United States Patent
Li et al.

(10) Patent No.: US 11,254,686 B1
(45) Date of Patent: Feb. 22, 2022

(54) COMPOUNDS AND METHODS FOR MODULATING ADENOSINE A2B RECEPTOR AND ADENOSINE A2A RECEPTOR

(71) Applicant: Corvus Pharmaceuticals, Inc., Burlingame, CA (US)

(72) Inventors: Zhihong Li, Millbrae, CA (US); Lubov Konstantinovna Filonova, Redwood City, CA (US); Erin Kathleen Bradley, San Mateo, CA (US); Erik Verner, Belmont, CA (US)

(73) Assignee: Corvus Pharmaceuticals, Inc., Burlingame, CA (US)

( * ) Notice: Subject to any disclaimer, the term of this patent is extended or adjusted under 35 U.S.C. 154(b) by 0 days.

(21) Appl. No.: 16/640,508

(22) PCT Filed: Aug. 31, 2018

(86) PCT No.: PCT/US2018/049206
§ 371 (c)(1),
(2) Date: Feb. 20, 2020

(87) PCT Pub. No.: WO2019/046784
PCT Pub. Date: Mar. 7, 2019

Related U.S. Application Data

(60) Provisional application No. 62/654,181, filed on Apr. 6, 2018, provisional application No. 62/553,006, filed on Aug. 31, 2017.

(51) Int. Cl.
*C07D 495/04* (2006.01)
*C07D 519/00* (2006.01)

(52) U.S. Cl.
CPC ......... *C07D 495/04* (2013.01); *C07D 519/00* (2013.01)

(58) Field of Classification Search
CPC .......................... C07D 495/04; A61K 31/519
USPC ....................................... 544/278; 514/260.1
See application file for complete search history.

(56) References Cited

U.S. PATENT DOCUMENTS

| | | | |
|---|---|---|---|
| 6,787,541 B1 | 9/2004 | Gillespie et al. | |
| 7,384,949 B2 | 6/2008 | Gillespie et al. | |
| 7,795,268 B2 | 9/2010 | Zeng et al. | |
| 8,354,415 B2 | 1/2013 | Jordan et al. | |
| 9,120,807 B2 | 9/2015 | Jordan et al. | |
| 9,610,290 B2 | 4/2017 | Jordan et al. | |
| 9,920,066 B2 | 3/2018 | Jordan et al. | |
| 10,556,911 B2 | 2/2020 | Jordan et al. | |
| 2010/0298349 A1 | 11/2010 | Jordan et al. | |
| 2020/0079793 A1 | 3/2020 | Li et al. | |

FOREIGN PATENT DOCUMENTS

| | | |
|---|---|---|
| WO | WO-2010/045008 A1 | 4/2010 |
| WO | WO-2016/081290 A1 | 5/2016 |

OTHER PUBLICATIONS

Bedford, S.T. et al. (2009, e-published Aug. 14, 2009). "Discovery and optimization of potent and selective functional antagonists of the human adenosine $A_{2B}$ receptor," *Bioorg. & Med. Chem. Lett.* 19(20):5945-5949.
Extended European Search Report issued in European Patent Application No. EP19194681.3, dated Jan. 21, 2020 (dated Jan. 21, 2020), 6 pages.
International Search Report and Written Opinion issued in International Application No. PCT/US2018/049206, dated Dec. 27, 2018. 17 pages.

*Primary Examiner* — Jeffrey H Murray
(74) *Attorney, Agent, or Firm* — Mintz, Levin, Cohn, Ferris, Glovsky and Popeo, P.C.

(57) ABSTRACT

Disclosed herein, inter alia, are certain substituted thieno[3,2-b]pyrimidine compositions and methods for modulating Adenosine Receptors, for example, having the formula:

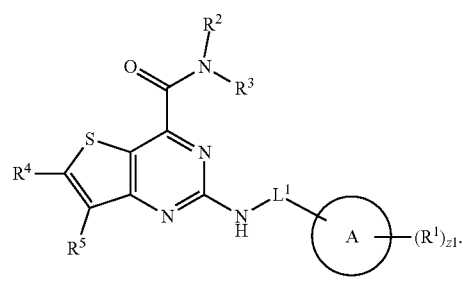

15 Claims, No Drawings
Specification includes a Sequence Listing.

COMPOUNDS AND METHODS FOR MODULATING ADENOSINE A2B RECEPTOR AND ADENOSINE A2A RECEPTOR

CROSS-REFERENCES TO RELATED APPLICATIONS

This application is the national stage filing under USC 371 of international application PCT/US2018/049206, filed Aug. 31, 2018, which claims the benefit of U.S. Provisional Application No. 62/553,006, filed Aug. 31, 2017, and U.S. Provisional Application No. 62/654,181, filed Apr. 6, 2018, which are incorporated herein by reference in their entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 048517-527N01US_Sequence_Listing_ST25.txt, created Feb. 18, 2020, 7,062 bytes, machine format IBM-PC, MS Windows operating system, is hereby incorporated by reference.

BACKGROUND

G protein-coupled receptors constitute a large superfamily of transmembrane proteins that represent the target for nearly half of all marketed drugs. Two of the GPCR family members, the Adenosine A2B Receptor and the Adenosine A2A Receptor are involved in many physiological functions. Thus there is a need in the art for Adenosine A2B Receptor modulators and Adenosine A2A Receptor modulators. Provided herein, inter alia, are solutions to these and other problems in the art.

BRIEF SUMMARY OF THE INVENTION

In an aspect is provided a compound having the formula:

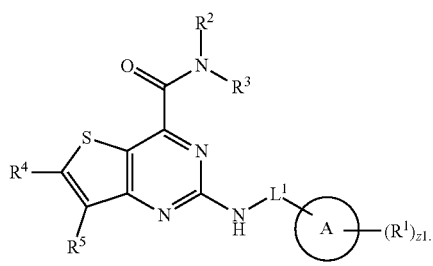

$L^1$ is substituted or unsubstituted alkylene, or substituted or unsubstituted heteroalkylene. Ring A is aryl or heteroaryl. $R^1$ is independently halogen, $-CX^1_3$, $-CHX^1_2$, $-CH_2X^1$, $-OCX^1_3$, $-OCH_2X^1$, $-OCHX^1_2$, $-CN$, $-SR^{1D}$, $-NR^{1A}R^{1B}$, $-C(O)R^{1C}$, $-C(O)OR^{1C}$, $-C(O)NR^{1A}R^{1B}$, $-OR^{1D}$, $-NR^{1A}C(O)R^{1C}$, $-NR^{1A}C(O)OR^{1C}$, $-SO_2R^{1D}$, $-SO_2NR^{1A}R^{1B}$, $-NR^{1A}SO_2R^{1D}$, substituted or unsubstituted alkyl, or substituted or unsubstituted heteroalkyl. The symbol z1 is an integer from 0 to 5. $R^2$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ and $R^3$ may optionally be joined to form a substituted or unsubstituted heterocycloalkyl. $R^4$ is independently hydrogen, halogen, $-CX^4_3$, $-CHX^4_2$, $-CH_2X^4$, $-OCX^4_3$, $-OCH_2X^4$, $-OCHX^4_2$, $-CN$, $-SR^{4D}$, $-NR^{4A}R^{4B}$, $-C(O)R^{4C}$, $-C(O)OR^{4C}$, $-C(O)NR^{4A}R^{4B}$, $-OR^{4D}$, $-NR^{4A}C(O)R^{4C}$, $-NR^{4A}C(O)OR^{4C}$, substituted or unsubstituted alkyl, or substituted or unsubstituted heteroalkyl. $R^5$ is independently hydrogen, halogen, $-CX^5_3$, $-CHX^5_2$, $-CH_2X^5$, $-OCX^5_3$, $-OCH_2X^5$, $-OCHX^5_2$, $-CN$, $-SR^{5D}$, $-NR^{5A}R^{5B}$, $-C(O)R^{5C}$, $-C(O)OR^{5C}$, $-C(O)NR^{5A}R^{5B}$, $-OR^{5D}$, $-NR^{5A}C(O)R^{5C}$, $-NR^{5A}C(O)OR^{5C}$, substituted or unsubstituted alkyl, or substituted or unsubstituted heteroalkyl. Each $R^{1A}$, $R^{1B}$, $R^{1C}$, $R^{1D}$, $R^{4A}$, $R^{4B}$, $R^{4C}$, $R^{4D}$, $R^{5A}$, $R^{5B}$, $R^{5C}$, and $R^{5D}$ is independently hydrogen, halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$ and $R^{1B}$ substituents bonded to the same nitrogen atom may optionally be joined to form a substituted or unsubstituted heterocycloalkyl. $R^{4A}$ and $R^{4B}$ substituents bonded to the same nitrogen atom may optionally be joined to form a substituted or unsubstituted heterocycloalkyl. $R^{5A}$ and $R^{5B}$ substituents bonded to the same nitrogen atom may optionally be joined to form a substituted or unsubstituted heterocycloalkyl. Each $X^1$, $X^4$, and $X^5$ is independently $-F$, $-Cl$, $-Br$, or $-I$.

In an aspect is provided a pharmaceutical composition including a compound as described herein, and a pharmaceutically acceptable excipient.

In an aspect is provided a method of inhibiting Adenosine A2B Receptor activity and Adenosine A2A Receptor activity, the method including contacting the Adenosine A2B Receptor and Adenosine A2A Receptor with a compound as described herein, including embodiments.

In another aspect is provided a method of inhibiting Adenosine A2B Receptor activity, the method including contacting the Adenosine A2B Receptor with a compound as described herein, including embodiments.

In an aspect is provided a method of treating cancer, the method including administering to a subject in need thereof an effective amount of a compound as described herein, including embodiments.

In an aspect is provided a method of treating fibrotic disease, said method comprising administering to a subject in need thereof an effective amount of a compound as described herein, including embodiments.

In an aspect is provided a method of treating a neurodegenerative disease, said method comprising administering to a subject in need thereof an effective amount of a compound as described herein, including embodiments.

In an aspect is provided a method of inhibiting a Adenosine Receptor activity, the method including contacting the Adenosine Receptor (e.g., A1, A2A, A2B, or A3) with a compound as described herein, including embodiments.

DETAILED DESCRIPTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—S—CH$_2$, —S(O)—CH$_3$, —CH$_2$—CH$_2$—S(O)$_2$—CH$_3$, —CH=CHO—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "〜〜" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

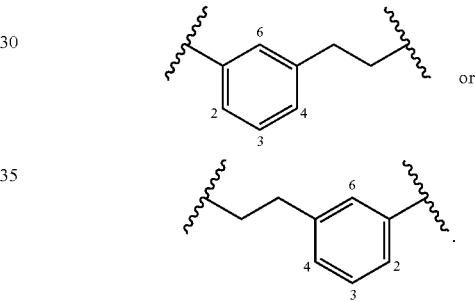

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$— $SO_3H$, —$OSO_3H$, —$SO_2NH_2$, —$NHNH_2$, —$ONH_2$, —NHC(O)$NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR"R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", ONR'R", —NR'C(O) NR"NR'"R"", —CN, —$NO_2$, —NR'SO$_2$R", —NR'C(O)R", —NR'C(O)—OR", —NR'OR", in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, —R, —N$_3$, —CH(Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

A "substituent group," as used herein, means a group selected from the following moieties:

(A) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:
  (i) oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and
  (ii) alkyl, heteroalkyl, cycloalkyl, heterocycloalkyl, aryl, heteroaryl, substituted with at least one substituent selected from:
    (a) oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and
    (b) alkyl, heteroalkyl, cycloalkyl, heterocycloalkyl, aryl, heteroaryl, substituted with at least one substituent selected from: oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{10}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{10}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroaryl ene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroaryl ene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroaryl ene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroaryl ene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroaryl ene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroaryl ene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroaryl ene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroaryl ene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroaryl ene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{10}$ alkyl, or unsubstituted 2 to 20 membered heteroalkyl," the group may contain one or more unsubstituted $C_1$-$C_{10}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

An "Adenosine A2B Receptor inhibitor" refers to a compound (e.g. compounds described herein) that reduces the activity of the Adenosine A2B Receptor when compared to a control, such as absence of the compound or a compound with known inactivity. An "Adenosine A2A Receptor inhibitor" refers to a compound (e.g. compounds described herein) that reduces the activity of Adenosine A2A Receptor when compared to a control, such as absence of the compound or a compound with known inactivity. An Adenosine A2B Receptor inhibitor may preferentially bind an Adenosine A2B Receptor (i.e., the Adenosine A2B Receptor inhibitor inhibits Adenosine A2B Receptor activity more than the Adenosine A2B Receptor inhibitor inhibits a different Adenosine Receptor (e.g., A2A, A1, or A3)).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

As defined herein, the term "activation", "activate", "activating", "activator" and the like in reference to a protein-inhibitor interaction means positively affecting (e.g. increasing) the activity or function of the protein relative to the activity or function of the protein in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein. The terms "agonist," "activator," "upregulator," etc. refer to a substance capable of detectably increasing the expression or activity of a given gene or protein relative to the absence of the agonist. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation). An "Adenosine A2B Receptor inhibitor" is a compound that negatively affects (e.g. decreases) the activity or function of Adenosine A2B Receptor relative to the activity or function of Adenosine A2B Receptor in the absence of the inhibitor. An "Adenosine A2A Receptor inhibitor" is a compound that negatively affects (e.g. decreases) the activity or function of Adenosine A2A Receptor relative to the activity or function of Adenosine A2A Receptor in the absence of the inhibitor.

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The terms "Adenosine A2A Receptor" and "AA2A Receptor" and "A2A" and "ADORA2A" refer to a protein (including homologs, isoforms, and functional fragments thereof) with adenylate cyclase activity. The term includes any recombinant or naturally-occurring form of Adenosine A2A Receptor variants thereof that maintain Adenosine A2A Receptor activity (e.g. within at least 30%, 40%, 50%, 60%, 70%, 80%, 90%, 95%, or 100% activity compared to wildtype Adenosine A2A Receptor). In embodiments, the Adenosine A2A Receptor protein encoded by the ADORA2A gene has the amino acid sequence set forth in or corresponding to Entrez 135, UniProt P29274, or RefSeq (protein) NP 000666. In embodiments, the ADORA2A gene has the nucleic acid sequence set forth in RefSeq (mRNA) NM 000675. In embodiments, the amino acid sequence or nucleic acid sequence is the sequence known at the time of filing of the present application. In embodiments, the sequence corresponds to GI: 156142194. In embodiments, the sequence corresponds to NM_000675.5. In embodiments, the sequence corresponds to NP_000667.2. In embodiments, the sequence corresponds to GI: 4501949. In embodiments, the A2A protein corresponds to the sequence:

```
                                            (SEQ ID NO: 1)
MPIMGSSVYITVELAIAVLAILGNVLVCWAVWLNSNLQNVTNYFVVS

LAAADIAVGVLAIPFAITISTGFCAACHGCLFIACEVLVLTQSSIFS

LLAIAIDRYIAIRIPLRYNGLVTGTRAKGIIAICWVLSFAIGLTPML

GWNNCGQPKEGKNHSQGCGEGQVACLFEDVPMNYMVYFNEFACVLVP

LLLMLGVYLRIFLAARRQLKQMESQPLPGERARSTLQKEVHAAKSLA

IIVGLFALCWLPLHIINCFTFFCPDCSHAPLWLMYLAIVLSHTNSVV

NPFIYAYRIREFRQTERKIIRSHVLRQQEPFKAAGTSARVLAAHGSD

GEQVSLRLNGUPPGVWANGSAPHPERRPNGYALGLVSGGSAQESQGN

TGLPDVELLSHELKGVCPEPPGLDDPLAQDGAGVS
```

The terms "Adenosine A2B Receptor" and "AA2B Receptor" and "A2B" and "ADORA2B" refer to a protein (including homologs, isoforms, and functional fragments thereof) with adenylate cyclase activity. The term includes any recombinant or naturally-occurring form of Adenosine A2B Receptor variants thereof that maintain Adenosine A2B Receptor activity (e.g. within at least 30%, 40%, 50%, 60%, 70%, 80%, 90%, 95%, or 100% activity compared to wildtype Adenosine A2B Receptor). In embodiments, the Adenosine A2B Receptor protein encoded by the ADORA2B gene has the amino acid sequence set forth in or corresponding to Entrez 136, UniProt P29275, or RefSeq (protein) NP 000667. In embodiments, the ADORA2B gene has the nucleic acid sequence set forth in RefSeq (mRNA) NM 000676. In embodiments, the amino acid sequence or nucleic acid sequence is the sequence known at the time of filing of the present application. In embodiments, the sequence corresponds to GI: 4501950. In embodiments, the sequence corresponds to NM_000676.2. In embodiments, the sequence corresponds to NP_000667.1. In embodiments, the A2B protein corresponds to the sequence:

```
                                            (SEQ ID NO: 2)
MLLETQDALYVALELVIAALSVAGNVLVCAAVGTANTLQTPTNYFLV

SLAAADVAVGLFAIPFAITISLGFCTDFYGCLFLACFVLVLTQSSIF

SLLAVAVDRYLAICVPLRYKSLVTGTRARGVIAVLWVLAFGIGLTPF

LGWNSKDSATNNCTEPWDGTTNESCCLVKCLFENVVPMSYMVYFNFF

GCVLPPLLIMLVIYIKIFLVACRQLQRTELMDHSRTTLQREIHAAKS

LAMIVGIFALCWLPVHAVNCVTLFQPAQGKNKPKWAMNMAILLSHAN

SVVNPIVYAYRNRDFRYTFHKIISRYLLCQADVKSGNGQAGVQPALG

VGL.
```

The terms "Adenosine A1 Receptor" and "A1 Receptor" refer to a protein (including homologs, isoforms, and functional fragments thereof) with adenylate cyclase activity. The term includes any recombinant or naturally-occurring form of Adenosine A1 Receptor variants thereof that maintain Adenosine A1 Receptor activity (e.g. within at least 30%, 40%, 50%, 60%, 70%, 80%, 90%, 95%, or 100% activity compared to wildtype Adenosine A1 Receptor). In embodiments, the Adenosine A1 Receptor protein encoded by the ADORA1 gene has the amino acid sequence set forth in or corresponding to Entrez 134, UniProt P30542, or RefSeq (protein) NP 000665. In embodiments, the ADORA1 gene has the nucleic acid sequence set forth in RefSeq (mRNA) NM 000674. In embodiments, the amino acid sequence or nucleic acid sequence is the sequence known at the time of filing of the present application.

The terms "Adenosine A3 Receptor" and "A3 Receptor" refer to a protein (including homologs, isoforms, and functional fragments thereof) with adenylate cyclase activity. The term includes any recombinant or naturally-occurring form of Adenosine A3 Receptor variants thereof that maintain Adenosine A3 Receptor activity (e.g. within at least 30%, 40%, 50%, 60%, 70%, 80%, 90%, 95%, or 100% activity compared to wildtype Adenosine A3 Receptor). In embodiments, the Adenosine A3 Receptor protein encoded by the ADORA3 gene has the amino acid sequence set forth in or corresponding to Entrez 140, UniProt P0DMS8, or RefSeq (protein) NP 000668. In embodiments, the ADORA3 gene has the nucleic acid sequence set forth in RefSeq (mRNA) NM_000677. In embodiments, the amino acid sequence or nucleic acid sequence is the sequence known at the time of filing of the present application.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The terms "disease" or "condition" refer to a state of being or health status of a patient or subject capable of being treated with the compounds or methods provided herein. The disease may be a cancer. The disease may be an autoimmune disease. The disease may be a fibrotic disorder (e.g., fibrosis). The disease may be an inflammatory disease. The disease may be an neurodegenerative disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "cancer" refers to all types of cancer, neoplasm or malignant tumors found in mammals (e.g. humans), including leukemia, lymphoma, carcinomas and sarcomas. Exemplary cancers that may be treated with a compound or method provided herein include brain cancer, glioma, glioblastoma, neuroblastoma, prostate cancer, colorectal cancer, pancreatic cancer, cervical cancer, gastric cancer, ovarian cancer, lung cancer, and cancer of the head. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Stemberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cunateous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, Schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms fully or partially remove the disease's underlying cause, shorten a disease's duration, or do a combination of these things. "Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "prevent" refers to a decrease in the occurrence of a disease or disease symptom in a patient (e.g., an Adenosine A2B Receptor or Adenosine A2A Receptor associated disease or disease symptom in a patient). As indicated above, the prevention may be complete (no detectable symptom) or partial, such that fewer symptoms or reduced severity of a symptom are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington; The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule. In some embodiments, an Adenosine A2B Receptor or Adenosine A2A Receptor associated disease modulator is a compound that reduces the severity of one or more symptoms of a disease associated with Adenosine A2B Receptor or Adenosine A2A Receptor (e.g. cancer). An Adenosine A2B Receptor or Adenosine A2A Receptor modulator is a compound that increases or decreases the activity or function or level of activity or level of function of Adenosine A2B Receptor or Adenosine A2A Receptor relative to the activity or function or level of activity or level of function of Adenosine A2B Receptor or Adenosine A2A Receptor in the absence of the Adenosine A2B Receptor or Adenosine A2A Receptor modulator.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease, a cancer associated with Adenosine A2B Receptor activity, Adenosine A2B Receptor associated cancer, Adenosine A2B Receptor associated disease (e.g., cancer)) means that the disease (e.g. cancer) is caused by (in whole or in part), or a symptom of the disease is caused by (in whole or in part) the substance or substance activity or function. For example, a cancer associated with Adenosine A2B Receptor or Adenosine A2A Receptor activity or function may be a cancer that results (entirely or partially) from aberrant Adenosine A2B Receptor or Adenosine A2A Receptor function (e.g. enzyme activity, protein-protein interaction, signaling pathway) or a cancer wherein a particular symptom of the disease is caused (entirely or partially) by aberrant Adenosine A2B Receptor or Adenosine A2A Receptor activity or function. As used herein, what is described as being associated with a disease, if a causative agent, could be a target for treatment of the disease. For example, a cancer associated with Adenosine A2B Receptor or Adenosine A2A Receptor activity or function or a Adenosine A2B Receptor or Adenosine A2A Receptor associated disease (e.g., cancer), may be treated with a Adenosine A2B Receptor or Adenosine A2A Receptor modulator or Adenosine A2B Receptor or Adenosine A2A Receptor inhibitor, in the instance where increased Adenosine A2B Receptor or Adenosine A2A Receptor activity or function (e.g. signaling pathway activity) causes the disease (e.g., cancer).

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components. For example, binding of a Adenosine A2B Receptor or Adenosine A2A Receptor with a compound as described herein may reduce the level of a product of the Adenosine A2B Receptor or Adenosine A2A Receptor catalyzed reaction or the level of a downstream derivative of the product or binding may reduce the interactions between the Adenosine A2B Receptor or Adenosine A2A Receptor or an Adenosine A2B Receptor or Adenosine A2A Receptor reaction product and downstream effectors or signaling pathway components, resulting in changes in cell growth, proliferation, or survival.

As used herein, the term "fibrosis" refers to the formation of excess fibrous connective tissue. The term "fibrotic disease" refers to a disease or condition caused by aberrant fibrosis or a disease or condition in which a symptom is aberrant fibrosis (e.g. relative to a control subject without the disease). Examples of fibrotic diseases that may be treated with a compound, pharmaceutical composition, or method described herein include idiopathic pulmonary fibrosis (IPF), myocardial infarction, cardiac hypertrophy, heart failure, cirrhosis, acetominophen (Tylenol) liver toxicity, hepatitis C liver disease, hepatosteatosis (fatty liver disease), and hepatic fibrosis.

As used herein, the term "neurodegenerative disease" refers to a disease or condition in which the function of a subject's nervous system becomes impaired (e.g. relative to a control subject who does not have the neurodegenerative disease). Examples of neurodegenerative diseases that may be treated with a compound, pharmaceutical composition, or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff s disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Wolfram Syndrome, transverse myelitis, Charcot-Marie-Tooth (CMT) disease, or Tabes dorsalis. Examples of neurodegenerative diseases that may be treated with a compound, pharmaceutical composition, or method described herein include retinitis pigmentosa, amyotrophic lateral sclerosis, retinal degeneration, macular degeneration, Parkinson's Disease, Alzheimer Disease, Huntington's Disease, Prion Disease, Creutzfeldt-Jakob Disease, or Kuru.

II. Compounds

In an aspect is provided a compound having the formula:

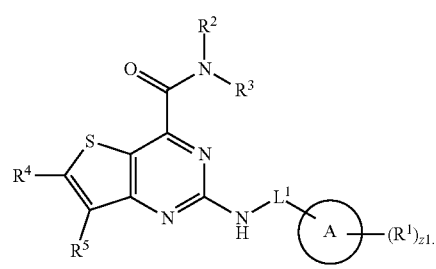

$L^1$ is a bond, substituted or unsubstituted alkylene, or substituted or unsubstituted heteroalkylene. In embodiments, $L^1$ is substituted or unsubstituted $C_1$-$C_3$ alkylene, or substituted or unsubstituted 2 to 3 membered heteroalkylene. Ring A is aryl or heteroaryl. $R^1$ is independently halogen, —CX$^1_3$, —CHX$^1_2$, —CH$_2$X$^1$, —OCX$^1_3$, —OCH$_2$X$^1$, —OCHX$^1_2$, —CN, —SR$^{1D}$, —NR$^{1A}$R$^{1B}$, —C(O)R$^{1C}$, —C(O)OR$^{1C}$, —C(O)NR$^{1A}$R$^{1B}$, —OR$^{1D}$, —NR$^{1A}$C(O)R$^{1C}$, —NR$^{1A}$C(O)OR$^{1C}$, —SO$_2$R$^{1D}$, —SO$_2$NR$^{1A}$R$^{1B}$, —NR$^{1A}$SO$_2$R$^{1D}$, substituted or unsubstituted alkyl, or substituted or unsubstituted heteroalkyl. The symbol z1 is an integer from 0 to 5.

R$^2$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^3$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^2$ and R$^3$ may optionally be joined to form a substituted or unsubstituted heterocycloalkyl.

R$^4$ is independently hydrogen, halogen, —CX$^4_3$, —CHX$^4_2$, —CH$_2$X$^4$, —OCX$^4_3$, —OCH$_2$X$^4$, —OCHX$^4_2$, —CN, —SR$^{4D}$, —NR$^{4A}$R$^{4B}$, —C(O)R$^{4C}$, —C(O)OR$^{4C}$, —C(O)NR$^{4A}$R$^{4B}$, —OR$^{4D}$, —NR$^{4A}$C(O)R$^{4C}$, —NR$^{4A}$C(O)OR$^{4C}$, substituted or unsubstituted alkyl, or substituted or unsubstituted heteroalkyl. R$^5$ is independently hydrogen, halogen, —CX$^5_3$, —CHX$^5_2$, —CH$_2$X$^5$, —OCX$^5_3$, —OCH$_2$X$^5$, —OCHX$^5_2$, —CN, —SR$^{5D}$, —NR$^{5A}$R$^{5B}$, —C(O)R$^{5C}$, —C(O)OR$^{5C}$, —C(O)NR$^{5A}$R$^{5B}$, —OR$^{5D}$, —NR$^{5A}$C(O)R$^{5C}$, —NR$^{5A}$C(O)OR$^{5C}$, substituted or unsubstituted alkyl, or substituted or unsubstituted heteroalkyl.

Each R$^{1A}$, R$^{1B}$, R$^{1C}$, R$^{1D}$, R$^{4A}$, R$^{4B}$, R$^{4C}$, R$^{4D}$, R$^{5A}$, R$^{5B}$, R$^{5C}$, and R$^{5D}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, each R$^{1A}$, R$^{1B}$, R$^{1C}$, R$^{1D}$, R$^{4A}$, R$^{4B}$, R$^{4C}$, R$^{4D}$, R$^{5A}$, R$^{5B}$, R$^{5C}$, and R$^{5D}$ independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, unsubstituted alkyl, unsubstituted heteroalkyl, unsubstituted cycloalkyl, unsubstituted heterocycloalkyl, unsubstituted aryl, or unsubstituted heteroaryl. R$^{1A}$ and R$^{1B}$ substituents bonded to the same nitrogen atom may optionally be joined to form a substituted or unsubstituted heterocycloalkyl or substituted or unsubstituted heteroaryl. R$^{4A}$ and R$^{4B}$ substituents bonded to the same nitrogen atom may optionally be joined to form a substituted or unsubstituted heterocycloalkyl or substituted or unsubstituted heteroaryl. R$^{5A}$ and R$^{5B}$ substituents bonded to the same nitrogen atom may optionally be joined to form a substituted or unsubstituted heterocycloalkyl or substituted or unsubstituted heteroaryl. Each X$^1$, X$^4$, and X$^5$ is independently —F, —Cl, —Br, or —I.

In embodiments, the compound has the formula:

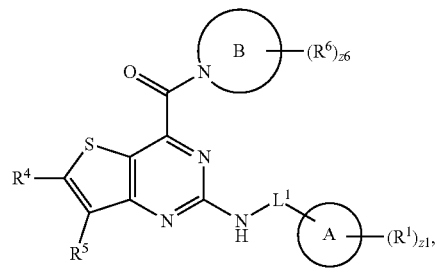

wherein Ring B is heterocycloalkyl, and R$^4$, R$^5$, L$^1$, Ring A, R$^1$, and z1 are as described herein, including embodiments. R$^6$ is independently halogen, —CX$^6_3$, —CHX$^6_2$, —CH$_2$X$^6$, —OCX$^6_3$, —OCH$_2$X$^6$, —OCHX$^6_2$, —CN, —SR$^{6D}$, —SO$_2$R$^{6D}$, —NR$^{6A}$R$^{6B}$, —C(O)R$^{6C}$, —C(O)OR$^{6C}$, —C(O)NR$^{6A}$R$^{6B}$, —OR$^{6D}$, —NR$^{6A}$C(O)R$^{6C}$, —NR$^{6A}$C(O)NR$^{6C}$—, —NR$^{6A}$C(O)OR$^{6C}$, —SO$_2$NR$^{6A}$R$^{6B}$, —NR$^{6A}$SO$_2$R$^{6D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol z6 is an integer from 0 to 10.

Each R$^{6A}$, R$^{6B}$, R$^{6C}$, and R$^{6D}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{6A}$ and R$^{6B}$ substituents bonded to the same nitrogen atom may optionally be joined to form a substituted or unsubstituted heterocycloalkyl or substituted or unsubstituted heteroaryl. The symbol X$^6$ is independently —F, —Cl, —Br, or —I.

In embodiments, the compound has the formula:

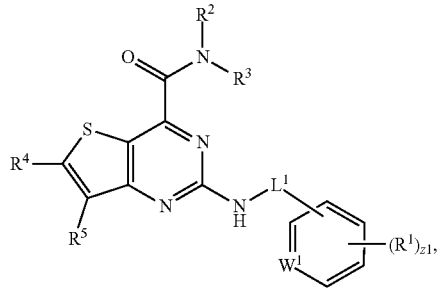

wherein R$^2$, R$^3$, R$^4$, R$^5$, L$^1$, R$^1$, and z1 are as described herein, including embodiments. The symbol W$^1$ is C(R$^1$), CH, or N.

In embodiments, the compound has the formula:

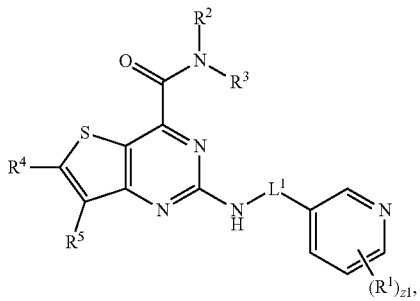

wherein R², R³, R⁴, R⁵, L¹, R¹, and z1 are as described herein, including embodiments.

In embodiments, the compound has the formula:

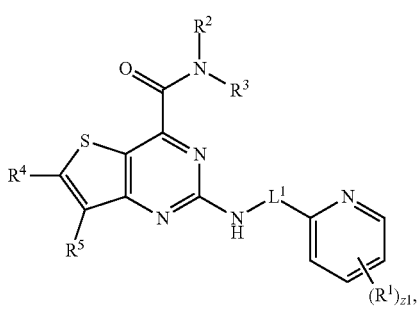

wherein R², R³, R⁴, R⁵, L¹, R¹, and z1 are as described herein, including embodiments.

In embodiments, the compound has formula:

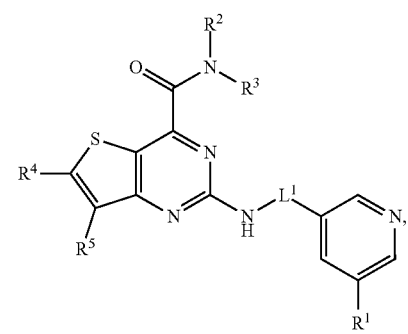

wherein R², R³, R⁴, R⁵, L¹, and R¹ are as described herein, including embodiments.

In embodiments, the compound has formula:

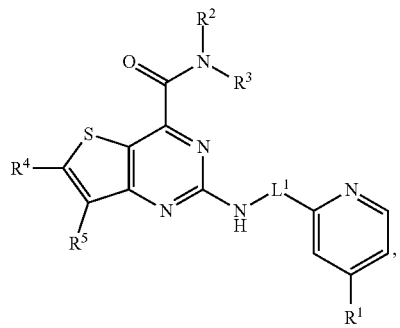

wherein R², R³, R⁴, R⁵, L¹, and R¹ are as described herein, including embodiments.

In embodiments, the compound has the formula:

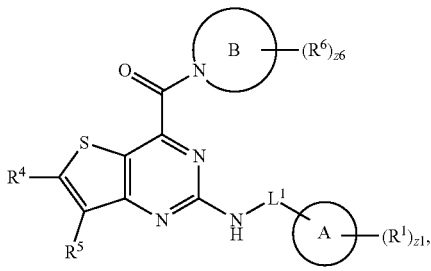

wherein Ring B is a heterocycloalkyl, and wherein R⁴, R⁵, L¹, R¹, Ring A, and z1 are as described herein, including embodiments.

In embodiments, the compound has the formula:

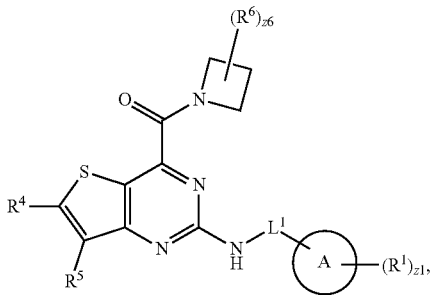

wherein R⁶, z6, R⁴, R⁵, L¹, R¹, Ring A, and z1 are as described herein, including embodiments.

In embodiments, the compound has the formula:

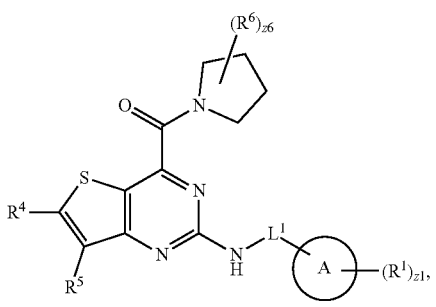

wherein $R^6$, z6, $R^4$, $R^5$, $L^1$, $R^1$, Ring A, and z1 are as described herein, including embodiments.

In embodiments, the compound has the formula:

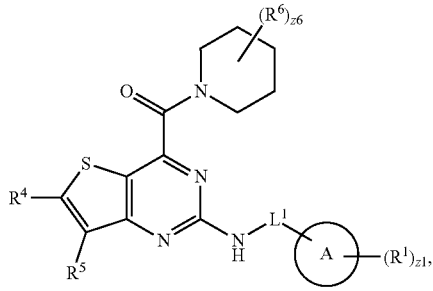

wherein $R^6$, z6, $R^4$, $R^5$, $L^1$, $R^1$, Ring A, and z1 are as described herein, including embodiments.

In embodiments, the compound has the formula:

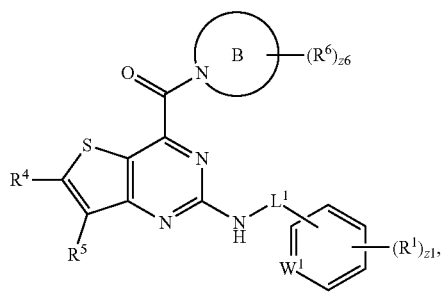

wherein $R^6$, z6, $R^4$, $R^5$, $L^1$, $R^1$, $W^1$, and z1 are as described herein, including embodiments.

In embodiments, the compound has the formula:

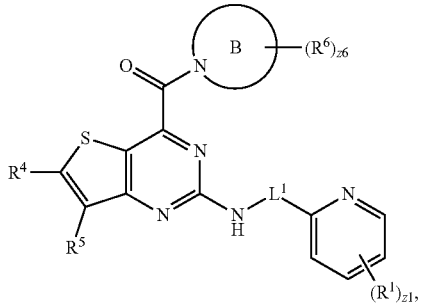

wherein $R^6$, z6, $R^4$, $R^5$, $L^1$, $R^1$, Ring B, and z1 are as described herein, including embodiments.

In embodiments, the compound has the formula:

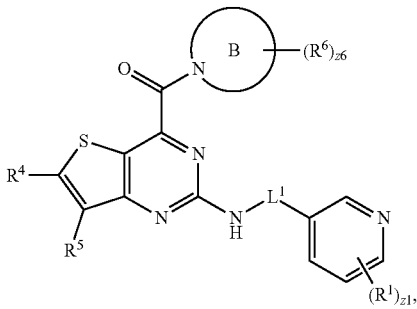

wherein $R^6$, z6, $R^4$, $R^5$, $L^1$, $R^1$, Ring B, and z1 are as described herein, including embodiments.

In embodiments, the compound has the formula:

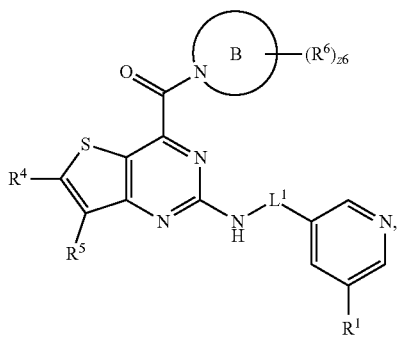

wherein $R^6$, z6, $R^4$, $R^5$, $L^1$, $R^1$, and Ring B are as described herein, including embodiments.

In embodiments, the compound has the formula:

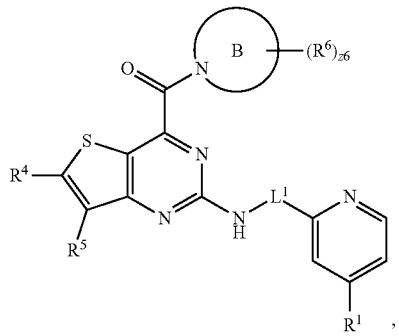

wherein $R^6$, z6, $R^4$, $R^5$, $L^1$, $R^1$, and Ring B are as described herein, including embodiments.

In embodiments, the compound has the formula:

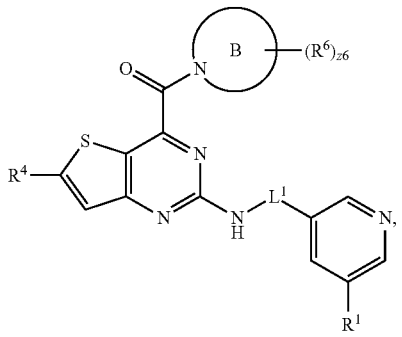

wherein $R^6$, z6, $R^4$, $L^1$, $R^1$, and Ring B are as described herein, including embodiments.

In embodiments, the compound has the formula:

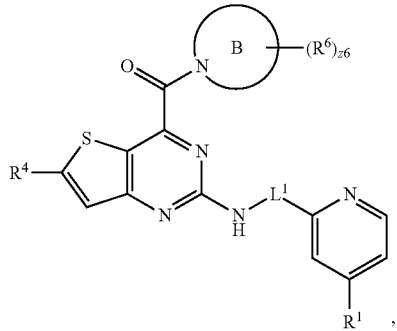

wherein $R^6$, z6, $R^4$, $L^1$, $R^1$, and Ring B are as described herein, including embodiments.

In embodiments, the compound has the formula:

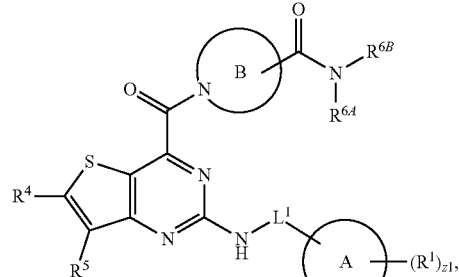

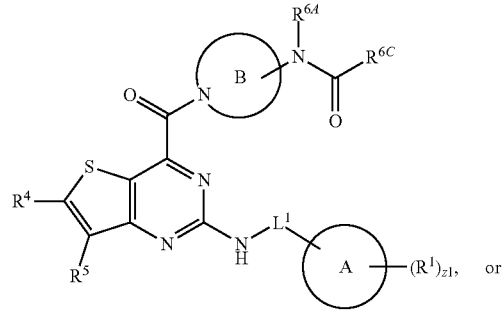

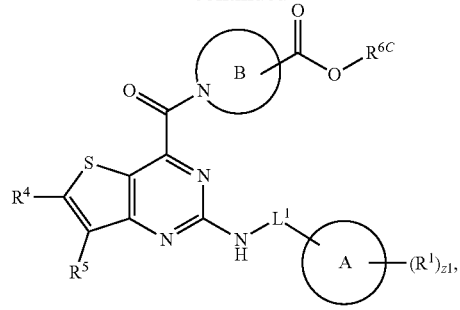

wherein $R^{6A}$, $R^{6B}$, $R^{6C}$, $R^4$, $R^5$, $L^1$, Ring A, z1, $R^1$, and Ring B are as described herein, including embodiments.

In embodiments, the compound has the formula:

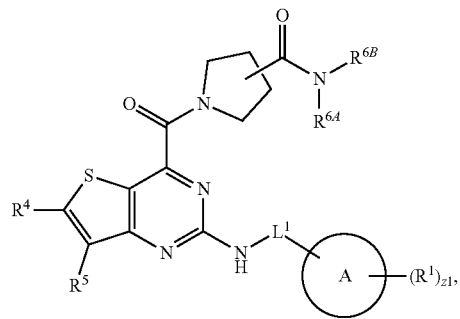

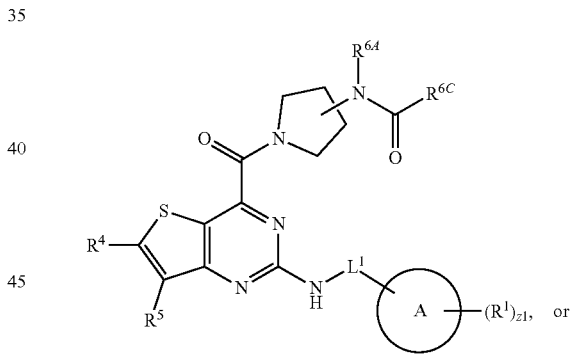

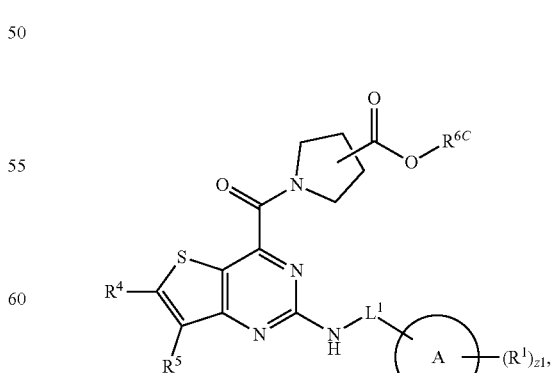

wherein $R^{6A}$, $R^{6B}$, $R^{6C}$, $R^4$, $R^5$, $L^1$, Ring A, z1, and $R^1$ are as described herein, including embodiments.

In embodiments, the compound has the formula:
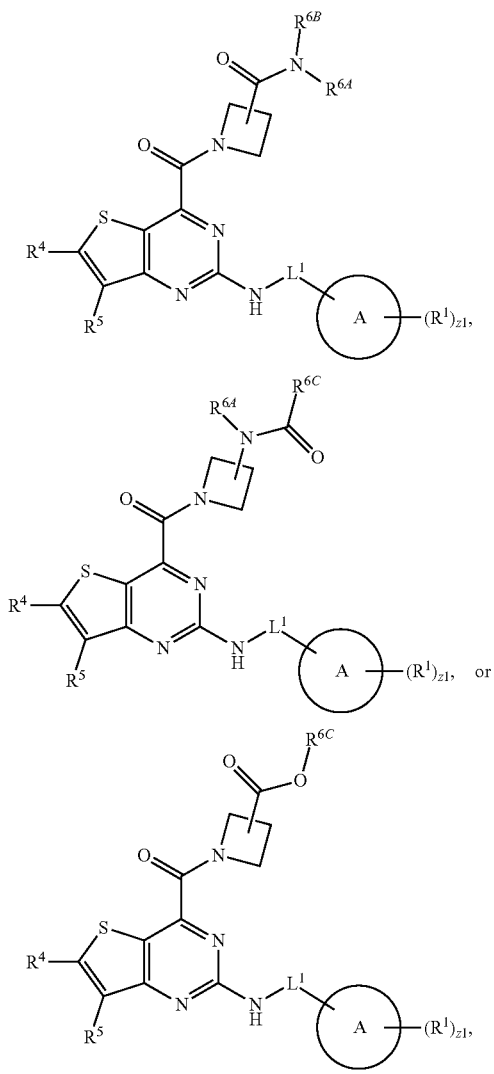
wherein $R^{6A}$, $R^{6B}$, $R^{6C}$, $R^4$, $R^5$, $L^1$, Ring A, z1, and $R^1$ are as described herein, including embodiments.
In embodiments, the compound has the formula:
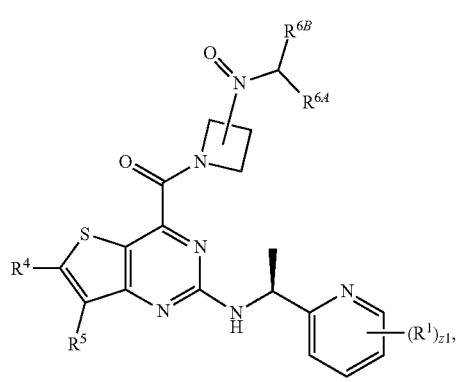
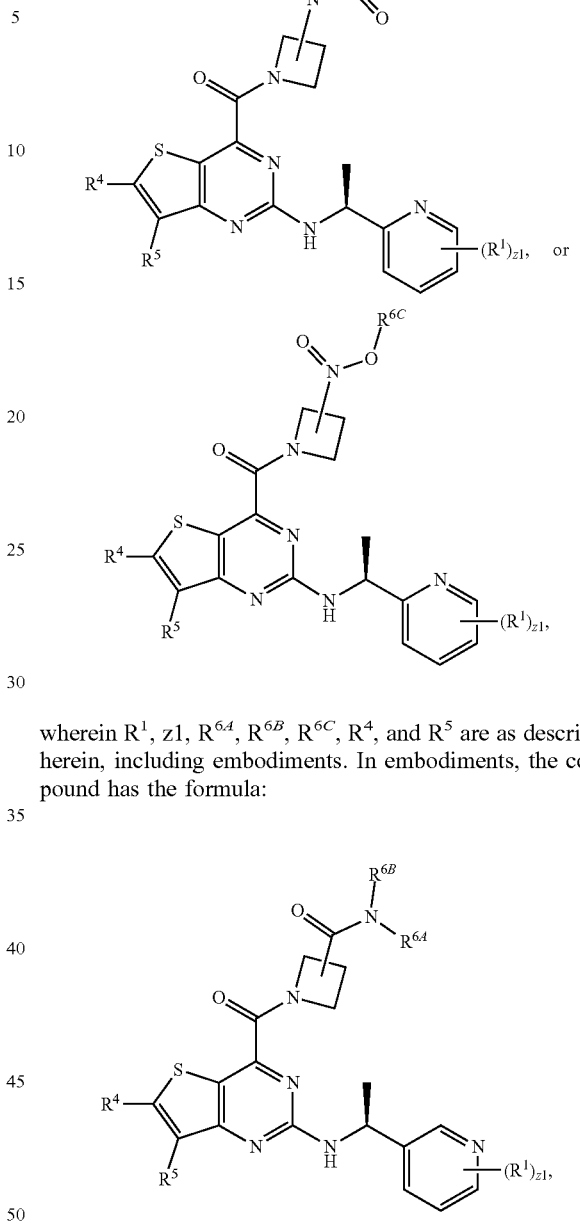
wherein $R^1$, z1, $R^{6A}$, $R^{6B}$, $R^{6C}$, $R^4$, and $R^5$ are as described herein, including embodiments. In embodiments, the compound has the formula:
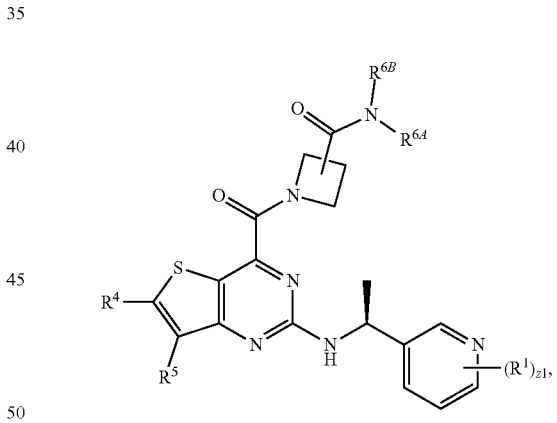
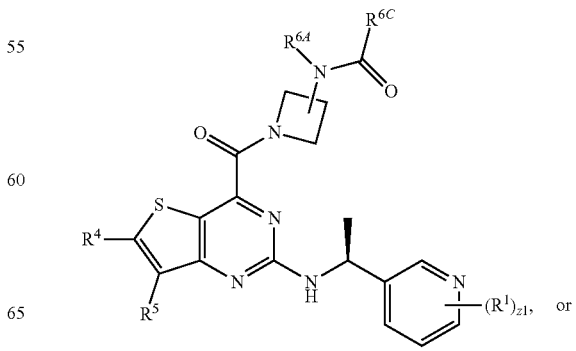

-continued

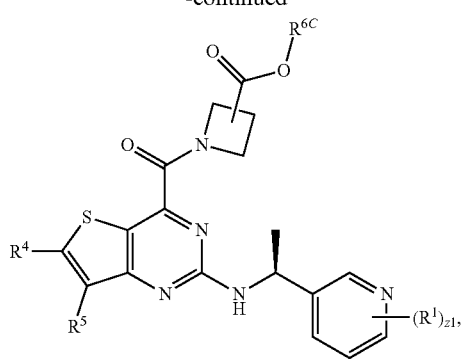

wherein $R^1$, z1, $R^{6A}$, $R^{6B}$, $R^{6C}$, $R^4$, and $R^5$ are as described herein, including embodiments.

In embodiments, the compound has the formula:

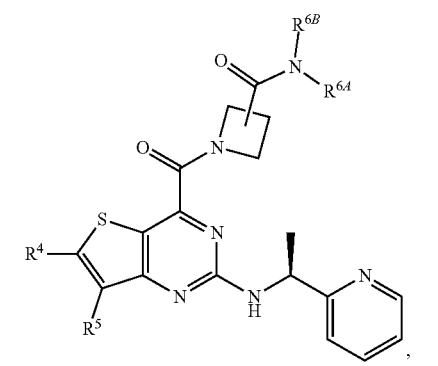

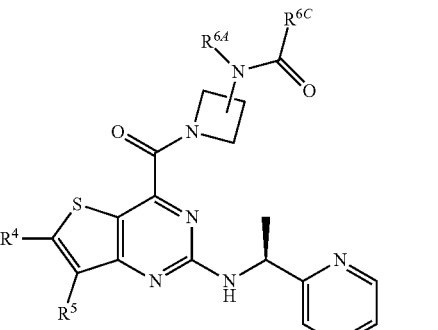

or

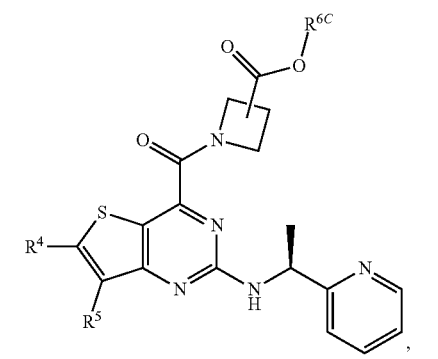

wherein $R^{6A}$, $R^{6B}$, $R^{6C}$, $R^4$, and $R^5$ are as described herein, including embodiments. In embodiments, the compound has the formula:

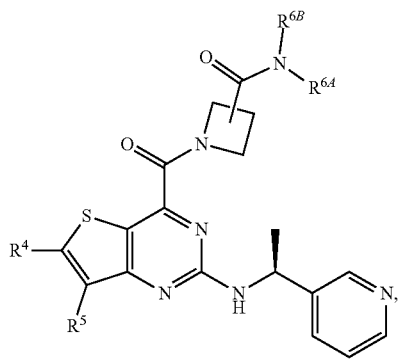

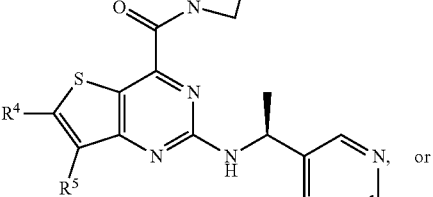

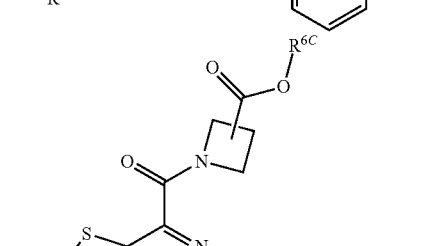

or

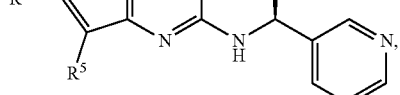

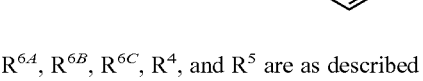

wherein $R^{6A}$, $R^{6B}$, $R^{6C}$, $R^4$, and $R^5$ are as described herein, including embodiments.

In embodiments, the compound has the formula:

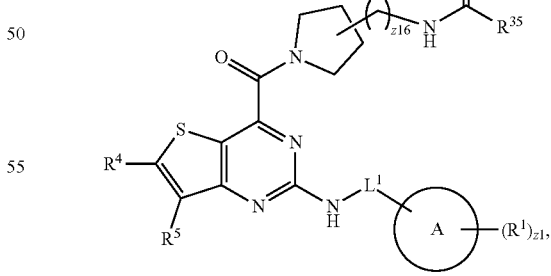

wherein $R^4$, $R^5$, $L^1$, Ring A, $R^1$, and z1 are as described herein, including embodiments; and z16 is an integer from 0 to 8. $R^{35}$ is oxo, halogen, —CCl₃, —CBr₃, —CF₃, —CI₃, CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the compound has the formula:

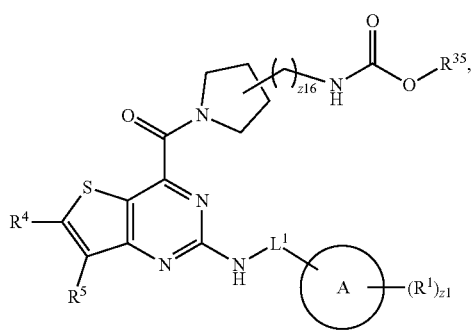

wherein R$^{35}$, R$^4$, R$^5$, L$^1$, Ring A, R$^1$, and z1 are as described herein, including embodiments; and z16 is an integer from 1 to 8.

In embodiments, the compound has the formula:

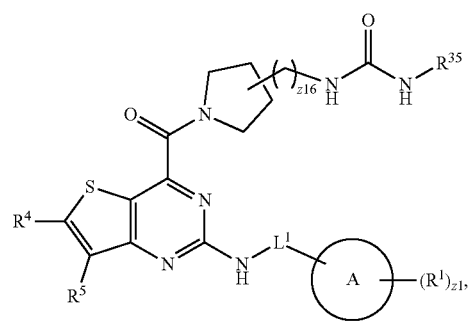

wherein R$^{35}$, R$^4$, R$^5$, L$^1$, Ring A, R$^1$, and z1 are as described herein, including embodiments; and z16 is an integer from 1 to 8.

In embodiments, the compound has the formula:

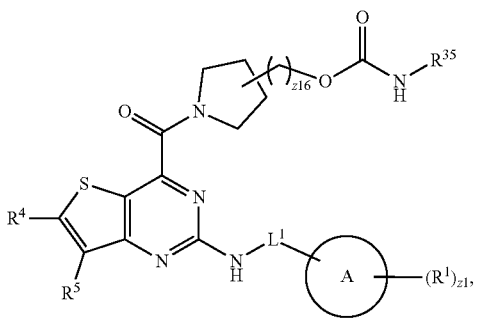

wherein R$^{35}$, R$^4$, R$^5$, L$^1$, Ring A, R$^1$, and z1 are as described herein, including embodiments; and z16 is an integer from 1 to 8.

In embodiments, the compound has the formula:

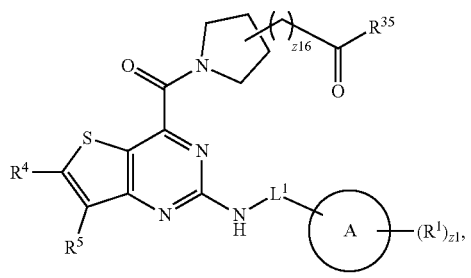

wherein R$^{35}$, R$^4$, R$^5$, L$^1$, Ring A, R$^1$, and z1 are as described herein, including embodiments; and z16 is an integer from 1 to 8.

In embodiments, the compound has the formula:

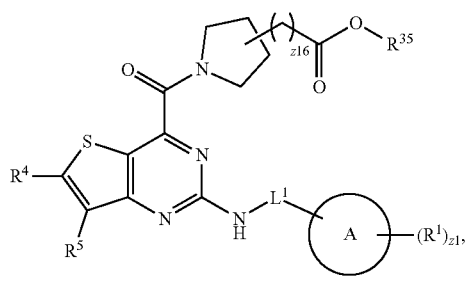

wherein R$^{35}$, R$^4$, R$^5$, L$^1$, Ring A, R$^1$, and z1 are as described herein, including embodiments; and z16 is an integer from 1 to 8.

In embodiments, the compound has the formula:

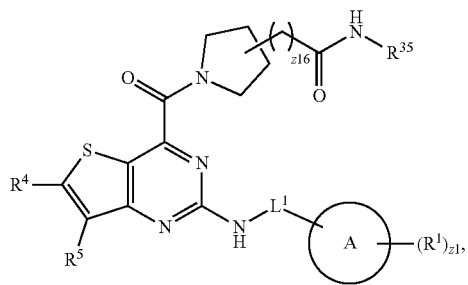

wherein R$^{35}$, R$^4$, R$^5$, L$^1$, Ring A, R$^1$, and z1 are as described herein, including embodiments; and z16 is an integer from 1 to 8.

In embodiments, the compound has the formula:

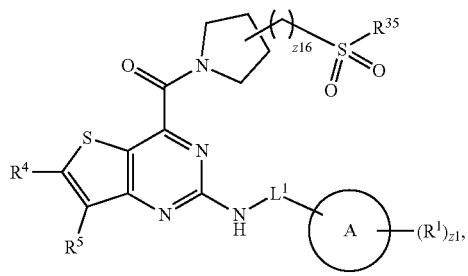

wherein $R^{35}$, $R^4$, $R^5$, $L^1$, Ring A, $R^1$, and z1 are as described herein, including embodiments; and z16 is an integer from 1 to 8.

In embodiments, the compound has the formula:

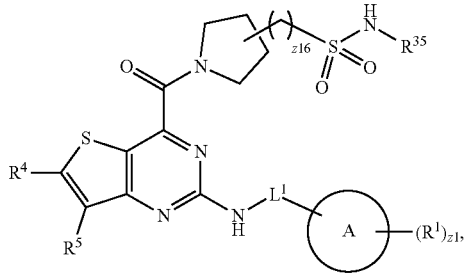

wherein $R^{35}$, $R^4$, $R^5$, $L^1$, Ring A, $R^1$, and z1 are as described herein, including embodiments; and z16 is an integer from 1 to 8.

In embodiments, the compound has the formula:

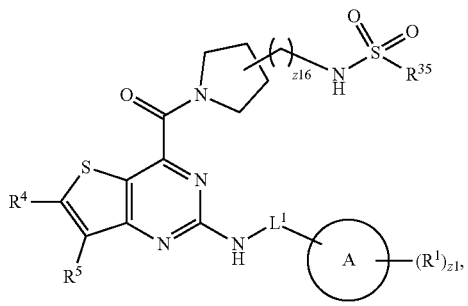

wherein $R^{35}$, $R^4$, $R^5$, $L^1$, Ring A, $R^1$, and z1 are as described herein, including embodiments; and z16 is an integer from 1 to 8.

In embodiments, the compound has the formula:

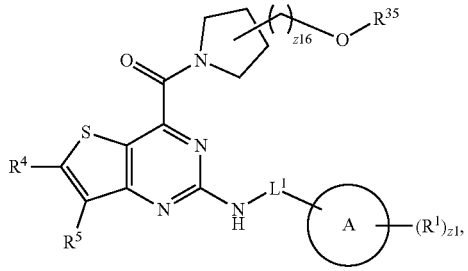

wherein $R^{35}$, $R^4$, $R^5$, $L^1$, Ring A, $R^1$, and z1 are as described herein, including embodiments; and z16 is an integer from 1 to 8.

In embodiments, the compound has the formula:

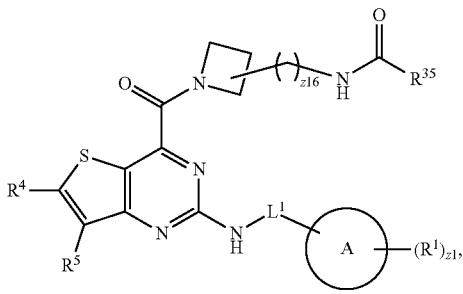

wherein $R^{35}$, $R^4$, $R^5$, $L^1$, Ring A, $R^1$, z16, and z1 are as described herein, including embodiments. In embodiments, the compound has the formula:

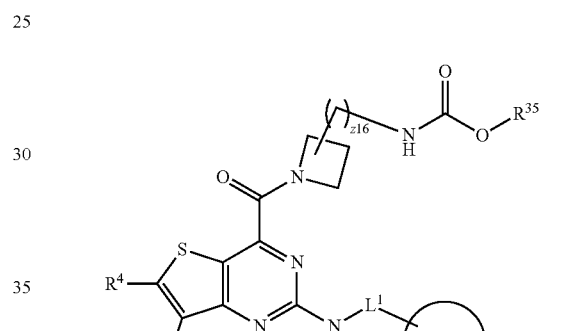

wherein $R^{35}$, $R^4$, $R^5$, $L^1$, Ring A, $R^1$, z16, and z1 are as described herein, including embodiments. In embodiments, the compound has the formula:

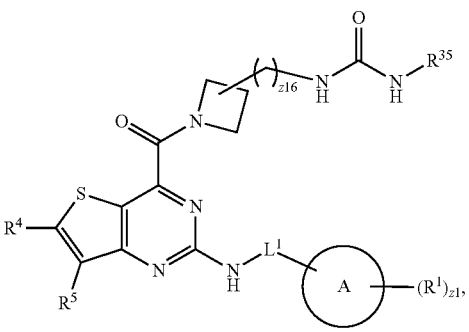

wherein $R^{35}$, $R^4$, $R^5$, $L^1$, Ring A, $R^1$, z16, and z1 are as described herein, including embodiments. In embodiments, the compound has the formula:

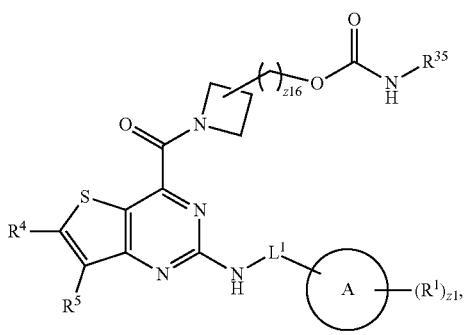

wherein $R^{35}$, $R^4$, $R^5$, $L^1$, Ring A, $R^1$, z16, and z1 are as described herein, including embodiments. In embodiments, the compound has the formula:

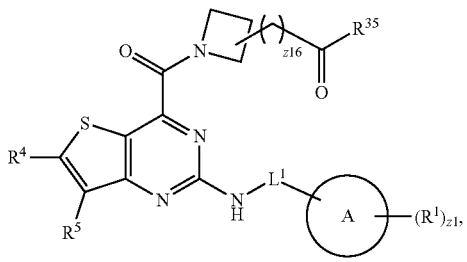

wherein $R^{35}$, $R^4$, $R^5$, $L^1$, Ring A, $R^1$, z16, and z1 are as described herein, including embodiments. In embodiments, the compound has the formula:

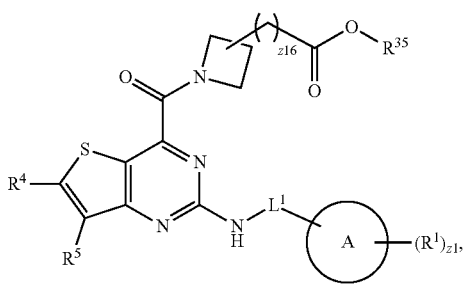

wherein $R^{35}$, $R^4$, $R^5$, $L^1$, Ring A, $R^1$, z16, and z1 are as described herein, including embodiments. In embodiments, the compound has the formula:

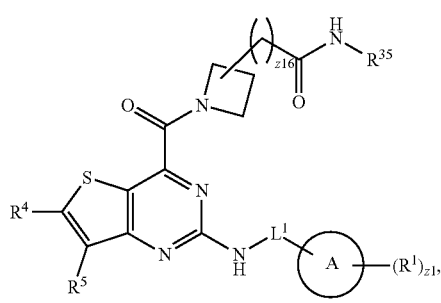

wherein $R^{35}$, $R^4$, $R^5$, $L^1$, Ring A, $R^1$, z16, and z1 are as described herein, including embodiments. In embodiments, the compound has the formula:

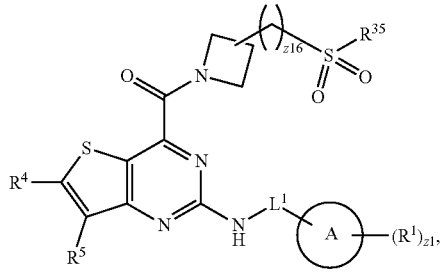

wherein $R^{35}$, $R^4$, $R^5$, $L^1$, Ring A, $R^1$, z16, and z1 are as described herein, including embodiments. In embodiments, the compound has the formula:

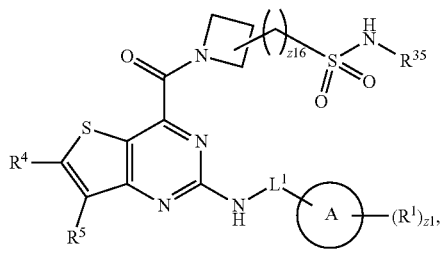

wherein $R^{35}$, $R^4$, $R^5$, $L^1$, Ring A, $R^1$, z16, and z1 are as described herein, including embodiments.

In embodiments, the compound has the formula:

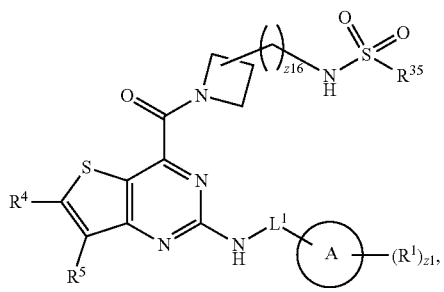

wherein $R^{35}$, $R^4$, $R^5$, $L^1$, Ring A, $R^1$, z16, and z1 are as described herein, including embodiments. In embodiments, the compound has the formula:

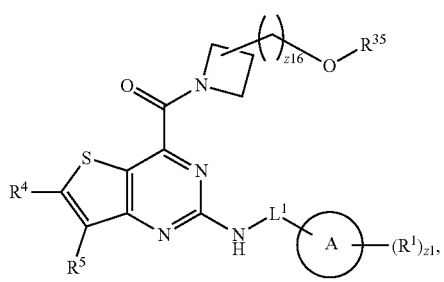

wherein $R^{35}$, $R^4$, $R^5$, $L^1$, Ring A, $R^1$, z16, and z1 are as described herein, including embodiments.

In embodiments, the compound has the formula:

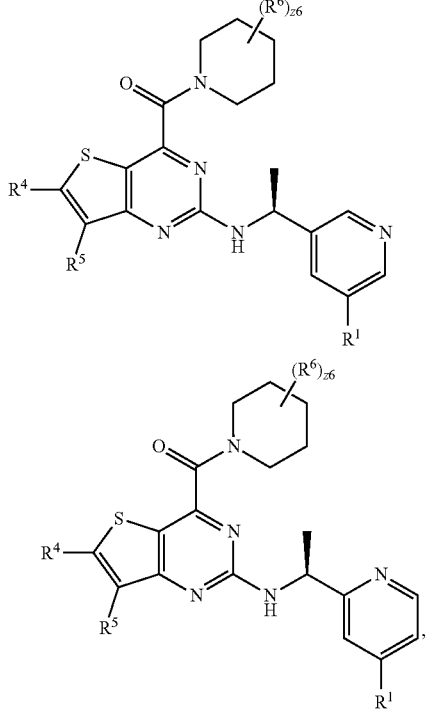

or

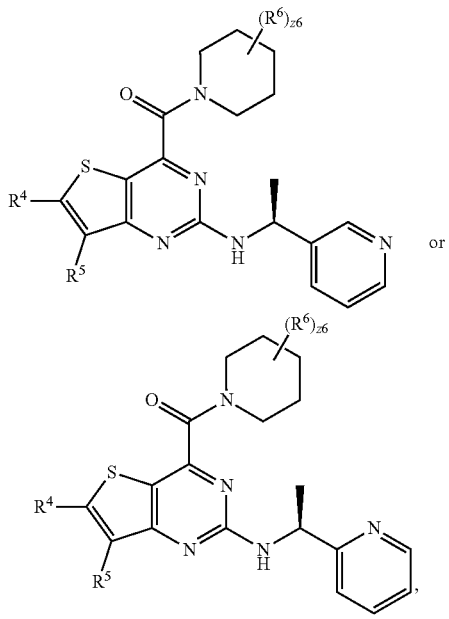

, wherein $R^6$, z6, $R^4$, $R^5$, and $R^1$ are as described herein, including embodiments.

In embodiments, the compound has the formula:

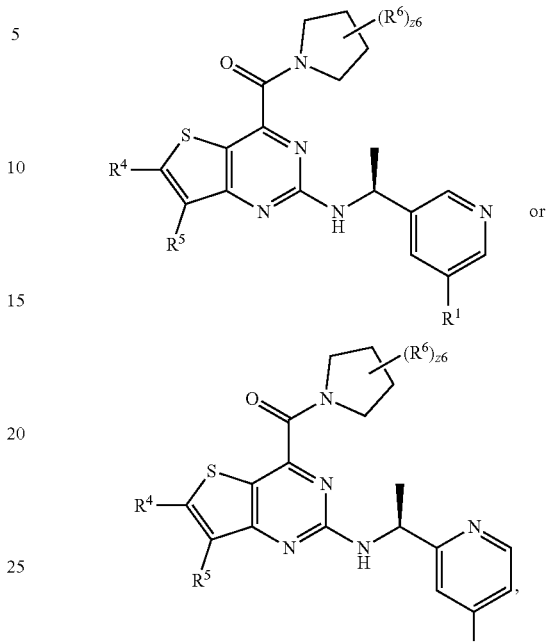

wherein $R^6$, z6, $R^4$, and $R^5$ are as described herein, including embodiments.

In embodiments, the compound has the formula:

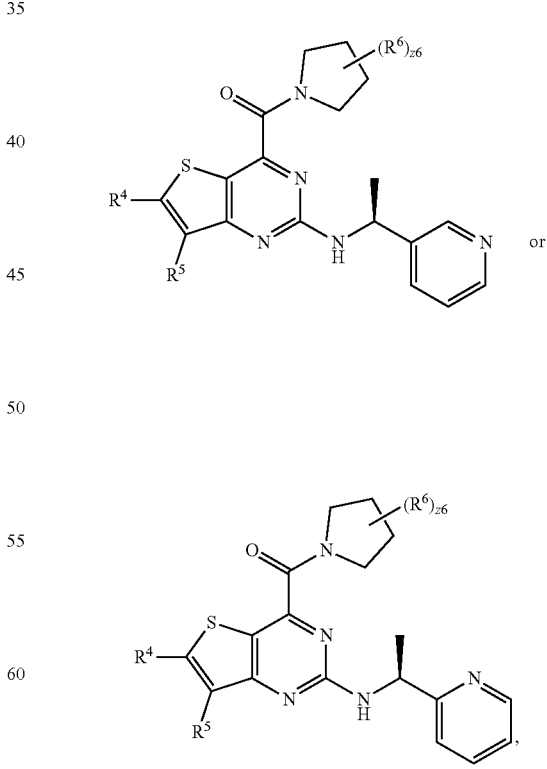

wherein $R^6$, z6, $R^4$, and $R^5$ are as described herein, including embodiments.

In embodiments, the compound has the formula:

wherein $R^6$, z6, $R^4$, $R^5$, and $R^1$ are as described herein, including embodiments.

In embodiments, the compound has the formula:

In embodiments, the compound has the formula:

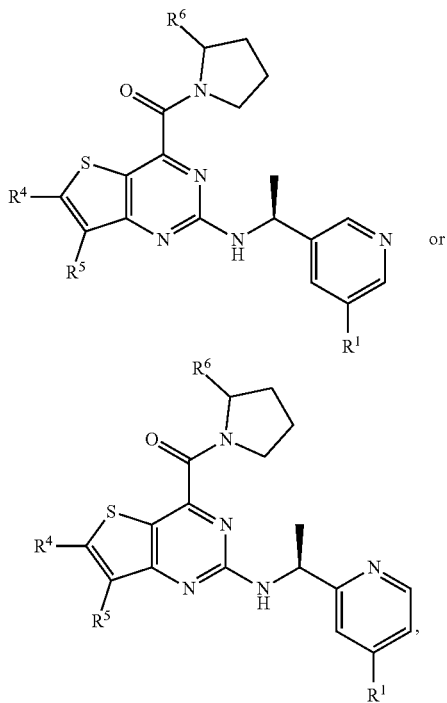

wherein R[6], R[4], R[5], and R[1] are as described herein, including embodiments.

In embodiments, the compound has the formula:

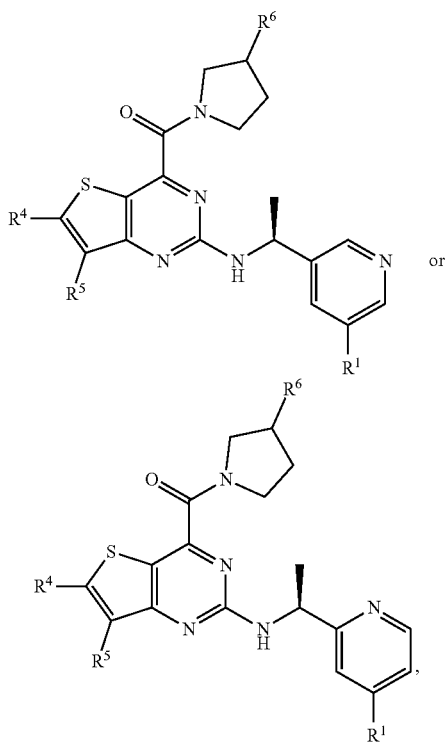

wherein R[6], R[4], R[5], and R[1] are as described herein, including embodiments.

In embodiments, the compound has the formula:

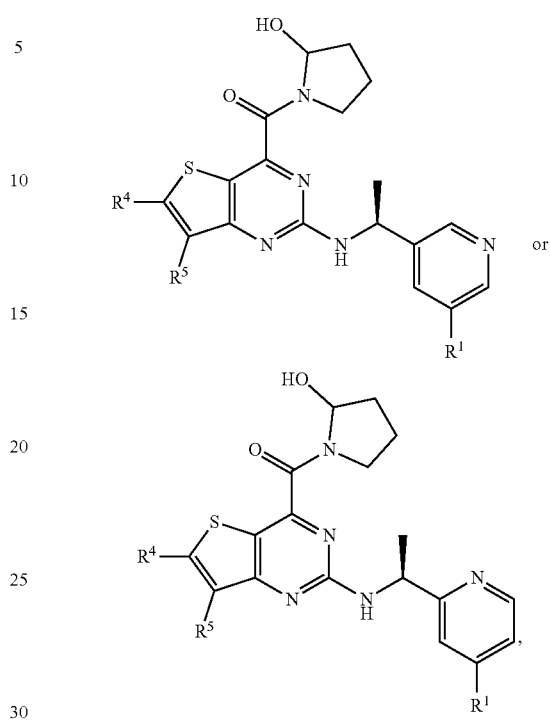

wherein R[1], R[4], and R[5] are as described herein.

In embodiments, the compound has the formula:

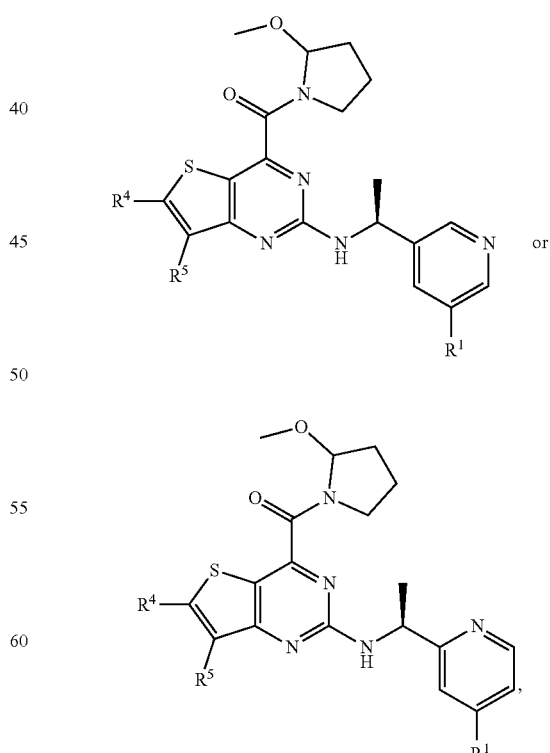

wherein R[1], R[4], and R[5] are as described herein.

In embodiments, the compound has the formula:

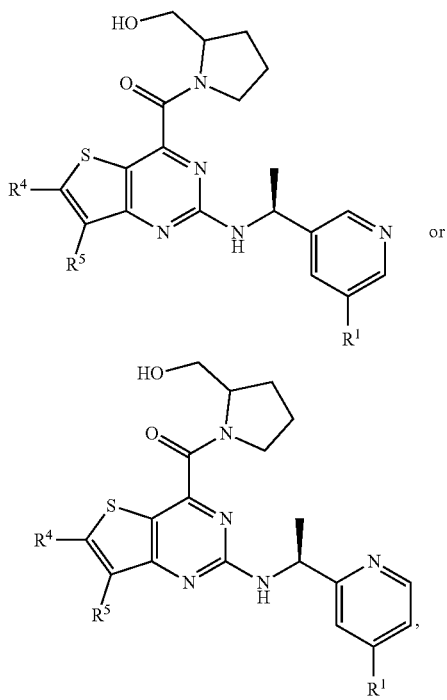

wherein $R^1$, $R^4$, and $R^5$ are as described herein.

In embodiments, the compound has the formula:

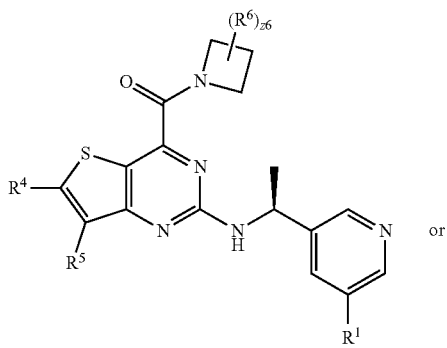

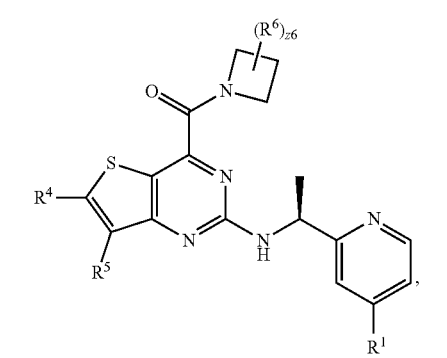

wherein $R^6$, z6, $R^1$, $R^4$, and $R^5$ are as described herein.

In embodiments, the compound has the formula:

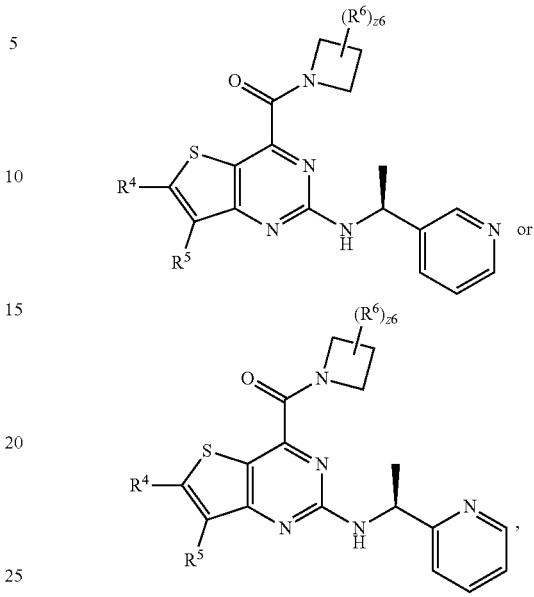

wherein $R^4$, $R^5$, z6, and $R^6$ are as described herein, including embodiments.

In embodiments, the compound has the formula:

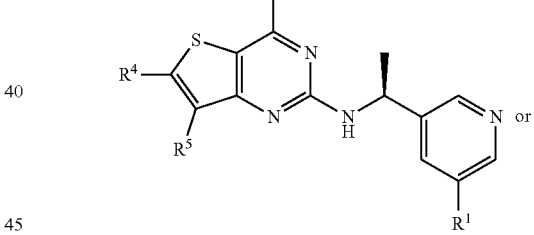

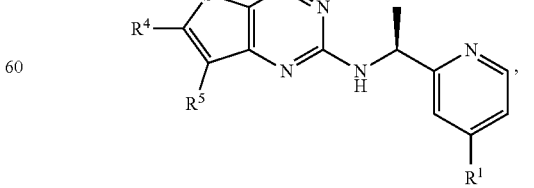

wherein $R^6$, $R^1$, $R^4$, and $R^5$ are as described herein.

In embodiments, the compound has the formula:

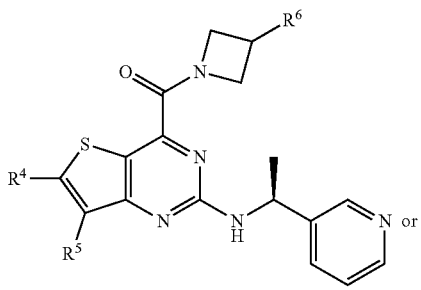

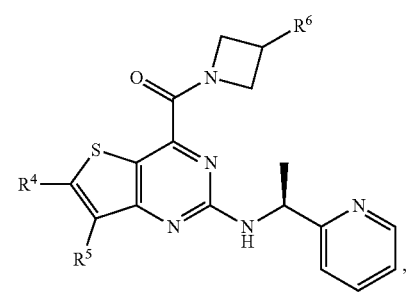

wherein $R^6$, $R^4$, and $R^5$ are as described herein.

In embodiments, the compound has the formula:

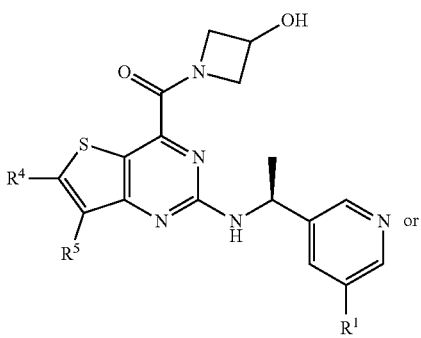

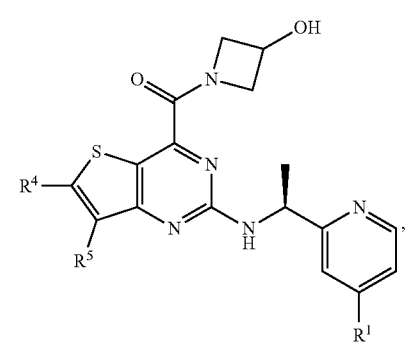

wherein $R^1$, $R^4$, and $R^5$ are as described herein, including embodiments.

In embodiments, the compound has the formula:

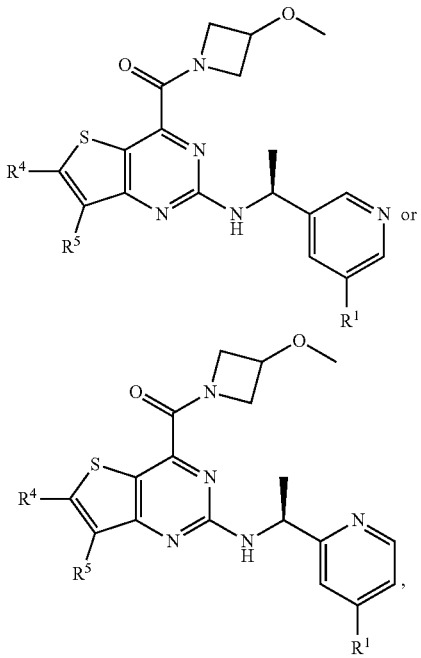

wherein $R^1$, $R^4$, and $R^5$ are as described herein, including embodiments.

In embodiments, the compound has the formula:

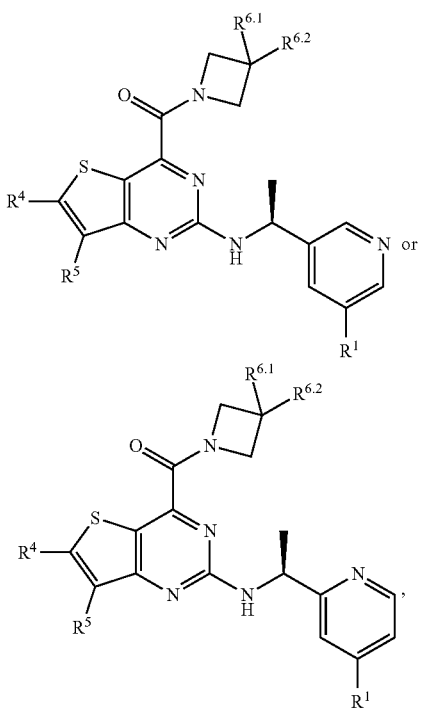

wherein $R^1$, $R^4$, and $R^5$ are as described herein, including embodiments; and wherein $R^{6.1}$ and $R^{6.2}$ are each $R^6$ at a fixed position on the attached ring. $R^{6.1}$ and $R^{6.2}$ may independently be any substituent of $R^6$ described herein, including in any aspect, embodiment, example, figure, or claim. $R^{6.1}$ and $R^{6.2}$ may be hydrogen.

In embodiments, the compound has the formula:

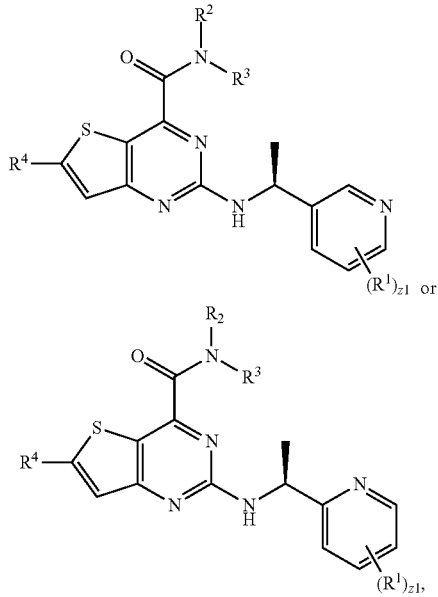

wherein $R^1$, z1, $R^2$, and $R^4$ are as described herein, including embodiments. In embodiments, the compound has the formula:

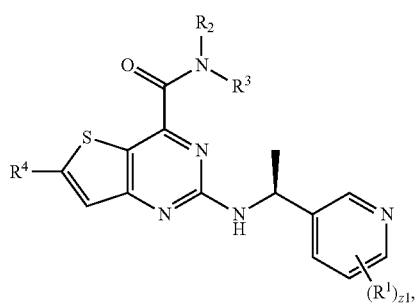

wherein $R^1$, z1, $R^2$, and $R^4$ are as described herein, including embodiments. In embodiments, the compound has the formula:

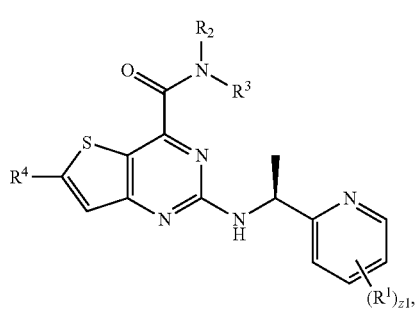

wherein $R^1$, z1, $R^2$, and $R^4$ are as described herein, including embodiments.

In embodiments, the compound has the formula:

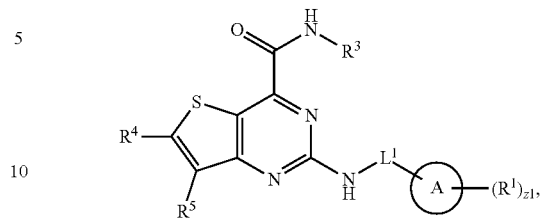

wherein $R^1$, z1, Ring A, $L^1$, $R^3$, $R^4$, and $R^5$ are as described herein, including embodiments.

In embodiments, the compound has the formula:

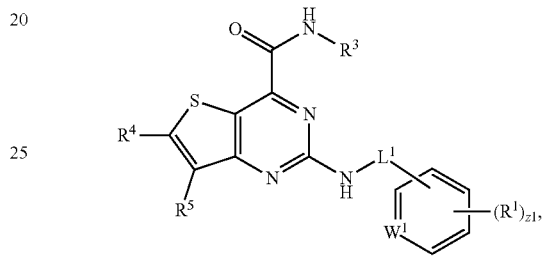

wherein $R^1$, z1, $W^1$, $L^1$, $R^3$, $R^4$, and $R^5$ are as described herein, including embodiments.

In embodiments, the compound has the formula:

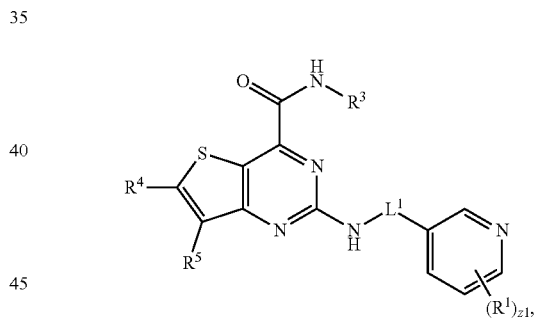

wherein $R^1$, z1, $L^1$, $R^3$, $R^4$, and $R^5$ are as described herein, including embodiments.

In embodiments, the compound has the formula:

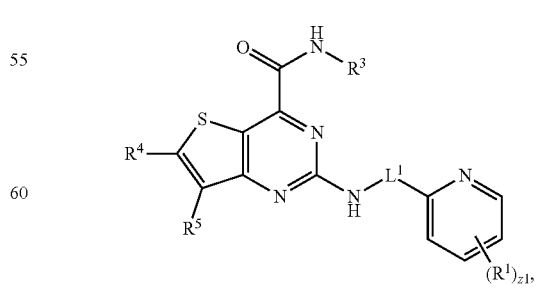

wherein $R^1$, z1, $L^1$, $R^3$, $R^4$, and $R^5$ are as described herein, including embodiments.

In embodiments, the compound has the formula:

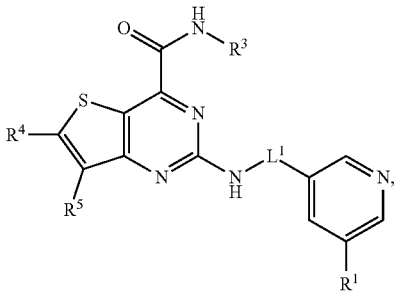

wherein $R^1$, $L^1$, $R^3$, $R^4$, and $R^5$ are as described herein, including embodiments.

In embodiments, the compound has the formula:

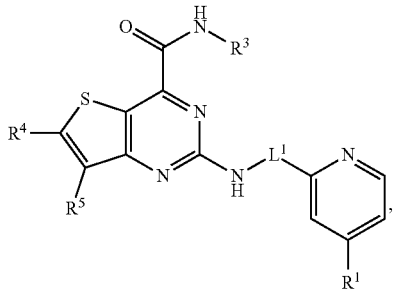

wherein $R^1$, $L^1$, $R^3$, $R^4$, and $R^5$ are as described herein, including embodiments.

In embodiments, the compound has the formula:

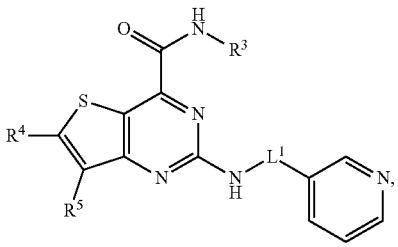

wherein $L^1$, $R^3$, $R^4$, and $R^5$ are as described herein, including embodiments.

In embodiments, the compound has the formula:

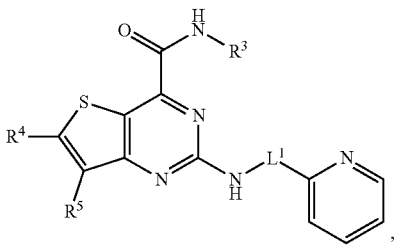

wherein $L^1$, $R^3$, $R^4$, and $R^5$ are as described herein, including embodiments.

In embodiments, the compound has the formula:

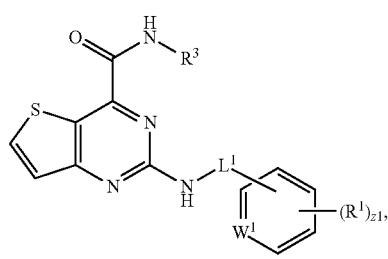

wherein $R^1$, $z1$, $W^1$, $L^1$, and $R^3$ are as described herein, including embodiments.

In embodiments, the compound has the formula:

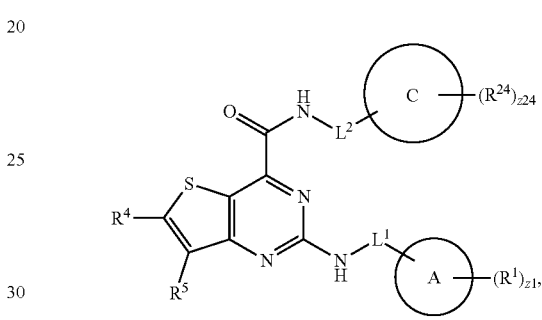

wherein $R^1$, $z1$, Ring A, $L^1$, $R^4$, and $R^5$ are as described herein, including embodiments; and wherein $L^2$ is bond, —S(O)$_2$—, —S(O)$_2$NH—, —NHS(O)$_2$—, —C(O)—, —C(O)NH—, —NHC(O)—, —NHC(O)O—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; Ring C is cycloalkyl, heterocycloalkyl, aryl, or heteroaryl; and z24 is an integer from 0 to 10. $R^{24}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, $R^{25}$-substituted or unsubstituted alkyl (e.g., C$_1$-C$_8$ alkyl, C$_1$-C$_6$ alkyl, or C$_1$-C$_4$ alkyl), $R^{25}$-substituted or unsubstituted heteroalkyl (e.g., 2 to 8 membered heteroalkyl, 2 to 6 membered heteroalkyl, or 2 to 4 membered heteroalkyl), $R^{25}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{25}$-substituted or unsubstituted heterocycloalkyl (e.g., 3 to 8 membered heterocycloalkyl, 3 to 6 membered heterocycloalkyl, or 5 to 6 membered heterocycloalkyl), $R^{25}$-substituted or unsubstituted aryl (e.g., C$_6$-C$_{10}$ aryl, C$_{10}$ aryl, or phenyl), or $R^{25}$-substituted or unsubstituted heteroaryl (e.g., 5 to 10 membered heteroaryl, 5 to 9 membered heteroaryl, or 5 to 6 membered heteroaryl). In embodiments z24 is 1. In embodiments, z24 is 2. In embodiments, z24 is 0.

In embodiments, the compound has the formula:

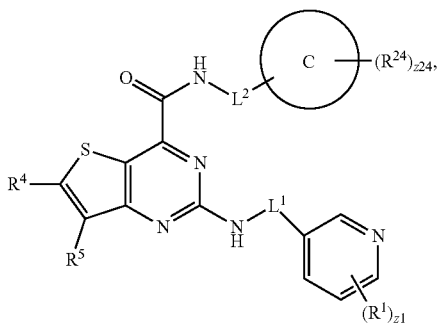

wherein $R^1$, z1, $L^1$, $R^4$, $R^5$, $L^2$, Ring C, $R^{24}$, and z24 are as described herein, including embodiments.

In embodiments, the compound has the formula:

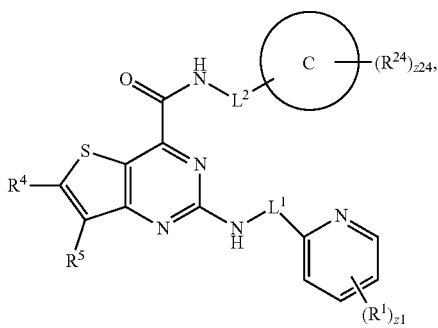

wherein $R^1$, z1, $L^1$, $R^4$, $R^5$, $L^2$, Ring C, $R^{24}$, and z24 are as described herein, including embodiments.

In embodiments, the compound has the formula:

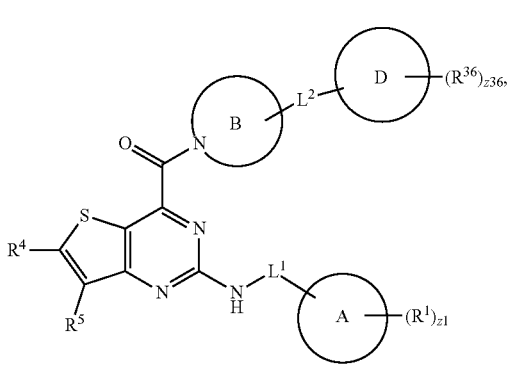

wherein $L^2$, $R^4$, $R^5$, $L^1$, Ring A, z1, $R^1$, and Ring B are as described herein, including embodiments. $R^{36}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, $R^{37}$-substituted or unsubstituted alkyl (e.g., C$_1$-C$_8$ alkyl, C$_1$-C$_6$ alkyl, or C$_1$-C$_4$ alkyl), $R^{37}$-substituted or unsubstituted heteroalkyl (e.g., 2 to 8 membered heteroalkyl, 2 to 6 membered heteroalkyl, or 2 to 4 membered heteroalkyl), $R^{37}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{37}$-substituted or unsubstituted heterocycloalkyl (e.g., 3 to 8 membered heterocycloalkyl, 3 to 6 membered heterocycloalkyl, or 5 to 6 membered heterocycloalkyl), $R^{37}$-substituted or unsubstituted aryl (e.g., C$_6$-C$_{10}$ aryl, C$_{10}$ aryl, or phenyl), or $R^{37}$-substituted or unsubstituted heteroaryl (e.g., 5 to 10 membered heteroaryl, 5 to 9 membered heteroaryl, or 5 to 6 membered heteroaryl). The symbol z36 is an integer from 0 to 10. In embodiments, z36 is 1. In embodiments, z36 is 2. In embodiments, when $R^{35}$ is substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl), $R^{35}$ may be referred to herein as (Ring D)-(R$^{36}$)$_{z36}$. In embodiments, $L^2$ is

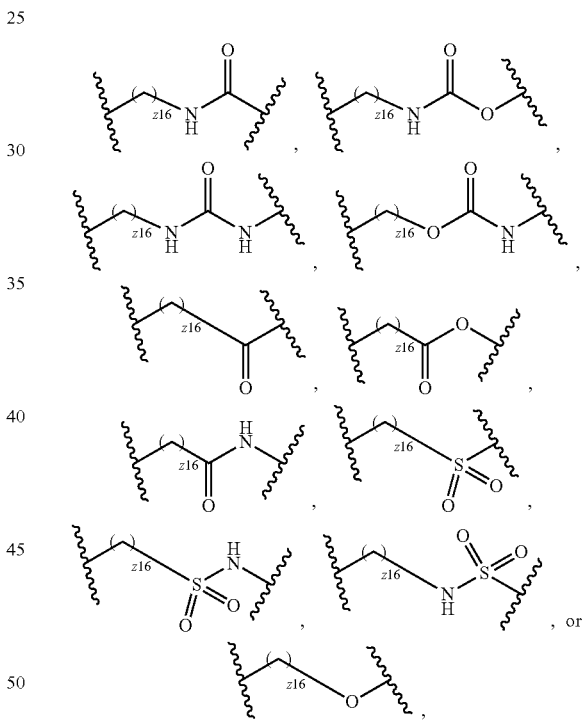

where z16 are as described herein, including embodiments. In embodiments, $L^2$ is

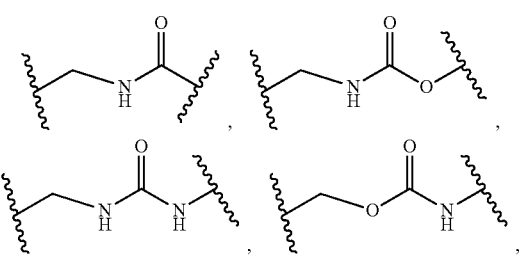

-continued

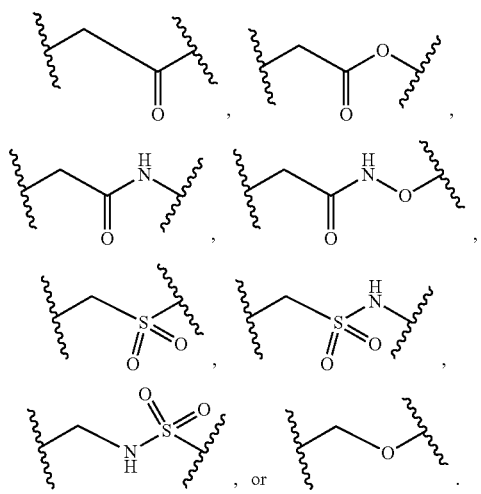

In embodiments, L² is

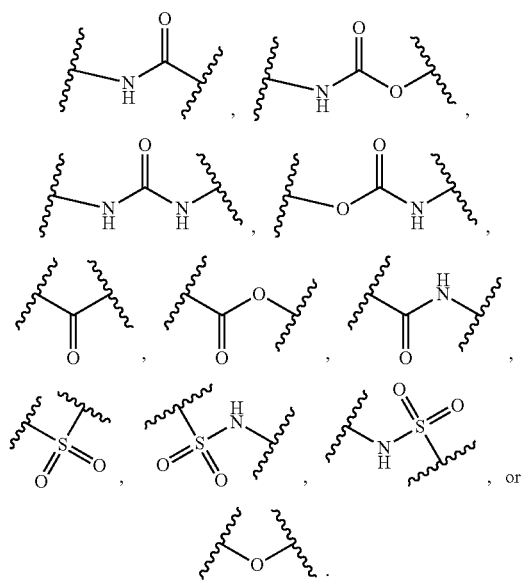, or

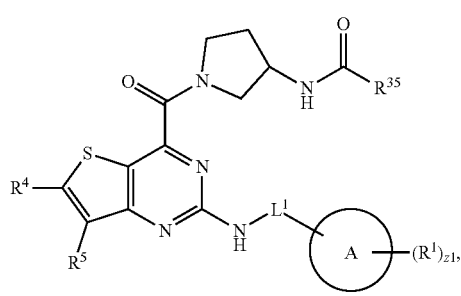.

In embodiments, the compound has the formula:

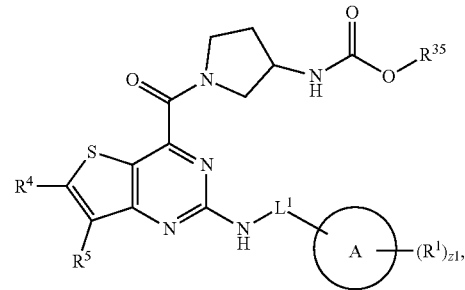

wherein $R^{35}$, $R^4$, $R^5$, $L^1$, Ring A, $R^1$, and z1 are as described herein, including embodiments.

In embodiments, the compound has the formula:

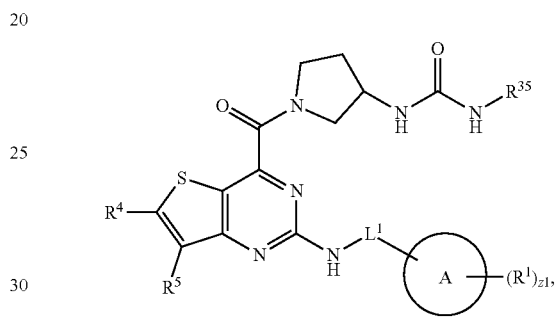

wherein $R^{35}$, $R^4$, $R^5$, $L^1$, Ring A, $R^1$, and z1 are as described herein, including embodiments.

In embodiments, the compound has the formula:

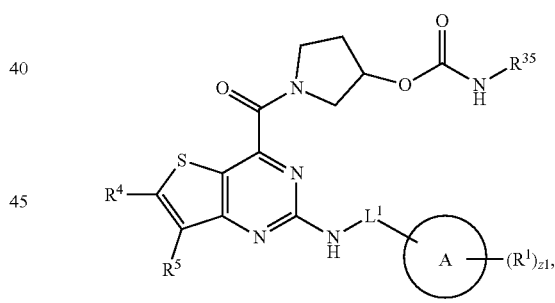

wherein $R^{35}$, $R^4$, $R^5$, $L^1$, Ring A, $R^1$, and z1 are as described herein, including embodiments.

In embodiments, the compound has the formula:

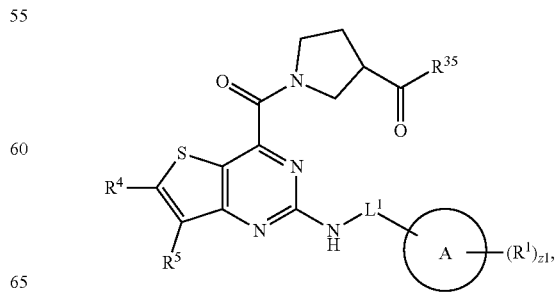

In embodiments, the compound has the formula:

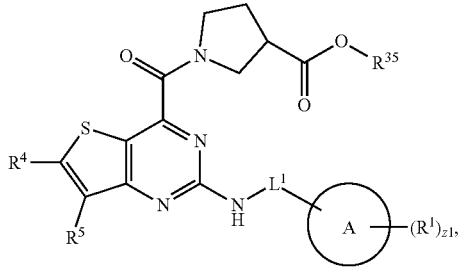

wherein $R^{35}$, $R^4$, $R^5$, $L^1$, Ring A, $R^1$, and z1 are as described herein, including embodiments.

In embodiments, the compound has the formula:

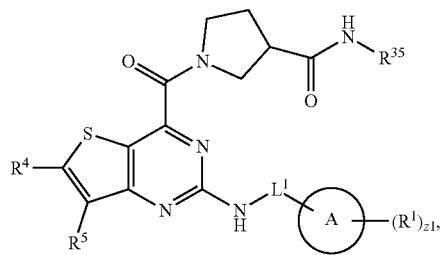

wherein $R^{35}$, $R^4$, $R^5$, $L^1$, Ring A, $R^1$, and z1 are as described herein, including embodiments.

In embodiments, the compound has the formula:

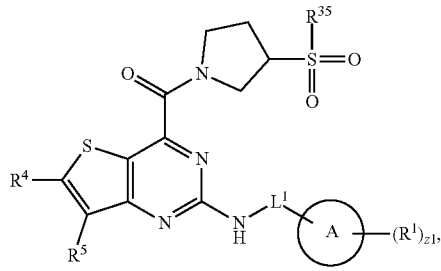

wherein $R^{35}$, $R^4$, $R^5$, $L^1$, Ring A, $R^1$, and z1 are as described herein, including embodiments.

In embodiments, the compound has the formula:

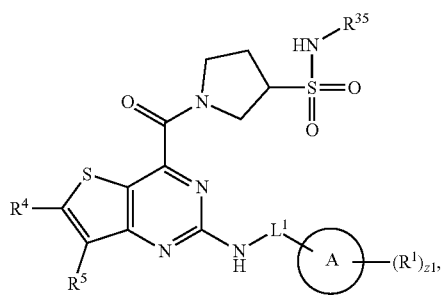

wherein $R^{35}$, $R^4$, $R^5$, $L^1$, Ring A, $R^1$, and z1 are as described herein, including embodiments.

In embodiments, the compound has the formula:

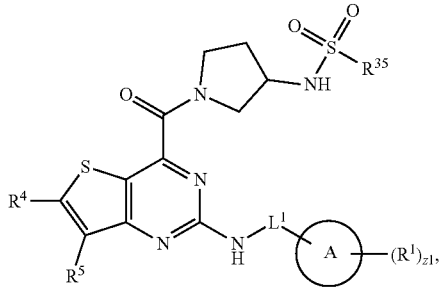

wherein $R^{35}$, $R^4$, $R^5$, $L^1$, Ring A, $R^1$, and z1 are as described herein, including embodiments.

In embodiments, the compound has the formula:

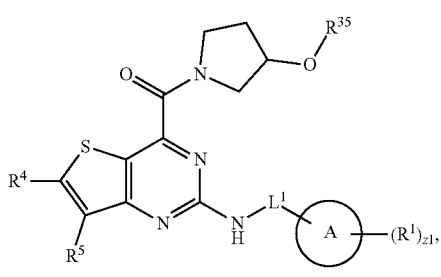

wherein $R^{35}$, $R^4$, $R^5$, $L^1$, Ring A, $R^1$, and z1 are as described herein, including embodiments.

In embodiments, the compound has the formula:

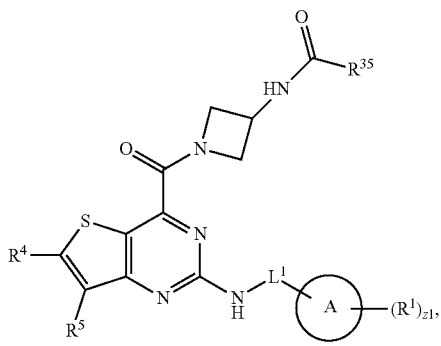

wherein $R^{35}$, $R^4$, $R^5$, $L^1$, Ring A, $R^1$, z16, and z1 are as described herein, including embodiments. In embodiments, the compound has the formula:

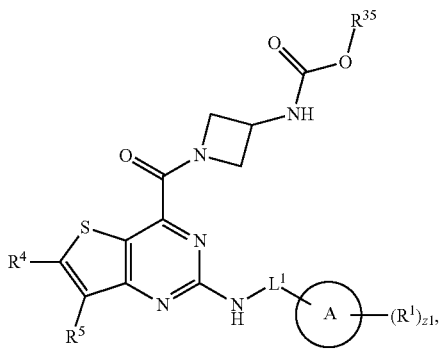

wherein $R^{35}$, $R^4$, $R^5$, $L^1$, Ring A, $R^1$, z16, and z1 are as described herein, including embodiments. In embodiments, the compound has the formula:

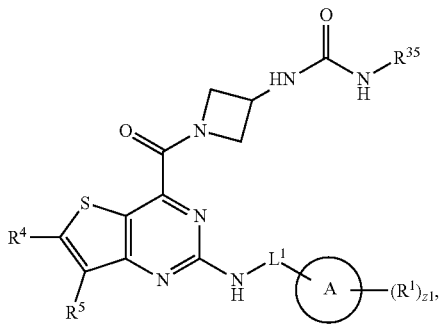

wherein $R^{35}$, $R^4$, $R^5$, $L^1$, Ring A, $R^1$, z16, and z1 are as described herein, including embodiments. In embodiments, the compound has the formula:

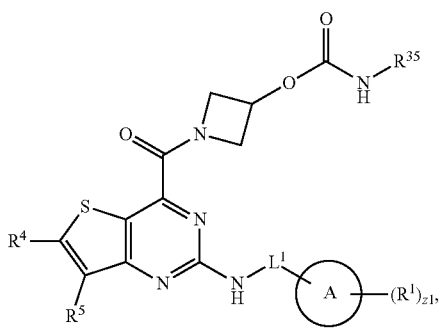

wherein $R^{35}$, $R^4$, $R^5$, $L^1$, Ring A, $R^1$, z16, and z1 are as described herein, including embodiments. In embodiments, the compound has the formula:

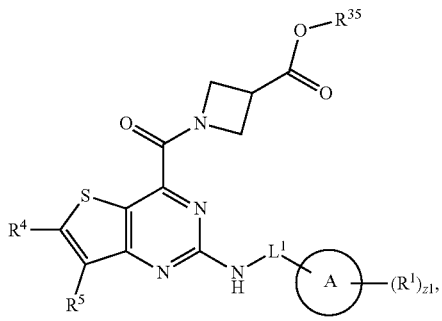

wherein $R^{35}$, $R^4$, $R^5$, $L^1$, Ring A, $R^1$, z16, and z1 are as described herein, including embodiments. In embodiments, the compound has the formula:

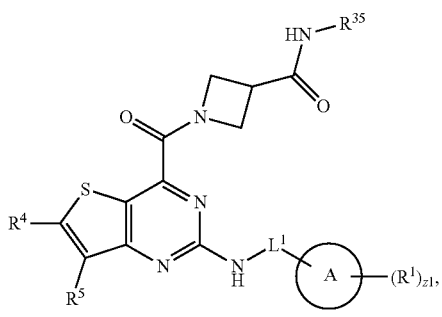

wherein $R^{35}$, $R^4$, $R^5$, $L^1$, Ring A, $R^1$, z16, and z1 are as described herein, including embodiments. In embodiments, the compound has the formula:

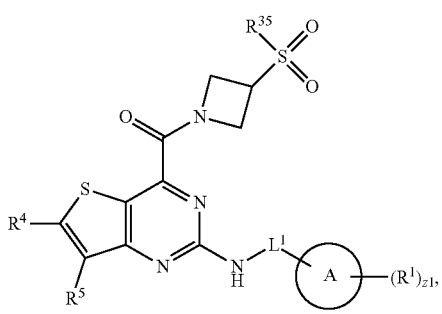

wherein $R^{35}$, $R^4$, $R^5$, $L^1$, Ring A, $R^1$, z16, and z1 are as described herein, including embodiments. In embodiments, the compound has the formula:

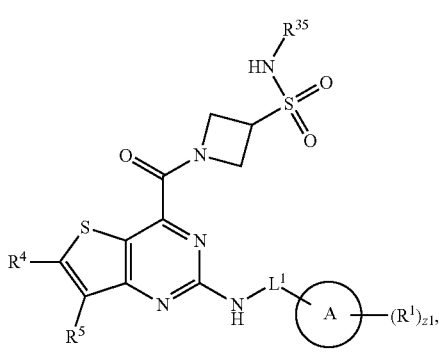

wherein $R^{35}$, $R^4$, $R^5$, $L^1$, Ring A, $R^1$, z16, and z1 are as described herein, including embodiments.

In embodiments, the compound has the formula:

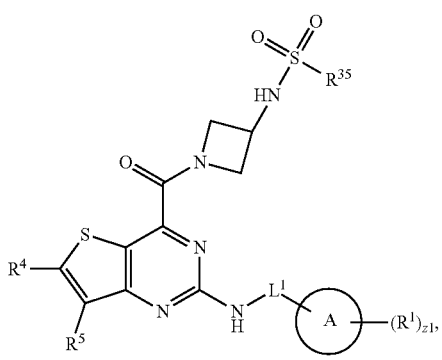

wherein $R^{35}$, $R^4$, $R^5$, $L^1$, Ring A, $R^1$, z16, and z1 are as described herein, including embodiments.

In embodiments, the compound has the formula:

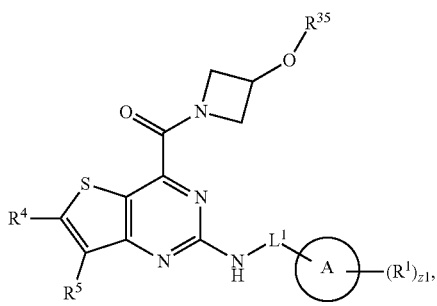

wherein $R^{35}$, $R^4$, $R^5$, $L^1$, Ring A, $R^1$, z16, and z1 are as described herein, including embodiments.

In embodiments, the compound is

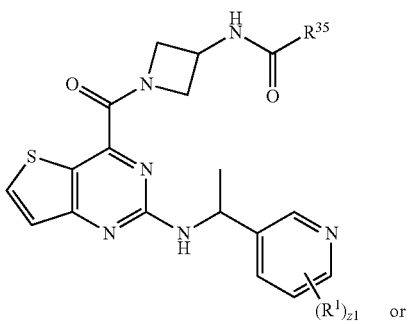 or

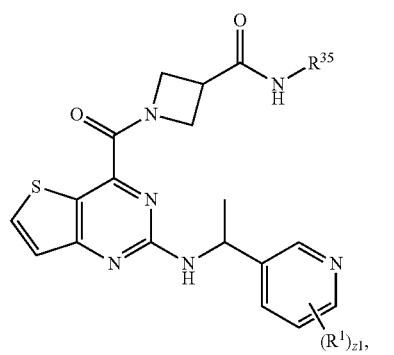

wherein $R^{35}$, $R^1$, and z1 are as described herein.

In embodiments, the compound is

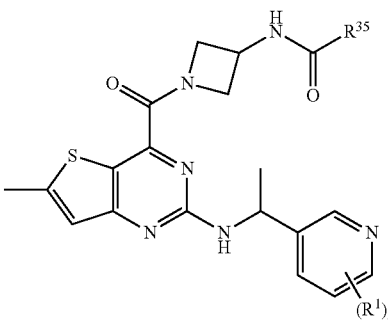 or

-continued
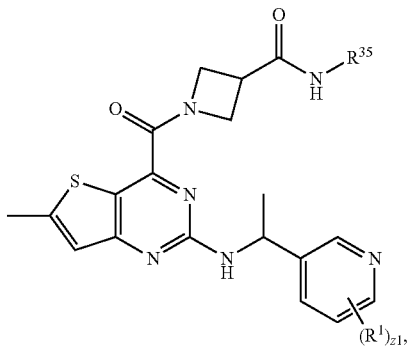
wherein $R^{35}$, $R^1$, and z1 are as described herein.
In embodiments, the compound is
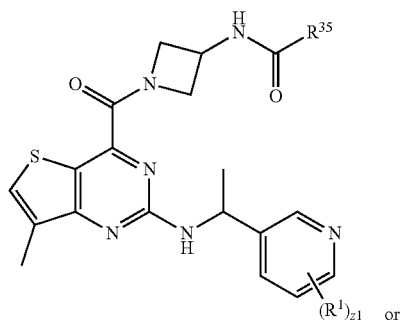
or
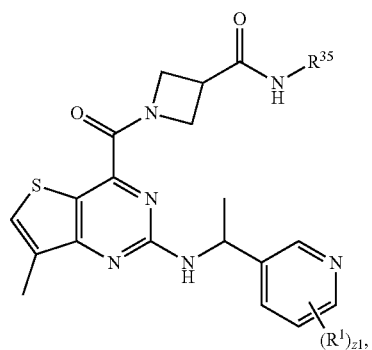
wherein $R^{35}$, $R^1$, and z1 are as described herein.
In embodiments, the compound is
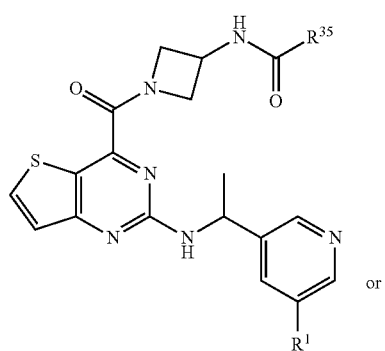
or
-continued
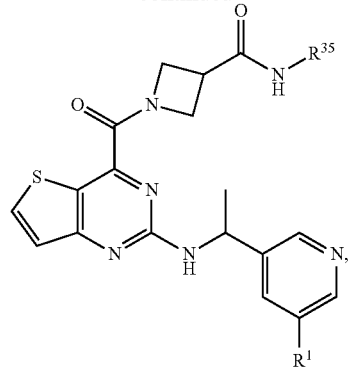
wherein $R^{35}$ and $R^1$ are as described herein.
In embodiments, the compound is
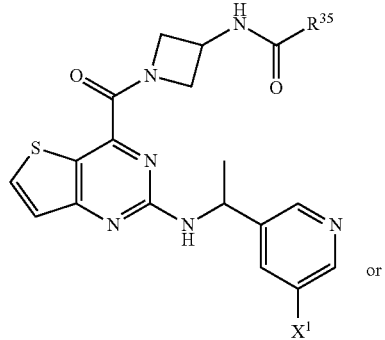
or
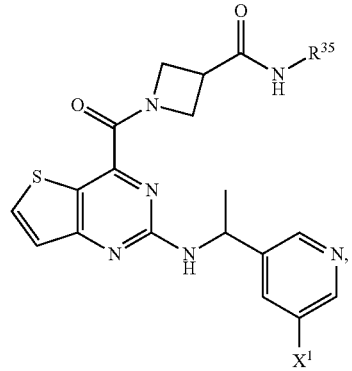
wherein $R^{35}$ and $X^1$ are as described herein.
In embodiments, the compound is
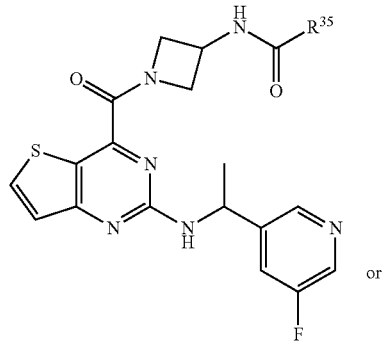
or -continued
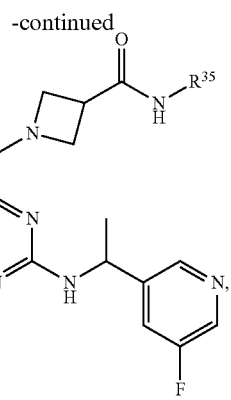
wherein R³⁵ is as described herein.
In embodiments, the compound is
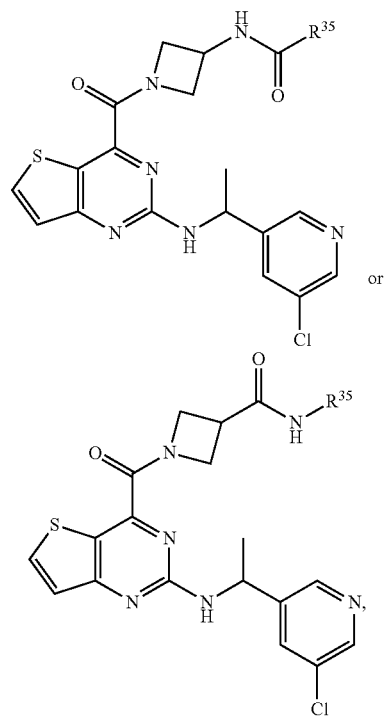
wherein R³⁵ is as described herein.
In embodiments, the compound is
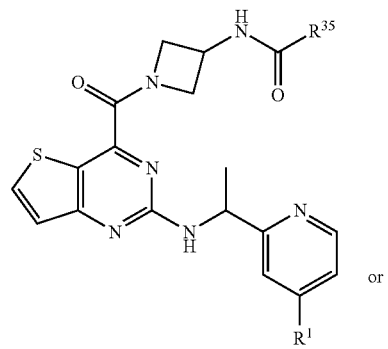
-continued
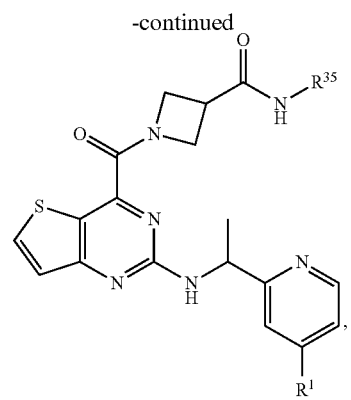
wherein R¹ and R³⁵ are as described herein.
In embodiments, the compound is
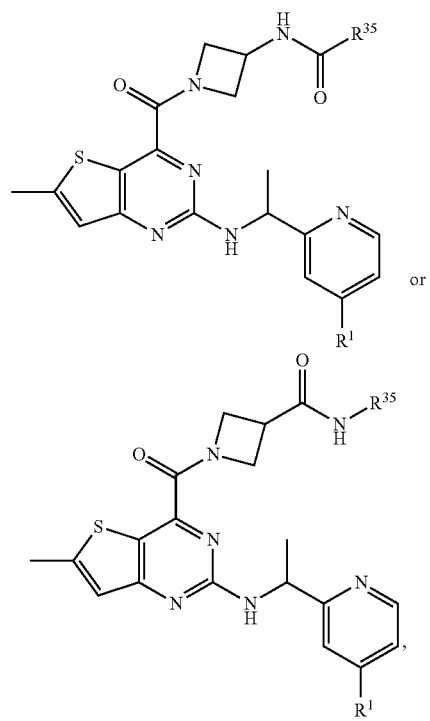
wherein R¹ and R³⁵ are as described herein.
In embodiments, the compound is 71
-continued
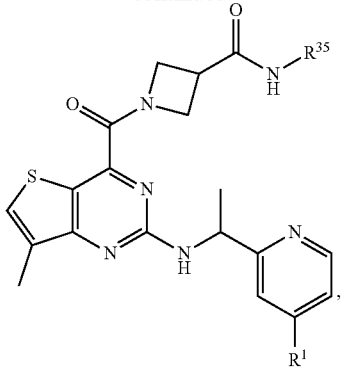
wherein R¹ and R³⁵ are as described herein.
In embodiments, the compound is
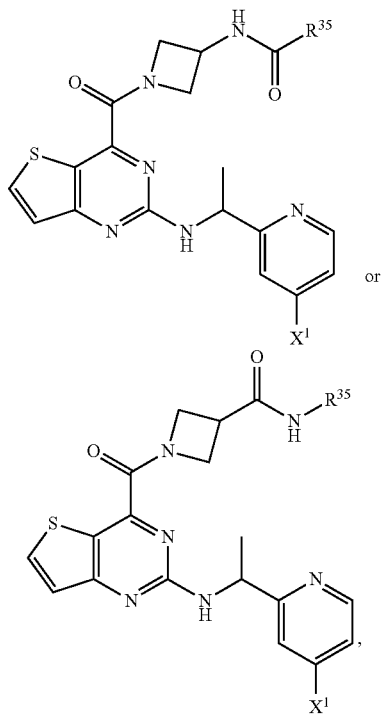
wherein X¹ and R³⁵ are as described herein.
In embodiments, the compound is
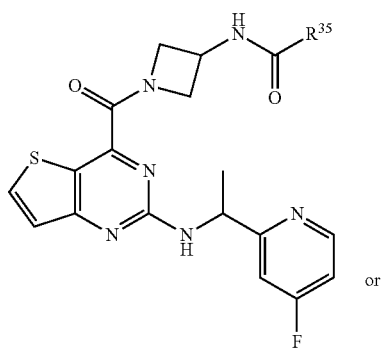
72
-continued
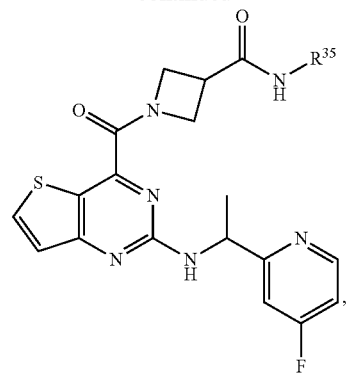
wherein R³⁵ is as described herein.
In embodiments, the compound is
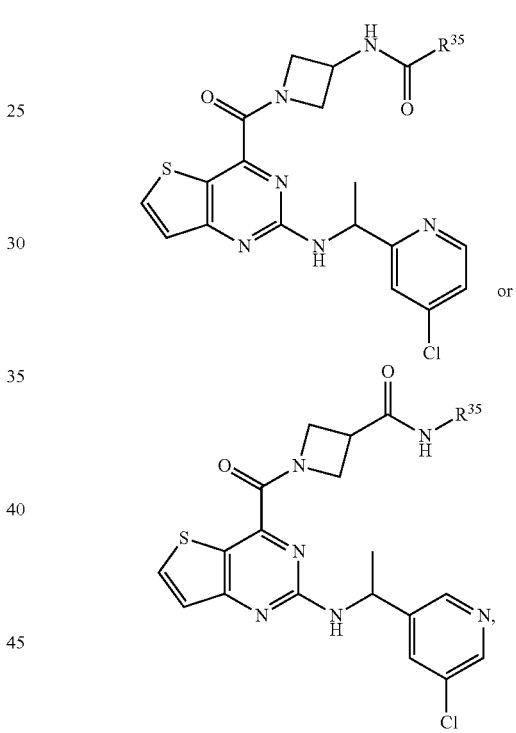
wherein R³⁵ is as described herein.
In embodiments, the compound is
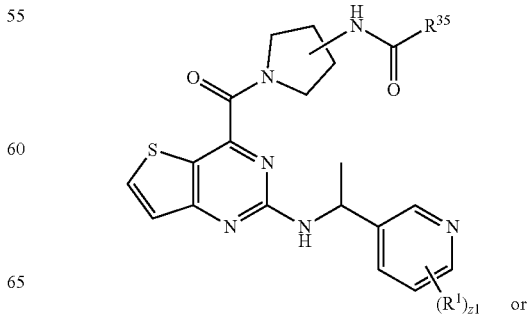
or

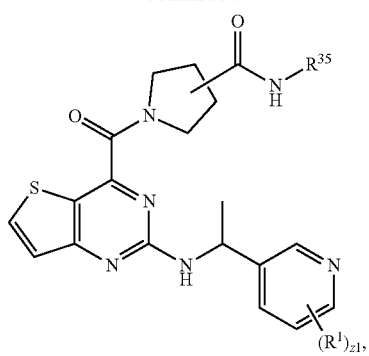
wherein $R^1$, z1, and $R^{35}$ are as described herein.
In embodiments, the compound is
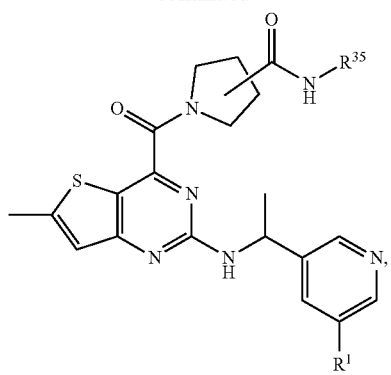
wherein $R^1$ and $R^{35}$ are as described herein.
In embodiments, the compound is
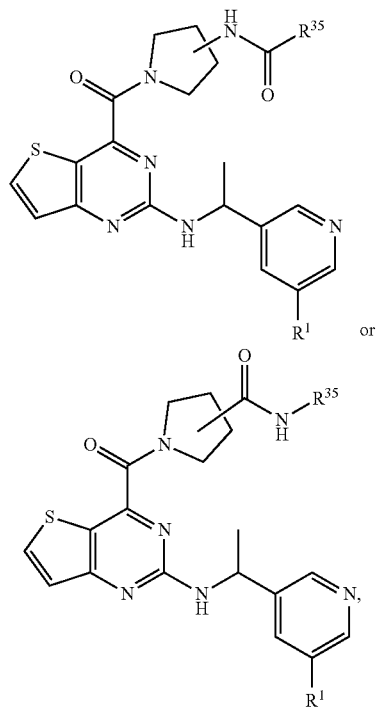
wherein $R^1$ and $R^{35}$ are as described herein.
In embodiments, the compound is
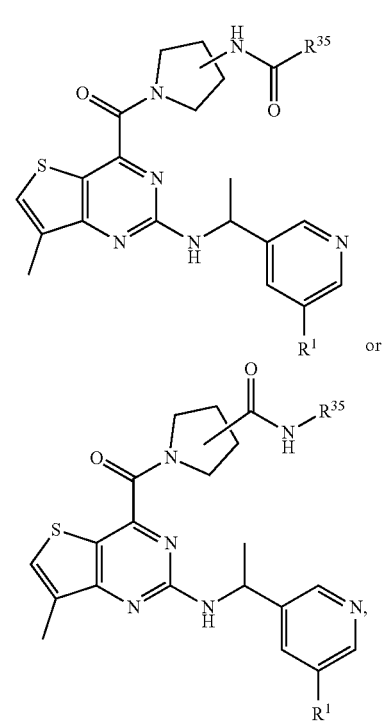
wherein $R^1$ and $R^{35}$ are as described herein.
In embodiments, the compound is
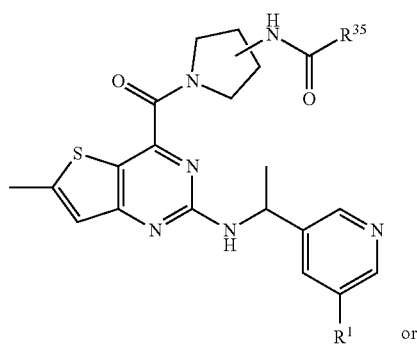
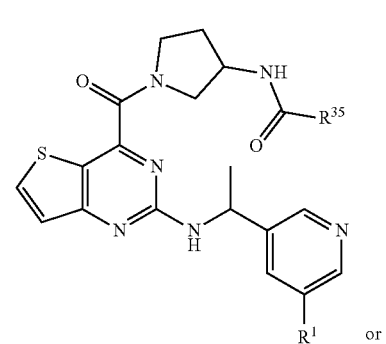

-continued

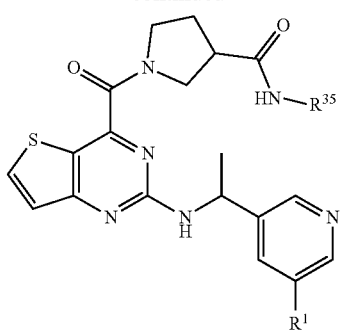

wherein R¹ and R³⁵ are as described herein.

In embodiments, the compound is

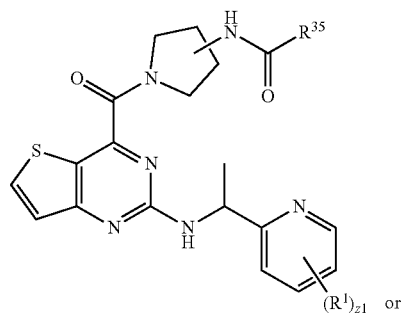

wherein z1, R¹, and R³⁵ are as described herein.

In embodiments, the compound is

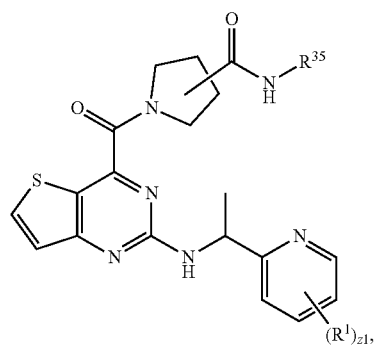

wherein z1, R¹, and R³⁵ are as described herein.

In embodiments, the compound is

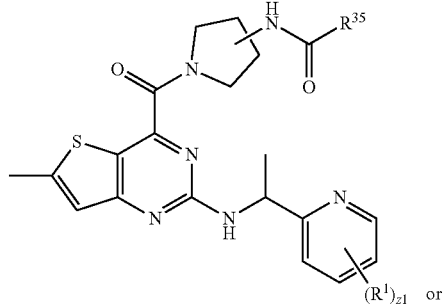

-continued

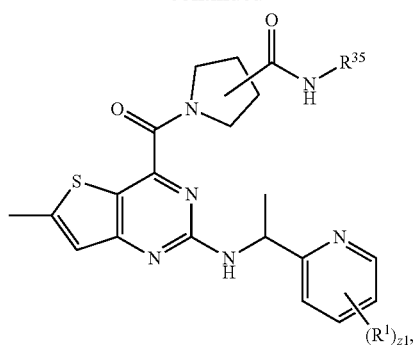

wherein R¹, z1, and R³⁵ are as described herein.

In embodiments, the compound is

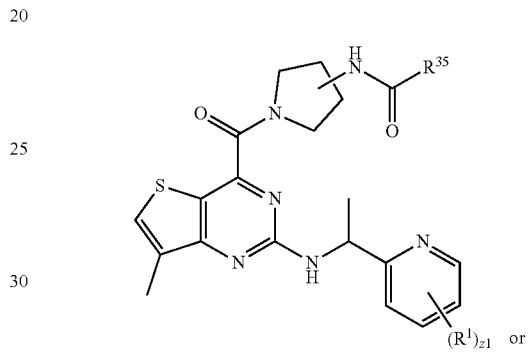

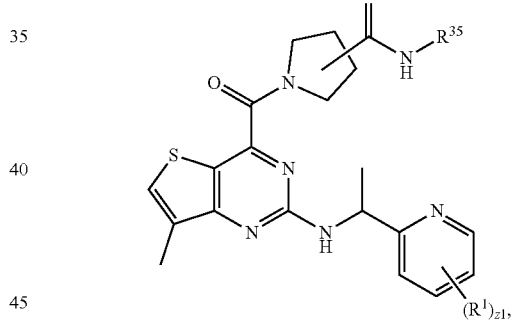

wherein z1, R¹, and R³⁵ are as described herein.

In embodiments, the compound is

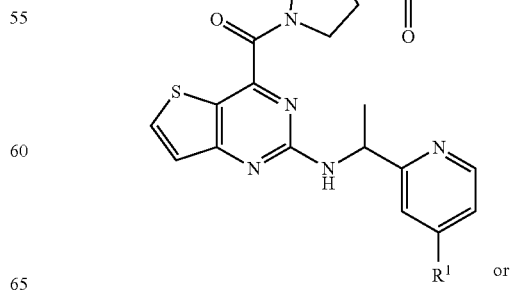

77

-continued

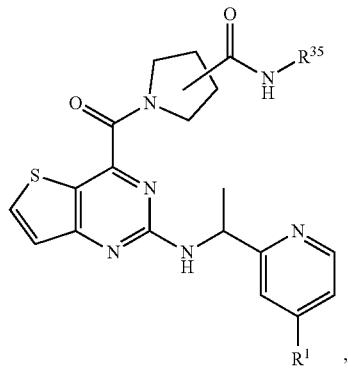

wherein R¹ and R³⁵ are as described herein.

In embodiments, the compound is

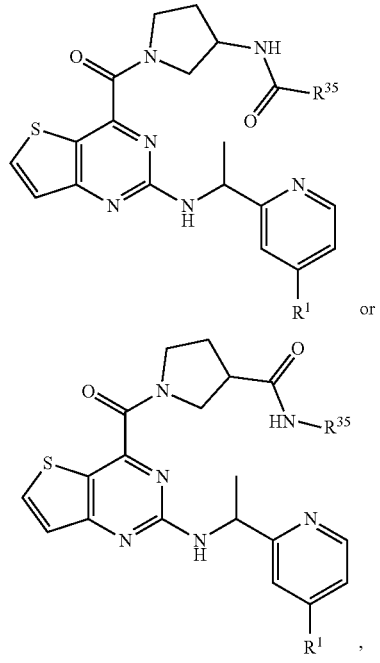

wherein R¹ and R³⁵ are as described herein.

In embodiments, the compound is

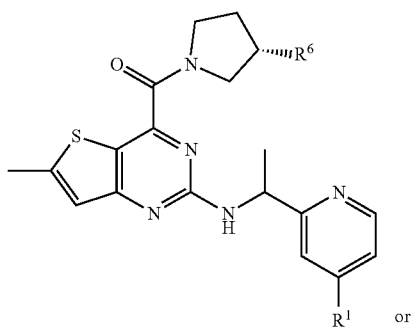

78

-continued

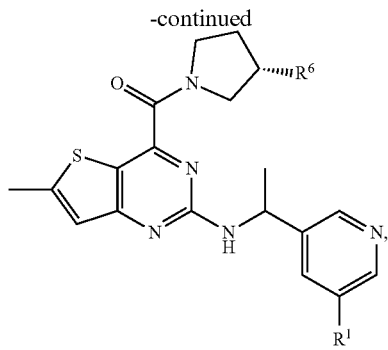

wherein R¹ and R³⁵ are as described herein.

In embodiments, $L^2$ is substituted or unsubstituted alkylene (e.g., $C_1$-$C_8$ alkylene, $C_1$-$C_6$ alkylene, or $C_1$-$C_4$ alkylene). In embodiments, $L^2$ is substituted alkylene (e.g., $C_1$-$C_8$ alkylene, $C_1$-$C_6$ alkylene, or $C_1$-$C_4$ alkylene). In embodiments, $L^2$ is an unsubstituted alkylene (e.g., $C_1$-$C_8$ alkylene, $C_1$-$C_6$ alkylene, or $C_1$-$C_4$ alkylene). In embodiments, $L^2$ is substituted or unsubstituted heteroalkylene (e.g., 2 to 8 membered heteroalkylene, 2 to 6 membered heteroalkylene, or 2 to 4 membered heteroalkylene). In embodiments, $L^2$ is substituted heteroalkylene (e.g., 2 to 8 membered heteroalkylene, 2 to 6 membered heteroalkylene, or 2 to 4 membered heteroalkylene). In embodiments, $L^2$ is an unsubstituted heteroalkylene (e.g., 2 to 8 membered heteroalkylene, 2 to 6 membered heteroalkylene, or 2 to 4 membered heteroalkylene). In embodiments, $L^2$ is substituted or unsubstituted $C_1$-$C_6$ alkylene. In embodiments, $L^2$ is substituted or unsubstituted $C_1$-$C_4$ alkylene. In embodiments, $L^2$ is substituted or unsubstituted $C_1$-$C_3$ alkylene. In embodiments, $L^2$ is substituted or unsubstituted $C_1$-$C_2$ alkylene.

In embodiments, $L^2$ is

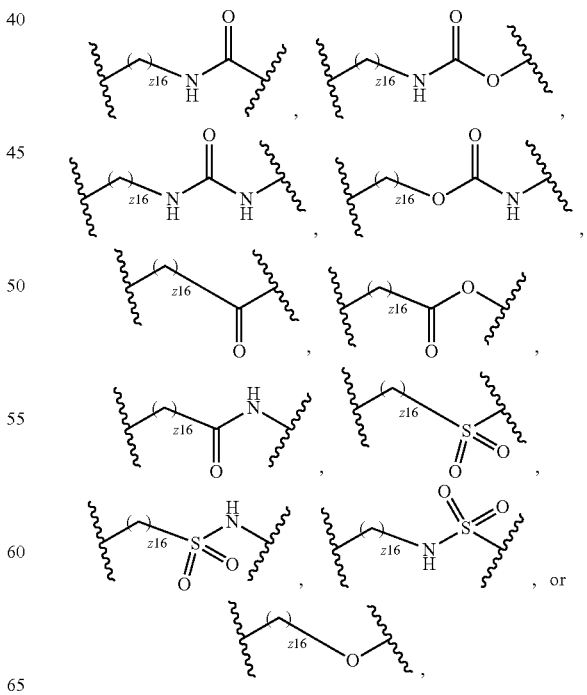

where z16 are as described herein, including embodiments.

In embodiments, $L^2$ is
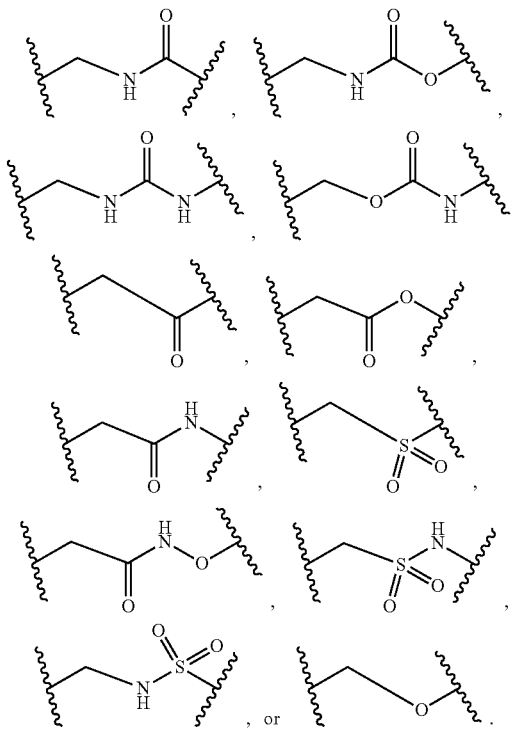
In embodiments, $L^2$ is
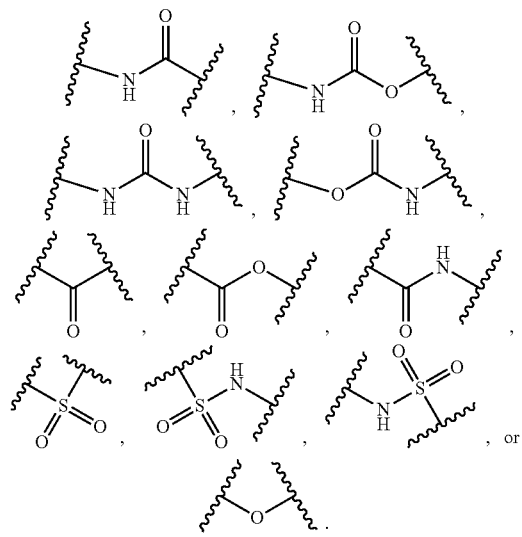
In embodiments, $L^2$ is
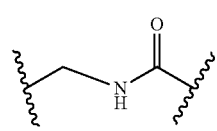
In embodiments, $L^2$ is
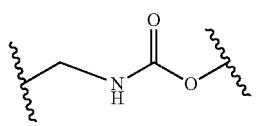
In embodiments, $L^2$ is
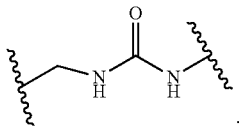
In embodiments, $L^2$ is
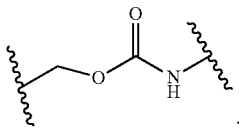 [SMILES: *COC(=O)N*]
In embodiments, $L^2$ is
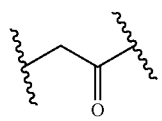
In embodiments, $L^2$ is
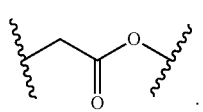 [SMILES: *CC(=O)O*]
In embodiments, $L^2$ is
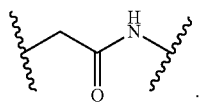 [SMILES: *CC(=O)N*]
In embodiments, $L^2$ is
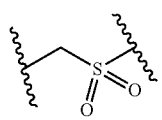

In embodiments, L² is

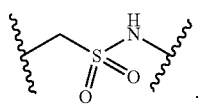 [SMILES: *CS(=O)(=O)N*]

In embodiments, L² is

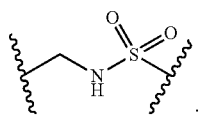 [SMILES: *CNS(*)(=O)=O]

In embodiments, L² is

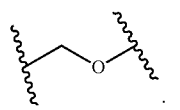 [SMILES: *CO*]

In embodiments L² is

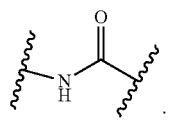 [SMILES: *NC(*)=O]

In embodiments, L² is

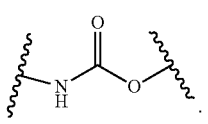 [SMILES: *NC(=O)O*]

In embodiments, L² is

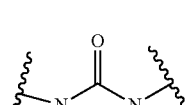

In embodiments, L² is

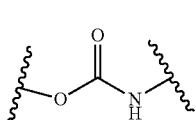

In embodiments, L² is

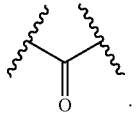

In embodiments, L² is

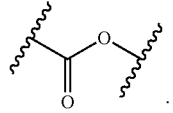

In embodiments, L² is

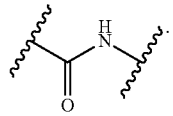

In embodiments, L is

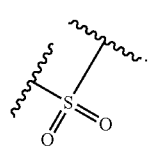 [SMILES: *S(*)(=O)=O]

In embodiments, L is

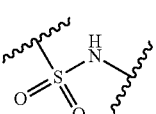

In embodiments, L² is

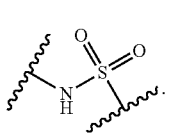

In embodiments, L² is

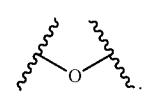

In embodiments, $R^1$ is substituted or unsubstituted $C_1$-$C_6$ alkyl, or substituted or unsubstituted 2 to 6 membered heteroalkyl.

In embodiments, $R^1$ is independently oxo, halogen, —CCl₃, —CBr₃, —CF₃, —CI₃, CHCl₂, —CHBr₂, —CHF₂, —CHI₂, —CH₂Cl, —CH₂Br, —CH₂F, —CH₂I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, R$^{20}$-substituted or unsubstituted alkyl (e.g., C$_1$-C$_8$ alkyl, C$_1$-C$_6$ alkyl, or C$_1$-C$_4$ alkyl), or R$^{20}$-substituted or unsubstituted heteroalkyl (e.g., 2 to 8 membered heteroalkyl, 2 to 6 membered heteroalkyl, or 2 to 4 membered heteroalkyl).

In embodiments, R$^1$ is R$^{20}$-substituted or unsubstituted alkyl (e.g., C$_1$-C$_8$ alkyl, C$_1$-C$_6$ alkyl, or C$_1$-C$_4$ alkyl). In embodiments, R$^1$ is R$^{20}$-substituted alkyl (e.g., C$_1$-C$_8$ alkyl, C$_1$-C$_6$ alkyl, or C$_1$-C$_4$ alkyl). In embodiments, R$^1$ is an unsubstituted alkyl (e.g., C$_1$-C$_8$ alkyl, C$_1$-C$_6$ alkyl, or C$_1$-C$_4$ alkyl). In embodiments, R$^1$ is R$^{20}$-substituted or unsubstituted heteroalkyl (e.g., 2 to 8 membered heteroalkyl, 2 to 6 membered heteroalkyl, or 2 to 4 membered heteroalkyl). In embodiments, R$^1$ is R$^{20}$-substituted heteroalkyl (e.g., 2 to 8 membered heteroalkyl, 2 to 6 membered heteroalkyl, or 2 to 4 membered heteroalkyl). In embodiments, R$^1$ is an unsubstituted heteroalkyl (e.g., 2 to 8 membered heteroalkyl, 2 to 6 membered heteroalkyl, or 2 to 4 membered heteroalkyl).

In embodiments, R$^{1A}$, R$^{1B}$, R$^{1C}$, and R$^{1D}$ are independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, R$^{20}$-substituted or unsubstituted alkyl (e.g., C$_1$-C$_8$ alkyl, C$_1$-C$_6$ alkyl, or C$_1$-C$_4$ alkyl), or R$^{20}$-substituted or unsubstituted heteroalkyl (e.g., 2 to 8 membered heteroalkyl, 2 to 6 membered heteroalkyl, or 2 to 4 membered heteroalkyl).

In embodiments, R$^{1A}$, R$^{1B}$, R$^{1C}$, R$^{1D}$ are independently R$^{20}$-substituted or unsubstituted alkyl (e.g., C$_1$-C$_8$ alkyl, C$_1$-C$_6$ alkyl, or C$_1$-C$_4$ alkyl). In embodiments, R$^{1A}$, R$^{1B}$, R$^{1C}$, and R$^{1D}$ are independently R$^{20}$-substituted alkyl (e.g., C$_1$-C$_8$ alkyl, C$_1$-C$_6$ alkyl, or C$_1$-C$_4$ alkyl). In embodiments, R$^{1A}$, R$^{1B}$, R$^{1C}$, and R$^{1D}$ are independently an unsubstituted alkyl (e.g., C$_1$-C$_8$ alkyl, C$_1$-C$_6$ alkyl, or C$_1$-C$_4$ alkyl). In embodiments, R$^{1A}$, R$^{1B}$, R$^{1C}$, R$^{1D}$ are independently R$^{20}$-substituted or unsubstituted heteroalkyl (e.g., 2 to 8 membered heteroalkyl, 2 to 6 membered heteroalkyl, or 2 to 4 membered heteroalkyl). In embodiments, R$^{1A}$, R$^{1B}$, R$^{1C}$, and R$^{1D}$ are independently R$^{20}$-substituted heteroalkyl (e.g., 2 to 8 membered heteroalkyl, 2 to 6 membered heteroalkyl, or 2 to 4 membered heteroalkyl). In embodiments, R$^{1A}$, R$^{1B}$, R$^{1C}$, and R$^{1D}$ are independently an unsubstituted heteroalkyl (e.g., 2 to 8 membered heteroalkyl, 2 to 6 membered heteroalkyl, or 2 to 4 membered heteroalkyl).

In embodiments, R$^{1A}$, R$^{1B}$, R$^{1C}$, and R$^{1D}$ are independently R$^{20}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{20}$-substituted or unsubstituted heterocycloalkyl (e.g., 3 to 8 membered heterocycloalkyl, 3 to 6 membered heterocycloalkyl, or 5 to 6 membered heterocycloalkyl), R$^{20}$-substituted or unsubstituted aryl (e.g., C$_6$-C$_{10}$ aryl, C$_{10}$ aryl, or phenyl), or R$^{20}$-substituted or unsubstituted heteroaryl (e.g., 5 to 10 membered heteroaryl, 5 to 9 membered heteroaryl, or 5 to 6 membered heteroaryl).

R$^{20}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, R$^{21}$-substituted or unsubstituted alkyl (e.g., C$_1$-C$_8$ alkyl, C$_1$-C$_6$ alkyl, or C$_1$-C$_4$ alkyl), R$^{21}$-substituted or unsubstituted heteroalkyl (e.g., 2 to 8 membered heteroalkyl, 2 to 6 membered heteroalkyl, or 2 to 4 membered heteroalkyl), R$^{21}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{21}$-substituted or unsubstituted heterocycloalkyl (e.g., 3 to 8 membered heterocycloalkyl, 3 to 6 membered heterocycloalkyl, or 5 to 6 membered heterocycloalkyl), R$^{21}$-substituted or unsubstituted aryl (e.g., C$_6$-C$_{10}$ aryl, C$_{10}$ aryl, or phenyl), or R$^{21}$-substituted or unsubstituted heteroaryl (e.g., 5 to 10 membered heteroaryl, 5 to 9 membered heteroaryl, or 5 to 6 membered heteroaryl).

R$^{21}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, R$^{22}$-substituted or unsubstituted alkyl (e.g., C$_1$-C$_8$ alkyl, C$_1$-C$_6$ alkyl, or C$_1$-C$_4$ alkyl), R$^{22}$-substituted or unsubstituted heteroalkyl (e.g., 2 to 8 membered heteroalkyl, 2 to 6 membered heteroalkyl, or 2 to 4 membered heteroalkyl), R$^{22}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{22}$-substituted or unsubstituted heterocycloalkyl (e.g., 3 to 8 membered heterocycloalkyl, 3 to 6 membered heterocycloalkyl, or 5 to 6 membered heterocycloalkyl), R$^{22}$-substituted or unsubstituted aryl (e.g., C$_6$-C$_{10}$ aryl, C$_{10}$ aryl, or phenyl), or R$^{22}$-substituted or unsubstituted heteroaryl (e.g., 5 to 10 membered heteroaryl, 5 to 9 membered heteroaryl, or 5 to 6 membered heteroaryl).

In embodiments, R$^1$ is R$^{20}$-substituted or unsubstituted alkyl (e.g., C$_1$-C$_8$ alkyl, C$_1$-C$_6$ alkyl, or C$_1$-C$_4$ alkyl). In embodiments, R$^1$ is R$^{20}$-substituted alkyl (e.g., C$_1$-C$_8$ alkyl, C$_1$-C$_6$ alkyl, or C$_1$-C$_4$ alkyl). In embodiments, R$^1$ is an unsubstituted alkyl (e.g., C$_1$-C$_8$ alkyl, C$_1$-C$_6$ alkyl, or C$_1$-C$_4$ alkyl). In embodiments, R$^1$ is R$^{20}$-substituted or unsubstituted heteroalkyl (e.g., 2 to 8 membered heteroalkyl, 2 to 6 membered heteroalkyl, or 2 to 4 membered heteroalkyl). In embodiments, R$^1$ is R$^{20}$-substituted heteroalkyl (e.g., 2 to 8 membered heteroalkyl, 2 to 6 membered heteroalkyl, or 2 to 4 membered heteroalkyl). In embodiments, R$^1$ is an unsubstituted heteroalkyl (e.g., 2 to 8 membered heteroalkyl, 2 to 6 membered heteroalkyl, or 2 to 4 membered heteroalkyl). In embodiments, R$^1$ is R$^{20}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^1$ is R$^{20}$-substituted cycloalkyl (e.g., C$_3$-C$_8$ cycloalkyl, C$_3$-C$_6$ cycloalkyl, or C$_5$-C$_6$ cycloalkyl). In embodiments, R$^1$ is an unsubstituted cycloalkyl (e.g., C$_3$-C$_8$ cycloalkyl, C$_3$-C$_6$ cycloalkyl, or C$_5$-C$_6$ cycloalkyl). In embodiments, R$^1$ is R$^{20}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^1$ is R$^{20}$-substituted heterocycloalkyl (e.g., 3 to 8 membered heterocycloalkyl, 3 to 6 membered heterocycloalkyl, or 5 to 6 membered heterocycloalkyl). In embodiments, R$^1$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^1$ is $R^{20}$-substituted or unsubstituted aryl (e.g., $C_6$-$C_{10}$ aryl, $C_{10}$ aryl, or phenyl). In embodiments, $R^1$ is $R^{20}$-substituted aryl (e.g., $C_6$-$C_{10}$ aryl, $C_{10}$ aryl, or phenyl). In embodiments, $R^1$ is an unsubstituted aryl (e.g., $C_6$-$C_{10}$ aryl, $C_{10}$ aryl, or phenyl). In embodiments, $R^1$ is $R^{20}$-substituted or unsubstituted heteroaryl (e.g., 5 to 10 membered heteroaryl, 5 to 9 membered heteroaryl, or 5 to 6 membered heteroaryl). In embodiments, $R^1$ is $R^{20}$-substituted heteroaryl (e.g., 5 to 10 membered heteroaryl, 5 to 9 membered heteroaryl, or 5 to 6 membered heteroaryl). In embodiments, $R^1$ is an unsubstituted heteroaryl (e.g., 5 to 10 membered heteroaryl, 5 to 9 membered heteroaryl, or 5 to 6 membered heteroaryl). In embodiments, $R^1$ is —$SO_2R^{1D}$, —$SO_2NR^{1A}R^{1B}$, or —$NR^{1A}SO_2R^{1D}$. In embodiments, $R^1$ is —$SO_2R^{1D}$. In embodiments, $R^1$ is —$SO_2NR^{1A}R^{1B}$. In embodiments, $R^1$ is —$NR^{1A}SO_2R^{1D}$.

In embodiments, $R^1$ is independently —OH. In embodiments, $R^1$ is independently —$OCH_3$. In embodiments, $R^1$ is independently —$OCH_2CH_3$. In embodiments, $R^1$ is independently unsubstituted $C_1$-$C_4$ alkoxy. In embodiments, $R^1$ is independently —Cl. In embodiments, $R^1$ is independently —F. In embodiments, $R^1$ is independently halogen. In embodiments, $R^1$ is independently —$CH_3$. In embodiments, $R^1$ is independently —$CH_2CH_3$. In embodiments, $R^1$ is independently unsubstituted $C_1$-$C_4$ alkyl. In embodiments, $R^1$ is independently —$CF_3$. In embodiments, $R^1$ is independently —$CXV$ In embodiments, $R^1$ is independently —$OCH_3$ or —F. In embodiments, $R^1$ is independently unsubstituted $C_1$-$C_4$ alkoxy or halogen. In embodiments, $R^1$ is independently —CN. In embodiments, $R^1$ is independently —$C(O)NH_2$. In embodiments, $R^1$ is independently —$C(O)NR^{1A}R^{1B}$. In embodiments, $R^{1A}$ is independently hydrogen. In embodiments, $R^{1A}$ is independently unsubstituted $C_1$-$C_4$ alkyl. In embodiments, $R^{1A}$ is independently —$CH_3$. In embodiments, $R^{1A}$ is independently —$CH_2CH_3$. In embodiments, $R^{1B}$ is independently hydrogen. In embodiments, $R^{1B}$ is independently unsubstituted $C_1$-$C_4$ alkyl. In embodiments, $R^{1B}$ is independently —$CH_3$. In embodiments, $R^{1B}$ is independently —$CH_2CH_3$. In embodiments, $R^{1C}$ is independently hydrogen. In embodiments, $R^{1C}$ is independently unsubstituted $C_1$-$C_4$ alkyl. In embodiments, $R^{1C}$ is independently —$CH_3$. In embodiments, $R^{1C}$ is independently —$CH_2CH_3$. In embodiments, $R^{1D}$ is independently hydrogen. In embodiments, $R^{1D}$ is independently unsubstituted $C_1$-$C_4$ alkyl. In embodiments, $R^{1D}$ is independently —$CH_3$. In embodiments, $R^{1D}$ is independently —$CH_2CH_3$.

In embodiments, $R^2$ is hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

In embodiments, $R^2$ is independently hydrogen, $R^{23}$-substituted or unsubstituted alkyl (e.g., $C_1$-$C_8$ alkyl, $C_1$-$C_6$ alkyl, or $C_1$-$C_4$ alkyl), $R^{23}$-substituted or unsubstituted heteroalkyl (e.g., 2 to 8 membered heteroalkyl, 2 to 6 membered heteroalkyl, or 2 to 4 membered heteroalkyl), $R^{23}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{23}$-substituted or unsubstituted heterocycloalkyl (e.g., 3 to 8 membered heterocycloalkyl, 3 to 6 membered heterocycloalkyl, or 5 to 6 membered heterocycloalkyl), $R^{23}$-substituted or unsubstituted aryl (e.g., $C_6$-$C_{10}$ aryl, $C_{10}$ aryl, or phenyl), or $R^{23}$-substituted or unsubstituted heteroaryl (e.g., 5 to 10 membered heteroaryl, 5 to 9 membered heteroaryl, or 5 to 6 membered heteroaryl). In embodiments, $R^2$ is independently hydrogen.

In embodiments, $R^2$ is $R^{23}$-substituted or unsubstituted alkyl (e.g., $C_1$-$C_8$ alkyl, $C_1$-$C_6$ alkyl, or $C_1$-$C_4$ alkyl). In embodiments, $R^2$ is $R^{23}$-substituted alkyl (e.g., $C_1$-$C_8$ alkyl, $C_1$-$C_6$ alkyl, or $C_1$-$C_4$ alkyl). In embodiments, $R^2$ is an unsubstituted alkyl (e.g., $C_1$-$C_8$ alkyl, $C_1$-$C_6$ alkyl, or $C_1$-$C_4$ alkyl). In embodiments, $R^2$ is $R^{23}$-substituted or unsubstituted heteroalkyl (e.g., 2 to 8 membered heteroalkyl, 2 to 6 membered heteroalkyl, or 2 to 4 membered heteroalkyl). In embodiments, $R^2$ is $R^{23}$-substituted heteroalkyl (e.g., 2 to 8 membered heteroalkyl, 2 to 6 membered heteroalkyl, or 2 to 4 membered heteroalkyl). In embodiments, $R^2$ is an unsubstituted heteroalkyl (e.g., 2 to 8 membered heteroalkyl, 2 to 6 membered heteroalkyl, or 2 to 4 membered heteroalkyl). In embodiments, $R^2$ is $R^{23}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^2$ is $R^{23}$-substituted cycloalkyl (e.g., $C_3$-$C_8$ cycloalkyl, $C_3$-$C_6$ cycloalkyl, or $C_5$-$C_6$ cycloalkyl). In embodiments, $R^2$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^2$ is $R^{23}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^2$ is $R^{23}$-substituted heterocycloalkyl (e.g., 3 to 8 membered heterocycloalkyl, 3 to 6 membered heterocycloalkyl, or 5 to 6 membered heterocycloalkyl). In embodiments, $R^2$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^2$ is $R^{23}$-substituted or unsubstituted aryl (e.g., $C_6$-$C_{10}$ aryl, $C_{10}$ aryl, or phenyl). In embodiments, $R^2$ is $R^{23}$-substituted aryl (e.g., $C_6$-$C_{10}$ aryl, $C_{10}$ aryl, or phenyl). In embodiments, $R^2$ is an unsubstituted aryl (e.g., $C_6$-$C_{10}$ aryl, $C_{10}$ aryl, or phenyl). In embodiments, $R^2$ is $R^{23}$-substituted or unsubstituted heteroaryl (e.g., 5 to 10 membered heteroaryl, 5 to 9 membered heteroaryl, or 5 to 6 membered heteroaryl). In embodiments, $R^2$ is $R^{23}$-substituted heteroaryl (e.g., 5 to 10 membered heteroaryl, 5 to 9 membered heteroaryl, or 5 to 6 membered heteroaryl). In embodiments, $R^2$ is an unsubstituted heteroaryl (e.g., 5 to 10 membered heteroaryl, 5 to 9 membered heteroaryl, or 5 to 6 membered heteroaryl). In embodiments, when $R^2$ is divalent it may be referred to herein as $L^2$.

$R^{23}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)$ $NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{24}$-substituted or unsubstituted alkyl (e.g., $C_1$-$C_8$ alkyl, $C_1$-$C_6$ alkyl, or $C_1$-$C_4$ alkyl), $R^{24}$-substituted or unsubstituted heteroalkyl (e.g., 2 to 8 membered heteroalkyl, 2 to 6 membered heteroalkyl, or 2 to 4 membered heteroalkyl), $R^{24}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{24}$-substituted or unsubstituted heterocycloalkyl (e.g., 3 to 8 membered heterocycloalkyl, 3 to 6 membered heterocycloalkyl, or 5 to 6 membered heterocycloalkyl), $R^{24}$-substituted or unsubstituted aryl (e.g., $C_6$-$C_{10}$ aryl, $C_{10}$ aryl, or phenyl), or $R^{24}$-substituted or unsubstituted heteroaryl (e.g., 5 to 10 membered heteroaryl, 5 to 9 membered heteroaryl, or 5 to 6 membered heteroaryl). In embodiments, when $R^{23}$ is $R^{24}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{24}$-substituted or unsubstituted heterocycloalkyl (e.g., 3 to 8 membered heterocycloalkyl, 3 to 6 membered heterocycloalkyl, or 5 to 6 membered heterocycloalkyl), $R^{24}$-substituted or unsubstituted aryl (e.g., $C_6$-$C_{10}$ aryl, $C_{10}$ aryl, or phenyl), or $R^{24}$-substituted or unsubstituted heteroaryl (e.g., 5 to 10 membered heteroaryl, 5 to 9 membered heteroaryl, or 5 to 6 membered heteroaryl) it may be referred to herein as $(R^{24})_{z4}$-substituted Ring C.

In embodiments, $R^{23}$ is independently oxo. In embodiments, $R^{23}$ is independently halogen. In embodiments, $R^{23}$ is independently —$CCl_3$. In embodiments, $R^{23}$ is independently —$CBr_3$. In embodiments, $R^{23}$ is independently —$CF_3$. In embodiments, $R^{23}$ is independently —$CI_3$. In embodiments, $R^{23}$ is independently $CHCl_2$. In embodiments, $R^{23}$ is independently —$CHBr_2$. In embodiments, $R^{23}$ is independently —$CHF_2$. In embodiments, $R^{23}$ is independently —$CHI_2$. In embodiments, $R^{23}$ is independently —$CH_2Cl$. In embodiments, $R^{23}$ is independently —$CH_2Br$. In embodiments, $R^{23}$ is independently —$CH_2F$. In embodiments, $R^{23}$ is independently —$CH_2I$. In embodiments, $R^{23}$ is independently —CN. In embodiments, $R^{23}$ is independently —OH. In embodiments, $R^{23}$ is independently —$NH_2$. In embodiments, $R^{23}$ is independently —COOH. In embodiments, $R^{23}$ is independently —$CONH_2$. In embodiments, $R^{23}$ is independently —$NO_2$. In embodiments, $R^{23}$ is independently —SH. In embodiments, $R^{23}$ is independently —$SO_3H$. In embodiments, $R^{23}$ is independently —$SO_4H$. In embodiments, $R^{23}$ is independently —$SO_2NH_2$. In embodiments, $R^{23}$ is independently —$NHNH_2$. In embodiments, $R^{23}$ is independently —$ONH_2$. In embodiments, $R^{23}$ is independently —$NHC(O)NHNH_2$. In embodiments, $R^{23}$ is independently —$NHC(O)NH_2$. In embodiments, $R^{23}$ is independently —$NHSO_2H$. In embodiments, $R^{23}$ is independently —$NHC(O)H$. In embodiments, $R^{23}$ is independently —$NHC(O)OH$. In embodiments, $R^{23}$ is independently —NHOH. In embodiments, $R^{23}$ is independently —$OCCl_3$. In embodiments, $R^{23}$ is independently —$OCF_3$. In embodiments, $R^{23}$ is independently —$OCBr_3$. In embodiments, $R^{23}$ is independently —$OCI_3$. In embodiments, $R^{23}$ is independently —$OCHCl_2$. In embodiments, $R^{23}$ is independently —$OCHBr_2$. In embodiments, $R^{23}$ is independently —$OCHI_2$. In embodiments, $R^{23}$ is independently —$OCHF_2$. In embodiments, $R^{23}$ is independently —$OCH_2Cl$. In embodiments, $R^{23}$ is independently —$OCH_2Br$. In embodiments, $R^{23}$ is independently —$OCH_2I$. In embodiments, $R^{23}$ is independently —$OCH_2F$. In embodiments, $R^{23}$ is independently —$N_3$.

In embodiments, $R^{23}$ is $R^{24}$-substituted or unsubstituted alkyl (e.g., $C_1$-$C_8$ alkyl, $C_1$-$C_6$ alkyl, or $C_1$-$C_4$ alkyl). In embodiments, $R^{23}$ is $R^{24}$-substituted alkyl (e.g., $C_1$-$C_8$ alkyl, $C_1$-$C_6$ alkyl, or $C_1$-$C_4$ alkyl). In embodiments, $R^{23}$ is an unsubstituted alkyl (e.g., $C_1$-$C_8$ alkyl, $C_1$-$C_6$ alkyl, or $C_1$-$C_4$ alkyl).

In embodiments, $R^{23}$ is $R^{24}$-substituted or unsubstituted heteroalkyl (e.g., 2 to 8 membered heteroalkyl, 2 to 6 membered heteroalkyl, or 2 to 4 membered heteroalkyl). In embodiments, $R^{23}$ is $R^{24}$-substituted heteroalkyl (e.g., 2 to 8 membered heteroalkyl, 2 to 6 membered heteroalkyl, or 2 to 4 membered heteroalkyl). In embodiments, $R^{23}$ is an unsubstituted heteroalkyl (e.g., 2 to 8 membered heteroalkyl, 2 to 6 membered heteroalkyl, or 2 to 4 membered heteroalkyl).

In embodiments, $R^{23}$ is $R^{24}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{23}$ is $R^{24}$-substituted cycloalkyl (e.g., $C_3$-$C_8$ cycloalkyl, $C_3$-$C_6$ cycloalkyl, or $C_5$-$C_6$ cycloalkyl). In embodiments, $R^{23}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{23}$ is $R^{24}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{23}$ is $R^{24}$-substituted heterocycloalkyl (e.g., 3 to 8 membered heterocycloalkyl, 3 to 6 membered heterocycloalkyl, or 5 to 6 membered heterocycloalkyl). In embodiments, $R^{23}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{23}$ is $R^{24}$-substituted or unsubstituted aryl (e.g., $C_6$-$C_{10}$ aryl, $C_{10}$ aryl, or phenyl). In embodiments, $R^{23}$ is $R^{24}$-substituted aryl (e.g., $C_6$-$C_{10}$ aryl, $C_{10}$ aryl, or phenyl). In embodiments, $R^{23}$ is an unsubstituted aryl (e.g., $C_6$-$C_{10}$ aryl, $C_{10}$ aryl, or phenyl).

In embodiments, $R^{23}$ is $R^{24}$-substituted or unsubstituted heteroaryl (e.g., 5 to 10 membered heteroaryl, 5 to 9 membered heteroaryl, or 5 to 6 membered heteroaryl). In embodiments, $R^{23}$ is $R^{24}$-substituted heteroaryl (e.g., 5 to 10 membered heteroaryl, 5 to 9 membered heteroaryl, or 5 to 6 membered heteroaryl). In embodiments, $R^{23}$ is an unsubstituted heteroaryl (e.g., 5 to 10 membered heteroaryl, 5 to 9 membered heteroaryl, or 5 to 6 membered heteroaryl).

In embodiments, $R^{23}$ is $R^{24}$-substituted or unsubstituted heteroaryl (e.g., 5 to 10 membered heteroaryl, 5 to 9 membered heteroaryl, or 5 to 6 membered heteroaryl). In embodiments, $R^{23}$ is substituted or unsubstituted pyridyl. In embodiments, $R^{23}$ is $R^{24}$-substituted pyridyl. In embodiments, $R^{23}$ is unsubstituted pyridyl. In embodiments, $R^{23}$ is substituted or unsubstituted pyrimidinyl. In embodiments, $R^{23}$ is $R^{24}$-substituted pyrimidinyl. In embodiments, $R^{23}$ is unsubstituted pyrimidinyl. In embodiments, $R^{23}$ is methoxy. In embodiments, $R^{23}$ is substituted or unsubstituted phenyl. In embodiments, $R^{23}$ is $R^{24}$-substituted phenyl. In embodiments, $R^{23}$ is unsubstituted phenyl. In embodiments, $R^{23}$ is substituted or unsubstituted pyridinazinyl. In embodiments, $R^{23}$ is $R^{24}$-substituted pyridinazinyl. In embodiments, $R^{24}$ is an unsubstituted pyridinazinyl.

In embodiments, $R^{24}$ is independently —OH. In embodiments, $R^{24}$ is independently —$OCH_3$. In embodiments, $R^{24}$ is independently —$OCH_2CH_3$. In embodiments, $R^{24}$ is independently —F. In embodiments, $R^{24}$ is independently —$NHC(O)CH_3$. In embodiments, $R^{24}$ is independently —COOH. In embodiments, $R^{24}$ is independently —$SO_2NH_2$.

In embodiments, $R^{24}$ is $R^{25}$-substituted or unsubstituted heteroaryl (e.g., 5 to 10 membered heteroaryl, 5 to 9 membered heteroaryl, or 5 to 6 membered heteroaryl). In embodiments, $R^{24}$ is substituted or unsubstituted pyridyl. In embodiments, $R^{24}$ is $R^{25}$-substituted pyridyl. In embodiments, $R^{24}$ is unsubstituted pyridyl. In embodiments, $R^{24}$ is substituted or unsubstituted pyrimidinyl. In embodiments, $R^{24}$ is $R^{25}$-substituted pyrimidinyl. In embodiments, $R^{24}$ is unsubstituted pyrimidinyl. In embodiments, $R^{24}$ is methoxy. In embodiments, $R^{24}$ is substituted or unsubstituted phenyl. In embodiments, $R^{24}$ is $R^{25}$-substituted phenyl. In embodiments, $R^{24}$ is unsubstituted phenyl. In embodiments, $R^{24}$ is substituted or unsubstituted pyridinazinyl. In embodiments, $R^{24}$ is $R^{25}$-substituted pyridinazinyl. In embodiments, $R^{24}$ is unsubstituted pyridinazinyl.

In embodiments, $R^2$ is $R^{23}$-substituted or unsubstituted alkyl (e.g., $C_1$-$C_8$ alkyl, $C_1$-$C_6$ alkyl, or $C_1$-$C_4$ alkyl). In embodiments, $R^2$ is $R^{23}$-substituted alkyl (e.g., $C_1$-$C_8$ alkyl, $C_1$-$C_6$ alkyl, or $C_1$-$C_4$ alkyl). In embodiments, $R^2$ is an unsubstituted alkyl (e.g., $C_1$-$C_8$ alkyl, $C_1$-$C_6$ alkyl, or $C_1$-$C_4$ alkyl). In embodiments, $R^2$ is $R^{23}$-substituted or unsubstituted heteroalkyl (e.g., 2 to 8 membered heteroalkyl, 2 to 6 membered heteroalkyl, or 2 to 4 membered heteroalkyl). In embodiments, $R^2$ is $R^{23}$-substituted heteroalkyl (e.g., 2 to 8 membered heteroalkyl, 2 to 6 membered heteroalkyl, or 2 to 4 membered heteroalkyl). In embodiments, $R^2$ is an unsubstituted heteroalkyl (e.g., 2 to 8 membered heteroalkyl, 2 to 6 membered heteroalkyl, or 2 to 4 membered heteroalkyl). In embodiments, $R^2$ is $R^{23}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^2$ is $R^{23}$-substituted cycloalkyl (e.g., $C_3$-$C_8$ cycloalkyl, $C_3$-$C_6$ cycloalkyl, or $C_5$-$C_6$ cycloalkyl). In embodiments, $R^2$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^2$ is $R^{23}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^2$ is $R^{23}$-substituted heterocycloalkyl (e.g., 3 to 8 membered heterocycloalkyl, 3 to 6 membered heterocycloalkyl, or 5 to 6 membered heterocycloalkyl). In embodiments, $R^2$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^2$ is $R^{23}$-substituted or unsubstituted aryl (e.g., $C_6$-$C_{10}$ aryl, $C_{10}$ aryl, or phenyl). In embodiments, $R^2$ is $R^{23}$-substituted aryl (e.g., $C_6$-$C_{10}$ aryl, $C_{10}$ aryl, or phenyl). In embodiments, $R^2$ is an unsubstituted aryl (e.g., $C_6$-$C_{10}$ aryl, $C_{10}$ aryl, or phenyl). In embodiments, $R^2$ is $R^{23}$-substituted or unsubstituted heteroaryl (e.g., 5 to 10 membered heteroaryl, 5 to 9 membered heteroaryl, or 5 to 6 membered heteroaryl). In embodiments, $R^2$ is $R^{23}$-substituted heteroaryl (e.g., 5 to 10 membered heteroaryl, 5 to 9 membered heteroaryl, or 5 to 6 membered heteroaryl). In embodiments, $R^2$ is an unsubstituted heteroaryl (e.g., 5 to 10 membered heteroaryl, 5 to 9 membered heteroaryl, or 5 to 6 membered heteroaryl). In embodiments, $R^2$ is substituted or unsubstituted $C_1$-$C_6$ alkyl. In embodiments, $R^2$ is substituted or unsubstituted $C_3$-$C_6$ cycloalkyl. In embodiments, $R^2$ is hydrogen.

In embodiments, $R^2$ is substituted or unsubstituted pyridyl-substituted ethyl. In embodiments, $R^2$ is substituted or unsubstituted 5 to 6 membered heteroaryl-substituted ethyl. In embodiments, $R^2$ is substituted or unsubstituted heteroaryl-substituted ethyl. In embodiments, $R^2$ is substituted or unsubstituted 5 to 6 membered heteroaryl-substituted $C_1$-$C_4$ alkyl. In embodiments, $R^2$ is substituted or unsubstituted heteroaryl-substituted $C_1$-$C_4$ alkyl. In embodiments, $R^2$ is substituted pyridyl-substituted ethyl. In embodiments, $R^2$ is substituted 5 to 6 membered heteroaryl-substituted ethyl. In embodiments, $R^2$ is substituted heteroaryl-substituted ethyl. In embodiments, $R^2$ is substituted 5 to 6 membered heteroaryl-substituted $C_1$-$C_4$ alkyl. In embodiments, $R^2$ is substituted heteroaryl-substituted $C_1$-$C_4$ alkyl. In embodiments, $R^2$ is substituted $C_1$-$C_4$ alkyl. In embodiments, $R^2$ is substituted ethyl. In embodiments, $R^2$ is unsubstituted pyridyl-substituted ethyl. In embodiments, $R^2$ is unsubstituted 5 to 6 membered heteroaryl-substituted ethyl. In embodiments, $R^2$ is unsubstituted heteroaryl-substituted ethyl. In embodiments, $R^2$ is unsubstituted 5 to 6 membered heteroaryl-substituted $C_1$-$C_4$ alkyl. In embodiments, $R^2$ is unsubstituted heteroaryl-substituted $C_1$-$C_4$ alkyl.

In embodiments, $R^2$ is substituted or unsubstituted pyrimidinyl-substituted methyl. In embodiments, $R^2$ is substituted or unsubstituted 5 to 6 membered heteroaryl-substituted methyl. In embodiments, $R^2$ is substituted or unsubstituted heteroaryl-substituted methyl. In embodiments, $R^2$ is substituted methyl. In embodiments, $R^2$ is substituted pyrimidinyl-substituted methyl. In embodiments, $R^2$ is substituted 5 to 6 membered heteroaryl-substituted methyl. In embodiments, $R^2$ is substituted heteroaryl-substituted methyl. In embodiments, $R^2$ is unsubstituted methyl. In embodiments, $R^2$ is substituted $C_1$-$C_4$ alkyl. In embodiments, $R^2$ is unsubstituted pyrimidinyl-substituted methyl. In embodiments, $R^2$ is unsubstituted 5 to 6 membered heteroaryl-substituted methyl. In embodiments, $R^2$ is unsubstituted heteroaryl-substituted methyl.

In embodiments, $R^2$ is substituted or unsubstituted pyridyl-substituted methyl. In embodiments, $R^2$ is methoxy-substituted pyridyl-substituted methyl. In embodiments, $R^2$ is substituted pyridyl-substituted methyl. In embodiments, $R^2$ is substituted pyridyl-substituted methyl. In embodiments, $R^2$ is unsubstituted pyridyl-substituted methyl.

In embodiments, $R^2$ is methoxy-substituted pyridyl-substituted $C_1$-$C_4$ alkyl. In embodiments, $R^2$ is substituted pyridyl-substituted $C_1$-$C_4$ alkyl. In embodiments, $R^2$ is substituted 5 to 6 membered heteroaryl-substituted $C_1$-$C_4$ alkyl. In embodiments, $R^2$ is substituted heteroaryl-substituted $C_1$-$C_4$ alkyl. In embodiments, $R^2$ is unsubstituted 5 to 6 membered heteroaryl-substituted $C_1$-$C_4$ alkyl. In embodiments, $R^2$ is unsubstituted heteroaryl-substituted $C_1$-$C_4$ alkyl.

In embodiments, $R^2$ is unsubstituted methyl. In embodiments, $R^2$ is unsubstituted $C_1$-$C_4$ alkyl. In embodiments, $R^2$ is methyl-substituted cyclopentyl. In embodiments, $R^2$ is $C_1$-$C_4$ alkyl-substituted cyclopentyl. In embodiments, $R^2$ is methyl-substituted $C_3$-$C_6$ cycloalkyl. In embodiments, $R^2$ is substituted $C_3$-$C_6$ cycloalkyl. In embodiments, $R^2$ is substituted cyclopentyl.

In embodiments, $R^2$ is substituted or unsubstituted pyridyl-substituted propyl. In embodiments, $R^2$ is substituted or unsubstituted 5 to 6 membered heteroaryl-substituted propyl. In embodiments, $R^2$ is substituted or unsubstituted heteroaryl-substituted propyl. In embodiments, $R^2$ is substituted propyl. In embodiments, $R^2$ is substituted or unsubstituted pyridyl-substituted $C_1$-$C_6$ alkyl. In embodiments, $R^2$ is substituted or unsubstituted 5 to 6 membered heteroaryl-substituted $C_1$-$C_6$ alkyl. In embodiments, $R^2$ is substituted or unsubstituted heteroaryl-substituted $C_1$-$C_6$ alkyl. In embodiments, $R^2$ is substituted pyridyl-substituted propyl. In embodiments, $R^2$ is substituted 5 to 6 membered heteroaryl-substituted propyl. In embodiments, $R^2$ is substituted heteroaryl-substituted propyl. In embodiments, $R^2$ is unsubstituted propyl. In embodiments, $R^2$ is substituted pyridyl-substituted $C_1$-$C_6$ alkyl. In embodiments, $R^2$ is substituted 5 to 6 membered heteroaryl-substituted $C_1$-$C_6$ alkyl. In embodiments, $R^2$ is substituted heteroaryl-substituted $C_1$-$C_6$ alkyl. In embodiments, $R^2$ is substituted $C_1$-$C_6$ alkyl. In embodiments, $R^2$ is unsubstituted pyridyl-substituted propyl. In embodiments, $R^2$ is unsubstituted 5 to 6 membered heteroaryl-substituted propyl. In embodiments, $R^2$ is unsubstituted heteroaryl-substituted propyl. In embodiments, $R^2$ is unsubstituted propyl. In embodiments, $R^2$ is unsubstituted pyridyl-substituted $C_1$-$C_6$ alkyl. In embodiments, $R^2$ is unsubstituted 5 to 6 membered heteroaryl-substituted $C_1$-$C_6$ alkyl. In embodiments, $R^2$ is unsubstituted heteroaryl-substituted $C_1$-$C_6$ alkyl.

In embodiments, $R^2$ is substituted or unsubstituted phenyl-substituted methyl. In embodiments, $R^2$ is substituted or unsubstituted aryl-substituted methyl. In embodiments, $R^2$ is substituted methyl. In embodiments, $R^2$ is substituted or unsubstituted phenyl-substituted $C_1$-$C_4$ alkyl. In embodiments, $R^2$ is substituted or unsubstituted aryl-substituted $C_1$-$C_4$ alkyl. In embodiments, $R^2$ is substituted $C_1$-$C_4$ alkyl. In embodiments, $R^2$ is unsubstituted phenyl-substituted methyl. In embodiments, $R^2$ is unsubstituted aryl-substituted methyl. In embodiments, $R^2$ is unsubstituted phenyl-substituted $C_1$-$C_4$ alkyl. In embodiments, $R^2$ is unsubstituted aryl-substituted $C_1$-$C_4$ alkyl. In embodiments, $R^2$ is substituted phenyl-substituted methyl. In embodiments, $R^2$ is substituted aryl-substituted methyl. In embodiments, $R^2$ is substituted phenyl-substituted $C_1$-$C_4$ alkyl. In embodiments, $R^2$ is substituted aryl-substituted $C_1$-$C_4$ alkyl.

In embodiments, $R^2$ is substituted or unsubstituted pyridazinyl-substituted methyl. In embodiments, $R^2$ is substituted or unsubstituted pyridazinyl-substituted $C_1$-$C_4$ alkyl. In embodiments, $R^2$ is substituted pyridazinyl-substituted methyl. In embodiments, $R^2$ is substituted pyridazinyl-substituted $C_1$-$C_4$ alkyl. In embodiments, $R^2$ is unsubstituted pyridazinyl-substituted methyl. In embodiments, $R^2$ is unsubstituted pyridazinyl-substituted $C_1$-$C_4$ alkyl.

In embodiments, $R^2$ is unsubstituted ethyl. In embodiments, $R^2$ is unsubstituted $C_1$-$C_4$ alkyl.

In embodiments, $R^2$ is methoxy-substituted pyridyl. In embodiments, $R^2$ is substituted pyridyl. In embodiments, $R^2$ is methoxy-substituted 5 to 6 membered heteroaryl. In embodiments, $R^2$ is substituted 5 to 6 membered heteroaryl. In embodiments, $R^2$ is substituted heteroaryl.

In embodiments, $R^2$ is substituted or unsubstituted benzyl-substituted piperidinyl-substituted methyl. In embodiments, $R^2$ is substituted benzyl-substituted piperidinyl-substituted methyl. In embodiments, $R^2$ is unsubstituted benzyl-substituted piperidinyl-substituted methyl. In embodiments, $R^2$ is substituted piperidinyl-substituted methyl. In embodiments, $R^2$ is substituted or unsubstituted 5 to 6 membered heterocycloalkyl-substituted methyl. In embodiments, $R^2$ is substituted 5 to 6 membered heterocycloalkyl-substituted methyl. In embodiments, $R^2$ is substituted or unsubstituted heterocycloalkyl-substituted methyl. In embodiments, $R^2$ is substituted heterocycloalkyl-substituted methyl. In embodiments, $R^2$ is substituted methyl. In embodiments, $R^2$ is substituted or unsubstituted benzyl-substituted piperidinyl-substituted $C_1$-$C_4$ alkyl. In embodiments, $R^2$ is substituted benzyl-substituted piperidinyl-substituted $C_1$-$C_4$ alkyl. In embodiments, $R^2$ is substituted piperidinyl-substituted $C_1$-$C_4$ alkyl. In embodiments, $R^2$ is substituted or unsubstituted 5 to 6 membered heterocycloalkyl-substituted $C_1$-$C_4$ alkyl. In embodiments, $R^2$ is substituted or unsubstituted heterocycloalkyl-substituted $C_1$-$C_4$ alkyl. In embodiments, $R^2$ is substituted $C_1$-$C_4$ alkyl. In embodiments, $R^2$ is unsubstituted benzyl-substituted piperidinyl-substituted methyl. In embodiments, $R^2$ is substituted piperidinyl-substituted methyl. In embodiments, $R^2$ is substituted 5 to 6 membered heterocycloalkyl-substituted methyl. In embodiments, $R^2$ is substituted heterocycloalkyl-substituted methyl. In embodiments, $R^2$ is unsubstituted benzyl-substituted piperidinyl-substituted $C_1$-$C_4$ alkyl. In embodiments, $R^2$ is substituted piperidinyl-substituted $C_1$-$C_4$ alkyl. In embodiments, $R^2$ is substituted 5 to 6 membered heterocycloalkyl-substituted $C_1$-$C_4$ alkyl. In embodiments, $R^2$ is substituted heterocycloalkyl-substituted $C_1$-$C_4$ alkyl.

In embodiments, $R^2$ is substituted or unsubstituted pyridyl-substituted 4 membered heteroalkyl. In embodiments, $R^2$ is substituted or unsubstituted 5 to 6 membered heteroaryl-substituted 4 membered heteroalkyl. In embodiments, $R^2$ is substituted or unsubstituted heteroaryl-substituted 4 membered heteroalkyl. In embodiments, $R^2$ is substituted or unsubstituted pyridyl-substituted 2 to 6 membered heteroalkyl. In embodiments, $R^2$ is substituted or unsubstituted 5 to 6 membered heteroaryl-substituted 2 to 6 membered heteroalkyl. In embodiments, $R^2$ is substituted pyridyl-substituted 4 membered heteroalkyl. In embodiments, $R^2$ is substituted 5 to 6 membered heteroaryl-substituted 4 membered heteroalkyl. In embodiments, $R^2$ is substituted heteroaryl-substituted 4 membered heteroalkyl. In embodiments, $R^2$ is substituted pyridyl-substituted 2 to 6 membered heteroalkyl. In embodiments, $R^2$ is substituted 5 to 6 membered heteroaryl-substituted 2 to 6 membered heteroalkyl. In embodiments, $R^2$ is substituted heteroaryl-substituted 2 to 6 membered heteroalkyl.

In embodiments, $R^2$ is unsubstituted pyridyl-substituted 4 membered heteroalkyl. In embodiments, $R^2$ is unsubstituted 5 to 6 membered heteroaryl-substituted 4 membered heteroalkyl. In embodiments, $R^2$ is unsubstituted heteroaryl-substituted 4 membered heteroalkyl. In embodiments, $R^2$ is unsubstituted pyridyl-substituted 2 to 6 membered heteroalkyl. In embodiments, $R^2$ is unsubstituted 5 to 6 membered heteroaryl-substituted 2 to 6 membered heteroalkyl. In embodiments, $R^2$ is unsubstituted heteroaryl-substituted 2 to 6 membered heteroalkyl.

In embodiments, $R^2$ is substituted or unsubstituted imidazolyl-substituted ethyl. In embodiments, $R^2$ is substituted or unsubstituted 5 to 6 membered heteroaryl-substituted ethyl. In embodiments, $R^2$ is substituted or unsubstituted heteroaryl-substituted ethyl. In embodiments, $R^2$ is substituted or unsubstituted imidazolyl-substituted $C_1$-$C_4$ alkyl. In embodiments, $R^2$ is substituted or unsubstituted 5 to 6 membered heteroaryl-substituted $C_1$-$C_4$ alkyl. In embodiments, $R^2$ is substituted or unsubstituted heteroaryl-substituted $C_1$-$C_4$ alkyl. In embodiments, $R^2$ is substituted imidazolyl-substituted ethyl. In embodiments, $R^2$ is substituted 5 to 6 membered heteroaryl-substituted ethyl. In embodiments, $R^2$ is substituted heteroaryl-substituted ethyl. In embodiments, $R^2$ is substituted imidazolyl-substituted $C_1$-$C_4$ alkyl. In embodiments, $R^2$ is substituted 5 to 6 membered heteroaryl-substituted $C_1$-$C_4$ alkyl. In embodiments, $R^2$ is substituted heteroaryl-substituted $C_1$-$C_4$ alkyl.

In embodiments, $R^2$ is unsubstituted imidazolyl-substituted ethyl. In embodiments, $R^2$ is unsubstituted 5 to 6 membered heteroaryl-substituted ethyl. In embodiments, $R^2$ is unsubstituted heteroaryl-substituted ethyl. In embodiments, $R^2$ is unsubstituted imidazolyl-substituted $C_1$-$C_4$ alkyl. In embodiments, $R^2$ is unsubstituted 5 to 6 membered heteroaryl-substituted $C_1$-$C_4$ alkyl. In embodiments, $R^2$ is unsubstituted heteroaryl-substituted $C_1$-$C_4$ alkyl.

In embodiments, $R^2$ is OH-substituted ethyl. In embodiments, $R^2$ is OH-substituted $C_1$-$C_4$ alkyl. In embodiments, $R^2$ is substituted ethyl. In embodiments, $R^2$ is substituted $C_1$-$C_4$ alkyl.

In embodiments, $R^2$ is unsubstituted 4 membered heteroalkyl-substituted piperidinyl-substituted methyl. In embodiments, $R^2$ is unsubstituted heteroalkyl substituted piperidinyl-substituted methyl. In embodiments, $R^2$ is substituted 5 to 6 membered heterocycloalkyl-substituted methyl. In embodiments, $R^2$ is unsubstituted 4 membered heteroalkyl-substituted piperidinyl-substituted $C_1$-$C_4$ alkyl. In embodiments, $R^2$ is unsubstituted heteroalkyl-substituted piperidinyl-substituted $C_1$-$C_4$ alkyl. In embodiments, $R^2$ is substituted 5 to 6 membered heterocycloalkyl-substituted $C_1$-$C_4$ alkyl. In embodiments, $R^2$ is substituted heterocycloalkyl-substituted $C_1$-$C_4$ alkyl.

In embodiments, $R^2$ is tert-butyloxycarbonyl-substituted pyrrolidinyl. In embodiments, $R^2$ is substituted 2 to 8 membered heteroalkyl-substituted pyrrolidinyl. In embodiments, $R^2$ is tert-butyloxycarbonyl-substituted 3 to 6 membered heterocycloalkyl. In embodiments, $R^2$ is substituted 3 to 6 membered heterocycloalkyl. In embodiments, $R^2$ is substituted heterocycloalkyl.

In embodiments, $R^2$ is unsubstituted 4 membered heteroalkyl. In embodiments, $R^2$ is unsubstituted 2 to 6 membered heteroalkyl. In embodiments, $R^2$ is unsubstituted heteroalkyl.

In embodiments, $R^2$ is unsubstituted cyclobutyl. In embodiments, $R^2$ is unsubstituted 3 to 6 membered cycloalkyl. In embodiments, $R^2$ is unsubstituted cycloalkyl.

In embodiments, $R^2$ is unsubstituted pyrrolidinyl. In embodiments, $R^2$ is unsubstituted 3 to 6 membered heterocycloalkyl. In embodiments, $R^2$ is unsubstituted heterocycloalkyl.

In embodiments, $R^2$ is OH-substituted cyclobutyl. In embodiments, $R^2$ is substituted cyclobutyl. In embodiments, $R^2$ is OH-substituted $C_3$-$C_6$ cycloalkyl. In embodiments, $R^2$ is substituted $C_3$-$C_6$ cycloalkyl.

In embodiments, $R^2$ is OH-substituted propyl. In embodiments, $R^2$ is OH-substituted $C_1$-$C_6$ alkyl. In embodiments, $R^2$ is substituted propyl. In embodiments, $R^2$ is substituted $C_1$-$C_6$ alkyl.

In embodiments, $R^2$ is tert-butyloxycarbonyl-substituted azetidinyl. In embodiments, $R^2$ is oxo-substituted 2 to 8 membered heteroalkyl-substituted azetidinyl. In embodiments, $R^2$ is oxo-substituted heteroalkyl-substituted azetidinyl. In embodiments, $R^2$ is substituted 2 to 8 membered heteroalkyl-substituted azetidinyl. In embodiments, $R^2$ is substituted heteroalkyl-substituted azetidinyl.

In embodiments, $R^2$ is unsubstituted cyclopentyl. In embodiments, $R^2$ is unsubstituted $C_3$-$C_6$ cycloalkyl. In embodiments, $R^2$ is unsubstituted cyclopropyl.

In embodiments, $R^2$ is unsubstituted cyclobutyl-substituted methyl. In embodiments, $R^2$ is unsubstituted $C_3$-$C_6$ cycloalkyl-substituted methyl. In embodiments, $R^2$ is unsubstituted cyclobutyl-substituted $C_1$-$C_4$ alkyl. In embodiments, $R^2$ is unsubstituted $C_3$-$C_6$ cycloalkyl-substituted $C_1$-$C_4$ alkyl.

In embodiments, $R^2$ is unsubstituted oxetanyl. In embodiments, $R^2$ is unsubstituted 3 to 6 membered heterocycloalkyl.

In embodiments, $R^2$ is unsubstituted isopropyl. In embodiments, $R^2$ is unsubstituted propyl. In embodiments, $R^2$ is unsubstituted tert-butyl. In embodiments, $R^2$ is unsubstituted butyl. In embodiments, $R^2$ is unsubstituted $C_1$-$C_6$ alkyl.

In embodiments, $R^2$ is oxo-substituted 4 membered heteroalkyl. In embodiments, $R^2$ is oxo-substituted 2 to 6 membered heteroalkyl. In embodiments, $R^2$ is substituted 4 membered heteroalkyl. In embodiments, $R^2$ is substituted 2 to 6 membered heteroalkyl. In embodiments, $R^2$ is substituted heteroalkyl.

In embodiments, $R^2$ is unsubstituted tetrahydropyran-substituted methyl. In embodiments, $R^2$ is tetrahydropyran-substituted methyl. In embodiments, $R^2$ is unsubstituted 5 to 6 membered heterocycloalkyl-substituted methyl. In embodiments, $R^2$ is unsubstituted tetrahydropyran-substituted $C_1$-$C_4$ alkyl. In embodiments, $R^2$ is tetrahydropyran-substituted $C_1$-$C_4$ alkyl. In embodiments, $R^2$ is unsubstituted 5 to 6 membered heterocycloalkyl-substituted $C_1$-$C_4$ alkyl.

In embodiments, $R^2$ is $CF_3$-substituted methyl. In embodiments, $R^2$ is $C(halo)_3$-substituted methyl. In embodiments, $R^2$ is $CF_3$-substituted $C_1$-$C_4$ alkyl. In embodiments, $R^2$ is $C(halo)_3$-substituted $C_1$-$C_4$ alkyl.

In embodiments, $R^2$ is tert-butyloxycarbonyl-substituted pyrrolidinyl-substituted methyl. In embodiments, $R^2$ is oxo-substituted 2 to 8 membered heteroalkyl-substituted pyrrolidinyl-substituted methyl. In embodiments, $R^2$ is substituted 2 to 8 membered heteroalkyl-substituted pyrrolidinyl-substituted methyl. In embodiments, $R^2$ is tert-butyloxycarbonyl-substituted 3 to 6 membered heterocycloalkyl-substituted methyl. In embodiments, $R^2$ is tert-butyloxycarbonyl-substituted pyrrolidinyl-substituted $C_1$-$C_4$ alkyl. In embodiments, $R^2$ is substituted 2 to 8 membered heteroalkyl-substituted pyrrolidinyl-substituted $C_1$-$C_4$ alkyl. In embodiments, $R^2$ is substituted 2 to 8 membered heteroalkyl-substituted 3 to 6 membered heterocycloalkyl-substituted $C_1$-$C_4$ alkyl. In embodiments, $R^2$ is substituted 3 to 6 membered heterocycloalkyl-substituted $C_1$-$C_4$ alkyl.

In embodiments, $R^2$ is OH-substituted butyl. In embodiments, $R^2$ is substituted butyl.

In embodiments, $R^2$ is OH-substituted pyridyl-substituted ethyl. In embodiments, $R^2$ is OH-substituted ethyl. In embodiments, $R^2$ is unsubstituted pyridyl-substituted ethyl. In embodiments, $R^2$ is OH-substituted and unsubstituted pyridyl-substituted $C_1$-$C_4$ alkyl. In embodiments, $R^2$ is OH-substituted $C_1$-$C_4$ alkyl. In embodiments, $R^2$ is unsubstituted pyridyl-substituted $C_1$-$C_4$ alkyl. In embodiments, $R^2$ is OH-substituted and unsubstituted 5 to 6 membered heteroaryl-substituted ethyl. In embodiments, $R^2$ is substituted ethyl. In embodiments, $R^2$ is unsubstituted 5 to 6 membered heteroaryl-substituted ethyl. In embodiments, $R^2$ is OH-substituted and unsubstituted 5 to 6 membered heteroaryl-substituted $C_1$-$C_4$ alkyl. In embodiments, $R^2$ is substituted $C_1$-$C_4$ alkyl. In embodiments, $R^2$ is unsubstituted 5 to 6 membered heteroaryl-substituted $C_1$-$C_4$ alkyl.

In embodiments, $R^2$ is substituted or unsubstituted methyl-substituted imidazolyl-substituted methyl. In embodiments, $R^2$ is substituted or unsubstituted methyl-substituted 5 to 6 membered heteroaryl-substituted methyl. In embodiments, $R^2$ is substituted or unsubstituted methyl-substituted heteroaryl-substituted methyl. In embodiments, $R^2$ is substituted methyl-substituted imidazolyl-substituted methyl. In embodiments, $R^2$ is substituted methyl-substituted 5 to 6 membered heteroaryl-substituted methyl. In embodiments, $R^2$ is substituted methyl-substituted heteroaryl-substituted methyl. In embodiments, $R^2$ is unsubstituted $C_1$-$C_4$ alkyl-substituted imidazolyl-substituted $C_1$-$C_4$ alkyl. In embodiments, $R^2$ is unsubstituted $C_1$-$C_4$ alkyl-substituted 5 to 6 membered heteroaryl-substituted $C_1$-$C_4$ alkyl. In embodiments, $R^2$ is unsubstituted $C_1$-$C_4$ alkyl-substituted heteroaryl-substituted $C_1$-$C_4$ alkyl.

In embodiments, $R^2$ is methoxy-substituted cyclobutyl. In embodiments, $R^2$ is 2 to 4 membered heteroalkyl-substituted cyclobutyl. In embodiments, $R^2$ is methoxy-substituted $C_3$-$C_6$ cycloalkyl. In embodiments, $R^2$ is 2 to 4 membered heteroalkyl-substituted $C_3$-$C_6$ cycloalkyl.

In embodiments, $R^2$ is unsubstituted phenyl. In embodiments, $R^2$ is unsubstituted aryl.

In embodiments, $R^2$ is substituted or unsubstituted imidazolyl-substituted methyl. In embodiments, $R^2$ is substituted or unsubstituted 5 to 6 membered heteroaryl-substituted methyl. In embodiments, $R^2$ is substituted or unsubstituted heteroaryl-substituted methyl. In embodiments, $R^2$ is substituted imidazolyl-substituted methyl. In embodiments, $R^2$ is substituted 5 to 6 membered heteroaryl-substituted methyl. In embodiments, $R^2$ is substituted heteroaryl-substituted methyl. In embodiments, $R^2$ is unsubstituted imidazolyl-substituted methyl. In embodiments, $R^2$ is unsubstituted 5 to 6 membered heteroaryl-substituted methyl. In embodiments, $R^2$ is unsubstituted heteroaryl-substituted methyl. In embodiments, $R^2$ is substituted or unsubstituted imidazolyl-substituted $C_1$-$C_4$ alkyl. In embodiments, $R^2$ is substituted or unsubstituted 5 to 6 membered heteroaryl-substituted $C_1$-$C_4$ alkyl. In embodiments, $R^2$ is substituted or unsubstituted heteroaryl-substituted $C_1$-$C_4$ alkyl. In embodiments, $R^2$ is unsubstituted imidazolyl-substituted $C_1$-$C_4$ alkyl. In embodiments, $R^2$ is unsubstituted 5 to 6 membered heteroaryl-substituted $C_1$-$C_4$ alkyl. In embodiments, $R^2$ is unsubstituted heteroaryl-substituted $C_1$-$C_4$ alkyl.

In embodiments, $R^2$ is OH-substituted cyclopentyl. In embodiments, $R^2$ is OH-substituted $C_3$-$C_6$ cycloalkyl. In embodiments, $R^2$ is substituted cyclopentyl. In embodiments, $R^2$ is substituted $C_3$-$C_6$ cycloalkyl.

In embodiments, $R^2$ is OH-substituted phenyl-substituted ethyl. In embodiments, $R^2$ is OH-substituted aryl-substituted ethyl. In embodiments, $R^2$ is substituted aryl-substituted ethyl. In embodiments, $R^2$ is OH-substituted phenyl-substituted $C_1$-$C_4$ alkyl. In embodiments, $R^2$ is OH-substituted aryl-substituted $C_1$-$C_4$ alkyl. In embodiments, $R^2$ is substituted aryl-substituted $C_1$-$C_4$ alkyl.

In embodiments, $R^2$ is tert-butyloxycarbonyl-substituted tetrahydropyran-substituted ethyl. In embodiments, $R^2$ is substituted 2 to 8 membered heteroalkyl-substituted tetrahydropyran-substituted ethyl. In embodiments, $R^2$ is tert-butyloxycarbonyl-substituted 3 to 6 membered heterocycloalkyl-substituted ethyl. In embodiments, $R^2$ is tert-butyloxycarbonyl-substituted tetrahydropyran-substituted $C_1$-$C_4$ alkyl.

In embodiments, $R^2$ is unsubstituted pyrrolidinyl-substituted ethyl. In embodiments, $R^2$ is unsubstituted 3 to 6 membered heterocycloalkyl-substituted ethyl. In embodiments, $R^2$ is unsubstituted pyrrolidinyl-substituted $C_1$-$C_4$ alkyl. In embodiments, $R^2$ is unsubstituted 5 to 6 membered heterocycloalkyl-substituted $C_1$-$C_4$ alkyl.

In embodiments, $R^2$ is tert-butyloxy carbonyl-substituted pyrrolidinyl-substituted ethyl. In embodiments, $R^2$ is substituted 2 to 8 membered heteroalkyl-substituted pyrrolidinyl-substituted ethyl. In embodiments, $R^2$ is tert-butyloxy carbonyl-substituted 3 to 6 membered heterocycloalkyl-substituted ethyl.

In embodiments, $R^2$ is tert-butyloxy carbonyl-substituted pyrrolidinyl-substituted $C_1$-$C_4$ alkyl. In embodiments, $R^2$ is substituted 2 to 8 membered heteroalkyl-substituted pyrrolidinyl-substituted $C_1$-$C_4$ alkyl. In embodiments, $R^2$ is tert-butyloxycarbonyl-substituted 3 to 6 membered heterocycloalkyl-substituted $C_1$-$C_4$ alkyl.

In embodiments, $R^2$ is unsubstituted pyrrolidinyl-substituted methyl. In embodiments, $R^2$ is unsubstituted 3 to 6 membered heterocycloalkyl-substituted methyl.

In embodiments, $R^2$ is unsubstituted pyrrolidinyl-substituted $C_1$-$C_4$ alkyl. In embodiments, $R^2$ is unsubstituted 3 to 6 membered heterocycloalkyl-substituted $C_1$-$C_4$ alkyl.

In embodiments, $R^2$ is unsubstituted morpholinyl-substituted ethyl. In embodiments, $R^2$ is unsubstituted morpholinyl-substituted ethyl. In embodiments, $R^2$ is unsubstituted 5 to 6 membered heterocycloalkyl-substituted ethyl. In embodiments, $R^2$ is unsubstituted morpholinyl-substituted $C_1$-$C_4$ alkyl.

In embodiments, $R^2$ is OH-substituted phenyl-substituted ethyl. In embodiments, $R^2$ is OH-substituted aryl-substituted ethyl. In embodiments, $R^2$ is substituted phenyl-substituted $C_1$-$C_4$ alkyl. In embodiments, $R^2$ is substituted aryl-substituted $C_1$-$C_4$ alkyl.

In embodiments, $R^2$ is unsubstituted piperidinyl-substituted methyl. In embodiments, $R^2$ is unsubstituted 5 to 6 membered heterocycloalkyl-substituted methyl. In embodiments, $R^2$ is unsubstituted heterocycloalkyl-substituted methyl. In embodiments, $R^2$ is unsubstituted piperidinyl-substituted $C_1$-$C_4$ alkyl. In embodiments, $R^2$ is unsubstituted 5 to 6 membered heterocycloalkyl-substituted $C_1$-$C_4$ alkyl. In embodiments, $R^2$ is unsubstituted heterocycloalkyl-substituted $C_1$-$C_4$ alkyl.

In embodiments, $R^2$ is OH-substituted methyl-substituted phenyl-substituted ethyl. In embodiments, $R^2$ is OH-substituted methyl-substituted aryl-substituted ethyl. In embodiments, $R^2$ is substituted phenyl-substituted ethyl. In embodiments, $R^2$ is substituted aryl-substituted ethyl. In embodiments, $R^2$ is substituted phenyl-substituted $C_1$-$C_4$ alkyl. In embodiments, $R^2$ is substituted aryl-substituted $C_1$-$C_4$ alkyl.

In embodiments, $R^2$ is Cl-substituted phenyl-substituted ethyl. In embodiments, $R^2$ is halo-substituted aryl-substituted ethyl. In embodiments, $R^2$ is halo-substituted phenyl-substituted ethyl. In embodiments, $R^2$ is Cl-substituted phenyl-substituted $C_1$-$C_4$ alkyl. In embodiments, $R^2$ is halo-substituted phenyl-substituted $C_1$-$C_4$ alkyl. In embodiments, $R^2$ is halo-substituted aryl-substituted $C_1$-$C_4$ alkyl.

In embodiments, $R^2$ is unsubstituted tetrahydrofuranyl-substituted methyl. In embodiments, $R^2$ is tetrahydrofuranyl-substituted methyl. In embodiments, $R^2$ is unsubstituted 3 to 6 membered heterocycloalkyl-substituted methyl. In embodiments, $R^2$ is unsubstituted tetrahydrofuranyl-substituted $C_1$-$C_4$ alkyl. In embodiments, $R^2$ is tetrahydrofuranyl-substituted $C_1$-$C_4$ alkyl.

In embodiments, $R^2$ is unsubstituted phenyl-substituted ethyl. In embodiments, $R^2$ is unsubstituted aryl-substituted ethyl. In embodiments, $R^2$ is unsubstituted phenyl-substituted $C_1$-$C_4$ alkyl. In embodiments, $R^2$ is unsubstituted aryl-substituted $C_1$-$C_4$ alkyl.

In embodiments, $R^2$ is unsubstituted azetidinyl. In embodiments, $R^2$ is unsubstituted 3 to 6 membered heterocycloalkyl In embodiments, $R^2$ is methoxy-substituted phenoxy-substituted pyridyl-substituted methyl. In embodiments, $R^2$ is 2 to 4 membered alkoxy-substituted phenoxy-substituted pyridyl-substituted methyl. In embodiments, $R^2$ is 2 to 4 membered alkoxy-substituted aryloxy-substituted pyridyl-substituted methyl. In embodiments, $R^2$ is 2 to 4 membered alkoxy-substituted aryl oxy-substituted 5 to 6 membered heteroaryl-substituted methyl. In embodiments, $R^2$ is 2 to 4 membered alkoxy-substituted aryloxy-substituted 5 to 6 membered heteroaryl-substituted $C_1$-$C_4$ alkyl.

In embodiments, $R^2$ is methoxy-substituted pyridyl-substituted ethyl. In embodiments, $R^2$ is 2 to 4 membered alkoxy-substituted pyridyl-substituted ethyl. In embodiments, $R^2$ is 2 to 4 membered alkoxy-substituted 5 to 6 membered heteroaryl-substituted ethyl. In embodiments, $R^2$ is 2 to 4 membered alkoxy-substituted 5 to 6 membered heteroaryl-substituted $C_1$-$C_4$ alkyl. In embodiments, $R^2$ is 2 to 4 membered alkoxy-substituted heteroaryl-substituted $C_1$-$C_4$ alkyl.

In embodiments, $R^2$ is methoxy-substituted phenyl-substituted ethyl. In embodiments, $R^2$ is 2 to 4 membered alkoxy-substituted phenyl-substituted ethyl. In embodiments, $R^2$ is 2 to 4 membered alkoxy-substituted aryl-substituted ethyl. In embodiments, $R^2$ is 2 to 4 membered alkoxy-substituted aryl-substituted $C_1$-$C_4$ alkyl.

In embodiments, $R^2$ is oxo-substituted 2 to 4 membered heteroalkyl-substituted phenyl-substituted ethyl. In embodiments, $R^2$ is substituted 2 to 4 membered heteroalkyl-substituted phenyl-substituted ethyl. In embodiments, $R^2$ is substituted 2 to 4 membered heteroalkyl-substituted aryl-substituted ethyl. In embodiments, $R^2$ is substituted 2 to 4 membered heteroalkyl-substituted aryl-substituted $C_1$-$C_4$ alkyl.

In embodiments, $R^2$ is methoxy-substituted phenyl-substituted propyl. In embodiments, $R^2$ is 2 to 4 membered alkoxy-substituted phenyl-substituted propyl. In embodiments, $R^2$ is 2 to 4 membered alkoxy-substituted aryl-substituted propyl. In embodiments, $R^2$ is 2 to 4 membered alkoxy-substituted aryl-substituted $C_1$-$C_4$ alkyl.

In embodiments, $R^2$ is oxo-substituted 2 to 4 membered heteroalkyl-substituted phenyl-substituted ethyl. In embodiments, $R^2$ is substituted 2 to 4 membered heteroalkyl-substituted phenyl-substituted ethyl. In embodiments, $R^2$ is substituted 2 to 4 membered heteroalkyl-substituted aryl-substituted ethyl. In embodiments, $R^2$ is substituted 2 to 4 membered heteroalkyl-substituted aryl-substituted $C_1$-$C_4$ alkyl.

In embodiments, $R^2$ is unsubstituted cyclopentyl-substituted ethyl. In embodiments, $R^2$ is unsubstituted $C_3$-$C_6$ cycloalkyl-substituted ethyl. In embodiments, $R^2$ is unsubstituted $C_3$-$C_6$ cycloalkyl-substituted $C_1$-$C_4$ alkyl.

In embodiments, $R^2$ is tert-butyloxycarbonyl-substituted pyrrolidinyl-substituted ethyl. In embodiments, $R^2$ is oxo-substituted 4 to 8 membered heteroalkyl-substituted pyrrolidinyl-substituted ethyl. In embodiments, $R^2$ is substituted 4 to 8 membered heteroalkyl-substituted pyrrolidinyl-substituted ethyl. In embodiments, $R^2$ is substituted 4 to 8 membered heteroalkyl-substituted 3 to 6 membered heterocycloalkyl-substituted ethyl. In embodiments, $R^2$ is substituted 4 to 8 membered heteroalkyl-substituted 3 to 6 membered heterocycloalkyl-substituted $C_1$-$C_4$ alkyl.

In embodiments, $R^2$ is tert-butyloxy carbonyl-substituted azetidinyl-substituted ethyl. In embodiments, $R^2$ is oxo-substituted 4 to 8 membered heteroalkyl-substituted azetidinyl-substituted ethyl. In embodiments, $R^2$ is substituted 4 to 8 membered heteroalkyl-substituted azetidinyl-substituted ethyl. In embodiments, $R^2$ is substituted 4 to 8 membered heteroalkyl-substituted azetidinyl-substituted $C_1$-$C_4$ alkyl.

In embodiments, $R^2$ is unsubstituted azetidinyl-substituted ethyl. In embodiments, $R^2$ is unsubstituted $C_3$-$C_6$ heterocycloalkyl-substituted ethyl. In embodiments, $R^2$ is unsubstituted $C_3$-$C_6$ heterocycloalkyl-substituted $C_1$-$C_4$ alkyl.

In embodiments, $R^2$ is CN-substituted phenyl-substituted ethyl. In embodiments, $R^2$ is substituted phenyl-substituted ethyl. In embodiments, $R^2$ is CN-substituted aryl-substituted ethyl. In embodiments, $R^2$ is CN-substituted aryl-substituted $C_1$-$C_4$ alkyl. In embodiments, $R^2$ is substituted aryl-substituted $C_1$-$C_4$ alkyl.

In embodiments, $R^2$ is unsubstituted phenyl-substituted ethyl-substituted piperidinyl-substituted methyl. In embodiments, $R^2$ is unsubstituted aryl-substituted ethyl-substituted piperidinyl-substituted methyl. In embodiments, $R^2$ is unsubstituted aryl-substituted $C_1$-$C_4$ alkyl-substituted piperidinyl-substituted methyl. In embodiments, $R^2$ is unsubstituted aryl-substituted $C_1$-$C_4$ alkyl-substituted 3 to 6 membered heterocycloalkyl-substituted methyl. In embodiments, $R^2$ is unsubstituted aryl-substituted $C_1$-$C_4$ alkyl-substituted 3 to 6 membered heterocycloalkyl-substituted $C_1$-$C_4$ alkyl.

In embodiments, $R^2$ is methoxy-substituted pyridyl-substituted methyl. In embodiments, $R^2$ is 2 to 4 membered alkoxy-substituted pyridyl-substituted methyl. In embodiments, $R^2$ is 2 to 4 membered alkoxy-substituted 5 to 6 membered heteroaryl-substituted methyl. In embodiments, $R^2$ is 2 to 4 membered alkoxy-substituted 5 to 6 membered heteroaryl-substituted $C_1$-$C_4$ alkyl.

In embodiments, $R^2$ is unsubstituted 2 to 4 membered alkoxy-substituted pyridyl-substituted methyl. In embodiments, $R^2$ is unsubstituted 2 to 4 membered alkoxy-substituted 5 to 6 membered heteroaryl-substituted methyl. In embodiments, $R^2$ is unsubstituted 2 to 4 membered alkoxy-substituted 5 to 6 membered heteroaryl-substituted $C_1$-$C_4$ alkyl.

In embodiments, $R^2$ is unsubstituted pyridyl-substituted methyl. In embodiments, $R^2$ is unsubstituted 5 to 6 membered heteroaryl-substituted methyl. In embodiments, $R^2$ is unsubstituted 5 to 6 membered heteroaryl-substituted $C_1$-$C_4$ alkyl.

In embodiments, $R^2$ is carboxyl-substituted phenyl-substituted ethyl. In embodiments, $R^2$ is substituted phenyl-substituted ethyl. In embodiments, $R^2$ is carboxyl-substituted aryl-substituted ethyl. In embodiments, $R^2$ is carboxyl-substituted aryl-substituted $C_1$-$C_4$ alkyl.

In embodiments, $R^2$ is $SO_2NH_2$-substituted phenyl-substituted ethyl. In embodiments, $R^2$ is $SO_2NH_2$-substituted aryl-substituted ethyl. In embodiments, $R^2$ is $SO_2NH_2$-substituted aryl-substituted $C_1$-$C_4$ alkyl. In embodiments, $R^2$ is hydrogen.

In embodiments, $R^2$ is tert-butylcarbamate-substituted phenyl-substituted ethyl. In embodiments, $R^2$ is oxo-substituted 6 to 8 membered heteroalkyl-substituted phenyl-substituted ethyl. In embodiments, $R^2$ is substituted 6 to 8 membered heteroalkyl-substituted phenyl-substituted ethyl. In embodiments, $R^2$ is substituted 6 to 8 membered heteroalkyl-substituted aryl-substituted ethyl. In embodiments, $R^2$ is substituted 6 to 8 membered heteroalkyl-substituted aryl-substituted $C_1$-$C_4$ alkyl.

In embodiments, $R^2$ is tert-butyloxycarbonyl-substituted piperidinyl-substituted ethyl. In embodiments, $R^2$ is oxo-substituted 5 to 7 membered heteroalkyl-substituted piperidinyl-substituted ethyl. In embodiments, $R^2$ is substituted 5 to 7 membered heteroalkyl-substituted piperidinyl-substituted ethyl. In embodiments, $R^2$ is substituted 5 to 7 membered heteroalkyl-substituted 5 to 6 membered heterocycloalkyl-substituted ethyl. In embodiments, $R^2$ is substituted 5 to 7 membered heteroalkyl-substituted 5 to 6 membered heterocycloalkyl-substituted $C_1$-$C_4$ alkyl.

In embodiments, $R^2$ is unsubstituted thiazolyl-substituted methyl. In embodiments, $R^2$ is unsubstituted 5 to 6 membered heteroaryl-substituted methyl. In embodiments, $R^2$ is unsubstituted 5 to 6 membered heteroaryl-substituted $C_1$-$C_4$ alkyl.

In embodiments, $R^2$ is $NH_2$-substituted phenyl-substituted ethyl. In embodiments, $R^2$ is $NH_2$-substituted aryl-substituted ethyl. In embodiments, $R^2$ is $NH_2$-substituted aryl-substituted $C_1$-$C_4$ alkyl. In embodiments, $R^2$ is substituted aryl-substituted $C_1$-$C_4$ alkyl.

In embodiments, $R^2$ is unsubstituted piperidinyl-substituted ethyl. In embodiments, $R^2$ is unsubstituted 5 to 6 membered heterocycloalkyl-substituted ethyl. In embodiments, $R^2$ is unsubstituted 5 to 6 membered heterocycloalkyl-substituted $C_1$-$C_4$ alkyl.

In embodiments, $R^2$ is oxo-substituted 2 to 6 membered heteroalkyl-substituted phenyl-substituted ethyl. In embodiments, $R^2$ is substituted 2 to 6 membered heteroalkyl-substituted phenyl-substituted ethyl. In embodiments, $R^2$ is substituted 2 to 6 membered heteroalkyl-substituted aryl-substituted ethyl. In embodiments, $R^2$ is substituted 2 to 6 membered heteroalkyl-substituted aryl-substituted $C_1$-$C_4$ alkyl.

In embodiments, $R^2$ is

In embodiments, R² is
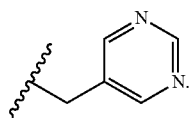 [SMILES: *Cc1cncnc1]
In embodiments, R² is
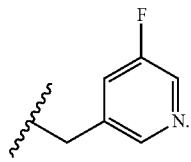 [SMILES: *Cc1cncc(F)c1]
In embodiments, R² is
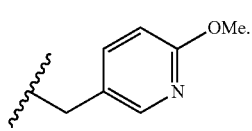 [SMILES: *Cc1ccc(OC)nc1]
In embodiments, R² is
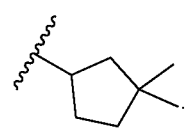 [SMILES: *C1CCC(C)(C)C1]
In embodiments, R² is
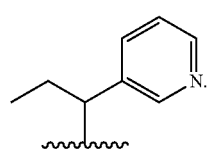 [SMILES: *C(CC)c1cccnc1]
In embodiments, R² is
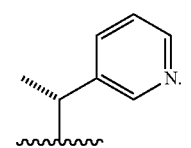
In embodiments, R² is
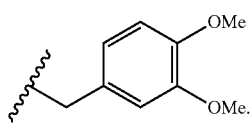 [SMILES: *Cc1ccc(OC)c(OC)c1]
In embodiments, R² is
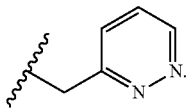 [SMILES: *Cc1cccnn1]
In embodiments, R² is
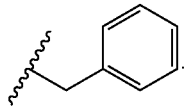
In embodiments, R² is
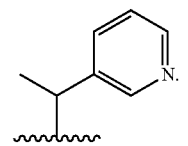
In embodiments, R² is
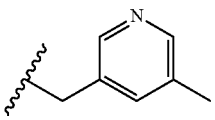
In embodiments, R² is
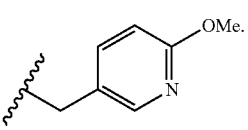 [SMILES: *Cc1ccc(OC)nc1]
In embodiments, R² is
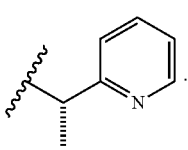 [SMILES: *[C@@H](C)c1ccccn1]
In embodiments, R² is
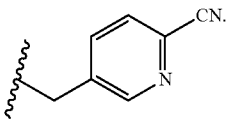 [SMILES: *Cc1ccc(C#N)nc1]

In embodiments, $R^2$ is
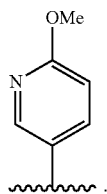
In embodiments, $R^2$ is
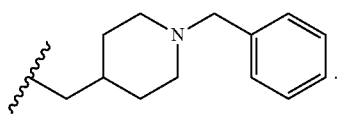 [SMILES: *CC1CCN(Cc2ccccc2)CC1]
In embodiments, $R^2$ is
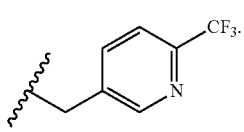
In embodiments, $R^2$ is
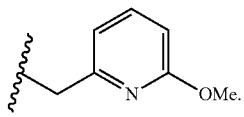 [SMILES: *Cc1cccc(OC)n1]
In embodiments, $R^2$ is
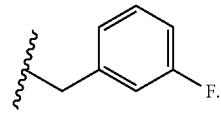 [SMILES: *Cc1cccc(F)c1]
In embodiments, $R^2$ is
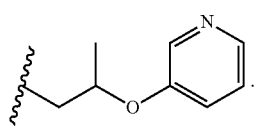 [SMILES: *CC(C)Oc1cccnc1]
In embodiments, $R^2$ is
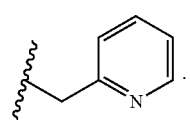 [SMILES: *Cc1ccccn1]
In embodiments, $R^2$ is
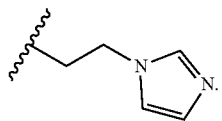 [SMILES: *CCn1ccnc1]
In embodiments, $R^2$ is
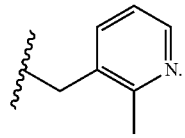 [SMILES: *Cc1cccnc1C]
In embodiments, $R^2$ is
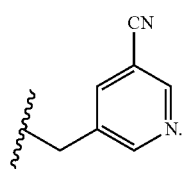 [SMILES: *Cc1cncc(C#N)c1]
In embodiments, $R^2$ is
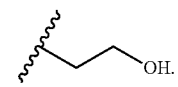 [SMILES: *CCO]
In embodiments, $R^2$ is
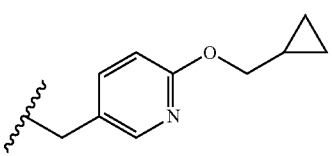
In embodiments, $R^2$ is
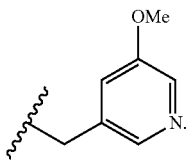
In embodiments, $R^2$ is
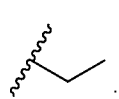

In embodiments, R² is
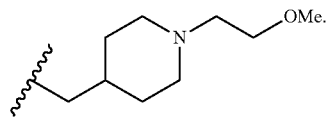 [SMILES: *CC1CCN(CCOC)CC1]
In embodiments, R² is
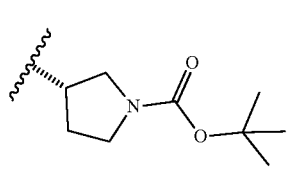
In embodiments, R² is
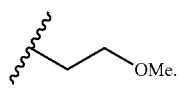 [SMILES: *CCOC]
In embodiments, R² is
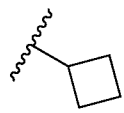
In embodiments, R² is
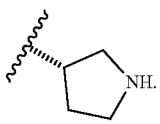
In embodiments, R² is
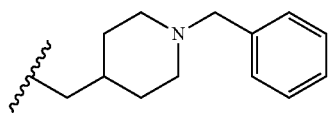
In embodiments, R² is
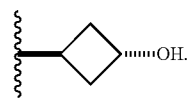 [SMILES: *[C@H]1C[C@H](O)C1]
In embodiments, R² is
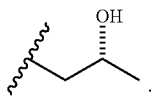
In embodiments, R² is
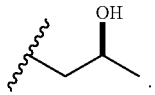 [SMILES: *C[C@H](C)O]
In embodiments, R² is
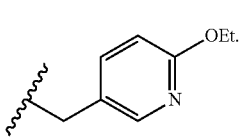
In embodiments, R² is
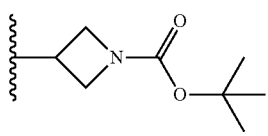
In embodiments, R² is
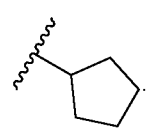
In embodiments, R² is
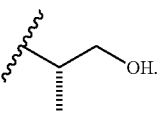
In embodiments, R² is
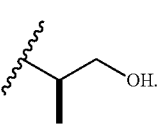 [SMILES: *[C@H](C)CO]

In embodiments, R² is
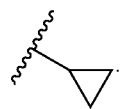
In embodiments, R² is
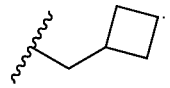
In embodiments, R² is
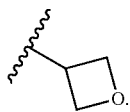 [SMILES: *C1COC1]
In embodiments, R² is
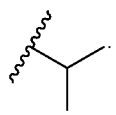
In embodiments, R² is
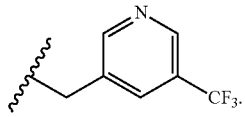 [SMILES: *Cc1cncc(C(F)(F)F)c1]
In embodiments, R² is
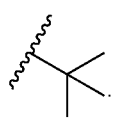
In embodiments, R² is
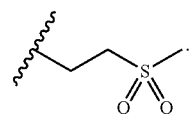 [SMILES: *CCS(C)(=O)=O]
In embodiments, R² is
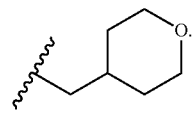 [SMILES: *CC1CCOCC1]
In embodiments, R² is
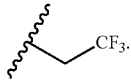
In embodiments, R² is
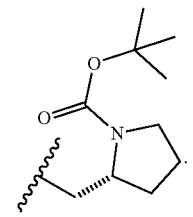
In embodiments, R² is
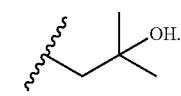 [SMILES: *CC(C)(C)O]
In embodiments, R² is
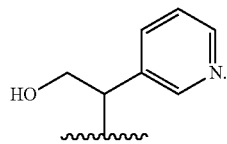 [SMILES: *C(CO)c1cccnc1]
In embodiments, R² is
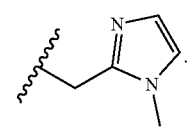 [SMILES: *Cc1nccn1C]
In embodiments, R² is
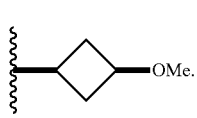

In embodiments, R² is
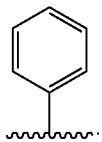
In embodiments, R² is
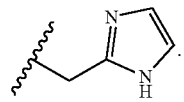
In embodiments, R² is
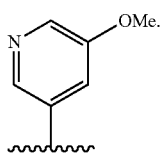
In embodiments, R² is
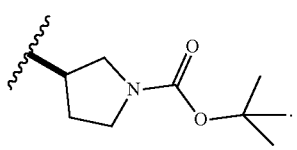 [SMILES: *[C@@H]1CCN(C(=O)OC(C)(C)C)C1]
In embodiments, R² is
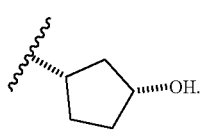
In embodiments, R² is
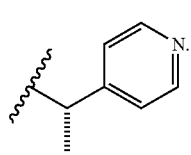 [SMILES: *[C@@H](C)c1ccncc1]
In embodiments, R² is
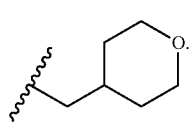
In embodiments, R² is
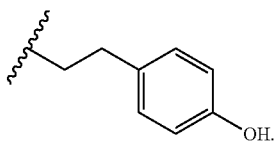 [SMILES: *CCc1ccc(O)cc1]
In embodiments, R² is
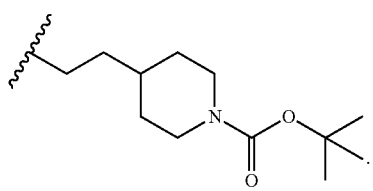 [SMILES: *CCC1CCN(C(=O)OC(C)(C)C)CC1]
In embodiments, R² is
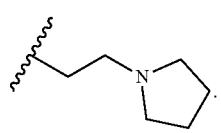 [SMILES: *CCN1CCCC1]
In embodiments, R² is
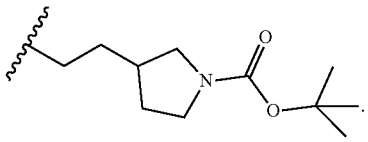 [SMILES: *CCC1CCN(C(=O)OC(C)(C)C)C1]
In embodiments, R² is
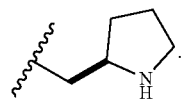
In embodiments, R² is
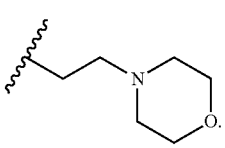 [SMILES: *CCN1CCOCC1]
In embodiments, R² is
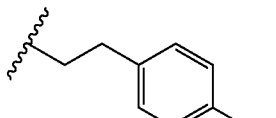

In embodiments, R² is
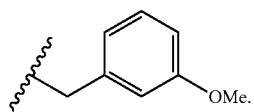 [SMILES: *Cc1cccc(OC)c1]
In embodiments, R² is
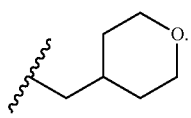
In embodiments, R² is
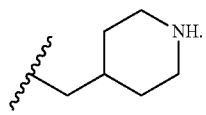
In embodiments, R² is
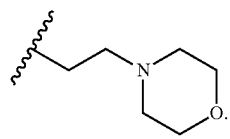
In embodiments, R² is
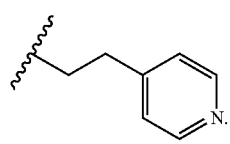 [SMILES: *CCc1ccncc1]
In embodiments, R² is
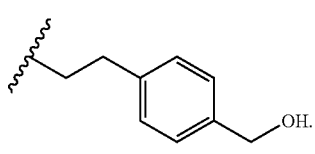 [SMILES: *CCc1ccc(CO)cc1]
In embodiments, R² is
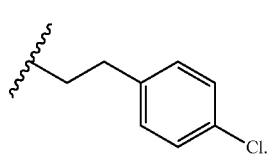 [SMILES: *CCc1ccc(Cl)cc1]
In embodiments, R² is
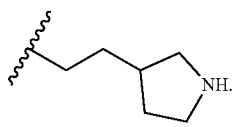
In embodiments, R² is
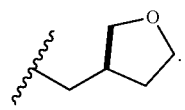
In embodiments, R² is
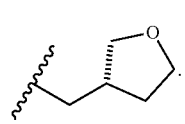
In embodiments, R² is
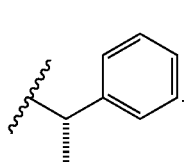 [SMILES: *[C@@H](C)c1ccccc1]
In embodiments, R² is
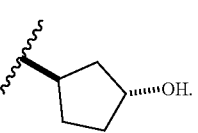 [SMILES: *[C@@H]1CC[C@@H](O)C1]
In embodiments, R² is
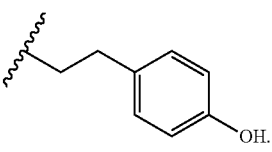 [SMILES: *CCc1ccc(O)cc1]
In embodiments, R² is
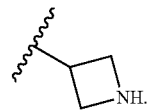

In embodiments, R² is
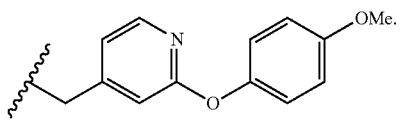 [SMILES: *Cc1ccnc(Oc2ccc(OC)cc2)c1]
In embodiments, R² is
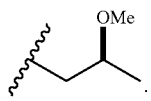 [SMILES: *C[C@H](C)OC]
In embodiments, R² is
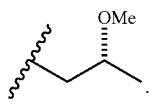
In embodiments, R² is
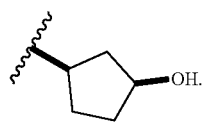
In embodiments, R² is
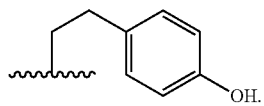 [SMILES: *CCc1ccc(O)cc1]
In embodiments, R² is
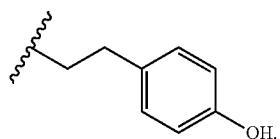 [SMILES: *CCc1ccc(O)cc1]
In embodiments, R² is
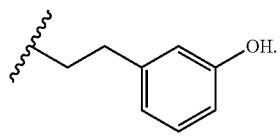 [SMILES: *CCc1cccc(O)c1]
In embodiments, R² is
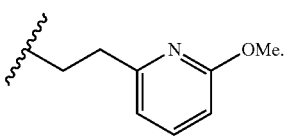 [SMILES: *CCc1cccc(OC)n1]
In embodiments, R² is
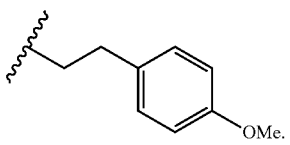 [SMILES: *CCc1ccc(OC)cc1]
In embodiments, R² is
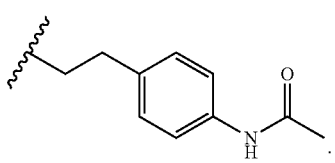
In embodiments, R² is
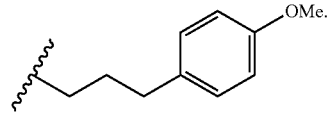 [SMILES: *CCCc1ccc(OC)cc1]
In embodiments, R² is
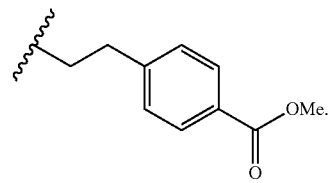 [SMILES: *CCc1ccc(C(=O)OC)cc1]
In embodiments, R² is
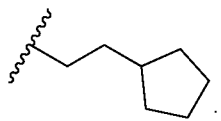 [SMILES: *CCC1CCCC1]

In embodiments, R² is
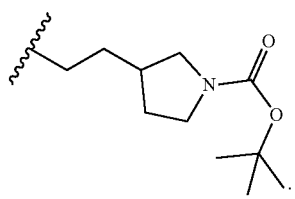 [SMILES: *CCC1CCN(C(=O)OC(C)(C)C)C1]
In embodiments, R² is
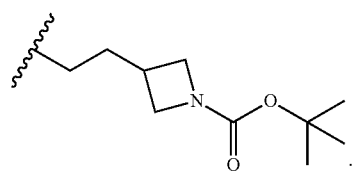 [SMILES: *CCC1CN(C(=O)OC(C)(C)C)C1]
In embodiments, R² is
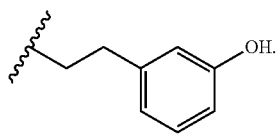
In embodiments, R² is
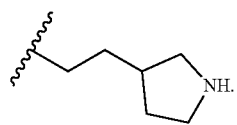 [SMILES: *CCC1CCNC1]
In embodiments, R² is
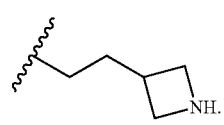 [SMILES: *CCC1CNC1]
In embodiments, R² is
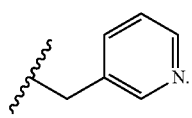 [SMILES: *Cc1cccnc1]
In embodiments, R² is
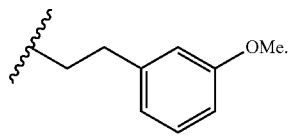 [SMILES: *CCc1cccc(OC)c1]
In embodiments, R² is
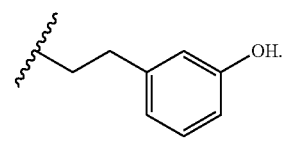 [SMILES: *CCc1cccc(O)c1]
In embodiments, R² is
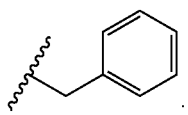 [SMILES: *Cc1ccccc1]
In embodiments, R² is
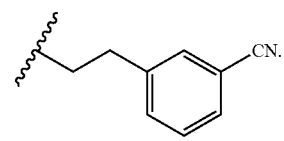
In embodiments, R² is
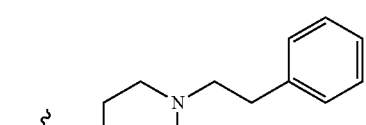
In embodiments, R² is
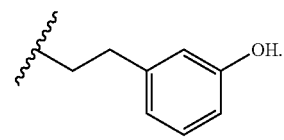 [SMILES: *CCc1cccc(O)c1]
In embodiments, R² is
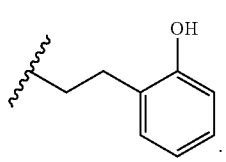 [SMILES: *CCc1ccccc1O]

In embodiments, R² is
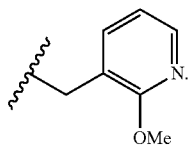 [SMILES: *Cc1cccnc1OC]
In embodiments, R² is
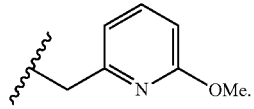 [SMILES: *Cc1cccc(OC)n1]
In embodiments, R² is
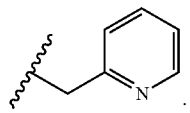
In embodiments, R² is
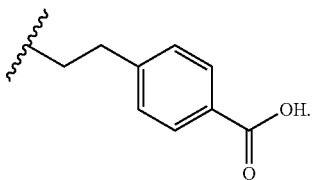 [SMILES: *CCc1ccc(C(=O)O)cc1]
In embodiments, R² is
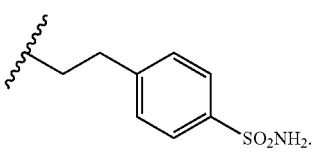 [SMILES: *CCc1ccc(S(N)(=O)=O)cc1]
In embodiments, R² is
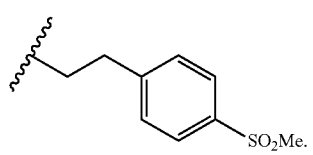 [SMILES: *CCc1ccc(S(C)(=O)=O)cc1]
In embodiments, R² is
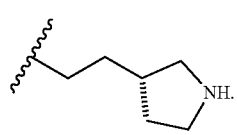 [SMILES: *CC[C@H]1CCNC1]
In embodiments, R² is
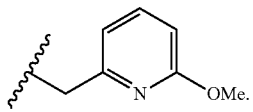 [SMILES: *Cc1cccc(OC)n1]
In embodiments, R² is
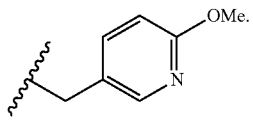
In embodiments, R² is
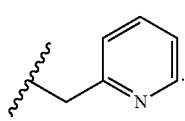 [SMILES: *Cc1ccccn1]
In embodiments, R² is
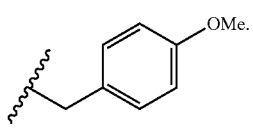 [SMILES: *Cc1ccc(OC)cc1]
In embodiments, R² is
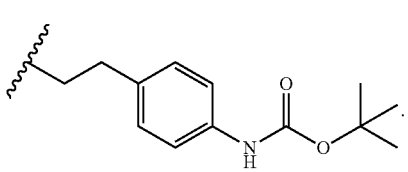 [SMILES: *CCc1ccc(NC(=O)OC(C)(C)C)cc1]
In embodiments, R² is
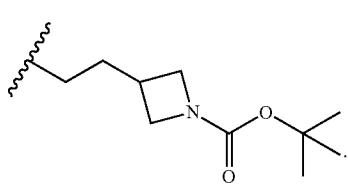 [SMILES: *CCC1CN(C(=O)OC(C)(C)C)C1]
In embodiments, R² is
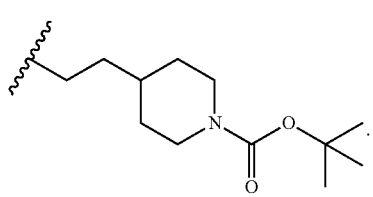 [SMILES: *CCC1CCN(C(=O)OC(C)(C)C)CC1]

In embodiments, R² is

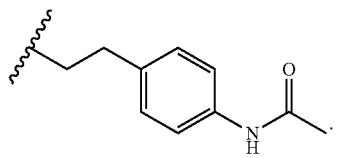 [SMILES: *CCc1ccc(NC(C)=O)cc1]

In embodiments, R² is

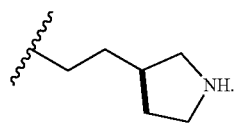 [SMILES: *CC[C@@H]1CCNC1]

In embodiments, R² is

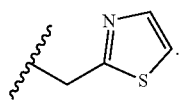 [SMILES: *Cc1nccs1]

In embodiments, R² is

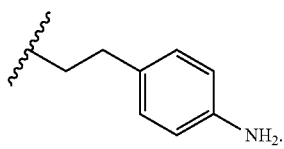

In embodiments, R² is

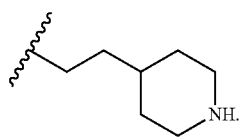 [SMILES: *CCC1CCNCC1]

In embodiments, R² is

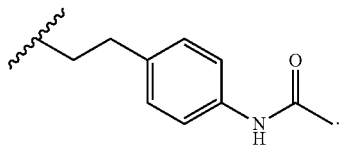 [SMILES: *CCc1ccc(NC(C)=O)cc1]

In embodiments, R² is

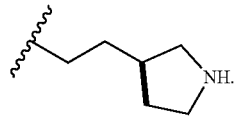 [SMILES: *CC[C@@H]1CCNC1]

In embodiments, R² is

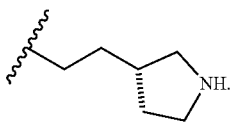

In embodiments, R² is

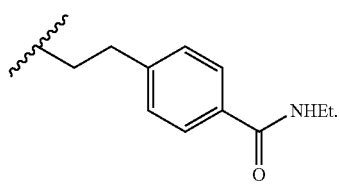

In embodiments, R³ is

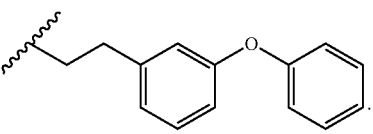 [SMILES: *CCc1cccc(Oc2ccccc2)c1]

In embodiments, R³ is hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

In embodiments, R³ is independently hydrogen, $R^{26}$-substituted or unsubstituted alkyl (e.g., $C_1$-$C_8$ alkyl, $C_1$-$C_6$ alkyl, or $C_1$-$C_4$ alkyl), $R^{26}$-substituted or unsubstituted heteroalkyl (e.g., 2 to 8 membered heteroalkyl, 2 to 6 membered heteroalkyl, or 2 to 4 membered heteroalkyl), $R^{26}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26}$-substituted or unsubstituted aryl (e.g., $C_6$-$C_{10}$ aryl, $C_{10}$ aryl, or phenyl), or $R^{26}$-substituted or unsubstituted heteroaryl (e.g., 5 to 10 membered heteroaryl, 5 to 9 membered heteroaryl, or 5 to 6 membered heteroaryl). In embodiments, R³ is independently hydrogen.

In embodiments, R³ is $R^{26}$-substituted or unsubstituted alkyl (e.g., $C_1$-$C_8$ alkyl, $C_1$-$C_6$ alkyl, or $C_1$-$C_4$ alkyl). In embodiments, R³ is $R^{26}$-substituted alkyl (e.g., $C_1$-$C_8$ alkyl, $C_1$-$C_6$ alkyl, or $C_1$-$C_4$ alkyl). In embodiments, R³ is an unsubstituted alkyl (e.g., $C_1$-$C_8$ alkyl, $C_1$-$C_6$ alkyl, or $C_1$-$C_4$ alkyl). In embodiments, R³ is $R^{26}$-substituted or unsubstituted heteroalkyl (e.g., 2 to 8 membered heteroalkyl, 2 to 6 membered heteroalkyl, or 2 to 4 membered heteroalkyl). In embodiments, R³ is $R^{26}$-substituted heteroalkyl (e.g., 2 to 8 membered heteroalkyl, 2 to 6 membered heteroalkyl, or 2 to 4 membered heteroalkyl). In embodiments, R³ is an unsubstituted heteroalkyl (e.g., 2 to 8 membered heteroalkyl, 2 to 6 membered heteroalkyl, or 2 to 4 membered heteroalkyl). In embodiments, R³ is $R^{26}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, R³ is $R^{26}$-substituted cycloalkyl (e.g., $C_3$-$C_8$ cycloalkyl, $C_3$-$C_6$ cycloalkyl, or $C_5$-$C_6$ cycloalkyl). In embodiments, R³ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^3$ is $R^{26}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^3$ is $R^{26}$-substituted heterocycloalkyl (e.g., 3 to 8 membered heterocycloalkyl, 3 to 6 membered heterocycloalkyl, or 5 to 6 membered heterocycloalkyl). In embodiments, $R^3$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^3$ is $R^{26}$-substituted or unsubstituted aryl (e.g., $C_6$-$C_{10}$ aryl, $C_{10}$ aryl, or phenyl). In embodiments, $R^3$ is $R^{26}$-substituted aryl (e.g., $C_6$-$C_{10}$ aryl, $C_{10}$ aryl, or phenyl). In embodiments, $R^3$ is an unsubstituted aryl (e.g., $C_6$-$C_{10}$ aryl, $C_{10}$ aryl, or phenyl). In embodiments, $R^3$ is $R^{26}$-substituted or unsubstituted heteroaryl (e.g., 5 to 10 membered heteroaryl, 5 to 9 membered heteroaryl, or 5 to 6 membered heteroaryl). In embodiments, $R^3$ is $R^{26}$-substituted heteroaryl (e.g., 5 to 10 membered heteroaryl, 5 to 9 membered heteroaryl, or 5 to 6 membered heteroaryl). In embodiments, $R^3$ is an unsubstituted heteroaryl (e.g., 5 to 10 membered heteroaryl, 5 to 9 membered heteroaryl, or 5 to 6 membered heteroaryl).

In embodiments, $R^{26}$ is independently oxo. In embodiments, $R^{26}$ is independently halogen. In embodiments, $R^{26}$ is independently —$CCl_3$. In embodiments, $R^{26}$ is independently —$CBr_3$. In embodiments, $R^{26}$ is independently —$CF_3$. In embodiments, $R^{26}$ is independently —$CI_3$. In embodiments, $R^{26}$ is independently $CHCl_2$. In embodiments, $R^{26}$ is independently —$CHBr_2$. In embodiments, $R^{26}$ is independently —$CHF_2$. In embodiments, $R^{26}$ is independently —$CHI_2$. In embodiments, $R^{26}$ is independently —$CH_2Cl$. In embodiments, $R^{26}$ is independently —$CH_2Br$. In embodiments, $R^{26}$ is independently —$CH_2F$. In embodiments, $R^{26}$ is independently —$CH_2I$. In embodiments, $R^{26}$ is independently —CN. In embodiments, $R^{26}$ is independently —OH. In embodiments, $R^{26}$ is independently —$NH_2$. In embodiments, $R^{26}$ is independently —COOH. In embodiments, $R^{26}$ is independently —$CONH_2$. In embodiments, $R^{26}$ is independently —$NO_2$. In embodiments, $R^{26}$ is independently —SH. In embodiments, $R^{26}$ is independently —$SO_3H$. In embodiments, $R^{26}$ is independently —$SO_4H$. In embodiments, $R^{26}$ is independently —$SO_2NH_2$. In embodiments, $R^{26}$ is independently —$NHNH_2$. In embodiments, $R^{26}$ is independently —$ONH_2$. In embodiments, $R^{26}$ is independently —$NHC(O)NHNH_2$. In embodiments, $R^{26}$ is independently —$NHC(O)NH_2$. In embodiments, $R^{26}$ is independently —$NHSO_2H$. In embodiments, $R^{26}$ is independently —$NHC(O)H$. In embodiments, $R^{26}$ is independently —$NHC(O)OH$. In embodiments, $R^{26}$ is independently —NHOH. In embodiments, $R^{26}$ is independently —$OCCl_3$. In embodiments, $R^{26}$ is independently —$OCF_3$. In embodiments, $R^{26}$ is independently —$OCBr_3$. In embodiments, $R^{26}$ is independently —$OCI_3$. In embodiments, $R^{26}$ is independently —$OCHCl_2$. In embodiments, $R^{26}$ is independently —$OCHBr_2$. In embodiments, $R^{26}$ is independently —$OCHI_2$. In embodiments, $R^{26}$ is independently —$OCHF_2$. In embodiments, $R^{26}$ is independently —$OCH_2Cl$. In embodiments, $R^{26}$ is independently —$OCH_2Br$. In embodiments, $R^{26}$ is independently —$OCH_2I$. In embodiments, $R^{26}$ is independently —$OCH_2F$. In embodiments, $R^{26}$ is independently —$N_3$.

In embodiments, $R^{26}$ is $R^{27}$-substituted or unsubstituted alkyl (e.g., $C_1$-$C_8$ alkyl, $C_1$-$C_6$ alkyl, or $C_1$-$C_4$ alkyl). In embodiments, $R^{26}$ is $R^{27}$-substituted alkyl (e.g., $C_1$-$C_8$ alkyl, $C_1$-$C_6$ alkyl, or $C_1$-$C_4$ alkyl). In embodiments, $R^{26}$ is an unsubstituted alkyl (e.g., $C_1$-$C_8$ alkyl, $C_1$-$C_6$ alkyl, or $C_1$-$C_4$ alkyl).

In embodiments, $R^{26}$ is $R^{27}$-substituted or unsubstituted heteroalkyl (e.g., 2 to 8 membered heteroalkyl, 2 to 6 membered heteroalkyl, or 2 to 4 membered heteroalkyl). In embodiments, $R^{26}$ is $R^{27}$-substituted heteroalkyl (e.g., 2 to 8 membered heteroalkyl, 2 to 6 membered heteroalkyl, or 2 to 4 membered heteroalkyl). In embodiments, $R^{26}$ is an unsubstituted heteroalkyl (e.g., 2 to 8 membered heteroalkyl, 2 to 6 membered heteroalkyl, or 2 to 4 membered heteroalkyl).

In embodiments, $R^{26}$ is $R^{27}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{26}$ is $R^{27}$-substituted cycloalkyl (e.g., $C_3$-$C_8$ cycloalkyl, $C_3$-$C_6$ cycloalkyl, or $C_5$-$C_6$ cycloalkyl). In embodiments, $R^{26}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{26}$ is $R^{27}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{26}$ is $R^{27}$-substituted heterocycloalkyl (e.g., 3 to 8 membered heterocycloalkyl, 3 to 6 membered heterocycloalkyl, or 5 to 6 membered heterocycloalkyl). In embodiments, $R^{26}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{26}$ is $R^{27}$-substituted or unsubstituted aryl (e.g., $C_6$-$C_{10}$ aryl, $C_{10}$ aryl, or phenyl). In embodiments, $R^{26}$ is $R^{27}$-substituted aryl (e.g., $C_6$-$C_{10}$ aryl, $C_{10}$ aryl, or phenyl). In embodiments, $R^{26}$ is an unsubstituted aryl (e.g., $C_6$-$C_{10}$ aryl, $C_{10}$ aryl, or phenyl).

In embodiments, $R^{26}$ is $R^{27}$-substituted or unsubstituted heteroaryl (e.g., 5 to 10 membered heteroaryl, 5 to 9 membered heteroaryl, or 5 to 6 membered heteroaryl). In embodiments, $R^{26}$ is $R^{27}$-substituted heteroaryl (e.g., 5 to 10 membered heteroaryl, 5 to 9 membered heteroaryl, or 5 to 6 membered heteroaryl). In embodiments, $R^{26}$ is an unsubstituted heteroaryl (e.g., 5 to 10 membered heteroaryl, 5 to 9 membered heteroaryl, or 5 to 6 membered heteroaryl).

$R^{26}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O) $NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{27}$-substituted or unsubstituted alkyl (e.g., $C_1$-$C_8$ alkyl, $C_1$-$C_6$ alkyl, or $C_1$-$C_4$ alkyl), $R^{27}$-substituted or unsubstituted heteroalkyl (e.g., 2 to 8 membered heteroalkyl, 2 to 6 membered heteroalkyl, or 2 to 4 membered heteroalkyl), $R^{27}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{27}$-substituted or unsubstituted heterocycloalkyl (e.g., 3 to 8 membered heterocycloalkyl, 3 to 6 membered heterocycloalkyl, or 5 to 6 membered heterocycloalkyl), $R^{27}$-substituted or unsubstituted aryl (e.g., $C_6$-$C_{10}$ aryl, $C_{10}$ aryl, or phenyl), or $R^{27}$-substituted or unsubstituted heteroaryl (e.g., 5 to 10 membered heteroaryl, 5 to 9 membered heteroaryl, or 5 to 6 membered heteroaryl).

$R^{27}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, R$^{28}$-substituted or unsubstituted alkyl (e.g., C$_1$-C$_8$ alkyl, C$_1$-C$_6$ alkyl, or C$_1$-C$_4$ alkyl), R$^{28}$-substituted or unsubstituted heteroalkyl (e.g., 2 to 8 membered heteroalkyl, 2 to 6 membered heteroalkyl, or 2 to 4 membered heteroalkyl), R$^{28}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{28}$-substituted or unsubstituted heterocycloalkyl (e.g., 3 to 8 membered heterocycloalkyl, 3 to 6 membered heterocycloalkyl, or 5 to 6 membered heterocycloalkyl), R$^{28}$-substituted or unsubstituted aryl (e.g., C$_6$-C$_{10}$ aryl, C$_{10}$ aryl, or phenyl), or R$^{28}$-substituted or unsubstituted heteroaryl (e.g., 5 to 10 membered heteroaryl, 5 to 9 membered heteroaryl, or 5 to 6 membered heteroaryl). In embodiments, R$^{27}$ is independently —OH. In embodiments, R$^{27}$ is independently —OCH$_3$. In embodiments, R$^{27}$ is independently —OCH$_2$CH$_3$. In embodiments, R$^{27}$ is independently —F. In embodiments, R$^{27}$ is independently —NHC(O)CH$_3$. In embodiments, R$^{27}$ is independently —COOH. In embodiments, R$^{27}$ is independently —SO$_2$NH$_2$.

In embodiments, R$^2$ and R$^3$ may optionally be joined to form a substituted or unsubstituted heterocycloalkyl (e.g., 3 to 8 membered heterocycloalkyl, 3 to 6 membered heterocycloalkyl, or 5 to 6 membered heterocycloalkyl) which may be referred to herein as "Ring B". In embodiments, R$^2$ and R$^3$ may optionally be joined to form a substituted or unsubstituted 3 to 8 membered heterocycloalkyl. In embodiments, R$^2$ and R$^3$ may optionally be joined to form a substituted or unsubstituted 3 membered heterocycloalkyl. In embodiments, R$^2$ and R$^3$ may optionally be joined to form a substituted or unsubstituted 4 membered heterocycloalkyl. In embodiments, R$^2$ and R$^3$ may optionally be joined to form a substituted or unsubstituted 5 membered heterocycloalkyl. In embodiments, R$^2$ and R$^3$ may optionally be joined to form a substituted or unsubstituted 6 membered heterocycloalkyl. In embodiments, R$^2$ and R$^3$ may optionally be joined to form a substituted or unsubstituted 7 membered heterocycloalkyl. In embodiments, R$^2$ and R$^3$ may optionally be joined to form a substituted or unsubstituted 8 membered heterocycloalkyl.

In embodiments, R$^2$ and R$^3$ may optionally be joined to form a substituted 3 to 8 membered heterocycloalkyl. In embodiments, R$^2$ and R$^3$ may optionally be joined to form a substituted 3 membered heterocycloalkyl. In embodiments, R$^2$ and R$^3$ may optionally be joined to form a substituted 4 membered heterocycloalkyl. In embodiments, R$^2$ and R$^3$ may optionally be joined to form a substituted 5 membered heterocycloalkyl. In embodiments, R$^2$ and R$^3$ may optionally be joined to form a substituted 6 membered heterocycloalkyl. In embodiments, R$^2$ and R$^3$ may optionally be joined to form a substituted 7 membered heterocycloalkyl. In embodiments, R$^2$ and R$^3$ may optionally be joined to form a substituted 8 membered heterocycloalkyl. In embodiments, R$^2$ and R$^3$ may optionally be joined to form a R$^6$-substituted 3 to 8 membered heterocycloalkyl. In embodiments, R$^2$ and R$^3$ may optionally be joined to form a R$^6$-substituted 3 membered heterocycloalkyl. In embodiments, R$^2$ and R$^3$ may optionally be joined to form a R$^6$-substituted 4 membered heterocycloalkyl. In embodiments, R$^2$ and R$^3$ may optionally be joined to form a R$^6$-substituted 5 membered heterocycloalkyl. In embodiments, R$^2$ and R$^3$ may optionally be joined to form a R$^6$-substituted 6 membered heterocycloalkyl. In embodiments, R$^2$ and R$^3$ may optionally be joined to form a R$^6$-substituted 7 membered heterocycloalkyl. In embodiments, R$^2$ and R$^3$ may optionally be joined to form a R$^6$-substituted 8 membered heterocycloalkyl. In embodiments, R$^2$ and R$^3$ may optionally be joined to form an unsubstituted 3 to 8 membered heterocycloalkyl. In embodiments, R$^2$ and R$^3$ may optionally be joined to form an unsubstituted 3 membered heterocycloalkyl. In embodiments, R$^2$ and R$^3$ may optionally be joined to form an unsubstituted 4 membered heterocycloalkyl. In embodiments, R$^2$ and R$^3$ may optionally be joined to form an unsubstituted 5 membered heterocycloalkyl. In embodiments, R$^2$ and R$^3$ may optionally be joined to form an unsubstituted 6 membered heterocycloalkyl. In embodiments, R$^2$ and R$^3$ may optionally be joined to form an unsubstituted 7 membered heterocycloalkyl. In embodiments, R$^2$ and R$^3$ may optionally be joined to form an unsubstituted 8 membered heterocycloalkyl.

In embodiments, R$^3$ is hydrogen, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl. In embodiments, R$^2$ and R$^3$ are joined to form a substituted or unsubstituted heterocycloalkyl.

In embodiments, R$^3$ is R$^{26}$-substituted or unsubstituted alkyl (e.g., C$_1$-C$_8$ alkyl, C$_1$-C$_6$ alkyl, or C$_1$-C$_4$ alkyl). In embodiments, R$^3$ is R$^{26}$-substituted alkyl (e.g., C$_1$-C$_8$ alkyl, C$_1$-C$_6$ alkyl, or C$_1$-C$_4$ alkyl). In embodiments, R$^3$ is an unsubstituted alkyl (e.g., C$_1$-C$_8$ alkyl, C$_1$-C$_6$ alkyl, or C$_1$-C$_4$ alkyl). In embodiments, R$^3$ is R$^{26}$-substituted or unsubstituted heteroalkyl (e.g., 2 to 8 membered heteroalkyl, 2 to 6 membered heteroalkyl, or 2 to 4 membered heteroalkyl). In embodiments, R$^3$ is R$^{26}$-substituted heteroalkyl (e.g., 2 to 8 membered heteroalkyl, 2 to 6 membered heteroalkyl, or 2 to 4 membered heteroalkyl). In embodiments, R$^3$ is an unsubstituted heteroalkyl (e.g., 2 to 8 membered heteroalkyl, 2 to 6 membered heteroalkyl, or 2 to 4 membered heteroalkyl). In embodiments, R$^3$ is R$^{26}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^3$ is R$^{26}$-substituted cycloalkyl (e.g., C$_3$-C$_8$ cycloalkyl, C$_3$-C$_6$ cycloalkyl, or C$_5$-C$_6$ cycloalkyl). In embodiments, R$^3$ is an unsubstituted cycloalkyl (e.g., C$_3$-C$_8$ cycloalkyl, C$_3$-C$_6$ cycloalkyl, or C$_5$-C$_6$ cycloalkyl). In embodiments, R$^3$ is R$^{26}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^3$ is R$^{26}$-substituted heterocycloalkyl (e.g., 3 to 8 membered heterocycloalkyl, 3 to 6 membered heterocycloalkyl, or 5 to 6 membered heterocycloalkyl). In embodiments, R$^3$ is an unsubstituted heterocycloalkyl (e.g., 3 to 8 membered heterocycloalkyl, 3 to 6 membered heterocycloalkyl, or 5 to 6 membered heterocycloalkyl). In embodiments, R$^3$ is R$^{26}$-substituted or unsubstituted aryl (e.g., C$_6$-C$_{10}$ aryl, C$_{10}$ aryl, or phenyl). In embodiments, R$^3$ is R$^{26}$-substituted aryl (e.g., C$_6$-C$_{10}$ aryl, C$_{10}$ aryl, or phenyl). In embodiments, R$^3$ is an unsubstituted aryl (e.g., C$_6$-C$_{10}$ aryl, C$_{10}$ aryl, or phenyl). In embodiments, R$^3$ is R$^{26}$-substituted or unsubstituted heteroaryl (e.g., 5 to 10 membered heteroaryl, 5 to 9 membered heteroaryl, or 5 to 6 membered heteroaryl). In embodiments, R$^3$ is R$^{26}$-substituted heteroaryl (e.g., 5 to 10 membered heteroaryl, 5 to 9 membered heteroaryl, or 5 to 6 membered heteroaryl). In embodiments, R$^3$ is an unsubstituted heteroaryl (e.g., 5 to 10 membered heteroaryl, 5 to 9 membered heteroaryl, or 5 to 6 membered heteroaryl). In embodiments, R$^3$ is substituted or unsubstituted C$_1$-C$_6$ alkyl. In embodiments, $R^3$ is substituted or unsubstituted $C_3$-$C_6$ cycloalkyl. In embodiments, $R^3$ is hydrogen.

In embodiments, $R^3$ is substituted or unsubstituted pyridyl-substituted ethyl. In embodiments, $R^3$ is substituted or unsubstituted 5 to 6 membered heteroaryl-substituted ethyl. In embodiments, $R^3$ is substituted or unsubstituted heteroaryl-substituted ethyl. In embodiments, $R^3$ is substituted or unsubstituted 5 to 6 membered heteroaryl-substituted $C_1$-$C_4$ alkyl. In embodiments, $R^3$ is substituted or unsubstituted heteroaryl-substituted $C_1$-$C_4$ alkyl. In embodiments, $R^3$ is substituted pyridyl-substituted ethyl. In embodiments, $R^3$ is substituted 5 to 6 membered heteroaryl-substituted ethyl. In embodiments, $R^3$ is substituted heteroaryl-substituted ethyl. In embodiments, $R^3$ is substituted 5 to 6 membered heteroaryl-substituted $C_1$-$C_4$ alkyl. In embodiments, $R^3$ is substituted heteroaryl-substituted $C_1$-$C_4$ alkyl. In embodiments, $R^3$ is substituted $C_1$-$C_4$ alkyl. In embodiments, $R^3$ is substituted ethyl. In embodiments, $R^3$ is unsubstituted pyridyl-substituted ethyl. In embodiments, $R^3$ is unsubstituted 5 to 6 membered heteroaryl-substituted ethyl. In embodiments, $R^3$ is unsubstituted heteroaryl-substituted ethyl. In embodiments, $R^3$ is unsubstituted 5 to 6 membered heteroaryl-substituted $C_1$-$C_4$ alkyl. In embodiments, $R^3$ is unsubstituted heteroaryl-substituted $C_1$-$C_4$ alkyl.

In embodiments, $R^3$ is substituted or unsubstituted pyrimidinyl-substituted methyl. In embodiments, $R^3$ is substituted or unsubstituted 5 to 6 membered heteroaryl-substituted methyl. In embodiments, $R^3$ is substituted or unsubstituted heteroaryl-substituted methyl. In embodiments, $R^3$ is substituted pyrimidinyl-substituted methyl. In embodiments, $R^3$ is substituted 5 to 6 membered heteroaryl-substituted methyl. In embodiments, $R^3$ is substituted heteroaryl-substituted methyl. In embodiments, $R^3$ is substituted methyl. In embodiments, $R^3$ is substituted $C_1$-$C_4$ alkyl. In embodiments, $R^3$ is unsubstituted pyrimidinyl-substituted methyl. In embodiments, $R^3$ is unsubstituted 5 to 6 membered heteroaryl-substituted methyl. In embodiments, $R^3$ is unsubstituted heteroaryl-substituted methyl.

In embodiments, $R^3$ is substituted or unsubstituted pyridyl-substituted methyl. In embodiments, $R^3$ is methoxy-substituted pyridyl-substituted methyl. In embodiments, $R^3$ is substituted pyridyl-substituted methyl. In embodiments, $R^3$ is unsubstituted pyridyl-substituted methyl.

In embodiments, $R^3$ is methoxy-substituted pyridyl-substituted $C_1$-$C_4$ alkyl. In embodiments, $R^3$ is substituted pyridyl-substituted $C_1$-$C_4$ alkyl. In embodiments, $R^3$ is an unsubstituted pyridyl-substituted $C_1$-$C_4$ alkyl. In embodiments, $R^3$ is substituted 5 to 6 membered heteroaryl-substituted $C_1$-$C_4$ alkyl. In embodiments, $R^3$ is substituted heteroaryl-substituted $C_1$-$C_4$ alkyl.

In embodiments, $R^3$ is unsubstituted methyl. In embodiments, $R^3$ is unsubstituted $C_1$-$C_4$ alkyl. In embodiments, $R^3$ is substituted or unsubstituted methyl-substituted cyclopentyl. In embodiments, $R^3$ is substituted or unsubstituted $C_1$-$C_4$ alkyl-substituted cyclopentyl. In embodiments, $R^3$ is substituted or unsubstituted methyl-substituted $C_3$-$C_6$ cycloalkyl. In embodiments, $R^3$ is substituted methyl-substituted cyclopentyl. In embodiments, $R^3$ is substituted $C_1$-$C_4$ alkyl-substituted cyclopentyl. In embodiments, $R^3$ is substituted methyl-substituted $C_3$-$C_6$ cycloalkyl. In embodiments, $R^3$ is substituted $C_3$-$C_6$ cycloalkyl. In embodiments, $R^3$ is substituted cyclopentyl.

In embodiments, $R^3$ is substituted or unsubstituted pyridyl-substituted propyl. In embodiments, $R^3$ is substituted or unsubstituted 5 to 6 membered heteroaryl-substituted propyl. In embodiments, $R^3$ is substituted or unsubstituted heteroaryl-substituted propyl. In embodiments, $R^3$ is substituted propyl. In embodiments, $R^3$ is substituted or unsubstituted pyridyl-substituted $C_1$-$C_6$ alkyl. In embodiments, $R^3$ is substituted pyridyl-substituted propyl. In embodiments, $R^3$ is substituted 5 to 6 membered heteroaryl-substituted propyl. In embodiments, $R^3$ is substituted heteroaryl-substituted propyl. In embodiments, $R^3$ is unsubstituted propyl. In embodiments, $R^3$ is substituted pyridyl-substituted $C_1$-$C_6$ alkyl. In embodiments, $R^3$ is unsubstituted pyridyl-substituted propyl. In embodiments, $R^3$ is unsubstituted 5 to 6 membered heteroaryl-substituted propyl. In embodiments, $R^3$ is unsubstituted heteroaryl-substituted propyl. In embodiments, $R^3$ is unsubstituted pyridyl-substituted $C_1$-$C_6$ alkyl.

In embodiments, $R^3$ is substituted or unsubstituted 5 to 6 membered heteroaryl-substituted $C_1$-$C_6$ alkyl. In embodiments, $R^3$ is substituted or unsubstituted heteroaryl-substituted $C_1$-$C_6$ alkyl. In embodiments, $R^3$ is substituted 5 to 6 membered heteroaryl-substituted $C_1$-$C_6$ alkyl. In embodiments, $R^3$ is substituted heteroaryl-substituted $C_1$-$C_6$ alkyl. In embodiments, $R^3$ is substituted 5 to 6 membered heteroaryl-substituted $C_1$-$C_6$ alkyl. In embodiments, $R^3$ is substituted heteroaryl-substituted $C_1$-$C_6$ alkyl. In embodiments, $R^3$ is an unsubstituted 5 to 6 membered heteroaryl-substituted $C_1$-$C_6$ alkyl. In embodiments, $R^3$ is an unsubstituted heteroaryl-substituted $C_1$-$C_6$ alkyl. In embodiments, $R^3$ is substituted $C_1$-$C_6$ alkyl. In embodiments, $R^3$ is unsubstituted pyridyl-substituted propyl. In embodiments, $R^3$ is unsubstituted 5 to 6 membered heteroaryl-substituted propyl. In embodiments, $R^3$ is unsubstituted heteroaryl-substituted propyl. In embodiments, $R^3$ is substituted propyl. In embodiments, $R^3$ is unsubstituted pyridyl-substituted $C_1$-$C_6$ alkyl. In embodiments, $R^3$ is unsubstituted 5 to 6 membered heteroaryl-substituted $C_1$-$C_6$ alkyl. In embodiments, $R^3$ is unsubstituted heteroaryl-substituted $C_1$-$C_6$ alkyl.

In embodiments, $R^3$ is substituted or unsubstituted phenyl-substituted methyl. In embodiments, $R^3$ is substituted or unsubstituted aryl-substituted methyl. In embodiments, $R^3$ is substituted methyl. In embodiments, $R^3$ is substituted or unsubstituted phenyl-substituted $C_1$-$C_4$ alkyl. In embodiments, $R^3$ is substituted or unsubstituted aryl-substituted $C_1$-$C_4$ alkyl. In embodiments, $R^3$ is substituted phenyl-substituted methyl. In embodiments, $R^3$ is substituted aryl-substituted methyl. In embodiments, $R^3$ is an unsubstituted methyl. In embodiments, $R^3$ is substituted phenyl-substituted $C_1$-$C_4$ alkyl. In embodiments, $R^3$ is substituted aryl-substituted $C_1$-$C_4$ alkyl. In embodiments, $R^3$ is substituted $C_1$-$C_4$ alkyl. In embodiments, $R^3$ is unsubstituted phenyl-substituted methyl. In embodiments, $R^3$ is unsubstituted aryl-substituted methyl. In embodiments, $R^3$ is unsubstituted phenyl-substituted $C_1$-$C_4$ alkyl. In embodiments, $R^3$ is unsubstituted aryl-substituted $C_1$-$C_4$ alkyl.

In embodiments, $R^3$ is substituted or unsubstituted pyridazinyl-substituted methyl. In embodiments, $R^3$ is substituted or unsubstituted pyridazinyl-substituted $C_1$-$C_4$ alkyl. In embodiments, $R^3$ is substituted pyridazinyl-substituted methyl. In embodiments, $R^3$ is substituted pyridazinyl-substituted $C_1$-$C_4$ alkyl. In embodiments, $R^3$ is unsubstituted pyridazinyl-substituted methyl. In embodiments, $R^3$ is unsubstituted pyridazinyl-substituted $C_1$-$C_4$ alkyl. In embodiments, $R^3$ is unsubstituted ethyl. In embodiments, $R^3$ is unsubstituted $C_1$-$C_4$ alkyl. In embodiments, $R^3$ is methoxy-substituted pyridyl. In embodiments, $R^3$ is substituted pyridyl. In embodiments, $R^3$ is methoxy-substituted 5 to 6 membered heteroaryl. In embodiments, $R^3$ is substituted 5 to 6 membered heteroaryl. In embodiments, $R^3$ is substituted heteroaryl.

In embodiments, $R^3$ is substituted or unsubstituted benzyl-substituted piperidinyl-substituted methyl. In embodiments, $R^3$ is substituted benzyl-substituted piperidinyl-substituted methyl. In embodiments, $R^3$ is unsubstituted benzyl-substituted piperidinyl-substituted methyl. In embodiments, $R^3$ is substituted piperidinyl-substituted methyl. In embodiments, $R^3$ is substituted or unsubstituted 5 to 6 membered heterocycloalkyl-substituted methyl. In embodiments, $R^3$ is substituted or unsubstituted heterocycloalkyl-substituted methyl. In embodiments, $R^3$ is substituted 5 to 6 membered heterocycloalkyl-substituted methyl. In embodiments, $R^3$ is substituted heterocycloalkyl-substituted methyl. In embodiments, $R^3$ is substituted methyl. In embodiments, $R^3$ is substituted or unsubstituted benzyl-substituted piperidinyl-substituted $C_1$-$C_4$ alkyl. In embodiments, $R^3$ is substituted piperidinyl-substituted $C_1$-$C_4$ alkyl. In embodiments, $R^3$ is substituted or unsubstituted 5 to 6 membered heterocycloalkyl-substituted $C_1$-$C_4$ alkyl. In embodiments, $R^3$ is substituted or unsubstituted heterocycloalkyl-substituted $C_1$-$C_4$ alkyl. In embodiments, $R^3$ is substituted benzyl-substituted piperidinyl-substituted $C_1$-$C_4$ alkyl. In embodiments, $R^3$ is an unsubstituted piperidinyl-substituted $C_1$-$C_4$ alkyl. In embodiments, $R^3$ is substituted 5 to 6 membered heterocycloalkyl-substituted $C_1$-$C_4$ alkyl. In embodiments, $R^3$ is substituted heterocycloalkyl-substituted $C_1$-$C_4$ alkyl. In embodiments, $R^3$ is substituted $C_1$-$C_4$ alkyl. In embodiments, $R^3$ is unsubstituted benzyl-substituted piperidinyl-substituted methyl. In embodiments, $R^3$ is substituted piperidinyl-substituted methyl. In embodiments, $R^3$ is substituted 5 to 6 membered heterocycloalkyl-substituted methyl. In embodiments, $R^3$ is substituted heterocycloalkyl-substituted methyl. In embodiments, $R^3$ is unsubstituted benzyl-substituted piperidinyl-substituted $C_1$-$C_4$ alkyl. In embodiments, $R^3$ is substituted piperidinyl-substituted $C_1$-$C_4$ alkyl. In embodiments, $R^3$ is substituted 5 to 6 membered heterocycloalkyl-substituted $C_1$-$C_4$ alkyl. In embodiments, $R^3$ is substituted heterocycloalkyl-substituted $C_1$-$C_4$ alkyl.

In embodiments, $R^3$ is substituted or unsubstituted pyridyl-substituted 4 membered heteroalkyl. In embodiments, $R^3$ is substituted or unsubstituted 5 to 6 membered heteroaryl-substituted 4 membered heteroalkyl. In embodiments, $R^3$ is substituted or unsubstituted heteroaryl-substituted 4 membered heteroalkyl. In embodiments, $R^3$ is substituted or unsubstituted pyridyl-substituted 2 to 6 membered heteroalkyl. In embodiments, $R^3$ is substituted or unsubstituted 5 to 6 membered heteroaryl-substituted 2 to 6 membered heteroalkyl. In embodiments, $R^3$ is substituted or unsubstituted heteroaryl-substituted 2 to 6 membered heteroalkyl. In embodiments, $R^3$ is substituted pyridyl-substituted 4 membered heteroalkyl. In embodiments, $R^3$ is substituted 5 to 6 membered heteroaryl-substituted 4 membered heteroalkyl. In embodiments, $R^3$ is substituted heteroaryl-substituted 4 membered heteroalkyl. In embodiments, $R^3$ is substituted pyridyl-substituted 2 to 6 membered heteroalkyl. In embodiments, $R^3$ is substituted 5 to 6 membered heteroaryl-substituted 2 to 6 membered heteroalkyl. In embodiments, $R^3$ is substituted heteroaryl-substituted 2 to 6 membered heteroalkyl. In embodiments, $R^3$ is unsubstituted pyridyl-substituted 4 membered heteroalkyl. In embodiments, $R^3$ is unsubstituted 5 to 6 membered heteroaryl-substituted 4 membered heteroalkyl. In embodiments, $R^3$ is unsubstituted heteroaryl-substituted 4 membered heteroalkyl. In embodiments, $R^3$ is unsubstituted pyridyl-substituted 2 to 6 membered heteroalkyl. In embodiments, $R^3$ is unsubstituted 5 to 6 membered heteroaryl-substituted 2 to 6 membered heteroalkyl. In embodiments, $R^3$ is unsubstituted heteroaryl-substituted 2 to 6 membered heteroalkyl.

In embodiments, $R^3$ is unsubstituted pyridyl-substituted 4 membered heteroalkyl. In embodiments, $R^3$ is unsubstituted 5 to 6 membered heteroaryl-substituted 4 membered heteroalkyl. In embodiments, $R^3$ is unsubstituted heteroaryl-substituted 4 membered heteroalkyl. In embodiments, $R^3$ is unsubstituted pyridyl-substituted 2 to 6 membered heteroalkyl. In embodiments, $R^3$ is unsubstituted 5 to 6 membered heteroaryl-substituted 2 to 6 membered heteroalkyl. In embodiments, $R^3$ is unsubstituted heteroaryl-substituted 2 to 6 membered heteroalkyl.

In embodiments, $R^3$ is substituted or unsubstituted imidazolyl-substituted ethyl. In embodiments, $R^3$ is substituted or unsubstituted 5 to 6 membered heteroaryl-substituted ethyl. In embodiments, $R^3$ is substituted or unsubstituted heteroaryl-substituted ethyl. In embodiments, $R^3$ is substituted or unsubstituted imidazolyl-substituted $C_1$-$C_4$ alkyl. In embodiments, $R^3$ is substituted or unsubstituted 5 to 6 membered heteroaryl-substituted $C_1$-$C_4$ alkyl. In embodiments, $R^3$ is substituted or unsubstituted heteroaryl-substituted $C_1$-$C_4$ alkyl. In embodiments, $R^3$ is substituted imidazolyl-substituted ethyl. In embodiments, $R^3$ is substituted 5 to 6 membered heteroaryl-substituted ethyl. In embodiments, $R^3$ is substituted heteroaryl-substituted ethyl. In embodiments, $R^3$ is substituted imidazolyl-substituted $C_1$-$C_4$ alkyl. In embodiments, $R^3$ is substituted 5 to 6 membered heteroaryl-substituted $C_1$-$C_4$ alkyl. In embodiments, $R^3$ is substituted heteroaryl-substituted $C_1$-$C_4$ alkyl. In embodiments, $R^3$ is unsubstituted imidazolyl-substituted ethyl. In embodiments, $R^3$ is unsubstituted 5 to 6 membered heteroaryl-substituted ethyl. In embodiments, $R^3$ is unsubstituted heteroaryl-substituted ethyl. In embodiments, $R^3$ is unsubstituted imidazolyl-substituted $C_1$-$C_4$ alkyl. In embodiments, $R^3$ is unsubstituted 5 to 6 membered heteroaryl-substituted $C_1$-$C_4$ alkyl. In embodiments, $R^3$ is unsubstituted heteroaryl-substituted $C_1$-$C_4$ alkyl.

In embodiments, $R^3$ is unsubstituted imidazolyl-substituted ethyl. In embodiments, $R^3$ is unsubstituted 5 to 6 membered heteroaryl-substituted ethyl. In embodiments, $R^3$ is unsubstituted heteroaryl-substituted ethyl. In embodiments, $R^3$ is unsubstituted imidazolyl-substituted $C_1$-$C_4$ alkyl. In embodiments, $R^3$ is unsubstituted 5 to 6 membered heteroaryl-substituted $C_1$-$C_4$ alkyl. In embodiments, $R^3$ is unsubstituted heteroaryl-substituted $C_1$-$C_4$ alkyl.

In embodiments, $R^3$ is OH-substituted ethyl. In embodiments, $R^3$ is OH-substituted $C_1$-$C_4$ alkyl. In embodiments, $R^3$ is substituted ethyl. In embodiments, $R^3$ is substituted $C_1$-$C_4$ alkyl.

In embodiments, $R^3$ is unsubstituted 4 membered heteroalkyl-substituted piperidinyl-substituted methyl. In embodiments, $R^3$ is unsubstituted heteroalkyl substituted piperidinyl-substituted methyl. In embodiments, $R^3$ is substituted 5 to 6 membered heterocycloalkyl-substituted methyl. In embodiments, $R^3$ is unsubstituted 4 membered heteroalkyl-substituted piperidinyl-substituted $C_1$-$C_4$ alkyl. In embodiments, $R^3$ is unsubstituted heteroalkyl-substituted piperidinyl-substituted $C_1$-$C_4$ alkyl. In embodiments, $R^3$ is substituted 5 to 6 membered heterocycloalkyl-substituted $C_1$-$C_4$ alkyl. In embodiments, $R^3$ is substituted heterocycloalkyl-substituted $C_1$-$C_4$ alkyl.

In embodiments, $R^3$ is tert-butyloxycarbonyl-substituted pyrrolidinyl. In embodiments, $R^3$ is substituted 2 to 8 membered heteroalkyl-substituted pyrrolidinyl. In embodiments, $R^3$ is an unsubstituted 2 to 8 membered heteroalkyl-substituted pyrrolidinyl. In embodiments, $R^3$ is tert-butyloxycarbonyl-substituted 3 to 6 membered heterocycloalkyl. In embodiments, $R^3$ is substituted 3 to 6 membered heterocycloalkyl. In embodiments, $R^3$ is substituted heterocycloalkyl. In embodiments, $R^3$ is unsubstituted 4 membered heteroalkyl. In embodiments, $R^3$ is unsubstituted 2 to 6 membered heteroalkyl. In embodiments, $R^3$ is unsubstituted heteroalkyl.

In embodiments, $R^3$ is unsubstituted cyclobutyl. In embodiments, $R^3$ is unsubstituted 3 to 6 membered cycloalkyl. In embodiments, $R^3$ is unsubstituted cycloalkyl. In embodiments, $R^3$ is unsubstituted pyrrolidinyl. In embodiments, $R^3$ is unsubstituted 3 to 6 membered heterocycloalkyl. In embodiments, $R^3$ is unsubstituted heterocycloalkyl.

In embodiments, $R^3$ is OH-substituted cyclobutyl. In embodiments, $R^3$ is substituted cyclobutyl. In embodiments, $R^3$ is OH-substituted $C_3$-$C_6$ cycloalkyl. In embodiments, $R^3$ is substituted $C_3$-$C_6$ cycloalkyl.

In embodiments, $R^3$ is OH-substituted propyl. In embodiments, $R^3$ is OH-substituted $C_1$-$C_6$ alkyl. In embodiments, $R^3$ is substituted propyl. In embodiments, $R^3$ is substituted $C_1$-$C_6$ alkyl.

In embodiments, $R^3$ is tert-butyloxycarbonyl-substituted azetidinyl. In embodiments, $R^3$ is oxo-substituted 2 to 8 membered heteroalkyl-substituted azetidinyl. In embodiments, $R^3$ is oxo-substituted heteroalkyl-substituted azetidinyl. In embodiments, $R^3$ is substituted 2 to 8 membered heteroalkyl-substituted azetidinyl. In embodiments, $R^3$ is substituted heteroalkyl-substituted azetidinyl.

In embodiments, $R^3$ is unsubstituted cyclopentyl. In embodiments, $R^3$ is unsubstituted $C_3$-$C_6$ cycloalkyl. In embodiments, $R^3$ is unsubstituted cyclopropyl.

In embodiments, $R^3$ is unsubstituted cyclobutyl-substituted methyl. In embodiments, $R^3$ is unsubstituted $C_3$-$C_6$ cycloalkyl-substituted methyl. In embodiments, $R^3$ is unsubstituted cyclobutyl-substituted $C_1$-$C_4$ alkyl. In embodiments, $R^3$ is unsubstituted $C_3$-$C_6$ cycloalkyl-substituted $C_1$-$C_4$ alkyl.

In embodiments, $R^3$ is unsubstituted oxetanyl. In embodiments, $R^3$ is unsubstituted 3 to 6 membered heterocycloalkyl.

In embodiments, $R^3$ is unsubstituted isopropyl. In embodiments, $R^3$ is unsubstituted propyl. In embodiments, $R^3$ is unsubstituted tert-butyl. In embodiments, $R^3$ is unsubstituted butyl. In embodiments, $R^3$ is unsubstituted $C_1$-$C_6$ alkyl.

In embodiments, $R^3$ is oxo-substituted 4 membered heteroalkyl. In embodiments, $R^3$ is oxo-substituted 2 to 6 membered heteroalkyl. In embodiments, $R^3$ is substituted 4 membered heteroalkyl. In embodiments, $R^3$ is substituted 2 to 6 membered heteroalkyl. In embodiments, $R^3$ is substituted heteroalkyl.

In embodiments, $R^3$ is unsubstituted tetrahydropyran-substituted methyl. In embodiments, $R^3$ is tetrahydropyran-substituted methyl. In embodiments, $R^3$ is unsubstituted 5 to 6 membered heterocycloalkyl-substituted methyl. In embodiments, $R^3$ is unsubstituted tetrahydropyran-substituted $C_1$-$C_4$ alkyl. In embodiments, $R^3$ is tetrahydropyran-substituted $C_1$-$C_4$ alkyl. In embodiments, $R^3$ is unsubstituted 5 to 6 membered heterocycloalkyl-substituted $C_1$-$C_4$ alkyl.

In embodiments, $R^3$ is $CF_3$-substituted methyl. In embodiments, $R^3$ is C(halo)$_3$-substituted methyl. In embodiments, $R^3$ is $CF_3$-substituted $C_1$-$C_4$ alkyl. In embodiments, $R^3$ is C(halo)$_3$-substituted $C_1$-$C_4$ alkyl.

In embodiments, $R^3$ is tert-butyloxycarbonyl-substituted pyrrolidinyl-substituted methyl. In embodiments, $R^3$ is oxo-substituted 2 to 8 membered heteroalkyl-substituted pyrrolidinyl-substituted methyl. In embodiments, $R^3$ is substituted 2 to 8 membered heteroalkyl-substituted pyrrolidinyl-substituted methyl. In embodiments, $R^3$ is tert-butyloxycarbonyl-substituted 3 to 6 membered heterocycloalkyl-substituted methyl. In embodiments, $R^3$ is tert-butyloxycarbonyl-substituted pyrrolidinyl-substituted $C_1$-$C_4$ alkyl. In embodiments, $R^3$ is substituted 2 to 8 membered heteroalkyl-substituted pyrrolidinyl-substituted $C_1$-$C_4$ alkyl. In embodiments, $R^3$ is substituted 2 to 8 membered heteroalkyl-substituted 3 to 6 membered heterocycloalkyl-substituted $C_1$-$C_4$ alkyl. In embodiments, $R^3$ is substituted 3 to 6 membered heterocycloalkyl-substituted $C_1$-$C_4$ alkyl.

In embodiments, $R^3$ is OH-substituted butyl. In embodiments, $R^3$ is substituted butyl.

In embodiments, $R^3$ is OH-substituted and unsubstituted pyridyl-substituted ethyl. In embodiments, $R^3$ is OH-substituted ethyl. In embodiments, $R^3$ is unsubstituted pyridyl-substituted ethyl. In embodiments, $R^3$ is OH-substituted and unsubstituted pyridyl-substituted $C_1$-$C_4$ alkyl. In embodiments, $R^3$ is OH-substituted $C_1$-$C_4$ alkyl. In embodiments, $R^3$ is unsubstituted pyridyl-substituted $C_1$-$C_4$ alkyl. In embodiments, $R^3$ is OH-substituted and unsubstituted 5 to 6 membered heteroaryl-substituted ethyl. In embodiments, $R^3$ is substituted ethyl. In embodiments, $R^3$ is unsubstituted 5 to 6 membered heteroaryl-substituted ethyl. In embodiments, $R^3$ is OH-substituted and unsubstituted 5 to 6 membered heteroaryl-substituted $C_1$-$C_4$ alkyl. In embodiments, $R^3$ is substituted $C_1$-$C_4$ alkyl. In embodiments, $R^3$ is unsubstituted 5 to 6 membered heteroaryl-substituted $C_1$-$C_4$ alkyl.

In embodiments, $R^3$ is methyl-substituted imidazolyl-substituted methyl. In embodiments, $R^3$ is methyl-substituted 5 to 6 membered heteroaryl-substituted methyl. In embodiments, $R^3$ is methyl-substituted heteroaryl-substituted methyl. In embodiments, $R^3$ is unsubstituted $C_1$-$C_4$ alkyl-substituted imidazolyl-substituted $C_1$-$C_4$ alkyl. In embodiments, $R^3$ is unsubstituted $C_1$-$C_4$ alkyl-substituted 5 to 6 membered heteroaryl-substituted $C_1$-$C_4$ alkyl. In embodiments, $R^3$ is unsubstituted $C_1$-$C_4$ alkyl-substituted heteroaryl-substituted $C_1$-$C_4$ alkyl.

In embodiments, $R^3$ is methoxy-substituted cyclobutyl. In embodiments, $R^3$ is 2 to 4 membered heteroalkyl-substituted cyclobutyl. In embodiments, $R^3$ is methoxy-substituted $C_3$-$C_6$ cycloalkyl. In embodiments, $R^3$ is 2 to 4 membered heteroalkyl-substituted $C_3$-$C_6$ cycloalkyl.

In embodiments, $R^3$ is unsubstituted phenyl. In embodiments, $R^3$ is unsubstituted aryl.

In embodiments, $R^3$ is imidazolyl-substituted methyl. In embodiments, $R^3$ is 5 to 6 membered heteroaryl-substituted methyl. In embodiments, $R^3$ is heteroaryl-substituted methyl. In embodiments, $R^3$ is unsubstituted imidazolyl-substituted methyl. In embodiments, $R^3$ is unsubstituted 5 to 6 membered heteroaryl-substituted methyl. In embodiments, $R^3$ is unsubstituted heteroaryl-substituted methyl. In embodiments, $R^3$ is imidazolyl-substituted $C_1$-$C_4$ alkyl. In embodiments, $R^3$ is 5 to 6 membered heteroaryl-substituted $C_1$-$C_4$ alkyl. In embodiments, $R^3$ is heteroaryl-substituted $C_1$-$C_4$ alkyl. In embodiments, $R^3$ is unsubstituted imidazolyl-substituted $C_1$-$C_4$ alkyl. In embodiments, $R^3$ is unsubstituted 5 to 6 membered heteroaryl-substituted $C_1$-$C_4$ alkyl. In embodiments, $R^3$ is unsubstituted heteroaryl-substituted $C_1$-$C_4$ alkyl.

In embodiments, $R^3$ is OH-substituted cyclopentyl. In embodiments, $R^3$ is OH-substituted $C_3$-$C_6$ cycloalkyl. In embodiments, $R^3$ is substituted cyclopentyl. In embodiments, $R^3$ is substituted $C_3$-$C_6$ cycloalkyl.

In embodiments, $R^3$ is OH-substituted phenyl-substituted ethyl. In embodiments, $R^3$ is OH-substituted aryl-substituted ethyl. In embodiments, $R^3$ is substituted aryl-substituted ethyl. In embodiments, $R^3$ is OH-substituted phenyl-substituted $C_1$-$C_4$ alkyl. In embodiments, $R^3$ is OH-substituted aryl-substituted $C_1$-$C_4$ alkyl. In embodiments, $R^3$ is substituted aryl-substituted $C_1$-$C_4$ alkyl.

In embodiments, $R^3$ is tert-butyloxycarbonyl-substituted tetrahydropyran-substituted ethyl. In embodiments, $R^3$ is substituted 2 to 8 membered heteroalkyl-substituted tetrahydropyran-substituted ethyl. In embodiments, $R^3$ is tert-butyloxycarbonyl-substituted 3 to 6 membered heterocycloalkyl-substituted ethyl. In embodiments, $R^3$ is tert-butyloxycarbonyl-substituted tetrahydropyran-substituted $C_1$-$C_4$ alkyl.

In embodiments, $R^3$ is unsubstituted pyrrolidinyl-substituted ethyl. In embodiments, $R^3$ is unsubstituted 3 to 6 membered heterocycloalkyl-substituted ethyl. In embodiments, $R^3$ is unsubstituted pyrrolidinyl-substituted $C_1$-$C_4$ alkyl. In embodiments, $R^3$ is unsubstituted 5 to 6 membered heterocycloalkyl-substituted $C_1$-$C_4$ alkyl.

In embodiments, $R^3$ is tert-butyloxy carbonyl-substituted pyrrolidinyl-substituted ethyl. In embodiments, $R^3$ is substituted 2 to 8 membered heteroalkyl-substituted pyrrolidinyl-substituted ethyl. In embodiments, $R^3$ is tert-butyloxy carbonyl-substituted 3 to 6 membered heterocycloalkyl-substituted ethyl.

In embodiments, $R^3$ is tert-butyloxy carbonyl-substituted pyrrolidinyl-substituted $C_1$-$C_4$ alkyl. In embodiments, $R^3$ is substituted 2 to 8 membered heteroalkyl-substituted pyrrolidinyl-substituted $C_1$-$C_4$ alkyl. In embodiments, $R^3$ is tert-butyloxycarbonyl-substituted 3 to 6 membered heterocycloalkyl-substituted $C_1$-$C_4$ alkyl.

In embodiments, $R^3$ is unsubstituted pyrrolidinyl-substituted methyl. In embodiments, $R^3$ is unsubstituted 3 to 6 membered heterocycloalkyl-substituted methyl.

In embodiments, $R^3$ is unsubstituted pyrrolidinyl-substituted $C_1$-$C_4$ alkyl. In embodiments, $R^3$ is unsubstituted 3 to 6 membered heterocycloalkyl-substituted $C_1$-$C_4$ alkyl.

In embodiments, $R^3$ is unsubstituted morpholinyl-substituted ethyl. In embodiments, $R^3$ is unsubstituted morpholinyl-substituted ethyl. In embodiments, $R^3$ is unsubstituted 5 to 6 membered heterocycloalkyl-substituted ethyl. In embodiments, $R^3$ is unsubstituted morpholinyl-substituted $C_1$-$C_4$ alkyl.

In embodiments, $R^3$ is OH-substituted phenyl-substituted ethyl. In embodiments, $R^3$ is OH-substituted aryl-substituted ethyl. In embodiments, $R^3$ is substituted phenyl-substituted $C_1$-$C_4$ alkyl. In embodiments, $R^3$ is substituted aryl-substituted $C_1$-$C_4$ alkyl.

In embodiments, $R^3$ is unsubstituted piperidinyl-substituted methyl. In embodiments, $R^3$ is unsubstituted 5 to 6 membered heterocycloalkyl-substituted methyl. In embodiments, $R^3$ is unsubstituted heterocycloalkyl-substituted methyl. In embodiments, $R^3$ is unsubstituted piperidinyl-substituted $C_1$-$C_4$ alkyl. In embodiments, $R^3$ is unsubstituted 5 to 6 membered heterocycloalkyl-substituted $C_1$-$C_4$ alkyl. In embodiments, $R^3$ is unsubstituted heterocycloalkyl-substituted $C_1$-$C_4$ alkyl.

In embodiments, $R^3$ is OH-substituted methyl-substituted phenyl-substituted ethyl. In embodiments, $R^3$ is OH-substituted methyl-substituted aryl-substituted ethyl. In embodiments, $R^3$ is substituted phenyl-substituted ethyl. In embodiments, $R^3$ is substituted aryl-substituted ethyl. In embodiments, $R^3$ is substituted phenyl-substituted $C_1$-$C_4$ alkyl. In embodiments, $R^3$ is substituted aryl-substituted $C_1$-$C_4$ alkyl.

In embodiments, $R^3$ is Cl-substituted phenyl-substituted ethyl. In embodiments, $R^3$ is halo-substituted aryl-substituted ethyl. In embodiments, $R^3$ is halo-substituted phenyl-substituted ethyl. In embodiments, $R^3$ is Cl-substituted phenyl-substituted $C_1$-$C_4$ alkyl. In embodiments, $R^3$ is halo-substituted phenyl-substituted $C_1$-$C_4$ alkyl. In embodiments, $R^3$ is halo-substituted aryl-substituted $C_1$-$C_4$ alkyl.

In embodiments, $R^3$ is unsubstituted tetrahydrofuranyl-substituted methyl. In embodiments, $R^3$ is tetrahydrofuranyl-substituted methyl. In embodiments, $R^3$ is unsubstituted 3 to 6 membered heterocycloalkyl-substituted methyl. In embodiments, $R^3$ is unsubstituted tetrahydrofuranyl-substituted $C_1$-$C_4$ alkyl. In embodiments, $R^3$ is tetrahydrofuranyl-substituted $C_1$-$C_4$ alkyl.

In embodiments, $R^3$ is unsubstituted phenyl-substituted ethyl. In embodiments, $R^3$ is unsubstituted aryl-substituted ethyl. In embodiments, $R^3$ is unsubstituted phenyl-substituted $C_1$-$C_4$ alkyl. In embodiments, $R^3$ is unsubstituted aryl-substituted $C_1$-$C_4$ alkyl.

In embodiments, $R^3$ is unsubstituted azetidinyl. In embodiments, $R^3$ is unsubstituted 3 to 6 membered heterocycloalkyl In embodiments, $R^3$ is methoxy-substituted phenoxy-substituted pyridyl-substituted methyl. In embodiments, $R^3$ is 2 to 4 membered alkoxy-substituted phenoxy-substituted pyridyl-substituted methyl. In embodiments, $R^3$ is 2 to 4 membered alkoxy-substituted aryloxy-substituted pyridyl-substituted methyl. In embodiments, $R^3$ is 2 to 4 membered alkoxy-substituted aryl oxy-substituted 5 to 6 membered heteroaryl-substituted methyl. In embodiments, $R^3$ is 2 to 4 membered alkoxy-substituted aryloxy-substituted 5 to 6 membered heteroaryl-substituted $C_1$-$C_4$ alkyl.

In embodiments, $R^3$ is methoxy-substituted pyridyl-substituted ethyl. In embodiments, $R^3$ is 2 to 4 membered alkoxy-substituted pyridyl-substituted ethyl. In embodiments, $R^3$ is 2 to 4 membered alkoxy-substituted 5 to 6 membered heteroaryl-substituted ethyl. In embodiments, $R^3$ is 2 to 4 membered alkoxy-substituted 5 to 6 membered heteroaryl-substituted $C_1$-$C_4$ alkyl. In embodiments, $R^3$ is 2 to 4 membered alkoxy-substituted heteroaryl-substituted $C_1$-$C_4$ alkyl.

In embodiments, $R^3$ is methoxy-substituted phenyl-substituted ethyl. In embodiments, $R^3$ is 2 to 4 membered alkoxy-substituted phenyl-substituted ethyl. In embodiments, $R^3$ is 2 to 4 membered alkoxy-substituted aryl-substituted ethyl. In embodiments, $R^3$ is 2 to 4 membered alkoxy-substituted aryl-substituted $C_1$-$C_4$ alkyl.

In embodiments, $R^3$ is oxo-substituted 2 to 4 membered heteroalkyl-substituted phenyl-substituted ethyl. In embodiments, $R^3$ is substituted 2 to 4 membered heteroalkyl-substituted phenyl-substituted ethyl. In embodiments, $R^3$ is substituted 2 to 4 membered heteroalkyl-substituted aryl-substituted ethyl. In embodiments, $R^3$ is substituted 2 to 4 membered heteroalkyl-substituted aryl-substituted $C_1$-$C_4$ alkyl.

In embodiments, $R^3$ is methoxy-substituted phenyl-substituted propyl. In embodiments, $R^3$ is 2 to 4 membered alkoxy-substituted phenyl-substituted propyl. In embodiments, $R^3$ is 2 to 4 membered alkoxy-substituted aryl-substituted propyl. In embodiments, $R^3$ is 2 to 4 membered alkoxy-substituted aryl-substituted $C_1$-$C_4$ alkyl.

In embodiments, $R^3$ is oxo-substituted 2 to 4 membered heteroalkyl-substituted phenyl-substituted ethyl. In embodiments, $R^3$ is substituted 2 to 4 membered heteroalkyl-substituted phenyl-substituted ethyl. In embodiments, $R^3$ is substituted 2 to 4 membered heteroalkyl-substituted aryl-substituted ethyl. In embodiments, $R^3$ is substituted 2 to 4 membered heteroalkyl-substituted aryl-substituted $C_1$-$C_4$ alkyl.

In embodiments, $R^3$ is unsubstituted cyclopentyl-substituted ethyl. In embodiments, $R^3$ is unsubstituted $C_3$-$C_6$ cycloalkyl-substituted ethyl. In embodiments, $R^3$ is unsubstituted $C_3$-$C_6$ cycloalkyl-substituted $C_1$-$C_4$ alkyl.

In embodiments, $R^3$ is tert-butyloxycarbonyl-substituted pyrrolidinyl-substituted ethyl. In embodiments, $R^3$ is oxo-substituted 4 to 8 membered heteroalkyl-substituted pyrrolidinyl-substituted ethyl. In embodiments, $R^3$ is substituted 4 to 8 membered heteroalkyl-substituted pyrrolidinyl-substituted ethyl. In embodiments, $R^3$ is substituted 4 to 8 membered heteroalkyl-substituted 3 to 6 membered heterocycloalkyl-substituted ethyl. In embodiments, $R^3$ is substituted 4 to 8 membered heteroalkyl-substituted 3 to 6 membered heterocycloalkyl-substituted $C_1$-$C_4$ alkyl.

In embodiments, $R^3$ is tert-butyloxy carbonyl-substituted azetidinyl-substituted ethyl. In embodiments, $R^3$ is oxo-substituted 4 to 8 membered heteroalkyl-substituted azetidinyl-substituted ethyl. In embodiments, $R^3$ is substituted 4 to 8 membered heteroalkyl-substituted azetidinyl-substituted ethyl. In embodiments, $R^3$ is substituted 4 to 8 membered heteroalkyl-substituted azetidinyl-substituted $C_1$-$C_4$ alkyl.

In embodiments, $R^3$ is unsubstituted azetidinyl-substituted ethyl. In embodiments, $R^3$ is unsubstituted $C_3$-$C_6$ heterocycloalkyl-substituted ethyl. In embodiments, $R^3$ is unsubstituted $C_3$-$C_6$ heterocycloalkyl-substituted $C_1$-$C_4$ alkyl.

In embodiments, $R^3$ is CN-substituted phenyl-substituted ethyl. In embodiments, $R^3$ is CN-substituted phenyl-substituted ethyl. In embodiments, $R^3$ is CN-substituted aryl-substituted ethyl. In embodiments, $R^3$ is CN-substituted aryl-substituted $C_1$-$C_4$ alkyl. In embodiments, $R^3$ is substituted aryl-substituted $C_1$-$C_4$ alkyl.

In embodiments, $R^3$ is unsubstituted phenyl-substituted ethyl-substituted piperidinyl-substituted methyl. In embodiments, $R^3$ is unsubstituted aryl-substituted ethyl-substituted piperidinyl-substituted methyl. In embodiments, $R^3$ is unsubstituted aryl-substituted $C_1$-$C_4$ alkyl-substituted piperidinyl-substituted methyl. In embodiments, $R^3$ is unsubstituted aryl-substituted $C_1$-$C_4$ alkyl-substituted 3 to 6 membered heterocycloalkyl-substituted methyl. In embodiments, $R^3$ is unsubstituted aryl-substituted $C_1$-$C_4$ alkyl-substituted 3 to 6 membered heterocycloalkyl-substituted $C_1$-$C_4$ alkyl.

In embodiments, $R^3$ is methoxy-substituted pyridyl-substituted methyl. In embodiments, $R^3$ is substituted or unsubstituted 2 to 4 membered alkoxy-substituted pyridyl-substituted methyl. In embodiments, $R^3$ is substituted or unsubstituted 2 to 4 membered alkoxy-substituted 5 to 6 membered heteroaryl-substituted methyl. In embodiments, $R^3$ is substituted or unsubstituted 2 to 4 membered alkoxy-substituted 5 to 6 membered heteroaryl-substituted $C_1$-$C_4$ alkyl. In embodiments, $R^3$ is substituted 2 to 4 membered alkoxy-substituted pyridyl-substituted methyl. In embodiments, $R^3$ is substituted 2 to 4 membered alkoxy-substituted 5 to 6 membered heteroaryl-substituted methyl. In embodiments, $R^3$ is substituted 2 to 4 membered alkoxy-substituted 5 to 6 membered heteroaryl-substituted $C_1$-$C_4$ alkyl. In embodiments, $R^3$ is unsubstituted 2 to 4 membered alkoxy-substituted pyridyl-substituted methyl. In embodiments, $R^3$ is unsubstituted 2 to 4 membered alkoxy-substituted 5 to 6 membered heteroaryl-substituted methyl. In embodiments, $R^3$ is unsubstituted 2 to 4 membered alkoxy-substituted 5 to 6 membered heteroaryl-substituted $C_1$-$C_4$ alkyl.

In embodiments, $R^3$ is unsubstituted 2 to 4 membered alkoxy-substituted pyridyl-substituted methyl. In embodiments, $R^3$ is unsubstituted 2 to 4 membered alkoxy-substituted 5 to 6 membered heteroaryl-substituted methyl. In embodiments, $R^3$ is unsubstituted 2 to 4 membered alkoxy-substituted 5 to 6 membered heteroaryl-substituted $C_1$-$C_4$ alkyl.

In embodiments, $R^3$ is unsubstituted pyridyl-substituted methyl. In embodiments, $R^3$ is unsubstituted 5 to 6 membered heteroaryl-substituted methyl. In embodiments, $R^3$ is unsubstituted 5 to 6 membered heteroaryl-substituted $C_1$-$C_4$ alkyl.

In embodiments, $R^3$ is carboxyl-substituted phenyl-substituted ethyl. In embodiments, $R^3$ is substituted phenyl-substituted ethyl. In embodiments, $R^3$ is carboxyl-substituted aryl-substituted ethyl. In embodiments, $R^3$ is carboxyl-substituted aryl-substituted $C_1$-$C_4$ alkyl.

In embodiments, $R^3$ is $SO_2NH_2$-substituted phenyl-substituted ethyl. In embodiments, $R^3$ is $SO_2NH_2$-substituted aryl-substituted ethyl. In embodiments, $R^3$ is $SO_2NH_2$-substituted aryl-substituted $C_1$-$C_4$ alkyl.

In embodiments, $R^3$ is hydrogen. In embodiments, $R^3$ is tert-butylcarbamate-substituted phenyl-substituted ethyl. In embodiments, $R^3$ is oxo-substituted 6 to 8 membered heteroalkyl-substituted phenyl-substituted ethyl. In embodiments, $R^3$ is substituted 6 to 8 membered heteroalkyl-substituted phenyl-substituted ethyl. In embodiments, $R^3$ is substituted 6 to 8 membered heteroalkyl-substituted aryl-substituted ethyl. In embodiments, $R^3$ is substituted 6 to 8 membered heteroalkyl-substituted aryl-substituted $C_1$-$C_4$ alkyl.

In embodiments, $R^3$ is tert-butyloxycarbonyl-substituted piperidinyl-substituted ethyl. In embodiments, $R^3$ is oxo-substituted 5 to 7 membered heteroalkyl-substituted piperidinyl-substituted ethyl. In embodiments, $R^3$ is substituted 5 to 7 membered heteroalkyl-substituted piperidinyl-substituted ethyl. In embodiments, $R^3$ is substituted 5 to 7 membered heteroalkyl-substituted 5 to 6 membered heterocycloalkyl-substituted ethyl. In embodiments, $R^3$ is substituted 5 to 7 membered heteroalkyl-substituted 5 to 6 membered heterocycloalkyl-substituted $C_1$-$C_4$ alkyl.

In embodiments, $R^3$ is unsubstituted thiazolyl-substituted methyl. In embodiments, $R^3$ is unsubstituted 5 to 6 membered heteroaryl-substituted methyl. In embodiments, $R^3$ is unsubstituted 5 to 6 membered heteroaryl-substituted $C_1$-$C_4$ alkyl.

In embodiments, $R^3$ is $NH_2$-substituted phenyl-substituted ethyl. In embodiments, $R^3$ is $NH_2$-substituted aryl-substituted ethyl. In embodiments, $R^3$ is $NH_2$-substituted aryl-substituted $C_1$-$C_4$ alkyl. In embodiments, $R^3$ is substituted aryl-substituted $C_1$-$C_4$ alkyl.

In embodiments, $R^3$ is unsubstituted piperidinyl-substituted ethyl. In embodiments, $R^3$ is unsubstituted 5 to 6 membered heterocycloalkyl-substituted ethyl. In embodiments, $R^3$ is unsubstituted 5 to 6 membered heterocycloalkyl-substituted $C_1$-$C_4$ alkyl.

In embodiments, $R^3$ is oxo-substituted 2 to 6 membered heteroalkyl-substituted phenyl-substituted ethyl. In embodiments, $R^3$ is substituted 2 to 6 membered heteroalkyl-substituted phenyl-substituted ethyl. In embodiments, $R^3$ is substituted 2 to 6 membered heteroalkyl-substituted aryl-substituted ethyl. In embodiments, $R^3$ is substituted 2 to 6 membered heteroalkyl-substituted aryl-substituted $C_1$-$C_4$ alkyl.

In embodiments, $R^3$ is

In embodiments, R³ is
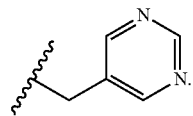 [SMILES: *Cc1cncnc1]
In embodiments, R³ is
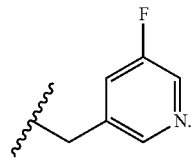 [SMILES: *Cc1cncc(F)c1]
In embodiments, R³ is
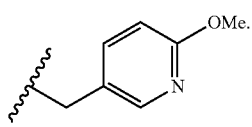 [SMILES: *Cc1ccc(OC)nc1]
In embodiments, R³ is
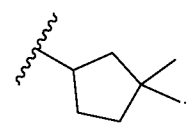 [SMILES: *C1CCC(C)(C)C1]
In embodiments, R³ is
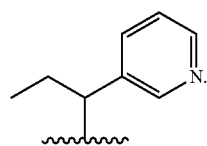 [SMILES: *C(CC)c1cccnc1]
In embodiments, R³ is
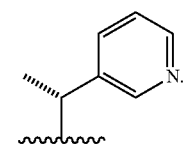
In embodiments, R³ is
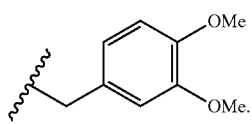 [SMILES: *Cc1ccc(OC)c(OC)c1]
In embodiments, R³ is
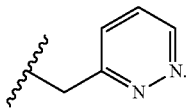 [SMILES: *Cc1cccnn1]
In embodiments, R³ is
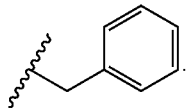 [SMILES: *Cc1ccccc1]
In embodiments, R³ is
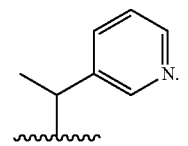
In embodiments, R³ is
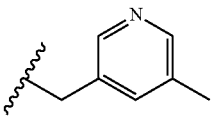
In embodiments, R³ is
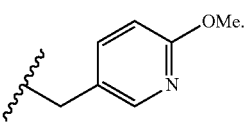
In embodiments, R³ is
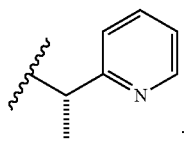 [SMILES: *[C@@H](C)c1ccccn1]
In embodiments, R³ is
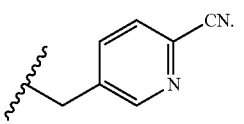 [SMILES: *Cc1ccc(C#N)nc1]

In embodiments, $R^3$ is
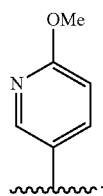 [SMILES: *c1ccc(OC)nc1]
In embodiments, $R^3$ is
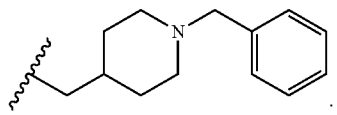 [SMILES: *CC1CCN(Cc2ccccc2)CC1]
In embodiments, $R^3$ is
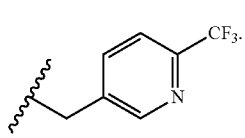
In embodiments, $R^3$ is
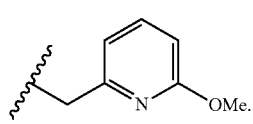 [SMILES: *Cc1cccc(OC)n1]
In embodiments, $R^3$ is
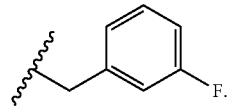
In embodiments, $R^3$ is
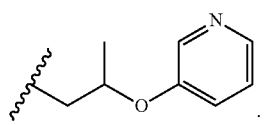 [SMILES: *CC(C)Oc1cccnc1]
In embodiments, $R^3$ is
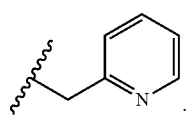
In embodiments, $R^3$ is
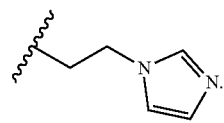 [SMILES: *CCn1ccnc1]
In embodiments, $R^3$ is
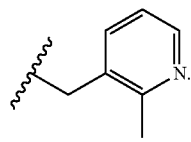 [SMILES: *Cc1cccnc1C]
In embodiments, $R^3$ is
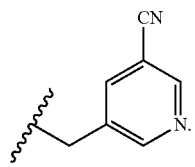
In embodiments, $R^3$ is
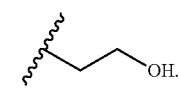
In embodiments, $R^3$ is
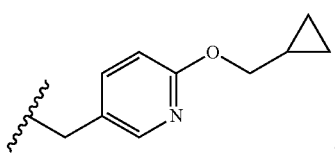
In embodiments, $R^3$ is
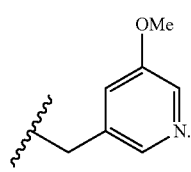 [SMILES: *Cc1cncc(OC)c1]
In embodiments, $R^3$ is
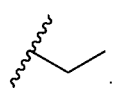

In embodiments, R³ is
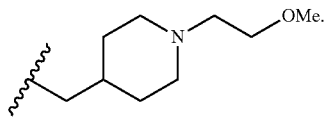 [SMILES: *CC1CCN(CCOC)CC1]
In embodiments, R³ is
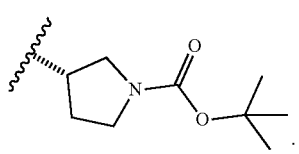 [SMILES: *[C@H]1CCN(C(=O)OC(C)(C)C)C1]
In embodiments, R³ is
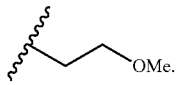
In embodiments, R³ is
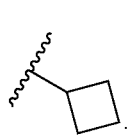
In embodiments, R³ is
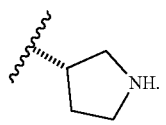
In embodiments, R³ is
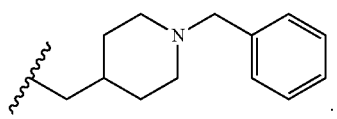 [SMILES: *CC1CCN(Cc2ccccc2)CC1]
In embodiments, R³ is
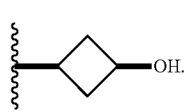
In embodiments, R³ is
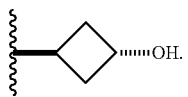
In embodiments, R³ is
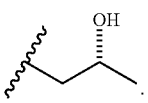
In embodiments, R³ is
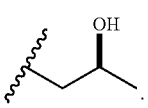
In embodiments, R³ is
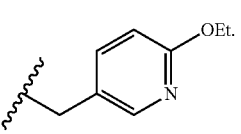
In embodiments, R³ is
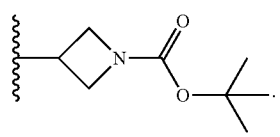 [SMILES: *C1CN(C(=O)OC(C)(C)C)C1]
In embodiments, R³ is
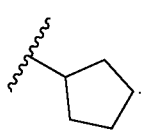
In embodiments, R³ is
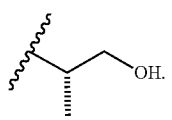 [SMILES: *[C@@H](C)CO]

In embodiments, R³ is
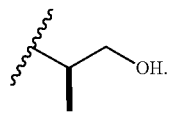 [SMILES: *[C@H](C)CO]
In embodiments, R³ is
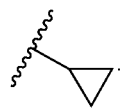
In embodiments, R³ is
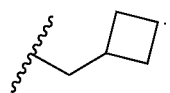 [SMILES: *CC1CCC1]
In embodiments, R³ is
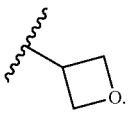
In embodiments, R³ is
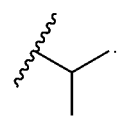
In embodiments, R³ is
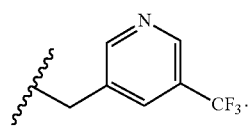 [SMILES: *Cc1cncc(C(F)(F)F)c1]
In embodiments, R³ is
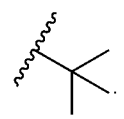 [SMILES: *C(C)(C)C]
In embodiments, R³ is
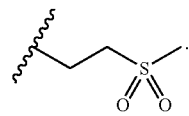 [SMILES: *CCS(C)(=O)=O]
In embodiments, R³ is
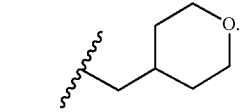 [SMILES: *CC1CCOCC1]
In embodiments, R³ is
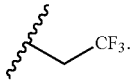
In embodiments, R³ is
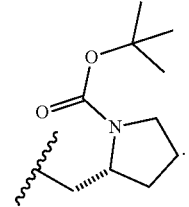
In embodiments, R³ is
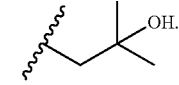 [SMILES: *CC(C)(C)O]
In embodiments, R³ is
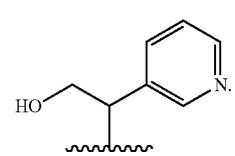 [SMILES: *C(CO)c1cccnc1]
In embodiments, R³ is
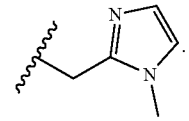

In embodiments, R³ is
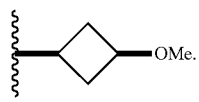 [SMILES: *[C@H]1C[C@@H](OC)C1]
In embodiments, R³ is
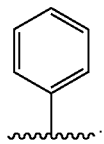
In embodiments, R³ is
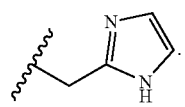 [SMILES: *Cc1ncc[nH]1]
In embodiments, R³ is
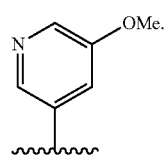
In embodiments, R³ is
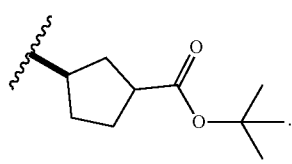
In embodiments, R³ is
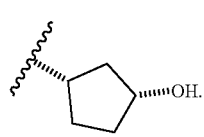
In embodiments, R³ is
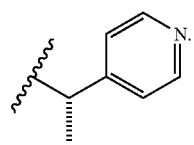 [SMILES: *[C@@H](C)c1ccncc1]
In embodiments, R³ is
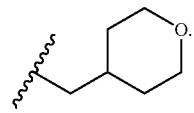 [SMILES: *CC1CCOCC1]
In embodiments, R³ is
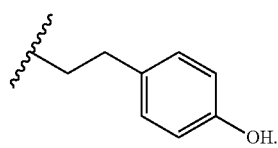 [SMILES: *CCc1ccc(O)cc1]
In embodiments, R³ is
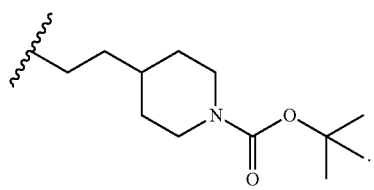 [SMILES: *CCC1CCN(C(=O)OC(C)(C)C)CC1]
In embodiments, R³ is
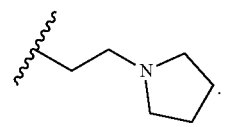 [SMILES: *CCN1CCCC1]
In embodiments, R³ is
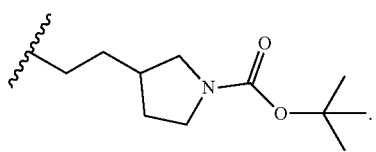 [SMILES: *CCC1CCN(C(=O)OC(C)(C)C)C1]
In embodiments, R³ is
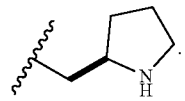
In embodiments, R³ is
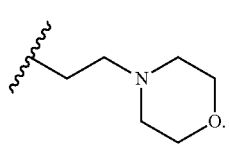 [SMILES: *CCN1CCOCC1]

In embodiments, R³ is
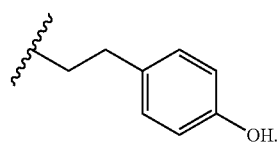 [SMILES: *CCc1ccc(O)cc1]
In embodiments, R³ is
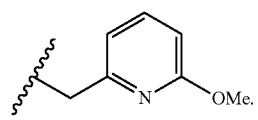 [SMILES: *Cc1cccc(OC)n1]
In embodiments, R³ is
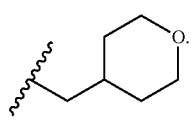
In embodiments, R³ is
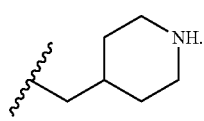
In embodiments, R³ is
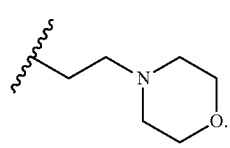 [SMILES: *CCN1CCOCC1]
In embodiments, R³ is
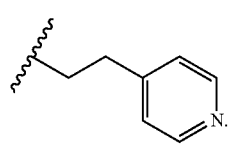 [SMILES: *CCc1ccncc1]
In embodiments, R³ is
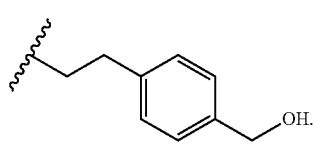 [SMILES: *CCc1ccc(CO)cc1]
In embodiments, R³ is
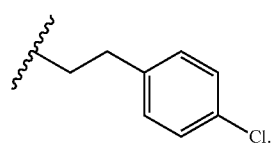 [SMILES: *CCc1ccc(Cl)cc1]
In embodiments, R³ is
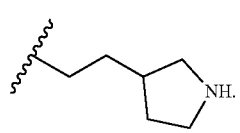 [SMILES: *CCC1CCNC1]
In embodiments, R³ is
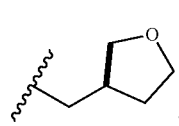
In embodiments, R³ is
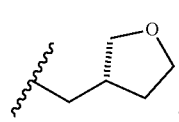
In embodiments, R³ is
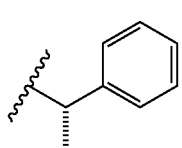
In embodiments, R³ is
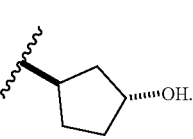
In embodiments, R³ is
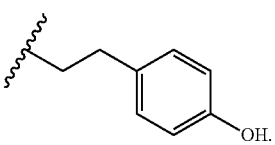 [SMILES: *CCc1ccc(O)cc1]

In embodiments, R³ is
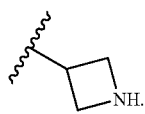 [SMILES: *C1CNC1]
In embodiments, R³ is
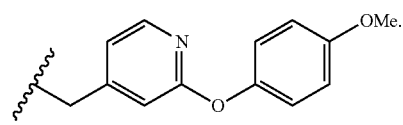 [SMILES: *Cc1ccnc(Oc2ccc(OC)cc2)c1]
In embodiments, R³ is
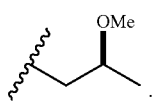
In embodiments, R³ is
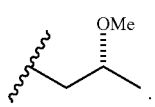
In embodiments, R³ is
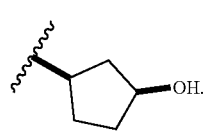
In embodiments, R³ is
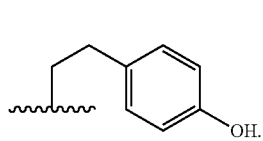 [SMILES: *CCc1ccc(O)cc1]
In embodiments, R³ is
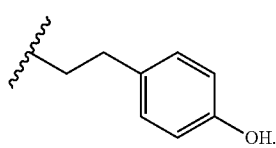 [SMILES: *CCc1ccc(O)cc1]
In embodiments, R³ is
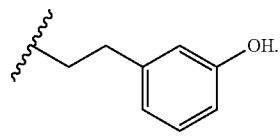 [SMILES: *CCc1cccc(O)c1]
In embodiments, R³ is
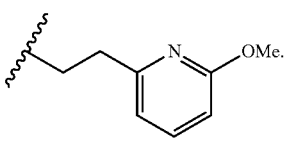 [SMILES: *CCc1cccc(OC)n1]
In embodiments, R³ is
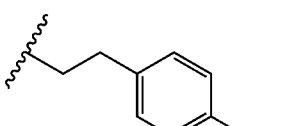
In embodiments, R³ is
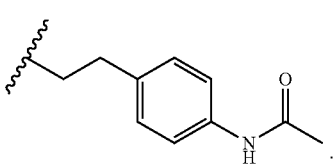 [SMILES: *CCc1ccc(NC(C)=O)cc1]
In embodiments, R³ is
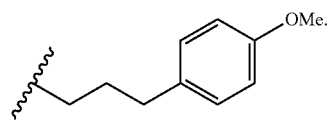 [SMILES: *CCCc1ccc(OC)cc1]
In embodiments, R³ is
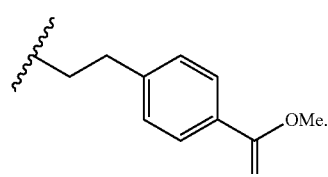

In embodiments, R³ is
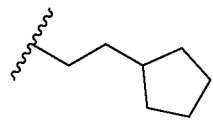
In embodiments, R³ is
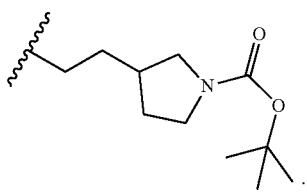 [SMILES: *CCC1CCN(C(=O)OC(C)(C)C)C1]
In embodiments, R³ is
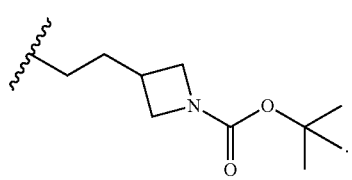 [SMILES: *CCC1CN(C(=O)OC(C)(C)C)C1]
In embodiments, R³ is
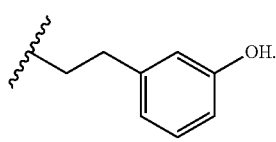 [SMILES: *CCc1cccc(O)c1]
In embodiments, R³ is
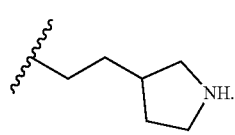
In embodiments, R³ is
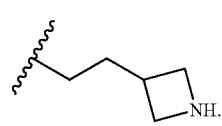 [SMILES: *CCC1CNC1]
In embodiments, R³ is
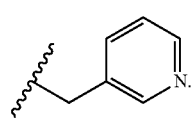
In embodiments, R³ is
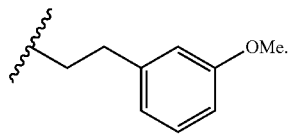
In embodiments, R³ is
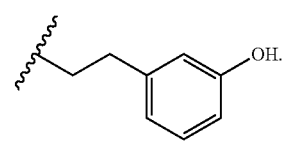 [SMILES: *CCc1cccc(O)c1]
In embodiments, R³ is
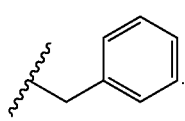 [SMILES: *Cc1ccccc1]
In embodiments, R³ is
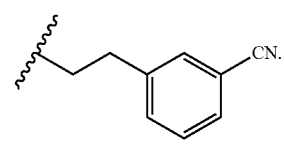
In embodiments, R³ is
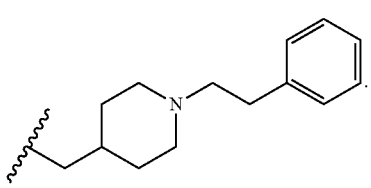 [SMILES: *CC1CCN(CCc2ccccc2)CC1]
In embodiments, R³ is
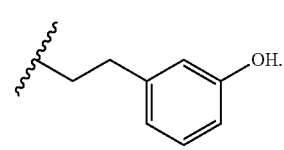 [SMILES: *CCc1cccc(O)c1]
In embodiments, R³ is
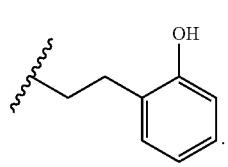 [SMILES: *CCc1ccccc1O]

149
In embodiments, R³ is
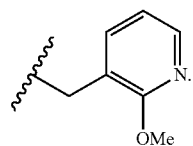 [SMILES: *Cc1cccnc1OC]
In embodiments, R³ is
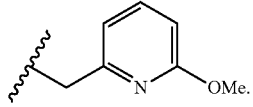 [SMILES: *Cc1cccc(OC)n1]
In embodiments, R³ is
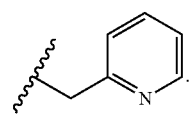
In embodiments, R³ is
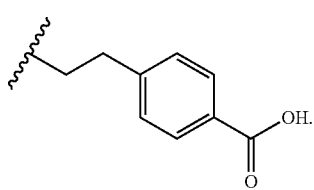 [SMILES: *CCc1ccc(C(=O)O)cc1]
In embodiments, R³ is
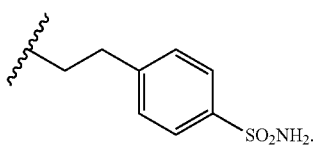 [SMILES: *CCc1ccc(S(N)(=O)=O)cc1]
In embodiments, R³ is
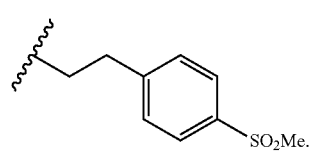 [SMILES: *CCc1ccc(S(C)(=O)=O)cc1]
In embodiments, R³ is
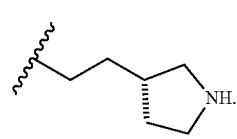
150
In embodiments, R³ is
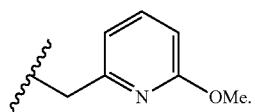 [SMILES: *Cc1cccc(OC)n1]
In embodiments, R³ is
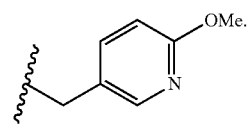 [SMILES: *Cc1ccc(OC)nc1]
In embodiments, R³ is
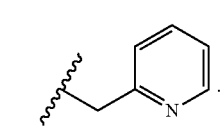
In embodiments, R³ is
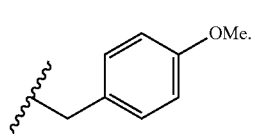
In embodiments, R³ is
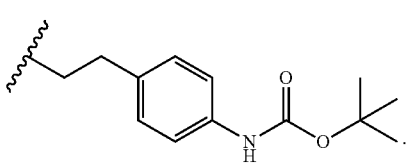 [SMILES: *CCc1ccc(NC(=O)OC(C)(C)C)cc1]
In embodiments, R³ is
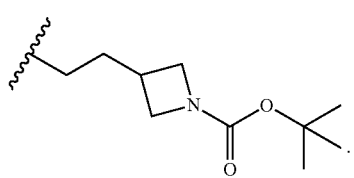 [SMILES: *CCC1CN(C(=O)OC(C)(C)C)C1]
In embodiments, R³ is
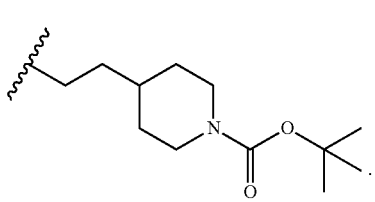 [SMILES: *CCC1CCN(C(=O)OC(C)(C)C)CC1]

In embodiments, $R^3$ is

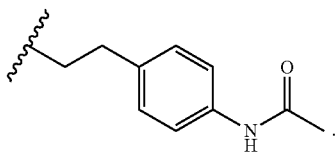 [SMILES: *CCc1ccc(NC(C)=O)cc1]

In embodiments, $R^3$ is

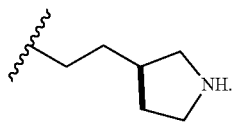

In embodiments, $R^3$ is

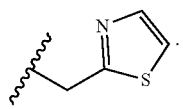 [SMILES: *Cc1nccs1]

In embodiments, $R^3$ is

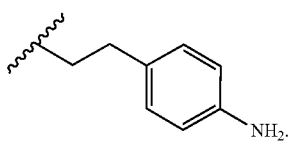 [SMILES: *CCc1ccc(N)cc1]

In embodiments, $R^3$ is

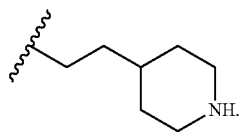

In embodiments, $R^3$ is

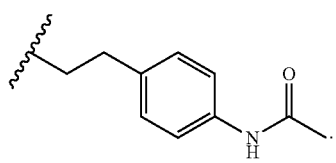 [SMILES: *CCc1ccc(NC(C)=O)cc1]

In embodiments, $R^3$ is

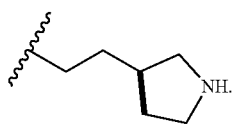 [SMILES: *CC[C@@H]1CCNC1]

In embodiments, $R^3$ is

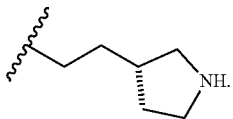

In embodiments, $R^3$ is

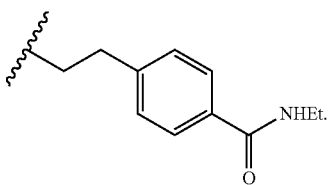

In embodiments, $R^3$ is

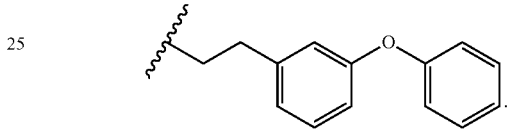

In embodiments, $R^4$ is hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

In embodiments, $R^4$ is independently halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, $R^{29}$-substituted or unsubstituted alkyl (e.g., $C_1$-$C_8$ alkyl, $C_1$-$C_6$ alkyl, or $C_1$-$C_4$ alkyl), or $R^{29}$-substituted or unsubstituted heteroalkyl (e.g., 2 to 8 membered heteroalkyl, 2 to 6 membered heteroalkyl, or 2 to 4 membered heteroalkyl).

In embodiments, $R^4$ is $R^{29}$-substituted or unsubstituted alkyl (e.g., $C_1$-$C_8$ alkyl, $C_1$-$C_6$ alkyl, or $C_1$-$C_4$ alkyl). In embodiments, $R^4$ is $R^{29}$-substituted alkyl (e.g., $C_1$-$C_8$ alkyl, $C_1$-$C_6$ alkyl, or $C_1$-$C_4$ alkyl). In embodiments, $R^4$ is an unsubstituted alkyl (e.g., $C_1$-$C_8$ alkyl, $C_1$—$C_6$ alkyl, or $C_1$-$C_4$ alkyl). In embodiments, $R^4$ is $R^{29}$-substituted or unsubstituted heteroalkyl (e.g., 2 to 8 membered heteroalkyl, 2 to 6 membered heteroalkyl, or 2 to 4 membered heteroalkyl). In embodiments, $R^4$ is $R^{29}$-substituted heteroalkyl (e.g., 2 to 8 membered heteroalkyl, 2 to 6 membered heteroalkyl, or 2 to 4 membered heteroalkyl). In embodiments, $R^4$ is an unsubstituted heteroalkyl (e.g., 2 to 8 membered heteroalkyl, 2 to 6 membered heteroalkyl, or 2 to 4 membered heteroalkyl).

In embodiments, $R^{4A}$, $R^{4B}$, $R^{4C}$, and $R^{4D}$ are independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, R$^{29}$-substituted or unsubstituted alkyl (e.g., C$_1$-C$_8$ alkyl, C$_1$-C$_6$ alkyl, or C$_1$-C$_4$ alkyl), R$^{29}$-substituted or unsubstituted heteroalkyl (e.g., 2 to 8 membered heteroalkyl, 2 to 6 membered heteroalkyl, or 2 to 4 membered heteroalkyl), R$^{29}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{29}$-substituted or unsubstituted heterocycloalkyl (e.g., 3 to 8 membered heterocycloalkyl, 3 to 6 membered heterocycloalkyl, or 5 to 6 membered heterocycloalkyl), R$^{29}$-substituted or unsubstituted aryl (e.g., C$_6$-C$_{10}$ aryl, C$_{10}$ aryl, or phenyl), or R$^{29}$-substituted or unsubstituted heteroaryl (e.g., 5 to 10 membered heteroaryl, 5 to 9 membered heteroaryl, or 5 to 6 membered heteroaryl).

In embodiments, R$^{4A}$, R$^{4B}$, R$^{4C}$, and R$^{4D}$ are independently R$^{29}$-substituted or unsubstituted alkyl (e.g., C$_1$-C$_8$ alkyl, C$_1$-C$_6$ alkyl, or C$_1$-C$_4$ alkyl). In embodiments, R$^{4A}$, R$^{4B}$, R$^{4C}$, and R$^{4D}$ are independently R$^{29}$-substituted alkyl (e.g., C$_1$-C$_8$ alkyl, C$_1$-C$_6$ alkyl, or C$_1$-C$_4$ alkyl). In embodiments, R$^{4A}$, R$^{4B}$, R$^{4C}$, and R$^{4D}$ are independently an unsubstituted alkyl (e.g., C$_1$-C$_8$ alkyl, C$_1$-C$_6$ alkyl, or C$_1$-C$_4$ alkyl). In embodiments, R$^{4A}$, R$^{4B}$, R$^{4C}$, and R$^{4D}$ are independently R$^{29}$-substituted or unsubstituted heteroalkyl (e.g., 2 to 8 membered heteroalkyl, 2 to 6 membered heteroalkyl, or 2 to 4 membered heteroalkyl). In embodiments, R$^{4A}$, R$^{4B}$, R$^{4C}$, and R$^{4D}$ are independently R$^{29}$-substituted heteroalkyl (e.g., 2 to 8 membered heteroalkyl, 2 to 6 membered heteroalkyl, or 2 to 4 membered heteroalkyl). In embodiments, R$^{4A}$, R$^{4B}$, R$^{4C}$, and R$^{4D}$ are independently an unsubstituted heteroalkyl (e.g., 2 to 8 membered heteroalkyl, 2 to 6 membered heteroalkyl, or 2 to 4 membered heteroalkyl). In embodiments, R$^{4A}$, R$^{4B}$, R$^{4C}$, and R$^{4D}$ are independently R$^{29}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{4A}$, R$^{4B}$, R$^{4C}$, and R$^{4D}$ are independently R$^{29}$-substituted cycloalkyl (e.g., C$_3$-C$_8$ cycloalkyl, C$_3$-C$_6$ cycloalkyl, or C$_5$-C$_6$ cycloalkyl). In embodiments, R$^{4A}$, R$^{4B}$, R$^{4C}$, and R$^{4D}$ are independently an unsubstituted cycloalkyl (e.g., C$_3$-C$_8$ cycloalkyl, C$_3$-C$_6$ cycloalkyl, or C$_5$-C$_6$ cycloalkyl). In embodiments, R$^{4A}$, R$^{4B}$, R$^{4C}$, and R$^{4D}$ are independently R$^{29}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{4A}$, R$^{4B}$, R$^{4C}$, and R$^{4D}$ are independently R$^{29}$-substituted heterocycloalkyl (e.g., 3 to 8 membered heterocycloalkyl, 3 to 6 membered heterocycloalkyl, or 5 to 6 membered heterocycloalkyl). In embodiments, R$^{4A}$, R$^{4B}$, R$^{4C}$, and R$^{4D}$ are independently an unsubstituted heterocycloalkyl (e.g., 3 to 8 membered heterocycloalkyl, 3 to 6 membered heterocycloalkyl, or 5 to 6 membered heterocycloalkyl). In embodiments, R$^{4A}$, R$^{4B}$, R$^{4C}$, and R$^{4D}$ are independently R$^{29}$-substituted or unsubstituted aryl (e.g., C$_6$-C$_{10}$ aryl, C$_{10}$ aryl, or phenyl). In embodiments, R$^{4A}$, R$^{4B}$, R$^{4C}$, and R$^{4D}$ are independently R$^{29}$-substituted aryl (e.g., C$_6$-C$_{10}$ aryl, C$_{10}$ aryl, or phenyl). In embodiments, R$^{4A}$, R$^{4B}$, R$^{4C}$, and R$^{4D}$ are independently an unsubstituted aryl (e.g., C$_6$-C$_{10}$ aryl, C$_{10}$ aryl, or phenyl). In embodiments, R$^{4A}$, R$^{4B}$, R$^{4C}$, and R$^{4D}$ are independently R$^{29}$-substituted or unsubstituted heteroaryl (e.g., 5 to 10 membered heteroaryl, 5 to 9 membered heteroaryl, or 5 to 6 membered heteroaryl). In embodiments, R$^{4A}$, R$^{4B}$, R$^{4C}$, and R$^{4D}$ are independently R$^{29}$-substituted heteroaryl (e.g., 5 to 10 membered heteroaryl, 5 to 9 membered heteroaryl, or 5 to 6 membered heteroaryl). In embodiments, R$^{4A}$, R$^{4B}$, R$^{4C}$, and R$^{4D}$ are independently an unsubstituted heteroaryl (e.g., 5 to 10 membered heteroaryl, 5 to 9 membered heteroaryl, or 5 to 6 membered heteroaryl).

R$^{29}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, R$^{30}$-substituted or unsubstituted alkyl (e.g., C$_1$-C$_8$ alkyl, C$_1$-C$_6$ alkyl, or C$_1$-C$_4$ alkyl), R$^{30}$-substituted or unsubstituted heteroalkyl (e.g., 2 to 8 membered heteroalkyl, 2 to 6 membered heteroalkyl, or 2 to 4 membered heteroalkyl), R$^{30}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{30}$-substituted or unsubstituted heterocycloalkyl (e.g., 3 to 8 membered heterocycloalkyl, 3 to 6 membered heterocycloalkyl, or 5 to 6 membered heterocycloalkyl), R$^{30}$-substituted or unsubstituted aryl (e.g., C$_6$-C$_{10}$ aryl, C$_{10}$ aryl, or phenyl), or R$^{30}$-substituted or unsubstituted heteroaryl (e.g., 5 to 10 membered heteroaryl, 5 to 9 membered heteroaryl, or 5 to 6 membered heteroaryl).

R$^{30}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, R$^{31}$-substituted or unsubstituted alkyl (e.g., C$_1$-C$_8$ alkyl, C$_1$-C$_6$ alkyl, or C$_1$-C$_4$ alkyl), R$^{31}$-substituted or unsubstituted heteroalkyl (e.g., 2 to 8 membered heteroalkyl, 2 to 6 membered heteroalkyl, or 2 to 4 membered heteroalkyl), R$^{31}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{31}$-substituted or unsubstituted heterocycloalkyl (e.g., 3 to 8 membered heterocycloalkyl, 3 to 6 membered heterocycloalkyl, or 5 to 6 membered heterocycloalkyl), R$^{31}$-substituted or unsubstituted aryl (e.g., C$_6$-C$_{10}$ aryl, C$_{10}$ aryl, or phenyl), or R$^{31}$-substituted or unsubstituted heteroaryl (e.g., 5 to 10 membered heteroaryl, 5 to 9 membered heteroaryl, or 5 to 6 membered heteroaryl).

In embodiments, R$^4$ is R$^{29}$-substituted or unsubstituted alkyl (e.g., C$_1$-C$_8$ alkyl, C$_1$-C$_6$ alkyl, or C$_1$-C$_4$ alkyl). In embodiments, R$^4$ is R$^{29}$-substituted alkyl (e.g., C$_1$-C$_8$ alkyl, C$_1$-C$_6$ alkyl, or C$_1$-C$_4$ alkyl). In embodiments, R$^4$ is an unsubstituted alkyl (e.g., C$_1$-C$_8$ alkyl, C$_1$-C$_6$ alkyl, or C$_1$-C$_4$ alkyl). In embodiments, R$^4$ is R$^{29}$-substituted or unsubstituted heteroalkyl (e.g., 2 to 8 membered heteroalkyl, 2 to 6 membered heteroalkyl, or 2 to 4 membered heteroalkyl). In embodiments, R$^4$ is R$^{29}$-substituted heteroalkyl (e.g., 2 to 8 membered heteroalkyl, 2 to 6 membered heteroalkyl, or 2 to 4 membered heteroalkyl). In embodiments, R$^4$ is an unsubstituted heteroalkyl (e.g., 2 to 8 membered heteroalkyl, 2 to 6 membered heteroalkyl, or 2 to 4 membered heteroalkyl). In embodiments, R$^4$ is hydrogen, halogen, —CX$^4_3$, —CHX$^4_2$, —CH$_2$X$^4$, —OCX$^4_3$, —OCH$_2$X$^4$, —OCHX$^4_2$, —CN, —SR$^{4D}$, —NR$^{4A}$R$^{4B}$, or substituted or unsubstituted C$_1$-C$_6$ alkyl. In embodiments, R$^4$ is hydrogen, halogen, —CX$^3$, —NR$^{4A}$R$^{4B}$, or substituted or unsubstituted C$_1$-C$_6$ alkyl. In embodiments, R$^4$ is hydrogen, halogen, —CF$_3$, —NH$_2$, —NH(CH$_3$) or unsubstituted C$_1$-C$_6$ alkyl. In embodiments, R$^4$ is hydrogen or unsubstituted methyl.

In embodiments, R$^4$ is hydrogen. In embodiments, R$^4$ is —NH(CH$_3$). In embodiments, R$^4$ is unsubstituted 2 to 3 membered heteroalkyl. In embodiments, R$^4$ is 2 to 3 membered heteroalkyl. In embodiments, R$^4$ is —NH$_2$. In embodiments, R$^4$ is —NH(R$^{4A}$). In embodiments, R$^4$ is —NR$^{4A}$R$^{4B}$.

In embodiments, R$^{4A}$ is R$^{29}$-substituted or unsubstituted alkyl (e.g., C$_1$-C$_8$ alkyl, C$_1$-C$_6$ alkyl, or C$_1$-C$_4$ alkyl). In embodiments, R$^{4A}$ is R$^{29}$-substituted alkyl (e.g., C$_1$-C$_8$ alkyl, C$_1$-C$_6$ alkyl, or C$_1$-C$_4$ alkyl). In embodiments, R$^{4A}$ is an unsubstituted alkyl (e.g., C$_1$-C$_8$ alkyl, C$_1$-C$_6$ alkyl, or C$_1$-C$_4$ alkyl). In embodiments, R$^{4A}$ is an unsubstituted C$_1$-C$_4$ alkyl. In embodiments, R$^{4A}$ is an unsubstituted C$_1$-C$_2$ alkyl. In embodiments, R$^{4A}$ is hydrogen.

In embodiments, R$^{4B}$ is R$^{29}$-substituted or unsubstituted alkyl (e.g., C$_1$-C$_8$ alkyl, C$_1$-C$_6$ alkyl, or C$_1$-C$_4$ alkyl). In embodiments, R$^{4B}$ is R$^{29}$-substituted alkyl (e.g., C$_1$-C$_8$ alkyl, C$_1$-C$_6$ alkyl, or C$_1$-C$_4$ alkyl). In embodiments, R$^{4B}$ is an unsubstituted alkyl (e.g., C$_1$-C$_8$ alkyl, C$_1$-C$_6$ alkyl, or C$_1$-C$_4$ alkyl). In embodiments, R$^{4B}$ is an unsubstituted C$_1$-C$_4$ alkyl. In embodiments, R$^{4B}$ is an unsubstituted C$_1$-C$_2$ alkyl. In embodiments, R$^{4B}$ is hydrogen.

In embodiments, R$^{4C}$ is R$^{29}$-substituted or unsubstituted alkyl (e.g., C$_1$-C$_8$ alkyl, C$_1$-C$_6$ alkyl, or C$_1$-C$_4$ alkyl). In embodiments, R$^{4C}$ is R$^{29}$-substituted alkyl (e.g., C$_1$-C$_8$ alkyl, C$_1$-C$_6$ alkyl, or C$_1$-C$_4$ alkyl). In embodiments, R$^{4C}$ is an unsubstituted alkyl (e.g., C$_1$-C$_8$ alkyl, C$_1$-C$_6$ alkyl, or C$_1$-C$_4$ alkyl). In embodiments, R$^{4C}$ is an unsubstituted C$_1$-C$_4$ alkyl. In embodiments, R$^{4C}$ is an unsubstituted C$_1$-C$_2$ alkyl. In embodiments, R$^{4C}$ is hydrogen.

In embodiments, R$^{4D}$ is R$^{29}$-substituted or unsubstituted alkyl (e.g., C$_1$-C$_8$ alkyl, C$_1$-C$_6$ alkyl, or C$_1$-C$_4$ alkyl). In embodiments, R$^{4D}$ is R$^{29}$-substituted alkyl (e.g., C$_1$-C$_8$ alkyl, C$_1$-C$_6$ alkyl, or C$_1$-C$_4$ alkyl). In embodiments, R$^{4D}$ is an unsubstituted alkyl (e.g., C$_1$-C$_8$ alkyl, C$_1$-C$_6$ alkyl, or C$_1$-C$_4$ alkyl). In embodiments, R$^{4D}$ is an unsubstituted C$_1$-C$_4$ alkyl. In embodiments, R$^{4D}$ is an unsubstituted C$_1$-C$_2$ alkyl. In embodiments, R$^{4D}$ is hydrogen.

In embodiments, R$^4$ is unsubstituted methyl. In embodiments, R$^4$ is unsubstituted C$_1$-C$_3$ alkyl. In embodiments, R$^4$ is unsubstituted ethyl.

In embodiments, R$^4$ is —CF$_3$. In embodiments, R$^4$ is —CHF$_2$. In embodiments, R$^4$ is —CH$_2$F. In embodiments, R$^4$ is-CX$^4{}_3$. In embodiments, R$^4$ is-CHX$^4{}_2$. In embodiments, R$^4$ is —CH$_2$X$^4$. X$^4$ is independently —F, —Cl, —Br, or —I.

In embodiments, R$^5$ is hydrogen, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl.

In embodiments, R$^5$ is independently halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O) NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, R$^{32}$-substituted or unsubstituted alkyl (e.g., C$_1$-C$_8$ alkyl, C$_1$-C$_6$ alkyl, or C$_1$-C$_4$ alkyl), or R$^{32}$-substituted or unsubstituted heteroalkyl (e.g., 2 to 8 membered heteroalkyl, 2 to 6 membered heteroalkyl, or 2 to 4 membered heteroalkyl).

In embodiments, R$^5$ is R$^{32}$-substituted or unsubstituted alkyl (e.g., C$_1$-C$_8$ alkyl, C$_1$-C$_6$ alkyl, or C$_1$-C$_4$ alkyl). In embodiments, R$^5$ is R$^{32}$-substituted alkyl (e.g., C$_1$-C$_8$ alkyl, C$_1$-C$_6$ alkyl, or C$_1$-C$_4$ alkyl). In embodiments, R$^5$ is an unsubstituted alkyl (e.g., C$_1$-C$_8$ alkyl, C$_1$-C$_6$ alkyl, or C$_1$-C$_4$ alkyl). In embodiments, R$^5$ is R$^{32}$-substituted or unsubstituted heteroalkyl (e.g., 2 to 8 membered heteroalkyl, 2 to 6 membered heteroalkyl, or 2 to 4 membered heteroalkyl). In embodiments, R$^5$ is R$^{32}$-substituted heteroalkyl (e.g., 2 to 8 membered heteroalkyl, 2 to 6 membered heteroalkyl, or 2 to 4 membered heteroalkyl). In embodiments, R$^5$ is an unsubstituted heteroalkyl (e.g., 2 to 8 membered heteroalkyl, 2 to 6 membered heteroalkyl, or 2 to 4 membered heteroalkyl).

In embodiments, R$^{5A}$, R$^{5B}$, R$^{5C}$, and R$^{5D}$ are independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_3$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, R$^{32}$-substituted or unsubstituted alkyl (e.g., C$_1$-C$_8$ alkyl, C$_1$-C$_6$ alkyl, or C$_1$-C$_4$ alkyl), R$^{32}$-substituted or unsubstituted heteroalkyl (e.g., 2 to 8 membered heteroalkyl, 2 to 6 membered heteroalkyl, or 2 to 4 membered heteroalkyl), R$^{32}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{32}$-substituted or unsubstituted heterocycloalkyl (e.g., 3 to 8 membered heterocycloalkyl, 3 to 6 membered heterocycloalkyl, or 5 to 6 membered heterocycloalkyl), R$^{32}$-substituted or unsubstituted aryl (e.g., C$_6$-C$_{10}$ aryl, C$_{10}$ aryl, or phenyl), or R$^{32}$-substituted or unsubstituted heteroaryl (e.g., 5 to 10 membered heteroaryl, 5 to 9 membered heteroaryl, or 5 to 6 membered heteroaryl).

In embodiments, R$^{5A}$, R$^{5B}$, R$^{5C}$, and R$^{5D}$ are independently R$^{32}$-substituted or unsubstituted alkyl (e.g., C$_1$-C$_8$ alkyl, C$_1$-C$_6$ alkyl, or C$_1$-C$_4$ alkyl). In embodiments, R$^{5A}$, R$^{5B}$, R$^{5C}$, and R$^{5D}$ are independently R$^{32}$-substituted alkyl (e.g., C$_1$-C$_8$ alkyl, C$_1$-C$_6$ alkyl, or C$_1$-C$_4$ alkyl). In embodiments, R$^{5A}$, R$^{5B}$, R$^{5C}$, and R$^{5D}$ are independently an unsubstituted alkyl (e.g., C$_1$-C$_8$ alkyl, C$_1$-C$_6$ alkyl, or C$_1$-C$_4$ alkyl). In embodiments, R$^{5A}$, R$^{5B}$, R$^{5C}$, and R$^{5D}$ are independently R$^{32}$-substituted or unsubstituted heteroalkyl (e.g., 2 to 8 membered heteroalkyl, 2 to 6 membered heteroalkyl, or 2 to 4 membered heteroalkyl). In embodiments, R$^{5A}$, R$^{5B}$, R$^{5C}$ and R$^{5D}$ are independently R$^{32}$-substituted heteroalkyl (e.g., 2 to 8 membered heteroalkyl, 2 to 6 membered heteroalkyl, or 2 to 4 membered heteroalkyl). In embodiments, R$^{5A}$, R$^{5B}$, R$^{5C}$ and R$^{5D}$ are independently an unsubstituted heteroalkyl (e.g., 2 to 8 membered heteroalkyl, 2 to 6 membered heteroalkyl, or 2 to 4 membered heteroalkyl). In embodiments, R$^{5A}$, R$^{5B}$, R$^{5C}$ and R$^{5D}$ are independently R$^{32}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{5A}$, R$^{5B}$, R$^{5C}$, and R$^{5D}$ are independently R$^{32}$-substituted cycloalkyl (e.g., C$_3$-C$_8$ cycloalkyl, C$_3$-C$_6$ cycloalkyl, or C$_5$-C$_6$ cycloalkyl). In embodiments, R$^{5A}$, R$^{5B}$, R$^{5C}$, and R$^{5D}$ are independently an unsubstituted cycloalkyl (e.g., C$_3$-C$_8$ cycloalkyl, C$_3$-C$_6$ cycloalkyl, or C$_5$-C$_6$ cycloalkyl). In embodiments, R$^{5A}$, R$^{5B}$, R$^{5C}$, and R$^{5D}$ are independently R$^{32}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{5A}$, R$^{5B}$, R$^{5C}$, and R$^{5D}$ are independently R$^{32}$-substituted heterocycloalkyl (e.g., 3 to 8 membered heterocycloalkyl, 3 to 6 membered heterocycloalkyl, or 5 to 6 membered heterocycloalkyl). In embodiments, R$^{5A}$, R$^{5B}$, R$^{5C}$, and R$^{5D}$ are independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{5A}$, $R^{5B}$, $R^{5C}$, and $R^{5D}$ are independently $R^{32}$-substituted or unsubstituted aryl (e.g., $C_6$-$C_{10}$ aryl, $C_{10}$ aryl, or phenyl). In embodiments, $R^{5A}$, $R^{5B}$, $R^{5C}$, and $R^{5D}$ are independently $R^{32}$-substituted aryl (e.g., $C_6$-$C_{10}$ aryl, $C_{10}$ aryl, or phenyl). In embodiments, $R^{5A}$, $R^{5B}$, $R^{5C}$, and $R^{5D}$ are independently an unsubstituted aryl (e.g., $C_6$-$C_{10}$ aryl, $C_{10}$ aryl, or phenyl). In embodiments, $R^{5A}$, $R^{5B}$, $R^{5C}$, and $R^{5D}$ are independently $R^{32}$-substituted or unsubstituted heteroaryl (e.g., 5 to 10 membered heteroaryl, 5 to 9 membered heteroaryl, or 5 to 6 membered heteroaryl). In embodiments, $R^{5A}$, $R^{5B}$, $R^{5C}$, and $R^{5D}$ are independently $R^{32}$-substituted heteroaryl (e.g., 5 to 10 membered heteroaryl, 5 to 9 membered heteroaryl, or 5 to 6 membered heteroaryl). In embodiments, $R^{5A}$, $R^{5B}$, $R^{5C}$, and $R^{5D}$ are independently an unsubstituted heteroaryl (e.g., 5 to 10 membered heteroaryl, 5 to 9 membered heteroaryl, or 5 to 6 membered heteroaryl).

$R^{32}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O) $NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{33}$-substituted or unsubstituted alkyl (e.g., $C_1$-$C_8$ alkyl, $C_1$-$C_6$ alkyl, or $C_1$-$C_4$ alkyl), $R^{33}$-substituted or unsubstituted heteroalkyl (e.g., 2 to 8 membered heteroalkyl, 2 to 6 membered heteroalkyl, or 2 to 4 membered heteroalkyl), $R^{33}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{33}$-substituted or unsubstituted heterocycloalkyl (e.g., 3 to 8 membered heterocycloalkyl, 3 to 6 membered heterocycloalkyl, or 5 to 6 membered heterocycloalkyl), $R^{33}$-substituted or unsubstituted aryl (e.g., $C_6$-$C_{10}$ aryl, $C_{10}$ aryl, or phenyl), or $R^{33}$-substituted or unsubstituted heteroaryl (e.g., 5 to 10 membered heteroaryl, 5 to 9 membered heteroaryl, or 5 to 6 membered heteroaryl).

$R^{33}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O) $NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{34}$-substituted or unsubstituted alkyl (e.g., $C_1$-$C_8$ alkyl, $C_1$-$C_6$ alkyl, or $C_1$-$C_4$ alkyl), $R^{34}$-substituted or unsubstituted heteroalkyl (e.g., 2 to 8 membered heteroalkyl, 2 to 6 membered heteroalkyl, or 2 to 4 membered heteroalkyl), $R^{34}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{34}$-substituted or unsubstituted heterocycloalkyl (e.g., 3 to 8 membered heterocycloalkyl, 3 to 6 membered heterocycloalkyl, or 5 to 6 membered heterocycloalkyl), $R^{34}$-substituted or unsubstituted aryl (e.g., $C_6$-$C_{10}$ aryl, $C_{10}$ aryl, or phenyl), or $R^{34}$-substituted or unsubstituted heteroaryl (e.g., 5 to 10 membered heteroaryl, 5 to 9 membered heteroaryl, or 5 to 6 membered heteroaryl).

In embodiments, $R^5$ is hydrogen, halogen, —$CX^5_3$, —$CHX^5_2$, —$CH_2X^5$, —$OCX^5_3$, —$OCH_2X^5$, —$OCHX^5_2$, —CN, —$SR^{5D}$, —$NR^{5A}R^{5B}$, or substituted or unsubstituted $C_1$-$C_6$ alkyl. In embodiments, $R^5$ is hydrogen, halogen, —$CX^5_3$, —$NR^{5A}R^{5B}$, or substituted or unsubstituted $C_1$-$C_6$ alkyl. In embodiments, $R^5$ is hydrogen, halogen, —$CF_3$, —$NH_2$, —$NH(CH_3)$ or unsubstituted $C_1$-$C_6$ alkyl. In embodiments, $R^5$ is hydrogen or unsubstituted methyl. In embodiments, $R^5$ is unsubstituted methyl. In embodiments, $R^5$ is unsubstituted $C_1$-$C_3$ alkyl. In embodiments, $R^5$ is unsubstituted ethyl. In embodiments, $R^5$ is unsubstituted methyl.

In embodiments, $R^5$ is $R^{32}$-substituted or unsubstituted alkyl (e.g., $C_1$-$C_8$ alkyl, $C_1$-$C_6$ alkyl, or $C_1$-$C_4$ alkyl). In embodiments, $R^5$ is $R^{32}$-substituted alkyl (e.g., $C_1$-$C_8$ alkyl, $C_1$-$C_6$ alkyl, or $C_1$-$C_4$ alkyl). In embodiments, $R^5$ is an unsubstituted alkyl (e.g., $C_1$-$C_8$ alkyl, $C_1$-$C_6$ alkyl, or $C_1$-$C_4$ alkyl). In embodiments, $R^5$ is $R^{32}$-substituted or unsubstituted heteroalkyl (e.g., 2 to 8 membered heteroalkyl, 2 to 6 membered heteroalkyl, or 2 to 4 membered heteroalkyl). In embodiments, $R^5$ is $R^{32}$-substituted heteroalkyl (e.g., 2 to 8 membered heteroalkyl, 2 to 6 membered heteroalkyl, or 2 to 4 membered heteroalkyl). In embodiments, $R^5$ is an unsubstituted heteroalkyl (e.g., 2 to 8 membered heteroalkyl, 2 to 6 membered heteroalkyl, or 2 to 4 membered heteroalkyl). In embodiments, $R^5$ is unsubstituted methyl. In embodiments, $R^5$ is unsubstituted $C_1$-$C_2$ alkyl. In embodiments, $R^5$ is unsubstituted $C_1$-$C_3$ alkyl. In embodiments, $R^5$ is hydrogen.

In embodiments, $R^6$ is halogen. In embodiments, $R^6$ is —$CX^6_3$. In embodiments, $R^6$ is —$CHX^6_2$. In embodiments, $R^6$ is —$CH_2X^6$. In embodiments, $R^6$ is —$OCX^6_3$. In embodiments, $R^6$ is —$OCH_2X^6$. In embodiments, $R^6$ is —$OCHX^6_2$. In embodiments, $R^6$ is —CN. In embodiments, $R^6$ is —$SR^{6D}$. In embodiments, $R^6$ is —$SO_2R^{6D}$. In embodiments, $R^6$ is —$NR^{6A}R^{6B}$. In embodiments, $R^6$ is —$C(O)R^{6C}$. In embodiments, $R^6$ is —$C(O)OR^{6C}$. In embodiments, $R^6$ is —$C(O)NR^{6A}R^{6B}$. In embodiments, $R^6$ is —$OR^{6D}$. In embodiments, $R^6$ is —$NR^{6A}C(O)R^{6C}$. In embodiments, $R^6$ is —$NR^{6A}C(O)OR^{6C}$. In embodiments, $R^6$ is —$SO_2NR^{6A}R^{6B}$. In embodiments, $R^6$ is —$NR^{6A}SO_2R^{6D}$. In embodiments, $R^6$ is —$C(O)NR^{6A}OR^{6B}$.

In embodiments, $R^6$ is substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^6$ is hydrogen, substituted or unsubstituted $C_1$-$C_8$ alkyl, or substituted or unsubstituted 2 to 8 membered heteroalkyl.

In embodiments, $R^6$ is independently halogen, —$CX^6_3$, —$CHX^6_2$, —$CH_2X^6$, —$OCX^6_3$, —$OCH_2X^6$, —$OCHX^6_2$, —CN, —$SR^{6D}$, —$SO_2R^{6D}$, —$NR^{6A}R^{6B}$, —$C(O)R^{6C}$, —$C(O)OR^{6C}$, —$C(O)NR^{6A}R^{6B}$, —$OR^{6D}$, —$NR^{6A}C(O)R^{6C}$, —$NR^{6A}C(O)OR^{6C}$, substituted or unsubstituted alkyl, or substituted or unsubstituted heteroalkyl.

In embodiments, $R^6$ is $R^{35}$-substituted or unsubstituted alkyl (e.g., $C_1$-$C_8$ alkyl, $C_1$-$C_6$ alkyl, or $C_1$-$C_4$ alkyl). In embodiments, $R^6$ is $R^{35}$-substituted alkyl (e.g., $C_1$-$C_8$ alkyl, $C_1$-$C_6$ alkyl, or $C_1$-$C_4$ alkyl). In embodiments, $R^6$ is an unsubstituted alkyl (e.g., $C_1$-$C_8$ alkyl, $C_1$-$C_6$ alkyl, or $C_1$-$C_4$ alkyl). In embodiments, $R^6$ is $R^{35}$-substituted or unsubstituted heteroalkyl (e.g., 2 to 8 membered heteroalkyl, 2 to 6 membered heteroalkyl, or 2 to 4 membered heteroalkyl). In embodiments, $R^6$ is $R^{35}$-substituted heteroalkyl (e.g., 2 to 8 membered heteroalkyl, 2 to 6 membered heteroalkyl, or 2 to 4 membered heteroalkyl). In embodiments, $R^6$ is an unsubstituted heteroalkyl (e.g., 2 to 8 membered heteroalkyl, 2 to 6 membered heteroalkyl, or 2 to 4 membered heteroalkyl). In embodiments, $R^6$ is —O-(substituted or unsubstituted $C_1$-$C_8$ alkyl). In embodiments, $R^6$ is —O-(substituted or unsubstituted $C_1$-$C_6$ alkyl). In embodiments, $R^6$ is —O-

(substituted or unsubstituted $C_1$-$C_4$ alkyl). In embodiments, $R^6$ is —$OCH_3$. In embodiments, $R^6$ is $R^{35}$-substituted or unsubstituted 3 to 8 membered heterocycloalkyl, wherein the heterocycloalkyl includes an oxygen atom. In embodiments, $R^6$ is $R^{35}$-substituted or unsubstituted 5 to 6 membered heterocycloalkyl, wherein the heterocycloalkyl includes an oxygen atom. In embodiments, $R^6$ is $R^{35}$-substituted or unsubstituted 5 membered heterocycloalkyl, wherein the heterocycloalkyl includes an oxygen atom. In embodiments, $R^6$ is $R^{35}$-substituted or unsubstituted 6 membered heterocycloalkyl, wherein the heterocycloalkyl includes an oxygen atom. In embodiments, $R^6$ is substituted or unsubstituted heteroalkyl, or substituted or unsubstituted heterocycloalkyl. In embodiments, $R^6$ is substituted or unsubstituted 2 to 8 membered heteroalkyl. In embodiments, $R^6$ is substituted or unsubstituted 2 to 6 membered heteroalkyl. In embodiments, $R^6$ is substituted or unsubstituted 2 to 4 membered heteroalkyl. In embodiments, $R^6$ is substituted or unsubstituted 2 membered heteroalkyl. In embodiments, $R^6$ is substituted or unsubstituted 3 membered heteroalkyl. In embodiments, $R^6$ is substituted or unsubstituted 4 membered heteroalkyl. In embodiments, $R^6$ is substituted or unsubstituted 5 membered heteroalkyl. In embodiments, $R^6$ is substituted or unsubstituted 6 membered heteroalkyl. In embodiments, $R^6$ is substituted or unsubstituted 7 membered heteroalkyl. In embodiments, $R^6$ is substituted or unsubstituted 8 membered heteroalkyl. In embodiments, $R^6$ is substituted 2 to 8 membered heteroalkyl. In embodiments, $R^6$ is substituted 2 to 6 membered heteroalkyl. In embodiments, $R^6$ is substituted 2 to 4 membered heteroalkyl. In embodiments, $R^6$ is substituted 2 membered heteroalkyl. In embodiments, $R^6$ is substituted 3 membered heteroalkyl. In embodiments, $R^6$ is substituted 4 membered heteroalkyl. In embodiments, $R^6$ is substituted 5 membered heteroalkyl. In embodiments, $R^6$ is substituted 6 membered heteroalkyl. In embodiments, $R^6$ is substituted 7 membered heteroalkyl. In embodiments, $R^6$ is substituted 8 membered heteroalkyl. In embodiments, $R^6$ is unsubstituted 2 to 8 membered heteroalkyl. In embodiments, $R^6$ is unsubstituted 2 to 6 membered heteroalkyl. In embodiments, $R^6$ is unsubstituted 2 to 4 membered heteroalkyl. In embodiments, $R^6$ is unsubstituted 2 membered heteroalkyl. In embodiments, $R^6$ is unsubstituted 3 membered heteroalkyl. In embodiments, $R^6$ is unsubstituted 4 membered heteroalkyl. In embodiments, $R^6$ is unsubstituted 5 membered heteroalkyl. In embodiments, $R^6$ is unsubstituted 6 membered heteroalkyl. In embodiments, $R^6$ is unsubstituted 7 membered heteroalkyl. In embodiments, $R^6$ is unsubstituted 8 membered heteroalkyl.

In embodiments, $R^6$ is $R^{35}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^6$ is $R^{35}$-substituted cycloalkyl (e.g., $C_3$-$C_8$ cycloalkyl, $C_3$-$C_6$ cycloalkyl, or $C_5$-$C_6$ cycloalkyl). In embodiments, $R^6$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^6$ is $R^{35}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^6$ is $R^{35}$-substituted heterocycloalkyl (e.g., 3 to 8 membered heterocycloalkyl, 3 to 6 membered heterocycloalkyl, or 5 to 6 membered heterocycloalkyl). In embodiments, $R^6$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^6$ is $R^{35}$-substituted or unsubstituted aryl (e.g., $C_6$-$C_{10}$ aryl, $C_{10}$ aryl, or phenyl). In embodiments, $R^6$ is $R^{35}$-substituted aryl (e.g., $C_6$-$C_{10}$ aryl, $C_{10}$ aryl, or phenyl). In embodiments, $R^6$ is an unsubstituted aryl (e.g., $C_6$-$C_{10}$ aryl, $C_{10}$ aryl, or phenyl).

In embodiments, $R^6$ is $R^{35}$-substituted or unsubstituted heteroaryl (e.g., 5 to 10 membered heteroaryl, 5 to 9 membered heteroaryl, or 5 to 6 membered heteroaryl). In embodiments, $R^6$ is $R^{35}$-substituted heteroaryl (e.g., 5 to 10 membered heteroaryl, 5 to 9 membered heteroaryl, or 5 to 6 membered heteroaryl). In embodiments, $R^6$ is an unsubstituted heteroaryl (e.g., 5 to 10 membered heteroaryl, 5 to 9 membered heteroaryl, or 5 to 6 membered heteroaryl).

In embodiments, $R^{35}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —$CN$, —$OH$, —$NH_2$, —$COOH$, —$CONH_2$, —$NO_2$, —$SH$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{36}$-substituted or unsubstituted alkyl (e.g., $C_1$-$C_8$ alkyl, $C_1$-$C_6$ alkyl, or $C_1$-$C_4$ alkyl), $R^{36}$-substituted or unsubstituted heteroalkyl (e.g., 2 to 8 membered heteroalkyl, 2 to 6 membered heteroalkyl, or 2 to 4 membered heteroalkyl), $R^{36}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{36}$-substituted or unsubstituted heterocycloalkyl (e.g., 3 to 8 membered heterocycloalkyl, 3 to 6 membered heterocycloalkyl, or 5 to 6 membered heterocycloalkyl), $R^{36}$-substituted or unsubstituted aryl (e.g., $C_6$-$C_{10}$ aryl, $C_{10}$ aryl, or phenyl), or $R^{36}$-substituted or unsubstituted heteroaryl (e.g., 5 to 10 membered heteroaryl, 5 to 9 membered heteroaryl, or 5 to 6 membered heteroaryl).

In embodiments, $R^{35}$ is independently unsubstituted phenyl. In embodiments, $R^{35}$ is independently unsubstituted methyl. In embodiments, $R^{35}$ is independently —$CF_3$. In embodiments, $R^{35}$ is independently —$NH_2$. In embodiments, $R^{35}$ is independently unsubstituted benzyl. In embodiments, $R^{35}$ is independently oxo. In embodiments, $R^{35}$ is independently halogen. In embodiments, $R^{35}$ is independently —$CCl_3$. In embodiments, $R^{35}$ is independently —$CBr_3$. In embodiments, $R^{35}$ is independently —$CF_3$. In embodiments, $R^{35}$ is independently —$CI_3$. In embodiments, $R^{35}$ is independently $CHCl_2$. In embodiments, $R^{35}$ is independently —$CHBr_2$. In embodiments, $R^{35}$ is independently —$CHF_2$. In embodiments, $R^{35}$ is independently —$CHI_2$. In embodiments, $R^{35}$ is independently —$CH_2Cl$. In embodiments, $R^{35}$ is independently —$CH_2Br$. In embodiments, $R^{35}$ is independently —$CH_2F$. In embodiments, $R^{35}$ is independently —$CH_2I$. In embodiments, $R^{35}$ is independently —$CN$. In embodiments, $R^{35}$ is independently —$OH$. In embodiments, $R^{35}$ is independently —$NH_2$. In embodiments, $R^{35}$ is independently —$COOH$. In embodiments, $R^{35}$ is independently —$CONH_2$. In embodiments, $R^{35}$ is independently —$NO_2$. In embodiments, $R^{35}$ is independently —$SH$. In embodiments, $R^{35}$ is independently —$SO_3H$. In embodiments, $R^{35}$ is independently —$SO_4H$. In embodiments, $R^{35}$ is independently —$SO_2NH_2$. In embodiments, $R^{35}$ is independently —$NHNH_2$. In embodiments, $R^{35}$ is independently —$ONH_2$. In embodiments, $R^{35}$ is independently —$NHC(O)NHNH_2$. In embodiments, $R^{35}$ is independently —$NHC(O)NH_2$. In embodiments, $R^{35}$ is independently —$NHSO_2H$. In embodiments, $R^{35}$ is independently —$NHC(O)H$. In embodiments, $R^{35}$ is independently —$NHC(O)OH$. In embodiments, $R^{35}$ is independently —$NHOH$. In embodiments, $R^{35}$ is independently —$OCCl_3$. In embodiments, $R^{35}$ is independently —$OCF_3$. In embodiments, $R^{35}$ is independently —OCBr$_3$. In embodiments, R$^{35}$ is independently —OCI$_3$. In embodiments, R$^{35}$ is independently —OCHCl$_2$. In embodiments, R$^{35}$ is independently —OCHBr$_2$. In embodiments, R$^{35}$ is independently —OCHI$_2$. In embodiments, R$^{35}$ is independently —OCHF$_2$. In embodiments, R$^{35}$ is independently —OCH$_2$Cl. In embodiments, R$^{35}$ is independently —OCH$_2$Br. In embodiments, R$^{35}$ is independently —OCH$_2$I. In embodiments, R$^{35}$ is independently —OCH$_2$F. In embodiments, R$^{35}$ is independently —O(C$_4$ alkyl). In embodiments, R$^{35}$ is independently In embodiments, R$^{35}$ is independently In embodiments, R$^{35}$ is R$^{36}$-substituted or unsubstituted alkyl (e.g., C$_1$-C$_8$ alkyl, C$_1$-C$_6$ alkyl, or C$_1$-C$_4$ alkyl). In embodiments, R$^{35}$ is R$^{36}$-substituted alkyl (e.g., C$_1$-C$_8$ alkyl, C$_1$-C$_6$ alkyl, or C$_1$-C$_4$ alkyl). In embodiments, R$^{35}$ is an unsubstituted alkyl (e.g., C$_1$-C$_8$ alkyl, C$_1$-C$_6$ alkyl, or C$_1$-C$_4$ alkyl).

In embodiments, R$^{35}$ is R$^{36}$-substituted or unsubstituted heteroalkyl (e.g., 2 to 8 membered heteroalkyl, 2 to 6 membered heteroalkyl, or 2 to 4 membered heteroalkyl). In embodiments, R$^{35}$ is R$^{36}$-substituted heteroalkyl (e.g., 2 to 8 membered heteroalkyl, 2 to 6 membered heteroalkyl, or 2 to 4 membered heteroalkyl). In embodiments, R$^{35}$ is an unsubstituted heteroalkyl (e.g., 2 to 8 membered heteroalkyl, 2 to 6 membered heteroalkyl, or 2 to 4 membered heteroalkyl). In embodiments, R$^{35}$ is substituted or unsubstituted 2 to 8 membered heteroalkyl. In embodiments, R$^{35}$ is substituted or unsubstituted 2 to 6 membered heteroalkyl. In embodiments, R$^{35}$ is substituted or unsubstituted 2 to 4 membered heteroalkyl. In embodiments, R$^{35}$ is substituted or unsubstituted 2 membered heteroalkyl. In embodiments, R$^{35}$ is substituted or unsubstituted 3 membered heteroalkyl. In embodiments, R$^{35}$ is substituted or unsubstituted 4 membered heteroalkyl. In embodiments, R$^{35}$ is substituted or unsubstituted 5 membered heteroalkyl. In embodiments, R$^{35}$ is substituted or unsubstituted 6 membered heteroalkyl. In embodiments, R$^{35}$ is substituted or unsubstituted 7 membered heteroalkyl. In embodiments, R$^{35}$ is substituted or unsubstituted 8 membered heteroalkyl. In embodiments, R$^{35}$ is substituted 2 to 8 membered heteroalkyl. In embodiments, R$^{35}$ is substituted 2 to 6 membered heteroalkyl. In embodiments, R$^{35}$ is substituted 2 to 4 membered heteroalkyl. In embodiments, R$^{35}$ is substituted 2 membered heteroalkyl. In embodiments, R$^{35}$ is substituted 3 membered heteroalkyl. In embodiments, R$^{35}$ is substituted 4 membered heteroalkyl. In embodiments, R$^{35}$ is substituted 5 membered heteroalkyl. In embodiments, R$^{35}$ is substituted 6 membered heteroalkyl. In embodiments, R$^{35}$ is substituted 7 membered heteroalkyl. In embodiments, R$^{35}$ is substituted 8 membered heteroalkyl. In embodiments, R$^{35}$ is unsubstituted 2 to 8 membered heteroalkyl. In embodiments, R$^{35}$ is unsubstituted 2 to 6 membered heteroalkyl. In embodiments, R$^{35}$ is unsubstituted 2 to 4 membered heteroalkyl. In embodiments, R$^{35}$ is unsubstituted 2 membered heteroalkyl. In embodiments, R$^{35}$ is unsubstituted 3 membered heteroalkyl. In embodiments, R$^{35}$ is unsubstituted 4 membered heteroalkyl. In embodiments, R$^{35}$ is unsubstituted 5 membered heteroalkyl. In embodiments, R$^{35}$ is unsubstituted 6 membered heteroalkyl. In embodiments, R$^{35}$ is unsubstituted 7 membered heteroalkyl. In embodiments, R$^{35}$ is unsubstituted 8 membered heteroalkyl.

In embodiments, R$^{35}$ is R$^{36}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{35}$ is R$^{36}$-substituted cycloalkyl (e.g., C$_3$-C$_8$ cycloalkyl, C$_3$-C$_6$ cycloalkyl, or C$_5$-C$_6$ cycloalkyl). In embodiments, R$^{35}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, R$^{35}$ is R$^{36}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{35}$ is R$^{36}$-substituted heterocycloalkyl (e.g., 3 to 8 membered heterocycloalkyl, 3 to 6 membered heterocycloalkyl, or 5 to 6 membered heterocycloalkyl). In embodiments, R$^{35}$ is an unsubstituted heterocycloalkyl (e.g., 3 to 8 membered heterocycloalkyl, 3 to 6 membered heterocycloalkyl, or 5 to 6 membered heterocycloalkyl). In embodiments, R$^{35}$ is R$^{36}$-substituted or unsubstituted 3 to 8 membered heterocycloalkyl. In embodiments, R$^{35}$ is R$^{36}$-substituted 3 to 8 membered heterocycloalkyl. In embodiments, R$^{35}$ is unsubstituted 3 to 8 membered heterocycloalkyl. In embodiments, R$^{35}$ is R$^{36}$-substituted or unsubstituted 3 to 6 membered heterocycloalkyl. In embodiments, R$^{35}$ is R$^{36}$-substituted 3 to 6 membered heterocycloalkyl. In embodiments, R$^{35}$ is unsubstituted 3 to 6 membered heterocycloalkyl. In embodiments, R$^{35}$ is R$^{36}$-substituted or unsubstituted 5 to 6 membered heterocycloalkyl. In embodiments, R$^{35}$ is R$^{36}$-substituted 5 to 6 membered heterocycloalkyl. In embodiments, R$^{35}$ is unsubstituted 5 to 6 membered heterocycloalkyl.

In embodiments, R$^{35}$ is R$^{36}$-substituted or unsubstituted aryl (e.g., C$_6$-C$_{10}$ aryl, C$_{10}$ aryl, or phenyl). In embodiments, R$^{35}$ is R$^{36}$-substituted aryl (e.g., C$_6$-C$_{10}$ aryl, C$_{10}$ aryl, or phenyl). In embodiments, R$^{35}$ is an unsubstituted aryl (e.g., C$_6$-C$_{10}$ aryl, C$_{10}$ aryl, or phenyl).

In embodiments, R$^{35}$ is R$^{36}$-substituted or unsubstituted heteroaryl (e.g., 5 to 10 membered heteroaryl, 5 to 9 membered heteroaryl, or 5 to 6 membered heteroaryl). In embodiments, R$^{35}$ is R$^{36}$-substituted heteroaryl (e.g., 5 to 10 membered heteroaryl, 5 to 9 membered heteroaryl, or 5 to 6 membered heteroaryl). In embodiments, R$^{35}$ is an unsubstituted heteroaryl (e.g., 5 to 10 membered heteroaryl, 5 to 9 membered heteroaryl, or 5 to 6 membered heteroaryl).

In embodiments, R$^{35}$ is

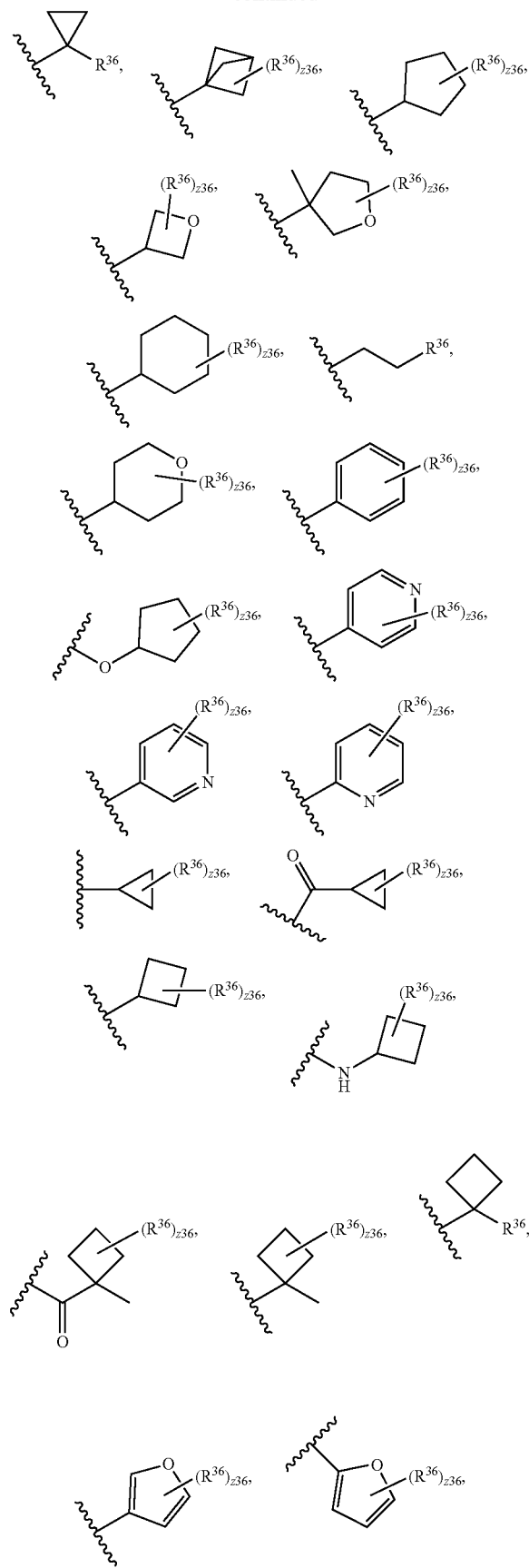
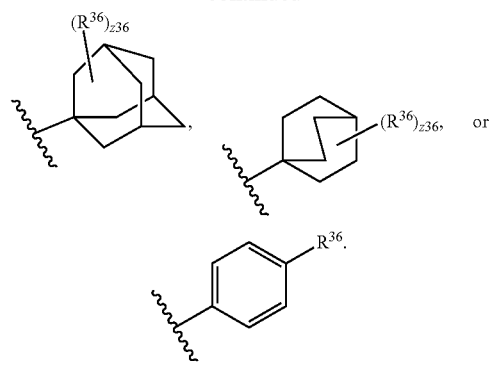
In embodiments, z36 is 0. In embodiments, z36 is 1. In embodiments, z36 is 2. In embodiments, z36 is 3. In embodiments, z36 is 4. In embodiments, z36 is 5. In embodiments, z36 is 6. In embodiments, z36 is 7. In embodiments, z36 is 8. In embodiments, z36 is an integer from 1 to 3. In embodiments, z36 is an integer from 1 to 2. In embodiments, z36 is an integer from 1 to 4.
In embodiments, $R^{35}$ is:
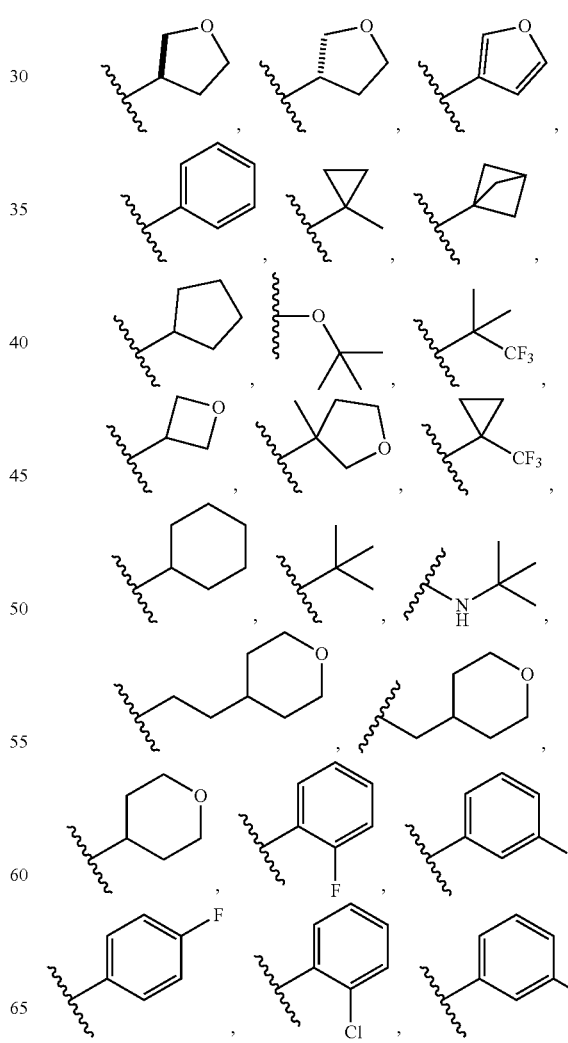

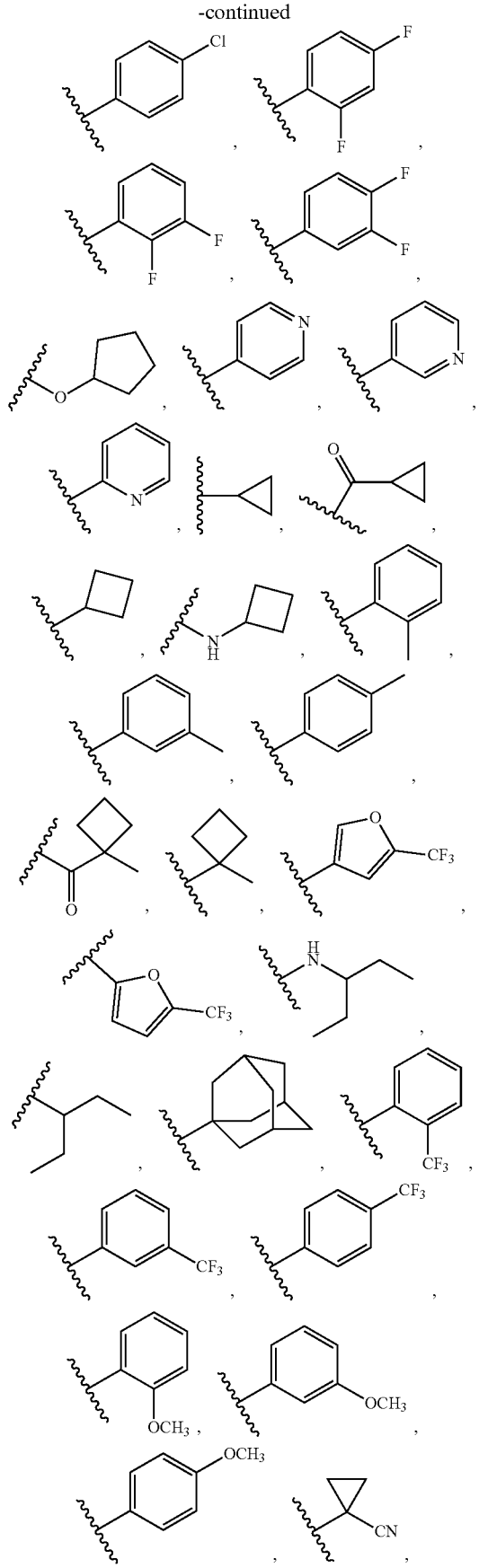
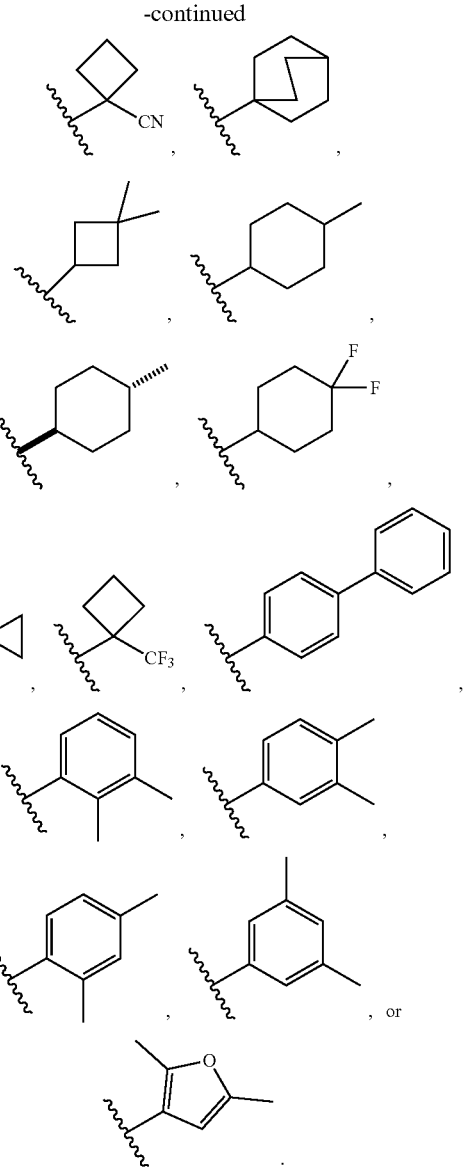
In embodiments, $R^{35}$ is:
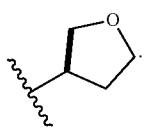
In embodiments, $R^{35}$ is
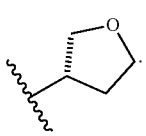

In embodiments, $R^{35}$ is
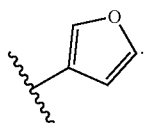 [SMILES: *c1ccoc1]
In embodiments, $R^{35}$ is
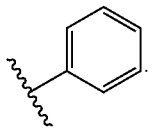 [SMILES: *c1ccccc1]
In embodiments, $R^{35}$ is
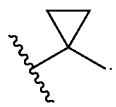
In embodiments, $R^{35}$ is
In embodiments, $R^{35}$ is
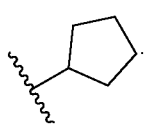 [SMILES: *C1CCCC1]
In embodiments, $R^{35}$ is
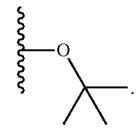 [SMILES: *OC(C)(C)C]
In embodiments, $R^{35}$ is
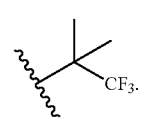
In embodiments, $R^{35}$ is
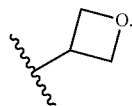 [SMILES: *C1COC1]
In embodiments, $R^{35}$ is
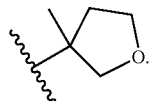 [SMILES: *C1(C)CCOC1]
In embodiments, $R^{35}$ is
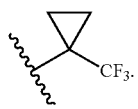 [SMILES: *C1(C(F)(F)F)CC1]
In embodiments, $R^{35}$ is
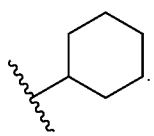
In embodiments, $R^{35}$ is
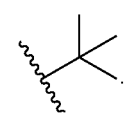
In embodiments, $R^{35}$ is
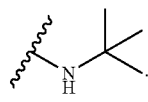 [SMILES: *NC(C)(C)C]
In embodiments, $R^{35}$ is
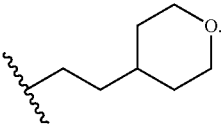 [SMILES: *CCC1CCOCC1]
In embodiments, $R^{35}$ is
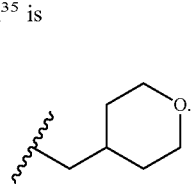

In embodiments, $R^{35}$ is
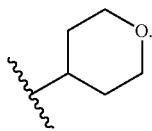 [SMILES: *C1CCOCC1]
In embodiments, $R^{35}$ is
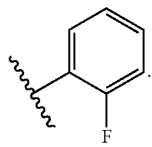 [SMILES: *c1ccccc1F]
In embodiments, $R^{35}$ is
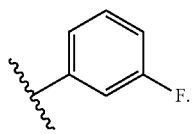 [SMILES: *c1cccc(F)c1]
In embodiments, $R^{35}$ is
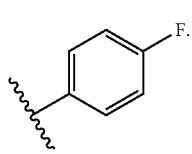 [SMILES: *c1ccc(F)cc1]
In embodiments, $R^{35}$ is
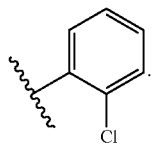 [SMILES: *c1ccccc1Cl]
In embodiments, $R^{35}$ is
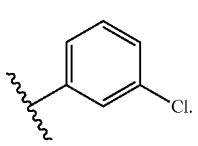 [SMILES: *c1cccc(Cl)c1]
In embodiments, $R^{35}$ is
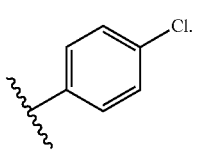 [SMILES: *c1ccc(Cl)cc1]
In embodiments, $R^{35}$ is
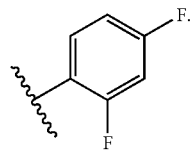 [SMILES: *c1ccc(F)cc1F]
In embodiments, $R^{35}$ is
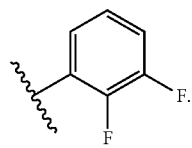 [SMILES: *c1cccc(F)c1F]
In embodiments, $R^{35}$ is
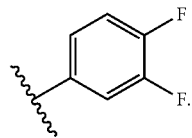 [SMILES: *c1ccc(F)c(F)c1]
In embodiments, $R^{35}$ is
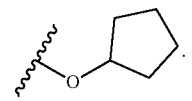 [SMILES: *OC1CCCC1]
In embodiments, $R^{35}$ is
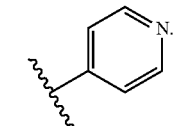 [SMILES: *c1ccncc1]
In embodiments, $R^{35}$ is
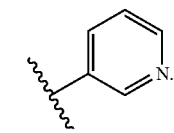
In embodiments, $R^{35}$ is
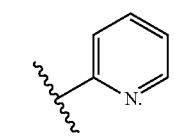 [SMILES: *c1ccccn1]

In embodiments, $R^{35}$ is
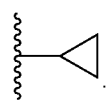
In embodiments, $R^{35}$ is
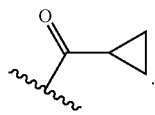 [SMILES: *C(=O)C1CC1]
In embodiments, $R^{35}$ is
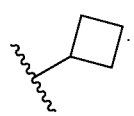
In embodiments, $R^{35}$ is
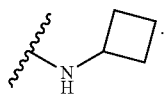
In embodiments, $R^{35}$ is
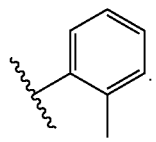 [SMILES: *c1ccccc1C]
In embodiments, $R^{35}$ is
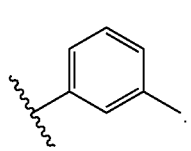 [SMILES: *c1cccc(C)c1]
In embodiments, $R^{35}$ is
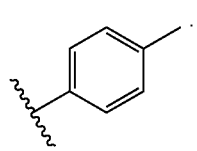
In embodiments, $R^{35}$ is
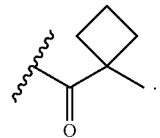 [SMILES: *C(=O)C1(C)CCC1]
In embodiments, $R^{35}$ is
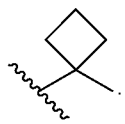
In embodiments, $R^{35}$ is
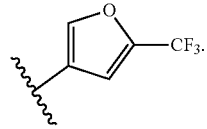 [SMILES: *c1coc(C(F)(F)F)c1]
In embodiments, $R^{35}$ is
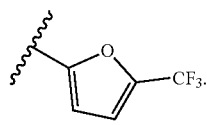 [SMILES: *c1ccc(C(F)(F)F)o1]
In embodiments, $R^{35}$ is
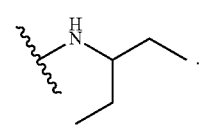 [SMILES: *NC(CC)CC]
In embodiments, $R^{35}$ is
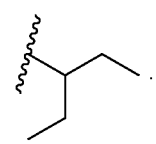 [SMILES: *C(CC)CC]
In embodiments, $R^{35}$ is
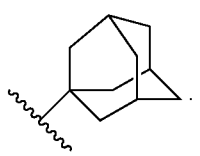 [SMILES: *C12CC3CC(CC(C3)C1)C2]

In embodiments, R$^{35}$ is
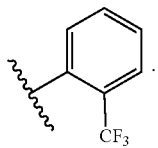
In embodiments, R$^{35}$ is
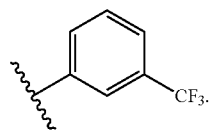 [SMILES: *c1cccc(C(F)(F)F)c1]
In embodiments, R$^{35}$ is
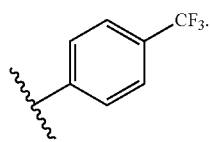 [SMILES: *c1ccc(C(F)(F)F)cc1]
In embodiments, R$^{35}$ is
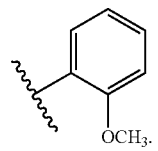 [SMILES: *c1ccccc1OC]
In embodiments, R$^{35}$ is
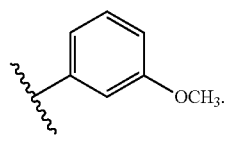
In embodiments, R$^{35}$ is
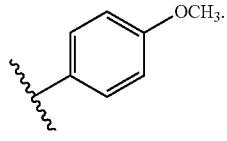 [SMILES: *c1ccc(OC)cc1]
In embodiments, R$^{35}$ is
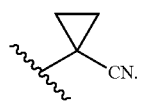 [SMILES: *C1(C#N)CC1]
In embodiments, R$^{35}$ is
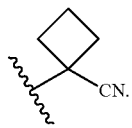 [SMILES: *C1(C#N)CCC1]
In embodiments, R$^{35}$ is
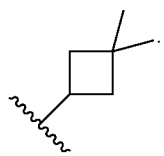 [SMILES: *C1CC(C)(C)C1]
In embodiments, R$^{35}$ is
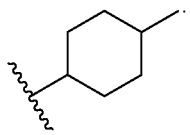 [SMILES: *C1CCC(C)CC1]
In embodiments, R$^{35}$ is
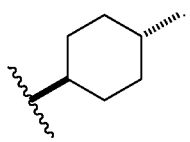 [SMILES: *[C@H]1CC[C@H](C)CC1]
In embodiments, R$^{35}$ is
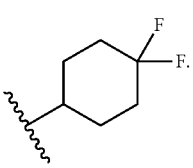 [SMILES: *C1CCC(F)(F)CC1]
In embodiments, R$^{35}$ is
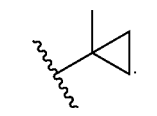

In embodiments, $R^{35}$ is
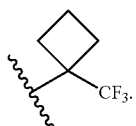 [SMILES: *C1(C(F)(F)F)CCC1]
In embodiments, $R^{35}$ is
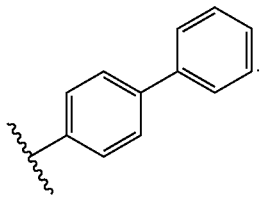 [SMILES: *c1ccc(-c2ccccc2)cc1]
In embodiments, $R^{35}$ is
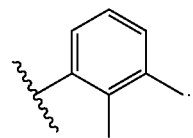 [SMILES: *c1cccc(C)c1C]
In embodiments, $R^{35}$ is
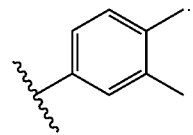 [SMILES: *c1ccc(C)c(C)c1]
In embodiments, $R^{35}$ is
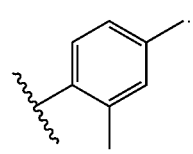 [SMILES: *c1ccc(C)cc1C]
In embodiments, $R^{35}$ is
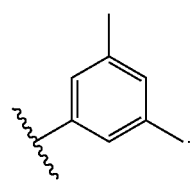 [SMILES: *c1cc(C)cc(C)c1]
In embodiments, $R^{35}$ is
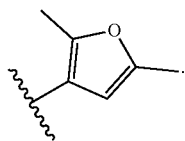 [SMILES: *c1cc(C)oc1C]
In embodiments, $R^{36}$ is
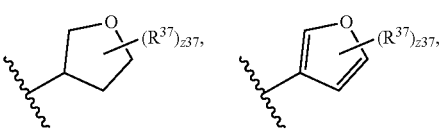
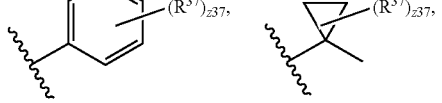
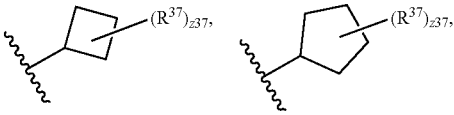
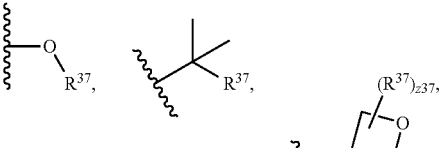
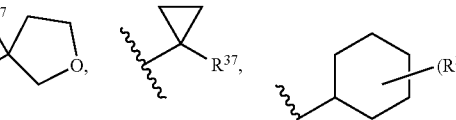
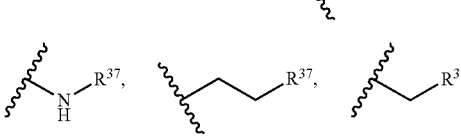
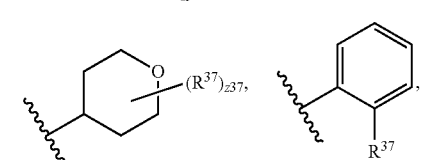
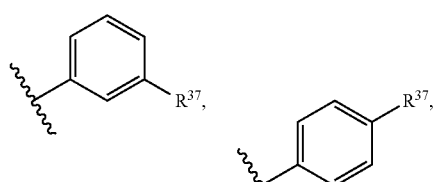

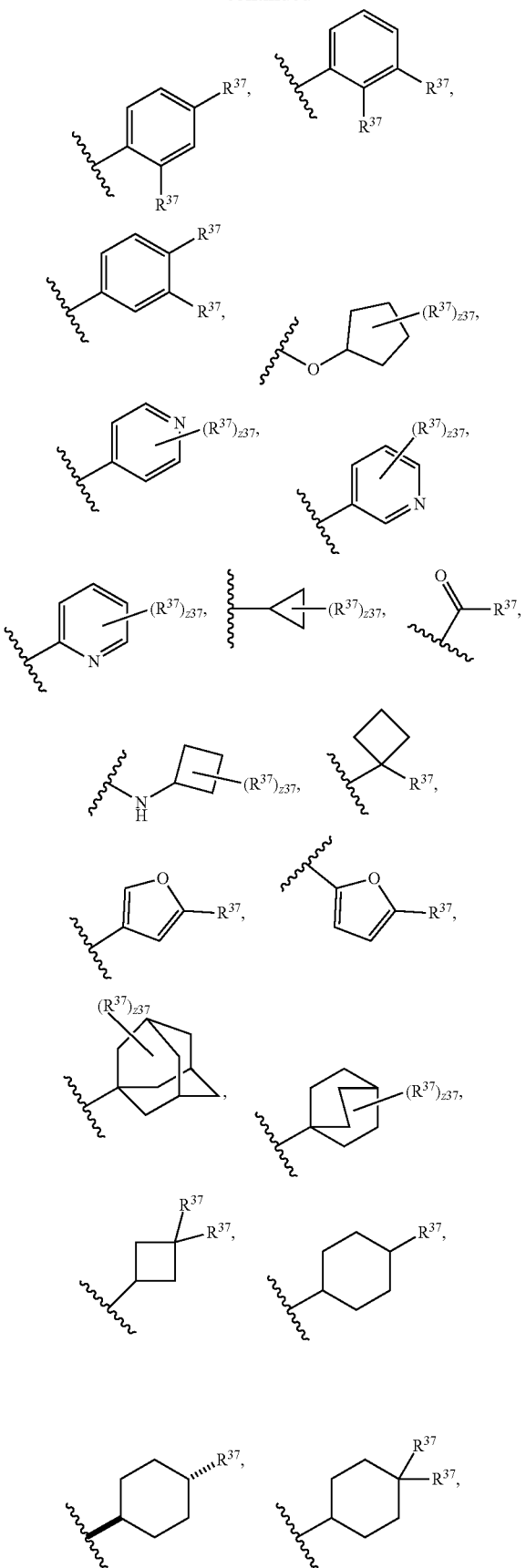
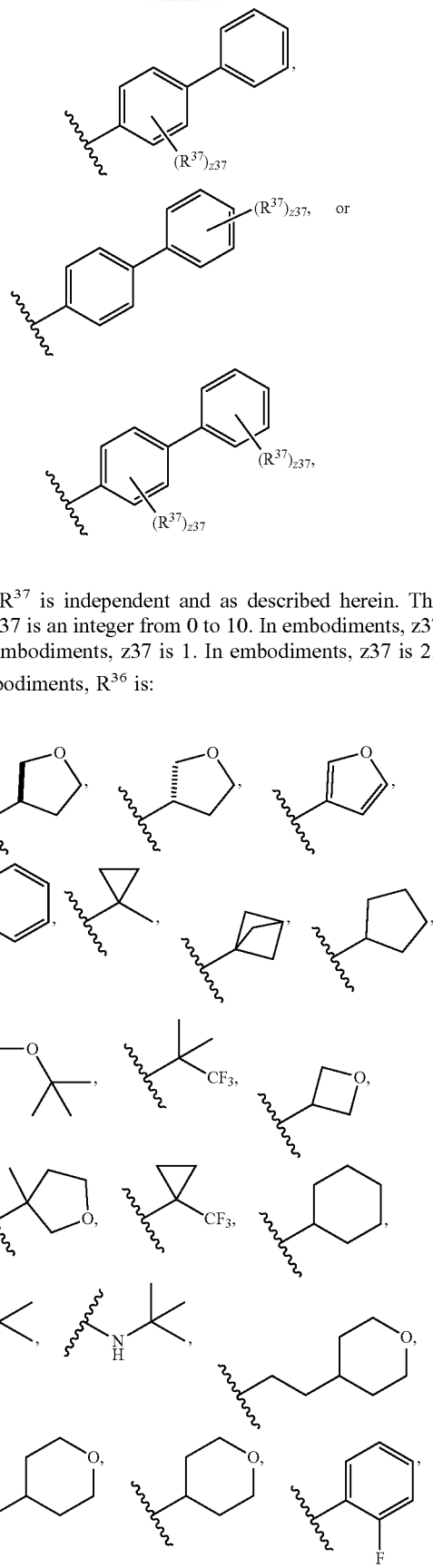
wherein R$^{37}$ is independent and as described herein. The symbol z37 is an integer from 0 to 10. In embodiments, z37 is 0. In embodiments, z37 is 1. In embodiments, z37 is 2.
In embodiments, R$^{36}$ is:

179
-continued
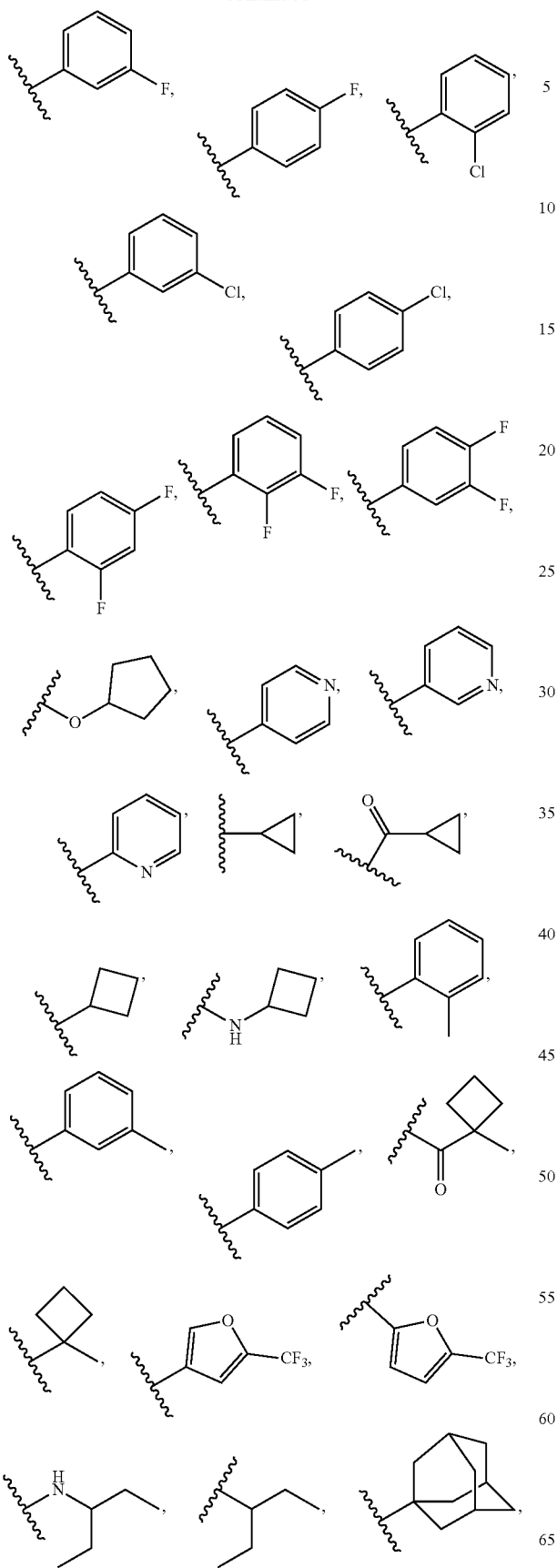
180
-continued
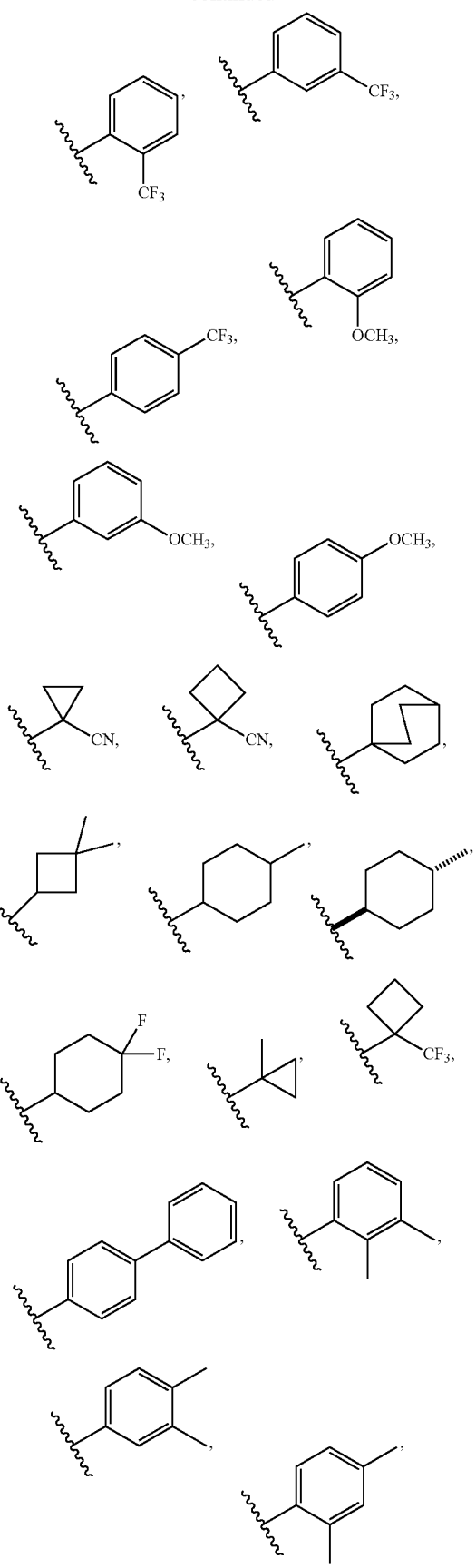

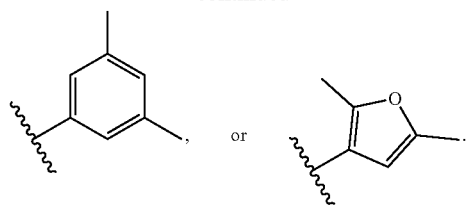 or 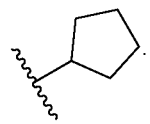,
In embodiments, $R^{36}$ is:
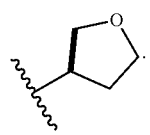.
In embodiments, $R^{36}$ is
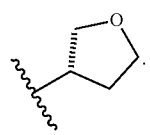.
In embodiments, $R^{36}$ is
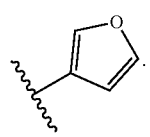 [SMILES: *c1ccoc1].
In embodiments, $R^{36}$ is
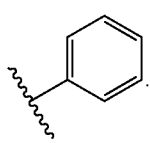 [SMILES: *c1ccccc1].
In embodiments, $R^{36}$ is
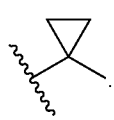 [SMILES: *C1(C)CC1].
In embodiments, $R^{36}$ is
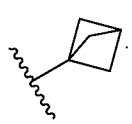
In embodiments, $R^{36}$ is
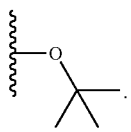 [SMILES: *OC(C)(C)C].
In embodiments, $R^{36}$ is
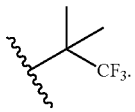 [SMILES: *C(C)(C)C(F)(F)F].
In embodiments, $R^{36}$ is
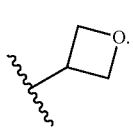 [SMILES: *C1COC1].
In embodiments, $R^{36}$ is
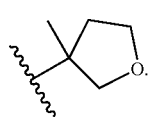 [SMILES: *C1(C)CCOC1].
In embodiments, $R^{36}$ is
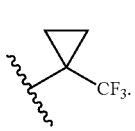.
In embodiments, $R^{36}$ is
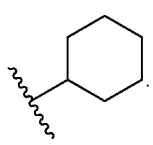.

In embodiments, $R^{36}$ is
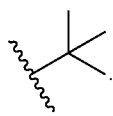
In embodiments, $R^{36}$ is
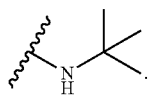 [SMILES: *NC(C)(C)C]
In embodiments, $R^{36}$ is
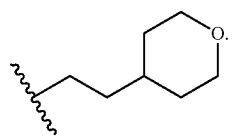 [SMILES: *CCC1CCOCC1]
In embodiments, $R^{36}$ is
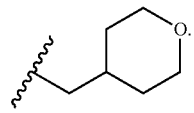 [SMILES: *CC1CCOCC1]
In embodiments, $R^{36}$ is
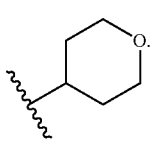 [SMILES: *C1CCOCC1]
In embodiments, $R^{36}$ is
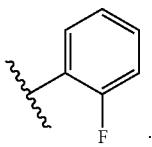 [SMILES: *c1ccccc1F]
In embodiments, $R^{36}$ is
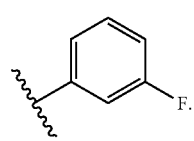
In embodiments, $R^{36}$ is
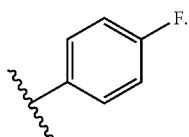 [SMILES: *c1ccc(F)cc1]
In embodiments, $R^{36}$ is
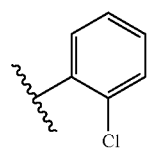
In embodiments, $R^{36}$ is
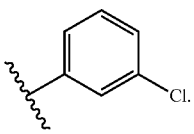 [SMILES: *c1cccc(Cl)c1]
In embodiments, $R^{36}$ is
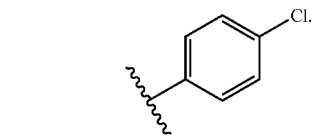 [SMILES: *c1ccc(Cl)cc1]
In embodiments, $R^{36}$ is
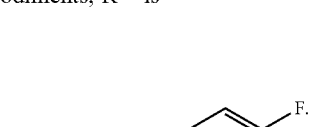
In embodiments, $R^{36}$ is
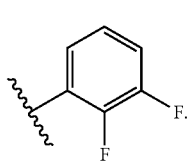 [SMILES: *c1cccc(F)c1F]

In embodiments, $R^{36}$ is S
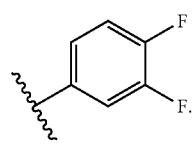
In embodiments, $R^{36}$ is
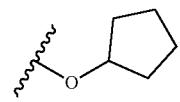
In embodiments, $R^{36}$ is
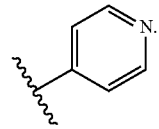 [SMILES: *c1ccncc1]
In embodiments, $R^{36}$ is
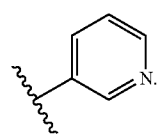 [SMILES: *c1cccnc1]
In embodiments, $R^{36}$ is
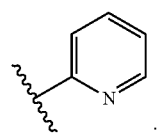 [SMILES: *c1ccccn1]
In embodiments, $R^{36}$ is
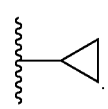
In embodiments, $R^{36}$ is
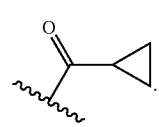 [SMILES: *C(=O)C1CC1]
In embodiments, $R^{36}$ is
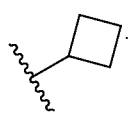 [SMILES: *C1CCC1]
In embodiments, $R^{36}$ is
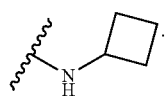 [SMILES: *NC1CCC1]
In embodiments, $R^{36}$ is
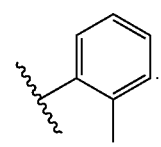
In embodiments, $R^{36}$ is
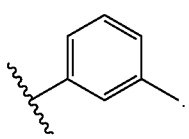 [SMILES: *c1cccc(C)c1]
In embodiments, $R^{36}$ is
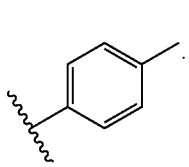 [SMILES: *c1ccc(C)cc1]
In embodiments, $R^{36}$ is
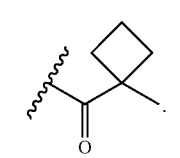 [SMILES: *C(=O)C1(C)CCC1]
In embodiments, $R^{36}$ is
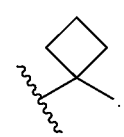

In embodiments, R³⁶ is
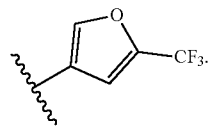 [SMILES: *c1coc(C(F)(F)F)c1]
In embodiments, R³⁶ is
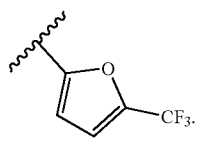 [SMILES: *c1ccc(C(F)(F)F)o1]
In embodiments, R³⁶ is
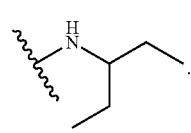 [SMILES: *NC(CC)CC]
In embodiments, R³⁶ is
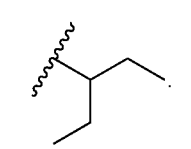 [SMILES: *C(CC)CC]
In embodiments, R³⁶ is
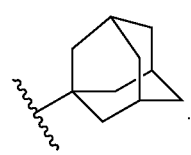
In embodiments, R³⁶ is
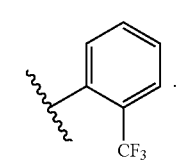
In embodiments, R³⁶ is
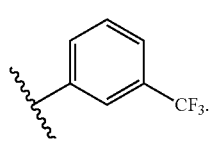 [SMILES: *c1cccc(C(F)(F)F)c1]
In embodiments, R³⁶ is
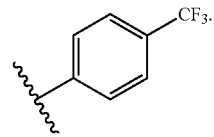
In embodiments, R³⁶ is
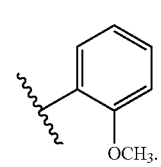
In embodiments, R³⁶ is
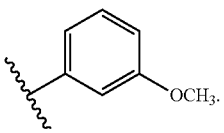 [SMILES: *c1cccc(OC)c1]
In embodiments, R³⁶ is
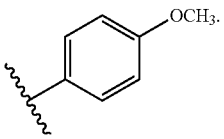 [SMILES: *c1ccc(OC)cc1]
In embodiments, R³⁶ is S
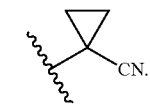 [SMILES: *C1(C#N)CC1]
In embodiments, R³⁶ is
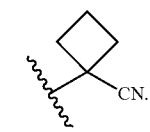
In embodiments, R³⁶ is
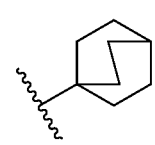

In embodiments, R³⁶ is

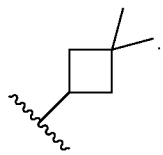 [SMILES: *C1CC(C)(C)C1]

In embodiments, R³⁶ is

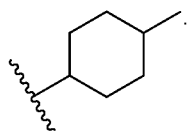 [SMILES: *C1CCC(C)CC1]

In embodiments, R³⁶ is

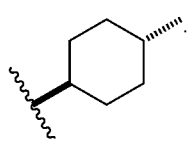 [SMILES: *[C@H]1CC[C@H](C)CC1]

In embodiments, R³⁶ is

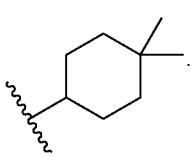 [SMILES: *C1CCC(C)(C)CC1]

In embodiments, R³⁶ is

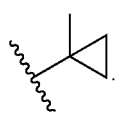

In embodiments, R³⁶ is

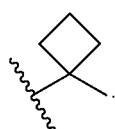

In embodiments, R³⁶ is

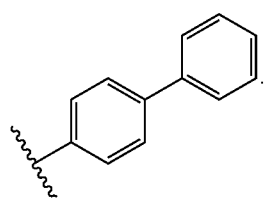 [SMILES: *c1ccc(-c2ccccc2)cc1]

In embodiments, R³⁶ is

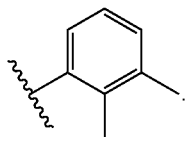 [SMILES: *c1cccc(C)c1C]

In embodiments, R³⁶ is

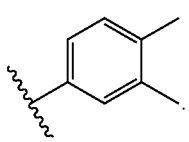 [SMILES: *c1ccc(C)c(C)c1]

In embodiments, R³⁶ is

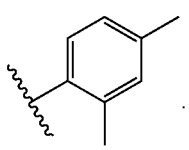 [SMILES: *c1ccc(C)cc1C]

In embodiments, R³⁶

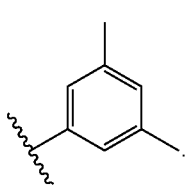 [SMILES: *c1cc(C)cc(C)c1]

In embodiments, R³⁶ is

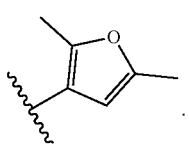 [SMILES: *c1cc(C)oc1C]

In embodiments, $R^6$ is independently halogen, $-CX^6_3$, $-CHX^6_2$, $-CH_2X^6$, $-OCX^6_3$, $-OCH_2X^6$, $-OCHX^6_2$, $-NR^{6A}R^{6B}$, $-C(O)R^{6C}$, substituted or unsubstituted $C_1$-$C_6$ alkyl, substituted or unsubstituted 2 to 6 membered heteroalkyl. In embodiments, $R^6$ is independently halogen, $-CX^6_3$, $-CHX^6_2$, $-CH_2X^6$, $-OCX^6_3$, $-OCH_2X^6$, $-OCHX^6_2$, $-CN$, $-SR^{6D}$, $-SO_2R^{6D}$, $-NR^{6A}R^{6B}$, $-C(O)R^{6C}$, $-C(O)OR^{6C}$, $-C(O)NR^{6A}R^{6B}$, $-OR^{6D}$, $-NR^{6A}C(O)R^{6C}$, $-NR^{6A}C(O)OR^{6C}$, substituted or unsubstituted $C_1$-$C_6$ alkyl, substituted or unsubstituted 2 to 6 membered heteroalkyl. In embodiments, $R^6$ is independently $-C(O)R^{6C}$, $-C(O)OR^{6C}$, $-C(O)NR^{6A}R^{6B}$, $-OR^{6D}$, $-NR^{6A}C(O)R^{6C}$, $-NR^{6A}C(O)OR^{6C}$, substituted or unsubstituted $C_1$-$C_6$ alkyl, substituted or unsubstituted 2 to 6 membered heteroalkyl. In embodiments, $R^6$ is $-F$, $-OH$, $-OCH_3$, $-OCH_2CH_3$, $-CH_2OH$, $-CH_2OCH_3$, $-NHC(O)CH_3$, $-CH_3$, $-N(CH_3)_2$, $-CH_2NH_2$, $-CH_2N(CH_3)_2$, $-NH_2$, $-NHCH_3$, $-COOH$, or $-SO_2CH_3$. In embodiments, $R^6$ is-OH, —OCH$_3$, —OCH$_2$CH$_3$, —CH$_2$OH, or —CH$_2$OCH$_3$. In embodiments, R$^6$ is substituted or unsubstituted C$_1$-C$_6$ alkyl, or substituted or unsubstituted 2 to 6 membered heteroalkyl. In embodiments, R$^6$ is R$^{35}$-substituted or unsubstituted C$_1$-C$_6$ alkyl, or R$^{35}$-substituted or unsubstituted 2 to 6 membered heteroalkyl.

In embodiments, R$^{6A}$ is hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, R$^{35A}$-substituted or unsubstituted alkyl (e.g., C$_1$-C$_8$ alkyl, C$_1$-C$_6$ alkyl, or C$_1$-C$_4$ alkyl), R$^{35A}$-substituted or unsubstituted heteroalkyl (e.g., 2 to 8 membered heteroalkyl, 2 to 6 membered heteroalkyl, or 2 to 4 membered heteroalkyl), R$^{35A}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{35A}$-substituted or unsubstituted heterocycloalkyl (e.g., 3 to 8 membered heterocycloalkyl, 3 to 6 membered heterocycloalkyl, or 5 to 6 membered heterocycloalkyl), R$^{35A}$-substituted or unsubstituted aryl (e.g., C$_6$-C$_{10}$ aryl, C$_{10}$ aryl, or phenyl), or R$^{35A}$-substituted or unsubstituted heteroaryl (e.g., 5 to 10 membered heteroaryl, 5 to 9 membered heteroaryl, or 5 to 6 membered heteroaryl).

In embodiments, R$^{6A}$ is R$^{35A}$-substituted or unsubstituted alkyl (e.g., C$_1$-C$_8$ alkyl, C$_1$-C$_6$ alkyl, or C$_1$-C$_4$ alkyl). In embodiments, R$^{6A}$ is R$^{35A}$-substituted alkyl (e.g., C$_1$-C$_8$ alkyl, C$_1$-C$_6$ alkyl, or C$_1$-C$_4$ alkyl). In embodiments, R$^{6A}$ is an unsubstituted alkyl (e.g., C$_1$-C$_8$ alkyl, C$_1$-C$_6$ alkyl, or C$_1$-C$_4$ alkyl). In embodiments, R$^{6A}$ is R$^{35A}$-substituted or unsubstituted heteroalkyl (e.g., 2 to 8 membered heteroalkyl, 2 to 6 membered heteroalkyl, or 2 to 4 membered heteroalkyl). In embodiments, R$^{6A}$ is R$^{35A}$-substituted heteroalkyl (e.g., 2 to 8 membered heteroalkyl, 2 to 6 membered heteroalkyl, or 2 to 4 membered heteroalkyl). In embodiments, R$^{6A}$ is an unsubstituted heteroalkyl (e.g., 2 to 8 membered heteroalkyl, 2 to 6 membered heteroalkyl, or 2 to 4 membered heteroalkyl). In embodiments, R$^{6A}$ is —O-(substituted or unsubstituted C$_1$-C$_8$ alkyl). In embodiments, R$^{6A}$ is —O-(substituted or unsubstituted C$_1$-C$_6$ alkyl). In embodiments, R$^{6A}$ is —O-(substituted or unsubstituted C$_1$-C$_4$ alkyl). In embodiments, R$^{6A}$ is —OCH$_3$. In embodiments, R$^{6A}$ is R$^{35A}$-substituted or unsubstituted 3 to 8 membered heterocycloalkyl, wherein the heterocycloalkyl includes an oxygen atom. In embodiments, R$^{6A}$ is R$^{35A}$-substituted or unsubstituted 5 to 6 membered heterocycloalkyl, wherein the heterocycloalkyl includes an oxygen atom. In embodiments, R$^{6A}$ is R$^{35A}$-substituted or unsubstituted 5 membered heterocycloalkyl, wherein the heterocycloalkyl includes an oxygen atom. In embodiments, R$^{6A}$ is R$^{35A}$-substituted or unsubstituted 6 membered heterocycloalkyl, wherein the heterocycloalkyl includes an oxygen atom.

In embodiments, R$^{6A}$ is R$^{35A}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{6A}$ is R$^{35A}$-substituted cycloalkyl (e.g., C$_3$-C$_8$ cycloalkyl, C$_3$-C$_6$ cycloalkyl, or C$_5$-C$_6$ cycloalkyl). In embodiments, R$^{6A}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, R$^{6A}$ is R$^{35A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{6A}$ is R$^{35A}$-substituted heterocycloalkyl (e.g., 3 to 8 membered heterocycloalkyl, 3 to 6 membered heterocycloalkyl, or 5 to 6 membered heterocycloalkyl). In embodiments, R$^{6A}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, R$^{6A}$ is R$^{35A}$-substituted or unsubstituted aryl (e.g., C$_6$-C$_{10}$ aryl, C$_{10}$ aryl, or phenyl). In embodiments, R$^{6A}$ is R$^{35A}$-substituted aryl (e.g., C$_6$-C$_{10}$ aryl, C$_{10}$ aryl, or phenyl). In embodiments, R$^{6A}$ is an unsubstituted aryl (e.g., C$_6$-C$_{10}$ aryl, C$_{10}$ aryl, or phenyl).

In embodiments, R$^{6A}$ is R$^{35A}$-substituted or unsubstituted heteroaryl (e.g., 5 to 10 membered heteroaryl, 5 to 9 membered heteroaryl, or 5 to 6 membered heteroaryl). In embodiments, R$^{6A}$ is R$^{35A}$-substituted heteroaryl (e.g., 5 to 10 membered heteroaryl, 5 to 9 membered heteroaryl, or 5 to 6 membered heteroaryl). In embodiments, R$^{6A}$ is an unsubstituted heteroaryl (e.g., 5 to 10 membered heteroaryl, 5 to 9 membered heteroaryl, or 5 to 6 membered heteroaryl).

In embodiments, R$^{6A}$ is:

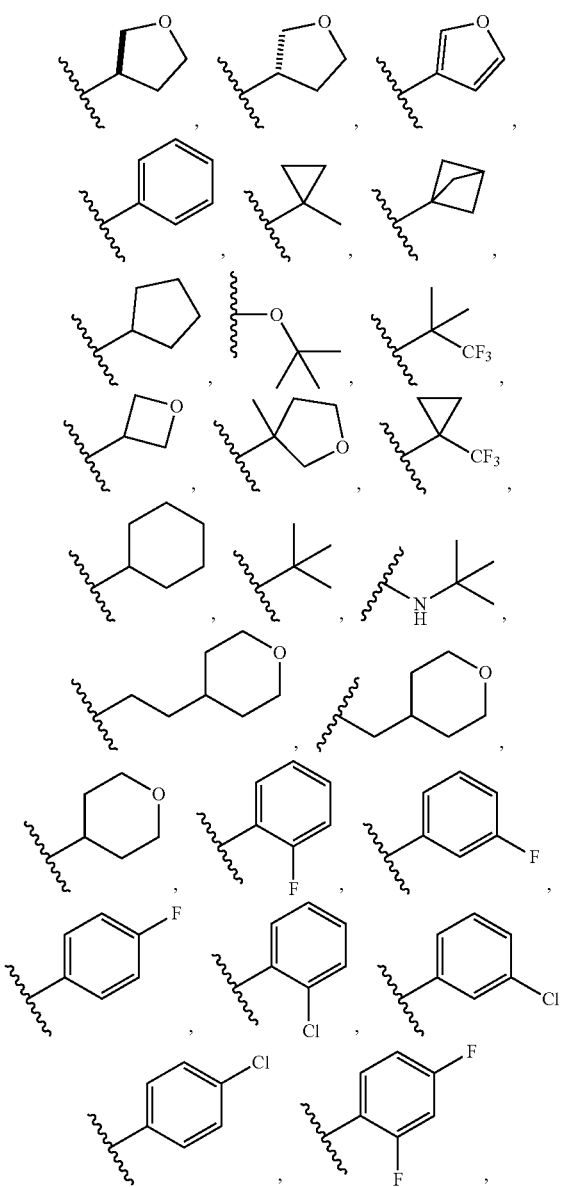

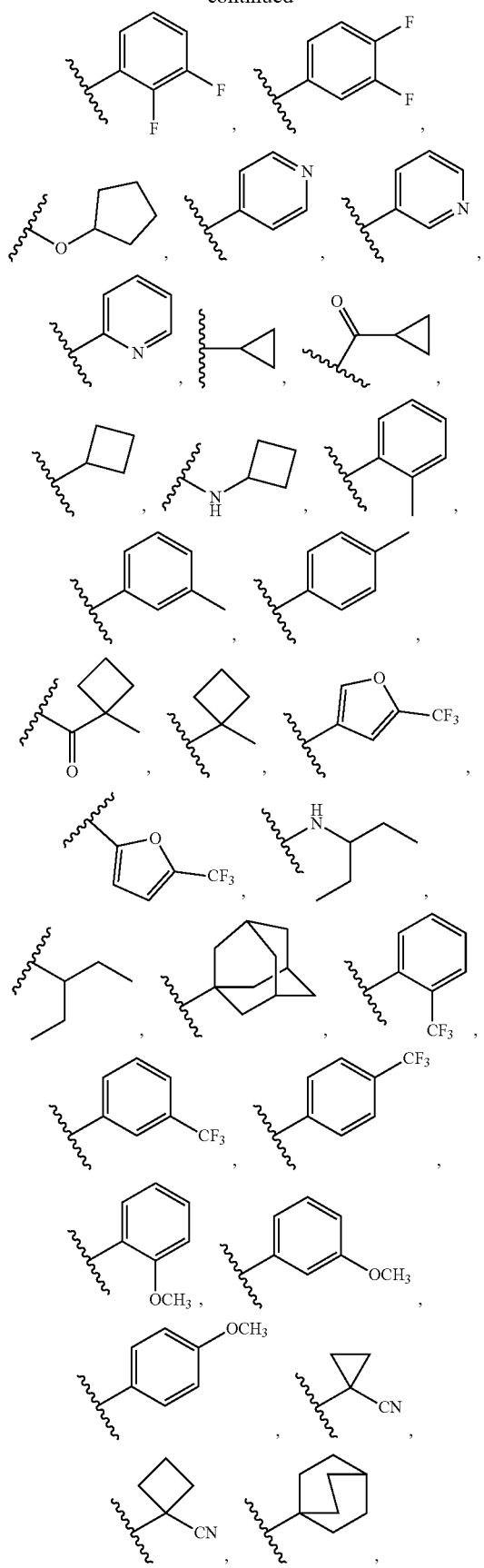
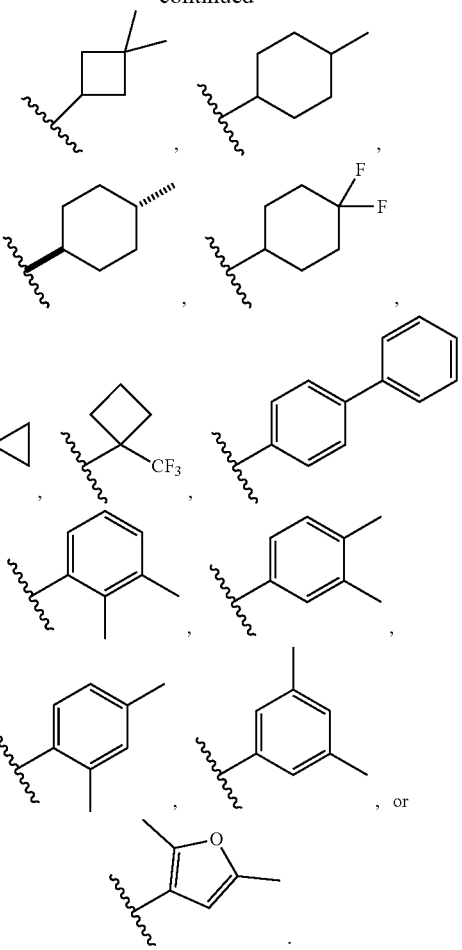
In embodiments, $R^{6A}$ is:
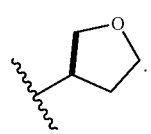
In embodiments, $R^{6A}$ is
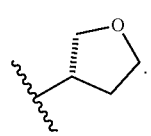
In embodiments, $R^{6A}$ is
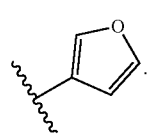 [SMILES: *c1ccoc1]

In embodiments, $R^{6A}$ is
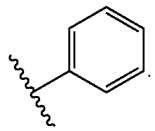 [SMILES: *c1ccccc1]
In embodiments, $R^{6A}$ is
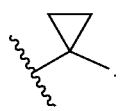 [SMILES: *C1(C)CC1]
In embodiments, $R^{6A}$ is
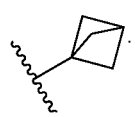
In embodiments, $R^{6A}$ is
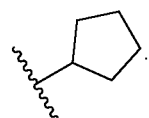 [SMILES: *C1CCCC1]
In embodiments, $R^{6A}$ is
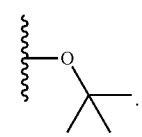 [SMILES: *OC(C)(C)C]
In embodiments, $R^{6A}$ is
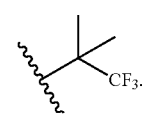
In embodiments, $R^{6A}$ is
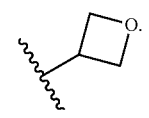
In embodiments, $R^{6A}$ is
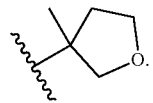 [SMILES: *C1(C)CCOC1]
In embodiments, $R^{6A}$ is
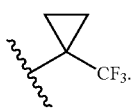
In embodiments, $R^{6A}$ is
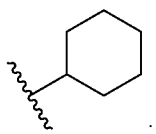
In embodiments, $R^{6A}$ is
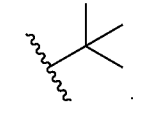 [SMILES: *C(C)(C)C]
In embodiments, $R^{6A}$ is
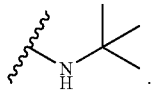
In embodiments, $R^{6A}$ is
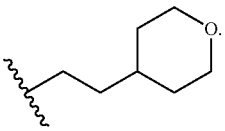 [SMILES: *CCC1CCOCC1]
In embodiments, $R^{6A}$ is
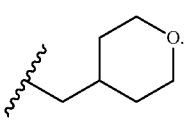

In embodiments, $R^{6A}$ is
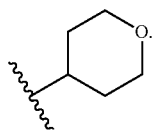 [SMILES: *C1CCOCC1]
In embodiments, $R^{6A}$ is
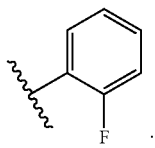
In embodiments, $R^{6A}$ is
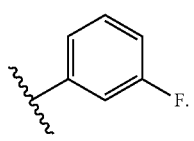
In embodiments, $R^{6A}$ is
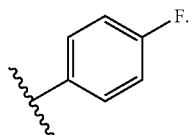
In embodiments, $R^{6A}$ is
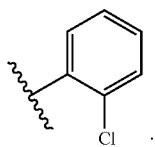 [SMILES: *c1ccccc1Cl]
In embodiments, $R^{6A}$ is
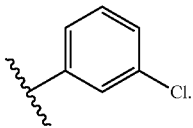
In embodiments, $R^{6A}$ is
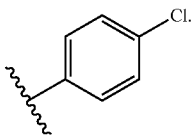
In embodiments, $R^{6A}$ is
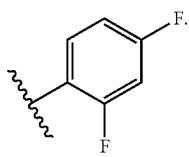 [SMILES: *c1ccc(F)cc1F]
In embodiments, $R^{6A}$ is
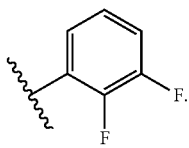
In embodiments, $R^{6A}$ is
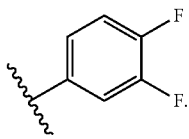 [SMILES: *c1ccc(F)c(F)c1]
In embodiments, $R^{6A}$ is
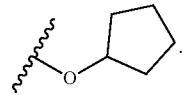 [SMILES: *OC1CCCC1]
In embodiments, $R^{6A}$ is
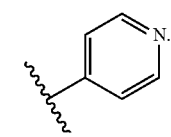 [SMILES: *c1ccncc1]
In embodiments, $R^{6A}$ is
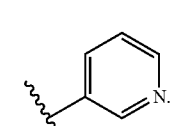
In embodiments, $R^{6A}$ is
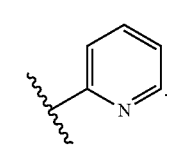

In embodiments, $R^{6A}$ is
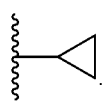
In embodiments, $R^{6A}$ is
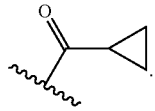 [SMILES: *C(=O)C1CC1]
In embodiments, $R^{6A}$ is
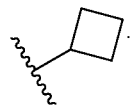
In embodiments, $R^{6A}$ is
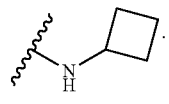
In embodiments, $R^{6A}$ is
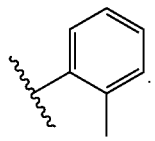 [SMILES: *c1ccccc1C]
In embodiments, $R^{6A}$ is
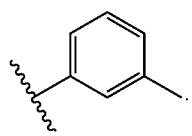
In embodiments, $R^{6A}$ is
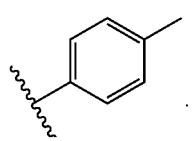 [SMILES: *c1ccc(C)cc1]
In embodiments, $R^{6A}$ is
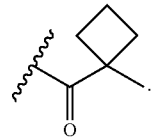 [SMILES: *C(=O)C1(C)CCC1]
In embodiments, $R^{6A}$ is
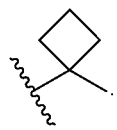
In embodiments, $R^{6A}$ is
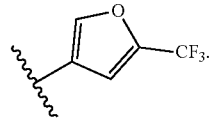 [SMILES: *c1coc(C(F)(F)F)c1]
In embodiments, $R^{6A}$ is
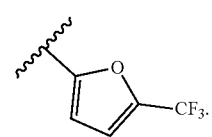 [SMILES: *c1ccc(C(F)(F)F)o1]
In embodiments, $R^{6A}$ is
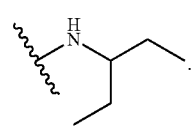 [SMILES: *NC(CC)CC]
In embodiments, $R^{6A}$ is
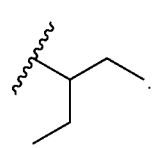
In embodiments, $R^{6A}$ is
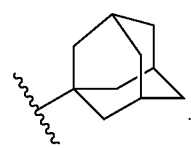 [SMILES: *C12CC3CC(CC(C3)C1)C2]

In embodiments, $R^{6A}$ is
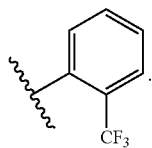
In embodiments, $R^{6A}$ is
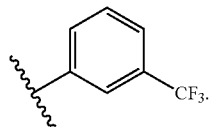 [SMILES: *c1cccc(C(F)(F)F)c1]
In embodiments, $R^{6A}$ is
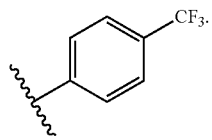 [SMILES: *c1ccc(C(F)(F)F)cc1]
In embodiments, $R^{6A}$ is
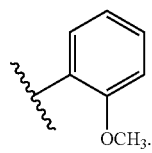 [SMILES: *c1ccccc1OC]
In embodiments, $R^{6A}$ is
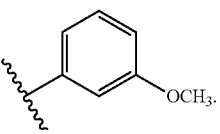 [SMILES: *c1cccc(OC)c1]
In embodiments, $R^{6A}$ is
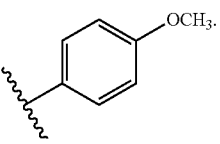 [SMILES: *c1ccc(OC)cc1]
In embodiments, $R^{6A}$ is
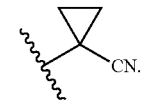
In embodiments, $R^{6A}$ is
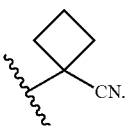 [SMILES: *C1(C#N)CCC1]
In embodiments, $R^{6A}$ is
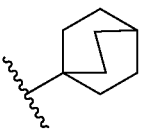
In embodiments, $R^{6A}$ is
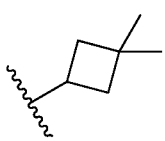
In embodiments, $R^{6A}$ is
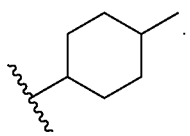 [SMILES: *C1CCC(C)CC1]
In embodiments, $R^{6A}$ is
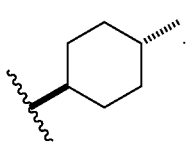
In embodiments, $R^{6A}$ is
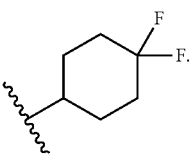
In embodiments, $R^{6A}$ is
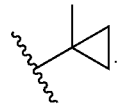

In embodiments, $R^{6A}$ is

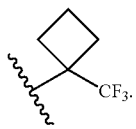

In embodiments, $R^{6A}$ is

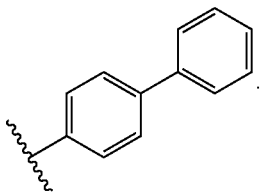 [SMILES: *c1ccc(-c2ccccc2)cc1]

In embodiments, $R^{6A}$ is

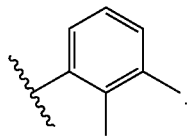 [SMILES: *c1cccc(C)c1C]

In embodiments, $R^{6A}$ is

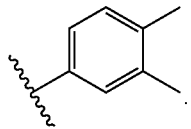 [SMILES: *c1ccc(C)c(C)c1]

In embodiments, $R^{6A}$ is

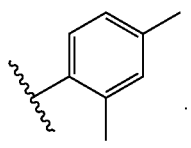 [SMILES: *c1ccc(C)cc1C]

In embodiments, $R^{6A}$ is

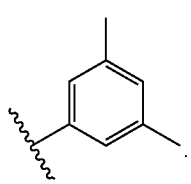 [SMILES: *c1cc(C)cc(C)c1]

In embodiments, $R^{6A}$ is

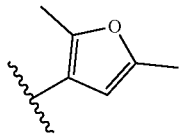

$R^{35A}$ is oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{35A}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_3$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, $R^{36A}$-substituted or unsubstituted alkyl (e.g., C$_1$-C$_8$ alkyl, C$_1$-C$_6$ alkyl, or C$_1$-C$_4$ alkyl), $R^{36A}$-substituted or unsubstituted heteroalkyl (e.g., 2 to 8 membered heteroalkyl, 2 to 6 membered heteroalkyl, or 2 to 4 membered heteroalkyl), $R^{36A}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{36A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{36A}$-substituted or unsubstituted aryl (e.g., C$_6$-C$_{10}$ aryl, C$_{10}$ aryl, or phenyl), or $R^{36A}$-substituted or unsubstituted heteroaryl (e.g., 5 to 10 membered heteroaryl, 5 to 9 membered heteroaryl, or 5 to 6 membered heteroaryl).

In embodiments, $R^{35A}$ is independently unsubstituted phenyl. In embodiments, $R^{35A}$ is independently unsubstituted methyl. In embodiments, $R^{35A}$ is independently —CF$_3$. In embodiments, $R^{35A}$ is independently —NH$_2$. In embodiments, $R^{35A}$ is independently unsubstituted benzyl. In embodiments, $R^{35A}$ is independently oxo. In embodiments, $R^{35A}$ is independently halogen. In embodiments, $R^{35A}$ is independently —CCl$_3$. In embodiments, $R^{35A}$ is independently —CBr$_3$. In embodiments, $R^{35A}$ is independently —CF$_3$. In embodiments, $R^{35A}$ is independently —CI$_3$. In embodiments, $R^{35A}$ is independently CHCl$_2$. In embodiments, $R^{35A}$ is independently —CHBr$_2$. In embodiments, $R^{35A}$ is independently —CHF$_2$. In embodiments, $R^{35A}$ is independently —CHI$_2$. In embodiments, $R^{35A}$ is independently —CH$_2$Cl. In embodiments, $R^{35A}$ is independently —CH$_2$Br. In embodiments, $R^{35A}$ is independently —CH$_2$F. In embodiments, $R^{35A}$ is independently —CH$_2$I. In embodiments, $R^{35A}$ is independently —CN. In embodiments, $R^{35A}$ is independently —OH. In embodiments, $R^{35A}$ is independently —NH$_2$. In embodiments, $R^{35A}$ is independently —COOH. In embodiments, $R^{35A}$ is independently —CONH$_2$. In embodiments, $R^{35A}$ is independently —NO$_2$. In embodiments, $R^{35A}$ is independently —SH. In embodiments, $R^{35A}$ is independently —SO$_3$H. In embodiments, $R^{35A}$ is independently —SO$_4$H. In embodiments, $R^{35A}$ is independently —SO$_2$NH$_2$. In embodiments, $R^{35A}$ is independently —NHNH$_2$. In embodiments, $R^{35A}$ is independently —ONH$_2$. In embodiments, $R^{35A}$ is independently —NHC(O)NHNH$_2$. In embodiments, $R^{35A}$ is independently —NHC(O)NH$_2$. In embodiments, $R^{35A}$ is independently —NHSO$_2$H. In embodiments, $R^{35A}$ is independently —NHC(O)H. In embodiments, $R^{35A}$ is independently —NHC(O)OH. In embodiments, $R^{35A}$ is independently —NHOH. In embodiments, $R^{35A}$ is independently —OCCl$_3$. In embodiments, $R^{35A}$ is independently —OCF$_3$. In embodiments, $R^{35A}$ is independently —OCBr$_3$. In embodiments, $R^{35A}$ is independently —OCI$_3$. In embodiments, $R^{35A}$ is independently —OCHCl$_2$. In embodiments, $R^{35A}$ is independently —OCHBr$_2$. In embodiments, $R^{35A}$ is independently —OCHI$_2$. In embodiments, $R^{35A}$ is independently —OCHF$_2$. In embodiments, $R^{35A}$ is independently —OCH$_2$Cl. In embodiments, $R^{35A}$ is independently —OCH$_2$Br. In embodiments, $R^{35A}$ is independently —OCH$_2$I. In embodiments, $R^{35A}$ is independently —OCH$_2$F.

$R^{36A}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, $R^{37A}$-substituted or unsubstituted alkyl (e.g., C$_1$-C$_8$ alkyl, C$_1$-C$_6$ alkyl, or C$_1$-C$_4$ alkyl), $R^{37A}$-substituted or unsubstituted heteroalkyl (e.g., 2 to 8 membered heteroalkyl, 2 to 6 membered heteroalkyl, or 2 to 4 membered heteroalkyl), $R^{37A}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{37A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{37A}$-substituted or unsubstituted aryl (e.g., C$_6$-C$_{10}$ aryl, C$_{10}$ aryl, or phenyl), or $R^{37A}$-substituted or unsubstituted heteroaryl (e.g., 5 to 10 membered heteroaryl, 5 to 9 membered heteroaryl, or 5 to 6 membered heteroaryl).

In embodiments, $R^{6B}$ is hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, $R^{35B}$-substituted or unsubstituted alkyl (e.g., C$_1$-C$_8$ alkyl, C$_1$-C$_6$ alkyl, or C$_1$-C$_4$ alkyl), $R^{35B}$-substituted or unsubstituted heteroalkyl (e.g., 2 to 8 membered heteroalkyl, 2 to 6 membered heteroalkyl, or 2 to 4 membered heteroalkyl), $R^{35B}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{35B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{35B}$-substituted or unsubstituted aryl (e.g., C$_6$-C$_{10}$ aryl, C$_{10}$ aryl, or phenyl), or $R^{35B}$-substituted or unsubstituted heteroaryl (e.g., 5 to 10 membered heteroaryl, 5 to 9 membered heteroaryl, or 5 to 6 membered heteroaryl).

In embodiments, $R^{6B}$ is $R^{35B}$-substituted or unsubstituted alkyl (e.g., C$_1$-C$_8$ alkyl, C$_1$-C$_6$ alkyl, or C$_1$-C$_4$ alkyl). In embodiments, $R^{6B}$ is $R^{35B}$-substituted alkyl (e.g., C$_1$-C$_8$ alkyl, C$_1$-C$_6$ alkyl, or C$_1$-C$_4$ alkyl). In embodiments, $R^{6B}$ is an unsubstituted alkyl (e.g., C$_1$-C$_8$ alkyl, C$_1$-C$_6$ alkyl, or C$_1$-C$_4$ alkyl). In embodiments, $R^{6B}$ is $R^{35B}$-substituted or unsubstituted heteroalkyl (e.g., 2 to 8 membered heteroalkyl, 2 to 6 membered heteroalkyl, or 2 to 4 membered heteroalkyl). In embodiments, $R^{6B}$ is $R^{35B}$-substituted heteroalkyl (e.g., 2 to 8 membered heteroalkyl, 2 to 6 membered heteroalkyl, or 2 to 4 membered heteroalkyl). In embodiments, $R^{6B}$ is an unsubstituted heteroalkyl (e.g., 2 to 8 membered heteroalkyl, 2 to 6 membered heteroalkyl, or 2 to 4 membered heteroalkyl). In embodiments, $R^{6B}$ is —O-(substituted or unsubstituted C$_1$-C$_8$ alkyl). In embodiments, $R^{6B}$ is —O-(substituted or unsubstituted C$_1$-C$_6$ alkyl). In embodiments, $R^{6B}$ is —O-(substituted or unsubstituted C$_1$-C$_4$ alkyl). In embodiments, $R^{6B}$ is —OCH$_3$. In embodiments, $R^{6B}$ is $R^{35B}$-substituted or unsubstituted 3 to 8 membered heterocycloalkyl, wherein the heterocycloalkyl includes an oxygen atom. In embodiments, $R^{6B}$ is $R^{35B}$-substituted or unsubstituted 5 to 6 membered heterocycloalkyl, wherein the heterocycloalkyl includes an oxygen atom. In embodiments, $R^{6B}$ is $R^{35B}$-substituted or unsubstituted 5 membered heterocycloalkyl, wherein the heterocycloalkyl includes an oxygen atom. In embodiments, $R^{6B}$ is $R^{35B}$-substituted or unsubstituted 6 membered heterocycloalkyl, wherein the heterocycloalkyl includes an oxygen atom.

In embodiments, $R^{6B}$ is $R^{35B}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{6B}$ is $R^{35B}$-substituted cycloalkyl (e.g., C$_3$-C$_8$ cycloalkyl, C$_3$-C$_6$ cycloalkyl, or C$_5$-C$_6$ cycloalkyl). In embodiments, $R^{6B}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, $R^{6B}$ is $R^{35B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{6B}$ is $R^{35B}$-substituted heterocycloalkyl (e.g., 3 to 8 membered heterocycloalkyl, 3 to 6 membered heterocycloalkyl, or 5 to 6 membered heterocycloalkyl). In embodiments, $R^{6B}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{6B}$ is $R^{35B}$-substituted or unsubstituted aryl (e.g., C$_6$-C$_{10}$ aryl, C$_{10}$ aryl, or phenyl). In embodiments, $R^{6B}$ is $R^{35B}$-substituted aryl (e.g., C$_6$-C$_{10}$ aryl, C$_{10}$ aryl, or phenyl). In embodiments, $R^{6B}$ is an unsubstituted aryl (e.g., C$_6$-C$_{10}$ aryl, C$_{10}$ aryl, or phenyl).

In embodiments, $R^{6B}$ is $R^{35B}$-substituted or unsubstituted heteroaryl (e.g., 5 to 10 membered heteroaryl, 5 to 9 membered heteroaryl, or 5 to 6 membered heteroaryl). In embodiments, $R^{6B}$ is $R^{35B}$-substituted heteroaryl (e.g., 5 to 10 membered heteroaryl, 5 to 9 membered heteroaryl, or 5 to 6 membered heteroaryl). In embodiments, $R^{6B}$ is an unsubstituted heteroaryl (e.g., 5 to 10 membered heteroaryl, 5 to 9 membered heteroaryl, or 5 to 6 membered heteroaryl).

In embodiments, $R^{6B}$ is:

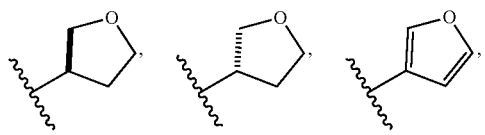

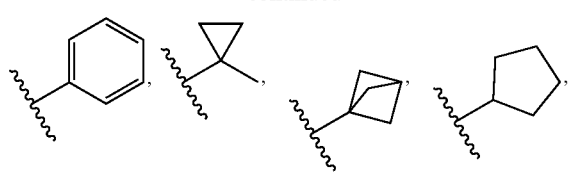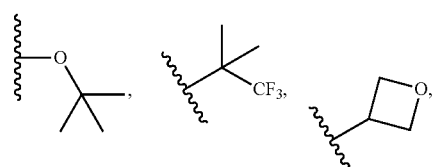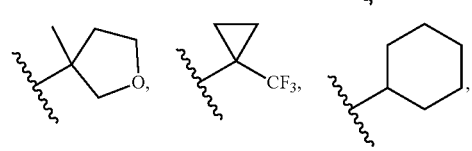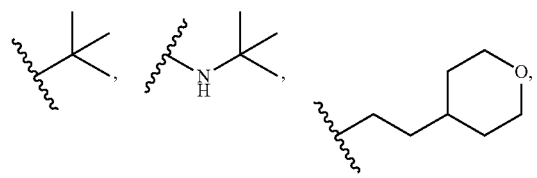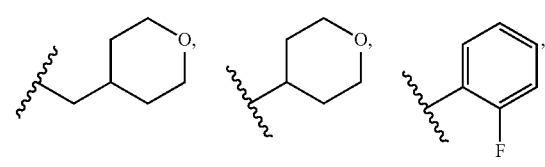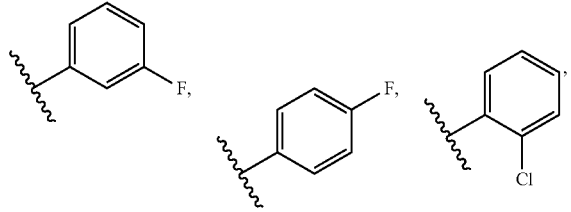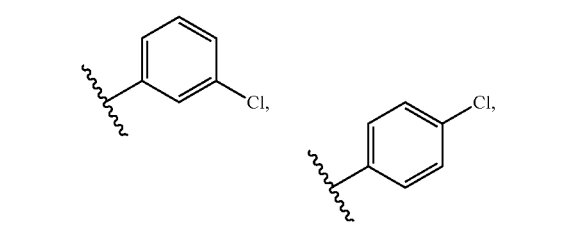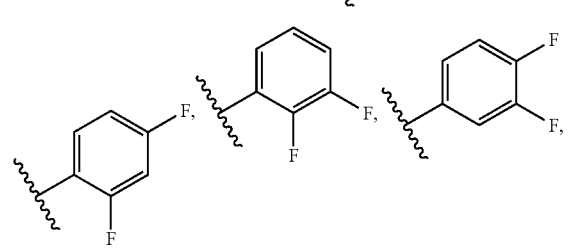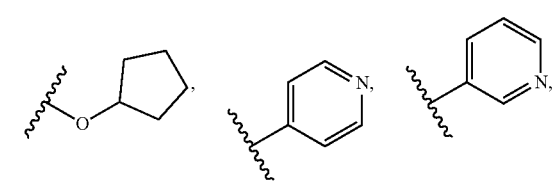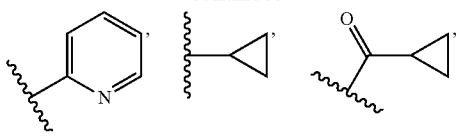

-continued
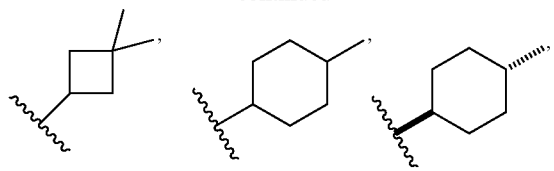
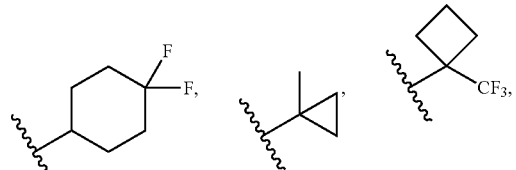
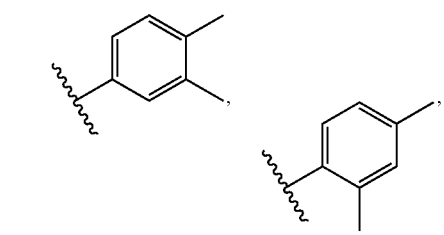
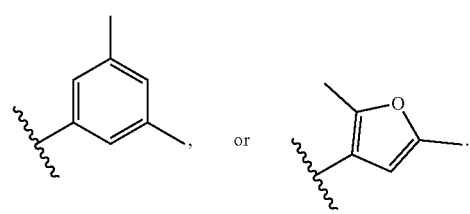, or 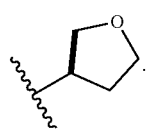
In embodiments, $R^{6B}$ is:
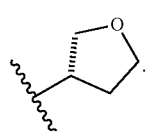
In embodiments, $R^{6B}$ is
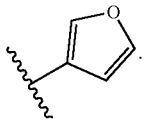
In embodiments, $R^{6B}$ is
In embodiments, $R^{6B}$ is
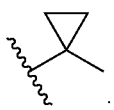 [SMILES: *C1(C)CC1]
In embodiments, $R^{6B}$ is
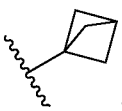
In embodiments, $R^{6B}$ is
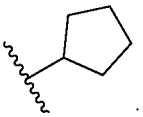 [SMILES: *C1CCCC1]
In embodiments, $R^{6B}$ is
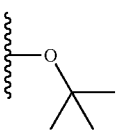
In embodiments, $R^{6B}$ is
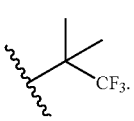

In embodiments, $R^{6B}$ is
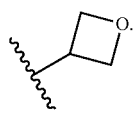 [SMILES: *C1COC1]
In embodiments, $R^{6B}$ is
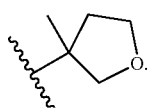
In embodiments, $R^{6B}$ is
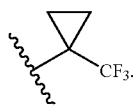
In embodiments, $R^{6B}$ is
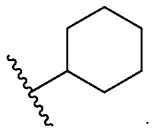 [SMILES: *C1CCCCC1]
In embodiments, $R^{6B}$ is
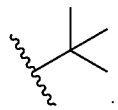 [SMILES: *C(C)(C)C]
In embodiments, $R^{6B}$ is
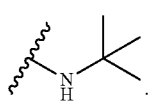
In embodiments, $R^{6B}$ is
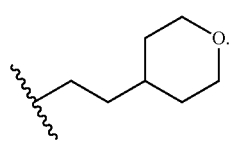 [SMILES: *CCC1CCOCC1]
In embodiments, $R^{6B}$ is
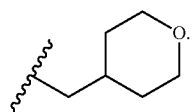 [SMILES: *CC1CCOCC1]
In embodiments, $R^{6B}$ is
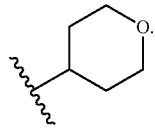 [SMILES: *C1CCOCC1]
In embodiments, $R^{6B}$ is
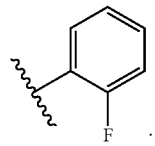
In embodiments, $R^{6B}$ is
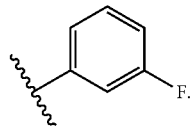
In embodiments, $R^{6B}$ is
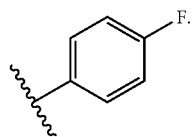
In embodiments, $R^{6B}$ is
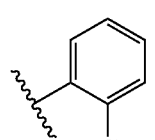
In embodiments, $R^{6B}$ is
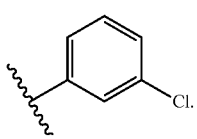 [SMILES: *c1cccc(Cl)c1]

In embodiments, $R^{6B}$ is
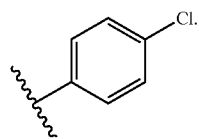 [SMILES: *c1ccc(Cl)cc1]
In embodiments, $R^{6B}$ is
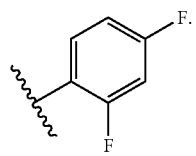
In embodiments, $R^{6B}$ is
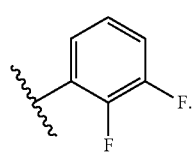 [SMILES: *c1cccc(F)c1F]
In embodiments, $R^{6B}$ is
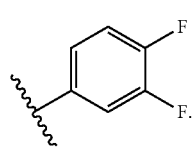 [SMILES: *c1ccc(F)c(F)c1]
In embodiments, $R^{6B}$ is
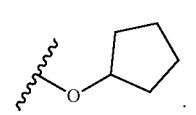 [SMILES: *OC1CCCC1]
In embodiments, $R^{6B}$ is
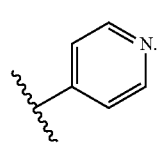 [SMILES: *c1ccncc1]
In embodiments, $R^{6B}$ is
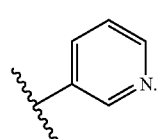 [SMILES: *c1cccnc1]
In embodiments, $R^{6B}$ is
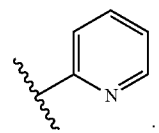
In embodiments, $R^{6B}$ is
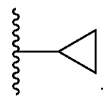 [SMILES: *C1CC1]
In embodiments, $R^{6B}$ is
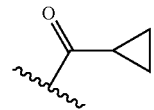
In embodiments, $R^{6B}$ is
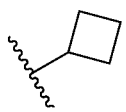
In embodiments, $R^{6B}$ is
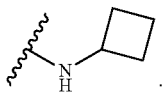
In embodiments, $R^{6B}$ is
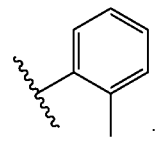 [SMILES: *c1ccccc1C]
In embodiments, $R^{6B}$ is
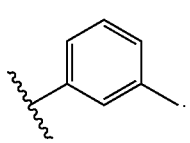

In embodiments, $R^{6B}$ is
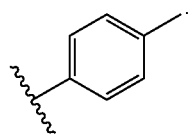 [SMILES: *c1ccc(C)cc1]
In embodiments, $R^{6B}$ is
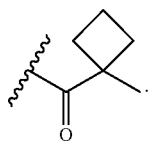
In embodiments, $R^{6B}$ is
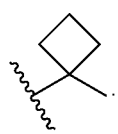
In embodiments, $R^{6B}$ is
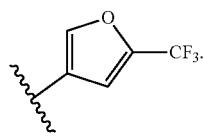 [SMILES: *c1coc(C(F)(F)F)c1]
In embodiments, $R^{6B}$ is
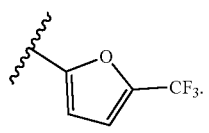 [SMILES: *c1ccc(C(F)(F)F)o1]
In embodiments, $R^{6B}$ is
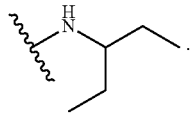 [SMILES: *NC(CC)CC]
In embodiments, $R^{6B}$ is
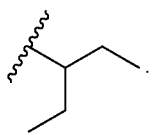 [SMILES: *C(CC)CC]
In embodiments, $R^{6B}$ is
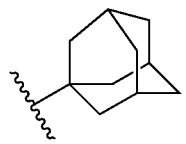
In embodiments, $R^{6B}$ is
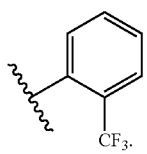 [SMILES: *c1ccccc1C(F)(F)F]
In embodiments, $R^{6B}$ is
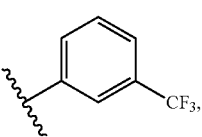 [SMILES: *c1cccc(C(F)(F)F)c1]
In embodiments, $R^{6B}$ is
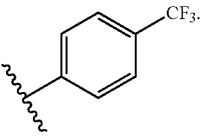 [SMILES: *c1ccc(C(F)(F)F)cc1]
In embodiments, $R^{6B}$ is
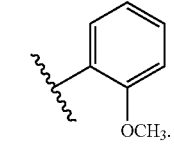
In embodiments, $R^{6B}$ is
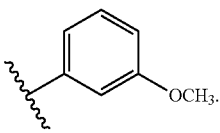 [SMILES: *c1cccc(OC)c1]

In embodiments, $R^{6B}$ is
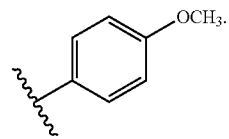 [SMILES: *c1ccc(OC)cc1]
In embodiments, $R^{6B}$ is
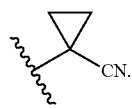 [SMILES: *C1(C#N)CC1]
In embodiments, $R^{6B}$ is S
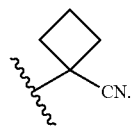 [SMILES: *C1(C#N)CCC1]
In embodiments, $R^{6B}$ is
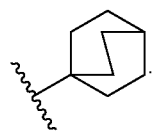 [SMILES: *C12CCC(CC1)CC2]
In embodiments, $R^{6B}$ is
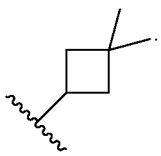 [SMILES: *C1CC(C)(C)C1]
In embodiments, $R^{6B}$ is
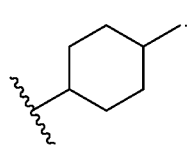 [SMILES: *C1CCC(C)CC1]
In embodiments, $R^{6B}$ is
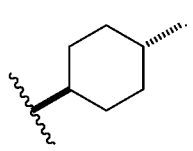 [SMILES: *[C@H]1CC[C@H](C)CC1]
In embodiments, $R^{6B}$ is
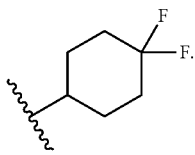 [SMILES: *C1CCC(F)(F)CC1]
In embodiments, $R^{6B}$ is
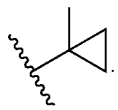 [SMILES: *C1(C)CC1]
In embodiments, $R^{6B}$ is
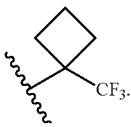 [SMILES: *C1(C(F)(F)F)CCC1]
In embodiments, $R^{6B}$ is
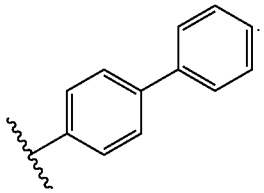 [SMILES: *c1ccc(-c2ccccc2)cc1]
In embodiments, $R^{6B}$ is
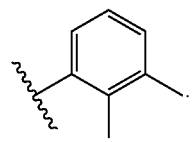 [SMILES: *c1cccc(C)c1C]
In embodiments, $R^{6B}$ is
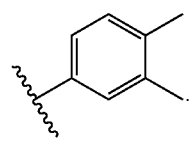 [SMILES: *c1ccc(C)c(C)c1]
In embodiments, $R^{6B}$ is
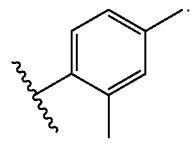 [SMILES: *c1ccc(C)cc1C]

In embodiments, $R^{6B}$ is

[Structure: 3,5-dimethylphenyl group with two wavy-line attachment points]

In embodiments, $R^{6B}$ is

[Structure: 2,5-dimethylfuran group with wavy-line attachment point]

$R^{35B}$ is oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{35B}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, $R^{36B}$-substituted or unsubstituted alkyl (e.g., C$_1$-C$_8$ alkyl, C$_1$-C$_6$ alkyl, or C$_1$-C$_4$ alkyl), $R^{36B}$-substituted or unsubstituted heteroalkyl (e.g., 2 to 8 membered heteroalkyl, 2 to 6 membered heteroalkyl, or 2 to 4 membered heteroalkyl), $R^{36B}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{36B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{36B}$-substituted or unsubstituted aryl (e.g., C$_6$-C$_{10}$ aryl, C$_{10}$ aryl, or phenyl), or $R^{36B}$-substituted or unsubstituted heteroaryl (e.g., 5 to 10 membered heteroaryl, 5 to 9 membered heteroaryl, or 5 to 6 membered heteroaryl).

In embodiments, $R^{35B}$ is independently unsubstituted phenyl. In embodiments, $R^{35B}$ is independently unsubstituted methyl. In embodiments, $R^{35B}$ is independently —CF$_3$. In embodiments, $R^{35B}$ is independently —NH$_2$. In embodiments, $R^{35B}$ is independently unsubstituted benzyl. In embodiments, $R^{35B}$ is independently oxo. In embodiments, $R^{35B}$ is independently halogen. In embodiments, $R^{35B}$ is independently —CCl$_3$. In embodiments, $R^{35B}$ is independently —CBr$_3$. In embodiments, $R^{35B}$ is independently —CF$_3$. In embodiments, $R^{35B}$ is independently —CI$_3$. In embodiments, $R^{35B}$ is independently CHCl$_2$. In embodiments, $R^{35B}$ is independently —CHBr$_2$. In embodiments, $R^{35B}$ is independently —CHF$_2$. In embodiments, $R^{35B}$ is independently —CHI$_2$. In embodiments, $R^{35B}$ is independently —CH$_2$Cl. In embodiments, $R^{35B}$ is independently —CH$_2$Br. In embodiments, $R^{35B}$ is independently —CH$_2$F. In embodiments, $R^{35B}$ is independently —CH$_2$I. In embodiments, $R^{35B}$ is independently —CN. In embodiments, $R^{35B}$ is independently —OH. In embodiments, $R^{35B}$ is independently —NH$_2$. In embodiments, $R^{35B}$ is independently —COOH. In embodiments, $R^{35B}$ is independently —CONH$_2$. In embodiments, $R^{35B}$ is independently —NO$_2$. In embodiments, $R^{35B}$ is independently —SH. In embodiments, $R^{35B}$ is independently —SO$_3$H. In embodiments, $R^{35B}$ is independently —SO$_4$H. In embodiments, $R^{35B}$ is independently —SO$_2$NH$_2$. In embodiments, $R^{35B}$ is independently —NHNH$_2$. In embodiments, $R^{35B}$ is independently —ONH$_2$. In embodiments, $R^{35B}$ is independently —NHC(O)NHNH$_2$. In embodiments, $R^{35B}$ is independently —NHC(O)NH$_2$. In embodiments, $R^{35B}$ is independently —NHSO$_2$H. In embodiments, $R^{35B}$ is independently —NHC(O)H. In embodiments, $R^{35B}$ is independently —NHC(O)OH. In embodiments, $R^{35B}$ is independently —NHOH. In embodiments, $R^{35B}$ is independently —OCCl$_3$. In embodiments, $R^{35B}$ is independently —OCF$_3$. In embodiments, $R^{35B}$ is independently —OCBr$_3$. In embodiments, $R^{35B}$ is independently —OCI$_3$. In embodiments, $R^{35B}$ is independently —OCHCl$_2$. In embodiments, $R^{35B}$ is independently —OCHBr$_2$. In embodiments, $R^{35B}$ is independently —OCHI$_2$. In embodiments, $R^{35B}$ is independently —OCHF$_2$. In embodiments, $R^{35B}$ is independently —OCH$_2$Cl. In embodiments, $R^{35B}$ is independently —OCH$_2$Br. In embodiments, $R^{35B}$ is independently —OCH$_2$I. In embodiments, $R^{35B}$ is independently —OCH$_2$F.

$R^{36B}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, $R^{37B}$-substituted or unsubstituted alkyl (e.g., C$_1$-C$_8$ alkyl, C$_1$-C$_6$ alkyl, or C$_1$-C$_4$ alkyl), $R^{37B}$-substituted or unsubstituted heteroalkyl (e.g., 2 to 8 membered heteroalkyl, 2 to 6 membered heteroalkyl, or 2 to 4 membered heteroalkyl), $R^{37B}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{37B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{37B}$-substituted or unsubstituted aryl (e.g., C$_6$-C$_{10}$ aryl, C$_{10}$ aryl, or phenyl), or $R^{37B}$-substituted or unsubstituted heteroaryl (e.g., 5 to 10 membered heteroaryl, 5 to 9 membered heteroaryl, or 5 to 6 membered heteroaryl).

In embodiments, $R^{6C}$ is hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, $R^{35C}$-substituted or unsubstituted alkyl (e.g., C$_1$-C$_8$ alkyl, C$_1$-C$_6$ alkyl, or C$_1$-C$_4$ alkyl), $R^{35C}$-substituted or unsubstituted heteroalkyl (e.g., 2 to 8 membered heteroalkyl, 2 to 6 membered heteroalkyl, or 2 to 4 membered heteroalkyl), $R^{35C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{35C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{35C}$-substituted or unsubstituted aryl (e.g., $C_6$-$C_{10}$ aryl, $C_{10}$ aryl, or phenyl), or $R^{35C}$-substituted or unsubstituted heteroaryl (e.g., 5 to 10 membered heteroaryl, 5 to 9 membered heteroaryl, or 5 to 6 membered heteroaryl).

In embodiments, $R^{6C}$ is $R^{35C}$-substituted or unsubstituted alkyl (e.g., $C_1$-$C_8$ alkyl, $C_1$-$C_6$ alkyl, or $C_1$-$C_4$ alkyl). In embodiments, $R^{6C}$ is $R^{35C}$-substituted alkyl (e.g., $C_1$-$C_8$ alkyl, $C_1$-$C_6$ alkyl, or $C_1$-$C_4$ alkyl). In embodiments, $R^{6C}$ is an unsubstituted alkyl (e.g., $C_1$-$C_8$ alkyl, $C_1$-$C_6$ alkyl, or $C_1$-$C_4$ alkyl). In embodiments, $R^{6C}$ is $R^{35C}$-substituted or unsubstituted heteroalkyl (e.g., 2 to 8 membered heteroalkyl, 2 to 6 membered heteroalkyl, or 2 to 4 membered heteroalkyl). In embodiments, $R^{6C}$ is $R^{35C}$-substituted heteroalkyl (e.g., 2 to 8 membered heteroalkyl, 2 to 6 membered heteroalkyl, or 2 to 4 membered heteroalkyl). In embodiments, $R^{6C}$ is an unsubstituted heteroalkyl (e.g., 2 to 8 membered heteroalkyl, 2 to 6 membered heteroalkyl, or 2 to 4 membered heteroalkyl). In embodiments, $R^{6C}$ is —O-(substituted or unsubstituted $C_1$-$C_8$ alkyl). In embodiments, $R^{6C}$ is —O-(substituted or unsubstituted $C_1$-$C_6$ alkyl). In embodiments, $R^{6C}$ is —O-(substituted or unsubstituted $C_1$-$C_4$ alkyl). In embodiments, $R^{6C}$ is —OCH$_3$. In embodiments, $R^{6C}$ is $R^{35C}$-substituted or unsubstituted 3 to 8 membered heterocycloalkyl, wherein the heterocycloalkyl includes an oxygen atom. In embodiments, $R^{6C}$ is $R^{35C}$-substituted or unsubstituted 5 to 6 membered heterocycloalkyl, wherein the heterocycloalkyl includes an oxygen atom. In embodiments, $R^{6C}$ is $R^{35C}$-substituted or unsubstituted 5 membered heterocycloalkyl, wherein the heterocycloalkyl includes an oxygen atom. In embodiments, $R^{6C}$ is $R^{35C}$-substituted or unsubstituted 6 membered heterocycloalkyl, wherein the heterocycloalkyl includes an oxygen atom.

In embodiments, $R^{6C}$ is $R^{35C}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{6C}$ is $R^{35C}$-substituted cycloalkyl (e.g., $C_3$-$C_8$ cycloalkyl, $C_3$-$C_6$ cycloalkyl, or $C_5$-$C_6$ cycloalkyl). In embodiments, $R^{6C}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{6C}$ is $R^{35C}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{6C}$ is $R^{35C}$-substituted heterocycloalkyl (e.g., 3 to 8 membered heterocycloalkyl, 3 to 6 membered heterocycloalkyl, or 5 to 6 membered heterocycloalkyl). In embodiments, $R^{6C}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{6C}$ is $R^{35C}$-substituted or unsubstituted aryl (e.g., $C_6$-$C_{10}$ aryl, $C_{10}$ aryl, or phenyl). In embodiments, $R^{6C}$ is $R^{35C}$-substituted aryl (e.g., $C_6$-$C_{10}$ aryl, $C_{10}$ aryl, or phenyl). In embodiments, $R^{6C}$ is an unsubstituted aryl (e.g., $C_6$-$C_{10}$ aryl, $C_{10}$ aryl, or phenyl).

In embodiments, $R^{6C}$ is $R^{35C}$-substituted or unsubstituted heteroaryl (e.g., 5 to 10 membered heteroaryl, 5 to 9 membered heteroaryl, or 5 to 6 membered heteroaryl). In embodiments, $R^{6C}$ is $R^{35C}$-substituted heteroaryl (e.g., 5 to 10 membered heteroaryl, 5 to 9 membered heteroaryl, or 5 to 6 membered heteroaryl). In embodiments, $R^{6C}$ is an unsubstituted heteroaryl (e.g., 5 to 10 membered heteroaryl, 5 to 9 membered heteroaryl, or 5 to 6 membered heteroaryl).

In embodiments, $R^{6C}$ is:

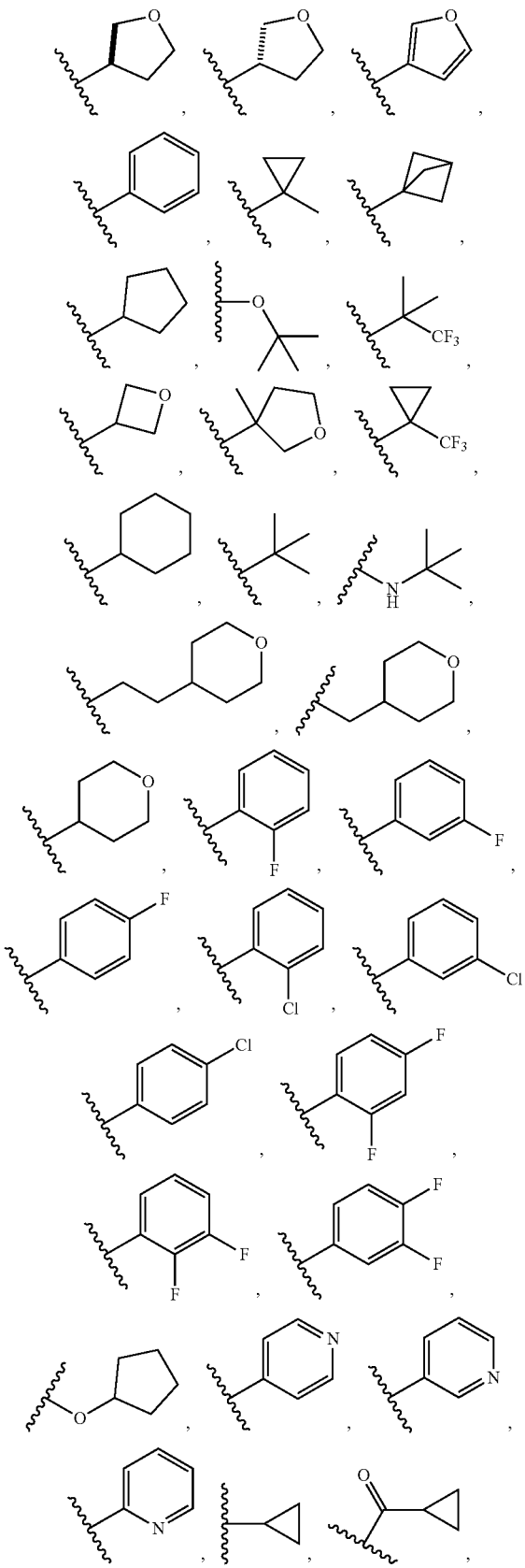

223
-continued
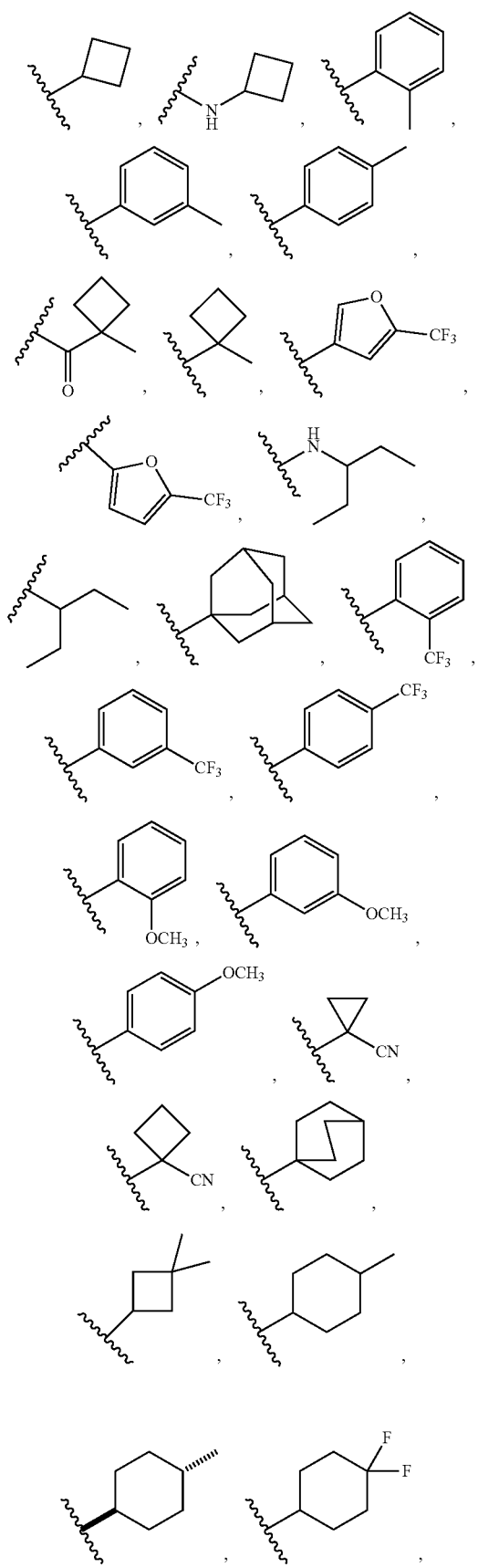
224
-continued
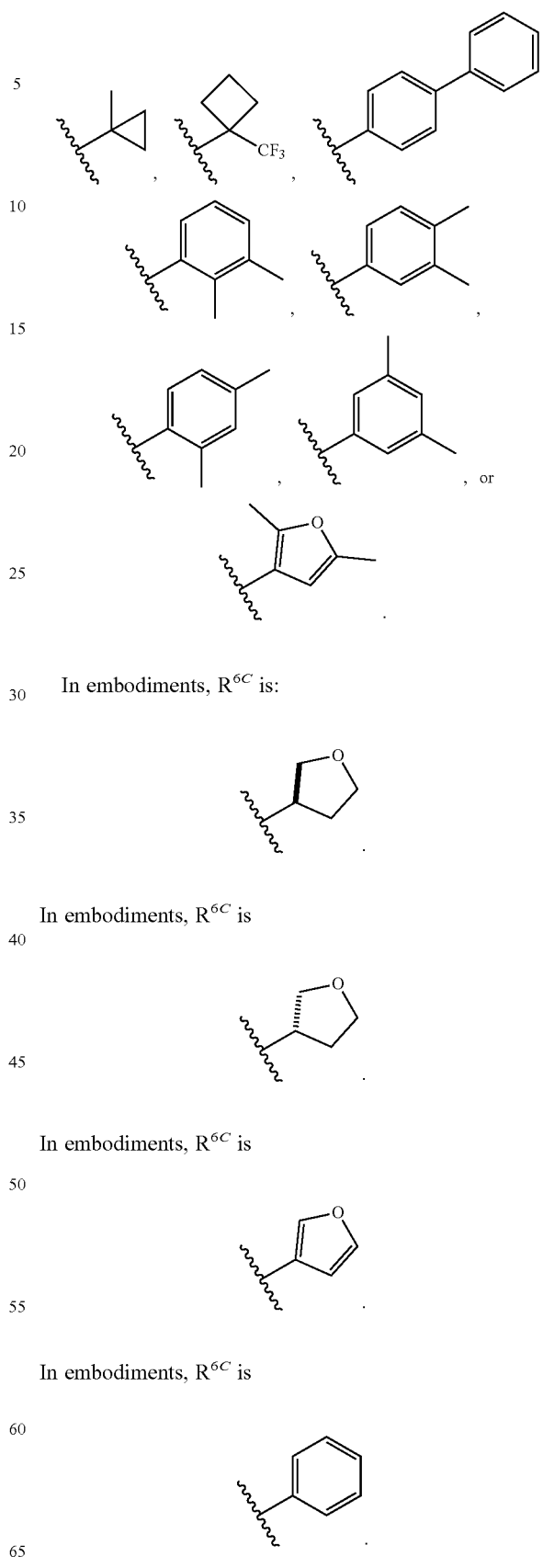
In embodiments, $R^{6C}$ is:
In embodiments, $R^{6C}$ is
In embodiments, $R^{6C}$ is
In embodiments, $R^{6C}$ is 225
In embodiments, $R^{6C}$ is
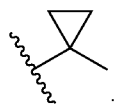 [SMILES: *C1(C)CC1]
In embodiments, $R^{6C}$ is
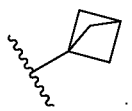
In embodiments, $R^{6C}$ is
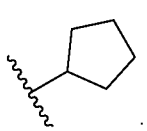
In embodiments, $R^{6C}$ is
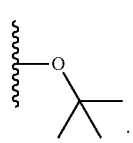 [SMILES: *OC(C)(C)C]
In embodiments, $R^{6C}$ is
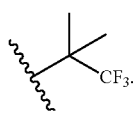 [SMILES: *C(C)(C)C(F)(F)F]
In embodiments, $R^{6C}$ is
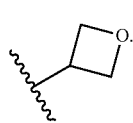 [SMILES: *C1COC1]
In embodiments, $R^{6C}$ is
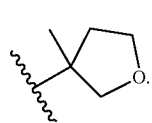
226
In embodiments, $R^{6C}$ is
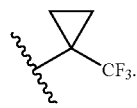
In embodiments, $R^{6C}$ is
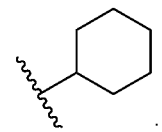
In embodiments, $R^{6C}$ is
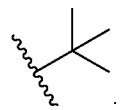
In embodiments, $R^{6C}$ is
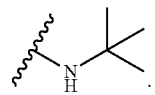 [SMILES: *NC(C)(C)C]
In embodiments, $R^{6C}$ is
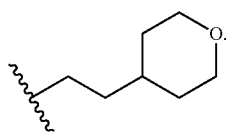 [SMILES: *CCC1CCOCC1]
In embodiments, $R^{6C}$ is
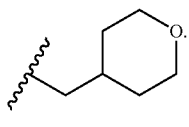
In embodiments, $R^{6C}$ is
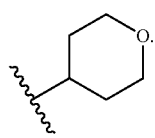 [SMILES: *C1CCOCC1]

In embodiments, R$^{6C}$ is
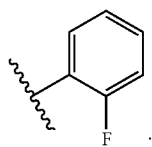
In embodiments, R$^{6C}$ is
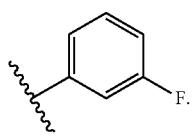
In embodiments, R$^{6C}$ is
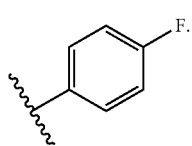 [SMILES: *c1ccc(F)cc1]
In embodiments, R$^{6C}$ is
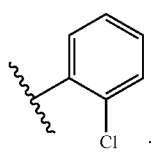
In embodiments, R$^{6C}$ is
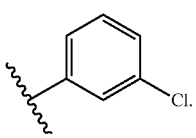 [SMILES: *c1cccc(Cl)c1]
In embodiments, R$^{6C}$ is
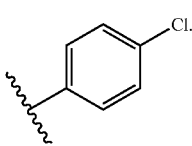
In embodiments, R$^{6C}$ is
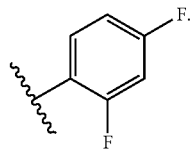 [SMILES: *c1ccc(F)cc1F]
In embodiments, R$^{6C}$ is
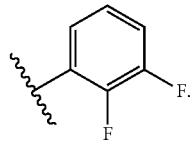
In embodiments, R$^{6C}$ is 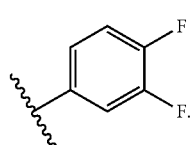
In embodiments R$^{6C}$ is
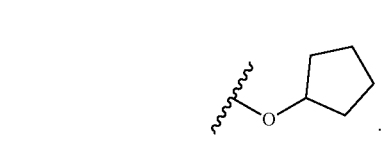
In embodiments, R$^{6C}$ is
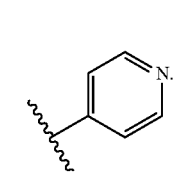 [SMILES: *c1ccncc1]
In embodiments, R$^{6C}$ is
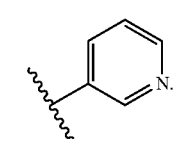
In embodiments, R$^{6C}$ is
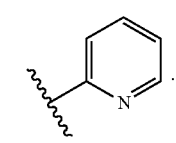

In embodiments, $R^{6C}$ is
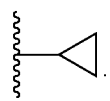
In embodiments, $R^{6C}$ is
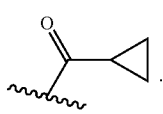 [SMILES: *C(=O)C1CC1]
In embodiments, $R^{6C}$ is
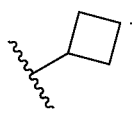
In embodiments, $R^{6C}$ is
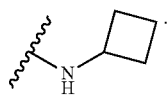
In embodiments, $R^{6C}$ is
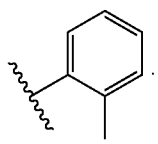 [SMILES: *c1ccccc1C]
In embodiments, $R^{6C}$ is
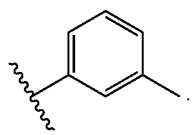 [SMILES: *c1cccc(C)c1]
In embodiments, $R^{6C}$ is
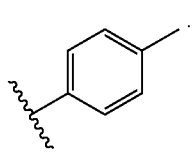
In embodiments, $R^{6C}$ is
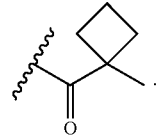
In embodiments, $R^{6C}$ is
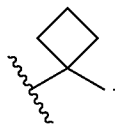 [SMILES: *C1(C)CCC1]
In embodiments, $R^{6C}$ is
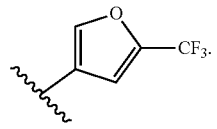 [SMILES: *c1coc(C(F)(F)F)c1]
In embodiments, $R^{6C}$ is
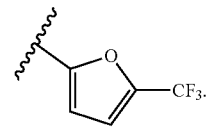 [SMILES: *c1ccc(C(F)(F)F)o1]
In embodiments, $R^{6C}$ is
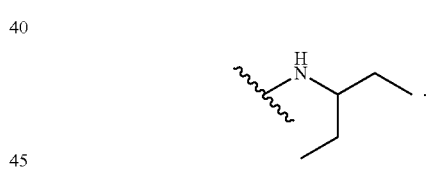
In embodiments, $R^{6C}$ is
In embodiments, $R^{6C}$ is
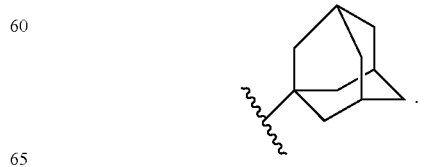

In embodiments, $R^{6C}$ is
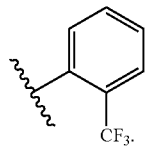
In embodiments, $R^{6C}$ is
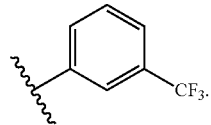 [SMILES: *c1cccc(C(F)(F)F)c1]
In embodiments, $R^{6C}$ is
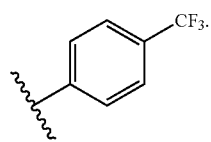 [SMILES: *c1ccc(C(F)(F)F)cc1]
In embodiments, $R^{6C}$ is
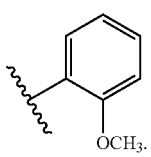
In embodiments, $R^{6C}$ is
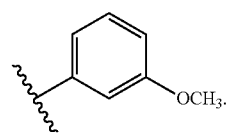 [SMILES: *c1cccc(OC)c1]
In embodiments, $R^{6C}$ is
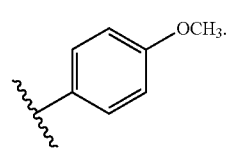 [SMILES: *c1ccc(OC)cc1]
In embodiments, $R^{6C}$ is
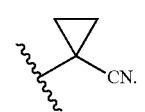 [SMILES: *C1(C#N)CC1]
In embodiments, $R^{6C}$ is
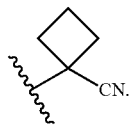 [SMILES: *C1(C#N)CCC1]
In embodiments, $R^{6C}$ is
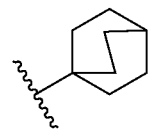
In embodiments, $R^{6C}$ is
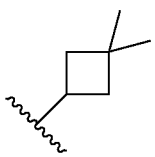
In embodiments, $R^{6C}$ is
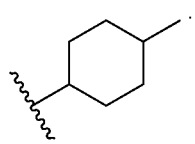 [SMILES: *C1CCC(C)CC1]
In embodiments, $R^{6C}$ is
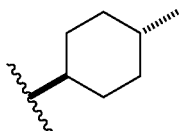
In embodiments, $R^{6C}$ is
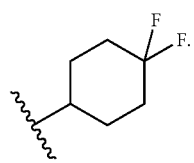 [SMILES: *C1CCC(F)(F)CC1]

In embodiments, $R^{6C}$ is

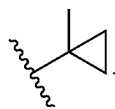

In embodiments, $R^{6C}$ is

In embodiments, $R^{6C}$ is

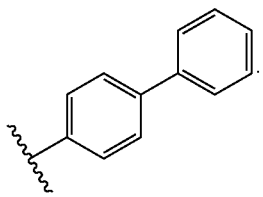 [SMILES: *c1ccc(-c2ccccc2)cc1]

In embodiments, $R^{6C}$ is

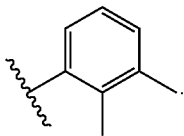 [SMILES: *c1cccc(C)c1C]

In embodiments, $R^{6C}$ is

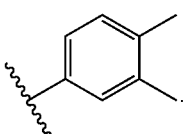 [SMILES: *c1ccc(C)c(C)c1]

In embodiments, $R^{6C}$ is

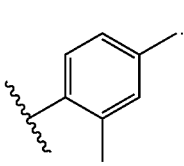 [SMILES: *c1ccc(C)cc1C]

In embodiments, $R^{6C}$ is

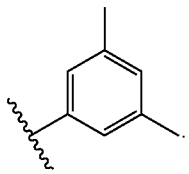 [SMILES: *c1cc(C)cc(C)c1]

In embodiments, $R^{6C}$ is

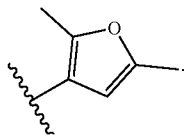 [SMILES: *c1cc(C)oc1C]

$R^{35C}$ is oxo, halogen, —CCl₃, —CBr₃, —CF₃, —CI₃, CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCH F₂, —OCH₂Cl, —OCH₂Br, —OCH₂I, —OCH₂F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{35C}$ is independently oxo, halogen, —CCl₃, —CBr₃, —CF₃, —CI₃, CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, $R^{36C}$-substituted or unsubstituted alkyl (e.g., $C_1$-$C_8$ alkyl, $C_1$-$C_6$ alkyl, or $C_1$-$C_4$ alkyl), $R^{36C}$-substituted or unsubstituted heteroalkyl (e.g., 2 to 8 membered heteroalkyl, 2 to 6 membered heteroalkyl, or 2 to 4 membered heteroalkyl), $R^{36C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{36C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{36C}$-substituted or unsubstituted aryl (e.g., $C_6$-$C_{10}$ aryl, $C_{10}$ aryl, or phenyl), or $R^{36C}$-substituted or unsubstituted heteroaryl (e.g., 5 to 10 membered heteroaryl, 5 to 9 membered heteroaryl, or 5 to 6 membered heteroaryl).

In embodiments, $R^{35C}$ is independently unsubstituted phenyl. In embodiments, $R^{35C}$ is independently unsubstituted methyl. In embodiments, $R^{35C}$ is independently —CF₃. In embodiments, $R^{35C}$ is independently —NH₂. In embodiments, $R^{35C}$ is independently unsubstituted benzyl. In embodiments, $R^{35C}$ is independently oxo. In embodiments, $R^{35C}$ is independently halogen. In embodiments, $R^{35C}$ is independently —CCl₃. In embodiments, $R^{35C}$ is independently —CBr₃. In embodiments, $R^{35C}$ is independently —CF₃. In embodiments, $R^{35C}$ is independently —CI₃. In embodiments, $R^{35C}$ is independently CHCl₂. In embodiments, $R^{35C}$ is independently —CHBr₂. In embodiments, $R^{35C}$ is independently —CHF₂. In embodiments, $R^{35C}$ is independently —CHB In embodiments, $R^{35C}$ is independently —CH$_2$Cl. In embodiments, R$^{35C}$ is independently —CH$_2$Br. In embodiments, R$^{35C}$ is independently —CH$_2$F. In embodiments, R$^{35C}$ is independently —CH$_2$I. In embodiments, R$^{35C}$ is independently —CN. In embodiments, R$^{35C}$ is independently —OH. In embodiments, R$^{35C}$ is independently —NH$_2$. In embodiments, R$^{35C}$ is independently —COOH. In embodiments, R$^{35C}$ is independently —CONH$_2$. In embodiments, R$^{35C}$ is independently —NO$_2$. In embodiments, R$^{35C}$ is independently —SH. In embodiments, R$^{35C}$ is independently —SO$_3$H. In embodiments, R$^{35C}$ is independently —SO$_4$H. In embodiments, R$^{35C}$ is independently —SO$_2$NH$_2$. In embodiments, R$^{35C}$ is independently —NHNH$_2$. In embodiments, R$^{35C}$ is independently —ONH$_2$. In embodiments, R$^{35C}$ is independently —NHC(O)NHNH$_2$. In embodiments, R$^{35C}$ is independently —NHC(O)NH$_2$. In embodiments, R$^{35C}$ is independently —NHSO$_2$H. In embodiments, R$^{35C}$ is independently —NHC(O)H. In embodiments, R$^{35C}$ is independently —NHC(O)OH. In embodiments, R$^{35C}$ is independently —NHOH. In embodiments, R$^{35C}$ is independently —OCCl$_3$. In embodiments, R$^{35C}$ is independently —OCF$_3$. In embodiments, R$^{35C}$ is independently —OCBr$_3$. In embodiments, R$^{35C}$ is independently —OCI$_3$. In embodiments, R$^{35C}$ is independently —OCHCl$_2$. In embodiments, R$^{35C}$ is independently —OCHBr$_2$. In embodiments, R$^{35C}$ is independently —OCHI$_2$. In embodiments, R$^{35C}$ is independently —OCHF$_2$. In embodiments, R$^{35C}$ is independently —OCH$_2$Cl. In embodiments, R$^{35C}$ is independently —OCH$_2$Br. In embodiments, R$^{35C}$ is independently —OCH$_2$I. In embodiments, R$^{35C}$ is independently —OCH$_2$F.

R$^{36C}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, R$^{37C}$-substituted or unsubstituted alkyl (e.g., C$_1$-C$_8$ alkyl, C$_1$-C$_6$ alkyl, or C$_1$-C$_4$ alkyl), R$^{37C}$-substituted or unsubstituted heteroalkyl (e.g., 2 to 8 membered heteroalkyl, 2 to 6 membered heteroalkyl, or 2 to 4 membered heteroalkyl), R$^{37C}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{37C}$-substituted or unsubstituted heterocycloalkyl (e.g., 3 to 8 membered heterocycloalkyl, 3 to 6 membered heterocycloalkyl, or 5 to 6 membered heterocycloalkyl), R$^{37C}$-substituted or unsubstituted aryl (e.g., C$_6$-C$_{10}$ aryl, C$_{10}$ aryl, or phenyl), or R$^{37C}$-substituted or unsubstituted heteroaryl (e.g., 5 to 10 membered heteroaryl, 5 to 9 membered heteroaryl, or 5 to 6 membered heteroaryl).

In embodiments, R$^{6D}$ is hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, R$^{35D}$-substituted or unsubstituted alkyl (e.g., C$_1$-C$_8$ alkyl, C$_1$-C$_6$ alkyl, or C$_1$-C$_4$ alkyl), R$^{35D}$-substituted or unsubstituted heteroalkyl (e.g., 2 to 8 membered heteroalkyl, 2 to 6 membered heteroalkyl, or 2 to 4 membered heteroalkyl), R$^{35D}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{35D}$-substituted or unsubstituted heterocycloalkyl (e.g., 3 to 8 membered heterocycloalkyl, 3 to 6 membered heterocycloalkyl, or 5 to 6 membered heterocycloalkyl), R$^{35D}$-substituted or unsubstituted aryl (e.g., C$_6$-C$_{10}$ aryl, C$_{10}$ aryl, or phenyl), or R$^{35D}$-substituted or unsubstituted heteroaryl (e.g., 5 to 10 membered heteroaryl, 5 to 9 membered heteroaryl, or 5 to 6 membered heteroaryl).

In embodiments, R$^{6D}$ is R$^{35D}$-substituted or unsubstituted alkyl (e.g., C$_1$-C$_8$ alkyl, C$_1$-C$_6$ alkyl, or C$_1$-C$_4$ alkyl). In embodiments, R$^{6D}$ is R$^{35D}$-substituted alkyl (e.g., C$_1$-C$_8$ alkyl, C$_1$-C$_6$ alkyl, or C$_1$-C$_4$ alkyl). In embodiments, R$^{6D}$ is an unsubstituted alkyl (e.g., C$_1$-C$_8$ alkyl, C$_1$-C$_6$ alkyl, or C$_1$-C$_4$ alkyl). In embodiments, R$^{6D}$ is R$^{35D}$-substituted or unsubstituted heteroalkyl (e.g., 2 to 8 membered heteroalkyl, 2 to 6 membered heteroalkyl, or 2 to 4 membered heteroalkyl). In embodiments, R$^{6D}$ is R$^{35D}$-substituted heteroalkyl (e.g., 2 to 8 membered heteroalkyl, 2 to 6 membered heteroalkyl, or 2 to 4 membered heteroalkyl). In embodiments, R$^{6D}$ is an unsubstituted heteroalkyl (e.g., 2 to 8 membered heteroalkyl, 2 to 6 membered heteroalkyl, or 2 to 4 membered heteroalkyl). In embodiments, R$^{6D}$ is —O-(substituted or unsubstituted C$_1$-C$_8$ alkyl). In embodiments, R$^{6D}$ is —O-(substituted or unsubstituted C$_1$-C$_6$ alkyl). In embodiments, R$^{6D}$ is —O-(substituted or unsubstituted C$_1$-C$_4$ alkyl). In embodiments, R$^{6D}$ is —OCH$_3$. In embodiments, R$^{6D}$ is R$^{35D}$-substituted or unsubstituted 3 to 8 membered heterocycloalkyl, wherein the heterocycloalkyl includes an oxygen atom. In embodiments, R$^{6D}$ is R$^{35D}$-substituted or unsubstituted 5 to 6 membered heterocycloalkyl, wherein the heterocycloalkyl includes an oxygen atom. In embodiments, R$^{6D}$ is R$^{35D}$-substituted or unsubstituted 5 membered heterocycloalkyl, wherein the heterocycloalkyl includes an oxygen atom. In embodiments, R$^{6D}$ is R$^{35D}$-substituted or unsubstituted 6 membered heterocycloalkyl, wherein the heterocycloalkyl includes an oxygen atom.

In embodiments, R$^{6D}$ is R$^{35D}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{6D}$ is R$^{35D}$-substituted cycloalkyl (e.g., C$_3$-C$_8$ cycloalkyl, C$_3$-C$_6$ cycloalkyl, or C$_5$-C$_6$ cycloalkyl). In embodiments, R$^{6D}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, R$^{6D}$ is R$^{35D}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{6D}$ is R$^{35D}$-substituted heterocycloalkyl (e.g., 3 to 8 membered heterocycloalkyl, 3 to 6 membered heterocycloalkyl, or 5 to 6 membered heterocycloalkyl). In embodiments, R$^{6D}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, R$^{6D}$ is R$^{35D}$-substituted or unsubstituted aryl (e.g., C$_6$-C$_{10}$ aryl, C$_{10}$ aryl, or phenyl). In embodiments, R$^{6D}$ is R$^{35D}$-substituted aryl (e.g., C$_6$-C$_{10}$ aryl, C$_{10}$ aryl, or phenyl). In embodiments, R$^{6D}$ is an unsubstituted aryl (e.g., C$_6$-C$_{10}$ aryl, C$_{10}$ aryl, or phenyl).

In embodiments, R$^{6D}$ is R$^{35D}$-substituted or unsubstituted heteroaryl (e.g., 5 to 10 membered heteroaryl, 5 to 9 membered heteroaryl, or 5 to 6 membered heteroaryl). In embodiments, R$^{6D}$ is R$^{35D}$-substituted heteroaryl (e.g., 5 to 10 membered heteroaryl, 5 to 9 membered heteroaryl, or 5 to 6 membered heteroaryl). In embodiments, R$^{6D}$ is an unsubstituted heteroaryl (e.g., 5 to 10 membered heteroaryl, 5 to 9 membered heteroaryl, or 5 to 6 membered heteroaryl).

In embodiments, $R^{6D}$ is:
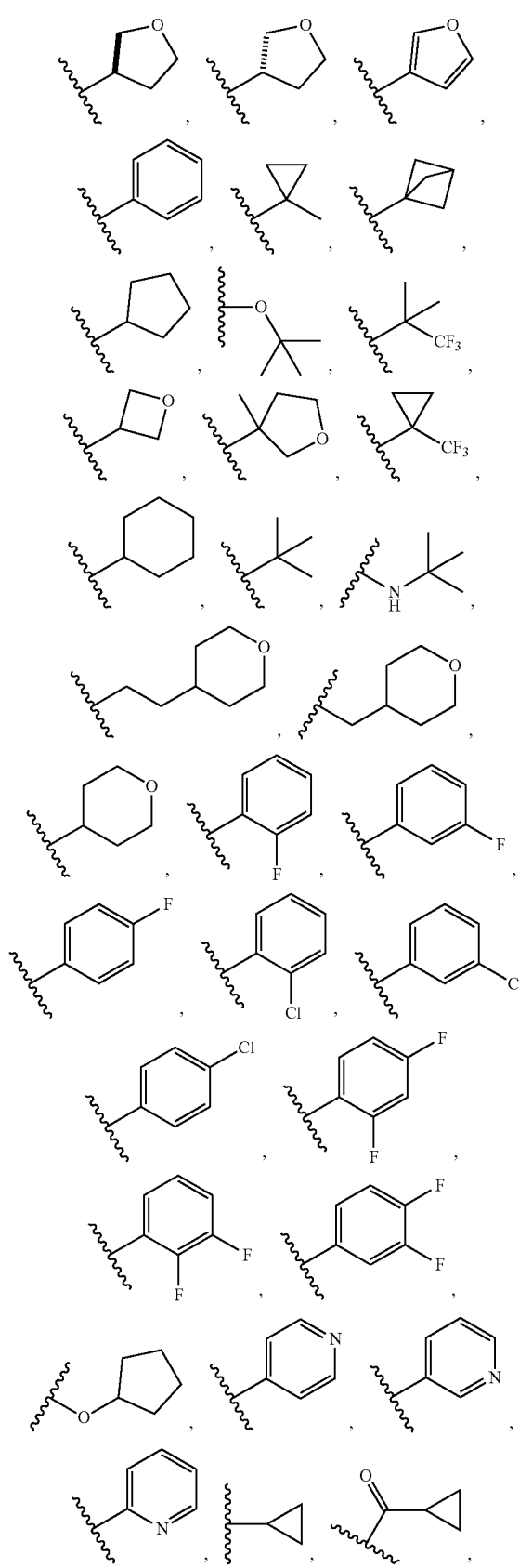
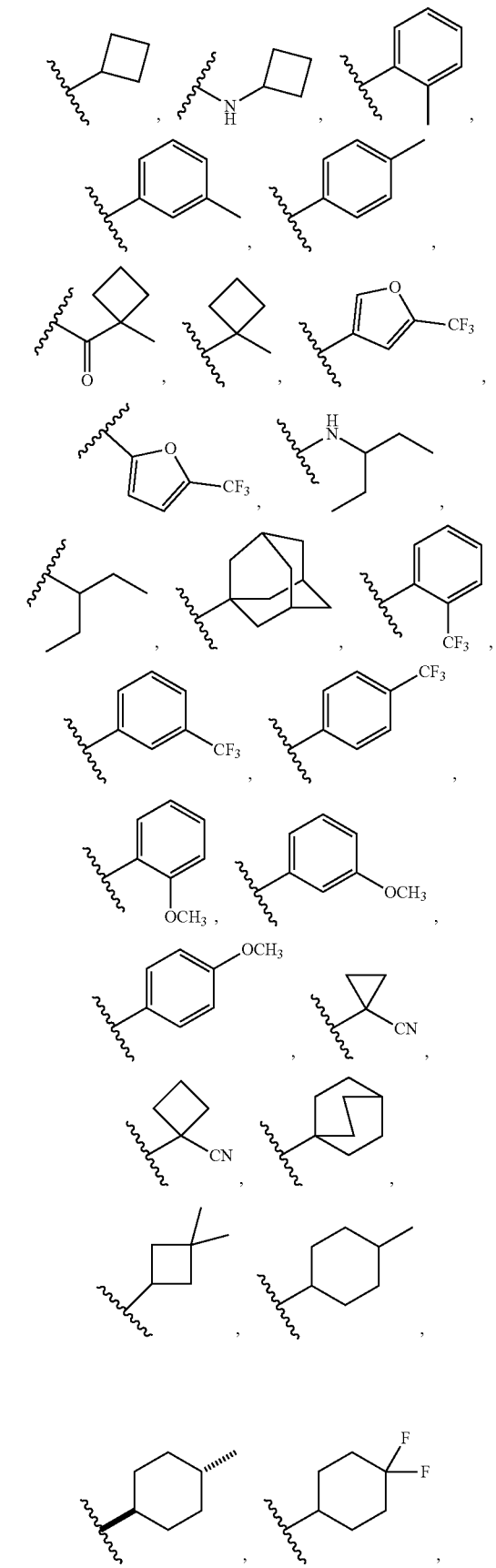

-continued
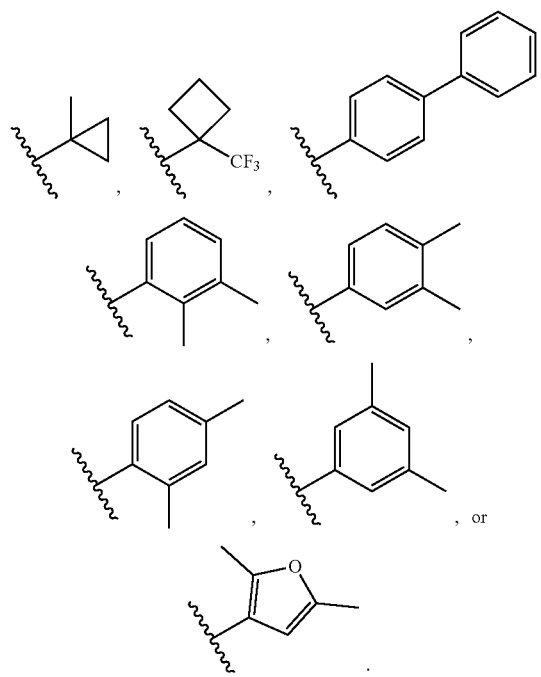
In embodiments, $R^{6D}$ is:
In embodiments, $R^{6D}$ is
In embodiments, $R^{6D}$ is
In embodiments, $R^{6D}$ is
In embodiments, $R^{6D}$ is 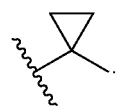
In embodiments, $R^{6D}$ is
In embodiments, $R^{6D}$ is
In embodiments, $R^{6D}$ is
In embodiments, $R^{6D}$ is
In embodiments, $R^{6D}$ is
In embodiments, $R^{6D}$ is
In embodiments, $R^{6D}$ is
In embodiments, $R^{6D}$ is In embodiments, $R^{6D}$ is
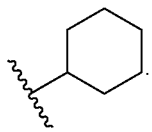 [SMILES: *C1CCCCC1]
In embodiments, $R^{6D}$ is
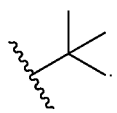
In embodiments, $R^{6D}$ is
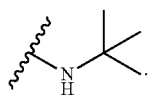 [SMILES: *NC(C)(C)C]
In embodiments, $R^{6D}$ is
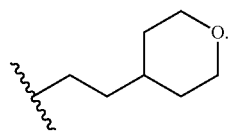 [SMILES: *CCC1CCOCC1]
In embodiments, $R^{6D}$ is
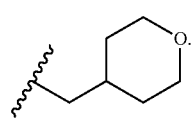
In embodiments, $R^{6D}$ is
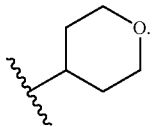 [SMILES: *C1CCOCC1]
In embodiments, $R^{6D}$ is
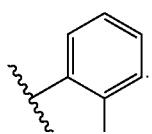
In embodiments, $R^{6D}$ is
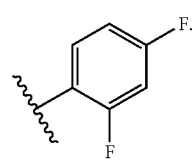 [SMILES: *c1ccc(F)cc1F]
In embodiments, $R^{6D}$ is
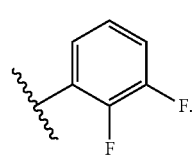 [SMILES: *c1cccc(F)c1F]
In embodiments, $R^{6D}$ is
In embodiments, $R^{6D}$ is
In embodiments, $R^{6D}$ is
In embodiments, $R^{6D}$ is
In embodiments, $R^{6D}$ is In embodiments, $R^{6D}$ is
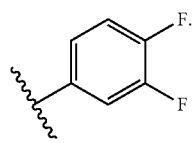 [SMILES: *c1ccc(F)c(F)c1]
In embodiments, $R^{6D}$ is
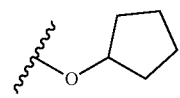
In embodiments, $R^{6D}$ is
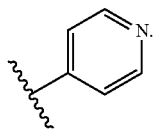 [SMILES: *c1ccncc1]
In embodiments, $R^{6D}$ is
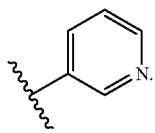 [SMILES: *c1cccnc1]
In embodiments, $R^{6D}$ is
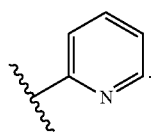 [SMILES: *c1ccccn1]
In embodiments, $R^{6D}$ is
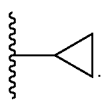 [SMILES: *C1CC1]
In embodiments, $R^{6D}$ is
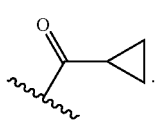 [SMILES: *C(=O)C1CC1]
In embodiments, $R^{6D}$ is
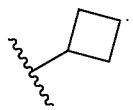 [SMILES: *C1CCC1]
In embodiments, $R^{6D}$ is
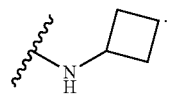
In embodiments, $R^{6D}$ is
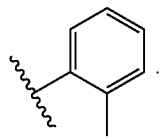
In embodiments, $R^{6D}$ is
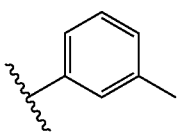
In embodiments, $R^{6D}$ is
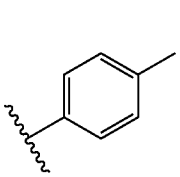
In embodiments, $R^{6D}$ is
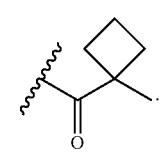 [SMILES: *C(=O)C1(C)CCC1]
In embodiments, $R^{6D}$ is
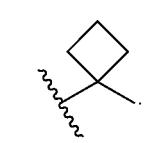 [SMILES: *C1(C)CCC1]

In embodiments, R$^{6D}$ is
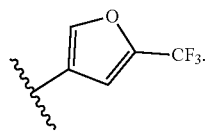 [SMILES: *c1coc(C(F)(F)F)c1]
In embodiments, R$^{6D}$ is
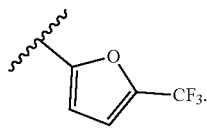 [SMILES: *c1ccc(C(F)(F)F)o1]
In embodiments, R$^{6D}$ is
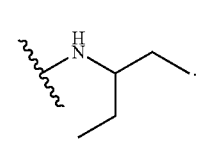 [SMILES: *NC(CC)CC]
In embodiments, R$^{6D}$ is
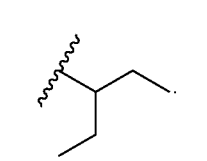 [SMILES: *C(CC)CC]
In embodiments, R$^{6D}$ is
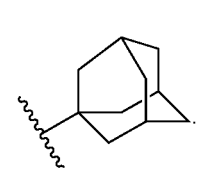 [SMILES: *C12CC3CC(CC(C3)C1)C2]
In embodiments, R$^{6D}$ is
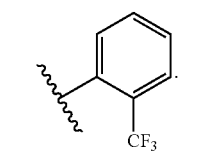
In embodiments, R$^{6D}$ is
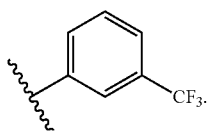 [SMILES: *c1cccc(C(F)(F)F)c1]
In embodiments, R$^{6D}$ is
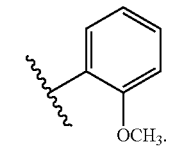
In embodiments, R$^{6D}$ is
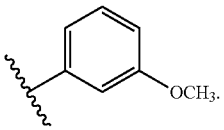 [SMILES: *c1cccc(OC)c1]
In embodiments, R$^{6D}$ is
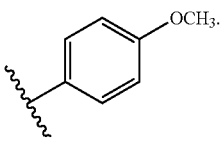 [SMILES: *c1ccc(OC)cc1]
In embodiments, R$^{6D}$ is
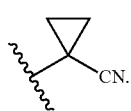 [SMILES: *C1(C#N)CC1]
In embodiments, R$^{6D}$ is
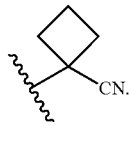 [SMILES: *C1(C#N)CCC1]
In embodiments, R$^{6D}$ is
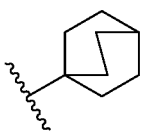

In embodiments, $R^{6D}$ is

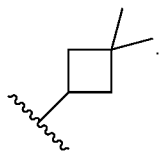

In embodiments, $R^{6D}$ is

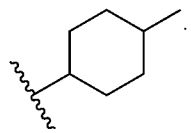 [SMILES: *C1CCC(C)CC1]

In embodiments, $R^{6D}$ is

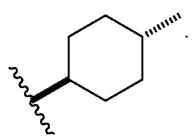

In embodiments, $R^{6D}$ is

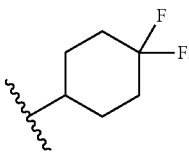

In embodiments, $R^{6D}$ is

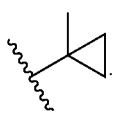 [SMILES: *C1(C)CC1]

In embodiments, $R^{6D}$ is

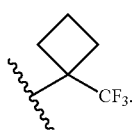

In embodiments, $R^{6D}$ is

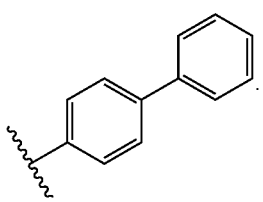 [SMILES: *c1ccc(-c2ccccc2)cc1]

In embodiments, $R^{6D}$ is

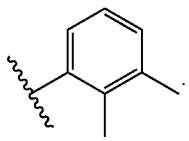 [SMILES: *c1cccc(C)c1C]

In embodiments, $R^{6D}$ is

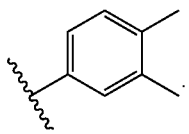

In embodiments, $R^{6D}$ is I

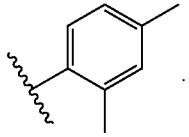 [SMILES: *c1ccc(C)cc1C]

In embodiments, $R^{6D}$ is

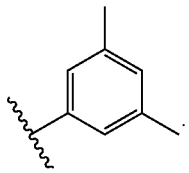 [SMILES: *c1cc(C)cc(C)c1]

In embodiments, $R^{6D}$ is

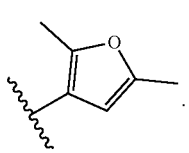 [SMILES: *c1cc(C)oc1C]

$R^{35D}$ is oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{35D}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, $R^{36D}$-substituted or unsubstituted alkyl (e.g., $C_1$-$C_8$ alkyl, $C_1$-$C_6$ alkyl, or $C_1$-$C_4$ alkyl), $R^{36D}$-substituted or unsubstituted heteroalkyl (e.g., 2 to 8 membered heteroalkyl, 2 to 6 membered heteroalkyl, or 2 to 4 membered heteroalkyl), $R^{36D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{36D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{36D}$-substituted or unsubstituted aryl (e.g., $C_6$-$C_{10}$ aryl, $C_{10}$ aryl, or phenyl), or $R^{36D}$-substituted or unsubstituted heteroaryl (e.g., 5 to 10 membered heteroaryl, 5 to 9 membered heteroaryl, or 5 to 6 membered heteroaryl).

In embodiments, $R^{35D}$ is unsubstituted phenyl. In embodiments, $R^{35D}$ is unsubstituted methyl. In embodiments, $R^{35D}$ is —CF$_3$. In embodiments, $R^{35D}$ is —NH$_2$. In embodiments, $R^{35D}$ is unsubstituted benzyl. In embodiments, $R^{35D}$ is oxo. In embodiments, $R^{35D}$ is halogen. In embodiments, $R^{35D}$ is —CCl$_3$. In embodiments, $R^{35D}$ is —CBr$_3$. In embodiments, $R^{35D}$ is —CF$_3$. In embodiments, $R^{35D}$ is —CI$_3$. In embodiments, $R^{35D}$ is CHCl$_2$. In embodiments, $R^{35D}$ is —CHBr$_2$. In embodiments, $R^{35D}$ is —CHF$_2$. In embodiments, $R^{35D}$ is —CHI$_2$. In embodiments, $R^{35D}$ is —CH$_2$Cl. In embodiments, $R^{35D}$ is —CH$_2$Br. In embodiments, $R^{35D}$ is —CH$_2$F. In embodiments, $R^{35D}$ is —CH$_2$I. In embodiments, $R^{35D}$ is —CN. In embodiments, $R^{35D}$ is —OH. In embodiments, $R^{35D}$ is —NH$_2$. In embodiments, $R^{35D}$ is —COOH. In embodiments, $R^{35D}$ is —CONH$_2$. In embodiments, $R^{35D}$ is —NO$_2$. In embodiments, $R^{35D}$ is —SH. In embodiments, $R^{35D}$ is —SO$_3$H. In embodiments, $R^{35D}$ is —SO$_4$H. In embodiments, $R^{35D}$ is —SO$_2$NH$_2$. In embodiments, $R^{35D}$ is —NHNH$_2$. In embodiments, $R^{35D}$ is —ONH$_2$. In embodiments, $R^{35D}$ is —NHC(O)NHNH$_2$. In embodiments, $R^{35D}$ is —NHC(O)NH$_2$. In embodiments, $R^{35D}$ is —NHSO$_2$H. In embodiments, $R^{35D}$ is —NHC(O)H. In embodiments, $R^{35D}$ is —NHC(O)OH. In embodiments, $R^{35D}$ is —NHOH. In embodiments, $R^{35D}$ is —OCCl$_3$. In embodiments, $R^{35D}$ is —OCF$_3$. In embodiments, $R^{35D}$ is —OCBr$_3$. In embodiments, $R^{35D}$ is —OCI$_3$. In embodiments, $R^{35D}$ is —OCHCl$_2$. In embodiments, $R^{35D}$ is —OCHBr$_2$. In embodiments, $R^{35D}$ is —OCHI$_2$. In embodiments, $R^{35D}$ is —OCHF$_2$. In embodiments, $R^{35D}$ is —OCH$_2$Cl. In embodiments, $R^{35D}$ is —OCH$_2$Br. In embodiments, $R^{35D}$ is —OCH$_2$I. In embodiments, $R^{35D}$ is —OCH$_2$F.

$R^{36D}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_3$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, $R^{37D}$-substituted or unsubstituted alkyl (e.g., $C_1$-$C_8$ alkyl, $C_1$-$C_6$ alkyl, or $C_1$-$C_4$ alkyl), $R^{37D}$-substituted or unsubstituted heteroalkyl (e.g., 2 to 8 membered heteroalkyl, 2 to 6 membered heteroalkyl, or 2 to 4 membered heteroalkyl), $R^{37D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{37D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{37D}$-substituted or unsubstituted aryl (e.g., $C_6$-$C_{10}$ aryl, $C_{10}$ aryl, or phenyl), or $R^{37D}$-substituted or unsubstituted heteroaryl (e.g., 5 to 10 membered heteroaryl, 5 to 9 membered heteroaryl, or 5 to 6 membered heteroaryl).

In embodiments, $R^6$ is

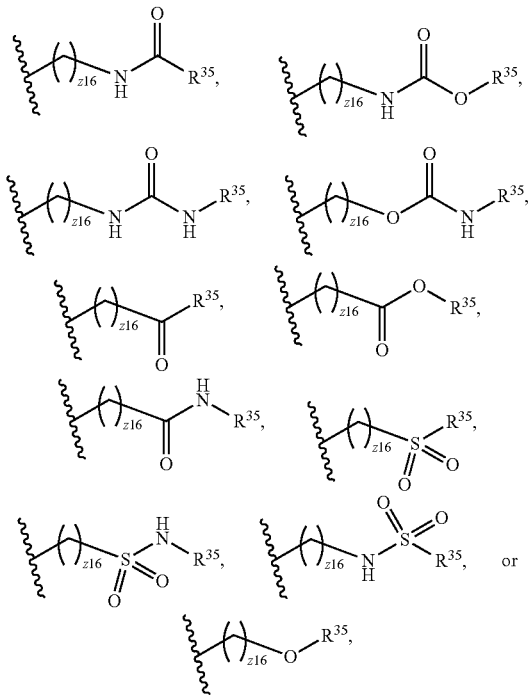

wherein $R^{35}$ and z16 are as described herein, including embodiments.

In embodiments, $R^6$ is

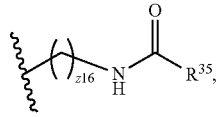

wherein $R^{35}$ and z16 are as described herein, including embodiments. In embodiments, $R^6$ is

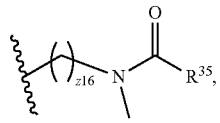

wherein $R^{35}$ and z16 are as described herein, including embodiments. In embodiments, $R^6$ is

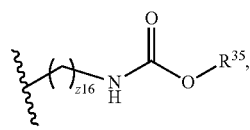

wherein $R^{35}$ and z16 are as described herein, including embodiments. In embodiments, $R^6$ is

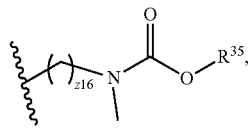

wherein $R^{35}$ and z16 are as described herein, including embodiments. In embodiments, $R^6$ is

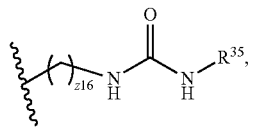

wherein $R^{35}$ and z16 are as described herein, including embodiments. In embodiments, $R^6$ is

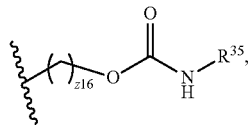

wherein $R^{35}$ and z16 are as described herein, including embodiments. In embodiments, $R^6$ is

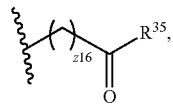

wherein $R^{35}$ and z16 are as described herein, including embodiments. In embodiments, $R^6$ is

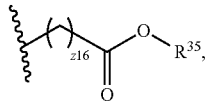

wherein $R^{35}$ and z16 are as described herein, including embodiments. In embodiments, $R^6$ is

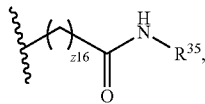

wherein $R^{35}$ and z16 are as described herein, including embodiments. In embodiments, $R^6$ is

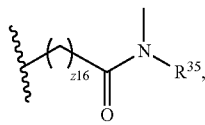

wherein $R^{35}$ and z16 are as described herein, including embodiments. In embodiments, $R^6$ is

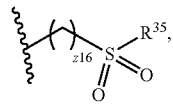

wherein $R^{35}$ and z16 are as described herein, including embodiments. In embodiments, $R^6$ is

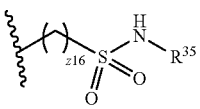

wherein $R^{35}$ and z16 are as described herein, including embodiments. In embodiments, $R^6$ is

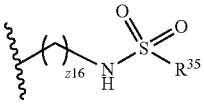

wherein R and z16 are as described herein, including embodiments. In embodiments, $R^6$ is

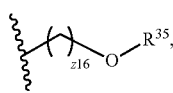

wherein $R^{35}$ and z16 are as described herein, including embodiments.

In embodiments, $R^6$ is

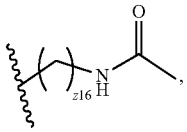 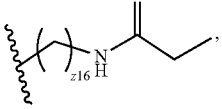

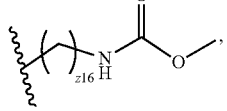 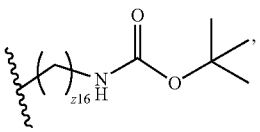

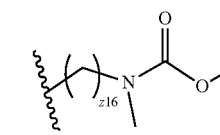 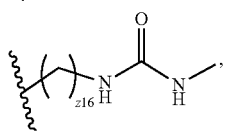

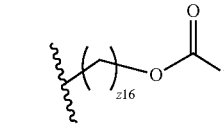 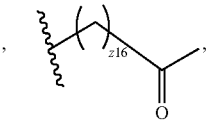

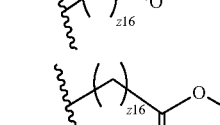 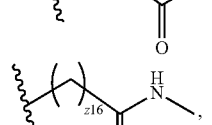

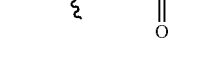 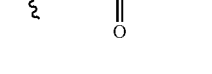

-continued

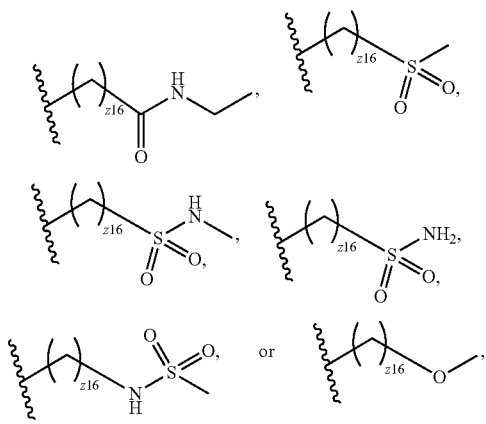

wherein z16 is as described herein, including embodiments. In embodiments, $R^6$ is

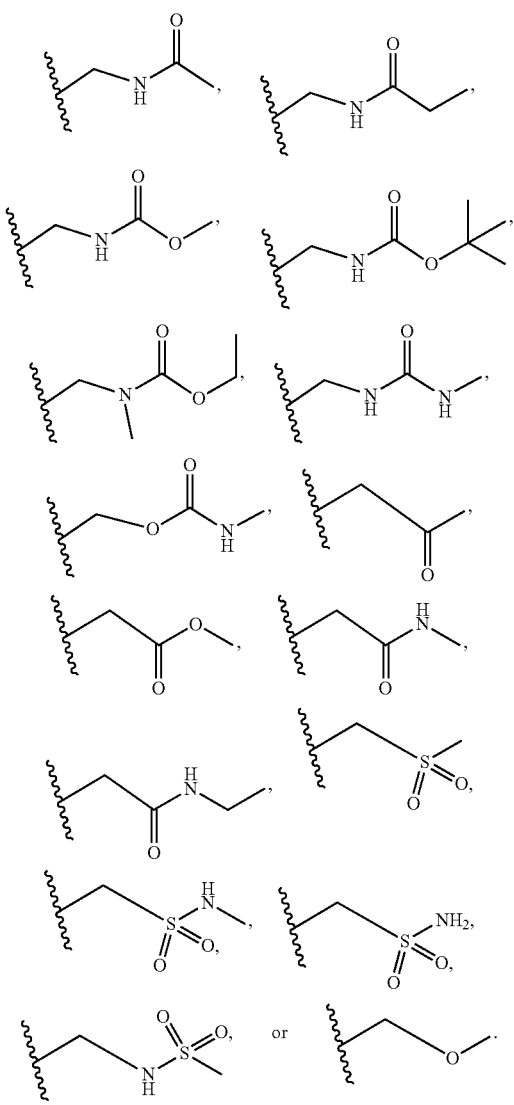

In embodiments, $R^6$ is

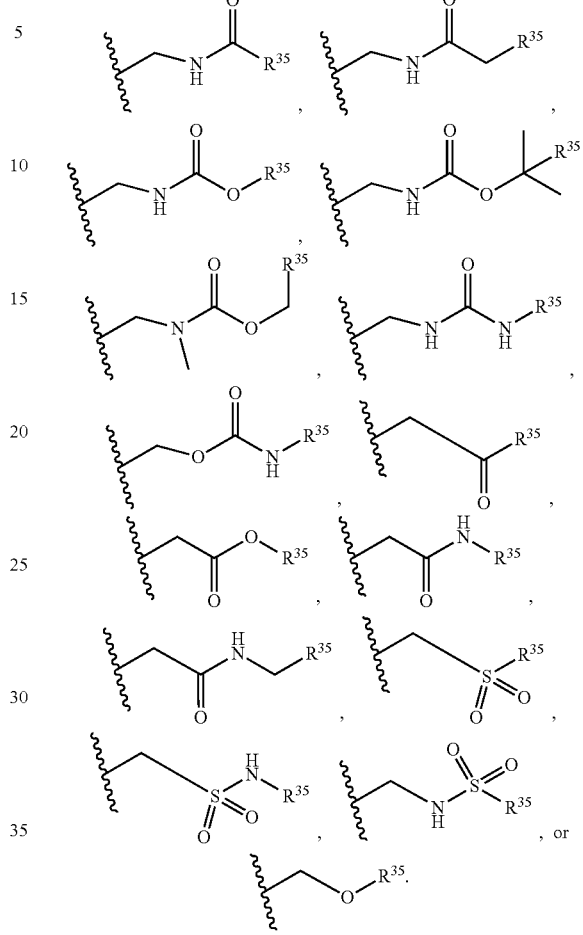

In embodiments, $R^6$ is

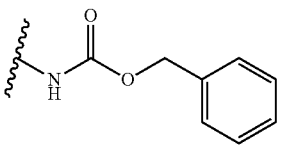

In embodiments, $R^6$ is

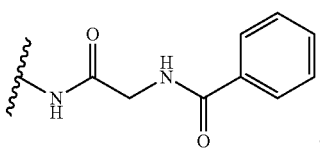

In embodiments, z16 is 1. In embodiments, z16 is 2. In embodiments, z16 is 3. In embodiments, z16 is 4. In embodiments, z16 is 5. In embodiments, z16 is 6. In embodiments, z16 is 7. In embodiments, z16 is 8. In embodiments, z16 is an integer from 1 to 3. In embodiments, z16 is an integer from 1 to 2. In embodiments, z16 is an integer from 1 to 4. In embodiments, z16 is 0.

In embodiments, $R^6$ is independently unsubstituted methyl. In embodiments, $R^6$ is independently unsubstituted $C_1$-$C_3$ alkyl.

In embodiments, $R^6$ is independently —F. In embodiments, $R^6$ is independently halogen.

In embodiments, $R^6$ is independently —$OCH_3$. In embodiments, $R^6$ is independently —$OCH_2CH_3$. In embodiments, $R^6$ is independently —$CH_2OCH_3$. In embodiments, $R^6$ is independently unsubstituted 2 to 3 membered heteroalkyl. In embodiments, $R^6$ is independently —OH.

In embodiments, $R^6$ is independently —$CH_2OH$. In embodiments, $R^6$ is independently substituted methyl. In embodiments, $R^6$ is independently OH-substituted $C_1$-$C_3$ alkyl. In embodiments, $R^6$ is independently substituted $C_1$-$C_3$ alkyl.

In embodiments, $R^6$ is independently unsubstituted phenyl-substituted propyl. In embodiments, $R^6$ is independently unsubstituted phenyl-substituted $C_2$-$C_6$ alkyl. In embodiments, $R^6$ is independently unsubstituted aryl-substituted $C_2$-$C_6$ alkyl.

In embodiments, $R^6$ is independently tert-butyloxycarbonyl. In embodiments, $R^6$ is independently oxo-substituted 6 membered heteroalkyl. In embodiments, $R^6$ is independently oxo-substituted 4 to 8 membered heteroalkyl. In embodiments, $R^6$ is substituted 6 membered heteroalkyl. In embodiments, $R^6$ is substituted 4 to 8 membered heteroalkyl. In embodiments, $R^6$ is independently tert-butylcarbamate.

In embodiments, $R^6$ is independently N-methyl-substituted tert-butylcarbamate. In embodiments, $R^6$ is independently oxo-substituted 6 to 10 membered heteroalkyl. In embodiments, $R^6$ is independently substituted 6 to 10 membered heteroalkyl.

In embodiments, $R^6$ is independently —$SO_2CH_3$. In embodiments, $R^6$ is independently —$SO_2$-(unsubstituted $C_1$-$C_3$ alkyl). In embodiments, $R^6$ is independently oxo-substituted 2 to 4 membered heteroalkyl.

In embodiments, $R^6$ is independently —$CH_2CF_3$. In embodiments, $R^6$ is independently halo-substituted ethyl. In embodiments, $R^6$ is independently halo-substituted $C_1$-$C_4$ alkyl.

In embodiments, $R^6$ is independently —$NHC(O)CH_3$. In embodiments, $R^6$ is independently -oxo-substituted 2 to 4 membered heteroalkyl. In embodiments, $R^6$ is independently —$CH_2NH_2$.

In embodiments, $R^6$ is independently —$NH(CH_3)$. In embodiments, $R^6$ is independently —$NR^{6A}R^{6B}$. In embodiments, $R^6$ is independently unsubstituted 2 to 3 membered heteroalkyl. In embodiments, $R^6$ is independently —$NH_2$.

In embodiments, $R^6$ is independently —COOH.

In embodiments, $R^6$ is independently oxo-substituted 8 membered heteroalkyl. In embodiments, $R^6$ is independently oxo-substituted 6 to 10 membered heteroalkyl. In embodiments, $R^6$ is independently substituted 8 membered heteroalkyl. In embodiments, $R^6$ is independently substituted 6 to 10 membered heteroalkyl.

In embodiments, $R^6$ is independently —$CH_2NH_2$. In embodiments, $R^6$ is independently $NH_2$-substituted $C_1$-$C_3$ alkyl.

In embodiments, $R^6$ is independently —$OCH_2CH_3$. In embodiments, $R^6$ is independently unsubstituted 2 to 4 membered alkoxy. In embodiments, $R^6$ is independently unsubstituted 2 to 4 membered heteroalkyl. In embodiments, $R^6$ is independently unsubstituted 2 to 4 membered heteroalkyl.

In embodiments, $R^6$ is independently unsubstituted benzyl carbamate. In embodiments, $R^6$ is independently OH-substituted and unsubstituted phenyl-substituted 2 to 5 membered heteroalkyl. In embodiments, $R^6$ is independently substituted 2 to 5 membered heteroalkyl.

In embodiments, $R^6$ is independently —$N(CH_3)_2$. In embodiments, $R^6$ is independently —$N$(unsubstituted $C_1$-$C_3$ alkyl)$_2$. In embodiments, $R^6$ is independently unsubstituted 2 to 6 membered heteroalkyl.

In embodiments, $R^6$ is independently —$CH_2C(O)NHCH_2CH_3$. In embodiments, $R^6$ is independently oxo-substituted 4 to 6 membered heteroalkyl. In embodiments, $R^6$ is independently substituted 4 to 6 membered heteroalkyl.

In embodiments, $R^6$ is independently —$CH_2N(CH_3)_2$. In embodiments, $R^6$ is independently unsubstituted 2 to 6 membered heteroalkyl.

In embodiments, $R^6$ is independently —$C(O)NH_2$. In embodiments, $R^6$ is independently oxo-substituted and $NH_2$-substituted methyl. In embodiments, $R^6$ is independently oxo-substituted and $NH_2$-substituted $C_1$-$C_4$ alkyl. In embodiments, $R^6$ is independently substituted $C_1$-$C_4$ alkyl.

In embodiments, $R^6$ is independently —$N(CH_3)C(O)OCH_2CH_3$. In embodiments, $R^6$ is independently oxo-substituted 4 to 8 membered heteroalkyl. In embodiments, $R^6$ is independently substituted 4 to 8 membered heteroalkyl.

In embodiments, $R^6$ is independently oxo-substituted 4 to 10 membered heteroalkyl. In embodiments, $R^6$ is independently substituted 4 to 10 membered heteroalkyl. In embodiments, $R^6$ is independently oxo-substituted 2 to 6 membered heteroalkyl. In embodiments, $R^6$ is independently substituted 2 to 6 membered heteroalkyl. In embodiments, $R^6$ is independently oxo-substituted 4 to 8 membered heteroalkyl. In embodiments, $R^6$ is independently substituted 4 to 8 membered heteroalkyl. In embodiments, $R^6$ is independently oxo-substituted and unsubstituted phenyl-substituted 3 to 8 membered heteroalkyl. In embodiments, $R^6$ is independently oxo-substituted and unsubstituted aryl-substituted 3 to 8 membered heteroalkyl. In embodiments, $R^6$ is independently oxo-substituted and unsubstituted aryl-substituted 4 to 6 membered heteroalkyl. In embodiments, $R^6$ is independently oxo-substituted and unsubstituted phenyl-substituted 4 to 6 membered heteroalkyl. In embodiments, $R^6$ is independently substituted 3 to 8 membered heteroalkyl. In embodiments, $R^6$ is independently substituted 4 to 6 membered heteroalkyl. In embodiments, $R^6$ is independently unsubstituted 2 to 4 membered heteroalkyl.

$R^{6.1}$ and $R^{6.2}$ are each hydrogen or $R^6$ at a fixed position on the attached ring. $R^{6.1}$ and $R^{6.2}$ may be any substituent of $R^6$ described herein, including in any aspect, embodiment, example, figure, or claim. $R^{6.1}$ is independently hydrogen, halogen, —$CX^6_3$, —$CHX^6_2$, —$CH_2X^6$, —$OCX^6_3$, —$OCH_2X^6$, —$OCHX^6_2$, —CN, —$SR^{6D}$, —$SO_2R^{6D}$, —$NR^{6A}R^{6B}$, —$C(O)R^{6C}$, —$C(O)OR^{6C}$, —$C(O)NR^{6A}R^{6B}$, —$OR^{6D}$, —$NR^{6A}C(O)R^{6C}$—, —$NR^{6A}C(O)NR^{6C}$—, —$NR^{6A}C(O)OR^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{6.2}$ is independently hydrogen, halogen, —$CX^6_3$, —$CHX^6_2$, —$CH_2X^6$, —$OCX^6_3$, —$OCH_2X^6$, —$OCHX^6_2$, —CN, —$SR^{6D}$, —$SO_2R^{6D}$, —$NR^{6A}R^{6B}$, —$C(O)R^{6C}$, —$C(O)OR^{6C}$, —$C(O)NR^{6A}R^{6B}$, —$OR^{6D}$, —$NR^{6A}C(O)R^{6C}$—, —$NR^{6A}C(O)NR^{6C}$—, —$NR^{6A}C(O)OR^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{6.1}$ is halogen. In embodiments, $R^{6.1}$ is —$CX^6{}_3$. In embodiments, $R^{6.1}$ is —$CHX^6{}_2$. In embodiments, $R^{6.1}$ is —$CH_2X^6$. In embodiments, $R^{6.1}$ is —$OCX^6{}_3$. In embodiments, $R^{6.1}$ is —$OCH_2X^6$. In embodiments, $R^{6.1}$ is —$OCHX^6{}_2$. In embodiments, $R^{6.1}$ is —CN. In embodiments, $R^{6.1}$ is —$SR^{6D}$. In embodiments, $R^{6.1}$ is —$SO_2R^{6D}$. In embodiments, $R^{6.1}$ is —$NR^{6A}R^{6B}$. In embodiments, $R^{6.1}$ is —$C(O)R^{6C}$. In embodiments, $R^{6.1}$ is —$C(O)OR^{6C}$. In embodiments, $R^{6.1}$ is —$C(O)NR^{6A}R^{6B}$. In embodiments, $R^{6.1}$ is —$OR^{6D}$. In embodiments, $R^{6.1}$ is —$NR^{6A}C(O)R^{6C}$. In embodiments, $R^{6.1}$ is —$NR^{6A}C(O)OR^{6C}$.

In embodiments, $R^{6.1}$ is substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{6.1}$ is hydrogen, substituted or unsubstituted $C_1$-$C_8$ alkyl, or substituted or unsubstituted 2 to 8 membered heteroalkyl.

In embodiments, $R^{6.1}$ is independently halogen, —$CX^6{}_3$, —$CHX^6{}_2$, —$CH_2X^6$, —$OCX^6{}_3$, —$OCH_2X^6$, —$OCHX^6{}_2$, —CN, —$SR^{6D}$, —$SO_2R^{6D}$, —$NR^{6A}R^{6B}$, —$C(O)R^{6C}$, —$C(O)OR^{6C}$, —$C(O)NR^{6A}R^{6B}$, —$OR^{6D}$, —$NR^{6A}C(O)R^{6C}$, —$NR^{6A}C(O)OR^{6C}$, substituted or unsubstituted alkyl, or substituted or unsubstituted heteroalkyl.

In embodiments, $R^{6.1}$ is $R^{35}$-substituted or unsubstituted alkyl (e.g., $C_1$-$C_8$ alkyl, $C_1$-$C_6$ alkyl, or $C_1$-$C_4$ alkyl). In embodiments, $R^{6.1}$ is $R^{35}$-substituted alkyl (e.g., $C_1$-$C_8$ alkyl, $C_1$-$C_6$ alkyl, or $C_1$-$C_4$ alkyl). In embodiments, $R^{6.1}$ is an unsubstituted alkyl (e.g., $C_1$-$C_8$ alkyl, $C_1$-$C_6$ alkyl, or $C_1$-$C_4$ alkyl). In embodiments, $R^{6.1}$ is $R^{35}$-substituted or unsubstituted heteroalkyl (e.g., 2 to 8 membered heteroalkyl, 2 to 6 membered heteroalkyl, or 2 to 4 membered heteroalkyl). In embodiments, $R^{6.1}$ is $R^{35}$-substituted heteroalkyl (e.g., 2 to 8 membered heteroalkyl, 2 to 6 membered heteroalkyl, or 2 to 4 membered heteroalkyl). In embodiments, $R^{6.1}$ is an unsubstituted heteroalkyl (e.g., 2 to 8 membered heteroalkyl, 2 to 6 membered heteroalkyl, or 2 to 4 membered heteroalkyl).

In embodiments, $R^{6.1}$ is $R^{35}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{6.1}$ is $R^{35}$-substituted cycloalkyl (e.g., $C_3$-$C_8$ cycloalkyl, $C_3$-$C_6$ cycloalkyl, or $C_5$-$C_6$ cycloalkyl). In embodiments, $R^{6.1}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{6.1}$ is $R^{35}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{6.1}$ is $R^{35}$-substituted heterocycloalkyl (e.g., 3 to 8 membered heterocycloalkyl, 3 to 6 membered heterocycloalkyl, or 5 to 6 membered heterocycloalkyl). In embodiments, $R^{6.1}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{6.1}$ is $R^{35}$-substituted or unsubstituted aryl (e.g., $C_6$-$C_{10}$ aryl, $C_{10}$ aryl, or phenyl). In embodiments, $R^{6.1}$ is $R^{35}$-substituted aryl (e.g., $C_6$-$C_{10}$ aryl, $C_{10}$ aryl, or phenyl). In embodiments, $R^{6.1}$ is an unsubstituted aryl (e.g., $C_6$-$C_{10}$ aryl, $C_{10}$ aryl, or phenyl).

In embodiments, $R^{6.1}$ is $R^{35}$-substituted or unsubstituted heteroaryl (e.g., 5 to 10 membered heteroaryl, 5 to 9 membered heteroaryl, or 5 to 6 membered heteroaryl). In embodiments, $R^{6.1}$ is $R^{35}$-substituted heteroaryl (e.g., 5 to 10 membered heteroaryl, 5 to 9 membered heteroaryl, or 5 to 6 membered heteroaryl). In embodiments, $R^{6.1}$ is an unsubstituted heteroaryl (e.g., 5 to 10 membered heteroaryl, 5 to 9 membered heteroaryl, or 5 to 6 membered heteroaryl).

In embodiments, $R^{6.2}$ is halogen. In embodiments, $R^{6.2}$ is —$CX^6{}_3$. In embodiments, $R^{6.2}$ is —$CHX^6{}_2$. In embodiments, $R^{6.2}$ is —$CH_2X^6$. In embodiments, $R^{6.2}$ is —$OCX^6{}_3$. In embodiments, $R^{6.2}$ is —$OCH_2X^6$. In embodiments, $R^{6.2}$ is —$OCHX^6{}_2$. In embodiments, $R^{6.2}$ is —CN. In embodiments, $R^{6.2}$ is —$SR^{6D}$. In embodiments, $R^{6.2}$ is —$SO_2R^{6D}$. In embodiments, $R^{6.2}$ is —$NR^{6A}R^{6B}$. In embodiments, $R^{6.2}$ is —$C(O)R^{6C}$. In embodiments, $R^{6.2}$ is —$C(O)OR^{6C}$. In embodiments, $R^{6.2}$ is —$C(O)NR^{6A}R^{6B}$. In embodiments, $R^{6.2}$ is —$OR^{6D}$. In embodiments, $R^{6.2}$ is —$NR^{6A}C(O)R^{6C}$. In embodiments, $R^{6.2}$ is —$NR^{6A}C(O)OR^{6C}$.

In embodiments, $R^{6.2}$ is substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^{6.2}$ is hydrogen, substituted or unsubstituted $C_1$-$C_8$ alkyl, or substituted or unsubstituted 2 to 8 membered heteroalkyl.

In embodiments, $R^{6.2}$ is independently halogen, —$CX^6{}_3$, —$CHX^6{}_2$, —$CH_2X^6$, —$OCX^6{}_3$, —$OCH_2X^6$, —$OCHX^6{}_2$, —CN, —$SR^{6D}$, —$SO_2R^{6D}$, —$NR^{6A}R^{6B}$, —$C(O)R^{6C}$, —$C(O)OR^{6C}$, —$C(O)NR^{6A}R^{6B}$, —$OR^{6D}$, —$NR^{6A}C(O)R^{6C}$, —$NR^{6A}C(O)OR^{6C}$, substituted or unsubstituted alkyl, or substituted or unsubstituted heteroalkyl.

In embodiments, $R^{6.2}$ is $R^{35}$-substituted or unsubstituted alkyl (e.g., $C_1$-$C_8$ alkyl, $C_1$-$C_6$ alkyl, or $C_1$-$C_4$ alkyl). In embodiments, $R^{6.2}$ is $R^{35}$-substituted alkyl (e.g., $C_1$-$C_8$ alkyl, $C_1$-$C_6$ alkyl, or $C_1$-$C_4$ alkyl). In embodiments, $R^{6.2}$ is an unsubstituted alkyl (e.g., $C_1$-$C_8$ alkyl, $C_1$-$C_6$ alkyl, or $C_1$-$C_4$ alkyl). In embodiments, $R^{6.2}$ is $R^{35}$-substituted or unsubstituted heteroalkyl (e.g., 2 to 8 membered heteroalkyl, 2 to 6 membered heteroalkyl, or 2 to 4 membered heteroalkyl). In embodiments, $R^{6.2}$ is $R^{35}$-substituted heteroalkyl (e.g., 2 to 8 membered heteroalkyl, 2 to 6 membered heteroalkyl, or 2 to 4 membered heteroalkyl). In embodiments, $R^{6.2}$ is an unsubstituted heteroalkyl (e.g., 2 to 8 membered heteroalkyl, 2 to 6 membered heteroalkyl, or 2 to 4 membered heteroalkyl).

In embodiments, $R^{6.2}$ is $R^{35}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{6.2}$ is $R^{35}$-substituted cycloalkyl (e.g., $C_3$-$C_8$ cycloalkyl, $C_3$-$C_6$ cycloalkyl, or $C_5$-$C_6$ cycloalkyl). In embodiments, $R^{6.2}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{6.2}$ is $R^{35}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{6.2}$ is $R^{35}$-substituted heterocycloalkyl (e.g., 3 to 8 membered heterocycloalkyl, 3 to 6 membered heterocycloalkyl, or 5 to 6 membered heterocycloalkyl). In embodiments, $R^{6.2}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{6.2}$ is $R^{35}$-substituted or unsubstituted aryl (e.g., $C_6$-$C_{10}$ aryl, $C_{10}$ aryl, or phenyl). In embodiments, $R^{6.2}$ is $R^{35}$-substituted aryl (e.g., $C_6$-$C_{10}$ aryl, $C_{10}$ aryl, or phenyl). In embodiments, $R^{6.2}$ is an unsubstituted aryl (e.g., $C_6$-$C_{10}$ aryl, $C_{10}$ aryl, or phenyl).

In embodiments, $R^{6.2}$ is $R^{35}$-substituted or unsubstituted heteroaryl (e.g., 5 to 10 membered heteroaryl, 5 to 9 membered heteroaryl, or 5 to 6 membered heteroaryl). In embodiments, $R^{6.2}$ is $R^{35}$-substituted heteroaryl (e.g., 5 to 10 membered heteroaryl, 5 to 9 membered heteroaryl, or 5 to 6 membered heteroaryl). In embodiments, $R^{6.2}$ is an unsubstituted heteroaryl (e.g., 5 to 10 membered heteroaryl, 5 to 9 membered heteroaryl, or 5 to 6 membered heteroaryl).

In embodiments, $R^{6.1}$ is independently —F. In embodiments, $R^{6.1}$ is independently halogen. In embodiments, $R^{6.1}$ is independently —OCH$_3$. In embodiments, $R^{6.1}$ is independently —OCH$_2$CH$_3$. In embodiments, $R^{6.1}$ is independently —CH$_2$OCH$_3$. In embodiments, $R^{6.1}$ is independently unsubstituted 2 to 3 membered heteroalkyl. In embodiments, $R^{6.1}$ is independently —OH. In embodiments, $R^{6.1}$ is independently —CH$_2$OH. In embodiments, $R^{6.1}$ is independently substituted methyl. In embodiments, $R^{6.1}$ is independently OH-substituted $C_1$-$C_3$ alkyl. In embodiments, $R^{6.1}$ is independently substituted $C_1$-$C_3$ alkyl. In embodiments, $R^{6.1}$ is independently unsubstituted phenyl-substituted propyl. In embodiments, $R^{6.1}$ is independently unsubstituted phenyl-substituted $C_2$-$C_6$ alkyl. In embodiments, $R^{6.1}$ is independently unsubstituted aryl-substituted $C_2$-$C_6$ alkyl. In embodiments, $R^{6.1}$ is independently tert-butyloxycarbonyl. In embodiments, $R^{6.1}$ is independently oxo-substituted 6 membered heteroalkyl. In embodiments, $R^{6.1}$ is independently oxo-substituted 4 to 8 membered heteroalkyl. In embodiments, $R^{6.1}$ is substituted 6 membered heteroalkyl. In embodiments, $R^{6.1}$ is substituted 4 to 8 membered heteroalkyl. In embodiments, $R^{6.1}$ is independently tert-butylcarbamate. In embodiments, $R^{6.1}$ is independently N-methyl-substituted tert-butylcarbamate. In embodiments, $R^{6.1}$ is independently oxo-substituted 6 to 10 membered heteroalkyl. In embodiments, $R^{6.1}$ is independently substituted 6 to 10 membered heteroalkyl. In embodiments, $R^{6.1}$ is independently —SO$_2$CH$_3$. In embodiments, $R^{6.1}$ is independently —SO$_2$-(unsubstituted $C_1$-$C_3$ alkyl). In embodiments, $R^{6.1}$ is independently oxo-substituted 2 to 4 membered heteroalkyl. In embodiments, $R^{6.1}$ is independently —CH$_2$CF$_3$. In embodiments, $R^{6.1}$ is independently halo-substituted ethyl. In embodiments, $R^{6.1}$ is independently halo-substituted $C_1$-$C_4$ alkyl. In embodiments, $R^{6.1}$ is independently —NHC(O)CH$_3$. In embodiments, $R^{6.1}$ is independently -oxo-substituted 2 to 4 membered heteroalkyl. In embodiments, $R^{6.1}$ is independently —CH$_2$NH$_2$. In embodiments, $R^{6.1}$ is independently —NH(CH$_3$). In embodiments, $R^{6.1}$ is independently —NR$^{6.1B}$R$^{6.1B}$. In embodiments, $R^{6.1}$ is independently unsubstituted 2 to 3 membered heteroalkyl. In embodiments, $R^{6.1}$ is independently —NH$_2$. In embodiments, $R^{6.1}$ is independently —COOH. In embodiments, $R^{6.1}$ is independently oxo-substituted 8 membered heteroalkyl. In embodiments, $R^{6.1}$ is independently oxo-substituted 6 to 10 membered heteroalkyl. In embodiments, $R^{6.1}$ is independently substituted 8 membered heteroalkyl. In embodiments, $R^{6.1}$ is independently substituted 6 to 10 membered heteroalkyl. In embodiments, $R^{6.1}$ is independently —CH$_2$NH$_2$. In embodiments, $R^{6.1}$ is independently NH$_2$-substituted $C_1$-$C_3$ alkyl. In embodiments, $R^{6.1}$ is independently —OCH$_2$CH$_3$. In embodiments, $R^{6.1}$ is independently unsubstituted 2 to 4 membered alkoxy. In embodiments, $R^{6.1}$ is independently unsubstituted 2 to 4 membered heteroalkyl. In embodiments, $R^{6.1}$ is independently unsubstituted 2 to 4 membered heteroalkyl. In embodiments, $R^{6.1}$ is independently unsubstituted benzyl carbamate. In embodiments, $R^{6.1}$ is independently OH-substituted and unsubstituted phenyl-substituted 2 to 5 membered heteroalkyl. In embodiments, $R^{6.1}$ is independently substituted 2 to 5 membered heteroalkyl. In embodiments, $R^{6.1}$ is independently —N(CH$_3$)$_2$. In embodiments, $R^{6.1}$ is independently —N(unsubstituted $C_1$-$C_3$ alkyl)$_2$. In embodiments, $R^{6.1}$ is independently unsubstituted 2 to 6 membered heteroalkyl. In embodiments, $R^{6.1}$ is independently —CH$_2$C(O)NHCH$_2$CH$_3$. In embodiments, $R^{6.1}$ is independently oxo-substituted 4 to 6 membered heteroalkyl. In embodiments, $R^{6.1}$ is independently substituted 4 to 6 membered heteroalkyl. In embodiments, $R^{6.1}$ is independently —CH$_2$N(CH$_3$)$_2$. In embodiments, $R^{6.1}$ is independently unsubstituted 2 to 6 membered heteroalkyl. In embodiments, $R^{6.1}$ is independently —C(O)NH$_2$. In embodiments, $R^{6.1}$ is independently oxo-substituted and NH$_2$-substituted methyl. In embodiments, $R^{6.1}$ is independently oxo-substituted and NH$_2$-substituted $C_1$-$C_4$ alkyl. In embodiments, $R^{6.1}$ is independently substituted $C_1$-$C_4$ alkyl. In embodiments, $R^{6.1}$ is independently —N(CH$_3$)C(O)OCH$_2$CH$_3$. In embodiments, $R^{6.1}$ is independently oxo-substituted 4 to 8 membered heteroalkyl. In embodiments, $R^{6.1}$ is independently substituted 4 to 8 membered heteroalkyl. In embodiments, $R^{6.1}$ is independently oxo-substituted 4 to 10 membered heteroalkyl. In embodiments, $R^{6.1}$ is independently substituted 4 to 10 membered heteroalkyl. In embodiments, $R^{6.1}$ is independently oxo-substituted 2 to 6 membered heteroalkyl. In embodiments, $R^{6.1}$ is independently substituted 2 to 6 membered heteroalkyl. In embodiments, $R^{6.1}$ is independently oxo-substituted 4 to 8 membered heteroalkyl. In embodiments, $R^{6.1}$ is independently substituted 4 to 8 membered heteroalkyl. In embodiments, $R^{6.1}$ is independently oxo-substituted and unsubstituted phenyl-substituted 3 to 8 membered heteroalkyl. In embodiments, $R^{6.1}$ is independently oxo-substituted and unsubstituted aryl-substituted 3 to 8 membered heteroalkyl. In embodiments, $R^{6.1}$ is independently oxo-substituted and unsubstituted aryl-substituted 4 to 6 membered heteroalkyl. In embodiments, $R^{6.1}$ is independently oxo-substituted and unsubstituted phenyl-substituted 4 to 6 membered heteroalkyl. In embodiments, $R^{6.1}$ is independently substituted 3 to 8 membered heteroalkyl. In embodiments, $R^{6.1}$ is independently substituted 4 to 6 membered heteroalkyl. In embodiments, $R^{6.1}$ is independently unsubstituted 2 to 4 membered heteroalkyl.

In embodiments, $R^{6.2}$ is independently —F. In embodiments, $R^{6.2}$ is independently halogen. In embodiments, $R^{6.2}$ is independently —OCH$_3$. In embodiments, $R^{6.2}$ is independently —OCH$_2$CH$_3$. In embodiments, $R^{6.2}$ is independently —CH$_2$OCH$_3$. In embodiments, $R^{6.2}$ is independently unsubstituted 2 to 3 membered heteroalkyl. In embodiments, $R^{6.2}$ is independently —OH. In embodiments, $R^{6.2}$ is independently —CH$_2$OH. In embodiments, $R^{6.2}$ is independently substituted methyl. In embodiments, $R^{6.2}$ is independently OH-substituted $C_1$-$C_3$ alkyl. In embodiments, $R^{6.2}$ is independently substituted $C_1$-$C_3$ alkyl. In embodiments, $R^{6.2}$ is independently unsubstituted phenyl-substituted propyl. In embodiments, $R^{6.2}$ is independently unsubstituted phenyl-substituted $C_2$-$C_6$ alkyl. In embodiments, $R^{6.2}$ is independently unsubstituted aryl-substituted $C_2$-$C_6$ alkyl. In embodiments, $R^{6.2}$ is independently tert-butyloxycarbonyl. In embodiments, $R^{6.2}$ is independently oxo-substituted 6 membered heteroalkyl. In embodiments, $R^{6.2}$ is independently oxo-substituted 4 to 8 membered heteroalkyl. In embodiments, $R^{6.2}$ is substituted 6 membered heteroalkyl. In embodiments, $R^{6.2}$ is substituted 4 to 8 membered heteroalkyl. In embodiments, $R^{6.2}$ is independently tert-butylcarbamate. In embodiments, $R^{6.2}$ is independently N-methyl-substituted tert-butylcarbamate. In embodiments, $R^{6.2}$ is independently oxo-substituted 6 to 10 membered heteroalkyl. In embodiments, $R^{6.2}$ is independently substituted 6 to 10 membered heteroalkyl. In embodiments, $R^{6.2}$ is independently —SO$_2$CH$_3$. In embodiments, $R^{6.2}$ is independently —SO$_2$-(unsubstituted $C_1$-$C_3$ alkyl). In embodiments, $R^{6.2}$ is independently oxo-substituted 2 to 4 membered heteroalkyl.

In embodiments, $R^{6.2}$ is independently —$CH_2CF_3$. In embodiments, $R^{6.2}$ is independently halo-substituted ethyl. In embodiments, $R^{6.2}$ is independently halo-substituted $C_1$-$C_4$ alkyl. In embodiments, $R^{6.2}$ is independently —NHC(O)$CH_3$. In embodiments, $R^{6.2}$ is independently -oxo-substituted 2 to 4 membered heteroalkyl. In embodiments, $R^{6.2}$ is independently —$CH_2NH_2$. In embodiments, $R^{6.2}$ is independently —NH($CH_3$). In embodiments, $R^{6.2}$ is independently —$NR^{6.2B}R^{6.2B}$. In embodiments, $R^{6.2}$ is independently unsubstituted 2 to 3 membered heteroalkyl. In embodiments, $R^{6.2}$ is independently —$NH_2$. In embodiments, $R^{6.2}$ is independently —COOH. In embodiments, $R^{6.2}$ is independently oxo-substituted 8 membered heteroalkyl. In embodiments, $R^{6.2}$ is independently oxo-substituted 6 to 10 membered heteroalkyl. In embodiments, $R^{6.2}$ is independently substituted 8 membered heteroalkyl. In embodiments, $R^{6.2}$ is independently substituted 6 to 10 membered heteroalkyl. In embodiments, $R^{6.2}$ is independently —$CH_2NH_2$. In embodiments, $R^{6.2}$ is independently $NH_2$-substituted $C_1$-$C_3$ alkyl. In embodiments, $R^{6.2}$ is independently —$OCH_2CH_3$. In embodiments, $R^{6.2}$ is independently unsubstituted 2 to 4 membered alkoxy. In embodiments, $R^{6.2}$ is independently unsubstituted 2 to 4 membered heteroalkyl. In embodiments, $R^{6.2}$ is independently unsubstituted 2 to 4 membered heteroalkyl. In embodiments, $R^{6.2}$ is independently unsubstituted benzyl carbamate. In embodiments, $R^{6.2}$ is independently OH-substituted and unsubstituted phenyl-substituted 2 to 5 membered heteroalkyl. In embodiments, $R^{6.2}$ is independently substituted 2 to 5 membered heteroalkyl. In embodiments, $R^{6.2}$ is independently —N($CH_3$)$_2$. In embodiments, $R^{6.2}$ is independently —N (unsubstituted $C_1$-$C_3$ alkyl)$_2$. In embodiments, $R^{6.2}$ is independently unsubstituted 2 to 6 membered heteroalkyl. In embodiments, $R^{6.2}$ is independently —$CH_2C(O)NHCH_2CH_3$. In embodiments, $R^{6.2}$ is independently oxo-substituted 4 to 6 membered heteroalkyl. In embodiments, $R^{6.2}$ is independently substituted 4 to 6 membered heteroalkyl. In embodiments, $R^{6.2}$ is independently —$CH_2N(CH_3)_2$. In embodiments, $R^{6.2}$ is independently unsubstituted 2 to 6 membered heteroalkyl. In embodiments, $R^{6.2}$ is independently —C(O)$NH_2$. In embodiments, $R^{6.2}$ is independently oxo-substituted and $NH_2$-substituted methyl. In embodiments, $R^{6.2}$ is independently oxo-substituted and $NH_2$-substituted $C_1$-$C_4$ alkyl. In embodiments, $R^{6.2}$ is independently substituted $C_1$-$C_4$ alkyl. In embodiments, $R^{6.2}$ is independently —N($CH_3$)C(O)$OCH_2CH_3$. In embodiments, $R^{6.2}$ is independently oxo-substituted 4 to 8 membered heteroalkyl. In embodiments, $R^{6.2}$ is independently substituted 4 to 8 membered heteroalkyl. In embodiments, $R^{6.2}$ is independently oxo-substituted 4 to 10 membered heteroalkyl. In embodiments, $R^{6.2}$ is independently substituted 4 to 10 membered heteroalkyl. In embodiments, $R^{6.2}$ is independently oxo-substituted 2 to 6 membered heteroalkyl. In embodiments, $R^{6.2}$ is independently substituted 2 to 6 membered heteroalkyl. In embodiments, $R^{6.2}$ is independently oxo-substituted 4 to 8 membered heteroalkyl. In embodiments, $R^{6.2}$ is independently substituted 4 to 8 membered heteroalkyl. In embodiments, $R^{6.2}$ is independently oxo-substituted and unsubstituted phenyl-substituted 3 to 8 membered heteroalkyl. In embodiments, $R^{6.2}$ is independently oxo-substituted and unsubstituted aryl-substituted 3 to 8 membered heteroalkyl. In embodiments, $R^{6.2}$ is independently oxo-substituted and unsubstituted aryl-substituted 4 to 6 membered heteroalkyl. In embodiments, $R^{6.2}$ is independently oxo-substituted and unsubstituted phenyl-substituted 4 to 6 membered heteroalkyl. In embodiments, $R^{6.2}$ is independently substituted 3 to 8 membered heteroalkyl. In embodiments, $R^{6.2}$ is independently substituted 4 to 6 membered heteroalkyl. In embodiments, $R^{6.2}$ is independently unsubstituted 2 to 4 membered heteroalkyl.

In embodiments, $L^1$ is $R^{38}$-substituted or unsubstituted alkylene (e.g., $C_1$-$C_8$ alkylene, $C_1$-$C_6$ alkylene, or $C_1$-$C_4$ alkylene) or $R^{38}$-substituted or unsubstituted heteroalkylene (e.g., 2 to 8 membered heteroalkylene, 2 to 6 membered heteroalkylene, or 2 to 4 membered heteroalkylene). In embodiments, $L^1$ is $R^{38}$-substituted or unsubstituted $C_1$-$C_6$ alkylene or $R^{38}$-substituted or unsubstituted 2 to 6 membered heteroalkylene. In embodiments, $L^1$ is methyl-substituted $C_1$-$C_6$ alkylene. In embodiments, $L^1$ is methyl-substituted $C_1$-$C_5$ alkylene. In embodiments, $L^1$ is methyl-substituted $C_1$-$C_4$ alkylene. In embodiments, $L^1$ is methyl-substituted $C_1$-$C_3$ alkylene. In embodiments, $L^1$ is methyl-substituted $C_1$-$C_2$ alkylene. In embodiments, $L^1$ is methyl-substituted methylene. In embodiments, $L^1$ is a bond. In embodiments, $L^1$ is substituted or unsubstituted $C_1$-$C_3$ alkylene, substituted or unsubstituted 2 to 3 membered heteroalkylene. In embodiments, $L^1$ is a bond. In embodiments, $L^1$ is a methyl substituted methylene.

In embodiments, $L^1$ is $R^{38}$-substituted or unsubstituted alkylene (e.g., $C_1$-$C_8$ alkylene, $C_1$-$C_6$ alkylene, or $C_1$-$C_4$ alkylene). In embodiments, $L^1$ is $R^{38}$-substituted alkylene (e.g., $C_1$-$C_8$ alkylene, $C_1$-$C_6$ alkylene, or $C_1$-$C_4$ alkylene). In embodiments, $L^1$ is an unsubstituted alkylene (e.g., $C_1$-$C_8$ alkylene, $C_1$-$C_6$ alkylene, or $C_1$-$C_4$ alkylene). In embodiments, $L^1$ is $R^{38}$-substituted or unsubstituted heteroalkylene (e.g., 2 to 8 membered heteroalkylene, 2 to 6 membered heteroalkylene, or 2 to 4 membered heteroalkylene). In embodiments, $L^1$ is $R^{38}$-substituted heteroalkylene (e.g., 2 to 8 membered heteroalkylene, 2 to 6 membered heteroalkylene, or 2 to 4 membered heteroalkylene). In embodiments, $L^1$ is an unsubstituted heteroalkylene (e.g., 2 to 8 membered heteroalkylene, 2 to 6 membered heteroalkylene, or 2 to 4 membered heteroalkylene).

$R^{38}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{39}$-substituted or unsubstituted alkyl (e.g., $C_1$-$C_8$ alkyl, $C_1$-$C_6$ alkyl, or $C_1$-$C_4$ alkyl), $R^{39}$-substituted or unsubstituted heteroalkyl (e.g., 2 to 8 membered heteroalkyl, 2 to 6 membered heteroalkyl, or 2 to 4 membered heteroalkyl), $R^{39}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{39}$-substituted or unsubstituted heterocycloalkyl (e.g., 3 to 8 membered heterocycloalkyl, 3 to 6 membered heterocycloalkyl, or 5 to 6 membered heterocycloalkyl), $R^{39}$-substituted or unsubstituted aryl (e.g., $C_6$-$C_{10}$ aryl, $C_{10}$ aryl, or phenyl), or $R^{39}$-substituted or unsubstituted heteroaryl (e.g., 5 to 10 membered heteroaryl, 5 to 9 membered heteroaryl, or 5 to 6 membered heteroaryl).

$R^{39}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{40}$- substituted or unsubstituted alkyl (e.g., $C_1$-$C_8$ alkyl, $C_1$-$C_6$ alkyl, or $C_1$-$C_4$ alkyl), $R^{40}$-substituted or unsubstituted heteroalkyl (e.g., 2 to 8 membered heteroalkyl, 2 to 6 membered heteroalkyl, or 2 to 4 membered heteroalkyl), $R^{40}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{40}$-substituted or unsubstituted heterocycloalkyl (e.g., 3 to 8 membered heterocycloalkyl, 3 to 6 membered heterocycloalkyl, or 5 to 6 membered heterocycloalkyl), $R^{40}$-substituted or unsubstituted aryl (e.g., $C_6$-$C_{10}$ aryl, $C_{10}$ aryl, or phenyl), or $R^{40}$-substituted or unsubstituted heteroaryl (e.g., 5 to 10 membered heteroaryl, 5 to 9 membered heteroaryl, or 5 to 6 membered heteroaryl).

In embodiments, $R^{39}$ is $R^{40}$-substituted or unsubstituted alkyl (e.g., $C_1$-$C_8$ alkyl, $C_1$-$C_6$ alkyl, or $C_1$-$C_4$ alkyl). In embodiments, $R^{39}$ is $R^{40}$-substituted alkyl (e.g., $C_1$-$C_8$ alkyl, $C_1$-$C_6$ alkyl, or $C_1$-$C_4$ alkyl). In embodiments, $R^{39}$ is an unsubstituted alkyl (e.g., $C_1$-$C_8$ alkyl, $C_1$-$C_6$ alkyl, or $C_1$-$C_4$ alkyl).

In embodiments, $L^1$ is substituted or unsubstituted $C_1$-$C_3$ alkylene. In embodiments, $L^1$ is substituted or unsubstituted methylene. In embodiments, $L^1$ is substituted or unsubstituted $C_1$-$C_6$ alkylene, or substituted or unsubstituted 2 to 6 membered heteroalkylene. In embodiments, $L^1$ is substituted or unsubstituted $C_1$-$C_3$ alkylene, or substituted or unsubstituted 2 to 3 membered heteroalkylene.

In embodiments, $L^1$ is —CH(CH$_3$)—. In embodiments, $L^1$ is unsubstituted ethyl. In embodiments, $L^1$ is unsubstituted $C_1$-$C_3$ alkylene. In embodiments, $L^1$ is unsubstituted methylene. In embodiments, $L^1$ is unsubstituted $C_2$-$C_3$ alkylene. In embodiments, $L^1$ is —CH(CH$_2$CH$_3$)—. In embodiments, $L^1$ is —C(CH$_3$)$_2$-. In embodiments, $L^1$ is —CH$_2$CH$_2$—

In embodiments, $L^1$ is —CH(CH$_2$OCH$_3$)—. In embodiments, $L^1$ is unsubstituted 3 membered heteroalkyl-substituted methylene. In embodiments, $L^1$ is unsubstituted 2 to 4 membered heteroalkyl-substituted methylene. In embodiments, $L^1$ is —CH(CH$_2$OH)—. In embodiments, $L^1$ is OH-substituted ethylene. In embodiments, $L^1$ is OH-substituted $C_1$-$C_3$ alkylene. In embodiments, $L^1$ is substituted ethylene. In embodiments, $L^1$ is substituted $C_1$-$C_3$ alkylene. In embodiments, $L^1$ is

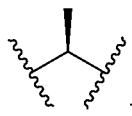

In embodiments. $L^1$ is

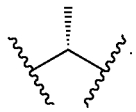

In embodiments, $L^2$ is a bond, —S(O)$_2$—, —C(O)—, —C(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^2$ is a bond. In embodiments, $L^2$ is —S(O)$_2$—. In embodiments, $L^2$ is —S(O)$_2$NH—. In embodiments, $L^2$ is —NHS(O)$_2$—. In embodiments, $L^2$ is —C(O)—. In embodiments, $L^2$ is —C(O)NH—. In embodiments, $L^2$ is —NHC(O)—. In embodiments, $L^2$ is —NHC(O)NH—. In embodiments, $L^2$ is —C(O)O—. In embodiments, $L^2$ is —OC(O)—.

In embodiments, $L^2$ is substituted or unsubstituted alkylene (e.g., $C_1$-$C_8$ alkylene, $C_1$-$C_6$ alkylene, or $C_1$-$C_4$ alkylene). In embodiments, $L^2$ is substituted alkylene (e.g., $C_1$-$C_8$ alkylene, $C_1$-$C_6$ alkylene, or $C_1$-$C_4$ alkylene). In embodiments, $L^2$ is an unsubstituted alkylene (e.g., $C_1$-$C_8$ alkylene, $C_1$-$C_6$ alkylene, or $C_1$-$C_4$ alkylene). In embodiments, $L^2$ is substituted or unsubstituted heteroalkylene (e.g., 2 to 8 membered heteroalkylene, 2 to 6 membered heteroalkylene, or 2 to 4 membered heteroalkylene). In embodiments, $L^2$ is substituted heteroalkylene (e.g., 2 to 8 membered heteroalkylene, 2 to 6 membered heteroalkylene, or 2 to 4 membered heteroalkylene). In embodiments, $L^2$ is an unsubstituted heteroalkylene (e.g., 2 to 8 membered heteroalkylene, 2 to 6 membered heteroalkylene, or 2 to 4 membered heteroalkylene). In embodiments, $L^2$ is substituted or unsubstituted $C_1$-$C_6$ alkylene. In embodiments, $L^2$ is substituted or unsubstituted $C_1$-$C_4$ alkylene. In embodiments, $L^2$ is substituted or unsubstituted $C_1$-$C_3$ alkylene. In embodiments, $L^2$ is substituted or unsubstituted $C_1$-$C_2$ alkylene.

In embodiments, Ring A is $C_6$-$C_{10}$ aryl or 5 to 10 membered heteroaryl. In embodiments, Ring A is $C_6$-$C_{10}$ aryl or 5 to 10 membered heteroaryl. In embodiments, Ring A is $C_6$-$C_{10}$ aryl. In embodiments, Ring A is phenyl. In embodiments, Ring A is naphthyl. In embodiments, Ring A is 5 to 10 membered heteroaryl. In embodiments, Ring A is 5 to 6 membered heteroaryl. In embodiments, Ring A is thienyl. In embodiments, Ring A is furanyl. In embodiments, Ring A is pyrrolyl. In embodiments, Ring A is imidazolyl. In embodiments, Ring A is pyrazolyl. In embodiments, Ring A is oxazolyl. In embodiments, Ring A is isoxazolyl. In embodiments, Ring A is thaizolyl. In embodiments, Ring A is pyridinyl. In embodiments, Ring A is pyridyl. In embodiments, Ring A is pyrazinyl. In embodiments, Ring A is pyrimidinyl. In embodiments, Ring A is pyridazinyl. In embodiments, Ring A is 1,2,3-triazinyl. In embodiments, Ring A is 1,2,4-triazinyl. In embodiments, Ring A is 1,3,5-triazinyl.

When Ring A is substituted (e.g., substituted $C_6$-$C_{10}$ aryl) it is understood z1 is not 0 (i.e., Ring A is $R^1$-substituted). In embodiments, Ring A is substituted $C_6$-$C_{10}$ aryl or substituted 5 to 10 membered heteroaryl. In embodiments, Ring A is substituted $C_6$-$C_{10}$ aryl or substituted 5 to 10 membered heteroaryl. In embodiments, Ring A is substituted $C_6$-$C_{10}$ aryl. In embodiments, Ring A is substituted phenyl. In embodiments, Ring A is substituted naphthyl. In embodiments, Ring A is substituted 5 to 10 membered heteroaryl. In embodiments, Ring A is substituted 5 to 6 membered heteroaryl. In embodiments, Ring A is substituted thienyl. In embodiments, Ring A is substituted furanyl. In embodiments, Ring A is substituted pyrrolyl. In embodiments, Ring A is substituted imidazolyl. In embodiments, Ring A is substituted pyrazolyl. In embodiments, Ring A is substituted oxazolyl. In embodiments, Ring A is substituted isoxazolyl. In embodiments, Ring A is substituted thaizolyl. In embodiments, Ring A is substituted pyridinyl. In embodiments, Ring A is substituted pyridyl. In embodiments, Ring A is substituted pyrazinyl. In embodiments, Ring A is substituted pyrimidinyl. In embodiments, Ring A is substituted pyridazinyl. In embodiments, Ring A is substituted 1,2,3-triazinyl. In embodiments, Ring A is substituted 1,2,4-triazinyl. In embodiments, Ring A is substituted 1,3,5-triazinyl.

In embodiments, Ring A is an unsubstituted $C_6$-$C_{10}$ aryl or unsubstituted 5 to 10 membered heteroaryl. In embodiments, Ring A is an unsubstituted $C_6$-$C_{10}$ aryl or unsubstituted 5 to 10 membered heteroaryl. In embodiments, Ring A is an unsubstituted $C_6$-$C_{10}$ aryl. In embodiments, Ring A is an unsubstituted phenyl. In embodiments, Ring A is an unsubstituted naphthyl. In embodiments, Ring A is an unsubstituted 5 to 10 membered heteroaryl. In embodiments, Ring A is an unsubstituted 5 to 6 membered heteroaryl. In embodiments, Ring A is an unsubstituted thienyl. In embodiments, Ring A is an unsubstituted furanyl. In embodiments, Ring A is an unsubstituted pyrrolyl. In embodiments, Ring A is an unsubstituted imidazolyl. In embodiments, Ring A is an unsubstituted pyrazolyl. In embodiments, Ring A is an unsubstituted oxazolyl. In embodiments, Ring A is an unsubstituted isoxazolyl. In embodiments, Ring A is an unsubstituted thaizolyl. In embodiments, Ring A is an unsubstituted pyridinyl. In embodiments, Ring A is an unsubstituted pyridyl. In embodiments, Ring A is an unsubstituted pyrazinyl. In embodiments, Ring A is an unsubstituted pyrimidinyl. In embodiments, Ring A is an unsubstituted pyridazinyl. In embodiments, Ring A is an unsubstituted 1,2,3-triazinyl. In embodiments, Ring A is an unsubstituted 1,2,4-triazinyl. In embodiments, Ring A is an unsubstituted 1,3,5-triazinyl.

In embodiments, Ring A is substituted with one $R^1$. In embodiments, Ring A is substituted with two optionally different $R^1$ substituents. In embodiments, Ring A is substituted with three optionally different $R^1$ substituents. In embodiments, Ring A is substituted with four optionally different $R^1$ substituents. In embodiments, Ring A is substituted with five optionally different $R^1$ substituents.

In embodiments, Ring A is phenyl, or 5 to 6 membered heteroaryl. In embodiments, Ring A is phenyl. In embodiments, Ring A is 5 to 6 membered heteroaryl. In embodiments, Ring A is a 5 membered heteroaryl. In embodiments, Ring A is a 5 membered heteroaryl.

In embodiments, Ring A is phenyl, pyridyl, pyrazolyl, imidazolyl, oxazolyl, isoxazolyl, thiazolyl, furanyl, pyrrolyl, thienyl, pyrazinyl, pyridazinyl, or pyrimidinyl. In embodiments, Ring A is phenyl. In embodiments, Ring A is pyridyl. In embodiments, Ring A is pyrazolyl. In embodiments, Ring A is imidazolyl. In embodiments, Ring A is oxazolyl. In embodiments, Ring A is isoxazolyl. In embodiments, Ring A is thiazolyl. In embodiments, Ring A is furanyl. In embodiments, Ring A is pyrrolyl. In embodiments, Ring A is thienyl. In embodiments, Ring A is pyrazinyl. In embodiments, Ring A is pyridazinyl. In embodiments, Ring A is pyrimidinyl. In embodiments, Ring A is phenyl or pyridyl. In embodiments, Ring A is pyridyl.

In embodiments, Ring A is phenyl.

In embodiments, Ring A is pyridin-3-yl. In embodiments, Ring A is pyridyl. In embodiments, Ring A is a 6 membered heteroaryl. In embodiments, Ring A is pyridin-2-yl. In embodiments, Ring A is pyridin-4-yl.

In embodiments, Ring A is pyrimidin-5-yl. In embodiments, Ring A is pyrimidinyl.

In embodiments, Ring A is pyridazin-3-yl. In embodiments, Ring A is pyridazinyl.

In embodiments, Ring A is pyrazin-2-yl. In embodiments, Ring A is pyrazinyl.

In embodiments, Ring A is imidazol-1-yl. In embodiments, Ring A is imidazolyl. In embodiments, Ring A is a 5 membered heteroaryl.

In embodiments, -(Ring A)-$(R^1)_{z1}$ is

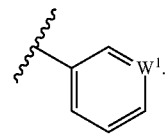

In embodiments, -(Ring A)-$(R^1)_{z1}$ is

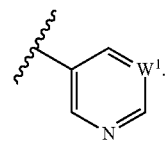

In embodiments, -(Ring A)-$(R^1)_{z1}$ is

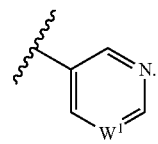

In embodiments, -(Ring A)-$(R^1)_{z1}$ is

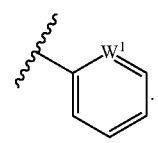

In embodiments, -(Ring A)-$(R^1)_{z1}$ is

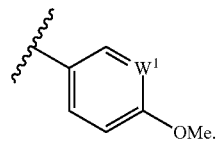

In embodiments, -(Ring A)-$(R^1)_{z1}$ is

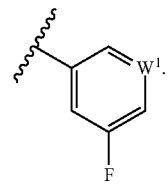

In embodiments, -(Ring A)-$(R^1)_{z1}$ is

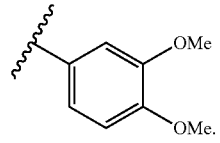 [SMILES: *c1ccc(OC)c(OC)c1]

In embodiments, -(Ring A)-(R$^1$)$_{z1}$ is

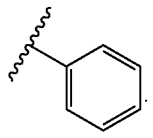 [SMILES: *c1ccccc1]

In embodiments, -(Ring A)-(R$^1$)$_{z1}$ is

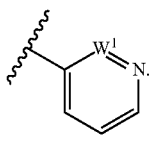

In embodiments, -(Ring A)-(R$^1$)$_{z1}$ is

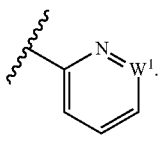

In embodiments, -(Ring A)-(R$^1$)$_{z1}$ is

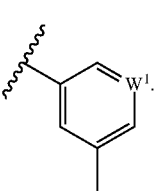

In embodiments, -(Ring A)-(R$^1$)$_{z1}$ is

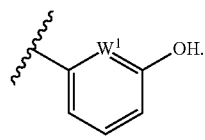

In embodiments, -(Ring A)-(R$^1$)$_{z1}$ is

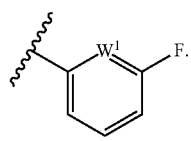

In embodiments, -(Ring A)-(R$^1$)$_{z1}$ is

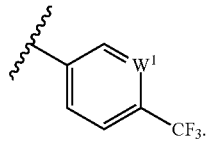

In embodiments, -(Ring A)-(R$^1$)$_{z1}$ is

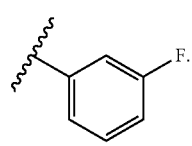 [SMILES: *c1cccc(F)c1]

In embodiments, -(Ring A)-(R$^1$)$_{z1}$ is

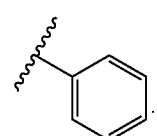

In embodiments, -(Ring A)-(R$^1$)$_{z1}$ is

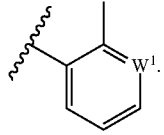

In embodiments, -(Ring A)-(R$^1$)$_{z1}$ is

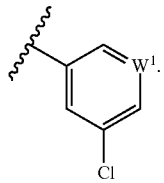

In embodiments, -(Ring A)-(R$^1$)$_{z1}$ is

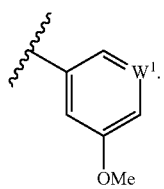

In embodiments, -(Ring A)-(R$^1$)$_{z1}$ is

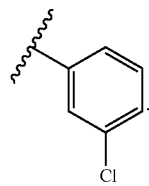

In embodiments, -(Ring A)-(R$^1$)$_{z1}$ is

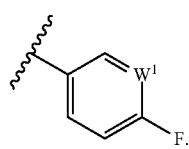

In embodiments, -(Ring A)-(R$^1$)$_{z1}$ is

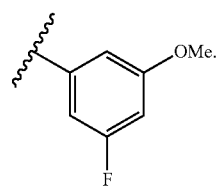 [SMILES: *c1cc(F)cc(OC)c1]

In embodiments, -(Ring A)-(R$^1$)$_{z1}$ is

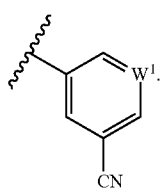

In embodiments, -(Ring A)-(R$^1$)$_{z1}$ is

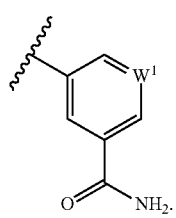

In embodiments, -(Ring A)-(R$^1$)$_{z1}$ is

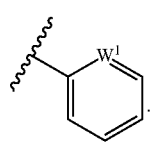

In embodiments, -(Ring A)-(R$^1$)$_{z1}$ is

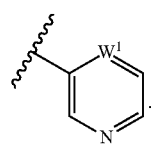

In embodiments, -(Ring A)-(R$^1$)$_{z1}$ is

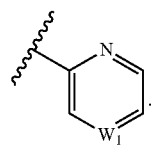

In embodiments, -(Ring A)-(R$^1$)$_{z1}$ is

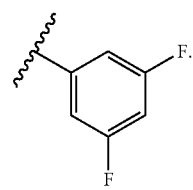 [SMILES: *c1cc(F)cc(F)c1]

In embodiments, -(Ring A)-(R$^1$)$_{z1}$ is

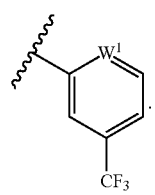

In embodiments, -(Ring A)-(R$^1$)$_{z1}$ is

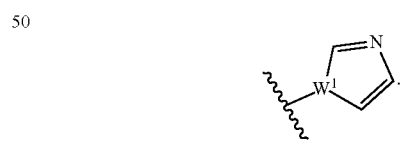

In embodiments, -(Ring A)-(R$^1$)$_{z1}$ is

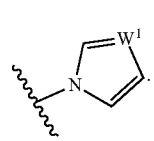

271

In embodiments, -(Ring A)-(R$^1$)$_{z1}$ is

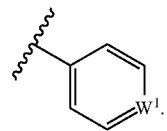

In embodiments, -(Ring A)-R$^1$)$_{z1}$ is

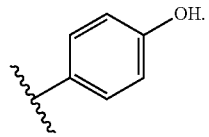 [SMILES: *c1ccc(O)cc1]

In embodiments, -(Ring A)-(R$^1$)$_{z1}$ is

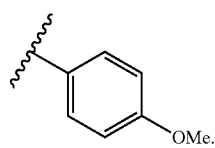

In embodiments, -(Ring A)-(R$^1$)$_{z1}$ is

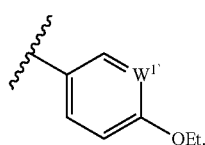

In embodiments, -(Ring A)-(R$^1$)$_{z1}$ is

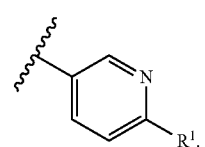

In embodiments, -(Ring A)-(R$^1$)$_{z1}$ is

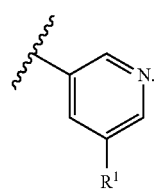

272

In embodiments, -(Ring A)-(R$^1$)$_{z1}$ is

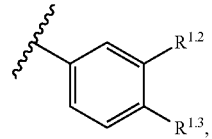

wherein R$^{1.2}$ and R$^{1.3}$ are each R$^1$ at a fixed position on the attached ring. R$^{1.2}$ and R$^{1.3}$ may independently be any substituent of R$^1$ described herein, including in any aspect, embodiment, example, figure, or claim. In embodiments, -(Ring A)-(R$^1$)$_{z1}$ is

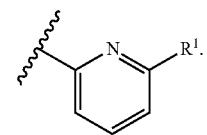

In embodiments, -(Ring A)-(R$^1$)$_{z1}$ is

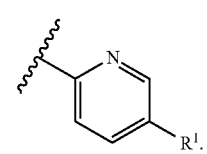

In embodiments, -(Ring A)-(R$^1$)$_{z1}$ is

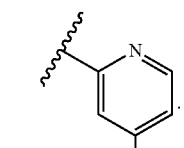

In embodiments, -(Ring A)-(R$^1$)$_{z1}$ is

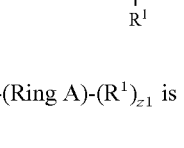

In embodiments, -(Ring A)-(R$^1$)$_{z1}$ is

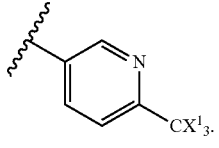

In embodiments, -(Ring A)-(R$^1$)$_{z1}$ is

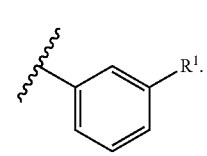

In embodiments, -(Ring A)-(R$^1$)$_{z1}$ is

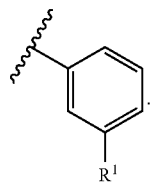

In embodiments, -(Ring A)-(R$^1$)$_{z1}$ is

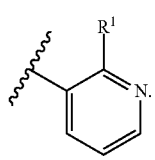

In embodiments, -(Ring A)-(R$^1$)$_{z1}$ is

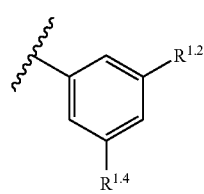

wherein R$^{1.2}$ and R$^{1.4}$ are each R$^1$ at a fixed position on the attached ring. R$^{1.2}$ and R$^{1.4}$ may independently be any substituent of R$^1$ described herein, including in any aspect, embodiment, example, figure, or claim. In embodiments, -(Ring A)-(R$^1$)$_{z1}$ is

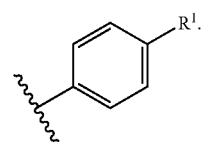

In embodiments, -(Ring A)-(R$^1$)$_{z1}$ is

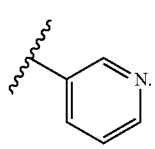

In embodiments, -(Ring A)-(R$^1$)$_{z1}$ is

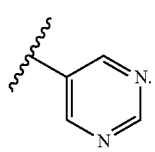

In embodiments, -(Ring A)-(R$^1$)$_{z1}$ is

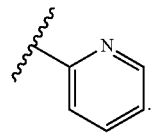 [SMILES: *c1ccccn1]

In embodiments, -(Ring A)-(R$^4$)$_{z1}$ is

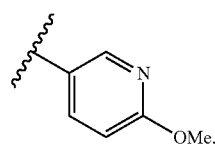

In embodiments, -(Ring A)-(R$^1$)$_{z1}$ is

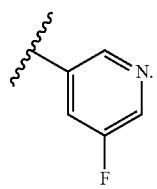 [SMILES: *c1cncc(F)c1]

In embodiments, -(Ring A)-(R$^1$)$_{z1}$ is

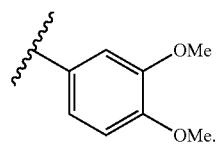

In embodiments, -(Ring A)-(R$^1$)$_{z1}$ is

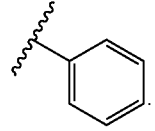 [SMILES: *c1ccccc1]

In embodiments, -(Ring A)-(R$^1$)$_{z1}$ is

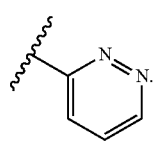 [SMILES: *c1cccnn1]

In embodiments, -(Ring A)-(R$^1$)$_{z1}$ is

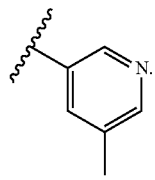 [SMILES: *c1cncc(C)c1]

In embodiments, -(Ring A)-(R$^1$)$_{z1}$ is

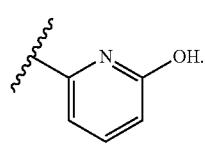 [SMILES: *c1cccc(O)n1]

In embodiments, -(Ring A)-(R$^1$)$_{z1}$ is

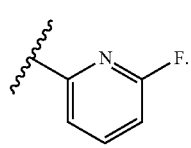

In embodiments, -(Ring A)-(R$^1$)$_{z1}$ is

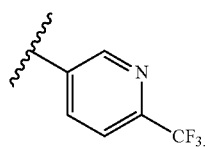

In embodiments, -(Ring A)-(R$^1$)$_{z1}$ is

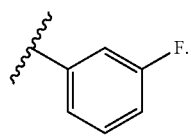

In embodiments, -(Ring A)-(R$^1$)$_{z1}$ is

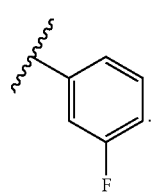 [SMILES: *c1cccc(F)c1]

In embodiments, -(Ring A)-(R$^1$)$_{z1}$ is

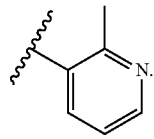 [SMILES: *c1cccnc1C]

In embodiments, -(Ring A)-(R$^1$)$_{z1}$ is

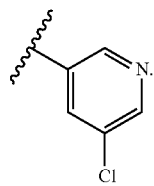 [SMILES: *c1cncc(Cl)c1]

In embodiments, -(Ring A)-(R$^1$)$_{z1}$ is

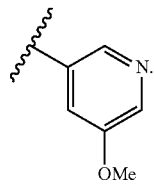 [SMILES: *c1cncc(OC)c1]

In embodiments, -(Ring A)-(R$^1$)$_{z1}$ is

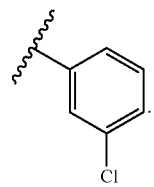 [SMILES: *c1cccc(Cl)c1]

In embodiments, -(Ring A)-(R$^1$)$_{z1}$ is

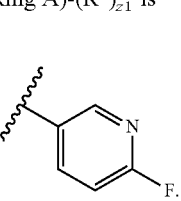

In embodiments, -(Ring A)-(R$^1$)$_{z1}$ is

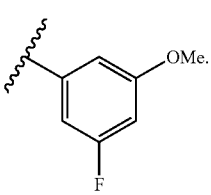 [SMILES: *c1cc(F)cc(OC)c1]

In embodiments, -(Ring A)-(R$^1$)$_{z1}$ is

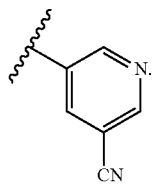

In embodiments, -(Ring A)-(R$^1$)$_{z1}$ is

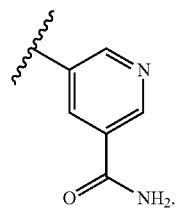 [SMILES: *c1cncc(C(N)=O)c1]

In embodiments, -(Ring A)-(R$^1$)$_{z1}$ is

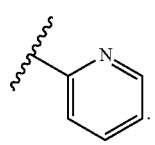

In embodiments, -(Ring A)-(R$^1$)$_{z1}$ is

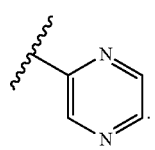

In embodiments, -(Ring A)-(R$^1$)$_{z1}$ is

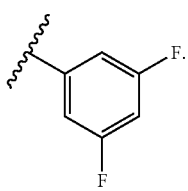 [SMILES: *c1cc(F)cc(F)c1]

In embodiments, -(Ring A)-(R$^1$)$_{z1}$ is

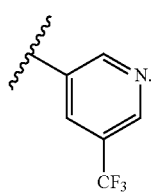

In embodiments, -(Ring A)-(R$^1$)$_{z1}$ is

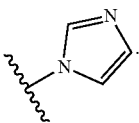

In embodiments, -(Ring A)-(R$^1$)$_{z1}$ is

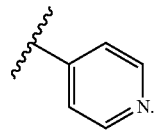

In embodiments, -(Ring A)-(R$^1$)$_{z1}$ is

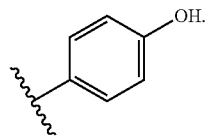 [SMILES: *c1ccc(O)cc1]

In embodiments, -(Ring A)-(R$^1$)$_{z1}$ is

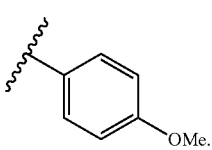 [SMILES: *c1ccc(OC)cc1]

In embodiments, -(Ring A)-(R$^1$)$_{z1}$ is

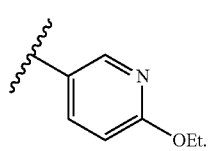 [SMILES: *c1ccc(OCC)nc1]

In embodiments, Ring B is a 4 to 8 membered heterocycloalkyl. In embodiments, Ring B is a 4 membered heterocycloalkyl. In embodiments, Ring B is a 5 membered heterocycloalkyl. In embodiments, Ring B is a 6 membered heterocycloalkyl. In embodiments, Ring B is a 7 membered heterocycloalkyl. In embodiments, Ring B is an 8 membered heterocycloalkyl. In embodiments, Ring B is a 4 to 6 membered heterocycloalkyl. In embodiments, Ring B is azetidinyl. When Ring B is substituted (e.g., substituted 4 to 8 membered heterocycloalkyl) it is understood z6 is not 0 (i.e., Ring B is R$^6$-substituted Ring B).

In embodiments, Ring B is a substituted or unsubstituted heterocycloalkyl. In embodiments, Ring B is a substituted heterocycloalkyl. In embodiments, Ring B is an unsubstituted heterocycloalkyl. In embodiments, Ring B is a substituted or unsubstituted 3 to 10 membered heterocycloalkyl. In embodiments, Ring B is a substituted 3 to 10 membered heterocycloalkyl. In embodiments, Ring B is an unsubstituted 3 to 10 membered heterocycloalkyl. In embodiments, Ring B is a R$^6$-substituted or unsubstituted 5 to 10 membered heterocycloalkyl. In embodiments, Ring B is a $R^6$-substituted 5 to 10 membered heterocycloalkyl. In embodiments, Ring B is an unsubstituted 5 to 10 membered heterocycloalkyl.

In embodiments, Ring B is a substituted or unsubstituted 3 membered heterocycloalkyl. In embodiments, Ring B is a substituted or unsubstituted 4 membered heterocycloalkyl. In embodiments, Ring B is a substituted or unsubstituted 5 membered heterocycloalkyl. In embodiments, Ring B is a substituted or unsubstituted 6 membered heterocycloalkyl. In embodiments, Ring B is a substituted 3 membered heterocycloalkyl. In embodiments, Ring B is a substituted 4 membered heterocycloalkyl. In embodiments, Ring B is a substituted 5 membered heterocycloalkyl. In embodiments, Ring B is a substituted 6 membered heterocycloalkyl. In embodiments, Ring B is an unsubstituted 3 membered heterocycloalkyl. In embodiments, Ring B is an unsubstituted 4 membered heterocycloalkyl. In embodiments, Ring B is an unsubstituted 5 membered heterocycloalkyl. In embodiments, Ring B is an unsubstituted 6 membered heterocycloalkyl.

In embodiments, Ring B is a substituted or unsubstituted aziridinyl, azirinyl, azetidinyl, dihydroazetyl, diazetidinyl, azetyl, pyrrolidinyl, pyrrolinyl, pyrrolyl, pyrazolidinyl, imidazolidinyl, pyrazolinyl, pyrazolyl, thiazolidinyl, thiazolyl, isothiazolyl, piperidinyl, piperazinyl, morpholinyl, oxazinyl, thiomorpholinyl, thiazinyl, decahydroquinolinyl, dihydroazepinyl, azepanyl, or azocanyl. In embodiments, Ring B is a substituted aziridinyl, azirinyl, azetidinyl, dihydroazetyl, diazetidinyl, azetyl, pyrrolidinyl, pyrrolinyl, pyrrolyl, pyrazolidinyl, imidazolidinyl, pyrazolinyl, pyrazolyl, thiazolidinyl, thiazolyl, isothiazolyl, piperidinyl, piperazinyl, morpholinyl, oxazinyl, thiomorpholinyl, thiazinyl, decahydroquinolinyl, dihydroazepinyl, azepanyl, or azocanyl. In embodiments, Ring B is an unsubstituted aziridinyl, azirinyl, azetidinyl, dihydroazetyl, diazetidinyl, azetyl, pyrrolidinyl, pyrrolinyl, pyrrolyl, pyrazolidinyl, imidazolidinyl, pyrazolinyl, pyrazolyl, thiazolidinyl, thiazolyl, isothiazolyl, piperidinyl, piperazinyl, morpholinyl, oxazinyl, thiomorpholinyl, thiazinyl, decahydroquinolinyl, dihydroazepinyl, azepanyl, or azocanyl.

In embodiments, Ring B is substituted with one $R^6$. In embodiments, Ring B is substituted with two optionally different $R^6$ substituents. In embodiments, Ring B is substituted with three optionally different $R^6$ substituents. In embodiments, Ring B is substituted with four optionally different $R^6$ substituents. In embodiments, Ring B is substituted with five optionally different $R^6$ substituents. In embodiments, Ring B is substituted with six optionally different $R^6$ substituents. In embodiments, Ring B is substituted with seven optionally different $R^6$ substituents. In embodiments, Ring B is substituted with eight optionally different $R^6$ substituents. In embodiments, Ring B is substituted with nine optionally different $R^6$ substituents. In embodiments, Ring B is substituted with ten optionally different $R^6$ substituents.

In embodiments, Ring B is azetidinyl. In embodiments, Ring B is 4 membered heterocycloalkyl. In embodiments, Ring B is 3 to 5 membered heterocycloalkyl. In embodiments, Ring B is 3 to 6 membered heterocycloalkyl. In embodiments, Ring B is pyrrolidinyl. In embodiments, Ring B is 5 membered heterocycloalkyl. In embodiments, Ring B is 4 to 6 membered heterocycloalkyl. In embodiments, Ring B is morpholinyl. In embodiments, Ring B is 6 membered heterocycloalkyl. In embodiments, Ring B is 5 to 7 membered heterocycloalkyl. In embodiments, Ring B is 2-oxa-6-azaspiro[3.3]heptanyl. In embodiments, Ring B is 2-oxa-6-azaspiro[3.3]heptan-6-yl. In embodiments, Ring B is 7 membered heterocycloalkyl. In embodiments, Ring B is 6 to 8 membered heterocycloalkyl. In embodiments, Ring B is 7 membered spirocyclic heterocycloalkyl. In embodiments, Ring B is 6 to 8 membered spirocyclic heterocycloalkyl. In embodiments, Ring B is piperidin-1-yl. In embodiments, Ring B is piperidinyl. In embodiments, Ring B is piperazin-1-yl. In embodiments, Ring B is piperazinyl. In embodiments, Ring B is oxazolidin-3-yl. In embodiments, Ring B is oxazolidinyl. In embodiments, Ring B is imidazolidinyl. In embodiments, Ring B is 1,3-oxazinanyl. In embodiments, Ring B is oxazinanyl.

In embodiments, -(Ring B)-$(R^6)_{z6}$ is

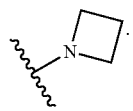

In embodiments, -(Ring B)-$(R^6)_{z6}$ is

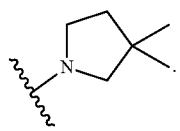 [SMILES: *N1CCC(C)(C)C1]

In embodiments, -(Ring B)-$(R^6)_{z6}$ is

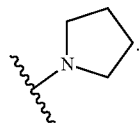 [SMILES: *N1CCCC1]

In embodiments, -(Ring B)-$(R^6)_{z6}$ is

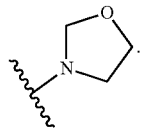

In embodiments, -(Ring B)-$(R^6)_{z6}$ is

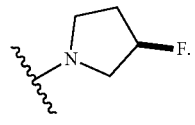 [SMILES: *N1CC[C@@H](F)C1]

In embodiments, -(Ring B)-$(R^6)_{z6}$ is

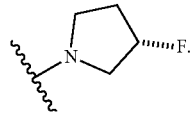 [SMILES: *N1CC[C@H](F)C1]

281

In embodiments, -(Ring B)-(R$^6$)$_{z6}$ is

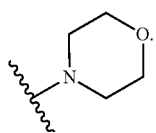 [SMILES: *N1CCOCC1]

In embodiments, -(Ring B)-(R$^6$)$_{z6}$ is

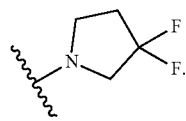 [SMILES: *N1CCC(F)(F)C1]

In embodiments, -(Ring B)-(R$^6$)$_{z6}$ is

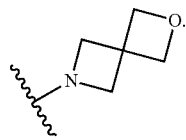 [SMILES: *N1CC2(COC2)C1]

In embodiments, -(Ring B)-(R$^6$)$_{z6}$ is

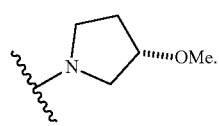 [SMILES: *N1CC[C@H](OC)C1]

In embodiments, -(Ring B)-(R$^6$)$_{z6}$ is

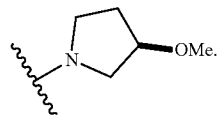 [SMILES: *N1CC[C@@H](OC)C1]

In embodiments, -(Ring B)-(R$^6$)$_{z6}$ is

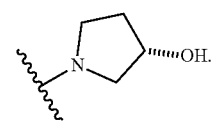 [SMILES: *N1CC[C@H](O)C1]

In embodiments, -(Ring B)-(R$^6$)$_{z6}$ is

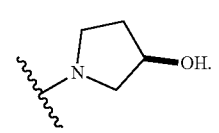 [SMILES: *N1CC[C@@H](O)C1]

282

In embodiments, -(Ring B)-(R$^6$)$_{z6}$ is

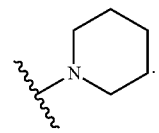 [SMILES: *N1CCCCC1]

In embodiments, -(Ring B)-(R$^6$)$_{z6}$ is

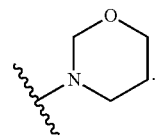 [SMILES: *N1CCCOC1]

In embodiments, -(Ring B)-(R$^6$)$_{z6}$ is

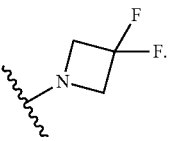 [SMILES: *N1CC(F)(F)C1]

In embodiments, -(Ring B)-(R$^6$)$_{z6}$ is

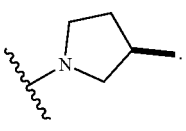 [SMILES: *N1CC[C@@H](C)C1]

In embodiments, -(Ring B)-(R$^6$)$_{z6}$ is

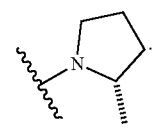

In embodiments, -(Ring B)-(R$^6$)$_{z6}$ is

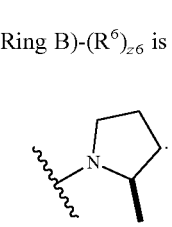

In embodiments, -(Ring B)-(R$^6$)$_{z6}$ is

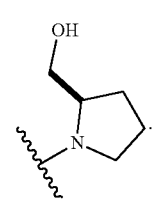 [SMILES: *N1CCC[C@@H]1CO]

In embodiments, -(Ring B)-(R$^6$)$_{z6}$ is

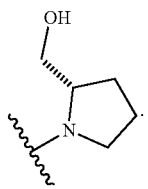 [SMILES: *N1CCC[C@H]1CO]

In embodiments, -(Ring B)-(R$^6$)$_{z6}$ is

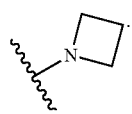

In embodiments, -(Ring B)-(R$^6$)$_{z6}$ is

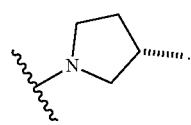 [SMILES: *N1CC[C@H](C)C1]

In embodiments, -(Ring B)-(R$^6$)$_{z6}$ is

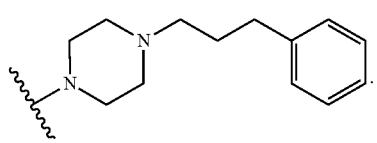 [SMILES: *N1CCN(CCCc2ccccc2)CC1]

In embodiments, -(Ring B)-(R$^6$)$_{z6}$ is

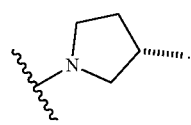 [SMILES: *N1CC[C@H](C)C1]

In embodiments, -(Ring B)-(R$^6$)$_{z6}$ is

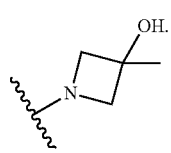 [SMILES: *N1CC(C)(O)C1]

In embodiments, -(Ring B)-(R$^6$)$_{z6}$ is

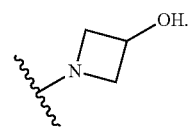 [SMILES: *N1CC(O)C1]

In embodiments, -(Ring B)-(R$^6$)$_{z6}$ is

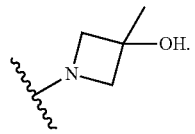 [SMILES: *N1CC(C)(O)C1]

In embodiments, -(Ring B)-(R$^6$)$_{z6}$ is

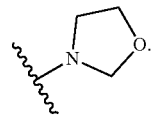 [SMILES: *N1CCOC1]

In embodiments, -(Ring B)-(R$^6$)$_{z6}$ is

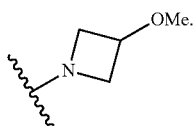 [SMILES: *N1CC(OC)C1]

In embodiments, -(Ring B)-(R$^6$)$_{z6}$ is

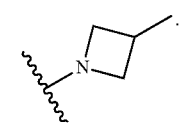 [SMILES: *N1CC(C)C1]

In embodiments, -(Ring B)-(R$^6$)$_{z6}$ is

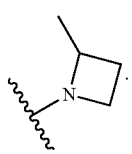 [SMILES: *N1CCC1C]

In embodiments, -(Ring B)-(R$^6$)$_{z6}$ is. In embodiments, -(Ring B)-(R$^6$)$_{z6}$ is

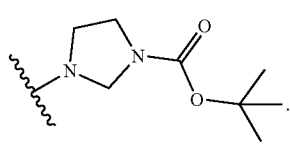 [SMILES: *N1CCN(C(=O)OC(C)(C)C)C1]

In embodiments, -(Ring B)-(R$^6$)$_{z6}$ is

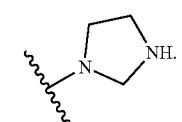

In embodiments, -(Ring B)-(R$^6$)$_{z6}$ is

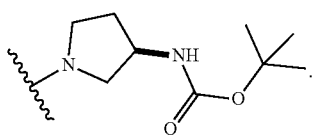 [SMILES: *N1CC[C@@H](NC(=O)OC(C)(C)C)C1]

In embodiments, -(Ring B)-(R$^6$)$_{z6}$ is

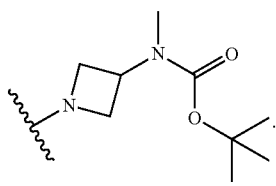 [SMILES: *N1CC(N(C)C(=O)OC(C)(C)C)C1]

In embodiments, -(Ring B)-(R$^6$)$_{z6}$ is

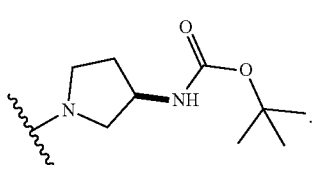 [SMILES: *N1CC[C@@H](NC(=O)OC(C)(C)C)C1]

In embodiments, -(Ring B)-(R$^6$)$_{z6}$ is

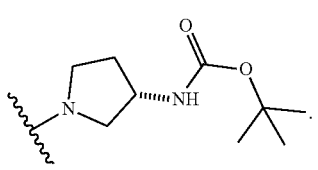 [SMILES: *N1CC[C@H](NC(=O)OC(C)(C)C)C1]

In embodiments, -(Ring B)-(R$^6$)$_{z6}$ is

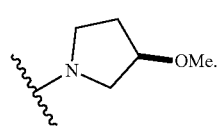 [SMILES: *N1CC[C@@H](OC)C1]

In embodiments, -(Ring B)-(R$^6$)$_{z6}$ is

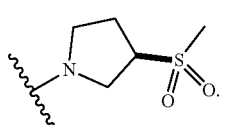 [SMILES: *N1CC[C@@H](S(C)(=O)=O)C1]

In embodiments, -(Ring B)-(R$^6$)$_{z6}$ is

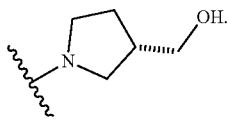 [SMILES: *N1CC[C@H](CO)C1]

In embodiments, -(Ring B)-(R$^6$)$_{z6}$ is

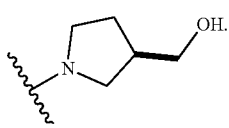 [SMILES: *N1CC[C@@H](CO)C1]

In embodiments, -(Ring B)-(R$^6$)$_{z6}$ is

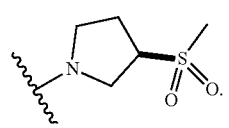 [SMILES: *N1CC[C@@H](S(C)(=O)=O)C1]

In embodiments, -(Ring B)-(R$^6$)$_{z6}$ is

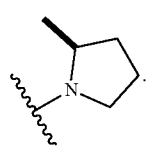

In embodiments, -(Ring B)-(R$^6$)$_{z6}$ is

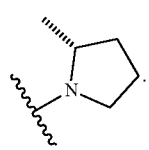

In embodiments, -(Ring B)-(R$^6$)$_{z6}$ is

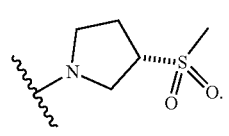 [SMILES: *N1CC[C@H](S(C)(=O)=O)C1]

In embodiments, -(Ring B)-(R$^6$)$_{z6}$ is

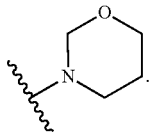 [SMILES: *N1CCCOC1]

US 11,254,686 B1

287

In embodiments, -(Ring B)-(R$^6$)$_{z6}$ is

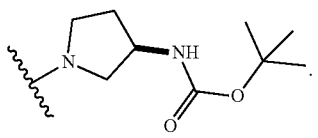 [SMILES: *N1CC[C@@H](NC(=O)OC(C)(C)C)C1]

In embodiments, -(Ring B)-(R$^6$)$_{z6}$ is

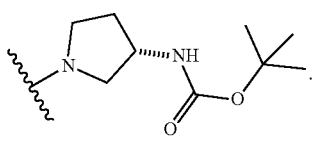 [SMILES: *N1CC[C@H](NC(=O)OC(C)(C)C)C1]

In embodiments, -(Ring B)-(R$^6$)$_{z6}$ is

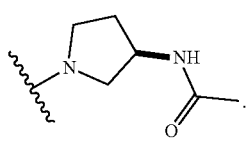 [SMILES: *N1CC[C@@H](NC(C)=O)C1]

In embodiments, -(Ring B)-(R$^6$)$_{z6}$ is

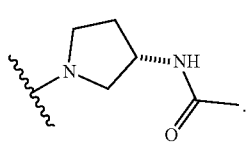 [SMILES: *N1CC[C@H](NC(C)=O)C1]

In embodiments, -(Ring B)-(R$^6$)$_{z6}$ is

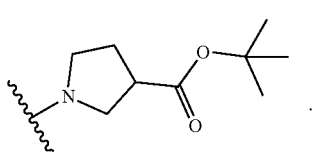 [SMILES: *N1CCC(C(=O)OC(C)(C)C)C1]

In embodiments, -(Ring B)-(R$^6$)$_{z6}$ is

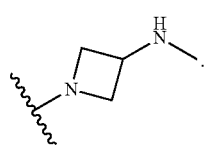 [SMILES: *N1CC(NC)C1]

In embodiments, -(Ring B)-(R$^6$)$_{z6}$ is

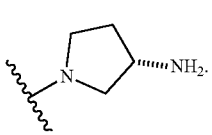 [SMILES: *N1CC[C@H](N)C1]

288

In embodiments, -(Ring B)-(R$^6$)$_{z6}$ is

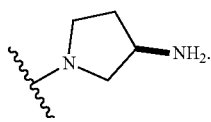 [SMILES: *N1CC[C@@H](N)C1]

In embodiments, -(Ring B)-(R$^6$)$_{z6}$ is

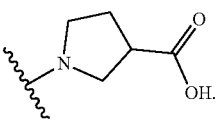 [SMILES: *N1CCC(C(=O)O)C1]

In embodiments, -(Ring B)-(R$^6$)$_{z6}$ is

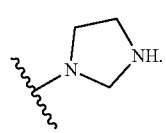 [SMILES: *N1CCNC1]

In embodiments, -(Ring B)-(R$^6$)$_{z6}$ is

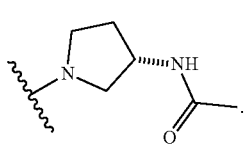 [SMILES: *N1CC[C@H](NC(C)=O)C1]

In embodiments, -(Ring B)-(R$^6$)$_{z6}$ is

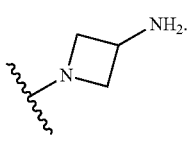 [SMILES: *N1CC(N)C1]

In embodiments, -(Ring B)-(R$^6$)$_{z6}$ is

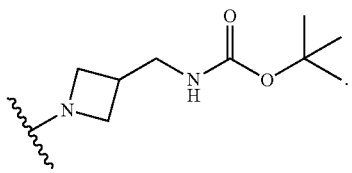 [SMILES: *N1CC(CNC(=O)OC(C)(C)C)C1]

In embodiments, -(Ring B)-(R$^6$)$_{z6}$ is

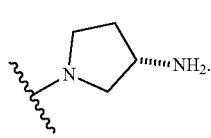

In embodiments, -(Ring B)-(R⁶)_{z6} is
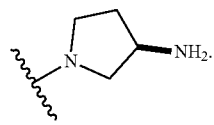 [SMILES: *N1CC[C@@H](N)C1]
In embodiments, -(Ring B)-(R⁶)_{z6} is
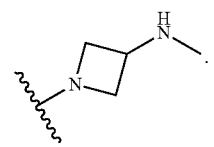 [SMILES: *N1CC(NC)C1]
In embodiments, -(Ring B)-(R⁶)_{z6} is
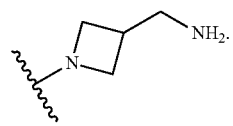 [SMILES: *N1CC(CN)C1]
In embodiments, -(Ring B)-(R⁶)_{z6} is
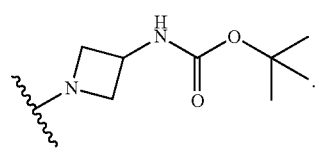 [SMILES: *N1CC(NC(=O)OC(C)(C)C)C1]
In embodiments, -(Ring B)-(R⁶)_{z6} is
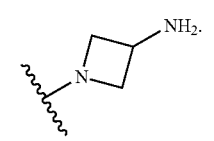 [SMILES: *N1CC(N)C1]
In embodiments, -(Ring B)-(R⁶)_{z6} is
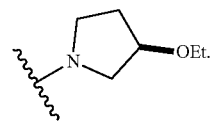 [SMILES: *N1CC[C@@H](OCC)C1]
In embodiments, -(Ring B)-(R⁶)_{z6} is
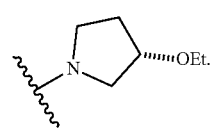 [SMILES: *N1CC[C@H](OCC)C1]
In embodiments, -(Ring B)-(R⁶)_{z6} is
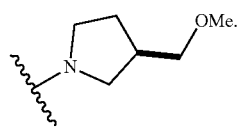 [SMILES: *N1CC[C@@H](COC)C1]
In embodiments, -(Ring B)-(R⁶)_{z6} is
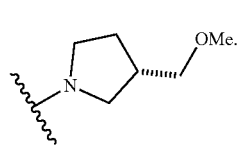 [SMILES: *N1CC[C@H](COC)C1]
In embodiments, -(Ring B)-(R⁶)_{z6} is
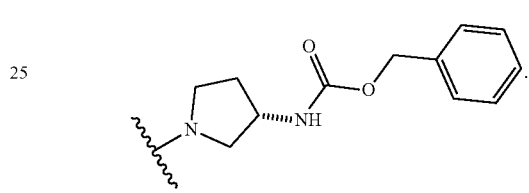
In embodiments, -(Ring B)-(R⁶)_{z6} is
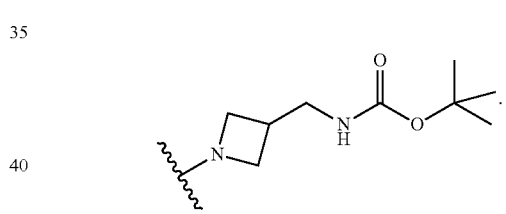
In embodiments, -(Ring B)-(R⁶)_{z6} is
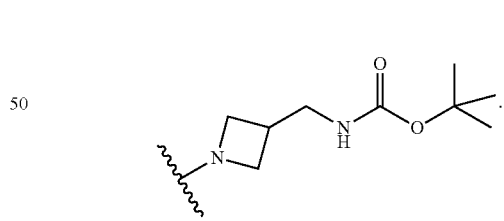
In embodiments, -(Ring B)-(R⁶)_{z6} is
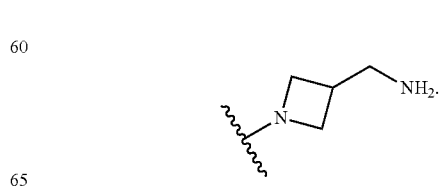

In embodiments, -(Ring B)-(R⁶)_z6 is
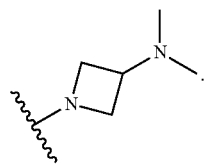 [SMILES: *N1CC(N(C)C)C1]
In embodiments, -(Ring B)-(R⁶)_z6 is
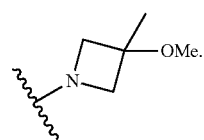 [SMILES: *N1CC(C)(OC)C1]
In embodiments, -(Ring B)-(R⁶)_z6 is
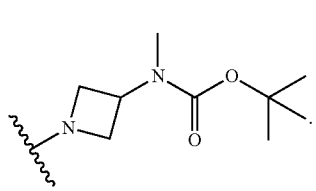 [SMILES: *N1CC(N(C)C(=O)OC(C)(C)C)C1]
In embodiments, -(Ring B)-(R⁶)_z6 is
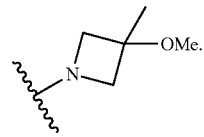 [SMILES: *N1CC(C)(OC)C1]
In embodiments, -(Ring B)-(R⁶)_z6 is
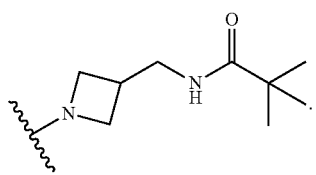 [SMILES: *N1CC(CNC(=O)C(C)(C)C)C1]
In embodiments, -(Ring B)-(R⁶)_z6 is
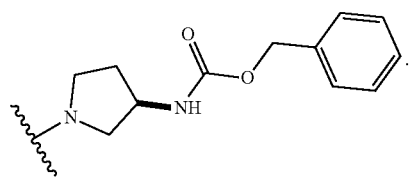 [SMILES: *N1CC[C@@H](NC(=O)OCc2ccccc2)C1]
In embodiments, -(Ring B)-(R⁶)_z6 is
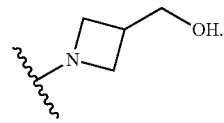 [SMILES: *N1CC(CO)C1]
In embodiments, -(Ring B)-(R⁶)_z6 is
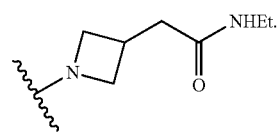
In embodiments, -(Ring B)-(R⁶)_z6 is
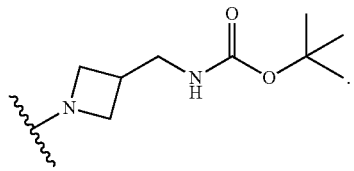 [SMILES: *N1CC(CNC(=O)OC(C)(C)C)C1]
In embodiments, -(Ring B)-(R⁶)_z6 is
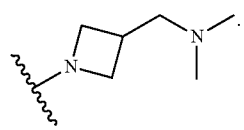 [SMILES: *N1CC(CN(C)C)C1]
In embodiments, -(Ring B)-(R⁶)_z6 is
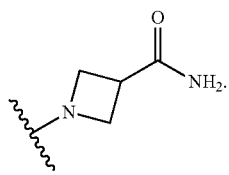 [SMILES: *N1CC(C(N)=O)C1]
In embodiments, -(Ring B)-(R⁶)_z6 is
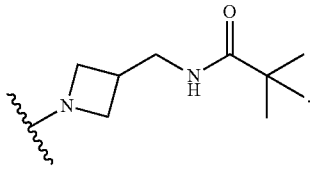 [SMILES: *N1CC(CNC(=O)C(C)(C)C)C1]

In embodiments, -(Ring B)-(R$^6$)$_{z6}$ is

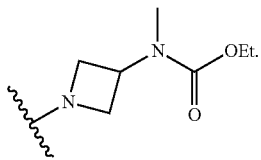 [SMILES: *N1CC(N(C)C(=O)OCC)C1]

In embodiments, -(Ring B)-(R$^6$)$_{z6}$ is

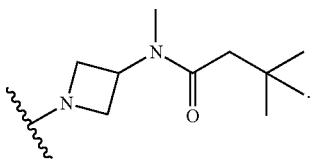 [SMILES: *N1CC(N(C)C(=O)CC(C)(C)C)C1]

In embodiments, -(Ring B)-(R$^6$)$_{z6}$ is

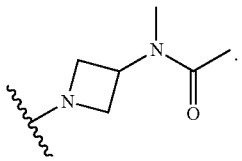 [SMILES: *N1CC(N(C)C(C)=O)C1]

In embodiments, -(Ring B)-(R$^6$)$_{z6}$ is

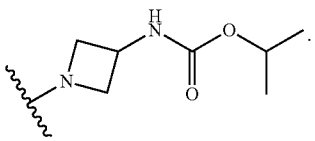 [SMILES: *N1CC(NC(=O)OC(C)C)C1]

In embodiments, -(Ring B)-(R$^6$)$_{z6}$ is

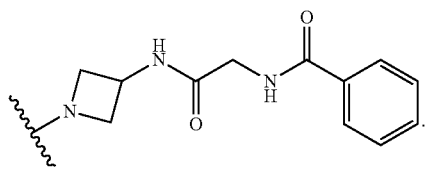 [SMILES: *N1CC(NC(=O)CNC(=O)c2ccccc2)C1]

In embodiments, -(Ring B)-(R$^6$)$_{z6}$ is

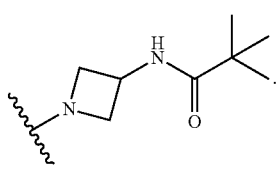 [SMILES: *N1CC(NC(=O)C(C)(C)C)C1]

In embodiments, -(Ring B)-(R$^6$)$_{z6}$ is

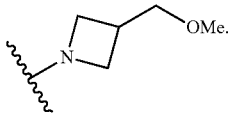 [SMILES: *N1CC(COC)C1]

In embodiments, Ring B is

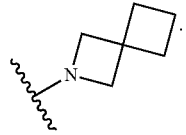 [SMILES: *N1CC2(CCC2)C1]

In embodiments, Ring C is a substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl. In embodiments, Ring C is a substituted or unsubstituted 5 to 6 membered heteroaryl. When Ring C is substituted (e.g., substituted C$_3$-C$_6$ cycloalkyl) it is understood z24 is not 0 (i.e., Ring C is R$^{24}$-substituted).

In embodiments, Ring C is substituted or unsubstituted cycloalkyl. In embodiments, Ring C is substituted or unsubstituted heterocycloalkyl. In embodiments, Ring C is substituted or unsubstituted aryl. In embodiments, Ring C is substituted or unsubstituted heteroaryl. In embodiments, Ring C is substituted or unsubstituted (C$_3$-C$_{10}$) cycloalkyl, substituted or unsubstituted 3 to 10 membered heterocycloalkyl, substituted or unsubstituted (C$_6$-C$_{10}$) aryl, or substituted or unsubstituted 5 to 10 membered heteroaryl. In embodiments, Ring C is substituted or unsubstituted (C$_3$-C$_{10}$) cycloalkyl. In embodiments, Ring C is substituted or unsubstituted 3 to 10 membered heterocycloalkyl. In embodiments, Ring C is substituted or unsubstituted (C$_6$-C$_{10}$) aryl. In embodiments, Ring C is substituted or unsubstituted 5 to 10 membered heteroaryl. In embodiments, Ring C is substituted or unsubstituted (C$_3$-C$_6$) cycloalkyl. In embodiments, Ring C is substituted or unsubstituted 3 to 6 membered heterocycloalkyl. In embodiments, Ring C is substituted or unsubstituted phenyl. In embodiments, Ring C is substituted or unsubstituted naphthyl. In embodiments, Ring C is substituted or unsubstituted 5 to 9 membered heteroaryl. In embodiments, Ring C is substituted or unsubstituted 5 to 6 membered heteroaryl. In embodiments, Ring C is an unsubstituted 5 to 6 membered heteroaryl. In embodiments, Ring C is substituted or unsubstituted 5 membered heteroaryl. In embodiments, Ring C is a substituted 5 membered heteroaryl. In embodiments, Ring C is an unsubstituted 5 membered heteroaryl.

In embodiments, Ring C is R$^{24}$-substituted or unsubstituted (C$_3$-C$_{10}$) cycloalkyl, R$^{24}$-substituted or unsubstituted 5 to 10 membered heterocycloalkyl, R$^{24}$-substituted or unsubstituted (C$_6$-C$_{10}$) aryl, or R$^{24}$-substituted or unsubstituted 5 to 10 membered heteroaryl. In embodiments, Ring C is R$^{24}$-substituted or unsubstituted (C$_3$-C$_{10}$) cycloalkyl or R$^{24}$-substituted or unsubstituted 5 to 10 membered heterocycloalkyl. In embodiments, Ring C is R$^{24}$-substituted or unsubstituted (C$_3$-C$_{10}$) cycloalkyl. In embodiments, Ring C is R$^{24}$-substituted or unsubstituted 3 to 10 membered heterocycloalkyl. In embodiments, Ring C is R$^{24}$-substituted or unsubstituted (C$_6$-C$_{10}$) aryl. In embodiments, Ring C is R$^{24}$-substituted or unsubstituted 5 to 10 membered heteroaryl. In embodiments, Ring C is R$^{24}$-substituted or unsubstituted ($C_3$-$C_6$) cycloalkyl. In embodiments, Ring C is $R^{24}$-substituted or unsubstituted 3 to 6 membered heterocycloalkyl. In embodiments, Ring C is $R^{24}$-substituted or unsubstituted phenyl. In embodiments, Ring C is $R^{24}$-substituted or unsubstituted naphthyl. In embodiments, Ring C is $R^{24}$-substituted or unsubstituted 5 to 9 membered heteroaryl. In embodiments, Ring C is $R^{24}$-substituted or unsubstituted 5 to 6 membered heteroaryl.

In embodiments, Ring C is $R^{24}$-substituted or unsubstituted thienyl. In embodiments, Ring C is $R^{24}$-substituted or unsubstituted phenyl. In embodiments, Ring C is $R^{24}$-substituted or unsubstituted benzothienyl. In embodiments, Ring C is $R^{24}$-substituted or unsubstituted naphthyl. In embodiments, Ring C is $R^{24}$-substituted or unsubstituted benzofuranyl. In embodiments, Ring C is $R^{24}$-substituted or unsubstituted furanyl. In embodiments, Ring C is $R^{24}$-substituted or unsubstituted pyrrolyl. In embodiments, Ring C is $R^{24}$-substituted or unsubstituted oxazolyl. In embodiments, Ring C is $R^{24}$-substituted or unsubstituted oxadiazolyl. In embodiments, Ring C is $R^{24}$-substituted or unsubstituted triazolyl. In embodiments, Ring C is $R^{24}$-substituted or unsubstituted thiazolyl.

In embodiments, Ring C is substituted cycloalkyl. In embodiments, Ring C is substituted heterocycloalkyl. In embodiments, Ring C is substituted aryl. In embodiments, Ring C is substituted heteroaryl. In embodiments, Ring C is substituted ($C_3$-$C_{10}$) cycloalkyl, substituted 3 to 10 membered heterocycloalkyl, substituted ($C_6$-$C_{10}$) aryl, or substituted 5 to 10 membered heteroaryl. In embodiments, Ring C is substituted ($C_3$-$C_{10}$) cycloalkyl. In embodiments, Ring C is substituted 3 to 10 membered heterocycloalkyl. In embodiments, Ring C is substituted ($C_6$-$C_{10}$) aryl. In embodiments, Ring C is substituted 5 to 10 membered heteroaryl. In embodiments, Ring C is substituted ($C_3$-$C_6$) cycloalkyl. In embodiments, Ring C is substituted 3 to 6 membered heterocycloalkyl. In embodiments, Ring C is substituted phenyl. In embodiments, Ring C is substituted naphthyl. In embodiments, Ring C is substituted 5 to 9 membered heteroaryl. In embodiments, Ring C is substituted 5 to 6 membered heteroaryl. In embodiments, Ring C is $R^{24}$-substituted ($C_3$-$C_{10}$) cycloalkyl, $R^{24}$-substituted 5 to 10 membered heterocycloalkyl, $R^{24}$-substituted ($C_6$-$C_{10}$) aryl, or $R^{24}$-substituted 5 to 10 membered heteroaryl. In embodiments, Ring C is $R^{24}$-substituted ($C_3$-$C_{10}$) cycloalkyl or $R^{24}$-substituted 5 to 10 membered heterocycloalkyl. In embodiments, Ring C is $R^{24}$-substituted ($C_3$-$C_{10}$) cycloalkyl. In embodiments, Ring C is $R^{24}$-substituted 3 to 10 membered heterocycloalkyl. In embodiments, Ring C is $R^{24}$-substituted ($C_6$-$C_{10}$) aryl. In embodiments, Ring C is $R^{24}$-substituted 5 to 10 membered heteroaryl. In embodiments, Ring C is $R^{24}$-substituted ($C_3$-$C_6$) cycloalkyl. In embodiments, Ring C is $R^{24}$-substituted 3 to 6 membered heterocycloalkyl. In embodiments, Ring C is $R^{24}$-substituted phenyl. In embodiments, Ring C is $R^{24}$-substituted naphthyl. In embodiments, Ring C is $R^{24}$-substituted 5 to 9 membered heteroaryl. In embodiments, Ring C is $R^{24}$-substituted 5 to 6 membered heteroaryl. In embodiments, Ring C is $R^{24}$-substituted thienyl. In embodiments, Ring C is $R^{24}$-substituted phenyl. In embodiments, Ring C is $R^{24}$-substituted benzothienyl. In embodiments, Ring C is $R^{24}$-substituted naphthyl. In embodiments, Ring C is $R^{24}$-substituted benzofuranyl. In embodiments, Ring C is $R^{24}$-substituted furanyl. In embodiments, Ring C is $R^{24}$-substituted pyrrolyl. In embodiments, Ring C is $R^{24}$-substituted oxazolyl. In embodiments, Ring C is $R^{24}$-substituted oxadiazolyl. In embodiments, Ring C is $R^{24}$-substituted triazolyl. In embodiments, Ring C is $R^{24}$-substituted thiazolyl.

In embodiments, Ring C is unsubstituted cycloalkyl. In embodiments, Ring C is unsubstituted heterocycloalkyl. In embodiments, Ring C is unsubstituted aryl. In embodiments, Ring C is unsubstituted heteroaryl. In embodiments, Ring C is unsubstituted ($C_3$-$C_{10}$) cycloalkyl, unsubstituted 3 to 10 membered heterocycloalkyl, unsubstituted ($C_6$-$C_{10}$) aryl, or unsubstituted 5 to 10 membered heteroaryl. In embodiments, Ring C is unsubstituted ($C_3$-$C_{10}$) cycloalkyl. In embodiments, Ring C is unsubstituted 3 to 10 membered heterocycloalkyl. In embodiments, Ring C is unsubstituted ($C_6$-$C_{10}$) aryl. In embodiments, Ring C is unsubstituted 5 to 10 membered heteroaryl. In embodiments, Ring C is unsubstituted ($C_3$-$C_6$) cycloalkyl. In embodiments, Ring C is unsubstituted 3 to 6 membered heterocycloalkyl. In embodiments, Ring C is unsubstituted phenyl. In embodiments, Ring C is unsubstituted naphthyl. In embodiments, Ring C is unsubstituted 5 to 9 membered heteroaryl. In embodiments, Ring C is unsubstituted 5 to 6 membered heteroaryl. In embodiments, Ring C is unsubstituted ($C_3$-$C_{10}$) cycloalkyl, unsubstituted 5 to 10 membered heterocycloalkyl, unsubstituted ($C_6$-$C_{10}$) aryl, or unsubstituted 5 to 10 membered heteroaryl. In embodiments, Ring C is unsubstituted ($C_3$-$C_{10}$) cycloalkyl or unsubstituted 5 to 10 membered heterocycloalkyl. In embodiments, Ring C is unsubstituted ($C_3$-$C_{10}$) cycloalkyl. In embodiments, Ring C is unsubstituted 3 to 10 membered heterocycloalkyl. In embodiments, Ring C is unsubstituted ($C_6$-$C_{10}$) aryl. In embodiments, Ring C is unsubstituted 5 to 10 membered heteroaryl. In embodiments, Ring C is unsubstituted ($C_3$-$C_6$) cycloalkyl. In embodiments, Ring C is unsubstituted 3 to 6 membered heterocycloalkyl. In embodiments, Ring C is unsubstituted phenyl. In embodiments, Ring C is unsubstituted naphthyl. In embodiments, Ring C is unsubstituted 5 to 9 membered heteroaryl. In embodiments, Ring C is unsubstituted 5 to 6 membered heteroaryl. In embodiments, Ring C is unsubstituted thienyl. In embodiments, Ring C is unsubstituted phenyl. In embodiments, Ring C is unsubstituted benzothienyl. In embodiments, Ring C is unsubstituted naphthyl. In embodiments, Ring C is unsubstituted benzofuranyl. In embodiments, Ring C is unsubstituted furanyl. In embodiments, Ring C is unsubstituted pyrrolyl. In embodiments, Ring C is an unsubstituted oxazolyl. In embodiments, Ring C is unsubstituted phenyl. In embodiments, Ring C is an unsubstituted oxadiazolyl. In embodiments, Ring C is an unsubstituted triazolyl. In embodiments, Ring C is an unsubstituted thiazolyl.

In embodiments, Ring C is $C_6$-$C_{10}$ aryl or 5 to 10 membered heteroaryl. In embodiments, Ring C is $C_6$-$C_{10}$ aryl or 5 to 10 membered heteroaryl. In embodiments, Ring C is $C_6$-$C_{10}$ aryl. In embodiments, Ring C is phenyl. In embodiments, Ring C is naphthyl. In embodiments, Ring C is 5 to 10 membered heteroaryl. In embodiments, Ring C is 5 to 6 membered heteroaryl. In embodiments, Ring C is thienyl. In embodiments, Ring C is furanyl. In embodiments, Ring C is pyrrolyl. In embodiments, Ring C is imidazolyl. In embodiments, Ring C is pyrazolyl. In embodiments, Ring C is oxazolyl. In embodiments, Ring C is isoxazolyl. In embodiments, Ring C is thaizolyl. In embodiments, Ring C is pyridinyl. In embodiments, Ring C is pyridyl. In embodiments, Ring C is pyrazinyl. In embodiments, Ring C is pyrimidinyl. In embodiments, Ring C is pyridazinyl. In embodiments, Ring C is 1,2,3-triazinyl. In embodiments, Ring C is 1,2,4-triazinyl. In embodiments, Ring C is 1,3,5-triazinyl.

In embodiments, Ring C is substituted $C_6$-$C_{10}$ aryl or substituted 5 to 10 membered heteroaryl. In embodiments, Ring C is substituted $C_6$-$C_{10}$ aryl or substituted 5 to 10 membered heteroaryl. In embodiments, Ring C is substituted $C_6$-$C_{10}$ aryl. In embodiments, Ring C is substituted phenyl. In embodiments, Ring C is substituted naphthyl. In embodiments, Ring C is substituted 5 to 10 membered heteroaryl. In embodiments, Ring C is substituted 5 to 6 membered heteroaryl. In embodiments, Ring C is substituted thienyl. In embodiments, Ring C is substituted furanyl. In embodiments, Ring C is substituted pyrrolyl. In embodiments, Ring C is substituted imidazolyl. In embodiments, Ring C is substituted pyrazolyl. In embodiments, Ring C is substituted oxazolyl. In embodiments, Ring C is substituted isoxazolyl. In embodiments, Ring C is substituted thaizolyl. In embodiments, Ring C is substituted pyridinyl. In embodiments, Ring C is substituted pyridyl. In embodiments, Ring C is substituted pyrazinyl. In embodiments, Ring C is substituted pyrimidinyl. In embodiments, Ring C is substituted pyridazinyl. In embodiments, Ring C is substituted 1,2,3-triazinyl. In embodiments, Ring C is substituted 1,2,4-triazinyl. In embodiments, Ring C is substituted 1,3,5-triazinyl.

In embodiments, Ring C is an unsubstituted $C_6$-$C_{10}$ aryl or unsubstituted 5 to 10 membered heteroaryl. In embodiments, Ring C is an unsubstituted $C_6$-$C_{10}$ aryl or unsubstituted 5 to 10 membered heteroaryl. In embodiments, Ring C is an unsubstituted $C_6$-$C_{10}$ aryl. In embodiments, Ring C is an unsubstituted phenyl. In embodiments, Ring C is an unsubstituted naphthyl. In embodiments, Ring C is an unsubstituted 5 to 10 membered heteroaryl. In embodiments, Ring C is an unsubstituted 5 to 6 membered heteroaryl. In embodiments, Ring C is an unsubstituted thienyl. In embodiments, Ring C is an unsubstituted furanyl. In embodiments, Ring C is an unsubstituted pyrrolyl. In embodiments, Ring C is an unsubstituted imidazolyl. In embodiments, Ring C is an unsubstituted pyrazolyl. In embodiments, Ring C is an unsubstituted oxazolyl. In embodiments, Ring C is an unsubstituted isoxazolyl. In embodiments, Ring C is an unsubstituted thaizolyl. In embodiments, Ring C is an unsubstituted pyridinyl. In embodiments, Ring C is an unsubstituted pyridyl. In embodiments, Ring C is an unsubstituted pyrazinyl. In embodiments, Ring C is an unsubstituted pyrimidinyl. In embodiments, Ring C is an unsubstituted pyridazinyl. In embodiments, Ring C is an unsubstituted 1,2,3-triazinyl. In embodiments, Ring C is an unsubstituted 1,2,4-triazinyl. In embodiments, Ring C is an unsubstituted 1,3,5-triazinyl.

In embodiments, Ring C is a 4 to 8 membered heterocycloalkyl. In embodiments, Ring C is a 4 membered heterocycloalkyl. In embodiments, Ring C is a 5 membered heterocycloalkyl. In embodiments, Ring C is a 6 membered heterocycloalkyl. In embodiments, Ring C is a 7 membered heterocycloalkyl. In embodiments, Ring C is an 8 membered heterocycloalkyl. In embodiments, Ring C is a 4 to 6 membered heterocycloalkyl. In embodiments, Ring C is azetidinyl.

In embodiments, Ring C is a substituted or unsubstituted heterocycloalkyl. In embodiments, Ring C is a substituted heterocycloalkyl. In embodiments, Ring C is an unsubstituted heterocycloalkyl. In embodiments, Ring C is a substituted or unsubstituted 3 to 10 membered heterocycloalkyl. In embodiments, Ring C is a substituted 3 to 10 membered heterocycloalkyl. In embodiments, Ring C is an unsubstituted 3 to 10 membered heterocycloalkyl. In embodiments, Ring C is a $R^6$-substituted or unsubstituted 5 to 10 membered heterocycloalkyl. In embodiments, Ring C is a $R^6$-substituted 5 to 10 membered heterocycloalkyl. In embodiments, Ring C is an unsubstituted 5 to 10 membered heterocycloalkyl.

In embodiments, Ring C is a substituted or unsubstituted 3 membered heterocycloalkyl. In embodiments, Ring C is a substituted or unsubstituted 4 membered heterocycloalkyl. In embodiments, Ring C is a substituted or unsubstituted 5 membered heterocycloalkyl. In embodiments, Ring C is a substituted or unsubstituted 6 membered heterocycloalkyl. In embodiments, Ring C is a substituted 3 membered heterocycloalkyl. In embodiments, Ring C is a substituted 4 membered heterocycloalkyl. In embodiments, Ring C is a substituted 5 membered heterocycloalkyl. In embodiments, Ring C is a substituted 6 membered heterocycloalkyl. In embodiments, Ring C is an unsubstituted 3 membered heterocycloalkyl. In embodiments, Ring C is an unsubstituted 4 membered heterocycloalkyl. In embodiments, Ring C is an unsubstituted 5 membered heterocycloalkyl. In embodiments, Ring C is an unsubstituted 6 membered heterocycloalkyl.

In embodiments, Ring C is a substituted or unsubstituted aziridinyl, azirinyl, azetidinyl, dihydroazetyl, diazetidinyl, azetyl, pyrrolidinyl, pyrrolinyl, pyrrolyl, pyrazolidinyl, imidazolidinyl, pyrazolinyl, pyrazolyl, thiazolidinyl, thiazolyl, isothiazolyl, piperidinyl, piperazinyl, morpholinyl, oxazinyl, thiomorpholinyl, thiazinyl, decahydroquinolinyl, dihydroazepinyl, azepanyl, or azocanyl. In embodiments, Ring C is a substituted aziridinyl, azirinyl, azetidinyl, dihydroazetyl, diazetidinyl, azetyl, pyrrolidinyl, pyrrolinyl, pyrrolyl, pyrazolidinyl, imidazolidinyl, pyrazolinyl, pyrazolyl, thiazolidinyl, thiazolyl, isothiazolyl, piperidinyl, piperazinyl, morpholinyl, oxazinyl, thiomorpholinyl, thiazinyl, decahydroquinolinyl, dihydroazepinyl, azepanyl, or azocanyl. In embodiments, Ring C is an unsubstituted aziridinyl, azirinyl, azetidinyl, dihydroazetyl, diazetidinyl, azetyl, pyrrolidinyl, pyrrolinyl, pyrrolyl, pyrazolidinyl, imidazolidinyl, pyrazolinyl, pyrazolyl, thiazolidinyl, thiazolyl, isothiazolyl, piperidinyl, piperazinyl, morpholinyl, oxazinyl, thiomorpholinyl, thiazinyl, decahydroquinolinyl, dihydroazepinyl, azepanyl, or azocanyl.

Ring C may be substituted with one $R^{24}$. Ring C may be substituted with two optionally different $R^{24}$ substituents. Ring C may be substituted with three optionally different $R^{24}$ substituents. Ring C may be substituted with four optionally different $R^{24}$ substituents. Ring C may be substituted with five optionally different $R^{24}$ substituents. Ring C may be substituted with six optionally different $R^{24}$ substituents. Ring C may be substituted with seven optionally different $R^{24}$ substituents. Ring C may be substituted with eight optionally different $R^{24}$ substituents. Ring C may be substituted with nine optionally different $R^{24}$ substituents. Ring C may be substituted with ten optionally different $R^{24}$ substituents.

In embodiments, Ring C is a substituted cyclopropyl. In embodiments, Ring C is a substituted cyclobutyl. In embodiments, Ring C is a substituted cyclohexyl. In embodiments, Ring C is a substituted cyclopentyl. In embodiments, Ring C is an OH-substituted cyclopentyl. In embodiments, Ring C is an OH-substituted cyclobutyl. In embodiments, Ring C is an unsubstituted cyclobutyl. In embodiments, Ring C is an unsubstituted cyclohexyl. In embodiments, Ring C is an unsubstituted cyclopentyl. In embodiments, Ring C is a OH-substituted phenyl. In embodiments, Ring C is a substituted phenyl. In embodiments, Ring C is an unsubstituted phenyl. In embodiments, Ring C is an unsubstituted tetrahydropyranyl. In embodiments, Ring C is a substituted tetrahydropyranyl. In embodiments, Ring C is an unsubstituted tetrahydrofuranyl. In embodiments, Ring C is a substituted tetrahydrofuranyl. In embodiments, Ring C is an unsubstituted cyclopropyl. In embodiments, Ring C is an unsubstituted pyridyl. In embodiments, Ring C is a substituted pyridyl. In embodiments, Ring C is an —OCH$_3$-substituted pyridyl. In embodiments, Ring C is a substituted piperidinyl. In embodiments, Ring C is an unsubstituted piperidinyl. In embodiments, Ring C is a substituted thiazolyl. In embodiments, Ring C is an unsubstituted thiazolyl. In embodiments, Ring C is a substituted pyrrolidinyl. In embodiments, Ring C is an unsubstituted pyrrolidinyl. In embodiments, Ring C is a substituted oxetanyl. In embodiments, Ring C is an unsubstituted oxetanyl. In embodiments, Ring C is a substituted azetidinyl. In embodiments, Ring C is an unsubstituted azetidinyl. In embodiments, Ring C is a substituted morpholinyl. In embodiments, Ring C is an unsubstituted morpholinyl. In embodiments, Ring C is a substituted imidazolyl. In embodiments, Ring C is an unsubstituted imidazolyl. In embodiments, Ring C is a substituted pyrimidinyl. In embodiments, Ring C is an unsubstituted pyrimidinyl. In embodiments, Ring C is a substituted pyridazinyl. In embodiments, Ring C is an unsubstituted pyridazinyl.

In embodiments, each $R^{1A}$, $R^{1B}$, $R^{1C}$, $R^{1D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, and $R^{6D}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{1A}$ is hydrogen. In embodiments, $R^{1B}$ is hydrogen. In embodiments, $R^{1C}$ is hydrogen. In embodiments, $R^{1D}$ is hydrogen. In embodiments, $R^{4A}$ is hydrogen. In embodiments, $R^{4B}$ is hydrogen. In embodiments, $R^{4C}$ is hydrogen. In embodiments, $R^{4D}$ is hydrogen. In embodiments, $R^{5A}$ is hydrogen. In embodiments, $R^{5B}$ is hydrogen. In embodiments, $R^{5C}$ is hydrogen. In embodiments, $R^{5D}$ is hydrogen. In embodiments, $R^{1A}$ is halogen. In embodiments, $R^{1B}$ is halogen. In embodiments, $R^{1C}$ is halogen. In embodiments, $R^{1D}$ is halogen. In embodiments, $R^{4A}$ is halogen. In embodiments, $R^{4B}$ is halogen. In embodiments, $R^{4C}$ is halogen. In embodiments, $R^{4D}$ is halogen. In embodiments, $R^{5A}$ is halogen. In embodiments, $R^{5B}$ is halogen. In embodiments, $R^{5C}$ is halogen. In embodiments, $R^{5D}$ is halogen. In embodiments, $R^{6A}$ is halogen. In embodiments, $R^{6B}$ is halogen. In embodiments, $R^{6C}$ is halogen. In embodiments, $R^{6D}$ is halogen.

In embodiments, $R^{1A}$ is unsubstituted alkyl (e.g., C$_1$-C$_8$ alkyl, C$_1$-C$_6$ alkyl, or C$_1$-C$_4$ alkyl). In embodiments, $R^{1B}$ is unsubstituted alkyl (e.g., C$_1$-C$_8$ alkyl, C$_1$-C$_6$ alkyl, or C$_1$-C$_4$ alkyl). In embodiments, $R^{1C}$ is unsubstituted alkyl (e.g., C$_1$-C$_8$ alkyl, C$_1$-C$_6$ alkyl, or C$_1$-C$_4$ alkyl). In embodiments, $R^{1D}$ is unsubstituted alkyl (e.g., C$_1$-C$_8$ alkyl, C$_1$-C$_6$ alkyl, or C$_1$-C$_4$ alkyl). In embodiments, $R^{4A}$ is unsubstituted alkyl (e.g., C$_1$-C$_8$ alkyl, C$_1$-C$_6$ alkyl, or C$_1$-C$_4$ alkyl). In embodiments, $R^{4B}$ is unsubstituted alkyl (e.g., C$_1$-C$_8$ alkyl, C$_1$-C$_6$ alkyl, or C$_1$-C$_4$ alkyl). In embodiments, $R^{4C}$ is unsubstituted alkyl (e.g., C$_1$-C$_8$ alkyl, C$_1$-C$_6$ alkyl, or C$_1$-C$_4$ alkyl). In embodiments, $R^{4D}$ is unsubstituted alkyl (e.g., C$_1$-C$_8$ alkyl, C$_1$-C$_6$ alkyl, or C$_1$-C$_4$ alkyl). In embodiments, $R^{5A}$ is unsubstituted alkyl (e.g., C$_1$-C$_8$ alkyl, C$_1$-C$_6$ alkyl, or C$_1$-C$_4$ alkyl). In embodiments, $R^{5B}$ is unsubstituted alkyl (e.g., C$_1$-C$_8$ alkyl, C$_1$-C$_6$ alkyl, or C$_1$-C$_4$ alkyl). In embodiments, $R^{5C}$ is unsubstituted alkyl (e.g., C$_1$-C$_8$ alkyl, C$_1$-C$_6$ alkyl, or C$_1$-C$_4$ alkyl). In embodiments, $R^{5D}$ is unsubstituted alkyl (e.g., C$_1$-C$_8$ alkyl, C$_1$-C$_6$ alkyl, or C$_1$-C$_4$ alkyl). In embodiments, $R^{6A}$ is unsubstituted alkyl (e.g., C$_1$-C$_8$ alkyl, C$_1$-C$_6$ alkyl, or C$_1$-C$_4$ alkyl). In embodiments, $R^{6B}$ is unsubstituted alkyl (e.g., C$_1$-C$_8$ alkyl, C$_1$-C$_6$ alkyl, or C$_1$-C$_4$ alkyl). In embodiments, $R^{6C}$ is unsubstituted alkyl (e.g., C$_1$-C$_8$ alkyl, C$_1$-C$_6$ alkyl, or C$_1$-C$_4$ alkyl). In embodiments, $R^{6D}$ is unsubstituted alkyl (e.g., C$_1$-C$_8$ alkyl, C$_1$-C$_6$ alkyl, or C$_1$-C$_4$ alkyl).

In embodiments, $R^{1A}$ is unsubstituted heteroalkyl (e.g., 2 to 8 membered heteroalkyl, 2 to 6 membered heteroalkyl, or 2 to 4 membered heteroalkyl). In embodiments, $R^{1B}$ is unsubstituted heteroalkyl (e.g., 2 to 8 membered heteroalkyl, 2 to 6 membered heteroalkyl, or 2 to 4 membered heteroalkyl). In embodiments, $R^{1C}$ is unsubstituted heteroalkyl (e.g., 2 to 8 membered heteroalkyl, 2 to 6 membered heteroalkyl, or 2 to 4 membered heteroalkyl). In embodiments, $R^{1D}$ is unsubstituted heteroalkyl (e.g., 2 to 8 membered heteroalkyl, 2 to 6 membered heteroalkyl, or 2 to 4 membered heteroalkyl). In embodiments, $R^{4A}$ is unsubstituted heteroalkyl (e.g., 2 to 8 membered heteroalkyl, 2 to 6 membered heteroalkyl, or 2 to 4 membered heteroalkyl). In embodiments, $R^{4B}$ is unsubstituted heteroalkyl (e.g., 2 to 8 membered heteroalkyl, 2 to 6 membered heteroalkyl, or 2 to 4 membered heteroalkyl). In embodiments, $R^{4C}$ is unsubstituted heteroalkyl (e.g., 2 to 8 membered heteroalkyl, 2 to 6 membered heteroalkyl, or 2 to 4 membered heteroalkyl). In embodiments, $R^{4D}$ is unsubstituted heteroalkyl (e.g., 2 to 8 membered heteroalkyl, 2 to 6 membered heteroalkyl, or 2 to 4 membered heteroalkyl). In embodiments, $R^{5A}$ is unsubstituted heteroalkyl (e.g., 2 to 8 membered heteroalkyl, 2 to 6 membered heteroalkyl, or 2 to 4 membered heteroalkyl). In embodiments, $R^{5B}$ is unsubstituted heteroalkyl (e.g., 2 to 8 membered heteroalkyl, 2 to 6 membered heteroalkyl, or 2 to 4 membered heteroalkyl). In embodiments, $R^{5C}$ is unsubstituted heteroalkyl (e.g., 2 to 8 membered heteroalkyl, 2 to 6 membered heteroalkyl, or 2 to 4 membered heteroalkyl). In embodiments, $R^{5D}$ is unsubstituted heteroalkyl (e.g., 2 to 8 membered heteroalkyl, 2 to 6 membered heteroalkyl, or 2 to 4 membered heteroalkyl). In embodiments, $R^{6A}$ is unsubstituted heteroalkyl (e.g., 2 to 8 membered heteroalkyl, 2 to 6 membered heteroalkyl, or 2 to 4 membered heteroalkyl). In embodiments, $R^{6B}$ is unsubstituted heteroalkyl (e.g., 2 to 8 membered heteroalkyl, 2 to 6 membered heteroalkyl, or 2 to 4 membered heteroalkyl). In embodiments, $R^{6C}$ is unsubstituted heteroalkyl (e.g., 2 to 8 membered heteroalkyl, 2 to 6 membered heteroalkyl, or 2 to 4 membered heteroalkyl). In embodiments, $R^{6D}$ is unsubstituted heteroalkyl (e.g., 2 to 8 membered heteroalkyl, 2 to 6 membered heteroalkyl, or 2 to 4 membered heteroalkyl).

In embodiments, $R^{1A}$ and $R^{1B}$ substituents bonded to the same nitrogen atom may optionally be joined to form a substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{4A}$ and $R^{4B}$ substituents bonded to the same nitrogen atom may optionally be joined to form a substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{5A}$ and $R^{5B}$ substituents bonded to the same nitrogen atom may optionally be joined to form a substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{6A}$ and $R^{6B}$ substituents bonded to the same nitrogen atom may optionally be joined to form a substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{1A}$ and $R^{1B}$ substituents bonded to the same nitrogen atom may optionally be joined to form a substituted heterocycloalkyl (e.g., 3 to 8 membered heterocycloalkyl, 3 to 6 membered heterocycloalkyl, or 5 to 6 membered heterocycloalkyl). In embodiments, $R^{4A}$ and $R^{4B}$ substituents bonded to the same nitrogen atom may optionally be joined to form a substituted heterocycloalkyl (e.g., 3 to 8 membered heterocycloalkyl, 3 to 6 membered heterocycloalkyl, or 5 to 6 membered heterocycloalkyl). In embodiments, $R^{5A}$ and $R^{5B}$ substituents bonded to the same nitrogen atom may optionally be joined to form a substituted heterocycloalkyl (e.g., 3 to 8 membered heterocycloalkyl, 3 to 6 membered heterocycloalkyl, or 5 to 6 membered heterocycloalkyl). In embodiments, $R^{6A}$ and $R^{6B}$ substituents bonded to the same nitrogen atom may optionally be joined to form a substituted heterocycloalkyl (e.g., 3 to 8 membered heterocycloalkyl, 3 to 6 membered heterocycloalkyl, or 5 to 6 membered heterocycloalkyl). In embodiments, $R^{1A}$ and $R^{1B}$ substituents bonded to the same nitrogen atom may optionally be joined to form an unsubstituted heterocycloalkyl (e.g., 3 to 8 membered heterocycloalkyl, 3 to 6 membered heterocycloalkyl, or 5 to 6 membered heterocycloalkyl). In embodiments, $R^{4A}$ and $R^{4B}$ substituents bonded to the same nitrogen atom may optionally be joined to form an unsubstituted heterocycloalkyl (e.g., 3 to 8 membered heterocycloalkyl, 3 to 6 membered heterocycloalkyl, or 5 to 6 membered heterocycloalkyl). In embodiments, $R^{5A}$ and $R^{5B}$ substituents bonded to the same nitrogen atom may optionally be joined to form an unsubstituted heterocycloalkyl (e.g., 3 to 8 membered heterocycloalkyl, 3 to 6 membered heterocycloalkyl, or 5 to 6 membered heterocycloalkyl). In embodiments, $R^{6A}$ and $R^{6B}$ substituents bonded to the same nitrogen atom may optionally be joined to form an unsubstituted heterocycloalkyl (e.g., 3 to 8 membered heterocycloalkyl, 3 to 6 membered heterocycloalkyl, or 5 to 6 membered heterocycloalkyl).

In embodiments, each $R^{1A}$, $R^{1B}$, $R^{1C}$, $R^{1D}$, $R^{4A}$, $R^{4B}$, $R^{4C}$, $R^{4D}$, $R^{5A}$, $R^{5B}$, $R^{5C}$, and $R^{5D}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

$R^{22}$, $R^{25}$, $R^{28}$, $R^{31}$, $R^{34}$, $R^{37}$, and $R^{40}$ are independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{22}$, $R^{25}$, $R^{28}$, $R^{31}$, $R^{34}$, $R^{37}$, and $R^{40}$ are independently oxo. In embodiments, $R^{22}$, $R^{25}$, $R^{28}$, $R^{31}$, $R^{34}$, $R^{37}$, and $R^{40}$ are independently halogen. In embodiments, $R^{22}$, $R^{25}$, $R^{28}$, $R^{31}$, $R^{34}$, $R^{37}$, and $R^{40}$ are independently —$CF_3$. In embodiments, $R^{22}$, $R^{25}$, $R^{28}$, $R^{31}$, $R^{34}$, $R^{37}$, and $R^{40}$ are independently —$CBr_3$. In embodiments, $R^{22}$, $R^{25}$, $R^{28}$, $R^{31}$, $R^{34}$, $R^{37}$, and $R^{40}$ are independently —$CCl_3$. In embodiments, $R^{22}$, $R^{25}$, $R^{28}$, $R^{31}$, $R^{34}$, $R^{37}$, and $R^{40}$ are independently —$CI_3$. In embodiments, $R^{22}$, $R^{25}$, $R^{28}$, $R^{31}$, $R^{34}$, $R^{37}$, and $R^{40}$ are independently —$CHF_2$. In embodiments, $R^{22}$, $R^{25}$, $R^{28}$, $R^{31}$, $R^{34}$, $R^{37}$, and $R^{40}$ are independently —$CHBr_2$. In embodiments, $R^{22}$, $R^{25}$, $R^{28}$, $R^{31}$, $R^{34}$, $R^{37}$, and $R^{40}$ are independently —$CHCl_2$. In embodiments, $R^{22}$, $R^{25}$, $R^{28}$, $R^{31}$, $R^{34}$, $R^{37}$, and $R^{40}$ are independently —$CHI_2$. In embodiments, $R^{22}$, $R^{25}$, $R^{28}$, $R^{31}$, $R^{34}$, $R^{37}$, and $R^{40}$ are independently —$CH_2F$. In embodiments, $R^{22}$, $R^{25}$, $R^{28}$, $R^{31}$, $R^{34}$, $R^{37}$, and $R^{40}$ are independently —$CH_2Br$. In embodiments, $R^{22}$, $R^{25}$, $R^{28}$, $R^{31}$, $R^{34}$, $R^{37}$, and $R^{40}$ are independently —$CH_2Cl$. In embodiments, $R^{22}$, $R^{25}$, $R^{28}$, $R^{31}$, $R^{34}$, $R^{37}$, and $R^{40}$ are independently —$CH_2I$. In embodiments, $R^{22}$, $R^{25}$, $R^{28}$, $R^{31}$, $R^{34}$, $R^{37}$, and $R^{40}$ are independently —$OCF_3$. In embodiments, $R^{22}$, $R^{25}$, $R^{28}$, $R^{31}$, $R^{34}$, $R^{37}$, and $R^{40}$ are independently —$OCBr_3$. In embodiments, $R^{22}$, $R^{25}$, $R^{28}$, $R^{31}$, $R^{34}$, $R^{37}$, and $R^{40}$ are independently —$OCCl_3$. In embodiments, $R^{22}$, $R^{25}$, $R^{28}$, $R^{31}$, $R^{34}$, $R^{37}$, and $R^{40}$ are independently —$OCI_3$. In embodiments, $R^{22}$, $R^{25}$, $R^{28}$, $R^{31}$, $R^{34}$, $R^{37}$, and $R^{40}$ are independently —$OCHF_2$. In embodiments, $R^{22}$, $R^{25}$, $R^{28}$, $R^{31}$, $R^{34}$, $R^{37}$, and $R^{40}$ are independently —$OCHBr_2$. In embodiments, $R^{22}$, $R^{25}$, $R^{28}$, $R^{31}$, $R^{34}$, $R^{37}$, and $R^{40}$ are independently —$OCHCl_2$. In embodiments, $R^{22}$, $R^{25}$, $R^{28}$, $R^{31}$, $R^{34}$, $R^{37}$, and $R^{40}$ are independently —$OCHI_2$. In embodiments, $R^{22}$, $R^{25}$, $R^{28}$, $R^{31}$, $R^{34}$, $R^{37}$, and $R^{40}$ are independently —$OCH_2F$. In embodiments, $R^{22}$, $R^{25}$, $R^{28}$, $R^{31}$, $R^{34}$, $R^{37}$, and $R^{40}$ are independently —$OCH_2Br$. In embodiments, $R^{22}$, $R^{25}$, $R^{28}$, $R^{31}$, $R^{34}$, $R^{37}$, and $R^{40}$ are independently —$OCH_2Cl$. In embodiments, $R^{22}$, $R^{25}$, $R^{28}$, $R^{31}$, $R^{34}$, $R^{37}$, and $R^{40}$ are independently —$OCH_2I$. In embodiments, $R^{22}$, $R^{25}$, $R^{28}$, $R^{31}$, $R^{34}$, $R^{37}$, and $R^{40}$ are independently —CN. In embodiments, $R^{22}$, $R^{25}$, $R^{28}$, $R^{31}$, $R^{34}$, $R^{37}$, and $R^{40}$ are independently —OH. In embodiments, $R^{22}$, $R^{25}$, $R^{28}$, $R^{31}$, $R^{34}$, $R^{37}$, and $R^{40}$ are independently —$NH_2$. In embodiments, $R^{22}$, $R^{25}$, $R^{28}$, $R^{31}$, $R^{34}$, $R^{37}$, and $R^{40}$ are independently —COOH. In embodiments, $R^{22}$, $R^{25}$, $R^{28}$, $R^{31}$, $R^{34}$, $R^{37}$, and $R^{40}$ are independently —$CONH_2$. In embodiments, $R^{22}$, $R^{25}$, $R^{28}$, $R^{31}$, $R^{34}$, $R^{37}$, and $R^{40}$ are independently —$NO_2$. In embodiments, $R^{22}$, $R^{25}$, $R^{28}$, $R^{31}$, $R^{34}$, $R^{37}$, and $R^{40}$ are independently —SH. In embodiments, $R^{22}$, $R^{25}$, $R^{28}$, $R^{31}$, $R^{34}$, $R^{37}$, and $R^{40}$ are independently —$SO_3H$. In embodiments, $R^{22}$, $R^{25}$, $R^{28}$, $R^{31}$, $R^{34}$, $R^{37}$, and $R^{40}$ are independently —$SO_4H$. In embodiments, $R^{22}$, $R^{25}$, $R^{28}$, $R^{31}$, $R^{34}$, $R^{37}$, and $R^{40}$ are independently —$SO_2NH_2$. In embodiments, $R^{22}$, $R^{25}$, $R^{28}$, $R^{31}$, $R^{34}$, $R^{37}$, and $R^{40}$ are independently —$NHNH_2$. In embodiments, $R^{22}$, $R^{25}$, $R^{28}$, $R^{31}$, $R^{34}$, $R^{37}$, and $R^{40}$ are independently —$ONH_2$, —NHC(O)$NHNH_2$. In embodiments, $R^{22}$, $R^{25}$, $R^{28}$, $R^{31}$, $R^{34}$, $R^{37}$, and $R^{40}$ are independently —NHC(O)$NH_2$. In embodiments, $R^{22}$, $R^{25}$, $R^{28}$, $R^{31}$, $R^{34}$, $R^{37}$, and $R^{40}$ are independently —$NHSO_2H$. In embodiments, $R^{22}$, $R^{25}$, $R^{28}$, $R^{31}$, $R^{34}$, $R^{37}$, and $R^{40}$ are independently —NHC(O)H. In embodiments, $R^{22}$, $R^{25}$, $R^{28}$, $R^{31}$, $R^{34}$, $R^{37}$, and $R^{40}$ are independently —NHC(O)OH. In embodiments, $R^{22}$, $R^{25}$, $R^{28}$, $R^{31}$, $R^{34}$, $R^{37}$, and $R^{40}$ are independently —NHOH. In embodiments, $R^{22}$, $R^{25}$, $R^{28}$, $R^{31}$, $R^{34}$, $R^{37}$, and $R^{40}$ are independently —$OCCl_3$. In embodiments, $R^{22}$, $R^{25}$, $R^{28}$, $R^{31}$, $R^{34}$, $R^{37}$, and $R^{40}$ are independently —$OCF_3$. In embodiments, $R^{22}$, $R^{25}$, $R^{28}$, $R^{31}$, $R^{34}$, $R^{37}$, and $R^{40}$ are independently —$OCBr_3$. In embodiments, $R^{22}$, $R^{25}$, $R^{28}$, $R^{31}$, $R^{34}$, $R^{37}$, and $R^{40}$ are independently —$OCI_3$. In embodiments, $R^{22}$, $R^{25}$, $R^{28}$, $R^{31}$, $R^{34}$, $R^{37}$, and $R^{40}$ are independently —$OCHCl_2$. In embodiments, $R^{22}$, $R^{25}$, $R^{28}$, $R^{31}$, $R^{34}$, $R^{37}$, and $R^{40}$ are independently —$OCHBr_2$. In embodiments, $R^{22}$, $R^{25}$, $R^{28}$, $R^{31}$, $R^{34}$, $R^{37}$, and $R^{40}$ are independently —$OCHI_2$. In embodiments, $R^{22}$, $R^{25}$, $R^{28}$, $R^{31}$, $R^{34}$, $R^{37}$, and $R^{40}$ are independently —$OCHF_2$. In embodiments, $R^{22}$, $R^{25}$, $R^{28}$, $R^{31}$, $R^{34}$, $R^{37}$, and $R^{40}$ are independently unsubstituted alkyl (e.g., $C_1$-$C_8$ alkyl, $C_1$-$C_6$ alkyl, or $C_1$-$C_4$ alkyl). In embodiments, $R^{22}$, $R^{25}$, $R^{28}$, $R^{31}$, $R^{34}$, $R^{37}$, and $R^{40}$ are independently unsubstituted heteroalkyl (e.g., 2 to 8 membered heteroalkyl, 2 to 6 membered heteroalkyl, or 2 to 4 membered heteroalkyl). In embodiments, $R^{22}$, $R^{25}$, $R^{28}$, $R^{31}$, $R^{34}$, $R^{37}$, and $R^{40}$ are independently unsubstituted cycloalkyl (e.g., $C_3$-$C_8$ cycloalkyl, $C_3$-$C_6$ cycloalkyl, or $C_5$-$C_6$ cycloalkyl). In embodiments, $R^{22}$, $R^{25}$, $R^{28}$, $R^{31}$, $R^{34}$, $R^{37}$, and $R^{40}$ are independently unsubstituted heterocycloalkyl (e.g., 3 to 8 membered heterocycloalkyl, 3 to 6 membered heterocycloalkyl, or 5 to 6 membered heterocycloalkyl). In embodiments, $R^{22}$, $R^{25}$, $R^{28}$, $R^{31}$, $R^{34}$, $R^{37}$, and $R^{40}$ are independently unsubstituted aryl (e.g., $C_6$-$C_{10}$ aryl, $C_{10}$ aryl, or phenyl). In embodiments, $R^{22}$, $R^{25}$, $R^{28}$, $R^{31}$, $R^{34}$, $R^{37}$, and $R^{40}$ are independently unsubstituted heteroaryl (e.g., 5 to 10 membered heteroaryl, 5 to 9 membered heteroaryl, or 5 to 6 membered heteroaryl). In embodiments, $R^{22}$, $R^{25}$, $R^{28}$, $R^{31}$, $R^{34}$, $R^{37}$, and $R^{40}$ are independently —$CH_3$. In embodiments, $R^{22}$, $R^{25}$, $R^{28}$, $R^{31}$, $R^{34}$, $R^{37}$, and $R^{40}$ are independently an unsubstituted $C_2$ alkyl. In embodiments, $R^{22}$, $R^{25}$, $R^{28}$, $R^{31}$, $R^{34}$, $R^{37}$, and $R^{40}$ are independently an unsubstituted $C_3$ alkyl. In embodiments, $R^{22}$, $R^{25}$, $R^{28}$, $R^{31}$, $R^{34}$, $R^{37}$, and $R^{40}$ are independently an unsubstituted $C_4$ alkyl. In embodiments, $R^{22}$, $R^{25}$, $R^{28}$, $R^{31}$, $R^{34}$, $R^{37}$, and $R^{40}$ are independently an unsubstituted $C_5$ alkyl. In embodiments, $R^{22}$, $R^{25}$, $R^{28}$, $R^{31}$, $R^{34}$, $R^{37}$, and $R^{40}$ are independently an unsubstituted $C_6$ alkyl. In embodiments, $R^{22}$, $R^{25}$, $R^{28}$, $R^{31}$, $R^{34}$, $R^{37}$, and $R^{40}$ are independently an unsubstituted $C_7$ alkyl. In embodiments, $R^{22}$, $R^{25}$, $R^{28}$, $R^{31}$, $R^{34}$, $R^{37}$, and $R^{40}$ are independently an unsubstituted $C_8$ alkyl.

$R^{37A}$, $R^{37B}$, $R^{37C}$, and $R^{37D}$ are independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{25}$ is —OH. In embodiments, $R^{25}$ is —$OCH_3$. In embodiments, $R^{25}$ is —$OCH_2CH_3$. In embodiments, $R^{25}$ is —F. In embodiments, $R^{25}$ is —NHC(O)$CH_3$. In embodiments, $R^{25}$ is —COOH. In embodiments, $R^{25}$ is —$SO_2NH_2$.

In embodiments, $R^{28}$ is —OH. In embodiments, $R^{28}$ is —$OCH_3$. In embodiments, $R^{28}$ is —$OCH_2CH_3$. In embodiments, $R^{28}$ is —F. In embodiments, $R^{28}$ is —NHC(O)$CH_3$. In embodiments, $R^{28}$ is —COOH. In embodiments, $R^{28}$ is —$SO_2NH_2$.

In embodiments, $X^1$ is —F. In embodiments, $X^1$ is —Cl. In embodiments, $X^1$ is —Br. In embodiments, $X^1$ is —I. In embodiments, $X^4$ is —F. In embodiments, $X^4$ is —Cl. In embodiments, $X^4$ is —Br. In embodiments, $X^4$ is —I. In embodiments, $X^5$ is —F. In embodiments, $X^5$ is —Cl. In embodiments, $X^5$ is —Br. In embodiments, $X^5$ is —I. In embodiments, $X^6$ is —F. In embodiments, $X^6$ is —Cl. In embodiments, $X^6$ is —Br. In embodiments, $X^6$ is —I.

In embodiments, z1 is an integer from 0 to 5. In embodiments, z1 is an integer from 0 to 2. In embodiments, z1 is 0. In embodiments, z1 is 1. In embodiments, z1 is 2. In embodiments, z1 is 3. In embodiments, z1 is 4. In embodiments, z1 is 5. In embodiments, z6 is an integer from 0 to 5. In embodiments, z6 is an integer from 0 to 2. In embodiments, z6 is 0. In embodiments, z6 is 1. In embodiments, z6 is 2. In embodiments, z6 is 3. In embodiments, z6 is 4. In embodiments, z6 is 5. In embodiments, z6 is 6. In embodiments, z6 is 7. In embodiments, z6 is 8. In embodiments, z6 is 9. In embodiments, z6 is 10. In embodiments, z16 is 1. In embodiments, z16 is 2. In embodiments, z16 is 3. In embodiments, z16 is 4. In embodiments, z16 is 5. In embodiments, z16 is 6. In embodiments, z16 is 7. In embodiments, z16 is 8. In embodiments, z24 is 0. In embodiments, z24 is 1. In embodiments, z24 is 2. In embodiments, z24 is 3. In embodiments, z24 is 4. In embodiments, z24 is 5. In embodiments, z24 is 6. In embodiments, z24 is 7. In embodiments, z24 is 8. In embodiments, z24 is 9. In embodiments, z24 is 10.

In embodiments, the compound is Z1. In embodiments, the compound is Z2. In embodiments, the compound is Z3. In embodiments, the compound is Z4. In embodiments, the compound is Z5. In embodiments, the compound is Z6. In embodiments, the compound is Z7. In embodiments, the compound is Z8. In embodiments, the compound is Z9. In embodiments, the compound is Z10. In embodiments, the compound is Z11. In embodiments, the compound is Z12. In embodiments, the compound is Z13. In embodiments, the compound is Z14. In embodiments, the compound is Z15. In embodiments, the compound is Z16. In embodiments, the compound is Z17. In embodiments, the compound is Z18. In embodiments, the compound is Z19. In embodiments, the compound is Z20. In embodiments, the compound is Z21. In embodiments, the compound is Z22. In embodiments, the compound is Z23. In embodiments, the compound is Z24. In embodiments, the compound is Z25. In embodiments, the compound is Z26. In embodiments, the compound is Z27. In embodiments, the compound is Z28. In embodiments, the compound is Z29. In embodiments, the compound is Z30. In embodiments, the compound is Z31. In embodiments, the compound is Z32. In embodiments, the compound is Z33. In embodiments, the compound is Z34. In embodiments, the compound is Z35. In embodiments, the compound is Z36. In embodiments, the compound is Z37. In embodiments, the compound is Z38. In embodiments, the compound is Z39. In embodiments, the compound is Z40. In embodiments, the compound is Z41. In embodiments, the compound is Z42. In embodiments, the compound is Z43. In embodiments, the compound is Z44. In embodiments, the compound is Z45. In embodiments, the compound is Z46. In embodiments, the compound is Z47. In embodiments, the compound is Z48. In embodiments, the compound is Z49. In embodiments, the compound is Z50. In embodiments, the compound is Z51. In embodiments, the compound is Z52. In embodiments, the compound is Z53. In embodiments, the compound is Z54. In embodiments, the compound is Z55. In embodiments, the compound is Z56. In embodiments, the compound is Z57. In embodiments, the compound is Z58. In embodiments, the compound is Z59. In embodiments, the compound is Z60. In embodiments, the compound is Z61. In embodiments, the compound is Z62. In embodiments, the compound is Z63. In embodiments, the compound is Z64. In embodiments, the compound is Z65. In embodiments, the compound is Z66. In embodiments, the compound is Z67. In embodiments, the compound is Z68. In embodiments, the compound is Z69. In embodiments, the compound is Z70. In embodiments, the compound is Z71. In embodiments, the compound is Z72. In embodiments, the compound is Z73. In embodiments, the compound is Z74. In embodiments, the compound is Z75. In embodiments, the compound is Z76. In embodiments, the compound is Z77. In embodiments, the compound is Z78. In embodiments, the compound is Z79. In embodiments, the compound is Z80. In embodiments, the compound is Z81. In embodiments, the compound is Z82. In embodiments, the compound is Z83. In embodiments, the compound is Z84. In embodiments, the compound is Z85. In embodiments, the compound is Z86. In embodiments, the compound is Z87. In embodiments, the compound is Z88. In embodiments, the compound is Z89. In embodiments, the compound is Z90. In embodiments, the compound is Z91. In embodiments, the compound is Z92. In embodiments, the compound is Z93. In embodiments, the compound is Z94. In embodiments, the compound is Z95. In embodiments, the compound is Z96. In embodiments, the compound is Z97. In embodiments, the compound is Z98. In embodiments, the compound is Z99. In embodiments, the compound is Z100. In embodiments, the compound is Z101. In embodiments, the compound is Z102. In embodiments, the compound is Z103. In embodiments, the compound is Z104. In embodiments, the compound is Z105. In embodiments, the compound is Z106. In embodiments, the compound is Z107. In embodiments, the compound is Z108. In embodiments, the compound is Z109. In embodiments, the compound is Z110. In embodiments, the compound is Z111. In embodiments, the compound is Z112. In embodiments, the compound is Z113. In embodiments, the compound is Z114. In embodiments, the compound is Z115. In embodiments, the compound is Z116. In embodiments, the compound is Z117. In embodiments, the compound is Z118. In embodiments, the compound is Z119. In embodiments, the compound is Z120. In embodiments, the compound is Z121. In embodiments, the compound is Z122. In embodiments, the compound is Z123. In embodiments, the compound is Z124. In embodiments, the compound is Z125. In embodiments, the compound is Z126. In embodiments, the compound is Z127. In embodiments, the compound is Z128. In embodiments, the compound is Z129. In embodiments, the compound is Z130. In embodiments, the compound is Z131. In embodiments, the compound is Z132. In embodiments, the compound is Z133. In embodiments, the compound is Z134. In embodiments, the compound is Z135. In embodiments, the compound is Z136. In embodiments, the compound is Z137. In embodiments, the compound is Z138. In embodiments, the compound is Z139. In embodiments, the compound is Z140. In embodiments, the compound is Z141. In embodiments, the compound is Z142. In embodiments, the compound is Z143. In embodiments, the compound is Z144. In embodiments, the compound is Z145. In embodiments, the compound is Z146. In embodiments, the compound is Z147. In embodiments, the compound is Z148. In embodiments, the compound is Z149. In embodiments, the compound is Z150. In embodiments, the compound is Z151. In embodiments, the compound is Z152. In embodiments, the compound is Z153. In embodiments, the compound is Z154. In embodiments, the compound is Z155. In embodiments, the compound is Z156. In embodiments, the compound is Z157. In embodiments, the compound is Z158. In embodiments, the compound is Z159. In embodiments, the compound is Z160. In embodiments, the compound is Z161. In embodiments, the compound is Z162. In embodiments, the compound is Z163. In embodiments, the compound is Z164. In embodiments, the compound is Z165. In embodiments, the compound is Z166. In embodiments, the compound is Z167. In embodiments, the compound is Z168. In embodiments, the compound is Z169. In embodiments, the compound is Z170. In embodiments, the compound is Z171. In embodiments, the compound is Z172. In embodiments, the compound is Z173. In embodiments, the compound is Z174. In embodiments, the compound is Z175. In embodiments, the compound is Z176. In embodiments, the compound is Z177. In embodiments, the compound is Z178. In embodiments, the compound is Z179. In embodiments, the compound is Z180. In embodiments, the compound is Z181. In embodiments, the compound is Z182. In embodiments, the compound is Z183. In embodiments, the compound is Z184. In embodiments, the compound is Z185. In embodiments, the compound is Z186. In embodiments, the compound is Z187. In embodiments, the compound is Z188. In embodiments, the compound is Z189. In embodiments, the compound is Z190. In embodiments, the compound is Z191. In embodiments, the compound is Z192. In embodiments, the compound is Z193. In embodiments, the compound is Z194. In embodiments, the compound is Z195. In embodiments, the compound is Z196. In embodiments, the compound is Z197. In embodiments, the compound is Z198. In embodiments, the compound is Z199. In embodiments, the compound is Z200. In embodiments, the compound is Z201. In embodiments, the compound is Z202. In embodiments, the compound is Z203. In embodiments, the compound is Z204. In embodiments, the compound is Z205. In embodiments, the compound is Z206. In embodiments, the compound is Z207. In embodiments, the compound is Z208. In embodiments, the compound is Z209. In embodiments, the compound is Z210. In embodiments, the compound is Z211. In embodiments, the compound is Z212. In embodiments, the compound is Z213. In embodiments, the compound is Z214. In embodiments, the compound is Z215. In embodiments, the compound is Z216. In embodiments, the compound is Z217. In embodiments, the compound is Z218. In embodiments, the compound is Z219. In embodiments, the compound is Z220. In embodiments, the compound is Z221. In embodiments, the compound is Z222. In embodiments, the compound is Z223. In embodiments, the compound is Z224. In embodiments, the compound is Z225. In embodiments, the compound is Z226. In embodiments, the compound is Z227. In embodiments, the compound is Z228. In embodiments, the compound is Z229. In embodiments, the compound is Z230. In embodiments, the compound is Z231. In embodiments, the compound is Z232. In embodiments, the compound is Z233. In embodiments, the compound is Z234. In embodiments, the compound is Z235. In embodiments, the compound is Z236. In embodiments, the compound is Z237. In embodiments, the compound is Z238. In embodiments, the compound is Z239. In embodiments, the compound is Z240. In embodiments, the compound is Z241. In embodiments, the compound is Z242. In embodiments, the compound is Z243. In embodiments, the compound is Z244. In embodiments, the compound is Z245. In embodiments, the compound is Z246. In embodiments, the compound is Z247. In embodiments, the compound is Z248. In embodiments, the compound is Z249. In embodiments, the compound is Z250. In embodiments, the compound is Z251. In embodiments, the compound is Z252. In embodiments, the compound is Z253. In embodiments, the compound is Z254. In embodiments, the compound is Z255. In embodiments, the compound is Z256. In embodiments, the compound is Z257. In embodiments, the compound is Z258. In embodiments, the compound is Z259. In embodiments, the compound is Z260. In embodiments, the compound is Z261. In embodiments, the compound is Z262. In embodiments, the compound is Z263. In embodiments, the compound is Z264. In embodiments, the compound is Z265. In embodiments, the compound is Z266. In embodiments, the compound is Z267. In embodiments, the compound is Z268. In embodiments, the compound is Z269. In embodiments, the compound is Z270. In embodiments, the compound is Z271. In embodiments, the compound is Z272. In embodiments, the compound is Z273. In embodiments, the compound is Z274. In embodiments, the compound is Z275. In embodiments, the compound is Z276. In embodiments, the compound is Z277. In embodiments, the compound is Z278. In embodiments, the compound is Z279. In embodiments, the compound is Z280. In embodiments, the compound is Z281. In embodiments, the compound is Z282. In embodiments, the compound is Z283. In embodiments, the compound is Z284. In embodiments, the compound is Z285. In embodiments, the compound is Z286. In embodiments, the compound is Z287. In embodiments, the compound is Z288. In embodiments, the compound is Z289. In embodiments, the compound is Z290. In embodiments, the compound is Z291. In embodiments, the compound is Z292. In embodiments, the compound is Z293. In embodiments, the compound is Z294. In embodiments, the compound is Z295. In embodiments, the compound is Z296. In embodiments, the compound is Z297. In embodiments, the compound is Z298. In embodiments, the compound is Z299. In embodiments, the compound is Z300. In embodiments, the compound is Z301. In embodiments, the compound is Z302. In embodiments, the compound is Z303. In embodiments, the compound is Z304. In embodiments, the compound is Z305. In embodiments, the compound is Z306. In embodiments, the compound is Z307. In embodiments, the compound is Z308. In embodiments, the compound is Z309. In embodiments, the compound is Z310. In embodiments, the compound is Z311. In embodiments, the compound is Z312. In embodiments, the compound is Z313. In embodiments, the compound is Z314. In embodiments, the compound is Z315. In embodiments, the compound is Z316. In embodiments, the compound is Z317. In embodiments, the compound is Z318. In embodiments, the compound is Z319. In embodiments, the compound is Z320. In embodiments, the compound is Z321. In embodiments, the compound is Z322. In embodiments, the compound is Z323. In embodiments, the compound is Z324. In embodiments, the compound is Z325. In embodiments, the compound is Z326. In embodiments, the compound is Z327. In embodiments, the compound is Z328. In embodiments, the compound is Z329. In embodiments, the compound is Z330. In embodiments, the compound is Z331. In embodiments, the compound is Z332. In embodiments, the compound is Z333. In embodiments, the compound is Z334. In embodiments, the compound is Z335. In embodiments, the compound is Z336. In embodiments, the compound is Z337. In embodiments, the compound is Z338. In embodiments, the compound is Z339. In embodiments, the compound is Z340. In embodiments, the compound is Z341. In embodiments, the compound is Z342. In embodiments, the compound is Z343. In embodiments, the compound is Z344. In embodiments, the compound is Z345. In embodiments, the compound is Z346. In embodiments, the compound is Z347. In embodiments, the compound is Z348. In embodiments, the compound is Z349. In embodiments, the compound is Z350. In embodiments, the compound is Z351. In embodiments, the compound is Z352. In embodiments, the compound is Z353. In embodiments, the compound is Z354. In embodiments, the compound is Z355. In embodiments, the compound is Z356. In embodiments, the compound is Z357. In embodiments, the compound is Z358. In embodiments, the compound is Z359. In embodiments, the compound is Z360. In embodiments, the compound is Z361. In embodiments, the compound is Z362. In embodiments, the compound is Z363. In embodiments, the compound is Z364. In embodiments, the compound is Z365. In embodiments, the compound is Z366. In embodiments, the compound is Z367. In embodiments, the compound is Z368. In embodiments, the compound is Z369. In embodiments, the compound is Z370. In embodiments, the compound is Z371. In embodiments, the compound is Z372. In embodiments, the compound is Z373. In embodiments, the compound is Z374. In embodiments, the compound is Z375. In embodiments, the compound is Z376. In embodiments, the compound is Z377. In embodiments, the compound is Z378. In embodiments, the compound is Z379. In embodiments, the compound is Z380. In embodiments, the compound is Z381. In embodiments, the compound is Z382. In embodiments, the compound is Z383. In embodiments, the compound is Z384. In embodiments, the compound is Z385. In embodiments, the compound is Z386. In embodiments, the compound is Z387. In embodiments, the compound is Z388. In embodiments, the compound is Z389. In embodiments, the compound is Z390. In embodiments, the compound is Z391. In embodiments, the compound is Z392. In embodiments, the compound is Z393. In embodiments, the compound is Z394. In embodiments, the compound is Z395. In embodiments, the compound is Z396. In embodiments, the compound is Z397. In embodiments, the compound is Z398. In embodiments, the compound is Z399. In embodiments, the compound is Z400. In embodiments, the compound is Z401. In embodiments, the compound is Z402. In embodiments, the compound is Z403. In embodiments, the compound is Z404. In embodiments, the compound is Z405. In embodiments, the compound is Z406. In embodiments, the compound is Z407. In embodiments, the compound is Z408. In embodiments, the compound is Z409. In embodiments, the compound is Z410. In embodiments, the compound is Z411. In embodiments, the compound is Z412. In embodiments, the compound is Z413. In embodiments, the compound is Z414. In embodiments, the compound is Z415. In embodiments, the compound is Z416. In embodiments, the compound is Z417. In embodiments, the compound is Z418. In embodiments, the compound is Z419. In embodiments, the compound is Z420. In embodiments, the compound is Z421. In embodiments, the compound is Z422. In embodiments, the compound is Z423. In embodiments, the compound is Z424. In embodiments, the compound is Z425. In embodiments, the compound is Z426. In embodiments, the compound is Z427. In embodiments, the compound is Z428. In embodiments, the compound is Z429. In embodiments, the compound is Z430. In embodiments, the compound is Z431. In embodiments, the compound is Z432. In embodiments, the compound is Z433. In embodiments, the compound is Z434. In embodiments, the compound is Z435. In embodiments, the compound is Z436. In embodiments, the compound is Z437. In embodiments, the compound is Z438. In embodiments, the compound is Z439. In embodiments, the compound is Z440. In embodiments, the compound is Z441. In embodiments, the compound is Z442. In embodiments, the compound is Z443. In embodiments, the compound is Z444. In embodiments, the compound is Z445. In embodiments, the compound is Z446. In embodiments, the compound is Z447. In embodiments, the compound is Z448. In embodiments, the compound is Z449. In embodiments, the compound is Z450. In embodiments, the compound is Z451. In embodiments, the compound is Z452. In embodiments, the compound is Z453. In embodiments, the compound is Z454. In embodiments, the compound is Z455. In embodiments, the compound is Z456. In embodiments, the compound is Z457. In embodiments, the compound is Z458. In embodiments, the compound is Z459. In embodiments, the compound is Z460. In embodiments, the compound is Z461. In embodiments, the compound is Z462. In embodiments, the compound is Z463. In embodiments, the compound is Z464. In embodiments, the compound is Z465. In embodiments, the compound is Z466. In embodiments, the compound is Z467. In embodiments, the compound is Z468. In embodiments, the compound is Z469. In embodiments, the compound is Z470. In embodiments, the compound is Z471. In embodiments, the compound is Z472. In embodiments, the compound is Z473. In embodiments, the compound is Z474. In embodiments, the compound is Z475. In embodiments, the compound is Z476. In embodiments, the compound is Z477. In embodiments, the compound is Z478. In embodiments, the compound is Z479. In embodiments, the compound is Z480. In embodiments, the compound is Z481. In embodiments, the compound is Z482. In embodiments, the compound is Z483. In embodiments, the compound is Z484. In embodiments, the compound is Z485. In embodiments, the compound is Z486. In embodiments, the compound is Z487. In embodiments, the compound is Z488. In embodiments, the compound is Z489. In embodiments, the compound is Z490. In embodiments, the compound is Z491. In embodiments, the compound is Z492. In embodiments, the compound is Z493. In embodiments, the compound is Z494. In embodiments, the compound is Z495. In embodiments, the compound is Z496. In embodiments, the compound is Z497. In embodiments, the compound is Z498. In embodiments, the compound is Z499. In embodiments, the compound is Z500. In embodiments, the compound is Z501. In embodiments, the compound is Z502. In embodiments, the compound is Z503. In embodiments, the compound is Z504. In embodiments, the compound is Z505. In embodiments, the compound is Z506. In embodiments, the compound is Z507. In embodiments, the compound is Z508. In embodiments, the compound is Z509. In embodiments, the compound is Z510. In embodiments, the compound is Z511. In embodiments, the compound is Z512. In embodiments, the compound is Z513. In embodiments, the compound is Z514. In embodiments, the compound is Z515. In embodiments, the compound is Z516. In embodiments, the compound is Z517. In embodiments, the compound is Z518. In embodiments, the compound is Z519. In embodiments, the compound is Z520. In embodiments, the compound is Z521. In embodiments, the compound is Z522. In embodiments, the compound is Z523. In embodiments, the compound is Z524. In embodiments, the compound is Z525. In embodiments, the compound is Z526. In embodiments, the compound is Z527. In embodiments, the compound is Z528. In embodiments, the compound is Z529. In embodiments, the compound is Z530. In embodiments, the compound is Z531. In embodiments, the compound is Z532. In embodiments, the compound is Z533. In embodiments, the compound is Z534. In embodiments, the compound is Z535. In embodiments, the compound is Z536. In embodiments, the compound is Z537. In embodiments, the compound is Z538. In embodiments, the compound is Z539. In embodiments, the compound is Z540. In embodiments, the compound is Z541. In embodiments, the compound is Z542. In embodiments, the compound is Z543. In embodiments, the compound is Z544. In embodiments, the compound is Z545. In embodiments, the compound is Z546. In embodiments, the compound is Z547. In embodiments, the compound is Z548. In embodiments, the compound is Z549. In embodiments, the compound is Z550. In embodiments, the compound is Z551. In embodiments, the compound is Z552. In embodiments, the compound is Z553. In embodiments, the compound is Z554. In embodiments, the compound is Z555. In embodiments, the compound is Z556. In embodiments, the compound is Z557. In embodiments, the compound is Z558. In embodiments, the compound is Z559. In embodiments, the compound is Z560. In embodiments, the compound is Z561. In embodiments, the compound is Z562. In embodiments, the compound is Z563. In embodiments, the compound is Z564. In embodiments, the compound is Z565. In embodiments, the compound is Z566. In embodiments, the compound is Z567. In embodiments, the compound is Z568. In embodiments, the compound is Z569. In embodiments, the compound is Z570. In embodiments, the compound is Z571. In embodiments, the compound is Z572. In embodiments, the compound is Z573. In embodiments, the compound is Z574. In embodiments, the compound is Z575. In embodiments, the compound is Z576. In embodiments, the compound is Z577. In embodiments, the compound is Z578. In embodiments, the compound is Z579. In embodiments, the compound is Z580. In embodiments, the compound is Z581. In embodiments, the compound is Z582. In embodiments, the compound is Z583. In embodiments, the compound is Z584. In embodiments, the compound is Z585. In embodiments, the compound is Z586. In embodiments, the compound is Z587. In embodiments, the compound is Z588. In embodiments, the compound is Z589. In embodiments, the compound is Z590. In embodiments, the compound is Z591. In embodiments, the compound is Z592. In embodiments, the compound is Z593. In embodiments, the compound is Z594. In embodiments, the compound is Z595. In embodiments, the compound is Z596. In embodiments, the compound is Z597. In embodiments, the compound is Z598. In embodiments, the compound is Z599. In embodiments, the compound is Z600. In embodiments, the compound is Z601. In embodiments, the compound is Z602. In embodiments, the compound is Z603. In embodiments, the compound is Z604. In embodiments, the compound is Z605. In embodiments, the compound is Z606. In embodiments, the compound is Z607. In embodiments, the compound is Z608. In embodiments, the compound is Z609. In embodiments, the compound is Z610. In embodiments, the compound is Z611. In embodiments, the compound is Z612. In embodiments, the compound is Z613. In embodiments, the compound is Z614. In embodiments, the compound is Z615. In embodiments, the compound is Z616. In embodiments, the compound is Z617. In embodiments, the compound is Z618. In embodiments, the compound is Z619. In embodiments, the compound is Z620. In embodiments, the compound is Z621. In embodiments, the compound is Z622. In embodiments, the compound is Z623. In embodiments, the compound is Z624. In embodiments, the compound is Z625. In embodiments, the compound is Z626. In embodiments, the compound is Z627. In embodiments, the compound is Z628. In embodiments, the compound is Z629. In embodiments, the compound is Z630. In embodiments, the compound is Z631. In embodiments, the compound is Z632. In embodiments, the compound is Z633. In embodiments, the compound is Z634. In embodiments, the compound is Z635. In embodiments, the compound is Z636. In embodiments, the compound is Z637. In embodiments, the compound is Z638. In embodiments, the compound is Z639. In embodiments, the compound is Z640. In embodiments, the compound is Z641. In embodiments, the compound is Z642. In embodiments, the compound is Z643. In embodiments, the compound is Z644. In embodiments, the compound is Z645. In embodiments, the compound is Z646. In embodiments, the compound is Z647.

In embodiments, the compound is not:

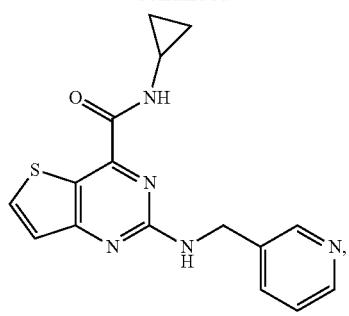

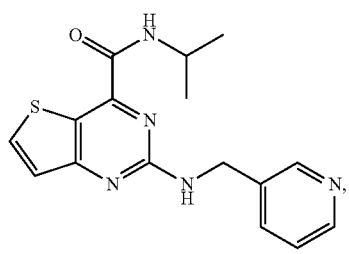

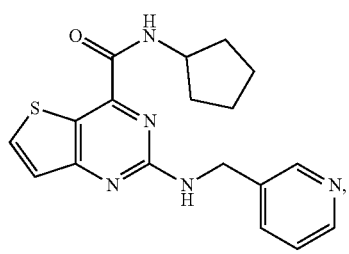

-continued

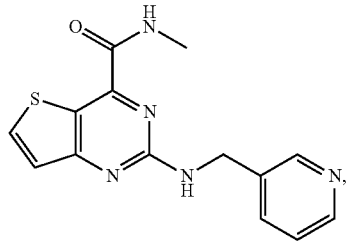

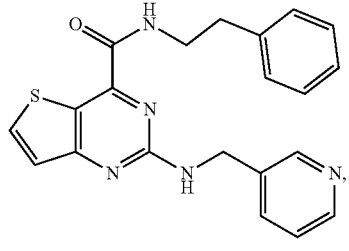

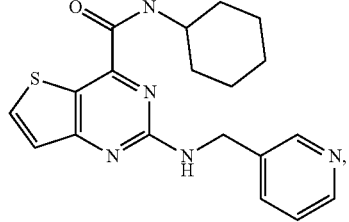

313
-continued
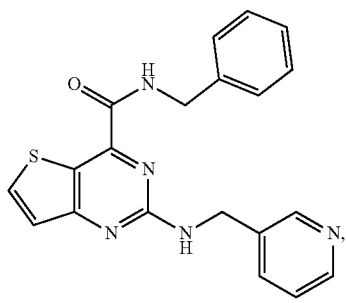
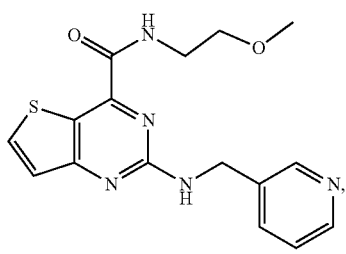
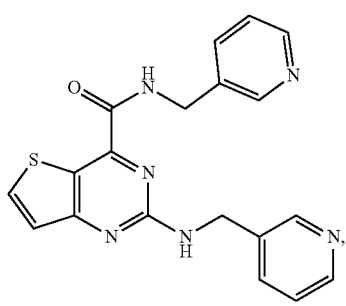
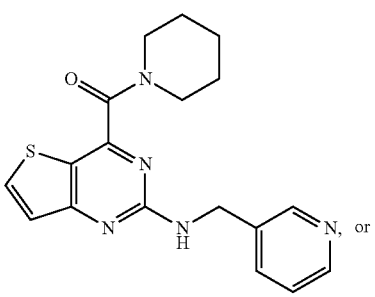, or
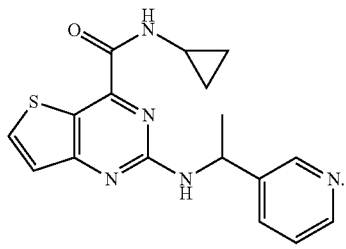
314
In embodiments, the compound is not
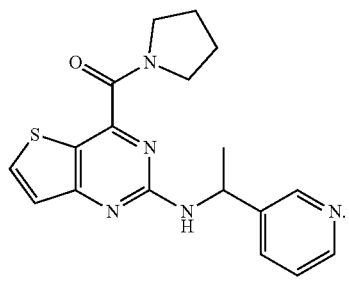 [SMILES: CC(Nc1nc(C(=O)N2CCCC2)c2sccc2n1)c1cccnc1]
In embodiments, the compound is not
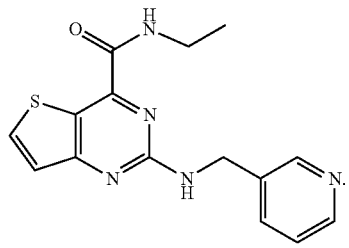 [SMILES: CCNC(=O)c1nc(NCc2cccnc2)nc2ccsc12]
In embodiments, the compound is not
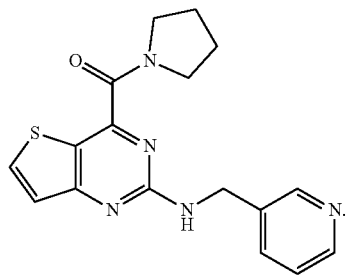 [SMILES: O=C(c1nc(NCc2cccnc2)nc2ccsc12)N1CCCC1]
In embodiments, the compound is not
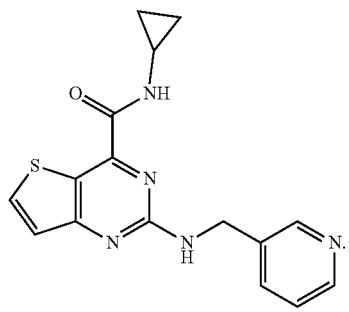 [SMILES: O=C(NC1CC1)c1nc(NCc2cccnc2)nc2ccsc12]

In embodiments, the compound is not
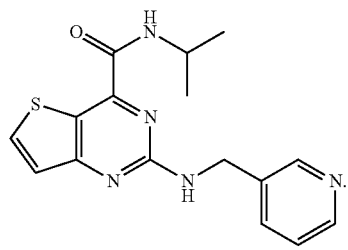 [SMILES: CC(C)NC(=O)c1nc(NCc2cccnc2)nc2ccsc12]
In embodiments, the compound is not
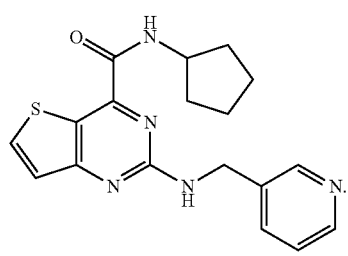 [SMILES: O=C(NC1CCCC1)c1nc(NCc2cccnc2)nc2ccsc12]
In embodiments, the compound is not
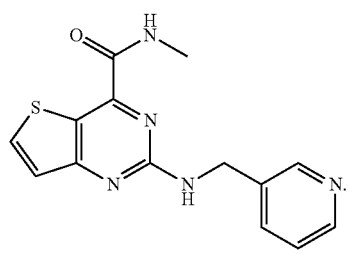 [SMILES: CNC(=O)c1nc(NCc2cccnc2)nc2ccsc12]
In embodiments, the compound is not
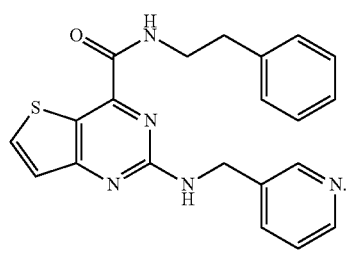 [SMILES: O=C(NCCc1ccccc1)c1nc(NCc2cccnc2)nc2ccsc12]
In embodiments, the compound is not
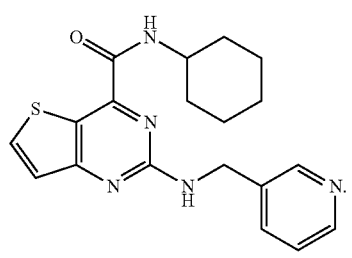 [SMILES: O=C(NC1CCCCC1)c1nc(NCc2cccnc2)nc2ccsc12]
In embodiments, the compound is not
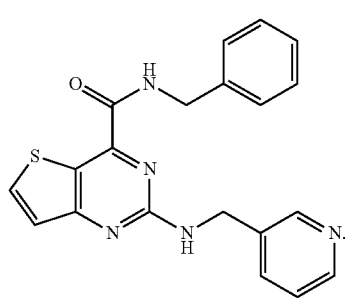
In embodiments, the compound is not
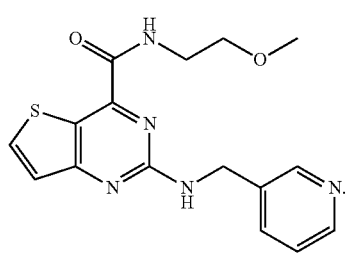 [SMILES: COCCNC(=O)c1nc(NCc2cccnc2)nc2ccsc12]
In embodiments, the compound is not
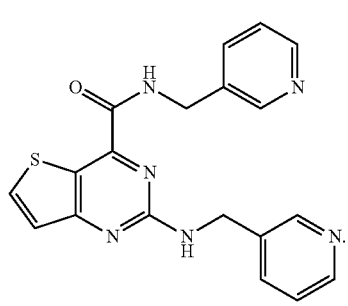 [SMILES: O=C(NCc1cccnc1)c1nc(NCc2cccnc2)nc2ccsc12]
In embodiments, the compound is not
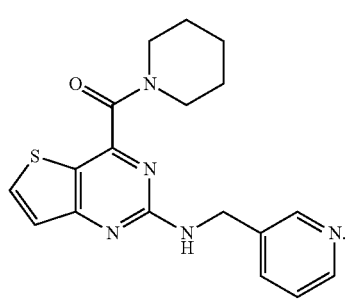 [SMILES: O=C(c1nc(NCc2cccnc2)nc2ccsc12)N1CCCCC1]

In embodiments, the compound is not

[Chemical structure: N-cyclopropyl thieno[3,2-d]pyrimidine-4-carboxamide with 2-(1-(pyridin-3-yl)ethylamino) substituent]

In embodiments, when $R^2$ and $R^3$ form an unsubstituted heterocycloalkyl and z1 is 0, $R^4$ is not hydrogen. In embodiments, when $R^2$ or $R^3$ is hydrogen and $L^1$ is unsubstituted methylene, $R^4$ is not hydrogen. In embodiments, when $R^2$ is hydrogen, $R^3$ is not unsubstituted cyclopropyl.

In embodiments, when $R^2$ and $R^3$ form an unsubstituted heterocycloalkyl (e.g., 3 to 8 membered heterocycloalkyl, 3 to 6 membered heterocycloalkyl, or 5 to 6 membered heterocycloalkyl) and z1 is 0, $R^4$ is not hydrogen. In embodiments, when $R^2$ and $R^3$ form an unsubstituted 3 to 8 membered heterocycloalkyl and z1 is 0, $R^4$ is not hydrogen. In embodiments, when $R^2$ and $R^3$ form an unsubstituted 5 to 6 membered heterocycloalkyl and z1 is 0, $R^4$ is not hydrogen. In embodiments, when $R^2$ and $R^3$ form an unsubstituted 5 membered heterocycloalkyl and z1 is 0, $R^4$ is not hydrogen. In embodiments, when $R^2$ and $R^3$ form an unsubstituted 6 membered heterocycloalkyl and z1 is 0, $R^4$ is not hydrogen. In embodiments, $R^2$ and $R^3$ do not form an unsubstituted 6 membered heterocycloalkyl. In embodiments, $R^2$ and $R^3$ do not form an unsubstituted 5 membered heterocycloalkyl.

In embodiments, when $R^2$ and $R^3$ form a substituted or unsubstituted heterocycloalkyl (e.g., 3 to 8 membered heterocycloalkyl, 3 to 6 membered heterocycloalkyl, or 5 to 6 membered heterocycloalkyl) and z1 is 0, $R^4$ is not hydrogen. In embodiments, when $R^2$ and $R^3$ form a substituted or unsubstituted 3 to 8 membered heterocycloalkyl and z1 is 0, $R^4$ is not hydrogen. In embodiments, when $R^2$ and $R^3$ form a substituted or unsubstituted 5 to 6 membered heterocycloalkyl and z1 is 0, $R^4$ is not hydrogen. In embodiments, when $R^2$ and $R^3$ form a substituted or unsubstituted 5 membered heterocycloalkyl and z1 is 0, $R^4$ is not hydrogen. In embodiments, when $R^2$ and $R^3$ form a substituted or unsubstituted 6 membered heterocycloalkyl and z1 is 0, $R^4$ is not hydrogen. In embodiments, $R^2$ and $R^3$ do not form a substituted or unsubstituted 6 membered heterocycloalkyl. In embodiments, $R^2$ and $R^3$ do not form a substituted or unsubstituted 5 membered heterocycloalkyl.

In embodiments, when $R^2$ or $R^3$ is hydrogen and $L^1$ is unsubstituted alkylene (e.g., $C_1$-$C_8$ alkylene, $C_1$-$C_6$ alkylene, or $C_1$-$C_4$ alkylene), $R^4$ is not hydrogen. In embodiments, when $R^2$ or $R^3$ is hydrogen and $L^1$ is unsubstituted $C_1$-$C_8$ alkylene, $R^4$ is not hydrogen. In embodiments, when $R^2$ or $R^3$ is hydrogen and $L^1$ is unsubstituted $C_1$-$C_6$ alkylene, $R^4$ is not hydrogen. In embodiments, when $R^2$ or $R^3$ is hydrogen and $L^1$ is unsubstituted $C_1$-$C_4$ alkylene, $R^4$ is not hydrogen. In embodiments, when $R^2$ or $R^3$ is hydrogen and $L^1$ is unsubstituted $C_1$-$C_2$ alkylene, $R^4$ is not hydrogen. In embodiments, when $R^2$ or $R^3$ is hydrogen, $L^1$ is not unsubstituted $C_1$-$C_2$ alkylene. In embodiments, when $R^2$ or $R^3$ is hydrogen, $L^1$ is not an unsubstituted $C_1$-$C_4$ alkylene.

In embodiments, when $R^2$ or $R^3$ is hydrogen and $L^1$ is substituted or unsubstituted alkylene (e.g., $C_1$-$C_8$ alkylene, $C_1$-$C_6$ alkylene, or $C_1$-$C_4$ alkylene), $R^4$ is not hydrogen. In embodiments, when $R^2$ or $R^3$ is hydrogen and $L^1$ is substituted or unsubstituted $C_1$-$C_8$ alkylene, $R^4$ is not hydrogen. In embodiments, when $R^2$ or $R^3$ is hydrogen and $L^1$ is substituted or unsubstituted $C_1$-$C_6$ alkylene, $R^4$ is not hydrogen. In embodiments, when $R^2$ or $R^3$ is hydrogen and $L^1$ is substituted or unsubstituted $C_1$-$C_4$ alkylene, $R^4$ is not hydrogen. In embodiments, when $R^2$ or $R^3$ is hydrogen and $L^1$ is substituted or unsubstituted $C_1$-$C_2$ alkylene, $R^4$ is not hydrogen. In embodiments, when $R^2$ or $R^3$ is hydrogen, $L^1$ is not substituted or unsubstituted $C_1$-$C_2$ alkylene. In embodiments, when $R^2$ or $R^3$ is hydrogen, $L^1$ is not an substituted or unsubstituted $C_1$-$C_4$ alkylene.

In embodiments, when $R^2$ is hydrogen, $R^3$ is not unsubstituted cyclopropyl. In embodiments, when $R^2$ is hydrogen, $R^3$ is not unsubstituted cycloalkyl (e.g., $C_3$-$C_8$ cycloalkyl, $C_3$-$C_6$ cycloalkyl, or $C_5$-$C_6$ cycloalkyl). In embodiments, when $R^2$ is hydrogen, $R^3$ is not unsubstituted $C_3$-$C_8$ cycloalkyl. In embodiments, when $R^2$ is hydrogen, $R^3$ is not unsubstituted $C_3$-$C_6$ cycloalkyl. In embodiments, when $R^2$ is hydrogen, $R^3$ is not unsubstituted $C_5$-$C_6$ cycloalkyl.

In embodiments, when $R^2$ is hydrogen, $R^3$ is not substituted or unsubstituted cyclopropyl. In embodiments, when $R^2$ is hydrogen, $R^3$ is not substituted or unsubstituted cycloalkyl (e.g., $C_3$-$C_8$ cycloalkyl, $C_3$-$C_6$ cycloalkyl, or $C_5$-$C_6$ cycloalkyl). In embodiments, when $R^2$ is hydrogen, $R^3$ is not substituted or unsubstituted $C_3$-$C_8$ cycloalkyl. In embodiments, when $R^2$ is hydrogen, $R^3$ is not substituted or unsubstituted $C_3$-$C_6$ cycloalkyl. In embodiments, when $R^2$ is hydrogen, $R^3$ is not substituted or unsubstituted $C_5$-$C_6$ cycloalkyl.

In embodiments, $R^4$ is not hydrogen. In embodiments, $R^2$ or $R^3$ are not hydrogen. In embodiments, $L^1$ is not unsubstituted methylene. In embodiments, $R^3$ is not unsubstituted cyclopropyl.

In embodiments, when $R^2$ and $R^3$ form an unsubstituted heterocycloalkyl (e.g., 3 to 8 membered heterocycloalkyl, 3 to 6 membered heterocycloalkyl, or 5 to 6 membered heterocycloalkyl), $R^4$ is not hydrogen. In embodiments, when $R^2$ and $R^3$ form an unsubstituted 3 to 8 membered heterocycloalkyl, $R^4$ is not hydrogen. In embodiments, when $R^2$ and $R^3$ form an unsubstituted 5 to 6 membered heterocycloalkyl, $R^4$ is not hydrogen. In embodiments, when $R^2$ and $R^3$ form an unsubstituted 5 membered heterocycloalkyl, $R^4$ is not hydrogen. In embodiments, when $R^2$ and $R^3$ form an unsubstituted 6 membered heterocycloalkyl, $R^4$ is not hydrogen. In embodiments, $R^2$ and $R^3$ do not form an unsubstituted 6 membered heterocycloalkyl. In embodiments, $R^2$ and $R^3$ do not form an unsubstituted 5 membered heterocycloalkyl.

In embodiments, when $L^1$ is unsubstituted alkylene (e.g., $C_1$-$C_8$ alkylene, $C_1$-$C_6$ alkylene, or $C_1$-$C_4$ alkylene), $R^4$ is not hydrogen. In embodiments, when $L^1$ is unsubstituted $C_1$-$C_8$ alkylene, $R^4$ is not hydrogen. In embodiments, when $L^1$ is unsubstituted $C_1$-$C_6$ alkylene, $R^4$ is not hydrogen. In embodiments, when $L^1$ is unsubstituted $C_1$-$C_4$ alkylene, $R^4$ is not hydrogen. In embodiments, when $L^1$ is unsubstituted $C_1$-$C_2$ alkylene, $R^4$ is not hydrogen. In embodiments, $L^1$ is not unsubstituted $C_1$-$C_2$ alkylene. In embodiments, $L^1$ is not an unsubstituted $C_1$-$C_4$ alkylene.

In embodiments, $R^3$ is not unsubstituted cyclopropyl. In embodiments, $R^3$ is not unsubstituted cycloalkyl (e.g., $C_3$-$C_8$ cycloalkyl, $C_3$-$C_6$ cycloalkyl, or $C_5$-$C_6$ cycloalkyl). In embodiments, $R^3$ is not unsubstituted $C_3$-$C_8$ cycloalkyl. In embodiments, $R^3$ is not unsubstituted $C_3$-$C_6$ cycloalkyl. In embodiments, $R^3$ is not unsubstituted $C_5$-$C_6$ cycloalkyl. In embodiments, $R^2$ is not unsubstituted cyclopropyl. In embodiments, $R^2$ is not unsubstituted cycloalkyl (e.g., $C_3$-$C_8$ cycloalkyl, $C_3$-$C_6$ cycloalkyl, or $C_5$-$C_6$ cycloalkyl). In embodiments, $R^2$ is not unsubstituted $C_3$-$C_8$ cycloalkyl. In embodiments, $R^2$ is not unsubstituted $C_3$-$C_6$ cycloalkyl. In embodiments, $R^2$ is not unsubstituted $C_5$-$C_6$ cycloalkyl.

In embodiments, $R^3$ is not substituted or unsubstituted cyclopropyl. In embodiments, $R^3$ is not substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^3$ is not substituted or unsubstituted $C_3$-$C_8$ cycloalkyl. In embodiments, $R^3$ is not substituted or unsubstituted $C_3$-$C_6$ cycloalkyl. In embodiments, $R^3$ is not substituted or unsubstituted $C_5$-$C_6$ cycloalkyl.

In embodiments, the compound is not Z1. In embodiments, the compound is not Z2. In embodiments, the compound is not Z3. In embodiments, the compound is not Z4. In embodiments, the compound is not Z5. In embodiments, the compound is not Z6. In embodiments, the compound is not Z7. In embodiments, the compound is not Z8. In embodiments, the compound is not Z9. In embodiments, the compound is not Z10. In embodiments, the compound is not Z11. In embodiments, the compound is not Z12. In embodiments, the compound is not Z13. In embodiments, the compound is not Z14. In embodiments, the compound is not Z15. In embodiments, the compound is not Z16. In embodiments, the compound is not Z17. In embodiments, the compound is not Z18. In embodiments, the compound is not Z19. In embodiments, the compound is not Z20. In embodiments, the compound is not Z21. In embodiments, the compound is not Z22. In embodiments, the compound is not Z23. In embodiments, the compound is not Z24. In embodiments, the compound is not Z25. In embodiments, the compound is not Z26. In embodiments, the compound is not Z27. In embodiments, the compound is not Z28. In embodiments, the compound is not Z29. In embodiments, the compound is not Z30. In embodiments, the compound is not Z31. In embodiments, the compound is not Z32. In embodiments, the compound is not Z33. In embodiments, the compound is not Z34. In embodiments, the compound is not Z35. In embodiments, the compound is not Z36. In embodiments, the compound is not Z37. In embodiments, the compound is not Z38. In embodiments, the compound is not Z39. In embodiments, the compound is not Z40. In embodiments, the compound is not Z41. In embodiments, the compound is not Z42. In embodiments, the compound is not Z43. In embodiments, the compound is not Z44. In embodiments, the compound is not Z45. In embodiments, the compound is not Z46. In embodiments, the compound is not Z47. In embodiments, the compound is not Z48. In embodiments, the compound is not Z49. In embodiments, the compound is not Z50. In embodiments, the compound is not Z51. In embodiments, the compound is not Z52. In embodiments, the compound is not Z53. In embodiments, the compound is not Z54. In embodiments, the compound is not Z55. In embodiments, the compound is not Z56. In embodiments, the compound is not Z57. In embodiments, the compound is not Z58. In embodiments, the compound is not Z59. In embodiments, the compound is not Z60. In embodiments, the compound is not Z61. In embodiments, the compound is not Z62. In embodiments, the compound is not Z63. In embodiments, the compound is not Z64. In embodiments, the compound is not Z65. In embodiments, the compound is not Z66. In embodiments, the compound is not Z67. In embodiments, the compound is not Z68. In embodiments, the compound is not Z69. In embodiments, the compound is not Z70. In embodiments, the compound is not Z71. In embodiments, the compound is not Z72. In embodiments, the compound is not Z73. In embodiments, the compound is not Z74. In embodiments, the compound is not Z75. In embodiments, the compound is not Z76. In embodiments, the compound is not Z77. In embodiments, the compound is not Z78. In embodiments, the compound is not Z79. In embodiments, the compound is not Z80. In embodiments, the compound is not Z81. In embodiments, the compound is not Z82. In embodiments, the compound is not Z83. In embodiments, the compound is not Z84. In embodiments, the compound is not Z85. In embodiments, the compound is not Z86. In embodiments, the compound is not Z87. In embodiments, the compound is not Z88. In embodiments, the compound is not Z89. In embodiments, the compound is not Z90. In embodiments, the compound is not Z91. In embodiments, the compound is not Z92. In embodiments, the compound is not Z93. In embodiments, the compound is not Z94. In embodiments, the compound is not Z95. In embodiments, the compound is not Z96. In embodiments, the compound is not Z97. In embodiments, the compound is not Z98. In embodiments, the compound is not Z99. In embodiments, the compound is not Z100. In embodiments, the compound is not Z101. In embodiments, the compound is not Z102. In embodiments, the compound is not Z103. In embodiments, the compound is not Z104. In embodiments, the compound is not Z105. In embodiments, the compound is not Z106. In embodiments, the compound is not Z107. In embodiments, the compound is not Z108. In embodiments, the compound is not Z109. In embodiments, the compound is not Z110. In embodiments, the compound is not Z111. In embodiments, the compound is not Z112. In embodiments, the compound is not Z113. In embodiments, the compound is not Z114. In embodiments, the compound is not Z115. In embodiments, the compound is not Z116. In embodiments, the compound is not Z117. In embodiments, the compound is not Z118. In embodiments, the compound is not Z119. In embodiments, the compound is not Z120. In embodiments, the compound is not Z121. In embodiments, the compound is not Z122. In embodiments, the compound is not Z123. In embodiments, the compound is not Z124. In embodiments, the compound is not Z125. In embodiments, the compound is not Z126. In embodiments, the compound is not Z127. In embodiments, the compound is not Z128. In embodiments, the compound is not Z129. In embodiments, the compound is not Z130. In embodiments, the compound is not Z131. In embodiments, the compound is not Z132. In embodiments, the compound is not Z133. In embodiments, the compound is not Z134. In embodiments, the compound is not Z135. In embodiments, the compound is not Z136. In embodiments, the compound is not Z137. In embodiments, the compound is not Z138. In embodiments, the compound is not Z139. In embodiments, the compound is not Z140. In embodiments, the compound is not Z141. In embodiments, the compound is not Z142. In embodiments, the compound is not Z143. In embodiments, the compound is not Z144. In embodiments, the compound is not Z145. In embodiments, the compound is not Z146. In embodiments, the compound is not Z147. In embodiments, the compound is not Z148. In embodiments, the compound is not Z149. In embodiments, the compound is not Z150. In embodiments, the compound is not Z151. In embodiments, the compound is not Z152. In embodiments, the compound is not Z153. In embodiments, the compound is not Z154. In embodiments, the compound is not Z155. In embodiments, the compound is not Z156. In embodiments, the compound is not Z157. In embodiments, the compound is not Z158. In embodiments, the compound is not Z159. In embodiments, the compound is not Z160. In embodiments, the compound is not Z161. In embodiments, the compound is not Z162. In embodiments, the compound is not Z163. In embodiments, the compound is not Z164. In embodiments, the compound is not Z165. In embodiments, the compound is not Z166. In embodiments, the compound is not Z167. In embodiments, the compound is not Z168. In embodiments, the compound is not Z169. In embodiments, the compound is not Z170. In embodiments, the compound is not Z171. In embodiments, the compound is not Z172. In embodiments, the compound is not Z173. In embodiments, the compound is not Z174. In embodiments, the compound is not Z175. In embodiments, the compound is not Z176. In embodiments, the compound is not Z177. In embodiments, the compound is not Z178. In embodiments, the compound is not Z179. In embodiments, the compound is not Z180. In embodiments, the compound is not Z181. In embodiments, the compound is not Z182. In embodiments, the compound is not Z183. In embodiments, the compound is not Z184. In embodiments, the compound is not Z185. In embodiments, the compound is not Z186. In embodiments, the compound is not Z187. In embodiments, the compound is not Z188. In embodiments, the compound is not Z189. In embodiments, the compound is not Z190. In embodiments, the compound is not Z191. In embodiments, the compound is not Z192. In embodiments, the compound is not Z193. In embodiments, the compound is not Z194. In embodiments, the compound is not Z195. In embodiments, the compound is not Z196. In embodiments, the compound is not Z197. In embodiments, the compound is not Z198. In embodiments, the compound is not Z199. In embodiments, the compound is not Z200. In embodiments, the compound is not Z201. In embodiments, the compound is not Z202. In embodiments, the compound is not Z203. In embodiments, the compound is not Z204. In embodiments, the compound is not Z205. In embodiments, the compound is not Z206. In embodiments, the compound is not Z207. In embodiments, the compound is not Z208. In embodiments, the compound is not Z209. In embodiments, the compound is not Z210. In embodiments, the compound is not Z211. In embodiments, the compound is not Z212. In embodiments, the compound is not Z213. In embodiments, the compound is not Z214. In embodiments, the compound is not Z215. In embodiments, the compound is not Z216. In embodiments, the compound is not Z217. In embodiments, the compound is not Z218. In embodiments, the compound is not Z219. In embodiments, the compound is not Z220. In embodiments, the compound is not Z221. In embodiments, the compound is not Z222. In embodiments, the compound is not Z223. In embodiments, the compound is not Z224. In embodiments, the compound is not Z225. In embodiments, the compound is not Z226. In embodiments, the compound is not Z227. In embodiments, the compound is not Z228. In embodiments, the compound is not Z229. In embodiments, the compound is not Z230. In embodiments, the compound is not Z231. In embodiments, the compound is not Z232. In embodiments, the compound is not Z233. In embodiments, the compound is not Z234. In embodiments, the compound is not Z235. In embodiments, the compound is not Z236. In embodiments, the compound is not Z237. In embodiments, the compound is not Z238. In embodiments, the compound is not Z239. In embodiments, the compound is not Z240. In embodiments, the compound is not Z241. In embodiments, the compound is not Z242. In embodiments, the compound is not Z243. In embodiments, the compound is not Z244. In embodiments, the compound is not Z245. In embodiments, the compound is not Z246. In embodiments, the compound is not Z247. In embodiments, the compound is not Z248. In embodiments, the compound is not Z249. In embodiments, the compound is not Z250. In embodiments, the compound is not Z251. In embodiments, the compound is not Z252. In embodiments, the compound is not Z253. In embodiments, the compound is not Z254. In embodiments, the compound is not Z255. In embodiments, the compound is not Z256. In embodiments, the compound is not Z257. In embodiments, the compound is not Z258. In embodiments, the compound is not Z259. In embodiments, the compound is not Z260. In embodiments, the compound is not Z261. In embodiments, the compound is not Z262. In embodiments, the compound is not Z263. In embodiments, the compound is not Z264. In embodiments, the compound is not Z265. In embodiments, the compound is not Z266. In embodiments, the compound is not Z267. In embodiments, the compound is not Z268. In embodiments, the compound is not Z269. In embodiments, the compound is not Z270. In embodiments, the compound is not Z271. In embodiments, the compound is not Z272. In embodiments, the compound is not Z273. In embodiments, the compound is not Z274. In embodiments, the compound is not Z275. In embodiments, the compound is not Z276. In embodiments, the compound is not Z277. In embodiments, the compound is not Z278. In embodiments, the compound is not Z279. In embodiments, the compound is not Z280. In embodiments, the compound is not Z281. In embodiments, the compound is not Z282. In embodiments, the compound is not Z283. In embodiments, the compound is not Z284. In embodiments, the compound is not Z285. In embodiments, the compound is not Z286. In embodiments, the compound is not Z287. In embodiments, the compound is not Z288. In embodiments, the compound is not Z289. In embodiments, the compound is not Z290. In embodiments, the compound is not Z291. In embodiments, the compound is not Z292. In embodiments, the compound is not Z293. In embodiments, the compound is not Z294. In embodiments, the compound is not Z295. In embodiments, the compound is not Z296. In embodiments, the compound is not Z297. In embodiments, the compound is not Z298. In embodiments, the compound is not Z299. In embodiments, the compound is not Z300. In embodiments, the compound is not Z301. In embodiments, the compound is not Z302. In embodiments, the compound is not Z303. In embodiments, the compound is not Z304. In embodiments, the compound is not Z305. In embodiments, the compound is not Z306. In embodiments, the compound is not Z307. In embodiments, the compound is not Z308. In embodiments, the compound is not Z309. In embodiments, the compound is not Z310. In embodiments, the compound is not Z311. In embodiments, the compound is not Z312. In embodiments, the compound is not Z313. In embodiments, the compound is not Z314. In embodiments, the compound is not Z315. In embodiments, the compound is not Z316. In embodiments, the compound is not Z317. In embodiments, the compound is not Z318. In embodiments, the compound is not Z319. In embodiments, the compound is not Z320. In embodiments, the compound is not Z321. In embodiments, the compound is not Z322. In embodiments, the compound is not Z323. In embodiments, the compound is not Z324. In embodiments, the compound is not Z325. In embodiments, the compound is not Z326. In embodiments, the compound is not Z327. In embodiments, the compound is not Z328. In embodiments, the compound is not Z329. In embodiments, the compound is not Z330. In embodiments, the compound is not Z331. In embodiments, the compound is not Z332. In embodiments, the compound is not Z333. In embodiments, the compound is not Z334. In embodiments, the compound is not Z335. In embodiments, the compound is not Z336. In embodiments, the compound is not Z337. In embodiments, the compound is not Z338. In embodiments, the compound is not Z339. In embodiments, the compound is not Z340. In embodiments, the compound is not Z341. In embodiments, the compound is not Z342. In embodiments, the compound is not Z343. In embodiments, the compound is not Z344. In embodiments, the compound is not Z345. In embodiments, the compound is not Z346. In embodiments, the compound is not Z347. In embodiments, the compound is not Z348. In embodiments, the compound is not Z349. In embodiments, the compound is not Z350. In embodiments, the compound is not Z351. In embodiments, the compound is not Z352. In embodiments, the compound is not Z353. In embodiments, the compound is not Z354. In embodiments, the compound is not Z355. In embodiments, the compound is not Z356. In embodiments, the compound is not Z357. In embodiments, the compound is not Z358. In embodiments, the compound is not Z359. In embodiments, the compound is not Z360. In embodiments, the compound is not Z361. In embodiments, the compound is not Z362. In embodiments, the compound is not Z363. In embodiments, the compound is not Z364. In embodiments, the compound is not Z365. In embodiments, the compound is not Z366. In embodiments, the compound is not Z367. In embodiments, the compound is not Z368. In embodiments, the compound is not Z369. In embodiments, the compound is not Z370. In embodiments, the compound is not Z371. In embodiments, the compound is not Z372. In embodiments, the compound is not Z373. In embodiments, the compound is not Z374. In embodiments, the compound is not Z375. In embodiments, the compound is not Z376. In embodiments, the compound is not Z377. In embodiments, the compound is not Z378. In embodiments, the compound is not Z379. In embodiments, the compound is not Z380. In embodiments, the compound is not Z381. In embodiments, the compound is not Z382. In embodiments, the compound is not Z383. In embodiments, the compound is not Z384. In embodiments, the compound is not Z385. In embodiments, the compound is not Z386. In embodiments, the compound is not Z387. In embodiments, the compound is not Z388. In embodiments, the compound is not Z389. In embodiments, the compound is not Z390. In embodiments, the compound is not Z391. In embodiments, the compound is not Z392. In embodiments, the compound is not Z393. In embodiments, the compound is not Z394. In embodiments, the compound is not Z395. In embodiments, the compound is not Z396. In embodiments, the compound is not Z397. In embodiments, the compound is not Z398. In embodiments, the compound is not Z399. In embodiments, the compound is not Z400. In embodiments, the compound is not Z401. In embodiments, the compound is not Z402. In embodiments, the compound is not Z403. In embodiments, the compound is not Z404. In embodiments, the compound is not Z405. In embodiments, the compound is not Z406. In embodiments, the compound is not Z407. In embodiments, the compound is not Z408. In embodiments, the compound is not Z409. In embodiments, the compound is not Z410. In embodiments, the compound is not Z411. In embodiments, the compound is not Z412. In embodiments, the compound is not Z413. In embodiments, the compound is not Z414. In embodiments, the compound is not Z415. In embodiments, the compound is not Z416. In embodiments, the compound is not Z417. In embodiments, the compound is not Z418. In embodiments, the compound is not Z419. In embodiments, the compound is not Z420. In embodiments, the compound is not Z421. In embodiments, the compound is not Z422. In embodiments, the compound is not Z423. In embodiments, the compound is not Z424. In embodiments, the compound is not Z425. In embodiments, the compound is not Z426. In embodiments, the compound is not Z427. In embodiments, the compound is not Z428. In embodiments, the compound is not Z429. In embodiments, the compound is not Z430. In embodiments, the compound is not Z431. In embodiments, the compound is not Z432. In embodiments, the compound is not Z433. In embodiments, the compound is not Z434. In embodiments, the compound is not Z435. In embodiments, the compound is not Z436. In embodiments, the compound is not Z437. In embodiments, the compound is not Z438. In embodiments, the compound is not Z439. In embodiments, the compound is not Z440. In embodiments, the compound is not Z441. In embodiments, the compound is not Z442. In embodiments, the compound is not Z443. In embodiments, the compound is not Z444. In embodiments, the compound is not Z445. In embodiments, the compound is not Z446. In embodiments, the compound is not Z447. In embodiments, the compound is not Z448. In embodiments, the compound is not Z449. In embodiments, the compound is not Z450. In embodiments, the compound is not Z451. In embodiments, the compound is not Z452. In embodiments, the compound is not Z453. In embodiments, the compound is not Z454. In embodiments, the compound is not Z455. In embodiments, the compound is not Z456. In embodiments, the compound is not Z457. In embodiments, the compound is not Z458. In embodiments, the compound is not Z459. In embodiments, the compound is not Z460. In embodiments, the compound is not Z461. In embodiments, the compound is not Z462. In embodiments, the compound is not Z463. In embodiments, the compound is not Z464. In embodiments, the compound is not Z465. In embodiments, the compound is not Z466. In embodiments, the compound is not Z467. In embodiments, the compound is not Z468. In embodiments, the compound is not Z469. In embodiments, the compound is not Z470. In embodiments, the compound is not Z471. In embodiments, the compound is not Z472. In embodiments, the compound is not Z473. In embodiments, the compound is not Z474. In embodiments, the compound is not Z475. In embodiments, the compound is not Z476. In embodiments, the compound is not Z477. In embodiments, the compound is not Z478. In embodiments, the compound is not Z479. In embodiments, the compound is not Z480. In embodiments, the compound is not Z481. In embodiments, the compound is not Z482. In embodiments, the compound is not Z483. In embodiments, the compound is not Z484. In embodiments, the compound is not Z485. In embodiments, the compound is not Z486. In embodiments, the compound is not Z487. In embodiments, the compound is not Z488. In embodiments, the compound is not Z489. In embodiments, the compound is not Z490. In embodiments, the compound is not Z491. In embodiments, the compound is not Z492. In embodiments, the compound is not Z493. In embodiments, the compound is not Z494. In embodiments, the compound is not Z495. In embodiments, the compound is not Z496. In embodiments, the compound is not Z497. In embodiments, the compound is not Z498. In embodiments, the compound is not Z499. In embodiments, the compound is not Z500. In embodiments, the compound is not Z501. In embodiments, the compound is not Z502. In embodiments, the compound is not Z503. In embodiments, the compound is not Z504. In embodiments, the compound is not Z505. In embodiments, the compound is not Z506. In embodiments, the compound is not Z507. In embodiments, the compound is not Z508. In embodiments, the compound is not Z509. In embodiments, the compound is not Z510. In embodiments, the compound is not Z511. In embodiments, the compound is not Z512. In embodiments, the compound is not Z513. In embodiments, the compound is not Z514. In embodiments, the compound is not Z515. In embodiments, the compound is not Z516. In embodiments, the compound is not Z517. In embodiments, the compound is not Z518. In embodiments, the compound is not Z519. In embodiments, the compound is not Z520. In embodiments, the compound is not Z521. In embodiments, the compound is not Z522. In embodiments, the compound is not Z523. In embodiments, the compound is not Z524. In embodiments, the compound is not Z525. In embodiments, the compound is not Z526. In embodiments, the compound is not Z527. In embodiments, the compound is not Z528. In embodiments, the compound is not Z529. In embodiments, the compound is not Z530. In embodiments, the compound is not Z531. In embodiments, the compound is not Z532. In embodiments, the compound is not Z533. In embodiments, the compound is not Z534. In embodiments, the compound is not Z535. In embodiments, the compound is not Z536. In embodiments, the compound is not Z537. In embodiments, the compound is not Z538. In embodiments, the compound is not Z539. In embodiments, the compound is not Z540. In embodiments, the compound is not Z541. In embodiments, the compound is not Z542. In embodiments, the compound is not Z543. In embodiments, the compound is not Z544. In embodiments, the compound is not Z545. In embodiments, the compound is not Z546. In embodiments, the compound is not Z547. In embodiments, the compound is not Z548. In embodiments, the compound is not Z549. In embodiments, the compound is not Z550. In embodiments, the compound is not Z551. In embodiments, the compound is not Z552. In embodiments, the compound is not Z553. In embodiments, the compound is not Z554. In embodiments, the compound is not Z555. In embodiments, the compound is not Z556. In embodiments, the compound is not Z557. In embodiments, the compound is not Z558. In embodiments, the compound is not Z559. In embodiments, the compound is not Z560. In embodiments, the compound is not Z561. In embodiments, the compound is not Z562. In embodiments, the compound is not Z563. In embodiments, the compound is not Z564. In embodiments, the compound is not Z565. In embodiments, the compound is not Z566. In embodiments, the compound is not Z567. In embodiments, the compound is not Z568. In embodiments, the compound is not Z569. In embodiments, the compound is not Z570. In embodiments, the compound is not Z571. In embodiments, the compound is not Z572. In embodiments, the compound is not Z573. In embodiments, the compound is not Z574. In embodiments, the compound is not Z575. In embodiments, the compound is not Z576. In embodiments, the compound is not Z577. In embodiments, the compound is not Z578. In embodiments, the compound is not Z579. In embodiments, the compound is not Z580. In embodiments, the compound is not Z581. In embodiments, the compound is not Z582. In embodiments, the compound is not Z583. In embodiments, the compound is not Z584. In embodiments, the compound is not Z585. In embodiments, the compound is not Z586. In embodiments, the compound is not Z587. In embodiments, the compound is not Z588. In embodiments, the compound is not Z589. In embodiments, the compound is not Z590. In embodiments, the compound is not Z591. In embodiments, the compound is not Z592. In embodiments, the compound is not Z593. In embodiments, the compound is not Z594. In embodiments, the compound is not Z595. In embodiments, the compound is not Z596. In embodiments, the compound is not Z597. In embodiments, the compound is not Z598. In embodiments, the compound is not Z599. In embodiments, the compound is not Z600. In embodiments, the compound is not Z601. In embodiments, the compound is not Z602. In embodiments, the compound is not Z603. In embodiments, the compound is not Z604. In embodiments, the compound is not Z605. In embodiments, the compound is not Z606. In embodiments, the compound is not Z607. In embodiments, the compound is not Z608. In embodiments, the compound is not Z609. In embodiments, the compound is not Z610. In embodiments, the compound is not Z611. In embodiments, the compound is not Z612. In embodiments, the compound is not Z613. In embodiments, the compound is not Z614. In embodiments, the compound is not Z615. In embodiments, the compound is not Z616. In embodiments, the compound is not Z617. In embodiments, the compound is not Z618. In embodiments, the compound is not Z619. In embodiments, the compound is not Z620. In embodiments, the compound is not Z621. In embodiments, the compound is not Z622. In embodiments, the compound is not Z623. In embodiments, the compound is not Z624. In embodiments, the compound is not Z625. In embodiments, the compound is not Z626. In embodiments, the compound is not Z627. In embodiments, the compound is not Z628. In embodiments, the compound is not Z629. In embodiments, the compound is not Z630. In embodiments, the compound is not Z631. In embodiments, the compound is not Z632. In embodiments, the compound is not Z633. In embodiments, the compound is not Z634. In embodiments, the compound is not Z635. In embodiments, the compound is not Z636. In embodiments, the compound is not Z637. In embodiments, the compound is not Z638. In embodiments, the compound is not Z639. In embodiments, the compound is not Z640. In embodiments, the compound is not Z641. In embodiments, the compound is not Z642. In embodiments, the compound is not Z643. In embodiments, the compound is not Z644. In embodiments, the compound is not Z645. In embodiments, the compound is not Z646. In embodiments, the compound is not Z647.

In embodiments, the compound has the formula:

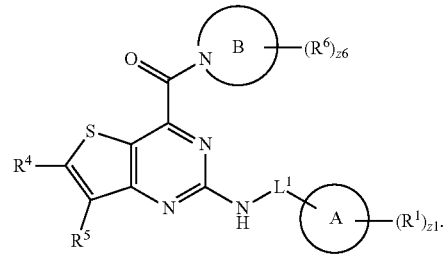

Ring A, Ring B, $L^1$, $R^1$, $R^4$, $R^5$, $R^6$, z1, and z6 are as described herein. In embodiments, $R^5$ is unsubstituted alkyl. In embodiments, $R^5$ is unsubstituted $C_1$-$C_4$ alkyl. In embodiments, $R^5$ is unsubstituted $C_1$-$C_3$ alkyl. In embodiments, $R^5$ is unsubstituted $C_1$-$C_2$ alkyl. In embodiments, $R^5$ is unsubstituted tert-butyl. In embodiments, $R^5$ is unsubstituted isobutyl. In embodiments, $R^5$ is unsubstituted secbutyl. In embodiments, $R^5$ is unsubstituted n-butyl. In embodiments, $R^5$ is unsubstituted isopropyl. In embodiments, $R^5$ is unsubstituted n-propyl. In embodiments, $R^5$ is unsubstituted ethyl. In embodiments, $R^5$ is unsubstituted methyl. In embodiments, $R^5$ is unsubstituted hydrogen. In embodiments, $R^4$ is unsubstituted alkyl. In embodiments, $R^4$ is unsubstituted $C_1$-$C_4$ alkyl. In embodiments, $R^4$ is unsubstituted $C_1$-$C_3$ alkyl. In embodiments, $R^4$ is unsubstituted $C_1$-$C_2$ alkyl. In embodiments, $R^4$ is unsubstituted tert-butyl. In embodiments, $R^4$ is unsubstituted isobutyl. In embodiments, $R^4$ is unsubstituted secbutyl. In embodiments, $R^4$ is unsubstituted n-butyl. In embodiments, $R^4$ is unsubstituted isopropyl. In embodiments, $R^4$ is unsubstituted n-propyl. In embodiments, $R^4$ is unsubstituted ethyl. In embodiments, $R^4$ is unsubstituted methyl. In embodiments, $R^4$ is unsubstituted hydrogen. In embodiments, $L^1$ is unsubstituted alkylene. In embodiments, $L^1$ is unsubstituted $C_1$-$C_4$ alkylene. In embodiments, $L^1$ is unsubstituted $C_1$-$C_3$ alkylene. In embodiments, $L^1$ is unsubstituted $C_1$-$C_2$ alkylene. In embodiments, $L^1$ is unsubstituted tert-butylene. In embodiments, $L^1$ is unsubstituted isobutylene. In embodiments, $L^1$ is unsubstituted secbutylene. In embodiments, $L^1$ is unsubstituted n-butylene. In embodiments, $L^1$ is unsubstituted isopropylene. In embodiments, $L^1$ is unsubstituted n-propylene. In embodiments, $L^1$ is unsubstituted ethylene. In embodiments, $L^1$ is unsubstituted methylene. In embodiments, $L^1$ is a bond. In embodiments, $L^1$ is

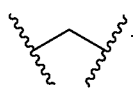

In embodiments, $L^1$ is

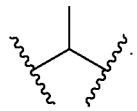 [SMILES: *C(*)C]

In embodiments, $L^1$ is

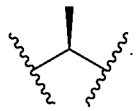

In embodiments, $L^1$ is

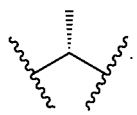

In embodiments, $L^1$ is

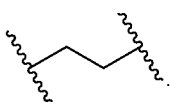 [SMILES: *CC*]

In embodiments, $L^1$ is

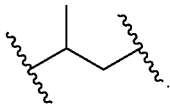 [SMILES: *CC(*)C]

In embodiments, $L^1$ is

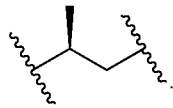 [SMILES: *C[C@@H](*)C]

In embodiments, $L^1$ is

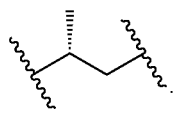 [SMILES: *C[C@H](*)C]

In embodiments, $L^1$ is

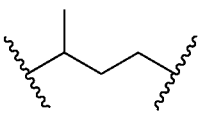

In embodiments, $L^1$ is

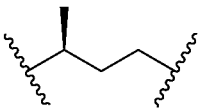

In embodiments, $L^1$ is

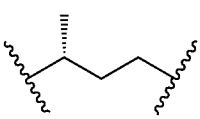

In embodiments, $L^1$ is

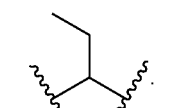

In embodiments, $L^1$ is

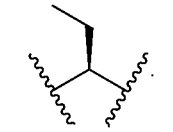

In embodiments. L¹ is

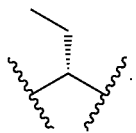

In embodiments, L¹ is

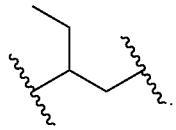 [SMILES: *CC(*)CC]

In embodiments, L¹ is

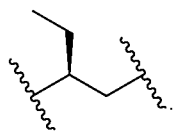 [SMILES: *C[C@@H](*)CC]

In embodiments, L¹ is

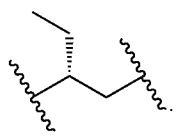 [SMILES: *C[C@H](*)CC]

In embodiments, L¹ is

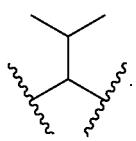

In embodiments, L¹ is

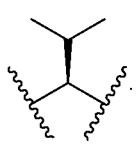

In embodiments, L¹ is

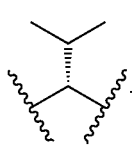

In embodiments, L¹ is

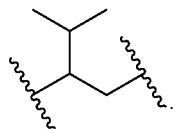 [SMILES: *CC(*)C(C)C]

In embodiments, L¹ is

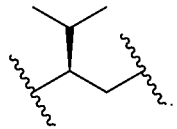 [SMILES: *C[C@@H](*)C(C)C]

In embodiments, L¹ is

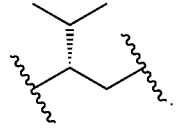 [SMILES: *C[C@H](*)C(C)C]

In embodiments, Ring A is pyridyl. In embodiments, Ring A is 2-pyridyl. In embodiments, Ring A is 3-pyridyl. In embodiments, Ring A is 4-pyridyl. In embodiments, Ring A is pyrrolyl. In embodiments, Ring A is 2-pyrrolyl. In embodiments, Ring A is 3-pyrrolyl. In embodiments, Ring A is azetyl. In embodiments, Ring A is 2-azetyl. In embodiments, Ring A is 3-azetyl. In embodiments, R¹ is independently —OH. In embodiments, R¹ is independently —OCH₃. In embodiments, R¹ is independently —OCH₂CH₃. In embodiments, R¹ is independently unsubstituted $C_1$-$C_4$ alkoxy. In embodiments, R¹ is independently —Cl. In embodiments, R¹ is independently —F. In embodiments, R¹ is independently halogen. In embodiments, R¹ is independently —CH₃. In embodiments, R¹ is independently —CH₂CH₃. In embodiments, R¹ is independently unsubstituted $C_1$-$C_4$ alkyl. In embodiments, R¹ is independently —CF₃. In embodiments, R¹ is independently —CXV In embodiments, z1 is an integer from 0 to 5. In embodiments, z1 is an integer from 0 to 2. In embodiments, z1 is 0. In embodiments, z1 is 1. In embodiments, z1 is 2. In embodiments, z1 is 3. In embodiments, z1 is 4. In embodiments, z1 is 5. In embodiments, R⁶ is independently —OH. In embodiments, R⁶ is independently —OCH₃. In embodiments, R⁶ is independently —OCH₂CH₃. In embodiments, R⁶ is independently unsubstituted $C_1$-$C_4$ alkoxy. In embodiments, R⁶ is independently —Cl. In embodiments, R⁶ is independently —F. In embodiments, R⁶ is independently —Br. In embodiments, R⁶ is independently —I. In embodiments, R⁶ is independently halogen. In embodiments, R⁶ is independently —CH₃. In embodiments, R⁶ is independently —CH₂CH₃. In embodiments, R⁶ is independently unsubstituted $C_1$-$C_4$ alkyl. In embodiments, R⁶ is independently —CF₃. In embodiments, R⁶ is independently —CCl₃. In embodiments, R⁶ is independently —CBr₃. In embodiments, R⁶ is independently —CI₃. In embodiments, R⁶ is independently —CX⁶₃. In embodiments, Ring B is a heterocycloalkyl. In embodiments, Ring B is a 4 to 6 membered heterocycloalkyl. In embodiments, Ring B is a 4 membered heterocycloalkyl. In embodiments, Ring B is a 5 membered heterocycloalkyl. In embodiments, Ring B is a 6 membered heterocycloalkyl. In embodiments, Ring B is a azetidinyl. In embodiments, Ring B is a pyrrolidinyl. In embodiments, Ring B is a piperdinyl. In embodiments, z6 is an integer from 0 to 8. In embodiments, z6 is an integer from 0 to 2. In embodiments, z6 is 0. In embodiments, z6 is 1. In embodiments, z6 is 2. In embodiments, z6 is 3. In embodiments, z6 is 4. In embodiments, z6 is 5. In embodiments, z6 is 6. In embodiments, z6 is 7. In embodiments, z6 is 8. In embodiments, z6 is 9. In embodiments, z6 is 10. In embodiments, -(Ring B)-$(R^6)_{z6}$ is

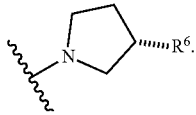

In embodiments, -(Ring B)-$(R^6)_{z6}$ is

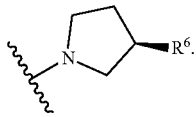

In embodiments, -(Ring B)-$(R^6)_{z6}$ is

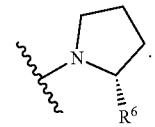

In embodiments, -(Ring B)-$(R^6)_{z6}$ is

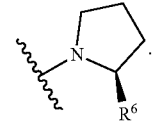

In embodiments, -(Ring B)-$(R^6)_{z6}$ is

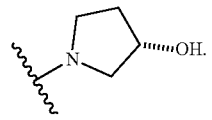

In embodiments, -(Ring B)-$(R^6)_{z6}$ is

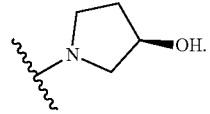

In embodiments, -(Ring B)-$(R^6)_{z6}$ is

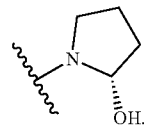

In embodiments, -(Ring B)-$(R^6)_{z6}$ is

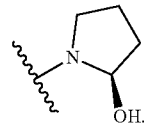

In embodiments, the compound is Z297.

III. Pharmaceutical Compositions

In an aspect is provided a pharmaceutical composition including a compound as described herein, and a pharmaceutically acceptable excipient.

In embodiments of the pharmaceutical compositions, the compound, or pharmaceutically acceptable salt thereof, is included in a therapeutically effective amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments of the pharmaceutical compositions, the second agent is an agent for treating cancer. In embodiments, the second agent is an anti-cancer agent. In embodiments, the second agent is a chemotherapeutic. In embodiments, the second agent is an anti-inflammatory agent. In embodiments, the administering does not include administration of any active agent other than the recited active agent (e.g., a compound described herein). In embodiments, the second agent is an anti-fibrotic agent. In embodiments, the second agent is an anti-neurodegenerative disease agent. In embodiments, the second agent is an agent for treating fibrosis. In embodiments, the second agent is an agent for treating a neurodegenerative disease.

IV. Methods of Use

In an aspect is provided a method of inhibiting Adenosine A2B Receptor activity and Adenosine A2A Receptor activity, the method including contacting the Adenosine A2B Receptor and Adenosine A2A Receptor with a compound as described herein, including embodiments. In embodiments, the compound contacts the Adenosine A2B Receptor. In embodiments, the compound contacts the Adenosine A2A Receptor. In embodiments, the compound is capable of independently contacting the Adenosine A2A Receptor and the Adenosine A2B Receptor. In embodiments, the compound does not contact the Adenosine A2A Receptor and the Adenosine A2B Receptor simultaneously.

In an aspect is provided a method of inhibiting Adenosine A2B Receptor activity and Adenosine A2A Receptor activity, the method including contacting the Adenosine A2B Receptor or Adenosine A2A Receptor with a compound as described herein, including embodiments. In embodiments, the method inhibits Adenosine A2B Receptor activity and Adenosine A2A Receptor activity relative to a control.

In embodiments, the method inhibits Adenosine A2B Receptor activity to Adenosine A2A Receptor activity at a ratio of about 1 to about 1. In embodiments, the method inhibits Adenosine A2B Receptor activity to Adenosine A2A Receptor activity at a ratio of about 2 to about 1. In embodiments, the method inhibits Adenosine A2B Receptor activity to Adenosine A2A Receptor activity at a ratio of about 3 to about 1. In embodiments, the method inhibits Adenosine A2B Receptor activity to Adenosine A2A Receptor activity at a ratio of about 4 to about 1. In embodiments, the method inhibits Adenosine A2B Receptor activity to Adenosine A2A Receptor activity at a ratio of about 5 to about 1. In embodiments, the method inhibits Adenosine A2B Receptor activity to Adenosine A2A Receptor activity at a ratio of about 6 to about 1. In embodiments, the method inhibits Adenosine A2B Receptor activity to Adenosine A2A Receptor activity at a ratio of about 7 to about 1. In embodiments, the method inhibits Adenosine A2B Receptor activity to Adenosine A2A Receptor activity at a ratio of about 8 to about 1. In embodiments, the method inhibits Adenosine A2B Receptor activity to Adenosine A2A Receptor activity at a ratio of about 9 to about 1. In embodiments, the method inhibits Adenosine A2B Receptor activity to Adenosine A2A Receptor activity at a ratio of about 10 to about 1. In embodiments, the method inhibits Adenosine A2B Receptor activity to Adenosine A2A Receptor activity at a ratio of about 20 to about 1. In embodiments, the method inhibits Adenosine A2B Receptor activity to Adenosine A2A Receptor activity at a ratio of about 25 to about 1. In embodiments, the method inhibits Adenosine A2B Receptor activity to Adenosine A2A Receptor activity at a ratio of about 30 to about 1. In embodiments, the method inhibits Adenosine A2B Receptor activity to Adenosine A2A Receptor activity at a ratio of about 40 to about 1. In embodiments, the method inhibits Adenosine A2B Receptor activity to Adenosine A2A Receptor activity at a ratio of about 50 to about 1. In embodiments, the method inhibits Adenosine A2B Receptor activity to Adenosine A2A Receptor activity at a ratio of about 100 to about 1. In embodiments, the method inhibits Adenosine A2B Receptor activity to Adenosine A2A Receptor activity at a ratio of about 200 to about 1. In embodiments, the method inhibits Adenosine A2B Receptor activity to Adenosine A2A Receptor activity at a ratio of about 300 to about 1. In embodiments, the method inhibits Adenosine A2B Receptor activity to Adenosine A2A Receptor activity at a ratio of about 400 to about 1. In embodiments, the method inhibits Adenosine A2B Receptor activity to Adenosine A2A Receptor activity at a ratio of about 500 to about 1. In embodiments, the method inhibits Adenosine A2B Receptor activity to Adenosine A2A Receptor activity at a ratio of about 600 to about 1. In embodiments, the method inhibits Adenosine A2B Receptor activity to Adenosine A2A Receptor activity at a ratio of about 700 to about 1. In embodiments, the method inhibits Adenosine A2B Receptor activity to Adenosine A2A Receptor activity at a ratio of about 800 to about 1. In embodiments, the method inhibits Adenosine A2B Receptor activity to Adenosine A2A Receptor activity at a ratio of about 900 to about 1. In embodiments, the method inhibits Adenosine A2B Receptor activity to Adenosine A2A Receptor activity at a ratio of about 1000 to about 1.

In another aspect is provided a method of inhibiting Adenosine A2B Receptor activity, said method comprising contacting the Adenosine A2B Receptor with a compound as described herein, including embodiments. In embodiments, the method inhibits Adenosine A2B Receptor activity relative to a control. In embodiments, the method inhibits Adenosine A2B Receptor activity greater than Adenosine A3 Receptor activity. In embodiments, the method inhibits Adenosine A2B Receptor activity greater than Adenosine A1 Receptor activity.

In embodiments, the method inhibits Adenosine A2B Receptor activity to Adenosine A3 Receptor activity at a ratio of about 1 to about 1. In embodiments, the method inhibits Adenosine A2B Receptor activity to Adenosine A3 Receptor activity at a ratio of about 2 to about 1. In embodiments, the method inhibits Adenosine A2B Receptor activity to Adenosine A3 Receptor activity at a ratio of about 3 to about 1. In embodiments, the method inhibits Adenosine A2B Receptor activity to Adenosine A3 Receptor activity at a ratio of about 4 to about 1. In embodiments, the method inhibits Adenosine A2B Receptor activity to Adenosine A3 Receptor activity at a ratio of about 5 to about 1. In embodiments, the method inhibits Adenosine A2B Receptor activity to Adenosine A3 Receptor activity at a ratio of about 6 to about 1. In embodiments, the method inhibits Adenosine A2B Receptor activity to Adenosine A3 Receptor activity at a ratio of about 7 to about 1. In embodiments, the method inhibits Adenosine A2B Receptor activity to Adenosine A3 Receptor activity at a ratio of about 8 to about 1. In embodiments, the method inhibits Adenosine A2B Receptor activity to Adenosine A3 Receptor activity at a ratio of about 9 to about 1. In embodiments, the method inhibits Adenosine A2B Receptor activity to Adenosine A3 Receptor activity at a ratio of about 10 to about 1. In embodiments, the method inhibits Adenosine A2B Receptor activity to Adenosine A3 Receptor activity at a ratio of about 20 to about 1. In embodiments, the method inhibits Adenosine A2B Receptor activity to Adenosine A3 Receptor activity at a ratio of about 25 to about 1. In embodiments, the method inhibits Adenosine A2B Receptor activity to Adenosine A3 Receptor activity at a ratio of about 30 to about 1. In embodiments, the method inhibits Adenosine A2B Receptor activity to Adenosine A3 Receptor activity at a ratio of about 40 to about 1. In embodiments, the method inhibits Adenosine A2B Receptor activity to Adenosine A3 Receptor activity at a ratio of about 50 to about 1. In embodiments, the method inhibits Adenosine A2B Receptor activity to Adenosine A3 Receptor activity at a ratio of about 100 to about 1. In embodiments, the method inhibits Adenosine A2B Receptor activity to Adenosine A3 Receptor activity at a ratio of about 200 to about 1. In embodiments, the method inhibits Adenosine A2B Receptor activity to Adenosine A3 Receptor activity at a ratio of about 300 to about 1. In embodiments, the method inhibits Adenosine A2B Receptor activity to Adenosine A3 Receptor activity at a ratio of about 400 to about 1. In embodiments, the method inhibits Adenosine A2B Receptor activity to Adenosine A3 Receptor activity at a ratio of about 500 to about 1. In embodiments, the method inhibits Adenosine A2B Receptor activity to Adenosine A3 Receptor activity at a ratio of about 600 to about 1. In embodiments, the method inhibits Adenosine A2B Receptor activity to Adenosine A3 Receptor activity at a ratio of about 700 to about 1. In embodiments, the method inhibits Adenosine A2B Receptor activity to Adenosine A3 Receptor activity at a ratio of about 800 to about 1. In embodiments, the method inhibits Adenosine A2B Receptor activity to Adenosine A3 Receptor activity at a ratio of about 900 to about 1. In embodiments, the method inhibits Adenosine A2B Receptor activity to Adenosine A3 Receptor activity at a ratio of about 1000 to about 1.

In embodiments, the method inhibits Adenosine A2B Receptor activity to Adenosine A1 Receptor activity at a ratio of about 1 to about 1. In embodiments, the method inhibits Adenosine A2B Receptor activity to Adenosine A1 Receptor activity at a ratio of about 2 to about 1. In embodiments, the method inhibits Adenosine A2B Receptor activity to Adenosine A1 Receptor activity at a ratio of about 3 to about 1. In embodiments, the method inhibits Adenosine A2B Receptor activity to Adenosine A1 Receptor activity at a ratio of about 4 to about 1. In embodiments, the method inhibits Adenosine A2B Receptor activity to Adenosine A1 Receptor activity at a ratio of about 5 to about 1. In embodiments, the method inhibits Adenosine A2B Receptor activity to Adenosine A1 Receptor activity at a ratio of about 6 to about 1. In embodiments, the method inhibits Adenosine A2B Receptor activity to Adenosine A1 Receptor activity at a ratio of about 7 to about 1. In embodiments, the method inhibits Adenosine A2B Receptor activity to Adenosine A1 Receptor activity at a ratio of about 8 to about 1. In embodiments, the method inhibits Adenosine A2B Receptor activity to Adenosine A1 Receptor activity at a ratio of about 9 to about 1. In embodiments, the method inhibits Adenosine A2B Receptor activity to Adenosine A1 Receptor activity at a ratio of about 10 to about 1. In embodiments, the method inhibits Adenosine A2B Receptor activity to Adenosine A1 Receptor activity at a ratio of about 20 to about 1. In embodiments, the method inhibits Adenosine A2B Receptor activity to Adenosine A1 Receptor activity at a ratio of about 25 to about 1. In embodiments, the method inhibits Adenosine A2B Receptor activity to Adenosine A1 Receptor activity at a ratio of about 30 to about 1. In embodiments, the method inhibits Adenosine A2B Receptor activity to Adenosine A1 Receptor activity at a ratio of about 40 to about 1. In embodiments, the method inhibits Adenosine A2B Receptor activity to Adenosine A1 Receptor activity at a ratio of about 50 to about 1. In embodiments, the method inhibits Adenosine A2B Receptor activity to Adenosine A1 Receptor activity at a ratio of about 100 to about 1. In embodiments, the method inhibits Adenosine A2B Receptor activity to Adenosine A1 Receptor activity at a ratio of about 200 to about 1. In embodiments, the method inhibits Adenosine A2B Receptor activity to Adenosine A1 Receptor activity at a ratio of about 300 to about 1. In embodiments, the method inhibits Adenosine A2B Receptor activity to Adenosine A1 Receptor activity at a ratio of about 400 to about 1. In embodiments, the method inhibits Adenosine A2B Receptor activity to Adenosine A1 Receptor activity at a ratio of about 500 to about 1. In embodiments, the method inhibits Adenosine A2B Receptor activity to Adenosine A1 Receptor activity at a ratio of about 600 to about 1. In embodiments, the method inhibits Adenosine A2B Receptor activity to Adenosine A1 Receptor activity at a ratio of about 700 to about 1. In embodiments, the method inhibits Adenosine A2B Receptor activity to Adenosine A1 Receptor activity at a ratio of about 800 to about 1. In embodiments, the method inhibits Adenosine A2B Receptor activity to Adenosine A1 Receptor activity at a ratio of about 900 to about 1. In embodiments, the method inhibits Adenosine A2B Receptor activity to Adenosine A1 Receptor activity at a ratio of about 1000 to about 1.

In embodiments, the method inhibits Adenosine A2B Receptor activity and does not inhibit Adenosine A3 Receptor activity.

In an aspect is provided a method of inhibiting Adenosine A2B Receptor activity, the method including contacting the Adenosine A2B Receptor with a compound as described herein, including embodiments.

In an aspect is provided a method of inhibiting Adenosine A2A Receptor activity, the method including contacting the A Adenosine A2A Receptor with a compound as described herein, including embodiments.

In an aspect is provided a method of treating cancer, said method comprising administering to a subject in need thereof an effective amount of a compound as described herein, including embodiments. In embodiments, the cancer is breast cancer, lung cancer, colon cancer, bladder cancer, kidney cancer, liver cancer, pancreatic cancer, melanoma, leukemia, lymphoma, or prostate cancer. In embodiments, the cancer is breast cancer. In embodiments, the cancer is lung cancer. In embodiments, the cancer is colon cancer. In embodiments, the cancer is bladder cancer. In embodiments, the cancer is kidney cancer. In embodiments, the cancer is liver cancer. In embodiments, the cancer is pancreatic cancer. In embodiments, the cancer is melanoma. In embodiments, the cancer is leukemia. In embodiments, the cancer is lymphoma. In embodiments, the cancer is prostate cancer.

In an aspect is provided a method of treating fibrotic disease, said method comprising administering to a subject in need thereof an effective amount of a compound as described herein, including embodiments. In embodiments, the fibrotic disease is pulmonary fibrosis. In embodiments, the fibrotic disease is idiopathic pulmonary fibrosis (IPF). In embodiments, the fibrotic disease is idiopathic pulmonary fibrosis (IPF), myocardial infarction, cardiac hypertrophy, heart failure, cirrhosis, acetominophen (Tylenol) liver toxicity, hepatitis C liver disease, hepatosteatosis (fatty liver disease), or hepatic fibrosis. In embodiments, the fibrotic disease is nonalcoholic steatohepatitis (NASH). In embodiments, the fibrotic disease is nonalcoholic fatty liver disease (NAFLD).

In an aspect is provided a method of treating a neurodegenerative disease, said method comprising administering to a subject in need thereof an effective amount of a compound as described herein, including embodiments. In embodiments, the neurodegenerative disease is Alzheimer's disease, Huntington's disease, Multiple sclerosis, Parkinson's disease, retinitis pigmentosa, amyotrophic lateral sclerosis, retinal degeneration, macular degeneration, Prion Disease, Creutzfeldt-Jakob Disease, or Kuru. In embodiments, the neurodegenerative disease is Alzheimer's disease. In embodiments, the neurodegenerative disease is Huntington's disease. In embodiments, the neurodegenerative disease is Multiple sclerosis. In embodiments, the neurodegenerative disease is Parkinson's disease. In embodiments, the neurodegenerative disease is Amyotrophic lateral sclerosis.

In embodiments, the method includes administering a second agent (e.g. therapeutic agent). In embodiments, the method includes administering a second agent (e.g. therapeutic agent) in a therapeutically effective amount. In embodiments, the second agent is an agent for treating cancer. In embodiments, the second agent is an anti-cancer agent. In embodiments, the second agent is a chemotherapeutic. In embodiments, the second agent is an anti-inflammatory agent. In embodiments, the second agent is an agent for treating fibrosis. In embodiments, the second agent is an agent for treating a neurodegenerative disease.

In an aspect is provided a method of inhibiting a Adenosine Receptor activity, the method including contacting the Adenosine Receptor (e.g., A1, A2A, A2B, or A3) with a compound as described herein, including embodiments.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EMBODIMENTS

Embodiment P1. A compound having the formula:

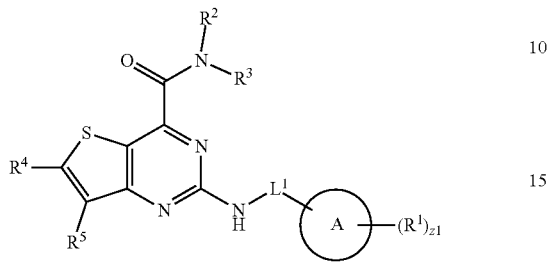

L$^1$ is substituted or unsubstituted C$_1$-C$_3$ alkylene, or substituted or unsubstituted 2 to 3 membered heteroalkylene;

Ring A is aryl or heteroaryl;

R$^1$ is independently halogen, —CX$^1_3$, —CHX$^1_2$, —CH$_2$X$^1$, —OCX$^1_3$, —OCH$_2$X$^1$, —OCHX$^1_2$, —CN, —SR$^{1D}$, —NR$^{1A}$R$^{1B}$, —C(O)R$^{1C}$, —C(O)OR$^{1C}$, —C(O)NR$^{1A}$R$^{1B}$, —OR$^{1D}$, —NR$^{1A}$C(O)R$^{1C}$, —NR$^{1A}$C(O)OR$^{1C}$, substituted or unsubstituted alkyl, or substituted or unsubstituted heteroalkyl;

z1 is an integer from 0 to 5;

R$^2$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^3$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^2$ and R$^3$ may optionally be joined to form a substituted or unsubstituted heterocycloalkyl;

R$^4$ is independently hydrogen, halogen, —CX$^4_3$, —CHX$^4_2$, —CH$_2$X$^4$, —OCX$^4_3$, —OCH$_2$X$^4$, —OCHX$^4_2$, —CN, —SR$^{4D}$, —NR$^{4A}$R$^{4B}$, —C(O)R$^{4C}$, —C(O)OR$^{4C}$, —C(O)NR$^{4A}$R$^{4B}$, —OR$^{4D}$, —NR$^{4A}$C(O)R$^{4C}$, —NR$^{4A}$C(O)OR$^{4C}$, substituted or unsubstituted alkyl, or substituted or unsubstituted heteroalkyl;

R$^5$ is independently hydrogen, halogen, —CX$^5_3$, —CHX$^5_2$, —CH$_2$X$^5$, —OCX$^5_3$, —OCH$_2$X$^5$, —OCHX$^5_2$, —CN, —SR$^{5D}$, —NR$^{5A}$R$^{5B}$, —C(O)R$^{5C}$, —C(O)OR$^{5C}$, —C(O)NR$^{5A}$R$^{5B}$, —OR$^{5D}$, —NR$^{5A}$C(O)R$^{5C}$, —NR$^{5A}$C(O)OR$^{5C}$, substituted or unsubstituted alkyl, or substituted or unsubstituted heteroalkyl;

each R$^{1A}$, R$^{1B}$, R$^{1C}$, R$^{1D}$, R$^{4A}$, R$^{4B}$, R$^{4C}$, R$^{4D}$, R$^{5A}$, R$^{5B}$, R$^{5C}$, and R$^{5D}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, unsubstituted alkyl, unsubstituted heteroalkyl, unsubstituted cycloalkyl, unsubstituted heterocycloalkyl, unsubstituted aryl, or unsubstituted heteroaryl;

R$^{1B}$ and R$^{1B}$ substituents bonded to the same nitrogen atom may optionally be joined to form a substituted or unsubstituted heterocycloalkyl;

R$^{4B}$ and R$^{4B}$ substituents bonded to the same nitrogen atom may optionally be joined to form a substituted or unsubstituted heterocycloalkyl;

R$^{5B}$ and R$^{5B}$ substituents bonded to the same nitrogen atom may optionally be joined to form a substituted or unsubstituted heterocycloalkyl;

each X$^1$, X$^4$, and X$^5$ is independently —F, —Cl, —Br, or —I; and wherein the compound is not

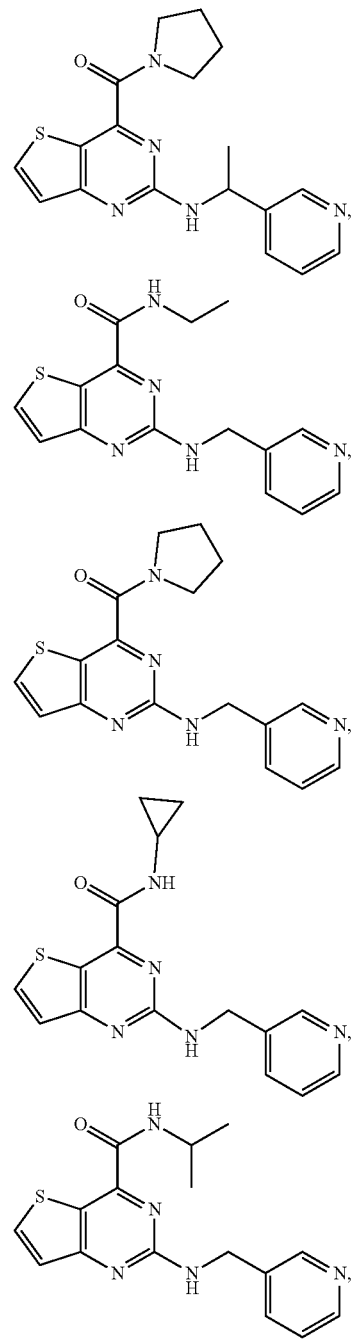

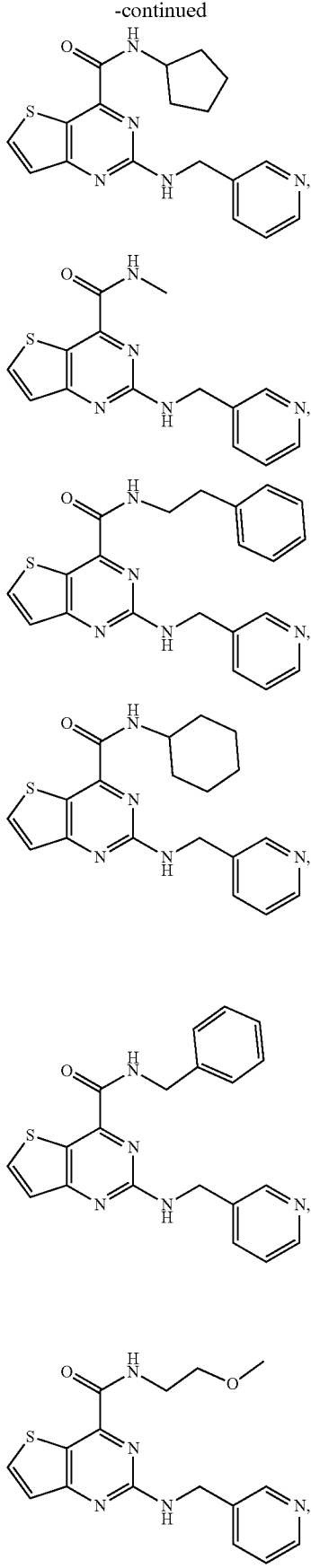

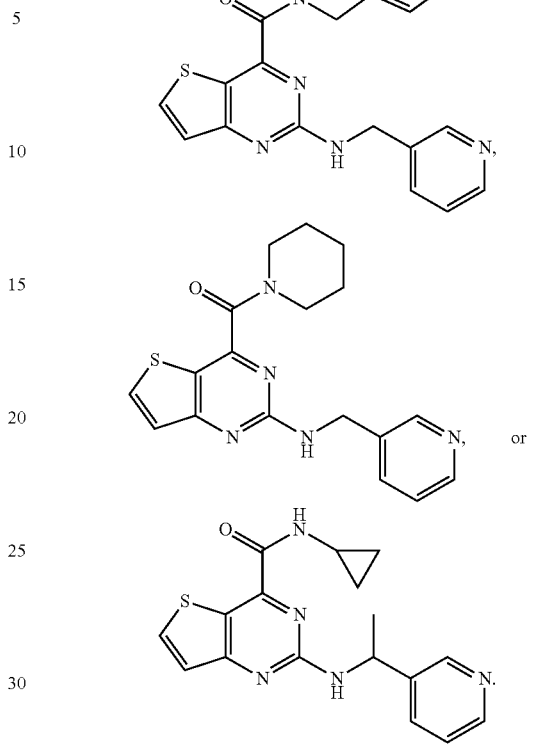

Embodiment P2. The compound of embodiment P1, wherein
when $R^2$ and $R^3$ form an unsubstituted heterocycloalkyl and z1 is 0, $R^4$ is not hydrogen;
when $R^2$ or $R^3$ is hydrogen and $L^1$ is unsubstituted methylene, $R^4$ is not hydrogen; or
when $R^2$ is hydrogen, $R^3$ is not unsubstituted cyclopropyl.

Embodiment P3. The compound of embodiments P1 or P2, wherein $R^2$ is hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment P4. The compound of embodiments P1 or P2, wherein $R^2$ is substituted or unsubstituted $C_1$-$C_6$ alkyl.

Embodiment P5. The compound of embodiments P1 or P2, wherein $R^2$ is substituted or unsubstituted $C_3$-$C_6$ cycloalkyl.

Embodiment P6. The compound of embodiment P1, wherein $R^2$ is hydrogen.

Embodiment P7. The compound of any one of embodiments P1 to P6, wherein $R^3$ is hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment P8. The compound of any one of embodiments P1 to P6, wherein $R^3$ is substituted or unsubstituted $C_1$-$C_6$ alkyl.

Embodiment P9. The compound of any one of embodiments P1 to P6, wherein $R^3$ is substituted or unsubstituted $C_3$-$C_6$ cycloalkyl.

Embodiment P10. The compound of any one of embodiments P1 to P6, wherein $R^3$ is hydrogen.

Embodiment P11. The compound of embodiment P1, wherein $R^2$ and $R^3$ are joined to form a substituted or unsubstituted heterocycloalkyl.

Embodiment P12. The compound of any one of embodiments P1 to P11, wherein Ring A is phenyl or 5 to 6 membered heteroaryl.

Embodiment P13. The compound of any one of embodiments P1 to P11, wherein Ring A is phenyl, pyridyl, pyrazolyl, imidazolyl, oxazolyl, isoxazolyl, thiazolyl, furanyl, pyrrolyl, thienyl, pyrazinyl, pyridazinyl, or pyrimidinyl.

Embodiment P14. The compound of any one of embodiments P1 to P11, wherein Ring A is phenyl or pyridyl.

Embodiment P15. The compound of any one of embodiments P1 to P11, wherein Ring A is pyridyl.

Embodiment P16. The compound of any one of embodiments P1 to P11, having the formula:

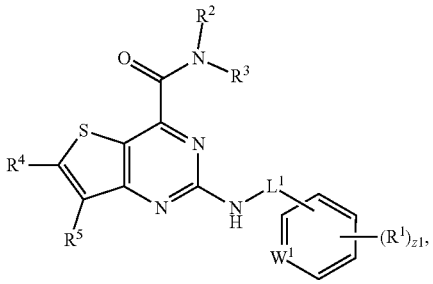

wherein $W^1$ is CH or N.

Embodiment P17. The compound of any one of embodiments P1 to P11, having the formula:

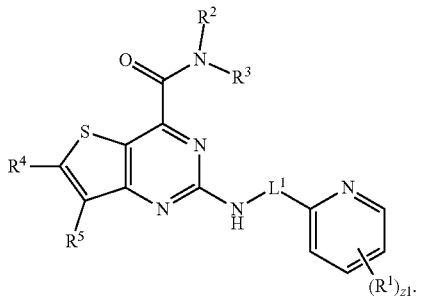

Embodiment P18. The compound of any one of embodiments P1 to P11, having the formula:

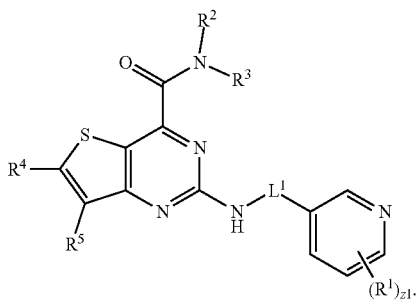

Embodiment P19. The compound of any one of embodiments P1 to P11, having the formula:

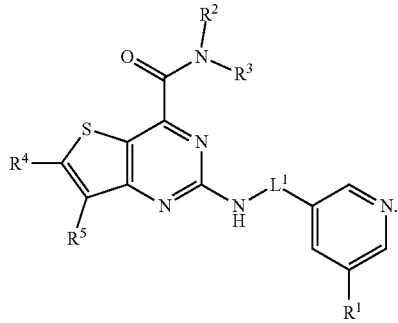

Embodiment P20. The compound of any one of embodiments P1 to P19, wherein $L^1$ is substituted or unsubstituted $C_1$-$C_3$ alkylene.

Embodiment P21. The compound of any one of embodiments P1 to P19, wherein $L^1$ is substituted or unsubstituted methylene.

Embodiment P22. The compound of any one of embodiments P1 to P21, wherein $R^4$ is hydrogen, halogen, —$CX^4_3$, —$CHX^4_2$, —$CH_2X^4$, —$OCX^4_3$, —$OCH_2X^4$, —$OCHX^4_2$, —CN, —$SR^{4D}$, —$NR^{4A}R^{4B}$, or substituted or unsubstituted $C_1$-$C_6$ alkyl.

Embodiment P23. The compound of any one of embodiments P1 to P21, wherein $R^4$ is hydrogen, halogen, —$CX_3$, —$NR^{4A}R^{4B}$, or substituted or unsubstituted $C_1$-$C_6$ alkyl.

Embodiment P24. The compound of any one of embodiments P1 to P21, wherein $R^4$ is hydrogen, halogen, —$CF_3$, —$NH_2$, —$NH(CH_3)$ or unsubstituted $C_1$-$C_6$ alkyl.

Embodiment P25. The compound of any one of embodiments P1 to P21, wherein $R^4$ is hydrogen or unsubstituted methyl.

Embodiment P26. The compound of any one of embodiments P1 to P25, wherein $R^5$ is hydrogen, halogen, —$CX^5_3$, —$CHX^5_2$, —$CH_2X^5$, —$OCX^5_3$, —$OCH_2X^5$, —$OCHX^5_2$, —CN, —$SR^{5D}$, —$NR^{5A}R^{5B}$, or substituted or unsubstituted $C_1$-$C_6$ alkyl.

Embodiment P27. The compound of any one of embodiments P1 to P25, wherein $R^5$ is hydrogen, halogen, —$CX_3$, —$NR^{5A}R^{5B}$, or substituted or unsubstituted $C_1$-$C_6$ alkyl.

Embodiment P28. The compound of any one of embodiments P1 to P25, wherein $R^5$ is hydrogen, halogen, —$CF_3$, —$NH_2$, —$NH(CH_3)$ or unsubstituted $C_1$-$C_6$ alkyl.

Embodiment P29. The compound of any one of embodiments P1 to P25, wherein $R^5$ is hydrogen or unsubstituted methyl.

Embodiment P30. The compound of any one of embodiments P1, or P11 to P29 having the formula:

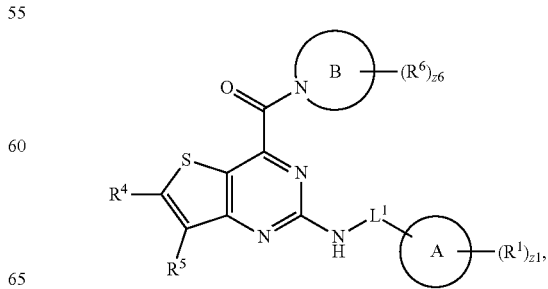

wherein

Ring B is heterocycloalkyl;

R⁶ is independently halogen, —CX⁶₃, —CHX⁶₂, —CH₂X⁶, —OCX⁶₃, —OCH₂X⁶, —OCHX⁶₂, —CN, —SR⁶ᴰ, —SO₂R⁶ᴰ, —NR⁶ᴬR⁶ᴮ, —C(O)R⁶ᶜ, —C(O)OR⁶ᶜ, —C(O)NR⁶ᴬR⁶ᴮ, —OR⁶ᴰ, —NR⁶ᴬC(O)R⁶ᶜ, —NR⁶ᴬC(O)OR⁶ᶜ, substituted or unsubstituted alkyl, or substituted or unsubstituted heteroalkyl;

z6 is an integer from 0 to 10;

each R⁶ᴬ, R⁶ᴮ, R⁶ᶜ, and R⁶ᴰ is independently hydrogen, halogen, —CF₃, —CBr₃, —CCl₃, —CI₃, —CHF₂, —CHBr₂, —CHCl₂, —CHI₂, —CH₂F, —CH₂Br, —CH₂Cl, —CH₂I, —OCF₃, —OCBr₃, —OCCl₃, —OCI₃, —OCHF₂, —OCHBr₂, —OCHCl₂, —OCHI₂, —OCH₂F, —OCH₂Br, —OCH₂Cl, —OCH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁶ᴬ and R⁶ᴮ substituents bonded to the same nitrogen atom may optionally be joined to form a substituted or unsubstituted heterocycloalkyl; and X⁶ is independently —F, —Cl, —Br, or —I.

Embodiment P31. The compound of embodiment P30, having the formula:

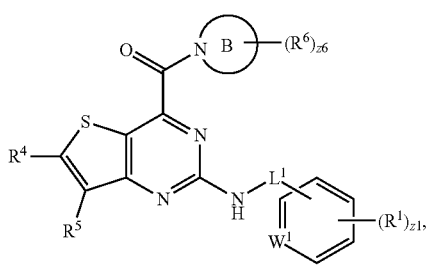

wherein W¹ is CH or N.

Embodiment P32. The compound of embodiment P30, having the formula:

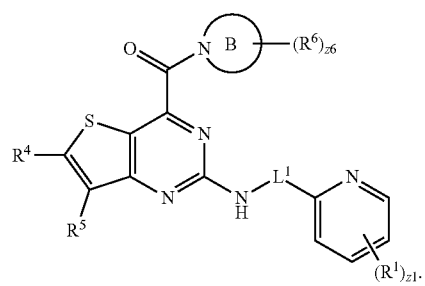

Embodiment P33. The compound of embodiment P30, having the formula:

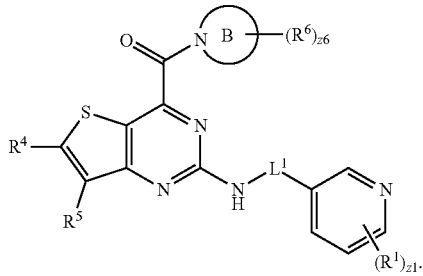

Embodiment P34. The compound of embodiment P30, having the formula:

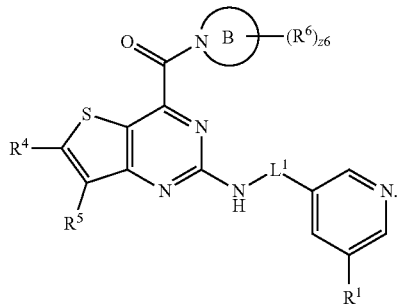

Embodiment P35. The compound of any one of embodiments P30 to P34, wherein Ring B is a 4 to 8 membered heterocycloalkyl.

Embodiment P36. The compound of any one of embodiments P30 to P34, wherein Ring B is a 4 to 6 membered heterocycloalkyl.

Embodiment P37. The compound of any one of embodiments P30 to P34, wherein Ring B is azetidinyl.

Embodiment P38. The compound of any one of embodiments P30 to P37, wherein z6 is 1.

Embodiment P39. The compound of any one of embodiments P30 to P38, wherein R⁶ is independently halogen, —CX⁶₃, —CHX⁶₂, —CH₂X⁶, —OCX⁶₃, —OCH₂X⁶, —OCHX⁶₂, —NR⁶ᴬR⁶ᴮ, —C(O)R⁶ᶜ, substituted or unsubstituted C₁-C₆ alkyl, or substituted or unsubstituted 2 to 6 membered heteroalkyl.

Embodiment P40. The compound of any one of embodiments P30 to P38, wherein R⁶ is independently halogen, —CX⁶₃, —CHX⁶₂, —CH₂X⁶, —OCX⁶₃, —OCH₂X⁶, —OCHX⁶₂, —CN, —SR⁶ᴰ, —SO₂R⁶ᴰ, —NR⁶ᴬR⁶ᴮ, —C(O)R⁶ᶜ, —C(O)OR⁶ᶜ, —C(O)NR⁶ᴬR⁶ᴮ, —OR⁶ᴰ, —NR⁶ᴬC(O)R⁶ᶜ, —NR⁶ᴬC(O)OR⁶ᶜ, substituted or unsubstituted C₁-C₆ alkyl, or substituted or unsubstituted 2 to 6 membered heteroalkyl.

Embodiment P41. The compound of any one of embodiments P30 to P38, wherein R⁶ is independently —C(O)R⁶ᶜ, —C(O)OR⁶ᶜ, —C(O)NR⁶ᴬR⁶ᴮ, —OR⁶ᴰ, —NR⁶ᴬC(O)R⁶ᶜ, —NR⁶ᴬC(O)OR⁶ᶜ, substituted or unsubstituted C₁-C₆ alkyl, substituted or unsubstituted 2 to 6 membered heteroalkyl.

Embodiment P42. The compound of any one of embodiments P30 to P38, wherein R⁶ is —F, —OH, —OCH₃, —OCH₂CH₃, —CH₂OH, —CH₂OCH₃, —NHC(O)CH₃, —CH₃, —N(CH₃)₂, —CH₂NH₂, —CH₂N(CH₃)₂, —NH₂, —NHCH₃, —COOH, or —SO₂CH₃.

Embodiment P43. The compound of any one of embodiments P30 to P38, wherein R⁶ is —OH, —OCH₃, —OCH₂CH₃, —CH₂OH, or —CH₂OCH₃.

Embodiment P44. The compound of any one of embodiments P30 to P38, wherein $R^6$ is substituted or unsubstituted $C_1$-$C_8$ alkyl or substituted or unsubstituted 2 to 8 membered heteroalkyl.

Embodiment P45. The compound of any one of embodiments P30 to P38, wherein $R^6$ is $R^{35}$-substituted or unsubstituted $C_1$-$C_8$ alkyl or $R^{35}$-substituted or unsubstituted 2 to 8 membered heteroalkyl; $R^{35}$ is oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P46. The compound of any one of embodiments P30 to P38, wherein $R^6$ is

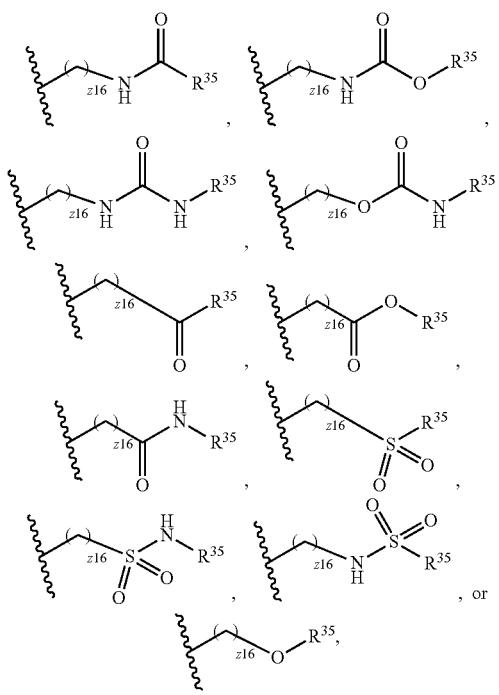

wherein z16 is an integer from 1 to 8; and
$R^{35}$ is oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P47. The compound of embodiment P30, having the formula:

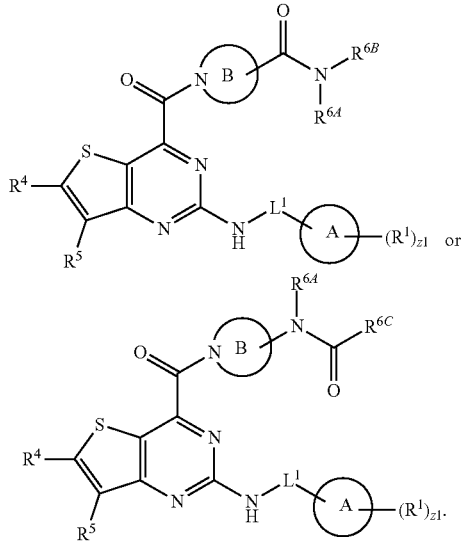

Embodiment P48. The compound of embodiment P30, having the formula:

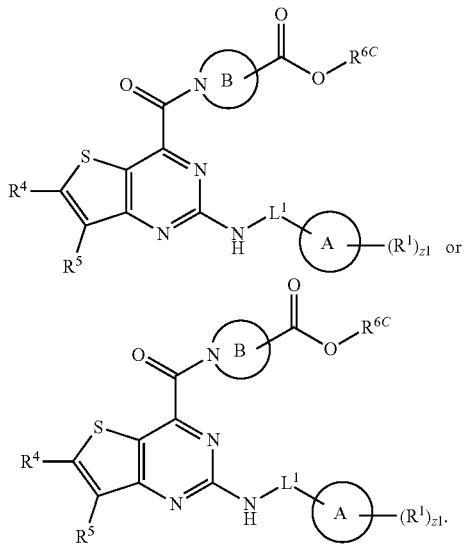

Embodiment P49. The compound of embodiment P30, having the formula:

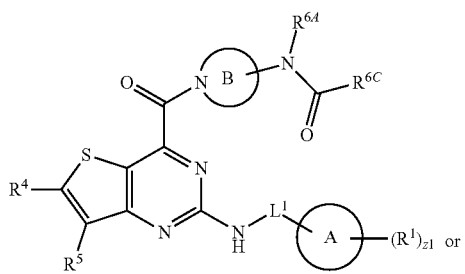

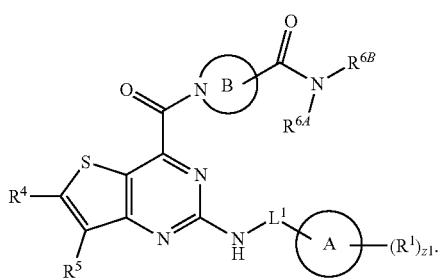
Embodiment P50. The compound of embodiment P30, having the formula:
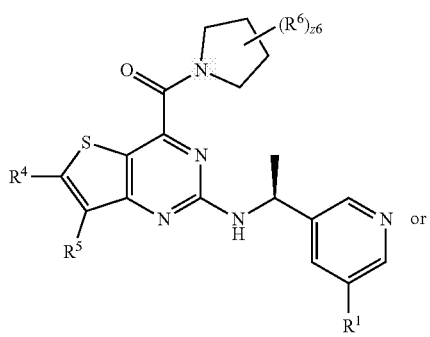
Embodiment P51. The compound of embodiment P30, having the formula:
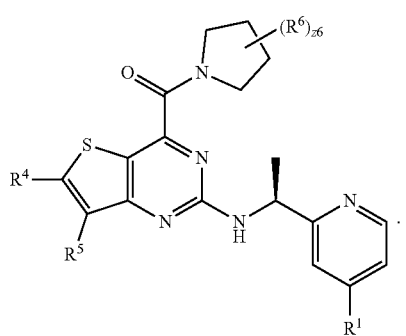
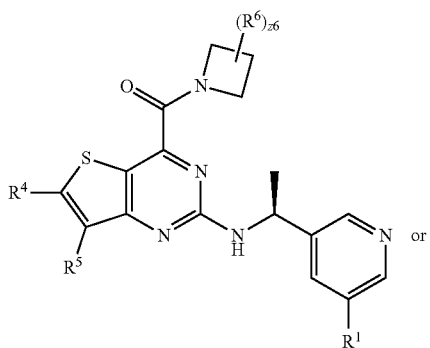
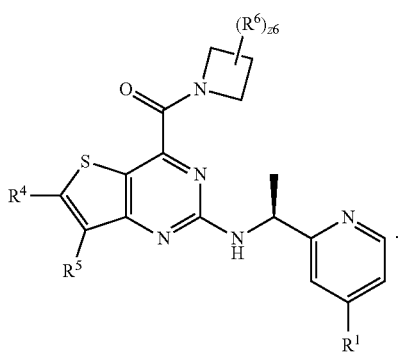
Embodiment P52. The compound of embodiment P30, having the formula:
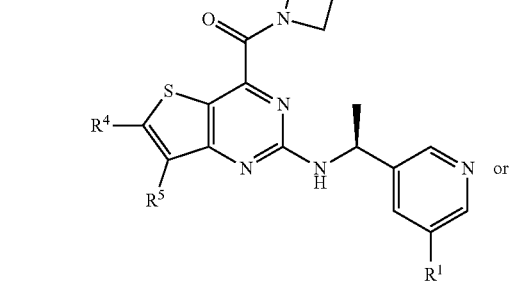
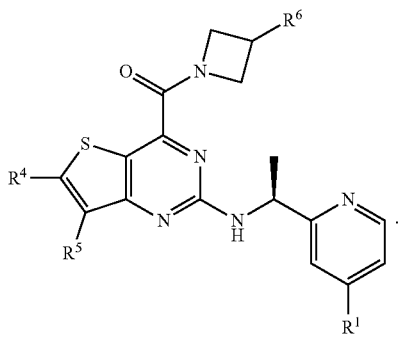
Embodiment P53. The compound of embodiment P1, having the formula:
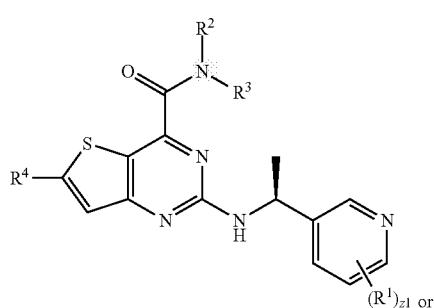

349

-continued

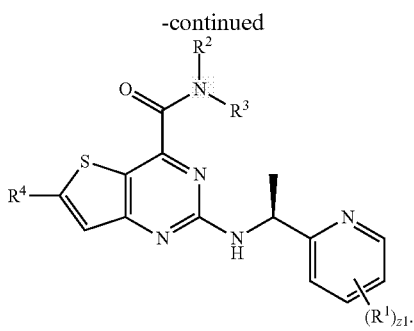

Embodiment P54. A pharmaceutical composition comprising the compound of any one of embodiments P1 to P53, and a pharmaceutically acceptable excipient.

Embodiment P55. A method of inhibiting Adenosine A2B Receptor activity and Adenosine A2A Receptor activity, said method comprising contacting the Adenosine A2B Receptor and Adenosine A2A Receptor with a compound of any one of embodiments P1 to P53.

Embodiment P56. A method of inhibiting Adenosine A2B Receptor activity, said method comprising contacting the Adenosine A2B Receptor with a compound of any one of embodiments P1 to P53.

Embodiment P57. A method of treating cancer, said method comprising administering to a subject in need thereof an effective amount of a compound of any one of embodiments P1 to P53.

Embodiment P58. The method of embodiment P57, wherein the cancer is breast cancer, lung cancer, colon cancer, bladder cancer, kidney cancer, liver cancer, pancreatic cancer, melanoma, leukemia, lymphoma, or prostate cancer.

Additional Embodiments

Embodiment 1. A compound having the formula:

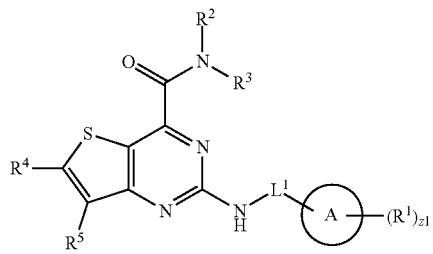

wherein
$L^1$ is substituted or unsubstituted $C_1$-$C_3$ alkylene, or substituted or unsubstituted 2 to 3 membered heteroalkylene;
Ring A is aryl or heteroaryl;
$R^1$ is independently halogen, —$CX^1_3$, —$CH^1_2$, —$CH_2X^1$, —$OCX^1_3$, —$OCH_2X^1$, —$OCHX^1_2$, —CN, —$SR^{1D}$, —$NR^{1A}R^{1B}$, —$C(O)R^{1C}$, —$C(O)OR^{1C}$, —$C(O)NR^{1A}R^{1B}$, —$OR^{1D}$, —$NR^{1A}C(O)R^{1C}$, —$NR^{1A}C(O)OR^{1C}$, —$SO_2R^{1D}$, —$SO_2NR^{1A}R^{1B}$, —$NR^{1A}SO_2R^{1D}$, substituted or unsubstituted alkyl, or substituted or unsubstituted heteroalkyl;
z1 is an integer from 0 to 5;
$R^2$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ and $R^3$ may optionally be joined to form a substituted or unsubstituted heterocycloalkyl;

$R^4$ is independently hydrogen, halogen, —$CX^4_3$, —$CHX^4_2$, —$CH_2X^4$, —$OCX^4_3$, —$OCH_2X^4$, —$OCHX^4_2$, —CN, —$SR^{4D}$, —$NR^{4A}R^{4B}$, —$C(O)R^{4C}$, —$C(O)OR^{4C}$, —$C(O)NR^{4A}R^{4B}$, —$OR^{4D}$, —$NR^{4A}C(O)R^{4C}$, —$NR^{4A}C(O)OR^{4C}$, substituted or unsubstituted alkyl, or substituted or unsubstituted heteroalkyl;

$R^5$ is independently hydrogen, halogen, —$CX^5_3$, —$CHX^5_2$, —$CH_2X^5$, —$OCX^5_3$, —$OCH_2X^5$, —$OCHX^5_2$, —CN, —$SR^{5D}$, —$NR^{5A}R^{5B}$, —$C(O)R^{5C}$, —$C(O)OR^{5C}$, —$C(O)NR^{5A}R^{5B}$, —$OR^{5D}$, —$NR^{5A}C(O)R^{5C}$, —$NR^{5A}C(O)OR^{5C}$, substituted or unsubstituted alkyl, or substituted or unsubstituted heteroalkyl;

each $R^{1A}$, $R^{1B}$, $R^{1C}$, $R^{1D}$, $R^{4A}$, $R^{4B}$, $R^{4C}$, $R^{4D}$, $R^{5A}$, $R^{5B}$, $R^{5C}$, and $R^{5D}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, unsubstituted alkyl, unsubstituted heteroalkyl, unsubstituted cycloalkyl, unsubstituted heterocycloalkyl, unsubstituted aryl, or unsubstituted heteroaryl;

$R^{1B}$ and $R^{1B}$ substituents bonded to the same nitrogen atom may optionally be joined to form a substituted or unsubstituted heterocycloalkyl;

$R^{4B}$ and $R^{4B}$ substituents bonded to the same nitrogen atom may optionally be joined to form a substituted or unsubstituted heterocycloalkyl;

$R^{5B}$ and $R^{5B}$ substituents bonded to the same nitrogen atom may optionally be joined to form a substituted or unsubstituted heterocycloalkyl;

each $X^1$, $X^4$, and $X^5$ is independently —F, —Cl, —Br, or —I; and wherein the compound is not

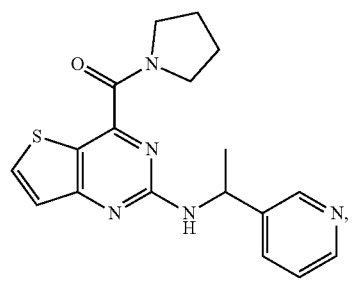

351
-continued
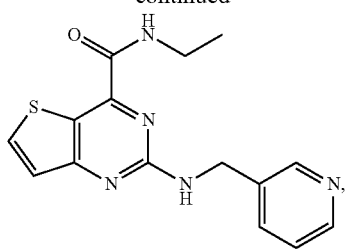
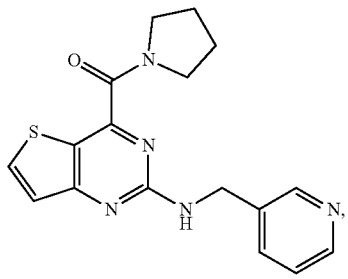
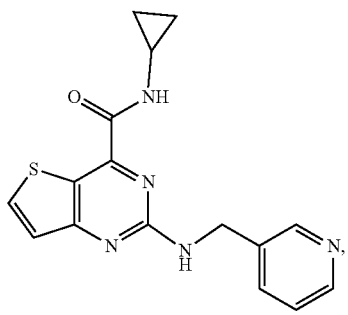
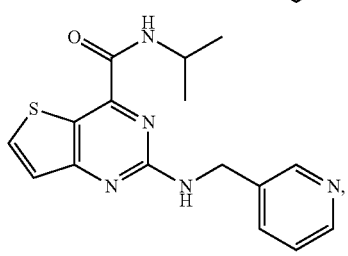
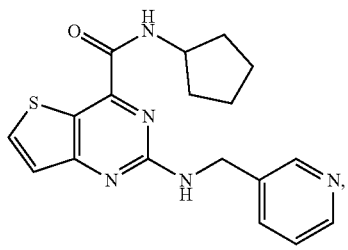
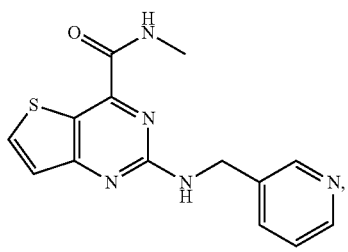
352
-continued
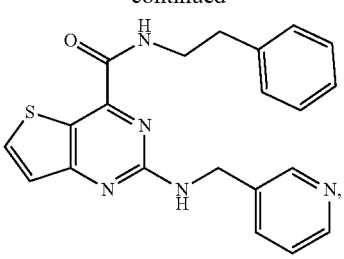
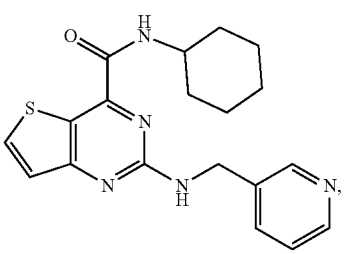
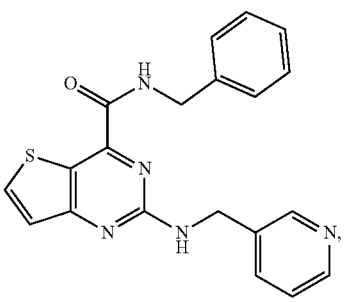
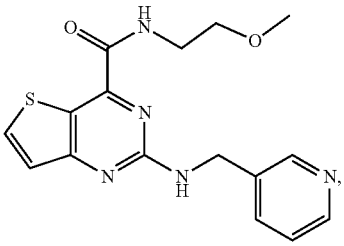
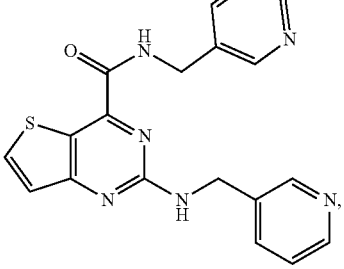
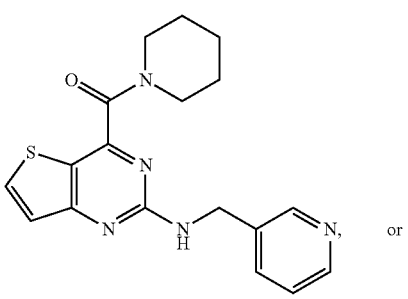
or

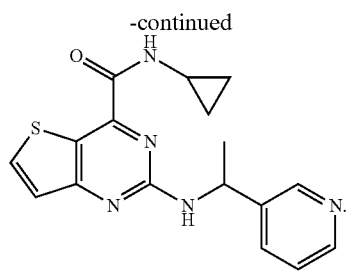

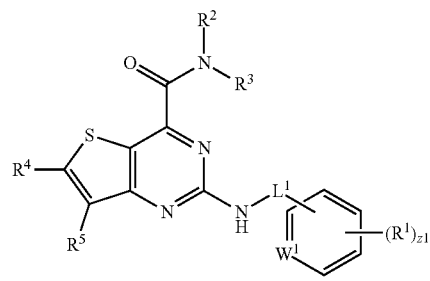

wherein $W^1$ is CH or N.

Embodiment 17. The compound of any one of embodiments 1 to 11, having the formula:

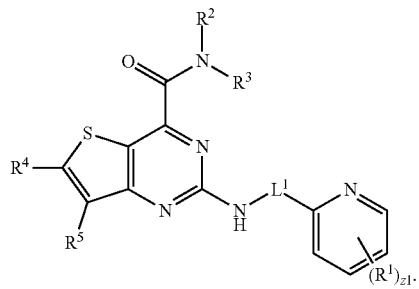

Embodiment 18. The compound of any one of embodiments 1 to 11, having the formula:

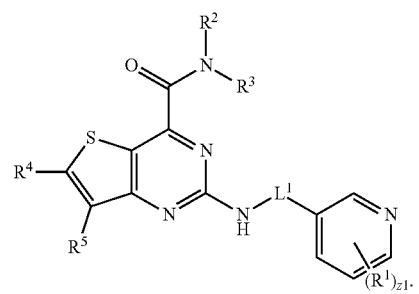

Embodiment 19. The compound of any one of embodiments 1 to 11, having the formula:

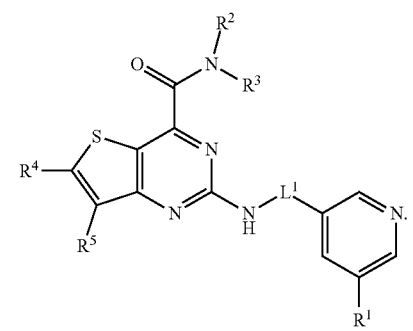

Embodiment 20. The compound of any one of embodiments 1 to 19, wherein $L^1$ is substituted or unsubstituted $C_1$-$C_3$ alkylene.

Embodiment 2. The compound of embodiment 1, wherein when $R^2$ and $R^3$ form an unsubstituted heterocycloalkyl and z1 is 0, $R^4$ is not hydrogen;

when $R^2$ or $R^3$ is hydrogen and $L^1$ is unsubstituted methylene, $R^4$ is not hydrogen; or when $R^2$ is hydrogen, $R^3$ is not unsubstituted cyclopropyl.

Embodiment 3. The compound of embodiments 1 or 2, wherein $R^2$ is hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 4. The compound of embodiments 1 or 2, wherein $R^2$ is substituted or unsubstituted $C_1$-$C_6$ alkyl.

Embodiment 5. The compound of embodiments 1 or 2, wherein $R^2$ is substituted or unsubstituted $C_3$-$C_6$ cycloalkyl.

Embodiment 6. The compound of embodiment 1, wherein $R^2$ is hydrogen.

Embodiment 7. The compound of any one of embodiments 1 to 6, wherein $R^3$ is hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 8. The compound of any one of embodiments 1 to 6, wherein $R^3$ is substituted or unsubstituted $C_1$-$C_6$ alkyl.

Embodiment 9. The compound of any one of embodiments 1 to 6, wherein $R^3$ is substituted or unsubstituted $C_3$-$C_6$ cycloalkyl.

Embodiment 10. The compound of any one of embodiments 1 to 6, wherein $R^3$ is hydrogen.

Embodiment 11. The compound of embodiment 1, wherein $R^2$ and $R^3$ are joined to form a substituted or unsubstituted heterocycloalkyl.

Embodiment 12. The compound of any one of embodiments 1 to 11, wherein Ring A is phenyl or 5 to 6 membered heteroaryl.

Embodiment 13. The compound of any one of embodiments 1 to 11, wherein Ring A is phenyl, pyridyl, pyrazolyl, imidazolyl, oxazolyl, isoxazolyl, thiazolyl, furanyl, pyrrolyl, thienyl, pyrazinyl, pyridazinyl, or pyrimidinyl.

Embodiment 14. The compound of any one of embodiments 1 to 11, wherein Ring A is phenyl or pyridyl.

Embodiment 15. The compound of any one of embodiments 1 to 11, wherein Ring A is pyridyl.

Embodiment 16. The compound of any one of embodiments 1 to 11, having the formula:

Embodiment 21. The compound of any one of embodiments 1 to 19, wherein $L^1$ is substituted or unsubstituted methylene.

Embodiment 22. The compound of any one of embodiments 1 to 21, wherein $R^4$ is hydrogen, halogen, —$CX^4_3$, —$CHX^4_2$, —$CH_2X^4$, —$OCX^4_3$, —$OCH_2X^4$, —$OCHX^4_2$, —CN, —$SR^{4D}$, —$NR^{4A}R^{4B}$, or substituted or unsubstituted $C_1$-$C_6$ alkyl.

Embodiment 23. The compound of any one of embodiments 1 to 21, wherein $R^4$ is hydrogen, halogen, —$CX_3$, —$NR^{4A}R^{4B}$, or substituted or unsubstituted $C_1$-$C_6$ alkyl.

Embodiment 24. The compound of any one of embodiments 1 to 21, wherein $R^4$ is hydrogen, halogen, —$CF_3$, —$NH_2$, —$NH(CH_3)$ or unsubstituted $C_1$-$C_6$ alkyl.

Embodiment 25. The compound of any one of embodiments 1 to 21, wherein $R^4$ is hydrogen or unsubstituted methyl.

Embodiment 26. The compound of any one of embodiments 1 to 25, wherein $R^5$ is hydrogen, halogen, —$CX^5_3$, —$CHX^5_2$, —$CH_2X^5$, —$OCX^5_3$, —$OCH_2X^5$, —$OCHX^5_2$, —CN, —$SR^{5D}$, —$NR^{5A}R^{5B}$, or substituted or unsubstituted $C_1$-$C_6$ alkyl.

Embodiment 27. The compound of any one of embodiments 1 to 25, wherein $R^5$ is hydrogen, halogen, —$CX_3$, —$NR^{5A}R^{5B}$, or substituted or unsubstituted $C_1$-$C_6$ alkyl.

Embodiment 28. The compound of any one of embodiments 1 to 25, wherein $R^5$ is hydrogen, halogen, —$CF_3$, —$NH_2$, —$NH(CH_3)$ or unsubstituted $C_1$-$C_6$ alkyl.

Embodiment 29. The compound of any one of embodiments 1 to 25, wherein $R^5$ is hydrogen or unsubstituted methyl.

Embodiment 30. The compound of any one of embodiments 1, or 11 to 29 having the formula:

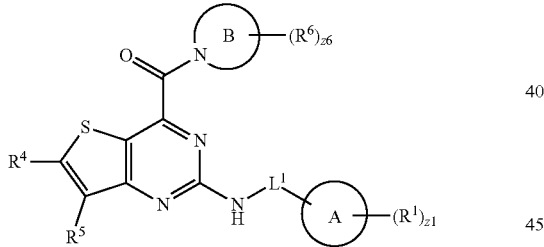

wherein Ring B is heterocycloalkyl; $R^6$ is independently halogen, —$CX^6_3$, —$CHX^6_2$, —$CH_2X^6$, —$OCX^6_3$, —$OCH_2X^6$, —$OCHX^6_2$, —CN, —$SR^{6D}$, —$SO_2R^{6D}$, —$NR^{6A}R^{6B}$, —$C(O)R^{6C}$, —$C(O)OR^{6C}$, —$C(O)NR^{6A}R^{6B}$, —$C(O)NR^{6A}OR^{6B}$, —$OR^{6D}$, —$NR^{6A}C(O)R^{6C}$, —$NR^{6A}C(O)OR^{6C}$, substituted or unsubstituted alkyl, or substituted or unsubstituted heteroalkyl;

z6 is an integer from 0 to 10;

each $R^{6A}$, $R^{6B}$, $R^{6C}$, and $R^{6D}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{6A}$ and $R^{6B}$ substituents bonded to the same nitrogen atom may optionally be joined to form a substituted or unsubstituted heterocycloalkyl; and $X^6$ is independently —F, —Cl, —Br, or —I.

Embodiment 31. The compound of embodiment 30, having the formula:

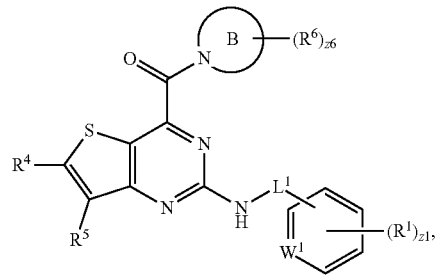

wherein $W^1$ is CH or N.

Embodiment 32. The compound of embodiment 30, having the formula:

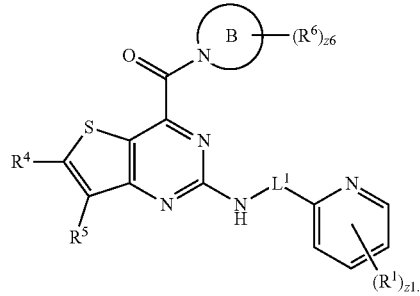

Embodiment 33. The compound of embodiment 30, having the formula:

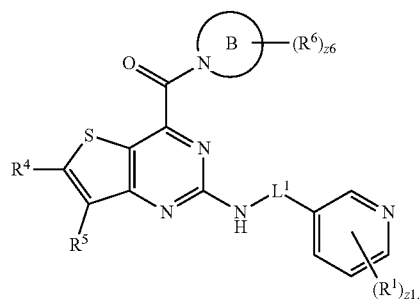

Embodiment 34. The compound of embodiment 30, having the formula:

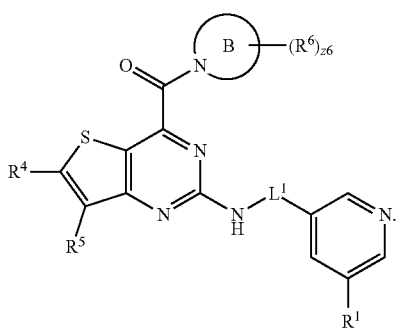

Embodiment 35. The compound of any one of embodiments 30 to 34, wherein Ring B is a 4 to 8 membered heterocycloalkyl.

Embodiment 36. The compound of any one of embodiments 30 to 34, wherein Ring B is a 4 to 6 membered heterocycloalkyl.

Embodiment 37. The compound of any one of embodiments 30 to 34, wherein Ring B is azetidinyl.

Embodiment 38. The compound of any one of embodiments 30 to 37, wherein z6 is 1.

Embodiment 39. The compound of any one of embodiments 30 to 38, wherein $R^6$ is independently halogen, $-CX^6{}_3$, $-CHX^6{}_2$, $-CH_2X^6$, $-OCX^6{}_3$, $-OCH_2X^6$, $-OCHX^6{}_2$, $-NR^{6A}R^{6B}$, $-C(O)R^{6C}$, substituted or unsubstituted $C_1$-$C_6$ alkyl, or substituted or unsubstituted 2 to 6 membered heteroalkyl.

Embodiment 40. The compound of any one of embodiments 30 to 38, wherein $R^6$ is independently halogen, $-CX^6{}_3$, $-CHX^6{}_2$, $-CH_2X^6$, $-OCX^6{}_3$, $-OCH_2X^6$, $-OCHX^6{}_2$, $-CN$, $-SR^{6D}$, $-SO_2R^{6D}$, $-NR^{6A}R^{6B}$, $-C(O)R^{6C}$, $-C(O)OR^{6C}$, $-C(O)NR^{6A}R^{6B}$, $-C(O)NR^{6A}OR^{6B}$, $-OR^{6D}$, $-NR^{6A}C(O)R^{6C}$, $-NR^{6A}C(O)OR^{6C}$, substituted or unsubstituted $C_1$-$C_6$ alkyl, or substituted or unsubstituted 2 to 6 membered heteroalkyl.

Embodiment 41. The compound of any one of embodiments 30 to 38, wherein $R^6$ is independently $-C(O)R^{6C}$, $-C(O)OR^{6C}$, $-C(O)NR^{6A}R^{6B}$, $-OR^{6D}$, $-NR^{6A}C(O)R^{6C}$, $-NR^{6A}C(O)OR^{6C}$, substituted or unsubstituted $C_1$-$C_6$ alkyl, substituted or unsubstituted 2 to 6 membered heteroalkyl.

Embodiment 42. The compound of any one of embodiments 30 to 38, wherein $R^6$ is $-F$, $-OH$, $-OCH_3$, $-OCH_2CH_3$, $-CH_2OH$, $-CH_2OCH_3$, $-NHC(O)CH_3$, $-CH_3$, $-N(CH_3)_2$, $-CH_2NH_2$, $-CH_2N(CH_3)_2$, $-NH_2$, $-NHCH_3$, $-COOH$, or $-SO_2CH_3$.

Embodiment 43. The compound of any one of embodiments 30 to 38, wherein $R^6$ is $-OH$, $-OCH_3$, $-OCH_2CH_3$, $-CH_2OH$, or $-CH_2OCH_3$.

Embodiment 44. The compound of any one of embodiments 30 to 38, wherein $R^6$ is substituted or unsubstituted $C_1$-$C_8$ alkyl or substituted or unsubstituted 2 to 8 membered heteroalkyl.

Embodiment 45. The compound of any one of embodiments 30 to 38, wherein $R^6$ is $R^{35}$-substituted or unsubstituted $C_1$-$C_8$ alkyl or $R^{35}$-substituted or unsubstituted 2 to 8 membered heteroalkyl; $R^{35}$ is oxo, halogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 46. The compound of any one of embodiments 30 to 38, wherein

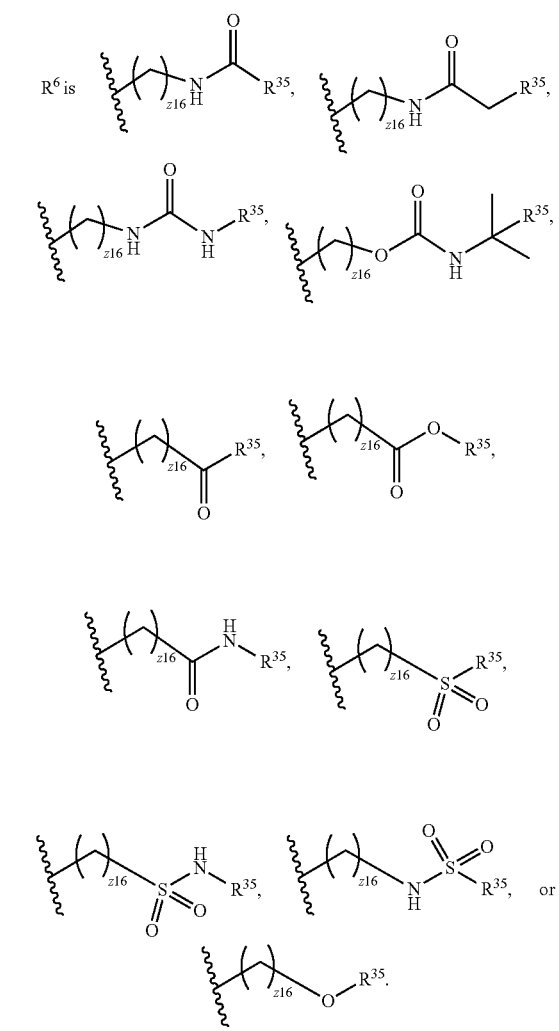

wherein z16 is an integer from 1 to 8; and
$R^{35}$ is oxo, halogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 47. The compound of embodiment 30, having the formula:

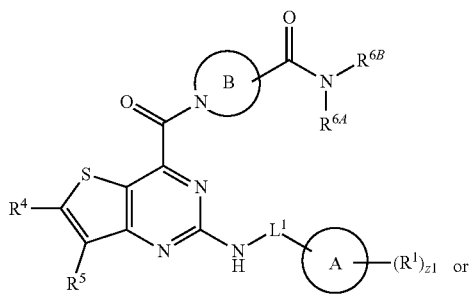
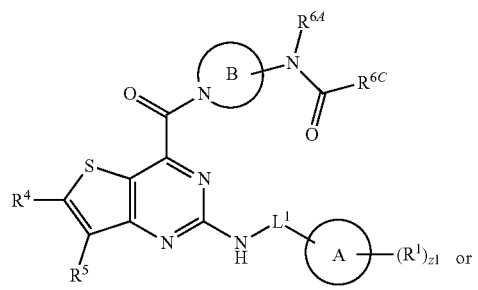
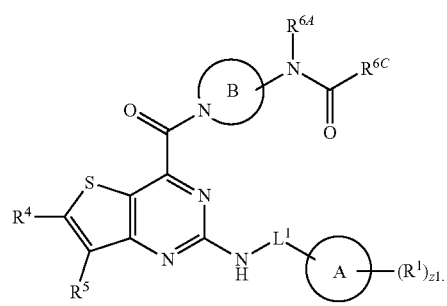
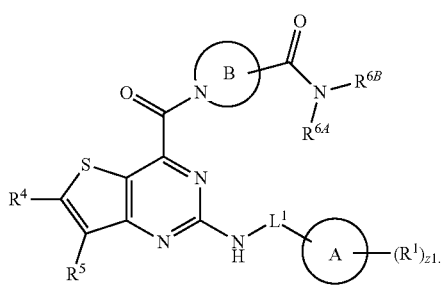
Embodiment 48. The compound of embodiment 30, having the formula:
Embodiment 50. The compound of embodiment 30, having the formula:
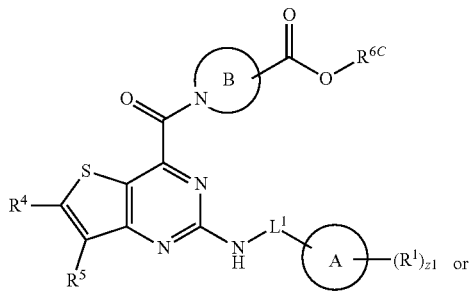
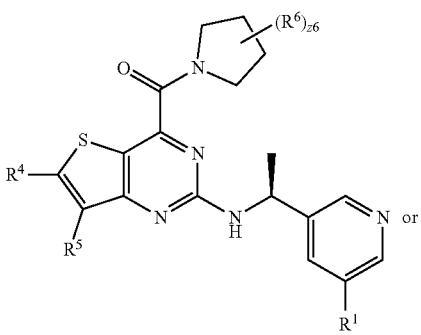
Embodiment 49. The compound of embodiment 30, having the formula:
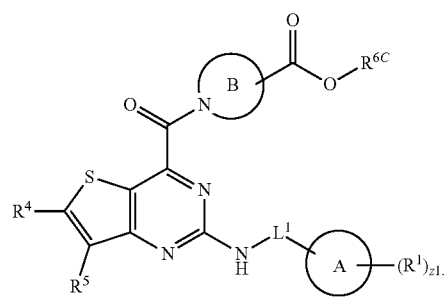
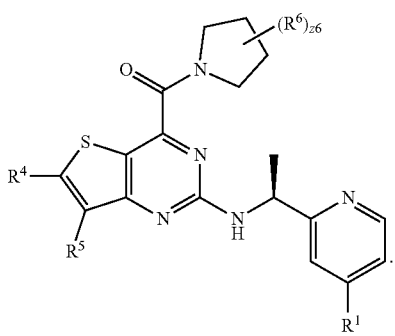
Embodiment 51. The compound of embodiment 30, having the formula:

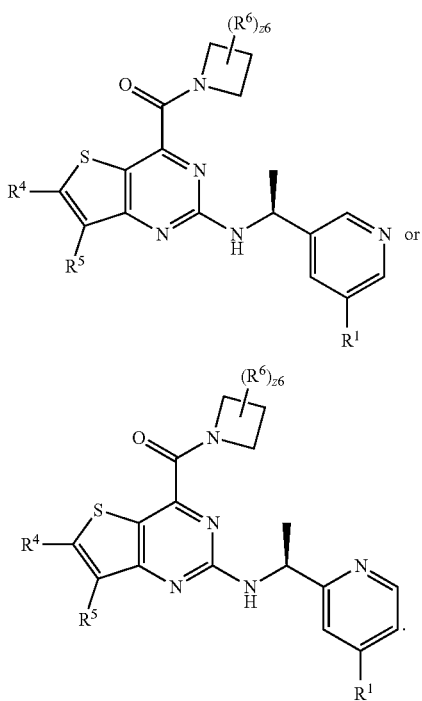

Embodiment 52. The compound of embodiment 30, having the formula:

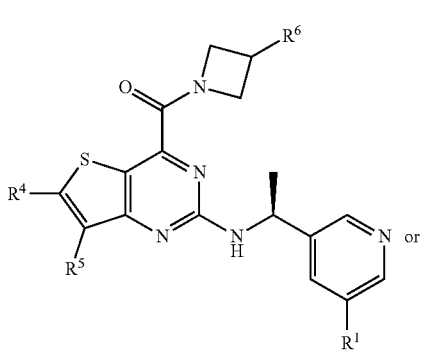

Embodiment 53. The compound of embodiment 30, having the formula:

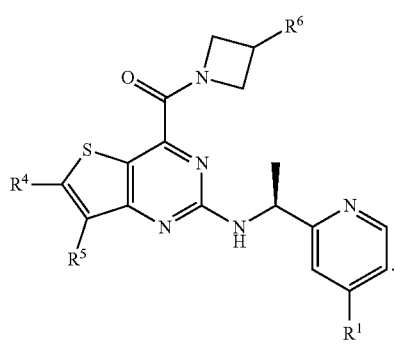

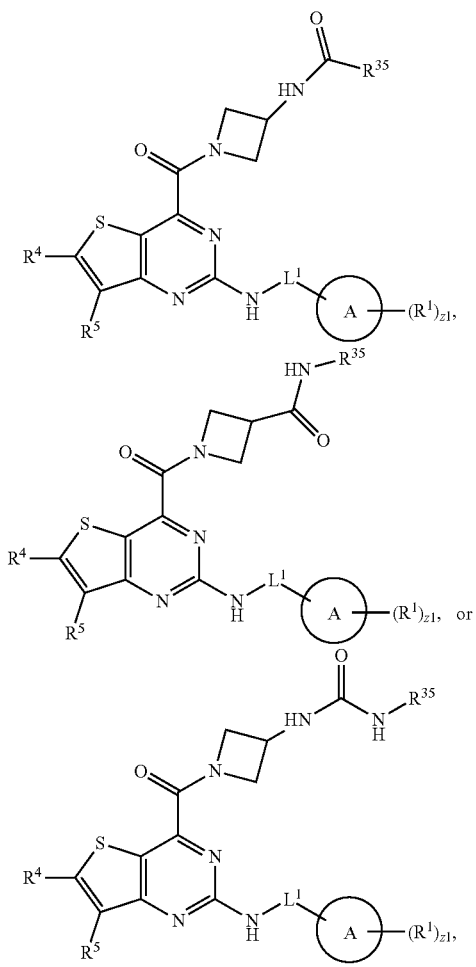

wherein $R^{35}$ is oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 54. The compound of embodiment 53, wherein $R^{35}$ is substituted or unsubstituted heteroalkyl, or substituted or unsubstituted heterocycloalkyl.

Embodiment 54. The compound of embodiment 53, wherein R is:

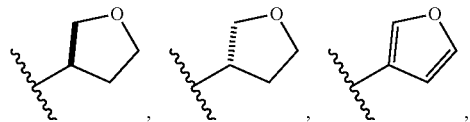

,

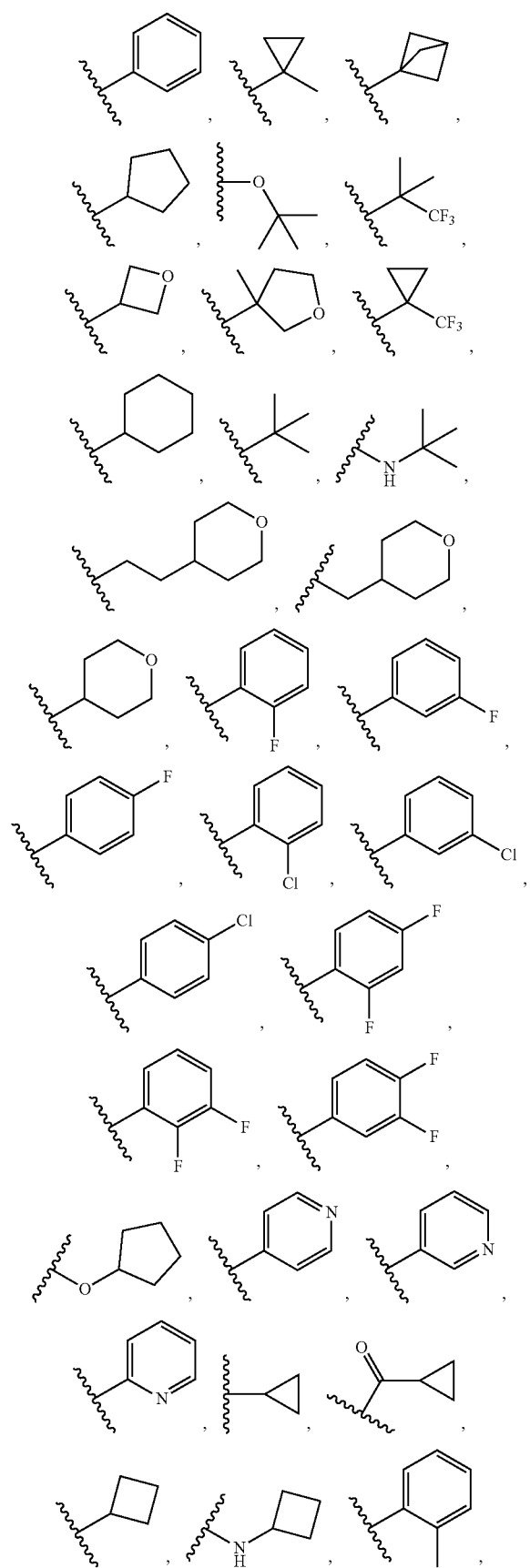
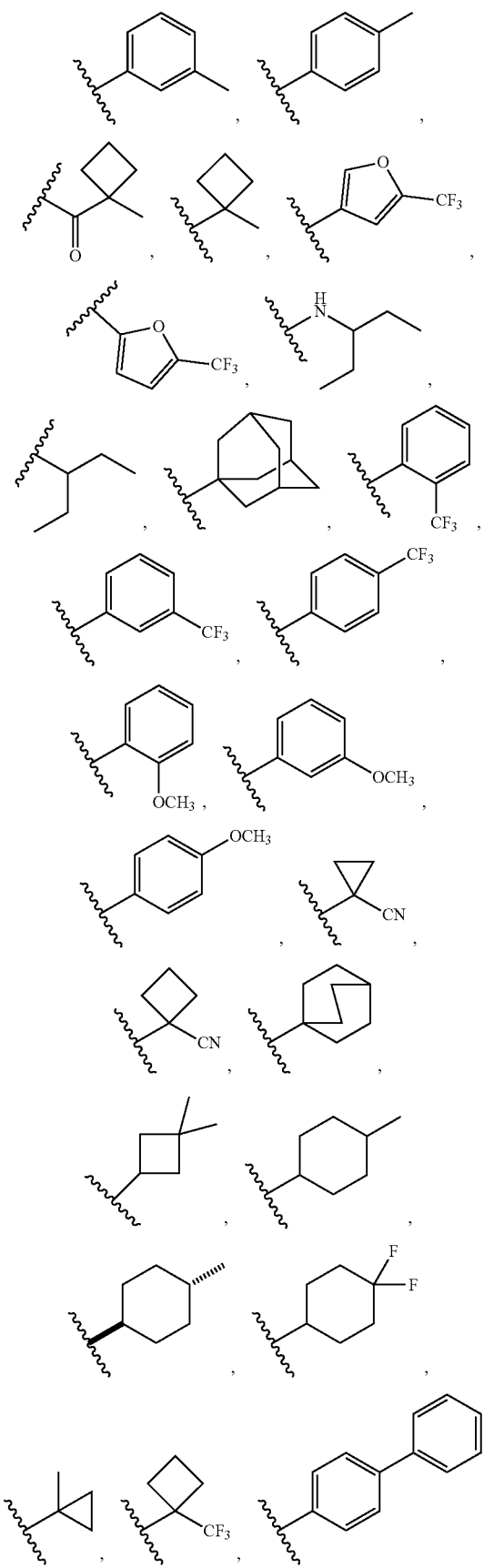

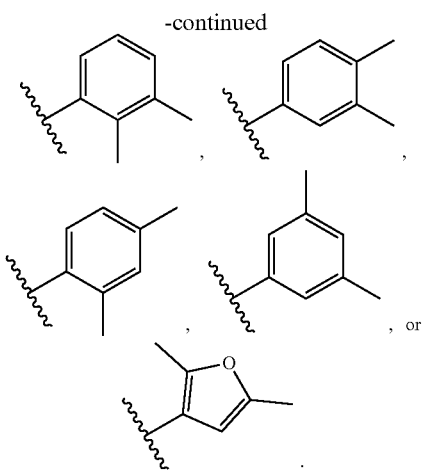

Embodiment 55. The compound of embodiment 1, having the formula:

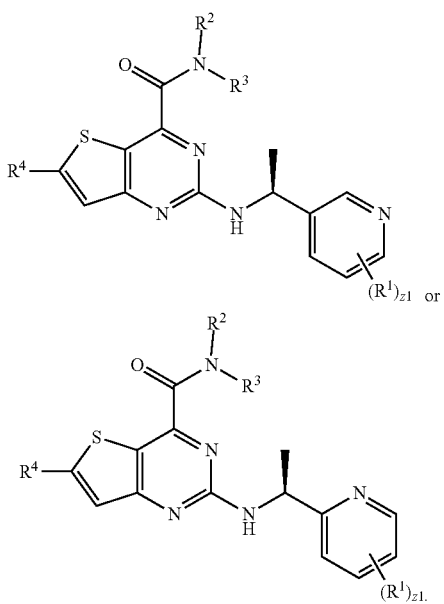

Embodiment 56. A pharmaceutical composition comprising the compound of any one of embodiments 1 to 55, and a pharmaceutically acceptable excipient.

Embodiment 57. A method of inhibiting Adenosine A2B Receptor activity and Adenosine A2A Receptor activity, said method comprising contacting the Adenosine A2B Receptor and Adenosine A2A Receptor with a compound of any one of embodiments 1 to 55.

Embodiment 58. A method of inhibiting Adenosine A2B Receptor activity, said method comprising contacting the Adenosine A2B Receptor with a compound of any one of embodiments 1 to 55.

Embodiment 59. A method of treating cancer, said method comprising administering to a subject in need thereof an effective amount of a compound of any one of embodiments 1 to 55.

Embodiment 60. The method of embodiment 57, wherein the cancer is breast cancer, lung cancer, colon cancer, bladder cancer, kidney cancer, liver cancer, pancreatic cancer, melanoma, leukemia, lymphoma, or prostate cancer.

Embodiment 61. A method of treating a neurodegenerative disease, said method comprising administering to a subject in need thereof an effective amount of a compound of any one of embodiments 1 to 55.

Embodiment 62. A method of treating a fibrotic disorder, said method comprising administering to a subject in need thereof an effective amount of a compound of any one of embodiments 1 to 55.

Embodiment 63. The method of embodiment 62, wherein the fibrotic disorder is pulmonary fibrosis.

Embodiment 64. The method of embodiment 62, wherein the fibrotic disorder is pulmonary fibrosis.

EXAMPLES

Unless otherwise stated, all compounds were obtained from commercial sources or were prepared using the methods and experimental procedures described herein. The following Abbreviations are used to refer to various reagents and solvents: Ac$_2$O: Acetic anhydride; AcOH: Acetic acid; DMAP: 4-Dimethylaminopyridine; DCM: Dichloromethane; DIEA: N,N-Diisopropylethylamine; DMF: N,N-Dimethylformamide; DMSO: Dimethylsulfoxide; EDCI: N-(3-Dimethylaminopropyl)-N'-ethylcarbodiimide hydrochloride; HOBt: 1-Hydroxybenzotriazole hydrate; HATU: 1-[Bis(dimethylamino)methylene]-1H-1,2,3-triazo[4,5-b]pyridinium 3-oxid hexafluorophosphate; LCMS: Liquid Chromatography Mass Spectrometry; MeOH: Methanol; NMP: N-Methyl-2-pyrrolidone; NMR: Nuclear magnetic resonance; TBS: t-Butyldimethylsilyl; TEA: Triethylamine; TFA: Trifluoroacetic acid; THF: Tetrahydrofuran; Tf$_2$O: Trifluoromethanesulfonic anhydride; TLC: Thin Layer Chromatography Example Z1. N—((S)-1-(Pyridin-3-yl)ethyl)-2-(((S)-1-(pyridin-3-yl)ethyl)amino)thieno[3,2-d]pyrimidine-4-carboxamide

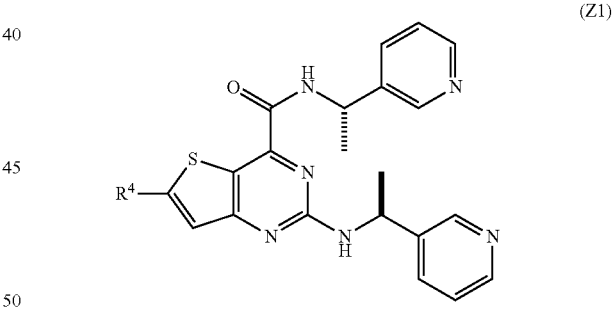

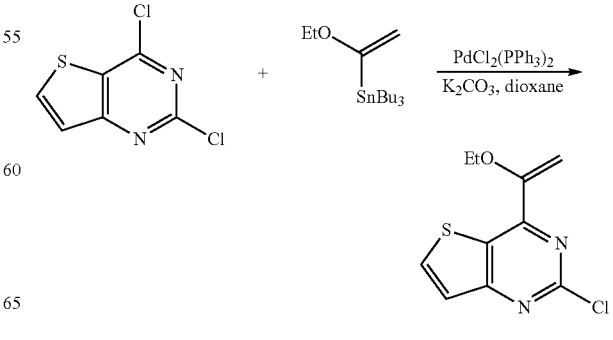

Synthesis of 2-chloro-4-(1-ethoxyvinyl)thieno[3,2-d]pyrimidine: To a solution of 2,4-dichlorothieno[3,2-d]pyrimidine (commercially obtained from AK Scientific, Union City, Calif.) (3.08 g, 15.0 mmol) in 1,4-dioxane (200 mL) was added a solution of potassium carbonate (4.15 g, 30 mmol) in water (40 mL). To the almost clear solution were added (1-ethoxyvinyl)-tributylstannane (commercially obtained from Sigma-Aldrich, St. Louis, Mo.) (5.07 mL, 15.0 mmol) and $PdCl_2(PPh_3)_2$ (526 mg, 0.75 mmol) under nitrogen atmosphere. The mixture was stirred at 100° C. for 30 min and LCMS analysis indicated completion of the reaction. After cooling to room temperature, the 1,4-dioxane was removed in vacuo and the residue was re-dissolved in DCM (100 mL) and water (50 mL) and transferred to a separating funnel. The aqueous layer was extracted with DCM, the combined organic layers were washed with water and brine, dried over $MgSO_4$, and the solvent was evaporated. The residue was purified by flash chromatography on silica gel eluting with chloroform to provide 2-chloro-4-(1-ethoxyvinyl)thieno[3,2-d]pyrimidine as an off-white solid (3.0 g, 83% yield). $^1$H NMR (400 MHz, DMSO-$d_6$) δ 1.49 (3H, t, J=7.0 Hz), 4.11 (2H, q, J=7.0 Hz), 4.88 (1H, d, J=2.5 Hz), 5.76 (1H, J=2.5 Hz), 7.59 (1H, d, J=6.0 Hz), 8.62 (1H, d, J=6.0 Hz) ppm. LCMS m/z=241.1 [M+H$^+$].

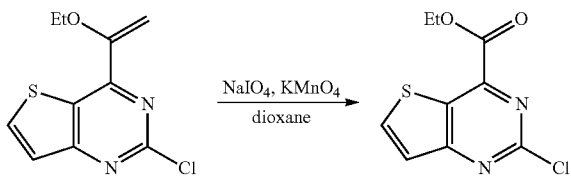

Synthesis of ethyl 2-chlorothieno[3,2-d]pyrimidine-4-carboxylate: Sodium periodate (3.42 g, 16 mmol) was suspended in water (40 mL) and sonicated until a clear solution was obtained. This solution was added to a solution of 2-chloro-4-(1-ethoxyvinyl)thieno[3,2-d]pyrimidine (1.93 g, 8 mmol) in 1,4-dioxane (80 mL). To the reaction mixture $KMnO_4$ (126 mg, 0.8 mmol) was added and the reaction mixture was stirred at room temperature for 2 h. Progress of the reaction was checked by TLC. After 2 h, remaining starting material was detected, additional $KMnO_4$ (126 mg) was added and the reaction mixture was stirred at room temperature for additional 2 h. The mixture was adjusted to pH 7-8 with sat. aqueous $K_2CO_3$ solution (1-2 mL). The precipitate was filtered off and the residue was rinsed thoroughly with DCM (4×20 mL). The combined filtrates were washed with water, dried over $MgSO_4$ and concentrated in vacuo. The residual solid was sonicated with ethyl acetate and collected by filtration to provide pure ethyl 2-chlorothieno[3,2-d]pyrimidine-4-carboxylate as white solid (1.43 g, yield 74%). The filtrate was concentrated and the residue was purified by flash chromatography on silica gel eluting with 10% to 45% ethyl acetate in hexanes to provide additional ethyl 2-chlorothieno[3,2-d]pyrimidine-4-carboxylate (147 mg, total yield 87%). $^1$H NMR (400 MHz, DMSO-$d_6$) δ 1.41 (3H, t, J=7.0 Hz), 4.50 (2H, q, J=7.0 Hz), 7.72 (1H, d, J=6.0 Hz), 8.76 (1H, d, J=6.0 Hz) ppm. LCMS: m/z=243.1 [M+H$^+$].

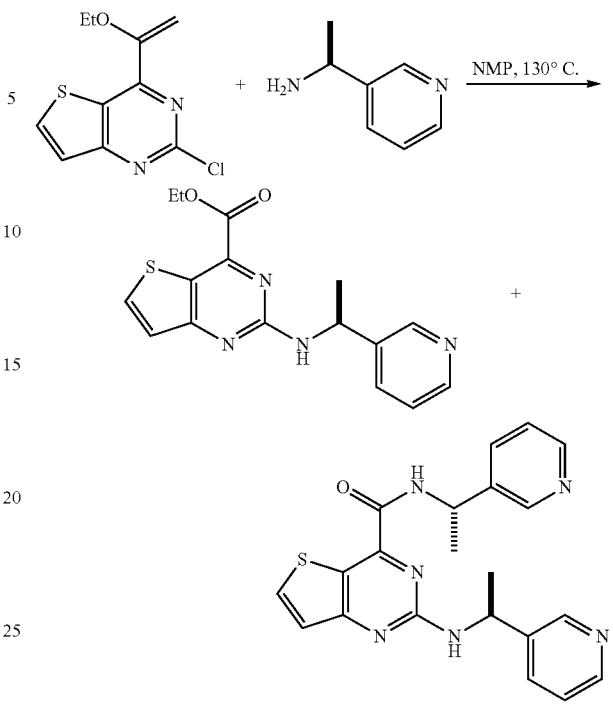

Syntheses of ethyl (S)-2-((1-(pyridin-3-yl)ethyl)amino)thieno[3,2-d]pyrimidine-4-carboxylate and N—((S)-1-(pyridin-3-yl)ethyl)-2-(((S)-1-(pyridin-3-yl)ethyl)amino)thieno[3,2-d]pyrimidine-4-carboxamide (1): To a solution of ethyl 2-chlorothieno[3,2-d]pyrimidine-4-carboxylate (420 mg, 1.73 mmol) in NMP (4 mL) was added (1S)-1-(3-pyridyl)ethanamine (commercially obtained from J&W Pharmalab, Levittown, Pa.) (0.62 mL, 5.19 mmol). The reaction mixture was stirred at 130° C. for 5 h. The reaction mixture was cooled to room temperature and diluted with ethyl acetate and washed with 25% aqueous NaCl solution, then with brine three times and dried. The solvent was evaporated and the residue was purified by flash chromatography (24 g, HP silica, Teledyne Isco) eluting with 10% to 50% solvent A (DCM/MeOH/NH$_4$OH, 100/10/1) in DCM to provide ethyl (S)-2-((1-(pyridin-3-yl)ethyl)amino)thieno[3,2-d]pyrimidine-4-carboxylate (185 mg, 33% yield) as a light yellow solid [$^1$H NMR (400 MHz, CDCl$_3$) δ 1.49 (3H, t, J=5.6 Hz), 1.63 (3H, d, J=5.6 Hz), 4.55 (2H, q, J=5.6 Hz), 5.30 (1H, m), 5.68 (1H, d, J=5.6 Hz), 7.19 (1H, d, J=4.4 Hz), 7.23 (1H, dd, J=6.4, 3.6 Hz), 7.74 (1H, dt, J=6.4, 1.6 Hz), 7.92 (1H, d, J=4.4 Hz), 8.48 (1H, dd, J=3.6, 1.6 Hz), 8.73 (1H, d, J=1.6 Hz) ppm, LCMS m/z=329.1[M+H$^+$]] and N—((S)-1-(pyridin-3-yl)ethyl)-2-(((S)-1-(pyridin-3-yl)ethyl)amino)thieno[3,2-d]pyrimidine-4-carboxamide as an yellow solid (175 mg, 25% yield). $^1$H NMR (400 MHz, CDCl$_3$) δ 1.65 (3H, d, J=6.8 Hz), 1.67 (3H, d, J=7.2 Hz), 5.15 (1H, q, J=6.8 Hz), 5.28 (1H, q, J=7.2 Hz), 5.49 (1H, d, J=6.0 Hz), 7.18 (1H, d, J=5.6 Hz), 7.21 (1H, dd, J=7.6, 4.0 Hz), 7.28 (1H, m), 7.57 (1H, m), 7.71 (1H, dt, J=8.0, 2.0 Hz), 7.91 (1H, m), 7.98 (1H, d, J=5.2 Hz), 8.48 (1H, dd, J=4.8, 1.6 Hz), 8.53 (1H, dd, J=4.8, 1.6 Hz), 8.58 (1H, m), 8.73 (1H, d, J=2.0 Hz) ppm. LCMS m/z=405.2[M+H$^+$].

369

Example Z2. (S)-Azetidin-1-yl(2-((1-(pyridin-3-yl)ethyl)amino)thieno[3,2-d]pyrimidin-4-yl)methanone (Z2)

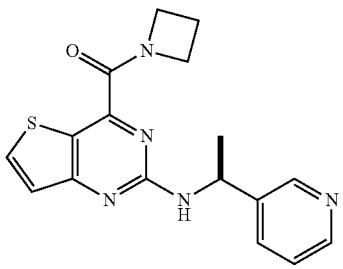 [SMILES: C[C@H](Nc1nc(C(=O)N2CCC2)c2sccc2n1)c1cccnc1]

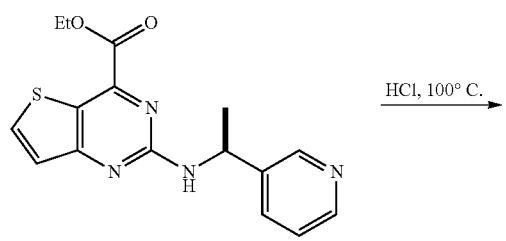

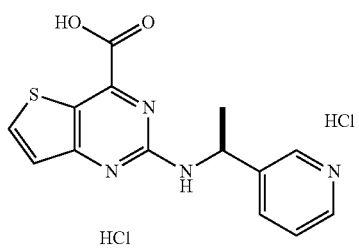

Synthesis of (S)-2-((1-(pyridin-3-yl)ethyl)amino)thieno[3,2-d]pyrimidine-4-carboxylic acid dihydrochloride: Ethyl 2-[[(1S)-1-(3-pyridyl)ethyl]amino]thieno[3,2-d]pyrimidine-4-carboxylate (100 mg, 0.30 mmol) was dissolved in 12 N HCl (6 mL) and stirred at 100° C. for 14 h. The reaction mixture was evaporated to dryness in vacuo at a bath temperature of 60° C. to provide (S)-2-((1-(pyridin-3-yl)ethyl)amino)thieno[3,2-d]pyrimidine-4-carboxylic acid as an yellow solid (112 mg) which was used in next step without further purification. LCMS m/z=301.1[M+H+].

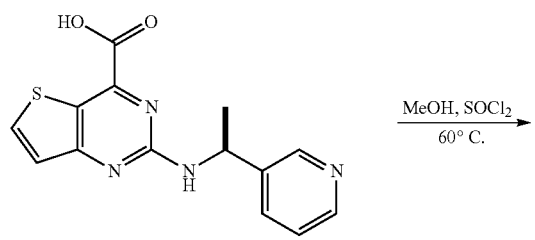

370

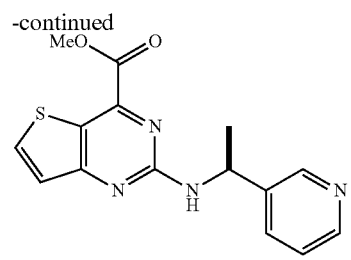

Synthesis of methyl (S)-2-((1-(pyridin-3-yl)ethyl)amino)thieno[3,2-d]pyrimidine-4-carboxylate: To a solution of 2-[[(1S)-1-(3-pyridyl)ethyl]amino]thieno[3,2-d]pyrimidine-4-carboxylic acid dihydrochloride (112 mg, 0.3 mmol) in MeOH (10 mL) was added thionyl chloride (0.220 mL, 3 mmol) at room temperature. The reaction mixture was stirred at 60° C. for 5 h. The reaction mixture was concentrated to dryness and the residue was dissolved in DCM/MeOH (10:1, 50 mL), washed with sat. NaHCO$_3$ and brine, dried over MgSO$_4$, concentrated to provide methyl (S)-2-((1-(pyridin-3-yl)ethyl)amino)thieno[3,2-d]pyrimidine-4-carboxylate as light yellow solid (26 mg, 92% yield). $^1$H NMR (400 MHz, CDCl$_3$) δ 1.63 (3H, d, J=6.8 Hz), 4.09 (3H, s), 5.30 (1H, m), 5.69 (1H, d, J=7.2 Hz), 7.20 (1H, d, J=5.6 Hz), 7.26 (1H, dd, J=8.0, 4.8 Hz), 7.76 (1H, dt, J=8.0, 1.6 Hz), 7.95 (1H, d, J=5.6 Hz), 8.48 (1H, dd, J=4.8, 1.6 Hz), 8.74 (1H, d, J=1.6 Hz) ppm. LCMS m/z=315.1[M+H+].

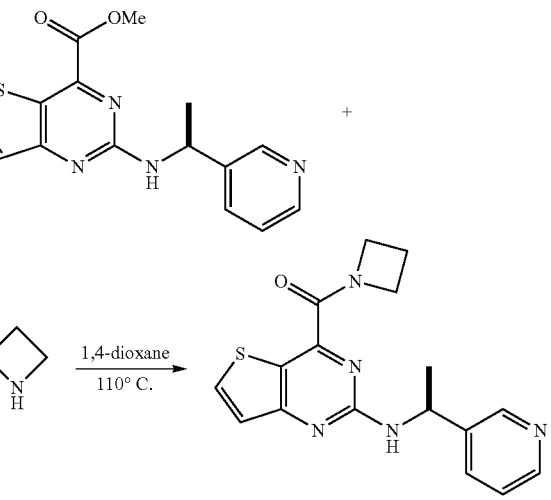

Synthesis of (S)-azetidin-1-yl(2-((1-(pyridin-3-yl)ethyl)amino)thieno[3,2-d]pyrimidin-4-yl)methanone (Z2): A solution of methyl 2-[[(1S)-1-(3-pyridyl)ethyl]amino]thieno[3,2-d]pyrimidine-4-carboxylate (15 mg, 0.05 mmol) and azetidine (64 uL, 0.1 mmol) in 1,4-dioxane (1 mL) was stirred at 110° C. for 3 h. The reaction mixture was concentrated in vacuo and the residue was purified by flash chromatography on silica gel (12 g, HP silica, Teledyne Isco) eluting with 10% to 50% solvent A (DCM:MeOH:NH$_4$OH, 100:10:1) in DCM to provide (S)-azetidin-1-yl(2-((1-(pyridin-3-yl)ethyl)amino)thieno[3,2-d]pyrimidin-4-yl)methanone as an off-white solid (15 mg, 93% yield). $^1$H NMR (400 MHz, CDCl$_3$) δ 1.63 (3H d, J=7.2 Hz), 2.33 (1H, m), 4.24 (2H, t, J=8.0 Hz), 4.42 (1H, m), 4.69 (1H, m), 5.23 (1H, quintet, J=7.2 Hz), 5.36 (1H, d, J=7.2 Hz), 7.16 (1H, d, J=5.6 Hz), 7.24 (1H, dd, J=8.0, 4.8 Hz), 7.69 (1H, d, J=4.8 Hz), 7.96 (1H, d, J=5.6 Hz), 8.50 (1H, dd, J=4.8, 0.8 Hz), 8.67 (1H, J=0.8 Hz) ppm. LCMS: m/z=340.2 [M+H⁺].

Example Z3. (S)-(3,3-Dimethylpyrrolidin-1-yl)(2-((1-(pyridin-3-yl)ethyl)amino)thieno[3,2-d]pyrimidin-4-yl)methanone (1H, dt, J=7.6, 2.0 Hz), 7.94 (1H, dd, J=5.6, 2.4 Hz), 8.49 (1H, td, J=6.8, 1.6 Hz), 8.68 (1H, t, J=2.0 Hz) ppm. LCMS: m/z=382.1 [M+H⁺].

Example Z4. N-(Pyrimidin-5-ylmethyl)-2-((pyrimidin-5-ylmethyl)amino)thieno[3,2-d]pyrimidine-4-carboxamide

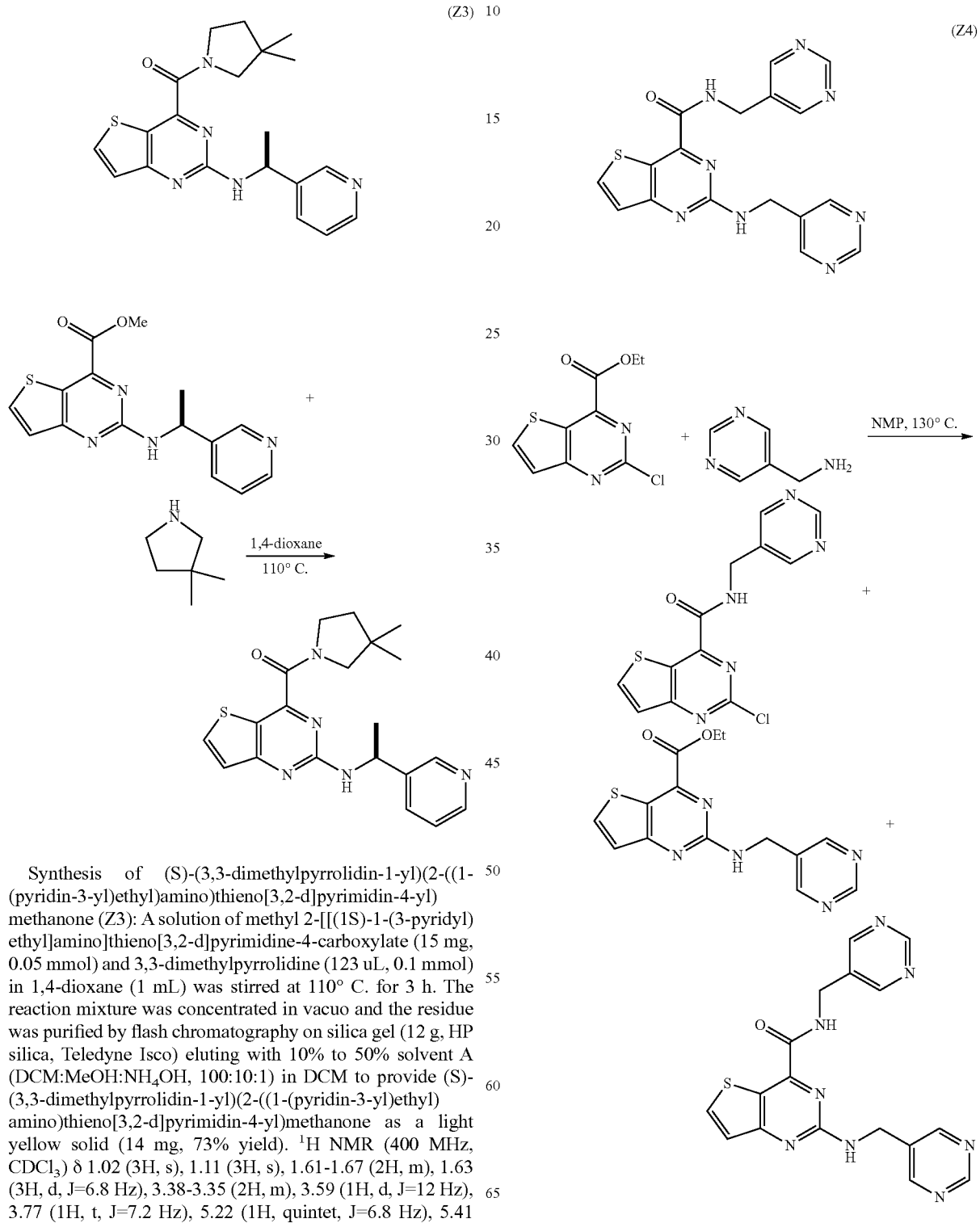

Synthesis of (S)-(3,3-dimethylpyrrolidin-1-yl)(2-((1-(pyridin-3-yl)ethyl)amino)thieno[3,2-d]pyrimidin-4-yl)methanone (Z3): A solution of methyl 2-[[(1S)-1-(3-pyridyl)ethyl]amino]thieno[3,2-d]pyrimidine-4-carboxylate (15 mg, 0.05 mmol) and 3,3-dimethylpyrrolidine (123 uL, 0.1 mmol) in 1,4-dioxane (1 mL) was stirred at 110° C. for 3 h. The reaction mixture was concentrated in vacuo and the residue was purified by flash chromatography on silica gel (12 g, HP silica, Teledyne Isco) eluting with 10% to 50% solvent A (DCM:MeOH:NH₄OH, 100:10:1) in DCM to provide (S)-(3,3-dimethylpyrrolidin-1-yl)(2-((1-(pyridin-3-yl)ethyl)amino)thieno[3,2-d]pyrimidin-4-yl)methanone as a light yellow solid (14 mg, 73% yield). ¹H NMR (400 MHz, CDCl₃) δ 1.02 (3H, s), 1.11 (3H, s), 1.61-1.67 (2H, m), 1.63 (3H, d, J=6.8 Hz), 3.38-3.35 (2H, m), 3.59 (1H, d, J=12 Hz), 3.77 (1H, t, J=7.2 Hz), 5.22 (1H, quintet, J=6.8 Hz), 5.41 (1H, d, J=6.8 Hz), 7.17 (1H, d, J=5.6 Hz), 7.22 (1H, m), 7.70

Syntheses of 2-chloro-N-(pyrimidin-5-ylmethyl)thieno[3,2-d]pyrimidine-4-carboxamide ethyl, 2-((pyrimidin-5-ylmethyl)amino)thieno[3,2-d]pyrimidine-4-carboxylate, and N-(pyrimidin-5-ylmethyl)-2-((pyrimidin-5-ylmethyl)amino)thieno[3,2-d]pyrimidine-4-carboxamide (Z4): To a solution of ethyl 2-chlorothieno[3,2-d]pyrimidine-4-carboxylate (72 mg, 0.29 mmol) in NMP (1 mL) was added pyrimidin-5-ylmethanamine (commercially obtained from Synthonix, Wake Forest, N.C.) (97 mg, 0.89 mmol). The reaction mixture was stirred at 130° C. for 3 h. The reaction mixture was cooled to room temperature, diluted with ethyl acetate and washed with 25% aqueous NaCl solution, then with brine three times and dried. The solvent was evaporated and the residue was purified by flash chromatography (24 g, HP silica, Teledyne Isco) eluting with 2% to 100% solvent A (DCM/MeOH/NH$_4$OH, 100/10/1) in DCM to provide 2-chloro-N-(pyrimidin-5-ylmethyl)thieno[3,2-d]pyrimidine-4-carboxamide (18 mg, 18% yield) as a light yellow solid (LCMS m/z=306.0 [M+H$^+$]), ethyl 2-((pyrimidin-5-ylmethyl)amino)thieno[3,2-d]pyrimidine-4-carboxylate (35 mg, 37% yield) as a light yellow solid (LCMS m/z=316.1 [M+H$^+$]), and N-(pyrimidin-5-ylmethyl)-2-((pyrimidin-5-ylmethyl)amino)thieno[3,2-d]pyrimidine-4-carboxamide (22.7 mg, 20% yield) as a light yellow solid (LCMS m/z=379.1[M+H$^+$]).

Example Z5. (2-((Pyrimidin-5-ylmethyl)amino)thieno[3,2-d]pyrimidin-4-yl)(pyrrolidin-1-yl)methanone

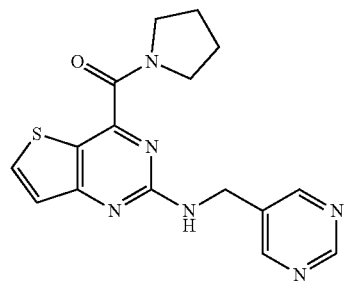 [SMILES: O=C(c1nc(NCc2cncnc2)nc2ccsc12)N1CCCC1]

(Z5)

Synthesis of 2-((pyrimidin-5-ylmethyl)amino)thieno[3,2-d]pyrimidine-4-carboxylic acid dihydrochloride: Ethyl 2-((pyrimidin-5-yl)ethyl)amino)thieno[3,2-d]pyrimidine-4-carboxylate (17 mg, 0.054 mmol) was dissolved in 12 N HCl (6 mL) and stirred at 100° C. for 14 h. The reaction mixture was evaporated to dryness in vacuo at a bath temperature of 60° C. to provide 2-((pyrimidin-5-ylmethyl)amino)thieno[3,2-d]pyrimidine-4-carboxylic acid dihydrochloride as an yellow solid (20 mg) which was used in next step without further purification. LCMS m/z=288.0 [M+H$^+$].

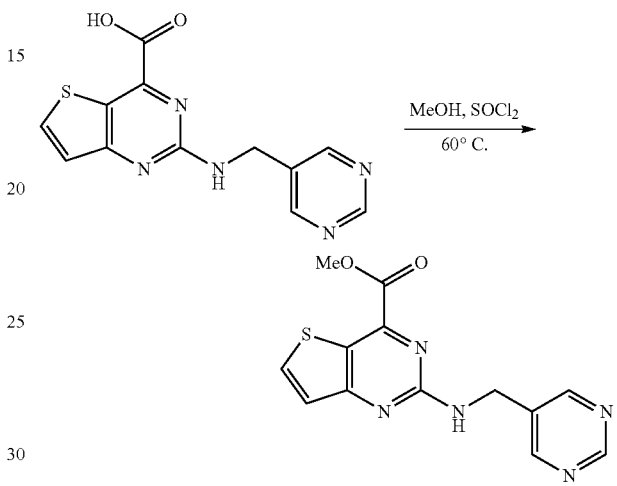

Synthesis of methyl 2-((pyrimidin-5-ylmethyl)amino)thieno[3,2-d]pyrimidine-4-carboxylate: To a solution of 2-((pyrimidin-5-ylmethyl)amino)thieno[3,2-d]pyrimidine-4-carboxylic acid dihydrochloride (20 mg, 0.067 mmol) in MeOH (10 mL) was added thionyl chloride (0.07 mL, 0.67 mmol) at room temperature. The reaction mixture was stirred at 60° C. for 5 h. The reaction mixture was concentrated to dryness, the residue was dissolved in DCM/MeOH (10:1, 20 mL), washed with sat. NaHCO$_3$ and brine, dried over MgSO$_4$, and concentrated to provide methyl 2-((pyrimidin-5-ylmethyl)amino)thieno[3,2-d]pyrimidine-4-carboxylate as light yellow solid (17 mg, 101% yield). LCMS m/z=302.0 [M+H$^+$].

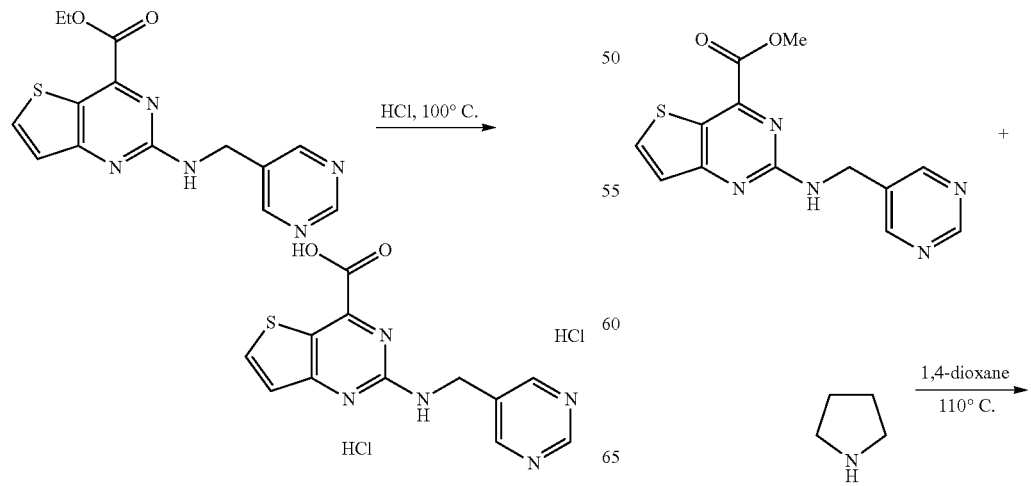

-continued

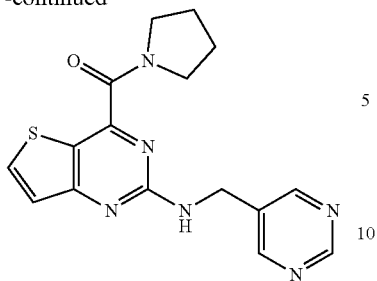

Synthesis of (2-((pyrimidin-5-ylmethyl)amino)thieno[3,2-d]pyrimidin-4-yl)(pyrrolidin-1-yl)methanone (Z5): A solution of methyl 2-((pyrimidin-5-ylmethyl)amino)thieno[3,2-d]pyrimidine-4-carboxylate (17 mg, 0.056 mmol) and pyrrolidine (47 uL, 0.56 mmol) in 1,4-dioxane (1 mL) was stirred at 110° C. for 3 h. The reaction mixture was concentrated in vacuo and the residue was purified by flash chromatography on silica gel (12 g, HP silica, Teledyne Isco) eluting with 10% to 50% solvent A (DCM:MeOH:NH$_4$OH, 100:10:1) in DCM to provide (2-((pyrimidin-5-ylmethyl)amino)thieno[3,2-d]pyrimidin-4-yl)(pyrrolidin-1-yl)methanone as light yellow solid (8.5 mg, 45% yield). $^1$H NMR (400 MHz, CDCl$_3$) δ 1.89-1.93 (4H, m), 3.71-3.74 (2H, m), 3.87 (2H, m), 4.75 (2H, d, J=6.0 Hz), 5.59 (1H, t, J=6.0 Hz), 7.22 (1H, d, J=5.6 Hz), 7.98 (1H, d, J=5.6 Hz), 8.79 (2H, s), 9.14 (1H, s) ppm. LCMS m/z=341.1 [M+H$^+$].

Example Z6. (S)-2-((1-(Pyridin-3-yl)ethyl)amino)-N-(pyrimidin-5-ylmethyl)thieno[3,2-d]pyrimidine-4-carboxamide Synthesis of (S)-2-((1-(pyridin-3-yl)ethyl)amino)-N-(pyrimidin-5-ylmethyl)thieno[3,2-d]pyrimidine-4-carboxamide (Z6): To a mixture of 2-chloro-N-(pyrimidin-5-ylmethyl)thieno[3,2-d]pyrimidine-4-carboxamide (20 mg, 0.066 mmol) and potassium carbonate (18 mg, 0.13 mmol) in NMP (2 mL) was added (1S)-1-(3-pyridyl)ethanamine (commercially obtained from J&W Pharmalab, Levittown, Pa.) (16.2 mg, 0.13 mmol). The reaction mixture was stirred at 130° C. for 5 h. The reaction mixture was cooled to room temperature and diluted with ethyl acetate and washed with 25% aqueous NaCl solution, then with brine three times and dried. The solvent was evaporated and the residue was purified by flash chromatography (24 g, HP silica, Teledyne Isco) eluting with 10% to 50% solvent A (DCM/MeOH/NH$_4$OH, 100/10/1) in DCM to provide (S)-2-((1-(pyridin-3-yl)ethyl)amino)-N-(pyrimidin-5-ylmethyl)thieno[3,2-d]pyrimidine-4-carboxamide (11.8 mg, 45% yield) as a light yellow solid. LCMS m/z=392.1 [M+H$^+$].

Example Z7. (3,3-Dimethylpyrrolidin-1-yl)(2-((pyrimidin-5-ylmethyl)amino)thieno[3,2-d]pyrimidin-4-yl)methanone

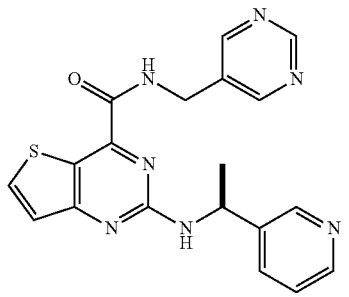 [SMILES: C[C@H](Nc1nc(C(=O)NCc2cncnc2)c2sccc2n1)c1cccnc1] (Z6)

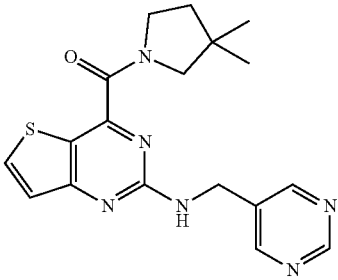 [SMILES: CC1(C)CCN(C(=O)c2nc(NCc3cncnc3)nc3ccsc23)C1] (Z7)

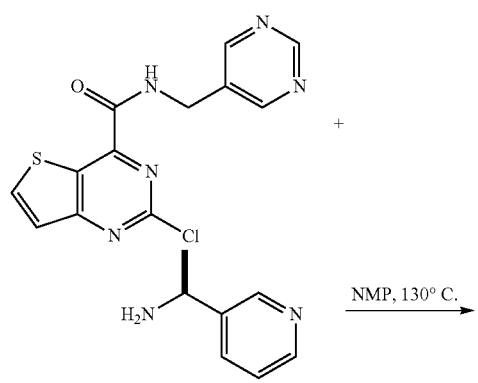

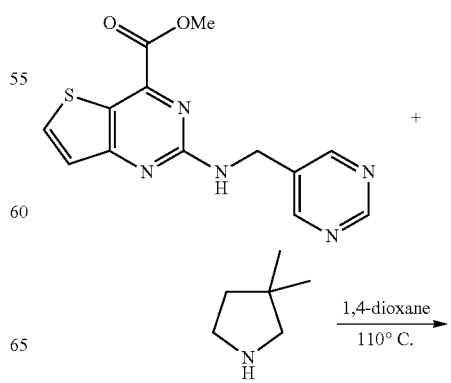

-continued

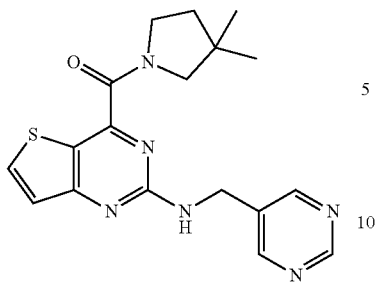

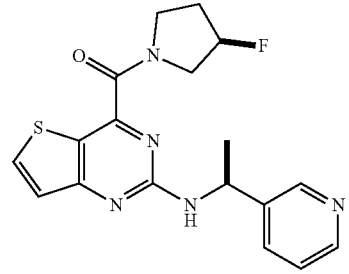 [SMILES: C[C@H](Nc1nc(C(=O)N2CC[C@@H](F)C2)c2sccc2n1)c1cccnc1]

Synthesis of (3, 3-dimethylpyrrolidin-1-yl)(2-((pyrimidin-5-ylmethyl)amino)thieno[3,2-d]pyrimidin-4-yl)methanone (Z7): A solution of methyl 2-((pyrimidin-5-ylmethyl)amino)thieno[3,2-d]pyrimidine-4-carboxylate (17 mg, 0.056 mmol) and 3,3-dimethylpyrrolidine (47 uL, 0.56 mmol) in 1,4-dioxane (1 mL) was stirred at 110° C. for 3 h. The reaction mixture was concentrated in vacuo and the residue was purified by flash chromatography on silica gel (12 g, HP silica, Teledyne Isco) eluting with 10% to 50% solvent A (DCM:MeOH:NH$_4$OH, 100:10:1) in DCM to provide (3, 3-dimethylpyrrolidin-1-yl)(2-((pyrimidin-5-ylmethyl)amino)thieno[3,2-d]pyrimidin-4-yl)methanone as light yellow solid (3.3 mg, 16% yield). LCMS m/z=369.2 [M+H$^+$].

Example Z8. ((R)-3-Fluoropyrrolidin-1-yl)(2-(((S)-1-(pyridin-3-yl)ethyl)amino)thieno[3,2-d]pyrimidin-4-yl)methanone (Z8)

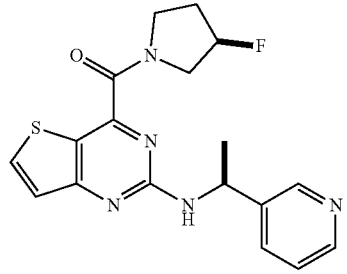

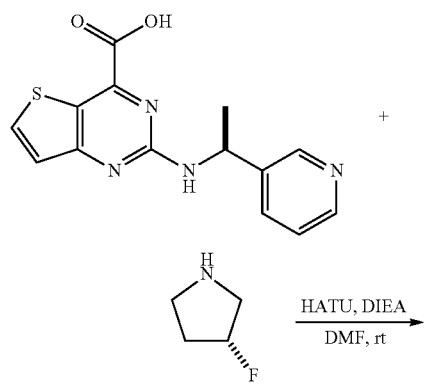

Synthesis of ((R)-3-fluoropyrrolidin-1-yl)(2-(((S)-1-(pyridin-3-yl)ethyl)amino)thieno[3,2-d]pyrimidin-4-yl) methanone (Z8): To a solution of 2-[[(1S)-1-(3-pyridyl)ethyl]amino]thieno[3,2-d]pyrimidine-4-carboxylic acid dihydrochloride (37 mg, 0.1 mmol) in DMF (2 mL) were added (3R)-3-fluoropyrrolidine hydrochloride (19 mg, 0.15 mmol), HATU (57 mg, 0.15 mmol), and DIEA (87 uL, 0.5 mmol). The mixture thus obtained was stirred at room temperature overnight. The reaction mixture was diluted with ethyl acetate and washed with 5% NaHCO$_3$, water, and brine, then dried over MgSO$_4$. The solvent was evaporated in vacuo and the residue was purified by flash chromatography on silica gel (12 g HP silica, Teledyne Isco) eluting with 10% to 50% solvent A (DCM/MeOH/NH$_4$OH, 100/10/1) in DCM to provide ((R)-3-fluoropyrrolidin-1-yl)(2-(((S)-1-(pyridin-3-yl)ethyl)amino)thieno[3,2-d]pyrimidin-4-yl)methanone (31 mg, 84% yield) as a light yellow solid. $^1$H NMR (400 MHz, CDCl$_3$) δ 1.64 (3H, d, J=7.2 Hz), 1.99 (1H, m), 2.27 (1H, m), 3.60-3.86 (2H, m), 3.97-4.15 (2H, m), 4.43 (1H, m), 5.20 (1H, m), 5.43 (1H, d, J=6.4 Hz), 7.18 (1H, d, J=5.2 Hz), 7.25 (1H, m), 7.71 (1H, dt, J=6.4, 1.6 Hz), 7.96 (1H, t, J=6.0 Hz), 8.49 (1H, dd, J=4.8, 1.6 Hz), 8.69 (1H, d, J=1.6 Hz) ppm. LCMS m/z=372.2 [M+H$^+$].

Example Z9. ((S)-3-Fluoropyrrolidin-1-yl)(2-(((S)-1-(pyridin-3-yl)ethyl)amino)thieno[3,2-d]pyrimidin-4-yl)methanone (Z9)

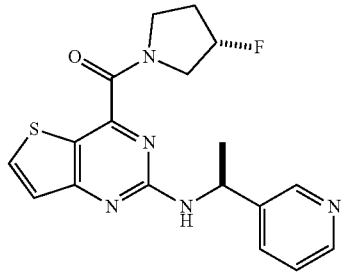 [SMILES: C[C@H](Nc1nc(C(=O)N2CC[C@H](F)C2)c2sccc2n1)c1cccnc1]

Synthesis of ((S)-3-fluoropyrrolidin-1-yl)(2-(((S)-1-(pyridin-3-yl)ethyl)amino)thieno[3,2-d]pyrimidin-4-yl)methanone (Z9): The title compound (9) was prepared from 2-[[(1S)-1-(3-pyridyl)ethyl]amino]thieno[3,2-d]pyrimidine-4-carboxylic acid dihydrochloride (37 mg, 0.10 mmol) using chemistry similar to that described in Example Z8 using (3S)-3-fluoropyrrolidine hydrochloride in place of its enantiomer (35 mg, 94% yield). $^1$H NMR (400 MHz, CDCl$_3$) δ 1.64 (3H, d, J=6.8 Hz), 1.93 (1H, m), 2.25 (1H, m), 3.70-3.87 (3H, m), 3.92-4.08 (2H, m), 5.18 (1H, m), 5.45 (1H, d, J=6.4 Hz), 7.19 (1H, d, J=5.6 Hz), 7.25 (1H, m), 7.71

(1H, m), 7.96 (1H, dd, J=6.0, 2.4 Hz), 8.49 (1H, ddd, J=8.0, 4.8, 1.6 Hz), 8.68 (1H, d, J=2.4 Hz) ppm. LCMS m/z=372.2 [M+H⁺].

Example Z10. (S)-(2-((1-(Pyridin-2-yl)ethyl)amino) thieno[3,2-d]pyrimidin-4-yl)(pyrrolidin-1-yl)methanone

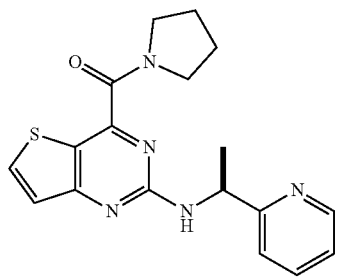 [SMILES: C[C@H](Nc1nc(C(=O)N2CCCC2)c2sccc2n1)c1ccccn1]

(Z10)

Synthesis of methyl (S)-2-((1-(pyridin-2-yl)ethyl)amino) thieno[3,2-d]pyrimidine-4-carboxylate: The title compound was prepared from ethyl 2-chlorothieno[3,2-d]pyrimidine-4-carboxylate using chemistry similar to that described in Example Z1 using (1S)-1-(2-pyridyl)ethanamine (commercially obtained from Ark Pharm, Libertyville, Ill.) in place of (1S)-1-(3-pyridyl)ethanamine. ¹H NMR (400 MHz, CDCl₃) δ 1.61 (3H, d, J=6.8 Hz), 4.09 (3H, s), 5.36 (1H, quintet, J=6.8 Hz), 6.43 (1H, d, J=6.8 Hz), 7.15 (1H, ddd, J=8.0, 4.8, 1.2 Hz), 7.23 (1H, d, J=5.6 Hz), 7.35 (1H, d, J=8.0 Hz), 7.62 (1H, td, J=8.0, 1.6 Hz), 7.93 (1H, d, J=5.6 Hz), 8.57 (1H, m) ppm. LCMS m/z=315.1[M+H⁺].

Synthesis of (S)-(2-((1-(pyridin-2-yl)ethyl)amino)thieno [3,2-d]pyrimidin-4-yl)(pyrrolidin-1-yl)methanone (Z10): The title compound (Z10) was prepared from methyl (S)-2-((1-(pyridin-2-yl)ethyl)amino)thieno[3,2-d]pyrimidine-4-carboxylate (31 mg, 0.10 mmol) using chemistry similar to that described in Example Z2 using pyrrolidine in place of azetidine (29 mg, 82% yield). ¹H NMR (400 MHz, CDCl₃) δ 1.62 (3H, d, J=5.6 Hz), 1.84-1.94 (4H, m), 3.62-3.75 (3H, m), 3.93 (1H, m), 5.25 (1H, m), 6.02 (1H, br s), 7.16 (1H, ddd, J=6.8, 4.8, 0.8 Hz), 7.19 (1H, d, J=4.4 Hz), 7.35 (1H, d, J=6.4 Hz), 7.62 (1H, td, J=6.0, 1.2 Hz), 7.92 (1H, d, J=4.4 Hz), 8.58 (1H, m) ppm. LCMS m/z=354.2 [M+H⁺].

Example Z11. (S)-Morpholino(2-((1-(pyridin-3-yl) ethyl)amino)thieno[3,2-d]pyrimidin-4-yl)methanone

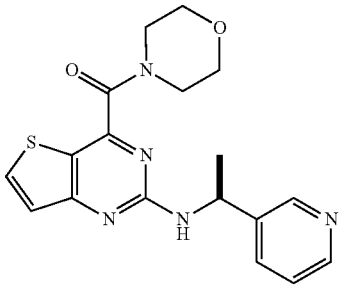 [SMILES: C[C@H](Nc1nc(C(=O)N2CCOCC2)c2sccc2n1)c1cccnc1]

(Z11)

Synthesis of (S)-morpholino(2-((1-(pyridin-3-yl)ethyl) amino)thieno[3,2-d]pyrimidin-4-yl)methanone (Z11): The title compound (Z11) was prepared from 2-[[(1S)-1-(3-pyridyl)ethyl]amino]thieno[3,2-d]pyrimidine-4-carboxylic acid dihydrochloride (37 mg, 0.10 mmol) using chemistry similar to that described in Example Z8 using morpholine in place of (R)-3-fluoropyrrolidine (35 mg, 95% yield). ¹H NMR (400 MHz, CDCl₃) δ 1.62 (3H, d, J=6.0 Hz), 3.45-3.56 (2H, m), 3.61-3.67 (2H, m), 3.73-3.87 (4H, m), 5.20 (1H, quintet, J=6.0 Hz), 5.44 (1H, d, J=6.0 Hz), 7.18 (1H, d, J=4.4 Hz), 7.24 (1H, m), 7.69 (1H, dt, J=6.8, 1.2 Hz), 7.92 (1H, d, J=4.0 Hz), 8.49 (1H, dd, J=4.0, 1.6 Hz), 8.68 (1H, d, J=1.6 Hz) ppm. LCMS m/z=370.1 [M+H⁺].

Example Z12. N-((6-Methoxypyridin-3-yl)methyl)-2-(((6-methoxypyridin-3-yl)methyl)amino)thieno[3,2-d]pyrimidine-4-carboxamide

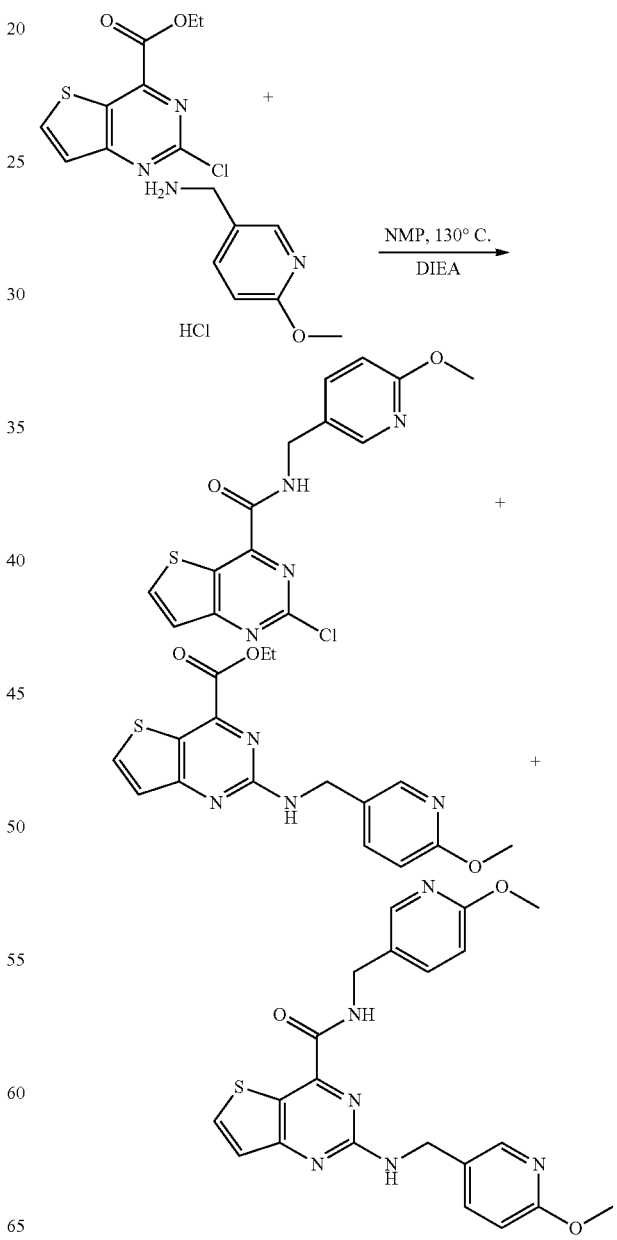

(Z12)

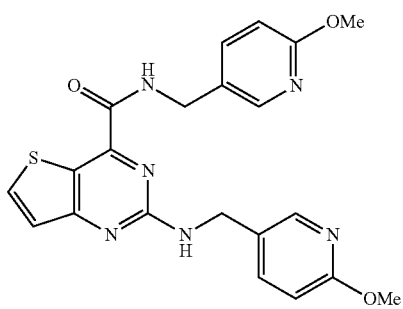 [SMILES: COc1ccc(CNC(=O)c2nc(NCc3ccc(OC)nc3)nc3ccsc23)cn1]

Synthesis of N-((6-methoxypyridin-3-yl)methyl)-2-((((6-methoxypyridin-3-yl)methyl)amino)thieno[3,2-d]pyrimidine-4-carboxamide (Z12): To a solution of ethyl 2-chlorothieno[3,2-d]pyrimidine-4-carboxylate (100 mg, 0.41 mmol) and DIEA (0.22 mL, 1.23 mmol) in NMP (3 mL) was added (6-methoxypyridin-3-yl)methanamine hydrochloride (commercially obtained from PharmaBlock, Sunnyvale, Calif.) (97 mg, 0.89 mmol). The reaction mixture was stirred at 130° C. for 3 h. The reaction mixture was cooled to room temperature, diluted with ethyl acetate and washed with 25% aqueous NaCl solution, then with brine three times and dried. The solvent was evaporated and the residue was purified by flash chromatography (24 g, HP silica, Teledyne Isco) eluting with 2% to 100% solvent A (DCM/MeOH/NH$_4$OH, 100/10/1) in DCM to provide 2-chloro-N-((6-methoxypyridin-3-yl)methyl)thieno[3,2-d]pyrimidine-4-carboxamide (21 mg, 15% yield) as a light yellow solid (LCMS m/z=335.1 [M+H$^+$]), ethyl 2-(((6-methoxypyridin-3-yl)methyl)amino)thieno[3,2-d]pyrimidine-4-carboxylate (15 mg, 11% yield) as a light yellow solid (LCMS m/z=345.2[M+H$^+$]), and N-((6-methoxypyridin-3-yl)methyl)-2-(((6-methoxypyridin-3-yl)methyl)amino)thieno[3,2-d]pyrimidine-4-carboxamide (30.3 mg, 17% yield) as a light yellow solid (LCMS m/z=437.1[M+H$^+$]).

Example Z13. (S)-(3,3-Difluoropyrrolidin-1-yl)(2-((1-(pyridin-3-yl)ethyl)amino)thieno[3,2-d]pyrimidin-4-yl)methanone (Z13)

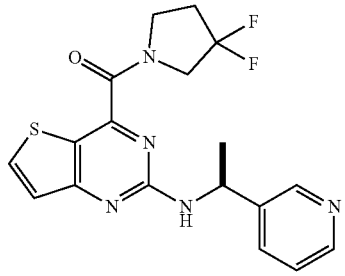 [SMILES: C[C@H](Nc1nc(C(=O)N2CCC(F)(F)C2)c2sccc2n1)c1cccnc1]

Synthesis of (S)-(3,3-difluoropyrrolidin-1-yl)(2-((1-(pyridin-3-yl)ethyl)amino)thieno[3,2-d]pyrimidin-4-yl)methanone (Z13): The title compound (Z13) was prepared from 2-[[(1S)-1-(3-pyridyl)ethyl]amino]thieno[3,2-d]pyrimidine-4-carboxylic acid dihydrochloride (37 mg, 0.10 mmol) using chemistry similar to that described in Example Z8 using 3,3-difluoropyrrolidine hydrochloride in place of (R)-3-fluoropyrrolidine (34 mg, 87% yield). $^1$H NMR (400 MHz, CDCl$_3$) δ 1.64 (3H, d, J=5.6 Hz), 2.25-2.39 (2H, m), 3.93 (1H, m), 4.00 (1H, m), 4.02 (1H, m), 4.30 (1H, m), 5.18 (1H, quintet, J=5.6 Hz), 5.45 (1H, d, J=5.6 Hz), 7.19 (1H, J=4.4 Hz), 7.25 (1H, m), 7.70 (1H, m), 7.97 (1H, d, J=4.4 Hz), 8.51 91H, dd, J=4.0, 1.6 Hz), 8.69 (1H, J=1.6 Hz) ppm. LCMS m/z=390.2 [M+H$^+$].

Example Z14. (S)-(2-((1-(Pyridin-3-yl)ethyl)amino) thieno[3,2-d]pyrimidin-4-yl)(2-oxa-6-azaspiro[3.3] heptan-6-yl)methanone (Z14)

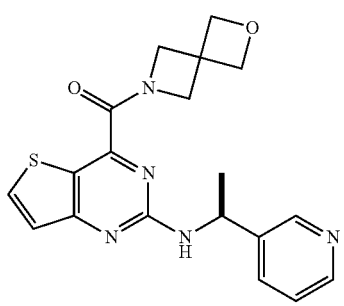 [SMILES: C[C@H](Nc1nc(C(=O)N2CC3(COC3)C2)c2sccc2n1)c1cccnc1]

Synthesis of (S)-(2-((1-(pyridin-3-yl)ethyl)amino)thieno[3,2-d]pyrimidin-4-yl)(2-oxa-6-azaspiro[3.3]heptan-6-yl)methanone (Z14): The title compound (Z14) was prepared from 2-[[(1S)-1-(3-pyridyl)ethyl]amino]thieno[3,2-d]pyrimidine-4-carboxylic acid dihydrochloride (37 mg, 0.10 mmol) using chemistry similar to that described in Example Z8 using 2-oxa-6-azaspiro[3.3]heptane in place of (R)-3-fluoropyrrolidine (6 mg, 16% yield). LCMS m/z=382.2 [M+H$^+$].

Example Z15. N-((5-Fluoropyridin-3-yl)methyl)-2-(((5-fluoropyridin-3-yl)methyl)amino)thieno[3,2-d] pyrimidine-4-carboxamide (Z15)

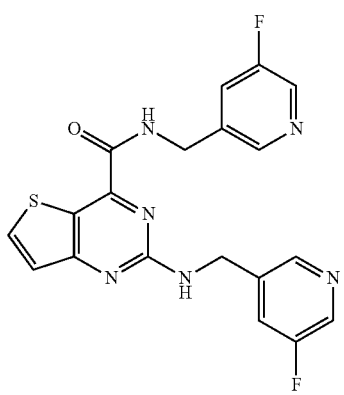 [SMILES: O=C(NCc1cncc(F)c1)c1nc(NCc2cncc(F)c2)nc2ccsc12]

-continued

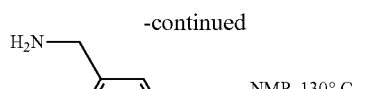

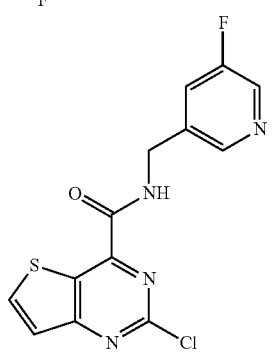

+

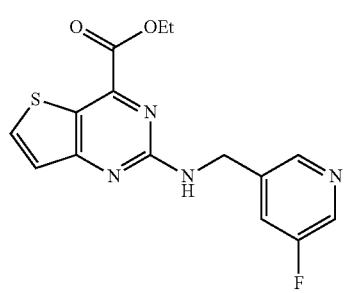

+

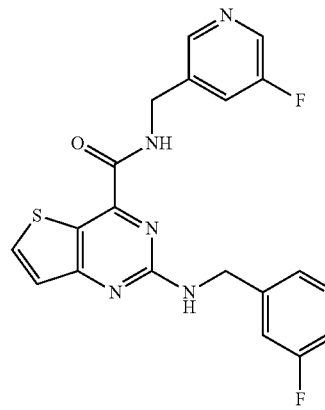

Synthesis of N-((5-fluoropyridin-3-yl)methyl)-2-(((5-fluoropyridin-3-yl)methyl)amino)thieno[3,2-d]pyrimidine-4-carboxamide (Z15): The title compound (Z15) was prepared from ethyl 2-chlorothieno[3,2-d]pyrimidine-4-carboxylate (114 mg, 0.47 mmol) using chemistry similar to that described in Example Z12 using (5-fluoropyridin-3-yl)methanamine (PharmaBlock, Sunnyvale, Calif.) (178 mg, 1.41 mmol) in place of (6-methoxypyridin-3-yl)methanamine hydrochloride (164 mg, 84% yield). LCMS m/z=413.1 [M+H⁺].

Example Z16. (S)—N-((6-Methoxypyridin-3-yl)methyl)-2-((1-(pyridin-2-yl)ethyl)amino)thieno[3,2-d]pyrimidine-4-carboxamide

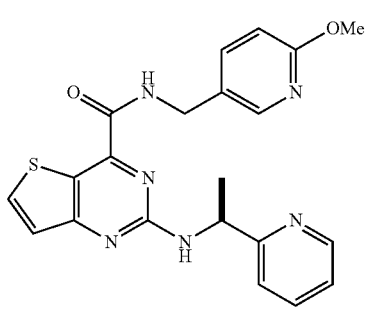 [SMILES: COc1ccc(CNC(=O)c2nc(N[C@@H](C)c3ccccn3)nc3ccsc23)cn1]
(Z16)

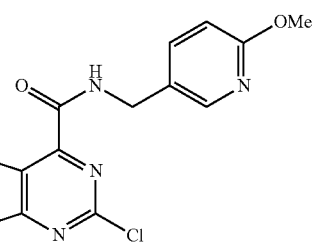

+

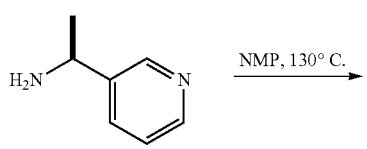

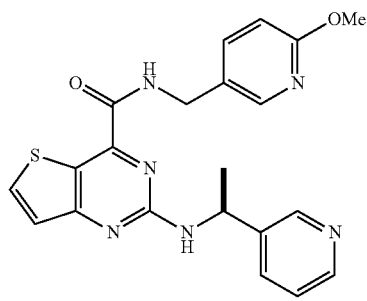

Synthesis of (S)—N-((6-methoxypyridin-3-yl)methyl)-2-((1-(pyridin-2-yl)ethyl)amino)thieno[3,2-d]pyrimidine-4-carboxamide (Z16): The title compound (Z16) was prepared from 2-chloro-N-((6-methoxypyridin-3-yl)methyl)thieno[3,2-d]pyrimidine-4-carboxamide using chemistry similar to that described in Example Z6. (52% yield). LCMS m/z=421.3 [M+H⁺].

Example Z17. (2-(((6-Methoxypyridin-3-yl)methyl)amino)thieno[3,2-d]pyrimidin-4-yl)(pyrrolidin-1-yl)methanone

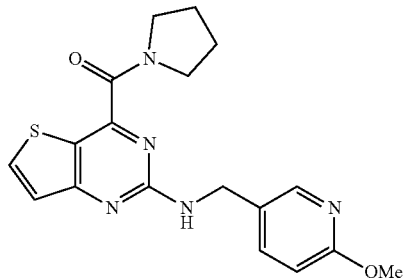 [SMILES: COc1ccc(CNc2nc(C(=O)N3CCCC3)c3sccc3n2)cn1]

(Z17)

Synthesis of 2-(((6-methoxypyridin-3-yl)methyl)amino)thieno[3,2-d]pyrimidine-4-carboxylic acid dihydrochloride: The title compound was prepared from ethyl 2-(((6-methoxypyridin-3-yl)methyl)amino)thieno[3,2-d]pyrimidine-4-carboxylate using chemistry similar to that described in Example Z5. (100% yield) LCMS m/z=317.1[M+H$^+$].

Synthesis of (2-(((6-methoxypyridin-3-yl)methyl)amino)thieno[3,2-d]pyrimidin-4-yl)(pyrrolidin-1-yl)methanone (Z17): The title compound (Z17) was prepared from 2-(((6-methoxypyridin-3-yl)methyl)amino)thieno[3,2-d]pyrimidine-4-carboxylic acid dihydrochloride using chemistry similar to that described in Example Z8 using pyrrolidine in place of (R)-3-fluoropyrrolidine (34% yield). LCMS m/z=370.1 [M+H$^+$].

Example Z18. ((S)-3-Methoxypyrrolidin-1-yl)(2-(((S)-1-(pyridin-3-yl)ethyl)amino)thieno[3,2-d]pyrimidin-4-yl)methanone

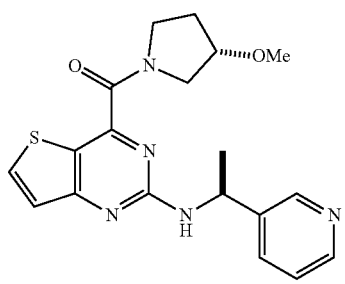 [SMILES: CO[C@H]1CCN(C(=O)c2nc(N[C@@H](C)c3cccnc3)nc3ccsc23)C1]

(Z18)

Synthesis of ((S)-3-methoxypyrrolidin-1-yl)(2-(((S)-1-(pyridin-3-yl)ethyl)amino)thieno[3,2-d]pyrimidin-4-yl)methanone (Z18): The title compound (Z18) was prepared from 2-[[(1S)-1-(3-pyridyl)ethyl]amino]thieno[3,2-d]pyrimidine-4-carboxylic acid dihydrochloride (37 mg, 0.10 mmol) using chemistry similar to that described in Example Z8 using (3S)-3-methoxypyrrolidine hydrochloride (commercially obtained from Enamine, Monmouth, N.J.) in place of (R)-3-fluoropyrrolidine (31 mg, 83% yield). $^1$H NMR (400 MHz, CDCl$_3$) δ 1.63 (3H, d, J=7.2 Hz), 1.84-1.93 (2H, m), 3.28 (3H, s), 3.67-3.96 (5H, m), 5.22 (1H, m), 5.47 (1H, m), 7.17 (1H, d, J=5.6 Hz), 7.28 (1H, m), 7.76 (1H, m), 7.95 (1H, dd, J=5.6, 1.6 Hz), 8.50 (1H, m), 8.69 (1H, dd, J=6.0, 2.0 Hz) ppm. LCMS m/z=384.2 [M+H$^+$].

Example Z19. ((R)-3-Methoxypyrrolidin-1-yl)(2-(((S)-1-(pyridin-3-yl)ethyl)amino)thieno[3,2-d]pyrimidin-4-yl)methanone

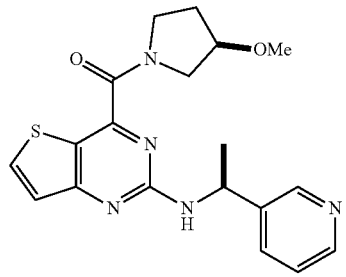 [SMILES: CO[C@@H]1CCN(C(=O)c2nc(N[C@@H](C)c3cccnc3)nc3ccsc23)C1]

(Z19)

Synthesis of ((R)-3-methoxypyrrolidin-1-yl)(2-(((S)-1-(pyridin-3-yl)ethyl)amino)thieno[3,2-d]pyrimidin-4-yl)methanone (Z19): The title compound (Z19) was prepared from 2-[[(1S)-1-(3-pyridyl)ethyl]amino]thieno[3,2-d]pyrimidine-4-carboxylic acid dihydrochloride (37 mg, 0.10 mmol) using chemistry similar to that described in Example Z8 using (3R)-3-methoxypyrrolidine hydrochloride (commercially obtained from Enamine, Monmouth, N.J.) in place of (R)-3-fluoropyrrolidine (27 mg, 70% yield). $^1$H NMR (400 MHz, CDCl$_3$) δ 1.64 (3H, d, J=7.2 Hz), 1.81-1.95 (2H, m), 3.34 (3H, s), 3.687-3.78 (2H, m), 3.86 (1H, m), 3.98 (1Hm), 4.14 (1H, m), 5.23 (1H, m), 5.47 (1H, m), 7.17 (1H, dd, J=5.6, 1.2 Hz), 7.28 (1H, dd, J=8.0, 4.8 Hz), 7.76 (1H, d, J=8.0 Hz), 7.95 (1H, dd, J=5.6, 3.6 Hz), 8.50 (1H, dd, J=4.8, 1.2 Hz), 8.70 (1H, s) ppm. LCMS m/z=384.2 [M+H$^+$].

Example Z20. (S)—N-((5-Fluoropyridin-3-yl)methyl)-2-((1-(pyridin-3-yl)ethyl)amino)thieno[3,2-d]pyrimidine-4-carboxamide

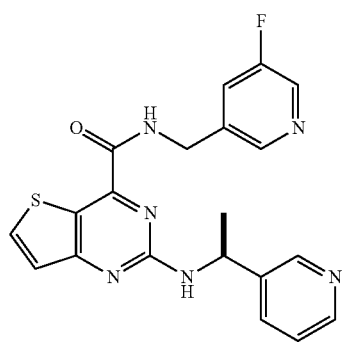 [SMILES: C[C@H](Nc1nc(C(=O)NCc2cncc(F)c2)c2sccc2n1)c1cccnc1]

(Z20)

Synthesis of (S)—N-((5-fluoropyridin-3-yl)methyl)-2-((1-(pyridin-3-yl)ethyl)amino)thieno[3,2-d]pyrimidine-4-carboxamide (Z20): The title compound (Z20) was prepared from 2-chloro-N-((5-fluoropyridin-3-yl)methyl)thieno[3,2-d]pyrimidine-4-carboxamide using chemistry similar to that described in Example Z6 (11% yield). LCMS m/z=409.3 [M+H$^+$].

Example Z21. (2-(((5-Fluoropyridin-3-yl)methyl)amino)thieno[3,2-d]pyrimidin-4-yl)(pyrrolidin-1-yl)methanone

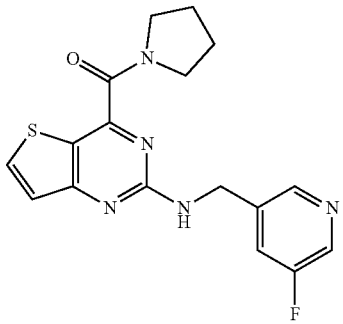 [SMILES: O=C(c1nc(NCc2cncc(F)c2)nc2ccsc12)N1CCCC1]

(Z21)

Synthesis of (2-(((5-Fluoropyridin-3-yl)methyl)amino)thieno[3,2-d]pyrimidin-4-yl)(pyrrolidin-1-yl)methanone (Z21): The title compound was prepared from ethyl 2-(((5-fluoropyridin-3-yl)methyl)amino)thieno[3,2-d]pyrimidine-4-carboxylate di-hydrochloride using chemistry similar to that described in Example Z17 using pyrrolidine in place of (R)-3-fluoropyrrolidine (56% yield). $^1$H NMR (400 MHz, CDCl$_3$) δ 1.88-1.92 (4H, m), 3.70-3.74 (2H, m), 3.86 (2H, m), 4.78 (2H, d, J=6.0 Hz), 5.57 (1H, t, J=6.0 Hz), 7.21 (1H, d, J=5.6 Hz), 7.45 (1H, m), 7.98 (1H, d, J=5.6 Hz), 8.38 (1H, d, J=2.8 Hz), 8.47 (1H, s) ppm. LCMS m/z=356.1 [M+H$^+$].

Example Z22. N-(3,3-Dimethylcyclopentyl)-2-(((5-fluoropyridin-3-yl)methyl)amino)-N-methylthieno[3,2-d]pyrimidine-4-carboxamide

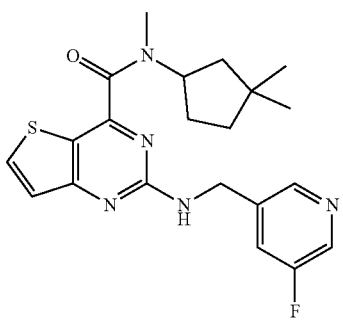 [SMILES: CN(C(=O)c1nc(NCc2cncc(F)c2)nc2ccsc12)C1CCC(C)(C)C1]

(Z22)

Synthesis of N-(3,3-Dimethylcyclopentyl)-2-(((5-fluoropyridin-3-yl)methyl)amino)-N-methylthieno[3,2-d]pyrimidine-4-carboxamide (Z22): The title compound was prepared from ethyl 2-(((5-fluoropyridin-3-yl)methyl)amino)thieno[3,2-d]pyrimidine-4-carboxylate dihydrochloride using chemistry similar to that described in Example Z17 using N,3,3-trimethylcyclopentan-1-amine in place of (R)-3-fluoropyrrolidine (29% yield). LCMS m/z=414.2 [M+H$^+$].

Example Z23. N-(1-(Pyridin-3-yl)propyl)-2-((1-(pyridin-3-yl)propyl)amino)thieno[3,2-d]pyrimidine-4-carboxamide

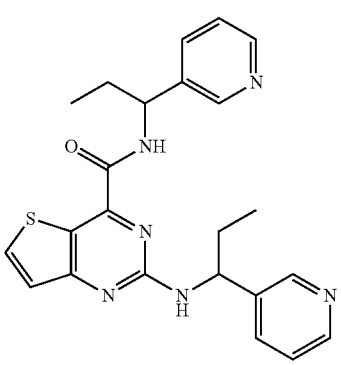 [SMILES: CCC(NC(=O)c1nc(NC(CC)c2cccnc2)nc2ccsc12)c1cccnc1]

(Z23)

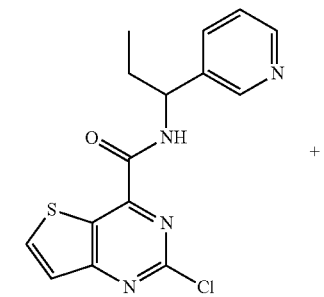

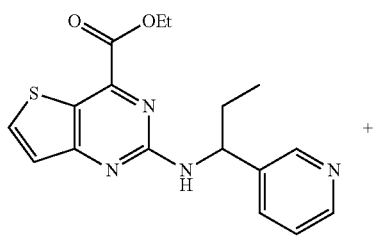

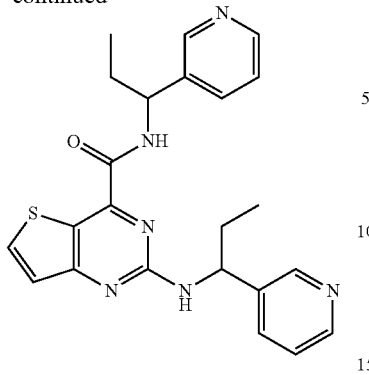

Synthesis of N-(1-(pyridin-3-yl)propyl)-2-((1-(pyridin-3-yl)propyl)amino)thieno[3,2-d]pyrimidine-4-carboxamide (Z23): The title compound (Z23) was prepared from ethyl 2-chlorothieno[3,2-d]pyrimidine-4-carboxylate (114 mg, 0.47 mmol) using chemistry similar to that described in Example Z12 using 1-(3-pyridyl)propan-1-amine (commercially obtained from Accella Bio, Shanghai, Conn.) (132 mg, 0.55 mmol) in place of (6-methoxypyridin-3-yl)methanamine hydrochloride (13.3 mg, 6% yield). LCMS m/z=433.3 [M+H$^+$]. Also isolated 2-chloro-N-(1-(pyridin-3-yl)propyl)thieno[3,2-d]pyrimidine-4-carboxamide (71.3 mg, 39% yield), LCMS m/z=333.1 [M+H$^+$], and ethyl 2-((1-(pyridin-3-yl)propyl)amino)thieno[3,2-d]pyrimidine-4-carboxylate (5323 mg, 28% yield), LCMS m/z=343.2 [M+H$^+$].

Example Z24. 2-(((S)-1-(Pyridin-3-yl)ethyl)amino)-N-(1-(pyridin-3-yl)propyl)thieno[3,2-d]pyrimidine-4-carboxamide

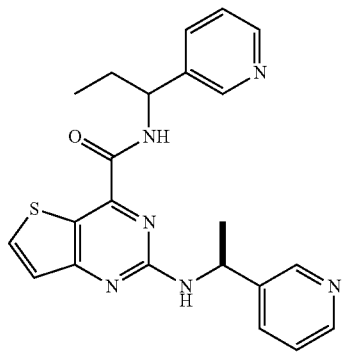 [SMILES: CCC(NC(=O)c1nc(N[C@@H](C)c2cccnc2)nc2ccsc12)c1cccnc1]

(Z24)

Synthesis of 2-(((S)-1-(pyridin-3-yl)ethyl)amino)-N-(1-(pyridin-3-yl)propyl)thieno[3,2-d]pyrimidine-4-carboxamide (Z24): The title compound (Z24) was prepared from 2-chloro-N-(1-(pyridin-3-yl)propyl)thieno[3,2-d]pyrimidine-4-carboxamide using chemistry similar to that described in Example Z6 (11% yield). LCMS m/z=419.1 [M+H$^+$].

Example Z25. (2-((1-(Pyridin-3-yl)propyl)amino)thieno[3,2-d]pyrimidin-4-yl)(pyrrolidin-1-yl)methanone

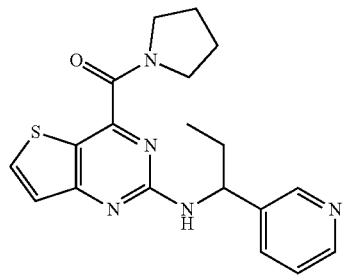 [SMILES: CCC(Nc1nc(C(=O)N2CCCC2)c2sccc2n1)c1cccnc1]

(Z25)

Synthesis of (2-((1-(pyridin-3-yl)propyl)amino)thieno[3,2-d]pyrimidin-4-yl)(pyrrolidin-1-yl)methanone (Z25): The title compound (Z25) was prepared from ethyl 2-((1-(pyridin-3-yl)propyl)amino)thieno[3,2-d]pyrimidine-4-carboxylate using chemistry similar to that described in Example Z17 using pyrrolidine in place of (R)-3-fluoropyrrolidine (71% yield). $^1$H NMR (400 Hz, CDCl$_3$) δ 1.03 (3H, t, J=7.4 Hz), 1.81-1.86 (4H, m), 1.91-1.98 (1H, m), 3.68 (4H, t, J=6.8 Hz), 3.77-3.79 (1H, m), 5.02 (1H, q, J=6.8 Hz), 5.36 (1H, d, J=2.4 Hz), 7.17 (1H, d, J=5.6 Hz), 7.26 (1H, m), 7.72 (1H, td, J=7.6, 1.8 Hz), 7.95 (1H, d, J=5.6 Hz), 8.49 (1H, dd, J=4.8, 0.8 Hz), 8.66 (1H, d, J=2.0 Hz) ppm. LCMS m/z=367.1 [M+H$^+$].

Example Z26. ((R)-3-Methoxypyrrolidin-1-yl)(2-((1-(pyridin-3-yl)propyl)amino)thieno[3,2-d]pyrimidin-4-yl)methanone

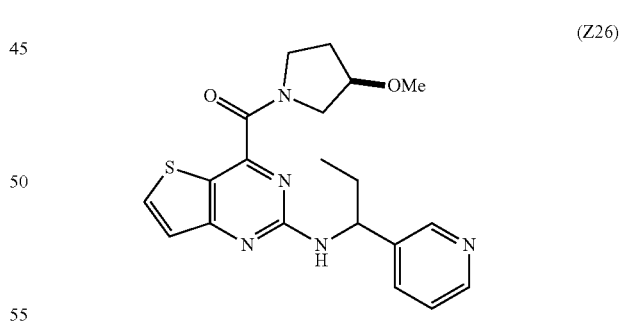

(Z26)

Synthesis of ((R)-3-methoxypyrrolidin-1-yl)(2-((1-(pyridin-3-yl)propyl)amino)thieno[3,2-d]pyrimidin-4-yl)methanone (Z26): The title compound (Z26) was prepared from ethyl 2-((1-(pyridin-3-yl)propyl)amino)thieno[3,2-d]pyrimidine-4-carboxylate dihydrochloride using chemistry similar to that described in Example Z17 using (3R)-3-methoxypyrrolidine hydrochloride (90% yield). LCMS m/z=398.1 [M+H$^+$].

Example Z27. (S)—N-((1-benzylpiperidin-4-yl)methyl)-2-((1-(pyridin-3-yl)ethyl)amino)thieno[3,2-d]pyrimidine-4-carboxamide

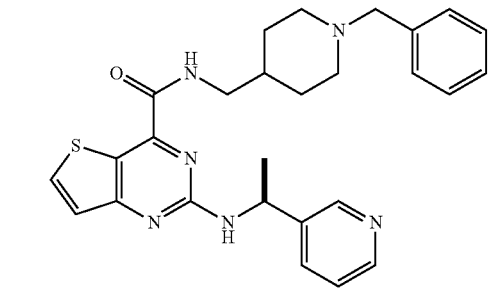

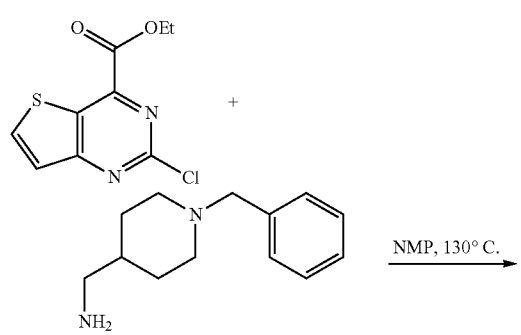

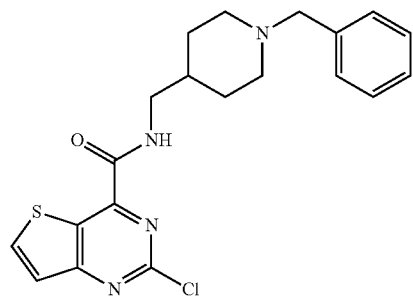

Synthesis of N-(2-(1-benzylpiperidin-4-yl)ethyl)-2-chlorothieno[3,2-d]pyrimidine-4-carboxamide. The title compound was prepared from ethyl 2-chlorothieno[3,2-d]pyrimidine-4-carboxylate (116 mg, 0.48 mmol) using chemistry similar to that described in Example Z12 using 2-(1-benzylpiperidin-4-yl)ethan-1-amine commercially available from Enamine, Monmouth Jct., N.J.) in place of (6-methoxypyridin-3-yl)methanamine hydrochloride (18% yield). LCMS m/z=401.1 [M+H⁺].

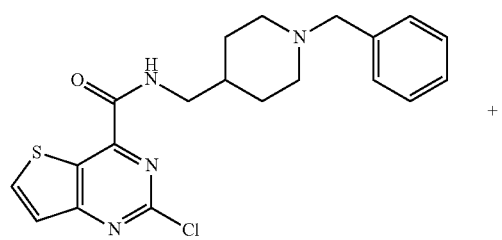

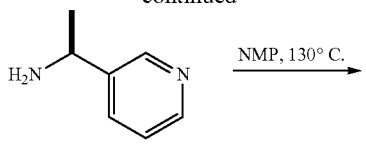

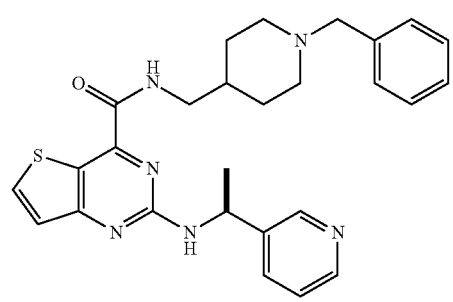 [SMILES: C[C@H](Nc1nc(C(=O)NCC2CCN(Cc3ccccc3)CC2)c2sccc2n1)c1cccnc1]

Synthesis of (S)—N-((1-benzylpiperidin-4-yl)methyl)-2-((1-(pyridin-3-yl)ethyl)amino)thieno[3,2-d]pyrimidine-4-carboxamide (Z27): The title compound (Z27) was prepared from N-(2-(1-benzylpiperidin-4-yl)ethyl)-2-chlorothieno[3,2-d]pyrimidine-4-carboxamide using chemistry similar to that described in Example Z6 (18% yield). LCMS m/z=487.3[M+H⁺].

Example Z28. ((S)-3-Hydroxypyrrolidin-1-yl)(2-(((S)-1-(pyridin-3-yl)ethyl)amino)thieno[3,2-d]pyrimidin-4-yl)methanone

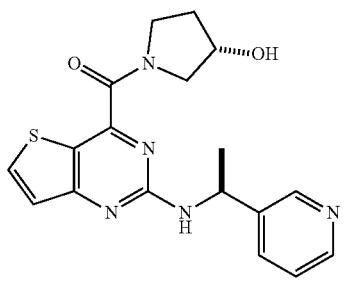

Synthesis of ((S)-3-hydroxypyrrolidin-1-yl)(2-(((S)-1-(pyridin-3-yl)ethyl)amino)thieno[3,2-d]pyrimidin-4-yl)methanone (Z28): The title compound (Z28) was prepared from 2-[[(1S)-1-(3-pyridyl)ethyl]amino]thieno[3,2-d]pyrimidine-4-carboxylic acid dihydrochloride (37 mg, 0.10 mmol) using chemistry similar to that described in Example Z8 using (S)-pyrrolidin-3-ol (commercially obtained from J&W Pharmalab, Levittown, Pa.) in place of (R)-3-fluoropyrrolidine (29 mg, 78% yield). ¹H NMR (400 MHz, CDCl₃) δ 1.63 (3H, d, J=7.2 Hz), 1.82-2.01 (2H, m), 3.55 (1H, m), 3.76-3.86 (3H, m), 4.48 (1H, m), 5.17 (1H, m), 5.50 (1H, d, J=6.8 Hz), 7.17 (1H, dd, J=6.0, 1.2 Hz), 7.29 (1H, dd, J=8.0, 4.8 Hz), 7.77 (1H, m), 7.95 (1H, t, J=5.6 Hz), 8.48 (1H, m), 8.69 (1H, m) ppm. LCMS m/z=370.3 [M+H⁺].

Example Z29. ((R)-3-Hydroxypyrrolidin-1-yl)(2-(((S)-1-(pyridin-3-yl)ethyl)amino)thieno[3,2-d]pyrimidin-4-yl)methanone

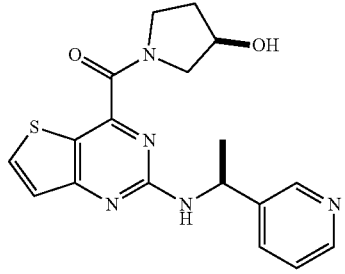

(Z29)

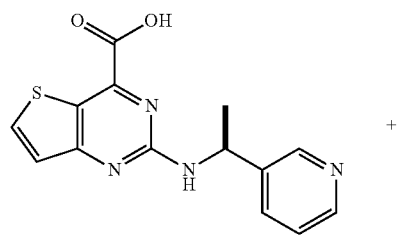

+

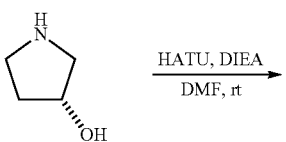

HATU, DIEA
———————→
DMF, rt

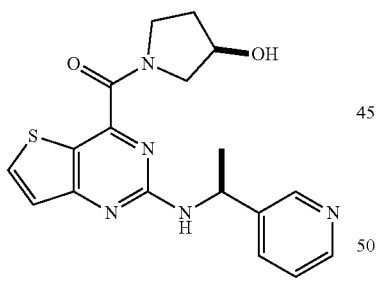

Synthesis of ((R)-3-hydroxypyrrolidin-1-yl)(2-(((S)-1-(pyridin-3-yl)ethyl)amino)thieno[3,2-d]pyrimidin-4-yl)methanone (Z29): The title compound (Z29) was prepared from 2-[[(1S)-1-(3-pyridyl)ethyl]amino]thieno[3,2-d]pyrimidine-4-carboxylic acid dihydrochloride (37 mg, 0.10 mmol) using chemistry similar to that described in Example Z8 using (R)-pyrrolidin-3-ol (commercially obtained from J&W Pharmalab, Levittown, Pa.) in place of (R)-3-fluoropyrrolidine (29 mg, 78% yield). $^1$H NMR (400 MHz, CDCl$_3$) δ 1.63 (3H, d, J=7.2 Hz), 1.91-2.05 (2H, m), 3.55 (1H, m), 3.73-3.84 (3H, m), 4.45 (1H, m), 5.18 (1H, m), 5.50 (1H, d, J=6.8 Hz), 7.17 (1H, d, J=5.6 Hz), 7.29 (1H, m), 7.78 (1H, dt, J=8.0, 1.6 Hz), 7.94 (1H, m), 8.48 (1H, m), 8.71 (1H, m) ppm. LCMS m/z=370.3 [M+H$^+$].

Example Z30. N—((R)-1-(Pyridin-3-yl)ethyl)-2-(((S)-1-(pyridin-3-yl)ethyl)amino)thieno[3,2-d]pyrimidine-4-carboxamide

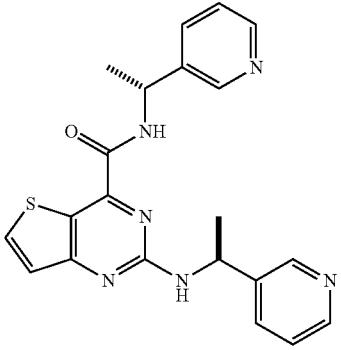 [SMILES: C[C@H](Nc1nc(C(=O)N[C@H](C)c2cccnc2)c2sccc2n1)c1cccnc1]

(Z30)

Synthesis of N—((R)-1-(pyridin-3-yl)ethyl)-2-(((S)-1-(pyridin-3-yl)ethyl)amino)thieno[3,2-d]pyrimidine-4-carboxamide (Z30): The title compound (Z30) was prepared from 2-[[(1S)-1-(3-pyridyl)ethyl]amino]thieno[3,2-d]pyrimidine-4-carboxylic acid dihydrochloride (37 mg, 0.10 mmol) using chemistry similar to that described in Example Z8 using (R)-1-(pyridin-3-yl)ethan-1-amine (commercially obtained from Ark Pharm, Libertyville, Ill.) in place of (R)-3-fluoropyrrolidine (40 mg, 99% yield). $^1$H NMR (400 MHz, CDCl$_3$) δ 1.59 (3H, d, J=7.2 Hz), 1.64 (3H, d, J=6.8 Hz), 5.14 (1H, m), 5.28 (1H, m), 5.50 (1H, d, J=6.0 Hz), 7.18 (1H, d, J=5.6 Hz), 7.26 (1H, dd, J=6.8, 5.6 Hz), 7.32 (1H, dd, J=8.0, 4.8 Hz), 7.72-7.75 (2H, m), 7.89 (1H, br s), 7.99 (1H, d, J=5.6 Hz), 8.51 (1H, dd, J=4.8, 1.6 Hz), 8.56 (1H, dd, J=4.8, 2.0 Hz), 8.69-8.71 (2H, m) ppm. LCMS m/z=405.2 [M+H$^+$].

Example Z31. (S)-Piperidin-1-yl(2-((1-(pyridin-3-yl)ethyl)amino)thieno[3,2-d]pyrimidin-4-yl)methanone

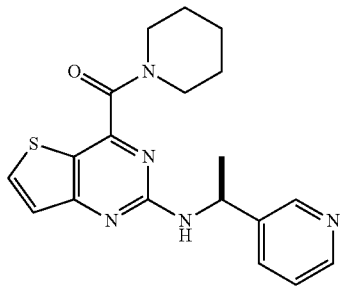 [SMILES: C[C@H](Nc1nc(C(=O)N2CCCCC2)c2sccc2n1)c1cccnc1]

(Z31)

Synthesis of (S)-piperidin-1-yl(2-((1-(pyridin-3-yl)ethyl)amino)thieno[3,2-d]pyrimidin-4-yl)methanone (Z31): The title compound (Z31) was prepared from 2-[[(1S)-1-(3-pyridyl)ethyl]amino]thieno[3,2-d]pyrimidine-4-carboxylic acid dihydrochloride (37 mg, 0.10 mmol) using chemistry similar to that described in Example Z8 using piperidine in place of (R)-3-fluoropyrrolidine (35 mg, 95% yield). $^1$H NMR (400 MHz, CDCl$_3$) δ 1.40-1.52 (2H, m), 1.62 (3H, d, J=7.2 Hz), 1.64-1.67 (4H, m), 3.43-3.46 (2H, m), 3.70-3.82

(2H, m), 5.25 (1H, quintet, J=7.2 Hz), 5.46 (1H, d, J=7.2 Hz), 7.17 (1H, d, J=5.6 Hz), 7.27 (1H, dd, J=8.0, 4.8 Hz), 7.75 (1H, dt, J=8.0, 1.6 Hz), 7.89 (1H, d, J=5.6 Hz), 8.48 (1H, dd, J=4.8, 1.2 Hz), 8.70 (1H, d, J=1.6 Hz) ppm. LCMS m/z=368.2 [M+H$^+$].

Example Z32. (S)-(3,3-Difluoroazetidin-1-yl)(2-((1-(pyridin-3-yl)ethyl)amino)thieno[3,2-d]pyrimidin-4-yl)methanone (Z32)

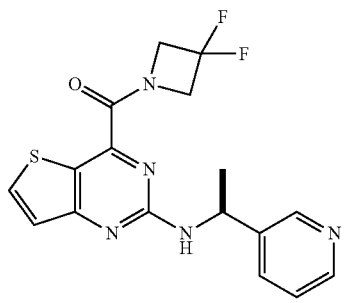 [SMILES: C[C@H](Nc1nc(C(=O)N2CC(F)(F)C2)c2sccc2n1)c1cccnc1]

Synthesis of (S)-(3,3-difluoroazetidin-1-yl)(2-((1-(pyridin-3-yl)ethyl)amino)thieno[3,2-d]pyrimidin-4-yl)methanone (Z32): The title compound (Z32) was prepared from 2-[[(1S)-1-(3-pyridyl)ethyl]amino]thieno[3,2-d]pyrimidine-4-carboxylic acid dihydrochloride (37 mg, 0.10 mmol) using chemistry similar to that described in Example Z8 using 3,3-difluoroazetidine hydrochloride in place of (R)-3-fluoropyrrolidine (33 mg, 88% yield). $^1$H NMR (400 MHz, CDCl$_3$) δ 1.66 (3H, d, J=7.2 Hz), 4.53 (2H, t, J=12.0 Hz), 4.63 (1H, m), 4.94 (1H, dd, J=12.0, 0.8 Hz), 5.20 (1H, m), 5.41 (1H, d, J=6.8 Hz), 7.19 (1H, d, J=5.6 Hz), 7.27 (1H, dd, J=8.0, 5.6 Hz), 7.70 (1H, dt, J=8.0, 1.6 Hz), 7.99 (1H, d, J=5.6 Hz), 8.52 (1H, dd, J=5.6, 1.6 Hz), 8.69 (1H, d, J=2.8 Hz) ppm. LCMS m/z=376.1 [M+H$^+$].

Example Z33. (S)—N-(3,4-Dimethoxybenzyl)-2-((1-(pyridin-3-yl)ethyl)amino)thieno[3,2-d]pyrimidine-4-carboxamide (Z33)

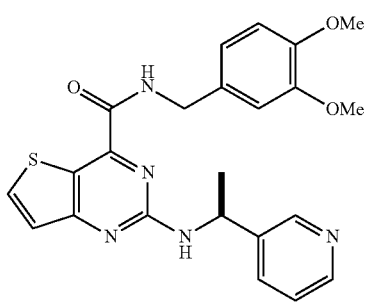 [SMILES: COc1ccc(CNC(=O)c2nc(N[C@@H](C)c3cccnc3)nc3ccsc23)cc1OC]

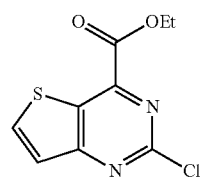

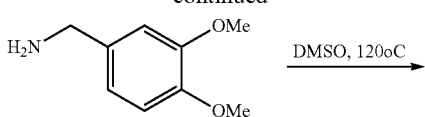

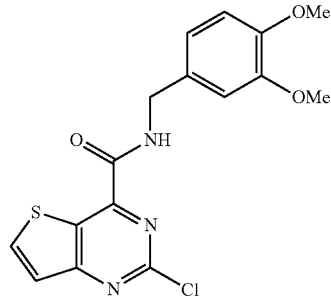

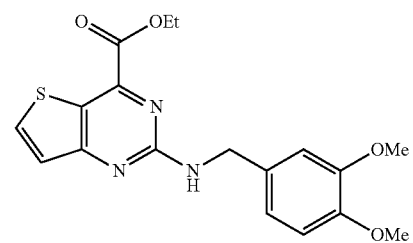

Synthesis of 2-chloro-N-(3,4-dimethoxybenzyl)thieno[3,2-d]pyrimidine-4-carboxamide. The title compound was prepared from ethyl 2-chlorothieno[3,2-d]pyrimidine-4-carboxylate (116 mg, 0.48 mmol) using chemistry similar to that described in Example Z12 using 3,4-dimethoxybenzylamine (commercially available from Combi-Blocks, San Diego, Calif.) in place of (6-methoxypyridin-3-yl)methanamine hydrochloride (27 mg, 36% yield). LCMS m/z=364.1 [M+H$^+$]. Also isolated was ethyl 2-((3,4-dimethoxybenzyl)amino)thieno[3,2-d]pyrimidine-4-carboxylate (26.6 mg, 34% yield). LCMS m/z=374.1 [M+H$^+$].

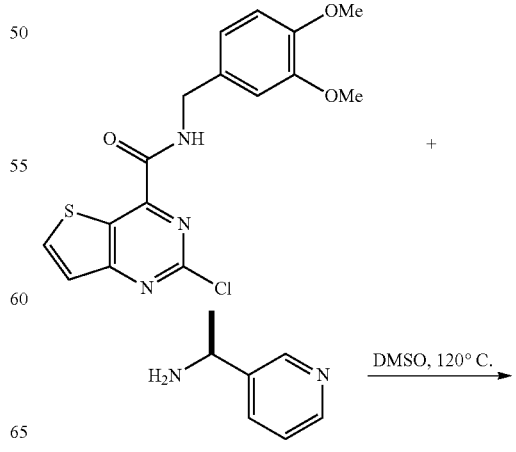

397

-continued

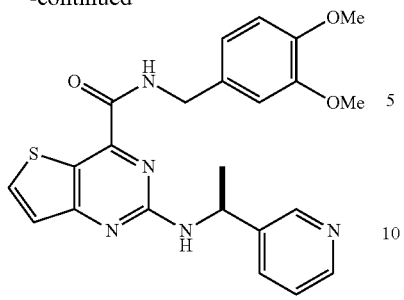

Synthesis of (S)—N-((1-benzylpiperidin-4-yl)methyl)-2-((1-(pyridin-3-yl)ethyl)amino)thieno[3,2-d]pyrimidine-4-carboxamide (Z33): The title compound (Z33) was prepared from 2-chloro-N-(3,4-dimethoxybenzyl)thieno[3,2-d]pyrimidine-4-carboxamide using chemistry similar to that described in Example Z6 (27% yield). LCMS m/z=450.2 [M+H$^+$].

Example Z34. ((R)-3-Methylpyrrolidin-1-yl)(2-(((S)-1-(pyridin-3-yl)ethyl)amino)thieno[3,2-d]pyrimidin-4-yl)methanone

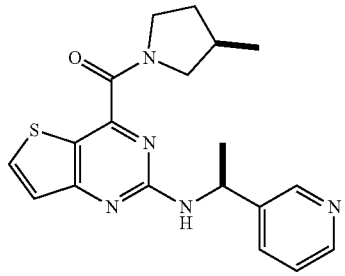

(Z34)

Synthesis of ((R)-3-methylpyrrolidin-1-yl)(2-(((S)-1-(pyridin-3-yl)ethyl)amino)thieno[3,2-d]pyrimidin-4-yl)methanone (Z34): The title compound (Z34) was prepared from 2-[[(1S)-1-(3-pyridyl)ethyl]amino]thieno[3,2-d]pyrimidine-4-carboxylic acid di-hydrochloride (37 mg, 0.10 mmol) using chemistry similar to that described in Example Z8 using (R)-3-methylpyrrolidine hydrochloride in place of (R)-3-fluoropyrrolidine (33 mg, 90% yield). $^1$H NMR (400 MHz, CDCl$_3$) δ 1.06 (3H, d, J=6.8 Hz), 1.45 (1H, m), 1.63 (3H, d, J=7.2 Hz), 2.00 (1H, m), 2.23 (1H, m), 3.23 (1H, m), 3.63 (1H, m), 3.78-3.88 (2H, m), 5.22 (1H, quintet, J=6.8 Hz), 5.43 (1H, d, J=6.8 Hz), 7.17 (1H, d, J=5.6 Hz), 7.24 (1H, m), 7.70 (1H, m), 7.94 (1H, d, J=5.6 Hz), 8.48 (1H, m), 8.68 (1H, m) ppm. LCMS m/z=368.1 [M+H$^+$].

398

Example Z35. N-(Pyridazin-3-ylmethyl)-2-((pyridazin-3-ylmethyl)amino)thieno[3,2-d]pyrimidine-4-carboxamide

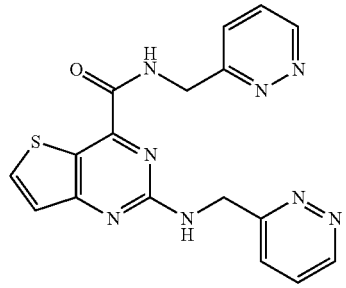 [SMILES: O=C(NCc1cccnn1)c1nc(NCc2cccnn2)nc2ccsc12]

(Z35)

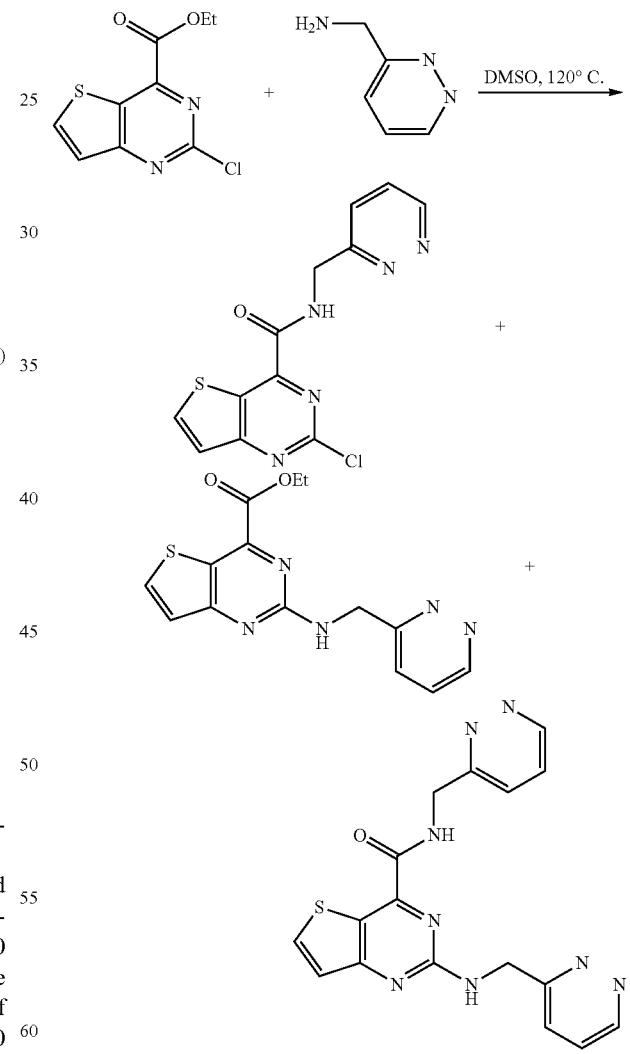

Synthesis of N-(1-(pyridin-3-yl)propyl)-2-((1-(pyridin-3-yl)propyl)amino)thieno[3,2-d]pyrimidine-4-carboxamide (Z35): The title compound (Z35) was prepared from ethyl 2-chlorothieno[3,2-d]pyrimidine-4-carboxylate (100 mg, 0.41 mmol) using chemistry similar to that described in Example Z12 using pyridazin-3-ylmethanamine (commercially available from Princeton Bio, Monmouth Jct., N.J.) in place of (6-methoxypyridin-3-yl)methanamine hydrochloride (7.2 mg, 4.6% yield). LCMS m/z=379.1 [M+H$^+$]. Also isolated were 2-chloro-N-(pyridazin-3-ylmethyl)thieno[3,2-d]pyrimidine-4-carboxamide (12 mg, 10% yield) LCMS m/z=306.2 [M+H$^+$], and ethyl 2-((pyridazin-3-ylmethyl)amino)thieno[3,2-d]pyrimidine-4-carboxylate (19 mg, 15% yield). LCMS m/z=316.1 [M+H$^+$].

Example Z36. ((S)-2-Methylpyrrolidin-1-yl)(2-(((S)-1-(pyridin-3-yl)ethyl)amino)thieno[3,2-d]pyrimidin-4-yl)methanone

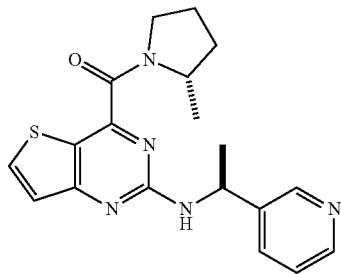 [SMILES: C[C@H](Nc1nc(C(=O)N2CCC[C@@H]2C)c2sccc2n1)c1cccnc1]

(Z36)

Synthesis of ((S)-2-methylpyrrolidin-1-yl)(2-(((S)-1-(pyridin-3-yl)ethyl)amino)thieno[3,2-d]pyrimidin-4-yl)methanone (Z36): The title compound (Z36) was prepared from 2-[[(1S)-1-(3-pyridyl)ethyl]amino]thieno[3,2-d]pyrimidine-4-carboxylic acid di-hydrochloride (37 mg, 0.10 mmol) using chemistry similar to that described in Example Z8 using (2S)-2-methylpyrrolidine in place of (R)-3-fluoropyrrolidine (37 mg, 100% yield). $^1$H NMR (400 MHz, CDCl$_3$) δ 1.33 (3H, d, J=6.0 Hz), 1.56-1.73 (2H, m), 1.63 (3H, d, J=6.8 Hz), 1.89 (1H, m), 1.97 (1H, m), 3.66-3.77 (2H, m), 4.38 (1H, m), 5.22 (1H, quintet, J=6.8 Hz), 5.43 (1H, d, J=6.8 Hz), 7.17 (1H, d, J=5.6 Hz), 7.24 (1H, dd, J=8.0, 4.8 Hz), 7.71 (1H, dt, J=8.0, 1.6 Hz), 7.94 (1H, d, J=5.6 Hz), 8.48 (1H, dd, J=4.8, 1.6 Hz), 8.68 (1H, d, J=1.6 Hz) ppm. LCMS m/z=368.1 [M+H$^+$].

Example Z37. ((R)-2-Methylpyrrolidin-1-yl)(2-(((S)-1-(pyridin-3-yl)ethyl)amino)thieno[3,2-d]pyrimidin-4-yl)methanone

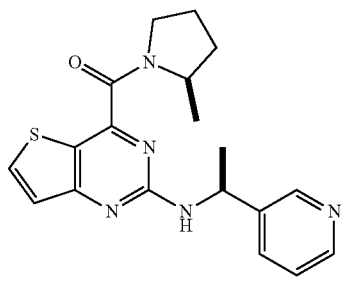 [SMILES: C[C@H](Nc1nc(C(=O)N2CCC[C@H]2C)c2sccc2n1)c1cccnc1]

(Z37)

Synthesis of ((R)-2-methylpyrrolidin-1-yl)(2-(((S)-1-(pyridin-3-yl)ethyl)amino)thieno[3,2-d]pyrimidin-4-yl)methanone (Z37): The title compound (Z37) was prepared from 2-[[(1S)-1-(3-pyridyl)ethyl]amino]thieno[3,2-d]pyrimidine-4-carboxylic acid di-hydrochloride (37 mg, 0.10 mmol) using chemistry similar to that described in Example Z8 using (2R)-2-methylpyrrolidine in place of (R)-3-fluoropyrrolidine (35 mg, 95% yield). $^1$H NMR (400 MHz, CDCl$_3$) δ 1.31 (3H, d, J=6.8 Hz), 1.61 (1H, m), 1.63 (3H, d, J=6.8 Hz), 1.82 (1H, m), 1.93-2.01 (2H, m), 3.70-3.84 (2H, m), 4.43 (1H, m), 5.22 (1H, quintet, J=6.8 Hz), 5.41 (1H, d, J=6.8 Hz), 7.17 (1H, d, J=5.6 Hz), 7.24 (1H, dd, J=8.0, 4.8 Hz), 7.71 (1H, dt, J=8.0, 1.6 Hz), 7.93 (1H, d, J=5.6 Hz), 8.49 (1H, dd, J=4.8, 1.6 Hz), 8.68 (1H, d, J=1.6 Hz) ppm. LCMS m/z=368.1 [M+H$^+$].

Example Z38. (2-((3,4-Dimethoxybenzyl)amino)thieno[3,2-d]pyrimidin-4-yl)(pyrrolidin-1-yl)methanone

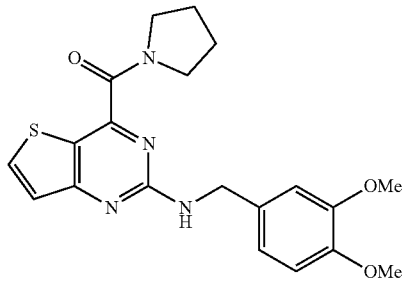 [SMILES: COc1ccc(CNc2nc(C(=O)N3CCCC3)c3sccc3n2)cc1OC]

(Z38)

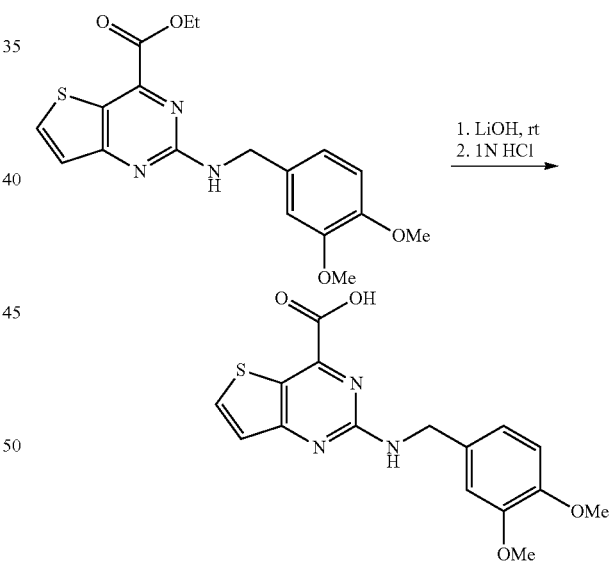

Synthesis of 2-[(3,4-dimethoxyphenyl)methylamino]thieno[3,2-d]pyrimidine-4-carboxylic acid hydrochloride: A mixture of hydroxylithium (4 mg, 0.1700 mmol) and ethyl 2-[(3,4-dimethoxyphenyl)methylamino]thieno[3,2-d]pyrimidine-4-carboxylate (13.3 mg, 0.04 mmol) in methanol (0.8 mL)/THF (0.2 mL)/water (0.2 mL) mixture was stirred at room temperature for 2 hours. The reaction mixture was concentrated, 1N HCl solution was used to adjust pH to 6, the resulting mixture was extracted with ethyl acetate, the organic extracts were dried over MgSO$_4$, filtered, and concentrated to provide crude 2-[(3,4-dimethoxyphenyl)methylamino]thieno[3,2-d]pyrimidine-4-carboxylic acid hydrochloride (15 mg, 112% yield). LCMS m/z=346.1 [M+H⁺].

Synthesis of (2-((3,4-dimethoxybenzyl)amino)thieno[3,2-d]pyrimidin-4-yl)(pyrrolidin-1-yl)methanone (Z38): The title compound (Z38) was prepared from crude 2-[(3,4-dimethoxyphenyl)methylamino]thieno[3,2-d]pyrimidine-4-carboxylic acid hydrochloride using chemistry similar to that described in Example Z8 using pyrrolidine in place of (R)-3-fluoropyrrolidine (38% yield). LCMS m/z=399.1 [M+H⁺].

Example Z39. (2-(Benzylamino)thieno[3,2-d]pyrimidin-4-yl)(pyrrolidin-1-yl)methanone

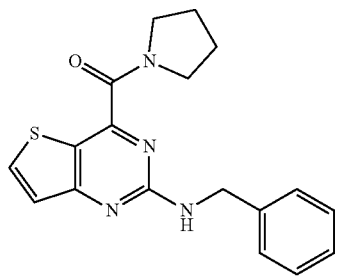 [SMILES: O=C(c1nc(NCc2ccccc2)nc2ccsc12)N1CCCC1]
(Z39)

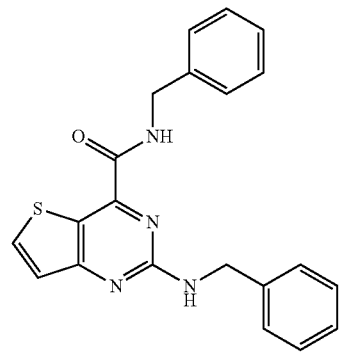

Synthesis of ethyl 2-(benzylamino)thieno[3,2-d]pyrimidine-4-carboxylate. The title compound was prepared from ethyl 2-chlorothieno[3,2-d]pyrimidine-4-carboxylate (124 mg, 0.51 mmol) using chemistry similar to that described in Example Z12 using benzylamine (commercially available from Sigma-Aldrich, St. Louis, Mo.) in place of (6-methoxypyridin-3-yl)methanamine hydrochloride (42 mg, 26% yield). LCMS m/z=314.1 [M+H⁺]. Also isolated were N-benzyl-2-chlorothieno[3,2-d]pyrimidine-4-carboxamide (12 mg, 9% yield), LCMS m/z=306.2 [M+H⁺], and N-benzyl-2-(benzylamino)thieno[3,2-d]pyrimidine-4-carboxamide (7.2 mg, 5% yield). LCMS m/z=379.1 [M+H⁺].

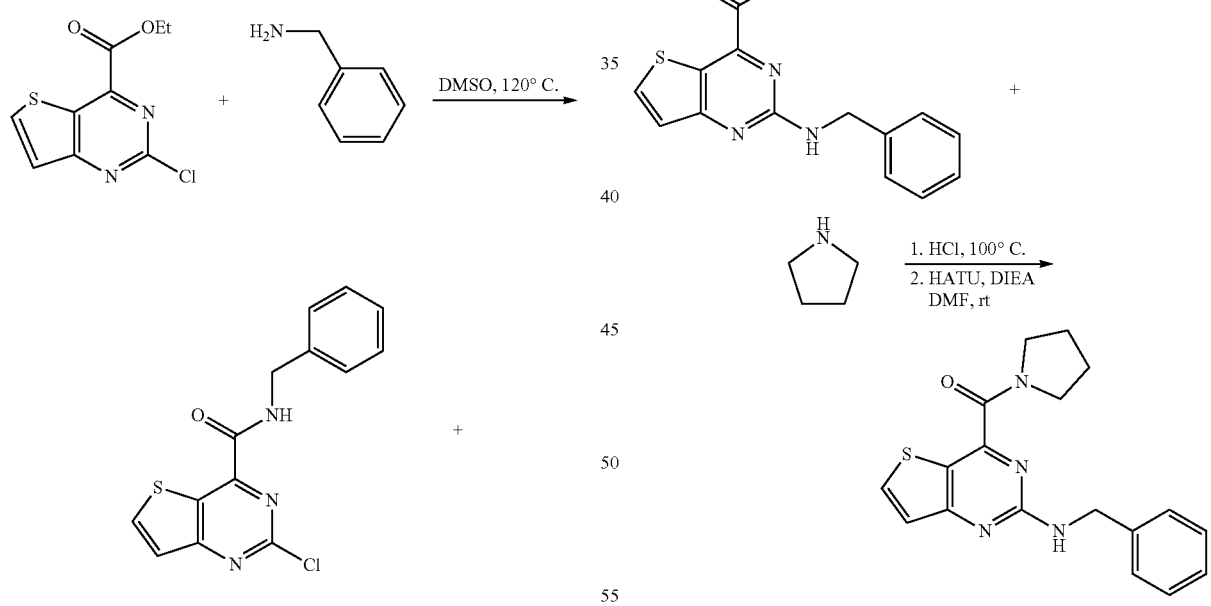

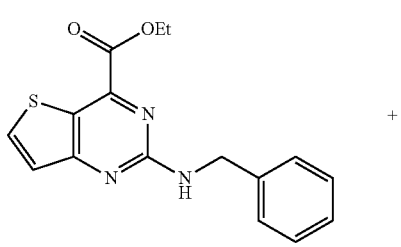

Synthesis of (2-(benzylamino)thieno[3,2-d]pyrimidin-4-yl)(pyrrolidin-1-yl)methanone (Z39): The title compound (Z39) was prepared from ethyl 2-(benzylamino)thieno[3,2-d]pyrimidine-4-carboxylate using chemistry similar to that described in Example Z17 using pyrrolidine in place of (3R)-3-methoxypyrrolidine hydrochloride (78% yield). ¹H NMR (400 MHz, DMSO-d₆) δ 1.75-1.79 (4H, m), 3.29 (2H, m), 3.52 (2H, m), 4.58 (2H, d, J=8.8 Hz), 7.18 (1H, m), 7.22 (1H, m), 7.27-7.32 (4H, m), 7.86 (1H, br t, J=6.8 Hz), 8.25 (1H, d, J=2.8 Hz) ppm. LCMS m/z=339.2 [M+H⁺].

Example Z40. (S)-(2-(Benzylamino)thieno[3,2-d]pyrimidin-4-yl)(3-hydroxypyrrolidin-1-yl)methanone

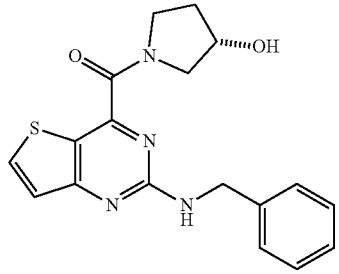 [SMILES: O=C(c1nc(NCc2ccccc2)nc2ccsc12)N1CC[C@H](O)C1]

(Z40)

Synthesis of (S)-(2-(benzylamino)thieno[3,2-d]pyrimidin-4-yl)(3-hydroxypyrrolidin-1-yl)methanone (Z40): The title compound (Z40) was prepared from ethyl 2-(benzylamino)thieno[3,2-d]pyrimidine-4-carboxylate using chemistry similar to that described in Example Z17 using pyrrolidine in place of (3R)-3-methoxypyrrolidine hydrochloride (24% yield). LCMS m/z=355.1 [M+H$^+$].

Example Z41. (S)—N,N-Diethyl-2-((1-(pyridin-3-yl)ethyl)amino)thieno[3,2-d]pyrimidine-4-carboxamide

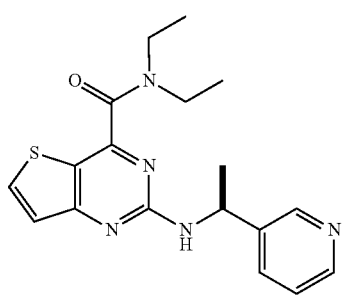 [SMILES: CCN(CC)C(=O)c1nc(N[C@@H](C)c2cccnc2)nc2ccsc12]

(Z41)

Synthesis of (S)—N,N-diethyl-2-((1-(pyridin-3-yl)ethyl)amino)thieno[3,2-d]pyrimidine-4-carboxamide (Z41): The title compound (Z41) was prepared from 2-[[(1S)-1-(3-pyridyl)ethyl]amino]thieno[3,2-d]pyrimidine-4-carboxylic acid di-hydrochloride using chemistry similar to that described in Example Z8 using diethylamine in place of (R)-3-fluoropyrrolidine (100% yield). $^1$H NMR (400 MHz, CDCl$_3$) δ 1.07 (3H, t, J=6.8 Hz), 1.27 (3H, t, J=7.2 Hz), 1.62 (3H, d, J=6.8 Hz), 3.38-3.48 (2H, m), 3.53-3.59 (2H, m), 5.26 (1H, quintet, J=6.8 Hz), 5.41 (1H, d, J=6.8 Hz), 7.17 (1H, d, J=5.6 Hz), 7.24 (1H, dd, J=8.0, 4.8 Hz), 7.70 (1H, dt, J=8.0, 2.0 Hz), 7.89 (1H, d, J=5.6 Hz), 8.48 (1H, dd, J=4.8, 2.0 Hz), 8.68 (1H, d, J=2.0 Hz) ppm. LCMS m/z=356.1 [M+H$^+$].

Example Z42. (S)—N-Benzyl-2-((1-(pyridin-3-yl)ethyl)amino)thieno[3,2-d]pyrimidine-4-carboxamide

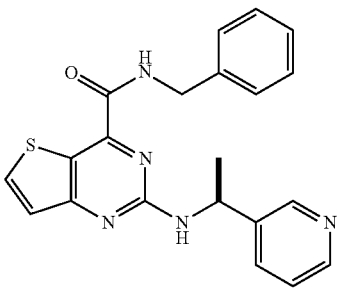 [SMILES: C[C@H](Nc1nc(C(=O)NCc2ccccc2)c2sccc2n1)c1cccnc1]

(Z42)

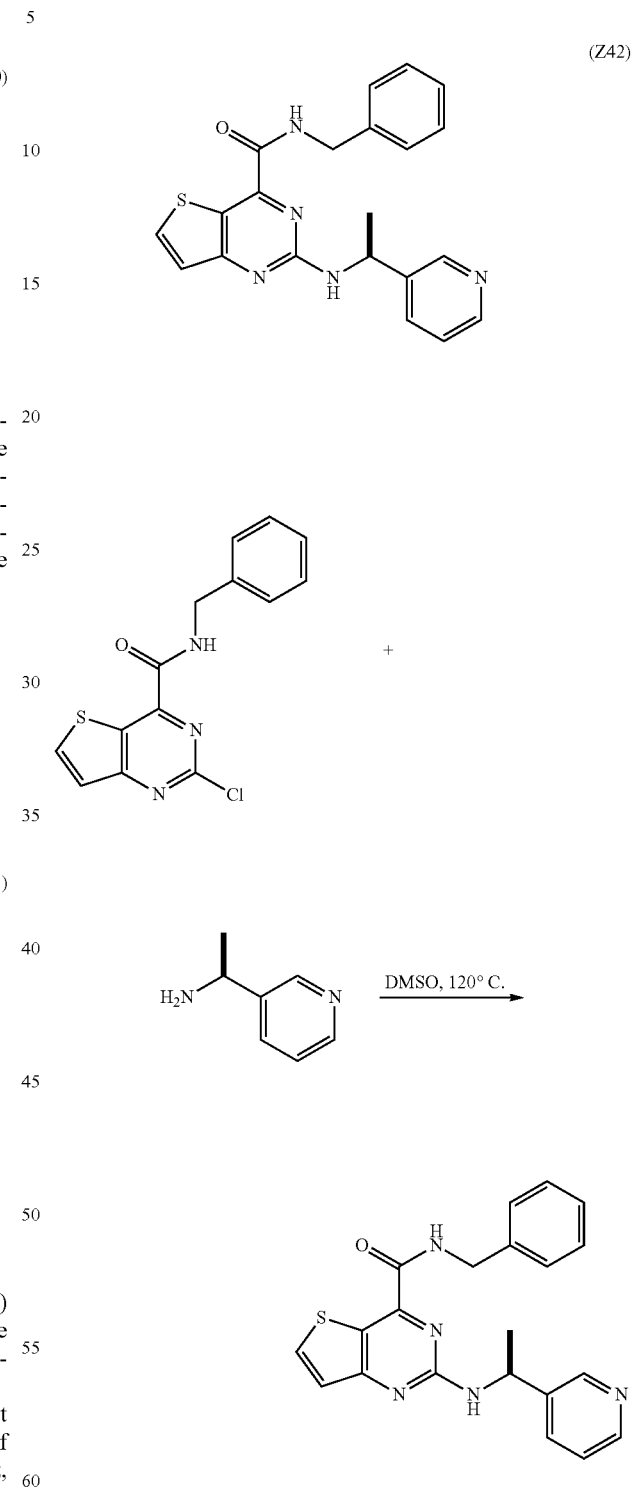

Synthesis of (S)—N-benzyl-2-((1-(pyridin-3-yl)ethyl)amino)thieno[3,2-d]pyrimidine-4-carboxamide (Z42): The title compound (Z42) was prepared from N-benzyl-2-chlorothieno[3,2-d]pyrimidine-4-carboxamide using chemistry similar to that described in Example Z6 (13% yield). LCMS m/z=390.2 [M+H$^+$].

Example Z43. (2-((Pyridazin-3-ylmethyl)amino) thieno[3,2-d]pyrimidin-4-yl)(pyrrolidin-1-yl)methanone

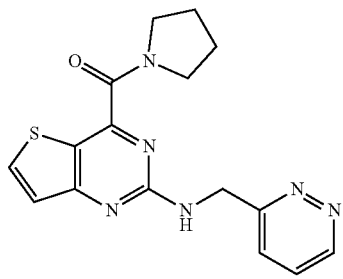 [SMILES: O=C(c1nc(NCc2cccnn2)nc2ccsc12)N1CCCC1]

(Z43)

Synthesis of (2-((pyridazin-3-ylmethyl)amino)thieno[3,2-d]pyrimidin-4-yl)(pyrrolidin-1-yl)methanone (Z43): The title compound (Z43) was prepared from ethyl 2-((pyridazin-3-ylmethyl)amino)thieno[3,2-d]pyrimidine-4-carboxylate using chemistry similar to that described in Example Z17 using pyrrolidine in place of (3R)-3-methoxy-pyrrolidine hydrochloride (89% yield). LCMS m/z=341.1 [M+H$^+$].

Example Z44. N-(1-(Pyridin-3-yl)ethyl)-2-((1-(pyridin-3-yl)ethyl)amino)thieno[3,2-d]pyrimidine-4-carboxamide (Z44)

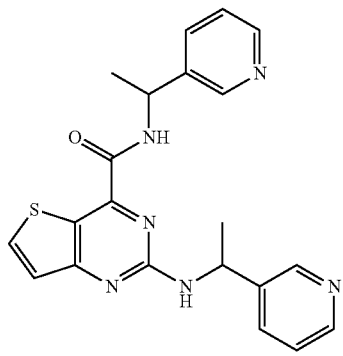 [SMILES: CC(NC(=O)c1nc(NC(C)c2cccnc2)nc2ccsc12)c1cccnc1]

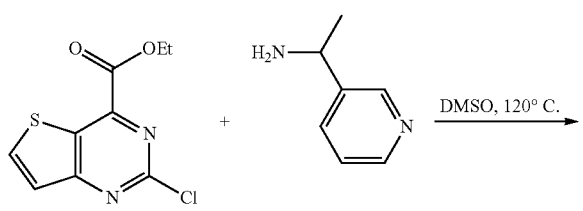

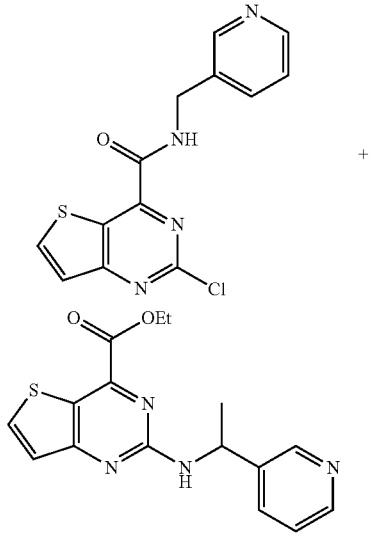

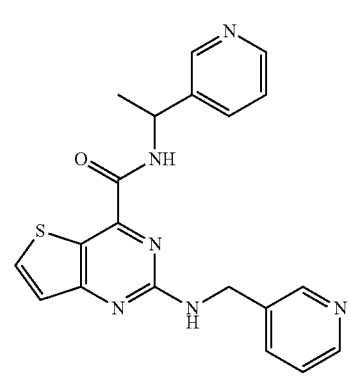

Synthesis of N-(1-(pyridin-3-yl)ethyl)-2-((1-(pyridin-3-yl)ethyl)amino)thieno[3,2-d]pyrimidine-4-carboxamide (Z44): The title compound (Z44) was prepared from ethyl 2-chlorothieno[3,2-d]pyrimidine-4-carboxylate (112 mg, 0.46 mmol) using chemistry similar to that described in Example Z12 using 1-(pyridin-3-yl)ethan-1-amine (Sigma-Aldrich, St. Louis, Mo.) in place of (6-methoxypyridin-3-yl)methanamine hydrochloride (32 mg, 17% yield). LCMS m/z=405.2 [M+H$^+$]. Also isolated were 2-chloro-N-(1-(pyridin-3-yl)ethyl)thieno[3,2-d]pyrimidine-4-carboxamide (16 mg, 11% yield), LCMS m/z=319.1 [M+H$^+$], and ethyl 2-((1-(pyridin-3-yl)ethyl)amino)thieno[3,2-d]pyrimidine-4-carboxylate hydrochloride (60 mg, 39% yield). LCMS m/z=329.1 [M+H$^+$].

Example Z45. N-((5-Methylpyridin-3-yl)methyl)-2-(((5-methylpyridin-3-yl)methyl)amino)thieno[3,2-d]pyrimidine-4-carboxamide

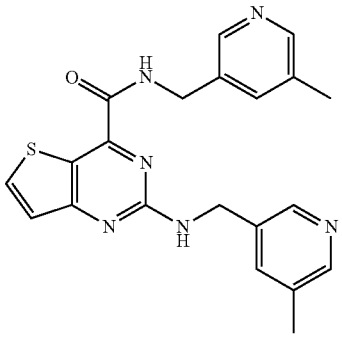 [SMILES: Cc1cncc(CNC(=O)c2nc(NCc3cncc(C)c3)nc3ccsc23)c1]
(Z45)

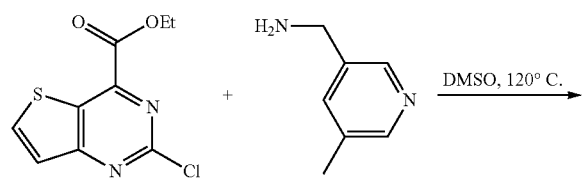

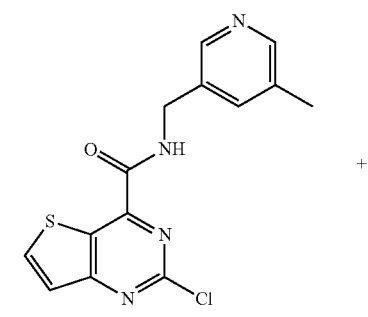

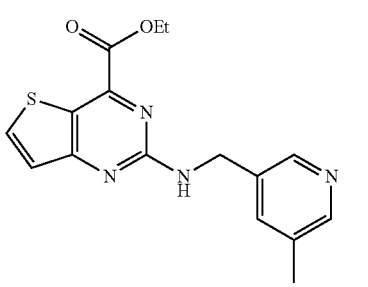

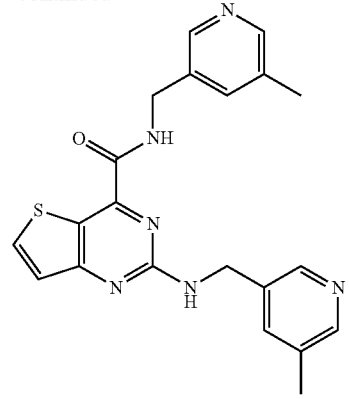

Synthesis of N-((5-methylpyridin-3-yl)methyl)-2-(((5-methylpyridin-3-yl)methyl)amino)thieno[3,2-d]pyrimidine-4-carboxamide (Z45): The title compound (Z45) was prepared from ethyl 2-chlorothieno[3,2-d]pyrimidine-4-carboxylate (112 mg, 0.46 mmol) using chemistry similar to that described in Example Z12 using (5-methyl-3-pyridyl)methanamine (commercially obtained from Oxchem, Wood Dale, Ill.) in place of (6-methoxypyridin-3-yl)methanamine hydrochloride (88 mg, 47% yield). LCMS m/z=405.2 [M+H$^+$]. Also isolated were 2-chloro-N-((5-methylpyridin-3-yl)methyl)thieno[3,2-d]pyrimidine-4-carboxamide (10 mg, 7% yield), LCMS m/z=319.2 [M+H$^+$], and ethyl 2-(((5-methylpyridin-3-yl)methyl)amino)thieno[3,2-d]pyrimidine-4-carboxylate (27 mg, 18% yield). LCMS m/z=329.1 [M+H$^+$].

Example Z46. ((R)-2-(Hydroxymethyl)pyrrolidin-1-yl)(2-(((S)-1-(pyridin-3-yl)ethyl)amino)thieno[3,2-d]pyrimidin-4-yl)methanone

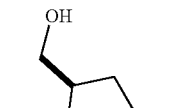
(Z46)

Synthesis of ((R)-2-(hydroxymethyl)pyrrolidin-1-yl)(2-(((S)-1-(pyridin-3-yl)ethyl)amino)thieno[3,2-d]pyrimidin-4-yl)methanone (Z46): The title compound (Z46) was prepared from 2-[[(1S)-1-(3-pyridyl)ethyl]amino]thieno[3,2-d]pyrimidine-4-carboxylic acid di-hydrochloride using chemistry similar to that described in Example Z8 using (R)-pyrrolidin-2-ylmethanol (commercially obtained from Sigma-Aldrich, St. Louis, Mo.) in place of (R)-3-fluoropyrrolidine (89% yield). $^1$H NMR (400 MHz, CDCl$_3$) δ 1.63 (3H, d, J=6.8 Hz), 1.64 (1H, m), 1.79 (1H, m), 1.95 (1H, m), 2.24 (1H, m), 3.54 (1H, m), 3.72-3.80 (2H, m), 4.25 (1H, m), 4.42 (1H, m), 5.19 (1H, quintet, J=6.8 Hz), 5.48 (1H, d, J=6.8 Hz), 7.17 (1H, d, J=5.6 Hz), 7.24 (1H, dd, J=8.0, 4.8 Hz), 7.70 (1H, dt, J=8.0, 1.6 Hz), 7.94 (1H, d, J=5.6 Hz), 8.48 (1H, dd, J=4.8, 1.6 Hz), 8.68 (1H, d, J=1.6 Hz) ppm. LCMS m/z=384.2 [M+H$^+$].

Example Z47. ((S)-2-(Hydroxymethyl)pyrrolidin-1-yl)(2-(((S)-1-(pyridin-3-yl)ethyl)amino)thieno[3,2-d]pyrimidin-4-yl)methanone

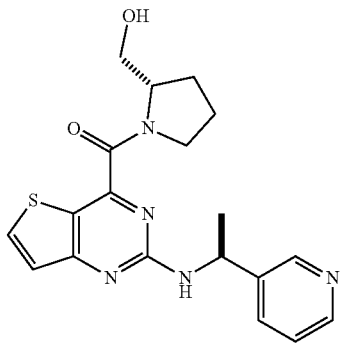 [SMILES: C[C@H](Nc1nc(C(=O)N2CCC[C@H]2CO)c2sccc2n1)c1cccnc1]

(Z47)

Synthesis of ((S)-2-(hydroxymethyl)pyrrolidin-1-yl)(2-(((S)-1-(pyridin-3-yl)ethyl)amino)thieno[3,2-d]pyrimidin-4-yl)methanone (Z47): The title compound (Z47) was prepared from 2-[[(1S)-1-(3-pyridyl)ethyl]amino]thieno[3,2-d]pyrimidine-4-carboxylic acid di-hydrochloride using chemistry similar to that described in Example Z8 using (S)-pyrrolidin-2-ylmethanol (commercially obtained from Sigma-Aldrich, St. Louis, Mo.) in place of (R)-3-fluoropyrrolidine (82% yield). $^1$H NMR (400 MHz, CDCl$_3$) δ 1.63 (3H, d, J=7.2 Hz), 1.70-1.84 (2H, m), 1.91 (1H, m), 2.08 (1H, m), 3.62 (1H, m), 3.73 (1H, dd, J=12.0, 6.4 Hz), 3.82 (1H, dd, J=12.0, 3.2 Hz), 3.96 (1H, m), 4.46 (1H, m), 5.19 (1H, m), 5.45 (1H, d, J=6.4 Hz), 7.18 (1H, d, J=5.6 Hz), 7.24 (1H, dd, J=8.0, 4.8 Hz), 7.70 (1H, dt, J=8.0, 1.6 Hz), 7.93 (1H, d, J=5.6 Hz), 8.47 (1H, dd, J=4.8, 1.6 Hz), 8.69 (1H, d, J=1.6 Hz) ppm. LCMS m/z=384.2 [M+H$^+$].

Example Z48. ((R)-3-Fluoropyrrolidin-1-yl)(2-((1-(pyridin-3-yl)ethyl)amino)thieno[3,2-d]pyrimidin-4-yl)methanone

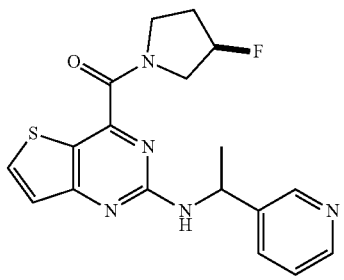 [SMILES: CC(Nc1nc(C(=O)N2CC[C@@H](F)C2)c2sccc2n1)c1cccnc1]

(Z48)

Synthesis of ((R)-3-fluoropyrrolidin-1-yl)(2-((1-(pyridin-3-yl)ethyl)amino)thieno[3,2-d]pyrimidin-4-yl)methanone (Z48): The title compound (Z48) was prepared from ethyl 2-((1-(pyridin-3-yl)ethyl)amino)thieno[3,2-d]pyrimidine-4-carboxylate using chemistry similar to that described in Example Z17 using (3R)-3-fluoropyrrolidine hydrochloride in place of (3R)-3-methoxypyrrolidine hydrochloride (87% yield).). LCMS m/z=372.2 [M+H$^+$].

Example Z49. N-((6-Methoxypyridin-3-yl)methyl)-2-((1-(pyridin-2-yl)ethyl)amino)thieno[3,2-d]pyrimidine-4-carboxamide

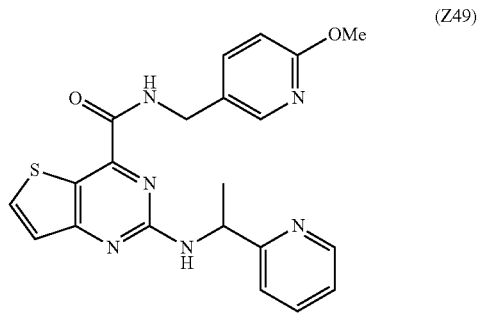

(Z49)

Synthesis of N-((6-methoxypyridin-3-yl)methyl)-2-((1-(pyridin-2-yl)ethyl)amino)thieno[3,2-d]pyrimidine-4-carboxamide (Z49): The title compound (Z49) was prepared from ethyl 2-((1-(pyridin-3-yl)ethyl)amino)thieno[3,2-d]pyrimidine-4-carboxylate using chemistry similar to that described in Example Z17 using (6-methoxypyridin-3-yl)methanamine (ACS Scientific, Berkeley Heights, N.J.) in place of (3R)-3-methoxypyrrolidine hydrochloride (51% yield).). LCMS m/z=421.3 [M+H$^+$].

Example Z50. (2-(((5-Methylpyridin-3-yl)methyl)amino)thieno[3,2-d]pyrimidin-4-yl)(pyrrolidin-1-yl)methanone

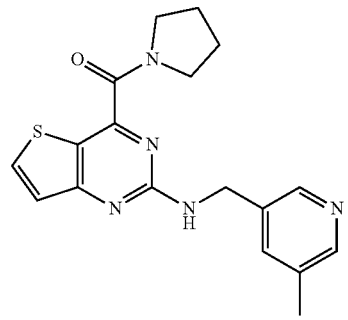 [SMILES: Cc1cncc(CNc2nc(C(=O)N3CCCC3)c3sccc3n2)c1]

(Z50)

Synthesis of (2-(((5-methylpyridin-3-yl)methyl)amino)thieno[3,2-d]pyrimidin-4-yl)(pyrrolidin-1-yl)methanone (Z50): The title compound (Z50) was prepared from ethyl 2-(((5-methylpyridin-3-yl)methyl)amino)thieno[3,2-d]pyrimidine-4-carboxylate using chemistry similar to that described in Example Z17 using pyrrolidine in place of (3R)-3-methoxypyrrolidine hydrochloride (85% yield).). LCMS m/z=354.2 [M+H$^+$].

Example Z51. N-Benzyl-2-(benzylamino)thieno[3,2-d]pyrimidine-4-carboxamide

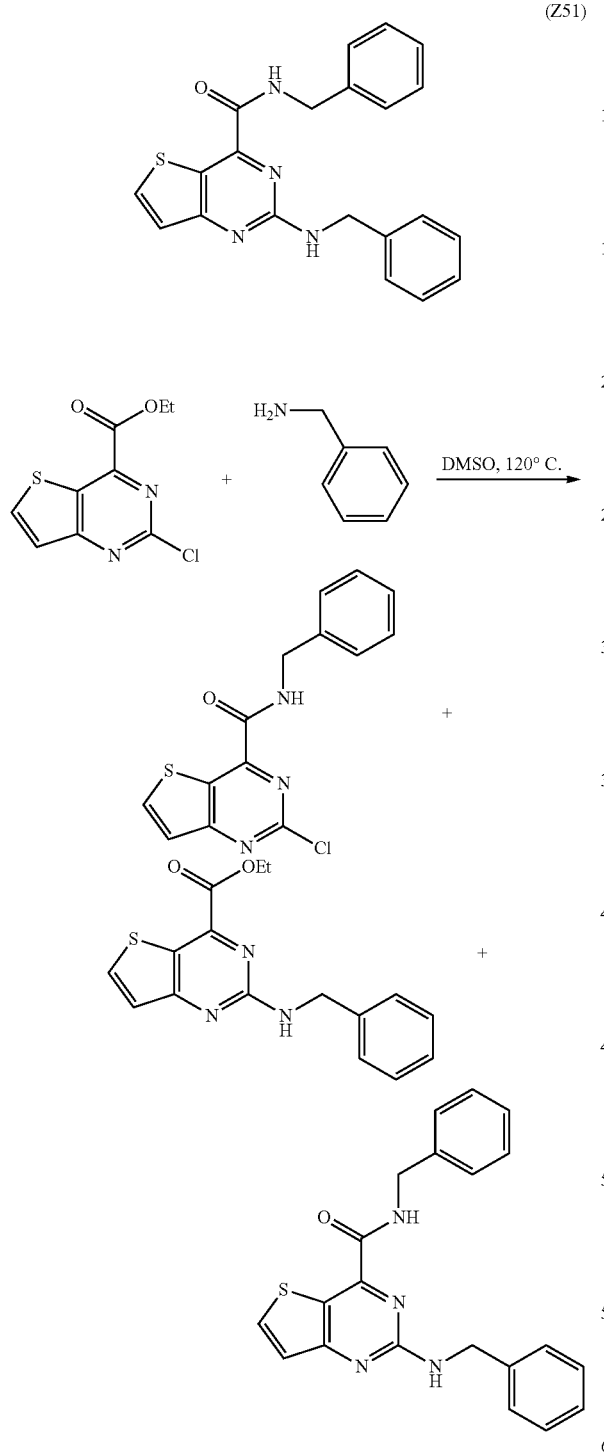

Synthesis of N-benzyl-2-(benzylamino)thieno[3,2-d]pyrimidine-4-carboxamide (Z51): The title compound (Z51) was prepared from ethyl 2-chlorothieno[3,2-d]pyrimidine-4-carboxylate (124 mg, 0.51 mmol) using chemistry similar to that described in Example Z12 using benzylamine in place of (6-methoxypyridin-3-yl)methanamine hydrochloride (82 mg, 43% yield). LCMS m/z=375.2 [M+H⁺]. Also isolated were N-benzyl-2-chlorothieno[3,2-d]pyrimidine-4-carboxamide (15 mg, 9% yield), LCMS m/z=304.1 [M+H⁺], and ethyl 2-(benzylamino)thieno[3,2-d]pyrimidine-4-carboxylate (42 mg, 26% yield). LCMS m/z=314.1 [M+H⁺].

Example Z52. ((R)-3-Fluoropyrrolidin-1-yl)(2-(((S)-1-(pyridin-2-yl)ethyl)amino)thieno[3,2-d]pyrimidin-4-yl)methanone

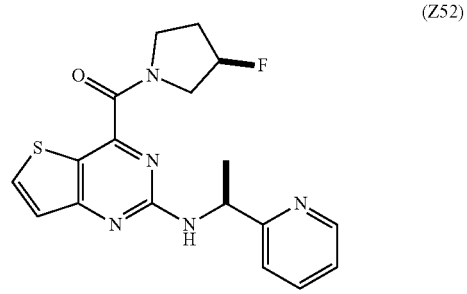

Synthesis of (S)-2-((1-(pyridin-2-yl)ethyl)amino)thieno[3,2-d]pyrimidine-4-carboxylic acid dihydrochloride: Methyl 2-[[(1S)-1-(2-pyridyl)ethyl]amino]thieno[3,2-d]pyrimidine-4-carboxylate (71 mg, 0.23 mmol) was dissolved in 6 N HCl (2.5 mL) and stirred at 100° C. for 2 h. The reaction mixture was evaporated to dryness in vacuo at a bath temperature of 60° C. and the residue was dried under high vacuum to provide (S)-2-((1-(pyridin-2-yl)ethyl)amino)thieno[3,2-d]pyrimidine-4-carboxylic acid di-hydrochloride salt as a yellow solid (84 mg, 100% yield) which was used in nest step without further purification. LCMS m/z=301.1 [M+H⁺].

Synthesis of ((R)-3-fluoropyrrolidin-1-yl)(2-(((S)-1-(pyridin-2-yl)ethyl)amino)thieno[3,2-d]pyrimidin-4-yl)methanone (Z52): The title compound (Z52) was prepared from (S)-2-((1-(pyridin-2-yl)ethyl)amino)thieno[3,2-d]pyrimidine-4-carboxylic acid di-hydrochloride using chemistry similar to that described in Example Z8 (93% yield). ¹H NMR (400 MHz, CDCl₃) δ 1.63 (3H, d, J=6.8 Hz), 2.00 (1H, m), 2.31 (1H, m), 3.76-4.12 (3H, m), 4.46 (1H, m), 5.21-5.35 (2H, m), 6.06 (1H, m), 7.17 (1H, dd, J=7.2, 4.8 Hz), 7.20 (1H, d, J=5.6 Hz), 7.36 (1H, m), 7.63 (1H, m), 7.94 (1H, dd, J=5.6, 2.4 Hz), 8.58 (1H, m) ppm. LCMS m/z=372.2 [M+H⁺].

Example Z53. ((S)-3-Fluoropyrrolidin-1-yl)(2-(((S)-1-(pyridin-2-yl)ethyl)amino)thieno[3,2-d]pyrimidin-4-yl)methanone

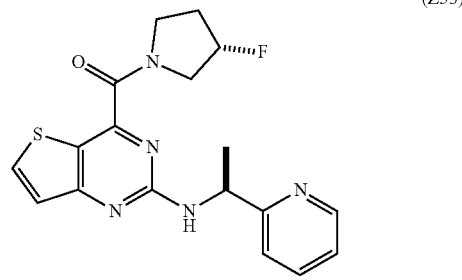

Synthesis of ((S)-3-fluoropyrrolidin-1-yl)(2-(((S)-1-(pyridin-2-yl)ethyl)amino)thieno[3,2-d]pyrimidin-4-yl)methanone (Z53): The title compound (Z53) was prepared from (S)-2-((1-(pyridin-2-yl)ethyl)amino)thieno[3,2-d]pyrimidine-4-carboxylic acid di-hydrochloride using chemistry similar to that described in Example Z8 (90% yield). ¹H NMR (400 MHz, CDCl₃) δ 1.62 (3H, d, J=6.8 Hz), 1.95 (1H, m), 2.25 (1H, m), 3.72-4.09 (4H, m), 5.10-5.32 (2H, m), 5.99 (1H, m), 7.15 (1H, m), 7.19 (1H, d, J=5.6 Hz), 7.36 (1H, m), 7.62 (1H, m), 7.94 (1H, dd, J=7.2, 5.6 Hz), 8.57 (1H, m) ppm. LCMS m/z=372.2 [M+H⁺].

Example Z54. N—((S)-1-(Pyridin-2-yl)ethyl)-2-(((S)-1-(pyridin-2-yl)ethyl)amino)thieno[3,2-d]pyrimidine-4-carboxamide

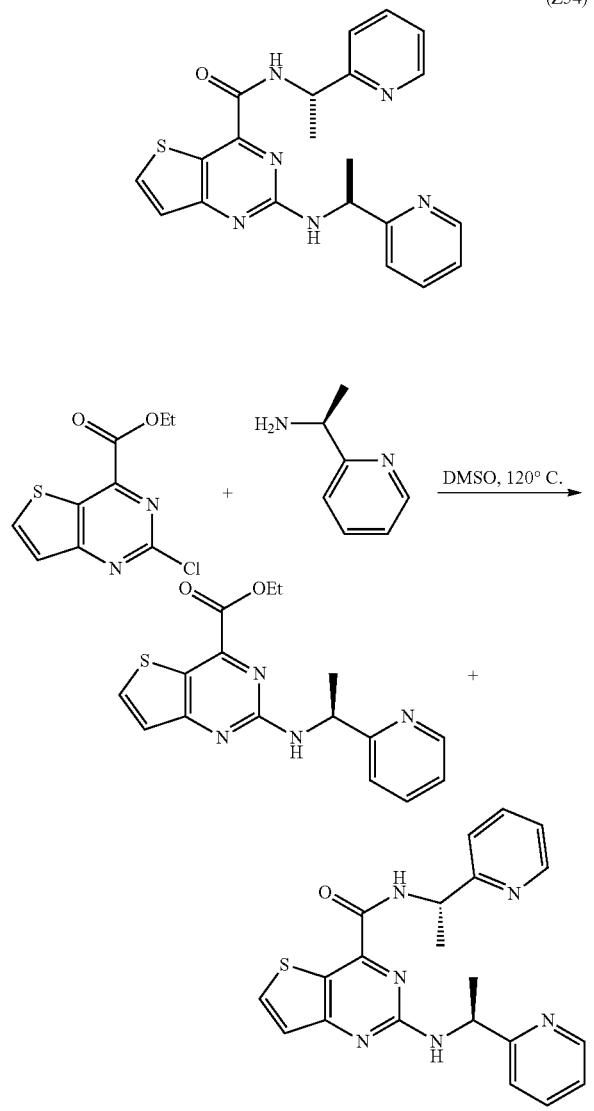

Synthesis of N—((S)-1-(pyridin-2-yl)ethyl)-2-(((S)-1-(pyridin-2-yl)ethyl)amino)thieno[3,2-d]pyrimidine-4-carboxamide (Z54): The title compound (Z54) was prepared from ethyl 2-chlorothieno[3,2-d]pyrimidine-4-carboxylate (92 mg, 0.38 mmol) using chemistry similar to that described in Example Z12 using 1S)-1-(2-pyridyl)ethanamine in place of (6-methoxypyridin-3-yl)methanamine hydrochloride (51 mg, 33% yield). LCMS m/z=405.2 [M+H⁺]. Also isolated was ethyl (S)-2-((1-(pyridin-2-yl)ethyl)amino)thieno[3,2-d]pyrimidine-4-carboxylate (62 mg, 50% yield). LCMS m/z=329.1 [M+H⁺].

Example Z55. Azetidin-1-yl(2-(((5-methylpyridin-3-yl)methyl)amino)thieno[3,2-d]pyrimidin-4-yl)methanone

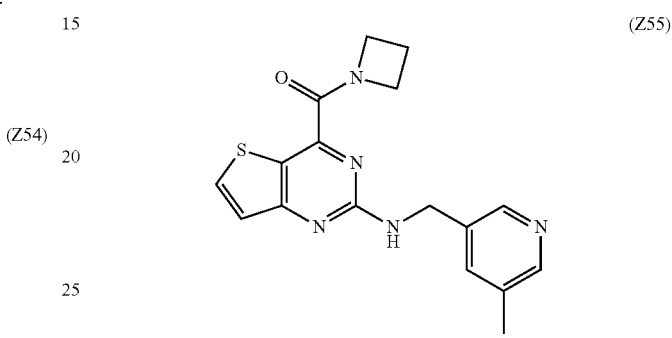

Synthesis of azetidin-1-yl(2-(((5-methylpyridin-3-yl)methyl)amino)thieno[3,2-d]pyrimidin-4-yl)methanone (Z55): The title compound (Z55) was prepared from ethyl 2-(((5-methylpyridin-3-yl)methyl)amino)thieno[3,2-d]pyrimidine-4-carboxylate using chemistry similar to that described in Example Z17 using azetidine in place of (3R)-3-methoxypyrrolidine hydrochloride (22% yield).). LCMS m/z=340.1 [M+H⁺].

Example Z56. (S)-(3-Hydroxypyrrolidin-1-yl)(2-(((5-methylpyridin-3-yl)methyl)amino)thieno[3,2-d]pyrimidin-4-yl)methanone

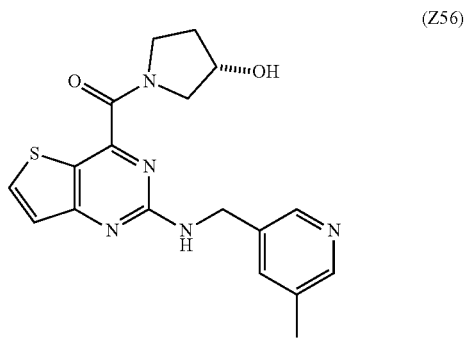

Synthesis of (S)-(3-hydroxypyrrolidin-1-yl)(2-(((5-methylpyridin-3-yl)methyl)amino)thieno[3,2-d]pyrimidin-4-yl)methanone (Z56): The title compound (Z56) was prepared from ethyl 2-(((5-methylpyridin-3-yl)methyl)amino)thieno[3,2-d]pyrimidine-4-carboxylate using chemistry similar to that described in Example Z17 using (3S)-pyrrolidin-3-ol in place of (3R)-3-methoxypyrrolidine hydrochloride (17% yield). LCMS m/z=370.3 [M+H⁺].

Example Z57. N-((6-Methoxypyridin-3-yl)methyl)-2-(((5-methylpyridin-3-yl)methyl)amino)thieno[3,2-d]pyrimidine-4-carboxamide

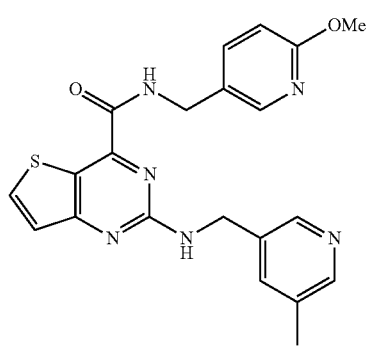 [SMILES: COc1ccc(CNC(=O)c2nc(NCc3cncc(C)c3)nc3ccsc23)cn1]

(Z57)

Synthesis of N-((6-methoxypyridin-3-yl)methyl)-2-(((5-methylpyridin-3-yl)methyl)amino)thieno[3,2-d]pyrimidine-4-carboxamide (Z57): The title compound (Z57) was prepared from ethyl 2-(((5-methylpyridin-3-yl)methyl)amino)thieno[3,2-d]pyrimidine-4-carboxylate using chemistry similar to that described in Example Z17 using (6-methoxy-3-pyridyl)methanamine hydrochloride in place of (3R)-3-methoxypyrrolidine hydrochloride (16% yield). LCMS m/z=421.3 [M+H$^+$].

Example Z58. ((S)-3-Hydroxypyrrolidin-1-yl)(2-(((S)-1-(pyridin-2-yl)ethyl)amino)thieno[3,2-d]pyrimidin-4-yl)methanone

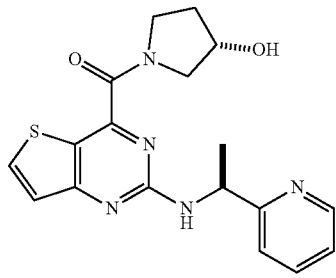 [SMILES: C[C@H](Nc1nc(C(=O)N2CC[C@H](O)C2)c2sccc2n1)c1ccccn1]

(Z58)

Synthesis of ((S)-3-hydroxypyrrolidin-1-yl)(2-(((S)-1-(pyridin-2-yl)ethyl)amino)thieno[3,2-d]pyrimidin-4-yl)methanone (Z58): The title compound (Z58) was prepared from (S)-2-((1-(pyridin-2-yl)ethyl)amino)thieno[3,2-d]pyrimidine-4-carboxylic acid di-hydrochloride using chemistry similar to that described in Example Z8 using (S)-pyrrolidin-3-ol in place of (R)-3-fluoropyrrolidine (13% yield). LCMS m/z=370.1 [M+H$^+$].

Example Z59. ((R)-3-Hydroxypyrrolidin-1-yl)(2-(((S)-1-(pyridin-2-yl)ethyl)amino)thieno[3,2-d]pyrimidin-4-yl)methanone

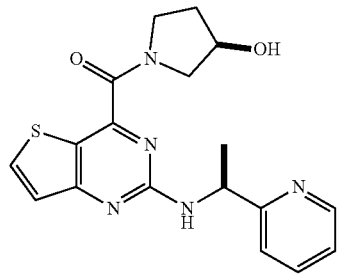

(Z59)

Synthesis of ((R)-3-hydroxypyrrolidin-1-yl)(2-(((S)-1-(pyridin-2-yl)ethyl)amino)thieno[3,2-d]pyrimidin-4-yl)methanone (Z59): The title compound (Z59) was prepared from (S)-2-((1-(pyridin-2-yl)ethyl)amino)thieno[3,2-d]pyrimidine-4-carboxylic acid di-hydrochloride using chemistry similar to that described in Example Z8 using (R)-pyrrolidin-3-ol in place of (R)-3-fluoropyrrolidine (39% yield). $^1$H NMR (400 MHz, CDCl$_3$) δ 1.62 (3H, d, J=6.8 Hz), 1.91-2.07 (2H, m), 3.62-3.88 (3H, m), 4.20 (1H, m), 4.51 (1H, m), 5.25 (1H, m), 6.03 (1H, m), 7.15-7.21 (2H, m), 7.38 (1H, m, 7.64 (1H, m), 7.94 (1H, d, J=5.6 Hz), 8.57 (1H, m) ppm. LCMS m/z=370.1 [M+H$^+$].

Example Z60. (R)-(2-(((5-Fluoropyridin-3-yl)methyl)amino)thieno[3,2-d]pyrimidin-4-yl)(3-fluoropyrrolidin-1-yl)methanone

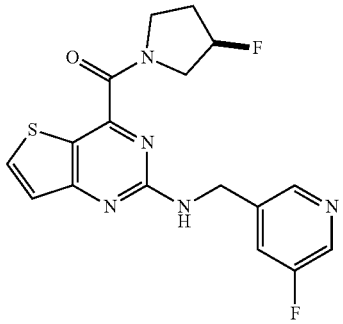 [SMILES: O=C(c1nc(NCc2cncc(F)c2)nc2ccsc12)N1CC[C@@H](F)C1]

(Z60)

Synthesis of (R)-(2-(((5-fluoropyridin-3-yl)methyl)amino)thieno[3,2-d]pyrimidin-4-yl)(3-fluoropyrrolidin-1-yl)methanone (Z60): The title compound (Z60) was prepared from ethyl 2-(((5-fluoropyridin-3-yl)methyl)amino)thieno[3,2-d]pyrimidine-4-carboxylate using chemistry similar to that described in Example Z17 using ((3R)-3-fluoropyrrolidine in place of (3R)-3-methoxypyrrolidine hydrochloride (55% yield). LCMS m/z=376.1 [M+H$^+$].

417

Example Z61. Azetidin-1-yl(2-(((5-fluoropyridin-3-yl)methyl)amino)thieno[3,2-d]pyrimidin-4-yl)methanone

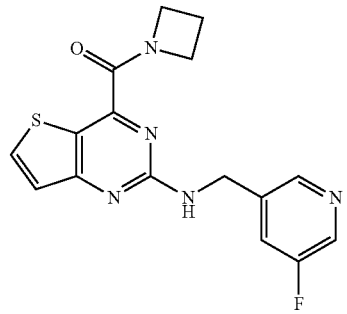 [SMILES: O=C(c1nc(NCc2cncc(F)c2)nc2ccsc12)N1CCC1]

(Z61)

Synthesis of azetidin-1-yl(2-(((5-fluoropyridin-3-yl)methyl)amino)thieno[3,2-d]pyrimidin-4-yl)methanone (Z61): The title compound (Z61) was prepared from ethyl 2-(((5-fluoropyridin-3-yl)methyl)amino)thieno[3,2-d]pyrimidine-4-carboxylate using chemistry similar to that described in Example Z17 using azetidine in place of (3R)-3-methoxypyrrolidine hydrochloride (51% yield). LCMS m/z=344.1 [M+H$^+$].

Example Z62. (S)-(2-(((5-Fluoropyridin-3-yl)methyl)amino)thieno[3,2-d]pyrimidin-4-yl)(3-hydroxypyrrolidin-1-yl)methanone

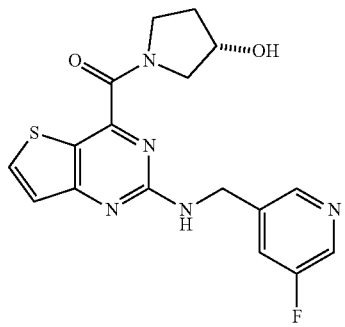 [SMILES: O=C(c1nc(NCc2cncc(F)c2)nc2ccsc12)N1CC[C@H](O)C1]

(Z62)

Synthesis of (S)-(2-(((5-fluoropyridin-3-yl)methyl)amino)thieno[3,2-d]pyrimidin-4-yl)(3-hydroxypyrrolidin-1-yl)methanone (Z62): The title compound (Z62) was prepared from ethyl 2-(((5-fluoropyridin-3-yl)methyl)amino)thieno[3,2-d]pyrimidine-4-carboxylate using chemistry similar to that described in Example Z17 using (3S)-pyrrolidin-3-ol in place of (3R)-3-methoxypyrrolidine hydrochloride (54% yield). $^1$H NMR (400 MHz, methanol-d$_4$) δ 1.94-2.03 (2H, m), 3.67-3.70 (1H, m) 3.76-3.79 (1H, m), 3.90 (2H, m), 4.40-4.45 (1H, m), 4.75 (2H, s), 7.20 (1H, dd, J=5.6, 0.8 Hz), 7.65 (1H, m), 8.13 (1H, dd, J=5.6, 0.8 Hz), 8.32 (1H, m), 8.45 (1H, m) ppm. LCMS m/z=374.1 [M+H$^+$].

418

Example Z63. ((S)-3-Methylpyrrolidin-1-yl)(2-(((S)-1-(pyridin-3-yl)ethyl)amino)thieno[3,2-d]pyrimidin-4-yl)methanone

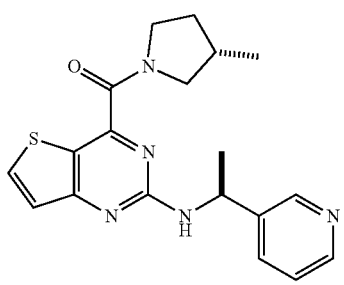 [SMILES: C[C@H]1CCN(C(=O)c2nc(N[C@@H](C)c3cccnc3)nc3ccsc23)C1]

(Z63)

Synthesis of ((S)-3-methylpyrrolidin-1-yl)(2-(((S)-1-(pyridin-3-yl)ethyl)amino)thieno[3,2-d]pyrimidin-4-yl)methanone (Z63): The title compound (Z63) was prepared from (S)-2-((1-(pyridin-3-yl)ethyl)amino)thieno[3,2-d]pyrimidine-4-carboxylic acid di-hydrochloride using chemistry similar to that described in Example Z8 using (S)-3-methylpyrrolidine in place of (R)-3-fluoropyrrolidine (83% yield). $^1$H NMR (400 MHz, CDCl$_3$) δ 1.05 (3H, d, J=5.6 Hz), 1.51 (1H, m), 1.63 (3H, d, J=7.2 Hz), 1.99 (1H, m), 2.25 (1H, m), 3.20 (1H, m), 3.64 (1H, m), 3.85 (1H, m), 4.04 (1H, m), 5.22 (1H, m), 5.42 (1H, m), 7.17 (1H, d, J=5.6 Hz), 7.24 (1H, m), 7.70 (1H, m), 7.94 (1H, d, J=5.6 Hz), 8.49 (1H, m) ppm. LCMS m/z=368.1 [M+H$^+$].

Example Z64. (S)—N-((6-Cyanopyridin-3-yl)methyl)-2-((1-(pyridin-2-yl)ethyl)amino)thieno[3,2-d]pyrimidine-4-carboxamide

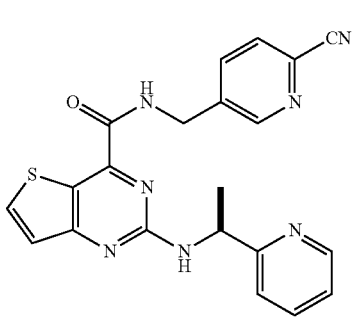 [SMILES: C[C@H](Nc1nc(C(=O)NCc2ccc(C#N)nc2)c2sccc2n1)c1ccccn1]

(Z64)

Synthesis of (S)—N-((6-cyanopyridin-3-yl)methyl)-2-((1-(pyridin-2-yl)ethyl)amino)thieno[3,2-d]pyrimidine-4-carboxamide (Z64): The title compound (Z64) was prepared from (S)-2-((1-(pyridin-2-yl)ethyl)amino)thieno[3,2-d]pyrimidine-4-carboxylic acid di-hydrochloride using chemistry similar to that described in Example Z8 using 5-(aminomethyl)pyridine-2-carbonitrile hydrochloride (commercially available from Sigma-Aldrich, St. Louis Mo.) in place of (R)-3-fluoropyrrolidine (65% yield). LCMS m/z=416.1 [M+H+].

Example Z65. (S)—N-(6-Methoxypyridin-3-yl)-2-((1-(pyridin-2-yl)ethyl)amino)thieno[3,2-d]pyrimidine-4-carboxamide

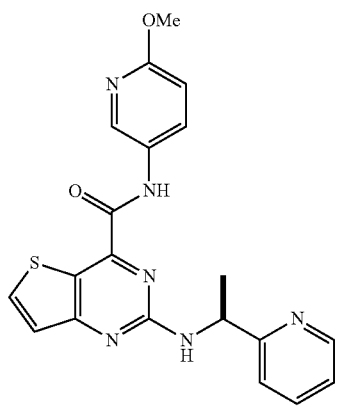 [SMILES: COc1ccc(NC(=O)c2nc(N[C@@H](C)c3ccccn3)nc3ccsc23)cn1]

(Z65)

Synthesis of (S)—N-(6-methoxypyridin-3-yl)-2-((1-(pyridin-2-yl)ethyl)amino)thieno[3,2-d]pyrimidine-4-carboxamide (Z65): The title compound (Z65) was prepared from (S)-2-((1-(pyridin-2-yl)ethyl)amino)thieno[3,2-d]pyrimidine-4-carboxylic acid di-hydrochloride using chemistry similar to that described in Example Z8 using 6-methoxypyridin-3-amine (commercially available from Pharma Block, Sunnyvale, Calif.) in place of (R)-3-fluoropyrrolidine (97% yield). LCMS m/z=407.1 [M+H$^+$].

Example Z66. (R)-(2-(((5-Fluoropyridin-3-yl)methyl)amino)thieno[3,2-d]pyrimidin-4-yl)(3-hydroxypyrrolidin-1-yl)methanone

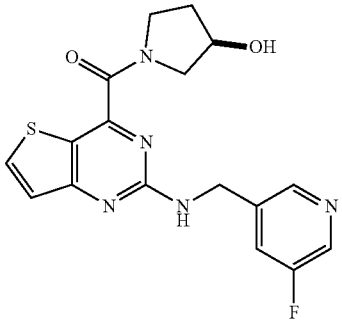 [SMILES: O=C(c1nc(NCc2cncc(F)c2)nc2ccsc12)N1CC[C@@H](O)C1]

(Z66)

Synthesis of (R)-(2-(((5-fluoropyridin-3-yl)methyl)amino)thieno[3,2-d]pyrimidin-4-yl)(3-hydroxypyrrolidin-1-yl)methanone (Z66): The title compound (Z66) was prepared from ethyl 2-(((5-fluoropyridin-3-yl)methyl)amino)thieno[3,2-d]pyrimidine-4-carboxylate using chemistry similar to that described in Example Z17 using (3R)-pyrrolidin-3-ol in place of (3R)-3-methoxypyrrolidine hydrochloride (11% yield). LCMS m/z=374.1 [M+H$^+$].

Example Z67. 2-(((5-Fluoropyridin-3-yl)methyl)amino)-N-((6-methoxypyridin-3-yl)methyl)thieno[3,2-d]pyrimidine-4-carboxamide

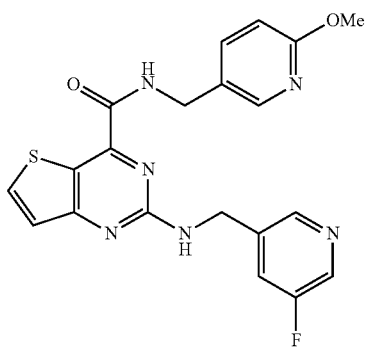 [SMILES: COc1ccc(CNC(=O)c2nc(NCc3cncc(F)c3)nc3ccsc23)cn1]

(Z67)

Synthesis of 2-(((5-fluoropyridin-3-yl)methyl)amino)-N-((6-methoxypyridin-3-yl)methyl)thieno[3,2-d]pyrimidine-4-carboxamide (Z67): The title compound (Z67) was prepared from ethyl 2-(((5-fluoropyridin-3-yl)methyl)amino)thieno[3,2-d]pyrimidine-4-carboxylate using chemistry similar to that described in Example Z17 using (6-methoxy-3-pyridyl)methanamine hydrochloride in place of (3R)-3-methoxypyrrolidine hydrochloride (57% yield). LCMS m/z=325.1 [M+H$^+$].

Example Z68. N-((1-Benzylpiperidin-4-yl)methyl)-2-(((5-fluoropyridin-3-yl)methyl)amino)thieno[3,2-d]pyrimidine-4-carboxamide

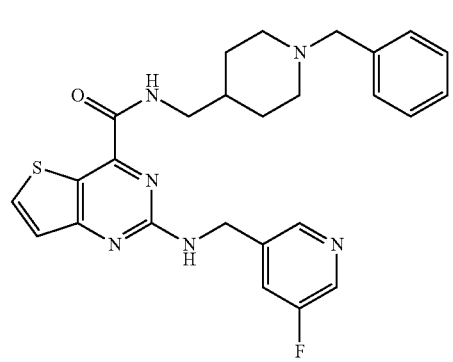 [SMILES: O=C(NCC1CCN(Cc2ccccc2)CC1)c1nc(NCc2cncc(F)c2)nc2ccsc12]

(Z68)

Synthesis of N-((1-benzylpiperidin-4-yl)methyl)-2-(((5-fluoropyridin-3-yl)methyl)amino)thieno[3,2-d]pyrimidine-4-carboxamide (Z68): The title compound (Z68) was prepared from ethyl 2-(((5-fluoropyridin-3-yl)methyl)amino)thieno[3,2-d]pyrimidine that described in Example-4-carboxylate using chemistry similar to that described in Example Z17 using (1-benzyl-4-piperidyl)methanamine (commercially obtained from Sigma-Aldrich, St. Louis, Mo.) in place of (3R)-3-methoxypyrrolidine hydrochloride (24% yield). LCMS m/z=492.2 [M+H$^+$].

Example Z69. (S)-(4-(3-Phenylpropyl)piperazin-1-yl)(2-((1-(pyridin-3-yl)ethyl)amino)thieno[3,2-d]pyrimidin-4-yl)methanone

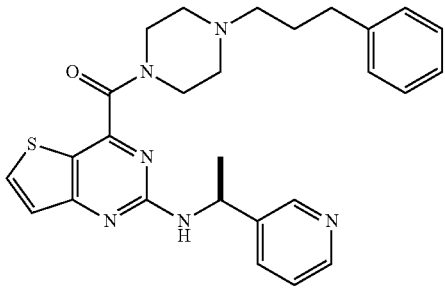 [SMILES: C[C@H](Nc1nc(C(=O)N2CCN(CCCc3ccccc3)CC2)c2sccc2n1)c1cccnc1]

(Z69)

Synthesis of (S)-(4-(3-phenylpropyl)piperazin-1-yl)(2-((1-(pyridin-3-yl)ethyl)amino)thieno[3,2-d]pyrimidin-4-yl)methanone (Z69): The title compound (Z69) was prepared from (S)-2-((1-(pyridin-3-yl)ethyl)amino)thieno[3,2-d]pyrimidine-4-carboxylic acid dihydrochloride using chemistry similar to that described in Example Z8 using 1-(3-phenylpropyl)piperazine (commercially obtained from Sigma-Aldrich, St. Louis, Mo.) in place of (R)-3-fluoropyrrolidine (68% yield). $^1$H NMR (400 MHz, CDCl$_3$) δ 1.62 (3H, d, J=7.2 Hz), 1.81 (2H, m), 2.28 (2H, m), 2.37 (2H, t, J=8.0 Hz), 2.51 (2H, m), 2.65 (2H, t, J=8.0 Hz), 3.60 (2H, m), 3.81 (2H, m), 5.21 (1H, quintet, J=7.2 Hz), 5.44 (1H, d, J=7.2 Hz), 7.17 (1H, d, J=5.6 Hz), 7.18-7.24 (4H, m), 7.27-7.31 (2H, m), 7.69 (1H, dt, J=8.0, 1.6 Hz), 7.90 (1H, d, J=5.6 Hz), 8.48 (1H, dd, J=4.8, 1.6 Hz), 8.68 (1H, d, J=1.6 Hz) ppm. LCMS m/z=487.3 [M+H$^+$].

Example Z70. (2-(((6-Hydroxypyridin-2-yl)methyl)amino)thieno[3,2-d]pyrimidin-4-yl)(pyrrolidin-1-yl)methanone

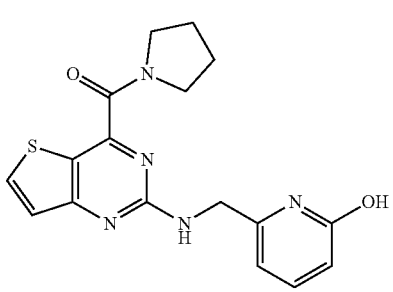 [SMILES: O=C(c1nc(NCc2cccc(O)n2)nc2ccsc12)N1CCCC1]

(Z70)

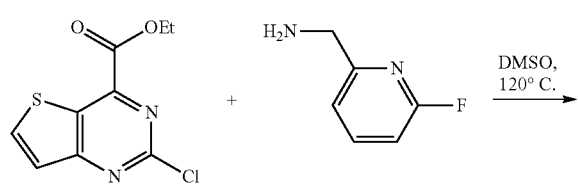

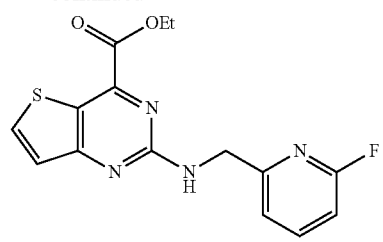

Synthesis of ethyl 2-(((6-fluoropyridin-2-yl)methyl)amino)thieno[3,2-d]pyrimidine-4-carboxylate: The title compound was prepared from ethyl 2-chlorothieno[3,2-d]pyrimidine-4-carboxylate (112 mg, 0.46 mmol) using chemistry similar to that described in Example Z12 using (6-fluoro-2-pyridyl)methanamine (commercially obtained from ACS Scientific, Berkeley Heights, N.J.) in place of (6-methoxypyridin-3-yl)methanamine hydrochloride (12 mg, 7% yield). LCMS m/z=333.2 [M+H$^+$].

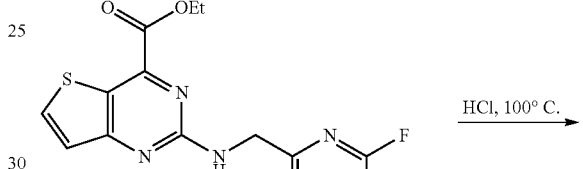

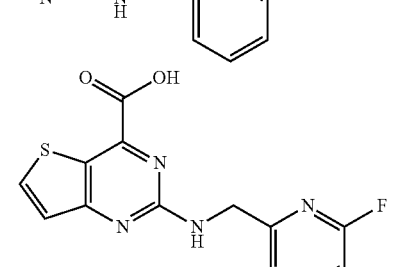

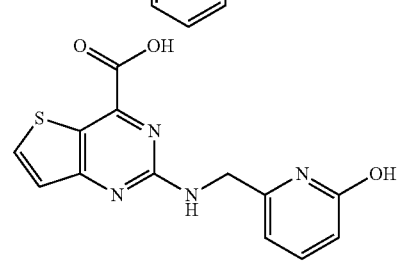

Synthesis of 2-(((6-fluoropyridin-2-yl)methyl)amino)thieno[3,2-d]pyrimidine-4-carboxylic acid and 2-(((6-hydroxypyridin-2-yl)methyl)amino)thieno[3,2-d]pyrimidine-4-carboxylic acid: A mixture of ethyl 2-(((6-fluoropyridin-2-yl)methyl)amino)thieno[3,2-d]pyrimidine-4-carboxylate (12 mg) and 4 M solution of HCl in 1,4-dioxane in DCM was stirred at 100° C. for 2 hours, concentrated, and coeluted with toluene to give a 2:1 mixture (by LCMS) of 2-[(6-fluoro-2-pyridyl)methylamino]thieno[3,2-d]pyrimidine-4-carboxylic acid di-hydrochloride (LCMS m/z=341.1 [M+H$^+$]) and 2-[(6-hydroxy-2-pyridyl)methylamino]thieno[3,2-d]pyrimidine-4-carboxylic acid di-hydrochloride (LCMS m/z=339.1 [M+H$^+$]). The mixture was used in the next step without further separation.

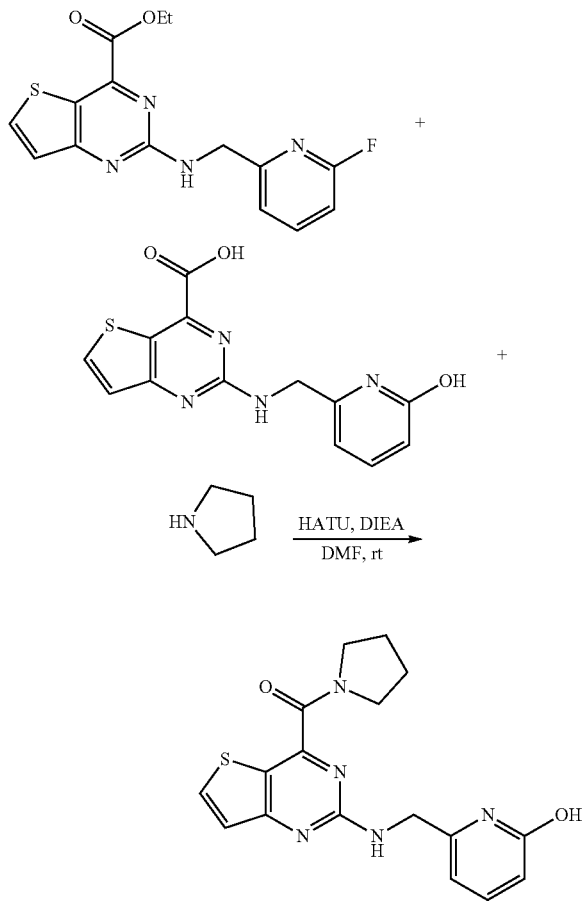

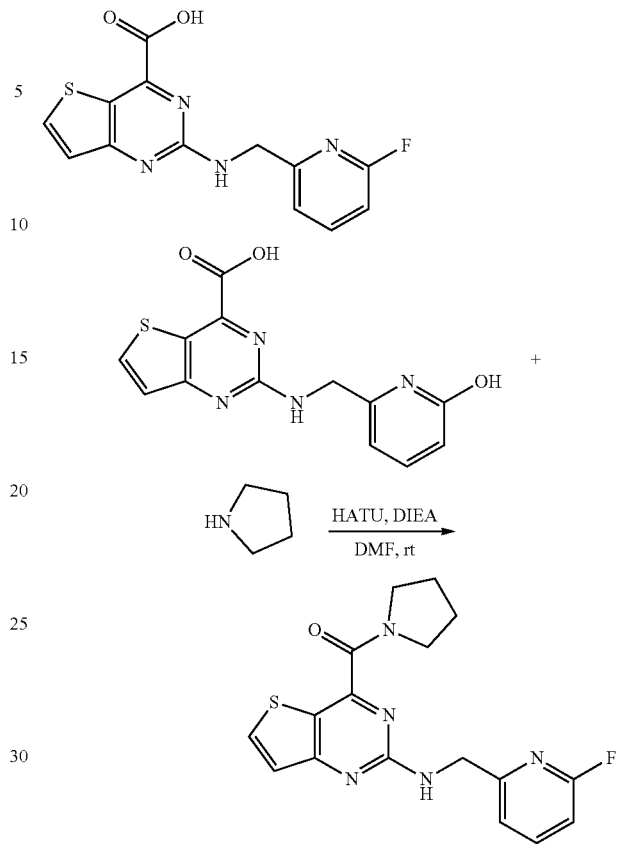

Synthesis of (2-(((6-hydroxypyridin-2-yl)methyl)amino)thieno[3,2-d]pyrimidin-4-yl)(pyrrolidin-1-yl)methanone (Z70): The title compound (Z70) was prepared by the condensation of the mixture of 2-[(6-fluoro-2-pyridyl)methylamino]thieno[3,2-d]pyrimidine-4-carboxylic acid di-hydrochloride and 2-[(6-hydroxy-2-pyridyl)methylamino]thieno[3,2-d]pyrimidine-4-carboxylic acid di-hydrochloride with pyrrolidine using chemistry similar to that described in Example Z17 (42% yield). LCMS m/z=356.1 [M+H$^+$].

Example Z71. (2-(((6-Fluoropyridin-2-yl)methyl)amino)thieno[3,2-d]pyrimidin-4-yl)(pyrrolidin-1-yl)methanone Synthesis of (2-(((6-fluoropyridin-2-yl)methyl)amino)thieno[3,2-d]pyrimidin-4-yl)(pyrrolidin-1-yl)methanone (Z71): The title compound (Z71) was prepared by the condensation of the mixture of 2-[(6-fluoro-2-pyridyl)methylamino]thieno[3,2-d]pyrimidine-4-carboxylic acid di-hydrochloride and 2-[(6-hydroxy-2-pyridyl)methylamino]thieno[3,2-d]pyrimidine-4-carboxylic acid di-hydrochloride prepared in Example Z70 with pyrrolidine using chemistry similar to that described in Example Z17 (32% yield). LCMS m/z=358.1 [M+H$^+$].

Example Z72. N-((6-(Trifluoromethyl)pyridin-3-yl)methyl)-2-(((6-(trifluoromethyl)pyridin-3-yl)methyl)amino)thieno[3,2-d]pyrimidine-4-carboxamide

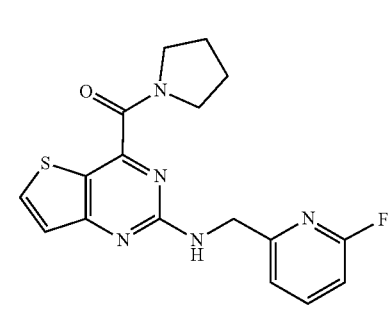 [SMILES: O=C(c1nc(NCc2cccc(F)n2)nc2ccsc12)N1CCCC1]

(Z71)

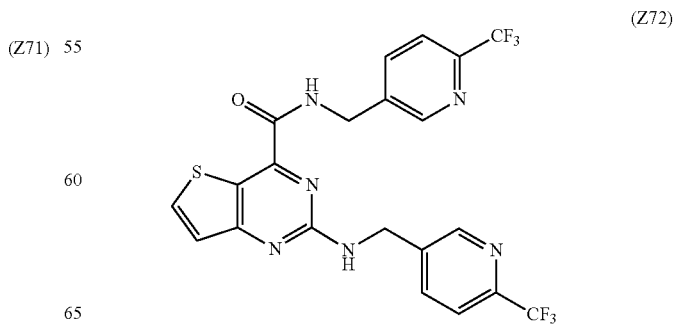

(Z72)

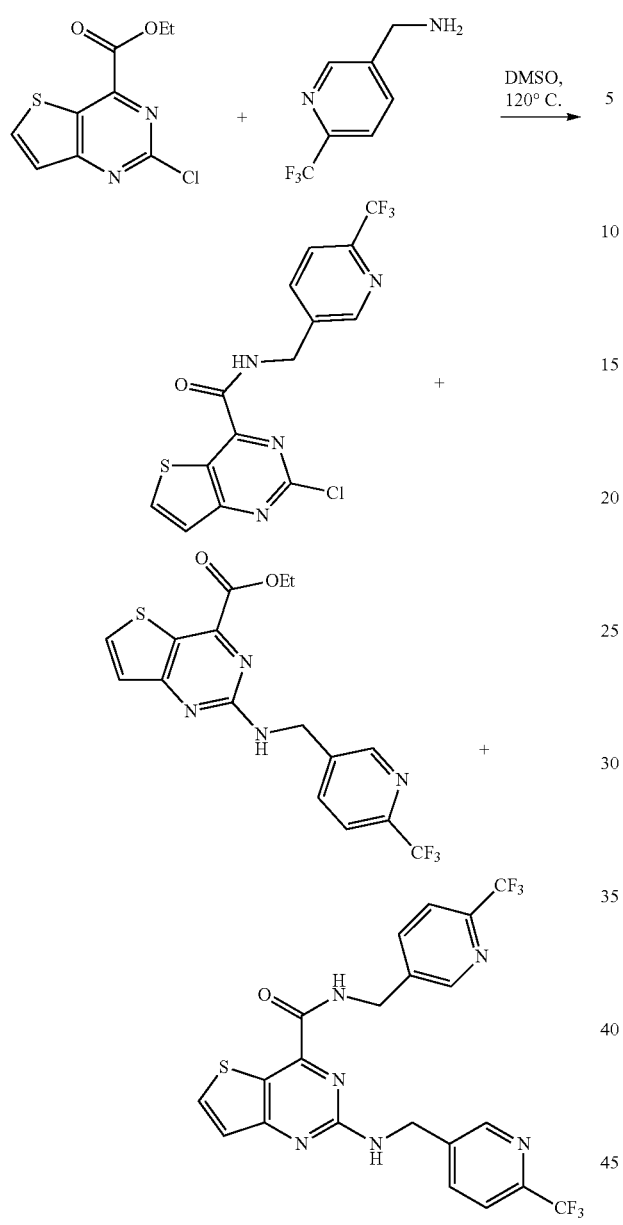

Synthesis of N-((6-(trifluoromethyl)pyridin-3-yl)methyl)-2-(((6-(trifluoromethyl)pyridin-3-yl)methyl)amino)thieno[3,2-d]pyrimidine-4-carboxamide (Z72): The title compound (Z72) was prepared from ethyl 2-chlorothieno[3,2-d]pyrimidine-4-carboxylate (120 mg, 0.49 mmol) using chemistry similar to that described in Example Z12 using [6-(trifluoromethyl)-3-pyridyl]methanamine (commercially obtained from CombiBlocks, San Diego, Calif.) in place of (6-methoxypyridin-3-yl)methanamine hydrochloride (26 mg, 10% yield). LCMS m/z=513.0 [M+H⁺]. Also were isolated 2-chloro-N-((6-(trifluoromethyl)pyridin-3-yl)methyl)thieno[3,2-d]pyrimidine-4-carboxamide (31 mg, 17% yield), LCMS m/z=373.1 [M+H⁺], and ethyl 2-(((6-(trifluoromethyl)pyridin-3-yl)methyl)amino)thieno[3,2-d]pyrimidine-4-carboxylate (54 mg, 29% yield), LCMS m/z=383.1 [M+H⁺].

Example Z73. (S)—N-((6-Methoxypyridin-2-yl)methyl)-2-((1-(pyridin-3-yl)ethyl)amino)thieno[3,2-d]pyrimidine-4-carboxamide

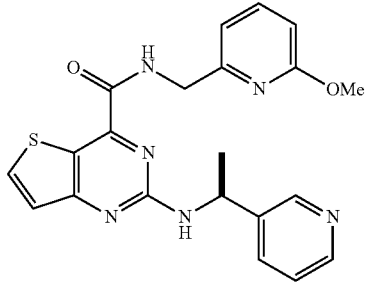 [SMILES: COc1cccc(CNC(=O)c2nc(N[C@@H](C)c3cccnc3)nc3ccsc23)n1]

(Z73)

Synthesis of (S)—N-((6-methoxypyridin-2-yl)methyl)-2-((1-(pyridin-3-yl)ethyl)amino)thieno[3,2-d]pyrimidine-4-carboxamide (Z73): The title compound (Z73) was prepared from (S)-2-((1-(pyridin-3-yl)ethyl)amino)thieno[3,2-d]pyrimidine-4-carboxylic acid di-hydrochloride using chemistry similar to that described in Example Z8 using (6-methoxypyridin-2-yl)methanamine (commercially obtained from ACS Scientific, Berkeley Heights, N.J.) in place of (R)-3-fluoropyrrolidine (51% yield). ¹H NMR (400 MHz, CDCl₃) δ 1.65 (3H, d, J=6.8 Hz), 3.96 (3H, s), 4.68 (2H, d, J=6.0 Hz), 5.28 (1H, quintet, J=6.8 Hz), 5.41 (1H, d, J=6.8 Hz), 6.67 (1H, d, J=7.6 Hz), 6.86 (1H, d, J=7.2 Hz), 7.18 (1H, d, J=5.6 Hz), 7.21 (1H, dd, J=7.6, 4.8 Hz), 7.56 (1H, dd, J=7.6, 7.2 Hz), 7.71 (1H, dt, J=7.6, 1.6 Hz), 7.99 (1H, d, J=5.6 Hz), 8.47 (1H, dd, J=4.8, 1.6 Hz), 8.56 (1H, m), 8.71 (1H, d, J=1.6 Hz) ppm. LCMS m/z=421.3 [M+H⁺].

Example Z74. N-(3-Fluorobenzyl)-2-((3-fluorobenzyl)amino)thieno[3,2-d]pyrimidine-4-carboxamide

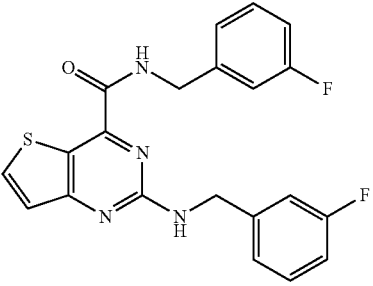 [SMILES: O=C(NCc1cccc(F)c1)c1nc(NCc2cccc(F)c2)nc2ccsc12]

(Z74)

Synthesis of N-(3-fluorobenzyl)-2-((3-fluorobenzyl)amino)thieno[3,2-d]pyrimidine-4-carboxamide (Z74): The title compound (Z74) was prepared from ethyl 2-chlorothieno[3,2-d]pyrimidine-4-carboxylate (123 mg, 0.5 mmol) using chemistry similar to that described in Example Z12 using 3-fluorobenzylamine (commercially obtained from Sigma-Aldrich, St. Louis, Mo.) in place of (6-methoxypyridin-3-yl)methanamine hydrochloride (55 mg, 26% yield). LCMS m/z=411.2 [M+H⁺]. Also was isolated ethyl 2-((3-fluorobenzyl)amino)thieno[3,2-d]pyrimidine-4-carboxylate (74 mg, 44% yield). LCMS m/z=332.1 [M+H⁺].

Example Z75. (S)-(3-Hydroxypyrrolidin-1-yl)(2-(((6-(trifluoromethyl)pyridin-3-yl)methyl)amino)thieno[3,2-d]pyrimidin-4-yl)methanone

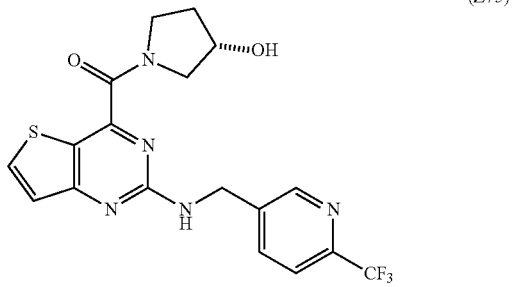

(Z75)

Synthesis of (S)-(3-hydroxypyrrolidin-1-yl)(2-(((6-(trifluoromethyl)pyridin-3-yl)methyl)amino)thieno[3,2-d]pyrimidin-4-yl)methanone (Z75): The title compound (Z75) was prepared from ethyl 2-(((6-(trifluoromethyl)pyridin-3-yl)methyl)amino)thieno[3,2-d]pyrimidine-4-carboxylate using chemistry similar to that described in Example Z17 using (3S)-pyrrolidin-3-ol in place of (3R)-3-methoxypyrrolidine hydrochloride (38% yield). LCMS m/z=424.1 [M+H$^+$].

Example Z76. Pyrrolidin-1-yl(2-(((6-(trifluoromethyl)pyridin-3-yl)methyl)amino)thieno[3,2-d]pyrimidin-4-yl)methanone

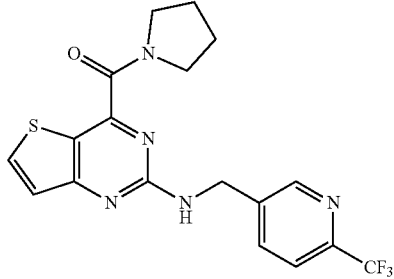 [SMILES: O=C(c1nc(NCc2ccc(C(F)(F)F)nc2)nc2ccsc12)N1CCCC1]

(Z76)

Synthesis of pyrrolidin-1-yl(2-(((6-(trifluoromethyl)pyridin-3-yl)methyl)amino)thieno[3,2-d]pyrimidin-4-yl)methanone (Z76): The title compound (Z76) was prepared from ethyl 2-(((6-(trifluoromethyl)pyridin-3-yl)methyl)amino)thieno[3,2-d]pyrimidine-4-carboxylate using chemistry similar to that described in Example Z17 using pyrrolidine in place of (3R)-3-methoxypyrrolidine hydrochloride (21% yield). LCMS m/z=408.2 [M+H$^+$].

Example Z77. 2-(((S)-1-(Pyridin-2-yl)ethyl)amino)-N-(2-(pyridin-3-yloxy)propyl)thieno[3,2-d]pyrimidine-4-carboxamide

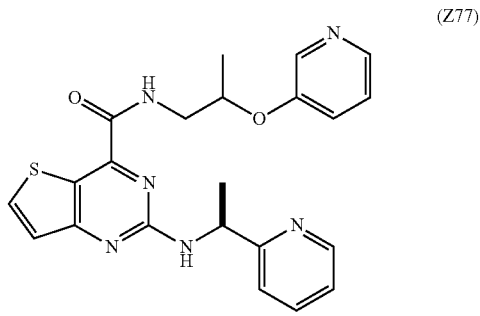

(Z77)

Synthesis of 2-(((S)-1-(pyridin-2-yl)ethyl)amino)-N-(2-(pyridin-3-yloxy)propyl)thieno[3,2-d]pyrimidine-4-carboxamide (Z77): The title compound (Z77) was prepared from (S)-2-((1-(pyridin-2-yl)ethyl)amino)thieno[3,2-d]pyrimidine-4-carboxylic acid di-hydrochloride using chemistry similar to that described in Example Z8 (69% yield). LCMS m/z=435.2 [M+H$^+$].

Example Z78. N-(Pyridin-2-ylmethyl)-2-((pyridin-2-ylmethyl)amino)thieno[3,2-d]pyrimidine-4-carboxamide

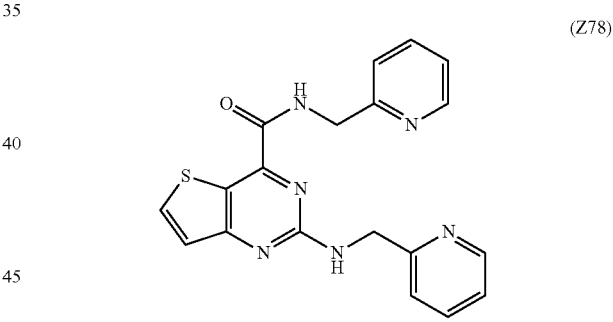

(Z78)

Synthesis of N-(pyridin-2-ylmethyl)-2-((pyridin-2-ylmethyl)amino)thieno[3,2-d]pyrimidine-4-carboxamide (Z78): To a solution of ethyl 2-chlorothieno[3,2-d]pyrimidine-4-carboxylate (242 mg, 1.0 mmol) in NMP (4 mL) was added 2-(aminomethyl)pyridine (commercially obtained from Sigma-Aldrich, St. Louis Mo.) (620 uL, 6.0 mmol). The reaction mixture was stirred at 130° C. overnight. The reaction mixture was diluted with ethyl acetate and washed with 25% NaCl aqueous solution, brine three times and dried. The solvent was evaporated and the residue was purified by flash chromatography (40 g, HP silica, Teledyne Isco) eluting with 20% to 55% solvent A (DCM/MeOH/NH$_4$OH, 100/10/1) in DCM to provide N-(pyridin-2-ylmethyl)-2-((pyridin-2-ylmethyl)amino)thieno[3,2-d]pyrimidine-4-carboxamide as a light yellow solid (315 mg, 84% yield). $^1$H NMR (400 MHz, CDCl$_3$) δ 4.81 (2H, d, J=6.0 Hz), 4.85 (2H, d, J=6.0 Hz), 6.28 (1H, m), 7.18 (1H, dd, J=6.8, 5.6 Hz), 7.22-7.25 (2H, m), 7.34 (1H, d, J=8.0 Hz), 7.39 (1H, d, J=8.0 Hz), 7.64 (1H, td, J=7.6, 1.6 Hz), 7.68

(1H, td, J=8.0, 1.6 Hz), 8.00 (1H, d, J=5.6 Hz), 8.57 (1H, d, J=4.8 Hz), 8.61 (1H, m), 8.91 (1H, m) ppm. LCMS: m/z=377.1 [M+H⁺].

Example Z79. (S)-2-((1-(Pyridin-2-yl)ethyl)amino)-N-((6-(trifluoromethyl)pyridin-3-yl)methyl)thieno[3,2-d]pyrimidine-4-carboxamide

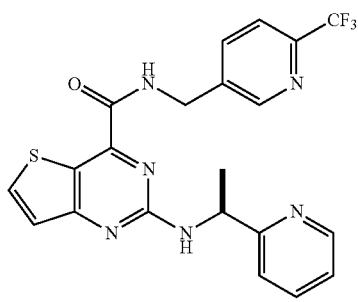 [SMILES: C[C@H](Nc1nc(C(=O)NCc2ccc(C(F)(F)F)nc2)c2sccc2n1)c1ccccn1]

(Z79)

Synthesis of (S)-2-((1-(pyridin-2-yl)ethyl)amino)-N-((6-(trifluoromethyl)pyridin-3-yl)methyl)thieno[3,2-d]pyrimidine-4-carboxamide (Z79): The title compound (Z79) was prepared from 2-chloro-N-((6-(trifluoromethyl)pyridin-3-yl)methyl)thieno[3,2-d]pyrimidine-4-carboxamide using chemistry similar to that described in Example Z12 using (S)-1-(pyridin-2-yl)ethan-1-amine in place of (6-methoxypyridin-3-yl)methanamine hydrochloride (35% yield). LCMS m/z=459.2 [M+H⁺].

Example Z80. (2-((3-Fluorobenzyl)amino)thieno[3,2-d]pyrimidin-4-yl)(4-(3-phenylpropyl)piperazin-1-yl)methanone

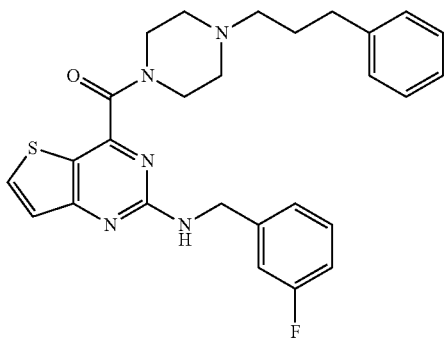 [SMILES: O=C(c1nc(NCc2cccc(F)c2)nc2ccsc12)N1CCN(CCCc2ccccc2)CC1]

(Z80)

Synthesis of (2-((3-fluorobenzyl)amino)thieno[3,2-d]pyrimidin-4-yl)(4-(3-phenylpropyl)piperazin-1-yl)methanone (Z80): The title compound (Z80) was prepared from ethyl 2-((3-fluorobenzyl)amino)thieno[3,2-d]pyrimidine-4-carboxylate using chemistry similar to that described in Example Z17 using 1-(3-phenylpropyl)piperazine (commercially obtained from Sigma-Aldrich, St. Louis, Mo.) in place of (3R)-3-methoxypyrrolidine hydrochloride (55% yield). LCMS m/z=490.3 [M+H⁺].

Example Z81. (R)-(2-((3-Fluorobenzyl)amino)thieno[3,2-d]pyrimidin-4-yl)(3-hydroxypyrrolidin-1-yl)methanone

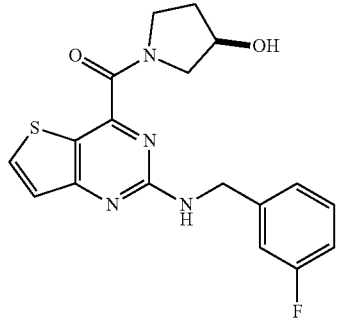 [SMILES: O=C(c1nc(NCc2cccc(F)c2)nc2ccsc12)N1CC[C@@H](O)C1]

(Z81)

Synthesis of (R)-(2-((3-fluorobenzyl)amino)thieno[3,2-d]pyrimidin-4-yl)(3-hydroxypyrrolidin-1-yl)methanone (Z81): The title compound (Z81) was prepared from ethyl 2-((3-fluorobenzyl)amino)thieno[3,2-d]pyrimidine-4-carboxylate using chemistry similar to that described in Example Z17 using (R)-3-hydroxypyrrolidine in place of (3R)-3-methoxypyrrolidine hydrochloride (72% yield). LCMS m/z=373.1 [M+H⁺].

Example Z82. 2-((3-Fluorobenzyl)amino)-N-((6-methoxypyridin-3-yl)methyl)thieno[3,2-d]pyrimidine-4-carboxamide

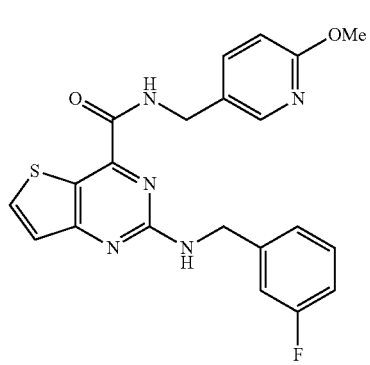 [SMILES: COc1ccc(CNC(=O)c2nc(NCc3cccc(F)c3)nc3ccsc23)cn1]

(Z82)

Synthesis of 2-((3-fluorobenzyl)amino)-N-((6-methoxypyridin-3-yl)methyl)thieno[3,2-d]pyrimidine-4-carboxamide (Z82): The title compound (Z82) was prepared from ethyl 2-((3-fluorobenzyl)amino)thieno[3,2-d]pyrimidine-4-carboxylate using chemistry similar to that described in Example Z17 using (6-methoxy-3-pyridyl)methanamine hydrochloride in place of (3R)-3-methoxypyrrolidine hydrochloride (17% yield). LCMS m/z=424.2 [M+H⁺].

Example Z83. N-((6-Methoxypyridin-3-yl)methyl)-2-((1-(pyridin-3-yl)propyl)amino)thieno[3,2-d]pyrimidine-4-carboxamide

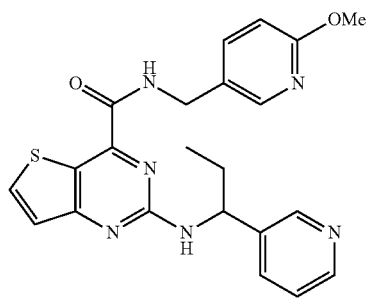 [SMILES: CCC(Nc1nc(C(=O)NCc2ccc(OC)nc2)c2sccc2n1)c1cccnc1]

(Z83)

Synthesis of N-((6-methoxypyridin-3-yl)methyl)-2-((1-(pyridin-3-yl)propyl)amino)thieno[3,2-d]pyrimidine-4-carboxamide (Z83): The title compound (Z83) was prepared from ethyl 2-((1-(pyridin-3-yl)propyl)amino)thieno[3,2-d]pyrimidine-4-carboxylate di-hydrochloride using chemistry similar to that described in Example Z17 using (6-methoxy-3-pyridyl)methanamine hydrochloride in place of (R)-3-fluoropyrrolidine (31% yield). LCMS m/z=434.3 [M+H$^+$].

Example Z84. (2-((3-Fluorobenzyl)amino)thieno[3,2-d]pyrimidin-4-yl)(pyrrolidin-1-yl)methanone

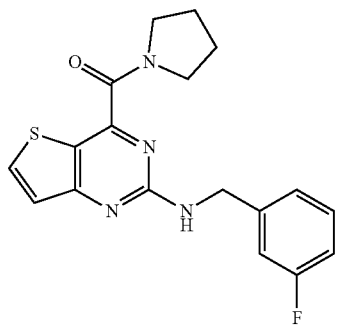 [SMILES: O=C(c1nc(NCc2cccc(F)c2)nc2ccsc12)N1CCCC1]

(Z84)

Synthesis of (2-((3-fluorobenzyl)amino)thieno[3,2-d]pyrimidin-4-yl)(pyrrolidin-1-yl)methanone (Z84): The title compound (Z84) was prepared from ethyl 2-((3-fluorobenzyl)amino)thieno[3,2-d]pyrimidine-4-carboxylate using chemistry similar to that described in Example Z17 using pyrrolidine in place of (3R)-3-methoxypyrrolidine hydrochloride (10% yield). LCMS m/z=357.2 [M+H$^+$].

Example Z85. N-(2-(1H-Imidazol-1-yl)ethyl)-2-(((5-fluoropyridin-3-yl)methyl)amino)thieno[3,2-d]pyrimidine-4-carboxamide

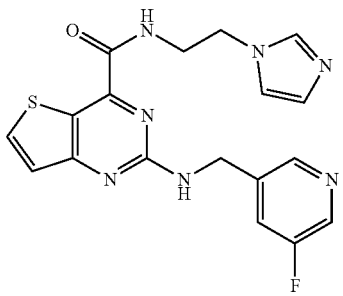 [SMILES: O=C(NCCn1ccnc1)c1nc(NCc2cncc(F)c2)nc2ccsc12]

(Z85)

Synthesis of N-(2-(1H-imidazol-1-yl)ethyl)-2-(((5-fluoropyridin-3-yl)methyl)amino)thieno[3,2-d]pyrimidine-4-carboxamide (Z85): The title compound (Z85) was prepared from ethyl 2-(((5-fluoropyridin-3-yl)methyl)amino)thieno[3,2-d]pyrimidine using chemistry similar to that described in Example Z17 using 2-imidazol-1-ylethanamine (commercially obtained from Sigma-Aldrich, St. Louis, Mo.) in place of (3R)-3-methoxypyrrolidine hydrochloride (20% yield). LCMS m/z=398.1 [M+H$^+$].

Example Z86. ((R)-3-Methylpyrrolidin-1-yl)(2-(((S)-1-(pyridin-2-yl)ethyl)amino)thieno[3,2-d]pyrimidin-4-yl)methanone

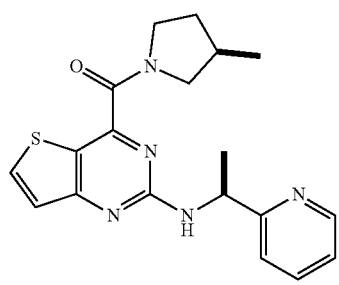 [SMILES: C[C@@H]1CCN(C(=O)c2nc(N[C@@H](C)c3ccccn3)nc3ccsc23)C1]

(Z86)

Synthesis of ((R)-3-methylpyrrolidin-1-yl)(2-(((S)-1-(pyridin-2-yl)ethyl)amino)thieno[3,2-d]pyrimidin-4-yl)methanone (Z86): The title compound (Z86) was prepared from (S)-2-((1-(pyridin-2-yl)ethyl)amino)thieno[3,2-d]pyrimidine-4-carboxylic acid di-hydrochloride using chemistry similar to that described in Example Z8 using (R)-3-methylpyrrolidine in place of (R)-3-fluoropyrrolidine (65% yield). $^1$H NMR (400 MHz, CDCl$_3$) δ 1.08 (3H, d, J=6.8 Hz), 1.49 (1H, m), 1.62 (3H, d, J=6.8 Hz), 2.01 (1H, m), 2.24 (1H, m), 3.20 (1H, m), 3.63-3.90 (3H, m), 5.27 (1H, m), 6.03 (1H, m), 7.16 (1H, m), 7.19 (1H, d, J=5.6 Hz), 7.35 (1H, d, J=8.0 Hz), 7.62 (1H, m), 7.92 (1H, d, J=5.6 Hz), 8.58 (1H, m) ppm. LCMS m/z=368.1 [M+H$^+$].

Example Z87. ((S)-3-Methylpyrrolidin-1-yl)(2-(((S)-1-(pyridin-2-yl)ethyl)amino)thieno[3,2-d]pyrimidin-4-yl)methanone

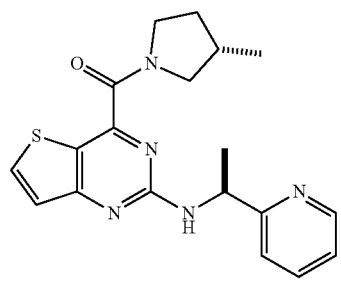 [SMILES: C[C@H]1CCN(C(=O)c2nc(N[C@@H](C)c3ccccn3)nc3ccsc23)C1]

(Z87)

Synthesis of ((S)-3-methylpyrrolidin-1-yl)(2-(((S)-1-(pyridin-2-yl)ethyl)amino)thieno[3,2-d]pyrimidin-4-yl)methanone (Z87): The title compound (Z87) was prepared from (S)-2-((1-(pyridin-2-yl)ethyl)amino)thieno[3,2-d]pyrimidine-4-carboxylic acid di-hydrochloride using chemistry similar to that described in Example Z8 using (S)-3-methylpyrrolidine in place of (R)-3-fluoropyrrolidine (71% yield). $^1$H NMR (400 MHz, CDCl$_3$) δ 1.07 (3H, d, J=6.8 Hz), 1.51 (1H, m), 1.62 (3H, d, J=6.8 Hz), 2.01 (1H, m), 2.26 (1H, m), 3.22 (1H, dd, J=12.4, 8.0 Hz), 3.66 (1H, m), 3.86 (1H, m), 4.14 (1H, m), 5.26 (1H, m), 6.03 (1H, m), 7.16 (1H, m), 7.20 (1H, d, J=5.6 Hz), 7.62 (1H, m), 7.92 (1H, d, J=5.6 Hz), 8.58 (1H, m) ppm. LCMS m/z=368.1 [M+H$^+$].

Example Z88. N-((2-Methylpyridin-3-yl)methyl)-2-(((2-methylpyridin-3-yl)methyl)amino)thieno[3,2-d]pyrimidine-4-carboxamide

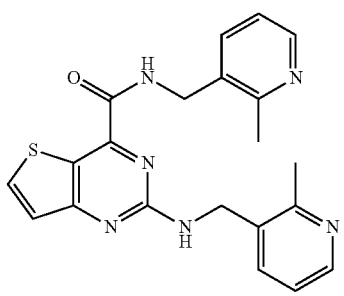 [SMILES: Cc1ncccc1CNC(=O)c1nc(NCc2cccnc2C)nc2ccsc12]

(Z88)

Synthesis of N-((2-methylpyridin-3-yl)methyl)-2-(((2-methylpyridin-3-yl)methyl)amino)thieno[3,2-d]pyrimidine-4-carboxamide (Z88). The title compound (Z88) was prepared from ethyl 2-chlorothieno[3,2-d]pyrimidine-4-carboxylate (120 mg, 0.49 mmol) using chemistry similar to that described in Example Z12 using (2-methyl-3-pyridyl)methanamine (commercially obtained from Princeton Bio-Molecular Research, Monmouth Junction, N.J.) in place of (6-methoxypyridin-3-yl)methanamine hydrochloride (78 mg, 39% yield). LCMS m/z=405.2 [M+H$^+$]. Also isolated was ethyl 2-(((2-methylpyridin-3-yl)methyl)amino)thieno[3,2-d]pyrimidine-4-carboxylate (45 mg, 28% yield). LCMS m/z=329.1 [M+H$^+$].

Example Z89. (S)—N-(Pyridin-2-ylmethyl)-2-((1-(pyridin-3-yl)ethyl)amino)thieno[3,2-d]pyrimidine-4-carboxamide

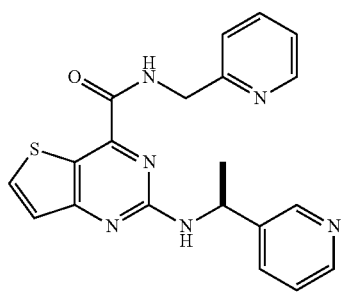 [SMILES: C[C@H](Nc1nc(C(=O)NCc2ccccn2)c2sccc2n1)c1cccnc1]

(Z89)

Synthesis of (S)—N-(pyridin-2-ylmethyl)-2-((1-(pyridin-3-yl)ethyl)amino)thieno[3,2-d]pyrimidine-4-carboxamide (Z89): The title compound (Z89) was prepared from (S)-2-((1-(pyridin-3-yl)ethyl)amino)thieno[3,2-d]pyrimidine-4-carboxylic acid di-hydrochloride using chemistry similar to that described in Example Z8 using pyridin-2-ylmethanamine in place of (R)-3-fluoropyrrolidine (72% yield). $^1$H NMR (400 MHz, CDCl$_3$) δ 1.66 (3H, d, J=7.2 Hz), 4.78 (2H, d, J=5.6 Hz), 5.29 (1H, quintet, J=7.2 Hz), 5.51 (1H, d, J=7.2 Hz), 7.18 (1H, d, J=5.6 Hz), 7.20 (1H, dd, J=8.0, 4.8 Hz), 7.26 (1H, m), 7.31 (1H, d, J=8.0 Hz), 7.70 (1H, td, J=8.0, 2.0 Hz), 7.77 (1H, dt, J=8.0, 2.0 Hz), 7.99 (1H, d, J=5.6 Hz), 8.46 (1H, dd, J=4.8, 2.0 Hz), 8.67 (1H, d, J=4.8 Hz), 8.77 (1H, d, J=2.0 Hz), 8.84 (1H, m) ppm. LCMS m/z=391.1 [M+H$^+$].

Example Z90. (S)-Azetidin-1-yl(2-((1-(pyridin-2-yl)ethyl)amino)thieno[3,2-d]pyrimidin-4-yl)methanone

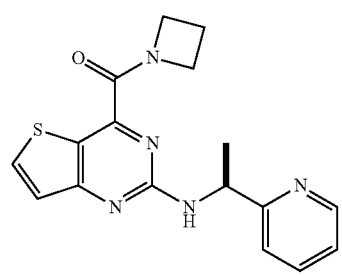 [SMILES: C[C@H](Nc1nc(C(=O)N2CCC2)c2sccc2n1)c1ccccn1]

(Z90)

Synthesis of (S)-azetidin-1-yl(2-((1-(pyridin-2-yl)ethyl)amino)thieno[3,2-d]pyrimidin-4-yl)methanone (Z90): To a solution of methyl 2-[[(1S)-1-(2-pyridyl)ethyl]amino]thieno[3,2-d]pyrimidine-4-carboxylate (31 mg, 0.10 mmol) in 1,4-dioxane (2 mL) was added azetidine (67 uL, 1.0 mmol). The mixture thus obtained was stirred at 110° C. for 3 h and LCMS indicated completion of the reaction. The reaction mixture was concentrated in vacuo and the residue was purified by flash chromatography on silica gel (12 g, HP silica, Teledyne Isco) eluting with 10% to 50% solvent A (DCM/MeOH/NH$_4$OH, 100/10/1) to provide (S)-azetidin-1-yl(2-((1-(pyridin-2-yl)ethyl)amino)thieno[3,2-d]pyrimidin-4-yl)methanone as a light yellow solid (30 mg, 88% yield). $^1$H NMR (400 MHz, CDCl$_3$) δ 1.62 (3H, d, J=6.8

Hz), 2.29-2.39 (2H, m), 4.24 (2H, t, J=7.2 Hz), 4.49 (1H, m), 4.77 (1H, m), 5.24 (1H, quintet, J=6.8 Hz), 6.02 (1H, d, J=6.8 Hz), 7.16-7.19 (2H, m), 7.43 (1H, d, J=8.0 Hz), 7.63 (1H, t, J=8.0 Hz), 7.94 (1H, d, J=5.6 Hz), 8.57 (1H, d, J=4.0 Hz) ppm. LCMS: 340.2 [M+H⁺].

Example Z91. (2-(((2-Methylpyridin-3-yl)methyl)amino)thieno[3,2-d]pyrimidin-4-yl)(pyrrolidin-1-yl)methanone

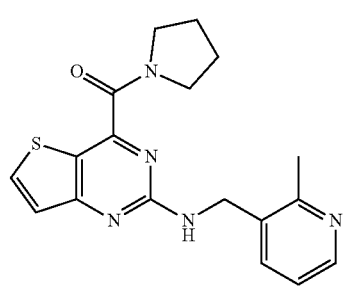 [SMILES: Cc1ncccc1CNc1nc(C(=O)N2CCCC2)c2sccc2n1]

(Z91)

Synthesis of (2-(((2-methylpyridin-3-yl)methyl)amino)thieno[3,2-d]pyrimidin-4-yl)(pyrrolidin-1-yl)methanone (Z91): The title compound (Z91) was prepared from ethyl 2-(((2-methylpyridin-3-yl)methyl)amino)thieno[3,2-d]pyrimidine-4-carboxylate using chemistry similar to that described in Example Z17 using pyrrolidine in place of (3R)-3-methoxypyrrolidine hydrochloride (83% yield). $^1$H NMR (400 MHz, CDCl$_3$) δ 1.86-1.89 (4H, m), 2.66 (3H, s), 3.69-3.72 (2H, m), 3.78 (2H, m), 4.71 (2H, d, J=6.0 Hz), 5.59 (1H, br s), 7.15 (1H, dd, J=7.8, 5.2 Hz) 7.22 (1H, d, J=5.6 Hz), 7.70 (1H, m), 7.97 (1H, d, J=5.6 Hz), 8.45 (1H, dd, J=4.8, 1.6 Hz) ppm. LCMS m/z=354.2 [M+H⁺].

Example Z92. (S)-(3,3-Difluoroazetidin-1-yl)(2-((1-(pyridin-2-yl)ethyl)amino)thieno[3,2-d]pyrimidin-4-yl)methanone

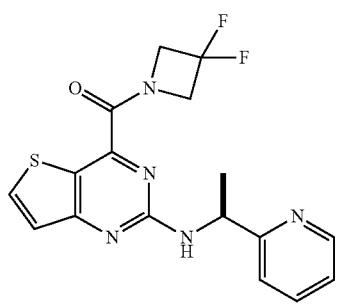 [SMILES: C[C@H](Nc1nc(C(=O)N2CC(F)(F)C2)c2sccc2n1)c1ccccn1]

(Z92)

Synthesis of (S)-(3,3-difluoroazetidin-1-yl)(2-((1-(pyridin-2-yl)ethyl)amino)thieno[3,2-d]pyrimidin-4-yl)methanone (Z92): The title compound (Z92) was prepared from (S)-2-((1-(pyridin-2-yl)ethyl)amino)thieno[3,2-d]pyrimidine-4-carboxylic acid di-hydrochloride using chemistry similar to that described in Example Z8 using 3,3-difluoroazetidine hydrochloride in place of (R)-3-fluoropyrrolidine (71% yield). $^1$H NMR (400 MHz, CDCl$_3$) δ 1.63 (3H, d, J=6.8 Hz), 4.51 (2H, t, J=8.0 Hz), 4.68 (1H, m), 5.01 (1H, m), 5.19 (1H, m), 6.07 (1H, m), 7.18-7.22 (2H, m), 7.35 (1H, d, J=8.0 Hz), 7.65 (1H, td, J=8.0, 1.6 Hz), 7.98 (1H, d, J=5.6 Hz), 8.59 (1H, dd, J=4.0, 1.6 Hz) ppm. LCMS m/z=376.1 [M+H⁺].

Example Z93. (2-(((5-Chloropyridin-3-yl)methyl)amino)thieno[3,2-d]pyrimidin-4-yl)(pyrrolidin-1-yl)methanone

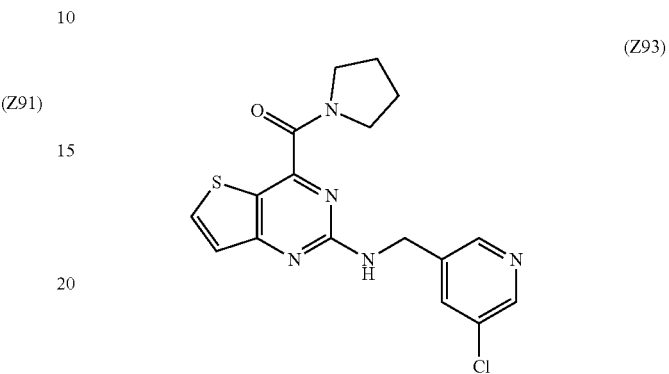

(Z93)

Synthesis of ethyl 2-(((5-chloropyridin-3-yl)methyl)amino)thieno[3,2-d]pyrimidine-4-carboxylate: The title compound was prepared from ethyl 2-chlorothieno[3,2-d]pyrimidine-4-carboxylate (100 mg, 0.41 mmol) using chemistry similar to that described in Example Z12 using (5-chloropyridin-3-yl)methanamine (commercially obtained from PharmaBlock, Sunnyvale, Calif.) in place of (6-methoxypyridin-3-yl)methanamine hydrochloride (13 mg, 9% yield). LCMS m/z=349.1 [M+H⁺].

Synthesis of (2-(((5-chloropyridin-3-yl)methyl)amino)thieno[3,2-d]pyrimidin-4-yl)(pyrrolidin-1-yl)methanone (Z93): The title compound (Z93) was prepared from ethyl 2-(((5-chloropyridin-3-yl)methyl)amino)thieno[3,2-d]pyrimidine-4-carboxylate using chemistry similar to that described in Example Z17 using pyrrolidine in place of (3R)-3-methoxypyrrolidine hydrochloride (20% yield). LCMS m/z=374.1 [M+H⁺].

Example Z94. N-((6-Methoxypyridin-3-yl)methyl)-2-(((2-methylpyridin-3-yl)methyl)amino)thieno[3,2-d]pyrimidine-4-carboxamide

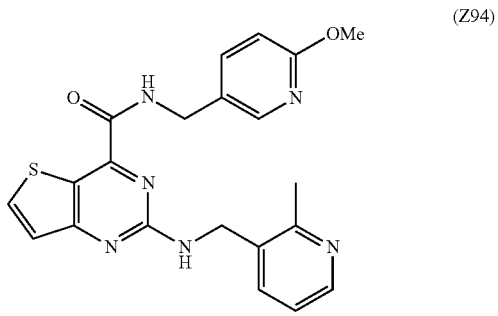

(Z94)

Synthesis of N-((6-methoxypyridin-3-yl)methyl)-2-(((2-methylpyridin-3-yl)methyl)amino)thieno[3,2-d]pyrimidine-4-carboxamideone (Z94): The title compound (Z94) was prepared from ethyl 2-(((2-methylpyridin-3-yl)methyl)amino)thieno[3,2-d]pyrimidine-4-carboxylate using chemistry similar to that described in Example Z17 using (6-methoxy-3-pyridyl)methanamine hydrochloride in place of (3R)-3-methoxypyrrolidine hydrochloride (29% yield). LCMS m/z=421.1 [M+H⁺].

Example Z95. (2-((Pyridin-2-ylmethyl)amino)thieno[3,2-d]pyrimidin-4-yl)(pyrrolidin-1-yl)methanone

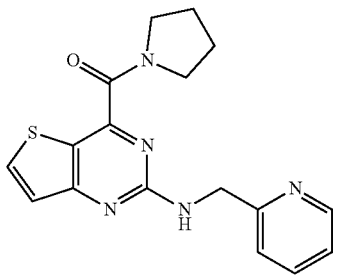 [SMILES: O=C(c1nc(NCc2ccccn2)nc2ccsc12)N1CCCC1]

(Z95)

Synthesis of methyl 2-((pyridin-2-ylmethyl)amino)thieno[3,2-d]pyrimidine-4-carboxylate: N-(2-Pyridylmethyl)-2-(2-pyridylmethylamino)thieno[3,2-d]pyrimidine-4-carboxamide (279 mg, 0.74 mmol) was dissolved in 12 N HCl (7.4 mL) and stirred at 100° C. for 36 h. The reaction mixture was evaporated to dryness in vacuo at a bath temperature of 60° C. and the residue was dissolved in methanol (15 mL). To the solution was added thionyl chloride (740 uL, 7.4 mmol) at room temperature. The reaction mixture was stirred at 60° C. for 4 h, then the reaction mixture was concentrated to dryness and the residue was dissolved in DCM/MeOH (10:1, 50 mL), washed with sat. NaHCO₃ and brine, dried over MgSO₄. The solvent was evaporated and the residue was purified by flash chromatography on silica gel (24 g HP silica, Teledyne Isco) eluting with 10% to 50% solvent A (DCM/MeOH/NH₄OH, 100/10/1) in DCM to provide methyl 2-((pyridin-2-ylmethyl)amino)thieno[3,2-d]pyrimidine-4-carboxylate (204 mg, 92% yield) as an yellow solid. LCMS m/z=301.1 [M+H⁺].

Synthesis of (2-((pyridin-2-ylmethyl)amino)thieno[3,2-d]pyrimidin-4-yl)(pyrrolidin-1-yl)methanone (Z95): To a solution of methyl 2-(2-pyridylmethylamino)thieno[3,2-d]pyrimidine-4-carboxylate (30 mg, 0.10 mmol) in 1,4-dioxane (2 mL) was added pyrrolidine (84 uL, 1.0 mmol). The mixture thus obtained was stirred at 110° C. for 3 h and completion of the reaction was observed. The reaction mixture was concentrated in vacuo and the residue was purified by flash chromatography on silica gel (12 g, HP silica, Teledyne Isco) eluting with 10% to 50% solvent A (DCM/MeOH/NH₄OH, 100/10/1) to provide (2-((pyridin-2-ylmethyl)amino)thieno[3,2-d]pyrimidin-4-yl)(pyrrolidin-1-yl)methanone as a light yellow solid (30 mg, 88% yield). ¹H NMR (400 MHz, CDCl₃) δ 1.90 (4H, m), 3.72 (2H, m), 3.92 (2H, m), 4.84 (2H, d, J=5.2 Hz), 6.13 (1H, t, J=5.2 Hz), 7.19 (1H, dd, J=8.0, 4.8 Hz), 7.23 (1H, d, J=5.6 Hz), 7.65 (1H, d, J=8.0 Hz), 7.64 (1H, td, J=8.0, 1.6 Hz), 7.95 (1H, d, J=5.6 Hz), 8.59 (1H, dd, J=4.8, 1.6 Hz) ppm. LCMS m/z=340.1 [M+H⁺].

Example Z96. (S)-(3,3-Difluoropyrrolidin-1-yl)(2-((1-(pyridin-2-yl)ethyl)amino)thieno[3,2-d]pyrimidin-4-yl)methanone

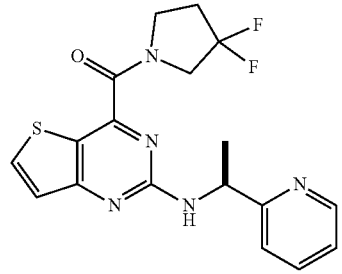 [SMILES: C[C@H](Nc1nc(C(=O)N2CCC(F)(F)C2)c2sccc2n1)c1ccccn1]

(Z96)

Synthesis of (S)-(3,3-difluoropyrrolidin-1-yl)(2-((1-(pyridin-2-yl)ethyl)amino)thieno[3,2-d]pyrimidin-4-yl)methanone (Z96): The title compound (Z96) was prepared from (S)-2-((1-(pyridin-2-yl)ethyl)amino)thieno[3,2-d]pyrimidine-4-carboxylic acid di-hydrochloride using chemistry similar to that described in Example Z8 using 3,3-difluoropyrrolidine hydrochloride in place of (R)-3-fluoropyrrolidine (67% yield). ¹H NMR (400 MHz, CDCl₃) δ 1.63 (3H, d, J=7.2 Hz), 2.31-2.39 (2H, m), 3.92 (2H, t, J=7.6 Hz), 4.01 (1H, t, J=12.4 Hz), 4.33 (1H, m), 5.20 (1H, m), 6.04 (1H, m), 7.18 (1H, m), 7.21 (1H, d, J=5.6 Hz), 7.36 (1H, d, J=8.0 Hz), 7.64 (1H, td, J=8.0, 1.6 Hz), 7.96 (1H, d, J=5.6 Hz), 8.59 (1H, dd, J=4.8, 1.6 Hz) ppm. LCMS m/z=390.0 [M+H⁺].

Example Z97. (3,3-Difluoroazetidin-1-yl)(2-(((5-fluoropyridin-3-yl)methyl)amino)thieno[3,2-d]pyrimidin-4-yl)methanone

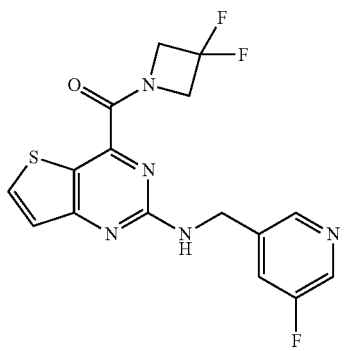 [SMILES: O=C(c1nc(NCc2cncc(F)c2)nc2ccsc12)N1CC(F)(F)C1]

(Z97)

Synthesis of (3,3-difluoroazetidin-1-yl)(2-(((5-fluoropyridin-3-yl)methyl)amino)thieno[3,2-d]pyrimidin-4-yl)methanone (Z97): The title compound (Z97) was prepared from ethyl 2-(((5-fluoropyridin-3-yl)methyl)amino)thieno[3,2-d]pyrimidine using chemistry similar to that described in Example Z17 using 3,3-difluoroazetidine hydrochloride (commercially obtained from Sigma-Aldrich, St. Louis Mo.) in place of (3R)-3-methoxypyrrolidine hydrochloride (53% yield). ¹H NMR (400 MHz, CDCl₃) δ 4.57 (2H, dt, J=12.0, 0.8 Hz), 4.77 (2H, d, J=6.4 Hz), 4.98 (2H, t, J=12.0 Hz), 5.51 (1H, t, J=4.8 Hz), 7.24 (1H, d, J=5.6 Hz), 7.45 (1H, m), 8.03 (1H, d, J=5.6 Hz), 8.40 (1H, d, J=2.8 Hz), 8.48 (1H, s) ppm. LCMS m/z=380.1 [M+H⁺].

Example Z98. (2-(((5-Fluoropyridin-3-yl)methyl)amino)thieno[3,2-d]pyrimidin-4-yl)(3-hydroxy-3-methylazetidin-1-yl)methanone

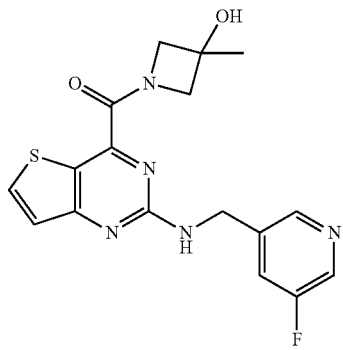 [SMILES: CC1(O)CN(C(=O)c2nc(NCc3cncc(F)c3)nc3ccsc23)C1]

(Z98)

Synthesis of (2-(((5-fluoropyridin-3-yl)methyl)amino)thieno[3,2-d]pyrimidin-4-yl)(3-hydroxy-3-methylazetidin-1-yl)methanone (Z98): The title compound (Z98) was prepared from ethyl 2-(((5-fluoropyridin-3-yl)methyl)amino)thieno[3,2-d]pyrimidine using chemistry similar to that described in Example Z17 using 3-methylazetidin-3-ol hydrochloride (commercially obtained from Parkway Scientific, New York, N.Y.) in place of (3R)-3-methoxypyrrolidine hydrochloride (47% yield). LCMS m/z=374.0 [M+H$^+$].

Example Z99. (S)-(2-(((5-Fluoropyridin-3-yl)methyl)amino)thieno[3,2-d]pyrimidin-4-yl)(3-fluoropyrrolidin-1-yl)methanone

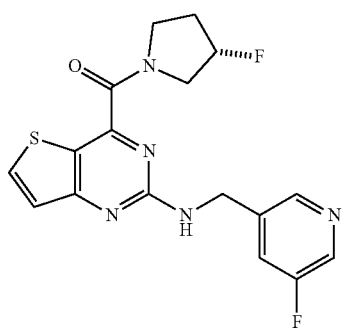

(Z99)

Synthesis of (S)-(2-(((5-fluoropyridin-3-yl)methyl)amino)thieno[3,2-d]pyrimidin-4-yl)(3-fluoropyrrolidin-1-yl)methanone (Z99): The title compound (Z99) was prepared from ethyl 2-(((5-fluoropyridin-3-yl)methyl)amino)thieno[3,2-d]pyrimidine using chemistry similar to that described in Example Z17 using (3S)-3-fluoropyrrolidine hydrochloride in place of (3R)-3-methoxypyrrolidine hydrochloride (56% yield). LCMS m/z=376.1 [M+H$^+$].

Example Z100. (S)-(3-Hydroxyazetidin-1-yl)(2-((1-(pyridin-2-yl)ethyl)amino)thieno[3,2-d]pyrimidin-4-yl)methanone

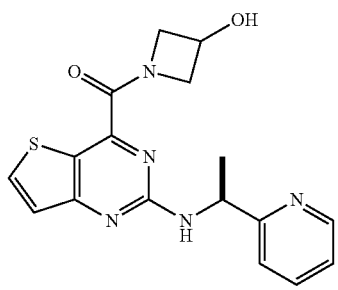 [SMILES: C[C@H](Nc1nc(C(=O)N2CC(O)C2)c2sccc2n1)c1ccccn1]

(Z100)

Synthesis of (S)-(3-hydroxyazetidin-1-yl)(2-((1-(pyridin-2-yl)ethyl)amino)thieno[3,2-d]pyrimidin-4-yl)methanone (Z100): The title compound (Z100) was prepared from (S)-2-((1-(pyridin-2-yl)ethyl)amino)thieno[3,2-d]pyrimidine-4-carboxylic acid di-hydrochloride using chemistry similar to that described in Example Z8 using azetidin-3-ol hydrochloride (commercially obtained from Matrix Scientific, Columbia, S.C.) in place of (R)-3-fluoropyrrolidine (54% yield). LCMS m/z=356.1 [M+H$^+$].

Example Z101. (S)-(3-Hydroxy-3-methylazetidin-1-yl)(2-((1-(pyridin-2-yl)ethyl)amino)thieno[3,2-d]pyrimidin-4-yl)methanone

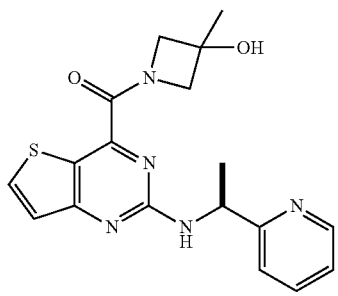 [SMILES: C[C@H](Nc1nc(C(=O)N2CC(C)(O)C2)c2sccc2n1)c1ccccn1]

(Z101)

Synthesis of (S)-(3-hydroxy-3-methylazetidin-1-yl)(2-((1-(pyridin-2-yl)ethyl)amino)thieno[3,2-d]pyrimidin-4-yl)methanone (Z101): The title compound (Z101) was prepared from (S)-2-((1-(pyridin-2-yl)ethyl)amino)thieno[3,2-d]pyrimidine-4-carboxylic acid di-hydrochloride using chemistry similar to that described in Example Z8 using 3-methylazetidin-3-ol hydrochloride in place of (R)-3-fluoropyrrolidine (54% yield). LCMS m/z=356.1 [M+H$^+$].

Example Z102. (S)—N-((5-Cyanopyridin-3-yl)methyl)-2-((1-(pyridin-2-yl)ethyl)amino)thieno[3,2-d]pyrimidine-4-carboxamide

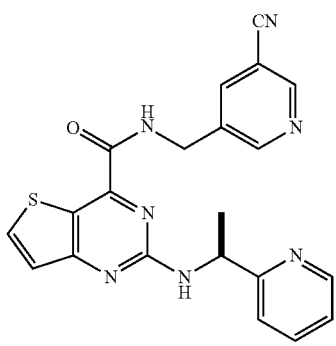
(Z102)

Synthesis of 2-chloro-N-((5-cyanopyridin-3-yl)methyl)thieno[3,2-d]pyrimidine-4-carboxamide and ethyl 2-(((5-cyanopyridin-3-yl)methyl)amino)thieno[3,2-d]pyrimidine-4-carboxylate: The title compounds were prepared from ethyl 2-chlorothieno[3,2-d]pyrimidine-4-carboxylate (200 mg, 0.82 mmol) using chemistry similar to that described in Example Z12 using 5-(aminomethyl)pyridine-3-carbonitrile (commercially obtained from Ox-Chem, Irwindale, Calif.) in place of (6-methoxypyridin-3-yl)methanamine hydrochloride to produce 2-chloro-N-((5-cyanopyridin-3-yl)methyl)thieno[3,2-d]pyrimidine-4-carboxamide (92 mg, 33% yield), LCMS m/z=340.1 [M+H$^+$], and ethyl 2-(((5-cyanopyridin-3-yl)methyl)amino)thieno[3,2-d]pyrimidine-4-carboxylate (51 mg, 20% yield). LCMS m/z=330.0 [M+H$^+$].

Synthesis of (S)—N-((5-cyanopyridin-3-yl)methyl)-2-((1-(pyridin-2-yl)ethyl)amino)thieno[3,2-d]pyrimidine-4-carboxamide (Z102): The title compound (Z102) was prepared from 2-chloro-N-((5-cyanopyridin-3-yl)methyl)thieno[3,2-d]pyrimidine-4-carboxamide (25 mg, 0.07 mmol) using chemistry similar to that described in Example Z12 using (1S)-1-(2-pyridyl)ethanamine in place of (6-methoxypyridin-3-yl)methanamine (14 mg, 49% yield). LCMS m/z=416.1 [M+H$^+$].

Example Z103. (R)-(3-Hydroxypyrrolidin-1-yl)(2-((pyridin-3-ylmethyl)amino)thieno[3,2-d]pyrimidin-4-yl)methanone

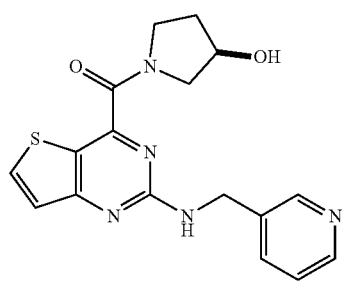 [SMILES: O=C(c1nc(NCc2cccnc2)nc2ccsc12)N1CC[C@@H](O)C1]
(Z103)

Synthesis of (R)-(3-hydroxypyrrolidin-1-yl)(2-((pyridin-3-ylmethyl)amino)thieno[3,2-d]pyrimidin-4-yl)methanone (Z103): The title compound (Z103) was prepared from 2-((pyridin-3-ylmethyl)amino)thieno[3,2-d]pyrimidine-4-carboxylic acid di-hydrochloride using chemistry similar to that described in Example Z8 using (R)-pyrrolidin-3-ol in place of (R)-3-fluoropyrrolidine (45% yield). $^1$H NMR (400 MHz, CDCl$_3$) δ 1.99-2.05 (2H, m), 3.81 (1H, m), 3.85-3.89 (2H, m), 4.06 (1H, m), 4.50 (1H, m), 4.71-4.78 (2H, m), 5.60 (1H, m), 7.21 (1H, d, J=5.6 Hz), 7.27 (1H, m), 7.72 (1H, td, J=4.8, 1.6 Hz), 7.97 (1H, d, J=5.6 Hz), 8.51 (1H, d, J=5.6 Hz), 8.66 (1H, dd, J=4.8, 1.6 Hz) ppm. LCMS m/z=356.1 [M+H$^+$].

Example Z104. (S)—N-((5-Cyanopyridin-3-yl)methyl)-2-((1-(pyridin-3-yl)ethyl)amino)thieno[3,2-d]pyrimidine-4-carboxamide

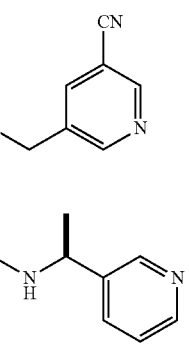
(Z104)

Synthesis of (S)—N-((5-cyanopyridin-3-yl)methyl)-2-((1-(pyridin-2-yl)ethyl)amino)thieno[3,2-d]pyrimidine-4-carboxamide (Z104): The title compound (Z104) was prepared from 2-chloro-N-((5-cyanopyridin-3-yl)methyl)thieno[3,2-d]pyrimidine-4-carboxamide (25 mg, 0.07 mmol) using chemistry similar to that described in Example Z12 using (1S)-1-(3-pyridyl)ethanamine in place of (6-methoxypyridin-3-yl)methanamine (16 mg, 51% yield). LCMS m/z=416.1 [M+H$^+$].

Example Z105 and 106. (S)-Oxazolidin-3-yl(2-((1-(pyridin-2-yl)ethyl)amino)thieno[3,2-d]pyrimidin-4-yl)methanone and (S)—N-(2-hydroxyethyl)-2-((1-(pyridin-2-yl)ethyl)amino)thieno[3,2-d]pyrimidine-4-carboxamide

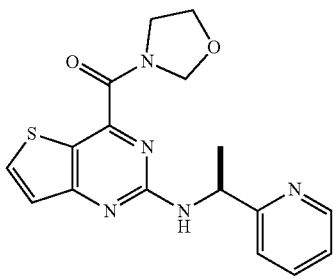 [SMILES: C[C@H](Nc1nc(C(=O)N2CCOC2)c2sccc2n1)c1ccccn1]
(Z105)

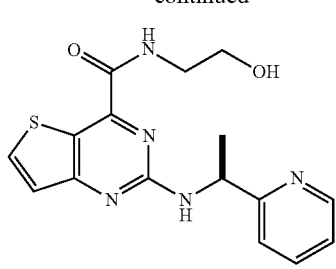

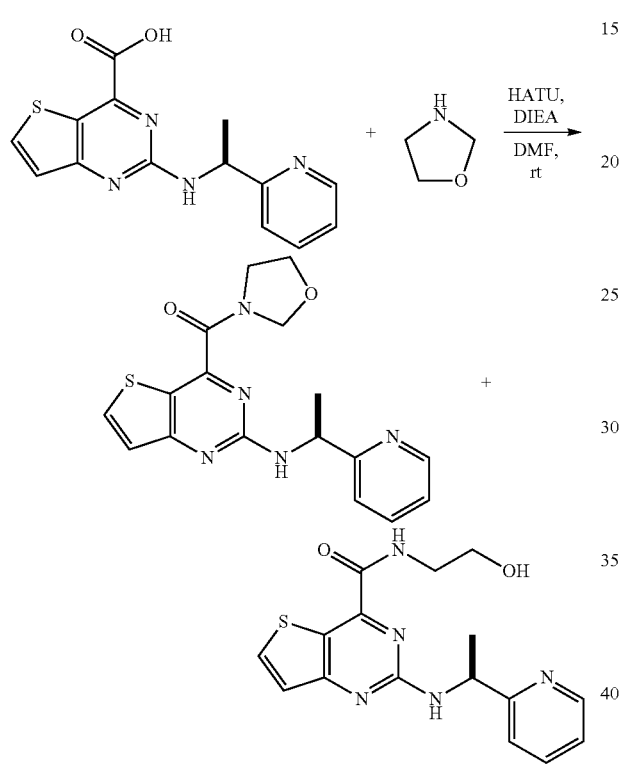

Syntheses of (S)-Oxazolidin-3-yl(2-((1-(pyridin-2-yl)ethyl)amino)thieno[3,2-d]pyrimidin-4-yl)methanone and (S)—N-(2-hydroxyethyl)-2-((1-(pyridin-2-yl)ethyl)amino)thieno[3,2-d]pyrimidine-4-carboxamide (Z105 and Z106): To a solution of 2-[[(1S)-1-(2-pyridyl)ethyl]amino]thieno[3,2-d]pyrimidine-4-carboxylic acid dihydrochloride (37 mg, 0.10 mmol) in DMF (2 mL) were added oxazolidine (14.6 mg, 0.2 mmol), HATU (57 mg, 0.15 mmol), and DIEA (70 uL, 0.4 mmol). The mixture thus obtained was stirred at room temperature for 4 h and the reaction mixture was diluted with ethyl acetate and washed with 5% NaHCO₃, water, and brine, then dried over MgSO4. The solvent was evaporated in vacuo and the residue was purified by flash chromatography on silica gel (12 g HP silica, Teledyne Isco) eluting with 15% to 50% solvent A (DCM/MeOH/NH₄OH, 100/10/1) in DCM to provide first eluted (S)-oxazolidin-3-yl(2-((1-(pyridin-2-yl)ethyl)amino)thieno[3,2-d]pyrimidin-4-yl)methanone (10 mg, 28% yield) as a light yellow solid (LCMS m/z=356.1 [M+H⁺]) and second eluted (S)—N-(2-hydroxyethyl)-2-((1-(pyridin-2-yl)ethyl)amino)thieno[3,2-d]pyrimidine-4-carboxamide (14 mg, 41% yield) as a light yellow solid (LCMS m/z=344.1 [M+H⁺]).

Example Z107. (S)—N-((6-(Cyclopropylmethoxy)pyridin-3-yl)methyl)-2-((1-(pyridin-2-yl)ethyl)amino)thieno[3,2-d]pyrimidine-4-carboxamide

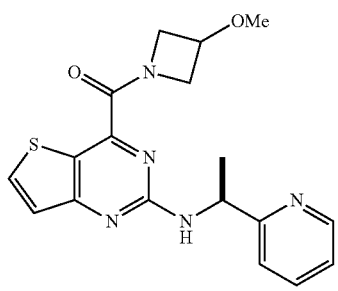 [SMILES: COC1CN(C(=O)c2nc(N[C@@H](C)c3ccccn3)nc3ccsc23)C1]

Synthesis of (S)—N-((6-(cyclopropylmethoxy)pyridin-3-yl)methyl)-2-((1-(pyridin-2-yl)ethyl)amino)thieno[3,2-d]pyrimidine-4-carboxamide (Z107): The title compound (Z107) was prepared from (S)-2-((1-(pyridin-2-yl)ethyl)amino)thieno[3,2-d]pyrimidine-4-carboxylic acid di-hydrochloride using chemistry similar to that described in Example Z8 using [6-(cyclopropyl-methoxy)-3-pyridyl]methanamine (commercially obtained from Enamine, Monmouth Jct., N.Y.) in place of (R)-3-fluoropyrrolidine (51% yield). LCMS m/z=461.1 [M+H⁺].

Example Z108. (S)-(3-Methoxyazetidin-1-yl)(2-((1-(pyridin-2-yl)ethyl)amino)thieno[3,2-d]pyrimidin-4-yl)methanone Synthesis of (S)-(3-methoxyazetidin-1-yl)(2-((1-(pyridin-2-yl)ethyl)amino)thieno[3,2-d]pyrimidin-4-yl)methanone (Z108): The title compound (Z108) was prepared from (S)-2-((1-(pyridin-2-yl)ethyl)amino)thieno[3,2-d]pyrimidine-4-carboxylic acid di-hydrochloride using chemistry similar to that described in Example Z8 using 3-methoxyazetidine hydrochloride (commercially obtained from PharmaBlock, Sunnyvale, Calif.) in place of (R)-3-fluoropyrrolidine (27% yield). LCMS m/z=370.1 [M+H⁺].

Example Z109. (2-(((5-Fluoropyridin-3-yl)methyl)amino)thieno[3,2-d]pyrimidin-4-yl)(3-hydroxyazetidin-1-yl)methanone

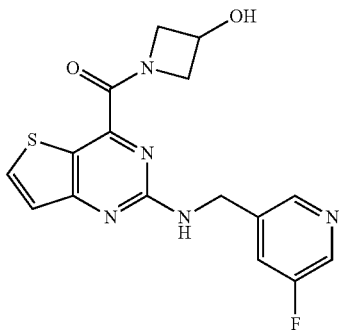 [SMILES: O=C(c1nc(NCc2cncc(F)c2)nc2ccsc12)N1CC(O)C1]
(Z109)

Synthesis of (2-(((5-fluoropyridin-3-yl)methyl)amino)thieno[3,2-d]pyrimidin-4-yl)(3-hydroxyazetidin-1-yl)methanone (Z109): The title compound (Z109) was prepared from ethyl 2-(((5-fluoropyridin-3-yl)methyl)amino)thieno[3,2-d]pyrimidine using chemistry similar to that described in Example Z17 using azetidin-3-ol hydrochloride (commercially obtained from Matrix Scientific, Elgin, S.C.) in place of (3R)-3-methoxypyrrolidine hydrochloride (41% yield). LCMS m/z=360.1 [M+H⁺].

Example Z110. (S)—N-((5-Methoxypyridin-3-yl)methyl)-2-((1-(pyridin-2-yl)ethyl)amino)thieno[3,2-d]pyrimidine-4-carboxamide

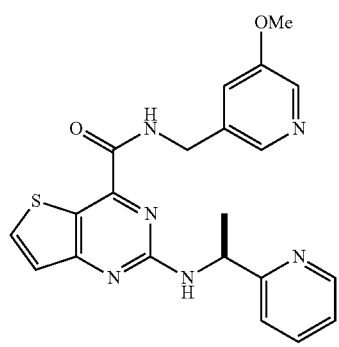
(Z110)

Synthesis of (S)—N-((5-methoxypyridin-3-yl)methyl)-2-((1-(pyridin-2-yl)ethyl)amino)thieno[3,2-d]pyrimidine-4-carboxamide (Z110): The title compound (Z110) was prepared from 2-chloro-N-((5-methoxypyridin-3-yl)methyl)thieno[3,2-d]pyrimidine-4-carbox-amide using chemistry similar to that described in Example Z12 using (1S)-1-(3-pyridyl)ethan-amine in place of (6-methoxypyridin-3-yl)methanamine (57% yield). LCMS m/z=421.1 [M+H⁺].

Example Z111. (S)—N-Ethyl-2-((1-(pyridin-2-yl)ethyl)amino)thieno[3,2-d]pyrimidine-4-carboxamide

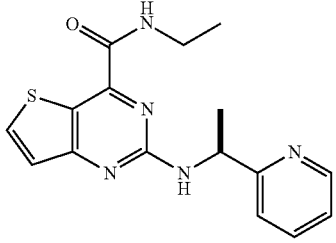 [SMILES: CCNC(=O)c1nc(N[C@@H](C)c2ccccn2)nc2ccsc12]
(Z111)

Synthesis of (S)—N-ethyl-2-((1-(pyridin-2-yl)ethyl)amino)thieno[3,2-d]pyrimidine-4-carboxamide (Z111): The title compound (Z111) was prepared from (S)-2-((1-(pyridin-2-yl)ethyl)amino)thieno[3,2-d]pyrimidine-4-carboxylic acid di-hydrochloride using chemistry similar to that described in Example Z8 using ethanamine hydrochloride in place of (R)-3-fluoropyrrolidine (52% yield). ¹H NMR (400 MHz, CDCl₃) δ 1.26 (3H, t, J=6.4 Hz), 1.63 (3H, d, J=6.8 Hz), 3.50 (2H, m), 5.26 (1H, quintet, J=6.8 Hz), 6.13 (1H, d, J=6.8 Hz), 7.18 (1H, ddd, J=8.0, 4.8, 1.2 Hz), 7.20 (1H, d, J=5.6 Hz), 7.36 (1H, d, J=8.0 Hz), 7.64 (1H, td, J=8.0, 2.0 Hz), 7.86 (1H, m), 7.97 (1H, d, J=5.6 Hz), 8.59 (1H, m) ppm. LCMS m/z=328.1 [M+H⁺].

Example Z112. (2-((2-(Pyridin-3-yl)propan-2-yl)amino)thieno[3,2-d]pyrimidin-4-yl)(pyrrolidin-1-yl)methanone

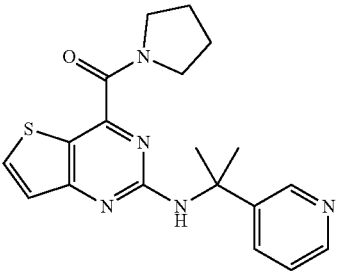 [SMILES: CC(C)(Nc1nc(C(=O)N2CCCC2)c2sccc2n1)c1cccnc1]
(Z112)

Synthesis of ethyl 2-((2-(pyridin-3-yl)propan-2-yl)amino)thieno[3,2-d]pyrimidine-4-carboxylate: The title compound was prepared from ethyl 2-chlorothieno[3,2-d]pyrimidine-4-carboxylate (200 mg, 0.82 mmol) using chemistry similar to that described in Example Z12 using 2-(3-pyridyl)propan-2-amine (commercially obtained from Astatech, Bristol, Pa.) in place of (6-methoxypyridin-3-yl)methanamine hydrochloride to produce ethyl 2-((2-(pyridin-3-yl)propan-2-yl)amino)thieno[3,2-d]pyrimidine-4-carboxylate (17 mg, 6% yield). LCMS m/z=341.1 [M+H⁺].

Synthesis of (2-((2-(pyridin-3-yl)propan-2-yl)amino)thieno[3,2-d]pyrimidin-4-yl)(pyrrolidin-1-yl)methanone (Z112): The title compound (Z112) was prepared from ethyl 2-((2-(pyridin-3-yl)propan-2-yl)amino)thieno[3,2-d]pyrimidine-4-carboxylate using chemistry similar to that described in Example Z17 using pyrrolidine in place of (R)-3-fluoropyrrolidine (43% yield). ¹H NMR (400 MHz, CDCl₃) δ 1.72-1.76 (2H, m), 1.61-1.64 (2H, m), 1.80 (6H, s), 3.04

(2H, m), 3.59 (2H, t, J=6.8 Hz), 5.77 (1H, s), 7.11 (1H, d, J=5.6 Hz), 7.28 (1H, m), 7.86 (1H, dt, J=8.0, 1.6 Hz), 7.92 (1H, d, J=5.6 Hz), 8.47 (1H, dd, J=4.8, 1.6 Hz), 8.78 (1H, dd, J=2.2, 0.8 Hz) ppm. LCMS m/z=368.1 [M+H$^+$].

Example Z113. (S)—N-((1-(2-Methoxyethyl)piperidin-4-yl)methyl)-2-((1-(pyridin-2-yl)ethyl)amino)thieno[3,2-d]pyrimidine-4-carboxamide

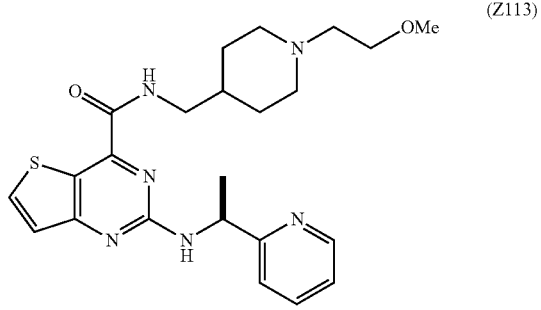

Synthesis of (S)-(3-methoxyazetidin-1-yl)(2-((1-(pyridin-2-yl)ethyl)amino)thieno[3,2-d]pyrimidin-4-yl)methanone (Z113): The title compound (Z113) was prepared from (S)-2-((1-(pyridin-2-yl)ethyl)amino)thieno[3,2-d]pyrimidine-4-carboxylic acid di-hydrochloride using chemistry similar to that described in Example Z8 using [1-(2-methoxyethyl)-4-piperidyl]methanamine (commercially obtained from Cambridge Chemical, Cambridge, UK) in place of (R)-3-fluoropyrrolidine (20% yield). LCMS m/z=355.1 [M+H$^+$].

Example Z114. (2-(((5-Methoxypyridin-3-yl)methyl)amino)thieno[3,2-d]pyrimidin-4-yl)(pyrrolidin-1-yl)methanone

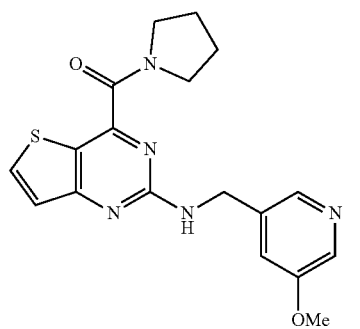 [SMILES: COc1cncc(CNc2nc(C(=O)N3CCCC3)c3sccc3n2)c1]

Synthesis of (2-((2-(pyridin-3-yl)propan-2-yl)amino)thieno[3,2-d]pyrimidin-4-yl)(pyrrolidin-1-yl)methanone (Z114): The title compound (Z114) was prepared from ethyl 2-(((5-methoxypyridin-3-yl)methyl)amino)thieno[3,2-d]pyrimidine-4-carboxylate using chemistry similar to that described in Example Z17 using pyrrolidine in place of (R)-3-fluoropyrrolidine (96% yield). LCMS m/z=370.1 [M+H$^+$].

Example Z115. (2-(((5-Fluoropyridin-3-yl)methyl)amino)thieno[3,2-d]pyrimidin-4-yl)(3-methoxyazetidin-1-yl)methanone

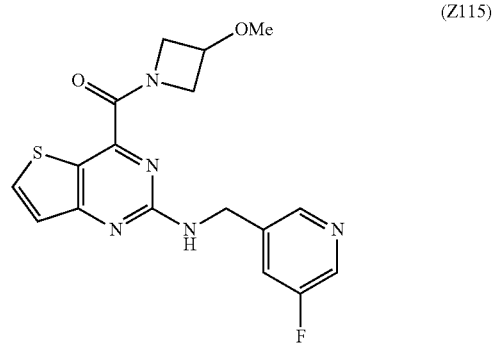

Synthesis of (2-(((5-fluoropyridin-3-yl)methyl)amino)thieno[3,2-d]pyrimidin-4-yl)(3-hydroxyazetidin-1-yl)methanone (Z115): The title compound (Z115) was prepared from ethyl 2-(((5-fluoropyridin-3-yl)methyl)amino)thieno[3,2-d]pyrimidine using chemistry similar to that described in Example Z17 using 3-methoxyazetidine hydrochloride (commercially obtained from PharmaBlock, Sunnyvale, Calif.) in place of (3R)-3-methoxypyrrolidine hydrochloride (44% yield). $^1$H NMR (400 MHz, CDCl$_3$) δ 3.30 (3H, s), 4.11 (1H, ddd, J=11.6, 3.8, 1.2 Hz), 4.22-4.25 (1H, m), 4.40 (1H, ddd, J=12.0, 6.4, 1.6 Hz), 4.45-4.50 (1H, m), 4.76-4.80 (3H, m), 5.50 (1H, m), 7.21 (1H, d, J=5.6 Hz), 7.44 (1H, dt, J=9.2, 2.0 Hz), 8.00 (1H, d, J=6.0 Hz), 8.39 (1H, d, J=2.8 Hz), 8.47 (1H, s) ppm. LCMS m/z=374.0 [M+H$^+$].

Example Z116. Azetidin-1-yl(2-(((5-methoxypyridin-3-yl)methyl)amino)thieno[3,2-d]pyrimidin-4-yl)methanone

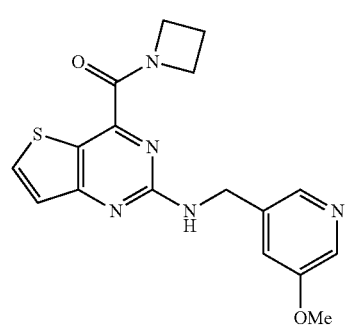 [SMILES: COc1cncc(CNc2nc(C(=O)N3CCC3)c3sccc3n2)c1]

Synthesis of azetidin-1-yl(2-(((5-methoxypyridin-3-yl)methyl)amino)thieno[3,2-d]pyrimidin-4-yl)methanone (Z116): The title compound (Z116) was prepared from ethyl 2-(((5-methoxypyridin-3-yl)methyl)amino)thieno[3,2-d]pyrimidine-4-carboxylate using chemistry similar to that described in Example Z17 using azetidine in place of (R)-3-fluoropyrrolidine (71% yield). LCMS m/z=356.1 [M+H$^+$].

Example Z117. (2-(((5-Methoxypyridin-3-yl)methyl)amino)thieno[3,2-d]pyrimidin-4-yl)(3-methylazetidin-1-yl)methanone

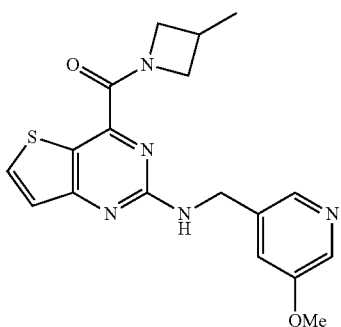 [SMILES: COc1cncc(CNc2nc(C(=O)N3CC(C)C3)c3sccc3n2)c1]
(Z117)

Synthesis of (2-(((5-methoxypyridin-3-yl)methyl)amino)thieno[3,2-d]pyrimidin-4-yl)(3-methylazetidin-1-yl)methanone (Z117): The title compound (Z117) was prepared from ethyl 2-(((5-methoxypyridin-3-yl)methyl)amino)thieno[3,2-d]pyrimidine-4-carboxylate using chemistry similar to that described in Example Z17 using 3-methylazetidine hydrochloride (commercially obtained from Sigma-Aldrich, St. Louis, Mo.) in place of (R)-3-fluoropyrrolidine (85% yield). LCMS m/z=370.1 [M+H$^+$].

Example Z118. (R)-(2-((3-Chlorobenzyl)amino)thieno[3,2-d]pyrimidin-4-yl)(3-hydroxypyrrolidin-1-yl)methanone

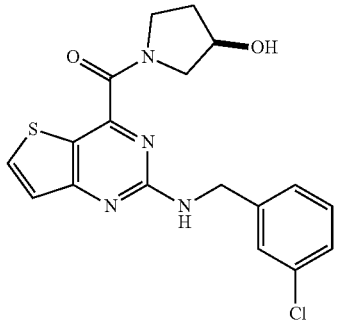 [SMILES: O=C(c1nc(NCc2cccc(Cl)c2)nc2ccsc12)N1CC[C@@H](O)C1]
(Z118)

Synthesis of (R)-(2-((3-chlorobenzyl)amino)thieno[3,2-d]pyrimidin-4-yl)(3-hydroxypyrrolidin-1-yl)methanone (Z118): The title compound (Z118) was prepared from ethyl 2-(((5-chloropyridin-3-yl)methyl)amino)thieno[3,2-d]pyrimidine-4-carboxylate using chemistry similar to that described in Example Z17 using (3R)-3-hydroxypyrrolidine in place of (3R)-3-methoxypyrrolidine hydrochloride (27% yield). LCMS m/z=389.1 [M+H$^+$].

Example Z119. (3-Hydroxyazetidin-1-yl)(2-(((5-methoxypyridin-3-yl)methyl)amino)thieno[3,2-d]pyrimidin-4-yl)methanone

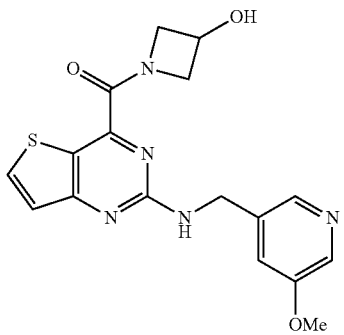 [SMILES: COc1cncc(CNc2nc(C(=O)N3CC(O)C3)c3sccc3n2)c1]
(Z119)

Synthesis of (3-hydroxyazetidin-1-yl)(2-(((5-methoxypyridin-3-yl)methyl)amino)thieno[3,2-d]pyrimidin-4-yl)methanone (Z119): The title compound (Z119) was prepared from ethyl 2-(((5-methoxypyridin-3-yl)methyl)amino)thieno[3,2-d]pyrimidine-4-carboxylate using chemistry similar to that described in Example Z17 using azetidin-3-ol hydrochloride in place of (R)-3-fluoropyrrolidine (59% yield). LCMS m/z=372.0 [M+H$^+$].

Example Z120. (2-((3-Chlorobenzyl)amino)thieno[3,2-d]pyrimidin-4-yl)(pyrrolidin-1-yl)methanone

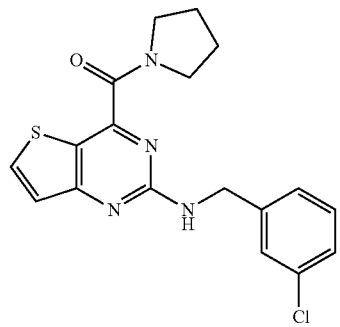 [SMILES: O=C(c1nc(NCc2cccc(Cl)c2)nc2ccsc12)N1CCCC1]
(Z120)

Synthesis of ethyl 2-((3-chlorobenzyl)amino)thieno[3,2-d]pyrimidine-4-carboxylate: The title compound was prepared from ethyl 2-chlorothieno[3,2-d]pyrimidine-4-carboxylate (220 mg, 0.92 mmol) using chemistry similar to that described in Example Z12 using 3-chlorobenzylamine (commercially obtained from Sigma-Aldrich, St. Louis, Mo.) in place of (6-methoxypyridin-3-yl)methanamine hydrochloride to produce ethyl 2-((3-chlorobenzyl)amino)thieno[3,2-d]pyrim-idine-4-carboxylate (115 mg, 36% yield). LCMS m/z=348.0 [M+H$^+$].

Synthesis of (2-((3-chlorobenzyl)amino)thieno[3,2-d]pyrimidin-4-yl)(pyrrolidin-1-yl)methanone (Z120): The title compound (Z120) was prepared from ethyl 2-((3-chlorobenzyl)amino)thieno[3,2-d]pyrimidine-4-carboxylate using chemistry similar to that described in Example Z17 using pyrrolidine in place of (3R)-3-methoxypyrrolidine hydrochloride (58% yield). LCMS m/z=373.1 [M+H$^+$].

Example Z121. Azetidin-1-yl(2-((3-chlorobenzyl)amino)thieno[3,2-d]pyrimidin-4-yl)methanone

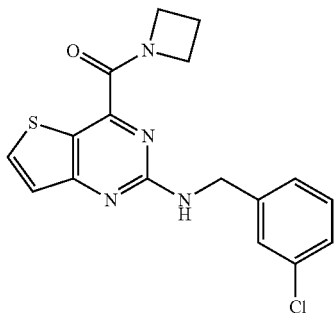 [SMILES: O=C(c1nc(NCc2cccc(Cl)c2)nc2ccsc12)N1CCC1]

(Z121)

Synthesis of azetidin-1-yl(2-((3-chlorobenzyl)amino)thieno[3,2-d]pyrimidin-4-yl)methanone (Z121): The title compound (Z121) was prepared from ethyl 2-((3-chlorobenzyl)amino)thieno[3,2-d]pyrimidine-4-carboxylate using chemistry similar to that described in Example Z17 using azetidine in place of (3R)-3-methoxypyrrolidine hydrochloride (47% yield). LCMS m/z=359.0 [M+H$^+$].

Example Z122. (2-((3-Chlorobenzyl)amino)thieno[3,2-d]pyrimidin-4-yl)(3-hydroxyazetidin-1-yl)methanone

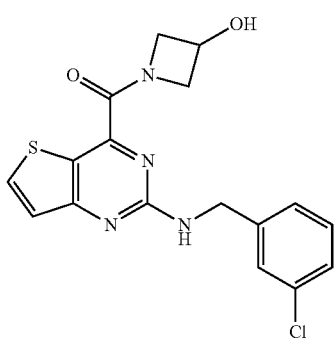 [SMILES: O=C(c1nc(NCc2cccc(Cl)c2)nc2ccsc12)N1CC(O)C1]

(Z122)

Synthesis of (2-((3-chlorobenzyl)amino)thieno[3,2-d]pyrimidin-4-yl)(3-hydroxyazetidin-1-yl)methanone (Z122): The title compound (Z122) was prepared from ethyl 2-((3-chlorobenzyl)-amino)thieno[3,2-d]pyrimidine-4-carboxylate using chemistry similar to that described in Example Z17 using azetidin-3-ol hydrochloride in place of (3R)-3-methoxypyrrolidine hydrochloride (44% yield). LCMS m/z=375.0 [M+H$^+$].

Example Z123. 2-(((5-Fluoropyridin-3-yl)methyl)amino)-N-(2-hydroxyethyl)thieno[3,2-d]pyrimidine-4-carboxamide

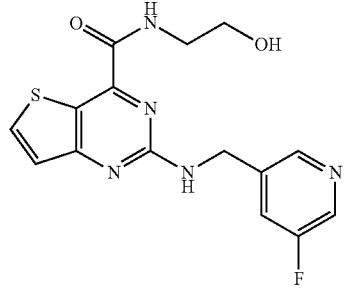 [SMILES: O=C(NCCO)c1nc(NCc2cncc(F)c2)nc2ccsc12]

(Z123)

Synthesis of 2-(((5-fluoropyridin-3-yl)methyl)amino)-N-(2-hydroxyethyl)thieno[3,2-d]pyrimidine-4-carboxamide (Z123): The title compound (Z123) was prepared from ethyl 2-(((5-fluoropyridin-3-yl)methyl)amino)thieno[3,2-d]pyrimidine using chemistry similar to that described in Example Z17 using 2-aminoethanol (commercially obtained from Combi-Blocks, San Diego, Calif.) in place of (3R)-3-methoxypyrrolidine hydrochloride (31% yield). $^1$H NMR (400 MHz, CDCl$_3$) δ 3.66 (2H, dt, J=10.4, 5.6 Hz), 3.85 (2H, t, J=4.8 Hz), 4.74 (2H, d, J=6.0 Hz), 5.65 (1H, m), 7.22 (1H, d, J=5.6 Hz), 7.48 (2H, dt, J=8.4, 2.0 Hz), 8.15 (1H, br s), 8.37 (1H, d, J=2.8 Hz), 8.55 (1H, s) ppm. LCMS m/z=348.0 [M+H$^+$].

Example Z124. ((S)-3-Hydroxypyrrolidin-1-yl)(2-((2-methoxy-1-(pyridin-3-yl)ethyl)amino)thieno[3,2-d]pyrimidin-4-yl)methanone

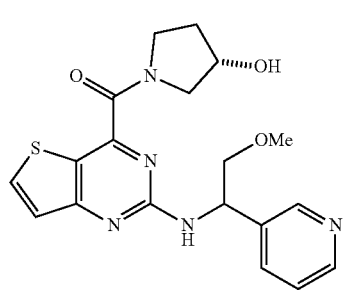 [SMILES: COCC(Nc1nc(C(=O)N2CC[C@H](O)C2)c2sccc2n1)c1cccnc1]

(Z124)

Synthesis of ethyl 2-((2-methoxy-1-(pyridin-3-yl)ethyl)amino)thieno[3,2-d]pyrimidine-4-carboxylate: The title compound was prepared from ethyl 2-chlorothieno[3,2-d]pyrimidine-4-carboxylate (215 mg, 0.88 mmol) using chemistry similar to that described in Example Z12 using 2-methoxy-1-(3-pyridyl)ethanamine hydrochloride (commercially obtained from Aurum Pharmatech, Franklin Park, N.J.) in place of (6-methoxypyridin-3-yl)methanamine hydrochloride to produce ethyl 2-((2-methoxy-1-(pyridin-3-yl)ethyl)amino)thieno[3,2-d]pyrimidine-4-carboxylate (58 mg, 18% yield). LCMS m/z=359.1 [M+H$^+$].

Synthesis of ((S)-3-hydroxypyrrolidin-1-yl)(2-((2-methoxy-1-(pyridin-3-yl)ethyl)amino)thieno[3,2-d]pyrimidin-4-yl)methanone (Z124): The title compound (Z124) was prepared from ethyl 2-((2-methoxy-1-(pyridin-3-yl)ethyl)

amino)thieno[3,2-d]pyrimidine-4-carboxylate using chemistry similar to that described in Example Z17 using (3S)-pyrrolidin-3-ol in place of (3R)-3-methoxypyrrolidine hydrochloride (31% yield). LCMS m/z=400.1 [M+H⁺].

Example Z125. (S)-(2-((1-(3-Fluorophenyl)ethyl)amino)thieno[3,2-d]pyrimidin-4-yl)(pyrrolidin-1-yl)methanone

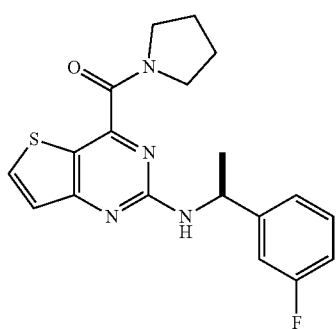 [SMILES: C[C@H](Nc1nc(C(=O)N2CCCC2)c2sccc2n1)c1cccc(F)c1]
(Z125)

Synthesis of (S)-2-((1-(3-fluorophenyl)ethyl)amino)thieno[3,2-d]pyrimidine-4-carboxylic acid hydrochloride: The title compound was prepared from ethyl 2-chlorothieno[3,2-d]pyrimidine-4-carboxylate using chemistry similar to that described in Example Z1 using (S)-1-(3-fluorophenyl)ethan-1-amine (commercially obtained from Ark Pharm, Libertyville, Ill.) in place of (1S)-1-(3-pyridyl)ethanamine. LCMS m/z=301.1 [M+H⁺].

Synthesis of (S)-2-((1-(3-fluorophenyl)ethyl)amino)thieno[3,2-d]pyrimidin-4-yl)(pyrrolidin-1-yl)methanone (Z125): The title compound (Z125) was prepared from (S)-2-((1-(3-fluorophenyl)ethyl)amino)thieno[3,2-d]pyrimidine-4-carboxylic acid hydrochloride and pyrrolidine using chemistry similar to that described in Example Z8 (28% yield). ¹H NMR (400 MHz, CDCl₃) δ 1.59 (3H, d, J=6.8 Hz), 1.76-1.89 (4H, m), 3.51 (1H, m), 3.63-3.71 (2H, m), 3.77 (1H, m), 5.15 (1H, quintet, J=6.8 Hz), 5.43 (1H, d, J=6.8 Hz), 6.91 (1H, m), 7.09 (1H, dt, J=9.6, 2.0 Hz), 7.16 (1H, d, J=8.0 Hz), 7.18 (1H, J=5.6 Hz), 7.28 (1H, m), 7.94 (1H, d, J=5.6 Hz) ppm. LCMS m/z=371.1 [M+H⁺].

Example Z126. Azetidin-1-yl(2-((2-methoxy-1-(pyridin-3-yl)ethyl)amino)thieno[3,2-d]pyrimidin-4-yl)methanone

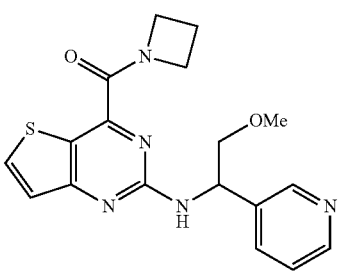
(Z126)

Synthesis of azetidin-1-yl(2-((2-methoxy-1-(pyridin-3-yl)ethyl)amino)thieno[3,2-d]pyrimidin-4-yl)methanone (Z126): The title compound (Z126) was prepared from ethyl 2-((2-methoxy-1-(pyridin-3-yl)ethyl)amino)thieno[3,2-d]pyrimidine-4-carboxylate using chemistry similar to that described in Example Z17 using azetidine in place of (3R)-3-methoxypyrrolidine hydrochloride (31% yield). LCMS m/z=400.1 [M+H⁺].

Example Z127. (2-((2-Methoxy-1-(pyridin-3-yl)ethyl)amino)thieno[3,2-d]pyrimidin-4-yl)(pyrrolidin-1-yl)methanone

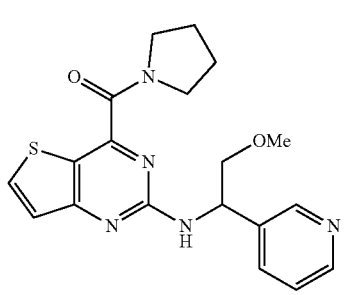
(Z127)

Synthesis of (2-((2-methoxy-1-(pyridin-3-yl)ethyl)amino)thieno[3,2-d]pyrimidin-4-yl)(pyrrolidin-1-yl)methanone (Z127): The title compound (Z127) was prepared from ethyl 2-(2-methoxy-1-(pyridin-3-yl)ethyl)amino)thieno[3,2-d]pyrimidine-4-carboxylate using chemistry similar to that described in Example Z17 using pyrrolidine in place of (3R)-3-methoxypyrrolidine hydrochloride (31% yield). LCMS m/z=400.1 [M+H⁺].

Example Z128. (S)-Azetidin-1-yl(2-((1-(3-fluorophenyl)ethyl)amino)thieno[3,2-d]pyrimidin-4-yl)methanone

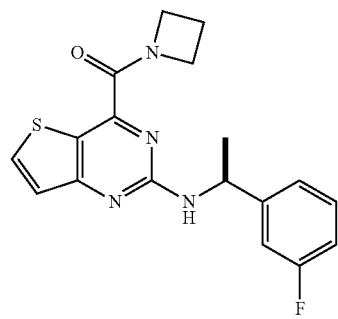 [SMILES: C[C@H](Nc1nc(C(=O)N2CCC2)c2sccc2n1)c1cccc(F)c1]
(Z128)

Synthesis of (S)-azetidin-1-yl(2-((1-(3-fluorophenyl)ethyl)amino)thieno[3,2-d]pyrimidin-4-yl)methanone (Z128): The title compound (Z128) was prepared from (S)-2-((1-(3-fluorophenyl)ethyl)amino)thieno[3,2-d]pyrimidine-4-carboxylic acid hydrochloride and azetidine using chemistry similar to that described in Example Z8 (25% yield). ¹H NMR (400 MHz, CDCl₃) δ 1.59 (3H, d, J=6.8 Hz), 2.26-2.39 (2H, m), 4.24 (2H, t, J=8.0 Hz), 4.40 (1H, m), 4.69 (1H, m), 5.18 (1H, quintet, J=6.8 Hz), 5.36 (1H, d, J=6.8 Hz), 6.92 (1H, td, J=8.0, 2.0 Hz), 7.08 (1H, dt, J=10.0, 2.0 Hz), 7.15 (1H, d, J=8.0 Hz), 7.17 (1H, d, J=5.6 Hz), 7.28 (1H, m), 7.96 (1H, d, J=5.6 Hz) ppm. LCMS m/z=357.2 [M+H⁺].

Example Z129. (2-(((S)-1-(3-Fluorophenyl)ethyl)amino)thieno[3,2-d]pyrimidin-4-yl)((S)-3-hydroxypyrrolidin-1-yl)methanone

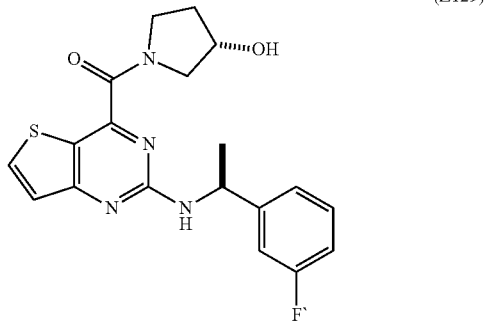

(Z129)

Synthesis of (2-(((S)-1-(3-fluorophenyl)ethyl)amino)thieno[3,2-d]pyrimidin-4-yl)((S)-3-hydroxypyrrolidin-1-yl)methanone (Z129): The title compound (Z129) was prepared from (S)-2-((1-(3-fluorophenyl)ethyl)amino)thieno[3,2-d]pyrimidine-4-carboxylic acid hydrochloride and (S)-pyrrolidin-3-ol using chemistry similar to that described in Example Z8 (44% yield). $^1$H NMR (400 MHz, CDCl$_3$) δ 1.59 (3H, d, J=6.8 Hz), 1.82-1.98 (2H, m), 3.66 (1H, m), 3.76 (1H, m), 3.81-3.85 (2H, m), 4.44 (1H, m), 5.13 (1H, quintet, J=6.8 Hz), 5.44 (1H, d, J=6.8 Hz), 6.92 (1H, m), 7.10 (1H, m), 7.16 (1H, d, J=8.0 Hz), 7.18 (1H, d, J=5.6 Hz), 7.28 (1H, m), 7.95 (1H, d, J=5.6 Hz) ppm. LCMS m/z=387.1 [M+H$^+$].

Example Z130. (2-(((6-Fluoropyridin-3-yl)methyl)amino)thieno[3,2-d]pyrimidin-4-yl)(pyrrolidin-1-yl)methanone

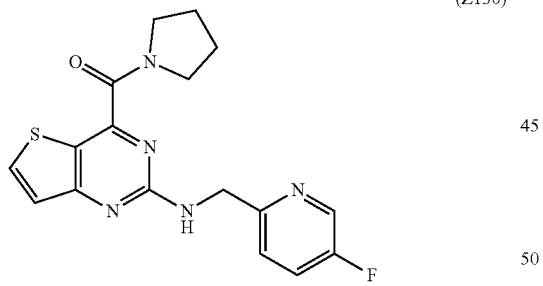

(Z130)

Synthesis of ethyl 2-(((5-fluoropyridin-2-yl)methyl)amino)thieno[3,2-d]pyrimidine-4-carboxylate: The title compound was prepared from ethyl 2-chlorothieno[3,2-d]pyrimidine-4-carboxylate (200 mg, 0.82 mmol) using chemistry similar to that described in Example Z12 using (5-fluoro-2-pyridyl)methanamine (commercially obtained from Ox-Chem, Wood Dale, Ill.) in place of (6-methoxypyridin-3-yl)methanamine hydrochloride to produce ethyl 2-(((5-fluoropyridin-2-yl)methyl)amino)thieno[3,2-d]pyrimidine-4-carboxylate (60 mg, 22% yield). $^1$H NMR (400 MHz, CDCl$_3$) δ 1.91 (4H, dt, J=10.0, 3.6 Hz), 3.73 (2H, m), 3.82 (2H, m), 4.81 (2H, dd, J=5.6, 1.2 Hz), 6.02 (1H, q, J=3.6 Hz), 7.22 (1H, d, J=5.6 Hz), 7.36 (2H, dd, J=6.4, 2.0 Hz), 7.95 (1H, d, J=6.4 Hz), 8.43 (1H, t, J=1.6 Hz) ppm. LCMS m/z=359.1 [M+H$^+$].

Synthesis of (2-(((5-fluoropyridin-3-yl)methyl)amino)thieno[3,2-d]pyrimidin-4-yl)(pyrrolidin-1-yl)methanone (Z130): The title compound (Z130) was prepared from ethyl 2-(((5-fluoropyridin-2-yl)methyl)amino)thieno[3,2-d]pyrimidine-4-carboxylate using chemistry similar to that described in Example Z17 using pyrrolidine in place of (3R)-3-methoxypyrrolidine hydrochloride (27% yield). LCMS m/z=358.1 [M+H$^+$].

Example Z131. (S)-(2-(((6-Fluoropyridin-3-yl)methyl)amino)thieno[3,2-d]pyrimidin-4-yl)(3-hydroxypyrrolidin-1-yl)methanone

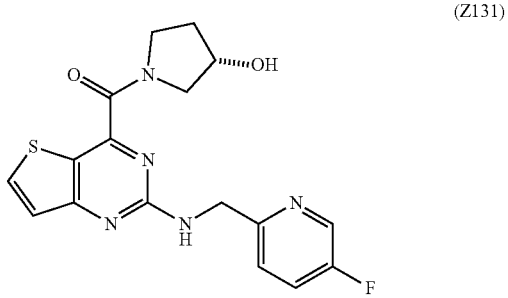

(Z131)

Synthesis of (S)-(2-(((5-fluoropyridin-2-yl)methyl)amino)thieno[3,2-d]pyrimidin-4-yl)(3-hydroxypyrrolidin-1-yl)methanone (Z131): The title compound (Z131) was prepared from ethyl 2-(((5-fluoropyridin-2-yl)methyl)amino)thieno[3,2-d]pyrimidine-4-carboxylate using chemistry similar to that described in Example Z17 using (3S)-pyrrolidin-3-ol in place of (3R)-3-methoxy-pyrrolidine hydrochloride (27% yield). LCMS m/z=358.1 [M+H$^+$].

Example Z132. (2-(((S)-1-(3-Fluorophenyl)ethyl)amino)thieno[3,2-d]pyrimidin-4-yl)((R)-3-hydroxypyrrolidin-1-yl)methanone

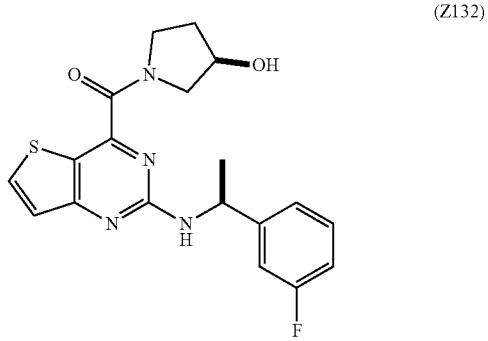

(Z132)

Synthesis of (2-(((S)-1-(3-fluorophenyl)ethyl)amino)thieno[3,2-d]pyrimidin-4-yl)((S)-3-hydroxypyrrolidin-1-yl)methanone (Z132): The title compound (Z132) was prepared from (S)-2-((1-(3-fluorophenyl)ethyl)amino)thieno[3,2-d]pyrimidine-4-carboxylic acid hydrochloride and (R)-pyrrolidin-3-ol using chemistry similar to that described in Example Z8 (49% yield). $^1$H NMR (400 MHz, CDCl$_3$) δ 1.59 (3H, d, J=6.8 Hz), 1.93-1.99 (2H, m), 3.66 (1H, m), 3.78 (1H, m), 3.85 (1H, m), 4.06 (1H, m), 4.48 (1H, m), 5.15 (1H, quintet, J=6.8 Hz), 5.43 (1H, d, J=6.8 Hz), 6.92 (1H, m), 7.10 (1H, m), 7.17 (1H, m), 7.18 (1H, d, J=5.6 Hz), 7.27 (1H, m), 7.94 (1H, d, J=5.6 Hz) ppm. LCMS m/z=387.2 [M+H⁺].

Example Z133. (2-Methylazetidin-1-yl)(2-(((S)-1-(pyridin-2-yl)ethyl)amino)thieno[3,2-d]pyrimidin-4-yl)methanone

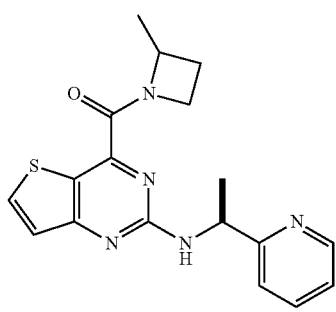 [SMILES: CC1CCN1C(=O)c1nc(N[C@@H](C)c2ccccn2)nc2ccsc12]

(Z133)

Synthesis of (2-methylazetidin-1-yl)(2-(((S)-1-(pyridin-2-yl)ethyl)amino)thieno[3,2-d]pyrimidin-4-yl)methanone (Z133): The title compound (Z133) was prepared from (S)-2-((1-(pyridin-2-yl)ethyl)amino)thieno[3,2-d]pyrimidine-4-carboxylic acid di-hydrochloride using chemistry similar to that described in Example Z8 using 2-methylazetidine (commercially obtained from Synnovator, Durham, N.C.) in place of (R)-3-fluoropyrrolidine (45% yield). LCMS m/z=354.2 [M+H⁺].

Example Z134. (S)-(2-((1-(5-Fluoropyridin-3-yl)ethyl)amino)thieno[3,2-d]pyrimidin-4-yl)(pyrrolidin-1-yl)methanone

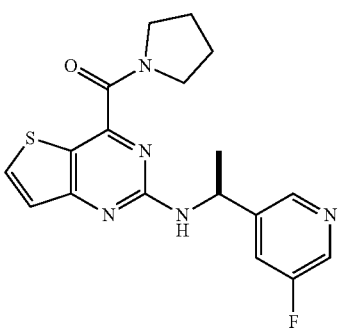 [SMILES: C[C@H](Nc1nc(C(=O)N2CCCC2)c2sccc2n1)c1cncc(F)c1]

(Z134)

Synthesis of methyl (S)-2-((1-(5-fluoropyridin-3-yl)ethyl)amino)thieno[3,2-d]pyrimidine-4-carboxylate: The title compound was prepared from ethyl 2-chlorothieno[3,2-d]pyrimidine-4-carboxylate using chemistry similar to that described in Example Z1 using (S)-1-(5-fluoropyridin-3-yl)ethan-1-amine (commercially obtained from Bellen, Beijing, China) in place of (1S)-1-(3-pyridyl)ethanamine. LCMS m/z=333.0 [M+H⁺].

Synthesis of (S)-(2-((1-(5-fluoropyridin-3-yl)ethyl)amino)thieno[3,2-d]pyrimidin-4-yl)(pyrrolidin-1-yl)methanone (Z134): The title compound (Z134) was prepared from methyl (S)-2-((1-(5-fluoropyridin-3-yl)ethyl)amino)thieno[3,2-d]pyrimidine-4-carboxylate using chemistry similar to that described in Example Z2 using pyrrolidine in place of azetidine (70% yield). ¹H NMR (400 MHz, CDCl₃) δ 1.64 (3H, d, J=6.8 Hz), 1.85-1.89 (4H, m), 3.58 (1H, m), 3.69 (2H, t, J=5.6 Hz), 3.78 (1H, m), 5.23 (1H, quintet, J=6.8 Hz), 5.41 (1H, d, J=6.8 Hz), 7.18 (1H, d, J=5.6 Hz), 7.44 (1H, dt, J=9.2, 2.4 Hz), 7.94 (1H, d, J=5.6 Hz), 8.34 (1H, d, J=2.4 Hz), 8.51 (1H, d, J=2.4 Hz) ppm. LCMS m/z=372.1 [M+H⁺].

Example Z135. tert-Butyl 3-(2-(((5-fluoropyridin-3-yl)methyl)amino)thieno[3,2-d]pyrimidine-4-carbonyl)imidazolidine-1-carboxylate

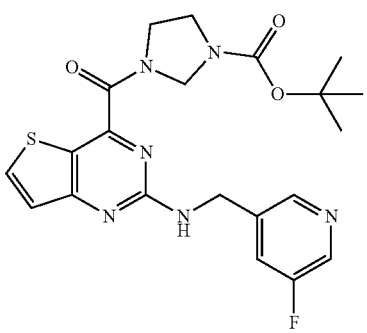

(Z135)

Synthesis of tert-butyl 3-(2-(((5-fluoropyridin-3-yl)methyl)amino)thieno[3,2-d]pyrimidine-4-carbonyl)imidazolidine-1-carboxylate (Z135): The title compound (Z135) was prepared from ethyl 2-(((5-fluoropyridin-3-yl)methyl)amino)thieno[3,2-d]pyrimidine using chemistry similar to that described in Example Z17 using tert-butyl imidazolidine-1-carboxylate (commercially obtained from OxChem, Wood Dale, Ill.) in place of (3R)-3-methoxypyrrolidine hydrochloride (59% yield). LCMS m/z=459.2 [M+H⁺].

Example Z136. (2-((3-Fluoro-5-methoxybenzyl)amino)thieno[3,2-d]pyrimidin-4-yl)(3-hydroxy-3-methylazetidin-1-yl)methanone

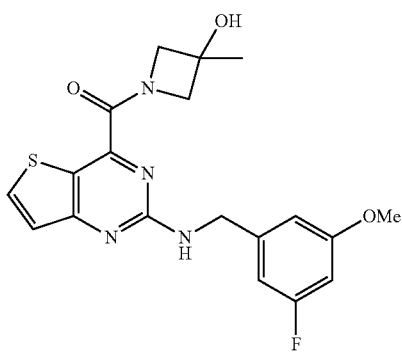 [SMILES: COc1cc(F)cc(CNc2nc(C(=O)N3CC(C)(O)C3)c3sccc3n2)c1]

(Z136)

Synthesis of ethyl 2-((3-fluoro-5-methoxybenzyl)amino)thieno[3,2-d]pyrimidine-4-carboxylate: The title compounds was prepared from ethyl 2-chlorothieno[3,2-d]pyrimidine-4-carboxylate (255 mg, 1.05 mmol) using chemistry similar to that described in Example Z12 using (3-fluoro-5-methoxy-phenyl)methanamine (commercially obtained from Activate Scientific, Shanghai, Conn.) in place of (6-methoxypyridin-3-yl)methanamine hydrochloride to produce ethyl 2-((3-fluoro-5-methoxybenzyl)amino)thieno[3,2-d]pyrimidine-4-carboxylate (58 mg, 15% yield). LCMS m/z=362.1 [M+H⁺].

Synthesis of (2-((3-fluoro-5-methoxybenzyl)amino)thieno[3,2-d]pyrimidin-4-yl)(3-hydroxy-3-methylazetidin-1-yl)methanone (Z136): The title compound (Z136) was prepared from ethyl 2-((3-fluoro-5-methoxybenzyl)amino)thieno[3,2-d]pyrimidine-4-carboxylate using chemistry similar to that described in Example Z17 using 3-methylazetidin-3-ol hydrochloride in place of (3R)-3-methoxypyrrolidine hydrochloride (36% yield). LCMS m/z=403.1 [M+H⁺].

Example Z137. (2-((3-Fluoro-5-methoxybenzyl)amino)thieno[3,2-d]pyrimidin-4-yl)(3-hydroxyazetidin-1-yl)methanone

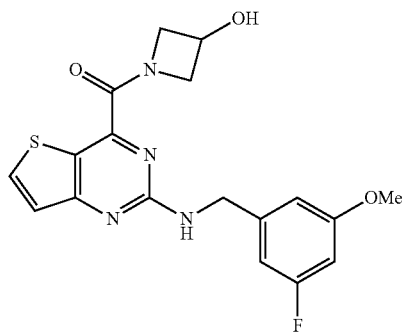 [SMILES: COc1cc(F)cc(CNc2nc(C(=O)N3CC(O)C3)c3sccc3n2)c1]

(Z137)

Synthesis of (2-((3-fluoro-5-methoxybenzyl)amino)thieno[3,2-d]pyrimidin-4-yl)(3-hydroxyazetidin-1-yl)methanone (Z137): The title compound (Z137) was prepared from ethyl 2-((3-fluoro-5-methoxybenzyl)amino)thieno[3,2-d]pyrimidine-4-carboxylate using chemistry similar to that described in Example Z17 using azetidin-3-ol hydrochloride in place of (3R)-3-methoxypyrrolidine hydrochloride (61% yield). LCMS m/z=389.1 [M+H⁺].

Example Z138. (S)-(3-Hydroxyazetidin-1-yl)(2-((1-(pyridin-3-yl)ethyl)amino)thieno[3,2-d]pyrimidin-4-yl)methanone

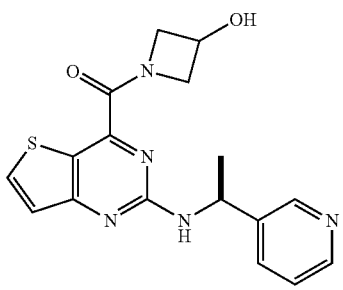 [SMILES: C[C@H](Nc1nc(C(=O)N2CC(O)C2)c2sccc2n1)c1cccnc1]

(Z138)

Synthesis of (S)-(3-hydroxyazetidin-1-yl)(2-((1-(pyridin-3-yl)ethyl)amino)thieno[3,2-d]pyrimidin-4-yl)methanone (Z138): The title compound (Z138) was prepared from (S)-2-((1-(pyridin-3-yl)ethyl)amino)thieno[3,2-d]pyrimidine-4-carboxylic acid di-hydrochloride and azetidin-3-ol hydrochloride using chemistry similar to that described in Example Z8 (27% yield). LCMS m/z=356.1 [M+H⁺].

Example Z139. (S)-(3-Methoxyazetidin-1-yl)(2-((1-(pyridin-3-yl)ethyl)amino)thieno[3,2-d]pyrimidin-4-yl)methanone

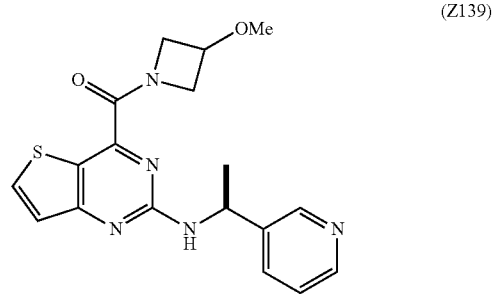

(Z139)

Synthesis of (S)-(3-methoxyazetidin-1-yl)(2-((1-(pyridin-3-yl)ethyl)amino)thieno[3,2-d]pyrimidin-4-yl)methanone (Z139): The title compound (Z139) was prepared from (S)-2-((1-(pyridin-3-yl)ethyl)amino)thieno[3,2-d]pyrimidine-4-carboxylic acid di-hydrochloride and 3-methoxyazetidine hydrochloride using chemistry similar to that described in Example Z8 (47% yield). LCMS m/z=370.1 [M+H⁺].

Example Z140. tert-Butyl (S)-3-(2-((1-(pyridin-3-yl)ethyl)amino)thieno[3,2-d]pyrimidine-4-carbonyl)imidazolidine-1-carboxylate

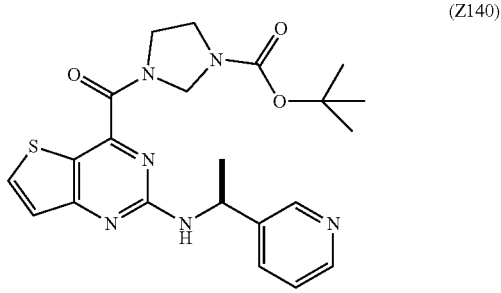

(Z140)

Synthesis of tert-butyl (S)-3-(2-((1-(pyridin-3-yl)ethyl)amino)thieno[3,2-d]pyrimidine-4-carbonyl)imidazolidine-1-carboxylate (Z140): The title compound (Z140) was prepared from ethyl (S)-2-((1-(pyridin-3-yl)ethyl)amino)thieno[3,2-d]pyrimidine-4-carboxylate using chemistry similar to that described in Example Z17 using tert-butyl imidazolidine-1-carboxylate in place of (3R)-3-methoxypyrrolidine hydrochloride (49% yield). LCMS m/z=455.1 [M+H⁺].

Example Z141. 5-(((4-(Pyrrolidine-1-carbonyl)thieno[3,2-d]pyrimidin-2-yl)amino)methyl)nicotinonitrile

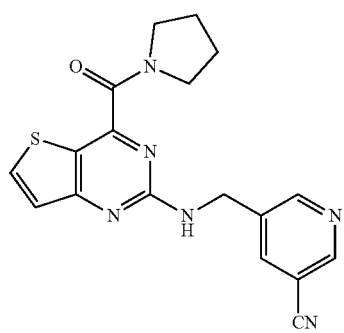 [SMILES: N#Cc1cncc(CNc2nc(C(=O)N3CCCC3)c3sccc3n2)c1]

(Z141)

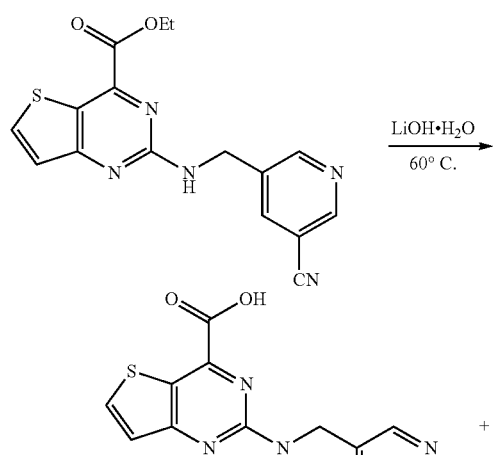

Synthesis of 2-(((5-cyanopyridin-3-yl)methyl)amino)thieno[3,2-d]pyrimidine-4-carboxylic acid: A mixture of ethyl 2-[(5-cyano-3-pyridyl)methylamino]thieno[3,2-d]pyrimidine-4-carboxylate (91 mg, 0.2700 mmol) and hydroxylithium hydrate (54.92 mg, 1.34 mmol) in methanol (0.8 mL)/THF (0.2 mL)/water (0.2 mL) was stirred at 60° C. for 2 hours. The reaction mixture was concentrated and coeluted with methanol, and then with toluene. The 1N HCl solution was used to adjust pH to 6, the resulting mixture was extracted with ethyl acetate, the organic extracts were dried over MgSO₄, filtered, and concentrated to provide a mixture of 2-[(5-cyano-3-pyridyl)methylamino]thieno[3,2-d]pyrimidine-4-carboxylic acid (40 mg, 48% yield), LCMS m/z=312.0 [M+H⁺], and 2-[(5-carbamoyl-3-pyridyl)methylamino]thieno[3,2-d]pyrimidine-4-carboxylic acid (40 mg, 45% yield), LCMS m/z=330.0 [M+H⁺].

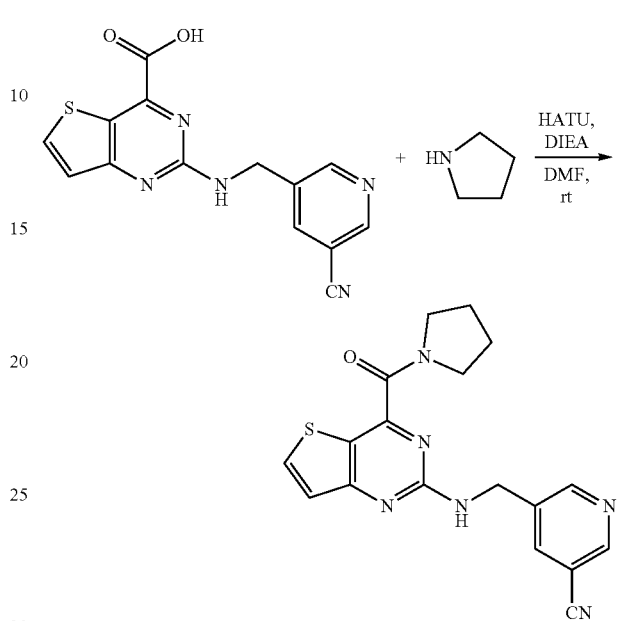

Synthesis of 5-(((4-(pyrrolidine-1-carbonyl)thieno[3,2-d]pyrimidin-2-yl)amino)methyl)nicotinonitrile (Z141): The title compound (Z141) was prepared from the mixture described in the previous step using chemistry similar to that described in Example Z8 using pyrrolidine in place of (R)-3-fluoropyrrolidine (28% yield). LCMS m/z=365.1 [M+H⁺].

Example Z142. 5-(((4-(Pyrrolidine-1-carbonyl)thieno[3,2-d]pyrimidin-2-yl)amino)methyl)nicotinamide

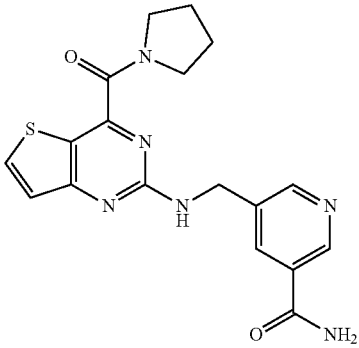 [SMILES: NC(=O)c1cncc(CNc2nc(C(=O)N3CCCC3)c3sccc3n2)c1]

(Z142)

Synthesis of 5-(((4-(pyrrolidine-1-carbonyl)thieno[3,2-d]pyrimidin-2-yl)amino)methyl)nicotinamide (Z142): The title compound (Z142) was prepared from the mixture obtained in the Example Z141 Step 1 using chemistry similar to that described in Example Z8 using pyrrolidine in place of (R)-3-fluoropyrrolidine (24% yield). LCMS m/z=383.1 [M+H⁺].

Example Z143. tert-Butyl (S)-3-(2-(((S)-1-(pyridin-2-yl)ethyl)amino)thieno[3,2-d]pyrimidine-4-carboxamido)pyrrolidine-1-carboxylate

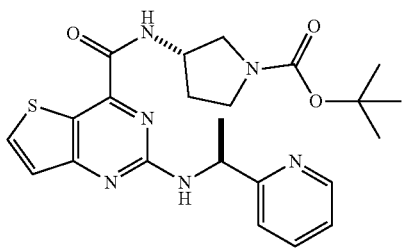

(Z143)

Synthesis of tert-butyl (S)-3-(2-(((S)-1-(pyridin-2-yl)ethyl)amino)thieno[3,2-d]pyrimidine-4-carboxamido)pyrrolidine-1-carboxylate (Z143): The title compound (Z143) was prepared from (S)-2-((1-(pyridin-2-yl)ethyl)amino)thieno[3,2-d]pyrimidine-4-carboxylic acid di-hydrochloride and tert-butyl (3S)-3-aminopyrrolidine-1-carboxylate (commercially obtained from PharmaBlock, Sunnyvale, Mo.) using chemistry similar to that described in Example Z8 (24% yield). $^1$H NMR (400 MHz, CDCl$_3$) δ 1.49 (9H, s), 1.62 (3H, d, J=6.8 Hz), 1.70 (1H, m), 2.0 (1H, m), 2.3 (1H, m), 3.31-3.30 (1H, m), 3.32-3.6 (2H, m), 3.70 (1H, m), 4.55-4.65 (1H, m), 5.15-5.30 (1H, m), 7.18-7.21 (2H, m), 7.35 (1H, d, J=8.0 Hz), 7.65 (1H, dt, J=7.6, 2.0 Hz), 7.95 (1H, m), 7.98 (1H, d, J=5.6 Hz), 8.59 (1H, d, J=4.0 Hz) ppm. LCMS m/z=469.3 [M+H$^+$].

Example Z144. (S)—N-(2-Methoxyethyl)-2-((1-(pyridin-2-yl)ethyl)amino)thieno[3,2-d]pyrimidine-4-carboxamide

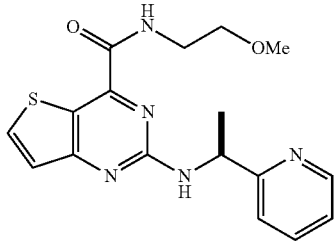

(Z144)

Synthesis of (S)—N-(2-methoxyethyl)-2-((1-(pyridin-2-yl)ethyl)amino)thieno[3,2-d]pyrimidine-4-carboxamide (Z144): The title compound (Z144) was prepared from (S)-2-((1-(pyridin-2-yl)ethyl)amino)thieno[3,2-d]pyrimidine-4-carboxylic acid di-hydrochloride and 2-methoxyethylamine (commercially obtained from Sigma-Aldrich, St. Louis, M)) using chemistry similar to that described in Example Z8 (49% yield). LCMS m/z=358.1 [M+H$^+$].

Example Z145. (S)—N-(2-Hydroxyethyl)-2-((1-(pyridin-3-yl)ethyl)amino)thieno[3,2-d]pyrimidine-4-carboxamide

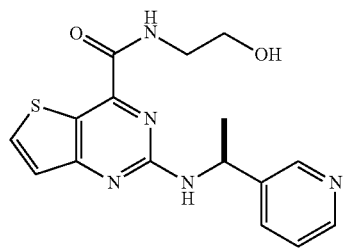 [SMILES: C[C@H](Nc1nc(C(=O)NCCO)c2sccc2n1)c1cccnc1]

(Z145)

Synthesis of (S)—N-(2-hydroxyethyl)-2-((1-(pyridin-3-yl)ethyl)amino)thieno[3,2-d]pyrimidine-4-carboxamide (Z145): The title compound (Z145) was prepared from (S)-2-((1-(pyridin-3-yl)ethyl)amino)thieno[3,2-d]pyrimidine-4-carboxylic acid di-hydrochloride and 2-aminoethanol using chemistry similar to that described in Example Z8 (49% yield). LCMS m/z=358.1 [M+H$^+$].

Example Z146. 2-(((5-Fluoropyridin-3-yl)methyl)amino)-N-(2-methoxyethyl)thieno[3,2-d]pyrimidine-4-carboxamide

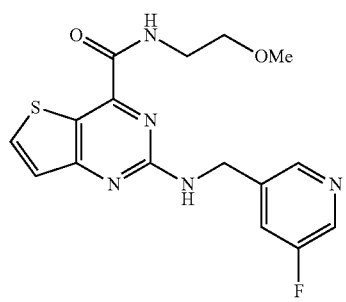

(Z146)

Synthesis of 2-(((5-fluoropyridin-3-yl)methyl)amino)-N-(2-methoxyethyl)thieno[3,2-d]pyrimidine-4-carboxamide (Z146): The title compound (Z146) was prepared from ethyl 2-(((5-fluoropyridin-3-yl)methyl)amino)thieno[3,2-d]pyrimidine using chemistry similar to that described in Example Z17 using 2-methoxyethylamine in place of (3R)-3-methoxypyrrolidine hydrochloride (85% yield). LCMS m/z=362.9 [M+H$^+$].

Example Z147. (S)—N-Cyclobutyl-2-((1-(pyridin-2-yl)ethyl)amino)thieno[3,2-d]pyrimidine-4-carboxamide

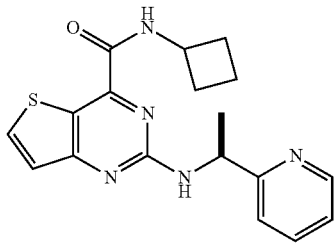

(Z147)

Synthesis of (S)—N-cyclobutyl-2-((1-(pyridin-2-yl)ethyl)amino)thieno[3,2-d]pyrimidine-4-carboxamide (Z147): The title compound (Z147) was prepared from (S)-2-((1-(pyridin-2-yl)ethyl)amino)thieno[3,2-d]pyrimidine-4-carboxylic acid di-hydrochloride and cyclobutylamine (commercially obtained from Sigma-Aldrich, St. Louis Mo.) using chemistry similar to that described in Example Z8 (56% yield). LCMS m/z=354.1 [M+H$^+$].

Example Z148. (S)-Imidazolidin-1-yl(2-((1-(pyridin-3-yl)ethyl)amino)thieno[3,2-d]pyrimidin-4-yl)methanone

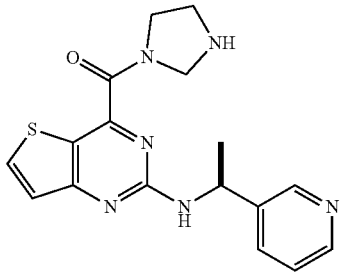 [SMILES: C[C@H](Nc1nc(C(=O)N2CCNC2)c2sccc2n1)c1cccnc1]

(Z148)

Synthesis of (S)-imidazolidin-1-yl(2-((1-(pyridin-3-yl)ethyl)amino)thieno[3,2-d]pyrimidin-4-yl)methanone (Z148): A solution of tert-butyl (S)-3-(2-((1-(pyridin-3-yl)ethyl)amino)thieno[3,2-d]pyrimidine-4-carbonyl)imidazolidine-1-carboxylate (26 mg, 0.05 mmol) in DCM was treated for 30 min with 4 M HCl solution in 1,4-dioxane. The resulting mixture was concentrated and the residue was purified by flash chromatography on silica gel (8 g HP silica, Teledyne Isco) eluting with 10% to 80% solvent A (DCM/MeOH/NH$_4$OH, 100/10/1) in DCM to provide (S)-imidazolidin-1-yl(2-((1-(pyridin-3-yl)ethyl)amino)thieno[3,2-d]pyrimidin-4-yl)methanone (24 mg, 100%). LCMS m/z=355.1 [M+H$^+$].

Example Z149. (2-(((5-Fluoropyridin-3-yl)methyl)amino)thieno[3,2-d]pyrimidin-4-yl)(imidazolidin-1-yl)methanone

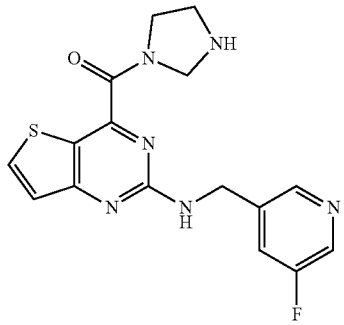 [SMILES: O=C(c1nc(NCc2cncc(F)c2)nc2ccsc12)N1CCNC1]

(Z149)

Synthesis of (2-(((5-fluoropyridin-3-yl)methyl)amino)thieno[3,2-d]pyrimidin-4-yl)(imidazolidin-1-yl)methanone (Z149): The title compound (Z149) was prepared from tert-butyl 3-(2-(((5-fluoropyridin-3-yl)methyl)amino)thieno[3,2-d]pyrimidine-4-carbonyl)imidazolidine-1-carboxylate using chemistry similar to that described in Example Z148 (100% yield). LCMS m/z=359.1 [M+H$^+$].

Example Z150. 2-(((S)-1-(pyridin-2-yl)ethyl)amino)-N—((S)-pyrrolidin-3-yl)thieno[3,2-d]pyrimidine-4-carboxamide

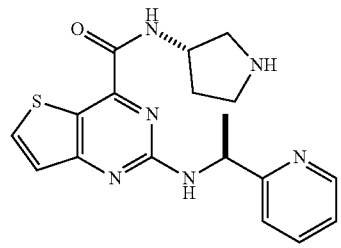

(Z150)

Synthesis of 2-(((S)-1-(pyridin-2-yl)ethyl)amino)-N—((S)-pyrrolidin-3-yl)thieno[3,2-d]pyrimidine-4-carboxamide (Z150): The title compound was prepared from tert-butyl (S)-3-(2-(((S)-1-(pyridin-2-yl)ethyl)amino)thieno[3,2-d]pyrimidine-4-carboxamido)pyrrolidine-1-carboxylate using chemistry similar to that described in Example Z148 (100% yield). LCMS m/z=369.2 [M+H$^+$].

Example Z151. (S)—N-((1-Benzylpiperidin-4-yl)methyl)-2-((1-(pyridin-2-yl)ethyl)amino)thieno[3,2-d]pyrimidine-4-carboxamide

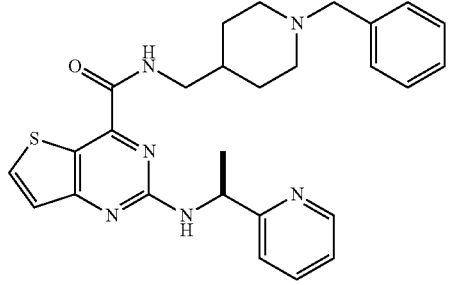 [SMILES: C[C@H](Nc1nc(C(=O)NCC2CCN(Cc3ccccc3)CC2)c2sccc2n1)c1ccccn1]
(Z151)

Synthesis of (S)—N-((1-benzylpiperidin-4-yl)methyl)-2-((1-(pyridin-2-yl)ethyl)amino)thieno[3,2-d]pyrimidine-4-carboxamide (Z151): The title compound (Z151) was prepared from (S)-2-((1-(pyridin-2-yl)ethyl)amino)thieno[3,2-d]pyrimidine-4-carboxylic acid di-hydrochloride and (1-benzyl-4-piperidyl)methanamine (commercially obtained from Sigma-Aldrich, St. Louis, Mo.) using chemistry similar to that described in Example Z8 (31% yield). LCMS m/z=387.3 [M+H$^+$].

Example Z152. (S)-(6-(Methylamino)-2-((1-(pyridin-3-yl)ethyl)amino)thieno[3,2-d]pyrimidin-4-yl)(pyrrolidin-1-yl)methanone

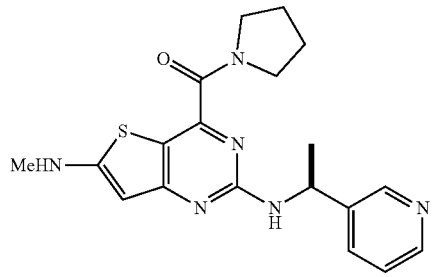 [SMILES: CNc1cc2nc(N[C@@H](C)c3cccnc3)nc(C(=O)N3CCCC3)c2s1]
(Z152)

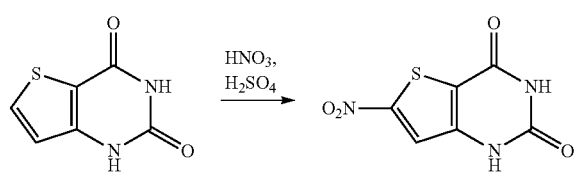

Synthesis of 6-nitrothieno[3,2-d]pyrimidine-2,4(1H,3H)-dione: To a mixture of sulfuric acid (80 mL) and HNO$_3$ (80 mL) was added thieno[3,2-d]pyrimidine-2,4(1H,3H)-dione (commercially obtained from Ark Pharm, Libertyville, Ill.) (15 g, 89.2 mmol) dropwise with stirring at 0° C. The resulting solution was stirred at room temperature for 30 min, and then ice/water was added. The precipitates were collected by filtration and dried under vacuo to provide 6-nitrothieno[3,2-d]pyrimidine-2,4(1H,3H)-dione as a yellow solid (10 g, 53% yield). LCMS m/z=244.7 [M+H$^+$].

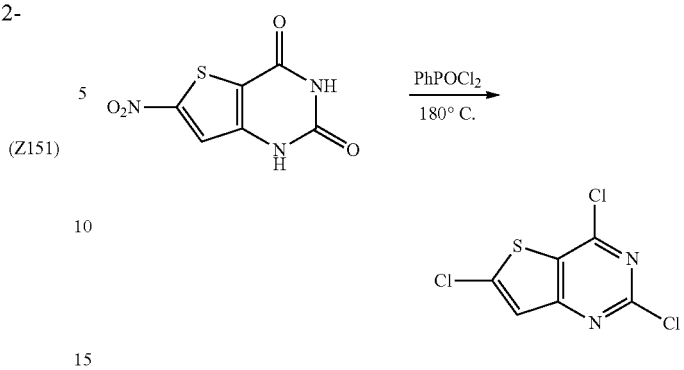

Synthesis of 2,4,6-trichlorothieno[3,2-d]pyrimidine: A solution of 6-nitrothieno[3,2-d]pyrimidine-2,4(1H,3H)-dione (10 g, 46.9 mmol) in phenylphosphonoyl dichloride (100 mL) was stirred at 180° C. for 4 h. The reaction mixture was cooled to 100° C. and iced water was added. The precipitates were collected by filtration and the filtrate was purified by column chromatography on silica gel eluting with dichloromethane/petroleum ether (100:1) to provide 2,4,6-trichlorothieno[3,2-d]pyrimidine as a white solid (2.5 g, 22% yield). $^1$H NMR (400 MHz, DMSO-d$_6$) δ 7.99 (1H, s) ppm. LCMS m/z=238.9 [M+H$^+$].

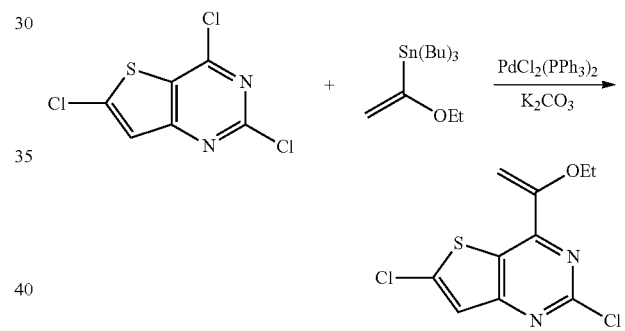

Synthesis of 2,6-dichloro-4-(1-ethoxyvinyl)thieno[3,2-d]pyrimidine: To a solution of 2,4,6-trichlorothieno[3,2-d]pyrimidine (20 g, 83.5 mmol) in 1,4-dioxane (300 mL) were added a solution of potassium carbonate (23.2 g, 168 mmol) in water (60 mL), tributyl(1-ethoxyethenyl)stannane (30.4 g, 84.2 mmol), PdCl$_2$(PPh$_3$)$_2$ (3 g, 4.3 mmol). The resulting solution was stirred for 1 h at 100° C., and then was extracted with ethyl acetate. The combined organic layer was dried over anhydrous sodium sulfate and concentrated under vacuum. The residue was purified by column chromatography on silica gel eluted with ethyl acetate/petroleum ether (3/100) to provide 2,6-dichloro-4-(1-ethoxyethenyl)thieno[3,2-d]pyrimidine as a yellow solid (19 g, 83% yield). LCMS m/z=274.8 [M+H$^+$].

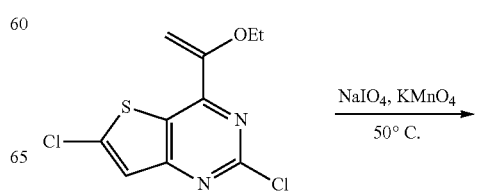

-continued

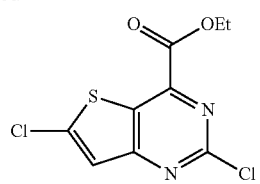

Synthesis of ethyl 2,6-dichlorothieno[3,2-d]pyrimidine-4-carboxylate: To a solution of 2,6-dichloro-4-(1-ethoxyethenyl)thieno[3,2-d]pyrimidine (20 g, 72.7 mmol) in dioxane (500 mL) were added a solution of NaIO₄ (31.24 g, 146 mmol) in water (250 mL) and KMnO₄ (2.3 g, 14.6 mmol). The resulting solution was stirred for 2 h at 50° C. and then was extracted with ethyl acetate. The combined organic layer was dried over anhydrous sodium sulfate and concentrated under vacuum. The residue was purified by flash chromatography on silica gel eluting with ethyl acetate/petroleum ether (5/100) to provide ethyl 2,6-dichlorothieno[3,2-d]pyrimidine-4-carboxylate as a white solid (12 g, 60% yield). ¹H NMR (400 MHz, DMSO-d₆) δ 1.41 (3H, t, J=4.0 Hz), 4.50 (2H, q, J=4.0 Hz), 7.9 (1H, s) ppm. LCMS m/z=276.9 [M+H⁺].

-continued

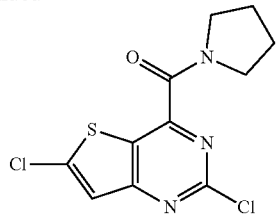

Synthesis of (2,6-dichlorothieno[3,2-d]pyrimidin-4-yl)(pyrrolidin-1-yl)methanone: To a solution of 2,6-dichlorothieno[3,2-d]pyrimidine-4-carboxylic acid (1 g, 4.0 mmol) in oxalic dichloride (10 mL) was added DMF (50 mg, 0.68 mmol) under nitrogen atmosphere and the solution thus obtained was stirred at room temperature for 2 h. The reaction mixture was concentrated under vacuum and the residue was dissolved in DCM (10 mL), and pyrrolidine (284 mg, 4.0 mmol), TEA (2 g, 20 mmol) were added. The reaction mixture was stirred at room temperature for 1 h and concentrated under vacuum. The residue was purified by flash chromatography on silica gel eluting with ethyl acetate/petroleum ether to provide (2,6-dichlorothieno[3,2-d]pyrimidin-4-yl)(pyrrolidin-1-yl)methanone as a yellow solid (866 mg, 71% yield). LCMS m/z=301.8 [M+H⁺].

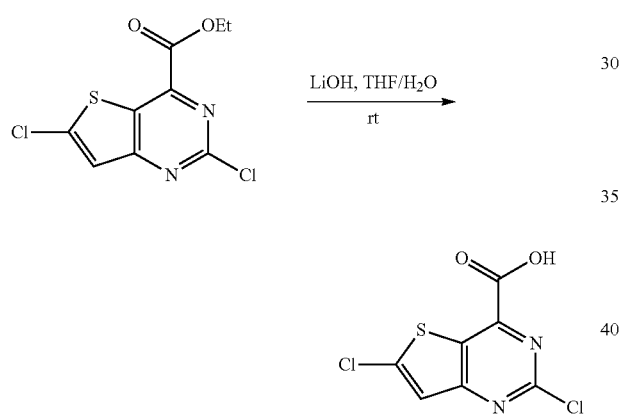

Synthesis of 2,6-dichlorothieno[3,2-d]pyrimidine-4-carboxylic acid: To a solution of ethyl 2,6-dichlorothieno[3,2-d]pyrimidine-4-carboxylate (12 g, 43.3 mmol) in tetrahydrofuran (200 mL) was added a solution of LiOH (4.2 g, 175.4 mmol) in water (50 mL). The resulting solution was stirred for 1 h at room temperature and was diluted with water. The pH value of the solution was adjusted to 2 with hydrogen chloride. The precipitates were collected by filtration and dried under vacuo to provide 2,6-dichlorothieno[3,2-d]pyrimidine-4-carboxylic acid as a brown solid (9.8 g, 91% yield). LCMS m/z=248.7 [M+H⁺].

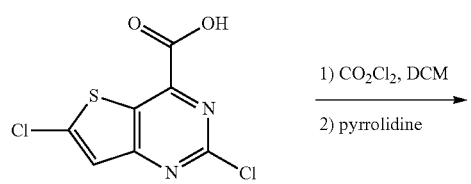

Synthesis of (S)-(6-chloro-2-((1-(pyridin-3-yl)ethyl)amino)thieno[3,2-d]pyrimidin-4-yl)(pyrrolidin-1-yl)methanone: To a solution of (2,6-dichlorothieno[3,2-d]pyrimidin-4-yl)(pyrrolidin-1-yl)methanone (750 mg, 2.48 mmol) in NMP (8 mL) were added (1S)-1-(pyridin-3-yl)ethan-1-amine (912 mg, 7.47 mmol) and DIEA (2.89 g, 22.36 mmol). The resulting solution was stirred for 3 h at 130° C. The reaction was then quenched by the addition of 100 mL of water and was extracted with 3×100 mL of ethyl acetate. The combined organic layer was concentrated and the residue was purified by flash chromatography on silica gel eluting with DCM/methanol (25/1) to provide (S)-(6-chloro-2-((1-(pyridin-3-yl)ethyl)amino)thieno[3,2-d]pyrimidin-4-yl)(pyrrolidin-1-yl)methanone as yellow solid (360 mg, 37% yield). LCMS m/z=387.9 [M+H⁺].

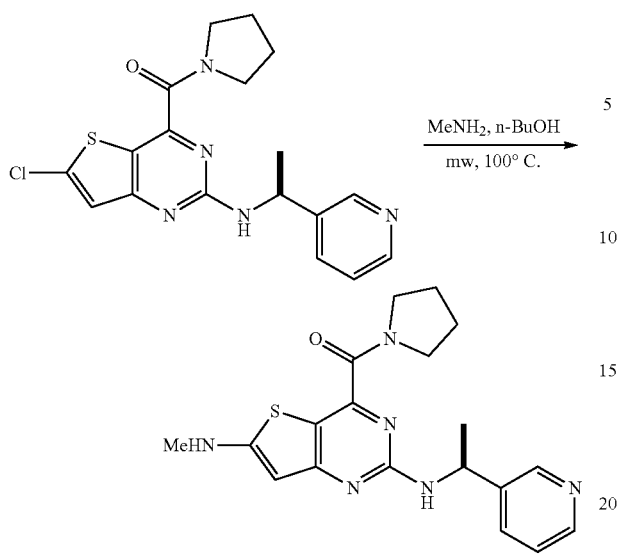

Synthesis of (S)-(6-(Methylamino)-2-((1-(pyridin-3-yl)ethyl)amino)thieno[3,2-d]pyrimidin-4-yl)(pyrrolidin-1-yl)methanone (Z152): To a solution of (S)-(6-chloro-2-((1-(pyridin-3-yl)ethyl)amino)thieno[3,2-d]pyrimidin-4-yl)(pyrrolidin-1-yl)methanone (300 mg, 0.775 mmol) in n-BuOH (1 mL) was added 2 M solution of methanamine in MeOH (1 mL). The resulting solution was stirred for 2 h at 110° C. under microwave irradiation. The reaction mixture was concentrated and the residue was purified by prep-HPLC (C-18 OBD column and a gradient elution system of water-acetonitrile) to provide (S)-(6-(methylamino)-2-((1-(pyridin-3-yl)ethyl)amino)thieno[3,2-d]pyrimidin-4-yl)(pyrrolidin-1-yl)methanone (70 mg). $^1$H NMR (400 MHz, DMSO-$d_6$) δ 1.46 (3H, d, J=6.8 Hz), 1.70-1.85 (4H, m), 2.83 (3H, d, J=4.8 Hz), 3.40-3.55 (3H, m), 3.85 (1H, m), 5.06 (1H, q, J=6.8 Hz), 5.70 (1H, s), 7.29-7.34 (2H, m), 7.70 (1H, m), 7.76 (1H, m), 8.38 (1H, dd, J=4.8, 1.6 Hz), 8.58 (1H, d, J=1.6 Hz) ppm. LCMS m/z=383.1 [M+H$^+$].

Example Z153. (S)-Azetidin-1-yl(6-(methylamino)-2-((1-(pyridin-3-yl)ethyl)amino)thieno[3,2-d]pyrimidin-4-yl)methanone (Z153)

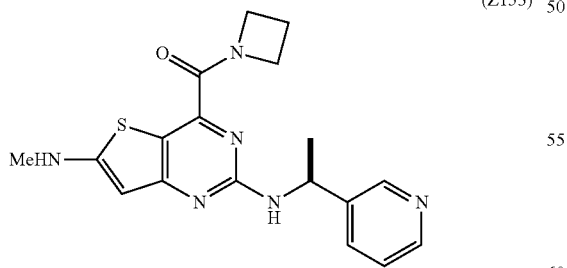

Synthesis of (S)-azetidin-1-yl(6-(methylamino)-2-((1-(pyridin-3-yl)ethyl)amino)thieno[3,2-d]pyrimidin-4-yl)methanone (Z153): The title compound (Z153) was prepared from 2,6-dichlorothieno[3,2-d]pyrimidine-4-carboxylic acid using chemistry similar to that described in Example Z152 using azetidine in place of pyrrolidine. $^1$H NMR (400 MHz, DMSO-$d_6$) δ 1.46 (3H, d, J=7.2 Hz), 2.23-2.29 (2H, m), 2.84 (3H, d, J=4.8 Hz), 3.95-4.06 (2H, m), 4.35 (1H, m), 4.67 (1H, m), 5.10 (1H, q, J=7.2 Hz), 5.68 (1H, s), 7.29-7.33 (2H, m), 7.73 (1H, m), 7.76 (1H, m), 8.39 (1H, dd, J=4.8, 1.6 Hz), 8.59 (1H, d, J=1.6 Hz) ppm. LCMS m/z=369.1 [M+H$^+$].

Example Z154. N-Cyclobutyl-2-((pyrazin-2-ylmethyl)amino)thieno[3,2-d]pyrimidine-4-carboxamide (Z154)

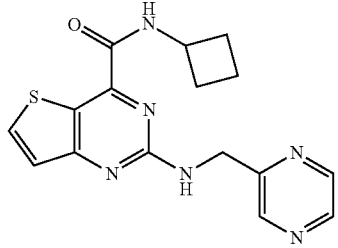 [SMILES: O=C(NC1CCC1)c1nc(NCc2cnccn2)nc2ccsc12]

Synthesis of ethyl 2-((pyrazin-2-ylmethyl)amino)thieno[3,2-d]pyrimidine-4-carboxylate: The title compound was prepared from ethyl 2-chlorothieno[3,2-d]pyrimidine-4-carboxylate (224 mg, 0.92 mmol) using chemistry similar to that described in Example Z12 using pyrazin-2-ylmethanamine (commercially obtained from Enamine, Monmouth Jct., N.J.) in place of (6-methoxypyridin-3-yl)methanamine hydrochloride (54 mg, 18% yield). LCMS m/z=316.1 [M+H$^+$].

Synthesis of N-cyclobutyl-2-((pyrazin-2-ylmethyl)amino)thieno[3,2-d]pyrimidine-4-carboxamide (Z154): The title compound (Z154) was prepared from ethyl 2-((pyrazin-2-ylmethyl)amino)thieno[3,2-d]pyrimidine-4-carboxylate using chemistry similar to that described in Example Z17 using cyclobutylamine in place of (3R)-3-methoxypyrrolidine hydrochloride (32% yield). LCMS m/z=341.1 [M+H$^+$].

Example Z155. Azetidin-1-yl(2-((pyrazin-2-ylmethyl)amino)thieno[3,2-d]pyrimidin-4-yl)methanone (Z155)

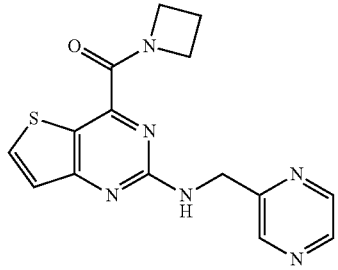 [SMILES: O=C(c1nc(NCc2cnccn2)nc2ccsc12)N1CCC1]

Synthesis of azetidin-1-yl(2-((pyrazin-2-ylmethyl)amino)thieno[3,2-d]pyrimidin-4-yl)methanone (Z155): The title compound (Z155) was prepared from ethyl 2-((pyrazin-2-ylmethyl)amino)thieno[3,2-d]pyrimidine-4-carboxylate using chemistry similar to that described in Example Z17 using azetidine in place of (3R)-3-methoxypyrrolidine hydrochloride (34% yield). $^1$H NMR (400 MHz, DMSO-$d_6$) δ 2.27 (2H, m), 4.08 (2H, t, J=7.2 Hz), 4.55 (2H, m), 4.72 (2H, d, J=6.0 Hz), 7.22 (1H, d, J=5.6 Hz), 7.90 (1H, t, J=6.0

Hz), 8.29 (1H, d, J=5.6 Hz), 8.52 (1H, m), 8.56 (1H, t, J=2.0 Hz) 8.64 (1H, s) ppm. LCMS m/z=327.0 [M+H⁺].

Example Z156. (S)-(3-Hydroxypyrrolidin-1-yl)(2-((pyrazin-2-ylmethyl)amino)thieno[3,2-d]pyrimidin-4-yl)methanone

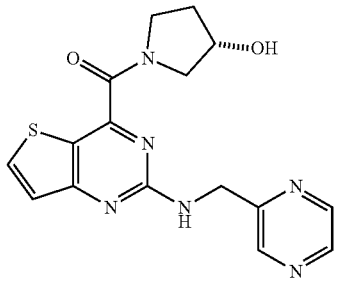 [SMILES: O=C(c1nc(NCc2cnccn2)nc2ccsc12)N1CC[C@H](O)C1]

(Z156)

Synthesis of (S)-(3-hydroxypyrrolidin-1-yl)(2-((pyrazin-2-ylmethyl)amino)thieno[3,2-d]pyrimidin-4-yl)methanone (Z156): The title compound (Z156) was prepared from ethyl 2-((pyrazin-2-ylmethyl)amino)thieno[3,2-d]pyrimidine-4-carboxylate using chemistry similar to that described in Example Z17 using (3S)-pyrrolidin-3-ol in place of (3R)-3-methoxypyrrolidine hydrochloride (38% yield). LCMS m/z=357.0 [M+H⁺].

Example Z157. N-(2-Methoxyethyl)-2-((pyrazin-2-ylmethyl)amino)thieno[3,2-d]pyrimidine-4-carboxamide

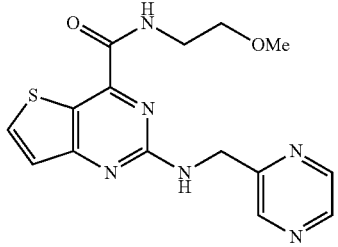 [SMILES: COCCNC(=O)c1nc(NCc2cnccn2)nc2ccsc12]

(Z157)

Synthesis of N-(2-methoxyethyl)-2-((pyrazin-2-ylmethyl)amino)thieno[3,2-d]pyrimidine-4-carboxamide (Z157): The title compound (Z157) was prepared from ethyl 2-((pyrazin-2-ylmethyl)amino)thieno[3,2-d]pyrimidine-4-carboxylate using chemistry similar to that described in Example Z17 using 2-methoxyethylamine in place of (3R)-3-methoxypyrrolidine hydrochloride (49% yield). LCMS m/z=345.0 [M+H⁺].

Example Z158. N-((1s,3R)-3-Hydroxycyclobutyl)-2-(((S)-1-(pyridin-2-yl)ethyl)amino)thieno[3,2-d]pyrimidine-4-carboxamide

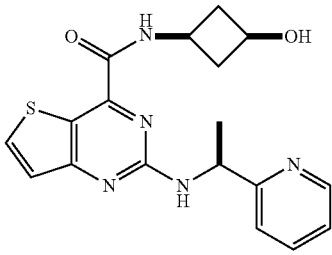

(Z158)

Synthesis of N-((1s,3R)-3-hydroxycyclobutyl)-2-(((S)-1-(pyridin-2-yl)ethyl)amino)thieno[3,2-d]pyrimidine-4-carboxamide (Z158): The title compound (Z158) was prepared from (S)-2-((1-(pyridin-2-yl)ethyl)amino)thieno[3,2-d]pyrimidine-4-carboxylic acid di-hydrochloride and 3-aminocyclobutanol hydrochloride (commercially obtained from Combi-Blocks, San Diego, Calif.) using chemistry similar to that described in Example Z8 (46% yield). LCMS m/z=370.1 [M+H⁺].

Example Z159. N-((1r,3S)-3-Hydroxycyclobutyl)-2-(((S)-1-(pyridin-2-yl)ethyl)amino)thieno[3,2-d]pyrimidine-4-carboxamide

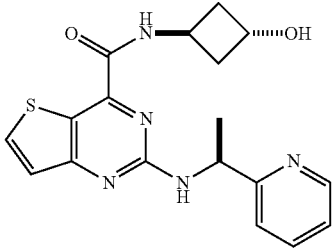

(Z159)

Synthesis of N-((1r,3S)-3-hydroxycyclobutyl)-2-(((S)-1-(pyridin-2-yl)ethyl)amino)thieno[3,2-d]pyrimidine-4-carboxamide (Z159): The title compound (Z159) was prepared from (S)-2-((1-(pyridin-2-yl)ethyl)amino)thieno[3,2-d]pyrimidine-4-carboxylic acid di-hydrochloride and trans-3-aminocyclobutanol hydrochloride (commercially obtained from PharmaBlock, Sunnyvale, Calif.) using chemistry similar to that described in Example Z8 (50% yield). LCMS m/z=370.1 [M+H⁺].

Example Z160. (6-(Methylamino)-2-((pyridin-2-ylmethyl)amino)thieno[3,2-d]pyrimidin-4-yl)(pyrrolidin-1-yl)methanone

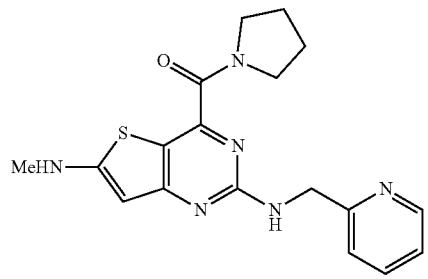 [SMILES: CNc1cc2nc(NCc3ccccn3)nc(C(=O)N3CCCC3)c2s1]

(Z160)

Synthesis of (6-(methylamino)-2-((pyridin-2-ylmethyl)amino)thieno[3,2-d]pyrimidin-4-yl)(pyrrolidin-1-yl)methanone (Z160): The title compound (Z160) was prepared from 2,6-dichlorothieno[3,2-d]pyrimidine-4-carboxylic acid using chemistry similar to that described in Example Z152 using pyridin-3-ylmethanamine in place of (S)-1-(pyridin-3-yl)ethan-1-amine. $^1$H NMR (400 MHz, DMSO-d$_6$) δ 1.65-1.82 (4H, m), 2.84 (3H, d, J=6.8 Hz), 3.40-3.80 (4H, m), 4.56 (2H, d, J=6.0 Hz), 5.73 (1H, s), 7.22 (1H, m), 7.30 1H, m), 7.33 (1H, m), 7.67-7.72 (2H, m), 8.49 (1H, d, J=4.0 Hz) ppm. LCMS m/z=369.1 [M+H$^+$].

Example Z161. ((R)-3-Fluoropyrrolidin-1-yl)(6-(methylamino)-2-(((S)-1-(pyridin-3-yl)ethyl)amino)thieno[3,2-d]pyrimidin-4-yl)methanone

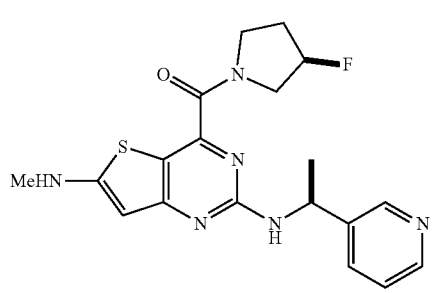 [SMILES: CNc1cc2nc(N[C@@H](C)c3cccnc3)nc(C(=O)N3CC[C@@H](F)C3)c2s1]

(Z161)

Synthesis of ((R)-3-fluoropyrrolidin-1-yl)(6-(methylamino)-2-(((S)-1-(pyridin-3-yl)ethyl)amino)thieno[3,2-d]pyrimidin-4-yl)methanone (Z161): The title compound (Z161) was prepared from 2,6-dichlorothieno[3,2-d]pyrimidine-4-carboxylic acid using chemistry similar to that described in Example Z152 using (R)-3-fluoropyrrolidine in place of pyrrolidine. $^1$H NMR (400 MHz, DMSO-d$_6$) δ 1.46 (3H, d, J=6.8 Hz), 1.90-2.20 (2H, m), 2.84 (3H, d, J=4.8 Hz), 3.51 (1H, m), 3.70-3.85 (2H, m), 4.32 (1H, m), 5.10 (1H, m), 5.34 (1H, m), 5.71 (1H, s), 7.31 (1H, m), 7.37 (1H, m), 7.74-7.79 (2H, m), 7.76 (1H, m), 8.39 (1H, dd, J=4.8, 1.6 Hz), 8.59 (1H, d, J=1.6 Hz) ppm. LCMS m/z=401.2 [M+H$^+$].

Example Z162. N—((R)-2-Hydroxypropyl)-2-(((S')-1-(pyridin-2-yl)ethyl)amino)thieno[3,2-d]pyrimidine-4-carboxamide

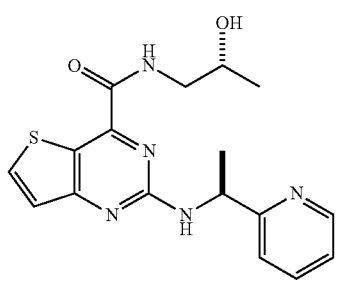 [SMILES: C[C@H](Nc1nc(C(=O)NC[C@@H](C)O)c2sccc2n1)c1ccccn1]

(Z162)

Synthesis of N—((R)-2-hydroxypropyl)-2-(((S)-1-(pyridin-2-yl)ethyl)amino)thieno[3,2-d]pyrimidine-4-carboxamide (Z162): The title compound (Z162) was prepared from (S)-2-((1-(pyridin-2-yl)ethyl)amino)thieno[3,2-d]pyrimidine-4-carboxylic acid di-hydrochloride and (R)-(−)-1-amino-2-propanol (commercially obtained from Combi-Blocks, San Diego, Calif.) using chemistry similar to that described in Example Z8 (35% yield). LCMS m/z=358.1 [M+H$^+$].

Example Z163. N—((S)-2-Hydroxypropyl)-2-(((S)-1-(pyridin-2-yl)ethyl)amino)thieno[3,2-d]pyrimidine-4-carboxamide

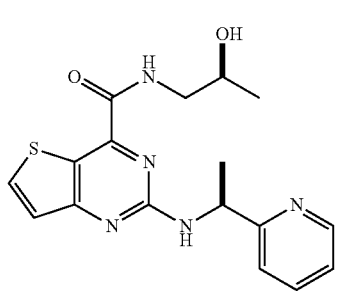 [SMILES: C[C@H](O)CNC(=O)c1nc(N[C@@H](C)c2ccccn2)nc2ccsc12]

(Z163)

Synthesis of N—((S)-2-hydroxypropyl)-2-(((S)-1-(pyridin-2-yl)ethyl)amino)thieno[3,2-d]pyrimidine-4-carboxamide (Z163): The title compound (Z163) was prepared from (S)-2-((1-(pyridin-2-yl)ethyl)amino)thieno[3,2-d]pyrimidine-4-carboxylic acid di-hydrochloride and (S)-1-amino-2-propanol (commercially obtained from Combi-Blocks, San Diego, Calif.) using chemistry similar to that described in Example Z8 (49% yield). LCMS m/z=358.1 [M+H$^+$].

Example Z164. (S)-Azetidin-1-yl(2-((1-(5-fluoropyridin-3-yl)ethyl)amino)thieno[3,2-d]pyrimidin-4-yl)methanone

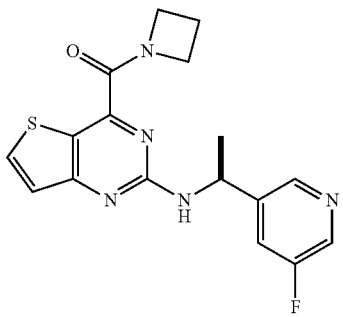 [SMILES: C[C@H](Nc1nc(C(=O)N2CCC2)c2sccc2n1)c1cncc(F)c1]

(Z164)

Synthesis of (S)-azetidin-1-yl(2-((1-(5-fluoropyridin-3-yl)ethyl)amino)thieno[3,2-d]pyrimidin-4-yl)methanone (Z164): The title compound (Z164) was prepared from (S)-2-((1-(5-fluoropyridin-3-yl)ethyl)amino)thieno[3,2-d]pyrimidine-4-carboxylic acid di-hydrochloride (39 mg, 0.10 mmol) using chemistry similar to that described in Example Z8 using azetidine in place of (R)-3-fluoropyrrolidine (16 mg, 45% yield). $^1$H NMR (400 MHz, CDCl$_3$) δ 1.64 (3H, d, J=6.8 Hz), 2.29-2.42 (2H, m), 4.25 (2H, t, J=8.0 Hz), 4.25 (1H, m), 4.69 (1H, m), 5.25 (1H, quintet, J=6.8 Hz), 5.36 (1H, d, J=6.8 Hz), 7.16 (1H, d, J=5.6 Hz), 7.43 (1H, dt, J=9.2, 2.0 Hz), 7.97 (1H, d, J=5.6 Hz), 8.35 (1H, d, J=2.8 Hz), 8.50 (1H, m) ppm. LCMS m/z=358.1 [M+H$^+$].

Example Z165. (2-(((S)-1-(5-Fluoropyridin-3-yl)ethyl)amino)thieno[3,2-d]pyrimidin-4-yl)((S)-3-hydroxypyrrolidin-1-yl)methanone

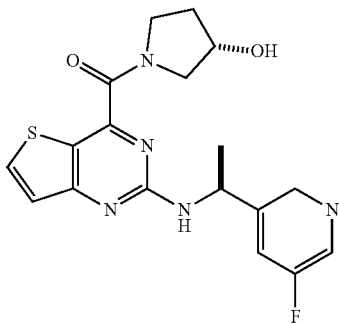 [SMILES: C[C@H](Nc1nc(C(=O)N2CC[C@H](O)C2)c2sccc2n1)c1cncc(F)c1]

(Z165)

Synthesis of (2-(((S)-1-(5-fluoropyridin-3-yl)ethyl)amino)thieno[3,2-d]pyrimidin-4-yl)((S)-3-hydroxypyrrolidin-1-yl)methanone (Z165): The title compound (Z165) was prepared from (S)-2-((1-(5-fluoropyridin-3-yl)ethyl)amino)thieno[3,2-d]pyrimidine-4-carboxylic acid di-hydrochloride (39 mg, 0.10 mmol) using chemistry similar to that described in Example Z8 using (S)-pyrrolidin-3-ol in place of (R)-3-fluoropyrrolidine (37 mg, 95% yield). $^1$H NMR (400 MHz, CDCl$_3$) δ 1.64 (3H, d, J=7.2 Hz), 1.90-2.05 (2H, m), 3.58 (1H, m), 3.77-3.86 (3H, m), 4.47 (1H, m), 5.21 (1H, m), 5.44 (1H, d, J=6.8 Hz), 7.18 (1H, m), 7.46 (1H, m), 7.96 (1H, m), 8.34 (1H, m), 8.53 (1H, m) ppm. LCMS m/z=388.1 [M+H$^+$].

Example Z166. (2-(((S)-1-(5-Fluoropyridin-3-yl)ethyl)amino)thieno[3,2-d]pyrimidin-4-yl)((R)-3-hydroxypyrrolidin-1-yl)methanone

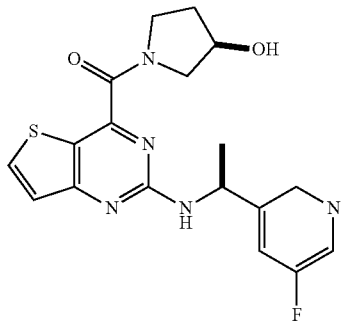

(Z166)

Synthesis of (2-(((S)-1-(5-fluoropyridin-3-yl)ethyl)amino)thieno[3,2-d]pyrimidin-4-yl)((R)-3-hydroxypyrrolidin-1-yl)methanone (Z166): The title compound (Z166) was prepared from (S)-2-((1-(5-fluoropyridin-3-yl)ethyl)amino)thieno[3,2-d]pyrimidine-4-carboxylic acid di-hydrochloride (39 mg, 0.10 mmol) using chemistry similar to that described in Example Z8 using (S)-pyrrolidin-3-ol in place of (S)-3-fluoropyrrolidine (36 mg, 93% yield). $^1$H NMR (400 MHz, CDCl$_3$) δ 1.64 (3H, d, J=7.2 Hz), 1.90-2.02 (2H, m), 3.50 (1H, m), 3.78-3.86 (3H, m), 4.47 (1H, m), 5.20 (1H, m), 5.44 (1H, m), 7.18 (1H, m), 7.47 (1H, m), 7.96 (1H, m), 8.34 (1H, m), 8.53 (1H, m) ppm. LCMS m/z=388.1 [M+H$^+$].

Example Z167. tert-Butyl (R)-(1-(2-((3,5-difluorobenzyl)amino)thieno[3,2-d]pyrimidine-4-carbonyl)pyrrolidin-3-yl)carbamate

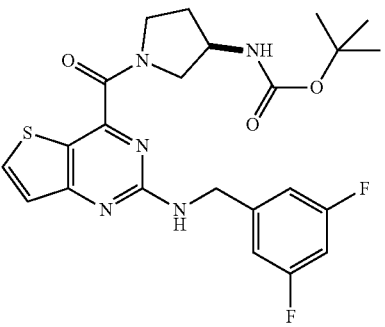 [SMILES: CC(C)(C)OC(=O)N[C@@H]1CCN(C(=O)c2nc(NCc3cc(F)cc(F)c3)nc3ccsc23)C1]

(Z167)

Synthesis of ethyl 2-((3,5-difluorobenzyl)amino)thieno[3,2-d]pyrimidine-4-carboxylate: The title compound was prepared from ethyl 2-chlorothieno[3,2-d]pyrimidine-4-carboxylate (200 mg, 0.82 mmol) using chemistry similar to that described in Example Z12 using 3,5-difluorobenzylamine pyrazin-2-ylmethanamine (commercially obtained from Sigma-Aldrich, St. Louis, Mo.) in place of (6-methoxypyridin-3-yl)methanamine hydrochloride (143 mg, 50% yield). LCMS m/z=316.1 [M+H$^+$].

Synthesis of tert-butyl (R)-(1-(2-((3,5-difluorobenzyl)amino)thieno[3,2-d]pyrimidine-4-carbonyl)pyrrolidin-3-yl)carbamate (Z167): The title compound (Z167) was prepared from ethyl 2-((3,5-difluorobenzyl)amino)thieno[3,2-d]pyrimidine-4-carboxylate using chemistry similar to that described in Example Z17 using tert-butyl N-[(3R)-pyrrolidin-3-yl]carbamate (commercially obtained from Combi-Blocks, San Diego, Calif.) in place of (3R)-3-methoxypyrrolidine hydrochloride (51% yield). LCMS m/z=490.1 [M+H$^+$].

Example Z168. Azetidin-1-yl(2-((3,5-difluorobenzyl)amino)thieno[3,2-d]pyrimidin-4-yl)methanone

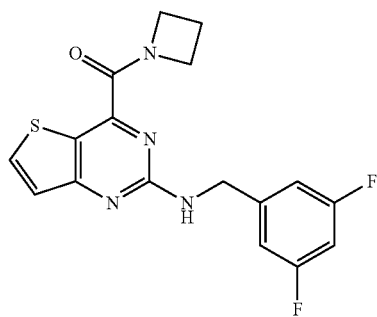 [SMILES: O=C(c1nc(NCc2cc(F)cc(F)c2)nc2ccsc12)N1CCC1]

(Z168)

Synthesis of azetidin-1-yl(2-((3,5-difluorobenzyl)amino)thieno[3,2-d]pyrimidin-4-yl)methanone (Z168): The title compound (Z168) was prepared from ethyl 2-((3,5-difluorobenzyl)amino)thieno[3,2-d]pyrimidine-4-carboxylate using chemistry similar to that described in Example Z17 using azetidine in place of (3R)-3-methoxypyrrolidine hydrochloride (30% yield). LCMS m/z=361.1 [M+H$^+$].

Example Z169. 2-((3,5-Difluorobenzyl)amino)-N-(2-hydroxyethyl)thieno[3,2-d]pyrimidine-4-carboxamide

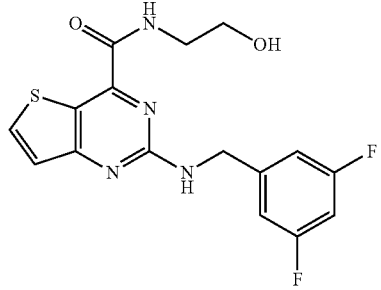 [SMILES: O=C(NCCO)c1nc(NCc2cc(F)cc(F)c2)nc2ccsc12]

(Z169)

Synthesis of 2-((3,5-difluorobenzyl)amino)-N-(2-hydroxyethyl)thieno[3,2-d]pyrimidine-4-carboxamide (Z169): The title compound (Z169) was prepared from ethyl 2-((3,5-difluorobenzyl)amino)thieno[3,2-d]pyrimidine-4-carboxylate using chemistry similar to that described in Example Z17 using 2-aminoethanol in place of (3R)-3-methoxypyrrolidine hydrochloride (42% yield). $^1$H NMR (400 MHz, DMSO-d$_6$) δ 3.42 (2H, q, J=12.0, 6.0 Hz), 3.56 (2H, q, J=12.0, 6.0 Hz), 4.55 (2H, m), 4.86 (1H, t, J=5.2 Hz), 7.02-7.10 (3H, m), 7.23 (1H, d, J=5.6 Hz), 7.88 (1H, t, J=6.8 Hz), 8.33 (1H, d, J=8.0 Hz) 8.65 (1H, br s) ppm. LCMS m/z=365.1 [M+H$^+$].

Example Z170. (S)—N-((6-ethoxypyridin-3-yl)methyl)-2-((1-(pyridin-2-yl)ethyl)amino)thieno[3,2-d]pyrimidine-4-carboxamide

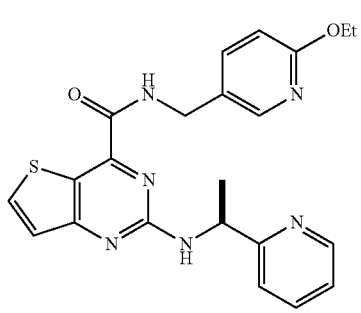

(Z170)

Synthesis of (S)—N-((6-ethoxypyridin-3-yl)methyl)-2-((1-(pyridin-2-yl)ethyl)amino)thieno[3,2-d]pyrimidine-4-carboxamide (Z170): The title compound (Z170) was prepared from (S)-2-((1-(pyridin-2-yl)ethyl)amino)thieno[3,2-d]pyrimidine-4-carboxylic acid di-hydrochloride and (6-ethoxy-3-pyridyl)methanamine (commercially obtained from Aurum Pharmatech, Franklin Park, N.J.) using chemistry similar to that described in Example Z8 (70% yield). LCMS m/z=435.2 [M+H$^+$].

Example Z171. N-Cyclobutyl-2-(((5-fluoropyridin-3-yl)methyl)amino)thieno[3,2-d]pyrimidine-4-carboxamide

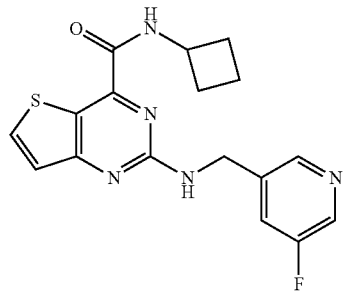 [SMILES: O=C(NC1CCC1)c1nc(NCc2cncc(F)c2)nc2ccsc12]

(Z171)

Synthesis of N-cyclobutyl-2-(((5-fluoropyridin-3-yl)methyl)amino)thieno[3,2-d]pyrimidine-4-carboxamide (Z171): The title compound (Z171) was prepared from 2-(((5-fluoropyridin-3-yl)methyl)amino)thieno[3,2-d]pyrimidine-4-carboxylic acid di-hydrochloride using chemistry similar to that described in Example Z17 using cyclobutylamine in place of (3R)-3-methoxypyrrolidine hydrochloride (38% yield). $^1$H NMR (400 MHz, DMSO-d$_6$) δ 1.66-1.75 (2H, m), 2.15-2.27 (4H, m), 4.73 (2H, m), 7.22 (1H, d, J=5.6 Hz), 7.72 (1H, d, J=10.0 Hz), 7.86 (1H, s), 8.33 (1H, d, J=5.2 Hz), 8.44 (1H, d, J=2.8 Hz), 8.53 (1H, s), 8.75 (1H, d, J=8.4 Hz) ppm. LCMS m/z=358.1 [M+H$^+$].

Example Z172. ((R)-3-Hydroxypyrrolidin-1-yl)(6-(methylamino)-2-(((S)-1-(pyridin-3-yl)ethyl)amino)thieno[3,2-d]pyrimidin-4-yl)methanone

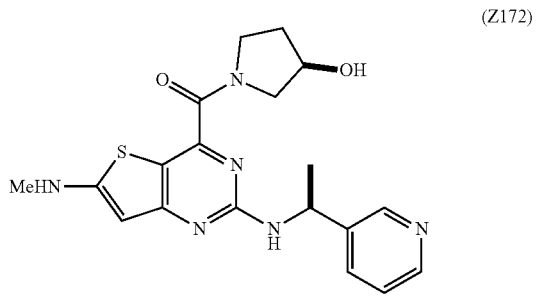

(Z172)

Synthesis of ((R)-3-Hydroxypyrrolidin-1-yl)(6-(methylamino)-2-(((S)-1-(pyridin-3-yl)ethyl)amino)thieno[3,2-d]pyrimidin-4-yl)methanone (Z172): The title compound (Z172) was prepared from 2,6-dichlorothieno[3,2-d]pyrimidine-4-carboxylic acid using chemistry similar to that described in Example Z152 using (R)-pyrrolidin-3-ol in place of pyrrolidine. $^1$H NMR (400 MHz, DMSO-$d_6$) δ 1.46 (3H, d, J=6.8 Hz), 1.89-1.90 (2H, m), 2.83 (3H, d, J=4.8 Hz), 3.35-3.58 (3H, m), 4.05 (1H, m), 4.24 (1H, m), 4.92 (1H, m), 5.10 (1H, m), 5.70 (1H, s), 7.30-7.34 (2H, m), 7.70 (1H, m), 7.78 (1H, m), 7.76 (1H, m), 8.39 (1H, dd, J=4.8, 1.6 Hz), 8.59 (1H, d, J=1.6 Hz) ppm. LCMS m/z=399.1 [M+H$^+$].

Example Z173. (S)-Azetidin-1-yl(6-(methylamino)-2-((1-(pyridin-2-yl)ethyl)amino)thieno[3,2-d]pyrimidin-4-yl)methanone

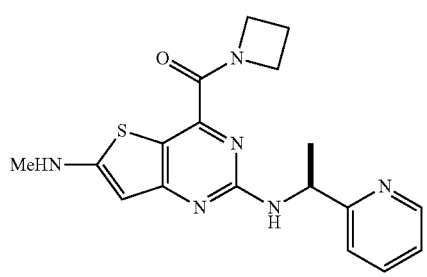 [SMILES: CNc1cc2nc(N[C@@H](C)c3ccccn3)nc(C(=O)N3CCC3)c2s1]

(Z173)

Synthesis of (S)-azetidin-1-yl(6-(methylamino)-2-((1-(pyridin-2-yl)ethyl)amino)thieno[3,2-d]pyrimidin-4-yl)methanone (Z173): The title compound (Z173) was prepared from 2,6-dichlorothieno[3,2-d]pyrimidine-4-carboxylic acid using chemistry similar to that described in Example Z152 using azetidine in place of pyrrolidine. $^1$H NMR (400 MHz, DMSO-$d_6$) δ 1.45 (3H, d, J=6.8 Hz), 2.11-2.28 (2H, m), 2.84 (3H, d, J=4.8 Hz), 3.91-4.05 (2H, m), 4.20 (1H, m), 4.59 (1H, m), 5.05 (1H, m), 5.69 (1H, s), 7.19-7.23 (2H, m), 7.37 (1H, d, J=8.0 Hz), 7.68-7.72 (2H, m), 8.49 (1H, d, J=4.0 Hz) ppm. LCMS m/z=369.1 [M+H$^+$].

Example Z174. (6-Amino-2-(((S)-1-(pyridin-2-yl)ethyl)amino)thieno[3,2-d]pyrimidin-4-yl)((R)-3-fluoropyrrolidin-1-yl)methanone

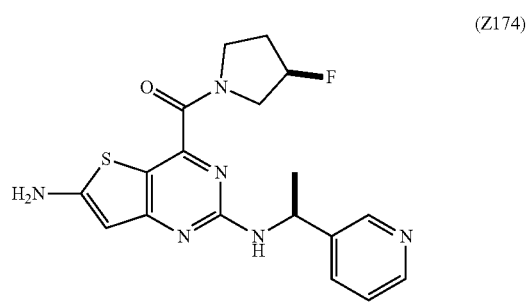

(Z174)

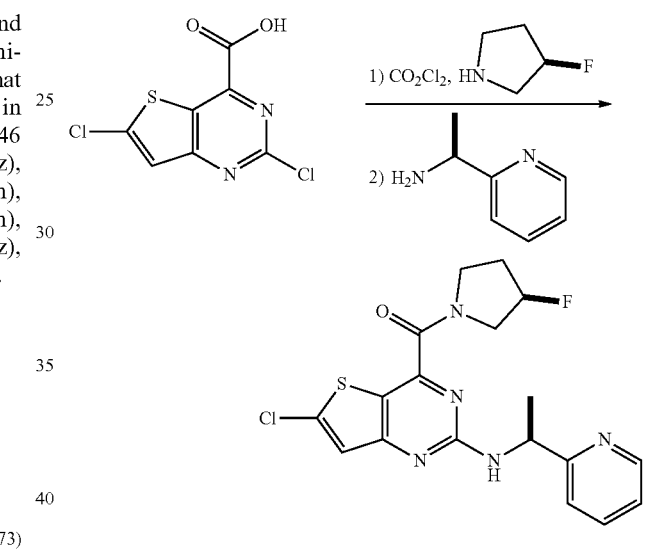

Synthesis of (6-chloro-2-(((S)-1-(pyridin-2-yl)ethyl)amino)thieno[3,2-d]pyrimidin-4-yl)((R)-3-fluoropyrrolidin-1-yl)methanone: The title compound was prepared from 2,6-dichlorothieno[3,2-d]pyrimidine-4-carboxylic acid using chemistry similar to that described in Example Z152 using (R)-3-fluoropyrrolidine in place of pyrrolidine. $^1$H NMR (400 MHz, DMSO-$d_6$) δ 1.53 (3H, d, J=6.8 Hz), 2.00-2.25 (2H, m), 3.25-3.40 (3H, m), 3.81 (1H, m), 5.14 (1H, m), 5.28 (1H, m), 7.32-7.41 (2H, m), 7.80 (1H, m), 8.12 (1H, m), 8.42 (1H, m), 8.63 (1H, m) ppm. LCMS m/z=406.0 [M+H$^+$].

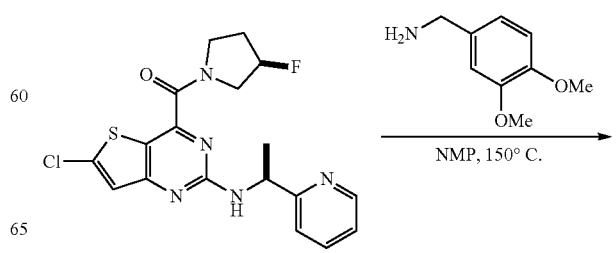

-continued

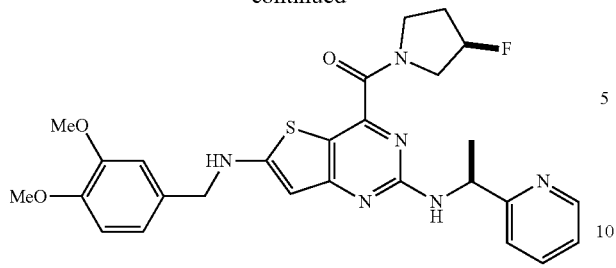

Synthesis of (6-((3,4-dimethoxybenzyl)amino)-2-(((S)-1-(pyridin-2-yl)ethyl)amino)thieno[3,2-d]pyrimidin-4-yl)((R)-3-fluoropyrrolidin-1-yl)methanone: To a solution of (6-chloro-2-(((S)-1-(pyridin-2-yl)ethyl)amino)thieno[3,2-d]pyrimidin-4-yl)((R)-3-fluoropyrrolidin-1-yl)methanone (300 mg, 0.74 mmol) in NMP (5 mL) was added (3,4-dimethoxyphenyl)methanamine (1.23 g, 7.4 mmol) and the resulting solution was stirred for 2 h at 150° C. The reaction mixture was extracted with ethyl acetate and the combined organic layer was dried over anhydrous sodium sulfate and concentrated under vacuum. The residue was purified by flash chromatography on silica gel eluting with DCM/methanol (30/1) to provide (6-((3,4-dimethoxybenzyl)amino)-2-(((S)-1-(pyridin-2-yl)ethyl)amino)thieno[3,2-d]pyrimidin-4-yl)((R)-3-fluoropyrrolidin-1-yl)methanone as a yellow solid (360 mg, 87% yield). $^1$H NMR (400 MHz, DMSO-$d_6$) δ 1.46 (3H, d, J=6.8 Hz), 1.90-2.14 (2H, m), 3.61-3.75 (4H, m), 3.65 (3H, s), 3.76 (3H, s), 4.33 (2H, m), 5.06 (1H, m), 5.25 (1H, m), 5.79 (1H, s), 6.91-7.01 (4H, m), 7.26-7.42 (2H, m), 7.75 (1H, m), 8.23 (1H, m), 8.39 (1H, m), 8.58 (1H, m) ppm. LCMS m/z=537.1 [M+H$^+$].

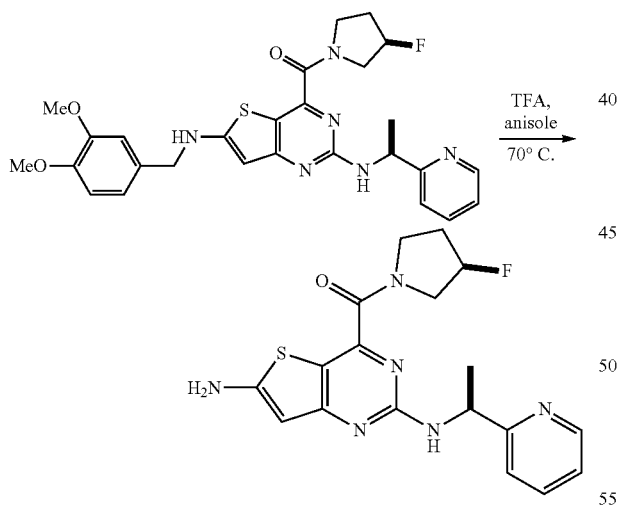

Synthesis of (6-amino-2-(((S)-1-(pyridin-2-yl)ethyl)amino)thieno[3,2-d]pyrimidin-4-yl)((R)-3-fluoropyrrolidin-1-yl)methanone (Z174): A solution of (6-((3,4-dimethoxybenzyl)amino)-2-(((S)-1-(pyridin-2-yl)ethyl)amino)thieno[3,2-d]pyrimidin-4-yl)((R)-3-fluoropyrrolidin-1-yl)methanone (280 mg, 0.52 mmol) in Anisole (2.5 mL) and TFA (2.5 mL) was stirred for 3 h at 70° C. and was concentrated under vacuum. The residue was purified by prep-HPLC (C-18 OBD column and a gradient elution system of water-acetonitrile) to provide (6-amino-2-(((S)-1-(pyridin-2-yl)ethyl)amino)thieno[3,2-d]pyrimidin-4-yl) ((R)-3-fluoropyrrolidin-1-yl)methanone as a light yellow solid (60 mg, 30% yield). $^1$H NMR (400 MHz, methanol-$d_4$) δ 1.60 (3H, d, J=6.8 Hz), 1.91-2.30 (2H, m), 3.35-3.87 (2H, m), 3.93 (1H, m), 4.33 (1H, m), 5.00-5.39 (2H, m), 5.90 (1H, s), 7.40 (1H, dd, J=8.0, 4.8 Hz), 7.89 (1H, ddd, J=8.0, 4.8, 4.0 Hz), 8.39 (1H, dd, J=4.0, 2.0 Hz), 8.59 (1H, d, J=2.0 Hz) ppm. LCMS m/z=387.0 [M+H$^+$].

Example Z175. ((R)-3-Fluoropyrrolidin-1-yl)(6-(methylamino)-2-(((S)-1-(pyridin-2-yl)ethyl)amino)thieno[3,2-d]pyrimidin-4-yl)methanone

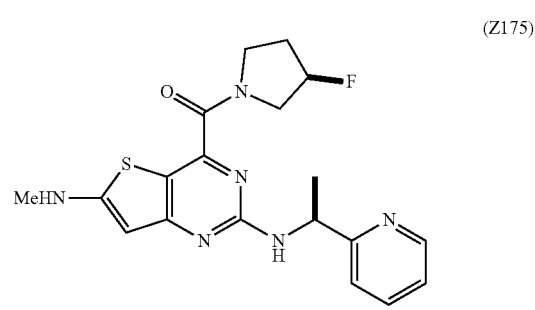

(Z175)

Synthesis of ((R)-3-fluoropyrrolidin-1-yl)(6-(methylamino)-2-(((S)-1-(pyridin-2-yl)ethyl)amino)thieno[3,2-d]pyrimidin-4-yl)methanone (Z175): The title compound (Z175) was prepared from 2,6-dichlorothieno[3,2-d]pyrimidine-4-carboxylic acid using chemistry similar to that described in Example Z152 using (R)-3-fluoropyrrolidine in place of pyrrolidine. $^1$H NMR (400 MHz, DMSO-$d_6$) δ 1.47 (3H, d, J=7.2 Hz), 1.69-2.24 (2H, m), 2.84 (3H, d, J=4.4 Hz), 3.35-3.88 (3H, m), 4.25 (1H, m), 5.03 (1H, m), 5.30 (1H, m), 5.71 (1H, s), 7.16-7.29 (2H, m), 7.38 (1H, dd, J=8.0, 4.0 Hz), 7.59-7.82 (2H, m), 8.50 (1H, d, J=4.0 Hz) ppm. LCMS m/z=401.1 [M+H$^+$].

Example Z176. ((R)-3-Hydroxypyrrolidin-1-yl)(6-(methylamino)-2-(((S)-1-(pyridin-2-yl)ethyl)amino)thieno[3,2-d]pyrimidin-4-yl)methanone

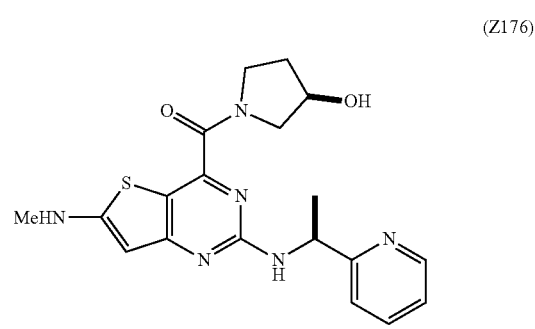

(Z176)

Synthesis of ((R)-3-hydroxypyrrolidin-1-yl)(6-(methylamino)-2-(((S)-1-(pyridin-2-yl)ethyl)amino)thieno[3,2-d]pyrimidin-4-yl)methanone (Z176): The title compound (Z176) was prepared from 2,6-dichlorothieno[3,2-d]pyrimidine-4-carboxylic acid using chemistry similar to that described in Example Z152 using (R)-pyrrolidin-3-ol in place of pyrrolidine. $^1$H NMR (400 MHz, DMSO-$d_6$) δ 1.47 (3H, d, J=6.8 Hz), 1.69-1.89 (2H, m), 2.83 (3H, d, J=4.8 Hz), 3.32-3.56 (3H, m), 3.39 (1H, m), 4.25 (1H, m), 4.92 (1H, m), 5.05 (1H, m), 5.71 (1H, s), 7.18-7.21 (2H, m), 7.38 (1H, m), 7.68-7.71 (2H, m), 8.49 (1H, m) ppm. LCMS m/z=399.1 [M+H$^+$].

Example Z177. N-Cyclobutyl-2-((3,5-difluorobenzyl)amino)thieno[3,2-d]pyrimidine-4-carboxamide

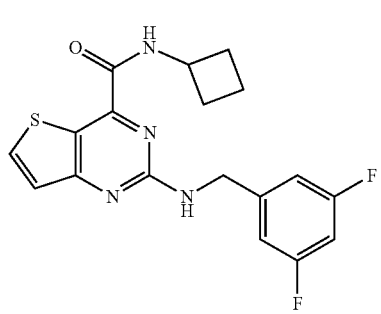
(Z177)

Synthesis of N-cyclobutyl-2-((3,5-difluorobenzyl)amino)thieno[3,2-d]pyrimidine-4-carboxamide (Z177): The title compound (Z177) was prepared from ethyl 2-((3,5-difluorobenzyl)amino)thieno[3,2-d]pyrimidine-4-carboxylate using chemistry similar to that described in Example Z17 using cyclobutylamine in place of (3R)-3-methoxypyrrolidine hydrochloride (30% yield). LCMS m/z=375.0 [M+H$^+$].

Example Z178. tert-Butyl 3-(2-(((5-fluoropyridin-3-yl)methyl)amino)thieno[3,2-d]pyrimidine-4-carboxamido)azetidine-1-carboxylate

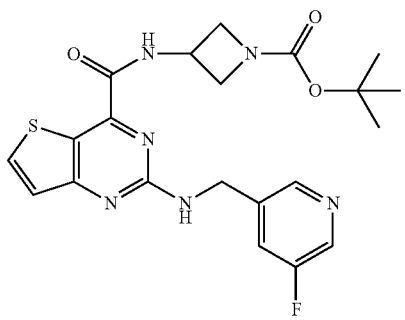 [SMILES: CC(C)(C)OC(=O)N1CC(NC(=O)c2nc(NCc3cncc(F)c3)nc3ccsc23)C1]
(Z178)

Synthesis of tert-butyl 3-(2-(((5-fluoropyridin-3-yl)methyl)amino)thieno[3,2-d]pyrimidine-4-carboxamido)azetidine-1-carboxylate (Z178): The title compound (Z178) was prepared from 2-(((5-fluoropyridin-3-yl)methyl)amino)thieno[3,2-d]pyrimidine-4-carboxylic acid di-hydrochloride using chemistry similar to that described in Example Z17 using tert-butyl 3-aminoazetidine-1-carboxylate (commercially obtained from CombiBlocks, San Diego, Calif.) in place of (3R)-3-methoxypyrrolidine hydrochloride (13% yield). LCMS m/z=459.2 [M+H$^+$].

Example Z179. tert-Butyl (S)-3-(2-((1-(pyridin-2-yl)ethyl)amino)thieno[3,2-d]pyrimidine-4-carboxamido)azetidine-1-carboxylate

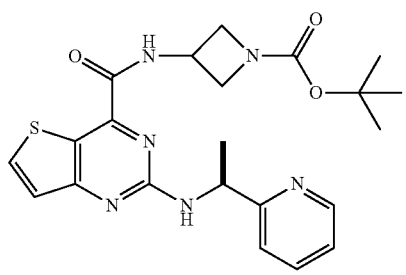 [SMILES: C[C@H](Nc1nc(C(=O)NC2CN(C(=O)OC(C)(C)C)C2)c2sccc2n1)c1ccccn1]
(Z179)

Synthesis of tert-butyl (S)-3-(2-((1-(pyridin-2-yl)ethyl)amino)thieno[3,2-d]pyrimidine-4-carboxamido)azetidine-1-carboxylate (Z179): The title compound (Z179) was prepared from (S)-2-((1-(pyridin-2-yl)ethyl)amino)thieno[3,2-d]pyrimidine-4-carboxylic acid di-hydrochloride and tert-butyl 3-aminoazetidine-1-carboxylate (commercially obtained from CombiBlocks, San Diego, Calif.) using chemistry similar to that described in Example Z8 (8% yield). LCMS m/z=455.1 [M+H$^+$].

Example Z180. (S)—N-Cyclopentyl-2-((1-(pyridin-2-yl)ethyl)amino)thieno[3,2-d]pyrimidine-4-carboxamide

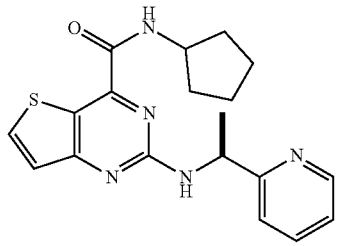 [SMILES: C[C@H](Nc1nc(C(=O)NC2CCCC2)c2sccc2n1)c1ccccn1]
(Z180)

Synthesis of (S)—N-cyclopentyl-2-((1-(pyridin-2-yl)ethyl)amino)thieno[3,2-d]pyrimidine-4-carboxamide (Z180): The title compound (Z180) was prepared from (S)-2-((1-(pyridin-2-yl)ethyl)amino)thieno[3,2-d]pyrimidine-4-carboxylic acid di-hydrochloride and cyclopentylamine (commercially obtained from CombiBlocks, San Diego, Calif.) using chemistry similar to that described in Example Z8 (25% yield). LCMS m/z=368.1 [M+H$^+$].

Example Z181. N—((S)-1-Hydroxypropan-2-yl)-2-(((S)-1-(pyridin-2-yl)ethyl)amino)thieno[3,2-d]pyrimidine-4-carboxamide

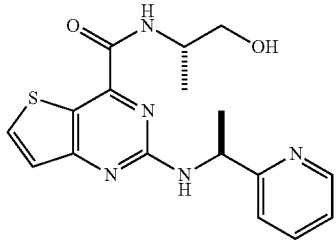 [SMILES: C[C@H](Nc1nc(C(=O)N[C@@H](C)CO)c2sccc2n1)c1ccccn1]

(Z181)

Synthesis of N—((S)-1-hydroxypropan-2-yl)-2-(((S)-1-(pyridin-2-yl)ethyl)amino)thieno[3,2-d]pyrimidine-4-carboxamide (Z181): The title compound (Z181) was prepared from (S)-2-((1-(pyridin-2-yl)ethyl)amino)thieno[3,2-d]pyrimidine-4-carboxylic acid di-hydrochloride and L-alaninol (commercially obtained from Sigma-Aldrich, St. Louis, Mo.) using chemistry similar to that described in Example Z8 (36% yield). LCMS m/z=358.1 [M+H$^+$].

Example Z182. N—((R)-1-Hydroxypropan-2-yl)-2-(((S)-1-(pyridin-2-yl)ethyl)amino)thieno[3,2-d]pyrimidine-4-carboxamide

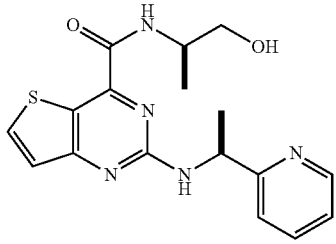 [SMILES: C[C@H](CO)NC(=O)c1nc(N[C@@H](C)c2ccccn2)nc2ccsc12]

(Z182)

Synthesis of N—((R)-1-hydroxypropan-2-yl)-2-(((S)-1-(pyridin-2-yl)ethyl)amino)thieno[3,2-d]pyrimidine-4-carboxamide (Z182): The title compound (Z182) was prepared from (S)-2-((1-(pyridin-2-yl)ethyl)amino)thieno[3,2-d]pyrimidine-4-carboxylic acid di-hydrochloride and D-alaninol (commercially obtained from Sigma-Aldrich, St. Louis, Mo.) using chemistry similar to that described in Example Z8 (37% yield). LCMS m/z=358.1 [M+H$^+$].

Example Z183. 2-(((5-Fluoropyridin-3-yl)methyl)amino)-N-((1s,3s)-3-hydroxycyclobutyl)thieno[3,2-d]pyrimidine-4-carboxamide

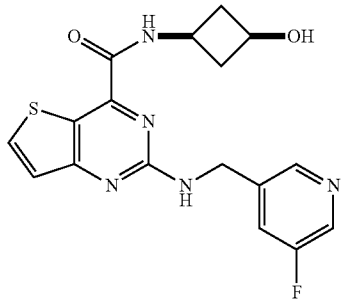

(Z183)

Synthesis of 2-(((5-fluoropyridin-3-yl)methyl)amino)-N-((1s,3s)-3-hydroxycyclo-butyl)thieno[3,2-d]pyrimidine-4-carboxamide (Z183): The title compound (Z183) was prepared from 2-(((5-fluoropyridin-3-yl)methyl)amino)thieno[3,2-d]pyrimidine-4-carboxylic acid di-hydrochloride using chemistry similar to that described in Example Z17 using cis-3-aminocyclobutanol hydrochloride (commercially obtained from Ark Pharm, Libertyville, Ill.) in place of (3R)-3-methoxypyrrolidine hydrochloride (30% yield). LCMS m/z=374.1 [M+H$^+$].

Example Z184. 2-(((5-Fluoropyridin-3-yl)methyl)amino)-N-((1r,3r)-3-hydroxycyclobutyl)thieno[3,2-d]pyrimidine-4-carboxamide (Z184)

Synthesis of 2-(((5-fluoropyridin-3-yl)methyl)amino)-N-((1r,3r)-3-hydroxycyclo-butyl)thieno[3,2-d]pyrimidine-4-carboxamide (Z184): The title compound (Z184) was prepared from 2-(((5-fluoropyridin-3-yl)methyl)amino)thieno[3,2-d]pyrimidine-4-carboxylic acid di-hydrochloride using chemistry similar to that described in Example Z17 using trans-3-aminocyclobutanol (commercially obtained from PharmaBlock, Sunnyvale, Calif.) in place of (3R)-3-methoxypyrrolidine hydrochloride (30% yield). LCMS m/z=374.0 [M+H$^+$].

Example Z185. (S)-(2-((1-(5-Fluoropyridin-3-yl)ethyl)amino)thieno[3,2-d]pyrimidin-4-yl)(3-methoxyazetidin-1-yl)methanone

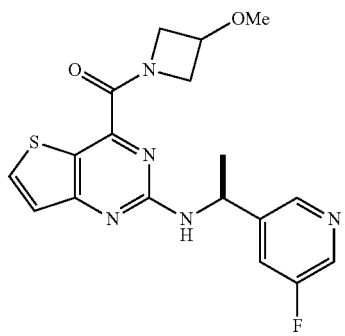
(Z185)

Synthesis of (S)-(2-((1-(5-fluoropyridin-3-yl)ethyl)amino)thieno[3,2-d]pyrimidin-4-yl)(3-methoxyazetidin-1-yl)methanone (Z185): The title compound (Z185) was prepared from (S)-2-((1-(5-fluoropyridin-3-yl)ethyl)amino)thieno[3,2-d]pyrimidine-4-carboxylic acid di-hydrochloride (39 mg, 0.10 mmol) using chemistry similar to that described in Example Z8 using 3-methoxyazetidine in place of (S)-3-fluoropyrrolidine (9 mg, 24% yield). $^1$H NMR (400 MHz, CDCl$_3$) δ 1.63 (3H, d, J=6.8 Hz), 3.32 (3H, s), 4.09 (1H, m), 4.22 (1H, m), 4.38 (1H, m), 4.49 (1H, m), 5.25 (1H, quintet, J=6.8 Hz), 5.37 (1H, d, J=6.8 Hz), 7.17 (1H, d, J=5.6 Hz), 7.43 (1H, d, J=9.2 Hz), 7.98 (1H, d, J=5.6 Hz), 8.35 (1H, d, J=2.4 Hz), 8.51 (1H, d, J=2.4 Hz) ppm. LCMS m/z=388.1 [M+H$^+$].

Example Z186. (6-Amino-2-((pyridin-3-ylmethyl)amino)thieno[3,2-d]pyrimidin-4-yl)(pyrrolidin-1-yl)methanone

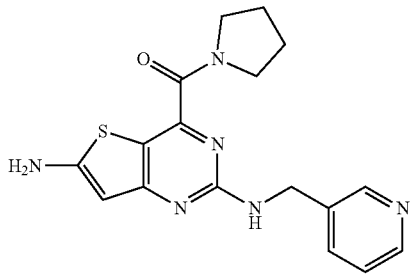 [SMILES: Nc1cc2nc(NCc3cccnc3)nc(C(=O)N3CCCC3)c2s1]
(Z186)

Synthesis of (6-amino-2-((pyridin-3-ylmethyl)amino)thieno[3,2-d]pyrimidin-4-yl)(pyrrolidin-1-yl)methanone (Z186): The title compound (Z186) was prepared from 2,6-dichlorothieno[3,2-d]pyrimidine-4-carboxylic acid using chemistry similar to that described in Example Z174 using phenylmethanamine in place of (S)-1-phenylethan-1-amine. $^1$H NMR (400 MHz, methanol-d$_4$) δ 1.81-1.93 (4H m), 3.56-3.60 (2H, m), 3.69-3.73 (2H, m), 4.67 (2H, s), 5.92 (1H, s), 7.40 (1H, dd, J=8.0, 4.8 Hz), 7.84 (1H, d, J=8.0 Hz), 8.40 (1H, dd, J=4.8, 1.2 Hz), 8.55 (1H, d, J=1.2 Hz) ppm. LCMS m/z=355.2 [M+H$^+$].

Example Z187. ((S)-3-Fluoropyrrolidin-1-yl)(6-(methylamino)-2-(((S)-1-(pyridin-3-yl)ethyl)amino)thieno[3,2-d]pyrimidin-4-yl)methanone

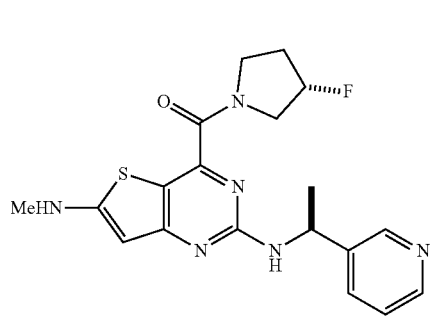 [SMILES: CNc1cc2nc(N[C@@H](C)c3cccnc3)nc(C(=O)N3CC[C@H](F)C3)c2s1]
(Z187)

Synthesis of ((S)-3-fluoropyrrolidin-1-yl)(6-(methylamino)-2-(((S)-1-(pyridin-3-yl)ethyl)amino)thieno[3,2-d]pyrimidin-4-yl)methanone (Z187): The title compound (Z187) was prepared from 2,6-dichlorothieno[3,2-d]pyrimidine-4-carboxylic acid using chemistry similar to that described in Example Z152 using (S)-3-fluoropyrrolidine in place of pyrrolidine. $^1$H NMR (300 MHz, methanol-d$_4$) δ 1.61 (3H, d, J=6.8 Hz), 1.82-2.27 (2H, m), 3.09 (3H, s), 3.56-3.89 (4H, m), 5.04-5.34 (2H, m), 5.82 (1H, s), 7.40 (1H, m), 7.88 (1H, m), 8.40 (1H, m), 8.60 (1H, m) ppm. LCMS m/z=401.1 [M+H$^+$].

Example Z188. ((S)-3-Hydroxypyrrolidin-1-yl)(6-(methylamino)-2-(((S)-1-(pyridin-3-yl)ethyl)amino)thieno[3,2-d]pyrimidin-4-yl)methanone

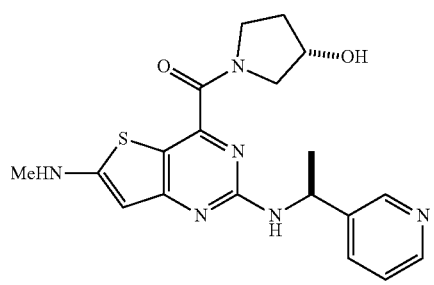
(Z188)

Synthesis of ((S)-3-hydroxypyrrolidin-1-yl)(6-(methylamino)-2-(((S)-1-(pyridin-3-yl)ethyl)amino)thieno[3,2-d]pyrimidin-4-yl)methanone (Z188): The title compound (Z188) was prepared from 2,6-dichlorothieno[3,2-d]pyrimidine-4-carboxylic acid using chemistry similar to that described in Example Z152 using (S)-pyrrolidin-3-ol in place of pyrrolidine. $^1$H NMR (300 MHz, methanol-d$_4$) δ 1.59 (3H, d, J=6.8 Hz), 1.85-1.94 (2H, m), 2.96 (3H, s), 3.44-3.83 (4H, m), 4.33 (1H, m), 4.24 (1H, m), 5.16 (1H, m), 5.81 (1H, s), 7.40 (1H, m), 7.91 (1H, m), 8.40 (1H, m), 8.61 (1H, m) ppm. LCMS m/z=399.1 [M+H$^+$].

Example Z189. (S)-(6-Amino-2-((1-(pyridin-2-yl)ethyl)amino)thieno[3,2-d]pyrimidin-4-yl)(azetidin-1-yl)methanone

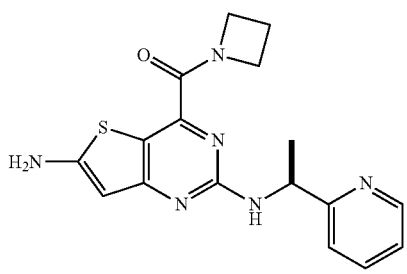 [SMILES: C[C@H](Nc1nc(C(=O)N2CCC2)c2sc(N)cc2n1)c1ccccn1]

Synthesis of (S)-(6-amino-2-((1-(pyridin-2-yl)ethyl)amino)thieno[3,2-d]pyrimidin-4-yl)(azetidin-1-yl)methanone (Z189): The title compound (Z189) was prepared from 2,6-dichlorothieno[3,2-d]pyrimidine-4-carboxylic acid using chemistry similar to that described in Example Z174 using azetidine in place of pyrrolidine. $^1$H NMR (400 MHz, DMSO-$d_6$) δ 1.45 (3H, d, J=7.2 Hz), 2.06-2.26 (2H, m), 3.96-3.98 (2H, m), 4.20 (1H, m), 4.56 (1H, m), 5.02 (1H, m), 5.71 (1H, s), 7.11 (1H, m), 7.13-7.24 (2H, m), 7.37 (1H, d, J=10.0 Hz), 7.70 (1H, dd, J=10.0, 8.8 Hz), 8.49 (1H, d, J=4.4 Hz) ppm. LCMS m/z=355.1 [M+H$^+$].

Example Z190. 2-(((S)-1-(5-Fluoropyridin-3-yl)ethyl)amino)-N—((R)-2-hydroxypropyl)thieno[3,2-d]pyrimidine-4-carboxamide

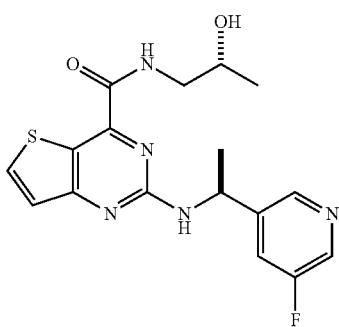 [SMILES: C[C@H](Nc1nc(C(=O)NC[C@@H](C)O)c2sccc2n1)c1cncc(F)c1]

Synthesis of 2-(((S)-1-(5-fluoropyridin-3-yl)ethyl)amino)-N—((R)-2-hydroxypropyl)thieno[3,2-d]pyrimidine-4-carboxamide (Z190): The title compound (Z190) was prepared from (S)-2-((1-(5-fluoropyridin-3-yl)ethyl)amino)thieno[3,2-d]pyrimidine-4-carboxylic acid di-hydrochloride (39 mg, 0.10 mmol) using chemistry similar to that described in Example Z8 using (R)-1-aminopropan-2-ol (commercially obtained from Ark Pharm, Libertyville, Ill.) in place of (S)-3-fluoropyrrolidine (31 mg, 83% yield). $^1$H NMR (400 MHz, CDCl$_3$) δ 1.26 (3H, d, J=6.8 Hz), 1.65 (3H, d, J=7.2 Hz), 3.21 (1H, m), 3.39 (1H, m), 3.75 (1H, m), 3.94 (1H, m), 5.14 (1H, m), 5.53 (1H, m), 7.17 (1H, d, J=5.6 Hz), 7.47 (1H, dt, J=9.6, 2.0 Hz), 8.00 (1H, d, J=5.6 Hz), 8.33 (1H, d, J=2.4 Hz), 8.60 (1H, m) ppm. LCMS m/z=376.1 [M+H$^+$].

Example Z191. 2-(((S)-1-(5-Fluoropyridin-3-yl)ethyl)amino)-N—((S)-2-hydroxypropyl)thieno[3,2-d]pyrimidine-4-carboxamide

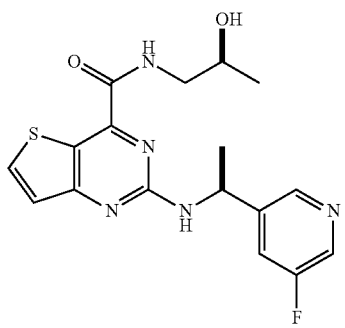

Synthesis of 2-(((S)-1-(5-fluoropyridin-3-yl)ethyl)amino)-N—((S)-2-hydroxypropyl)thieno[3,2-d]pyrimidine-4-carboxamide (Z191): The title compound (Z191) was prepared from (S)-2-((1-(5-fluoropyridin-3-yl)ethyl)amino)thieno[3,2-d]pyrimidine-4-carboxylic acid di-hydrochloride (39 mg, 0.10 mmol) using chemistry similar to that described in Example Z8 using (S)-1-aminopropan-2-ol (commercially obtained from Ark Pharm, Libertyville, Ill.) in place of (S)-3-fluoropyrrolidine (28 mg, 75% yield). $^1$H NMR (400 MHz, CDCl$_3$) δ 1.24 (3H, d, J=6.0 Hz), 1.63 (3H, d, J=6.8 Hz), 3.19 (1H, m), 3.67 (1H, m), 3.98 (1H, m), 5.14 (1H, m), 5.51 (1H, m), 7.16 (1H, d, J=5.6 Hz), 7.46 (1H, dt, J=9.2, 2.0 Hz), 7.99 (1H, d, J=5.6 Hz), 8.31 (1H, d, J=2.4 Hz), 8.59 (1H, m) ppm. LCMS m/z=376.1 [M+H$^+$].

Example Z192. (S)—N-Cyclopropyl-2-((1-(pyridin-2-yl)ethyl)amino)thieno[3,2-d]pyrimidine-4-carboxamide

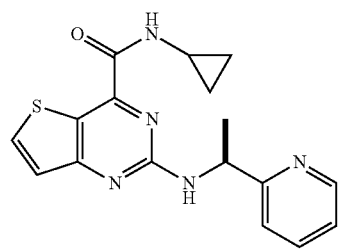 [SMILES: C[C@H](Nc1nc(C(=O)NC2CC2)c2sccc2n1)c1ccccn1]

Synthesis of (S)—N-cyclopropyl-2-((1-(pyridin-2-yl)ethyl)amino)thieno[3,2-d]pyrimidine-4-carboxamide (Z192): The title compound (Z192) was prepared from (S)-2-((1-(pyridin-2-yl)ethyl)amino)thieno[3,2-d]pyrimidine-4-carboxylic acid di-hydrochloride (37 mg, 0.1 mmol) using chemistry similar to that described in Example Z8 using cyclopropanamine in place of (R)-3-fluoropyrrolidine (17 mg, 50% yield). $^1$H NMR (400 MHz, CDCl$_3$) δ 0.64-0.68 (2H, m), 0.87-0.92 (2H, m), 1.61 (3H, d, J=6.8 Hz), 5.22 (1H, quintet, J=6.8 Hz), 6.10 (1H, d, J=6.8 Hz), 7.18 (1H, ddd, J=8.0, 4.8, 1.6 Hz), 7.19 (1H, d, J=5.6 Hz), 7.35 (1H, d, J=8.0 Hz), 7.34 (1H, td, J=8.0, 1.6 Hz), 7.88 (1H br s), 7.98 (1H, d, J=5.6 Hz), 8.59 (1H, dt, J=4.8, 1.6 Hz) ppm. LCMS m/z=340.1 [M+H$^+$].

Example Z193. (S)—N-(Cyclobutylmethyl)-2-((1-(pyridin-2-yl)ethyl)amino)thieno[3,2-d]pyrimidine-4-carboxamide

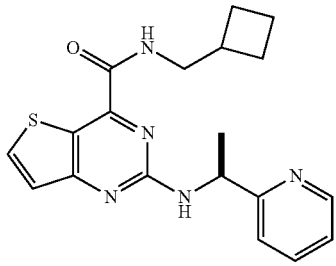 [SMILES: C[C@H](Nc1nc(C(=O)NCC2CCC2)c2sccc2n1)c1ccccn1]

(Z193)

Synthesis of (S)—N-(cyclobutylmethyl)-2-((1-(pyridin-2-yl)ethyl)amino)thieno[3,2-d]pyrimidine-4-carboxamide (Z193): The title compound (Z193) was prepared from (S)-2-((1-(pyridin-2-yl)ethyl)amino)thieno[3,2-d]pyrimidine-4-carboxylic acid di-hydrochloride and cyclobutylmethanamine (commercially obtained from Sigma-Aldrich, St. Louis, Mo.) using chemistry similar to that described in Example Z8 (25% yield). LCMS m/z=368.1 [M+H$^+$].

Example Z194. (S)—N-(Oxetan-3-yl)-2-((1-(pyridin-2-yl)ethyl)amino)thieno[3,2-d]pyrimidine-4-carboxamide

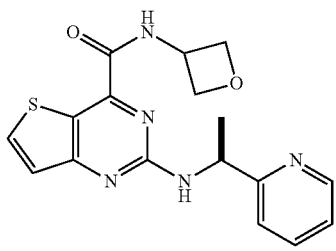 [SMILES: C[C@H](Nc1nc(C(=O)NC2COC2)c2sccc2n1)c1ccccn1]

(Z194)

Synthesis of (S)—N-(oxetan-3-yl)-2-((1-(pyridin-2-yl)ethyl)amino)thieno[3,2-d]pyrimidine-4-carboxamide (Z194): The title compound (Z194) was prepared from (S)-2-((1-(pyridin-2-yl)ethyl)amino)thieno[3,2-d]pyrimidine-4-carboxylic acid di-hydrochloride and oxetan-3-amine (commercially obtained from PharmaBlock, Sunnyvale, Calif.) using chemistry similar to that described in Example Z8 (24% yield). $^1$H NMR (400 MHz, DMSO-d$_6$) δ 1.52 (3H, d, J=6.8), 4.63 (1H, m), 4.70 (1H, t, J=2.4 Hz), 4.77-4.82 (2H, m), 5.05 (1H, m), 5.36 (1H, br s), 7.23 (1H, d, J=1.6 Hz), 7.25 (1H, m), 7.42 (1H, m), 7.43 (1H, td, J=8.0, 2.0 Hz), 7.50 (1H, d, J=8.0 Hz), 8.32 (1H, d, J=5.4 Hz), 8.54 (1H, d, J=4.0 Hz), 9.34 (1H, br s) ppm. LCMS m/z=356.1 [M+H$^+$].

Example Z195. (6-Amino-2-(((S)-1-(pyridin-3-yl)ethyl)amino)thieno[3,2-d]pyrimidin-4-yl)((R)-3-fluoropyrrolidin-1-yl)methanone

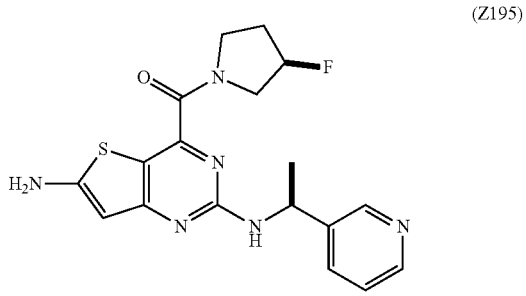

(Z195)

Synthesis of (6-amino-2-(((S)-1-(pyridin-3-yl)ethyl)amino)thieno[3,2-d]pyrimidin-4-yl)((R)-3-fluoropyrrolidin-1-yl)methanone (Z195): The title compound (Z195) was prepared from 2,6-dichlorothieno[3,2-d]pyrimidine-4-carboxylic acid using chemistry similar to that described in Example Z174 using (R)-3-fluoropyrrolidine in place of pyrrolidine. $^1$H NMR (400 MHz, methanol-d$_4$) δ 1.59 (3H, d, J=7.2 Hz), 2.04 (1H, m), 2.21 (1H, m), 3.60-3.70 (2H, m), 3.85 (1H, m), 4.30 (1H, m), 5.15 (1H, m), 5.23 (1H, m), 5.90 (1H, s), 7.40 (1H, dd, J=8.0, 4.8 Hz), 7.89 (1H, m), 8.38 (1H, m), 8.59 (1H, m) ppm. LCMS m/z=387.0 [M+H$^+$].

Example Z196. (6-Amino-2-(((S)-1-(pyridin-3-yl)ethyl)amino)thieno[3,2-d]pyrimidin-4-yl)((S)-3-hydroxypyrrolidin-1-yl)methanone

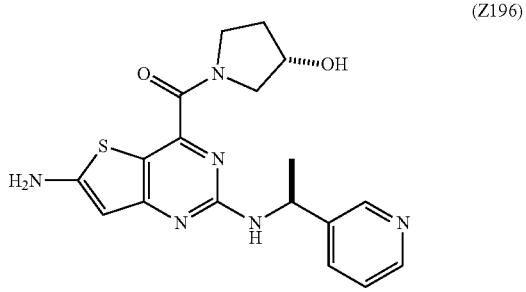

(Z196)

Synthesis of (6-amino-2-(((S)-1-(pyridin-3-yl)ethyl)amino)thieno[3,2-d]pyrimidin-4-yl)((S)-3-hydroxypyrrolidin-1-yl)methanone (Z196): The title compound (Z196) was prepared from 2,6-dichlorothieno[3,2-d]pyrimidine-4-carboxylic acid using chemistry similar to that described in Example Z174 using (S)-pyrrolidin-3-ol in place of pyrrolidine. $^1$H NMR (300 MHz, methanol-d$_4$) δ 1.58 (3H, d, J=7.2 Hz), 1.83-2.00 (2H, m), 3.30-3.87 (4H, m), 4.32 (1H, m), 5.17 (1H, m), 5.90 (1H, s), 7.39 (1H, m), 7.90 (1H, m), 8.38 (1H, m), 8.63 (1H, m) ppm. LCMS m/z=385.2 [M+H$^+$].

Example Z197. (2-(((S)-1-(5-Fluoropyridin-3-yl)ethyl)amino)-6-(methylamino)thieno[3,2-d]pyrimidin-4-yl)((S)-3-hydroxypyrrolidin-1-yl)methanone

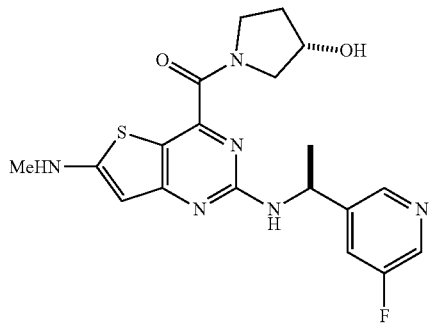 [SMILES: CNc1cc2nc(N[C@@H](C)c3cncc(F)c3)nc(C(=O)N3CC[C@H](O)C3)c2s1]

(Z197)

Synthesis of (2-(((S)-1-(5-fluoropyridin-3-yl)amino)-6-(methylamino)thieno[3,2-d]pyrimidin-4-yl)((S)-3-hydroxypyrrolidin-1-yl)methanone (Z197): The title compound (Z197) was prepared from 2,6-dichlorothieno[3,2-d]pyrimidine-4-carboxylic acid using chemistry similar to that described in Example Z152 using (S)-pyrrolidin-3-ol in place of pyrrolidine. $^1$H NMR (400 MHz, methanol-$d_4$) δ 1.59 (3H, d, J=6.8 Hz), 1.88-1.97 (2H, m), 2.96 (3H, s), 3.40-3.65 (2H, m), 3.66-3.92 (2H, m), 4.40 (1H, m), 5.20 (1H, q, J=6.8 Hz), 5.82 (1H, d, J=1.2 Hz), 7.68 (1H, m), 8.32 (1H, m), 8.48 (1H, m) ppm. LCMS m/z=417.0 [M+H$^+$].

Example Z198. (S)-(2-((1-(5-Fluoropyridin-3-yl)ethyl)amino)thieno[3,2-d]pyrimidin-4-yl)(3-hydroxyazetidin-1-yl)methanone

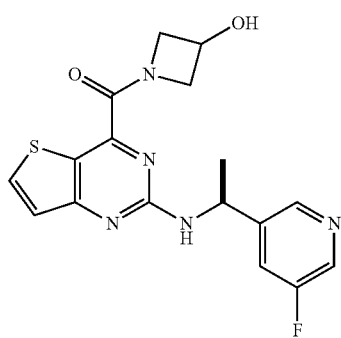 [SMILES: C[C@H](Nc1nc(C(=O)N2CC(O)C2)c2sccc2n1)c1cncc(F)c1]

(Z198)

Synthesis of (S)-(2-((1-(5-fluoropyridin-3-yl)ethyl)amino)thieno[3,2-d]pyrimidin-4-yl)(3-hydroxyazetidin-1-yl)methanone (Z198): The title compound (Z198) was prepared from (S)-2-((1-(5-fluoropyridin-3-yl)ethyl)amino)thieno[3,2-d]pyrimidine-4-carboxylic acid di-hydrochloride (39 mg, 0.10 mmol) using chemistry similar to that described in Example Z8 using azetidin-3-ol in place of (S)-3-fluoropyrrolidine (18 mg, 48% yield). $^1$H NMR (400 MHz, DMSO-$d_6$) δ 1.53 (3H, d, J=6.8 Hz), 3.82 (1H, m), 4.30 (1H, dd, J=10.8, 6.8 Hz), 4.41-4.54 (2H, m), 4.92 (1H, m), 5.25 (1H, quintet, J=6.8 Hz), 5.75 (1H, d, J=6.8 Hz), 7.18 (1H, d, J=5.6 Hz), 7.73 (1H, dt, J=9.6, 1.6 Hz), 7.86 (1H, m), 8.26 (1H, d, J=5.6 Hz), 8.40 (1H, d, J=2.4 Hz), 8.53 (1H, br s) ppm. LCMS m/z=374.1 [M+H$^+$].

Example Z199. (S)—N-Isopropyl-2-((1-(pyridin-2-yl)ethyl)amino)thieno[3,2-d]pyrimidine-4-carboxamide

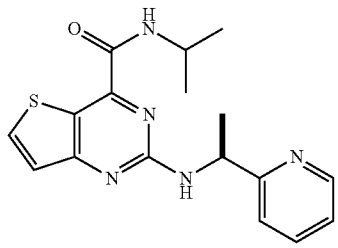 [SMILES: CC(C)NC(=O)c1nc(N[C@@H](C)c2ccccn2)nc2ccsc12]

(Z199)

Synthesis of (S)—N-isopropyl-2-((1-(pyridin-2-yl)ethyl)amino)thieno[3,2-d]pyrimidine-4-carboxamide (Z199): The title compound (Z199) was prepared from (S)-2-((1-(pyridin-2-yl)ethyl)amino)thieno[3,2-d]pyrimidine-4-carboxylic acid di-hydrochloride (37 mg, 0.1 mmol) using chemistry similar to that described in Example Z8 using propan-2-amine in place of (R)-3-fluoropyrrolidine (28 mg, 82% yield). $^1$H NMR (400 MHz, CDCl$_3$) δ 1.25 (3H, d, J=6.8 Hz), 1.30 (3H, d, J=6.4 Hz), 1.63 (3H, d, J=7.2 Hz), 4.24 (1H, m), 5.25 (1H, m), 6.11 (1H, m), 7.18 (1H, ddd, J=8.0, 4.8, 1.2 Hz), 7.20 (1H, d, J=5.6 Hz), 7.36 (1H, d, J=8.0 Hz), 7.64 (1H, td, J=8.0, 2.0 Hz), 7.69 (1H, br s), 7.97 (1H, d, J=5.6 Hz), 8.60 (1H, m) ppm. LCMS m/z=342.2 [M+H$^+$].

Example Z200. (S)-2-((1-(Pyridin-2-yl)ethyl)amino)-N-((5-(trifluoromethyl)pyridin-3-yl)methyl)thieno[3,2-d]pyrimidine-4-carboxamide

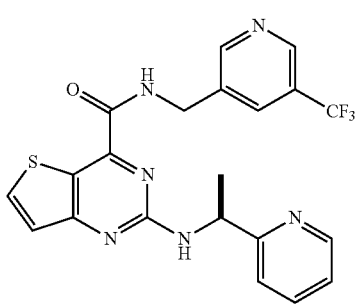 [SMILES: C[C@H](Nc1nc(C(=O)NCc2cncc(C(F)(F)F)c2)c2sccc2n1)c1ccccn1]

(Z200)

Synthesis of 2-chloro-N-((5-(trifluoromethyl)pyridin-3-yl)methyl)thieno[3,2-d]pyrimidine-4-carboxamide: The title compound was prepared from ethyl 2-chlorothieno[3,2-d]pyrimidine-4-carboxylate (200 mg, 0.82 mmol) using chemistry similar to that described in Example Z12 using [5-(trifluoromethyl)-3-pyridyl]methanamine (commercially obtained from Sigma-Aldrich, St. Louis, Mo.) in place of (6-methoxypyridin-3-yl)methanamine hydrochloride (22 mg, 8% yield). LCMS m/z=373.0 [M+H$^+$]. Also was isolated ethyl 2-(((5-(trifluoromethyl)pyridin-3-yl)methyl)amino)thieno[3,2-d]pyrimidine-4-carboxylate (96 mg, 30% yield). LCMS m/z=383.1 [M+H$^+$].

Synthesis of (S)-2-((1-(pyridin-2-yl)ethyl)amino)-N-((5-(trifluoromethyl)pyridin-3-yl)methyl)thieno[3,2-d]pyrimidine-4-carboxamide (Z200): The title compound (Z200) was prepared from 2-chloro-N-((5-(trifluoromethyl)pyridin-3- yl)methyl)thieno[3,2-d]pyrimidine-4-carboxamide using chemistry similar to that described in Example Z12 using (1S)-1-(2-pyridyl)-ethanamine in place of (6-methoxypyridin-3-yl)methanamine hydrochloride (28% yield). LCMS m/z=459.0 [M+H⁺].

Example Z201. (S)—N-(tert-Butyl)-2-((1-(pyridin-2-yl)ethyl)amino)thieno[3,2-d]pyrimidine-4-carboxamide

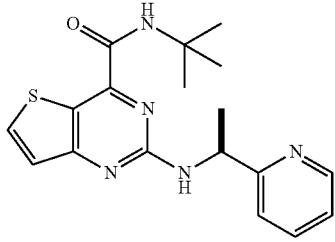

(Z201)

Synthesis of (S)—N-(tert-butyl)-2-((1-(pyridin-2-yl)ethyl)amino)thieno[3,2-d]pyrimidine-4-carboxamide (Z201): The title compound (Z201) was prepared from (S)-2-((1-(pyridin-2-yl)ethyl)amino)thieno[3,2-d]pyrimidine-4-carboxylic acid di-hydrochloride (37 mg, 0.1 mmol) using chemistry similar to that described in Example Z8 using 2-methylpropan-2-amine in place of (R)-3-fluoropyrrolidine (36 mg, 100% yield). $^1$H NMR (400 MHz, CDCl$_3$) δ 1.47 (9H, s), 1.62 (3H, d, J=6.4 Hz), 5.25 (1H, m), 6.11 (1H, m), 7.18 (1H, ddd, J=8.0, 4.8, 1.2 Hz), 7.19 (1H, d, J=5.6 Hz), 7.36 (1H, d, J=8.0 Hz), 7.64 (1H, td, J=8.0, 1.6 Hz), 7.83 (1H, br s), 7.97 (1H, d, J=5.6 Hz), 8.59 (1H, m) ppm. LCMS m/z=356.1 [M+H⁺].

Example Z202. N-Cyclopropyl-2-((2-methoxy-1-(pyridin-3-yl)ethyl)amino)thieno[3,2-d]pyrimidine-4-carboxamide

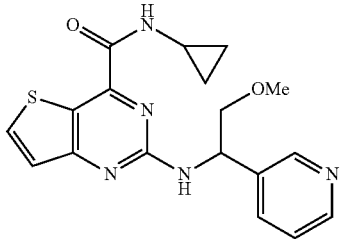 [SMILES: COCC(Nc1nc(C(=O)NC2CC2)c2sccc2n1)c1cccnc1]

(Z202)

Synthesis of N-cyclopropyl-2-((2-methoxy-1-(pyridin-3-yl)ethyl)amino)thieno[3,2-d]pyrimidine-4-carboxamid (Z202): The title compound (Z202) was prepared from ethyl 2-((2-methoxy-1-(pyridin-3-yl)ethyl)amino)thieno[3,2-d]pyrimidine-4-carboxylate using chemistry similar to that described in Example Z17 using cyclopropylamine in place of (3R)-3-methoxy-pyrrolidine hydrochloride (25% yield). $^1$H NMR (400 MHz, CDCl$_3$) δ 0.64 (2H, m), 0.86-0.91 (2H, m), 2.87-2.92 (1H, m), 3.38 (3H, s), 3.78-3.82 (1H, m), 3.86-3.90 (1H, m), 5.31 (1H, s), 6.31 (1H, d, J=6.0 Hz), 7.18-7.21 (2H, m), 7.41 (1H, d, J=8.0 Hz), 7.63 (1H, td, J=7.6, 1.6 Hz), 7.82 (1H, s), 7.98 (1H, d, J=5.6 Hz), 8.61 (1H, m) ppm. LCMS m/z=370.1 [M+H⁺].

Example Z203. (S)-(6-Amino-2-((1-(pyridin-3-yl)ethyl)amino)thieno[3,2-d]pyrimidin-4-yl)(azetidin-1-yl)methanone

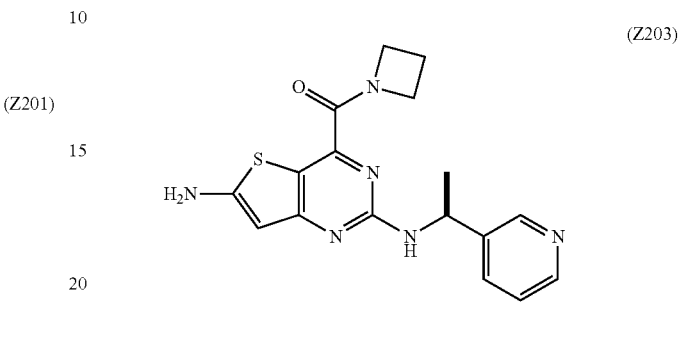

(Z203)

Synthesis of (S)-(6-amino-2-((1-(pyridin-3-yl)ethyl)amino)thieno[3,2-d]pyrimidin-4-yl)(azetidin-1-yl)methanone (Z203): The title compound (Z203) was prepared from 2,6-dichlorothieno[3,2-d]pyrimidine-4-carboxylic acid using chemistry similar to that described in Example Z174 using azetidine in place of pyrrolidine. $^1$H NMR (300 MHz, DMSO-d$_6$) δ 1.58 (3H, d, J=6.8 Hz), 2.27-2.36 (2H, m), 4.12-4.16 (2H, m), 4.33 (1H, m), 4.71 (1H, m), 5.17 (1H, m), 5.88 (1H, s), 7.39 (1H, m), 7.88 (1H, m), 8.39 (1H, m), 8.58 (1H, m) ppm. LCMS m/z=355.0 [M+H⁺].

Example Z204. (6-Amino-2-(((S)-1-(pyridin-3-yl)ethyl)amino)thieno[3,2-d]pyrimidin-4-yl)((S)-3-fluoropyrrolidin-1-yl)methanone

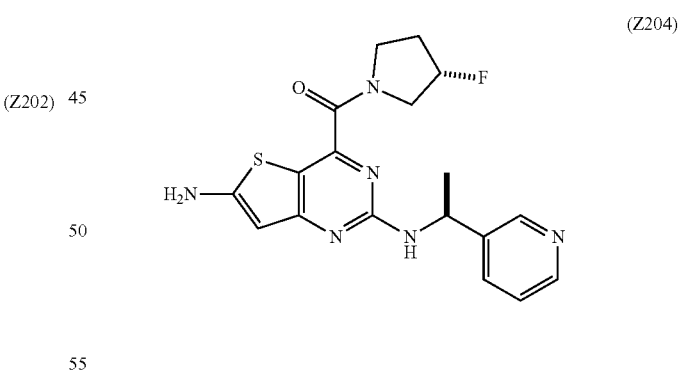

(Z204)

Synthesis of (6-amino-2-(((S)-1-(pyridin-3-yl)ethyl)amino)thieno[3,2-d]pyrimidin-4-yl)((S)-3-fluoropyrrolidin-1-yl)methanone (Z204): The title compound (Z204) was prepared from 2,6-dichlorothieno[3,2-d]pyrimidine-4-carboxylic acid using chemistry similar to that described in Example Z174 using (S)-3-fluoropyrrolidine in place of pyrrolidine. $^1$H NMR (400 MHz, methanol-d$_4$) δ 1.59 (3H, d, J=6.8 Hz), 2.09-2.12 (2H, m), 3.60-3.95 (4H, m), 5.06-5.19 (2H, m), 5.91 (1H, s), 7.41 (1H, m), 7.89 (1H, m), 8.40 (1H, m), 8.60 (1H, m) ppm. LCMS m/z=387.1 [M+H⁺].

Example Z205. (S)-(6-Amino-2-((1-(pyridin-2-yl)ethyl)amino)thieno[3,2-d]pyrimidin-4-yl)(3-hydroxyazetidin-1-yl)methanone

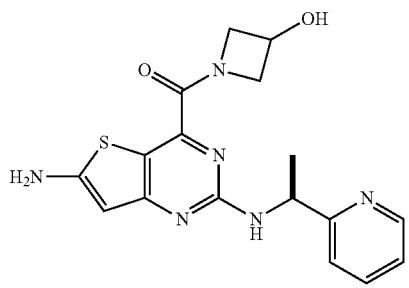 [SMILES: C[C@H](Nc1nc(C(=O)N2CC(O)C2)c2sc(N)cc2n1)c1ccccn1]

(Z205)

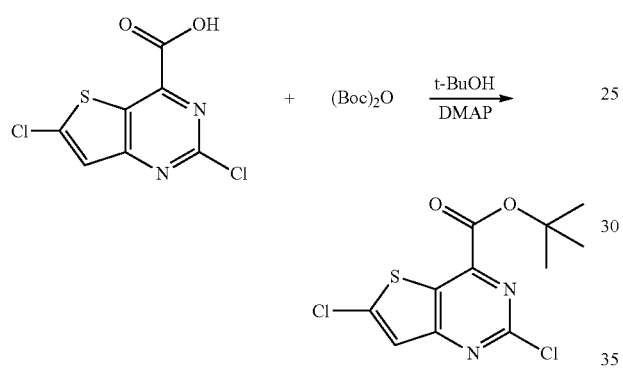

Synthesis of tert-butyl 2,6-dichlorothieno[3,2-d]pyrimidine-4-carboxylate: To a solution of 2,6-dichlorothieno[3,2-d]pyrimidine-4-carboxylic acid (4.6 g, 18.5 mmol) in t-butanol (200 mL) and DCM (100 mL) were added di-tert-butyl dicarbonate (6.06 g, 27.8 mmol), 4-dimethylaminopyridine (225.7 mg, 1.85 mmol) and pyridine (5 mL). The resulting solution was stirred for 16 h at room temperature and was extracted with DCM (3×200 mL). The combined organic layer was washed with brine (3×200 mL) and dried over anhydrous sodium sulfate, and then was concentrated under vacuum. The residue was purified by flash chromatography on silica gel eluting with ethyl acetate/petroleum ether (1:49) to provide tert-butyl 2,6-dichlorothieno[3,2-d]pyrimidine-4-carboxylate as a solid (2.1 g, 93% yield). LCMS m/z=305.0 [M+H$^+$].

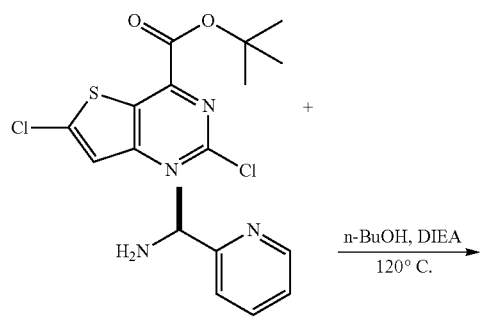

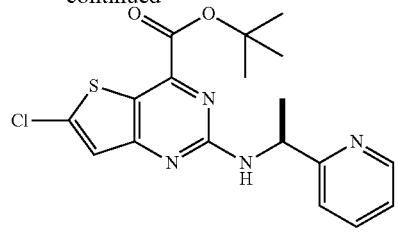

Synthesis of tert-butyl (S)-6-chloro-2-((1-(pyridin-2-yl)ethyl)amino)thieno[3,2-d]pyrimidine-4-carboxylate: To a solution of tert-butyl 2,6-dichlorothieno[3,2-d]pyrimidine-4-carboxylate (2.1 g, 6.88 mmol) in n-butanol (21 mL) were added (1S)-1-(pyridin-2-yl)ethan-1-amine (1.26 g, 10.31 mmol), DIEA (2.68 g, 20.74 mmol). The resulting solution was stirred for 2 h at 120° C. and then was concentrated under vacuum. The residue was purified by flash chromatography on silica gel eluting with ethyl acetate/petroleum ether (1/1) to provide tert-butyl (S)-6-chloro-2-((1-(pyridin-2-yl)ethyl)amino)thieno[3,2-d]pyrimidine-4-carboxylate as yellow oil (600 mg, 22% yield). LCMS m/z=391.0 [M+H$^+$].

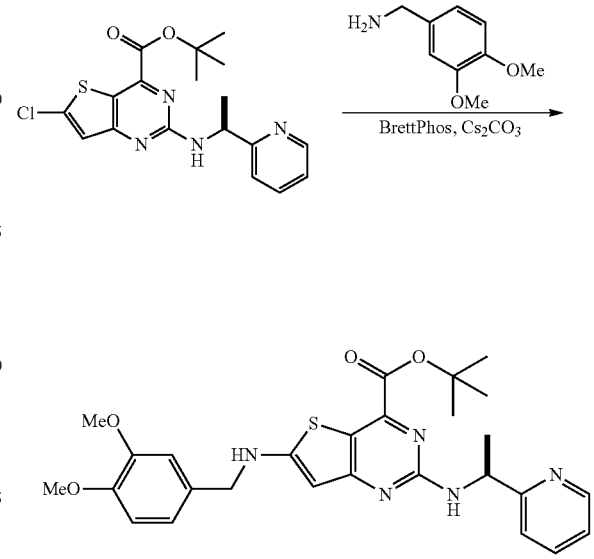

Synthesis of tert-butyl (S)-6-((3,4-dimethoxybenzyl)amino)-2-((1-(pyridin-2-yl)ethyl)amino)thieno[3,2-d]pyrimidine-4-carboxylate: To a solution of tert-butyl (S)-6-chloro-2-((1-(pyridin-2-yl)ethyl)amino)thieno[3,2-d]pyrimidine-4-carboxylate (500 mg, 1.28 mmol) in 1,4-dioxane (20 mL) were added (3,4-dimethoxyphenyl)methanamine (325 mg, 1.94 mmol), a solution of Cs$_2$CO$_3$ (835 mg, 2.56 mmol) in water (4 mL), and 3rd generation BrettPhos precatalyst (100 mg, 0.11 mmol). The resulting solution was stirred for 2 h at 100° C. and the precipitates were filtered out. The filtrate was extracted with ethyl acetate and the combined organic layer was concentrated under vacuum. The residue was purified by flash chromatography on silica gel eluting with DCM/methanol (20/1) to provide tert-butyl (S)-6-((3,4-dimethoxybenzyl)amino)-2-((1-(pyridin-2-yl)ethyl)amino)thieno[3,2-d]pyrimidine-4-carboxylate as yellow oil (300 mg, 45% yield). LCMS m/z=522.1 [M+H$^+$].

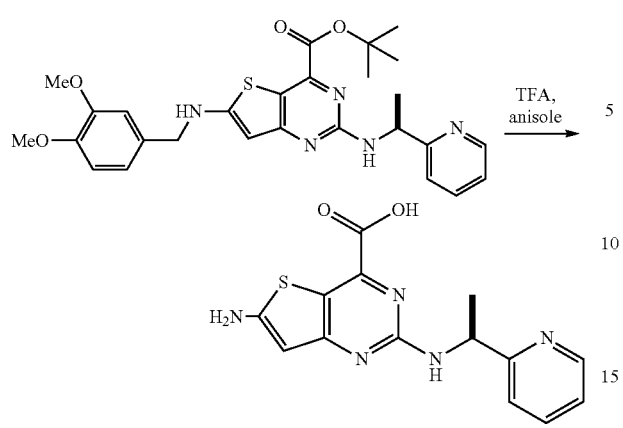

Synthesis of (S)-6-amino-2-((1-(pyridin-2-yl)ethyl)amino)thieno[3,2-d]pyrimidine-4-carboxylic acid: A solution of tert-butyl (S)-6-((3,4-dimethoxybenzyl)amino)-2-((1-(pyridin-2-yl)ethyl)amino)thieno[3,2-d]pyrimidine-4-carboxylate (300 mg, 0.58 mmol) in TFA (3 mL) and anisole (3 mL) was stirred for 2 h at 70° C. The reaction mixture was concentrated under vacuum to provide a crude (S)-6-amino-2-((1-(pyridin-2-yl)ethyl)amino)thieno[3,2-d]pyrimidine-4-carboxylic acid as yellow oil (150 mg, 83% yield) which was used in next step without further purification. $^1$H NMR (300 MHz, DMSO-$d_6$) δ 1.50 (3H, d, J=6.8 Hz), 5.28 (1H, m), 5.96 (1H, s), 7.39 (1H, m), 7.53 (1H, m), 7.88 (1H, m), 8.09 (1H, m), 8.62 (1H, m), 8.72 (2H, m) ppm. LCMS m/z=316.0 [M+H$^+$].

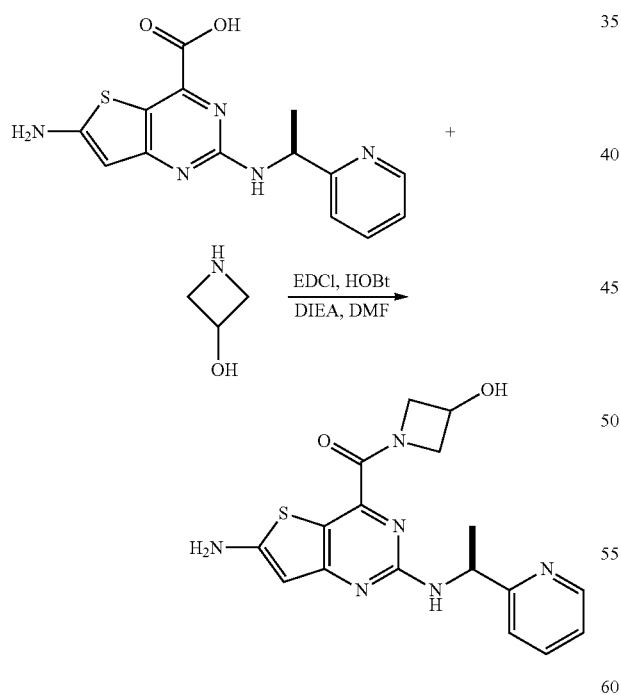

Synthesis of (S)-(6-amino-2-((1-(pyridin-2-yl)ethyl)amino)thieno[3,2-d]pyrimidin-4-yl)(3-hydroxyazetidin-1-yl)methanone (Z205): To a solution of (S)-6-amino-2-((1-(pyridin-2-yl)ethyl)amino)thieno[3,2-d]pyrimidine-4-carboxylic acid (100 mg, 0.32 mmol) in DMF (2 mL), were added azetidin-3-ol hydrochloride (52.3 mg, 0.48 mmol), HOBt (64.8 mg, 0.48 mmol), EDCI (92.2 mg, 0.48 mmol), and DIEA (123.8 mg, 0.96 mmol). The resulting solution was stirred for 16 h at room temperature and then was extracted with ethyl acetate. The combined organic layer was dried over anhydrous sodium sulfate and concentrated under vacuum. The residue was purified by prep-HPLC (C-18 OBD column and a gradient elution system of water-acetonitrile) to provide (S)-(6-amino-2-((1-(pyridin-2-yl)ethyl)amino)thieno[3,2-d]pyrimidin-4-yl)(3-hydroxyazetidin-1-yl)methanone as a light yellow solid (22 mg, 29% yield). $^1$H NMR (300 MHz, methanol-$d_4$) δ 1.58 (3H, d, J=6.8 Hz), 3.82-3.99 (2H, m), 4.27-4.66 (3H, m), 5.11 (1H, m), 5.88 (1H, s), 7.28 (1H, m), 7.48 (1H, m), 7.77 (1H, m), 8.51 (1H, m) ppm. LCMS m/z=371.1 [M+H$^+$].

Example Z206. (6-Amino-2-(((S)-1-(pyridin-2-yl)ethyl)amino)thieno[3,2-d]pyrimidin-4-yl)((R)-3-methylpyrrolidin-1-yl)methanone

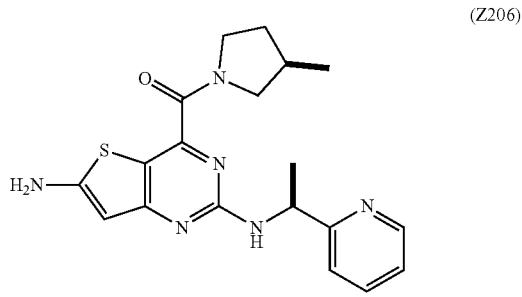

(Z206)

Synthesis of (6-amino-2-(((S)-1-(pyridin-2-yl)ethyl)amino)thieno[3,2-d]pyrimidin-4-yl)((R)-3-methylpyrrolidin-1-yl)methanone (Z206): The title compound (Z206) was prepared from 2,6-dichlorothieno[3,2-d]pyrimidine-4-carboxylic acid using chemistry similar to that described in Example Z174 using (R)-3-methylpyrrolidine in place of pyrrolidine. $^1$H NMR (400 MHz, methanol-$d_4$) δ 1.03 (3H, d, J=6.4 Hz), 1.46 (1H, m), 1.57 (3H, d, J=6.8 Hz), 1.95 (1H, m), 2.17 (1H, m), 3.10 (1H, m), 3.52-3.74 (3H, m), 5.03 (1H, m), 5.90 (1H, s), 7.27 (1H, m), 7.48 (1H, d, J=8.0 Hz), 7.76 (1H, m), 8.49 (1H, m) ppm. LCMS m/z=383.2 [M+H$^+$].

Example Z207. (6-(Methylamino)-2-(((S)-1-(pyridin-2-yl)ethyl)amino)thieno[3,2-d]pyrimidin-4-yl)((R)-3-methylpyrrolidin-1-yl)methanone

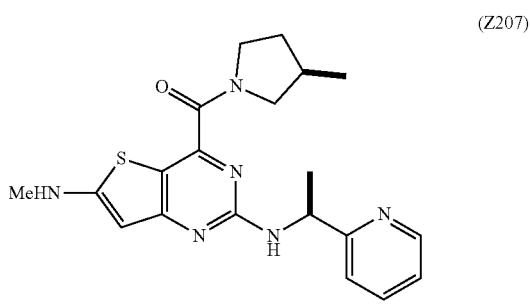

(Z207)

Synthesis of (6-(methylamino)-2-(((S)-1-(pyridin-2-yl)ethyl)amino)thieno[3,2-d]pyrimidin-4-yl)((R)-3-methylpyrrolidin-1-yl)methanone (Z207): The title compound (Z207) was prepared from 2,6-dichlorothieno[3,2-d]pyrimidine-4- carboxylic acid using chemistry similar to that described in Example Z152 using (R)-3-methylpyrrolidine in place of pyrrolidine. ¹H NMR (400 MHz, methanol-d₄) δ 1.04 (3H, d, J=6.4 Hz), 1.40 (1H, m), 1.58 (3H, d, J=6.8 Hz), 1.95 (1H, m), 2.16 (1H, m), 2.96 (3H, s), 3.12 (1H, m), 3.50-3.78 (3H, m), 5.13 (1H, m), 5.81 (1H, s), 7.27 (1H, m), 7.49 (1H, d, J=7.2 Hz), 7.77 (1H, m), 8.49 (1H, m) ppm. LCMS m/z=397.2 [M+H⁺].

Example Z208. (6-Amino-2-(((S)-1-(pyridin-2-yl)ethyl)amino)thieno[3,2-d]pyrimidin-4-yl)((R)-3-hydroxypyrrolidin-1-yl)methanone

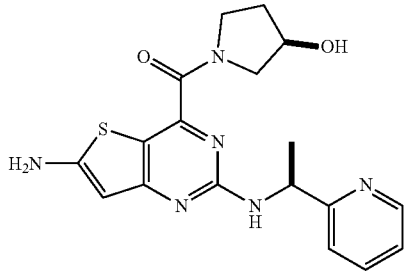

(Z208)

Synthesis of (6-amino-2-(((S)-1-(pyridin-2-yl)ethyl)amino)thieno[3,2-d]pyrimidin-4-yl)((R)-3-hydroxypyrrolidin-1-yl)methanone (Z208): The title compound (Z208) was prepared from 2,6-dichlorothieno[3,2-d]pyrimidine-4-carboxylic acid using chemistry similar to that described in Example Z174 using (R)-pyrrolidin-3-ol in place of pyrrolidine. ¹H NMR (400 MHz, DMSO-d₆) δ 1.61 (3H, d, J=6.8 Hz), 1.81-1.98 (2H, m), 3.58-3.74 (3H, m), 4.08 (1H, m), 4.39 (1H, m), 5.16 (1H, m), 5.97 (1H, s), 7.32 (1H, m), 7.53 (1H, m), 7.82 (1H, m), 8.52 (1H, m) ppm. LCMS m/z=385.0 [M+H⁺].

Example Z209. (S)-6-Amino-N-(2-hydroxyethyl)-2-((1-(pyridin-2-yl)ethyl)amino)thieno[3,2-d]pyrimidine-4-carboxamide

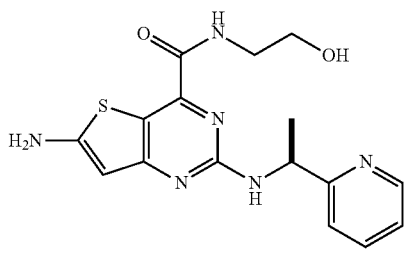 [SMILES: C[C@H](Nc1nc(C(=O)NCCO)c2sc(N)cc2n1)c1ccccn1]

(Z209)

Synthesis of (S)-6-amino-N-(2-hydroxyethyl)-2-((1-(pyridin-2-yl)ethyl)amino)thieno[3,2-d]pyrimidine-4-carboxamide (Z209): The title compound (Z209) was prepared from (S)-6-amino-2-((1-(pyridin-2-yl)ethyl)amino)thieno[3,2-d]pyrimidine-4-carboxylic acid using chemistry similar to that described in Example Z205 using 2-((tert-butyldimethylsilyl)oxy)ethan-1-amine in place of azetidin-3-ol. ¹H NMR (300 MHz, methanol-d₄) δ 1.55 (3H, d, J=7.2 Hz), 3.44-3.48 (2H, m), 3.66-3.69 (2H, m), 5.17 (1H, q, J=7.2 Hz), 5.85 (1H, s), 7.25 (1H, m), 7.51 (1H, d, J=8.0 Hz), 7.76 (1H, m), 8.48 (1H, m) ppm. LCMS m/z=359.1 [M+H⁺].

Example Z210. (S)-(2-((1-(5-Fluoropyridin-3-yl)ethyl)amino)-6-(methylamino)thieno[3,2-d]pyrimidin-4-yl)(pyrrolidin-1-yl)methanone

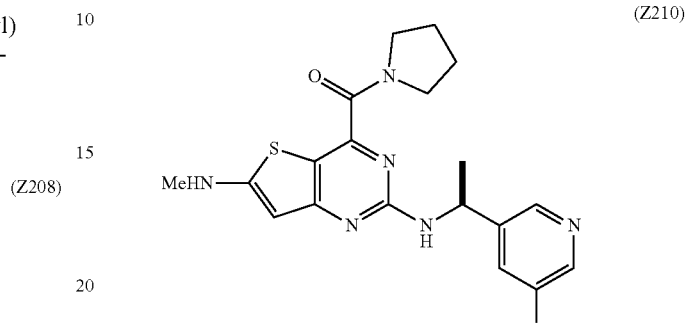

(Z210)

Synthesis of (S)-(2-((1-(5-fluoropyridin-3-yl)ethyl)amino)-6-(methylamino)thieno[3,2-d]pyrimidin-4-yl)(pyrrolidin-1-yl)methanone (Z210): The title compound (Z210) was prepared from 2,6-dichlorothieno[3,2-d]pyrimidine-4-carboxylic acid using chemistry similar to that described in Example Z152 using (S)-1-(5-fluoropyridin-3-yl)ethan-1-amine in place of (S)-1-(pyridin-3-yl)ethan-1-amine. ¹H NMR (400 MHz, methanol-d₄) δ 1.59 (3H, d, J=6.8 Hz), 1.79-1.91 (4H, m), 2.96 (3H, s), 3.50-3.59 (3H, m), 3.78 (1H, m), 5.18 (1H, q, J=6.8 Hz), 5.81 (1H, s), 7.69 (1H, m), 8.31 (1H, d, J=2.8 Hz), 8.47 (1H, s) ppm. LCMS m/z=401.0 [M+H⁺].

Example Z211. (S)-Azetidin-1-yl(2-((1-(5-fluoropyridin-3-yl)ethyl)amino)-6-(methylamino)thieno[3,2-d]pyrimidin-4-yl)methanone

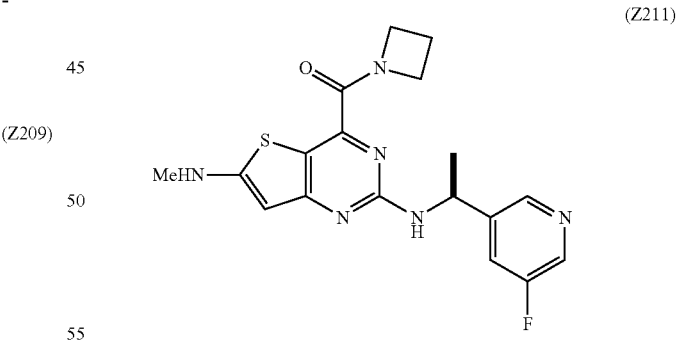

(Z211)

Synthesis of (S)-azetidin-1-yl(2-((1-(5-fluoropyridin-3-yl)ethyl)amino)-6-(methylamino)thieno[3,2-d]pyrimidin-4-yl)methanone (Z211): The title compound (Z211) was prepared from 2,6-dichlorothieno[3,2-d]pyrimidine-4-carboxylic acid using chemistry similar to that described in Example Z152 using azetidine in place of pyrrolidine. ¹H NMR (400 MHz, DMSO-d₆) δ 1.59 (3H, d, J=6.8 Hz), 2.27-2.41 (2H, m), 2.96 (3H, s), 4.14-4.18 (2H, m), 4.39 (1H, m), 4.74 (1H, m), 5.22 (1H, q, J=6.8 Hz), 5.80 (1H, s), 7.68 (1H, m), 8.32 (1H, d, J=2.8 Hz), 8.47 (1H, s) ppm. LCMS m/z=387.1 [M+H⁺].

Example Z212. (6-Amino-2-(((S)-1-(5-fluoropyridin-3-yl)ethyl)amino)thieno[3,2-d]pyrimidin-4-yl)((S)-3-hydroxypyrrolidin-1-yl)methanone

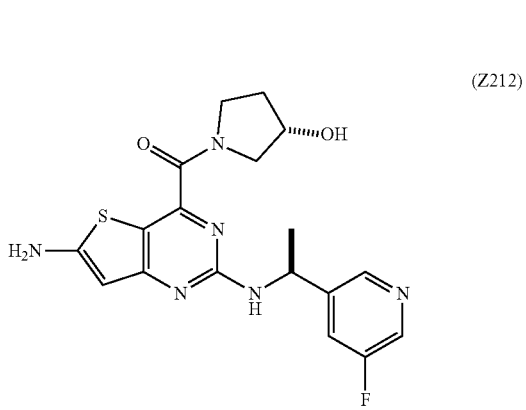

(Z212)

Synthesis of (6-amino-2-(((S)-1-(5-fluoropyridin-3-yl)ethyl)amino)thieno[3,2-d]pyrimidin-4-yl)((S)-3-hydroxypyrrolidin-1-yl)methanone (Z212): The title compound (Z212) was prepared from 2,6-dichlorothieno[3,2-d]pyrimidine-4-carboxylic acid using chemistry similar to that described in Example Z174 using (S)-pyrrolidin-3-ol in place of pyrrolidine. $^1$H NMR (400 MHz, methanol-$d_4$) δ 1.59 (3H, d, J=6.8 Hz), 1.86-1.97 (2H, m), 3.50-3.71 (4H, m), 4.40 (1H, m), 5.20 (1H, q, J=6.8 Hz), 5.90 (1H, s), 7.69 (1H, m), 8.32 (1H, m), 8.48 (1H, m) ppm. LCMS m/z=403.0 [M+H$^+$].

Example Z213. (S)-(6-Methyl-2-((1-(pyridin-3-yl)ethyl)amino)thieno[3,2-d]pyrimidin-4-yl)(pyrrolidin-1-yl)methanone

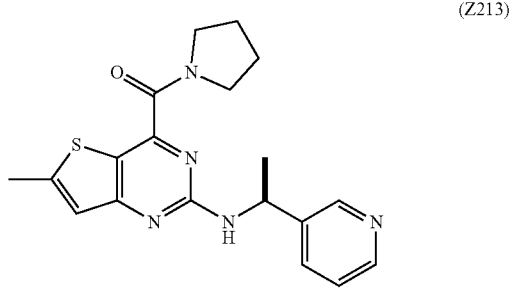

(Z213)

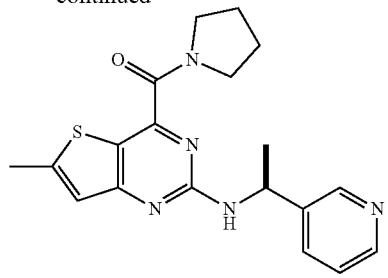

Synthesis of (S)-(6-methyl-2-((1-(pyridin-3-yl)ethyl)amino)thieno[3,2-d]pyrimidin-4-yl)(pyrrolidin-1-yl)methanone (Z213): To a solution of (S)-(6-chloro-2-((1-(pyridin-3-yl)ethyl)amino)thieno[3,2-d]pyrimidin-4-yl)(pyrrolidin-1-yl)methanone (200 mg, 0.52 mmol) in 1,4-dioxane (8 mL) were added trimethyl-1,3,5,2,4,6-trioxatriborinane (260 mg, 2.07 mmol), 2$^{nd}$ generation XPhos precatalyst (40 mg, 0.05 mmol), Cs$_2$CO$_3$ (335 mg, 1.03 mmol). The resulting solution was stirred for 30 min at 110° C. and was diluted with ethyl acetate (200 mL). The resulting mixture was washed with water and brine, then dried over anhydrous sodium sulfate. The residue was purified by prep-HPLC (C-18 OBD column and a gradient elution system of water-acetonitrile) to provide (S)-(6-methyl-2-((1-(pyridin-3-yl)ethyl)amino)thieno[3,2-d]pyrimidin-4-yl)(pyrrolidin-1-yl)methanone as a yellow solid (50 mg, 26% yield). $^1$H NMR (400 MHz, methanol-$d_4$) δ 1.62 (3H, d, J=7.2 Hz), 1.86-1.90 (4H, m), 2.60 (3H, s), 3.56-3.63 (3H, m), 3.78 (1H, m), 5.20 (1H, q, J=7.2 Hz), 6.89 (1H, s), 7.39 (1H, m), 7.91 (1H, m), 8.39 (1H, dd, J=4.8, 1.2 Hz), 8.62 (1H, d, J=1.2 Hz) ppm. LCMS m/z=368.0 [M+H$^+$].

Example Z214. (S)-(6-Ethyl-2-((1-(pyridin-3-yl)ethyl)amino)thieno[3,2-d]pyrimidin-4-yl)(pyrrolidin-1-yl)methanone

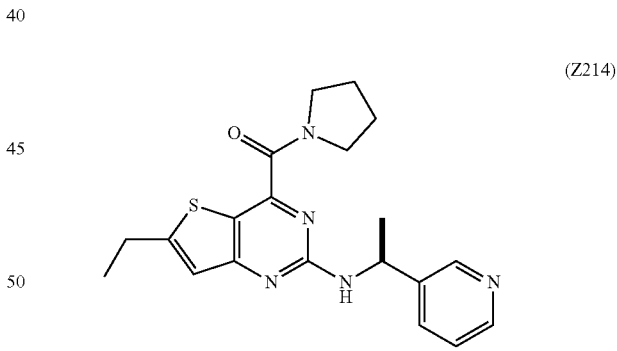

(Z214)

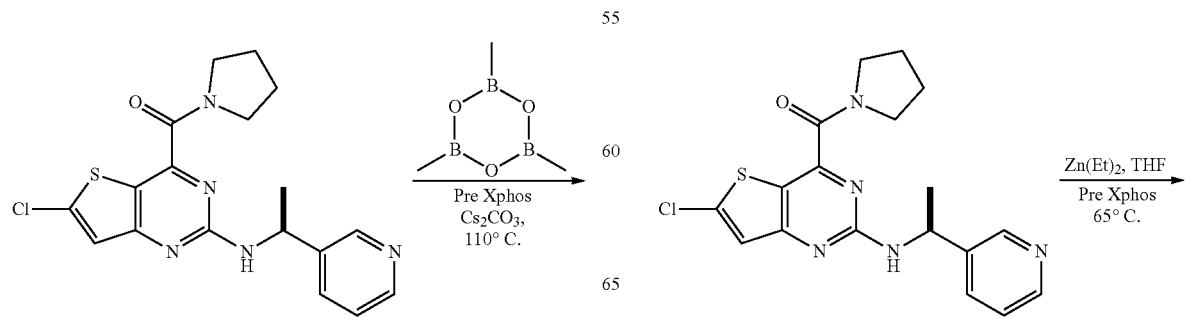

-continued

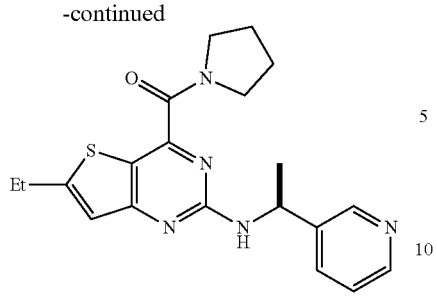

Synthesis of (S)-(6-ethyl-2-((1-(pyridin-3-yl)ethyl)amino)thieno[3,2-d]pyrimidin-4-yl)(pyrrolidin-1-yl)methanone (Z214): To a solution of (S)-(6-chloro-2-((1-(pyridin-3-yl)ethyl)amino)thieno[3,2-d]pyrimidin-4-yl)(pyrrolidin-1-yl)methanone (150 mg, 0.39 mmol) in THE (5 mL) were added 2$^{rd}$ generation XPhos precatalyst (30 mg, 0.04 mmol) and a solution of 1 M diethylzine in tetrahydrofuran (0.4 mL). The resulting solution was stirred for 45 min at 65° C. and then was diluted with ethyl acetate (200 mL), washed with water and brine. The organic layer was dried over anhydrous sodium sulfate and was concentrated under vacuum. The residue was purified by prep-HPLC (C-18 OBD column and a gradient elution system of water-acetonitrile) to provide (S)-(6-ethyl-2-((1-(pyridin-3-yl)ethyl)amino)thieno[3,2-d]pyrimidin-4-yl)(pyrrolidin-1-yl)methanone as an off-white solid (33 mg, 22% yield). $^1$H NMR (400 MHz, methanol-d$_4$) δ 1.38 (3H, t, J=7.2 Hz), 1.62 (3H, d, J=7.2 Hz), 1.87-1.91 (4H, m), 2.98 (2H, q, J=7.2 Hz), 3.50-3.76 (3H, m), 3.81 (1H, m), 5.21 (1H, q, J=6.8 Hz), 6.93 (1H, s), 7.40 (1H, dd, J=8.0, 5.2), 7.91 (1H, m), 8.40 (1H, dd, J=4.8, 1.2 Hz), 8.62 (1H, d, J=1.2 Hz) ppm. LCMS m/z=382.0 [M+H$^+$].

Example Z215. (S)—N-(2-(Methylsulfonyl)ethyl)-2-((1-(pyridin-2-yl)ethyl)amino)thieno[3,2-d]pyrimidine-4-carboxamide (Z215)

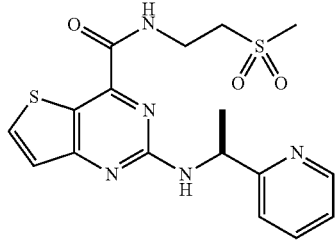 [SMILES: C[C@H](Nc1nc(C(=O)NCCS(C)(=O)=O)c2sccc2n1)c1ccccn1]

Synthesis of (S)—N-(2-(methylsulfonyl)ethyl)-2-((1-(pyridin-2-yl)ethyl)amino)thieno[3,2-d]pyrimidine-4-carboxamide (Z215): The title compound (Z215) was prepared from (S)-2-((1-(pyridin-2-yl)ethyl)amino)thieno[3,2-d]pyrimidine-4-carboxylic acid di-hydrochloride (37 mg, 0.1 mmol) using chemistry similar to that described in Example Z8 using 2-methylsulfonylethanamine hydrochloride in place of (R)-3-fluoropyrrolidine (29 mg, 72% yield). $^1$H NMR (400 MHz, CDCl$_3$) δ 1.62 (3H, d, J=7.2 Hz), 2.99 (3H, s), 3.38 (3H, t, J=6.4 Hz), 4.00 (1H, q, J=6.4 Hz), 5.27 (1H, quintet, J=7.2 Hz), 6.27 (1H, d, J=7.2 Hz), 7.18 (1H, ddd, J=8.0, 4.8, 1.6 Hz), 7.21 (1H, d, J=5.6 Hz), 7.38 (1H, d, J=8.0 Hz), 7.65 (1H, td, J=8.0, 1.6 Hz), 7.98 (1H, d, J=5.6 Hz), 8.50 (1H, t, J=6.4 Hz), 8.60 (1H, dt, J=4.8, 1.6 Hz) ppm. LCMS m/z=406.1 [M+H$^+$].

Example Z216. 2-((2-Methoxy-1-(pyridin-3-yl)ethyl)amino)-N-(oxetan-3-yl)thieno[3,2-d]pyrimidine-4-carboxamide (Z216)

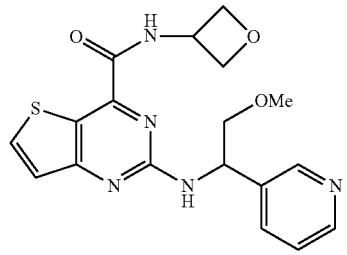 [SMILES: COCC(Nc1nc(C(=O)NC2COC2)c2sccc2n1)c1cccnc1]

Synthesis of 2-((2-methoxy-1-(pyridin-3-yl)ethyl)amino)-N-(oxetan-3-yl)thieno[3,2-d]pyrimidine-4-carboxamide (Z216): The title compound (Z216) was prepared from ethyl 2-((2-methoxy-1-(pyridin-3-yl)ethyl)amino)thieno[3,2-d]pyrimidine-4-carboxylate using chemistry similar to that described in Example Z17 using oxetan-3-amine in place of (3R)-3-methoxy-pyrrolidine hydrochloride (26% yield). LCMS m/z=386.1 [M+H$^+$].

Example Z217. (2-((2-Methoxy-1-(pyridin-3-yl)ethyl)amino)thieno[3,2-d]pyrimidin-4-yl)(3-methoxyazetidin-1-yl)methanone (Z217)

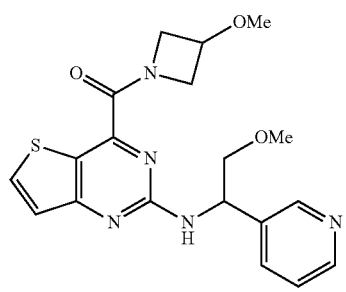 [SMILES: COCC(Nc1nc(C(=O)N2CC(OC)C2)c2sccc2n1)c1cccnc1]

Synthesis of 2-((2-methoxy-1-(pyridin-3-yl)ethyl)amino)-N-(3-methoxycyclo-butyl)thieno[3,2-d]pyrimidine-4-carboxamide (Z217): The title compound (Z217) was prepared from ethyl 2-((2-methoxy-1-(pyridin-3-yl)ethyl)amino)thieno[3,2-d]pyrimidine-4-carboxylate using chemistry similar to that described in Example Z17 using 3-methoxyazetidine hydrochloride (commercially obtained from PharmaBlock, Sunnyvale Calif.) in place of (3R)-3-methoxypyrrolidine hydrochloride (27% yield). LCMS m/z=400.3 [M+H$^+$]

Example Z218. N-((1s,3s)-3-Hydroxycyclobutyl)-2-((2-methoxy-1-(pyridin-3-yl)ethyl)amino)thieno[3,2-d]pyrimidine-4-carboxamide

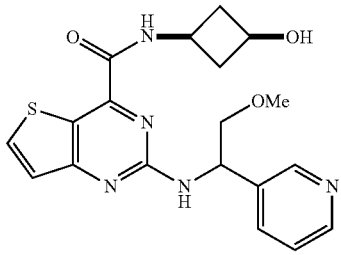

(Z218)

Synthesis of N-((1s,3s)-3-hydroxycyclobutyl)-2-((2-methoxy-1-(pyridin-3-yl)ethyl)amino)thieno[3,2-d]pyrimidine-4-carboxamide (Z218): The title compound (Z218) was prepared from ethyl 2-((2-methoxy-1-(pyridin-3-yl)ethyl)amino)thieno[3,2-d]pyrimidine-4-carboxylate using chemistry similar to that described in Example Z17 using cis-3-amino-cyclobutanol hydrochloride in place of (3R)-3-methoxypyrrolidine hydrochloride (42% yield). LCMS m/z=400.1 [M+H$^+$]

Example Z219. 2-(((5-Fluoropyridin-3-yl)methyl)amino)-N-((tetrahydro-2H-pyran-4-yl)methyl)thieno[3,2-d]pyrimidine-4-carboxamide

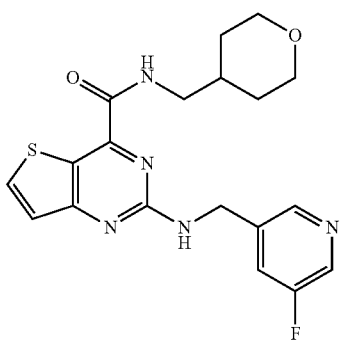

(Z219)

Synthesis of 2-(((5-fluoropyridin-3-yl)methyl)amino)-N-((tetrahydro-2H-pyran-4-yl)methyl)thieno[3,2-d]pyrimidine-4-carboxamide (Z219): The title compound (Z219) was prepared from ethyl 2-(((5-fluoropyridin-3-yl)methyl)amino)thieno[3,2-d]pyrimidine using chemistry similar to that described in Example Z17 using tetrahydropyran-4-ylmethanamine (commercially obtained from Sigma-Aldrich, St Louis, Mo.) in place of (3R)-3-methoxy-pyrrolidine hydrochloride (76% yield). $^1$H NMR (400 MHz, CDCl$_3$) δ 1.35-1.50 (4H, m), 1.85-1.92 (1H, m), 3.35-3.41 (4H, m), 3.99 (2H, dd, J=9.6, 3.2 Hz), 4.78 (2H, d, J=6.4 Hz), 5.60 (1H, m), 7.24 (1H, d, J=5.6 Hz), 7.46-7.49 (1H, m), 7.91 (1H, s), 8.05 (1H, d, J=5.6 Hz), 8.39 (1H, d, J=2.8 Hz), 8.50 (1H, s) ppm. LCMS m/z=402.2 [M+H$^+$].

Example Z220. (6-Amino-2-(((S)-1-(pyridin-3-yl)ethyl)amino)thieno[3,2-d]pyrimidin-4-yl)((R)-3-hydroxypyrrolidin-1-yl)methanone

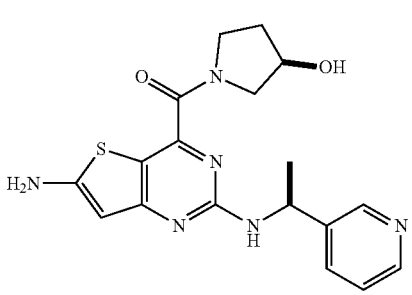

(Z220)

Synthesis of (6-amino-2-(((S)-1-(pyridin-3-yl)amino)thieno[3,2-d]pyrimidin-4-yl)((R)-3-hydroxypyrrolidin-1-yl)methanone (Z220): The title compound (Z220) was prepared from 2,6-dichlorothieno[3,2-d]pyrimidine-4-carboxylic acid using chemistry similar to that described in Example Z174 using (R)-pyrrolidin-3-ol in place of pyrrolidine. $^1$H NMR (400 MHz, DMSO-d$_6$) δ 1.60 (3H, d, J=6.8 Hz), 1.92-1.97 (2H, m), 3.61-3.73 (3H, m), 4.09 (1H, m), 4.40 (1H, m), 5.18 (1H, m), 5.90 (1H, s), 7.39 (1H, m), 7.90 (1H, m), 8.39 (1H, m), 8.59 (1H, m) ppm. LCMS m/z=385.1 [M+H$^+$].

Example Z221. (S)-(3-Hydroxyazetidin-1-yl)(6-(methylamino)-2-((1-(pyridin-2-yl)ethyl)amino)thieno[3,2-d]pyrimidin-4-yl)methanone

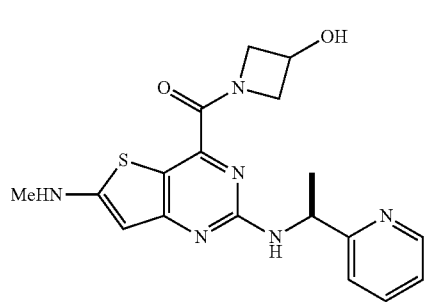 [SMILES: CNc1cc2nc(N[C@@H](C)c3ccccn3)nc(C(=O)N3CC(O)C3)c2s1]

(Z221)

Synthesis of (S)-(3-hydroxyazetidin-1-yl)(6-(methylamino)-2-((1-(pyridin-2-yl)ethyl)amino)thieno[3,2-d]pyrimidin-4-yl)methanone (Z221): The title compound (Z221) was prepared from 2,6-dichlorothieno[3,2-d]pyrimidine-4-carboxylic acid using chemistry similar to that described in Example Z152 using azetidin-3-ol in place of pyrrolidine. $^1$H NMR (400 MHz, methanol-d$_4$) δ 1.60 (3H, d, J=6.8 Hz), 2.96 (3H, s), 3.91 (1H, m), 4.09 (1H, m), 4.35 (1H, m), 4.41-4.59 (2H, m), 5.20 (1H, q, J=6.8 Hz), 5.80 (1H, s), 7.41 (1H, dd, J=8.0, 4.8 Hz), 7.89 (1H, m), 8.40 (1H, dd, J=4.8, 1.6 Hz), 8.60 (1H, d, J=1.6 Hz) ppm. LCMS m/z=385.1 [M+H$^+$].

Example Z222. (S)—N-(2-Hydroxyethyl)-6-(methylamino)-2-((1-(pyridin-2-yl)ethyl)amino)thieno[3,2-d]pyrimidine-4-carboxamide

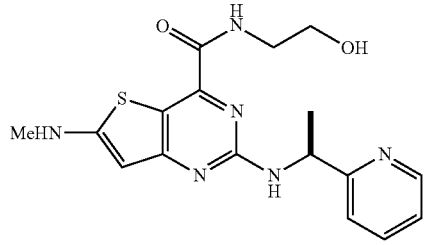 [SMILES: CNc1cc2nc(N[C@@H](C)c3ccccn3)nc(C(=O)NCCO)c2s1]

(Z222)

Synthesis of (S)-6-chloro-N-(2-hydroxyethyl)-2-((1-(pyridin-2-yl)ethyl)amino)thieno[3,2-d]pyrimidine-4-carboxamide: To a solution of (S)-6-chloro-2-((1-(pyridin-2-yl)ethyl)amino)thieno[3,2-d]pyrimidine-4-carboxylic acid (200 mg, 0.64 mmol) in DMF (4 mL), were added 2-aminoethan-1-ol (59 mg, 0.96 mmol), HOBt (130 mg, 0.96 mmol), EDCI (184 mg, 0.96 mmol), and DIEA (248 mg, 1.92 mmol). The resulting solution was stirred for 16 h at room temperature and then was extracted with ethyl acetate. The combined organic layer was dried over anhydrous sodium sulfate and concentrated under vacuum. The residue was purified flash chromatography on silica gel eluting with ethyl acetate/petroleum ether (1/2) to provide (S)-6-chloro-N-(2-hydroxyethyl)-2-((1-(pyridin-2-yl)ethyl)amino)thieno[3,2-d]pyrimidine-4-carboxamide as a light yellow solid (120 mg, 50% yield). $^1$H NMR (300 MHz, methanol-$d_4$) δ 1.52 (3H, d, J=6.8 Hz), 3.41 (2H, m), 3.55 (2H, m), 4.89 (1H, m), 5.31 (1H, m), 7.24 (1H, m), 7.38 (1H, m), 7.47 (1H, m), 7.71-7.83 (2H, m), 8.53 (1H, m), 8.64 (1H, m) ppm. LCMS m/z=378.3 [M+H$^+$].

Synthesis of (S)—N-(2-hydroxyethyl)-6-(methylamino)-2-((1-(pyridin-2-yl)ethyl)amino)thieno[3,2-d]pyrimidine-4-carboxamide (Z222): To a solution of (S)-6-chloro-N-(2-hydroxyethyl)-2-((1-(pyridin-2-yl)ethyl)amino)thieno[3,2-d]pyrimidine-4-carboxamide (150 mg, 0.40 mmol) in n-butanol (1.5 mL) was added a solution of MeNH2 (62 mg, 2.0 mmol) in ethanol (1 mL) and the solution thus obtained was irradiated with microwave radiation for 2 h at 130° C. The reaction mixture was concentrated under vacuum and the residue was purified by prep-HPLC (C-18 OBD column and a gradient elution system of water-acetonitrile) to provide (S)—N-(2-hydroxyethyl)-6-(methylamino)-2-((1-(pyridin-2-yl)ethyl)amino)thieno[3,2-d]pyrimidine-4-carboxamide as an yellow solid (15 mg, 10% yield). $^1$H NMR (300 MHz, methanol-$d_4$) δ 1.58 (3H, d, J=6.8 Hz), 2.96 (3H, s), 3.42-3.50 (2H, m), 3.68-3.72 (2H, m), 5.20 (1H, q, J=6.8 Hz), 5.79 (1H, s), 7.28 (1H, m), 7.54 (1H, d, J=10.8 Hz), 7.79 (1H, m), 8.50 (1H, m) ppm. LCMS m/z=373.1 [M+H$^+$].

Example Z223. (S)-(6-Amino-2-((1-(5-fluoropyridin-3-yl)ethyl)amino)thieno[3,2-d]pyrimidin-4-yl)(pyrrolidin-1-yl)methanone

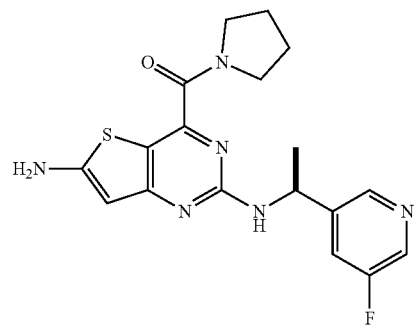 [SMILES: C[C@H](Nc1nc(C(=O)N2CCCC2)c2sc(N)cc2n1)c1cncc(F)c1]

(Z223)

Synthesis of (S)-(6-amino-2-((1-(5-fluoropyridin-3-yl)ethyl)amino)thieno[3,2-d]pyrimidin-4-yl)(pyrrolidin-1-yl)methanone (Z223): The title compound (Z223) was prepared from 2,6-dichlorothieno[3,2-d]pyrimidine-4-carboxylic acid using chemistry similar to that described in Example Z152 using (S)-1-(5-fluoropyridin-3-yl)ethan-1-amine in place of (S)-1-(pyridin-3-yl)ethan-1-amine. $^1$H NMR (400 MHz, methanol-$d_4$) δ 1.59 (3H, d, J=6.8 Hz), 1.79-1.91 (4H, m), 3.50 (1H, m), 3.55-3.58 (2H, m), 3.76 (1H, m), 5.17 (1H, q, J=6.8 Hz), 5.90 (1H, s), 7.69 (1H, m), 8.31 (1H, d, J=2.8 Hz), 8.47 (1H, s) ppm. LCMS m/z=387.0 [M+H$^+$].

Example Z224. (2-(((S)-1-(5-Fluoropyridin-3-yl)ethyl)amino)-6-(methylamino)thieno[3,2-d]pyrimidin-4-yl)((R)-3-hydroxypyrrolidin-1-yl)methanone

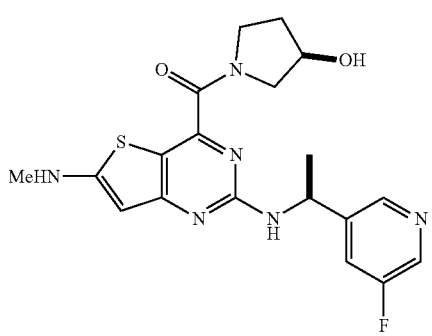 [SMILES: CNc1cc2nc(N[C@@H](C)c3cncc(F)c3)nc(C(=O)N3CC[C@@H](O)C3)c2s1]

(Z224)

Synthesis of (2-(((S)-1-(5-fluoropyridin-3-yl)ethyl)amino)-6-(methylamino)thieno[3,2-d]pyrimidin-4-yl)((R)-3-hydroxypyrrolidin-1-yl)methanone (Z224): The title compound (Z224) was prepared from 2,6-dichlorothieno[3,2-d]pyrimidine-4-carboxylic acid using chemistry similar to that described in Example Z152 using (R)-pyrrolidin-3-ol in place of pyrrolidine. $^1$H NMR (400 MHz, DMSO-$d_6$) δ 1.60 (3H, d, J=6.8 Hz), 1.93-2.02 (2H, m), 2.96 (3H, s), 3.62-3.74 (3H, m), 4.12 (1H, m), 4.41 (1H, m), 5.21 (1H, q, J=6.8 Hz), 5.81 (1H, s), 7.69 (1H, m), 8.31 (1H, d, J=2.8 Hz), 8.48 (1H, s) ppm. LCMS m/z=417.0 [M+H$^+$].

Example Z225. (2-(((S)-1-(5-Fluoropyridin-3-yl)ethyl)amino)thieno[3,2-d]pyrimidin-4-yl)((S)-3-fluoropyrrolidin-1-yl)methanone

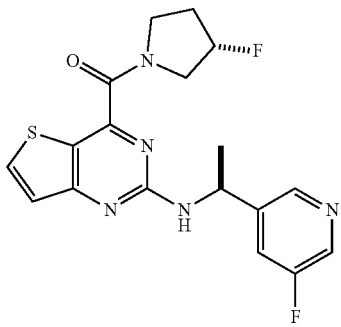 [SMILES: C[C@H](Nc1nc(C(=O)N2CC[C@H](F)C2)c2sccc2n1)c1cncc(F)c1]

(Z225)

Synthesis of (2-(((S)-1-(5-fluoropyridin-3-yl)amino)thieno[3,2-d]pyrimidin-4-yl)((S)-3-fluoropyrrolidin-1-yl)methanone (Z225): The title compound (Z225) was prepared from (S)-2-((1-(5-fluoropyridin-3-yl)ethyl)amino)thieno[3,2-d]pyrimidine-4-carboxylic acid di-hydrochloride (39 mg, 0.10 mmol) using chemistry similar to that described in Example Z8 (35 mg, 90% yield). $^1$H NMR (400 MHz, CDCl$_3$) δ 1.65 (3H, d, J=7.2 Hz), 1.97 (1H, m), 2.26 (1H, m), 3.75-4.10 (4H, m), 5.19-5.35 (2H, m), 5.43 (1H, m), 7.19 (1H, d, J=5.6 Hz), 7.45 (1H, m), 7.98 (1H, d, J=5.6 Hz), 8.36 (1H, m), 8.51 (1H, m) ppm. LCMS m/z=390.1 [M+H$^+$].

Example Z226. (S)-2-((1-(Pyridin-2-yl)ethyl)amino)-N-(2,2,2-trifluoroethyl)thieno[3,2-d]pyrimidine-4-carboxamide

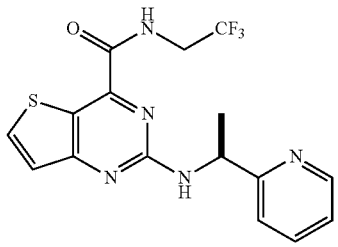

(Z226)

Synthesis of (S)-2-((1-(pyridin-2-yl)ethyl)amino)-N-(2,2,2-trifluoroethyl)thieno[3,2-d]pyrimidine-4-carboxamide (Z226): The title compound (Z226) was prepared from (S)-2-((1-(pyridin-2-yl)ethyl)amino)thieno[3,2-d]pyrimidine-4-carboxylic acid di-hydrochloride (37 mg, 0.1 mmol) using chemistry similar to that described in Example Z8 using 2-2,2,2-trifluoroethanamine hydrochloride in place of (R)-3-fluoropyrrolidine (28 mg, 73% yield). $^1$H NMR (400 MHz, CDCl$_3$) δ 1.63 (3H, d, J=6.8 Hz), 4.02-4.19 (2H, m), 5.24 (1H, m), 6.21 (1H, m), 7.18 (1H, ddd, J=8.0, 4.8, 1.6 Hz), 7.22 (1H, d, J=5.6 Hz), 7.36 (1H, d, J=8.0 Hz), 7.65 (1H, td, J=8.0, 1.6 Hz), 7.80 (1H, d, J=5.6 Hz), 8.17 (1H, m), 8.59 (1H, dt, J=4.8, 1.6 Hz) ppm. LCMS m/z=382.1 [M+H$^+$].

Example Z227. (S)-2-((1-(Pyridin-2-yl)ethyl)amino)-N-((tetrahydro-2H-pyran-4-yl)methyl)thieno[3,2-d]pyrimidine-4-carboxamide

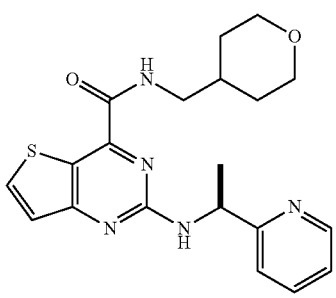 [SMILES: C[C@H](Nc1nc(C(=O)NCC2CCOCC2)c2sccc2n1)c1ccccn1]

(Z227)

Synthesis of (S)-2-((1-(pyridin-2-yl)ethyl)amino)-N-((tetrahydro-2H-pyran-4-yl)methyl)thieno[3,2-d]pyrimidine-4-carboxamide (Z227): The title compound (Z227) was prepared from (S)-2-((1-(pyridin-2-yl)ethyl)amino)thieno[3,2-d]pyrimidine-4-carboxylic acid di-hydrochloride and tetrahydropyran-4-ylmethanamine using chemistry similar to that described in Example Z8 (47% yield). LCMS m/z=398.1 [M+H$^+$].

Example Z228. tert-Butyl (R)-2-((2-(((S)-1-(pyridin-2-yl)ethyl)amino)thieno[3,2-d]pyrimidine-4-carboxamido)methyl)pyrrolidine-1-carboxylate

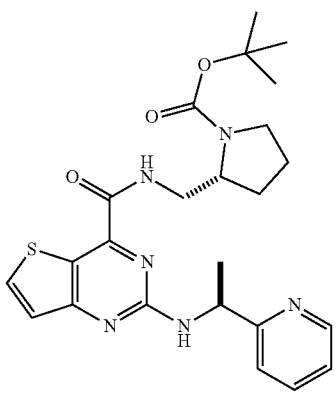

(Z228)

Synthesis of tert-butyl (R)-2-((2-(((S)-1-(pyridin-2-yl)ethyl)amino)thieno[3,2-d]pyrimidine-4-carboxamido)methyl)pyrrolidine-1-carboxylate (Z228): The title compound (Z228) was prepared from (S)-2-((1-(pyridin-2-yl)ethyl)amino)thieno[3,2-d]pyrimidine-4-carboxylic acid di-hydrochloride and tert-butyl (2R)-2-(aminomethyl)pyrrolidine-1-carboxylate (commercially obtained from Advanced ChemBlocks, Burlingame, Calif.) using chemistry similar to that described in Example Z8 (36% yield). LCMS m/z=483.2 [M+H$^+$].

Example Z229. tert-Butyl (R)-2-((2-(((5-fluoropyridin-3-yl)methyl)amino)thieno[3,2-d]pyrimidine-4-carboxamido)methyl)pyrrolidine-1-carboxylate

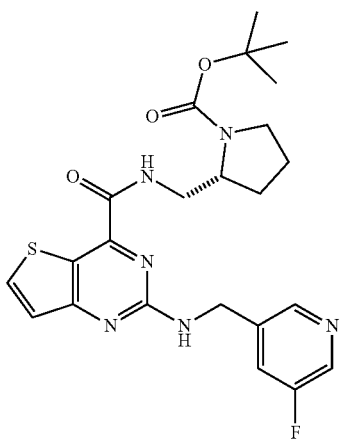

(Z229)

Synthesis of tert-butyl (R)-2-((2-(((5-fluoropyridin-3-yl)methyl)amino)thieno[3,2-d]pyrimidine-4-carboxamido)methyl)pyrrolidine-1-carboxylate (Z229): The title compound (Z229) was prepared from 2-(((5-fluoropyridin-3-yl)methyl)amino)thieno[3,2-d]pyrimidine-4-carboxylic acid using chemistry similar to that described in Example Z17 using tert-butyl (2R)-2-(aminomethyl)pyrrolidine-1-carboxylate in place of (3R)-3-methoxypyrrolidine hydrochloride (36% yield). LCMS m/z=383.2 [M+H$^+$].

Example Z230. (S)—N-(2-Hydroxy-2-methylpropyl)-2-((1-(pyridin-2-yl)ethyl)amino)thieno[3,2-d]pyrimidine-4-carboxamide

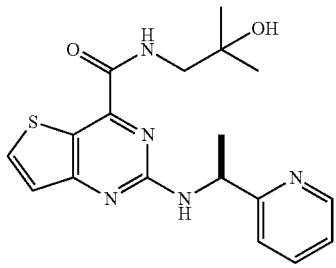 [SMILES: C[C@H](Nc1nc(C(=O)NCC(C)(C)O)c2sccc2n1)c1ccccn1]

(Z230)

Synthesis of (S)—N-(2-hydroxy-2-methylpropyl)-2-((1-(pyridin-2-yl)ethyl)amino)thieno[3,2-d]pyrimidine-4-carboxamide (Z230): The title compound (Z230) was prepared from (S)-2-((1-(pyridin-2-yl)ethyl)amino)thieno[3,2-d]pyrimidine-4-carboxylic acid di-hydrochloride (37 mg, 0.1 mmol) using chemistry similar to that described in Example Z8 using 1-amino-2-methyl-propan-2-ol in place of (R)-3-fluoropyrrolidine (25 mg, 67% yield). $^1$H NMR (400 MHz, CDCl$_3$) δ 1.39 (3H, s), 1.30 (3H, s), 1.62 (3H, d, J=6.8 Hz), 2.27 (1H, br s), 3.43-3.53 (2H, m), 5.27 (1H, m), 6.16 (1H, m), 7.18 (1H, ddd, J=8.0, 4.8, 1.2 Hz), 7.21 (1H, d, J=5.6 Hz), 7.37 (1H, d, J=8.0 Hz), 7.64 (1H, td, J=8.0, 1.6 Hz), 7.98 (1H, d, J=5.6 Hz), 8.28 (1H, m), 8.59 (1H, m) ppm. LCMS m/z=372.2 [M+H$^+$].

Example Z231. (S)-(2-((1-(5-Chloropyridin-3-yl)ethyl)amino)thieno[3,2-d]pyrimidin-4-yl)(pyrrolidin-1-yl)methanone

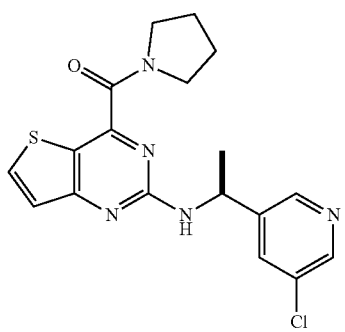 [SMILES: C[C@H](Nc1nc(C(=O)N2CCCC2)c2sccc2n1)c1cncc(Cl)c1]

(Z231)

Synthesis of ethyl (S)-2-((1-(5-chloropyridin-3-yl)ethyl)amino)thieno[3,2-d]pyrimidine-4-carboxylate: The title compound was prepared from ethyl 2-chlorothieno[3,2-d]pyrimidine-4-carboxylate (400 mg, 1.65 mmol) using chemistry similar to that described in Example Z12 using (1S)-1-(5-chloro-3-pyridyl)ethanamine (commercially obtained from Bellen, Shanghai, China) in place of (6-methoxypyridin-3-yl)methanamine hydrochloride (197 mg, 32% yield). LCMS m/z=363.0 [M+H$^+$].

Synthesis of (S)-(2-((1-(5-chloropyridin-3-yl)ethyl)amino)thieno[3,2-d]pyrimidin-4-yl)(pyrrolidin-1-yl)methanone (Z231): The title compound (Z231) was prepared from of ethyl (S)-2-((1-(5-chloropyridin-3-yl)ethyl)amino)thieno[3,2-d]pyrimidine-4-carboxylate using chemistry similar to that described in Example Z17 using pyrrolidine in place of (3R)-3-methoxypyrrolidine hydrochloride (77% yield). $^1$H NMR (400 MHz, CDCl$_3$) δ 1.63 (3H, d, J=6.8 Hz), 1.83-1.91 (4H, m), 3.50-3.60 (1H, m), 3.69 (2H, t, J=6.0, 6.8 Hz), 3.75-3.80 (1H, m), 5.16-5.21 (1H, m), 5.49 (1H, d, J=6.4 Hz), 7.18 (1H, d, J=5.6 Hz), 7.70 (1H, t, J=2.0, 1.6 Hz), 7.96 (1H, d, J=5.6 Hz), 8.44 (1H, d, J=2.4 Hz), 8.56 (1H, d, J=2.0 Hz) ppm. LCMS m/z=388.1 [M+H$^+$]

Example Z232. (S)-Azetidin-1-yl(2-((1-(5-chloropyridin-3-yl)ethyl)amino)thieno[3,2-d]pyrimidin-4-yl)methanone

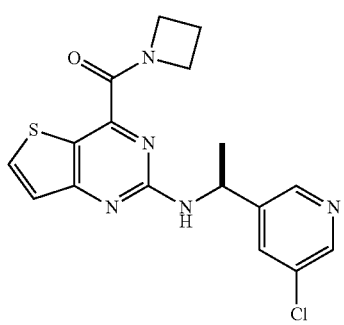 [SMILES: C[C@H](Nc1nc(C(=O)N2CCC2)c2sccc2n1)c1cncc(Cl)c1]

(Z232)

Synthesis of (S)-azetidin-1-yl(2-((1-(5-chloropyridin-3-yl)ethyl)amino)thieno[3,2-d]pyrimidin-4-yl)methanone (Z232): The title compound (Z232) was prepared from of ethyl (S)-2-((1-(5-chloropyridin-3-yl)ethyl)amino)thieno[3,2-d]pyrimidine-4-carboxylate using chemistry similar to that described in Example Z17 using azetidine in place of (3R)-3-methoxypyrrolidine hydrochloride (46% yield). ¹H NMR (400 MHz, CDCl₃) δ 1.63 (3H, d, J=7.6 Hz), 2.31-2.40 (2H, m), 4.25 (2H, t, J=8.0 Hz), 4.34-4.45 (1H, br s), 4.66-4.72 (1H, m), 5.26-5.25 (1H, m), 5.34 (1H, d, J=6.8 Hz), 7.16 (1H, d, J=5.6 Hz), 7.70 (1H, t, J=1.6 Hz), 7.97 (1H, d, J=5.6 Hz), 8.45 (1H, d, J=1.6 Hz), 8.55 (1H, d, J=2.0 Hz) ppm. LCMS m/z=374.0 [M+H⁺]

Example Z233. (S)-(2-((1-(5-Chloropyridin-3-yl)ethyl)amino)thieno[3,2-d]pyrimidin-4-yl)(3-methoxyazetidin-1-yl)methanone

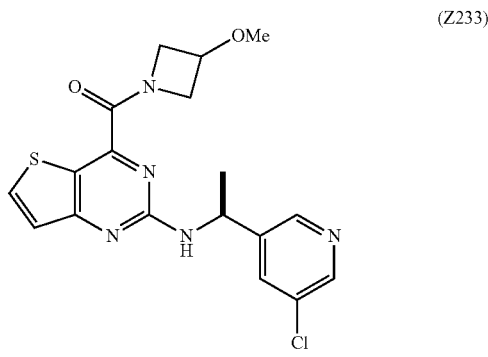

Synthesis of (S)-(2-((1-(5-chloropyridin-3-yl)ethyl)amino)thieno[3,2-d]pyrimidin-4-yl)(pyrrolidin-1-yl)methanone (Z233): The title compound (Z233) was prepared from of ethyl (S)-2-((1-(5-chloropyridin-3-yl)ethyl)amino)thieno[3,2-d]pyrimidine-4-carboxylate using chemistry similar to that described in Example Z17 using 3-methoxyazetidine hydrochloride in place of (3R)-3-methoxypyrrolidine hydrochloride (79% yield). ¹H NMR (400 MHz, CDCl₃) δ 1.64 (3H, d, J=7.2 Hz), 3.32 (3H, d, J=12.8 Hz), 4.07-4.11 (1H, m), 4.18-4.26 (2H, m), 4.35-4.41 (1H, m), 4.89-4.93 (1H, m), 5.19-5.23 (1H, m), 5.45 (1H, t, J=5.2 Hz), 7.18 (1H, dd, J=4.8, 0.8 Hz), 7.71 (1H, dd, J=4.0, 2.0 Hz), 7.98 (1H, dd, J=6.0, 2.0 Hz), 8.46 (1H, d, J=2.4 Hz), 8.56 (1H, dd, J=2.4, 2.0 Hz) ppm. LCMS m/z=404.1 [M+H⁺]

Example Z234. (2-(((S)-1-(5-Fluoropyridin-3-yl)ethyl)amino)thieno[3,2-d]pyrimidin-4-yl)((R)-3-fluoropyrrolidin-1-yl)methanone

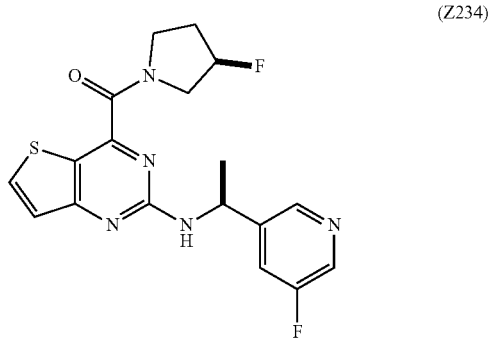

Synthesis of (2-(((S)-1-(5-fluoropyridin-3-yl)ethyl)amino)thieno[3,2-d]pyrimidin-4-yl)((R)-3-fluoropyrrolidin-1-yl)methanone (Z234): The title compound (Z234) was prepared from (S)-2-((1-(5-fluoropyridin-3-yl)ethyl)amino)thieno[3,2-d]pyrimidine-4-carboxylic acid di-hydrochloride (39 mg, 0.10 mmol) using chemistry similar to that described in Example Z8 (36 mg, 92% yield). ¹H NMR (400 MHz, CDCl₃) δ 1.65 (3H, d, J=6.8 Hz), 1.99 (1H, m), 2.29 (1H, m), 3.63-4.10 (4H, m), 5.19-5.35 (2H, m), 5.44 (1H, m), 7.19 (1H, d, J=5.6 Hz), 7.45 (1H, m), 7.97 (1H, d, J=5.6 Hz), 8.35 (1H, m), 8.52 (1H, m) ppm. LCMS m/z=390.2 [M+H⁺].

Example Z235. tert-Butyl (1-(2-(((5-fluoropyridin-3-yl)methyl)amino)thieno[3,2-d]pyrimidine-4-carbonyl)azetidin-3-yl)(methyl)carbamate

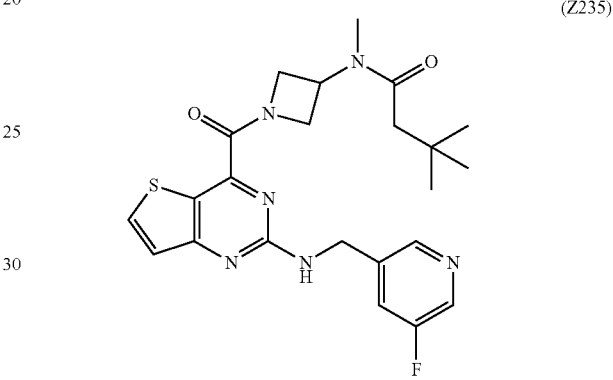

Synthesis of tert-butyl (1-(2-(((5-fluoropyridin-3-yl)methyl)amino)thieno[3,2-d]pyrimidine-4-carbonyl)azetidin-3-yl)(methyl)carbamate (Z235): The title compound (Z235) was prepared from 2-(((5-fluoropyridin-3-yl)methyl)amino)thieno[3,2-d]pyrimidine-4-carboxylic acid using chemistry similar to that described in Example Z17 using tert-butyl N-(azetidin-3-yl)-N-methyl-carbamate hydrochloride (commercially obtained from PharmaBlock, Sunnyvale, Calif.) in place of (3R)-3-methoxypyrrolidine hydrochloride (53% yield). LCMS m/z=473.1 [M+H⁺].

Example Z236. (2-(((S)-1-(5-Chloropyridin-3-yl)ethyl)amino)thieno[3,2-d]pyrimidin-4-yl)((S)-3-hydroxypyrrolidin-1-yl)methanone

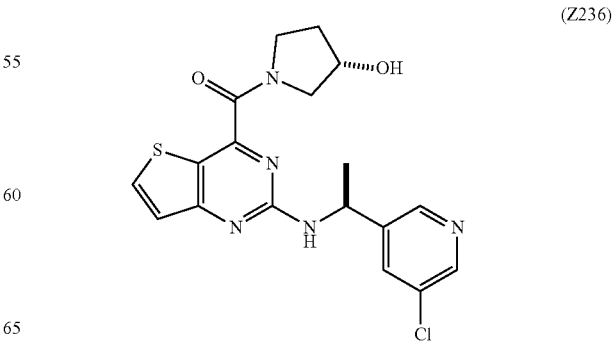

Synthesis of (2-(((S)-1-(5-chloropyridin-3-yl)ethyl)amino)thieno[3,2-d]pyrimidin-4-yl)((S)-3-hydroxypyrrolidin-1-yl)methanone (Z236): The title compound (Z236) was prepared from ethyl (S)-2-((1-(5-chloropyridin-3-yl)ethyl)amino)thieno[3,2-d]pyrimidine-4-carboxylate using chemistry similar to that described in Example Z17 using (3S)-pyrrolidin-3-ol in place of (3R)-3-methoxypyrrolidine hydrochloride (77% yield). $^1$H NMR (400 MHz, CDCl$_3$) δ 1.64 (3H, d, J=6.8 Hz), 1.93-2.03 (2H, m), 3.45-3.57 (1H, m), 3.76-3.79 (2H, m), 3.84 (2H, t, J=6.8 Hz), 4.41-4.55 (1H, m), 5.13-5.19 (1H, m), 5.56-5.60 (1H, m), 7.19 (1H, dd, J=4.8, 1.2 Hz), 7.71-7.76 (1H, m), 7.95-7.98 (1H, m), 8.44 (1H, d, J=2.4 Hz), 8.55 (1H, dd, J=7.2, 2.0 Hz) ppm. LCMS m/z=404.0 [M+H$^+$]

Example Z237. (2-(((S)-1-(5-Chloropyridin-3-yl)ethyl)amino)thieno[3,2-d]pyrimidin-4-yl)((R)-3-hydroxypyrrolidin-1-yl)methanone

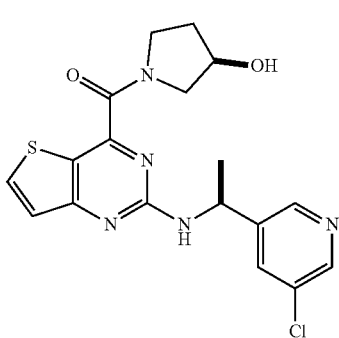 [SMILES: C[C@H](Nc1nc(C(=O)N2CC[C@@H](F)C2)c2sccc2n1)c1cncc(F)c1]

(Z237)

Synthesis of (2-(((S)-1-(5-chloropyridin-3-yl)ethyl)amino)thieno[3,2-d]pyrimidin-4-yl)((R)-3-hydroxypyrrolidin-1-yl)methanone (Z237): The title compound (Z237) was prepared from of ethyl (S)-2-((1-(5-chloropyridin-3-yl)ethyl)amino)thieno[3,2-d]pyrimidine-4-carboxylate using chemistry similar to that described in Example Z17 using (3R)-pyrrolidin-3-ol in place of (3R)-3-methoxypyrrolidine hydrochloride (77% yield). $^1$H NMR (400 MHz, CDCl$_3$) δ 1.64 (3H, d, J=6.8 Hz), 1.93-2.03 (2H, m), 3.55-3.70 (2H, m), 3.76-3.86 (3H, m), 4.41-4.55 (1H, m), 5.13-5.19 (1H, m), 5.56-5.60 (1H, m), 7.19 (1H, dd, J=4.8, 1.2 Hz), 7.72-7.76 (1H, m), 7.95-7.98 (1H, m), 8.44 (1H, m), 8.56-8.59 (1H, m) ppm. LCMS m/z=404.0 [M+H$^+$]

Example Z238. (S)-2-((1-(5-Fluoropyridin-3-yl)ethyl)amino)-N-(2-hydroxy-2-methylpropyl)thieno[3,2-d]pyrimidine-4-carboxamide

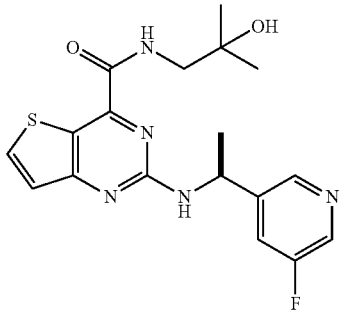 [SMILES: C[C@H](Nc1nc(C(=O)NCC(C)(C)O)c2sccc2n1)c1cncc(F)c1]

(Z238)

Synthesis of (S)-2-((1-(5-fluoropyridin-3-yl)ethyl)amino)-N-(2-hydroxy-2-methylpropyl)thieno[3,2-d]pyrimidine-4-carboxamide (Z238): The title compound (Z238) was prepared from (S)-2-((1-(5-fluoropyridin-3-yl)ethyl)amino)thieno[3,2-d]pyrimidine-4-carboxylic acid di-hydrochloride (39 mg, 0.10 mmol) using chemistry similar to that described in Example Z8 using 1-amino-2-methylpropan-2-ol in place of (S)-3-fluoropyrrolidine (26 mg, 67% yield). $^1$H NMR (400 MHz, CDCl$_3$) δ 1.21 (3H, s), 1.31 (3H, s), 1.65 (3H, d, J=6.8 Hz), 2.78 (1H, br s), 3.37 (1H, dd, J=13.6, 4.8 Hz), 3.56 (1H, dd, J=13.6, 7.2 Hz), 5.16 (1H, m), 5.55 (1H, d, J=5.6 Hz), 7.17 (1H, d, J=5.6 Hz), 7.47 (1H, dt, J=9.2, 1.6 Hz), 8.01 (1H, d, J=5.6 Hz), 8.04 (1H, m), 8.31 (1H, d, J=2.8 Hz), 8.60 (1H, t, J=1.6 Hz) ppm. LCMS m/z=390.2 [M+H$^+$].

Example Z239. tert-Butyl (R)-(1-(2-(((5-fluoropyridin-3-yl)methyl)amino)thieno[3,2-d]pyrimidine-4-carbonyl)pyrrolidin-3-yl)carbamate

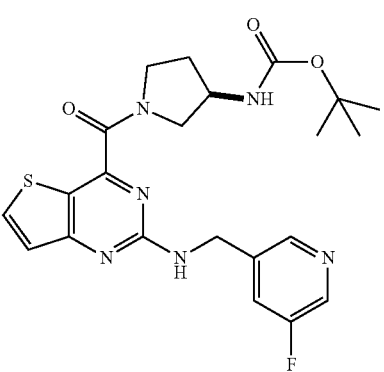

(Z239)

Synthesis of tert-butyl (R)-(1-(2-(((5-fluoropyridin-3-yl)methyl)amino)thieno[3,2-d]pyrimidine-4-carbonyl)pyrrolidin-3-yl)carbamate (Z239): The title compound (Z239) was prepared from 2-(((5-fluoropyridin-3-yl)methyl)amino)thieno[3,2-d]pyrimidine-4-carboxylic acid di-hydrochloride using chemistry similar to that described in Example Z17 using tert-butyl N-[(3S)-pyrrolidin-3-yl]carbamate (commercially obtained from CombiBlocks, San Diego Calif.) in place of (3R)-3-methoxypyrrolidine hydrochloride (76% yield). LCMS m/z=473.1 [M+H$^+$].

Example Z240. (S)-(3-Hydroxyazetidin-1-yl)(6-(methylamino)-2-((1-(pyridin-3-yl)ethyl)amino)thieno[3,2-d]pyrimidin-4-yl)methanone

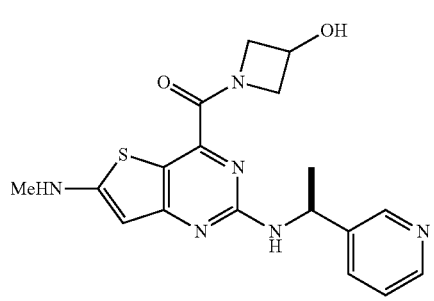 [SMILES: CNc1cc2nc(N[C@@H](C)c3cccnc3)nc(C(=O)N3CC(O)C3)c2s1]

(Z240)

Synthesis of (S)-(3-hydroxyazetidin-1-yl)(6-(methylamino)-2-((1-(pyridin-3-yl)ethyl)amino)thieno[3,2-d]pyrimidin-4-yl)methanone (Z240): The title compound (Z240) was prepared from 2,6-dichlorothieno[3,2-d]pyrimidine-4-carboxylic acid using chemistry similar to that described in Example Z152 using azetidin-3-ol in place of pyrrolidine. ¹H NMR (400 MHz, methanol-d₄) δ 1.60 (3H, d, J=7.2 Hz), 2.96 (3H, s), 3.89 (1H, m), 4.09 (1H, m), 4.33-4.61 (3H, m), 5.20 (1H, q, J=7.2 Hz), 5.80 (1H, s), 7.41 (1H, dd, J=8.0, 4.8 Hz), 7.89 (1H, m), 8.40 (1H, m), 8.60 (1H, s) ppm. LCMS m/z=385.1 [M+H⁺].

Example Z241. (S)-(6-Amino-2-((1-(5-fluoropyridin-3-yl)ethyl)amino)thieno[3,2-d]pyrimidin-4-yl)(azetidin-1-yl)methanone

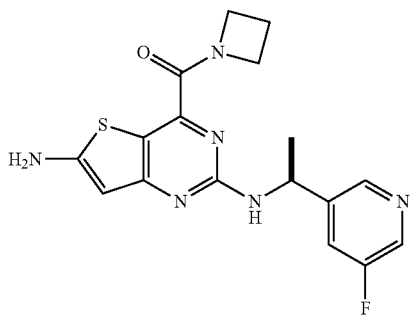 [SMILES: C[C@H](Nc1nc(C(=O)N2CCC2)c2sc(N)cc2n1)c1cncc(F)c1]

(Z241)

Synthesis of (S)-(6-amino-2-((1-(5-fluoropyridin-3-yl)ethyl)amino)thieno[3,2-d]pyrimidin-4-yl)(azetidin-1-yl)methanone (Z241): The title compound (Z241) was prepared from 2,6-dichlorothieno[3,2-d]pyrimidine-4-carboxylic acid using chemistry similar to that described in Example Z174 using azetidine in place of pyrrolidine. ¹H NMR (400 MHz, DMSO-d₆) δ 1.59 (3H, d, J=6.8 Hz), 2.27-2.40 (2H, m), 4.13-4.17 (2H, m), 4.36 (1H, m), 4.73 (1H, q, J=6.8 Hz), 5.20 (1H, q, J=6.8 Hz), 5.89 (1H, s), 7.68 (1H, m), 8.32 (1H, d, J=2.4 Hz), 8.47 (1H, s) ppm. LCMS m/z=373.1 [M+H⁺].

Example Z242. (6-Amino-2-(((S)-1-(5-fluoropyridin-3-yl)ethyl)amino)thieno[3,2-d]pyrimidin-4-yl)((R)-3-hydroxypyrrolidin-1-yl)methanone

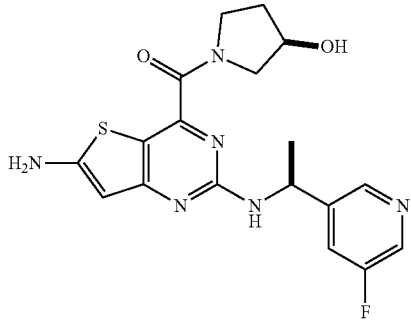 [SMILES: C[C@H](Nc1nc(C(=O)N2CC[C@@H](O)C2)c2sc(N)cc2n1)c1cncc(F)c1]

(Z242)

Synthesis of (6-amino-2-(((S)-1-(5-fluoropyridin-3-yl)ethyl)amino)thieno[3,2-d]pyrimidin-4-yl)((R)-3-hydroxypyrrolidin-1-yl)methanone (Z242): The title compound (Z242) was prepared from 2,6-dichlorothieno[3,2-d]pyrimidine-4-carboxylic acid using chemistry similar to that described in Example Z174 using (R)-pyrrolidin-3-ol in place of pyrrolidine. ¹H NMR (400 MHz, methanol-d₄) δ 1.60 (3H, d, J=6.8 Hz), 1.88-2.01 (2H, m), 3.59-3.74 (3H, m), 4.08 (1H, m), 4.41 (1H, m), 5.20 (1H, m), 5.90 (1H, s), 7.68 (1H, m), 8.32 (1H, d, J=2.8 Hz), 8.47 (1H, s) ppm. LCMS m/z=403.0 [M+H⁺].

Example Z243. (S)-(2-((1-(5-Fluoropyridin-3-yl)ethyl)amino)-6-(methylamino)thieno[3,2-d]pyrimidin-4-yl)(3-methoxyazetidin-1-yl)methanone

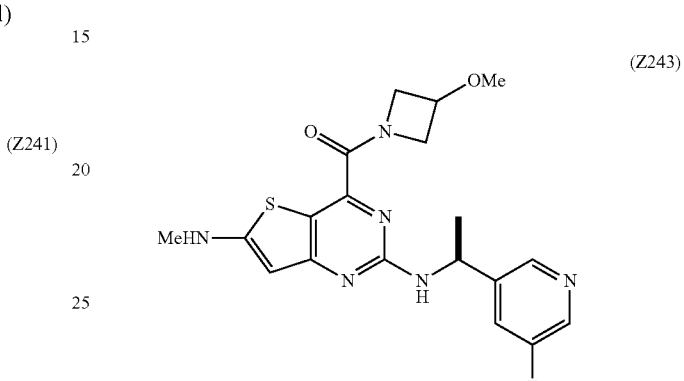

(Z243)

Synthesis of (S)-(2-((1-(5-fluoropyridin-3-yl)ethyl)amino)-6-(methylamino)thieno[3,2-d]pyrimidin-4-yl)(3-methoxyazetidin-1-yl)methanone (Z243): The title compound (Z243) was prepared from 2,6-dichlorothieno[3,2-d]pyrimidine-4-carboxylic acid using chemistry similar to that described in Example Z152 using 3-methoxyazetidine in place of pyrrolidine. ¹H NMR (400 MHz, DMSO-d₆) δ 1.47 (3H, d, J=7.2 Hz), 2.85 (3H, d, J=4.4 Hz), 3.24 (3H, s), 3.79 (1H, m), 4.17-4.21 (2H, m), 4.37 (1H, m), 4.84 (1H, m), 5.14 (1H, m), 5.70 (1H, s), 7.33 (1H, m), 7.70 (1H, m), 7.77 (1H, m), 8.40 (1H, d, J=2.8 Hz), 8.49 (1H, m) ppm. LCMS m/z=417.0 [M+H⁺].

Example Z244. (S)-(6-Methyl-2-((1-(pyridin-2-yl)ethyl)amino)thieno[3,2-d]pyrimidin-4-yl)(pyrrolidin-1-yl)methanone

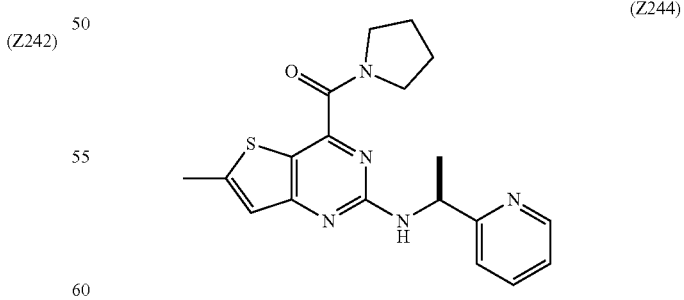

(Z244)

Synthesis of (S)-(6-chloro-2-((1-(pyridin-2-yl)ethyl)amino)thieno[3,2-d]pyrimidin-4-yl)(pyrrolidin-1-yl)methanone: To a solution of (2,6-dichlorothieno[3,2-d]pyrimidin-4-yl)(pyrrolidin-1-yl)methanone (500 mg, 1.65 mmol) in NMP (15 mL) were added (1S)-1-(pyridin-2-yl)ethan-1-amine (303 mg, 2.48 mmol) and DIEA (640 mg, 4.95 mmol). The resulting solution was stirred for 2 h at 120° C. under microwave irradiation. The reaction mixture was diluted with 100 mL of ethyl acetate and was washed with water (3×100 mL) and brine (1×100 mL), then was dried over anhydrous sodium sulfate. The solvent was evaporated under vacuum and the residue was purified column chromatography on silica gel eluting with 5% methanol in DCM to provide (S)-(6-chloro-2-((1-(pyridin-2-yl)ethyl)amino)thieno[3,2-d]pyrimidin-4-yl)(pyrrolidin-1-yl)methanone as yellow solid (335 mg, 52% yield). LCMS m/z=388.3 [M+H$^+$].

Synthesis of (S)-(6-methyl-2-((1-(pyridin-2-yl)ethyl)amino)thieno[3,2-d]pyrimidin-4-yl)(pyrrolidin-1-yl)methanone (Z244): The title compound (Z244) was prepared from (S)-(6-chloro-2-((1-(pyridin-2-yl)ethyl)amino)thieno[3,2-d]pyrimidin-4-yl)(pyrrolidin-1-yl)methanone using chemistry similar to that described in Example Z213. $^1$H NMR (400 MHz, methanol-d$_4$) δ 1.61 (3H, d, J=7.2 Hz), 1.86-1.90 (4H, m), 2.61 (3H, s), 3.39 (1H, m), 3.49-3.51 (2H, m), 3.72 (1H, m), 5.16 (1H, q, J=7.2 Hz), 6.90 (1H, s), 7.28 (1H, m), 7.51 (1H, d, J=8.0 Hz), 7.77 (1H, m), 8.51 (1H, m) ppm. LCMS m/z=368.0 [M+H$^+$].

Example Z245. tert-Butyl (S)-(1-(2-(((5-fluoropyridin-3-yl)methyl)amino)thieno[3,2-d]pyrimidine-4-carbonyl)pyrrolidin-3-yl)carbamate

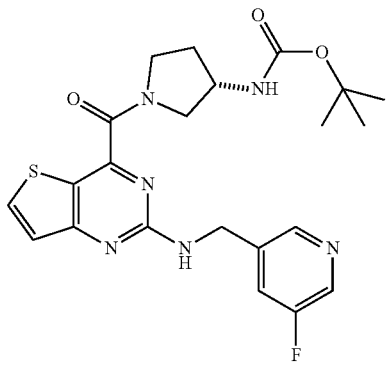
(Z245)

Synthesis of tert-butyl (S)-(1-(2-(((5-fluoropyridin-3-yl)methyl)amino)thieno[3,2-d]pyrimidine-4-carbonyl)pyrrolidin-3-yl)carbamate (Z245): The title compound (Z245) was prepared from 2-(((5-fluoropyridin-3-yl)methyl)amino)thieno[3,2-d]pyrimidine-4-carboxylic acid di-hydrochloride using chemistry similar to that described in Example Z17 using tert-butyl N-[(3S)-pyrrolidin-3-yl]carbamate (commercially obtained from CombiBlocks, San Diego, Calif.) in place of (3R)-3-methoxypyrrolidine hydrochloride (76% yield). LCMS m/z=473.1 [M+H$^+$].

Example Z246. tert-Butyl ((R)-1-(2-(((S)-1-(pyridin-2-yl)ethyl)amino)thieno[3,2-d]pyrimidine-4-carbonyl)pyrrolidin-3-yl)carbamate

(Z246)

Synthesis of tert-butyl ((R)-1-(2-(((S)-1-(pyridin-2-yl)ethyl)amino)thieno[3,2-d]pyrimidine-4-carbonyl)pyrrolidin-3-yl)carbamate (Z246): The title compound (Z246) was prepared from (S)-2-((1-(pyridin-2-yl)ethyl)amino)thieno[3,2-d]pyrimidine-4-carboxylic acid di-hydrochloride using chemistry similar to that described in Example Z17 using tert-butyl N-[(3R)-pyrrolidin-3-yl]carbamate (commercially obtained from CombiBlocks, San Diego, Calif.) in place of (3R)-3-methoxypyrrolidine hydrochloride (76% yield). LCMS m/z=473.1 [M+H$^+$].

Example Z247. ((R)-3-Methoxypyrrolidin-1-yl)(2-(((S)-1-(pyridin-2-yl)ethyl)amino)thieno[3,2-d]pyrimidin-4-yl)methanone

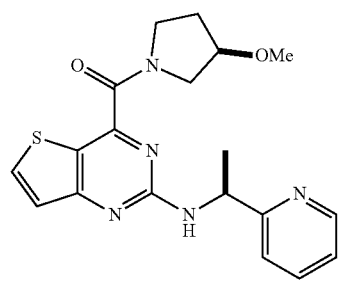
(Z247)

Synthesis of ((R)-3-methoxypyrrolidin-1-yl)(2-(((S)-1-(pyridin-2-yl)ethyl)amino)thieno[3,2-d]pyrimidin-4-yl)methanone (Z247): The title compound (Z247) was prepared from (S)-2-((1-(pyridin-2-yl)ethyl)amino)thieno[3,2-d]pyrimidine-4-carboxylic acid di-hydrochloride using chemistry similar to that described in Example Z17 using (3S)-3-methoxypyrrolidine hydrochloride (commercially obtained from Enamine, Monmouth Jct., N.J.) in place of (3R)-3-methoxypyrrolidine hydrochloride (29% yield). LCMS m/z=384.1 [M+H$^+$].

Example Z248. (S)-(6-Amino-2-((1-(pyridin-3-yl)ethyl)amino)thieno[3,2-d]pyrimidin-4-yl)(3-hydroxyazetidin-1-yl)methanone

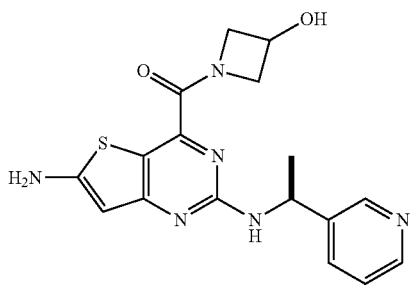 [SMILES: C[C@H](Nc1nc(C(=O)N2CC(O)C2)c2sc(N)cc2n1)c1cccnc1]

(Z248)

Synthesis of (S)-(6-amino-2-((1-(pyridin-3-yl)ethyl)amino)thieno[3,2-d]pyrimidin-4-yl)(3-hydroxyazetidin-1-yl)methanone (Z248): The title compound (Z248) was prepared from 2,6-dichlorothieno[3,2-d]pyrimidine-4-carboxylic acid using chemistry similar to that described in Example Z174 using azetidin-3-ol in place of pyrrolidine. $^1$H NMR (400 MHz, methanol-$d_4$) δ 1.60 (3H, d, J=7.2 Hz), 3.89 (1H, m), 4.09 (1H, m), 4.35 (1H, m), 4.36-4.60 (2H, m), 5.19 (1H, q, J=7.2 Hz), 5.88 (1H, s), 7.41 (1H, dd, J=8.0, 4.8 Hz), 7.89 (1H, m), 8.40 (1H, dd, J=4.8, 1.2 Hz), 8.59 (1H, d, J=1.2 Hz) ppm. LCMS m/z=371.1 [M+H$^+$].

Example Z249. (2-(((S)-1-(5-Fluoropyridin-3-yl)ethyl)amino)-6-methylthieno[3,2-d]pyrimidin-4-yl)((S)-3-hydroxypyrrolidin-1-yl)methanone

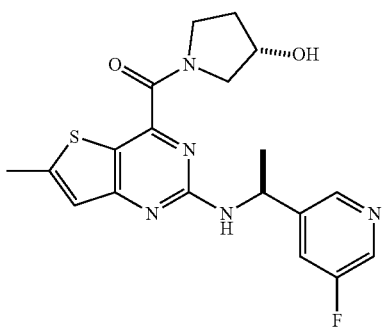 [SMILES: Cc1cc2nc(N[C@@H](C)c3cncc(F)c3)nc(C(=O)N3CC[C@H](O)C3)c2s1]

(Z249)

Synthesis of (6-chloro-2-(((S)-1-(5-fluoropyridin-3-yl)ethyl)amino)thieno[3,2-d]pyrimidin-4-yl)((S)-3-hydroxypyrrolidin-1-yl)methanone: The title compound was prepared from 2,6-dichlorothieno[3,2-d]pyrimidine-4-carboxylic acid using chemistry similar to that described in Example Z152 using (S)-pyrrolidin-3-ol in place of pyrrolidine. LCMS m/z=422.3 [M+H$^+$].

Synthesis of (2-(((S)-1-(5-fluoropyridin-3-yl)ethyl)amino)-6-methylthieno[3,2-d]pyrimidin-4-yl)((S)-3-hydroxypyrrolidin-1-yl)methanone (Z249): The title compound (Z249) was prepared from (6-chloro-2-(((S)-1-(5-fluoropyridin-3-yl)ethyl)amino)thieno[3,2-d]pyrimidin-4-yl)((S)-3-hydroxypyrrolidin-1-yl)methanone using chemistry similar to that described in Example Z213. $^1$H NMR (300 MHz, methanol-$d_4$) δ 1.61 (3H, d, J=7.2 Hz), 1.94-2.03 (2H, m), 2.60 (3H, s), 3.35-3.79 (4H, m), 4.39 (1H, m), 5.25 (1H, q, J=7.2 Hz), 6.90 (1H, s), 7.71 (1H, m), 8.31 (1H, m), 8.50 (1H, m) ppm. LCMS m/z=402.1 [M+H$^+$].

Example Z250. (2-(((S)-1-(5-Fluoropyridin-3-yl)ethyl)amino)-6-methylthieno[3,2-d]pyrimidin-4-yl)((R)-3-hydroxypyrrolidin-1-yl)methanone

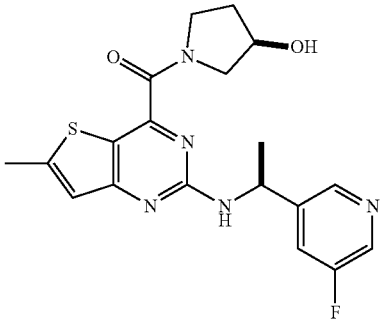 [SMILES: Cc1cc2nc(N[C@@H](C)c3cncc(F)c3)nc(C(=O)N3CC[C@@H](O)C3)c2s1]

(Z250)

Synthesis of (6-chloro-2-(((S)-1-(5-fluoropyridin-3-yl)ethyl)amino)thieno[3,2-d]pyrimidin-4-yl)((R)-3-hydroxypyrrolidin-1-yl)methanone: The title compound was prepared from 2,6-dichlorothieno[3,2-d]pyrimidine-4-carboxylic acid using chemistry similar to that described in Example Z152 using (R)-pyrrolidin-3-ol in place of pyrrolidine. LCMS m/z=422.3 [M+H$^+$].

Synthesis of (2-(((S)-1-(5-fluoropyridin-3-yl)ethyl)amino)-6-methylthieno[3,2-d]pyrimidin-4-yl)((R)-3-hydroxypyrrolidin-1-yl)methanone (Z250): The title compound (Z250) was prepared from (6-chloro-2-(((S)-1-(5-fluoropyridin-3-yl)ethyl)amino)thieno[3,2-d]pyrimidin-4-yl)((R)-3-hydroxypyrrolidin-1-yl)methanone using chemistry similar to that described in Example Z213. $^1$H NMR (400 MHz, methanol-$d_4$) δ 1.63 (3H, d, J=7.2 Hz), 1.98-2.06 (2H, m), 2.60 (3H, s), 3.68 (1H, m), 3.76-3.85 (2H, m), 4.07 (1H, m), 4.45 (1H, m), 5.25 (1H, q, J=7.2 Hz), 6.90 (1H, s), 7.72 (1H, m), 8.32 (1H, m), 8.51 (1H, m) ppm. LCMS m/z=402.1 [M+H$^+$].

Example Z251. (2-(((S)-1-(5-Fluoropyridin-3-yl)ethyl)amino)thieno[3,2-d]pyrimidin-4-yl)((R)-3-methoxypyrrolidin-1-yl)methanone

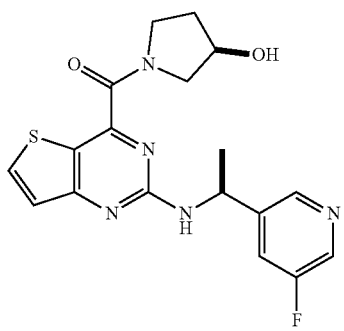

(Z251)

Synthesis of (2-(((S)-1-(5-fluoropyridin-3-yl)ethyl)amino)thieno[3,2-d]pyrimidin-4-yl)((R)-3-methoxypyrrolidin-1-yl)methanone (Z251): The title compound (Z251) was prepared from (S)-2-((1-(5-fluoropyridin-3-yl)ethyl)amino)thieno[3,2-d]pyrimidine-4-carboxylic acid di-hydrochloride (39 mg, 0.10 mmol) using chemistry similar to that described in Example Z8 using (3R)-3-methoxypyrrolidine hydrochloride in place of (R)-3-fluoropyrrolidine (32 mg, 80% yield). ¹H NMR (400 MHz, CDCl₃) δ 1.62-1.65 (3H, m), 1.92 (1H, m), 2.06 (1H, m), 3.35 (3H, s), 3.64-3.89 (4H, m), 3.98 (1H, m), 5.24 (1H, m), 5.42 (1H, m), 7.18 (1H, d, J=5.6 Hz), 7.45 (1H, m), 7.96 (1H, m), 8.34 (1H, d, J=2.4 Hz), 8.52 (1H, m) ppm. LCMS m/z=402.2 [M+H⁺].

Example Z252. (2-(((S)-1-(5-Fluoropyridin-3-yl)ethyl)amino)thieno[3,2-d]pyrimidin-4-yl)((S)-3-methoxypyrrolidin-1-yl)methanone

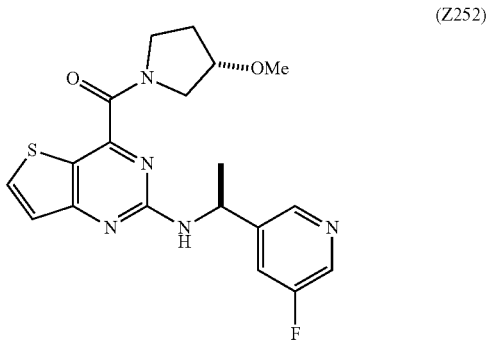

(Z252)

Synthesis of (2-(((S)-1-(5-fluoropyridin-3-yl)ethyl)amino)thieno[3,2-d]pyrimidin-4-yl)((S)-3-methoxypyrrolidin-1-yl)methanone (Z252): The title compound (Z252) was prepared from (S)-2-((1-(5-fluoropyridin-3-yl)ethyl)amino)thieno[3,2-d]pyrimidine-4-carboxylic acid di-hydrochloride (39 mg, 0.10 mmol) using chemistry similar to that described in Example Z8 using (3S)-3-methoxypyrrolidine hydrochloride in place of (R)-3-fluoropyrrolidine (32 mg, 80% yield). ¹H NMR (400 MHz, CDCl₃) δ 1.62-1.65 (3H, m), 1.91 (1H, m), 2.06 (1H, m), 3.35 (3H, s), 3.67-3.91 (4H, m), 3.97 (1H, m), 5.23 (1H, m), 5.42 (1H, m), 7.18 (1H, d, J=5.6 Hz), 7.44 (1H, m), 7.96 (1H, m), 8.34 (1H, m), 8.51 (1H, m) ppm. LCMS m/z=402.1 [M+H⁺].

Example Z253. (2-(((S)-1-(5-Chloropyridin-3-yl)ethyl)amino)thieno[3,2-d]pyrimidin-4-yl)((R)-3-methoxypyrrolidin-1-yl)methanone

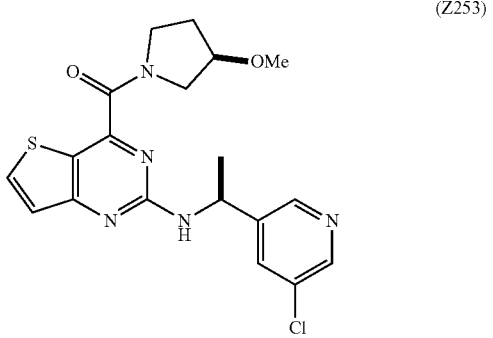

(Z253)

Synthesis of (2-(((S)-1-(5-chloropyridin-3-yl)amino)thieno[3,2-d]pyrimidin-4-yl)((R)-3-methoxypyrrolidin-1-yl)methanone (Z253): The title compound (Z253) was prepared from ethyl (S)-2-((1-(5-chloropyridin-3-yl)ethyl)amino)thieno[3,2-d]pyrimidine-4-carboxylate using chemistry similar to that described in Example Z17 using (3R)-3-methoxypyrrolidine in place of (3R)-3-methoxypyrrolidine hydrochloride (29% yield). ¹H NMR (400 MHz, CDCl₃) δ 1.65 (3H, dd, J=6.8, 2.8 Hz), 1.80-1.95 (1H, m), 2.01-2.12 (1H, m), 3.34 (3H, d, J=1.2 Hz), 3.64-3.90 (4H, m), 3.96-3.99 (1H, m), 5.20 (1H, q, J=6.8 Hz), 5.69 (1H, br s), 7.20-7.22 (1H, m), 7.71-7.74 (1H, m), 7.98 (1H, dt, J=6.4, 0.8 Hz), 8.45 (1H, m), 8.55-8.57 (1H, m) ppm. LCMS m/z=418.1 [M+H⁺]

Example Z254. (2-(((S)-1-(5-Chloropyridin-3-yl)ethyl)amino)thieno[3,2-d]pyrimidin-4-yl)((S)-3-methoxypyrrolidin-1-yl)methanone

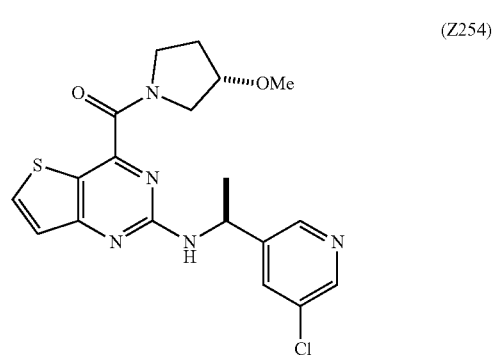

(Z254)

Synthesis of (2-(((S)-1-(5-chloropyridin-3-yl)ethyl)amino)thieno[3,2-d]pyrimidin-4-yl)((S)-3-methoxypyrrolidin-1-yl)methanone (Z254): The title compound (Z254) was prepared from ethyl (S)-2-((1-(5-chloropyridin-3-yl)ethyl)amino)thieno[3,2-d]pyrimidine-4-carboxylate using chemistry similar to that described in Example Z17 using (3S)-3-methoxypyrrolidine in place of (3R)-3-methoxypyrrolidine hydrochloride (55% yield). ¹H NMR (400 MHz, CDCl₃) δ 1.65 (3H, dd, J=6.8, 2.4 Hz), 1.80-1.98 (1H, m), 2.04 (1H, m), 3.19 (1H, s), 3.33 (2H, d, J=6.8 Hz), 3.60-3.85 (4H, m), 3.95 (1H, m), 5.17 (1H, q, J=5.6 Hz), 5.69 (1H, br s), 7.19-7.21 (1H, m), 7.70-7.72 (1H, m), 7.96 (1H, t, J=5.6 Hz), 8.45 (1H, m), 8.55-8.57 (1H, m) ppm. LCMS m/z=418.1 [M+H⁺]

Example Z255. ((S)-3-Methoxypyrrolidin-1-yl)(2-(((S)-1-(pyridin-2-yl)ethyl)amino)thieno[3,2-d]pyrimidin-4-yl)methanone

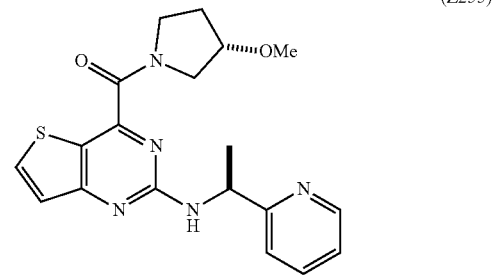

(Z255)

Synthesis of ((S)-3-methoxypyrrolidin-1-yl)(2-(((S)-1-(pyridin-2-yl)ethyl)amino)thieno[3,2-d]pyrimidin-4-yl)methanone (Z255): The title compound (Z255) was prepared from (S)-2-((1-(pyridin-2-yl)ethyl)amino)thieno[3,2-d]pyrimidine-4-carboxylic acid di-hydrochloride using chemistry similar to that described in Example Z17 using (3S)-3-methoxypyrrolidine hydrochloride (commercially obtained from Enamine, Monmouth Jct., N.J.) in place of (3R)-3-methoxypyrrolidine hydrochloride (15% yield). LCMS m/z=384.2 [M+H$^+$].

Example Z256. ((R)-3-(Methylsulfonyl)pyrrolidin-1-yl)(2-(((S)-1-(pyridin-2-yl)ethyl)amino)thieno[3,2-d]pyrimidin-4-yl)methanone

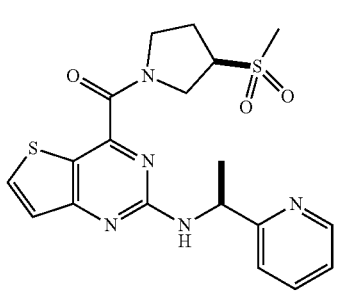 [SMILES: C[C@H](Nc1nc(C(=O)N2CC[C@@H](S(C)(=O)=O)C2)c2sccc2n1)c1ccccn1]
(Z256)

Synthesis of ((R)-3-(methylsulfonyl)pyrrolidin-1-yl)(2-(((S)-1-(pyridin-2-yl)ethyl)amino)thieno[3,2-d]pyrimidin-4-yl)methanone (Z256): The title compound (Z256) was prepared from (S)-2-((1-(pyridin-2-yl)ethyl)amino)thieno[3,2-d]pyrimidine-4-carboxylic acid di-hydrochloride using chemistry similar to that described in Example Z17 using (3R)-3-methyl-sulfonylpyrrolidine (commercially obtained from Enamine, Monmouth Jct., N.J.) in place of (3R)-3-methoxypyrrolidine hydrochloride (15% yield). $^1$H NMR (400 MHz, CDCl$_3$) δ 1.62 (3H, d, J=6.8 Hz), 2.35-2.59 (3H, m), 2.96 (3H, d, J=12 Hz), 3.62-4.02 (2H, m), 4.16 (1H, d, J=7.2 Hz), 4.35-4.52 (1H, m), 4.58-4.65 (1H, m), 5.18-5.30 (1H, m), 6.13-6.20 (1H, m), 7.20 (1H, dd, J=5.2, 0.4 Hz), 7.34-7.43 (1H, m), 7.96 (1H, qd, J=7.6, 2.0 Hz), 8.45 (1H, dd, J=5.6, 1.6 Hz), 8.57-8.58 (1H, m) ppm. LCMS m/z=384.2 [M+H$^+$].

Example Z257. Azetidin-1-yl(2-(((5-(trifluoromethyl)pyridin-3-yl)methyl)amino)thieno[3,2-d]pyrimidin-4-yl)methanone

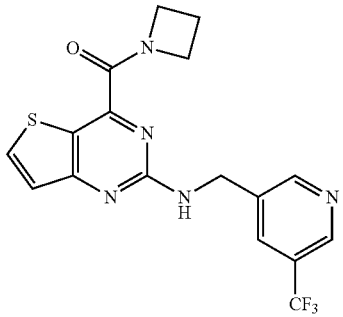 [SMILES: O=C(c1nc(NCc2cncc(C(F)(F)F)c2)nc2ccsc12)N1CCC1]
(Z257)

Synthesis of azetidin-1-yl(2-(((5-(trifluoromethyl)pyridin-3-yl)methyl)amino)thieno[3,2-d]pyrimidin-4-yl)methanone (Z257): The title compound (Z257) was prepared from ethyl 2-(((5-(trifluoromethyl)pyridin-3-yl)methyl)amino)thieno[3,2-d]pyrimidine-4-carboxylate using chemistry similar to that described in Example Z17 using azetidine in place of (3R)-3-methoxy-pyrrolidine hydrochloride (32% yield). $^1$H NMR (400 MHz, CDCl$_3$) δ 2.37 (2H, q, J=3.6 Hz), 4.27 (2H, t, J=6.4 Hz), 4.66 (2H, t, J=7.6 Hz), 4.82 (2H, d, J=6.0 Hz), 5.23 (1H, t, J=6.0 Hz), 7.21 (1H, d, J=5.6 Hz), 7.96 (1H, m), 8.00 (1H, d, J=2.0 Hz), 8.80 (1H, d, J=1.2 Hz), 8.84 (1H, d, J=1.6 Hz) ppm. LCMS m/z=394.1 [M+H$^+$].

Example Z258. (2-(Phenethylamino)thieno[3,2-d]pyrimidin-4-yl)(pyrrolidin-1-yl)methanone

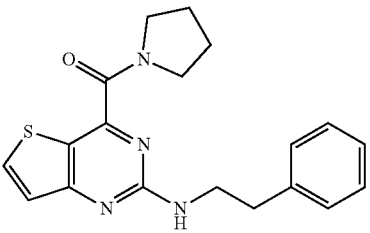 [SMILES: O=C(c1nc(NCCc2ccccc2)nc2ccsc12)N1CCCC1]
(Z258)

Synthesis of (2-(phenethylamino)thieno[3,2-d]pyrimidin-4-yl)(pyrrolidin-1-yl)methanone (Z258): To a solution of (2-chlorothieno[3,2-d]pyrimidin-4-yl)(pyrrolidin-1-yl)methanone (267 mg, 1.0 mmol) in NMP (3 mL) were added 2-phenylethan-1-amine (363 mg, 3.0 mmol) and DIEA (387 mg, 3.0 mmol). The resulting solution was stirred for 2 h at 130° C. in an oil bath. The resulting mixture was concentrated under vacuum and the residue was purified by prep-HPLC (C-18 OBD column and a gradient elution system of water-acetonitrile) to provide (2-(phenethylamino)thieno[3,2-d]pyrimidin-4-yl)(pyrrolidin-1-yl)methanone as an yellow solid (270 mg, 77% yield). $^1$H NMR (400 MHz, methanol-d$_4$) δ 1.94-2.05 (4H, m), 2.96 (2H, t, J=7.2 Hz), 3.68-3.73 (4H, m), 4.03-4.07 (2H, m), 7.17-7.20 (2H, m), 7.23-7.31 (4H, m), 8.12 (1H, d, J=6.4 Hz) ppm. LCMS m/z=353.1 [M+H$^+$].

Example Z259. ((S)-3-(Hydroxymethyl)pyrrolidin-1-yl)(2-(((S)-1-(pyridin-3-yl)ethyl)amino)thieno[3,2-d]pyrimidin-4-yl)methanone

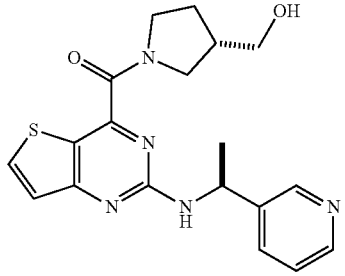 [SMILES: C[C@H](Nc1nc(C(=O)N2CC[C@H](CO)C2)c2sccc2n1)c1cccnc1]
(Z259)

Synthesis of ((S)-3-(hydroxymethyl)pyrrolidin-1-yl)(2-(((S)-1-(pyridin-3-yl)ethyl)amino)thieno[3,2-d]pyrimidin- 4-yl)methanone (Z259): The title compound (Z259) was prepared from (S)-2-((1-(pyridin-3-yl)ethyl)amino)thieno[3,2-d]pyrimidine-4-carboxylic acid di-hydrochloride (37 mg, 0.10 mmol) using chemistry similar to that described in Example Z8 using (S)-pyrrolidin-3-ylmethanol (commercially obtained from Ark Pharm, Libertyville, Ill.) in place of (R)-3-fluoropyrrolidine (22 mg, 57% yield). ¹H NMR (400 MHz, CDCl₃) δ 1.62 (3H, d, J=6.8 Hz), 1.72 (1H, m), 1.96 (1H, m), 2.44 (1H, m), 3.22-3.53 (2H, m), 3.61-3.71 (3H, m), 3.81 (1H, m), 5.18 (1H, m), 5.47 (1H, d, J=6.2 Hz), 7.17 (1H, d, J=5.6 Hz), 7.25 (1H, m), 7.73 (1H, dt, J=8.0, 2.0 Hz), 7.95 (1H, d, J=5.6 Hz), 8.47 (1H, m), 8.68 (1H, m) ppm. LCMS m/z=384.2 [M+H⁺].

Example Z260. ((R)-3-(Hydroxymethyl)pyrrolidin-1-yl)(2-(((S)-1-(pyridin-3-yl)ethyl)amino)thieno[3,2-d]pyrimidin-4-yl)methanone

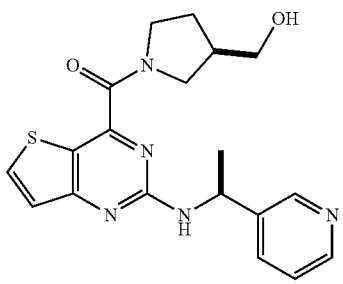 [SMILES: C[C@H](Nc1nc(C(=O)N2CC[C@@H](CO)C2)c2sccc2n1)c1cccnc1]

(Z260)

Synthesis of ((R)-3-(hydroxymethyl)pyrrolidin-1-yl)(2-(((S)-1-(pyridin-3-yl)ethyl)amino)thieno[3,2-d]pyrimidin-4-yl)methanone (Z260): The title compound (Z260) was prepared from (S)-2-((1-(pyridin-3-yl)ethyl)amino)thieno[3,2-d]pyrimidine-4-carboxylic acid di-hydrochloride (37 mg, 0.10 mmol) using chemistry similar to that described in Example Z8 using (R)-pyrrolidin-3-ylmethanol (commercially obtained from Ark Pharm, Libertyville, Ill.) in place of (R)-3-fluoropyrrolidine (23 mg, 60% yield). ¹H NMR (400 MHz, CDCl₃) δ 1.62 (3H, d, J=7.2 Hz), 1.73 (1H, m), 1.96 (1H, m), 2.25 (1H, m), 3.44-3.55 (2H, m), 3.58-3.71 (3H, m), 3.80 (1H, m), 5.18 (1H, quintet, J=7.2 Hz), 5.48 (1H, d, J=7.2 Hz), 7.17 (1H, d, J=5.6 Hz), 7.26 (1H, m), 7.74 (1H, dt, J=8.0, 1.6 Hz), 7.95 (1H, d, J=5.6 Hz), 8.47 (1H, dd, J=4.8, 1.6 Hz), 8.68 (1H, d, J=2.8 Hz) ppm. LCMS m/z=384.2 [M+H⁺].

Example Z261. (R)-(2-(((5-Fluoropyridin-3-yl)methyl)amino)thieno[3,2-d]pyrimidin-4-yl)(3-(methylsulfonyl)pyrrolidin-1-yl)methanone

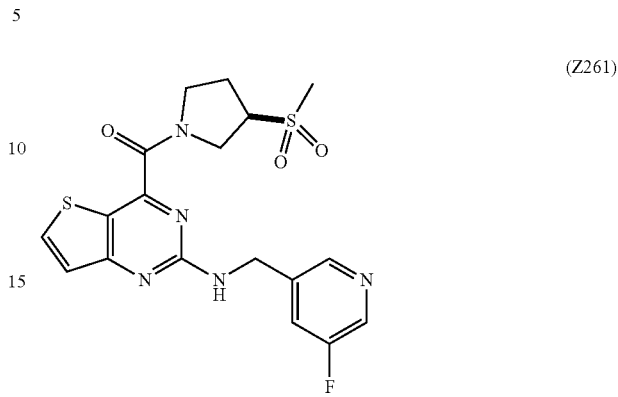

(Z261)

Synthesis of (R)-(2-(((5-fluoropyridin-3-yl)methyl)amino)thieno[3,2-d]pyrimidin-4-yl)(3-(methylsulfonyl)pyrrolidin-1-yl)methanone (Z261): The title compound (Z261) was prepared from 2-(((5-fluoropyridin-3-yl)methyl)amino)thieno[3,2-d]pyrimidine-4-carboxylic acid di-hydrochloride using chemistry similar to that described in Example Z17 using (3R)-3-methylsulfonylpyrrolidine (commercially obtained from CombiBlocks, San Diego Calif.) in place of (3R)-3-methoxypyrrolidine hydrochloride (52% yield). LCMS m/z=436.1 [M+H⁺].

Example Z262. ((R)-3-(Methylsulfonyl)pyrrolidin-1-yl)(2-(((S)-1-(pyridin-3-yl)ethyl)amino)thieno[3,2-d]pyrimidin-4-yl)methanone

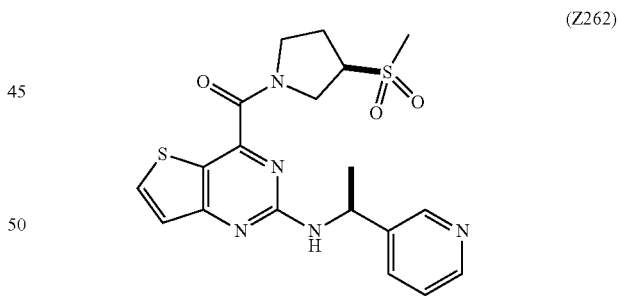

(Z262)

Synthesis of ((R)-3-(methylsulfonyl)pyrrolidin-1-yl)(2-(((S)-1-(pyridin-3-yl)ethyl)amino)thieno[3,2-d]pyrimidin-4-yl)methanone (Z262): The title compound (Z262) was prepared from (S)-2-((1-(pyridin-3-yl)ethyl)amino)thieno[3,2-d]pyrimidine-4-carboxylic acid di-hydrochloride using chemistry similar to that described in Example Z17 using (3R)-3-methylsulfonylpyrrolidine (commercially obtained from Enamine, Monmouth Jct., N.J.) in place of (3R)-3-methoxypyrrolidine hydrochloride (56% yield). LCMS m/z=432.1 [M+H⁺].

Example Z263. (S)-2-((1-(5-Fluoropyridin-3-yl)ethyl)amino)-N-(2,2,2-trifluoroethyl)thieno[3,2-d]pyrimidine-4-carboxamide

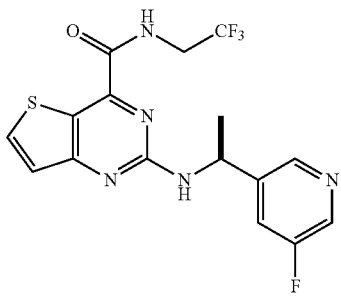 [SMILES: C[C@H](Nc1nc(C(=O)NCC(F)(F)F)c2sccc2n1)c1cncc(F)c1]

Synthesis of (S)-2-((1-(5-fluoropyridin-3-yl)ethyl)amino)-N-(2,2,2-trifluoroethyl)thieno[3,2-d]pyrimidine-4-carboxamide (Z263): The title compound (Z263) was prepared from (S)-2-((1-(5-fluoropyridin-3-yl)ethyl)amino)thieno[3,2-d]pyrimidine-4-carboxylic acid di-hydrochloride (39 mg, 0.10 mmol) using chemistry similar to that described in Example Z8 using 2,2,2-trifluoroethanamine hydrochloride in place of (R)-3-fluoropyrrolidine (26 mg, 65% yield). $^1$H NMR (400 MHz, CDCl$_3$) δ 1.66 (3H, d, J=6.8 Hz), 4.07-4.12 (2H, m), 5.22 (1H, m), 5.51 (1H, d, J=6.0 Hz), 7.20 (1H, d, J=5.6 Hz), 7.46 (1H, dt, J=9.2, 2.0 Hz), 7.96 (1H, m), 8.03 (1H, d, J=5.6 Hz), 8.36 (1H, d, J=2.0 Hz), 8.55 (1H, t, J=2.0 Hz) ppm. LCMS m/z=400.1 [M+H$^+$].

Example Z264. (S)-(3-Hydroxypyrrolidin-1-yl)(2-(((5-(trifluoromethyl)pyridin-3-yl)methyl)amino)thieno[3,2-d]pyrimidin-4-yl)methanone

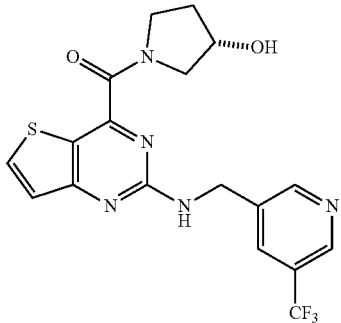 [SMILES: O=C(c1nc(NCc2cncc(C(F)(F)F)c2)nc2ccsc12)N1CC[C@H](O)C1]

Synthesis of (S)-(3-hydroxypyrrolidin-1-yl)(2-(((5-(trifluoromethyl)pyridin-3-yl)methyl)amino)thieno[3,2-d]pyrimidin-4-yl)methanone (Z264): The title compound (Z264) was prepared from ethyl 2-(((5-(trifluoromethyl)pyridin-3-yl)methyl)amino)thieno[3,2-d]pyrimidine-4-carboxylate using chemistry similar to that described in Example Z17 using (3S)-pyrrolidin-3-ol in place of (3R)-3-methoxypyrrolidine hydrochloride (28% yield). LCMS m/z=424.1 [M+H$^+$].

Example Z265. (S)—N-(2-Hydroxypropyl)-2-(((5-(trifluoromethyl)pyridin-3-yl)methyl)amino)thieno[3,2-d]pyrimidine-4-carboxamide

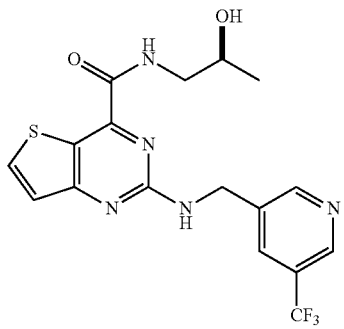 [SMILES: C[C@H](O)CNC(=O)c1nc(NCc2cncc(C(F)(F)F)c2)nc2ccsc12]

Synthesis of (S)—N-(2-hydroxypropyl)-2-(((5-(trifluoromethyl)pyridin-3-yl)methyl)amino)thieno[3,2-d]pyrimidine-4-carboxamide (Z265): The title compound (Z265) was prepared from ethyl 2-(((5-(trifluoromethyl)pyridin-3-yl)methyl)amino)thieno[3,2-d]pyrimidine-4-carboxylate using chemistry similar to that described in Example Z17 using (S)-(+)-1-amino-2 propanol in place of (3R)-3-methoxypyrrolidine hydrochloride (55% yield). LCMS m/z=412.1 [M+H$^+$].

Example Z266. (R)—N-(2-Hydroxypropyl)-2-(((5-(trifluoromethyl)pyridin-3-yl)methyl)amino)thieno[3,2-d]pyrimidine-4-carboxamide

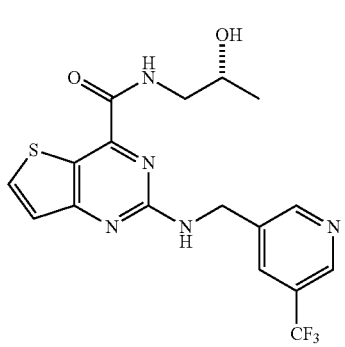 [SMILES: C[C@@H](O)CNC(=O)c1nc(NCc2cncc(C(F)(F)F)c2)nc2ccsc12]

Synthesis of (R)—N-(2-hydroxypropyl)-2-(((5-(trifluoromethyl)pyridin-3-yl)methyl)amino)thieno[3,2-d]pyrimidine-4-carboxamide (Z266): The title compound (Z266) was prepared from ethyl 2-(((5-(trifluoromethyl)pyridin-3-yl)methyl)amino)thieno[3,2-d]pyrimidine-4-carboxylate using chemistry similar to that described in Example Z17 using (R)-(−)-1-amino-2 propanol in place of (3R)-3-methoxypyrrolidine hydrochloride (50% yield). $^1$H NMR (400 MHz, CDCl$_3$) δ 1.27 (3H, d, J=6.4 Hz), 2.65-3.10 (1H, br s), 3.30-3.34 (1H, m), 3.68-3.74 (1H, m), 4.04-4.08 (1H, m), 4.80 (2H, d, J=2.0 Hz), 5.91 (1H, br s), 7.23 (1H, d, J=5.6 Hz), 8.02-8.04 (2H, m), 8.19 (1H, br s), 8.78 (1H, s), 8.84 (1H, d, J=1.6 Hz) ppm. LCMS m/z=412.1 [M+H$^+$].

Example Z267. (S)-(2-((1-(5-Fluoropyridin-3-yl)
ethyl)amino)-6-methylthieno[3,2-d]pyrimidin-4-yl)
(3-hydroxyazetidin-1-yl)methanone

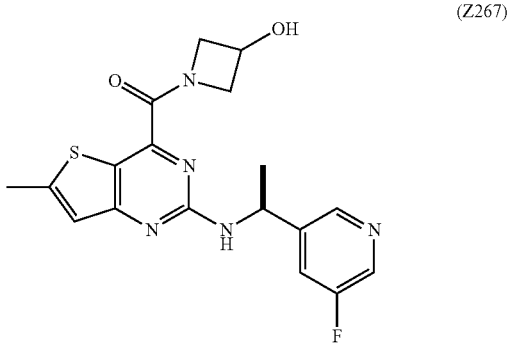

(Z267)

Synthesis of ethyl 2-chloro-6-methylthieno[3,2-d]pyrimidine-4-carboxylate: The title compound was prepared from 2,4-dichloro-6-methylthieno[3,2-d]pyrimidine (commercially obtained from PharmaBlock, Sunnyvale, Calif.) using chemistry similar to that described in Example Z1. $^1$H NMR (400 MHz, DMSO-$d_6$) δ 1.41 (3H, t, J=7.2 Hz), 2.75 (3H, s), 4.48 (2H, q, J=7.2 Hz), 7.46 (1H, s) ppm. LCMS m/z=257.2 [M+H$^+$].

Synthesis of ethyl (S)-2-((1-(5-fluoropyridin-3-yl)ethyl)amino)-6-methylthieno[3,2-d]pyrimidine-4-carboxylate and N—((S)-1-(5-fluoropyridin-3-yl)ethyl)-2-(((S)-1-(5-fluoropyridin-3-yl)ethyl)amino)-6-methylthieno[3,2-d]pyrimidine-4-carboxamide: To a solution of ethyl 2-chloro-6-methyl-thieno[3,2-d]pyrimidine-4-carboxylate (513 mg, 2.0 mmol) in NMP (4 mL) was added (1S)-1-(5-fluoro-3-pyridyl)ethanamine (620 uL, 5 mmol) and the reaction mixture was stirred at 130° C. for 8 h. The reaction mixture was diluted with ethyl acetate and washed with 25% NaCl aqueous solution two times, brine two times, and dried. The solvent was evaporated and the residue was purified by flash chromatography (80 g, HP silica, Teledyne Isco) eluting with 10% to 50% solvent A (DCM/MeOH/NH$_4$OH, 100/10/1) in DCM to provide first eluted ethyl (S)-2-((1-(5-fluoropyridin-3-yl)ethyl)amino)-6-methylthieno[3,2-d]pyrimidine-4-carboxylate as an yellow solid (233 mg, 32% yield) (LCMS: m/z=361.1 [M+H$^+$]) and second eluted N—((S)-1-(5-fluoropyridin-3-yl)ethyl)-2-(((S)-1-(5-fluoropyridin-3-yl)ethyl)amino)-6-methylthieno[3,2-d]pyrimidine-4-carboxamide as an yellow foam (340 mg, 37% yield). LCMS: m/z=455.1 [M+H$^+$].

Synthesis of (S)-2-((1-(5-fluoropyridin-3-yl)ethyl)amino)-6-methylthieno[3,2-d]pyrimidine-4-carboxylic acid: Ethyl 2-[[(1S)-1-(5-fluoro-3-pyridyl)ethyl]amino]-6-methyl-thieno[3,2-d]pyrimidine-4-carboxylate (233 mg, 0.65 mmol) was dissolved in 6 N HCl (3.2 mL) and stirred at 100° C. for 4 h and completion of the reaction was observed. The reaction mixture was evaporated to dryness in vacuo at a bath temperature of 60° C. and the residue was dried under high vacuum to provide (S)-2-((1-(5-fluoropyridin-3-yl)ethyl)amino)-6-methylthieno[3,2-d]pyrimidine-4-carboxylic acid di-hydrochloride salt as a brown solid (261 mg, 100% yield) which was used in next step without further purification. LCMS m/z=333.0 [M+H$^+$].

Synthesis of (S)-(2-((1-(5-fluoropyridin-3-yl)ethyl)amino)-6-methylthieno[3,2-d]pyrimidin-4-yl)(3-hydroxyazetidin-1-yl)methanone (Z267): The title compound (Z267) was prepared from (S)-2-((1-(5-fluoropyridin-3-yl)ethyl)amino)-6-methylthieno[3,2-d]pyrimidine-4-carboxylic acid di-hydrochloride (150 mg, 0.45 mmol) using chemistry similar to that described in Example Z8 using azetidin-3-ol in place of (R)-3-fluoropyrrolidine (45 mg, 26% yield). $^1$H NMR (400 MHz, methanol-$d_4$) δ 1.63 (3H, d, J=6.8 Hz), 2.61 (3H, s), 3.96 (1H, m), 4.39-4.45 (2H, m), 4.53-4.66 (2H, m), 5.28 (1H, q, J=6.8 Hz), 6.90 (1H, s), 7.71 (1H, m), 8.33 (1H, d, J=2.8 Hz), 8.51 (1H, m) ppm. LCMS m/z=388.0 [M+H$^+$].

Example Z268. (S)-(2-((1-(5-Fluoropyridin-3-yl)
ethyl)amino)-6-methylthieno[3,2-d]pyrimidin-4-yl)
(3-methoxyazetidin-1-yl)methanone

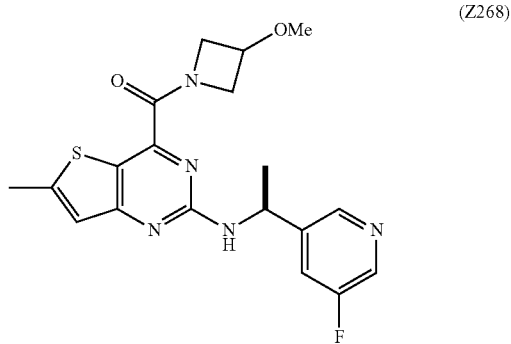

(Z268)

Synthesis of (S)-(2-((1-(5-fluoropyridin-3-yl)ethyl)amino)-6-methylthieno[3,2-d]pyrimidin-4-yl)(3-methoxyazetidin-1-yl)methanone (Z268): The title compound (Z268) was prepared from (S)-2-((1-(5-fluoropyridin-3-yl)ethyl)amino)-6-methylthieno[3,2-d]pyrimidine-4-carboxylic acid di-hydrochloride (120 mg, 0.36 mmol) using chemistry similar to that described in Example Z8 using 3-methoxyazetidine in place of (R)-3-fluoropyrrolidine (21 mg, 15% yield). $^1$H NMR (400 MHz, methanol-$d_4$) δ 1.63 (3H, d, J=7.2 Hz), 2.61 (3H, s), 3.50 (3H, s), 3.99 (1H, m), 4.26-4.39 (2H, m), 4.55-4.90 (2H, m), 5.27 (1H, q, J=7.2 Hz), 6.90 (1H, s), 7.72 (1H, m), 8.33 (1H, d, J=2.8 Hz), 8.51 (1H, m) ppm. LCMS m/z=402.4 [M+H$^+$].

Example Z269. N-(2-Hydroxy-1-(pyridin-3-yl)
ethyl)-2-(((S)-1-(pyridin-2-yl)ethyl)amino)thieno[3,
2-d]pyrimidine-4-carboxamide

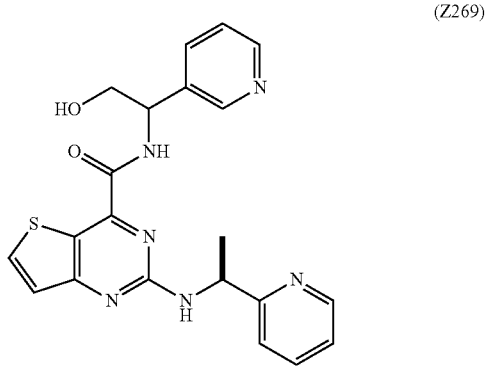

(Z269)

Synthesis of 2-chloro-N-[2-hydroxy-1-(3-pyridyl)ethyl]thieno[3,2-d]pyrimidine-4-carboxamide and ethyl 2-[[2-hydroxy-1-(3-pyridyl)ethyl]amino]thieno[3,2-d]pyrimidine-4-carboxylate: The title compounds were prepared from ethyl 2-chlorothieno[3,2-d]pyrimidine-4-carboxylate (260 mg, 1.07 mmol) using chemistry similar to that described in Example Z12 using 2-amino-2-(3-pyridyl)ethanol di-hydrochloride (commercially obtained from Aurum Pharmatech, Franklin Park, N.J.) in place of (6-methoxypyridin-3-yl)methanamine hydrochloride to produce 2-chloro-N-[2-hydroxy-1-(3-pyridyl)ethyl]thieno[3,2-d]pyrimidine-4-carboxamide (47 mg, 13% yield), LCMS m/z=359.1 [M+H$^+$], and ethyl 2-[[2-hydroxy-1-(3-pyridyl)ethyl]amino]thieno[3,2-d]pyrimidine-4-carboxylate (23 mg, 6%), LCMS m/z=342.1 [M+H$^+$].

Synthesis of N-(2-hydroxy-1-(pyridin-3-yl)ethyl)-2-(((S)-1-(pyridin-2-yl)ethyl)amino)thieno[3,2-d]pyrimidine-4-carboxamide (Z269): The title compound (Z269) was prepared from 2-chloro-N-[2-hydroxy-1-(3-pyridyl)ethyl]thieno[3,2-d]pyrimidine-4-carboxamide using chemistry similar to that described in Example Z12 using (1S)-1-(2-pyridyl)ethanamine in place of (6-methoxypyridin-3-yl)methanamine hydrochloride (22% yield). LCMS m/z=421.1 [M+H$^+$].

Example Z270. (2-((2-Hydroxy-1-(pyridin-3-yl)ethyl)amino)thieno[3,2-d]pyrimidin-4-yl)(pyrrolidin-1-yl)methanone

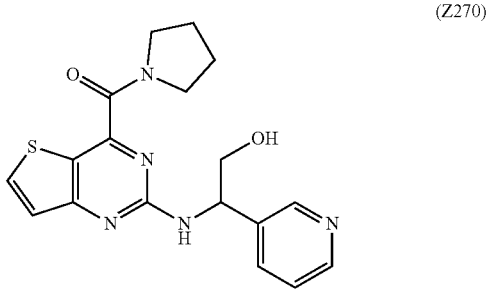

(Z270)

Synthesis of (2-((2-hydroxy-1-(pyridin-3-yl)ethyl)amino)thieno[3,2-d]pyrimidin-4-yl)(pyrrolidin-1-yl)methanone (Z270): The title compound (Z270) was prepared from ethyl 2-[[2-hydroxy-1-(3-pyridyl)ethyl]amino]thieno[3,2-d]pyrimidine-4-carboxylate using chemistry similar to that described in Example Z17 using pyrrolidine in place of (3R)-3-methoxypyrrolidine hydrochloride (36% yield). $^1$H NMR (400 MHz, CDCl$_3$) δ 1.82-1.90 (4H, m), 3.55-3.59 (1H, m), 3.68 (2H, t, J=6.0 Hz), 3.76-3.82 (1H, m), 3.99 (1H, dd, J=11.2, 5.6 Hz), 4.11 (1H, dd, J=10.8, 4.0 Hz), 5.23 (1H, dd, J=6.4, 2.0 Hz), 6.03 (1H, d, J=5.2 Hz), 7.19 (1H, d, J=6.0 Hz), 7.27-7.31 (1H, m), 7.78 (1H, dt, J=8.0, 1.6 Hz), 7.95 (1H, d, J=5.6 Hz), 8.52 (1H, dd, J=5.6, 2.0 Hz), 8.70 (1H, d, J=2.0 Hz) ppm. LCMS m/z=370.1 [M+H$^+$].

Example Z271. (2-(((S)-1-(5-Fluoropyridin-3-yl)ethyl)amino)thieno[3,2-d]pyrimidin-4-yl)((S)-2-methylpyrrolidin-1-yl)methanone

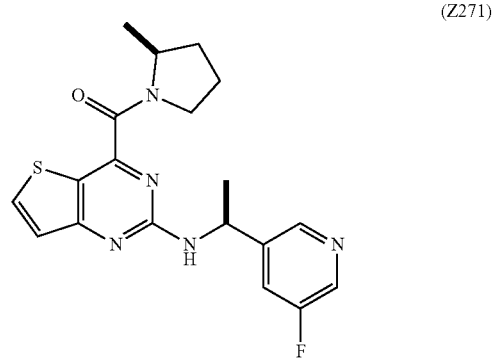

(Z271)

Synthesis of (2-(((S)-1-(5-fluoropyridin-3-yl)ethyl)amino)thieno[3,2-d]pyrimidin-4-yl)((S)-2-methylpyrrolidin-1-yl)methanone (Z271): The title compound (Z271) was prepared from (S)-2-((1-(5-fluoropyridin-3-yl)ethyl)amino)thieno[3,2-d]pyrimidine-4-carboxylic acid di-hydrochloride (39 mg, 0.10 mmol) using chemistry similar to that described in Example Z8 using (2S)-2-methylpyrrolidine in place of (R)-3-fluoropyrrolidine (33 mg, 86% yield). $^1$H NMR (400 MHz, CDCl$_3$) δ 1.33 (3H, d, J=6.4 Hz), 1.56-1.71 (2H, m), 1.63 (3H, d, J=6.8 Hz), 1.80-2.03 (2H, m), 3.64-3.85 (2H, m), 4.40 (1H, m), 5.24 (1H, m), 5.42 (1H, m), 7.17 (1H, m), 7.95 (1H, d, J=5.6 Hz), 8.34 (1H, m), 8.51 (1H, m) ppm. LCMS m/z=386.1 [M+H$^+$].

Example Z272. (2-(((S)-1-(5-Fluoropyridin-3-yl)ethyl)amino)thieno[3,2-d]pyrimidin-4-yl)((R)-2-methylpyrrolidin-1-yl)methanone

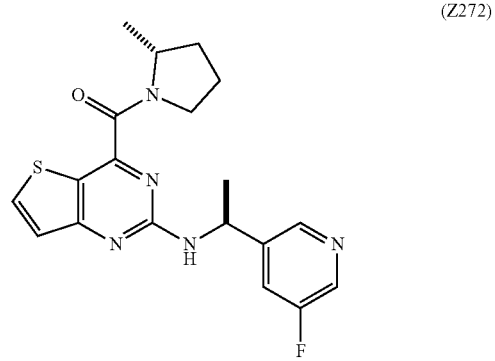

(Z272)

Synthesis of (2-(((S)-1-(5-fluoropyridin-3-yl)ethyl)amino)thieno[3,2-d]pyrimidin-4-yl)((R)-2-methylpyrrolidin-1-yl)methanone (Z272): The title compound (Z272) was prepared from (S)-2-((1-(5-fluoropyridin-3-yl)ethyl)amino)thieno[3,2-d]pyrimidine-4-carboxylic acid di-hydrochloride (39 mg, 0.10 mmol) using chemistry similar to that described in Example Z8 using (2R)-2-methylpyrrolidine in place of (R)-3-fluoropyrrolidine (35 mg, 91% yield). $^1$H NMR (400 MHz, CDCl$_3$) δ 1.33 (3H, d, J=6.4 Hz), 1.62 (1H, m), 1.64 (3H, d, J=6.8 Hz), 1.82 (1H, m), 1.88-2.05 (2H, m), 3.65-3.81 (2H, m), 4.42 (1H, m), 5.23 (1H, m), 5.41 (1H, m), 7.17 (1H, d, J=5.6 Hz), 7.44 (1H, m), 7.95 (1H, d, J=5.6 Hz), 8.34 (1H, d, J=1.6 Hz), 8.51 (1H, m) ppm. LCMS m/z=386.1 [M+H$^+$].

Example Z273. (2-((2-(1H-Imidazol-1-yl)ethyl)amino)thieno[3,2-d]pyrimidin-4-yl)(pyrrolidin-1-yl)methanone

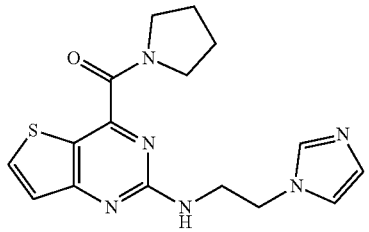

(Z273)

Synthesis of ethyl 2-((2-(1H-imidazol-1-yl)ethyl)amino)thieno[3,2-d]pyrimidine-4-carboxylate: The title compound was prepared from ethyl 2-chlorothieno[3,2-d]pyrimidine-4-carboxylate (260 mg, 1.07 mmol) using chemistry similar to that described in Example Z12 using 2-imidazol-1-ylethanamine (commercially obtained from Sigma-Aldrich, St. Louis, Mo.) in place of (6-methoxypyridin-3-yl)methanamine hydrochloride to produce ethyl 2-((2-(1H-imidazol-1-yl)ethyl)amino)thieno[3,2-d]pyrimidine-4-carboxylate (66 mg, 35% yield). LCMS m/z=318.2 [M+H$^+$].

Synthesis of (2-((2-(1H-imidazol-1-yl)ethyl)amino)thieno[3,2-d]pyrimidin-4-yl)(pyrrolidin-1-yl)methanone (Z273): The title compound (Z273) was prepared from ethyl 2-((2-(1H-imidazol-1-yl)ethyl)amino)thieno[3,2-d]pyrimidine-4-carboxylate using chemistry similar to that described in Example Z17 using pyrrolidine in place of (3R)-3-methoxypyrrolidine hydrochloride (26% yield). $^1$H NMR (400 MHz, CDCl$_3$) δ 1.92-2.01 (4H, m), 3.73 (2H, t, J=6.4 Hz), 3.95-3.99 (4H, m), 4.55 (2H, t, J=4.4 Hz), 7.22 (1H, s), 7.24 (1H, d, J=5.6 Hz), 2.26 (1H, s), 7.30 (1H, d, J=1.2 Hz), 8.06 (1H, d, J=5.6 Hz), 8.99 (1H, s) ppm. LCMS m/z=343.1 [M+H$^+$].

Example Z274. ((S)-3-(Methylsulfonyl)pyrrolidin-1-yl)(2-(((S)-1-(pyridin-2-yl)ethyl)amino)thieno[3,2-d]pyrimidin-4-yl)methanone

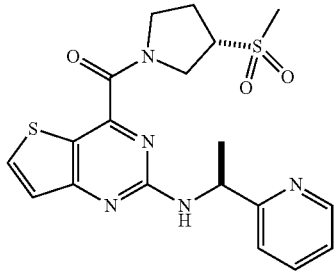

(Z274)

Synthesis of ((S)-3-(methylsulfonyl)pyrrolidin-1-yl)(2-(((S)-1-(pyridin-3-yl)ethyl)amino)thieno[3,2-d]pyrimidin-4-yl)methanone (Z274): The title compound (Z274) was prepared from (S)-2-((1-(pyridin-2-yl)ethyl)amino)thieno[3,2-d]pyrimidine-4-carboxylic acid di-hydrochloride using chemistry similar to that described in Example Z17 using (3S)-3-methylsulfonylpyrrolidine (commercially obtained from Enamine, Monmouth Jct., N.J.) in place of (3R)-3-methoxypyrrolidine hydrochloride (30% yield). $^1$H NMR (400 MHz, CDCl$_3$) δ 1.60-1.63 (3H, m), 2.25-2.38 (1H, m), 2.40-2.55 (1H, m), 2.93 (2H, s), 3.04 (1H, s), 3.63-3.86 (2H, m), 4.03-4.13 (2H, m), 5.19-5.25 (1H, m), 5.95-6.15 (1H, m), 6.13-6.20 (1H, m), 7.15-7.21 (2H, m), 7.34-7.37 (1H, m), 7.61-7.64 (1H, m), 7.50 (1H, d, J=5.2 Hz), 8.57 (1H, dd, J=11.2, 4.8 Hz) ppm. LCMS m/z=432.0 [M+H$^+$].

Example Z275. (S)-2-((1-(5-Fluoropyridin-3-yl)ethyl)amino)-N-(2-hydroxyethyl)thieno[3,2-d]pyrimidine-4-carboxamide

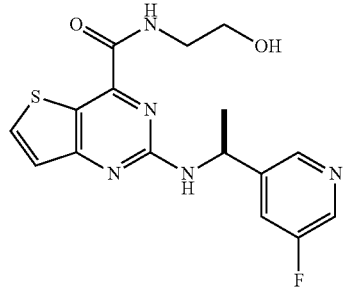 [SMILES: C[C@H](Nc1nc(C(=O)NCCO)c2sccc2n1)c1cncc(F)c1]

(Z275)

Synthesis of (S)-2-((1-(5-fluoropyridin-3-yl)ethyl)amino)-N-(2-hydroxyethyl)thieno[3,2-d]pyrimidine-4-carboxamide (Z275): The title compound (Z275) was prepared from (S)-2-((1-(5-fluoropyridin-3-yl)ethyl)amino)thieno[3,2-d]pyrimidine-4-carboxylic acid di-hydrochloride (39 mg, 0.10 mmol) using chemistry similar to that described in Example Z8 using 2-aminoethan-1-ol in place of (R)-3-fluoropyrrolidine (14 mg, 33% yield). LCMS m/z=362.1 [M+H$^+$].

Example Z276. (S)-Azetidin-1-yl(2-((1-(5-fluoropyridin-3-yl)ethyl)amino)-6-methylthieno[3,2-d]pyrimidin-4-yl)methanone

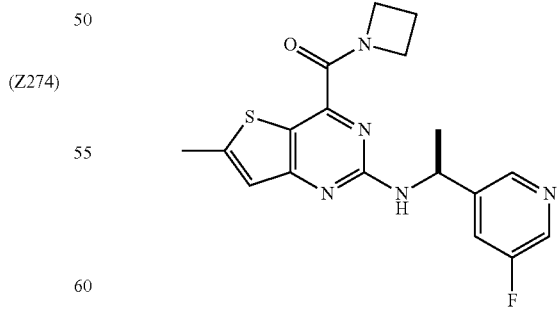

(Z276)

Synthesis of (S)-azetidin-1-yl(2-((1-(5-fluoropyridin-3-yl)ethyl)amino)-6-methylthieno[3,2-d]pyrimidin-4-yl)methanone (Z276): The title compound (Z276) was prepared from (S)-2-((1-(5-fluoropyridin-3-yl)ethyl)amino)-6-methylthieno[3,2-d]pyrimidine-4-carboxylic acid di-hydrochloride (200 mg, 0.60 mmol) using chemistry similar to that described in Example Z8 using azetidine in place of (R)-3-fluoropyrrolidine (59 mg, 26% yield). ¹H NMR (400 MHz, methanol-d₄) δ 1.63 (3H, d, J=6.8 Hz), 2.35-2.46 (2H, m), 2.61 (3H, s), 4.20-4.24 (2H, m), 4.57 (1H, m), 4.82 (1H, m), 5.28 (1H, q, J=6.8 Hz), 6.90 (1H, s), 7.74 (1H, m), 8.34 (1H, m), 8.51 (1H, m) ppm. LCMS m/z=372.1 [M+H⁺].

Example Z277. 2-(((S)-1-(5-Fluoropyridin-3-yl)ethyl)amino)-N—((S)-2-hydroxypropyl)-6-methylthieno[3,2-d]pyrimidine-4-carboxamide

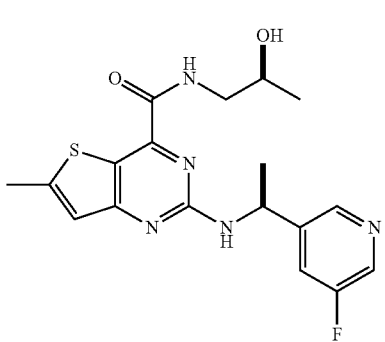 [SMILES: Cc1cc2nc(N[C@@H](C)c3cncc(F)c3)nc(C(=O)NC[C@H](C)O)c2s1]

(Z277)

Synthesis of 2-(((S)-1-(5-fluoropyridin-3-yl)ethyl)amino)-N—((S)-2-hydroxypropyl)-6-methylthieno[3,2-d]pyrimidine-4-carboxamide (Z277): The title compound (Z277) was prepared from (S)-2-((1-(5-fluoropyridin-3-yl)ethyl)amino)-6-methylthieno[3,2-d]pyrimidine-4-carboxylic acid di-hydrochloride (200 mg, 0.60 mmol) using chemistry similar to that described in Example Z8 using (S)-1-aminopropan-2-ol in place of (R)-3-fluoropyrrolidine (54 mg, 23% yield). ¹H NMR (400 MHz, methanol-d₄) δ 1.22 (3H, d, J=6.4 Hz), 1.64 (3H, d, J=6.8 Hz), 2.62 (3H, s), 3.33 (1H, m), 3.51 (1H, m), 3.98 (1H, m), 5.35 (1H, q, J=6.8 Hz), 6.90 (1H, s), 7.83 (1H, m), 8.37 (1H, m), 8.58 (1H, m) ppm. LCMS m/z=390.1 [M+H⁺].

Example Z278. 2-(((S)-1-(5-Fluoropyridin-3-yl)ethyl)amino)-N—((R)-2-hydroxypropyl)-6-methylthieno[3,2-d]pyrimidine-4-carboxamide

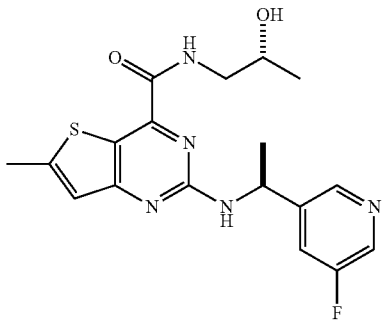 [SMILES: Cc1cc2nc(N[C@@H](C)c3cncc(F)c3)nc(C(=O)NC[C@@H](C)O)c2s1]

(Z278)

Synthesis of 2-(((S)-1-(5-fluoropyridin-3-yl)ethyl)amino)-N—((R)-2-hydroxypropyl)-6-methylthieno[3,2-d]pyrimidine-4-carboxamide (Z278): The title compound (Z278) was prepared from (S)-2-((1-(5-fluoropyridin-3-yl)ethyl)amino)-6-methylthieno[3,2-d]pyrimidine-4-carboxylic acid di-hydrochloride (200 mg, 0.60 mmol) using chemistry similar to that described in Example Z8 using (R)-1-aminopropan-2-ol in place of (R)-3-fluoropyrrolidine (42 mg, 18% yield). ¹H NMR (400 MHz, methanol-d₄) δ 1.20 (3H, d, J=6.4 Hz), 1.61 (3H, d, J=7.2 Hz), 2.60 (3H, s), 3.31 (1H, m), 3.50 (1H, dd, J=13.5, 4.4 Hz), 3.95 (1H, m), 5.30 (1H, q, J=6.8 Hz), 6.87 (1H, s), 7.72 (1H, m), 8.29 (1H, d, J=2.8 Hz), 8.53 (1H, m) ppm. LCMS m/z=390.1 [M+H⁺].

Example Z279. (S)-(2-((1-(5-Fluoropyridin-3-yl)ethyl)amino)-6-methylthieno[3,2-d]pyrimidin-4-yl)(pyrrolidin-1-yl)methanone

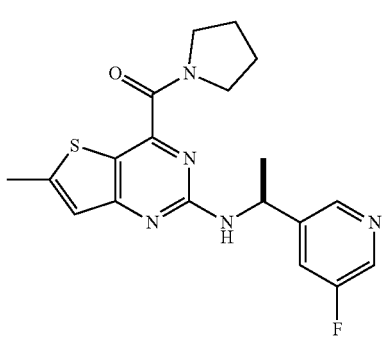 [SMILES: Cc1cc2nc(N[C@@H](C)c3cncc(F)c3)nc(C(=O)N3CCCC3)c2s1]

(Z279)

Synthesis of (S)-(2-((1-(5-fluoropyridin-3-yl)ethyl)amino)-6-methylthieno[3,2-d]pyrimidin-4-yl)(pyrrolidin-1-yl)methanone (Z279): The title compound (Z279) was prepared from (S)-2-((1-(5-fluoropyridin-3-yl)ethyl)amino)-6-methylthieno[3,2-d]pyrimidine-4-carboxylic acid di-hydrochloride (110 mg, 0.33 mmol) using chemistry similar to that described in Example Z8 using pyrrolidine in place of (R)-3-fluoropyrrolidine (45 mg, 35% yield). ¹H NMR (400 MHz, methanol-d₄) δ 1.60 (3H, d, J=7.2 Hz), 1.82-1.95 (4H, m), 2.59 (3H, s), 3.55-3.65 (3H, m), 3.82 (1H, m), 5.22 (1H, q, J=7.2 Hz), 6.89 (1H, s), 7.69 (1H, m), 8.30 (1H, m), 8.48 (1H, m) ppm. LCMS m/z=386.1 [M+H⁺].

Example Z280. (S)-2-((1-(5-Fluoropyridin-3-yl)ethyl)amino)-6-methyl-N-(2,2,2-trifluoroethyl)thieno[3,2-d]pyrimidine-4-carboxamide

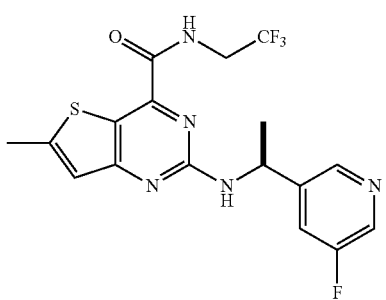 [SMILES: Cc1cc2nc(N[C@@H](C)c3cncc(F)c3)nc(C(=O)NCC(F)(F)F)c2s1]

(Z280)

Synthesis of (S)-2-((1-(5-fluoropyridin-3-yl)ethyl)amino)-6-methyl-N-(2,2,2-trifluoroethyl)thieno[3,2-d]pyrimidine-4-carboxamide (Z280): The title compound (Z280) was prepared from (S)-2-((1-(5-fluoropyridin-3-yl)ethyl)amino)- amino)-6-methylthieno[3,2-d]pyrimidine-4-carboxylic acid di-hydrochloride (150 mg, 0.45 mmol) using chemistry similar to that described in Example Z8 using 2,2,2-trifluoroethan-1-amine in place of (R)-3-fluoropyrrolidine (45 mg, 24% yield). $^1$H NMR (400 MHz, methanol-d$_4$) δ 1.64 (3H, d, J=7.2 Hz), 2.62 (3H, s), 4.10 (1H, m), 4.18 (1H, m), 5.38 (1H, q, J=7.2 Hz), 6.91 (1H, s), 7.74 (1H, m), 8.31 (1H, m), 8.54 (1H, m) ppm. LCMS m/z=414.3 [M+H$^+$].

Example Z281. ((R)-3-Hydroxypyrrolidin-1-yl)(6-methyl-2-(((S)-1-(pyridin-3-yl)ethyl)amino)thieno[3,2-d]pyrimidin-4-yl)methanone (Z281)

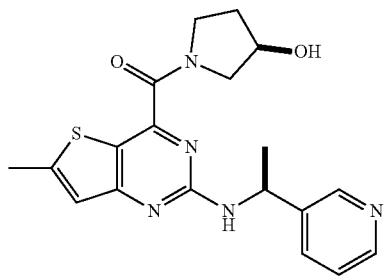

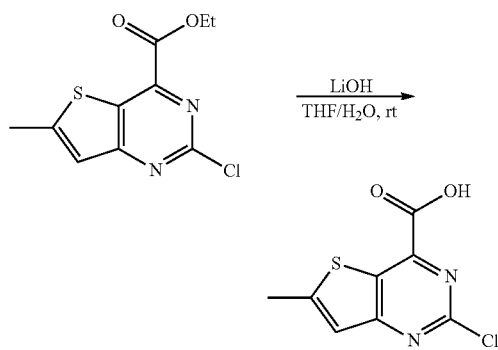

Synthesis of 2-chloro-6-methylthieno[3,2-d]pyrimidine-4-carboxylic acid: To a solution of ethyl 2-chloro-6-methylthieno[3,2-d]pyrimidine-4-carboxylate (1.2 g, 4.67 mmol) in THF (12 mL) and water (3 mL) was added lithium hydroxide (448 mg, 18.7 mmol) and the resulting solution was stirred for 2 h at room temperature. The reaction mixture was concentrated under vacuum and conc. hydrogen chloride was employed to adjust the pH to 1-2. The precipitates were collected by filtration and were dried under vacuum to provide 2-chloro-6-methylthieno[3,2-d]pyrimidine-4-carboxylic acid as a light yellow solid (1.0 g, 94% yield). LCMS m/z=229.0 [M+H$^+$].

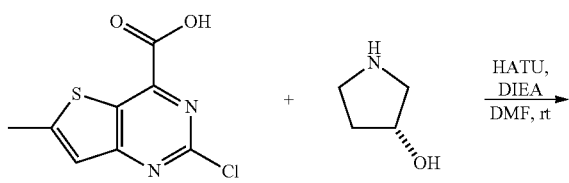

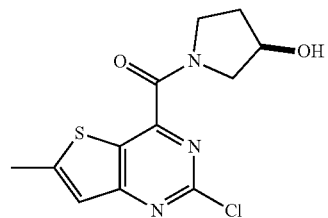

Synthesis of (R)-(2-chloro-6-methylthieno[3,2-d]pyrimidin-4-yl)(3-hydroxypyrrolidin-1-yl)methanone: The title compound was prepared from 2-chloro-6-methylthieno[3,2-d]pyrimidine-4-carboxylic acid (500 mg, 2.19 mmol) using chemistry similar to that described in Example Z8 using (R)-pyrrolidin-3-ol in place of (R)-3-fluoropyrrolidine (520 mg, 80% yield). LCMS m/z=298.0 [M+H$^+$].

Synthesis of ((R)-3-hydroxypyrrolidin-1-yl)(6-methyl-2-(((S)-1-(pyridin-3-yl)ethyl)amino)thieno[3,2-d]pyrimidin-4-yl)methanone (Z281): To a solution of (R)-(2-chloro-6-methylthieno[3,2-d]pyrimidin-4-yl)(3-hydroxypyrrolidin-1-yl)methanone (200 mg, 0.67 mmol) in NMP (2 mL) were (S)-1-(pyridin-3-yl)ethan-1-amine hydrogen chloride salt (194 mg, 1.59 mmol) and DIEA (782 mg, 6.06 mmol). The resulting solution was stirred for 2 h at 160° C. in an oil bath. The crude product was purified by prep-HPLC (C-18 OBD column and a gradient elution system of water-acetonitrile) to provide ((R)-3-hydroxypyrrolidin-1-yl)(6-methyl-2-(((S)-1-(pyridin-3-yl)ethyl)amino)thieno[3,2-d]pyrimidin-4-yl)methanone as an yellow solid (37 mg. 14% yield). $^1$H NMR (400 MHz, DMSO-d$_6$) δ 1.60 (3H, d, J=7.2 Hz), 1.93-2.00 (2H, m), 2.58 (3H, s), 3.65 (1H, m), 3.73-3.77 (2H, m), 4.05 (1H, m), 4.42 (1H, m), 5.21 (1H, q, J=7.2 Hz), 6.87 (1H, s), 7.37 (1H, dd, J=8.0, 4.8 Hz), 8.37 (1H, m), 8.61 (1H, m) ppm. LCMS m/z=384.1 [M+H$^+$].

Example Z282. ((S)-3-Hydroxypyrrolidin-1-yl)(6-methyl-2-(((S)-1-(pyridin-2-yl)ethyl)amino)thieno[3,2-d]pyrimidin-4-yl)methanone

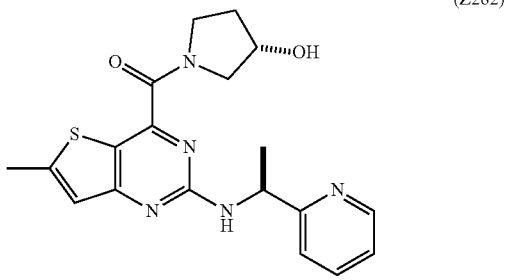

(Z282)

Synthesis of ethyl (S)-6-methyl-2-((1-(pyridin-2-yl)ethyl)amino)thieno[3,2-d]pyrimidine-4-carboxylate: To a solution of ethyl 2-chloro-6-methylthieno[3,2-d]pyrimidine-4-carboxylate (1.5 g, 5.84 mmol) in NMP (15 mL) were added (S)-1-(pyridin-2-yl)ethan-1-amine (2.14 g, 17.5 mmol) and DIEA (1.5 g, 11.6 mmol). The resulting solution was stirred for 4 h at 130° C. in an oil bath. The reaction mixture was diluted with 100 mL of H$_2$O and then was extracted with ethyl acetate. The combined organic layer was washed with brine and was dried over anhydrous sodium sulfate and then concentrated under vacuum. The residue was purified by flash chromatography on silica gel eluting with ethyl acetate/petroleum ether (2:1) to provide (S)-6-methyl-2-((1-(pyridin-2-yl)ethyl)amino)thieno[3,2-d]pyrimidine-4-carboxylate as an yellow solid (1.3 g, 65% yield). LCMS m/z=343.0 [M+H$^+$].

Synthesis of (S)-6-methyl-2-((1-(pyridin-2-yl)ethyl)amino)thieno[3,2-d]pyrimidine-4-carboxylic acid: A solution of (S)-6-methyl-2-((1-(pyridin-2-yl)ethyl)amino)thieno[3,2-d]pyrimidine-4-carboxylate (1.3 g, 3.80 mmol) in 6N HCl (30 mL) was stirred for 8 h at 100° C. in an oil bath. The reaction mixture was concentrated under vacuum and the residue was dried under vacuum overnight to provide (S)-6-methyl-2-((1-(pyridin-2-yl)ethyl)amino)thieno[3,2-d]pyrimidine-4-carboxylic acid di-hydrochloride as an yellow solid (1.2 g, 90% yield). LCMS m/z=315.0 [M+H$^+$].

Synthesis of ((S)-3-hydroxypyrrolidin-1-yl)(6-methyl-2-(((S)-1-(pyridin-2-yl)ethyl)amino)thieno[3,2-d]pyrimidin-4-yl)methanone (Z282): The title compound (Z282) was prepared from (S)-6-methyl-2-((1-(pyridin-2-yl)ethyl)amino)thieno[3,2-d]pyrimidine-4-carboxylic acid di-hydrochloride (150 mg, 0.45 mmol) using chemistry similar to that described in Example Z8 using (S)-pyrrolidin-3-ol in place of (R)-3-fluoropyrrolidine (31 mg, 18% yield). $^1$H NMR (300 MHz, methanol-d$_4$) δ 1.61 (3H, d, J=7.2 Hz), 1.90-1.97 (2H, m), 2.61 (3H, s), 3.64-3.80 (4H, m), 4.41 (1H, m), 5.17 (1H, q, J=7.2 Hz), 6.91 (1H, s), 7.30 (1H, m), 7.52 (1H, m), 7.77 (1H, m), 8.51 (1H, m) ppm. LCMS m/z=384.0 [M+H$^+$].

Example Z283. (S)-Azetidin-1-yl(6-methyl-2-((1-(pyridin-3-yl)ethyl)amino)thieno[3,2-d]pyrimidin-4-yl)methanone

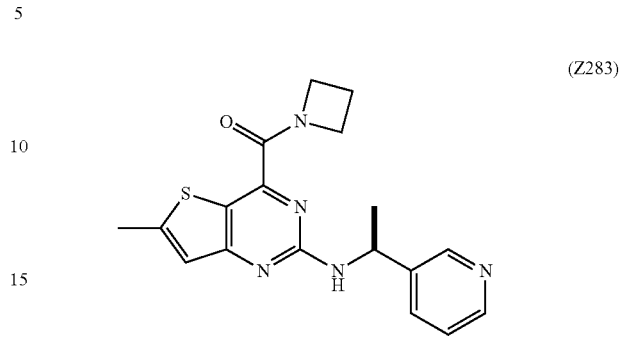

(Z283)

Synthesis of (S)-azetidin-1-yl(6-methyl-2-((1-(pyridin-3-yl)ethyl)amino)thieno[3,2-d]pyrimidin-4-yl)methanone (Z283): The title compound (Z283) was prepared from 2-chloro-6-methylthieno[3,2-d]pyrimidine-4-carboxylic acid using chemistry similar to that described in Example Z281 using azetidine in place of (R)-pyrrolidin-3-ol. $^1$H NMR (400 MHz, DMSO-d$_6$) δ 1.62 (3H, d, J=7.2 Hz), 2.35-2.42 (2H, m), 2.60 (3H, s), 4.19-4.23 (2H, m), 4.50 (1H, m), 4.64 (1H, m), 5.24 (1H, q, J=7.2 Hz), 6.88 (1H, s), 7.40 (1H, dd, J=8.0, 4.8 Hz), 7.92 (1H, m), 8.40 (1H, dd, J=4.8, 1.6 Hz), 8.62 (1H, d, J=1.6 Hz) ppm. LCMS m/z=354.1 [M+H$^+$].

Example Z284. (S)-Azetidin-1-yl(6-methyl-2-((1-(pyridin-2-yl)ethyl)amino)thieno[3,2-d]pyrimidin-4-yl)methanone

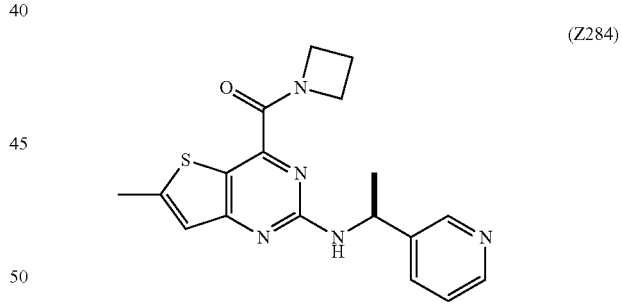

(Z284)

Synthesis of (S)-azetidin-1-yl(6-methyl-2-((1-(pyridin-2-yl)ethyl)amino)thieno[3,2-d]pyrimidin-4-yl)methanone (Z284): The title compound (Z284) was prepared from (S)-6-methyl-2-((1-(pyridin-2-yl)ethyl)amino)thieno[3,2-d]pyrimidine-4-carboxylic acid di-hydrochloride (150 mg, 0.45 mmol) using chemistry similar to that described in Example Z8 using azetidine in place of (R)-3-fluoropyrrolidine (15 mg, 9% yield). $^1$H NMR (400 MHz, methanol-d$_4$) δ 1.61 (3H, d, J=7.2 Hz), 2.33-2.40 (2H, m), 2.60 (3H, s), 4.13-4.21 (2H, m), 4.24 (1H, m), 4.34 (1H, m), 5.18 (1H, q, J=7.2 Hz), 6.89 (1H, s), 7.29 (1H, m), 7.50 (1H, d, J=3.6 Hz), 7.77 (1H, m), 8.51 (1H, m) ppm. LCMS m/z=354.1 [M+H$^+$].

Example Z285. (S)-(3-Hydroxyazetidin-1-yl)(6-methyl-2-((1-(pyridin-2-yl)ethyl)amino)thieno[3,2-d]pyrimidin-4-yl)methanone

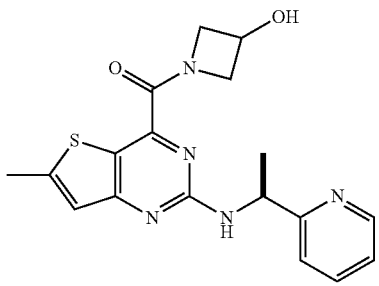 [SMILES: Cc1cc2nc(N[C@@H](C)c3ccccn3)nc(C(=O)N3CC(O)C3)c2s1]

(Z285)

Synthesis of (S)-(3-hydroxyazetidin-1-yl)(6-methyl-2-((1-(pyridin-2-yl)ethyl)amino)thieno[3,2-d]pyrimidin-4-yl)methanone (Z285): The title compound (Z285) was prepared from (S)-6-methyl-2-((1-(pyridin-2-yl)ethyl)amino)thieno[3,2-d]pyrimidine-4-carboxylic acid di-hydrochloride (250 mg, 0.80 mmol) using chemistry similar to that described in Example Z8 using azetidin-3-ol hydrochloride in place of (R)-3-fluoropyrrolidine (50 mg, 17% yield). $^1$H NMR (400 MHz, methanol-$d_4$) δ 1.61 (3H, d, J=6.8 Hz), 2.60 (3H, s), 3.94 (1H, m), 4.34-4.63 (4H, m), 5.18 (1H, q, J=6.8 Hz), 6.89 (1H, s), 7.29 (1H, m), 7.50 (1H, d, J=8.0 Hz), 7.77 (1H, td, J=7.8, 1.8 Hz), 8.52 (1H, d, J=4.8 Hz) ppm. LCMS m/z=370.0 [M+H$^+$].

Example Z286. (S)-(3-Methoxyazetidin-1-yl)(6-methyl-2-((1-(pyridin-3-yl)ethyl)amino)thieno[3,2-d]pyrimidin-4-yl)methanone

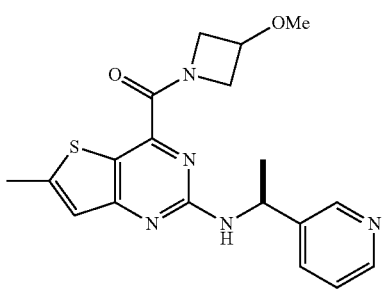

(Z286)

Synthesis of (S)-(3-methoxyazetidin-1-yl)(6-methyl-2-((1-(pyridin-3-yl)ethyl)amino)thieno[3,2-d]pyrimidin-4-yl)methanone (Z286): The title compound (Z286) was prepared from 2-chloro-6-methylthieno[3,2-d]pyrimidine-4-carboxylic acid using chemistry similar to that described in Example Z281 using 3-methoxyazetidine in place of (R)-pyrrolidin-3-ol. $^1$H NMR (400 MHz, methanol-$d_4$) δ 1.61 (3H, d, J=7.2 Hz), 2.58 (3H, s), 3.33 (3H, s), 4.21-4.35 (3H, m), 4.52-4.88 (2H, m), 5.21 (1H, q, J=7.2 Hz), 6.87 (1H, s), 7.38 (1H, dd, J=8.0, 4.8 Hz), 7.89 (1H, m), 8.38 (1H, dd, J=4.8, 1.2 Hz), 8.61 (1H, d, J=1.2 Hz) ppm. LCMS m/z=384.1 [M+H$^+$].

Example Z287. N—((S)-2-Hydroxypropyl)-6-methyl-2-(((S)-1-(pyridin-2-yl)ethyl)amino)thieno[3,2-d]pyrimidine-4-carboxamide

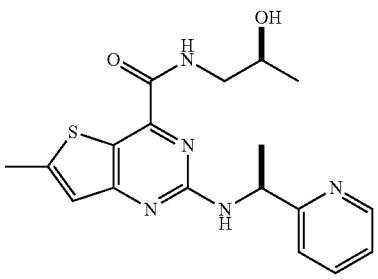 [SMILES: Cc1cc2nc(N[C@@H](C)c3ccccn3)nc(C(=O)NC[C@H](C)O)c2s1]

(Z287)

Synthesis of N—((S)-2-hydroxypropyl)-6-methyl-2-(((S)-1-(pyridin-2-yl)ethyl)amino)thieno[3,2-d]pyrimidine-4-carboxamide (Z287): The title compound (Z287) was prepared from (S)-6-methyl-2-((1-(pyridin-2-yl)ethyl)amino)thieno[3,2-d]pyrimidine-4-carboxylic acid di-hydrochloride (250 mg, 0.80 mmol) using chemistry similar to that described in Example Z8 using (S)-1-aminopropan-2-ol in place of (R)-3-fluoropyrrolidine (50 mg, 17% yield). $^1$H NMR (400 MHz, methanol-$d_4$) δ 1.21 (3H, d, J=6.4 Hz), 1.61 (3H, d, J=7.2 Hz), 2.61 (3H, s), 3.33 (1H, m), 3.50 (1H, m), 3.97 (1H, m), 5.26 (1H, q, J=7.2 Hz), 6.87 (1H, s), 7.27 (1H, m), 7.54 (1H, d, J=8.0 Hz), 7.77 (1H, dt, J=8.0, 2.0 Hz), 8.50 (1H, m) ppm. LCMS m/z=372.3 [M+H$^+$].

Example Z288. N—((R)-2-Hydroxypropyl)-6-methyl-2-(((S)-1-(pyridin-2-yl)ethyl)amino)thieno[3,2-d]pyrimidine-4-carboxamide

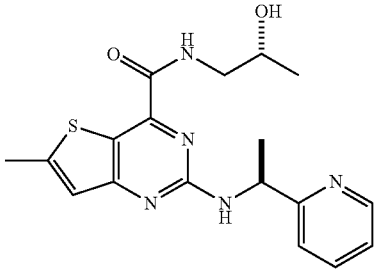 [SMILES: Cc1cc2nc(N[C@@H](C)c3ccccn3)nc(C(=O)NC[C@@H](C)O)c2s1]

(Z288)

Synthesis of N—((R)-2-hydroxypropyl)-6-methyl-2-(((S)-1-(pyridin-2-yl)ethyl)amino)thieno[3,2-d]pyrimidine-4-carboxamide (Z288): The title compound (Z288) was prepared from (S)-6-methyl-2-((1-(pyridin-2-yl)ethyl)amino)thieno[3,2-d]pyrimidine-4-carboxylic acid di-hydrochloride (250 mg, 0.80 mmol) using chemistry similar to that described in Example Z8 using (R)-1-aminopropan-2-ol in place of (R)-3-fluoropyrrolidine (50 mg, 17% yield). $^1$H NMR (300 MHz, methanol-$d_4$) δ 1.22 (3H, d, J=6.4 Hz), 1.61 (3H, d, J=7.2 Hz), 2.61 (3H, s), 3.32 (1H, m), 3.49 (1H, dd, J=13.5, 4.6 Hz), 3.96 (1H, m), 5.25 (1H, q, J=7.2 Hz), 6.87 (1H, s), 7.28 (1H, m), 7.54 (1H, d, J=8.0 Hz), 7.78 (1H, m), 8.50 (1H, m) ppm. LCMS m/z=372.0 [M+H$^+$].

Example Z289. (S)-(1,3-Oxazinan-3-yl)(2-((1-(pyridin-2-yl)ethyl)amino)thieno[3,2-d]pyrimidin-4-yl)methanone

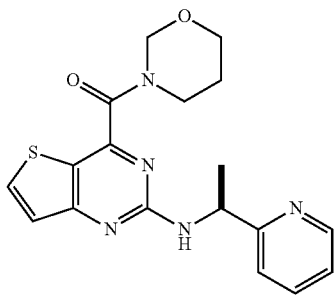 [SMILES: C[C@H](Nc1nc(C(=O)N2CCCOC2)c2sccc2n1)c1ccccn1]

Synthesis of (S)-(1,3-oxazinan-3-yl)(2-((1-(pyridin-2-yl)ethyl)amino)thieno[3,2-d]pyrimidin-4-yl)methanone (Z289): The title compound (Z289) was prepared from (S)-2-((1-(pyridin-2-yl)ethyl)amino)thieno[3,2-d]pyrimidine-4-carboxylic acid di-hydrochloride using chemistry similar to that described in Example Z17 using 1,3-oxazinane (commercially obtained from Sigma-Aldrich, St. Louis, Mo.) in place of (3R)-3-methoxypyrrolidine hydrochloride (35% yield). LCMS m/z=370.1 [M+H$^+$].

Example Z290. (S)—N-((1-Methyl-1H-imidazol-2-yl)methyl)-2-((1-(pyridin-2-yl)ethyl)amino)thieno[3,2-d]pyrimidine-4-carboxamide

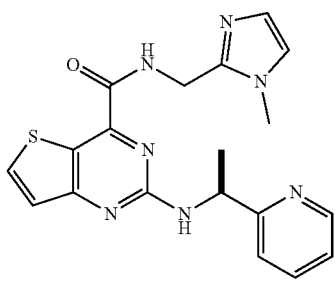 [SMILES: C[C@H](Nc1nc(C(=O)NCc2nccn2C)c2sccc2n1)c1ccccn1]

Synthesis of (S)—N-((1-methyl-1H-imidazol-2-yl)methyl)-2-((1-(pyridin-2-yl)ethyl)amino)thieno[3,2-d]pyrimidine-4-carboxamide (Z290): The title compound (Z290) was prepared from (S)-2-((1-(pyridin-2yl)ethyl)amino)thieno[3,2-d]pyrimidine-4-carboxylic acid di-hydrochloride using chemistry similar to that described in Example Z17 using (1-methyl-imidazol-2-yl)methanamine (commercially obtained from Enamine, Monmouth Jct., N.J.) in place of (3R)-3-methoxypyrrolidine hydrochloride (61% yield). LCMS m/z=394.1 [M+H$^+$].

Example Z291. (S)-2-((1-(5-Chloropyridin-3-yl)ethyl)amino)-N-(2-hydroxyethyl)thieno[3,2-d]pyrimidine-4-carboxamide

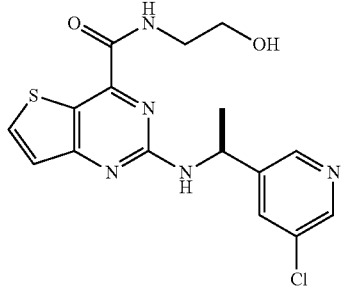

Synthesis of (S)-2-((1-(5-chloropyridin-3-yl)ethyl)amino)-N-(2-hydroxyethyl)thieno[3,2-d]pyrimidine-4-carboxamide (Z291): The title compound (Z291) was prepared from ethyl (S)-2-((1-(5-chloropyridin-3-yl)ethyl)amino)thieno[3,2-d]pyrimidine-4-carboxylate using chemistry similar to that described in Example Z17 using 2-aminoethanol in place of (3R)-3-methoxy-pyrrolidine hydrochloride (22% yield). LCMS m/z=378.0 [M+H$^+$].

Example Z292. 2-(((S)-1-(5-Chloropyridin-3-yl)ethyl)amino)-N—((S)-2-hydroxypropyl)thieno[3,2-d]pyrimidine-4-carboxamide

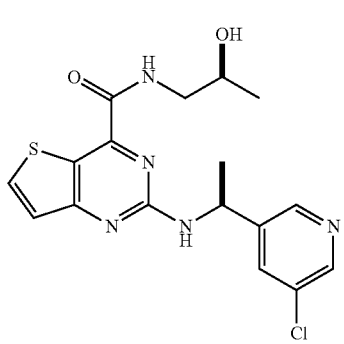 [SMILES: C[C@H](O)CNC(=O)c1nc(N[C@@H](C)c2cncc(Cl)c2)nc2ccsc12]

Synthesis of 2-(((S)-1-(5-chloropyridin-3-yl)ethyl)amino)-N—((S)-2-hydroxypropyl)thieno[3,2-d]pyrimidine-4-carboxamide (Z292): The title compound (Z292) was prepared from ethyl (S)-2-((1-(5-chloropyridin-3-yl)ethyl)amino)thieno[3,2-d]pyrimidine-4-carboxylate using chemistry similar to that described in Example Z17 using (S)-(+)-1-amino-2-propanol in place of (3R)-3-methoxypyrrolidine hydrochloride (38% yield). LCMS m/z=392.1 [M+H$^+$].

Example Z293. 2-(((S)-1-(5-Chloropyridin-3-yl)ethyl)amino)-N—((R)-2-hydroxypropyl)thieno[3,2-d]pyrimidine-4-carboxamide

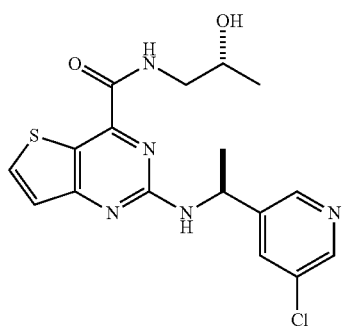 [SMILES: C[C@H](Nc1nc(C(=O)NC[C@@H](C)O)c2sccc2n1)c1cncc(Cl)c1]
(Z293)

Synthesis of 2-(((S)-1-(5-chloropyridin-3-yl)ethyl)amino)-N—((R)-2-hydroxy-propyl)thieno[3,2-d]pyrimidine-4-carboxamide (Z293): The title compound (Z293) was prepared from ethyl (S)-2-((1-(5-chloropyridin-3-yl)ethyl)amino)thieno[3,2-d]pyrimidine-4-carboxylate using chemistry similar to that described in Example Z17 using (R)-(−)-1-amino-2-propanol in place of (3R)-3-methoxypyrrolidine hydrochloride (31% yield). LCMS m/z=392.1 [M+H⁺].

Example Z294. (2-(((S)-1-(5-Fluoropyridin-3-yl)ethyl)amino)thieno[3,2-d]pyrimidin-4-yl)((S)-3-(hydroxymethyl)pyrrolidin-1-yl)methanone

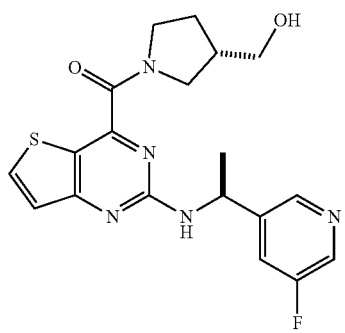 [SMILES: C[C@H](Nc1nc(C(=O)N2CC[C@H](CO)C2)c2sccc2n1)c1cncc(F)c1]
(Z294)

Synthesis of (2-(((S)-1-(5-fluoropyridin-3-yl)ethyl)amino)thieno[3,2-d]pyrimidin-4-yl)((S)-3-(hydroxymethyl)pyrrolidin-1-yl)methanone (Z294): The title compound (Z294) was prepared from (S)-2-((1-(5-fluoropyridin-3-yl)ethyl)amino)thieno[3,2-d]pyrimidine-4-carboxylic acid di-hydrochloride (39 mg, 0.10 mmol) using chemistry similar to that described in Example Z8 using (S)-pyrrolidin-3-ylmethanol in place of (R)-3-fluoropyrrolidine (28 mg, 70% yield). ¹H NMR (400 MHz, CDCl₃) δ 1.64 (3H, d, J=6.8 Hz), 1.71 (1H, m), 1.98 (1H, m), 2.45 (1H, m), 3.50 (1H, m), 3.57-3.75 (4H, m), 3.85 (1H, m), 5.23 (1H, m), 5.53 (1H, m), 7.17 (1H, d, J=5.6 Hz), 7.47 (1H, m), 7.95 (1H, m), 8.34 (1h, m), 8.51 (1H, m) ppm. LCMS m/z=402.1 [M+H⁺].

Example Z295. (2-(((S)-1-(5-Fluoropyridin-3-yl)ethyl)amino)thieno[3,2-d]pyrimidin-4-yl)((R)-3-(hydroxymethyl)pyrrolidin-1-yl)methanone

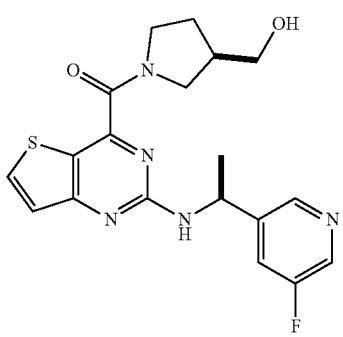 [SMILES: C[C@H](Nc1nc(C(=O)N2CC[C@@H](CO)C2)c2sccc2n1)c1cncc(F)c1]
(Z295)

Synthesis of (2-(((S)-1-(5-fluoropyridin-3-yl)ethyl)amino)thieno[3,2-d]pyrimidin-4-yl)((R)-3-(hydroxymethyl)pyrrolidin-1-yl)methanone (Z295): The title compound (Z295) was prepared from (S)-2-((1-(5-fluoropyridin-3-yl)ethyl)amino)thieno[3,2-d]pyrimidine-4-carboxylic acid di-hydrochloride (39 mg, 0.10 mmol) using chemistry similar to that described in Example Z8 using (R)-pyrrolidin-3-ylmethanol in place of (R)-3-fluoropyrrolidine (29 mg, 72% yield). ¹H NMR (400 MHz, CDCl₃) δ 1.62 (3H, d, J=6.8 Hz), 1.75 (1H, m), 1.98 (1H, m), 2.45 (1H, m), 3.49 (1H, m), 3.56-3.73 (4H, m), 3.81 (1H, m), 5.22 (1H, m), 5.47 (1H, m), 7.96 (1H, m), 8.33 (1H, m), 8.52 (1H, m) ppm. LCMS m/z=402.2 [M+H⁺].

Example Z296. N-((1s,3R)-3-Methoxycyclobutyl)-2-(((S)-1-(pyridin-3-yl)ethyl)amino)thieno[3,2-d]pyrimidine-4-carboxamide

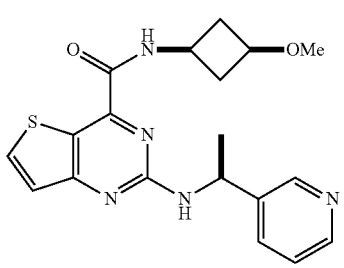
(Z296)

Synthesis of N-((1s,3R)-3-methoxycyclobutyl)-2-(((S)-1-(pyridin-3-yl)ethyl)amino)thieno[3,2-d]pyrimidine-4-carboxamide (Z296): The title compound (Z296) was prepared from (S)-2-((1-(pyridin-3-yl)ethyl)amino)thieno[3,2-d]pyrimidine-4-carboxylic acid di-hydrochloride using chemistry similar to that described in Example Z17 using 3-methoxycyclo-butanamine (commercially obtained from Enamine, Monmouth Jct., N.J.) in place of (3R)-3-methoxypyrrolidine hydrochloride (42% yield). LCMS m/z=384.2 [M+H⁺].

Example Z297. ((S)-3-Hydroxypyrrolidin-1-yl)(6-methyl-2-(((S)-1-(pyridin-3-yl)ethyl)amino)thieno[3,2-d]pyrimidin-4-yl)methanone

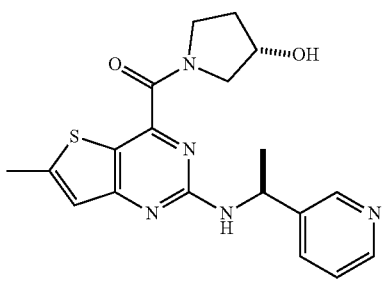

(Z297)

Synthesis of ((S)-3-hydroxypyrrolidin-1-yl)(6-methyl-2-(((S)-1-(pyridin-3-yl)ethyl)amino)thieno[3,2-d]pyrimidin-4-yl)methanone (Z297): The title compound (Z297) was prepared from 2-chloro-6-methylthieno[3,2-d]pyrimidine-4-carboxylic acid using chemistry similar to that described in Example Z281 using (S)-pyrrolidin-3-ol in place of (R)-pyrrolidin-3-ol. $^1$H NMR (400 MHz, DMSO-$d_6$) δ 1.50 (3H, d, J=7.2 Hz), 1.79-1.88 (2H, m), 2.55 (3H, s), 3.34-3.60 (3H, m), 3.82 (1H, m), 4.27 (1H, m), 4.99 (1H, m), 5.14 (1H, q, J=7.2 Hz), 6.94 (1H, s), 7.32 (1H, m), 7.78-7.85 (2H, m), 8.40 (1H, m), 8.62 (1H, m) ppm. LCMS m/z=384.1 [M+H$^+$].

Example Z298. ((R)-3-Hydroxypyrrolidin-1-yl)(6-methyl-2-(((S)-1-(pyridin-2-yl)ethyl)amino)thieno[3,2-d]pyrimidin-4-yl)methanone

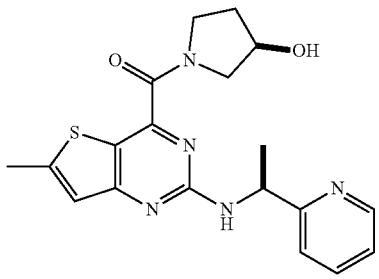 [SMILES: Cc1cc2nc(N[C@@H](C)c3ccccn3)nc(C(=O)N3CC[C@@H](O)C3)c2s1]

(Z298)

Synthesis of ((R)-3-hydroxypyrrolidin-1-yl)(6-methyl-2-(((S)-1-(pyridin-2-yl)ethyl)amino)thieno[3,2-d]pyrimidin-4-yl)methanone (Z298): The title compound (Z298) was prepared from (S)-6-methyl-2-((1-(pyridin-2-yl)ethyl)amino)thieno[3,2-d]pyrimidine-4-carboxylic acid di-hydrochloride (150 mg, 0.45 mmol) using chemistry similar to that described in Example Z8 using (R)-pyrrolidin-3-ol in place of (R)-3-fluoropyrrolidine (32 mg, 19% yield). $^1$H NMR (300 MHz, methanol-$d_4$) δ 1.61 (3H, d, J=7.2 Hz), 1.94-2.00 (2H, m), 2.61 (3H, s), 3.65-3.78 (2H, m), 4.07 (1H, m), 4.23-4.65 (2H, m), 5.18 (1H, q, J=7.2 Hz), 6.90 (1H, s), 7.28 (1H, m), 7.51 (1H, dd, J=8.0, 1.2 Hz), 7.77 (1H, m), 8.51 (1H, m) ppm. LCMS m/z=384.0 [M+H$^+$].

Example Z299. (S)-(3-Hydroxyazetidin-1-yl)(6-methyl-2-((1-(pyridin-3-yl)ethyl)amino)thieno[3,2-d]pyrimidin-4-yl)methanone

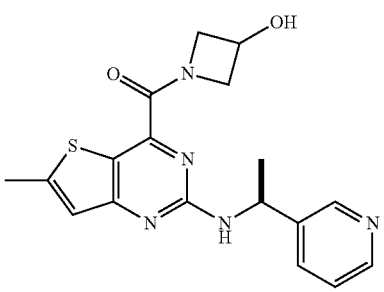 [SMILES: Cc1cc2nc(N[C@@H](C)c3cccnc3)nc(C(=O)N3CC(O)C3)c2s1]

(Z299)

Synthesis of (S)-(3-hydroxyazetidin-1-yl)(6-methyl-2-((1-(pyridin-3-yl)ethyl)amino)thieno[3,2-d]pyrimidin-4-yl)methanone (Z299): The title compound (Z299) was prepared from 2-chloro-6-methylthieno[3,2-d]pyrimidine-4-carboxylic acid using chemistry similar to that described in Example Z281 using azetidin-3-ol in place of (R)-pyrrolidin-3-ol. $^1$H NMR (400 MHz, DMSO-$d_6$) δ 1.51 (3H, d, J=6.8 Hz), 2.57 (3H, s), 3.79 (1H, m), 4.28 (1H, m), 4.43-4.52 (3H, m), 5.17 (1H, q, J=6.8 Hz), 5.76 (1H, m), 6.93 (1H, s), 7.33 (1H, dd, J=8.0, 4.8 Hz), 7.80 (1H, m), 8.41 (1H, dd, J=4.8, 1.6 Hz), 8.62 (1H, d, J=1.6 Hz) ppm. LCMS m/z=370.1 [M+H$^+$].

Example Z300. (S)-(3-Methoxyazetidin-1-yl)(6-methyl-2-((1-(pyridin-2-yl)ethyl)amino)thieno[3,2-d]pyrimidin-4-yl)methanone

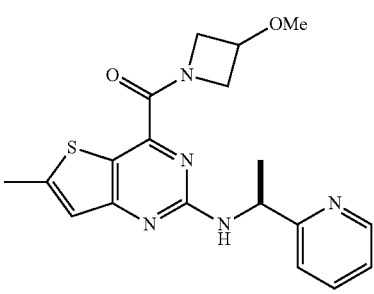 [SMILES: COC1CN(C(=O)c2nc(N[C@@H](C)c3ccccn3)nc3cc(C)sc23)C1]

(Z300)

Synthesis of (S)-(3-methoxyazetidin-1-yl)(6-methyl-2-((1-(pyridin-2-yl)ethyl)amino)thieno[3,2-d]pyrimidin-4-yl)methanone (Z300): The title compound (Z300) was prepared from (S)-6-methyl-2-((1-(pyridin-2-yl)ethyl)amino)thieno[3,2-d]pyrimidine-4-carboxylic acid di-hydrochloride (250 mg, 0.80 mmol) using chemistry similar to that described in Example Z8 using 3-methoxyazetidine hydrochloride in place of (R)-3-fluoropyrrolidine (50 mg, 16% yield). $^1$H NMR (400 MHz, methanol-$d_4$) δ 1.61 (3H, d, J=7.2 Hz), 2.60 (3H, s), 3.36 (3H, s), 3.95 (1H, m), 4.20-4.35 (3H, m), 4.47 (1H, m), 5.16 (1H, m), 6.88 (1H, s), 7.29 (1H, m), 7.50 (1H, d, J=8.0 Hz), 7.77 (1H, m), 8.52 (1H, m) ppm. LCMS m/z=384.0 [M+H$^+$].

Example Z301. (2-(((S)-1-(5-Fluoropyridin-3-yl)ethyl)amino)-6-methylthieno[3,2-d]pyrimidin-4-yl)((S)-3-methoxypyrrolidin-1-yl)methanone

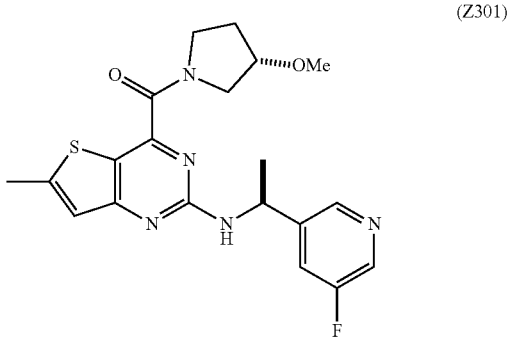

(Z301)

Synthesis of (2-(((S)-1-(5-fluoropyridin-3-yl)ethyl)amino)-6-methylthieno[3,2-d]pyrimidin-4-yl)((S)-3-methoxypyrrolidin-1-yl)methanone (Z301): The title compound (Z301) was prepared from (S)-2-((1-(5-fluoropyridin-3-yl)ethyl)amino)-6-methylthieno[3,2-d]pyrimidine-4-carboxylic acid di-hydrochloride (150 mg, 0.45 mmol) using chemistry similar to that described in Example Z8 using (S)-3-methoxypyrrolidine in place of (R)-3-fluoropyrrolidine (43 mg, 23% yield). $^1$H NMR (400 MHz, methanol-$d_4$) δ 1.62 (3H, d, J=6.8 Hz), 1.94 (1H, m), 2.09 (1H, m), 2.61 (3H, s), 3.38 (3H, s), 3.61-3.77 (4H, m), 4.03 (1H, m), 5.25 (1H, q, J=6.8 Hz), 6.91 (1H, s), 7.72 (1H, m), 8.33 (1H, m), 8.51 (1H, m) ppm. LCMS m/z=416.2 [M+H$^+$].

Example Z302. (2-(((S)-1-(5-Fluoropyridin-3-yl)ethyl)amino)-6-methylthieno[3,2-d]pyrimidin-4-yl)((R)-3-methoxypyrrolidin-1-yl)methanone

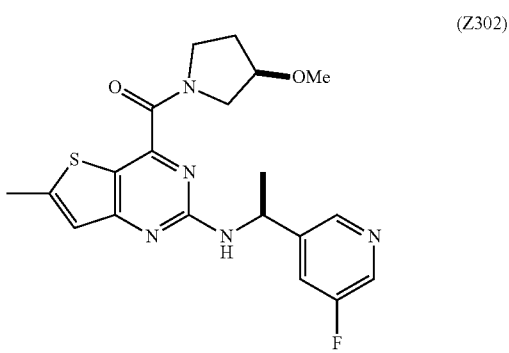

(Z302)

Synthesis of (2-(((S)-1-(5-fluoropyridin-3-yl)ethyl)amino)-6-methylthieno[3,2-d]pyrimidin-4-yl)((R)-3-methoxypyrrolidin-1-yl)methanone (Z302): The title compound (Z302) was prepared from (S)-2-((1-(5-fluoropyridin-3-yl)ethyl)amino)-6-methylthieno[3,2-d]pyrimidine-4-carboxylic acid di-hydrochloride (200 mg, 0.60 mmol) using chemistry similar to that described in Example Z8 using (R)-3-methoxypyrrolidine in place of (R)-3-fluoropyrrolidine (40 mg, 16% yield). $^1$H NMR (400 MHz, methanol-$d_4$) δ 1.62 (3H, d, J=7.2 Hz), 1.98 (1H, m), 2.13 (1H, m), 2.61 (3H, s), 3.38 (3H, s), 3.64-3.80 (3H, m), 4.05-4.13 (2H, m), 5.25 (1H, q, J=7.2 Hz), 6.91 (1H, s), 7.71 (1H, m), 8.32 (1H, m), 8.50 (1H, m) ppm. LCMS m/z=416.0 [M+H$^+$].

Example Z303. (S)—N-Phenyl-2-((1-(pyridin-2-yl)ethyl)amino)thieno[3,2-d]pyrimidine-4-carboxamide

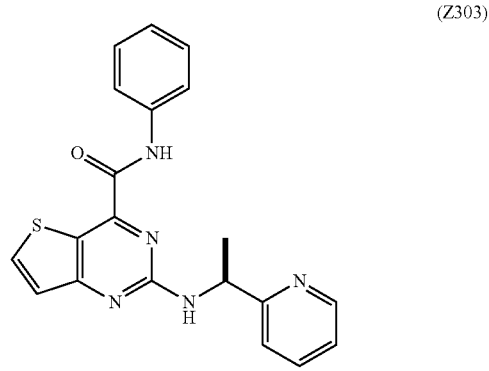

(Z303)

Synthesis of (S)—N-phenyl-2-((1-(pyridin-2-yl)ethyl)amino)thieno[3,2-d]pyrimidine-4-carboxamide (Z303): The title compound (Z303) was prepared from (S)-2-((1-(pyridin-2-yl)ethyl)amino)thieno[3,2-d]pyrimidine-4-carboxylic acid di-hydrochloride using chemistry similar to that described in Example Z17 using aniline in place of (3R)-3-methoxypyrrolidine hydrochloride (92% yield). $^1$H NMR (400 MHz, CDCl$_3$) δ 1.66 (3H, d, J=6.8 Hz), 5.30 (1H, m), 7.17-7.20 (2H, m), 7.23 (1H, d, J=5.6 Hz), 7.39-7.43 (3H, m), 7.67 (1H, t, J=5.6 Hz), 7.82 (2H, d, J=7.6 Hz), 8.02 (1H, d, J=5.6 Hz), 8.02 (1H, d, J=5.6 Hz), 8.61 (1H, d, J=4.4 Hz), 9.86 (1H, s) ppm. LCMS m/z=376.1 [M+H$^+$].

Example Z304. (S)—N-((1H-Imidazol-2-yl)methyl)-2-((1-(pyridin-2-yl)ethyl)amino)thieno[3,2-d]pyrimidine-4-carboxamide

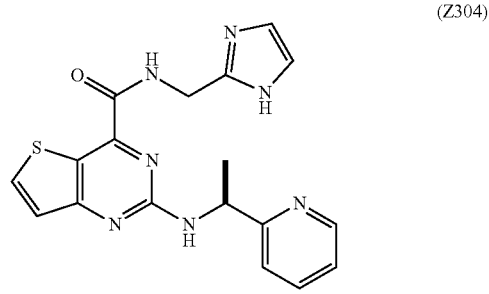

(Z304)

Synthesis of (S)—N-((1H-imidazol-2-yl)methyl)-2-((1-(pyridin-2-yl)ethyl)amino)thieno[3,2-d]pyrimidine-4-carboxamide (Z304): The title compound (Z304) was prepared from (S)-2-((1-(pyridin-2-yl)ethyl)amino)thieno[3,2-d]pyrimidine-4-carboxylic acid di-hydrochloride using chemistry similar to that described in Example Z17 using (1H-imidazol-2-yl)methanamine (commercially obtained from Sigma-Aldrich, St. Louis, Mo.) in place of (3R)-3-methoxypyrrolidine hydrochloride (73% yield). LCMS m/z=380.1 [M+H$^+$].

Example Z305. 2-(((S)-1-(5-Chloropyridin-3-yl)ethyl)amino)-N-((1s,3R)-3-hydroxycyclobutyl)thieno[3,2-d]pyrimidine-4-carboxamide

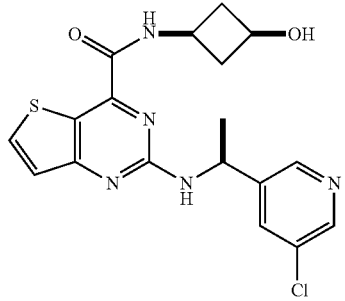

(Z305)

Synthesis of 2-(((S)-1-(5-chloropyridin-3-yl)ethyl)amino)-N-((1s,3R)-3-hydroxycyclobutyl)thieno[3,2-d]pyrimidine-4-carboxamide (Z305): The title compound (Z305) was prepared from ethyl (S)-2-((1-(5-chloropyridin-3-yl)ethyl)amino)thieno[3,2-d]pyrimidine-4-carboxylate using chemistry similar to that described in Example Z17 using 3-aminocyclobutanol hydrochloride in place of (3R)-3-methoxypyrrolidine hydrochloride (51% yield). $^1$H NMR (400 MHz, CDCl$_3$) δ 1.43-1.52 (1H, m), 1.63 (3H, d, J=7.2 Hz), 2.03-2.10 (1H, m), 3.04 (1H, s), 2.87-3.02 (2H, m), 4.13 (2H, m), 5.10 (1H, m), 5.67 (1H, m), 7.20 (1H, d, J=5.6 Hz), 7.65-7.75 (1H, m), 7.78 (1H, t, J=2.0 Hz), 8.01 (1H, d, J=5.2 Hz), 8.49 (1H, d, J=2.4 Hz), 8.68 (1H, dd, J=6.4, 2.0 Hz) ppm. LCMS m/z=404.0 [M+H$^+$].

Example Z306. 2-(((S)-1-(5-Chloropyridin-3-yl)ethyl)amino)-N-((1r,3S)-3-hydroxycyclobutyl)thieno[3,2-d]pyrimidine-4-carboxamide

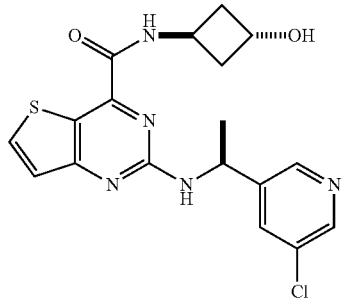

(Z306)

Synthesis of 2-(((S)-1-(5-chloropyridin-3-yl)ethyl)amino)-N-((1r,3S)-3-hydroxycyclo-butyl)thieno[3,2-d]pyrimidine-4-carboxamide (Z306): The title compound (Z306) was prepared from ethyl (S)-2-((1-(5-chloropyridin-3-yl)ethyl)amino)thieno[3,2-d]pyrimidine-4-carboxylate using chemistry similar to that described in Example Z17 using trans-3-aminocyclobutanol in place of (3R)-3-methoxypyrrolidine hydrochloride (65% yield). LCMS m/z=404.1 [M+H$^+$].

Example Z307. (S)—N-(5-Methoxypyridin-3-yl)-2-((1-(pyridin-2-yl)ethyl)amino)thieno[3,2-d]pyrimidine-4-carboxamide

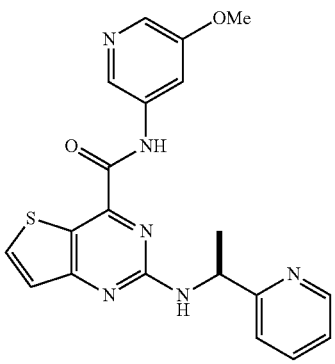 [SMILES: COc1cncc(NC(=O)c2nc(N[C@@H](C)c3ccccn3)nc3ccsc23)c1]

(Z307)

Synthesis of (S)—N-(5-methoxypyridin-3-yl)-2-((1-(pyridin-2-yl)ethyl)amino)thieno[3,2-d]pyrimidine-4-carboxamide (Z307): The title compound (Z307) was prepared from (S)-2-((1-(pyridin-2-yl)ethyl)amino)thieno[3,2-d]pyrimidine-4-carboxylic acid di-hydrochloride using chemistry similar to that described in Example Z17 using 5-methoxypyridin-3-amine (commercially obtained from CombiBlocks, San Diego, Calif.) in place of (3R)-3-methoxy-pyrrolidine hydrochloride (57% yield). $^1$H NMR (400 MHz, CDCl$_3$) δ 1.66 (3H, d, J=6.8 Hz), 3.92 (3H, s), 5.30 (1H, m), 7.17-7.20 (1H, m), 7.24 (2H, d, J=5.6 Hz), 7.40 (1H, d, J=8.0 Hz), 7.67 (2H, td, J=7.6, 1.6 Hz), 8.02 (1H, d, J=5.4 Hz), 8.14 (1H, d, J=2.4 Hz), 8.18 (1H, t, J=2.4 Hz), 8.35 (1H, d, J=2.0 Hz), 8.62 (1H, d, J=4.0 Hz), 9.94 (1H, s) ppm. LCMS m/z=407.1 [M+H$^+$].

Example Z308. (S)-2-((1-(5-Fluoropyridin-3-yl)ethyl)amino)-N-(2-hydroxy-2-methylpropyl)-6-methylthieno[3,2-d]pyrimidine-4-carboxamide

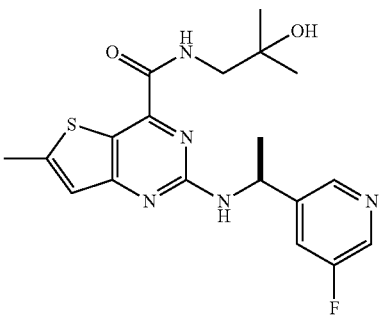 [SMILES: Cc1cc2nc(N[C@@H](C)c3cncc(F)c3)nc(C(=O)NCC(C)(C)O)c2s1]

(Z308)

Synthesis of (S)-2-((1-(5-fluoropyridin-3-yl)ethyl)amino)-N-(2-hydroxy-2-methylpropyl)-6-methylthieno[3,2-d]pyrimidine-4-carboxamide (Z308): The title compound (Z308) was prepared from ((S)-2-((1-(5-fluoropyridin-3-yl)ethyl)amino)-6-methylthieno[3,2-d]pyrimidine-4-carboxylic acid di-hydrochloride (150 mg, 0.45 mmol) using chemistry similar to that described in Example Z8 using 1-amino-2-methylpropan-2-ol in place of (R)-3-fluoropyrrolidine (52 mg, 29% yield). $^1$H NMR (400 MHz, methanol-d$_4$) δ 1.25 (6H, m), 1.64 (3H, d, J=7.2 Hz), 2.62 (3H, s), 3.41 (2H, s), 5.33 (1H, q, J=7.2 Hz), 6.91 (1H, s), 7.80 (1H, m), 8.35 (1H, m), 8.57 (1H, m) ppm. LCMS m/z=404.1 [M+H$^+$].

Example Z309. (2-(((S)-1-(5-Fluoropyridin-3-yl) ethyl)amino)-6-methylthieno[3,2-d]pyrimidin-4-yl) ((S)-3-(hydroxymethyl)pyrrolidin-1-yl)methanone

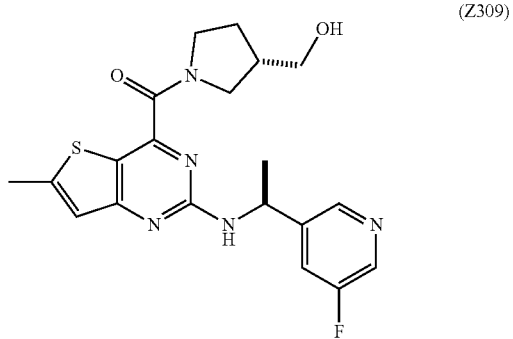

(Z309)

Synthesis of (2-(((S)-1-(5-fluoropyridin-3-yl)ethyl) amino)-6-methylthieno[3,2-d]pyrimidin-4-yl)((S)-3-(hydroxymethyl)pyrrolidin-1-yl)methanone (Z309): The title compound (Z309) was prepared from ((S)-2-((1-(5-fluoropyridin-3-yl)ethyl)amino)-6-methylthieno[3,2-d]pyrimidine-4-carboxylic acid di-hydrochloride (150 mg, 0.45 mmol) using chemistry similar to that described in Example Z8 using (S)-pyrrolidin-3-ylmethanol in place of (R)-3-fluoropyrrolidine (43 mg, 24% yield). $^1$H NMR (400 MHz, DMSO-d$_6$) δ 1.51 (3H, d, J=6.8 Hz), 1.64 (1H, m), 1.86 (1H, m), 2.25 (1H, m), 2.55 (3H, s), 3.28-3.44 (4H, m), 3.98 (1H, m), 4.74 (1H, m), 5.18 (1H, m), 6.95 (1H, s), 7.72 (1H, m), 7.84 (1H, br s), 8.40 (1H, m), 8.52 (1H, m) ppm. LCMS m/z=416.1 [M+H$^+$].

Example Z310. (2-(((S)-1-(5-Fluoropyridin-3-yl) ethyl)amino)-6-methylthieno[3,2-d]pyrimidin-4-yl) ((R)-3-(hydroxymethyl)pyrrolidin-1-yl)methanone

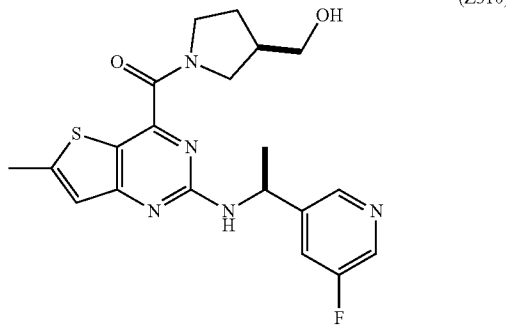

(Z310)

Synthesis of (2-(((S)-1-(5-fluoropyridin-3-yl)ethyl) amino)-6-methylthieno[3,2-d]pyrimidin-4-yl)((R)-3-(hydroxymethyl)pyrrolidin-1-yl)methanone (Z310): The title compound (Z310) was prepared from ((S)-2-((1-(5-fluoropyridin-3-yl)ethyl)amino)-6-methylthieno[3,2-d]pyrimidine-4-carboxylic acid di-hydrochloride (150 mg, 0.45 mmol) using chemistry similar to that described in Example Z8 using (R)-pyrrolidin-3-ylmethanol in place of (R)-3-fluoropyrrolidine (54 mg, 30% yield). $^1$H NMR (400 MHz, DMSO-d$_6$) δ 1.51 (3H, d, J=6.8 Hz), 1.63 (1H, m), 1.90 (1H, m), 2.27 (1H, m), 2.55 (3H, s), 3.34-3.61 (5H, m), 4.73 (1H, m), 5.20 (1H, m), 6.95 (1H, s), 7.73 (1H, m), 7.84 (1H, br s), 8.40 (1H, m), 8.51 (1H, m) ppm. LCMS m/z=416.1 [M+H$^+$].

Example Z311. ((S)-3-Methoxypyrrolidin-1-yl)(6-methyl-2-(((S)-1-(pyridin-2-yl)ethyl)amino)thieno[3,2-d]pyrimidin-4-yl)methanone

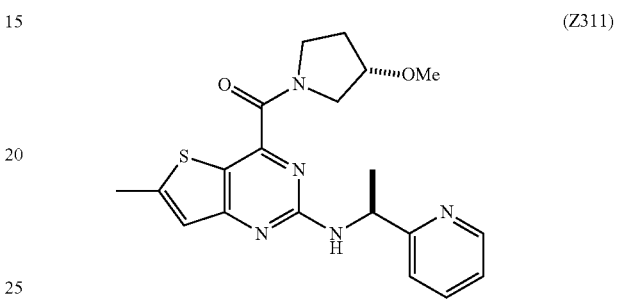

(Z311)

Synthesis of ((S)-3-methoxypyrrolidin-1-yl)(6-methyl-2-(((S)-1-(pyridin-2-yl)ethyl)amino)thieno[3,2-d]pyrimidin-4-yl)methanone (Z311): The title compound (Z311) was prepared from (S)-6-methyl-2-((1-(pyridin-2-yl)ethyl) amino)thieno[3,2-d]pyrimidine-4-carboxylic acid di-hydrochloride (250 mg, 0.80 mmol) using chemistry similar to that described in Example Z8 using (S)-3-methoxypyrrolidine in place of (R)-3-fluoropyrrolidine (48 mg, 15% yield). $^1$H NMR (400 MHz, methanol-d$_4$) δ 1.61 (3H, d, J=7.2 Hz), 1.91 (1H, m), 2.09 (1H, m), 2.61 (3H, s), 3.17 (1H, m), 3.37 (3H, s), 3.50-3.63 (3H, m), 3.94 (1H, m), 5.17 (1H, q, J=7.2 Hz), 6.91 (1H, s), 7.29 (1H, m), 7.55 (1H, m), 7.77 (1H, m), 8.52 (1H, m) ppm. LCMS m/z=398.3 [M+H$^+$].

Example Z312. ((R)-3-Methoxypyrrolidin-1-yl)(6-methyl-2-(((S)-1-(pyridin-2-yl)ethyl)amino)thieno[3,2-d]pyrimidin-4-yl)methanone

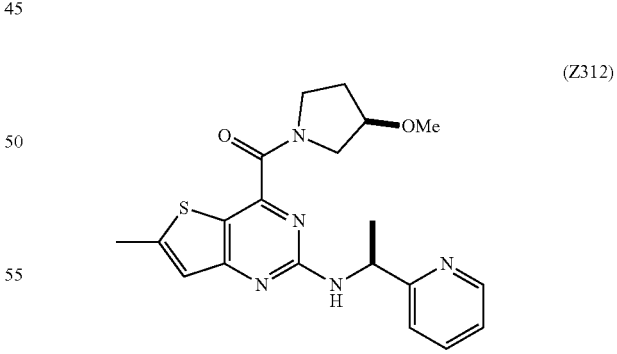

(Z312)

Synthesis of ((R)-3-methoxypyrrolidin-1-yl)(6-methyl-2-(((S)-1-(pyridin-2-yl)ethyl)amino)thieno[3,2-d]pyrimidin-4-yl)methanone (Z312): The title compound (Z312) was prepared from (S)-6-methyl-2-((1-(pyridin-2-yl)ethyl) amino)thieno[3,2-d]pyrimidine-4-carboxylic acid di-hydrochloride (250 mg, 0.80 mmol) using chemistry similar to that described in Example Z8 using (R)-3-methoxypyrrolidine in place of (R)-3-fluoropyrrolidine (50 mg, 16% yield).

¹H NMR (400 MHz, methanol-d₄) δ 1.61 (3H, d, J=7.2 Hz), 1.95 (1H, m), 2.09 (1H, m), 2.61 (3H, s), 3.35 (3H, s), 3.61-3.84 (3H, m), 4.02-4.10 (2H, m), 5.18 (1H, q, J=6.8 Hz), 6.90 (1H, s), 7.29 (1H, m), 7.50 (1H, m), 7.76 (1H, m), 8.51 (1H, m) ppm. LCMS m/z=398.3 [M+H⁺].

Example Z313. tert-Butyl ((R)-1-(2-(((S)-1-(pyridin-3-yl)ethyl)amino)thieno[3,2-d]pyrimidine-4-carbonyl)pyrrolidin-3-yl)carbamate

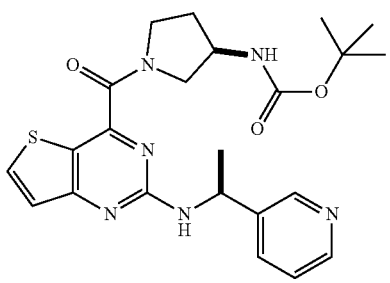

(Z313)

Synthesis of tert-butyl ((R)-1-(2-(((S)-1-(pyridin-3-yl)ethyl)amino)thieno[3,2-d]pyrimidine-4-carbonyl)pyrrolidin-3-yl)carbamate (Z313): The title compound (Z313) was prepared from (S)-2-((1-(pyridin-3-yl)ethyl)amino)thieno[3,2-d]pyrimidine-4-carboxylic acid di-hydrochloride using chemistry similar to that described in Example Z17 using tert-butyl N-[(3R)-pyrrolidin-3-yl]carbamate in place of (3R)-3-methoxypyrrolidine hydrochloride (61% yield). LCMS m/z=469.3 [M+H⁺].

Example Z314. tert-Butyl ((S)-1-(2-(((S)-1-(pyridin-3-yl)ethyl)amino)thieno[3,2-d]pyrimidine-4-carbonyl)pyrrolidin-3-yl)carbamate

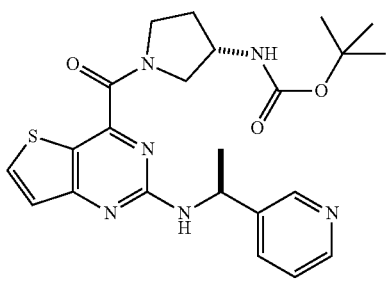

(Z314)

Synthesis of tert-butyl ((S)-1-(2-(((S)-1-(pyridin-3-yl)ethyl)amino)thieno[3,2-d]pyrimidine-4-carbonyl)pyrrolidin-3-yl)carbamate (Z314): The title compound (Z314) was prepared from (S)-2-((1-(pyridin-3-yl)ethyl)amino)thieno[3,2-d]pyrimidine-4-carboxylic acid di-hydrochloride using chemistry similar to that described in Example Z17 using tert-butyl N-[(3S)-pyrrolidin-3-yl]carbamate (commercially obtained from PharmaBlock, Sunnyvale, Calif.) in place of (3R)-3-methoxypyrrolidine hydrochloride (55% yield). LCMS m/z=469.3 [M+H+].

Example Z315. tert-Butyl ((S)-1-(2-(((S)-1-(pyridin-2-yl)ethyl)amino)thieno[3,2-d]pyrimidine-4-carbonyl)pyrrolidin-3-yl)carbamate

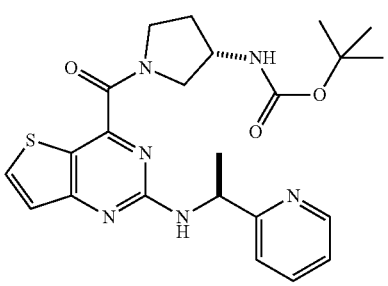

(Z315)

Synthesis of tert-butyl ((S)-1-(2-(((S)-1-(pyridin-2-yl)ethyl)amino)thieno[3,2-d]pyrimidine-4-carbonyl)pyrrolidin-2-yl)carbamate (Z315): The title compound (Z315) was prepared from (S)-2-((1-(pyridin-2-yl)ethyl)amino)thieno[3,2-d]pyrimidine-4-carboxylic acid di-hydrochloride using chemistry similar to that described in Example Z17 using tert-butyl N-[(3S)-pyrrolidin-3-yl]carbamate in place of (3R)-3-methoxypyrrolidine hydrochloride (61% yield). LCMS m/z=469.3 [M+H⁺].

Example Z316. N—((R)-1-(2-(((S)-1-(Pyridin-3-yl)ethyl)amino)thieno[3,2-d]pyrimidine-4-carbonyl)pyrrolidin-3-yl)acetamide

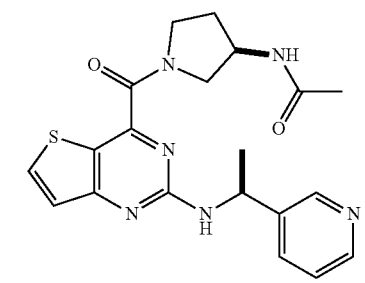

(Z316)

Synthesis of N—((R)-1-(2-(((S)-1-(pyridin-3-yl)ethyl)amino)thieno[3,2-d]pyrimidine-4-carbonyl)pyrrolidin-3-yl)acetamide (Z316): The title compound (Z316) was prepared from (S)-2-((1-(pyridin-3-yl)ethyl)amino)thieno[3,2-d]pyrimidine-4-carboxylic acid di-hydrochloride using chemistry similar to that described in Example Z17 using N-[(3R)-pyrrolidin-3-yl]acetamide (commercially obtained from PharmaBlock, Sunnyvale, Calif.) in place of (3R)-3-methoxypyrrolidine hydrochloride (48% yield). LCMS m/z=411.2 [M+H⁺].

Example Z317. N—((R)-1-(2-(((S)-1-(Pyridin-2-yl)ethyl)amino)thieno[3,2-d]pyrimidine-4-carbonyl)pyrrolidin-3-yl)acetamide

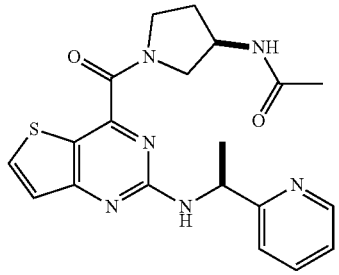

(Z317)

Synthesis of N—((R)-1-(2-(((S)-1-(pyridin-2-yl)ethyl)amino)thieno[3,2-d]pyrimidine-4-carbonyl)pyrrolidin-3-yl)acetamide (Z317): The title compound (Z317) was prepared from (S)-2-((1-(pyridin-2-yl)ethyl)amino)thieno[3,2-d]pyrimidine-4-carboxylic acid di-hydrochloride using chemistry similar to that described in Example Z17 using N-[(3R)-pyrrolidin-3-yl]acetamide in place of (3R)-3-methoxypyrrolidine hydrochloride (53% yield). LCMS m/z=411.2 [M+H$^+$].

Example Z318. (R)—N-(1-(2-(((5-Fluoropyridin-3-yl)methyl)amino)thieno[3,2-d]pyrimidine-4-carbonyl)pyrrolidin-3-yl)acetamide

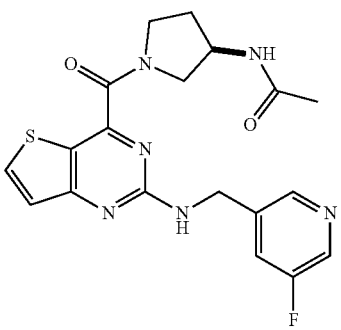 [SMILES: CC(=O)N[C@@H]1CCN(C(=O)c2nc(NCc3cncc(F)c3)nc3ccsc23)C1]

(Z318)

Synthesis of (R)—N-(1-(2-(((5-fluoropyridin-3-yl)methyl)amino)thieno[3,2-d]pyrimidine-4-carbonyl)pyrrolidin-3-yl)acetamide (Z318): The title compound (Z318) was prepared from 2-(((5-fluoropyridin-3-yl)methyl)amino)thieno[3,2-d]pyrimidine-4-carboxylic acid di-hydro-chloride using chemistry similar to that described in Example Z17 using N-[(3R)-pyrrolidin-3-yl]acetamide in place of (3R)-3-methoxypyrrolidine hydrochloride (61% yield). LCMS m/z=415.1 [M+H$^+$].

Example Z319. N—((R)-1-(2-(((S)-1-(5-Fluoropyridin-3-yl)ethyl)amino)thieno[3,2-d]pyrimidine-4-carbonyl)pyrrolidin-3-yl)acetamide

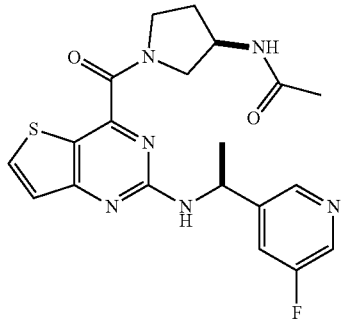 [SMILES: CC(=O)N[C@@H]1CCN(C(=O)c2nc(N[C@@H](C)c3cncc(F)c3)nc3ccsc23)C1]

(Z319)

Synthesis of N—((R)-1-(2-(((S)-1-(5-fluoropyridin-3-yl)ethyl)amino)thieno[3,2-d]pyrimidine-4-carbonyl)pyrrolidin-3-yl)acetamide (Z319): The title compound (Z319) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using N-[(3R)-pyrrolidin-3-yl]acetamide in place of (3R)-3-methoxypyrrolidine hydrochloride (30% yield). $^1$H NMR (400 MHz, CDCl$_3$) δ 1.63 (3H, dd, J=6.8, 3.2 Hz), 1.79-1.91 (1H, m), 2.00 (3H, d, J=8.8 Hz), 2.13-2.27 (1H, m), 3.77-3.83 (3H, m), 3.88-3.93 (1H, m), 4.41-4.54 (1H, m), 5.18 (1H, t, J=9.6 Hz), 5.45 (1H, t, J=6.8 Hz), 5.63-5.72 (1H, m), 7.17 (1H, d, J=5.6 Hz), 7.41-7.70 (1H, m), 7.96 (1H, dd, J=7.6, 5.6 Hz), 8.33 (1H, t, J=5.6 Hz), 8.50-8.54 (1H, m) ppm. LCMS m/z=429.2 [M+H$^+$].

Example Z320. N—((S)-2-Hydroxypropyl)-2-(((S)-2-methoxy-1-(pyridin-3-yl)ethyl)amino)thieno[3,2-d]pyrimidine-4-carboxamide

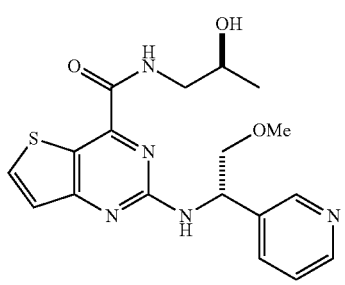 [SMILES: COC[C@@H](Nc1nc(C(=O)NC[C@H](C)O)c2sccc2n1)c1cccnc1]

(Z320)

Synthesis of ethyl (S)-2-((2-methoxy-1-(pyridin-3-yl)ethyl)amino)thieno[3,2-d]pyrimidine-4-carboxylate: The title compound was prepared from ethyl 2-chlorothieno[3,2-d]pyrimidine-4-carboxylate (400 mg, 1.65 mmol) using chemistry similar to that described in Example Z12 using (1S)-2-methoxy-1-(3-pyridyl)ethanamine hydrochloride (commercially obtained from Bellen, Shanghai, Conn.) in place of (6-methoxypyridin-3-yl)methanamine hydrochloride (89 mg, 15% yield). LCMS m/z=359.1 [M+H$^+$].

Synthesis of N—((S)-2-hydroxypropyl)-2-(((S)-2-methoxy-1-(pyridin-3-yl)ethyl)amino)thieno[3,2-d]pyrimidine-4-carboxamide (Z320): The title compound (Z320) was prepared from ethyl (S)-2-((2-methoxy-1-(pyridin-3-yl)ethyl)amino)thieno[3,2-d]pyrimidine-4-carboxylate using chemistry similar to that described in Example Z17 using (S)-(+)-1-amino-2-propanol in place of (3R)-3-methoxypyrrolidine hydrochloride (36% yield). LCMS m/z=388.1 [M+H⁺].

Example Z321. N—((R)-2-Hydroxypropyl)-2-(((S)-2-methoxy-1-(pyridin-3-yl)ethyl)amino)thieno[3,2-d]pyrimidine-4-carboxamide

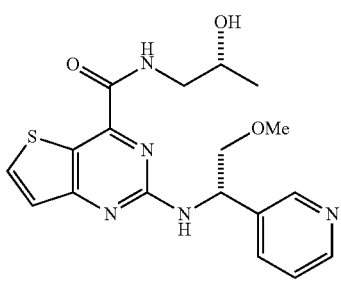 [SMILES: COC[C@@H](Nc1nc(C(=O)NC[C@@H](C)O)c2sccc2n1)c1cccnc1]

(Z321)

Synthesis of N—((R)-2-hydroxypropyl)-2-(((S)-2-methoxy-1-(pyridin-3-yl)ethyl)amino)thieno[3,2-d]pyrimidine-4-carboxamide (Z321): The title compound (Z321) was prepared from ethyl (S)-2-((2-methoxy-1-(pyridin-3-yl)ethyl)amino)thieno[3,2-d]pyrimidine-4-carboxylate using chemistry similar to that described in Example Z17 using (R)-(−)-1-amino-2-propanol in place of (3R)-3-methoxypyrrolidine hydrochloride (38% yield). LCMS m/z=388.2 [M+H⁺].

Example Z322. N—((S)-1-(2-(((S)-1-(Pyridin-3-yl)ethyl)amino)thieno[3,2-d]pyrimidine-4-carbonyl)pyrrolidin-3-yl)acetamide

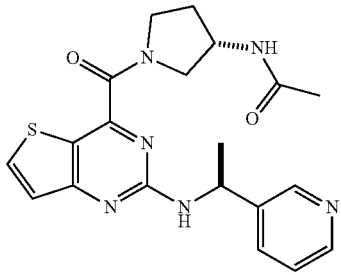 [SMILES: CC(=O)N[C@H]1CCN(C(=O)c2nc(N[C@@H](C)c3cccnc3)nc3ccsc23)C1]

(Z322)

Synthesis of N—((S)-1-(2-(((S)-1-(pyridin-3-yl)ethyl)amino)thieno[3,2-d]pyrimidine-4-carbonyl)pyrrolidin-3-yl)acetamide (Z322): The title compound (Z322) was prepared from (S)-2-((1-(pyridin-3-yl)ethyl)amino)thieno[3,2-d]pyrimidine-4-carboxylic acid di-hydrochloride using chemistry similar to that described in Example Z17 using N-[(3S)-pyrrolidin-3-yl]acetamide (commercially obtained from PharmaBlock, Sunnyvale Calif.) in place of (3R)-3-methoxypyrrolidine hydrochloride (28% yield). LCMS m/z=411.2 [M+H⁺].

Example Z323. N—((S)-2-Hydroxypropyl)-2-(((R)-2-methoxy-1-(pyridin-3-yl)ethyl)amino)thieno[3,2-d]pyrimidine-4-carboxamide

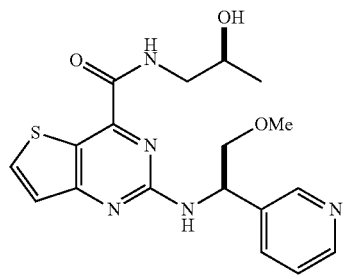 [SMILES: COC[C@H](Nc1nc(C(=O)NC[C@H](C)O)c2sccc2n1)c1cccnc1]

(Z323)

Synthesis of ethyl (R)-2-((2-methoxy-1-(pyridin-3-yl)ethyl)amino)thieno[3,2-d]pyrimidine-4-carboxylate: The title compound was prepared from ethyl 2-chlorothieno[3,2-d]pyrimidine-4-carboxylate (400 mg, 1.65 mmol) using chemistry similar to that described in Example Z12 using (1R)-2-methoxy-1-(3-pyridyl)ethanamine hydrochloride (commercially obtained from Bellen, Shanghai, Conn.) in place of (6-methoxypyridin-3-yl)methanamine hydrochloride (95 mg, 16% yield). LCMS m/z=359.1[M+H⁺].

Synthesis of N—((S)-2-hydroxypropyl)-2-(((R)-2-methoxy-1-(pyridin-3-yl)ethyl)amino)thieno[3,2-d]pyrimidine-4-carboxamide (Z323): The title compound (Z323) was prepared from ethyl (R)-2-((2-methoxy-1-(pyridin-3-yl)ethyl)amino)thieno[3,2-d]pyrimidine-4-carboxylate using chemistry similar to that described in Example Z17 using (S)-(+)-1-amino-2-propanol in place of (3R)-3-methoxypyrrolidine hydrochloride (20% yield). LCMS m/z=388.1 [M+H⁺].

Example Z324. N—((S)-1-(2-(((S)-1-(Pyridin-2-yl)ethyl)amino)thieno[3,2-d]pyrimidine-4-carbonyl)pyrrolidin-3-yl)acetamide

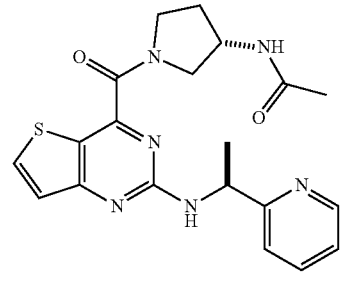 [SMILES: CC(=O)N[C@H]1CCN(C(=O)c2nc(N[C@@H](C)c3ccccn3)nc3ccsc23)C1]

(Z324)

Synthesis of N—((S)-1-(2-(((S)-1-(pyridin-2-yl)ethyl)amino)thieno[3,2-d]pyrimidine-4-carbonyl)pyrrolidin-3-yl)acetamide (Z324): The title compound (Z324) was prepared from (S)-2-((1-(pyridin-2-yl)ethyl)amino)thieno[3,2-d]pyrimidine-4-carboxylic acid di-hydrochloride using chemistry similar to that described in Example Z17 using N-[(3S)-pyrrolidin-3-yl]acetamide (commercially obtained from PharmaBlock, Sunnyvale, Calif.) in place of (3R)-3-methoxy-pyrrolidine hydrochloride (46% yield). ¹H NMR (400 MHz, CDCl₃) δ 1.61 (3H, d, J=6.8 Hz), 1.82-1.92 (1H, m), 2.00 (3H, d, J=14.8 Hz), 2.14-2.23 (1H, m), 3.59-3.69

(1H, m), 3.76-3.87 (2H, m), 3.99-4.11 (1H, m), 4.50 (1H, m), 5.22 (1H, m), 5.83-5.93 (2H, m), 7.18 (2H, t, J=6.0 Hz), 7.37 (1H, t, J=6.8 Hz), 7.62-7.65 (1H, m), 7.92 (1H, dd, J=12.4, 5.6 Hz), 8.55 (1H, m) ppm. LCMS m/z=411.2 [M+H$^+$].

Example Z325. N—((R)-2-Hydroxypropyl)-2-(((R)-2-methoxy-1-(pyridin-3-yl)ethyl)amino)thieno[3,2-d]pyrimidine-4-carboxamide

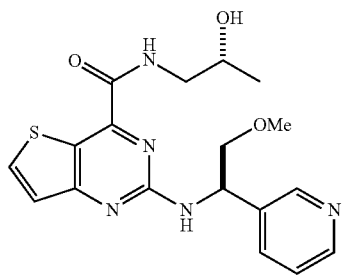 [SMILES: COC[C@H](Nc1nc(C(=O)NC[C@@H](C)O)c2sccc2n1)c1cccnc1]

(Z325)

Synthesis of N—((R)-2-hydroxypropyl)-2-(((R)-2-methoxy-1-(pyridin-3-yl)ethyl)amino)thieno[3,2-d]pyrimidine-4-carboxamide (Z325): The title compound (Z325) was prepared from ethyl (R)-2-((2-methoxy-1-(pyridin-3-yl)ethyl)amino)thieno[3,2-d]pyrimidine-4-carboxylate using chemistry similar to that described in Example Z17 using (R)-(−)-1-amino-2-propanol in place of (3R)-3-methoxypyrrolidine hydrochloride (17% yield). LCMS m/z=388.1 [M+H$^+$].

Example Z326. tert-Butyl (R)-3-(2-(((S)-1-(pyridin-2-yl)ethyl)amino)thieno[3,2-d]pyrimidine-4-carboxamido)pyrrolidine-1-carboxylate

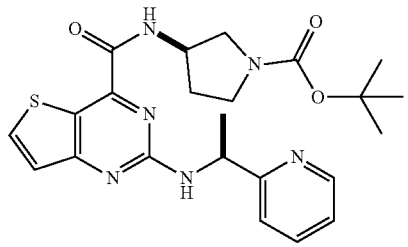

(Z326)

Synthesis of tert-butyl (R)-3-(2-(((S)-1-(pyridin-2-yl)ethyl)amino)thieno[3,2-d]pyrimidine-4-carboxamido)pyrrolidine-1-carboxylate (Z326): The title compound (Z326) was prepared from (S)-2-((1-(pyridin-2-yl)ethyl)amino)thieno[3,2-d]pyrimidine-4-carboxylic acid di-hydrochloride using chemistry similar to that described in Example Z17 using tert-butyl (3R)-3-aminopyrrol-idine-1-carboxylate (commercially obtained from PharmaBlock, Sunnyvale, Calif.) in place of (3R)-3-methoxypyrrolidine hydrochloride (42% yield). $^1$H NMR (400 MHz, CDCl$_3$) δ 1.47 (9H, s), 1.65 (3H, dd, J=24.0, 5.6 Hz), 1.82-1.92 (1H, m), 2.00 (1H, d, J=14.8 Hz), 3.25-3.63 (3H, m), 3.74 (1H, dd, J=11.2, 6.8 Hz), 4.59 (1H, m), 5.25 (1H, m), 6.22 (1H, s), 7.21 (1H, d, J=7.2 Hz), 7.39 (1H, d, J=1.2 Hz), 7.39 (1H, d, J=6.0 Hz), 7.69 (1H, t, J=8.0 Hz,), 7.96 (2H, d, J=6.8 Hz), 8.59 (1H, d, J=4.4 Hz) ppm. LCMS m/z=469.3 [M+H$^+$].

Example Z327. (S)-(2-((1-(Pyridin-3-yl)ethyl)amino)-6-(trifluoromethyl)thieno[3,2-d]pyrimidin-4-yl)(pyrrolidin-1-yl)methanone

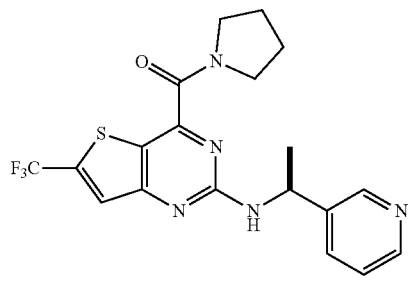 [SMILES: C[C@H](Nc1nc(C(=O)N2CCCC2)c2sc(C(F)(F)F)cc2n1)c1cccnc1]

(Z327)

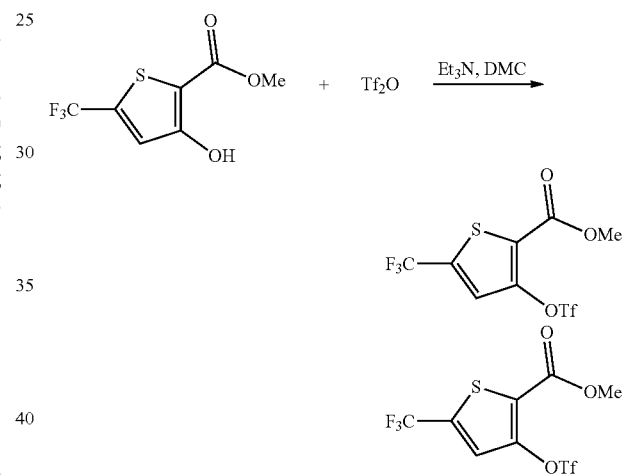

Synthesis of methyl 5-(trifluoromethyl)-3-((((trifluoromethyl)sulfonyl)oxy)thiophene-2-carboxylate: To a solution of methyl 3-hydroxy-5-(trifluoromethyl)thiophene-2-carboxylate (5 g, 22.1 mmol) and triethylamine (3.35 g, 33.1 mmol) in DCM (100 mL) was added trifluoromethanesulfonic anhydride (8.11 g, 28.7 mmol) dropwise with stirring at −78° C. in 10 min. The resulting solution was stirred for 1 h at −78° C. and then was extracted with DCM (2×150 mL). The combined organic layer was dried over anhydrous sodium sulfate and concentrated under vacuum to provide methyl 5-(trifluoromethyl)-3-(((trifluoromethyl)sulfonyl)oxy)thiophene-2-carboxylate as a light brown oil (6.9 g, 87% yield). $^1$H NMR (400 MHz, methanol-d$_4$) δ 3.92 (3H, s), 8.26 (1H, s) ppm.

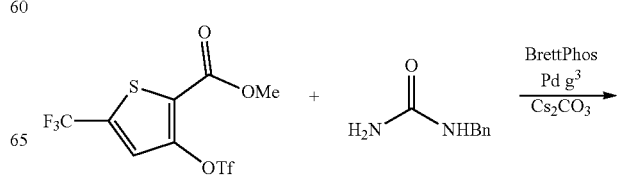

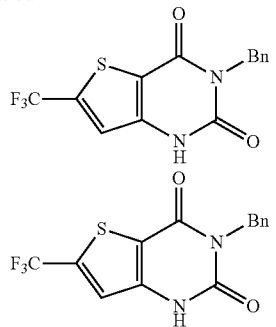

Synthesis of 3-benzyl-6-(trifluoromethyl)thieno[3,2-d]pyrimidine-2,4(1H,3H)-dione: To a solution of methyl 5-(trifluoromethyl)-3-(((trifluoromethyl)sulfonyl)oxy)thiophene-2-carboxylate (6.9 g, 19.3 mmol) in 1,4-dioxane (100 mL) were added Cs₂CO₃ (12.56 g, 38.5 mmol), benzylurea (3.47 g, 23.1 mmol) and 3$^{rd}$ generation BrettPhos precatalyst (1.75 g, 1.93 mmol). The resulting solution was stirred for 2 h at 80° C. and then was extracted with ethyl acetate (3×400 mL). The combined organic layer was washed with brine, dried over anhydrous sodium sulfate and concentrated under vacuum. The residue was purified by flash chromatography on silica gel eluting with ethyl acetate/petroleum ether (1:5) to provide 3-benzyl-6-(trifluoromethyl)thieno[3,2-d]pyrimidine-2,4(1H,3H)-dione as a brown solid (4 g, 64% yield). LCMS m/z=326.9 [M+H⁺].

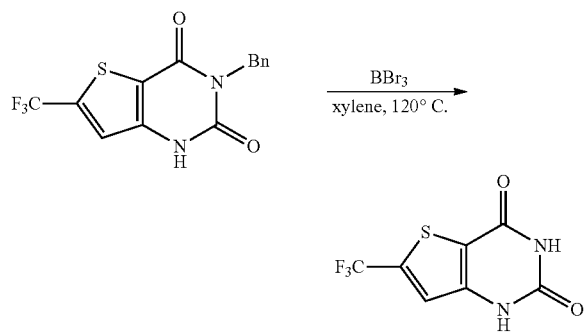

Synthesis of 6-(trifluoromethyl)thieno[3,2-d]pyrimidine-2,4(1H,3H)-dione: To a solution of 3-benzyl-6-(trifluoromethyl)thieno[3,2-d]pyrimidine-2,4(1H,3H)-dione (4 g, 12.3 mmol) in xylene (100 mL) was added BBr₃ (17 mL, 123 mmol) and the resulting solution was stirred for 1 h at 120° C. The reaction mixture was extracted with ethyl acetate (3×300 mL) and the combined organic layer was dried over anhydrous sodium sulfate and concentrated under vacuum. The residue was purified by flash chromatography on silica gel eluting with DCM/methanol (30:1) to provide 6-(trifluoromethyl)thieno[3,2-d]pyrimidine-2,4(1H,3H)-dione as a light brown solid (2.0 g, 69% yield). LCMS m/z=236.9 [M+H⁺].

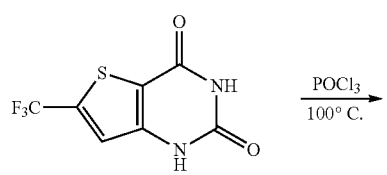

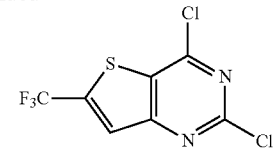

Synthesis of 2,4-dichloro-6-(trifluoromethyl)thieno[3,2-d]pyrimidine: To a solution of 6-(trifluoromethyl)thieno[3,2-d]pyrimidine-2,4(1H,3H)-dione (2 g, 8.47 mmol) in POCl₃ (90 mL) was added DIEA (2.18 g, 16.9 mmol). The resulting solution was stirred overnight at 100° C. and then was extracted with ethyl acetate (3×150 mL). The combined organic layer was dried over anhydrous sodium sulfate and concentrated under vacuum. The residue was purified by flash chromatography on silica gel eluting with ethyl acetate/petroleum ether (1:30) to provide 2,4-dichloro-6-(trifluoromethyl)thieno[3,2-d]pyrimidine as a brown solid (1.9 g, 82% yield). LCMS m/z=272.8 [M+H⁺].

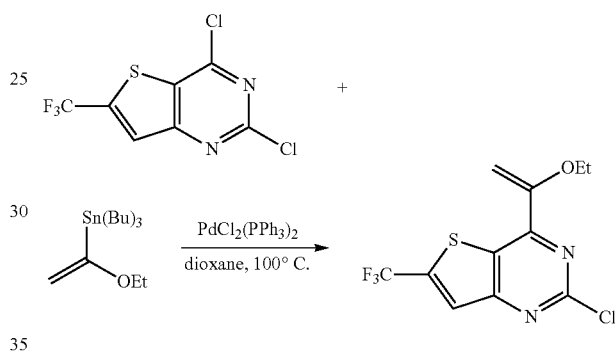

Synthesis of 2-chloro-4-(1-ethoxyvinyl)-6-(trifluoromethyl)thieno[3,2-d]pyrimidine: To a solution of 2,4-dichloro-6-(trifluoromethyl)thieno[3,2-d]pyrimidine (1.9 g, 6.96 mmol) in dioxane/H₂O (75/15 mL) were added tributyl (1-ethoxyethenyl)stannane (1.85 g, 5.12 mmol), potassium carbonate (1.41 g) and bis(triphenylphosphine)palladium (II) dichloride (180 mg, 0.26 mmol). The resulting solution was stirred for 1 h at 100° C. and then was extracted with ethyl acetate (3×150 mL). The combined organic layer was dried over anhydrous sodium sulfate and concentrated under vacuum. The residue was purified by flash chromatography on silica gel eluting with ethyl acetate/petroleum ether (1:50) to provide 2-chloro-4-(1-ethoxyvinyl)-6-(trifluoromethyl)thieno[3,2-d]pyrimidine as a light brown solid (900 mg, 42% yield). LCMS m/z=309.1 [M+H⁺].

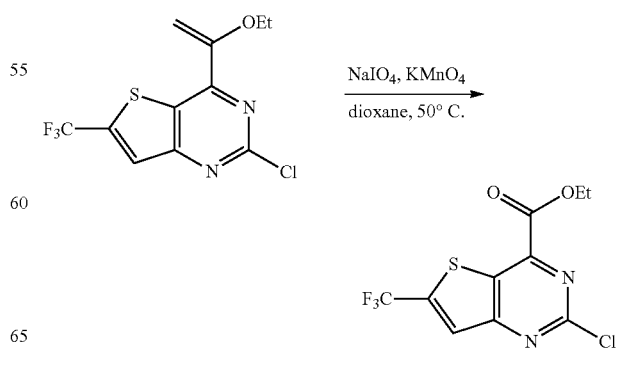

Synthesis of ethyl 2-chloro-6-(trifluoromethyl)thieno[3,2-d]pyrimidine-4-carboxylate: To a solution of 2-chloro-4-(1-ethoxyvinyl)-6-(trifluoromethyl)thieno[3,2-d]pyrimidine (900 mg, 2.92 mmol) in dioxane (36 mL) were added sodium periodate (1.25 g, 5.84 mmol) and potassium permanganate (230 mg, 1.46 mmol). The resulting solution was stirred for 1 h at 50° C. and the solids were filtered out. The filtrate was extracted with ethyl acetate (2×100 mL) and the combined organic layer was dried and and concentrated under vacuum. The residue was purified by flash chromatography on silica gel eluting with ethyl acetate/petroleum ether (1:30) to provide ethyl 2-chloro-6-(trifluoromethyl)thieno[3,2-d]pyrimidine-4-carboxylate as a white solid (600 mg, 66% yield). LCMS m/z=311.1

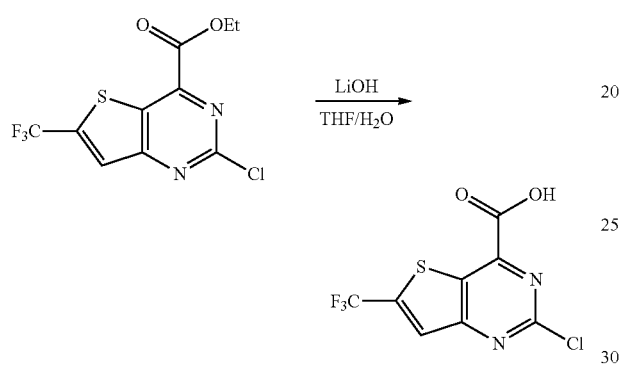

Synthesis of 2-chloro-6-(trifluoromethyl)thieno[3,2-d]pyrimidine-4-carboxylic acid: To a solution of ethyl 2-chloro-6-(trifluoromethyl)thieno[3,2-d]pyrimidine-4-carboxylate (200 mg, 0.64 mmol) in tetrahydrofuran/H₂O (10/2.5 mL) was added lithium hydroxide (76 mg, 3.17 mmol) and the resulting solution was stirred for 2 h at 5° C. The pH value of the reaction mixture was adjusted to 3-4 with 1N hydrogen chloride. The reaction mixture was dried over anhydrous sodium sulfate and concentrated under vacuum to provide 2-chloro-6-(trifluoromethyl)thieno[3,2-d]pyrimidine-4-carboxylic acid as an yellow solid (180 mg, 99% yield). LCMS m/z=282.8 [M+H⁺].

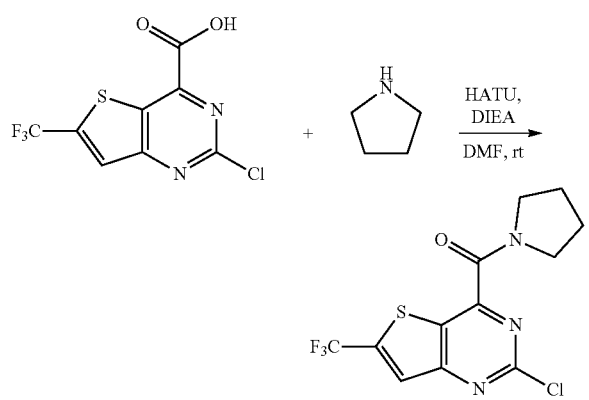

Synthesis of (2-chloro-6-(trifluoromethyl)thieno[3,2-d]pyrimidin-4-yl)(pyrrolidin-1-yl)methanone: To a solution of 2-chloro-6-(trifluoromethyl)thieno[3,2-d]pyrimidine-4-carboxylic acid (120 mg, 0.42 mmol) in DMF (6 mL) were added HATU (306 mg, 0.84 mmol), DIEA (164 mg, 1.26 mmol) and pyrrolidine (30 mg, 0.42 mmol). The resulting solution was stirred for 2 h at room temperature and then was extracted with ethyl acetate (2×50 mL). The combined organic layer was dried over anhydrous sodium sulfate and concentrated under vacuum. The residue was purified by flash chromatography on silica gel eluting with ethyl acetate/petroleum ether (1:4). To provide (2-chloro-6-(trifluoromethyl)thieno[3,2-d]pyrimidin-4-yl)(pyrrolidin-1-yl)methanone as an yellow solid (60 mg, 42% yield). LCMS m/z=336.2 [M+H⁺].

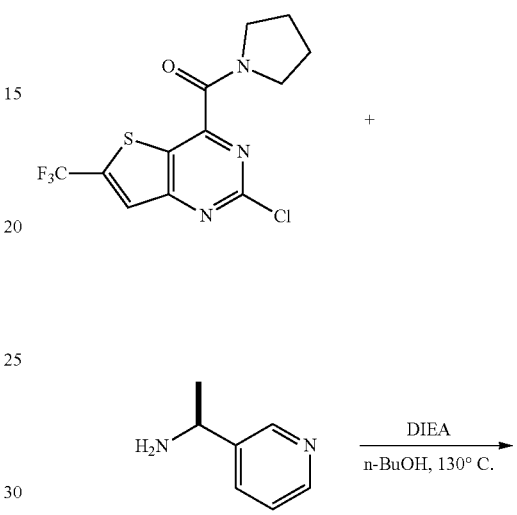

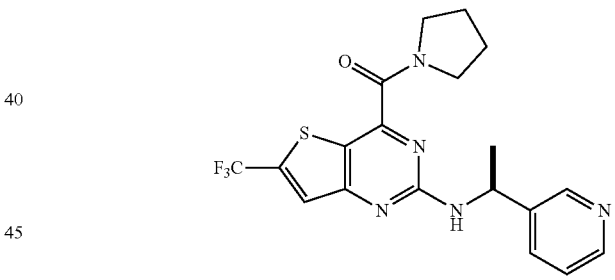

Synthesis of (S)-(2-((1-(pyridin-3-yl)ethyl)amino)-6-(trifluoromethyl)thieno[3,2-d]pyrimidin-4-yl)(pyrrolidin-1-yl)methanone (Z327): To a solution of (2-chloro-6-(trifluoromethyl)thieno[3,2-d]pyrimidin-4-yl)(pyrrolidin-1-yl)methanone (60 mg, 0.18 mmol) in n-butanol (3 mL) were added (S)-1-(pyridin-3-yl)ethan-1-amine (32 mg, 0.26 mmol) and DIEA (70 mg, 0.54 mmol). The resulting solution was stirred for 3 h at 130° C. The crude product was purified by prep-HPLC (C-18 OBD column and a gradient elution system of water-acetonitrile) to provide (S)-(2-((1-(pyridin-3-yl)ethyl)amino)-6-(trifluoromethyl)thieno[3,2-d]pyrimidin-4-yl)(pyrrolidin-1-yl)methanone as a light yellow solid (11 mg, 14% yield). ¹H NMR (300 MHz, methanol-d₄) δ 1.63 (3H, d, J=7.2 Hz), 1.83-2.00 (4H, m), 3.60-3.70 (2H, m), 3.90-4.10 (2H, m), 5.23 (1H, q, J=7.2 Hz), 7.39 (1H, dd, J=8.0, 4.8 Hz), 7.60 (1H, s), 7.91 (1H, d, J=8.0 Hz), 8.39 (1H, dd, J=4.8, 1.5 Hz), 8.62 (1H, d, J=1.5 Hz) ppm. LCMS m/z=422.1 [M+H⁺].

Example Z328. N—((S)-2-Hydroxypropyl)-6-methyl-2-(((S)-1-(pyridin-3-yl)ethyl)amino)thieno[3,2-d]pyrimidine-4-carboxamide

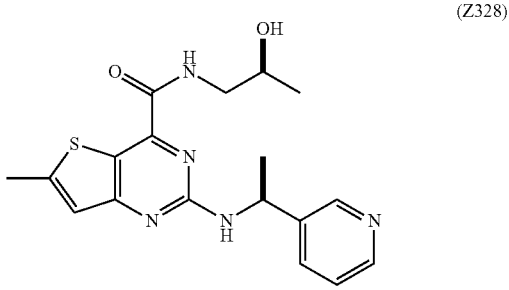

(Z328)

Synthesis of ethyl (S)-6-methyl-2-((1-(pyridin-3-yl)ethyl)amino)thieno[3,2-d]pyrimidine-4-carboxylate: To a solution of ethyl 2-chloro-6-methylthieno[3,2-d]pyrimidine-4-carboxylate (1 g, 3.90 mmol) in DMSO (20 mL) were added (S)-1-(pyridin-3-yl)ethan-1-amine (953 mg, 7.80 mmol) and DIEA (1.5 g, 11.6 mmol) and the resulting solution was stirred for 3 h at 130° C. The reaction mixture was extracted with ethyl acetate and the combined organic layer was dried over anhydrous sodium sulfate and concentrated under vacuum. The residue was purified by flash chromatography on silica gel eluting with ethyl acetate/petroleum ether to provide ethyl (S)-6-methyl-2-((1-(pyridin-3-yl)ethyl)amino)thieno[3,2-d]pyrimidine-4-carboxylate as an yellow solid (560 mg, 42% yield). $^1$H NMR (300 MHz, DMSO-$d_6$) δ 1.38 (3H, t, J=6.4 Hz), 1.51 (3H, d, J=6.8 Hz), 2.58 (3H, s), 4.42 (2H, q, J=6.4 Hz), 5.17 (1H, q, J=6.8 Hz), 6.99 (1H, s), 7.32 (1H, m), 7.84 (1H, m), 8.14 (1H, br s), 8.40 (1H, m), 8.66 (1H, m) ppm. LCMS m/z=343.3 [M+H$^+$].

Synthesis of (S)-6-methyl-2-((1-(pyridin-3-yl)ethyl)amino)thieno[3,2-d]pyrimidine-4-carboxylic acid di-hydrochloride: A solution of ethyl (S)-6-methyl-2-((1-(pyridin-3-yl)ethyl)amino)thieno[3,2-d]pyrimidine-4-carboxylate (500 mg, 1.46 mmol) in 6N hydrogen chloride (25 mL) was stirred for 1.5 h at 90° C. The reaction mixture was concentrated under vacuum and the crude product was dried under high vacuum overnight to provide (S)-6-methyl-2-((1-(pyridin-3-yl)ethyl)amino)thieno[3,2-d]pyrimidine-4-carboxylic acid di-hydrochloride as an yellow solid (565 mg, 100% yield). LCMS m/z=315.2 [M+H$^+$].

Synthesis of N—((S)-2-hydroxypropyl)-6-methyl-2-(((S)-1-(pyridin-3-yl)ethyl)amino)thieno[3,2-d]pyrimidine-4-carboxamide (Z328): The title compound (Z328) was prepared from (S)-6-methyl-2-((1-(pyridin-3-yl)ethyl)amino)thieno[3,2-d]pyrimidine-4-carboxylic acid di-hydrochloride (120 mg, 0.31 mmol) using chemistry similar to that described in Example Z8 using (S)-1-aminopropan-2-ol in place of (R)-3-fluoropyrrolidine (56 mg, 49% yield). $^1$H NMR (400 MHz, methanol-$d_4$) δ 1.22 (3H, d, J=7.2 Hz), 1.63 (3H, d, J=7.2 Hz), 2.61 (3H, s), 3.35 (1H, m), 3.52 (1H, dd, J=13.6, 4.0 Hz), 3.97 (1H, m), 5.29 (1H, q, J=7.2 Hz), 6.89 (1H, s), 7.40 (1H, dd, J=7.6, 4.8 Hz), 7.95 (1H, d, J=7.6 Hz), 8.39 (1H, dd, J=4.8, 2.0 Hz), 8.68 (1H, d, J=2.0 Hz) ppm. LCMS m/z=372.3 [M+H$^+$].

Example Z329. 2-(((S)-1-(5-Fluoropyridin-3-yl)ethyl)amino)-N-((1S,3R)-3-hydroxycyclopentyl)thieno[3,2-d]pyrimidine-4-carboxamide

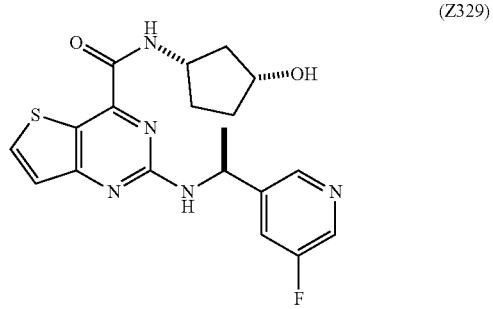

(Z329)

Synthesis of 2-(((S)-1-(5-fluoropyridin-3-yl)ethyl)amino)-N-((1S,3R)-3-hydroxycyclopentyl)thieno[3,2-d]pyrimidine-4-carboxamide (Z329): The title compound (Z329) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using (1R,3S)-3-aminocyclopentanol (commercially available from LabNetwork, Shanghai, Conn.) in place of (3R)-3-methoxypyrrolidine hydrochloride (42% yield). LCMS m/z=402.2 [M+H$^+$].

Example Z330. (S)—N-(1-(2-(((5-Fluoropyridin-3-yl)methyl)amino)thieno[3,2-d]pyrimidine-4-carbonyl)pyrrolidin-3-yl)acetamide

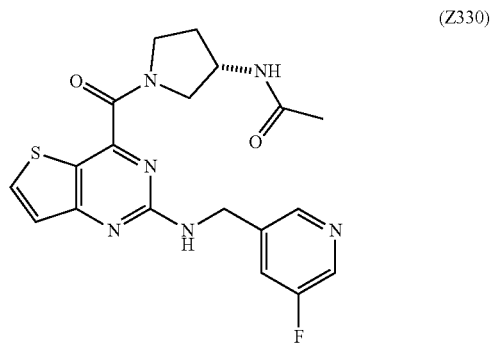

(Z330)

Synthesis of (S)—N-(1-(2-(((5-fluoropyridin-3-yl)methyl)amino)thieno[3,2-d]pyrimidine-4-carbonyl)pyrrolidin-3-yl)acetamide (Z330): The title compound (Z330) was prepared from 2-(((5-fluoropyridin-3-yl)methyl)amino)thieno[3,2-d]pyrimidine-4-carboxylic acid di-hydrochloride using chemistry similar to that described in Example Z17 using N-[(3S)-pyrrolidin-3-yl]acetamide in place of (3R)-3-methoxypyrrolidine hydrochloride (61% yield). $^1$H NMR (400 MHz, CDCl$_3$) δ 1.83-1.96 (1H, m), 2.01 (3H, d, J=10.4 Hz), 2.11-2.23 (1H, m), 3.76-3.92 (3H, m), 4.15-4.20 (1H, m), 4.47-4.54 (1H, m), 4.72 (2H, dd, J=10.8, 6.0 Hz), 5.67 (1H, dt, J=28.4, 6.4 Hz), 6.00 (1H, dd, J=22.0, 6.4 Hz), 7.20 (1H, dd, J=6.4, 5.6 Hz), 7.43-7.47 (1H, m), 7.96 (1H, dd, J=8.8, 5.6 Hz), 8.36 (1H, d, J=2.8 Hz), 8.47 (1H, m) ppm. LCMS m/z=415.1 [M+H$^+$].

Example Z331. N—((S)-1-(2-(((S)-1-(5-Fluoropyridin-3-yl)ethyl)amino)thieno[3,2-d]pyrimidine-4-carbonyl)pyrrolidin-3-yl)acetamide

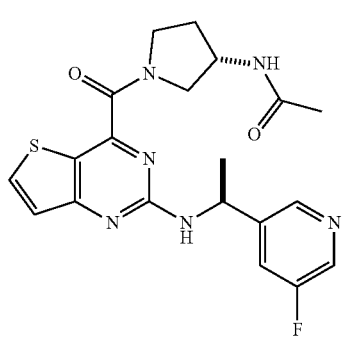 [SMILES: CC(=O)N[C@H]1CCN(C(=O)c2nc(N[C@@H](C)c3cncc(F)c3)nc3ccsc23)C1]
(Z331)

Synthesis of N—((S)-1-(2-(((S)-1-(5-fluoropyridin-3-yl)ethyl)amino)thieno[3,2-d]pyrimidine-4-carbonyl)pyrrolidin-3-yl)acetamide (Z331): The title compound (Z331) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using N-[(3S)-pyrrolidin-3-yl]acetamide in place of (3R)-3-methoxypyrrolidine hydrochloride (20% yield). 1H NMR (400 MHz, CDCl3) δ 1.63 (3H, d, J=8.0 Hz), 1.77-1.89 (1H, m), 2.04 (3H, d, J=3.6 Hz), 2.15-2.24 (1H, m), 3.42-3.87 (3H, m), 4.28 (1H, dd, J=12.4, 6.0 Hz), 4.48-4.52 (1H, m), 5.09-5.19 (1H, m), 5.46 (1H, dd, J=16.4, 5.6 Hz), 6.84 (1H, m), 7.17 (1H, dd, J=5.6, 4.0 Hz), 7.44 (1H, dt, J=9.2, 2.0 Hz), 7.96 (1H, dd, J=5.2, 1.2 Hz), 8.33 (1H, t, J=2.4 Hz), 8.47-8.50 (1H, m) ppm. LCMS m/z=429.2 [M+H$^+$].

Example Z332. N-((1S,3R)-3-Hydroxycyclopentyl)-2-(((S)-1-(pyridin-2-yl)ethyl)amino)thieno[3,2-d]pyrimidine-4-carboxamide

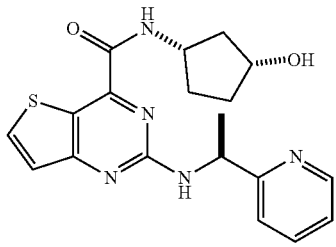
(Z332)

Synthesis of N-((1S,3R)-3-hydroxycyclopentyl)-2-(((S)-1-(pyridin-2-yl)ethyl)amino)thieno[3,2-d]pyrimidine-4-carboxamide (Z332): The title compound (Z332) was prepared from (S)-2-((1-(pyridin-2-yl)ethyl)amino)thieno[3,2-d]pyrimidine-4-carboxylic acid di-hydrochloride using chemistry similar to that described in Example Z17 using (1R,3S)-3-aminocyclopentanol in place of (3R)-3-methoxypyrrolidine hydrochloride (52% yield). LCMS m/z=484.2 [M+H$^+$].

Example Z333. ((S)-3-Hydroxypyrrolidin-1-yl)(2-(((S)-1-(pyridin-3-yl)ethyl)amino)-6-(trifluoromethyl)thieno[3,2-d]pyrimidin-4-yl)methanone

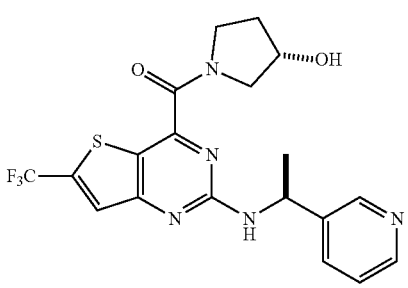 [SMILES: C[C@H](Nc1nc(C(=O)N2CC[C@H](O)C2)c2sc(C(F)(F)F)cc2n1)c1cccnc1]
(Z333)

Synthesis of ((S)-3-hydroxypyrrolidin-1-yl)(2-(((S)-1-(pyridin-3-yl)ethyl)amino)-6-(trifluoromethyl)thieno[3,2-d]pyrimidin-4-yl)methanone (Z333): The title compound (Z333) was prepared from (S)-2-((1-(pyridin-3-yl)ethyl)amino)-6-(trifluoromethyl)thieno[3,2-d]pyrimidine-4-carboxylic acid di-hydrochloride (55 mg, 0.12 mmol) using chemistry similar to that described in Example Z8 using (S)-pyrrolidin-3-ol in place of (R)-3-fluoropyrrolidine (25 mg, 48% yield). $^1$H NMR (400 MHz, methanol-d$_4$) δ 1.65 (3H, d, J=7.2 Hz), 1.92-2.10 (2H, m), 3.50-3.80 (2H, m), 3.90-4.25 (2H, m), 4.46 (1H, m), 5.27 (1H, q, J=7.2 Hz), 7.41 (1H, m), 7.63 (1H, s), 7.94 (1H, m), 8.41 (1H, m), 8.65 (1H, m) ppm. LCMS m/z=438.1 [M+H$^+$].

Example Z334. N—((R)-2-Hydroxypropyl)-6-methyl-2-(((S')-1-(pyridin-3-yl)ethyl)amino)thieno[3,2-d]pyrimidine-4-carboxamide

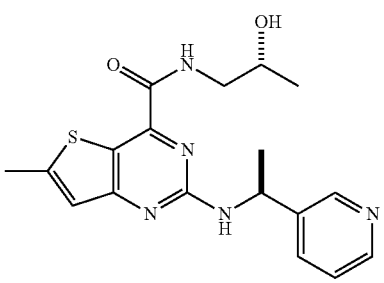 [SMILES: Cc1cc2nc(N[C@@H](C)c3cccnc3)nc(C(=O)NC[C@@H](C)O)c2s1]
(Z334)

Synthesis of N—((R)-2-hydroxypropyl)-6-methyl-2-(((S)-1-(pyridin-3-yl)ethyl)amino)thieno[3,2-d]pyrimidine-4-carboxamide (Z334): The title compound (Z334) was prepared from (S)-6-methyl-2-((1-(pyridin-3-yl)ethyl)amino)thieno[3,2-d]pyrimidine-4-carboxylic acid di-hydrochloride (120 mg, 0.31 mmol) using chemistry similar to that described in Example Z8 using (R)-1-aminopropan-2-ol in place of (R)-3-fluoropyrrolidine (60 mg, 52% yield). $^1$H NMR (300 MHz, methanol-d$_4$) δ 1.23 (3H, d, J=6.4 Hz), 1.63 (3H, d, J=6.8 Hz), 2.61 (3H, s), 3.36 (1H, m), 3.52 (1H, dd, J=13.5, 4.2 Hz), 3.97 (1H, m), 5.28 (1H, q, J=6.8 Hz), 6.88 (1H, s), 7.40 (1H, dd, J=7.8, 4.8 Hz), 7.95 (1H, d, J=7.8 Hz), 8.39 (1H, dd, J=4.8, 2.0 Hz), 8.67 (1H, d, J=2.0 Hz) ppm. LCMS m/z=372.2 [M+H$^+$].

Example Z335. ((R)-3-(Hydroxymethyl)pyrrolidin-1-yl)(6-methyl-2-(((S)-1-(pyridin-3-yl)ethyl)amino)thieno[3,2-d]pyrimidin-4-yl)methanone

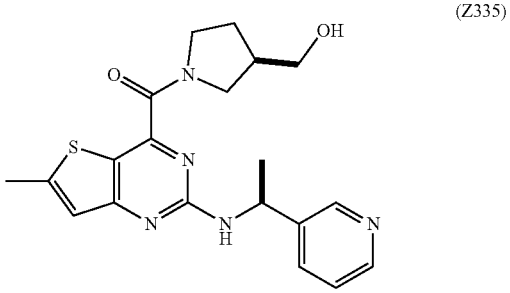

(Z335)

Synthesis of ((R)-3-(hydroxymethyl)pyrrolidin-1-yl)(6-methyl-2-(((S)-1-(pyridin-3-yl)ethyl)amino)thieno[3,2-d]pyrimidin-4-yl)methanone (Z335): The title compound (Z335) was prepared from (S)-6-methyl-2-((1-(pyridin-3-yl)ethyl)amino)thieno[3,2-d]pyrimidine-4-carboxylic acid di-hydrochloride (120 mg, 0.31 mmol) using chemistry similar to that described in Example Z8 using (R)-pyrrolidin-3-ylmethanol in place of (R)-3-fluoropyrrolidine (62 mg, 50% yield). $^1$H NMR (300 MHz, methanol-$d_4$) δ 1.62 (3H, d, J=7.2 Hz), 1.71 (1H, m), 2.01 (1H, m), 2.41 (1H, m), 2.60 (3H, s), 3.40 (1H, m), 3.45-3.64 (2H, m), 3.65-3.80 (2H, m), 3.92 (1H, m), 5.23 (1H, m), 6.90 (1H, s), 7.40 (1H, m), 7.92 (1H, m), 8.40 (1H, m), 8.62 (1H, m) ppm. LCMS m/z=398.1 [M+H$^+$].

Example Z336. ((S)-3-(Hydroxymethyl)pyrrolidin-1-yl)(6-methyl-2-(((S)-1-(pyridin-3-yl)ethyl)amino)thieno[3,2-d]pyrimidin-4-yl)methanone

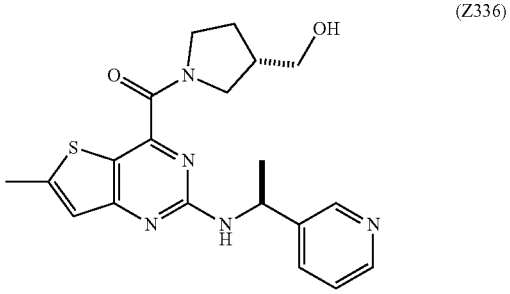

(Z336)

Synthesis of ((S)-3-(hydroxymethyl)pyrrolidin-1-yl)(6-methyl-2-(((S)-1-(pyridin-3-yl)ethyl)amino)thieno[3,2-d]pyrimidin-4-yl)methanone (Z336): The title compound (Z336) was prepared from (S)-6-methyl-2-((1-(pyridin-3-yl)ethyl)amino)thieno[3,2-d]pyrimidine-4-carboxylic acid di-hydrochloride (120 mg, 0.31 mmol) using chemistry similar to that described in Example Z8 using (S)-pyrrolidin-3-ylmethanol in place of (R)-3-fluoropyrrolidine (50 mg, 41% yield). $^1$H NMR (300 MHz, methanol-$d_4$) δ 1.62 (3H, d, J=7.2 Hz), 1.74 (1H, m), 2.03 (1H, m), 2.42 (1H, m), 2.60 (3H, s), 3.38 (1H, m), 3.45-3.64 (2H, m), 3.65-3.80 (2H, m), 3.92 (1H, m), 5.23 (1H, m), 6.90 (1H, s), 7.40 (1H, dd, J=8.0, 4.8 Hz), 7.92 (1H, m), 8.40 (1H, m), 8.62 (1H, m) ppm. LCMS m/z=398.2 [M+H$^+$].

Example Z337. ((R)-3-Hydroxypyrrolidin-1-yl)(2-(((S)-1-(pyridin-3-yl)ethyl)amino)-6-(trifluoromethyl)thieno[3,2-d]pyrimidin-4-yl)methanone

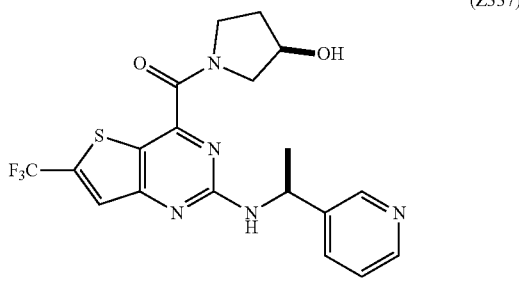

(Z337)

Synthesis of ((R)-3-hydroxypyrrolidin-1-yl)(2-(((S)-1-(pyridin-3-yl)ethyl)amino)-6-(trifluoromethyl)thieno[3,2-d]pyrimidin-4-yl)methanone (Z337): The title compound (Z337) was prepared from (S)-2-((1-(pyridin-3-yl)ethyl)amino)-6-(trifluoromethyl)thieno[3,2-d]pyrimidine-4-carboxylic acid di-hydrochloride (66 mg, 0.15 mmol) using chemistry similar to that described in Example Z8 using (R)-pyrrolidin-3-ol in place of (R)-3-fluoropyrrolidine (30 mg, 46% yield). $^1$H NMR (400 MHz, methanol-$d_4$) δ 1.64 (3H, d, J=6.8 Hz), 1.90-2.01 (2H, m), 3.52-3.82 (2H, m), 3.90-4.26 (2H, m), 4.66 (1H, m), 5.25 (1H, q, J=6.8 Hz), 7.39 (1H, m), 7.60 (1H, s), 7.92 (1H, d, J=8.0 Hz), 8.39 (1H, m), 8.64 (1H, m) ppm. LCMS m/z=438.1 [M+H$^+$].

Example Z338. N—((S)-1-(Pyridin-4-yl)ethyl)-2-(((S)-1-(pyridin-4-yl)ethyl)amino)thieno[3,2-d]pyrimidine-4-carboxamide

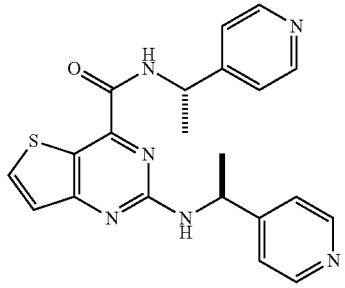 [SMILES: C[C@H](NC(=O)c1nc(N[C@@H](C)c2ccncc2)nc2ccsc12)c1ccncc1]

(Z338)

Synthesis of N—((S)-1-(pyridin-4-yl)ethyl)-2-(((S)-1-(pyridin-4-yl)ethyl)amino)thieno[3,2-d]pyrimidine-4-carboxamide (Z338) and ethyl (S)-2-((1-(pyridin-4-yl)ethyl)amino)thieno[3,2-d]pyrimidine-4-carboxylate: The title compounds were prepared from ethyl 2-chlorothieno[3,2-d]pyrimidine-4-carboxylate (450 mg, 1.85 mmol) using chemistry similar to that described in Example Z12 using (1S)-1-(4-pyridyl)ethanamine di-hydrochloride (commercially obtained from Accela ChemBio, San Diego, Calif.) in place of (6-methoxypyridin-3-yl)methanamine hydro-chloride to produce N—((S)-1-(pyridin-4-yl)ethyl)-2-(((S)-1-(pyridin-4-yl)ethyl)amino)thieno[3,2-d]pyrimidine-4-carboxamide (338) (324 mg, 43% yield), LCMS m/z=405.2 [M+H$^+$], and ethyl (S)-2-((1-(pyridin-4-yl)ethyl)amino)thieno[3,2-d]pyrimidine-4-carboxylate (328 mg, 25%), LCMS m/z=329.1 [M+H$^+$].

Example Z339. (S)-2-((1-(5-Fluoropyridin-3-yl)ethyl)amino)-N-((tetrahydro-2H-pyran-4-yl)methyl)thieno[3,2-d]pyrimidine-4-carboxamide

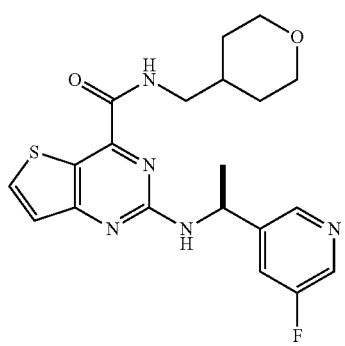 [SMILES: C[C@H](Nc1nc(C(=O)NCC2CCOCC2)c2sccc2n1)c1cncc(F)c1]

(Z339)

Synthesis of (S)-2-((1-(5-fluoropyridin-3-yl)ethyl)amino)-N-((tetrahydro-2H-pyran-4-yl)methyl)thieno[3,2-d]pyrimidine-4-carboxamide (Z339): The title compound (Z339) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using tetrahydropyran-4-ylmethanamine (commercially obtained from PharmaBlock, Sunnyvale Calif.) in place of (3R)-3-methoxypyrrolidine hydrochloride (37% yield). LCMS m/z=416.1 [M+H⁺].

Example Z340. (S)-2-((1-(5-Fluoropyridin-3-yl)ethyl)amino)-N-(4-hydroxyphenethyl)thieno[3,2-d]pyrimidine-4-carboxamide

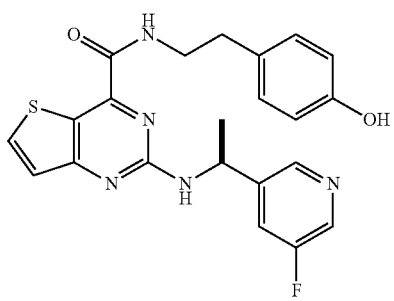 [SMILES: C[C@H](Nc1nc(C(=O)NCCc2ccc(O)cc2)c2sccc2n1)c1cncc(F)c1]

(Z340)

Synthesis of (S)-2-((1-(5-fluoropyridin-3-yl)ethyl)amino)-N-(4-hydroxyphenethyl)thieno[3,2-d]pyrimidine-4-carboxamide (Z340): The title compound (Z340) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using 4-(2-aminoethyl)phenol (commercially obtained from AK Scientific, Union City, Calif.) in place of (3R)-3-methoxypyrrolidine hydrochloride (41% yield). ¹H NMR (400 MHz, CDCl₃) δ 1.59 (3H, d, J=6.8 Hz), 2.81-2.85 (2H, m), 3.61-3.75 (2H, m), 5.15-5.18 (1H, m), 5.40 (1H, d, J=6.8 Hz), 6.33 (1H, m), 6.79 (2H, d, J=8.4 Hz), 7.06 (2H, d, J=8.4 Hz), 7.17 (1H, d, J=5.6 Hz), 7.40 (1H, d, J=7.6 Hz), 7.65-7.75 (1H, m), 8.01 (1H, d, J=4.2 Hz), 8.34 (2H, d, J=2.8 Hz) ppm. LCMS m/z=438.0 [M+H⁺].

Example Z341. (S)-Azetidin-1-yl(2-((2-methoxy-1-(pyridin-3-yl)ethyl)amino)thieno[3,2-d]pyrimidin-4-yl)methanone

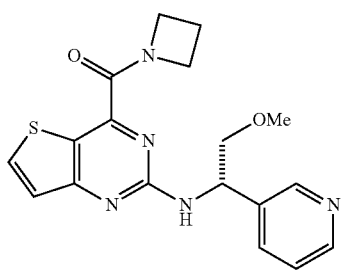 [SMILES: COC[C@@H](Nc1nc(C(=O)N2CCC2)c2sccc2n1)c1cccnc1]

(Z341)

Synthesis of (S)-azetidin-1-yl(2-((2-methoxy-1-(pyridin-3-yl)ethyl)amino)thieno[3,2-d]pyrimidin-4-yl)methanone (Z341): The title compound (Z341) was prepared from ethyl (S)-2-((2-methoxy-1-(pyridin-3-yl)ethyl)amino)thieno[3,2-d]pyrimidine-4-carboxylate using chemistry similar to that described in Example Z17 using azetidine in place of (3R)-3-methoxypyrrolidine hydrochloride (69% yield). ¹H NMR (400 MHz, CDCl₃) δ 2.28-2.41 (2H, m), 3.39 (3H, s), 3.71 (1H, dd, J=9.6, 4.0 Hz), 3.81 (1H, dd, J=9.6, 4.0 Hz), 4.23 (2H, d, J=8.0 Hz), 4.39 (1H, m), 4.67-4.28 (1H, m), 5.23-5.30 (1H, m), 5.92 (1H, d, J=6.4 Hz), 7.17 (1H, d, J=5.6 Hz), 7.22-7.26 (1H, m), 7.73 (1H, dt, J=7.6, 1.6 Hz), 7.95 (1H, d, J=6.4 Hz), 8.50 (1H, dd, J=4.8, 1.6 Hz), 8.68 (1H, d, J=1.6 Hz) ppm. LCMS m/z=370.1 [M+H⁺].

Example Z342. tert-Butyl (S)-4-(2-(2-((1-(Pyridin-2-yl)ethyl)amino)thieno[3,2-d]pyrimidine-4-carboxamido)ethyl)piperidine-1-carboxylate

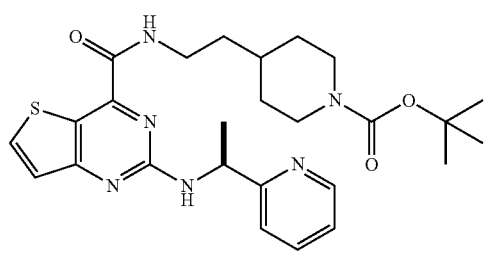 [SMILES: C[C@H](Nc1nc(C(=O)NCCC2CCN(C(=O)OC(C)(C)C)CC2)c2sccc2n1)c1ccccn1]

(Z342)

Synthesis of tert-butyl (S)-4-(2-(2-((1-(pyridin-2-yl)ethyl)amino)thieno[3,2-d]pyrimidine-4-carboxamido)ethyl)piperidine-1-carboxylate (Z342): The title compound (Z342) was prepared from (S)-2-((1-(pyridin-2-yl)ethyl)amino)thieno[3,2-d]pyrimidine-4-carboxylic acid di-hydrochloride using chemistry similar to that described in Example Z17 using tert-butyl 4-(2-aminoethyl)piperidine-1-carboxylate (commercially obtained from PharmaBlock, Sunnyvale, Calif.) in place of (3R)-3-methoxypyrrolidine hydrochloride (68% yield). LCMS m/z=511.3 [M+H⁺].

Example Z343. tert-Butyl (S)-4-(2-(2-((1-(5-Fluoro-pyridin-3-yl)ethyl)amino)thieno[3,2-d]pyrimidine-4-carboxamido)ethyl)piperidine-1-carboxylate

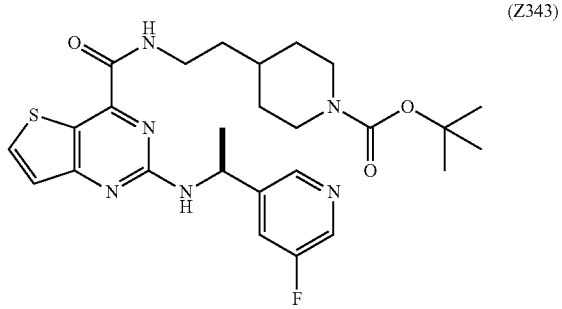

(Z343)

Synthesis of tert-butyl (S)-4-(2-(2-((1-(5-fluoropyridin-3-yl)ethyl)amino)thieno[3,2-d]pyrimidine-4-carboxamido)ethyl)piperidine-1-carboxylate (Z343): The title compound (Z343) was prepared from (S)-2-((1-(5-fluoropyridin-3-yl)ethyl)amino)thieno[3,2-d]pyrimidine-4-carboxylic acid dihydrochloride using chemistry similar to that described in Example Z17 using tert-butyl 4-(2-aminoethyl)piperidine-1-carboxylate in place of (3R)-3-methoxypyrrolidine hydrochloride (41% yield). $^1$H NMR (400 MHz, CDCl$_3$) δ 1.24-1.32 (2H, m), 1.45 (7H, s), 1.54-1.59 (2H, m), 1.64 (4H, dd, J=7.2, 3.2 Hz), 1.70-1.73 (2H, m), 3.39-3.63 (2H, m), 3.61-3.75 (2H, m), 4.08-4.20 (2H, m), 5.15-5.18 (1H, m), 5.19-5.28 (1H, m), 5.45 (1H, d, J=5.2 Hz), 7.18 (1H, d, J=5.6 Hz), 7.44-7.50 (1H, m), 7.65-7.75 (1H, m), 8.00 (1H, d, J=6.4 Hz), 8.34 (1H, dd, J=11.2, 6.8 Hz), 8.50-8.58 (1H, m) ppm. LCMS m/z=438.0 [M+H$^+$].

Example Z344. (S)-(2-((1-(Pyridin-4-yl)ethyl)amino)thieno[3,2-d]pyrimidin-4-yl)(pyrrolidin-1-yl)methanone

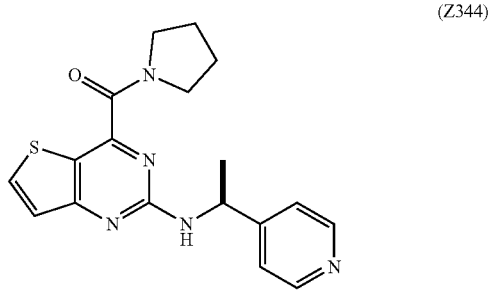

(Z344)

Synthesis of (S)-(2-((1-(pyridin-4-yl)ethyl)amino)thieno[3,2-d]pyrimidin-4-yl)(pyrrolidin-1-yl)methanone (Z344): The title compound (Z344) was prepared from ethyl (S)-2-((1-(pyridin-4-yl)ethyl)amino)thieno[3,2-d]pyrimidine-4-carboxylate using chemistry similar to that described in Example Z17 using pyrrolidine in place of (3R)-3-methoxypyrrolidine hydrochloride (28% yield). $^1$H NMR (400 MHz, CDCl$_3$) δ 1.59 (3H, d, J=7.2 Hz), 1.65-1.88 (4H, m), 3.40-3.75 (2H, m), 3.67 (2H, t, J=6.0 Hz), 5.13 (1H, q, J=6.8 Hz), 5.42 (1H, d, J=6.4 Hz), 7.17 (1H, d, J=5.6 Hz), 7.30 (2H, dd, J=6.0, 1.6 Hz), 7.95 (1H, d, J=5.2 Hz), 8.52 (2H, dd, J=4.8, 1.6 Hz) ppm. LCMS m/z=354.0 [M+H$^+$].

Example Z345. (S)—N-((6-Methoxypyridin-3-yl)methyl)-2-((1-(pyridin-4-yl)ethyl)amino)thieno[3,2-d]pyrimidine-4-carboxamide

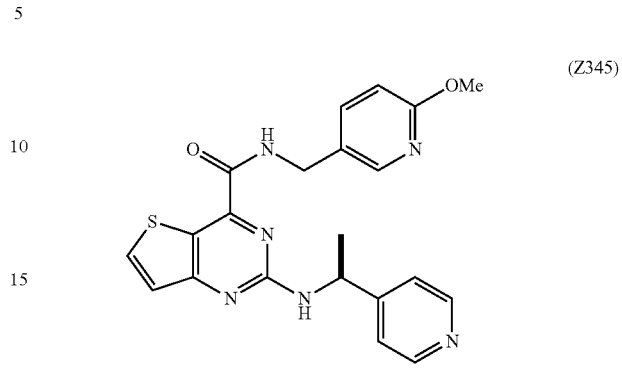

(Z345)

Synthesis of (S)—N-((6-methoxypyridin-3-yl)methyl)-2-((1-(pyridin-4-yl)ethyl)amino)thieno[3,2-d]pyrimidine-4-carboxamide (Z345): The title compound (Z345) was prepared from ethyl (S)-2-((1-(pyridin-4-yl)ethyl)amino)thieno[3,2-d]pyrimidine-4-carboxylate using chemistry similar to that described in Example Z17 using (6-methoxy-3-pyridyl)methan-amine hydrochloride in place of (3R)-3-methoxypyrrolidine hydrochloride (12% yield). LCMS m/z=421.1 [M+H$^+$].

Example Z346. (2-(((S)-1-(5-Fluoropyridin-3-yl)ethyl)amino)-6-(trifluoromethyl)thieno[3,2-d]pyrimidin-4-yl)((S)-3-hydroxypyrrolidin-1-yl)methanone

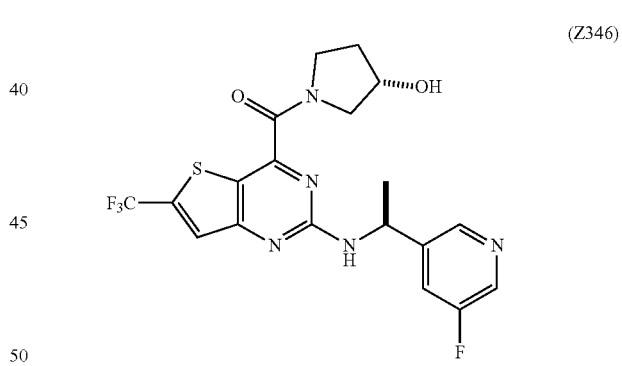

(Z346)

Synthesis of (S)-(2-chloro-6-(trifluoromethyl)thieno[3,2-d]pyrimidin-4-yl)(3-hydroxypyrrolidin-1-yl)methanone: To a solution of 2-chloro-6-(trifluoromethyl)thieno[3,2-d]pyrimidine-4-carboxylic acid (115 mg, 0.41 mmol) in DMF (4 mL) were added HATU (310 mg, 0.82 mmol), DIEA (158 mg, 1.23 mmol) and (3S)-pyrrolidin-3-ol (65 mg, 0.75 mmol). The resulting solution was stirred for 2 h at room temperature and then was extracted with ethyl acetate (2×20 mL). The combined organic layer was dried over anhydrous sodium sulfate and concentrated under vacuum. The residue was flash chromatography on silica gel eluting with ethyl acetate/petroleum ether (1.5:1) to provide (S)-(2-chloro-6-(trifluoromethyl)thieno[3,2-d]pyrimidin-4-yl)(3-hydroxy-pyrrolidin-1-yl)methanone as an yellow solid (65 mg, 45% yield). LCMS m/z=315.9 [M+H$^+$].

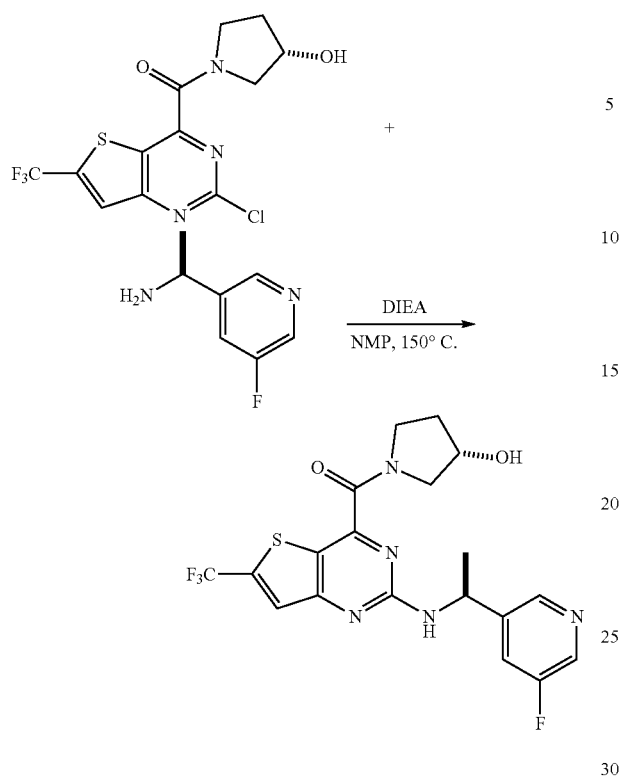

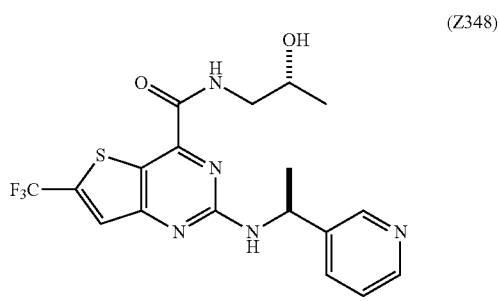

Synthesis of (2-(((S)-1-(5-fluoropyridin-3-yl)ethyl) amino)-6-(trifluoromethyl)thieno[3,2-d]pyrimidin-4-yl) ((S)-3-hydroxypyrrolidin-1-yl)methanone (Z346): To a solution of (S)-(2-chloro-6-(trifluoromethyl)thieno[3,2-d] pyrimidin-4-yl)(3-hydroxypyrrolidin-1-yl)methanone (65 mg, 0.18 mmol) in NMP (2 mL) were added (1S)-1-(5-fluoropyridin-3-yl)ethan-1-amine (80 mg, 0.57 mmol) and DIEA (96 mg, 0.72 mmol). The resulting solution was stirred for 4 h at 150° C. The crude product was purified by prep-HPLC (C-18 OBD column and a gradient elution system of water-acetonitrile) to provide (2-(((S)-1-(5-fluoropyridin-3-yl)ethyl)amino)-6-(trifluoromethyl)thieno[3,2-d]pyrimidin-4-yl)((S)-3-hydroxypyrrolidin-1-yl)methanone as an yellow solid (39 mg, 46% yield). $^1$H NMR (300 MHz, methanol-$d_4$) δ 1.63 (3H, d, J=7.2 Hz), 1.90-2.01 (2H, m), 3.61-3.85 (2H, m), 3.90-4.26 (2H, m), 4.45 (1H, m), 5.25 (1H, q, J=7.2 Hz), 7.61 (1H, s), 7.75 (1H, m), 8.35 (1H, m), 8.54 (1H, m) ppm. LCMS m/z=456.1 [M+H$^+$].

Example Z347. N—((S)-2-Hydroxypropyl)-2-(((S)-1-(pyridin-3-yl)ethyl)amino)-6-(trifluoromethyl) thieno[3,2-d]pyrimidine-4-carboxamide Synthesis of N—((S)-2-hydroxypropyl)-2-(((S)-1-(pyridin-3-yl)ethyl)amino)-6-(trifluoromethyl)thieno[3,2-d]pyrimidine-4-carboxamide (Z347): The title compound (Z347) was prepared from (S)-2-((1-(pyridin-3-yl)ethyl)amino)-6-(trifluoromethyl)thieno[3,2-d]pyrimidine-4-carboxylic acid di-hydrochloride (104 mg, 0.24 mmol) using chemistry similar to that described in Example Z8 using (S)-1-aminopropan-2-ol in place of (R)-3-fluoropyrrolidine (49 mg, 49% yield). $^1$H NMR (300 MHz, methanol-$d_4$) δ 1.21 (3H, d, J=6.4 Hz), 1.63 (3H, d, J=6.8 Hz), 3.32 (1H, m), 3.54 (1H, dd, J=13.5, 4.0 Hz), 3.97 (1H, m), 5.30 (1H, q, J=6.8 Hz), 7.39 (1H, dd, J=7.8, 4.8 Hz), 7.60 (1H, s), 7.94 (1H, d, J=7.6 Hz), 8.38 (1H, dd, J=4.8, 1.6 Hz), 8.65 (1H, d, J=1.6 Hz) ppm. LCMS m/z=426.1 [M+H$^+$].

Example Z348. N—((R)-2-Hydroxypropyl)-2-(((S)-1-(pyridin-3-yl)ethyl)amino)-6-(trifluoromethyl) thieno[3,2-d]pyrimidine-4-carboxamide (Z348)

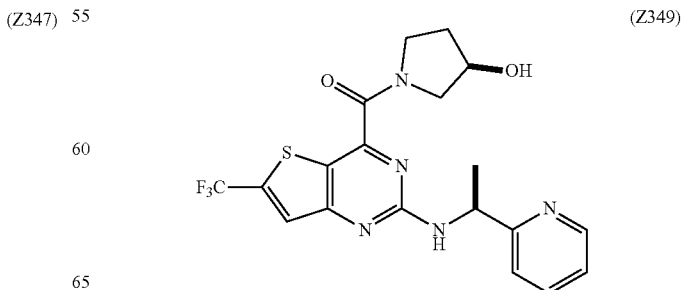

Synthesis of N—((R)-2-hydroxypropyl)-2-(((S)-1-(pyridin-3-yl)ethyl)amino)-6-(trifluoromethyl)thieno[3,2-d]pyrimidine-4-carboxamide (Z348): The title compound (Z348) was prepared from (S)-2-((1-(pyridin-3-yl)ethyl)amino)-6-(trifluoromethyl)thieno[3,2-d]pyrimidine-4-carboxylic acid di-hydrochloride (104 mg, 0.24 mmol) using chemistry similar to that described in Example Z8 using (S)-1-aminopropan-2-ol in place of (R)-3-fluoropyrrolidine (50 mg, 50% yield). $^1$H NMR (400 MHz, methanol-$d_4$) δ 1.22 (3H, d, J=6.4 Hz), 1.64 (3H, d, J=6.8 Hz), 3.31 (1H, m), 3.52 (1H, dd, J=13.5, 4.0 Hz), 3.97 (1H, m), 5.30 (1H, q, J=6.8 Hz), 7.45 (1H, dd, J=8.0, 4.8 Hz), 7.60 (1H, s), 8.02 (1H, d, J=8.0 Hz), 8.42 (1H, dd, J=4.8, 1.6 Hz), 8.67 (1H, d, J=1.6 Hz) ppm. LCMS m/z=426.1 [M+H$^+$].

Example Z349. ((R)-3-Hydroxypyrrolidin-1-yl)(2-(((S)-1-(pyridin-2-yl)ethyl)amino)-6-(trifluoromethyl)thieno[3,2-d]pyrimidin-4-yl)methanone (Z347)

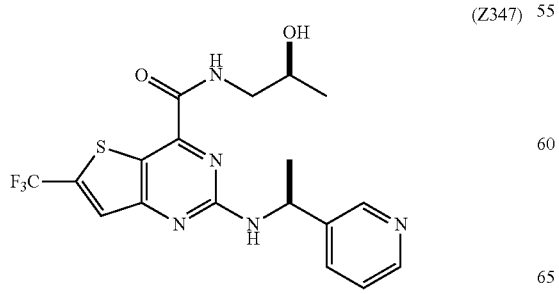

(Z349)

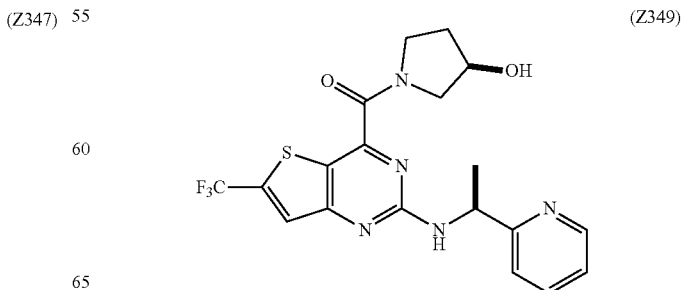

Synthesis of ethyl (S)-2-((1-(pyridin-2-yl)ethyl)amino)-6-(trifluoromethyl)thieno[3,2-d]pyrimidine-4-carboxylate: To a solution of ethyl 2-chloro-6-(trifluoromethyl)thieno[3,2-d]pyrimidine-4-carboxylate (100 mg, 0.32 mmol) in DMSO (5 mL) were added (1S)-1-(pyridin-2-yl)ethan-1-amine (47 mg, 0.38 mmol) and DIEA (125 mg, 0.97 mmol). The resulting solution was stirred for 2 h at 90° C. and then was extracted with ethyl acetate (3×20 mL). The combined organic layer was dried over anhydrous sodium sulfate and concentrated under vacuum. The residue was purified by flash chromatography on silica gel eluting with ethyl acetate/petroleum ether (1:1) to provide ethyl (S)-2-((1-(pyridin-2-yl)ethyl)amino)-6-(trifluoromethyl)thieno[3,2-d]pyrimidine-4-carboxylate as a green solid (100 mg, 78% yield). LCMS m/z=397.0 [M+H$^+$].

Synthesis of (S)-2-((1-(pyridin-2-yl)ethyl)amino)-6-(trifluoromethyl)thieno[3,2-d]pyrimidine-4-carboxylic acid: A solution of ethyl (S)-2-((1-(pyridin-2-yl)ethyl)amino)-6-(trifluoromethyl)thieno[3,2-d]pyrimidine-4-carboxylate (100 mg, 0.25 mmol) in 12 N hydrogen chloride (10 mL) was stirred for 2 h at 80° C. and then was concentrated under vacuum. The residue was dried under high vacuum overnight to provide (S)-2-((1-(pyridin-2-yl)ethyl)amino)-6-(trifluoromethyl)thieno[3,2-d]pyrimidine-4-carboxylic acid di-hydrochloride as an yellow solid (110 mg, 100% yield). LCMS m/z=369.2 [M+H$^+$].

Synthesis of ((R)-3-hydroxypyrrolidin-1-yl)(2-(((S)-1-(pyridin-2-yl)ethyl)amino)-6-(trifluoromethyl)thieno[3,2-d]pyrimidin-4-yl)methanone (Z349): The title compound (Z349) was prepared from (S)-2-((1-(pyridin-2-yl)ethyl)amino)-6-(trifluoromethyl)thieno[3,2-d]pyrimidine-4-carboxylic acid di-hydrochloride (104 mg, 0.24 mmol) using chemistry similar to that described in Example Z8 using (R)-pyrrolidin-3-ol in place of (R)-3-fluoropyrrolidine (56 mg, 53% yield). $^1$H NMR (400 MHz, methanol-d$_4$) δ 1.62 (3H, d, J=6.8 Hz), 1.90-2.15 (2H, m), 3.68-3.80 (2H, m), 4.15-4.30 (2H, m), 4.45 (1H, m), 5.21 (1H, q, J=6.8 Hz), 7.27 (1H, m), 7.50 (1H, d, J=8.0 Hz), 7.59 (1H, s), 7.76 (1H, m), 8.50 (1H, m) ppm. LCMS m/z=438.0 [M+H$^+$].

Example Z350. ((S)-3-Methoxypyrrolidin-1-yl)(6-methyl-2-(((S)-1-(pyridin-3-yl)ethyl)amino)thieno[3,2-d]pyrimidin-4-yl)methanone

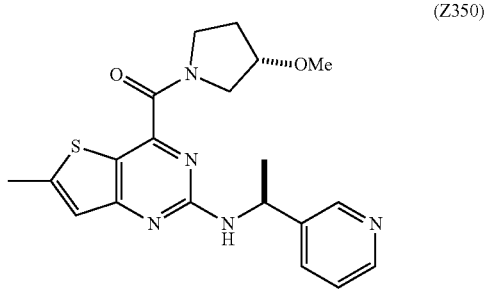

(Z350)

Synthesis of ((S)-3-methoxypyrrolidin-1-yl)(6-methyl-2-(((S)-1-(pyridin-3-yl)ethyl)amino)thieno[3,2-d]pyrimidin-4-yl)methanone (Z350): The title compound (Z350) was prepared from (S)-6-methyl-2-((1-(pyridin-3-yl)ethyl)amino)thieno[3,2-d]pyrimidine-4-carboxylic acid di-hydrochloride (55 mg, 0.14 mmol) using chemistry similar to that described in Example Z8 using (S)-3-methoxypyrrolidine in place of (R)-3-fluoropyrrolidine (27 mg, 48% yield). $^1$H NMR (300 MHz, DMSO-d$_6$) δ 1.50 (3H, d, J=6.8 Hz), 1.83-1.95 (2H, m), 2.55 (3H, s), 3.26 (3H, s), 3.44-3.95 (5H, m), 5.12 (1H, m), 6.94 (1H, s), 7.32 (1H, m), 7.77-7.88 (2H, m), 8.41 (1H, m), 8.61 (1H, m) ppm. LCMS m/z=398.3 [M+H$^+$].

Example Z351. ((R)-3-Methoxypyrrolidin-1-yl)(6-methyl-2-(((S)-1-(pyridin-3-yl)ethyl)amino)thieno[3,2-d]pyrimidin-4-yl)methanone

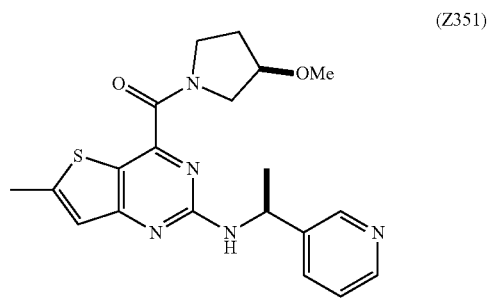

(Z351)

Synthesis of ((R)-3-methoxypyrrolidin-1-yl)(6-methyl-2-(((S)-1-(pyridin-3-yl)ethyl)amino)thieno[3,2-d]pyrimidin-4-yl)methanone (Z351): The title compound (Z351) was prepared from (S)-6-methyl-2-((1-(pyridin-3-yl)ethyl)amino)thieno[3,2-d]pyrimidine-4-carboxylic acid di-hydrochloride (55 mg, 0.14 mmol) using chemistry similar to that described in Example Z8 using (R)-3-methoxypyrrolidine in place of (R)-3-fluoropyrrolidine (35 mg, 63% yield). $^1$H NMR (400 MHz, methanol-d$_4$) δ 1.61 (3H, d, J=7.2 Hz), 1.94 (1H, m), 2.08 (1H, m), 2.58 (3H, s), 3.30 (3H, s), 3.61-3.77 (3H, m), 4.01-4.10 (2H, m), 5.20 (1H, m), 6.88 (1H, s), 7.37 (1H, dd, J=8.0, 4.8 Hz), 7.89 (1H, m), 8.37 (1H, m), 8.60 (1H, m) ppm. LCMS m/z=398.3 [M+H$^+$].

Example Z352. (S)—N-Cyclobutyl-6-methyl-2-((1-(pyridin-2-yl)ethyl)amino)thieno[3,2-d]pyrimidine-4-carboxamide

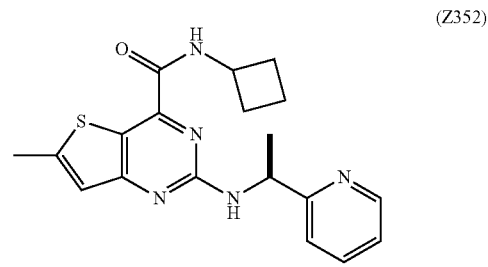

(Z352)

Synthesis of (S)—N-cyclobutyl-6-methyl-2-((1-(pyridin-2-yl)ethyl)amino)thieno[3,2-d]pyrimidine-4-carboxamide (Z352): The title compound (Z352) was prepared from (S)-6-methyl-2-((1-(pyridin-2-yl)ethyl)amino)thieno[3,2-d]pyrimidine-4-carboxylic acid di-hydrochloride using chemistry similar to that described in Example Z8 using cyclobutanamine in place of (R)-3-fluoropyrrolidine. $^1$H NMR (300 MHz, methanol-d$_4$) δ 1.62 (3H, d, J=6.8 Hz), 1.80-1.89 (2H, m), 2.11-2.23 (2H, m), 2.35-2.41 (2H, m), 2.60 (3H, s), 4.47 (1H, m), 5.21 (1H, q, J=6.8 Hz), 6.87 (1H, s), 7.29 (1H, m), 7.54 (1H, d, J=7.8 Hz), 7.78 (1H, td, J=7.8. 1.5), 8.54 (1H, m) ppm. LCMS m/z=368.3 [M+H⁺].

Example Z353. (S)—N-(2-Hydroxyethyl)-6-methyl-2-((1-(pyridin-2-yl)ethyl)amino)thieno[3,2-d]pyrimidine-4-carboxamide

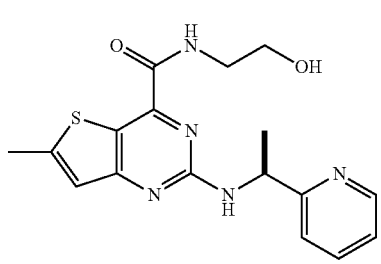 [SMILES: Cc1cc2nc(N[C@@H](C)c3ccccn3)nc(C(=O)NCCO)c2s1]
(Z353)

Synthesis of (S)—N-(2-hydroxyethyl)-6-methyl-2-((1-(pyridin-2-yl)ethyl)amino)thieno[3,2-d]pyrimidine-4-carboxamide (Z353): The title compound (Z353) was prepared from (S)-6-methyl-2-((1-(pyridin-2-yl)ethyl)amino)thieno[3,2-d]pyrimidine-4-carboxylic acid di-hydrochloride using chemistry similar to that described in Example Z8 using 2-aminoethan-1-ol in place of (R)-3-fluoropyrrolidine. ¹H NMR (300 MHz, methanol-d₄) δ 1.59 (3H, d, J=7.2 Hz), 2.57 (3H, s), 3.52 (2H, m), 3.72 (2H, m), 5.24 (1H, q, J=7.2 Hz), 6.84 (1H, s), 7.26 (1H, m), 7.53 (1H, d, J=7.8 Hz), 7.77 (1H, td, J=7.8. 1.5), 8.49 (1H, m) ppm. LCMS m/z=358.0 [M+H⁺].

Example Z354. tert-Butyl 1-(2-(((S)-1-(5-fluoropyridin-3-yl)ethyl)amino)thieno[3,2-d]pyrimidine-4-carbonyl)pyrrolidine-3-carboxylate

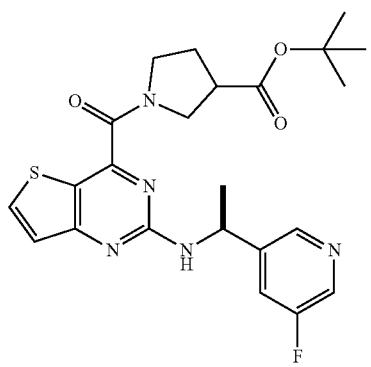
(Z354)

Synthesis of tert-butyl 1-(2-(((S)-1-(5-fluoropyridin-3-yl)ethyl)amino)thieno[3,2-d]pyrimidine-4-carbonyl)pyrrolidine-3-carboxylate (Z354): The title compound (Z354) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using tert-butyl pyrrolidine-3-carboxylate (commercially obtained from Accela Bio, Shanghai, Conn.) in place of (3R)-3-methoxypyrrolidine hydrochloride (45% yield). ¹H NMR (400 MHz, CDCl₃) δ 1.45 (4H, d, J=12.8 Hz), 1.47 (5H, d, J=0.8 Hz), 1.63 (3H, dd, J=6.8, 2.4 Hz), 2.09-2.17 (2H, m), 2.95-3.01 (1H, m), 3.88-3.93 (1H, m), 3.65-4.04 (3H, m), 5.28 (1H, m), 5.41 (1H, m), 7.17 (1H, dd, J=5.6, 1.2 Hz), 7.42-7.50 (1H, m), 7.96 (1H, dd, J=5.6, 2.8 Hz), 8.33 (1H, m), 8.50-8.53 (1H, m) ppm. LCMS m/z=472.3 [M+H⁺].

Example Z355. tert-Butyl 1-(2-(((S)-1-(pyridin-2-yl)ethyl)amino)thieno[3,2-d]pyrimidine-4-carbonyl)pyrrolidine-3-carboxylate

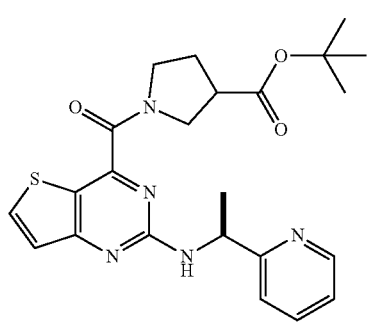
(Z355)

Synthesis of tert-butyl 1-(2-(((S)-1-(pyridin-2-yl)ethyl)amino)thieno[3,2-d]pyrimidine-4-carbonyl)pyrrolidine-3-carboxylate (Z355): The title compound (Z355) was prepared from (S)-2-((1-(pyridin-2-yl)ethyl)amino)thieno[3,2-d]pyrimidine-4-carboxylic acid di-hydrochloride using chemistry similar to that described in Example Z17 using tert-butyl pyrrolidine-3-carboxylate in place of (3R)-3-methoxypyrrolidine hydrochloride (24% yield). LCMS m/z=454.3 [M+H⁺].

Example Z356. (S)-2-((1-(Pyridin-2-yl)ethyl)amino)-N-(2-(pyrrolidin-1-yl)ethyl)thieno[3,2-d]pyrimidine-4-carboxamide

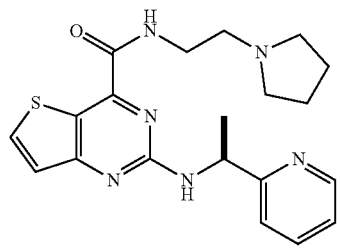 [SMILES: C[C@H](Nc1nc(C(=O)NCCN2CCCC2)c2sccc2n1)c1ccccn1]
(Z356)

Synthesis of (S)-2-((1-(pyridin-2-yl)ethyl)amino)-N-(2-(pyrrolidin-1-yl)ethyl)thieno[3,2-d]pyrimidine-4-carboxamide (Z356): The title compound (Z356) was prepared from (S)-2-((1-(pyridin-2-yl)ethyl)amino)thieno[3,2-d]pyrimidine-4-carboxylic acid di-hydrochloride using chemistry similar to that described in Example Z17 using N-(2-aminoethyl)pyrrolidine (commercially obtained from Sigma-Aldrich, St. Louis, Mo.) in place of (3R)-3-methoxypyrrolidine hydrochloride (12% yield). LCMS m/z=397.3 [M+H⁺].

Example Z357. (S)-2-((1-(5-Fluoropyridin-3-yl)ethyl)amino)-N-(2-(pyrrolidin-1-yl)ethyl)thieno[3,2-d]pyrimidine-4-carboxamide

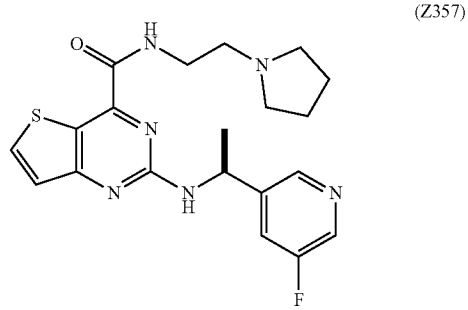

(Z357)

Synthesis of (S)-2-((1-(5-fluoropyridin-3-yl)ethyl)amino)-N-(2-(pyrrolidin-1-yl)ethyl)thieno[3,2-d]pyrimidine-4-carboxamide (Z357): The title compound (Z357) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using N-(2-aminoethyl)pyrrolidine in place of (3R)-3-methoxypyrrolidine hydrochloride (15% yield). LCMS m/z=415.1 [M+H$^+$].

Example Z358. (2-(((5-Fluoropyridin-3-yl)methyl)amino)thieno[3,2-d]pyrimidin-4-yl)(3-(methylamino)azetidin-1-yl)methanone

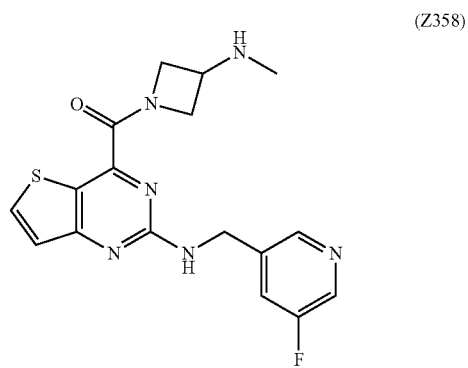

(Z358)

Synthesis of (2-(((5-fluoropyridin-3-yl)methyl)amino)thieno[3,2-d]pyrimidin-4-yl)(3-(methylamino)azetidin-1-yl)methanone (Z358): To a solution of tert-butyl N-[1-[2-[(5-fluoro-3-pyridyl)methylamino]thieno[3,2-d]pyrimidine-4-carbonyl]azetidin-3-yl]-N-methyl-carbamate (23 mg, 0.05 mmol) in DCM (0.5 mL) was added TFA (0.2 mL, 0.65 mmol) (a mixture turned bright red), and the resulting mixture was stirred for 1 hour. A reaction mixture was concentrated, and the residue was purified by flash chromatography on silica gel eluting with 10% to 70% solvent A (DCM/MeOH/NH$_4$OH-100/10/1) in DCM. The fractions containing the desired product were combined, concentrated, dissolved in water, and freeze-dried to provide (2-(((5-fluoropyridin-3-yl)methyl)amino)thieno[3,2-d]pyrimidin-4-yl)(3-(methylamino)azetidin-1-yl)methanone as light yellow solids (17.8 mg, 98% yield). $^1$H NMR (400 MHz, CDCl$_3$) δ 2.53 (2H, s), 3.64 (1H, t, J=4.4 Hz), 3.78 (2H, t, J=4.4 Hz), 4.18-4.21 (1H, m), 4.42-4.47 (1H, m), 4.64 (1H, m), 4.74 (2H, d, J=6.0 Hz), 4.84 (1H, m), 5.79 (1H, m), 7.17 (1H, d, J=5.6 Hz), 7.42-7.46 (1H, m), 7.96 (1H, d, J=5.6 Hz), 8.33 (1H, d, J=1.2 Hz), 8.50 (1H, m) ppm. LCMS m/z=373.1 [M+H$^+$].

Example Z359. (2-((4-Hydroxyphenethyl)amino)thieno[3,2-d]pyrimidin-4-yl)(pyrrolidin-1-yl)methanone

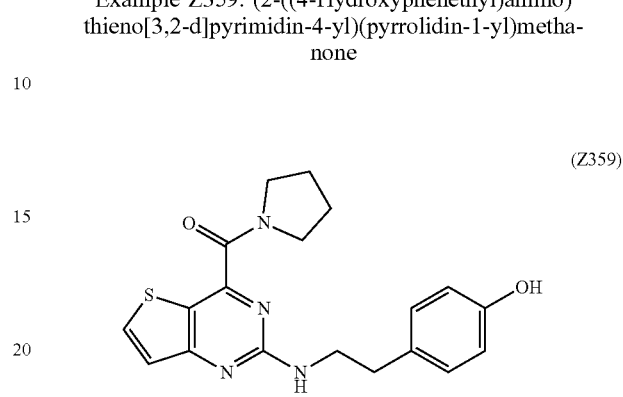

(Z359)

Synthesis of ethyl 2-((4-hydroxyphenethyl)amino)thieno[3,2-d]pyrimidine-4-carboxylate: The title compounds were prepared from ethyl 2-chlorothieno[3,2-d]pyrimidine-4-carboxylate (300 mg, 1.23 mmol) using chemistry similar to that described in Example Z12 using 4-(2-aminoethyl)phenol (commercially obtained from AK Scientific, Union City Calif.) in place of (6-methoxypyridin-3-yl)methanamine hydrochloride to produce the title compound (40 mg, 9% yield). LCMS m/z=344.0 [M+H$^+$].

Synthesis of (2-((4-hydroxyphenethyl)amino)thieno[3,2-d]pyrimidin-4-yl)(pyrrolidin-1-yl)methanone (Z359): The title compound (Z359) was prepared from ethyl 2-((4-hydroxyphenethyl)amino)thieno[3,2-d]pyrimidine-4-carboxylate using chemistry similar to that described in Example Z17 using pyrrolidine in place of (3R)-3-methoxypyrrolidine hydrochloride (23% yield). $^1$H NMR (400 MHz, CDCl$_3$) δ 1.90-2.02 (4H, m), 2.88 (2H, t, J=6.8 Hz), 3.75 (4H, q, J=7.2 Hz), 4.06 (2H, t, J=6.4 Hz), 6.77 (2H, dd, J=6.4, 2.0 Hz), 7.06 (2H, d, J=7.2 Hz), 7.19 (1H, d, J=5.2 Hz), 7.24 (1H, m), 7.94 (1H, d, J=5.2 Hz) ppm. LCMS m/z=369.2 [M+H$^+$].

Example Z360. (S)-(3-Aminopyrrolidin-1-yl)(2-(((5-fluoropyridin-3-yl)methyl)amino)thieno[3,2-d]pyrimidin-4-yl)methanone

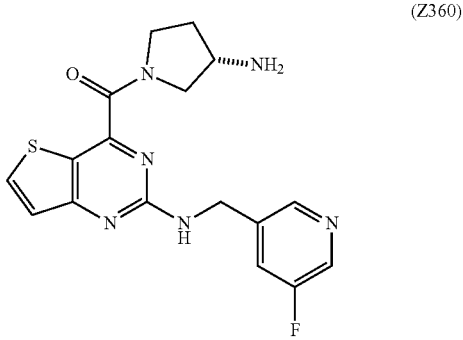

(Z360)

Synthesis of (S)-(3-aminopyrrolidin-1-yl)(2-(((5-fluoropyridin-3-yl)methyl)amino)thieno[3,2-d]pyrimidin-4-yl)

methanone (Z360): The title compound (Z360) was prepared from tert-butyl (S)-(1-(2-(((5-fluoropyridin-3-yl)methyl)amino)thieno[3,2-d]pyrimidine-4-carbonyl)pyrrolidin-3-yl)carbamate using chemistry similar to that described in Example Z358 (94% yield). LCMS m/z=373.1 [M+H$^+$].

Example Z361. (R)-(3-Aminopyrrolidin-1-yl)(2-(((5-fluoropyridin-3-yl)methyl)amino)thieno[3,2-d]pyrimidin-4-yl)methanone

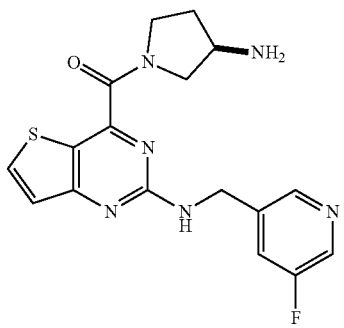 [SMILES: N[C@@H]1CCN(C(=O)c2nc(NCc3cncc(F)c3)nc3ccsc23)C1]

(Z361)

Synthesis of (R)-(3-aminopyrrolidin-1-yl)(2-(((5-fluoropyridin-3-yl)methyl)amino)thieno[3,2-d]pyrimidin-4-yl)methanone (Z361): The title compound (Z361) was prepared from tert-butyl (R)-(1-(2-(((5-fluoropyridin-3-yl)methyl)amino)thieno[3,2-d]pyrimidine-4-carbonyl)pyrrolidin-3-yl)carbamate using chemistry similar to that described in Example Z358 (72% yield). LCMS m/z=373.1 [M+H$^+$].

Example Z362. ((S)-3-Aminopyrrolidin-1-yl)(2-(((S)-1-(5-fluoropyridin-3-yl)ethyl)amino)thieno[3,2-d]pyrimidin-4-yl)methanone

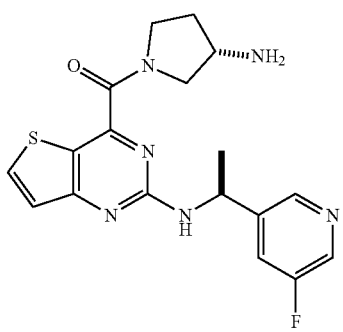

(Z362)

Synthesis of tert-butyl ((S)-1-(2-(((S)-1-(5-fluoropyridin-3-yl)ethyl)amino)thieno[3,2-d]pyrimidine-4-carbonyl)pyrrolidin-3-yl)carbamate: The title compound was prepared from (S)-2-((1-(5-fluoropyridin-3-yl)ethyl)amino)thieno[3,2-d]pyrimidine-4-carboxylic acid di-hydrochloride (39 mg, 0.10 mmol) using chemistry similar to that described in Example Z8 using tert-butyl (S)-pyrrolidin-3-ylcarbamate in place of (R)-3-fluoropyrrolidine (43 mg, 88% yield). LCMS m/z=487.1 [M+H$^+$].

Synthesis of ((S)-3-aminopyrrolidin-1-yl)(2-(((S)-1-(5-fluoropyridin-3-yl)ethyl)amino)thieno[3,2-d]pyrimidin-4-yl)methanone (Z362): To a solution of tert-butyl N-[(3S)-1-[2-[[(1S)-1-(5-fluoro-3-pyridyl)ethyl]amino]thieno[3,2-d]pyrimidine-4-carbonyl]pyrrolidin-3-yl]carbamate (43 mg, 0.06 mmol) in DCM (1.2 mL) was added TFA (0.6 mL) and the mixture thus obtained was stirred at room temperature for 1 h and LCMS analysis indicated completion of the reaction. The solvent was evaporated and the residue was purified by flash chromatography (12 g, HP silica, Teledyne Isco) eluting with 20% to 70% solvent A (DCM/MeOH/NH$_4$OH, 100/10/1) in DCM to provide ((S)-3-aminopyrrolidin-1-yl)(2-(((S)-1-(5-fluoropyridin-3-yl)ethyl)amino)thieno[3,2-d]pyrimidin-4-yl)methanone as an off-white solid (15 mg, 59% yield). $^1$H NMR (400 MHz, CDCl$_3$) δ 1.64 (3H, d, J=6.8 Hz), 1.68 (1H, m), 2.07 (1H, m), 3.43-3.67 (2H, m), 3.72-3.90 (2H, m), 4.05 (1H, m), 5.23 (1H, m), 5.42 (1H, m), 7.18 (1H, d, J=5.6 Hz), 7.44 (1H, m), 7.96 (1H, d, J=5.6 Hz), 8.34 (1H, m), 8.52 (1H, m) ppm. LCMS: m/z=387.2 [M+H$^+$].

Example Z363. ((S)-3-Aminopyrrolidin-1-yl)(2-(((S)-1-(pyridin-2-yl)ethyl)amino)thieno[3,2-d]pyrimidin-4-yl)methanone

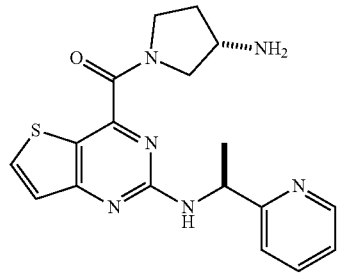 [SMILES: C[C@H](Nc1nc(C(=O)C2CC[C@H](N)C2)c2sccc2n1)c1ccccn1]

(Z363)

Synthesis of ((S)-3-aminopyrrolidin-1-yl)(2-(((S)-1-(pyridin-2-yl)ethyl)amino)thieno[3,2-d]pyrimidin-4-yl)methanone (Z363): The title compound (Z363) was prepared from tert-butyl ((S)-1-(2-(((S)-1-(pyridin-2-yl)ethyl)amino)thieno[3,2-d]pyrimidine-4-carbonyl)pyrrolidin-3-yl)carbamate using chemistry similar to that described in Example Z358 (99% yield). LCMS m/z=369.2 [M+H$^+$].

Example Z364. ((R)-3-Aminopyrrolidin-1-yl)(2-(((S)-1-(pyridin-2-yl)ethyl)amino)thieno[3,2-d]pyrimidin-4-yl)methanone

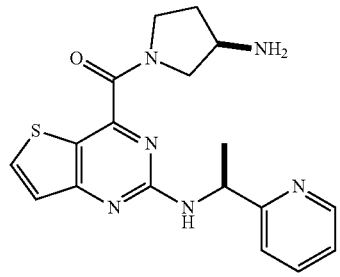 [SMILES: C[C@H](Nc1nc(C(=O)N2CC[C@@H](N)C2)c2sccc2n1)c1ccccn1]

(Z364)

Synthesis of ((R)-3-aminopyrrolidin-1-yl)(2-(((S)-1-(pyridin-2-yl)ethyl)amino)thieno[3,2-d]pyrimidin-4-yl)methanone (Z364): The title compound (Z364) was prepared from tert-butyl ((R)-1-(2-(((S)-1-(pyridin-2-yl)ethyl)amino)

thieno[3,2-d]pyrimidine-4-carbonyl)pyrrolidin-3-yl)carbamate using chemistry similar to that described in Example Z358 (99% yield). LCMS m/z=369.2 [M+H⁺].

Example Z365. tert-Butyl 3-(2-(2-(((S)-1-(5-fluoropyridin-3-yl)ethyl)amino)thieno[3,2-d]pyrimidine-4-carboxamido)ethyl)pyrrolidine-1-carboxylate

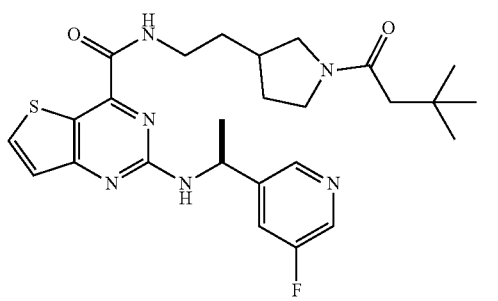

(Z365)

Synthesis of tert-butyl 3-(2-(2-(((S)-1-(5-fluoropyridin-3-yl)ethyl)amino)thieno[3,2-d]pyrimidine-4-carboxamido)ethyl)pyrrolidine-1-carboxylate (Z365): The title compound (Z365) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using tert-butyl 3-(2-aminoethyl)pyrrolidine-1-carboxylate (commercially obtained from Astatech, Bristol, Pa.) in place of (3R)-3-methoxypyrrolidine hydrochloride (53% yield). LCMS m/z=515.2 [M+H⁺].

Example Z366. ((R)-3-Aminopyrrolidin-1-yl)(2-(((S)-1-(pyridin-3-yl)ethyl)amino)thieno[3,2-d]pyrimidin-4-yl)methanone

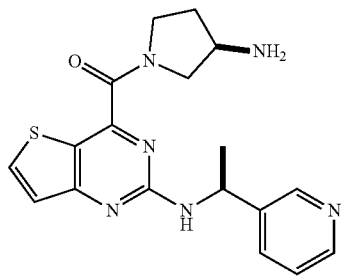 [SMILES: C[C@H](Nc1nc(C(=O)N2CC[C@@H](N)C2)c2sccc2n1)c1cccnc1]

(Z366)

Synthesis of ((R)-3-aminopyrrolidin-1-yl)(2-(((S)-1-(pyridin-3-yl)ethyl)amino)thieno[3,2-d]pyrimidin-4-yl)methanone (Z366): The title compound (Z366) was prepared from tert-butyl ((R)-1-(2-(((S)-1-(pyridin-3-yl)ethyl)amino)thieno[3,2-d]pyrimidine-4-carbonyl)pyrrolidin-3-yl)carbamate using chemistry similar to that described in Example Z358 (101% yield). LCMS m/z=369.2 [M+H⁺].

Example Z367. ((S)-3-Aminopyrrolidin-1-yl)(2-(((S)-1-(pyridin-3-yl)ethyl)amino)thieno[3,2-d]pyrimidin-4-yl)methanone

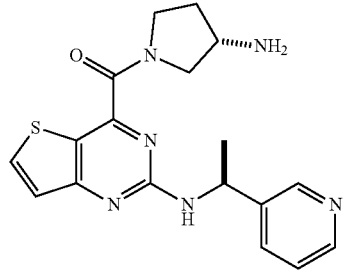 [SMILES: C[C@H](Nc1nc(C(=O)N2CC[C@H](N)C2)c2sccc2n1)c1cccnc1]

(Z367)

Synthesis of ((S)-3-aminopyrrolidin-1-yl)(2-(((S)-1-(pyridin-3-yl)ethyl)amino)thieno[3,2-d]pyrimidin-4-yl)methanone (Z367): The title compound (Z367) was prepared from tert-butyl ((S)-1-(2-(((S)-1-(pyridin-3-yl)ethyl)amino)thieno[3,2-d]pyrimidine-4-carbonyl)pyrrolidin-3-yl)carbamate using chemistry similar to that described in Example Z358 (100% yield). LCMS m/z=369.2 [M+H⁺].

Example Z368. (S)—N-(2-Hydroxyethyl)-6-methyl-2-((1-(pyridin-3-yl)ethyl)amino)thieno[3,2-d]pyrimidine-4-carboxamide

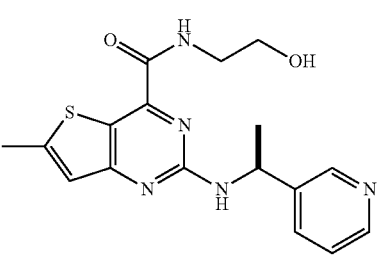 [SMILES: Cc1cc2nc(N[C@@H](C)c3cccnc3)nc(C(=O)NCCO)c2s1]

(Z368)

Synthesis of (S)—N-(2-hydroxyethyl)-6-methyl-2-((1-(pyridin-3-yl)ethyl)amino)thieno[3,2-d]pyrimidine-4-carboxamide (Z368): The title compound (Z368) was prepared from (S)-6-methyl-2-((1-(pyridin-3-yl)ethyl)amino)thieno[3,2-d]pyrimidine-4-carboxylic acid di-hydrochloride using chemistry similar to that described in Example Z8 using 2-aminoethan-1-ol in place of (R)-3-fluoropyrrolidine. ¹H NMR (300 MHz, methanol-d₄) δ 1.61 (3H, d, J=6.8 Hz), 2.58 (3H, s), 3.54 (2H, m), 3.73 (2H, m), 5.27 (1H, q, J=6.8 Hz), 6.86 (1H, s), 7.37 (1H, dd, J=7.5, 4.8 Hz), 7.93 (1H, m), 8.37 (1H, m), 8.65 (1H, m) ppm. LCMS m/z=358.2 [M+H⁺].

Example Z369. (R)-2-(((5-Fluoropyridin-3-yl)methyl)amino)-N-(pyrrolidin-2-ylmethyl)thieno[3,2-d]pyrimidine-4-carboxamide

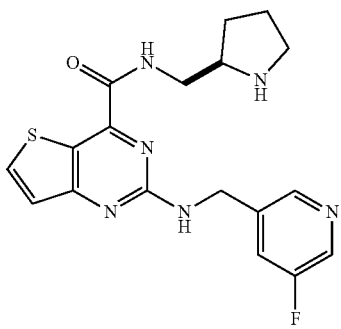
(Z369)

Synthesis of (R)-2-(((5-fluoropyridin-3-yl)methyl)amino)-N-(pyrrolidin-2-ylmethyl)thieno[3,2-d]pyrimidine-4-carboxamide (Z369): The title compound (Z369) was prepared from tert-butyl (R)-2-((2-(((5-fluoropyridin-3-yl)methyl)amino)thieno[3,2-d]pyrimidine-4-carboxamido)methyl)pyrrolidine-1-carboxylate using chemistry similar to that described in Example Z358 (93% yield). LCMS m/z=387.0 [M+H$^+$].

Example Z370. (R)-2-((Pyridin-2-ylmethyl)amino)-N-(pyrrolidin-2-ylmethyl)thieno[3,2-d]pyrimidine-4-carboxamide

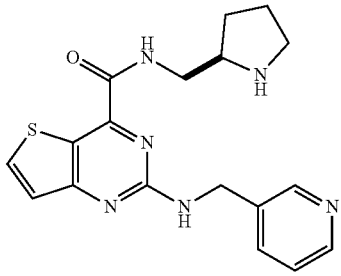
(Z370)

Synthesis of 2-(((S)-1-(pyridin-2-yl)ethyl)amino)-N-(((R)-pyrrolidin-2-yl)methyl)thieno[3,2-d]pyrimidine-4-carboxamide (Z370): The title compound (Z370) was prepared from tert-butyl (R)-2-((2-(((S)-1-(pyridin-2-yl)ethyl)amino)thieno[3,2-d]pyrimidine-4-carboxamido)methyl)pyrrolidine-1-carboxylate using chemistry similar to that described in Example Z358 (83% yield). LCMS m/z=383.1 [M+H$^+$].

Example Z371. (S)-(3-Aminopyrrolidin-1-yl)(2-((3,5-difluorobenzyl)amino)thieno[3,2-d]pyrimidin-4-yl)methanone

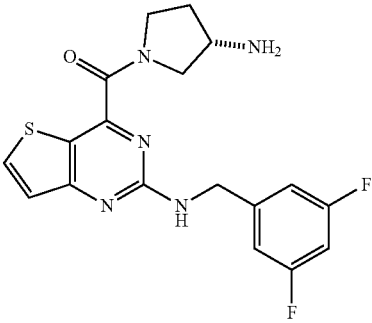 [SMILES: N[C@H]1CCN(C(=O)c2nc(NCc3cc(F)cc(F)c3)nc3ccsc23)C1]
(Z371)

Synthesis of (S)-(3-aminopyrrolidin-1-yl)(2-((3,5-difluorobenzyl)amino)thieno[3,2-d]pyrimidin-4-yl)methanone (Z371): The title compound (Z371) was prepared from tert-butyl (S)-(1-(2-((3,5-difluorobenzyl)amino)thieno[3,2-d]pyrimidine-4-carbonyl)pyrrolidin-3-yl)carbamate using chemistry similar to that described in Example Z358 (102% yield). LCMS m/z=390.0 [M+H$^+$].

Example Z372. (S)-2-((1-(5-Fluoropyridin-3-yl)ethyl)amino)-6-methyl-N-(2-morpholinoethyl)thieno[3,2-d]pyrimidine-4-carboxamide

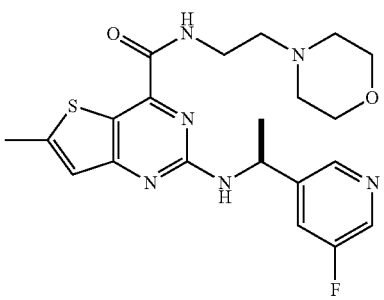 [SMILES: Cc1cc2nc(N[C@@H](C)c3cncc(F)c3)nc(C(=O)NCCN3CCOCC3)c2s1]
(Z372)

Synthesis of (S)-2-((1-(5-fluoropyridin-3-yl)ethyl)amino)-6-methyl-N-(2-morpholinoethyl)thieno[3,2-d]pyrimidine-4-carboxamide (Z372): The title compound (Z372) was prepared from ((S)-2-((1-(5-fluoropyridin-3-yl)ethyl)amino)-6-methylthieno[3,2-d]pyrimidine-4-carboxylic acid di-hydrochloride (40.5 mg, 0.10 mmol) using chemistry similar to that described in Example Z8 using 2-morpholinoethan-1-amine in place of (R)-3-fluoropyrrolidine (37 mg, 83% yield). $^1$H NMR (400 MHz, CDCl$_3$) δ 1.66 (3H, d, J=7.2 Hz), 2.55 (4H, m), 2.61 (3H, s), 2.62 (2H, m), 3.57 (2H, q, J=5.6 Hz), 3.76 (4H, t, J=4.8 Hz), 5.23 (1H, m), 5.37 (1H, d, J=6.8 Hz), 6.85 (1H, s), 7.46 (1H, dt, J=9.2, 2.4 Hz), 8.04 (1H, br s), 8.40 (1H, m), 8.34 (1H, d, J=2.4 Hz), 8.64 (1H, m) ppm. LCMS m/z=445.3 [M+H$^+$].

Example Z373. (S)-2-((1-(5-Fluoropyridin-3-yl)ethyl)amino)-N-(4-hydroxyphenethyl)-6-methylthieno[3,2-d]pyrimidine-4-carboxamide

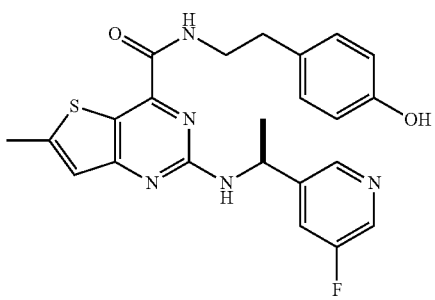 [SMILES: Cc1cc2nc(N[C@@H](C)c3cncc(F)c3)nc(C(=O)NCCc3ccc(O)cc3)c2s1]
(Z373)

Synthesis of (S)-2-((1-(5-fluoropyridin-3-yl)ethyl)amino)-N-(4-hydroxyphenethyl)-6-methylthieno[3,2-d]pyrimidine-4-carboxamide (Z373): The title compound (Z373) was prepared from (S)-2-((1-(5-fluoropyridin-3-yl)ethyl)amino)-6-methylthieno[3,2-d]pyrimidine-4-carboxylic acid di-hydrochloride using chemistry similar to that described in Example Z17 using 4-(2-aminoethyl)phenol (commercially obtained from AK Scientific, Union City, Calif.) in place of (3R)-3-methoxypyrrolidine hydrochloride (30% yield). LCMS m/z=452.1 [M+H$^+$].

Example Z374. (S)-2-((1-(5-Fluoropyridin-3-yl)ethyl)amino)-N-((6-methoxypyridin-2-yl)methyl)-6-methylthieno[3,2-d]pyrimidine-4-carboxamide

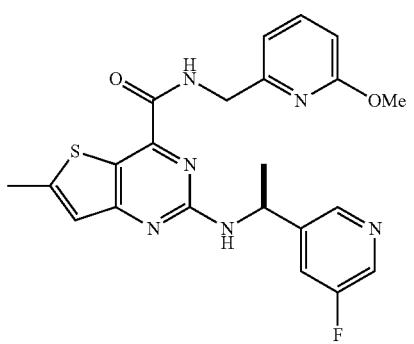 [SMILES: COc1cccc(CNC(=O)c2nc(N[C@@H](C)c3cncc(F)c3)nc3cc(C)sc23)n1]
(Z374)

Synthesis of (S)-2-((1-(5-fluoropyridin-3-yl)ethyl)amino)-N-((6-methoxypyridin-2-yl)methyl)-6-methylthieno[3,2-d]pyrimidine-4-carboxamide (Z374): The title compound (Z374) was prepared from ((S)-2-((1-(5-fluoropyridin-3-yl)ethyl)amino)-6-methylthieno[3,2-d]pyrimidine-4-carboxylic acid di-hydrochloride (40.5 mg, 0.10 mmol) using chemistry similar to that described in Example Z8 using (6-methoxypyridin-2-yl)methanamine in place of (R)-3-fluoropyrrolidine (40 mg, 88% yield). $^1$H NMR (400 MHz, CDCl$_3$) δ 1.63 (3H, d, J=6.8 Hz), 2.62 (3H, s), 3.96 (3H, s), 4.67 (2H, d, J=6.0 Hz), 5.27 (1H, quintet, J=6.8 Hz), 5.33 (1H, d, J=6.8 Hz), 6.67 (1H, d, J=8.0 Hz), 6.85 (1H, d, J=7.2 Hz), 6.86 (1H, s), 7.43 (1H, dt, J=8.8, 2.0 Hz), 7.56 (1H, dd, J=8.0, 7.8 Hz), 8.31 (1H, d, J=2.8 Hz), 8.50 (1H, m), 8.52 (1H, t, J=2.0 Hz) ppm. LCMS m/z=453.2 [M+H$^+$].

Example Z375. (S)-6-Methyl-2-((1-(pyridin-3-yl)ethyl)amino)-N-((tetrahydro-2H-pyran-4-yl)methyl)thieno[3,2-d]pyrimidine-4-carboxamide

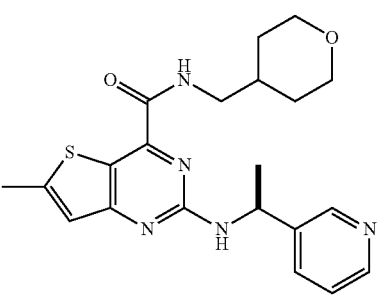 [SMILES: Cc1cc2nc(N[C@@H](C)c3cccnc3)nc(C(=O)NCC3CCOCC3)c2s1]
(Z375)

Synthesis of (S)-6-methyl-2-((1-(pyridin-3-yl)ethyl)amino)-N-((tetrahydro-2H-pyran-4-yl)methyl)thieno[3,2-d]pyrimidine-4-carboxamide (Z375): The title compound (Z375) was prepared from (S)-6-methyl-2-((1-(pyridin-3-yl)ethyl)amino)thieno[3,2-d]pyrimidine-4-carboxylic acid di-hydrochloride (60 mg, 0.155 mmol) using chemistry similar to that described in Example Z8 using (tetrahydro-2H-pyran-4-yl)methanamine in place of (R)-3-fluoropyrrolidine (30 mg, 47% yield). $^1$H NMR (300 MHz, methanol-d$_4$) δ 1.31-1.41 (2H, m), 1.58-1.72 (2H, m), 1.63 (3H, d, J=7.2 Hz), 1.90 (1H, m), 2.61 (3H, s), 3.24-3.47 (4H, m), 3.95-4.00 (2H, m), 5.31 (1H, q, J=7.2 Hz), 6.89 (1H, s), 7.39 (1H, dd, J=8.0, 4.8 Hz), 7.94 (1H, dt, J=8.0, 1.8 Hz), 8.40 (1H, dd, J=4.8, 2.0 Hz), 8.66 (1H, m) ppm. LCMS m/z=411.9 [M+H$^+$].

Example Z376. (S)-2-((1-(5-Fluoropyridin-3-yl)ethyl)amino)-6-methyl-N-((tetrahydro-2H-pyran-4-yl)methyl)thieno[3,2-d]pyrimidine-4-carboxamide

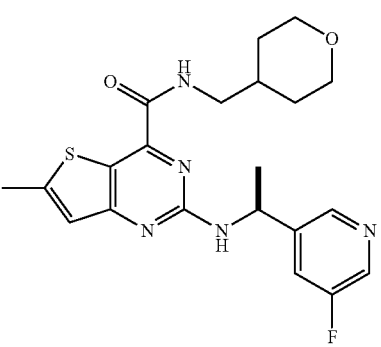 [SMILES: Cc1cc2nc(N[C@@H](C)c3cncc(F)c3)nc(C(=O)NCC3CCOCC3)c2s1]
(Z376)

Synthesis of (S)-2-((1-(5-fluoropyridin-3-yl)ethyl)amino)-6-methyl-N-((tetrahydro-2H-pyran-4-yl)methyl)thieno[3,2-d]pyrimidine-4-carboxamide (Z376): The title compound (Z376) was prepared from ((S)-2-((1-(5-fluoropyridin-3-yl)ethyl)amino)-6-methylthieno[3,2-d]pyrimidine-4-carboxylic acid di-hydrochloride (70 mg, 0.17 mmol) using chemistry similar to that described in Example Z8 using (tetrahydro-2H-pyran-4-yl)methanamine in place of (R)-3-fluoropyrrolidine (41 mg, 55% yield). $^1$H NMR (300 MHz, methanol-d$_4$) δ 1.31-1.41 (2H, m), 1.65 (3H, d, J=7.2 Hz), 1.66-1.68 (2H, m), 1.91 (1H, m), 2.62 (3H, s), 3.23-

3.48 (4H, m), 3.95-4.00 (2H, m), 5.35 (1H, q, J=7.2 Hz), 6.90 (1H, s), 7.73 (1H, m), 8.32 (1H, m), 8.54 (1H, m) ppm. LCMS m/z=430.0 [M+H$^+$].

Example Z377. (S)-6-Methyl-N-(piperidin-4-ylmethyl)-2-((1-(pyridin-3-yl)ethyl)amino)thieno[3,2-d]pyrimidine-4-carboxamide (Z377)

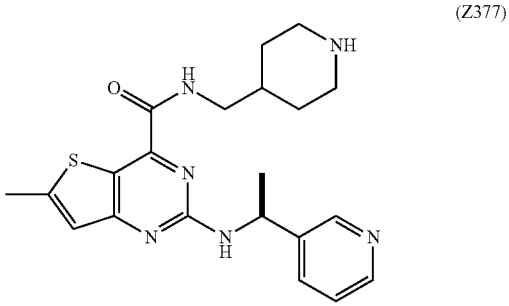
(Z377)

Synthesis of tert-butyl (S)-4-((6-methyl-2-((1-(pyridin-3-yl)ethyl)amino)thieno[3,2-d]pyrimidine-4-carboxamido)methyl)piperidine-1-carboxylate: The title compound was prepared from (S)-6-methyl-2-((1-(pyridin-3-yl)ethyl)amino)thieno[3,2-d]pyrimidine-4-carboxylic acid di-hydrochloride (60 mg, 0.155 mmol) using chemistry similar to that described in Example Z8 using tert-butyl 4-(aminomethyl)piperidine-1-carboxylate in place of (R)-3-fluoropyrrolidine (50 mg, 63% yield). LCMS m/z=515.5 [M+H$^+$].

Synthesis of (S)-6-methyl-N-(piperidin-4-ylmethyl)-2-((1-(pyridin-3-yl)ethyl)amino)thieno[3,2-d]pyrimidine-4-carboxamide (Z377): The title compound (Z377) was prepared from tert-butyl (S)-4-((6-methyl-2-((1-(pyridin-3-yl)ethyl)amino)thieno[3,2-d]pyrimidine-4-carboxamido)methyl)piperidine-1-carboxylate (50 mg, 0.10 mmol) using chemistry similar to that described in Example Z362 (31 mg, 77% yield). $^1$H NMR (300 MHz, methanol-d$_4$) δ 1.19-1.31 (2H, m), 1.62 (3H, d, J=7.2 Hz), 1.72-1.82 (3H, m), 2.60 (3H, s), 2.62 (2H, m), 3.11 (2H, m), 3.27-3.32 (2H, m), 5.30 (1H, q, J=7.2 Hz), 6.88 (1H, s), 7.39 (1H, m), 7.93 (1H, m), 8.39 (1H, dd, J=4.8, 2.0 Hz), 8.65 (1H, m) ppm. LCMS m/z=411.4 [M+H$^+$].

Example Z378. (S)-6-Methyl-N-(2-morpholinoethyl)-2-((1-(pyridin-3-yl)ethyl)amino)thieno[3,2-d]pyrimidine-4-carboxamide

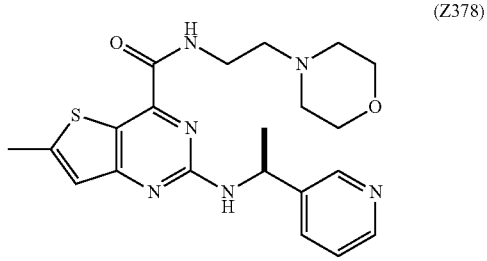
(Z378)

Synthesis of (S)-6-methyl-N-(2-morpholinoethyl)-2-((1-(pyridin-3-yl)ethyl)amino)thieno[3,2-d]pyrimidine-4-carboxamide (Z378): The title compound (Z378) was prepared from (S)-6-methyl-2-((1-(pyridin-3-yl)ethyl)amino)thieno[3,2-d]pyrimidine-4-carboxylic acid di-hydrochloride (50 mg, 0.13 mmol) using chemistry similar to that described in Example Z8 using 2-morpholinoethan-1-amine in place of (R)-3-fluoropyrrolidine (20 mg, 36% yield). $^1$H NMR (300 MHz, methanol-d$_4$) δ 1.62 (3H, d, J=6.8 Hz), 2.21-2.62 (6H, m), 2.59 (3H, s), 3.57 (2H, q, J=6.6 Hz), 3.71 (4H, t, J=4.8 Hz), 5.32 (1H, q, J=6.8 Hz), 6.87 (1H, s), 7.38 (1H, m Hz), 7.93 (1H, dt, J=6.6, 1.8 Hz), 8.38 (1H, dd, J=4.8, 1.8 Hz), 8.65 (1H, d, J=1.8 Hz) ppm. LCMS m/z=426.9 [M+H$^+$].

Example Z379. 1-(2-(((S)-1-(5-Fluoropyridin-3-yl)ethyl)amino)thieno[3,2-d]pyrimidine-4-carbonyl)pyrrolidine-3-carboxylic acid

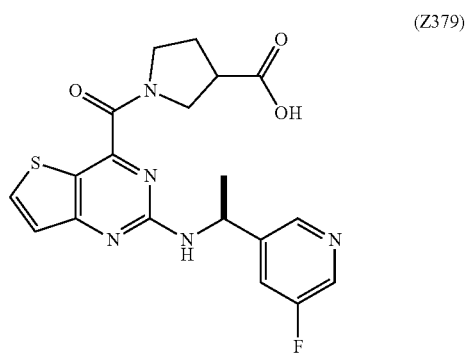
(Z379)

Synthesis of 1-(2-(((S)-1-(5-fluoropyridin-3-yl)ethyl)amino)thieno[3,2-d]pyrimidine-4-carbonyl)pyrrolidine-3-carboxylic acid (Z379): The title compound (Z379) was prepared from tert-butyl 1-(2-(((S)-1-(5-fluoropyridin-3-yl)ethyl)amino)thieno[3,2-d]pyrimidine-4-carbonyl)pyrrolidine-3-carboxylate using chemistry similar to that described in Example 358 (73% yield). $^1$H NMR (400 MHz, CDCl$_3$) δ 1.63 (3H, d, J=7.2 Hz), 2.19-2.25 (2H, m), 3.09-3.15 (1H, m), 3.70-3.77 (1H, m), 3.84-4.05 (3H, m), 4.15-4.21 (1H, m), 5.17-5.31 (1H, m), 6.27 (1H, m), 7.17 (1H, dd, J=5.6, 2.0 Hz), 7.48-7.58 (1H, m), 7.98 (1H, td, J=5.6, 0.8 Hz), 8.32 (1H, m), 8.51-8.59 (1H, m) ppm. LCMS m/z=416.1 [M+H$^+$].

Example Z380. 1-(2-(((S)-1-(Pyridin-2-yl)ethyl)amino)thieno[3,2-d]pyrimidine-4-carbonyl)pyrrolidine-3-carboxylic acid

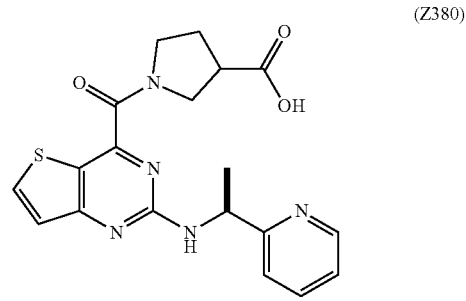
(Z380)

Synthesis of 1-(2-(((S)-1-(pyridin-2-yl)ethyl)amino)thieno[3,2-d]pyrimidine-4-carbonyl)pyrrolidine-3-carboxylic acid (Z380): The title compound (Z380) was prepared from tert-butyl 1-(2-(((S)-1-(pyridin-2-yl)ethyl)amino) thieno[3,2-d]pyrimidine-4-carbonyl)pyrrol-idine-3-carboxylate using chemistry similar to that described in Example 358 (84% yield). ¹H NMR (400 MHz, CDCl₃) δ 1.65 (3H, dt, J=7.2, 2.0 Hz), 2.14-2.29 (2H, m), 3.09-3.15 (1H, m), 3.64-4.40 (3H, m), 5.17-5.31 (1H, m), 6.75 (1H, m), 7.17-7.22 (1H, m), 7.27-7.29 (1H, m), 7.32-7.35 (1H, m), 7.50-7.57 (1H, m), 7.73-7.82 (1H, m), 7.96 (1H, d, J=6.4 Hz), 8.60-8.71 (1H, m) ppm. LCMS m/z=398.1 [M+H⁺].

Example Z381. (S)-2-((1-(5-Fluoropyridin-3-yl) ethyl)amino)thieno[3,2-d]pyrimidin-4-yl)(imidazolidin-1-yl)methanone

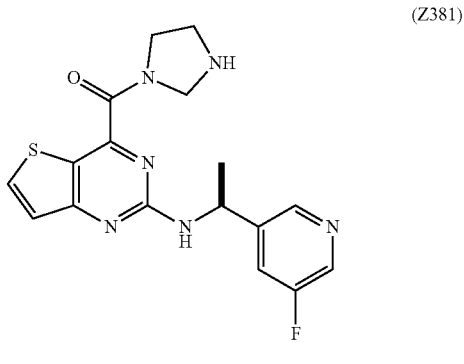

(Z381)

Synthesis of (S)-(2-((1-(5-fluoropyridin-3-yl)ethyl) amino)thieno[3,2-d]pyrimidin-4-yl)(imidazolidin-1-yl) methanone (Z381): The title compound (Z381) was prepared from tert-butyl (S)-3-(2-((1-(5-fluoropyridin-3-yl)ethyl) amino)thieno[3,2-d]pyrimidine-4-carbonyl)imidazol-idine-1-carboxylate using chemistry similar to that described in Example Z358 (33% yield). ¹H NMR (400 MHz, CDCl₃) δ 1.61 (3H, dtd, J=25.6, 8.0, 5.2 Hz), 3.20-3.31 (2H, m), 3.49-3.69 (1H, m), 3.75-3.80 (3H, m), 5.23 (1H, m), 6.27 (1H, m), 7.09-7.12 (1H, m), 7.17-7.19 (1H, m), 7.45-7.52 (1H, m), 7.98 (1H, td, J=26.8, 6.0 Hz), 8.27-8.32 (1H, m), 8.52-8.56 (1H, m) ppm. LCMS m/z=373.1 [M+H⁺].

Example Z382. (S)-2-((1-(5-Fluoropyridin-3-yl) ethyl)amino)-N-(2-(pyridin-4-yl)ethyl)thieno[3,2-d] pyrimidine-4-carboxamide

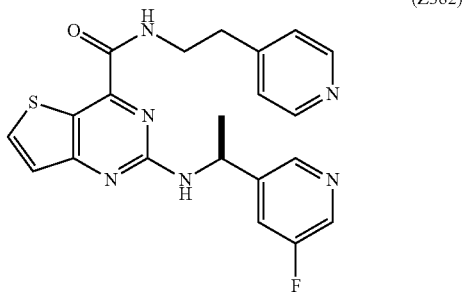

(Z382)

Synthesis of (S)-2-((1-(5-fluoropyridin-3-yl)ethyl) amino)-N-(2-(pyridin-4-yl)ethyl)thieno[3,2-d]pyrimidine-4-carboxamide (Z382): The title compound (Z382) was prepared from (S)-2-((1-(5-fluoropyridin-3-yl)ethyl)amino) thieno[3,2-d]pyrimidine-4-carboxylic acid di-hydrochloride using chemistry similar to that described in Example Z17 using 2-(4-pyridyl)ethanamine (commercially obtained from CombiBlocks, San Diego, Calif.) in place of (3R)-3-methoxypyrrolidine hydrochloride (42% yield). ¹H NMR (400 MHz, CDCl₃) δ 1.63 (3H, d, J=7.2 Hz), 2.95 (2H, t, J=7.2 Hz), 3.65-3.81 (2H, m), 5.12 (1H, t, J=6.4 Hz), 5.43 (1H, d, J=5.6 Hz), 7.18 (1H, d, J=5.6 Hz), 7.20 (2H, dd, J=4.8, 1.6 Hz), 7.39 (1H, dt, J=9.2, 2.0 Hz), 7.70 (1H, br s), 8.01 (1H, d, J=5.6 Hz), 8.34 (1H, d, J=2.4 Hz), 8.44 (1H, s), 8.56 (2H, dd, J=4.8, 1.6 Hz) ppm. LCMS m/z=423.2 [M+H⁺].

Example Z383. N—((S)-1-(2-(((S)-1-(5-Fluoropyridin-3-yl)ethyl)amino)-6-methylthieno[3,2-d]pyrimidine-4-carbonyl)pyrrolidin-3-yl)acetamide

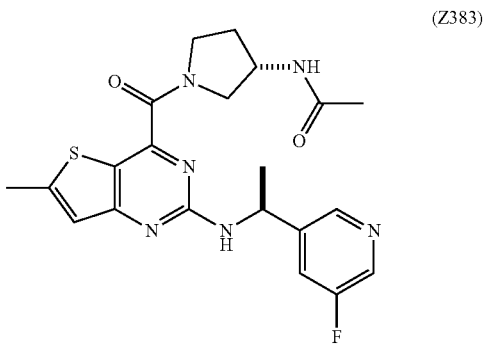

(Z383)

Synthesis of N—((S)-1-(2-(((S)-1-(5-fluoropyridin-3-yl) ethyl)amino)-6-methylthieno[3,2-d]pyrimidine-4-carbonyl) pyrrolidin-3-yl)acetamide (Z383): The title compound (Z383) was prepared from (S)-2-((1-(5-fluoropyridin-3-yl) ethyl)amino)-6-methylthieno[3,2-d]pyrimidine-4-carboxylic acid di-hydrochloride using chemistry similar to that described in Example Z17 using 4-(2-aminoethyl)phenol (commercially obtained from AK Scientific, Union City, Calif.) in place of (3R)-3-methoxypyrrolidine hydrochloride (19% yield). ¹H NMR (400 MHz, CDCl₃) δ 1.61 (3H, d, J=2.0 Hz), 1.73-1.85 (1H, m), 2.04 (3H, s), 2.11-2.24 (1H, m), 2.59 (3H, t, J=1.2 Hz), 3.55-3.90 (4H, m), 4.37-4.50 (1H, m), 5.15 (1H, q, J=6.8 Hz), 5.38 (1H, t, J=6.0 Hz), 5.68 (1H, m), 6.84 (1H, m), 7.42-7.49 (1H, m), 8.30-8.33 (1H, m), 8.44 (1H, s), 8.45-8.53 (1H, m) ppm. LCMS m/z=443.1 [M+H⁺].

Example Z384. (S)-2-((1-(5-Fluoropyridin-3-yl) ethyl)amino)-N-(4-(hydroxymethyl)phenethyl)thieno [3,2-d]pyrimidine-4-carboxamide

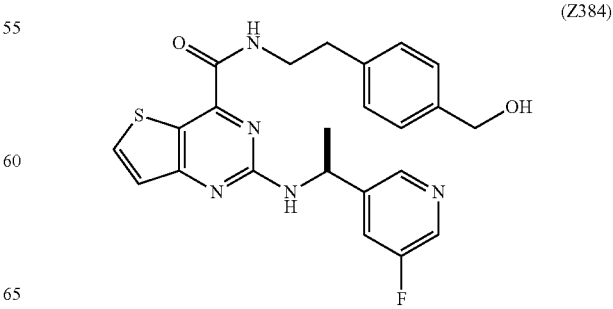

(Z384)

Synthesis of (S)-2-((1-(5-fluoropyridin-3-yl)ethyl)amino)-N-(2-(pyridin-4-yl)ethyl)thieno[3,2-d]pyrimidine-4-carboxamide (Z384): The title compound (Z384) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using [4-(2-aminoethyl)phenyl]methanol (commercially obtained from Enamine, Monmouth Jct., N.J.) in place of (3R)-3-methoxypyrrolidine hydrochloride (44% yield). $^1$H NMR (400 MHz, CDCl$_3$) δ 1.60 (3H, d, J=7.2 Hz), 2.88-2.99 (3H, m), 3.68-3.78 (2H, m), 4.07 (2H, s), 5.14 (1H, t, J=5.4 Hz), 5.40 (1H, d, J=6.8 Hz), 7.16 (1H, d, J=5.6 Hz), 7.23 (2H, d, J=8.4 Hz), 7.38 (1H, m), 7.35 (2H, d, J=8.4 Hz), 7.67 (1H, m), 8.02 (1H, d, J=5.6 Hz), 8.23 (1H, br s), 8.30 (1H, d, J=2.8 Hz) ppm. LCMS m/z=452.1 [M+H$^+$].

Example Z385. (S)—N-(4-Chlorophenethyl)-2-((1-(5-fluoropyridin-3-yl)ethyl)amino)thieno[3,2-d]pyrimidine-4-carboxamide

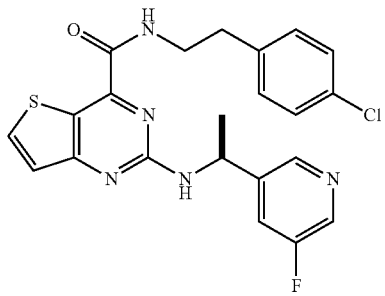 [SMILES: C[C@H](Nc1nc(C(=O)NCCc2ccc(Cl)cc2)c2sccc2n1)c1cncc(F)c1]

(Z385)

Synthesis of (S)—N-(4-chlorophenethyl)-2-((1-(5-fluoropyridin-3-yl)ethyl)amino)thieno[3,2-d]pyrimidine-4-carboxamide (Z385): The title compound (Z385) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using 2-(4-chlorophenyl)ethylamine (commercially obtained from AK Scientific, Union City, Calif.) in place of (3R)-3-methoxypyrrol-idine hydrochloride (37% yield). LCMS m/z=456.0 [M+H$^+$].

Example Z386. 2-(((S)-1-(5-Fluoropyridin-3-yl)ethyl)amino)-N-(2-(pyrrolidin-3-yl)ethyl)thieno[3,2-d]pyrimidine-4-carboxamide

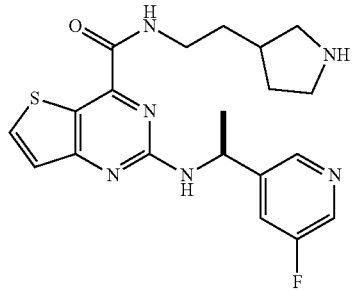

(Z386)

Synthesis of 2-(((S)-1-(5-fluoropyridin-3-yl)ethyl)amino)-N-(2-(pyrrolidin-3-yl)ethyl)thieno[3,2-d]pyrimidine-4-carboxamide (Z386): The title compound (Z386) was prepared from tert-butyl 3-(2-(2-(((S)-1-(5-fluoropyridin-3-yl)ethyl)amino)thieno[3,2-d]pyrimidine-4-carboxamido)ethyl)pyrrolidine-1-carboxylate using chemistry similar to that described in Example Z358 (77% yield). LCMS m/z=415.3 [M+H$^+$].

Example Z387. 6-Methyl-2-(((S)-1-(pyridin-3-yl)ethyl)amino)-N—(((S)-tetrahydrofuran-3-yl)methyl)thieno[3,2-d]pyrimidine-4-carboxamide

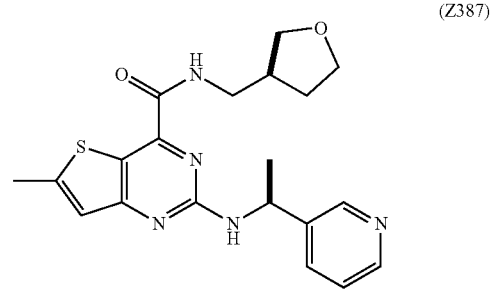

(Z387)

Synthesis of 6-methyl-2-(((S)-1-(pyridin-3-yl)ethyl)amino)-N—(((S)-tetrahydrofuran-3-yl)methyl)thieno[3,2-d]pyrimidine-4-carboxamide (Z387): The title compound (Z387) was prepared from (S)-6-methyl-2-((1-(pyridin-3-yl)ethyl)amino)thieno[3,2-d]pyrimidine-4-carboxylic acid di-hydrochloride (19 mg, 0.049 mmol) using chemistry similar to that described in Example Z8 using [(3S)-tetrahydrofuran-3-yl]methanamine (commercially obtained from PharmaBlock, Sunnyvale, Calif.) in place of (R)-3-fluoropyrrolidine (8 mg, 41% yield). LCMS m/z=398.1 [M+H$^+$].

Example Z388. 6-Methyl-2-(((S)-1-(pyridin-3-yl)ethyl)amino)-N—(((R)-tetrahydrofuran-3-yl)methyl)thieno[3,2-d]pyrimidine-4-carboxamide

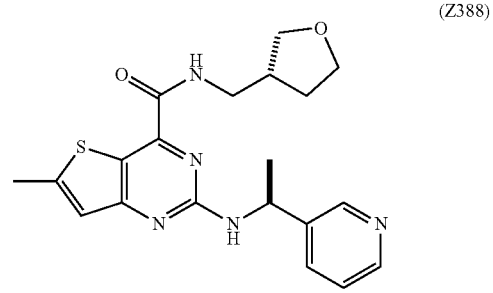

(Z388)

Synthesis of 6-methyl-2-(((S)-1-(pyridin-3-yl)ethyl)amino)-N—(((R)-tetrahydrofuran-3-yl)methyl)thieno[3,2-d]pyrimidine-4-carboxamide (Z388): The title compound (Z388) was prepared from (S)-6-methyl-2-((1-(pyridin-3-yl)ethyl)amino)thieno[3,2-d]pyrimidine-4-carboxylic acid di-hydrochloride (19.4 mg, 0.05 mmol) using chemistry similar to that described in Example Z8 using [(3R)-tetrahydrofuran-3-yl]methanamine (commercially obtained from PharmaBlock, Sunnyvale, Calif.) in place of (R)-3-fluoropyrrolidine (11 mg, 56% yield). $^1$H NMR (400 MHz, CDCl$_3$) δ 1.63 (3H, d, J=6.8 Hz), 1.64 (1H, m), 2.05 (1H, m), 2.40 (1H, m), 2.61 (3H, d, J=1.2 Hz), 3.40-3.49 (2H, m), 3.57 (1H, m), 3.77 (1H, m), 3.83 (1H, m), 3.90 (1H, m), 5.15 (1H, quintet, J=6.8 Hz), 5.40 (1H, d, J=6.8 Hz), 6.85 (1H, d, J=1.2 Hz), 7.25 (1H, dd, J=8.0, 4.8 Hz), 7.72 (1H, dt, J=8.0, 1.6 Hz), 7.78 (1H, m), 8.50 (1H, dd, J=4.8, 1.6 Hz), 8.71 (1H, d, J=1.6 Hz) ppm. LCMS m/z=398.1 [M+H$^+$].

Example Z389. 2-(((S)-1-(5-Fluoropyridin-3-yl)ethyl)amino)-6-methyl-N—(((S)-tetrahydrofuran-3-yl)methyl)thieno[3,2-d]pyrimidine-4-carboxamide

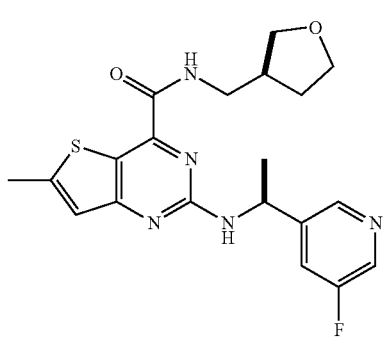

(Z389)

Synthesis of 2-(((S)-1-(5-fluoropyridin-3-yl)ethyl)amino)-6-methyl-N—(((S)-tetrahydrofuran-3-yl)methyl)thieno[3,2-d]pyrimidine-4-carboxamide (Z389): The title compound (Z389) was prepared from ((S)-2-((1-(5-fluoropyridin-3-yl)ethyl)amino)-6-methylthieno[3,2-d]pyrimidine-4-carboxylic acid di-hydrochloride (40.5 mg, 0.10 mmol) using chemistry similar to that described in Example Z8 using (S)-(tetrahydrofuran-3-yl)methanamine in place of (R)-3-fluoropyrrolidine (35 mg, 84% yield). $^1$H NMR (400 MHz, CDCl$_3$) δ 1.64 (3H, d, J=7.2 Hz), 1.66 (1H, m), 2.06 (1H, m), 2.57 (1H, m), 2.62 (3H, d, J=1.2 Hz), 3.43-3.48 (2H, m), 3.58 (1H, m), 3.76 (1H, m), 3.84 (1H, m), 3.91 (1H, m), 5.19 (1H, m), 5.38 (1H, m), 6.85 (1H, d, J=1.2 Hz), 7.45 (1H, m), 7.79 (1H, m), 8.35 (1H, d, J=2.8 Hz), 8.54 (1H, m) ppm. LCMS m/z=416.1 [M+H$^+$].

Example Z390. 2-(((S)-1-(5-Fluoropyridin-3-yl)ethyl)amino)-6-methyl-N—(((R)-tetrahydrofuran-3-yl)methyl)thieno[3,2d]pyrimidine-4-carboxamide

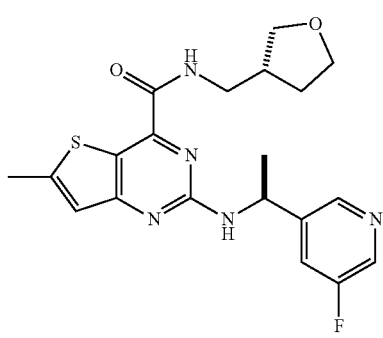

(Z390)

Synthesis of 2-(((S)-1-(5-fluoropyridin-3-yl)ethyl)amino)-6-methyl-N—(((R)-tetrahydrofuran-3-yl)methyl)thieno[3,2-d]pyrimidine-4-carboxamide (Z390): The title compound (Z390) was prepared from ((S)-2-((1-(5-fluoropyridin-3-yl)ethyl)amino)-6-methylthieno[3,2-d]pyrimidine-4-carboxylic acid di-hydrochloride (40.5 mg, 0.10 mmol) using chemistry similar to that described in Example Z8 using (R)-(tetrahydrofuran-3-yl)methanamine in place of (R)-3-fluoropyrrolidine (19 mg, 46% yield). $^1$H NMR (400 MHz, CDCl$_3$) δ 1.64 (3H, d, J=7.2 Hz), 1.66 (1H, m), 2.06 (1H, m), 2.57 (1H, m), 2.62 (3H, d, J=1.2 Hz), 3.43-3.48 (2H, m), 3.58 (1H, m), 3.76 (1H, m), 3.84 (1H, m), 3.91 (1H, m), 5.19 (1H, m), 5.38 (1H, m), 6.85 (1H, d, J=1.2 Hz), 7.45 (1H, m), 7.79 (1H, m), 8.35 (1H, d, J=2.8 Hz), 8.54 (1H, m) ppm. LCMS m/z=416.1 [M+H$^+$].

Example Z391. (2-(((S)-1-(5-Fluoropyridin-3-yl)ethyl)amino)-6-(trifluoromethyl)thieno[3,2-d]pyrimidin-4-yl)((R)-3-hydroxypyrrolidin-1-yl)methanone

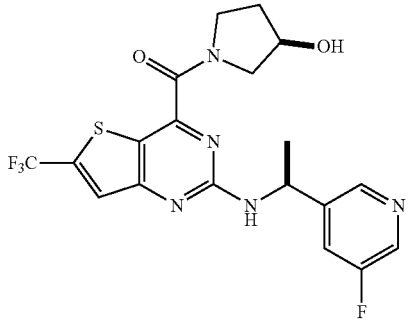 [SMILES: C[C@H](Nc1nc(C(=O)N2CC[C@@H](O)C2)c2sc(C(F)(F)F)cc2n1)c1cncc(F)c1]

Synthesis of ethyl (S)-2-((1-(5-fluoropyridin-3-yl)ethyl)amino)-6-(trifluoromethyl)thieno[3,2-d]pyrimidine-4-carboxylate: To a solution of ethyl 2-chloro-6-(trifluoromethyl)thieno[3,2-d]pyrimidine-4-carboxylate (220 mg, 0.71 mmol) in DMSO (4 mL) were added (1S)-1-(5-fluoropyridin-3-yl)ethan-1-amine (224 mg, 1.60 mmol) and DIEA (366 mg, 2.83 mmol). The resulting solution was stirred for 2 h at 100° C. and then was extracted with ethyl acetate (3×50 mL). The combined organic layer was dried over anhydrous sodium sulfate and concentrated under vacuum. The residue was purified by flash chromatography on silica gel eluting with ethyl acetate/petroleum ether (5:1) to provide (S)-2-((1-(5-fluoropyridin-3-yl)ethyl)amino)-6-(trifluoromethyl)thieno[3,2-d]pyrimidine-4-carboxylate as an yellow solid (190 mg, 65% yield). LCMS m/z=415.2 [M+H$^+$].

Synthesis of (S)-2-((1-(5-fluoropyridin-3-yl)ethyl)amino)-6-(trifluoromethyl)thieno[3,2-d]pyrimidine-4-carboxylic acid: A solution of (S)-2-((1-(5-fluoropyridin-3-yl)ethyl)amino)-6-(trifluoromethyl)thieno[3,2-d]pyrimidine-4-carboxylate (190 mg, 0.46 mmol) in 12N hydrogen chloride (10 mL) was stirred for 2 h at 80° C. The reaction mixture was concentrated under vacuum and the residue was dried under high vacuum overnight to provide (S)-2-((1-(5-fluoropyridin-3-yl)ethyl)amino)-6-(trifluoromethyl)thieno[3,2-d]pyrimidine-4-carboxylic acid di-hydrochloride as an yellow solid (190 mg, 90% yield). LCMS m/z=387.2 [M+H$^+$].

Synthesis of (2-(((S)-1-(5-fluoropyridin-3-yl)ethyl)amino)-6-(trifluoromethyl)thieno[3,2-d]pyrimidin-4-yl)((R)-3-hydroxypyrrolidin-1-yl)methanone (Z391): The title compound (Z391) was prepared from (S)-2-((1-(5-fluoropyridin-3-yl)ethyl)amino)-6-(trifluoromethyl)thieno[3,2-d]

pyrimidine-4-carboxylic acid di-hydrochloride (50 mg, 0.109 mmol) using chemistry similar to that described in Example Z8 using (R)-pyrrolidin-3-ol in place of (R)-3-fluoropyrrolidine (20 mg, 40% yield). $^1$H NMR (400 MHz, methanol-$d_4$) δ 1.64 (3H, d, J=7.2 Hz), 1.98-2.08 (2H, m), 3.70 (1H, m), 3.79 (1H, m), 4.22-4.44 (2H, m), 4.47 (1H, m), 5.28 (1H, q, J=7.2 Hz), 7.61 (1H, s), 7.71 (1H, dd, J=9.5, 2.0 Hz), 8.31 (1H, m), 8.52 (1H, m) ppm. LCMS m/z=456.1 [M+H$^+$].

Example Z392. 2-(((S)-1-(5-Fluoropyridin-3-yl)ethyl)amino)-N—((S)-2-hydroxypropl)-6-(trifluoromethyl)thieno[3,2-d]pyrimidine-4-carboxamide

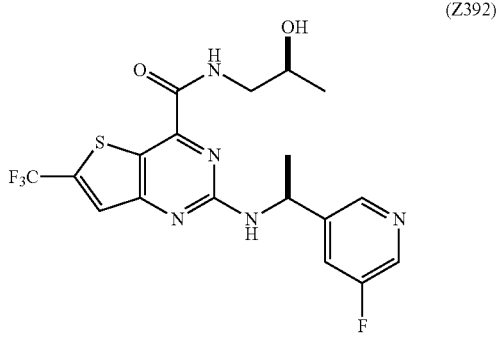

Synthesis of 2-(((S)-1-(5-fluoropyridin-3-yl)ethyl)amino)-N—((S)-2-hydroxypropyl)-6-(trifluoromethyl)thieno[3,2-d]pyrimidine-4-carboxamide (Z392): The title compound (Z392) was prepared from (S)-2-((1-(5-fluoropyridin-3-yl)ethyl)amino)-6-(trifluoromethyl)thieno[3,2-d]pyrimidine-4-carboxylic acid di-hydrochloride (46 mg, 0.10 mmol) using chemistry similar to that described in Example Z8 using (S)-1-aminopropan-2-ol in place of (R)-3-fluoropyrrolidine (20 mg, 45% yield). $^1$H NMR (400 MHz, methanol-$d_4$) δ 1.22 (3H, d, J=6.0 Hz), 1.63 (3H, d, J=6.8 Hz), 3.31 (1H, m), 3.54 (1H, dd, J=13.5, 4.0 Hz), 4.00 (1H, m), 5.37 (1H, q, J=6.8 Hz), 7.61 (1H, s), 7.73 (1H, m), 8.31 (1H, m), 8.54 (1H, m) ppm. LCMS m/z=444.1 [M+H$^+$].

Example Z393. 2-(((S)-1-(5-Fluoropyridin-3-yl)ethyl)amino)-N—((R)-2-hydroxypropyl)-6-(trifluoromethyl)thieno[3,2-d]pyrimidine-4-carboxamide

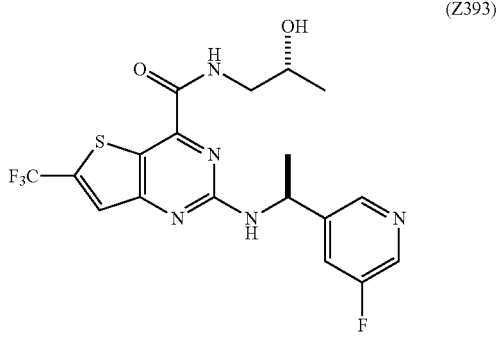

Synthesis of 2-(((S)-1-(5-fluoropyridin-3-yl)ethyl)amino)-N—((R)-2-hydroxypropyl)-6-(trifluoromethyl)thieno[3,2-d]pyrimidine-4-carboxamide (Z393): The title compound (Z393) was prepared from (S)-2-((1-(5-fluoropyridin-3-yl)ethyl)amino)-6-(trifluoromethyl)thieno[3,2-d]pyrimidine-4-carboxylic acid di-hydrochloride (23 mg, 0.05 mmol) using chemistry similar to that described in Example Z8 using (R)-1-aminopropan-2-ol in place of (R)-3-fluoropyrrolidine (7 mg, 32% yield). $^1$H NMR (400 MHz, methanol-$d_4$) δ 1.21 (3H, d, J=6.3 Hz), 1.63 (3H, d, J=7.2 Hz), 3.30 (1H, m), 3.52 (1H, dd, J=13.5, 4.0 Hz), 3.97 (1H, m), 5.34 (1H, q, J=7.2 Hz), 7.61 (1H, s), 7.73 (1H, dd, J=9.6, 1.8 Hz), 8.30 (1H, m), 8.55 (1H, m) ppm. LCMS m/z=444.1 [M+H$^+$].

Example Z394. N—((S)-1-Phenylethyl)-2-(((S)-1-phenylethyl)amino)thieno[3,2-d]pyrimidine-4-carboxamide

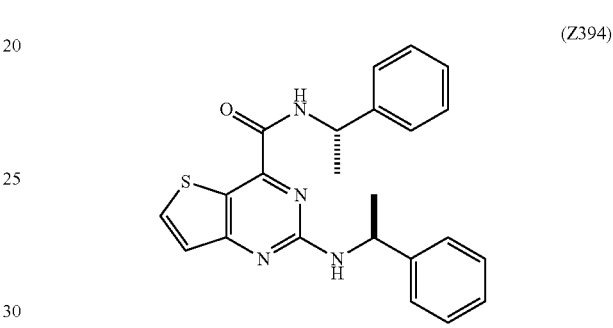

Synthesis of N—((S)-1-phenylethyl)-2-(((S)-1-phenylethyl)amino)thieno[3,2-d]pyrimidine-4-carboxamide (Z394) and ethyl (S)-2-((1-phenylethyl)amino)thieno[3,2-d]pyrimidine-4-carboxylate: The title compounds were prepared from ethyl 2-chlorothieno[3,2-d]pyrimidine-4-carboxylate (450 mg, 1.85 mmol) using chemistry similar to that described in Example Z12 using (S)-(−)-1-phenethylamine (commercially obtained from Ark Pharm, Libertyville, Ill.) in place of (6-methoxypyridin-3-yl)methanamine hydrochloride to provide N—((S)-1-phenylethyl)-2-(((S)-1-phenylethyl)amino)thieno[3,2-d]pyrimidine-4-carboxamide (394) (281 mg, 38% yield), LCMS m/z=403.2 [M+H$^+$], and ethyl (S)-2-((1-phenylethyl)amino)thieno[3,2-d]pyrimidine-4-carboxylate (200 mg, 33% yield), LCMS m/z=328.0 [M+H$^+$].

Example Z395. 2-(((S)-1-(5-Fluoropyridin-3-yl)ethyl)amino)-N-((1R,3R)-3-hydroxycyclopentyl)thieno[3,2-d]pyrimidine-4-carboxamide

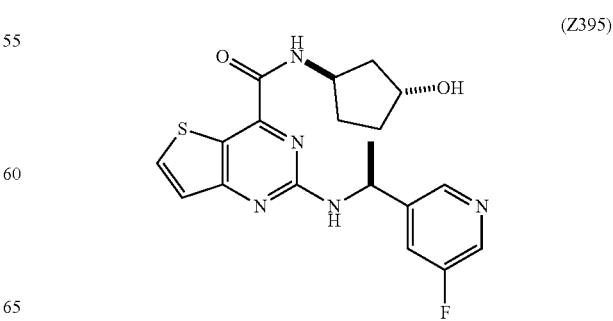

Synthesis of 2-(((S)-1-(5-fluoropyridin-3-yl)ethyl)amino)-N-((1R,3R)-3-hydroxycyclopentyl)thieno[3,2-d]pyrimidine-4-carboxamide (Z395): The title compound (Z395) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using (1R,3R)-3-aminocyclopentanol (commercially obtained from LabNetwork, Shanghai, Conn.)) in place of (3R)-3-methoxypyrrolidine hydrochloride (87% yield). LCMS m/z=402.2 [M+H$^+$].

Example Z396. (S)-2-((1-(5-Fluoropyridin-3-yl)ethyl)amino)-N-(4-hydroxyphenethyl)-N-methylthieno[3,2-d]pyrimidine-4-carboxamide

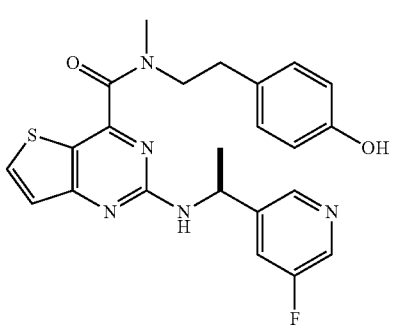 [SMILES: C[C@H](Nc1nc(C(=O)N(C)CCc2ccc(O)cc2)c2sccc2n1)c1cncc(F)c1]

(Z396)

Synthesis of (S)-2-((1-(5-fluoropyridin-3-yl)amino)-N-(4-hydroxyphenethyl)-N-methylthieno[3,2-d]pyrimidine-4-carboxamide (Z396): The title compound (Z396) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using 4-[2-(methyl-amino)ethyl]phenol (commercially obtained from CombiBlocks, San Diego, Calif.) in place of (3R)-3-methoxypyrrolidine hydrochloride (73% yield). $^1$H NMR (400 MHz, CDCl$_3$) δ 1.61 (3H, dd, J=11.2, 5.6 Hz), 2.81 (2H, s), 2.88 (1H, m), 2.90-2.93 (1H, m), 3.14 (2H, s), 3.65-3.91 (2H, m), 5.12 (1H, m), 5.46 (1H, m), 6.49 (1H, d, J=8.4 Hz), 6.67 (1H, d, J=7.6 Hz), 6.76 (1H, d, J=8.8 Hz), 7.14 (2H, dd, J=14.4, 5.6 Hz), 7.43 (1H, dd, J=9.2, 2.0 Hz), 7.90 (1H, dd, J=14.4, 5.6 Hz), 8.33 (1H, d, J=2.4 Hz), 8.47 (1H, d, J=21.6 Hz) ppm. LCMS m/z=452.1 [M+H$^+$].

Example Z397. (S)—N-(Azetidin-3-yl)-2-((1-(5-fluoropyridin-3-yl)ethyl)amino)thieno[3,2-d]pyrimidine-4-carboxamide

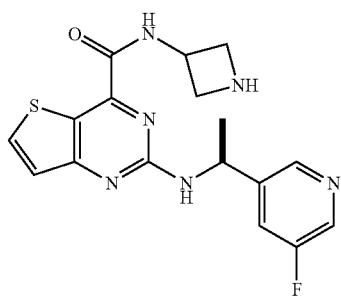 [SMILES: C[C@H](Nc1nc(C(=O)NC2CNC2)c2sccc2n1)c1cncc(F)c1]

(Z397)

Synthesis of tert-butyl (S)-3-(2-((1-(5-fluoropyridin-3-yl)ethyl)amino)thieno[3,2-d]pyrimidine-4-carboxamido)azetidine-1-carboxylate: The title compound was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using tert-butyl 3-aminoazetidine-1-carboxylate (commercially obtained from CombiBlocks, San Diego, Calif.) in place of (3R)-3-methoxypyrrolidine hydrochloride (88% yield). LCMS m/z=473.1 [M+H$^+$].

Synthesis of (S)—N-(azetidin-3-yl)-2-((1-(5-fluoropyridin-3-yl)ethyl)amino)thieno[3,2-d]pyrimidine-4-carboxamide (Z397): The title compound (Z397) was prepared from tert-butyl (S)-3-(2-((1-(5-fluoropyridin-3-yl)ethyl)amino)thieno[3,2-d]pyrimidine-4-carboxamido)azetidine-1-carboxylate using chemistry similar to that described in Example Z358 (80% yield). LCMS m/z=373.1 [M+H$^+$].

Example Z398. (S)-2-((1-(5-Fluoropyridin-3-yl)ethyl)amino)-N-((2-(4-methoxyphenoxy)pyridin-4-yl)methyl)thieno[3,2-d]pyrimidine-4-carboxamide

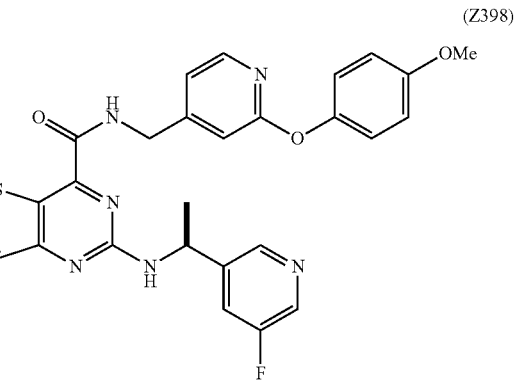

(Z398)

Synthesis of (S)-2-((1-(5-fluoropyridin-3-yl)ethyl)amino)-N-((2-(4-methoxyphenoxy)pyridin-4-yl)methyl)thieno[3,2-d]pyrimidine-4-carboxamide (Z398): The title compound (Z398) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using [6-(4-methoxyphenoxy)-3-pyridyl]methanamine (commercially obtained from Enamine, Monmouth Jct., N.J.) in place of (3R)-3-methoxypyrrolidine hydrochloride (44% yield). LCMS m/z=531.2 [M+H$^+$].

Example Z399. N—((S)-2-Methoxypropyl)-6-methyl-2-(((S)-1-(pyridin-3-yl)ethyl)amino)thieno[3,2-d]pyrimidine-4-carboxamide

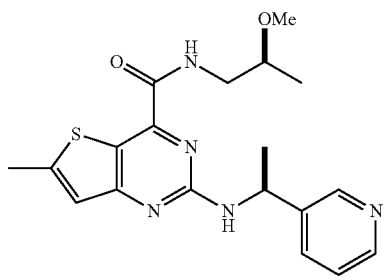 [SMILES: CO[C@@H](C)CNC(=O)c1nc(N[C@@H](C)c2cccnc2)nc2cc(C)sc12]

(Z399)

Synthesis of N—((S)-2-methoxypropyl)-6-methyl-2-(((S)-1-(pyridin-3-yl)ethyl)amino)thieno[3,2-d]pyrimidine-4-carboxamide (Z399): The title compound (Z399) was prepared from ((S)-2-((1-(5-fluoropyridin-3-yl)ethyl)amino)-6-methylthieno[3,2-d]pyrimidine-4-carboxylic acid di-hydrochloride (39 mg, 0.10 mmol) using chemistry similar to that described in Example Z8 using (2S)-2-methoxypropan-1-amine in place of (R)-3-fluoropyrrolidine (35 mg, 93% yield). $^1$H NMR (400 MHz, CDCl$_3$) δ 1.19 (3H, d, J=6.4 Hz), 1.64 (3H, d, J=7.2 Hz), 2.61 (3H, d, J=1.2 Hz), 3.32 (1H, m), 3.40 (3H, s), 3.54 (1H, m), 3.67 (1H, m), 5.20 (1H, quintet, J=7.2 Hz), 5.42 (1H, d, J=7.2 Hz), 6.85 (1H, d, J=1.2 Hz), 7.24 (1H, dd, J=8.0, 4.8 Hz), 7.72 (1H, dt, J=8.0, 1.6 Hz), 8.03 (1H, m), 8.49 (1H, dd, J=4.8, 1.6 Hz), 8.71 (1H, d, J=1.6 Hz) ppm. LCMS m/z=386.1 [M+H$^+$].

Example Z400. N—((R)-2-Methoxypropyl)-6-methyl-2-(((S)-1-(pyridin-3-yl)ethyl)amino)thieno[3,2-d]pyrimidine-4-carboxamide (Z400)

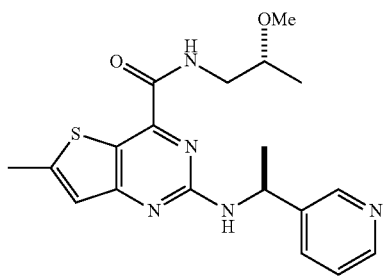 [SMILES: CO[C@H](C)CNC(=O)c1nc(N[C@@H](C)c2cccnc2)nc2cc(C)sc12]

(Z400)

Synthesis of N—((R)-2-methoxypropyl)-6-methyl-2-(((S)-1-(pyridin-3-yl)ethyl)amino)thieno[3,2-d]pyrimidine-4-carboxamide (Z400): The title compound (Z400) was prepared from ((S)-2-((1-(5-fluoropyridin-3-yl)ethyl)amino)-6-methylthieno[3,2-d]pyrimidine-4-carboxylic acid di-hydrochloride (39 mg, 0.10 mmol) using chemistry similar to that described in Example Z8 using (2R)-2-methoxypropan-1-amine in place of (R)-3-fluoropyrrolidine (39 mg, 100% yield). $^1$H NMR (400 MHz, CDCl$_3$) δ 1.17 (3H, d, J=6.4 Hz), 1.63 (3H, d, J=6.8 Hz), 2.61 (3H, d, J=1.2 Hz), 3.31 (1H, m), 3.42 (3H, s), 3.55 (1H, m), 3.67 (1H, m), 5.18 (1H, quintet, J=6.8 Hz), 5.42 (1H, d, J=6.8 Hz), 6.85 (1H, d, J=1.2 Hz), 7.25 (1H, dd, J=8.0, 4.8 Hz), 7.72 (1H, dt, J=8.0, 2.0 Hz), 8.04 (1H, m), 8.49 (1H, dd, J=4.8, 2.0 Hz), 8.71 (1H, d, J=2.0 Hz) ppm. LCMS m/z=386.1 [M+H$^+$].

Example Z401. (S)-(3-Aminoazetidin-1-yl)(2-((1-(5-fluoropyridin-3-yl)ethyl)amino)thieno[3,2-d]pyrimidin-4-yl)methanone

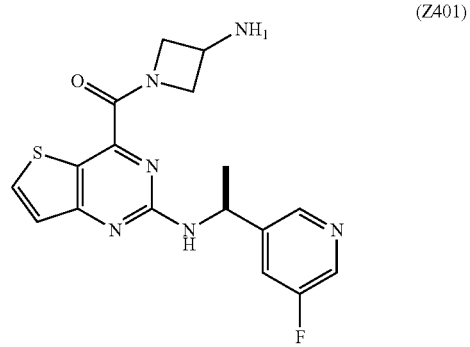

(Z401)

Synthesis of (S)-(3-aminoazetidin-1-yl)(2-((1-(5-fluoropyridin-3-yl)ethyl)amino)thieno[3,2-d]pyrimidin-4-yl)methanone (Z401): The title compound (Z401) was prepared from tert-butyl (S)-(1-(2-((1-(5-fluoropyridin-3-yl)ethyl)amino)thieno[3,2-d]pyrimidine-4-carbonyl)azetidin-3-yl)carbamate using chemistry similar to that described in Example Z358 (80% yield). LCMS m/z=387.3 [M+H$^+$].

Example Z402. 2-(((S)-1-(5-Fluoropyridin-3-yl)ethyl)amino)-N-((1R,3S)-3-hydroxycyclopentyl)thieno[3,2-d]pyrimidine-4-carboxamide

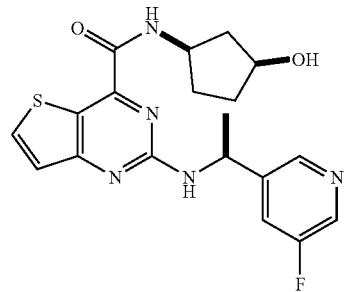

(Z402)

Synthesis of 2-(((S)-1-(5-fluoropyridin-3-yl)ethyl)amino)-N-((1R,3S)-3-hydroxycyclopentyl)thieno[3,2-d]pyrimidine-4-carboxamide (Z402): The title compound (Z402) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using (1S,3R)-3-aminocyclopentanol (commercially obtained from LabNetwork, Shanghai, Conn.)) in place of (3R)-3-methoxypyrrolidine hydrochloride (87% yield). LCMS m/z=402.2 [M+H$^+$].

Example Z403. (S)—N-(4-Hydroxyphenethyl)-2-((2-methoxy-1-(pyridin-3-yl)ethyl)amino)thieno[3,2-d]pyrimidine-4-carboxamide

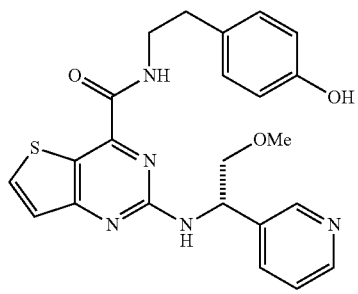 [SMILES: COC[C@@H](Nc1nc(C(=O)NCCc2ccc(O)cc2)c2sccc2n1)c1cccnc1]
(Z403)

Synthesis of (S)—N-(4-hydroxyphenethyl)-2-((2-methoxy-1-(pyridin-3-yl)ethyl)amino)thieno[3,2-d]pyrimidine-4-carboxamide (Z403): The title compound (Z403) was prepared from ethyl (S)-2-((2-methoxy-1-(pyridin-3-yl)ethyl)amino)thieno[3,2-d]pyrimidine-4-carboxylate using chemistry similar to that described in Example Z17 using 4-(2-amino-ethyl)phenol in place of (3R)-3-methoxypyrrolidine hydrochloride (43% yield). $^1$H NMR (400 MHz, CDCl$_3$) δ 2.83 (2H, t, J=5.6 Hz), 3.37 (3H, s), 3.63-3.69 (3H, m), 3.75 (1H, dd, J=9.6, 4.4 Hz), 5.21 (1H, q, J=0.8 Hz), 5.97 (1H, d, J=7.2 Hz), 6.80 (2H, dt, J=8.4, 5.6 Hz), 7.20 (2H, dt, J=8.4, 2.8 Hz), 7.16 (1H, d, J=14.0 Hz), 7.27 (1H, dd, J=8.8, 5.6 Hz), 7.65 (1H, br s), 7.75 (1H, dt, J=7.6, 2.0 Hz), 7.90 (1H, d, J=5.6 Hz), 8.46 (1H, s), 8.51 (1H, dd, J=4.2, 1.6 Hz) ppm. LCMS m/z=450.2 [M+H$^+$].

Example Z404. tert-Butyl (S)-((1-(2-((1-(5-fluoropyridin-3-yl)ethyl)amino)thieno[3,2-d]pyrimidine-4-carbonyl)azetidin-3-yl)methyl)carbamate

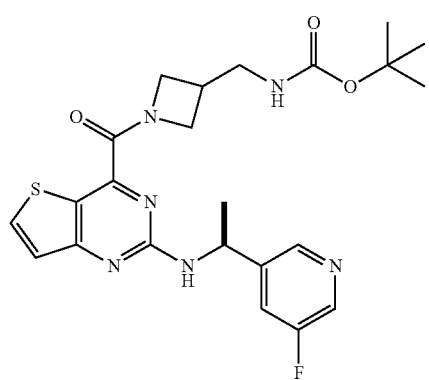 [SMILES: C[C@H](Nc1nc(C(=O)N2CC(CNC(=O)OC(C)(C)C)C2)c2sccc2n1)c1cncc(F)c1]
(Z404)

Synthesis of tert-butyl (S)-((1-(2-((1-(5-fluoropyridin-3-yl)ethyl)amino)thieno[3,2-d]pyrimidine-4-carbonyl)azetidin-3-yl)methyl)carbamate (Z404): The title compound (Z404) was prepared from (S)-2-((1-(5-fluoropyridin-3-yl)ethyl)amino)thieno[3,2-d]pyrimidine-4-carboxylic acid dihydrochloride using chemistry similar to that described in Example Z17 using tert-butyl N-(azetidin-3-ylmethyl)carbamate (commercially obtained from PharmaBlock, Sunnyvale, Calif.) in place of (3R)-3-methoxypyrrolidine hydrochloride (88% yield). $^1$H NMR (400 MHz, CDCl$_3$) δ 1.46 (9H, s), 1.64 (3H, dd, J=6.8, 3.2 Hz), 2.79-2.90 (1H, m), 3.17-3.30 (1H, m), 3.32-3.41 (2H, m), 3.84-3.90 (1H, m), 3.90-4.05 (1H, m), 4.24-4.32 (2H, m), 4.69 (1H t, J=9.2 Hz), 4.87 (1H, br s), 5.21 (1H, q, J=6.8 Hz), 5.42 (1H, d, J=6.0 Hz), 7.17 (1H, d, J=5.6 Hz), 7.45 (1H, dd, J=9.6, 2.0 Hz), 7.97 (1H, dd, J=5.6, 0.8 Hz), 8.36 (1H, t, J=2.8 Hz), 8.50 (1H, dd, J=3.6, 1.6 Hz) ppm. LCMS m/z=487.3 [M+H$^+$].

Example Z405. (S)-2-((1-(2-Fluoropyridin-4-yl)ethyl)amino)-N-(4-hydroxyphenethyl)thieno[3,2-d]pyrimidine-4-carboxamide

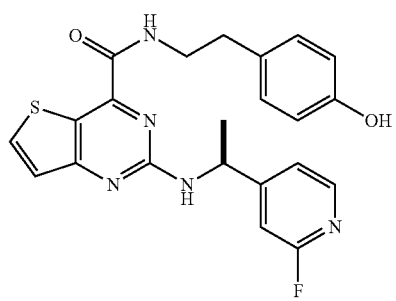 [SMILES: C[C@H](Nc1nc(C(=O)NCCc2ccc(O)cc2)c2sccc2n1)c1ccnc(F)c1]
(Z405)

Synthesis of ethyl (S)-2-((1-(2-fluoropyridin-4-yl)ethyl)amino)thieno[3,2-d]pyrimidine-4-carboxylateethyl: The title compound was prepared from ethyl 2-chlorothieno[3,2-d]pyramid-ine-4-carboxylate (400 mg, 1.65 mmol) using chemistry similar to that described in Example Z12 using (1S)-1-(2-fluoro-4-pyridyl)ethanamine (commercially obtained from AP Bioscience, LLC, Princeton, N.J.) in place of (6-methoxypyridin-3-yl)methanamine hydrochloride (138 mg, 24% yield). LCMS m/z=347.1 [M+H$^+$].

Synthesis of (S)-2-((1-(2-fluoropyridin-4-yl)ethyl)amino)-N-(4-hydroxyphen-ethyl)thieno[3,2-d]pyrimidine-4-carboxamide (Z405): The title compound (Z405) was prepared from ethyl (S)-2-((1-(2-fluoropyridin-4-yl)ethyl)amino)thieno[3,2-d]pyrimidine-4-carboxylate using chemistry similar to that described in Example Z17 using 4-(2-amino-ethyl)phenol in place of (3R)-3-methoxypyrrolidine hydrochloride (41% yield). $^1$H NMR (400 MHz, CDCl$_3$) δ 1.56 (3H, d, J=5.6 Hz), 2.77-2.88 (2H, m), 3.53-3.58 (1H, m), 3.68-3.76 (1H, m), 5.03 (1H, m), 5.57 (1H, q, J=0.8 Hz), 7.78-6.82 (3H, m), 7.06-7.08 (3H, m), 7.18 (1H, d, J=5.6 Hz), 7.62-7.65 (1H, m), 8.10 (1H, d, J=5.6 Hz), 8.18 (1H, d, J=5.2 Hz) ppm. LCMS m/z=438.2 [M+H$^+$]

Example Z406. (S)-(2-((1-(2-Fluoropyridin-4-yl)ethyl)amino)thieno[3,2-d]pyrimidin-4-yl)(pyrrolidin-1-yl)methanone

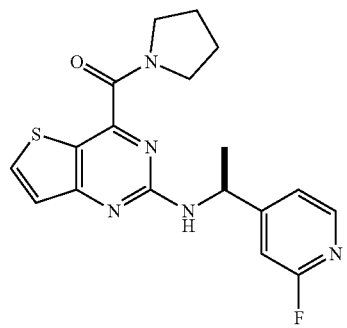

(Z406)

Synthesis of (S)-(2-((1-(2-fluoropyridin-4-yl)ethyl)amino)thieno[3,2-d]pyrimidin-4-yl)(pyrrolidin-1-yl)methanone (Z406): The title compound (Z406) was prepared from ethyl (S)-2-((1-(2-fluoropyridin-4-yl)ethyl)amino)thieno[3,2-d]pyrimidine-4-carboxylate using chemistry similar to that described in Example Z17 using pyrrolidine in place of (3R)-3-methoxypyrrolidine hydrochloride (42% yield). LCMS m/z=472.0 [M+H$^+$]

Example Z407. (2-(((S)-1-(2-Fluoropyridin-4-yl)ethyl)amino)thieno[3,2-d]pyrimidin-4-yl)((S)-3-hydroxypyrrolidin-1-yl)methanone

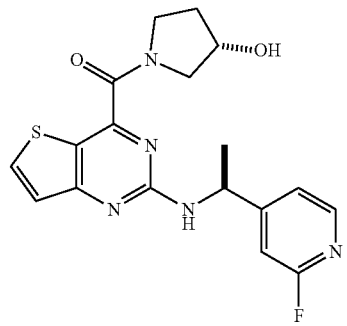

(Z407)

Synthesis of (2-(((S)-1-(2-fluoropyridin-4-yl)ethyl)amino)thieno[3,2-d]pyrimidin-4-yl)((S)-3-hydroxypyrrolidin-1-yl)methanone (Z407): The title compound (Z407) was prepared from ethyl (S)-2-((1-(2-fluoropyridin-4-yl)ethyl)amino)thieno[3,2-d]pyrimidine-4-carboxylate using chemistry similar to that described in Example Z17 using (3S)-pyrrolidin-3-ol in place of (3R)-3-methoxypyrrolidine hydrochloride (57% yield). $^1$H NMR (400 MHz, CDCl$_3$) δ 1.61 (3H, d, J=7.2 Hz), 1.91-2.01 (3H, m), 3.76 (2H, m), 3.83 (2H, d, J=9.6, 5.6 Hz), 4.52 (1H, m), 5.13 (1H, q, J=5.6 Hz), 5.45 (1H, m), 6.96 (1H, m), 7.18 (1H, dd, J=5.6, 2.4 Hz), 7.20-7.23 (1H, m), 7.97 (1H, dd, J=5.6, 0.8 Hz), 8.14 (1H, t, J=5.2 Hz) ppm. LCMS m/z=388.1 [M+H$^+$].

Example Z408. (2-(((S)-1-(2-Fluoropyridin-4-yl)ethyl)amino)thieno[3,2-d]pyrimidin-4-yl)((R)-3-hydroxypyrrolidin-1-yl)methanone

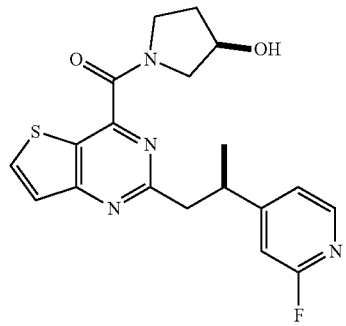 [SMILES: C[C@H](Nc1nc(C(=O)N2CC[C@@H](O)C2)c2sccc2n1)c1ccnc(F)c1]

(Z408)

Synthesis of (2-(((S)-1-(2-fluoropyridin-4-yl)ethyl)amino)thieno[3,2-d]pyrimidin-4-yl)((R)-3-hydroxypyrrolidin-1-yl)methanone (Z408): The title compound (Z408) was prepared from ethyl (S)-2-((1-(2-fluoropyridin-4-yl)ethyl)amino)thieno[3,2-d]pyrimidine-4-carboxylate using chemistry similar to that described in Example Z17 using (3R)-pyrrolidin-3-ol in place of (3R)-3-methoxypyrrolidine hydrochloride (58% yield). $^1$H NMR (400 MHz, CDCl$_3$) δ 1.62 (3H, d, J=6.8 Hz), 1.65-1.70 (1H, m), 1.92-2.10 (1H, m), 3.41-4.00 (6H, m), 5.19 (1H, q, J=6.8 Hz), 5.35 (1H, m), 6.85 (1H, d, J=1.2 Hz), 7.41-7.45 (2H, m), 8.33 (1H, t, J=3.2 Hz), 8.51 (1H, m) ppm. LCMS m/z=388.1 [M+H$^+$].

Example Z409. (S)-2-((1-(5-Fluoropyridin-3-yl)ethyl)amino)-N-(3-hydroxyphenethyl)thieno[3,2-d]pyrimidine-4-carboxamide

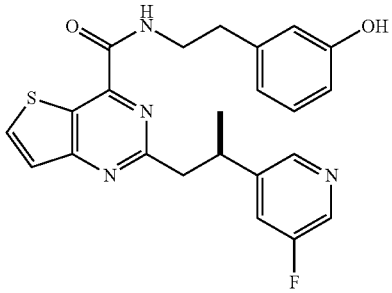

(Z409)

Synthesis of (S)-2-((1-(5-fluoropyridin-3-yl)ethyl)amino)-N-(3-hydroxyphen-ethyl)thieno[3,2-d]pyrimidine-4-carboxamide (Z409): The title compound (Z409) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using 3-(2-amino-ethyl)phenol hydrochloride (commercially obtained from LabNetwork, Shanghai, Conn.) in place of (3R)-3-methoxypyrrolidine hydrochloride (57% yield). $^1$H NMR (400 MHz, CDCl$_3$) δ 1.59 (3H, d, J=6.8 Hz), 2.82-2.92 (2H, m), 3.59-3.65 (1H, m), 3.88-3.93 (1H, m), 5.12 (1H, q, J=6.8 Hz), 5.51 (1H, d, J=6.8 Hz), 6.73-6.83 (3H, m), 7.15 (1H, d, J=5.6 Hz), 7.22 (1H, d, J=9.6 Hz), 7.25 (1H, d, J=2.0 Hz), 7.45 (1H, dt, J=9.2, 2.0 Hz), 7.68 (1H, t, J=4.4 Hz), 8.01 (1H, d, J=5.6 Hz), 8.35 (1H, d, J=3.6 Hz), 8.41 (1H, t, J=1.2 Hz) ppm. LCMS m/z=438.0 [M+H⁺].

Example Z410. (S)—N-(4-Hydroxyphenethyl)-2-((1-(pyridin-2-yl)ethyl)amino)thieno[3,2-d]pyrimidine-4-carboxamide

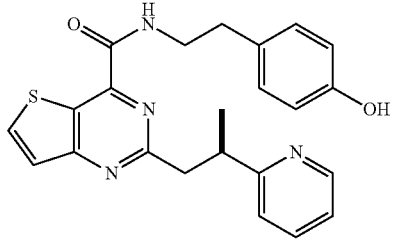

(Z410)

Synthesis of ((S)—N-(4-hydroxyphenethyl)-2-((1-(pyridin-2-yl)ethyl)amino)thieno[3,2-d]pyrimidine-4-carboxamide (Z410): The title compound (Z410) was prepared from (S)-2-((1-(pyridin-2-yl)ethyl)amino)thieno[3,2-d]pyrimidine-4-carboxylic acid di-hydrochloride using chemistry similar to that described in Example Z8 using 4-(2-aminoethyl)phenol in place of (R)-3-fluoropyrrolidine (29% yield). ¹H NMR (400 MHz, CDCl₃) δ 1.58 (3H, d, J=6.8 Hz), 2.85 (2H, t, J=6.8 Hz), 3.68 (2H, q, J=6.8 Hz), 5.21 (1H, q, J=6.8 Hz), 5.98 (1H, d, J=6.8 Hz), 6.84 (2H, dt, J=5.6, 2.0 Hz), 7.08 (2H, dt, J=5.6, 2.4 Hz), 7.18 (1H, d, J=5.6 Hz), 7.22 (1H, td, J=5.6, 1.2 Hz), 7.36 (1H, d, J=8.0 Hz), 7.68 (1H, td, J=8.0, 2.0 Hz), 7.86 (1H, m), 7.97 (1H, d, J=7.2 Hz), 8.59 (1H, dq, J=4.8, 0.8 Hz) ppm. LCMS m/z=420.2 [M+H⁺].

Example Z411. (S)-2-((1-(5-Fluoropyridin-3-yl)ethyl)amino)-N-(2-(6-methoxypyridin-2-yl)ethyl)thieno[3,2-d]pyrimidine-4-carboxamide

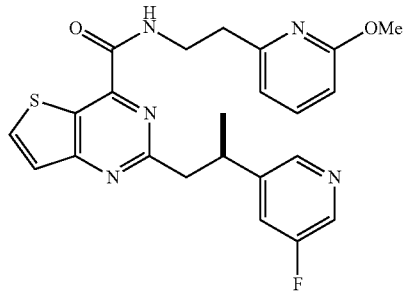 [SMILES: COc1cccc(CCNC(=O)c2nc(N[C@@H](C)c3cncc(F)c3)nc3ccsc23)n1]

(Z411)

Synthesis of (S)-2-((1-(5-fluoropyridin-3-yl)ethyl)amino)-N-(2-(6-methoxypyridin-2-yl)ethyl)thieno[3,2-d]pyrimidine-4-carboxamide (Z411): The title compound (Z411) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using 2-(6-methoxy-2-pyridyl)ethanamine di-hydrochloride (commercially obtained from Enamine, Monmouth Jct., N.J.) in place of (3R)-3-methoxypyrrolidine hydrochloride (67% yield). LCMS m/z=453.2 [M+H⁺].

Example Z412. ((S)-3-Aminopyrrolidin-1-yl)(2-(((S)-1-(5-fluoropyridin-3-yl)ethyl)amino)-6-methylthieno[3,2-d]pyrimidin-4-yl)methanone

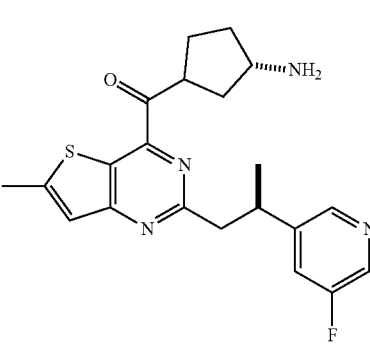

(Z412)

Synthesis of ((S)-3-aminopyrrolidin-1-yl)(2-(((S)-1-(5-fluoropyridin-3-yl)ethyl)amino)-6-methylthieno[3,2-d]pyrimidin-4-yl)methanone (Z412): The title compound (Z412) was prepared from tert-butyl ((S)-1-(2-(((S)-1-(5-fluoropyridin-3-yl)ethyl)amino)-6-methylthieno[3,2-d]pyrimidine-4-carbonyl)pyrrolidin-3-yl)carbamate using chemistry similar to that described in Example Z358 (77% yield). ¹H NMR (400 MHz, CDCl₃) δ 1.61 (3H, d, J=7.2 Hz), 1.64-1.70 (2H, m), 1.95-2.11 (1H, m), 2.59 (3H, d, J=1.2 Hz), 3.41-4.00 (6H, m), 5.19 (1H, quintet, J=7.2 Hz), 5.35 (1H, m), 6.85 (1H, d, J=1.2 Hz), 7.43 (1H, m), 8.33 (1H, t, J=3.6 Hz), 8.51 (1H, dd, J=8.0, 2.0 Hz) ppm. LCMS m/z=401.1 [M+H⁺].

Example Z413. ((R)-3-Aminopyrrolidin-1-yl)(2-(((S)-1-(5-fluoropyridin-3-yl)ethyl)amino)-6-methylthieno[3,2-d]pyrimidin-4-yl)methanone

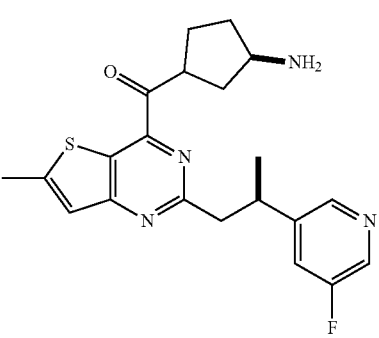 [SMILES: Cc1cc2nc(N[C@@H](C)c3cncc(F)c3)nc(C(=O)N3CC[C@@H](N)C3)c2s1]

(Z413)

Synthesis of ((R)-3-aminopyrrolidin-1-yl)(2-(((S)-1-(5-fluoropyridin-3-yl)ethyl)amino)-6-methylthieno[3,2-d]pyrimidin-4-yl)methanone (Z413): The title compound (Z413) was prepared from tert-butyl ((R)-1-(2-(((S)-1-(5-fluoropyridin-3-yl)ethyl)amino)-6-methylthieno[3,2-d]pyrimidine-4-carbonyl)pyrrolidin-3-yl)carbamate using chemistry similar to that described in Example Z358 (60% yield). ¹H NMR (400 MHz, CDCl₃) δ 1.61 (3H, d, J=7.2 Hz), 1.63-1.70 (2H, m), 1.95-2.11 (1H, m), 2.59 (3H, d, J=1.2 Hz), 3.41-4.00 (6H, m), 5.19 (1H, quintet, J=7.2 Hz), 5.35 (1H, m), 6.85 (1H, d, J=1.2 Hz), 7.43 (1H, m), 8.50 (1H, m) ppm. LCMS m/z=401.1 [M+H⁺].

Example Z414. (S)-(2-((1-(5-Fluoropyridin-3-yl)ethyl)amino)-7-methylthieno[3,2-d]pyrimidin-4-yl)(pyrrolidin-1-yl)methanone

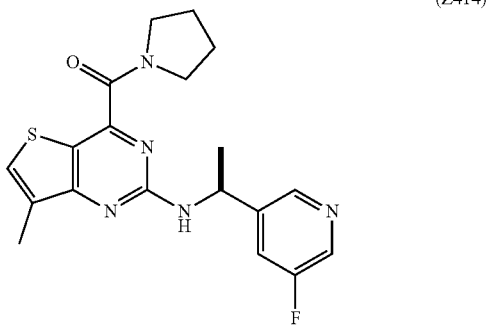

(Z414)

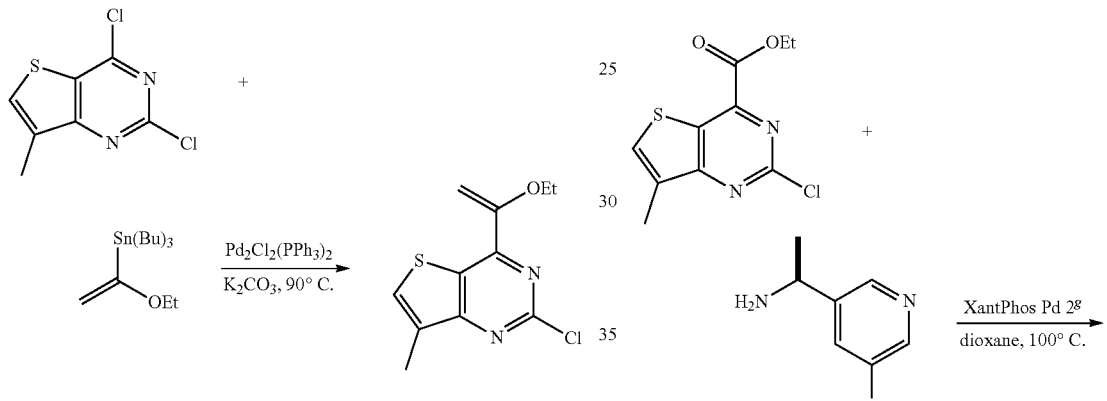

Synthesis of 2-chloro-4-(1-ethoxyvinyl)-7-methylthieno[3,2-d]pyrimidine: To a solution of 2,4-dichloro-7-methylthieno[3,2-d]pyrimidine (commercially obtained from AK Scientific, Union City, Calif.) (3.0 g, 13.7 mmol) in 1,4-dioxane (100 mL) were added tributyl(1-ethoxyethenyl)stannane (4.98 g, 13.7 mmol), PdCl$_2$(PPh$_3$)$_2$ (483 mg, 0.69 mmol) and potassium carbonate (3.81 g, 27.6 mmol) in dioxane (30 mL) and water (6 mL). The resulting solution was stirred for 2 h at 90° C. The reaction mixture was filtered and the filtrate was concentrated under reduced pressure. The residue was purified by flash chromatography on silica gel eluting with ethyl acetate/petroleum ether (1/20) to provide 2-chloro-4-(1-ethoxyvinyl)-7-methylthieno[3,2-d]pyrimidine as an off-white solid (3.2 g, 92% yield). This resulted in 3.2 g (92%) of 2-chloro-4-(1-ethoxyethenyl)-7-methylthieno[3,2-d]pyrimidine as an off-white solid. LCMS m/z=254.9 [M+H]$^+$.

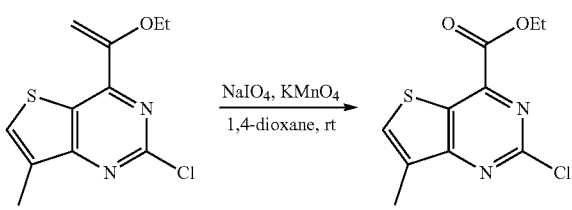

Synthesis of ethyl 2-chloro-7-methylthieno[3,2-d]pyrimidine-4-carboxylate: Sodium periodate (2.14 g, 10 mmol) was suspended in water (25 mL) and sonicated until a clear solution was obtained. This solution was added to a solution of 2-chloro-4-(1-ethoxyvinyl)-7-methylthieno[3,2-d]pyrimidine (1.27 g, 5 mmol) in 1,4-dioxane (50 mL). To the reaction mixture KMnO4 (79 mg, 0.5 mmol) was added and the reaction mixture was stirred at room temperature and progress of the reaction was checked by TLC. After 4 h, remaining starting material was detected, additional KMnO$_4$ (79 mg) was added and the reaction mixture was stirred at room temperature for additional 4 h. The mixture was adjusted to pH 7-8 with sat. aqueous K$_2$CO$_3$ solution (1-2 mL). The precipitate was filtered off and the residue was rinsed thoroughly with DCM (4×10 mL). The combined filtrates were washed with water, dried over MgSO$_4$ and concentrated in vacuo. The residue was purified by flash chromatography on silica gel (80 g, HP silica, Teledyne Isco) eluting with 0% to 30% ethyl acetate in hexanes to provide ethyl 2-chloro-7-methylthieno[3,2-d]pyrimidine-4-carboxylate as a white solid (496 mg, 39% yield). LCMS m/z=257.0 [M+H]$^+$.

Synthesis of ethyl (S)-2-((1-(5-fluoropyridin-3-yl)ethyl)amino)-7-methylthieno[3,2-d]pyrimidine-4-carboxylate: To a solution of ethyl 2-chloro-7-methylthieno[3,2-d]pyrimidine-4-carboxylate (982 mg, 3.83 mmol) in dioxane (10 mL) were added (S)-1-(5-fluoropyridin-3-yl)ethan-1-amine hydrogen chloride salt (976 mg, 4.60 mmol), 2$^{nd}$ generation Xantphos precatalyst (68.2 mg, 0.08 mmol) and Cs$_2$CO$_3$ (3.75 g, 11.50 mmol). The resulting solution was stirred for 8 h at 100° C. The precipitates were filtered out and the filtrate was extracted with ethyl acetate (3×100 mL) and the combined organic layer was concentrated in vacuo. The residue was purified by flash chromatography on silica gel eluting with ethyl acetate/petroleum ether (1/5) to provide (S)-2-((1-(5-fluoropyridin-3-yl)ethyl)amino)-7-methylthieno[3,2-d]pyrimidine-4-carboxylate as an yellow solid (720 mg, 52% yield). LCMS m/z=361.0 [M+H]$^+$.

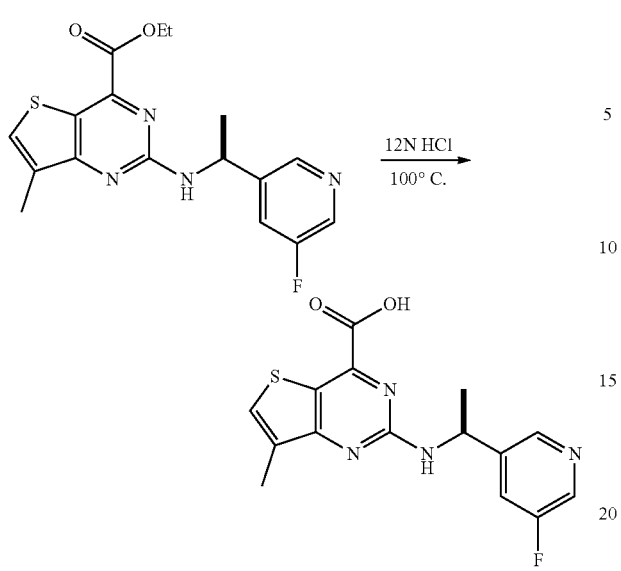

Synthesis of (S)-2-((1-(5-fluoropyridin-3-yl)ethyl)amino)-7-methylthieno[3,2-d]pyrimidine-4-carboxylic acid: A solution of (S)-2-((1-(5-fluoropyridin-3-yl)ethyl)amino)-7-methylthieno[3,2-d]pyrimidine-4-carboxylate (700 mg, 1.94 mmol) in 12N hydrogen chloride (10 mL) was stirred for 6 h at 100° C. The reaction mixture was concentrated under vacuum and the residue was dried overnight under high vacuum to provide (S)-2-((1-(5-fluoropyridin-3-yl)ethyl)amino)-7-methylthieno[3,2-d]pyrimidine-4-carboxylic acid di-hydrochloride (750 mg, 96% yield). LCMS m/z=333.0 [M+H]$^+$.

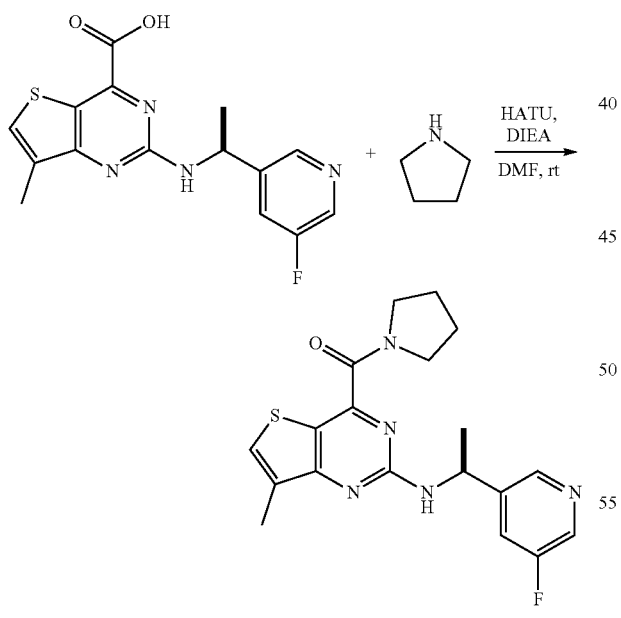

Synthesis of (S)-(2-((1-(5-fluoropyridin-3-yl)ethyl)amino)-7-methylthieno[3,2-d]pyrimidin-4-yl)(pyrrolidin-1-yl)methanone (Z414): The title compound (Z414) was prepared from (S)-2-((1-(5-fluoropyridin-3-yl)ethyl)amino)-7-methylthieno[3,2-d]pyrimidine-4-carboxylic acid di-hydrochloride (200 mg, 0.49 mmol) using chemistry similar to that described in Example Z8 using pyrrolidine in place of (R)-3-fluoropyrrolidine (62 mg, 33% yield). $^1$H NMR (400 MHz, DMSO-d$_6$) δ 1.54 (3H, d, J=6.8 Hz), 1.75-1.90 (4H, m), 2.27 (3H, s), 3.47-3.55 (2H, m), 3.70-3.92 (2H, m), 5.20 (1H, m), 7.75 (1H, m), 7.91 (1H, s), 7.96 (1H, m), 8.41 (1H, m), 8.55 (1H, m) ppm. LCMS m/z=386.3 [M+H$^+$].

Example Z415. (S)-Azetidin-1-yl(2-((1-(5-fluoropyridin-3-yl)ethyl)amino)-7-methylthieno[3,2-d]pyrimidin-4-yl)methanone (Z415)

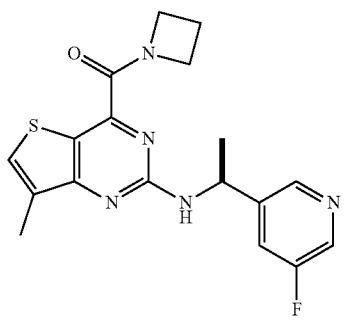 [SMILES: Cc1csc2c(C(=O)N3CCC3)nc(N[C@@H](C)c3cncc(F)c3)nc12]

Synthesis of (S)-azetidin-1-yl(2-((1-(5-fluoropyridin-3-yl)ethyl)amino)-7-methylthieno[3,2-d]pyrimidin-4-yl)methanone (Z415): The title compound (Z415) was prepared from (S)-2-((1-(5-fluoropyridin-3-yl)ethyl)amino)-7-methylthieno[3,2-d]pyrimidine-4-carboxylic acid di-hydrochloride (200 mg, 0.49 mmol) using chemistry similar to that described in Example Z8 using azetidine hydrochloride in place of (R)-3-fluoropyrrolidine (23 mg, 13% yield). $^1$H NMR (400 MHz, DMSO-d$_6$) δ 1.54 (3H, d, J=6.8 Hz), 2.26 (3H, s), 2.26-2.32 (2H, m), 4.09 (2H, t, J=7.6 Hz), 4.43 (1H, m), 4.71 (1H, m), 5.22 (1H, m), 7.77 (1H, m), 7.85-7.95 (2H, m), 8.41 (1H, m), 8.55 (1H, m) ppm. LCMS m/z=372.2 [M+H$^+$].

Example Z416. (2-(((S)-1-(5-Fluoropyridin-3-yl)ethyl)amino)-7-methylthieno[3,2-d]pyrimidin-4-yl)((S)-3-hydroxypyrrolidin-1-yl)methanone (Z416)

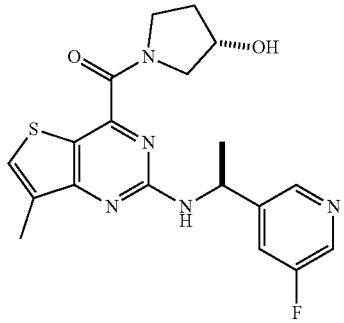 [SMILES: Cc1csc2c(C(=O)N3CC[C@H](O)C3)nc(N[C@@H](C)c3cncc(F)c3)nc12]

Synthesis of (2-(((S)-1-(5-fluoropyridin-3-yl)ethyl)amino)-7-methylthieno[3,2-d]pyrimidin-4-yl)((S)-3-hydroxypyrrolidin-1-yl)methanone (Z416): The title compound (Z416) was prepared from (S)-2-((1-(5-fluoropyridin-3-yl)ethyl)amino)-7-methylthieno[3,2-d]pyrimidine-4- carboxylic acid di-hydrochloride (200 mg, 0.49 mmol) using chemistry similar to that described in Example Z8 using (S)-pyrrolidin-3-ol in place of (R)-3-fluoropyrrolidine (83 mg, 42% yield). $^1$H NMR (400 MHz, DMSO-d$_6$) δ 1.54 (3H, d, J=6.8 Hz), 1.81-1.90 (2H, m), 2.27 (3H, s), 3.44-3.62 (2H, m), 3.62-3.95 (2H, m), 4.28 (1H, m), 5.00 (1H, m), 5.21 (1H, m), 7.76 (1H, m), 7.91 (1H, s), 7.98 (1H, br s), 8.41 (1H, m), 8.56 (1H, m) ppm. LCMS m/z=402.3 [M+H$^+$].

Example Z417. (S)-2-((1-(5-Fluoropyridin-3-yl)ethyl)amino)-N-(3-phenoxyphenethyl)thieno[3,2-d]pyrimidine-4-carboxamide

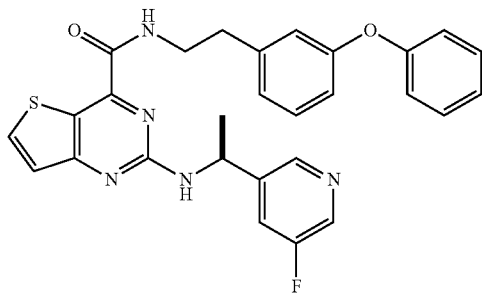 [SMILES: C[C@H](Nc1nc(C(=O)NCCc2cccc(Oc3ccccc3)c2)c2sccc2n1)c1cncc(F)c1]

(Z417)

Synthesis of (S)-2-((1-(5-fluoropyridin-3-yl)ethyl)amino)-N-(3-phenoxyphen-ethyl)thieno[3,2-d]pyrimidine-4-carboxamide (Z417): The title compound (Z417) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using 2-(3-phenoxy-phenyl)ethanamine (commercially obtained from Oakwood Chemicals, Estill, S.C.) in place of (3R)-3-methoxypyrrolidine hydrochloride (51% yield). LCMS m/z=514.3 [M+H$^+$].

Example Z418. (S)-(2-((1-(5-Fluoropyridin-3-yl)ethyl)amino)-6-methylthieno[3,2-d]pyrimidin-4-yl)(3-(methylamino)azetidin-1-yl)methanone

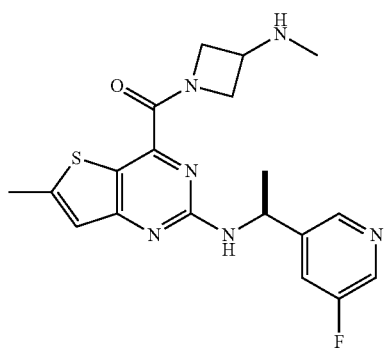 [SMILES: CNC1CN(C(=O)c2nc(N[C@@H](C)c3cncc(F)c3)nc3cc(C)sc23)C1]

(Z418)

Synthesis of (S)-(2-((1-(5-fluoropyridin-3-yl)ethyl)amino)-6-methylthieno[3,2-d]pyrimidin-4-yl)(3-(methylamino)azetidin-1-yl)methanone (Z418) was prepared from tert-butyl (S)-(1-(2-((1-(5-fluoropyridin-3-yl)ethyl)amino)-6-methylthieno[3,2-d]pyramid-ine-4-carbonyl)azetidin-3-yl)(methyl)carbamate using chemistry similar to that described in Example Z358 (85% yield). $^1$H NMR (400 MHz, CDCl$_3$) δ 1.62 (3H, d, J=6.8 Hz), 2.39-2.43 (3H, d, J=18.8 Hz), 2.60 (3H, d, J=0.8 Hz), 3.58-3.62 (1H, m), 3.87-3.90 (1H, m), 4.32-4.38 (1H, m), 4.40-4.49 (1H, m), 4.72-4.80 (1H, m), 5.20 (1H, q, J=6.4 Hz), 5.29 (1H, d, J=6.4 Hz), 6.84 (1H, d, J=1.2 Hz), 7.41 (1H, dt, J=9.2, 2.4 Hz), 8.34 (1H, dd, J=2.8, 0.8 Hz), 8.49 (1H, m) ppm. LCMS m/z=401.1 [M+H$^+$].

Example Z419. (S)-(3-(Aminomethyl)azetidin-1-yl)(2-((1-(5-fluoropyridin-3-yl)ethyl)amino)thieno[3,2-d]pyrimidin-4-yl)methanone

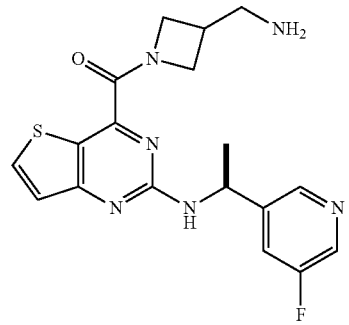 [SMILES: C[C@H](Nc1nc(C(=O)N2CC(CN)C2)c2sccc2n1)c1cncc(F)c1]

(Z419)

Synthesis of (S)-(3-(aminomethyl)azetidin-1-yl)(2-((1-(5-fluoropyridin-3-yl)ethyl)amino)thieno[3,2-d]pyrimidin-4-yl)methanone (Z419): The title compound (Z419) was prepared from tert-butyl (S)-((1-(2-((1-(5-fluoropyridin-3-yl)ethyl)amino)thieno[3,2-d]pyrim-idine-4-carbonyl)azetidin-3-yl)methyl)carbamate using chemistry similar to that described in Example Z358 (60% yield). $^1$H NMR (400 MHz, CDCl$_3$) δ 1.64 (3H, d, J=6.8 Hz), 2.68-2.71 (1H, m), 2.87-3.00 (2H, m), 3.84-3.91 (1H, m), 4.00-4.10 (1H, m), 4.28 (1H, t, J=8.8 Hz), 4.40-4.50 (1H, m), 4.73 (1H, m), 5.22 (1H, q, J=6.4 Hz), 5.39 (1H, d, J=6.4 Hz), 7.16 (1H, dd, J=6.4, 2.0 Hz), 7.44 (1H, ddd, J=9.6, 4.4, 2.0 Hz), 7.96 (1H, dd, J=5.6, 2.8 Hz), 8.34 (1H, t, J=2.0 Hz), 8.51 (1H, m) ppm. LCMS m/z=401.1 [M+H$^+$].

Example Z420. (S)-2-((1-(5-Fluoropyridin-3-yl)ethyl)amino)-N-(4-methoxyphenethyl)thieno[3,2-d]pyrimidine-4-carboxamide

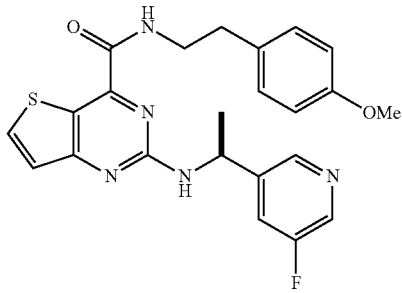 [SMILES: COc1ccc(CCNC(=O)c2nc(N[C@@H](C)c3cncc(F)c3)nc3ccsc23)cc1]

(Z420)

Synthesis of (S)-2-((1-(5-fluoropyridin-3-yl)ethyl)amino)-N-(4-methoxyphenethyl)thieno[3,2-d]pyrimidine-4-carboxamide (Z420): The title compound (Z420) was prepared from (S)-2-((1-(5-fluoropyridin-3-yl)ethyl)amino) thieno[3,2-d]pyrimidine-4-carboxylic acid di-hydrochloride using chemistry similar to that described in Example Z17 using 2-(4-methoxyphen-ethyl)ethylamine in place of (3R)-3-methoxypyrrolidine hydrochloride (45% yield). LCMS m/z=452.1 [M+H⁺].

Example Z421. (S)—N-(4-Acetamidophenethyl)-2-((1-(5-fluoropyridin-3-yl)ethyl)amino)thieno[3,2-d]pyrimidine-4-carboxamide

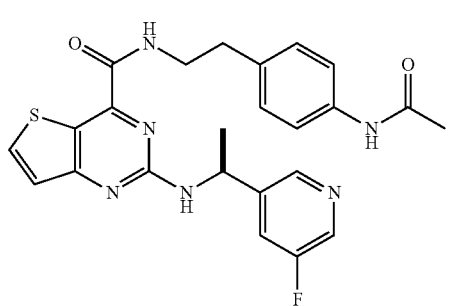 [SMILES: CC(=O)Nc1ccc(CCNC(=O)c2nc(N[C@@H](C)c3cncc(F)c3)nc3ccsc23)cc1]

(Z421)

Synthesis of (S)-2-((1-(5-fluoropyridin-3-yl) amino)-N-(4-methoxyphen-ethyl)thieno[3,2-d]pyrimidine-4-carboxamide (Z421): The title compound (Z421) was prepared from (S)-2-((1-(5-fluoropyridin-3-yl)ethyl)amino) thieno[3,2-d]pyrimidine-4-carboxylic acid di-hydrochloride using chemistry similar to that described in Example Z17 using N-[4-(2-amino-ethyl)phenyl]acetamide hydrochloride (commercially obtained from Enamine, Monmouth Jct., N.J.) in place of (3R)-3-methoxypyrrolidine hydrochloride (45% yield). ¹H NMR (400 MHz, CDCl₃) δ 1.62 (3H, d, J=5.6 Hz), 2.17 (3H, s), 2.89 (2H, t, J=5.6 Hz), 3.61-3.66 (1H, m), 3.70-3.77 (1H, m), 5.16 (1H, q, J=4.0 Hz), 5.44 (1H, d, J=6.8 Hz), 7.17 (1H, d, J=5.6 Hz), 7.19 (2H, d, J=8.4 Hz), 7.34 (1H, s), 7.40 (1H, dt, J=9.6, 2.0 Hz), 7.45 (2H, d, J=8.8 Hz), 7.65-7.75 (1H, m), 7.99 (1H, d, J=5.6 Hz), 8.33 (1H, d, J=2.4 Hz), 8.40 (1H, m) ppm. LCMS m/z=452.1 [M+H⁺].

Example Z422. (S)-2-((1-(5-Fluoropyridin-3-yl) ethyl)amino)-N-(3-(4-methoxyphenyl)propyl)thieno [3,2-d]pyrimidine-4-carboxamide

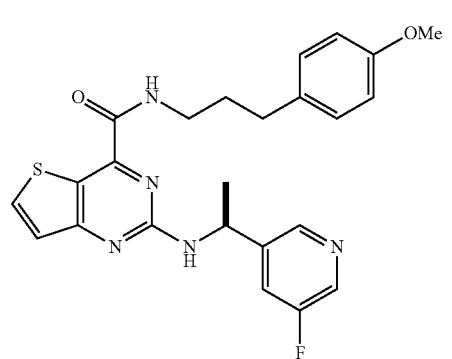 [SMILES: COc1ccc(CCCNC(=O)c2nc(N[C@@H](C)c3cncc(F)c3)nc3ccsc23)cc1]

(Z422)

Synthesis of (S)-2-((1-(5-fluoropyridin-3-yl)ethyl) amino)-N-(3-(4-methoxyphenyl)prop-yl)thieno[3,2-d]py-rimidine-4-carboxamide (Z422): The title compound (Z422) was prepared from (S)-2-((1-(5-fluoropyridin-3-yl)ethyl) amino)thieno[3,2-d]pyrimidine-4-carboxylic acid di-hydrochloride using chemistry similar to that described in Example Z17 using 3-(4-methoxy-phenyl)propan-1-amine (commercially obtained from Enamine, Monmouth Jct., N.J.) in place of (3R)-3-methoxypyrrolidine hydrochloride (70% yield). LCMS m/z=466.1 [M+H⁺].

Example Z423. Methyl (S)-4-(2-(2-((1-(5-fluoro-pyridin-3-yl)ethyl)amino)thieno[3,2-d]pyrimidine-4-carboxamido)ethyl)benzoate

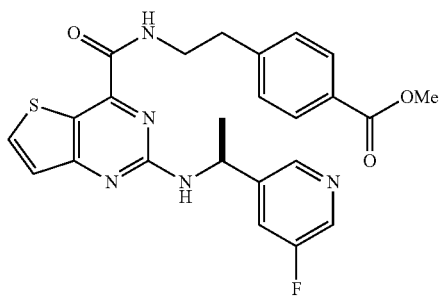 [SMILES: COC(=O)c1ccc(CCNC(=O)c2nc(N[C@@H](C)c3cncc(F)c3)nc3ccsc23)cc1]

(Z423)

Synthesis of methyl (S)-4-(2-(2-((1-(5-fluoropyridin-3-yl)ethyl)amino)thieno[3,2-d]pyrimidine-4-carboxamido) ethyl)benzoate (Z423): The title compound (Z423) was prepared from (S)-2-((1-(5-fluoropyridin-3-yl)ethyl)amino) thieno[3,2-d]pyrimidine-4-carboxylic acid di-hydrochloride using chemistry similar to that described in Example Z17 using methyl 4-(2-aminoethyl)benzoate hydrochloride (commercially obtained from J&W PharmLab, Levittown, Pa.) in place of (3R)-3-methoxypyrrolidine hydrochloride (68% yield). LCMS m/z=480.2 [M+H⁺].

Example Z424. (S)—N-(2-Cyclopentylethyl)-2-((1-(pyridin-2-yl)ethyl)amino)thieno[3,2-d]pyrimidine-4-carboxamide

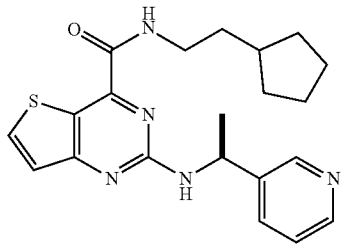

(Z424)

Synthesis of (S)—N-(2-cyclopentylethyl)-2-((1-(pyridin-2-yl)ethyl)amino)thieno[3,2-d]pyrimidine-4-carboxamide (Z424): The title compound (Z424) was prepared from (S)-2-((1-(pyridin-2-yl)ethyl)amino)thieno[3,2-d]pyrimidine-4-carboxylic acid di-hydrochloride using chemistry similar to that described in Example Z8 using 2-cyclopentylethanamine (commercially obtained from Combi Blocks, San Diego, Calif.) in place of (R)-3-fluoropyrrolidine (23% yield). LCMS m/z=396.2 [M+H⁺].

Example Z425. tert-Butyl 3-(2-(2-(((S)-1-(pyridin-2-yl)ethyl)amino)thieno[3,2-d]pyrimidine-4-carboxamido)ethyl)pyrrolidine-1-carboxylate

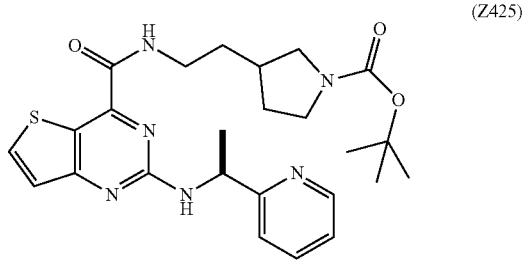

(Z425)

Synthesis of tert-butyl 3-(2-(2-(((S)-1-(pyridin-2-yl)ethyl)amino)thieno[3,2-d]pyrimidine-4-carboxamido)ethyl)pyrrolidine-1-carboxylate (Z425): The title compound (Z425) was prepared from (S)-2-((1-(pyridin-2-yl)ethyl)amino)thieno[3,2-d]pyrimidine-4-carboxylic acid di-hydrochloride using chemistry similar to that described in Example Z8 using tert-butyl 3-(2-aminoethyl)pyrrolidine-1-carboxylate (commercially obtained from Astatech, Bristol, Pa.) in place of (R)-3-fluoropyrrolidine (64% yield). LCMS m/z=497.3 [M+H$^+$].

Example Z426. tert-Butyl (S)-3-(2-(2-((1-(pyridin-2-yl)ethyl)amino)thieno[3,2-d]pyrimidine-4-carboxamido)ethyl)azetidine-1-carboxylate

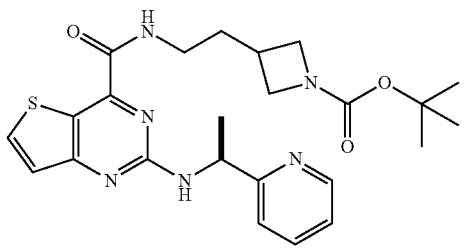 [SMILES: C[C@H](Nc1nc(C(=O)NCCC2CC(C(=O)OC(C)(C)C)C2)c2sccc2n1)c1ccccn1]

(Z426)

Synthesis of tert-butyl (S)-3-(2-(2-((1-(pyridin-2-yl)ethyl)amino)thieno[3,2-d]pyrimidine-4-carboxamido)ethyl)azetidine-1-carboxylate (Z426): The title compound (Z426) was prepared from (S)-2-((1-(pyridin-2-yl)ethyl)amino)thieno[3,2-d]pyrimidine-4-carboxylic acid di-hydrochloride using chemistry similar to that described in Example Z8 using tert-butyl 3-(2-aminoethyl)azetidine-1-carboxylate (commercially obtained from PharmaBlock, Sunnyvale, Calif.) in place of (R)-3-fluoropyrrolidine (46% yield). LCMS m/z=483.2 [M+H$^+$].

Example Z427. (S)—N-(3-Hydroxyphenethyl)-2-((1-(pyridin-3-yl)ethyl)amino)thieno[3,2-d]pyrimidine-4-carboxamide

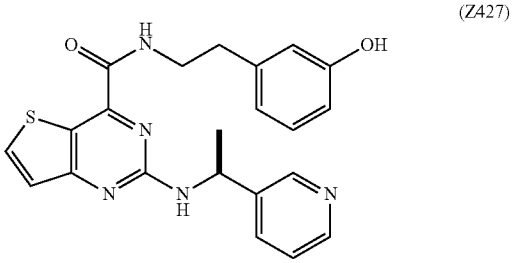

(Z427)

Synthesis of (S)—N-(3-hydroxyphenethyl)-2-((1-(pyridin-3-yl)ethyl)amino)thieno[3,2-d]pyrimidine-4-carboxamide (Z427): The title compound (Z427) was prepared from (S)-2-((1-(pyridin-3-yl)ethyl)amino)thieno[3,2-d]pyrimidine-4-carboxylic acid di-hydrochloride using chemistry similar to that described in Example Z8 using 3-(2-aminoethyl)phenol hydrochloride (commercially obtained from LabNetwork, Shanghai, Conn.) in place of (R)-3-fluoropyrrolidine (10% yield). LCMS m/z=420.2 [M+H$^+$].

Example Z428. (S)—N-(3-Hydroxyphenethyl)-2-((1-(pyridin-2-yl)ethyl)amino)thieno[3,2-d]pyrimidine-4-carboxamide (Z428)

Synthesis of (S)—N-(3-hydroxyphenethyl)-2-((1-(pyridin-2-yl)ethyl)amino)thieno[3,2-d]pyrimidine-4-carboxamide (Z428): The title compound (Z428) was prepared from (S)-2-((1-(pyridin-2-yl)ethyl)amino)thieno[3,2-d]pyrimidine-4-carboxylic acid di-hydrochloride using chemistry similar to that described in Example Z8 using 3-(2-aminoethyl)phenol hydrochloride in place of (R)-3-fluoropyrrolidine (11% yield). LCMS m/z=420.0 [M+H$^+$].

Example Z429. tert-Butyl (S)-(1-(2-((1-(5-Fluoro-pyridin-3-yl)ethyl)amino)-6-methylthieno[3,2-d]pyrimidine-4-carbonyl)azetidin-3-yl)carbamate

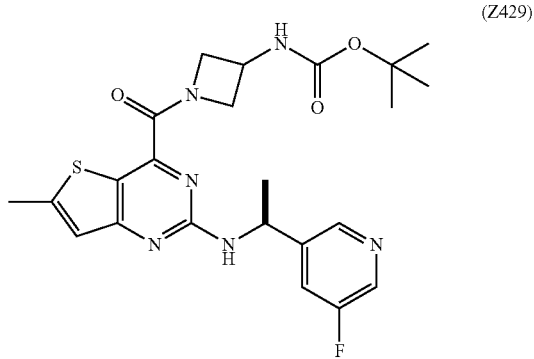

(Z429)

Synthesis of tert-butyl (S)-(1-(2-((1-(5-fluoropyridin-3-yl)ethyl)amino)-6-methylthieno[3,2-d]pyrimidine-4-carbonyl)azetidin-3-yl)carbamate (Z429): The title compound (Z429) was prepared from (S)-2-((1-(5-fluoropyridin-3-yl)ethyl)amino)-6-methylthieno[3,2-d]pyrimidine-4-carboxylic acid di-hydrochloride using chemistry similar to that described in Example Z8 using tert-butyl N-(azetidin-3-yl)carbamate (commercially obtained from CombiBlocks, San Diego, Calif.) in place of (R)-3-fluoropyrrolidine (67% yield). LCMS m/z=487.3 [M+H⁺].

Example Z430. (S)-(3-Aminoazetidin-1-yl)(2-((1-(5-fluoropyridin-3-yl)amino)-6-methylthieno[3,2-d]pyrimidin-4-yl)methanone

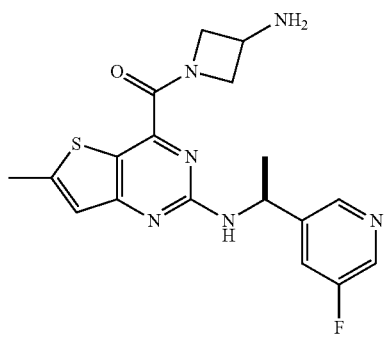 [SMILES: Cc1cc2nc(N[C@@H](C)c3cncc(F)c3)nc(C(=O)N3CC(N)C3)c2s1]

(Z430)

Synthesis of (S)-(3-aminoazetidin-1-yl)(2-((1-(5-fluoropyridin-3-yl)ethyl)amino)-6-methylthieno[3,2-d]pyrimidin-4-yl)methanone (Z430): The title compound (Z430) was prepared from tert-butyl (S)-(1-(2-((1-(5-fluoropyridin-3-yl)ethyl)amino)-6-methylthieno[3,2-d]pyramid-ine-4-carbonyl)azetidin-3-yl)carbamate using chemistry similar to that described in Example Z358 (91% yield). ¹H NMR (400 MHz, DMSO-d₆) δ 1.52 (3H, d, J=6.4 Hz), 2.54 (3H, s), 2.66-2.75 (2H, m), 3.67-3.78 (2H, m), 4.22 (1H, t, J=9.6 Hz), 4.32 (1H, q, J=1.0 Hz), 5.21 (1H, q, J=7.2 Hz), 6.92 (1H, d, J=1.2 Hz), 7.73 (1H, dt, J=10.0, 2.0 Hz), 8.07 (1H, d, J=6.0 Hz), 8.41 (1H, d, J=2.8 Hz), 8.52 (1H, s) ppm. LCMS m/z=387.2 [M+H⁺].

Example Z431. 2-(((S)-1-(Pyridin-2-yl)ethyl)amino)-N-(2-(pyrrolidin-3-yl)ethyl)thieno[3,2-d]pyrimidine-4-carboxamide

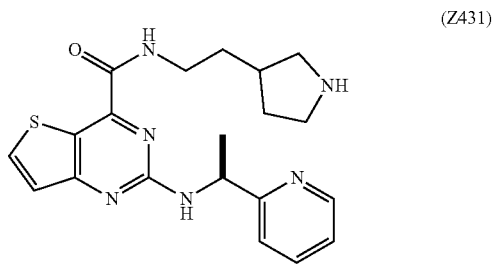

(Z431)

Synthesis of 2-(((S)-1-(pyridin-2-yl)ethyl)amino)-N-(2-(pyrrolidin-3-yl)ethyl)thieno[3,2-d]pyrimidine-4-carboxamide (Z431): The title compound (Z431) was prepared from tert-butyl 3-(2-(2-(((S)-1-(pyridin-2-yl)ethyl)amino)thieno[3,2-d]pyrimidine-4-carboxamido)ethyl)pyrrol-idine-1-carboxylate using chemistry similar to that described in Example Z358 (85% yield). ¹H NMR (400 MHz, CDCl₃) δ 1.63 (3H, d, J=6.8 Hz), 1.68-1.84 (3H, m), 2.22-2.30 (1H, m), 2.36-2.40 (1H, m), 2.92 (1H, q, J=11.2 Hz), 3.20-3.25 (1H, m), 3.36-3.45 (1H, m), 3.47-3.52 (2H, m), 5.29 (1H, m), 6.20-6.38 (1H, br s), 7.18 (1H, d, J=5.2 Hz), 7.22-7.25 (1H, m), 7.42 (1H, d, J=8.0 Hz), 7.69-7.72 (1H, m), 7.97 (1H, d, J=7.2 Hz), 8.07 (1H, m), 8.58 (1H, d, J=4.8 Hz), 9.81 (2H, br s) ppm. LCMS m/z=397.3 [M+H⁺].

Example Z432. (S)—N-(2-(Azetidin-3-yl)ethyl)-2-((1-(pyridin-2-yl)ethyl)amino)thieno[3,2-d]pyrimidine-4-carboxamide

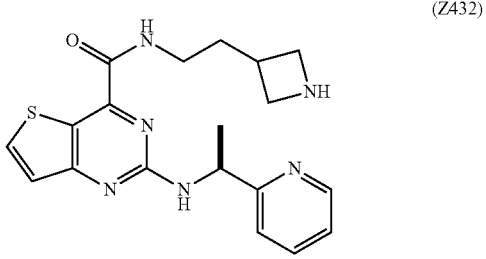

(Z432)

Synthesis of (S)—N-(2-(azetidin-3-yl)ethyl)-2-((1-(pyridin-2-yl)ethyl)amino)thieno[3,2-d]pyrimidine-4-carboxamide (Z432): The title compound (Z432) was prepared from tert-butyl (S)-3-(2-(2-((1-(pyridin-2-yl)ethyl)amino)thieno[3,2-d]pyrimidine-4-carboxamido)ethyl)azetidine-1-carboxylate using chemistry similar to that described in Example Z358 (99% yield). LCMS m/z=383.1 [M+H⁺].

Example Z433. Azetidin-1-yl(2-(((6-methoxypyridin-3-yl)methyl)amino)thieno[3,2-d]pyrimidin-4-yl)methanone

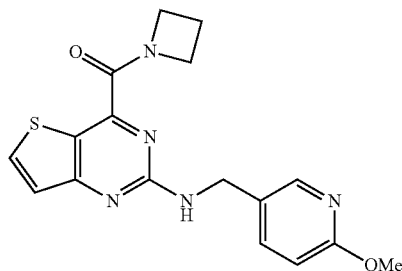

(Z433)

Synthesis of azetidin-1-yl(2-(((6-methoxypyridin-3-yl)methyl)amino)thieno[3,2-d]pyrimidin-4-yl)methanone (Z433): The title compound (Z433) was prepared from ethyl 2-(((6-methoxypyridin-3-yl)methyl)amino)thieno[3,2-d]pyrimidine-4-carboxylate using chemistry similar to that described in Example Z17 using azetidine in place of (3R)-3-methoxypyrrolidine hydrochloride (15% yield). LCMS m/z=356.1 [M+H$^+$]

Example Z434. N-Cyclobutyl-2-(((6-methoxypyridin-3-yl)methyl)amino)thieno[3,2-d]pyrimidine-4-carboxamide

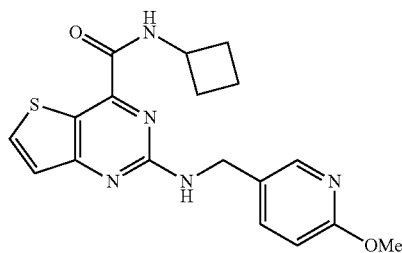 [SMILES: COc1ccc(CNc2nc(C(=O)NC3CCC3)c3sccc3n2)cn1]

(Z434)

Synthesis of N-cyclobutyl-2-(((6-methoxypyridin-3-yl)methyl)amino)thieno[3,2-d]pyrimidine-4-carboxamide (Z434): The title compound (Z434) was prepared from ethyl 2-(((6-methoxypyridin-3-yl)methyl)amino)thieno[3,2-d]pyrimidine-4-carboxylate using chemistry similar to that described in Example Z17 using cyclobutylamine in place of (3R)-3-methoxy-pyrrolidine hydrochloride (74% yield). LCMS m/z=370.1 [M+H$^+$]

Example Z435. (S)-2-((1-(4-Methoxyphenyl)ethyl)amino)-N-(pyridin-3-ylmethyl)thieno[3,2-d]pyrimidine-4-carboxamide

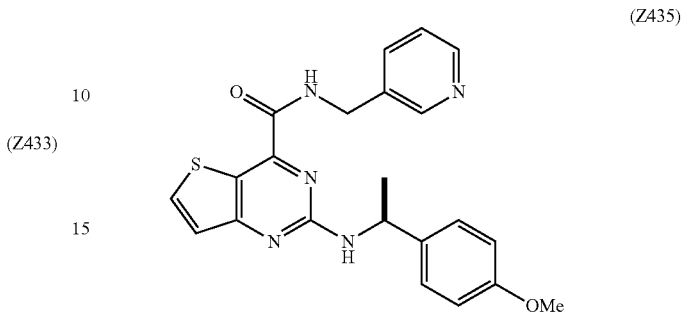

(Z435)

Synthesis of ethyl (S)-2-((1-(4-methoxyphenyl)ethyl)amino)thieno[3,2-d]pyrimidine-4-carboxylate and N—((S)-1-(4-methoxyphenyl)ethyl)-2-(((S)-1-(4-methoxyphenyl)ethyl)-amino)thieno[3,2-d]pyrimidine-4-carboxamide: The title compounds were prepared from ethyl 2-chlorothieno[3,2-d]pyrimidine-4-carboxylate (500 mg, 2.06 mmol) using chemistry similar to that described in Example Z12 using (1S)-1-(4-methoxyphenyl)ethanamine (commercially obtained from Cambridge, Cambridge, UK) in place of (6-methoxypyridin-3-yl)methanamine hydrochloride to provide ethyl (S)-2-((1-(4-methoxyphenyl)ethyl)amino)-thieno[3,2-d]pyrimidine-4-carboxylate (354 mg, 48% yield), LCMS m/z=358.1 [M+H$^+$], and N—((S)-1-(4-methoxyphenyl)ethyl)-2-(((S)-1-(4-methoxyphenyl)ethyl)amino)thieno[3,2-d]pyrimidine-4-carboxamide (235 mg, 25% yield). LCMS m/z=463.3 [M+H$^+$].

Synthesis of (S)-2-((1-(4-methoxyphenyl)ethyl)amino)thieno[3,2-d]pyrimidine-4-carboxylic acid: Ethyl (S)-2-((1-(4-methoxyphenyl)ethyl)amino)thieno[3,2-d]pyrimidine-4-carboxylate carboxylate (10 mg, 0.03 mmol) was dissolved in methanol (1 mL), then a solution of hydroxylithium hydrate (4.7 mg, 0.11 mmol) in water (0.3 mL) was added, and the resulting mixture was stirred at room temperature for 5 hours. The reaction mixture was concentrated, the residue was dissolved in methanol (0.2 mL) and passed through a silica gel (4 g HP silica, Teledyne Isco) eluting with 1% to 10% solvent A (DCM/MeOH/NH$_4$OH, 100/10/1) in DCM. The fractions containing the desired product were combined, concentrated, dissolved in water, and freeze-dried to provide (S)-2-((1-(4-methoxyphenyl)ethyl)amino)thieno[3,2-d]pyrimidine-4-carboxylic acid (8 mg, 85% yield). LCMS m/z=330.0 [M+H$^+$].

Synthesis of (S)-2-((1-(4-methoxyphenyl)ethyl)amino)-N-(pyridin-3-ylmethyl)thieno[3,2-d]pyrimidine-4-carboxamide (Z435): The title compound (Z435) was prepared from (S)-2-((1-(4-methoxyphenyl)ethyl)amino)thieno[3,2-d]pyrimidine-4-carboxylic acid using chemistry similar to that described in Example Z8 using 3-(aminomethyl)pyridine (commercially obtained from Ark Pharmaceuticals, Arlington Heights, Ill.) in place of (R)-3-fluoropyrrolidine (79% yield). LCMS m/z=420.0 [M+H$^+$]

Example Z436. 2-(((6-Methoxypyridin-3-yl)methyl)amino)-N-(pyridin-3-ylmethyl)thieno[3,2-d]pyrimidine-4-carboxamide

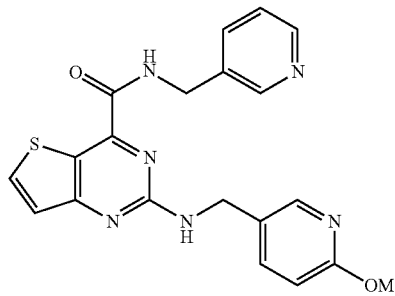

(Z436)

Synthesis of 2-(((6-methoxypyridin-3-yl)methyl)amino)-N-(pyridin-3-ylmethyl)thieno[3,2-d]pyrimidine-4-carboxamide (Z436): The title compound (Z436) was prepared from ethyl 2-(((6-methoxypyridin-3-yl)methyl)amino)thieno[3,2-d]pyrimidine-4-carboxylate using chemistry similar to that described in Example Z17 using 3-(aminomethyl)pyridine in place of (3R)-3-methoxypyrrolidine hydrochloride (63% yield). LCMS m/z=407.1 [M+H$^+$].

Example Z437. (S)—N-(3-Methoxyphenethyl)-2-((1-(pyridin-2-yl)ethyl)amino)thieno[3,2-d]pyrimidine-4-carboxamide

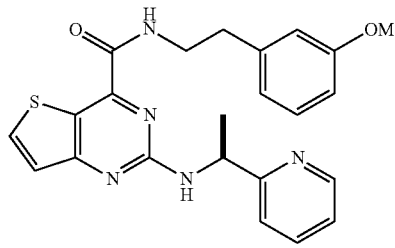

(Z437)

Synthesis of (S)—N-(3-methoxyphenethyl)-2-((1-(pyridin-2-yl)ethyl)amino)thieno[3,2-d]pyrimidine-4-carboxamide (Z437): The title compound (Z437) was prepared from (S)-2-((1-(pyridin-2-yl)ethyl)amino)thieno[3,2-d]pyrimidine-4-carboxylic acid di-hydrochloride using chemistry similar to that described in Example Z8 using 3-methoxyphenethylamine (commercially obtained from Ark Pharm, Libertyville, Ill.) in place of (R)-3-fluoropyrrolidine (41% yield). LCMS m/z=438.2 [M+H$^+$].

Example Z438. ((R)-3-Ethoxypyrrolidin-1-yl)(2-(((S)-1-(pyridin-2-yl)ethyl)amino)thieno[3,2-d]pyrimidin-4-yl)methanone

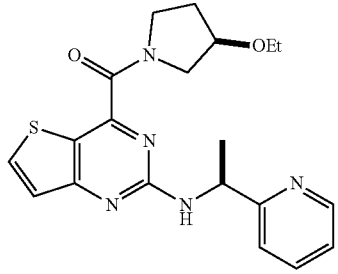

(Z438)

Synthesis of ((R)-3-ethoxypyrrolidin-1-yl)(2-(((S)-1-(pyridin-2-yl)ethyl)amino)thieno[3,2-d]pyrimidin-4-yl)methanone (Z438): The title compound (Z438) was prepared from (S)-2-((1-(pyridin-2-yl)ethyl)amino)thieno[3,2-d]pyrimidine-4-carboxylic acid di-hydrochloride using chemistry similar to that described in Example Z8 using (3R)-3-ethoxypyrrolidine (commercially obtained from J&W Pharmalab, Levittown, Pa.) in place of (R)-3-fluoropyrrolidine (53% yield). LCMS m/z=398.1 [M+H$^+$].

Example Z439. 2-(((6-Ethoxypyridin-3-yl)methyl)amino)-N-(3-hydroxyphenethyl)thieno[3,2-d]pyrimidine-4-carboxamide

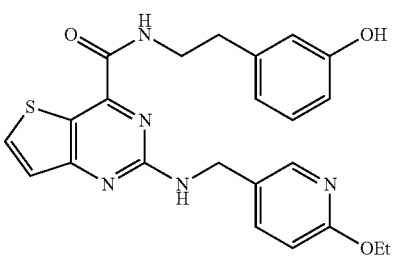 [SMILES: CCOc1ccc(CNc2nc(C(=O)NCCc3cccc(O)c3)c3sccc3n2)cn1]

(Z439)

Synthesis of ethyl 2-(((6-ethoxypyridin-3-yl)methyl)amino)thieno[3,2-d]pyrimidine-4-carboxylate: The title compound was prepared from ethyl 2-chlorothieno[3,2-d]pyrimidine-4-carboxylate (200 mg, 0.82 mmol) using chemistry similar to that described in Example Z12 using (6-ethoxy-3-pyridyl)methanamine (commercially available from Aurum Pharmatech, Franklin Park, N.J.) in place of (6-methoxypyridin-3-yl)methanamine hydrochloride (108 mg, 37% yield). LCMS m/z=359.1 [M+H$^+$].

Synthesis of 2-(((6-ethoxypyridin-3-yl)methyl)amino)-N-(3-hydroxyphenethyl)thieno[3,2-d]pyrimidine-4-carboxamide (Z439): The title compound (Z439) was prepared from ethyl 2-(((6-ethoxypyridin-3-yl)methyl)amino)thieno[3,2-d]pyrimidine-4-carboxylate using chemistry similar to that described in Example Z17 using 3-(2-aminoethyl)phenol hydrochloride in place of (3R)-3-methoxypyrrolidine hydrochloride (52% yield). LCMS m/z=450.2 [M+H$^+$].

Example Z440. ((S)-3-Methoxypyrrolidin-1-yl)(7-methyl-2-(((S)-1-(pyridin-2-yl)ethyl)amino)thieno[3,2-d]pyrimidin-4-yl)methanone

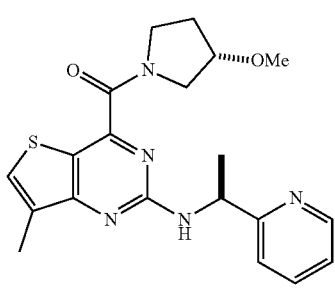 [SMILES: CO[C@H]1CCN(C(=O)c2nc(N[C@@H](C)c3ccccn3)nc3c(C)csc23)C1]

(Z440)

Synthesis of ethyl (S)-7-methyl-2-((1-(pyridin-2-yl)ethyl)amino)thieno[3,2-d]pyrimidine-4-carboxylate: To a solution of ethyl 2-chloro-7-methylthieno[3,2-d]pyrimidine-4-carboxylate (465 mg, 1.8 mmol) in NMP (7.25 mL) was added (1S)-1-(2-pyridyl)ethanamine (544 uL, 4.53 mmol). The reaction mixture was stirred at 130° C. for 5 h. The reaction mixture was diluted with ethyl acetate and washed with 25% NaCl aqueous solution three times and dried. The solvent was evaporated and the residue was purified by flash chromatography (40 g, HP silica, Teledyne Isco) eluting with 10% to 50% solvent A (DCM/MeOH/NH$_4$OH, 100/10/1) in DCM to provide ethyl (S)-7-methyl-2-((1-(pyridin-2-yl)ethyl)amino)thieno[3,2-d]pyrimidine-4-carboxylate as a light yellow solid (266 mg, 43% yield). $^1$H NMR (400 Hz, CDCl$_3$) δ 1.49 (3H, t, J=7.2 Hz), 1.63 (3H, d, J=6.8 Hz), 2.31 (3H, s), 4.54 (2H, q, J=7.2 Hz), 5.37 (1H, m), 6.29 (1H, d, J=7.6 Hz), 7.14 (1H, ddd, J=7.6, 5.2, 1.2 Hz), 7.38 (1H, d, J=7.6 Hz), 7.53 (1H, dd, J=2.4, 1.2 Hz), 7.61 (1H, td, J=7.6, 2.4 Hz), 7.58 (1H, m) ppm. LCMS m/z=343.1 [M+H$^+$].

Synthesis of (S)-7-methyl-2-((1-(pyridin-2-yl)ethyl)amino)thieno[3,2-d]pyrimidine-4-carboxylic acid: Ethyl (S)-7-methyl-2-((1-(pyridin-2-yl)ethyl)amino)thieno[3,2-d]pyrimidine-4-carboxylate (265 mg, 0.77 mmol) was dissolved in 6 N HCl (3.8 mL) and stirred at 100° C. for 4 h and LCMS indicated completion of the reaction. The reaction mixture was evaporated to dryness in vacuo at a bath temperature of 60° C. and the residue was dried under high vacuum to provide (S)-7-methyl-2-((1-(pyridin-2-yl)ethyl)amino)thieno[3,2-d]pyrimidine-4-carboxylic acid di-hydrochloride salt as an yellow solid (300 mg, 100% yield). LCMS m/z=315.0 [M+H$^+$].

Synthesis of ((S)-3-methoxypyrrolidin-1-yl)(7-methyl-2-(((S)-1-(pyridin-2-yl)ethyl)amino)thieno[3,2-d]pyrimidin-4-yl)methanone (Z440): The title compound (Z440) was prepared from (S)-7-methyl-2-((1-(pyridin-2-yl)ethyl)amino)thieno[3,2-d]pyrimidine-4-carboxylic acid di-hydrochloride (39 mg, 0.10 mmol) using chemistry similar to that described in Example Z8 using (S)-3-methoxypyrrolidine in place of (R)-3-fluoropyrrolidine (32 mg, 80% yield). $^1$H NMR (400 MHz, CDCl$_3$) δ 1.63 (3H, d, J=6.8 Hz), 1.87 (1H, m), 2.06 (1H, m), 2.36 (3H, d, J=1.6 Hz), 3.28 (3H, s), 3.68-3.75 (2H, m), 3.79-3.87 (2H, m), 3.96 (1H, m), 5.26 (1H, m), 5.95 (1H, m), 7.15 (1H, m), 7.38 (1H, dd, J=11.2, 8.0 Hz), 7.55 (1H, m), 7.62 (1H, m), 8.57 (1H, m) ppm. LCMS m/z=398.1 [M+H$^+$].

Example Z441. ((R)-3-Methoxypyrrolidin-1-yl)(7-methyl-2-(((S)-1-(pyridin-2-yl)ethyl)amino)thieno[3,2-d]pyrimidin-4-yl)methanone

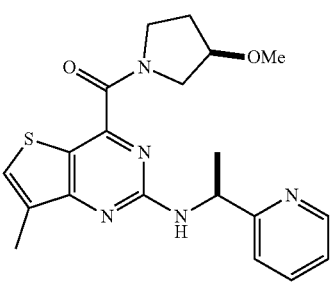 [SMILES: CO[C@@H]1CCN(C(=O)c2nc(N[C@@H](C)c3ccccn3)nc3c(C)csc23)C1]

(Z441)

Synthesis of ((R)-3-methoxypyrrolidin-1-yl)(7-methyl-2-(((S)-1-(pyridin-2-yl)ethyl)amino)thieno[3,2-d]pyrimidin-4-yl)methanone (Z441): The title compound (Z441) was prepared from (S)-7-methyl-2-((1-(pyridin-2-yl)ethyl)amino)thieno[3,2-d]pyrimidine-4-carboxylic acid di-hydrochloride (39 mg, 0.10 mmol) using chemistry similar to that described in Example Z8 using (R)-3-methoxypyrrolidine in place of (R)-3-fluoropyrrolidine (32 mg, 81% yield). $^1$H NMR (400 MHz, CDCl$_3$) δ 1.63 (3H, d, J=6.8 Hz), 1.93 (1H, m), 2.05 (1H, m), 2.36 (3H, s), 3.34 (3H, s), 3.67-3.88 (3H, m), 3.98 (1H, m), 4.17 (1H, m), 5.26 (1H, m), 5.98 (1H, d, J=6.8 Hz), 7.15 (1H, m), 7.37 (1H, dd, J=8.0, 3.2 Hz), 7.54 (1H, m), 7.62 (1H, m), 8.57 (1H, m) ppm. LCMS m/z=398.1 [M+H$^+$].

Example Z442. ((S)-3-Ethoxypyrrolidin-1-yl)(2-(((S)-1-(pyridin-2-yl)ethyl)amino)thieno[3,2-d]pyrimidin-4-yl)methanone

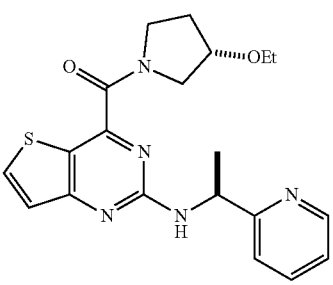 [SMILES: CCO[C@H]1CCN(C(=O)c2nc(N[C@@H](C)c3ccccn3)nc3ccsc23)C1]

(Z442)

Synthesis of ((S)-3-ethoxypyrrolidin-1-yl)(2-(((S)-1-(pyridin-2-yl)ethyl)amino)thieno[3,2-d]pyrimidin-4-yl)methanone (Z442): The title compound (Z442) was prepared from (S)-2-((1-(pyridin-2-yl)ethyl)amino)thieno[3,2-d]pyrimidine-4-carboxylic acid di-hydrochloride using chemistry similar to that described in Example Z8 using (3S)-3-ethoxypyrrolidine (commercially obtained from PharmaBlock, Sunnyvale, Calif.) in place of (R)-3-fluoropyrrolidine (61% yield). LCMS m/z=398.1 [M+H$^+$].

Example Z443. (S)—N-Benzyl-7-methyl-2-((1-(pyridin-2-yl)ethyl)amino)thieno[3,2-d]pyrimidine-4-carboxamide

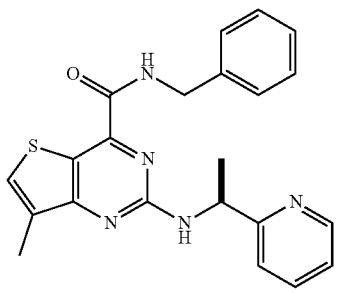

(Z443)

Synthesis of (S)—N-benzyl-7-methyl-2-((1-(pyridin-2-yl)ethyl)amino)thieno[3,2-d]pyrimidine-4-carboxamide (Z443): The title compound (Z443) was prepared from (S)-7-methyl-2-((1-(pyridin-2-yl)ethyl)amino)thieno[3,2-d]pyrimidine-4-carboxylic acid di-hydrochloride (39 mg, 0.10 mmol) using chemistry similar to that described in Example Z8 using benzylamine in place of (R)-3-fluoropyrrolidine (33 mg, 83% yield). $^1$H NMR (400 MHz, CDCl$_3$) δ 1.60 (3H, d, J=7.2 Hz), 2.35 (3H, d, J=1.2 Hz), 4.57 (1H, dd, J=15.2, 5.6 Hz), 4.71 (1H, dd, J=15.2, 6.8 Hz), 5.20 (1H, m), 6.02 (1H, m), 7.05 (1H, m), 7.30-7.39 (6H, m), 7.54 (1H, m), 7.60 (1H, d, J=1.2 Hz), 8.14 (1H, m), 8.37 (1H, m) ppm. LCMS m/z=404.1 [M+H$^+$].

Example Z444. (S)—N-(3-Methoxyphenethyl)-7-methyl-2-((1-(pyridin-2-yl)ethyl)amino)thieno[3,2-d]pyrimidine-4-carboxamide

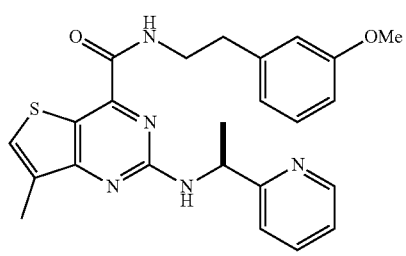 [SMILES: COc1cccc(CCNC(=O)c2nc(N[C@@H](C)c3ccccn3)nc3c(C)csc23)c1]

(Z444)

Synthesis of (S)—N-(3-methoxyphenethyl)-7-methyl-2-((1-(pyridin-2-yl)ethyl)amino)thieno[3,2-d]pyrimidine-4-carboxamide (Z444): The title compound (Z444) was prepared from (S)-7-methyl-2-((1-(pyridin-2-yl)ethyl)amino)thieno[3,2-d]pyrimidine-4-carboxylic acid di-hydrochloride (39 mg, 0.10 mmol) using chemistry similar to that described in Example Z8 using 2-(3-methoxyphenyl)ethan-1-amine in place of (R)-3-fluoropyrrolidine (40 mg, 89% yield). $^1$H NMR (400 MHz, CDCl$_3$) δ 1.61 (3H, d, J=6.8 Hz), 2.34 (3H, d, J=1.2 Hz), 2.91 (2H, t, J=6.8 Hz), 3.67-3.74 (2H, m), 3.80 (3H, s), 5.20 (1H, m), 6.07 (1H, d, J=6.4 Hz), 6.81 (1H, dd, J=8.0, 2.0 Hz), 6.82 (1H, s), 6.86 (1H, d, J=8.0 Hz), 7.15 (1H, ddd, J=8.0, 4.8, 1.2 Hz), 7.26 (1H, m), 7.30 (1H, d, J=8.0 Hz), 7.59 (1H, d, J=1.2 Hz), 7.61 (1H, td, J=8.0, 2.0 Hz), 7.99 (1H, m), 8.56 (1H, m) ppm. LCMS m/z=448.2 [M+H$^+$].

Example Z445. (S)—N-(3-Cyanophenethyl)-2-((1-(5-fluoropyridin-3-yl)ethyl)amino)thieno[3,2-d]pyrimidine-4-carboxamide

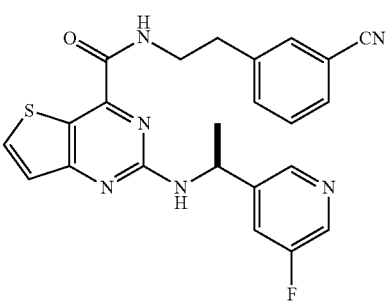

(Z445)

Synthesis of (S)—N-(3-cyanophenethyl)-2-((1-(5-fluoropyridin-3-yl)ethyl)amino)thieno[3,2-d]pyrimidine-4-carboxamide (Z445): The title compound (Z445) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using methyl 3-(2-aminoethyl)benzo-nitrile (commercially obtained from Enamine, Monmouth Jct., N.J.) in place of (3R)-3-methoxypyrrolidine hydrochloride (67% yield). LCMS m/z=447.2 [M+H$^+$].

Example Z446. (S)—N-((1-Phenethylpiperidin-4-yl)methyl)-2-((1-(pyridin-2-yl)ethyl)amino)thieno[3,2-d]pyrimidine-4-carboxamide

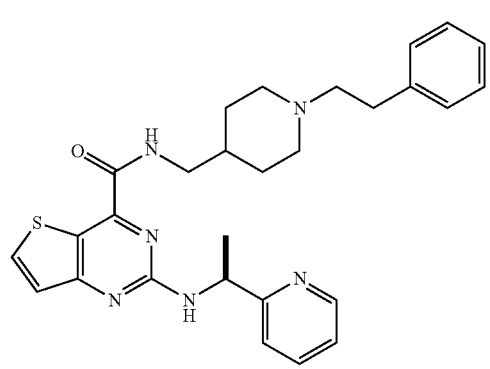 [SMILES: C[C@H](Nc1nc(C(=O)NCC2CCN(CCc3ccccc3)CC2)c2sccc2n1)c1ccccn1]

(Z446)

Synthesis of (S)—N-((1-phenethylpiperidin-4-yl)methyl)-2-((1-(pyridin-2-yl)ethyl)amino)thieno[3,2-d]pyrimidine-4-carboxamide (Z446): The title compound (Z446) was prepared from (S)-2-((1-(pyridin-2-yl)ethyl)amino)thieno[3,2-d]pyrimidine-4-carboxylic acid di-hydrochloride using chemistry similar to that described in Example Z8 using [1-(2-phenylethyl)-4-piperidyl]methanamine (commercially obtained from ChemBridge, San Diego, Calif.) in place of (R)-3-fluoropyrrolidine (70% yield). LCMS m/z=501.2 [M+H$^+$].

Example Z447. (S)—N-(3-Hydroxyphenethyl)-7-methyl-2-((1-(pyridin-2-yl)ethyl)amino)thieno[3,2-d]pyrimidine-4-carboxamide

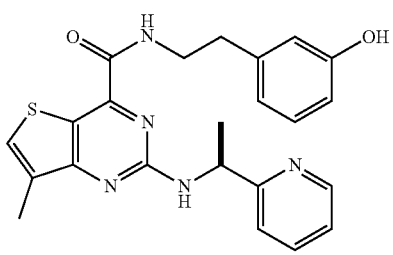

(Z447)

Synthesis of (S)—N-(3-hydroxyphenethyl)-7-methyl-2-((1-(pyridin-2-yl)ethyl)amino)thieno[3,2-d]pyrimidine-4-carboxamide (Z447): The title compound (Z447) was prepared from (S)-7-methyl-2-((1-(pyridin-2-yl)ethyl)amino)thieno[3,2-d]pyrimidine-4-carboxylic acid di-hydrochloride (39 mg, 0.10 mmol) using chemistry similar to that described in Example Z8 using 3-(2-aminoethyl)phenol in place of (R)-3-fluoropyrrolidine (13 mg, 30% yield). $^1$H NMR (400 MHz, CDCl$_3$) δ 1.66 (3H, d, J=7.2 Hz), 2.38 (3H, d, J=1.2 Hz), 2.48 (1H, m), 2.96 (1H, dt, J=14.0, 3.6 Hz), 3.91 (1H, m), 4.03 (1H, m), 5.38 (1H, quintet, J=7.2 Hz), 5.63 (1H, d, J=7.2 Hz), 6.71-6.74 (2H, m), 6.88 (1H, m), 7.29 (1H, d, J=8.0 Hz), 7.31 (1H, ddd, J=8.0, 4.8, 2.0 Hz), 7.50 (1H, d, J=8.0 Hz), 7.63 (1H, d, J=1.2 Hz), 7.50 (1H, d, J=8.0 Hz), 7.63 (1H, d, J=1.2 Hz), 7.74 (1H, td, J=8.0, 2.0 Hz), 7.81 (1H, m), 8.84 (1H, m), 11.60 (1H, br s) ppm. LCMS m/z=434.1 [M+H$^+$].

Example Z448. (S)-2-((1-(5-Fluoropyridin-3-yl)ethyl)amino)-N-2-hydroxyphenethyl)thieno[3,2-d]pyrimidine-4-carboxamide

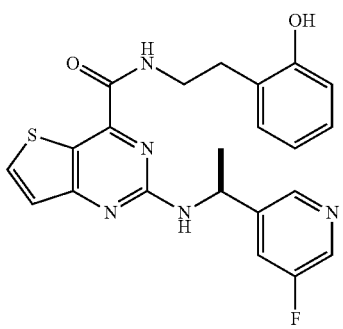 [SMILES: C[C@H](Nc1nc(C(=O)NCCc2ccccc2O)c2sccc2n1)c1cncc(F)c1]

(Z448)

Synthesis of (S)-2-((1-(5-fluoropyridin-3-yl)ethyl)amino)-N-(2-hydroxyphen-ethyl)thieno[3,2-d]pyrimidine-4-carboxamide (Z448): The title compound (Z448) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using 2-(2-amino-ethyl)phenol (commercially obtained from Enamine, Monmouth Jct., N.J.) in place of (3R)-3-methoxypyrrolidine hydrochloride (67% yield). $^1$H NMR (400 MHz, CDCl$_3$) δ 1.62 (3H, d, J=6.8 Hz), 2.88-2.96 (1H, t, J=5.6 Hz), 2.98-3.05 (1H, m), 3.68-3.73 (2H, m), 5.11 (1H, q, J=4.0 Hz), 5.56 (1H, d, J=5.6 Hz), 6.85-6.91 (2H, m), 7.13 (2H, d, J=7.6 Hz), 7.17 (1H, d, J=5.6 Hz), 7.40 (1H, dt, J=9.6, 2.0 Hz), 7.89-7.93 (1H, m), 8.01 (1H, d, J=6.4 Hz), 8.35 (1H, dd, J=7.6, 2.8 Hz), 8.38 (1H, s), 8.71 (1H, dd, J=4.4, 1.6 Hz) ppm. LCMS m/z=447.2 [M+H$^+$].

Example Z449. (S)—N-((2-Methoxypyridin-3-yl)methyl)-2-((1-(pyridin-2-yl)ethyl)amino)thieno[3,2-d]pyrimidine-4-carboxamide

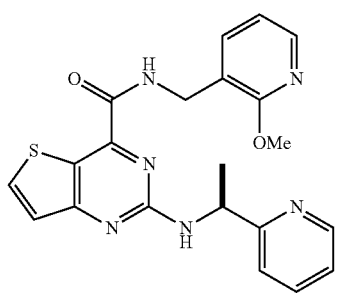 [SMILES: COc1ncccc1CNC(=O)c1nc(N[C@@H](C)c2ccccn2)nc2ccsc12]

(Z449)

Synthesis of (S)—N-((2-methoxypyridin-3-yl)methyl)-2-((1-(pyridin-2-yl)ethyl)amino)thieno[3,2-d]pyrimidine-4-carboxamide (Z449): The title compound (Z449) was prepared from (S)-2-((1-(pyridin-2-yl)ethyl)amino)thieno[3,2-d]pyrimidine-4-carboxylic acid di-hydrochloride using chemistry similar to that described in Example Z8 using (2-methoxy-3-pyridyl)methanamine (commercially obtained from Enamine, Monmouth Jct., N.J.) in place of (R)-3-fluoropyrrolidine (56% yield). LCMS m/z=421.2 [M+H$^+$].

Example Z450. (S)—N-((6-Methoxypyridin-2-yl)methyl)-7-methyl-2-((1-(pyridin-2-yl)ethyl)amino)thieno[3,2-d]pyrimidine-4-carboxamide

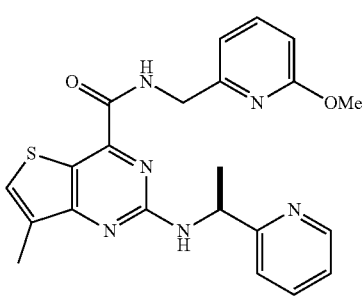 [SMILES: COc1cccc(CNC(=O)c2nc(N[C@@H](C)c3ccccn3)nc3c(C)csc23)n1]

(Z450)

Synthesis of (S)—N-((6-methoxypyridin-2-yl)methyl)-7-methyl-2-((1-(pyridin-2-yl)ethyl)amino)thieno[3,2-d]pyrimidine-4-carboxamide (Z450): The title compound (Z450) was prepared from (S)-7-methyl-2-((1-(pyridin-2-yl)ethyl)amino)thieno[3,2-d]pyrimidine-4-carboxylic acid di-hydrochloride (39 mg, 0.10 mmol) using chemistry similar to that described in Example Z8 using (6-methoxypyridin-2-yl)methanamine in place of (R)-3-fluoropyrrolidine (35 mg, 81% yield). $^1$H NMR (400 MHz, CDCl$_3$) δ 1.63 (3H, d, J=6.8 Hz), 2.36 (3H, d, J=1.2 Hz), 4.01 (3H, s), 4.64-4.74 (2H, m), 5.30 (1H, quintet, J=6.8 Hz), 6.15 (1H, d, J=6.8 Hz), 6.68 (1H, d, J=8.0 Hz), 6.85 (1H, d, J=7.2 Hz), 7.12

(1H, dd, J=6.8, 4.8 Hz), 7.36 (1H, d, J=8.0 Hz), 7.55 (1H, d, J=8.0, 6.8 Hz), 7.58-7.62 (2H, m), 8.50 (1H, d, J=4.0 Hz), 8.71 (1H, br s) ppm. LCMS m/z=435.2 [M+H⁺].

Example Z451. (S)-7-Methyl-2-((1-(pyridin-2-yl)ethyl)amino)-N-(pyridin-2-ylmethyl)thieno[3,2-d]pyrimidine-4-carboxamide

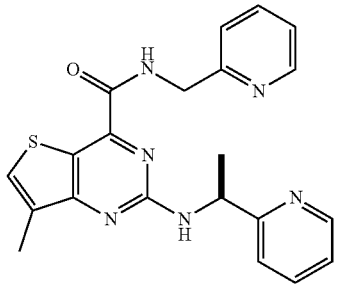

(Z451)

Synthesis of (S)-7-methyl-2-((1-(pyridin-2-yl)ethyl)amino)-N-(pyridin-2-ylmethyl)thieno[3,2-d]pyrimidine-4-carboxamide (Z451): The title compound (Z451) was prepared from (S)-7-methyl-2-((1-(pyridin-2-yl)ethyl)amino)thieno[3,2-d]pyrimidine-4-carboxylic acid di-hydrochloride (39 mg, 0.10 mmol) using chemistry similar to that described in Example Z8 using pyridin-2-ylmethanamine in place of (R)-3-fluoropyrrolidine (27 mg, 67% yield). ¹H NMR (400 MHz, CDCl₃) δ 1.64 (3H, d, J=6.8 Hz), 2.35 (3H, d, J=1.2 Hz), 4.78-4.80 (2H, m), 5.31 (1H, quintet, J=6.8 Hz), 6.13 (1H, d, J=6.8 Hz), 7.12 (1H, m), 7.24 (2H, m), 7.31 (1H, d, J=8.0 Hz), 7.41 (1H, d, J=8.0 Hz), 7.58-7.62 (2H, m), 7.68 (1H, td, J=8.0, 2.0 Hz), 8.52 (1H, d, J=4.4 Hz), 8.63 (1H, m), 8.81 (1H, m) ppm. LCMS m/z=405.2 [M+H⁺].

Example Z452. (S)-4-(2-(2-((1-(5-Fluoropyridin-3-yl)ethyl)amino)thieno[3,2-d]pyrimidine-4-carboxamido)ethyl)benzoic acid

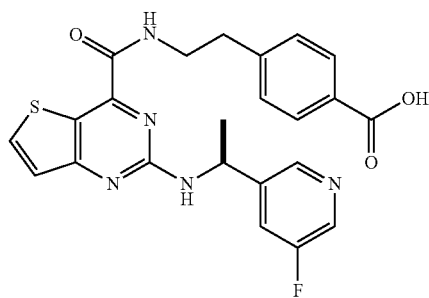 [SMILES: C[C@H](Nc1nc(C(=O)NCCc2ccc(C(=O)O)cc2)c2sccc2n1)c1cncc(F)c1]

(Z452)

Synthesis of (S)-4-(2-(2-((1-(5-fluoropyridin-3-yl)ethyl)amino)thieno[3,2-d]pyrimidine-4-carboxamido)ethyl)benzoic acid (Z452): The title compound (Z452) was prepared from methyl (S)-4-(2-(2-((1-(5-fluoropyridin-3-yl)ethyl)amino)thieno[3,2-d]pyrimidine-4-carboxamido)-ethyl)benzoate using chemistry similar to that described in Example Z435 (62% yield). LCMS m/z=466.1 [M+H⁺].

Example Z453. Azetidin-1-yl(2-(((6-ethoxypyridin-3-yl)methyl)amino)thieno[3,2-d]pyrimidin-4-yl)methanone

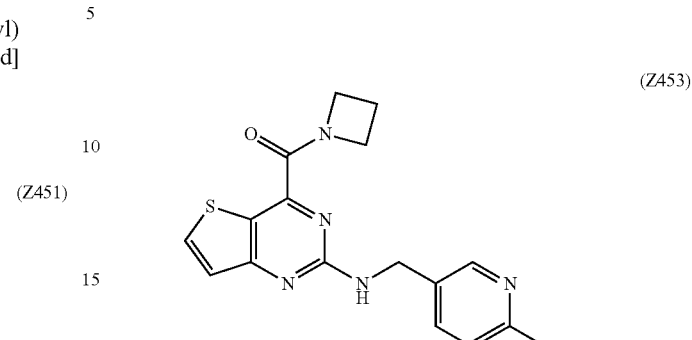

(Z453)

Synthesis of azetidin-1-yl(2-(((6-ethoxypyridin-3-yl)methyl)amino)thieno[3,2-d]pyrimidin-4-yl)methanone (Z453): The title compound (Z453) was prepared from ethyl 2-(((6-ethoxypyridin-3-yl)methyl)amino)thieno[3,2-d]pyrimidine-4-carboxylate using chemistry similar to that described in Example Z17 using azetidine in place of (3R)-3-methoxypyrrolidine hydrochloride (8% yield). LCMS m/z=370.1 [M+H⁺].

Example Z454. (S)-2-((1-(5-Fluoropyridin-3-yl)ethyl)amino)-N-(4-sulfamoylphenethyl)thieno[3,2-d]pyrimidine-4-carboxamide

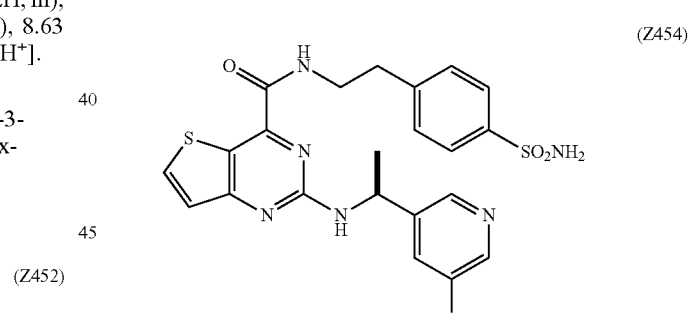

(Z454)

Synthesis of (S)-2-((1-(5-fluoropyridin-3-yl)ethyl)amino)-N-(4-sulfamoylphen-ethyl)thieno[3,2-d]pyrimidine-4-carboxamide (Z454): The title compound (Z454) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using 4-(2-aminoethyl)benzenesulfonamide (commercially obtained from AK Scientific, Union City, Calif.) in place of (3R)-3-methoxypyrrolidine hydrochloride (37% yield). ¹H NMR (400 MHz, CDCl₃) δ 1.62 (3H, d, J=6.8 Hz), 2.98-3.05 (2H, m), 3.71-3.77 (2H, m), 5.15 (1H, q, J=6.4 Hz), 5.34 (2H, br s), 5.43 (1H, d, J=6.4 Hz), 7.17 (1H, d, J=6.4 Hz), 7.35 (2H, d, J=8.4 Hz), 7.40 (1H, dt, J=9.2, 2.0 Hz), 7.64-7.66 (1H, m), 7.87 (2H, dt, J=8.4, 2.0 Hz), 8.04 (1H, d, J=5.2 Hz), 8.30 (1H, s), 8.34 (1H, d, J=2.0 Hz) ppm. LCMS m/z=501.0 [M+H⁺].

Example Z455. (S)-2-((1-(5-Fluoropyridin-3-yl)ethyl)amino)-N-(4-(methylsulfonyl)phenethyl)thieno[3,2-d]pyrimidine-4-carboxamide

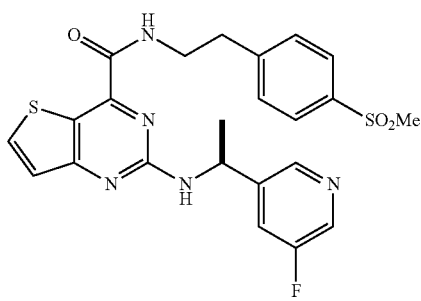 [SMILES: C[C@H](Nc1nc(C(=O)NCCc2ccc(S(C)(=O)=O)cc2)c2sccc2n1)c1cncc(F)c1]
(Z455)

Synthesis of (S)-2-((1-(5-fluoropyridin-3-yl)ethyl)amino)-N-(4-(methylsulfonyl)phen-ethyl)thieno[3,2-d]pyrimidine-4-carboxamide (Z455): The title compound (Z455) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using 2-(4-methyl-sulfonylphenyl)ethanamine (commercially obtained from Enamine, Monmouth Jct., N.J.) in place of (3R)-3-methoxypyrrolidine hydrochloride (58% yield). LCMS m/z=500.1 [M+H⁺].

Example Z456. (S)—N-Cyclobutyl-7-methyl-2-((1-(pyridin-2-yl)ethyl)amino)thieno[3,2-d]pyrimidine-4-carboxamide

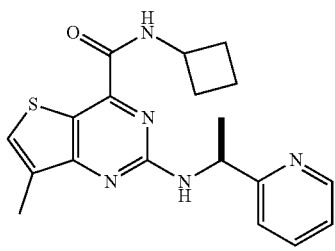
(Z456)

Synthesis of (S)—N-cyclobutyl-7-methyl-2-((1-(pyridin-2-yl)ethyl)amino)thieno[3,2-d]pyrimidine-4-carboxamide (Z456): The title compound (Z456) was prepared from (S)-7-methyl-2-((1-(pyridin-2-yl)ethyl)amino)thieno[3,2-d]pyrimidine-4-carboxylic acid di-hydrochloride (39 mg, 0.10 mmol) using chemistry similar to that described in Example Z8 using cyclobutanamine in place of (R)-3-fluoropyrrolidine (20 mg, 73% yield). $^1$H NMR (400 MHz, CDCl$_3$) δ 1.64 (3H, d, J=6.8 Hz), 1.75-1.84 (2H, m), 1.97-2.09 (2H, m), 2.35 (3H, d, J=1.2 Hz), 2.35-2.45 (2H, m), 4.53 (1H, m), 5.25 (1H, m), 6.03 (1H, m), 7.17 (1H, ddd, J=8.0, 4.8, 1.2 Hz), 7.40 (1H, d, J=8.0 Hz), 7.58 (1H, d, J=1.2 Hz), 7.64 (1H, td, J=8.0, 2.0 Hz), 7.96 (1H, m), 8.60 (1H, m) ppm. LCMS m/z=368.1 [M+H⁺].

Example Z457. (S)-6-Methyl-N-(pyridin-2-ylmethyl)-2-((1-(pyridin-3-yl)ethyl)amino)thieno[3,2-d]pyrimidine-4-carboxamide

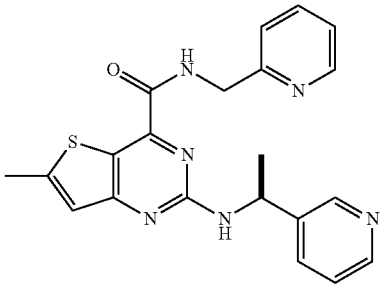 [SMILES: Cc1cc2nc(N[C@@H](C)c3cccnc3)nc(C(=O)NCc3ccccn3)c2s1]
(Z457)

Synthesis of (S)-6-methyl-N-(pyridin-2-ylmethyl)-2-((1-(pyridin-3-yl)ethyl)amino)thieno[3,2-d]pyrimidine-4-carboxamide (Z457): The title compound (Z457) was prepared from (S)-6-methyl-2-((1-(pyridin-3-yl)ethyl)amino)thieno[3,2-d]pyrimidine-4-carboxylic acid di-hydrochloride (39 mg, 0.10 mmol) using chemistry similar to that described in Example Z8 using pyridin-2-ylmethanamine in place of (R)-3-fluoropyrrolidine (28 mg, 63% yield). $^1$H NMR (400 MHz, CDCl$_3$) δ 1.64 (3H, d, J=6.8 Hz), 2.61 (3H, d, J=1.2 Hz), 4.76 (2H, d, J=5.2 Hz), 5.25 (1H, quintet, J=6.8 Hz), 5.43 (1H, d, J=6.8 Hz), 6.85 (1H, d, J=1.2 Hz), 7.19 (1H, dd, J=8.0, 4.8 Hz), 7.25 (1H, m), 7.30 91H, d, J=8.0 Hz), 7.69 (1H, td, J=8.0, 2.0 Hz), 7.75 (1H, dt, J=8.0, 2.0 Hz), 8.45 (1H, dd, J=4.8, 1.6 Hz), 8.66 (1H, d, J=2.4 Hz), 8.80 (1H, m) ppm. LCMS m/z=405.2 [M+H⁺].

Example Z458. (S)-7-Methyl-2-((1-(pyridin-2-yl)ethyl)amino)-N-(pyridin-3-ylmethyl)thieno[3,2-d]pyrimidine-4-carboxamide

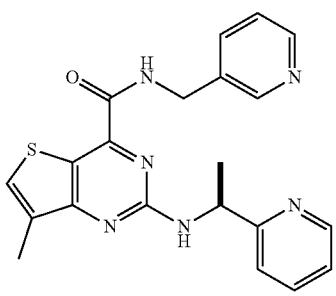 [SMILES: Cc1csc2c(C(=O)NCc3cccnc3)nc(N[C@@H](C)c3ccccn3)nc12]
(Z458)

Synthesis of (S)-7-methyl-2-((1-(pyridin-2-yl)ethyl)amino)-N-(pyridin-3-ylmethyl)thieno[3,2-d]pyrimidine-4-carboxamide (Z458): The title compound (Z458) was prepared from (S)-7-methyl-2-((1-(pyridin-2-yl)ethyl)amino)thieno[3,2-d]pyrimidine-4-carboxylic acid di-hydrochloride (39 mg, 0.10 mmol) using chemistry similar to that described in Example Z8 using pyridin-3-ylmethanamine in place of (R)-3-fluoropyrrolidine (18 mg, 59% yield). $^1$H NMR (400 MHz, CDCl$_3$) δ 1.61 (3H, d, J=6.8 Hz), 2.36 (3H, d, J=1.2 Hz), 4.58 (1H, dd, J=15.2, 5.6 Hz), 4.72 (1H, dd, J=15.2, 6.8 Hz), 5.20 (1H, m), 6.04 (1H, m), 7.07 (1H, m), 7.29 (1H, ddd, J=8.0, 4.8, 1.2 Hz), 7.34 (1H, d, J=8.0 Hz), 7.57 (1H, td, J=8.0, 2.0 Hz), 7.61 (1H, d, J=1.2 Hz), 7.67

(1H, d, J=8.0 Hz), 8.21 (1H, m), 8.41 (1H, m), 8.58 (1H, dd, J=4.8, 1.2 Hz), 8.60 (1H, d, J=2.0 Hz) ppm. LCMS m/z=405.0 [M+H⁺].

Example Z459. (S)-(7-Methyl-2-((1-pyridin-2-yl) ethyl)amino)thieno[3,2-d]pyrimidin-4-yl)(pyrrolidin-1-yl)methanone

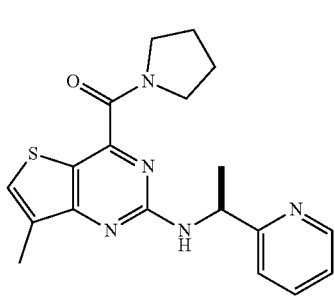 [SMILES: Cc1csc2c(C(=O)N3CCCC3)nc(N[C@@H](C)c3ccccn3)nc12]

(Z459)

Synthesis of (S)-(7-methyl-2-((1-(pyridin-2-yl)ethyl) amino)thieno[3,2-d]pyrimidin-4-yl)(pyrrolidin-1-yl)methanone (Z459): The title compound (Z459) was prepared from (S)-7-methyl-2-((1-(pyridin-2-yl)ethyl)amino)thieno[3,2-d] pyrimidine-4-carboxylic acid di-hydrochloride (29 mg, 0.075 mmol) using chemistry similar to that described in Example Z8 using pyrrolidine in place of (R)-3-fluoropyrrolidine (13 mg, 47% yield). ¹H NMR (400 MHz, CDCl₃) δ 1.63 (3H, d, J=6.8 Hz), 1.82-1.90 (4H, m), 2.36 (3H, d, J=1.2 Hz), 3.62-3.72 (3H, m), 3.88 (1H, m), 5.25 (1H, quintet, J=6.8 Hz), 5.95 (1H, d, J=6.8 Hz), 7.15 (1H, dd, J=8.0, 4.8, 1.2 Hz), 7.38 (1H, d, J=8.0 Hz), 7.54 (1H, d, J=1.2 Hz), 7.61 (1H, td, J=8.0, 1.6 Hz), 8.58 (1H, m) ppm. LCMS m/z=368.1 [M+H⁺].

Example Z460. N-Ethyl-2-((4-hydroxyphenethyl) amino)thieno[3,2-d]pyrimidine-4-carboxamide

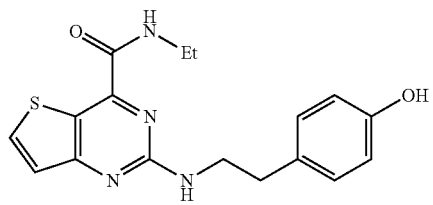 [SMILES: CCNC(=O)c1nc(NCCc2ccc(O)cc2)nc2ccsc12]

(Z460)

Synthesis of 2-chloro-N-ethylthieno[3,2-d]pyrimidine-4-carboxamide: The title compound was prepared from ethyl 2-chlorothieno[3,2-d]pyrimidine-4-carboxylate (500 mg, 2.06 mmol) using chemistry similar to that described in Example Z12 using ethanamine hydrochloride (commercially obtained from Sigma-Aldrich, St. Louis, Mo.) in place of (6-methoxypyridin-3-yl)methanamine hydrochloride (57 mg, 11% yield), LCMS m/z=242.0 [M+H⁺].

Synthesis of N-ethyl-2-((4-hydroxyphenethyl)amino) thieno[3,2-d]pyrimidine-4-carboxamide (Z460): The title compound (Z460) was prepared from 2-chloro-N-ethylthieno[3,2-d]pyrimidine-4-carboxamide using chemistry similar to that described in Example Z12 using 4-(2-aminoethyl) phenol in place of (6-methoxypyridin-3-yl)methanamine hydrochloride (92% yield). ¹H NMR (400 MHz, CDCl₃) δ 1.32 (3H, t, J=6.8 Hz), 2.90 (2H, t, J=6.8 Hz), 3.54 (2H, dt, J=13.6, 6.4 Hz), 3.74 (2H, q, J=6.4 Hz), 5.15 (1H, q, J=6.4 Hz), 5.49 (1H, br s), 6.78 (2H, dt, J=8.4, 2.4 Hz), 7.11 (2H, dt, J=8.4, 2.8 Hz), 7.21 (1H, d, J=5.6 Hz), 7.89 (1H, m), 7.98 (1H, d, J=5.6 Hz) ppm. LCMS m/z=343.1 [M+H⁺].

Example Z461. (S)-6-Methyl-2-((1-(pyridin-2-yl) ethyl)amino)-N-(pyridin-2-ylmethyl)thieno[3,2-d] pyrimidine-4-carboxamide

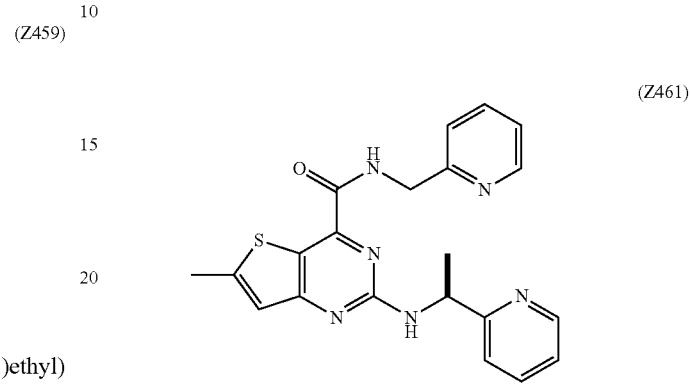

(Z461)

Synthesis of (S)-6-methyl-2-((1-(pyridin-2-yl)ethyl) amino)-N-(pyridin-2-ylmethyl)thieno[3,2-d]pyrimidine-4-carboxamide (Z461): The title compound (Z461) was prepared from (S)-6-methyl-2-((1-(pyridin-2-yl)ethyl)amino) thieno[3,2-d]pyrimidine-4-carboxylic acid di-hydrochloride (39 mg, 0.10 mmol) using chemistry similar to that described in Example Z8 using pyridin-2-ylmethanamine in place of (R)-3-fluoropyrrolidine (20 mg, 49% yield). ¹H NMR (400 MHz, CDCl₃) δ 1.62 (3H, d, J=6.8 Hz), 2.61 (3H, d, J=1.2 Hz), 4.73-4.83 (2H, m), 5.28 (1H, quintet, J=6.8 Hz), 6.11 (1H, d, J=6.8 Hz), 6.88 (1H, d, J=1.2 Hz), 7.12 (1H, dd, J=6.4, 4.8 Hz), 7.23 (1H, dd, J=6.4, 4.8 Hz), 7.31 (1H, d, J=8.0 Hz), 7.38 (1H, d, J=8.0 Hz), 7.60 (1H, td, J=8.0, 2.0 Hz), 7.67 (1H, td, J=7.2, 2.0 Hz), 8.52 (1H, d, J=4.8 Hz), 8.62 (1H, d, J=4.8 Hz), 8.79 (1H, m) ppm. LCMS m/z=405.2 [M+H⁺].

Example Z462. (S)-6-Methyl-2-((1-(pyridin-2-yl) ethyl)amino)-N-(pyridin-3-ylmethyl)thieno[3,2-d] pyrimidine-4-carboxamide

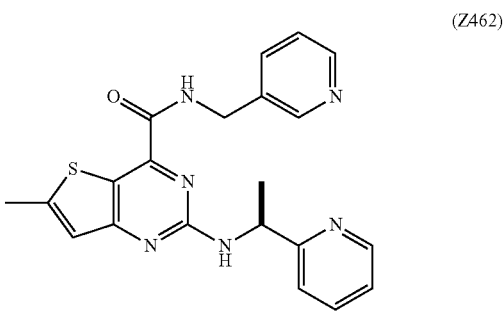

(Z462)

Synthesis of (S)-6-methyl-2-((1-(pyridin-2-yl)ethyl) amino)-N-(pyridin-3-ylmethyl)thieno[3,2-d]pyrimidine-4-carboxamide (Z462): The title compound (Z462) was prepared from (S)-6-methyl-2-((1-(pyridin-2-yl)ethyl)amino) thieno[3,2-d]pyrimidine-4-carboxylic acid di-hydrochloride (39 mg, 0.10 mmol) using chemistry similar to that described in Example Z8 using pyridin-3-ylmethanamine in place of (R)-3-fluoropyrrolidine (15 mg, 37% yield). ¹H NMR (400 MHz, CDCl₃) δ 1.58 (3H, d, J=6.8 Hz), 2.61 (3H, d, J=0.8 Hz), 4.57 (1H, dd, J=15.2, 6.4 Hz), 4.71 (1H, dd, J=15.2, 6.8 Hz), 5.17 (1H, quintet, J=6.8 Hz), 5.99 (1H, d, J=6.8 Hz), 6.89 (1H, d, J=0.8 Hz), 7.08 (1H, dd, J=6.8, 4.8 Hz), 7.28-7.32 (2H, m), 7.57 (1H, td, J=8.0, 1.6 Hz), 7.66 (1H, d, J=8.0 Hz), 8.21 (1H, m), 8.40 (1H, m), 8.57 (1H, dd, J=4.8, 1.2 Hz), 8.59 (1H, d, J=1.6 Hz) ppm. LCMS m/z=405.2 [M+H⁺].

Example Z463. 2-(((S)-1-(5-Fluoropyridin-3-yl)ethyl)amino)-6-methyl-N-(2-((R)-pyrrolidin-3-yl)ethyl)thieno[3,2-d]pyrimidine-4-carboxamide

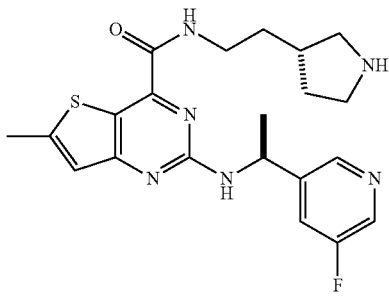 [SMILES: Cc1cc2nc(N[C@@H](C)c3cncc(F)c3)nc(C(=O)NCC[C@H]3CCNC3)c2s1]

Synthesis of tert-butyl (S)-3-(2-(2-(((S)-1-(5-fluoropyridin-3-yl)ethyl)amino)-6-methylthieno[3,2-d]pyrimidine-4-carboxamido)ethyl)pyrrolidine-1-carboxylate: The title compound was prepared from (S)-2-((1-(5-fluoropyridin-3-yl)ethyl)amino)-6-methylthieno[3,2-d]pyrimidine-4-carboxylic acid di-hydrochloride (40.5 mg, 0.10 mmol) using chemistry similar to that described in Example Z8 using tert-butyl (S)-3-(2-aminoethyl)pyrrolidine-1-carboxylate (commercially obtained from Ark Pham, Arlington Heights, Ill.) in place of (R)-3-fluoropyrrolidine (53 mg, 100% yield). LCMS m/z=529.3 [M+H⁺].

Synthesis of 2-(((S)-1-(5-fluoropyridin-3-yl)ethyl)amino)-6-methyl-N-(2-((R)-pyrrolidin-3-yl)ethyl)thieno[3,2-d]pyrimidine-4-carboxamide (Z463): A solution of tert-butyl (S)-3-(2-(2-(((S)-1-(5-fluoropyridin-3-yl)ethyl)amino)-6-methylthieno[3,2-d]pyrimidine-4-carboxamido)ethyl)pyrrolidine-1-carboxylate (53 mg, 0.1 mmol) in TFA/DCM (1/1, 2 mL) was stirred at room temperature for 1 h and LCMS indicated completion of the reaction. The reaction mixture was concentrated and the residue was purified by flash chromatography on silica gel (12 g HP silica, Teledyne Isco) eluting with 25% to 75% solvent A (DCM/MeOH/NH₄OH, 100/10/1) in DCM to provide 2-(((S)-1-(5-fluoropyridin-3-yl)ethyl)amino)-6-methyl-N-(2-((R)-pyrrolidin-3-yl)ethyl)thieno[3,2-d]pyrimidine-4-carboxamide as a light yellow solid (43 mg, 100% yield). ¹H NMR (400 MHz, CDCl₃) δ 1.62 (3H, d, J=6.8 Hz), 1.68-1.81 (3H, m), 2.24 (1H, m), 2.35 (1H, m), 2.61 (3H, d, J=1.2 Hz), 2.92 (1H, m), 3.27 (1H, m), 3.42-3.65 (4H, m), 5.19 (1H, m), 5.70 (1H, m), 6.85 (1H, d, J=1.2 Hz), 7.48 (1H, d, J=7.2 Hz), 7.83 (1H, m), 8.32 (1H, m), 8.57 (1H, m), 9.77 (1H, m), 9.96 (1H, m) ppm. LCMS m/z=429.2[M+H⁺].

Example Z464. (S)—N-((6-Methoxypyridin-2-yl)methyl)-6-methyl-2-((1-(pyridin-2-yl)ethyl)amino)thieno[3,2-d]pyrimidine-4-carboxamide

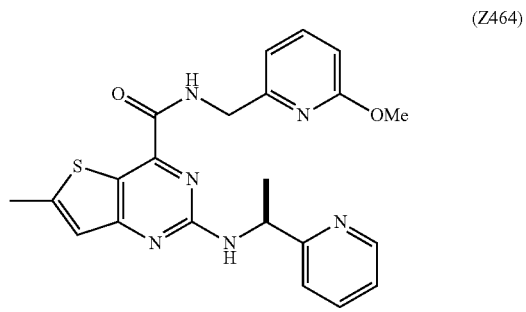

Synthesis of (S)—N-((6-methoxypyridin-2-yl)methyl)-6-methyl-2-((1-(pyridin-2-yl)ethyl)amino)thieno[3,2-d]pyrimidine-4-carboxamide (Z464): The title compound (Z464) was prepared from (S)-6-methyl-2-((1-(pyridin-2-yl)ethyl)amino)thieno[3,2-d]pyrimidine-4-carboxylic acid di-hydrochloride (39 mg, 0.10 mmol) using chemistry similar to that described in Example Z8 using (6-methoxypyridin-2-yl)methanamine in place of (R)-3-fluoropyrrolidine (25 mg, 58% yield). ¹H NMR (400 MHz, CDCl₃) δ 1.60 (3H, d, J=7.2 Hz), 2.62 (3H, d, J=1.2 Hz), 4.00 (3H, s), 4.63-4.73 (2H, m), 5.27 (1H, quintet, J=7.2 Hz), 6.12 (1H, d, J=7.2 Hz), 6.66 (1H, d, J=8.0 Hz), 6.85 (1H, d, J=8.0 Hz), 6.89 (1H, d, J=1.2 Hz), 7.12 (1H, dd, J=6.4, 4.8 Hz), 7.32 (1H, d, J=8.0 Hz), 7.54 (1H, t, J=8.0 Hz), 7.60 (1H, td, J=8.0, 1.6 Hz), 8.50 (1H, d, J=4.8 Hz), 8.71 (1H, m) ppm. LCMS m/z=435.2 [M+H⁺].

Example Z465. (R)-2-((1-(4-Methoxyphenyl)ethyl)amino)-N-((6-methoxypyridin-3-yl)methyl)thieno[3,2-d]pyrimidine-4-carboxamide

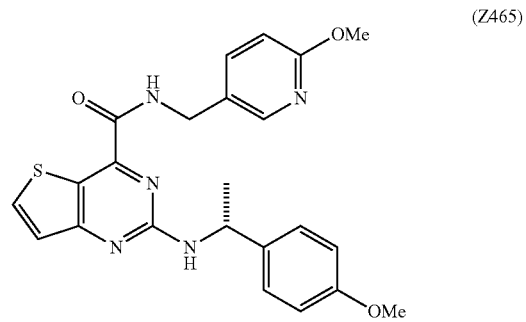

Synthesis of (R)-2-((1-(4-methoxyphenyl)ethyl)amino)thieno[3,2-d]pyrimidine-4-carboxylic acid: The title compound was prepared from ethyl 2-chlorothieno[3,2-d]pyrimidine-4-carboxyl-ate (500 mg, 2.06 mmol) using chemistry similar to that described in Example Z435 using (1R)-1-(4-methoxyphenyl)ethanamine (commercially obtained from Cambridge, Cambridge, UK) in place of (6-methoxypyridin-3-yl)methanamine hydrochloride to provide (R)-2-((1-(4-methoxy-phenyl)ethyl)amino)thieno[3,2-d]pyrimidine-4-carboxylic acid (374 mg, 50% yield). LCMS m/z=358.1 [M+H⁺].

Synthesis of (R)-2-((1-(4-methoxyphenyl)ethyl)amino)-N-((6-methoxypyridin-3-yl)methyl)thieno[3,2-d]pyrimidine-4-carboxamide (Z465): The title compound (Z465) was prepared from (R)-2-((1-(4-methoxyphenyl)ethyl)amino)thieno[3,2-d]pyrimidine-4-carboxylic acid using chemistry similar to that described in Example Z8 using (6-methoxy-3-pyridyl)meth-an amine (commercially obtained from Combi Blocks, San Diego, Calif.) in place of (R)-3-fluoropyrrolidine (31% yield). $^1$H NMR (400 MHz, CDCl$_3$) δ 1.56 (3H, t, J=6.8 Hz), 3.75 (3H, s), 3.94 (3H, s), 4.54 (2H, dd, J=6.0, 1.6 Hz), 5.02 (1H, m), 5.40 (1H, d, J=6.8 Hz), 6.74 (1H, d, J=8.4 Hz), 6.78 (2H, d, J=8.8 Hz), 7.18 (1H, dd, J=5.6, 2.8 Hz), 7.24 (1H, m), 7.28 (1H, m), 7.55 (1H, dd, J=8.8, 2.8 Hz), 7.90-7.97 (1H, m), 7.99 (1H, dd, J=5.2, 1.6 Hz), 8.14 (1H, d, J=2.4 Hz) ppm. LCMS m/z=450.2 [M+H$^+$]

Example Z466. (S)-2-((1-(4-Methoxyphenyl)ethyl)amino)-N-(pyridin-2-ylmethyl)thieno[3,2-d]pyrimidine-4-carboxamide

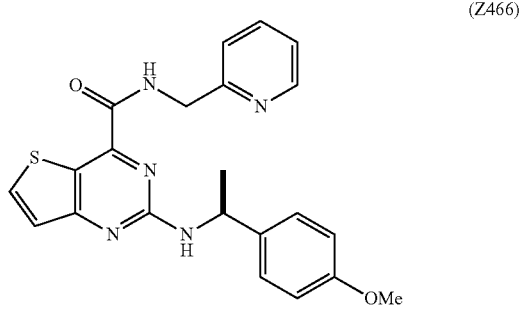

(Z466)

Synthesis of (S)-2-((1-(4-methoxyphenyl)ethyl)amino)-N-(pyridin-2-ylmethyl)thieno[3,2-d]pyrimidine-4-carboxamide (Z466): The title compound (Z466) was prepared from (S)-2-((1-(4-methoxyphenyl)ethyl)amino)thieno[3,2-d]pyrimidine-4-carboxylic acid using chemistry similar to that described in Example Z8 using 2-(aminomethyl)pyridine (commercially obtained from Sigma-Aldrich, St. Louis, Mo.) in place of (R)-3-fluoropyrrolidine (38% yield). $^1$H NMR (400 MHz, CDCl$_3$) δ 1.60 (3H, d, J=6.8 Hz), 3.74 (3H, s), 4.77 (2H, d, J=4.2 Hz), 5.18 (1H, q, J=8.0 Hz), 5.46 (1H, d, J=7.6 Hz), 6.78-6.82 (2H, m), 7.18 (1H, d, J=5.6 Hz), 7.24 (1H, m), 7.30 (1H, d, J=8.0 Hz), 7.37 (2H, dd, J=7.6, 2.0 Hz), 7.69 (1H, dt, J=8.0, 2.0 Hz), 7.97 (1H, d, J=5.6 Hz), 8.64 (1H, dt, J=4.0, 0.8 Hz), 8.80 (1H, m) ppm. LCMS m/z=420.2 [M+H$^+$]

Example Z467. ((R)-3-(Methoxymethyl)pyrrolidin-1-yl)(6-methyl-2-(((S)-1-(pyridin-2-yl)ethyl)amino)thieno[3,2-d]pyrimidin-4-yl)methanone

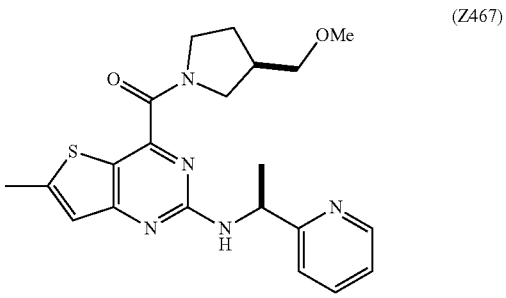

(Z467)

Synthesis of ((R)-3-(methoxymethyl)pyrrolidin-1-yl)(6-methyl-2-(((S)-1-(pyridin-2-yl)ethyl)amino)thieno[3,2-d]pyrimidin-4-yl)methanone (Z467): The title compound (Z467) was prepared from (S)-6-methyl-2-((1-(pyridin-2-yl)ethyl)amino)thieno[3,2-d]pyrimidine-4-carboxylic acid dihydrochloride (39 mg, 0.10 mmol) using chemistry similar to that described in Example Z8 using (R)-3-(methoxymethyl)pyrrolidine in place of (R)-3-fluoropyrrolidine (24 mg, 58% yield). $^1$H NMR (400 MHz, CDCl$_3$) δ 1.60 (3H, d, J=6.8 Hz), 1.70 (1H, m), 2.00 (1H, m), 2.47 (1H, m), 2.59 (3H, d, J=1.2 Hz), 3.31-3.43 (5H, m), 3.64-3.84 (3H, m), 4.01 (1H, m), 5.23 (1H, m), 5.94 (1H, m), 6.86 (1H, d, J=1.2 Hz), 7.15 (1H, m), 7.34 (1H, m), 7.61 (1H, m), 8.57 (1H, m) ppm. LCMS m/z=412.3 [M+H$^+$].

Example Z468. ((S)-3-(Methoxymethyl)pyrrolidin-1-yl)(6-methyl-2-(((S)-1-(pyridin-2-yl)ethyl)amino)thieno[3,2-d]pyrimidin-4-yl)methanone

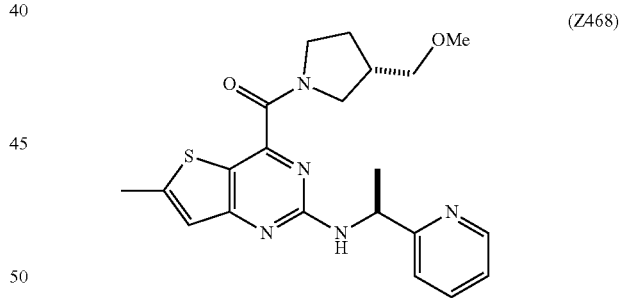

(Z468)

Synthesis of ((S)-3-(methoxymethyl)pyrrolidin-1-yl)(6-methyl-2-(((S)-1-(pyridin-2-yl)ethyl)amino)thieno[3,2-d]pyrimidin-4-yl)methanone (Z468): The title compound (Z468) was prepared from (S)-6-methyl-2-((1-(pyridin-2-yl)ethyl)amino)thieno[3,2-d]pyrimidine-4-carboxylic acid dihydrochloride (39 mg, 0.10 mmol) using chemistry similar to that described in Example Z8 using (S)-3-(methoxymethyl)pyrrolidine in place of (R)-3-fluoropyrrolidine (26 mg, 63% yield). $^1$H NMR (400 MHz, CDCl$_3$) δ 1.60 (3H, d, J=6.8 Hz), 1.72 (1H, m), 2.01 (1H, m), 2.47 (1H, m), 2.59 (3H, d, J=1.2 Hz), 3.27 (1H, m), 3.34-3.38 (4H, m), 3.43 (1H, m), 3.68 (1H, m), 3.81 (1H, m), 4.10 (1H, m), 5.22 (1H, m), 5.94 (1H, m), 6.86 (1H, d, J=1.2 Hz), 7.15 (1H, m), 7.34 (1H, d, J=8.0 Hz), 7.61 (1H, m), 8.57 (1H, m) ppm. LCMS m/z=412.3 [M+H$^+$].

Example Z469. (S)—N-((6-Methoxypyridin-3-yl)methyl)-6-methyl-2-((1-(pyridin-2-yl)ethyl)amino)thieno[3,2-d]pyrimidine-4-carboxamide

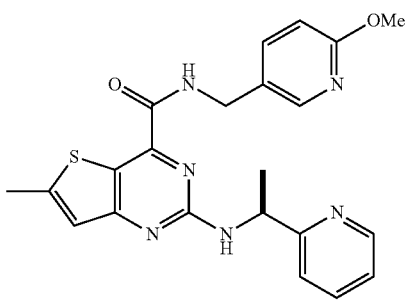 [SMILES: COc1ccc(CNC(=O)c2nc(N[C@@H](C)c3ccccn3)nc3cc(C)sc23)cn1]

(Z469)

Synthesis of (S)—N-((6-methoxypyridin-3-yl)methyl)-6-methyl-2-((1-(pyridin-2-yl)ethyl)amino)thieno[3,2-d]pyrimidine-4-carboxamide (Z469): The title compound (Z469) was prepared from (S)-6-methyl-2-((1-(pyridin-2-yl)ethyl)amino)thieno[3,2-d]pyrimidine-4-carboxylic acid di-hydrochloride (39 mg, 0.10 mmol) using chemistry similar to that described in Example Z8 using (6-methoxypyridin-3-yl)methanamine in place of (R)-3-fluoropyrrolidine (9 mg, 21% yield). $^1$H NMR (400 MHz, CDCl$_3$) δ 1.58 (3H, d, J=6.8 Hz), 2.62 (3H, d, J=1.2 Hz), 3.95 (3H, s), 4.48 (1H, dd, J=14.8, 5.6 Hz), 4.61 (1H, dd, J=14.8, 6.8 Hz), 5.16 (1H, m), 5.98 (1H, m), 6.73 (1H, d, J=8.0 Hz), 6.88 (1H, d, J=1.2 Hz), 7.08 (1H, dd, J=6.8, 4.8 Hz), 7.29 (1H, d, J=8.0 Hz), 7.52-7.58 (2H, m), 8.08 (1H, m), 8.13 (1H, d, J=2.0 Hz), 8.43 (1H, m) ppm. LCMS m/z=435.2 [M+H$^+$].

Example Z470. ((S)-3-(Methoxymethyl)pyrrolidin-1-yl)(2-(((S)-1-(pyridin-2-yl)ethyl)amino)thieno[3,2-d]pyrimidin-4-yl)methanone

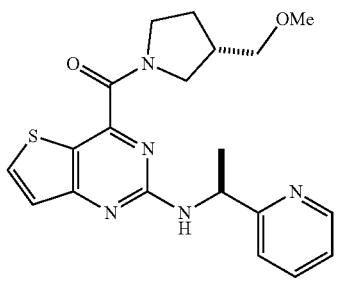 [SMILES: COC[C@H]1CCN(C(=O)c2nc(N[C@@H](C)c3ccccn3)nc3ccsc23)C1]

(Z470)

Synthesis of ((S)-3-(methoxymethyl)pyrrolidin-1-yl)(2-(((S)-1-(pyridin-2-yl)ethyl)amino)thieno[3,2-d]pyrimidin-4-yl)methanone (Z470): The title compound (Z470) was prepared from (S)-2-((1-(pyridin-2-yl)ethyl)amino)thieno[3,2-d]pyrimidine-4-carboxylic acid di-hydrochloride (37 mg, 0.10 mmol) using chemistry similar to that described in Example Z8 using (S)-3-(methoxymethyl)pyrrolidine in place of (R)-3-fluoropyrrolidine (31 mg, 78% yield). $^1$H NMR (400 MHz, CDCl$_3$) δ 1.62 (3H, d, J=6.8 Hz), 1.74 (1H, m), 2.01 (1H, m), 2.50 (1H, m), 3.29-3.49 (5H, m), 3.66-3.88 (3H, m), 4.13 (1H, m), 5.26 (1H, m), 6.06 (1H, m), 7.16 (1H, m), 7.19 (1H, d, J=5.2 Hz), 7.35 (1H, d, J=8.0 Hz), 7.62 (1H, m), 7.92 (1H, dd, J=5.6, 2.0 Hz), 8.58 (1H, m) ppm. LCMS m/z=398.1 [M+H$^+$].

Example Z471. ((R)-3-(Methoxymethyl)pyrrolidin-1-yl)(2-(((S)-1-(pyridin-2-yl)ethyl)amino)thieno[3,2-d]pyrimidin-4-yl)methanone

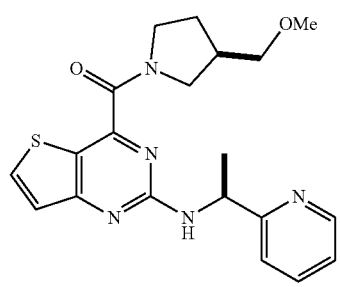 [SMILES: COC[C@@H]1CCN(C(=O)c2nc(N[C@@H](C)c3ccccn3)nc3ccsc23)C1]

(Z471)

Synthesis of ((R)-3-(methoxymethyl)pyrrolidin-1-yl)(2-(((S)-1-(pyridin-2-yl)ethyl)amino)thieno[3,2-d]pyrimidin-4-yl)methanone (Z471): The title compound (Z471) was prepared from (S)-2-((1-(pyridin-2-yl)ethyl)amino)thieno[3,2-d]pyrimidine-4-carboxylic acid di-hydrochloride (37 mg, 0.10 mmol) using chemistry similar to that described in Example Z8 using (R)-3-(methoxymethyl)pyrrolidine in place of (R)-3-fluoropyrrolidine (32 mg, 81% yield). $^1$H NMR (400 MHz, CDCl$_3$) δ 1.62 (3H, d, J=6.8 Hz), 1.74 (1H, m), 2.02 (1H, m), 2.50 (1H, m), 3.33-3.46 (5H, m), 3.67-3.86 (3H, m), 4.06 (1H, m), 5.27 (1H, m), 6.05 (1H, m), 7.16 (1H, m), 7.19 (1H, d, J=5.6 Hz), 7.35 (1H, d, J=8.0 Hz), 7.62 (1H, m), 7.92 (1H, dd, J=5.6, 4.0 Hz), 8.58 (1H, m) ppm. LCMS m/z=398.1 [M+H$^+$].

Example Z472. Benzyl ((S)-1-(2-(((S)-1-(5-fluoropyridin-3-yl)ethyl)amino)thieno[3,2-d]pyrimidine-4-carbonyl)pyrrolidin-3-yl)carbamate

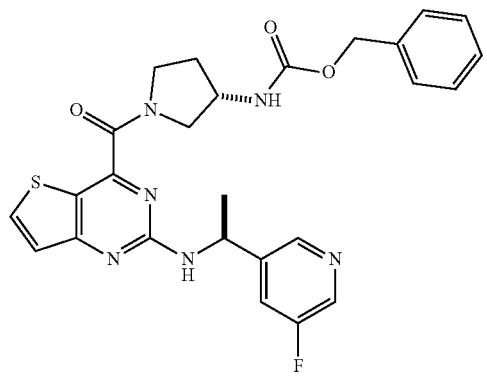 [SMILES: C[C@H](Nc1nc(C(=O)N2CC[C@H](NC(=O)OCc3ccccc3)C2)c2sccc2n1)c1cncc(F)c1]

(Z472)

Synthesis of benzyl ((S)-1-(2-(((S)-1-(5-fluoropyridin-3-yl)ethyl)amino)thieno[3,2-d]pyrimidine-4-carbonyl)pyrrolidin-3-yl)carbamate (Z472): The title compound (Z472) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using benzyl N-[(3S)-pyrrolidin-3-yl]carbamate (commercially obtained from Ark Pharm, Libertyville, Ill.) in place of (3R)-3-methoxypyrrolidine hydrochloride (86% yield). $^1$H NMR (400 MHz, CDCl$_3$) δ 1.62 (3H, dd, J=6.8, 2.4 Hz), 1.82-1.95 (2H, m), 2.05-2.20 (1H, m), 3.63-3.70 (1H, m), 3.78-3.92 (2H, m), 4.21-4.30 (1H, m), 4.87-5.05 (1H, m), 5.12 (2H, m), 5.19 (1H, m), 5.48 (1H, d, J=6.0 Hz), 7.17 (1H, dd, J=5.6, 1.6 Hz), 7.31-7.38 (4H, m), 7.41 (1H, m), 7.95 (1H, d, J=5.6 Hz), 8.32 (1H, q, 2.8 Hz), 8.50 (1H, m) ppm. LCMS m/z=521.2 [M+H$^+$].

Example Z473. Benzyl ((S)-1-(2-(((S)-1-(5-fluoropyridin-3-yl)ethyl)amino)-6-methylthieno[3,2-d]pyrimidine-4-carbonyl)pyrrolidin-3-yl)carbamate

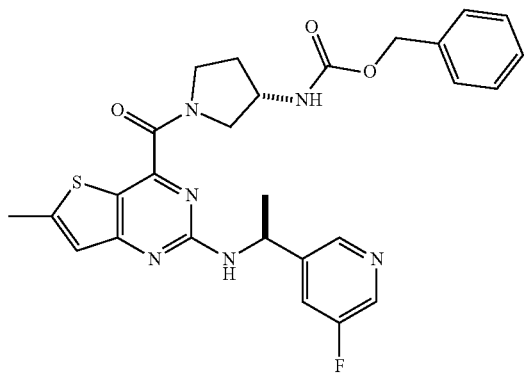 [SMILES: Cc1cc2nc(N[C@@H](C)c3cncc(F)c3)nc(C(=O)N3CC[C@H](NC(=O)OCc4ccccc4)C3)c2s1]

(Z473)

Synthesis of benzyl ((S)-1-(2-(((S)-1-(5-fluoropyridin-3-yl)ethyl)amino)-6-methylthieno[3,2-d]pyrimidine-4-carbonyl)pyrrolidin-3-yl)carbamate (Z473): The title compound (Z473) was prepared from (S)-2-((1-(5-fluoropyridin-3-yl)ethyl)amino)-6-methylthieno[3,2-d]pyrimidine-4-carboxylic acid di-hydrochloride using chemistry similar to that described in Example Z17 using benzyl N-[(3S)-pyrrolidin-3-yl]carbamate (commercially obtained from Ark Pharm, Libertyville, Ill.) in place of (3R)-3-methoxypyrrolidine hydrochloride (78% yield). $^1$H NMR (400 MHz, CDCl$_3$) δ 1.62 (3H, dd, J=6.4, 3.6 Hz), 1.82-1.95 (1H, m), 2.08-2.19 (1H, m), 2.59 (3H, s), 3.60-3.65 (1H, m), 3.75-3.92 (4H, m), 4.17-4.35 (1H, m), 4.85-4.96 (1H, m), 5.12-5.17 (3H, m), 5.42 (1H, d, J=6.0 Hz), 6.88 (1H, m), 7.33-7.38 (4H, m), 7.41 (1H, m), 8.32 (1H, q, J=2.8 Hz), 8.47 (1H, d, J=6.0 Hz) ppm. LCMS m/z=535.3 [M+H$^+$].

Example Z474. (S)—N-(4-Methoxybenzyl)-2-((1-(pyridin-2-yl)ethyl)amino)thieno[3,2-d]pyrimidine-4-carboxamide

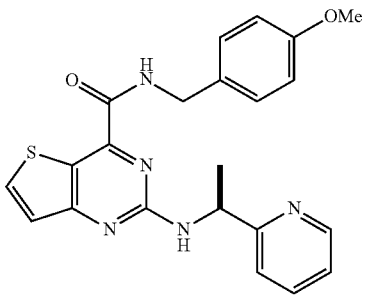

(Z474)

Synthesis of (S)—N-(4-methoxybenzyl)-2-((1-(pyridin-2-yl)ethyl)amino)thieno[3,2-d]pyrimidine-4-carboxamide (Z474): The title compound (Z474) was prepared from (S)-2-((1-(pyridin-2-yl)ethyl)amino)thieno[3,2-d]pyrimidine-4-carboxylic acid di-hydrochloride using chemistry similar to that described in Example Z8 using 4-methoxybenzylamine (commercially obtained from Enamine, Monmouth Jct., N.J.) in place of (R)-3-fluoropyrrolidine (56% yield). $^1$H NMR (400 MHz, CDCl$_3$) δ 1.61 (3H, d, J=6.8 Hz), 3.81 (3H, s), 4.51 (1H, dd, J=14.8, 4.8 Hz), 4.63 (1H, dd, J=14.8, 4.8 Hz), 5.18 (1H, q, J=6.0 Hz), 6.14 (1H, dd, J=2.4, 1.6 Hz), 6.88 (2H, dt, J=4.8, 2.4 Hz), 7.15 (1H, m), 7.18 (1H, d, J=5.6 Hz), 7.28 (1H, d, J=7.2 Hz), 7.38 (1H, d, J=7.6 Hz), 7.66 (1H, dt, J=7.2, 2.0 Hz), 7.97 (1H, d, J=5.2 Hz), 8.15 (1H, m), 8.43 (1H, m) ppm. LCMS m/z=420.2 [M+H$^+$].

Example Z475. tert-Butyl (S)-((1-(2-((1-(5-fluoropyridin-3-yl)ethyl)amino)-6-methylthieno[3,2-d]pyrimidine-4-carbonyl)azetidin-3-yl)methyl)carbamate

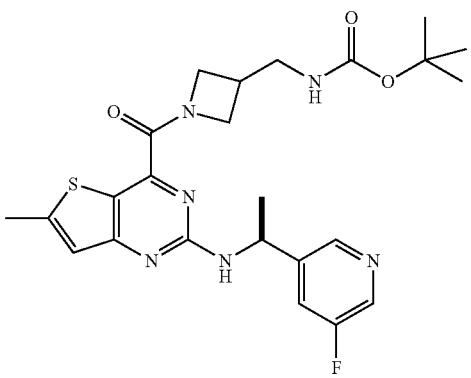 [SMILES: Cc1cc2nc(N[C@@H](C)c3cncc(F)c3)nc(C(=O)N3CC(CNC(=O)OC(C)(C)C)C3)c2s1]

(Z475)

Synthesis of tert-butyl (S)-((1-(2-((1-(5-fluoropyridin-3-yl)ethyl)amino)-6-methylthieno[3,2-d]pyrimidine-4-carbonyl)azetidin-3-yl)methyl)carbamate (Z475): The title compound (Z475) was prepared from (S)-2-((1-(5-fluoropyridin-3-yl)ethyl)amino)-6-methylthieno[3,2-d]pyrimidine-4-carboxylic acid di-hydrochloride using chemistry similar to that described in Example Z17 using tert-butyl N-(azetidin- 3-ylmethyl)carbamate (commercially obtained from PharmaBlock, Sunnyvale, Calif.) in place of (3R)-3-methoxypyrrolidine hydrochloride (35% yield). LCMS m/z=501.2 [M+H⁺].

Example Z476. tert-Butyl (S)-((1-(6-methyl-2-((1-(pyridin-2-yl)ethyl)amino)thieno[3,2-d]pyrimidine-4-carbonyl)azetidin-3-yl)methyl)carbamate

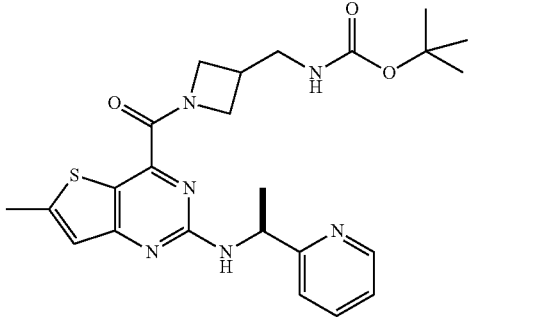 [SMILES: Cc1cc2nc(N[C@@H](C)c3ccccn3)nc(C(=O)N3CC(CNC(=O)OC(C)(C)C)C3)c2s1]

(Z476)

Synthesis of tert-butyl (S)-((1-(6-methyl-2-((1-(pyridin-2-yl)ethyl)amino)thieno[3,2-d]pyrimidine-4-carbonyl)azetidin-3-yl)methyl)carbamate (Z476): The title compound (Z476) was prepared from (S)-6-methyl-2-((1-(pyridin-2-yl)ethyl)amino)thieno[3,2-d]pyrimidine-4-carboxylic acid di-hydrochloride using chemistry similar to that described in Example Z8 using tert-butyl N-(azetidin-3-ylmethyl)carbamate in place of (R)-3-fluoropyrrolidine (23% yield). LCMS m/z=483.2 [M+H⁺].

Example Z477. (S)—N-(4-Methoxybenzyl)-6-methyl-2-((1-(pyridin-2-yl)ethyl)amino)thieno[3,2-d]pyrimidine-4-carboxamide

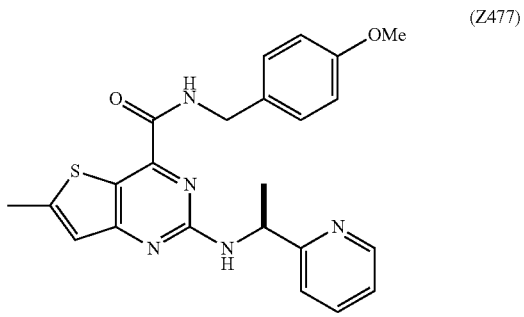

(Z477)

Synthesis of (S)—N-(4-methoxybenzyl)-6-methyl-2-((1-(pyridin-2-yl)ethyl)amino)thieno[3,2-d]pyrimidine-4-carboxamide (Z477): The title compound (Z477) was prepared from (S)-6-methyl-2-((1-(pyridin-2-yl)ethyl)amino)thieno[3,2-d]pyrimidine-4-carboxylic acid di-hydrochloride (39 mg, 0.10 mmol) using chemistry similar to that described in Example Z8 using (4-methoxyphenyl)methanamine in place of (R)-3-fluoropyrrolidine (15 mg, 35% yield). ¹H NMR (400 MHz, CDCl₃) δ 1.57 (3H, d, J=6.8 Hz), 2.61 (3H, d, J=1.2 Hz), 3.82 (3H, s), 4.49 (1H, dd, J=14.4, 6.0 Hz), 4.62 (1H, dd, J=14.4, 6.8 Hz), 5.16 (1H, m), 5.97 (1H, m), 6.86-6.91 (3H, m), 7.06 (1H, m), 7.20-7.29 (3H, m), 7.55 (1H, m), 8.06 (1H, m), 8.40 (1H, m) ppm. LCMS m/z=434.1 [M+H⁺].

Example Z478. (S)-(3-(Aminomethyl)azetidin-1-yl)(2-((1-(5-fluoropyridin-3-yl)ethyl)amino)-6-methyl-thieno[3,2-d]pyrimidin-4-yl)methanone

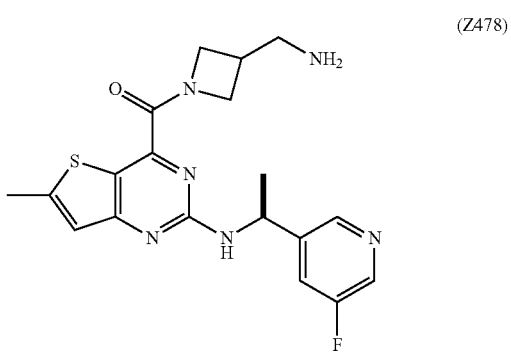

(Z478)

Synthesis of (S)-(3-(aminomethyl)azetidin-1-yl)(2-((1-(5-fluoropyridin-3-yl)ethyl)amino)-6-methylthieno[3,2-d]pyrimidin-4-yl)methanone (Z478): The title compound (Z478) was prepared from tert-butyl (S)-((1-(2-((1-(5-fluoropyridin-3-yl)ethyl)amino)-6-methylthieno[3,2-d]pyrim-idine-4-carbonyl)azetidin-3-yl)methyl)carbamate using chemistry similar to that described in Example Z358 (80% yield). ¹H NMR (400 MHz, CDCl₃) δ 1.61 (3H, d, J=6.8 Hz), 2.59 (3H, s), 2.63-2.73 (1H, m), 2.88 (1H, d, J=6.4 Hz), 2.99 (1H, d, J=7.2 Hz), 3.63-3.65 (1H, m), 3.80-3.88 (1H, m), 4.27 (1H, m), 4.37 (1H, m), 4.75 (1H, m), 5.17 (1H, q, J=7.6 Hz), 5.87 (1H, m), 6.85 (1H, d, J=1.2 Hz), 7.16 (1H, ddd, J=8.4, 4.8, 0.8 Hz), 7.35 (1H, d, J=8.0 Hz), 7.62 (1H, td, J=8.0, 1.6 Hz), 8.55 (1H, d, J=4.8 Hz) ppm. LCMS m/z=401.1 [M+H⁺].

Example Z479. (S)-(3-(Aminomethyl)azetidin-1-yl)(6-methyl-2-((1-(pyridin-2-yl)ethyl)amino)thieno[3,2-d]pyrimidin-4-yl)methanone

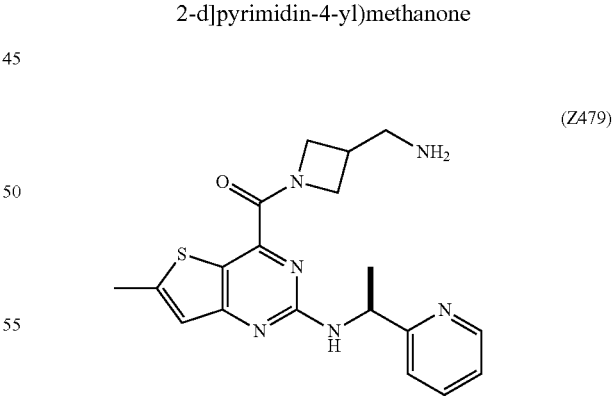

(Z479)

Synthesis of (S)-(3-(aminomethyl)azetidin-1-yl)(6-methyl-2-((1-(pyridin-2-yl)ethyl)amino)thieno[3,2-d]pyrimidin-4-yl)methanone (Z479): The title compound (Z479) was prepared from tert-butyl (S)-((1-(6-methyl-2-((1-(pyridin-2-yl)ethyl)amino)thieno[3,2-d]pyrim-idine-4-carbonyl)azetidin-3-yl)methyl)carbamate using chemistry similar to that described in Example Z358 (62% yield). LCMS m/z=383.1[M+H⁺].

Example Z480. (S)-6-Methyl-2-((1-(pyridin-2-yl)ethyl)amino)thieno[3,2-d]pyrimidine-4-carboxamide

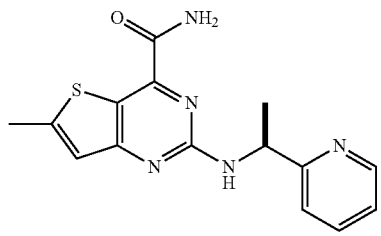 [SMILES: Cc1cc2nc(N[C@@H](C)c3ccccn3)nc(C(N)=O)c2s1]
(Z480)

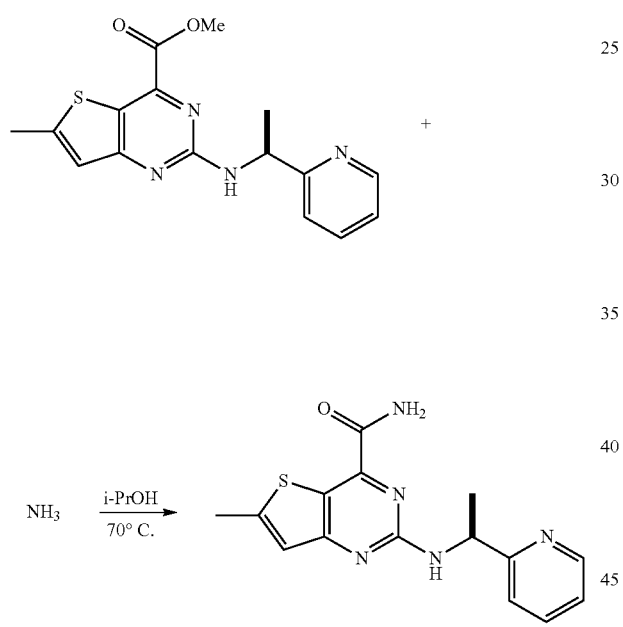

Synthesis of (S)-6-methyl-2-((1-(pyridin-2-yl)ethyl)amino)thieno[3,2-d]pyrimidine-4-carboxamide (480): To a solution of methyl 6-methyl-2-[[(1S)-1-(2-pyridyl)ethyl]amino]thieno[3,2-d]pyrimidine-4-carboxylate (33 mg, 0.10 mmol) in iso-propanol (1 mL) was added 2.0 M amonia solution in isoprpanol (2 mmol, 1 mL) and the solution was stirred at 70° C. for 2 days. The reaction mixture was concentrated and the residue was purified by flash chromatography on silica gel (12 g HP silica, Teledyne Isco) eluting with 10% to 50% solvent A (DCM/MeOH/NH$_4$OH, 100/10/1) in DCM to provide (S)-6-methyl-2-((1-(pyridin-2-yl)ethyl)amino)thieno[3,2-d]pyrimidine-4-carboxamide as an off-white solid (19 mg, 61% yield). $^1$H NMR (400 MHz, CDCl$_3$) δ 1.61 (3H, d, J=6.8 Hz), 2.61 (3H, d, J=1.2 Hz), 5.23 (1H, quintet, J=6.8 Hz), 5.62 (1H, br s), 6.09 (1H, m), 6.89 (1H, d, J=1.2 Hz), 7.17 (1H, ddd, J=8.0, 4.8, 1.2 Hz), 7.34 (1H, d, J=8.0 Hz), 7.64 (1H, td, J=8.0, 2.0 Hz), 7.69 (1H, br s), 8.57 (1H, m) ppm. LCMS m/z=314.1 [M+H$^+$].

Example Z481. (S)-(3-(Dimethylamino)azetidin-1-yl)(2-((1-(5-fluoropyridin-3-yl)ethyl)amino)-6-methylthieno[3,2-d]pyrimidin-4-yl)methanone

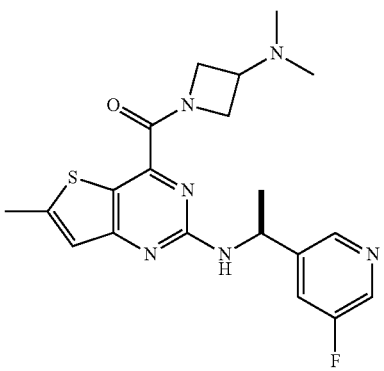 [SMILES: Cc1cc2nc(N[C@@H](C)c3cncc(F)c3)nc(C(=O)N3CC(N(C)C)C3)c2s1]
(Z481)

Synthesis of (S)-(3-(dimethylamino)azetidin-1-yl)(2-((1-(5-fluoropyridin-3-yl)ethyl)amino)-6-methylthieno[3,2-d]pyrimidin-4-yl)methanone (Z481): The title compound (Z481) was prepared from (S)-2-((1-(5-fluoropyridin-3-yl)ethyl)amino)-6-methylthieno[3,2-d]pyrimidine-4-carboxylic acid di-hydrochloride using chemistry similar to that described in Example Z17 using N,N-dimethylazetidin-3-amine di-hydrochloride (commercially obtained from Enamine, Monmouth Jct., N.J.) in place of (3R)-3-methoxy-pyrrolidine hydrochloride (20% yield). $^1$H NMR (400 MHz, CDCl$_3$) δ 1.63 (3H, d, J=6.8 Hz), 2.14 (3H, s), 2.19 (3H, s), 2.60 (3H, d, J=0.8 Hz), 3.03-3.11 (1H, m), 3.98-4.02 (1H, m), 4.16-4.21 (2H, m), 4.36-4.60 (1H, m), 5.20 (1H, q, J=6.8 Hz), 5.29 (1H, d, J=6.4 Hz), 6.84 (1H, d, J=1.2 Hz), 7.42 (1H, dt, J=9.6, 2.0 Hz), 8.33 (1H, dd, J=4.0, 2.8 Hz), 8.49 (1H, m) ppm. LCMS m/z=415.3 [M+H$^+$].

Example Z482. tert-Butyl (S)-(4-(2-(2-((1-(5-fluoropyridin-3-yl)ethyl)amino)thieno[3,2-d]pyrimidine-4-carboxamido)ethyl)phenyl)carbamate

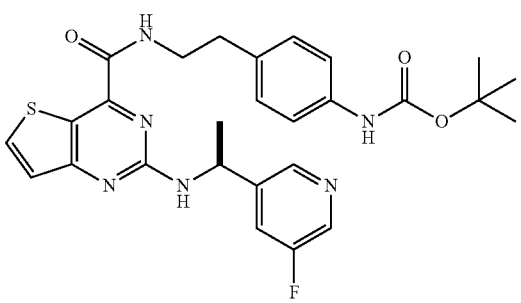 [SMILES: C[C@H](Nc1nc(C(=O)NCCc2ccc(NC(=O)OC(C)(C)C)cc2)c2sccc2n1)c1cncc(F)c1]
(Z482)

Synthesis of tert-butyl (S)-(4-(2-(2-((1-(5-fluoropyridin-3-yl)ethyl)amino)thieno[3,2-d]pyrimidine-4-carboxamido)ethyl)phenyl)carbamate (Z482): The title compound (Z482) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using tert-butyl N-[4-(2-aminoethyl)phenyl]carbamate (commercially obtained from J&W Pharmalab, Levittown, Pa.) in place of (3R)-3-methoxypyrrolidine hydrochloride (71% yield). LCMS m/z=537.2 [M+H⁺].

Example Z483. (S)-(3-Methoxy-3-methylazetidin-1-yl)(6-methyl-2-((1-(pyridin-2-yl)ethyl)amino)thieno[3,2-d]pyrimidin-4-yl)methanone

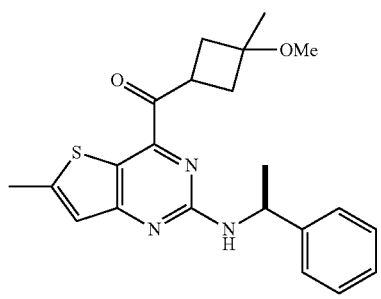 [SMILES: COC1(C)CN(C(=O)c2nc(N[C@@H](C)c3ccccn3)nc3cc(C)sc23)C1]

(Z483)

Synthesis of (S)-(3-methoxy-3-methylazetidin-1-yl)(6-methyl-2-((1-(pyridin-2-yl)ethyl)amino)thieno[3,2-d]pyrimidin-4-yl)methanone (Z483): The title compound (Z483) was prepared from (S)-6-methyl-2-((1-(pyridin-2-yl)ethyl)amino)thieno[3,2-d]pyrimidine-4-carboxylic acid di-hydrochloride (39 mg, 0.10 mmol) using chemistry similar to that described in Example Z8 using 3-methoxy-3-methylazetidine in place of (R)-3-fluoropyrrolidine (10 mg, 25% yield). ¹H NMR (400 MHz, CDCl₃) δ 1.46 (3H, s), 1.61 (3H, d, J=6.8 Hz), 2.60 (3H, d, J=1.2 Hz), 3.26 (3H, s), 3.93 (1H, m), 4.02-4.34 (2H, m), 4.52 (1H, d, J=11.6 Hz), 5.19 (1H, m), 5.87 (1H, m), 6.86 (1H, d, J=1.2 Hz), 7.16 (1H, m), 7.35 (1H, m), 7.62 (1H, m), 8.57 (1H, m) ppm. LCMS m/z=398.1 [M+H⁺].

Example Z484. tert-Butyl (S)-(1-(2-((1-(5-fluoropyridin-3-yl)ethyl)amino)-6-methylthieno[3,2-d]pyrimidine-4-carbonyl)azetidin-3-yl)(methyl)carbamate

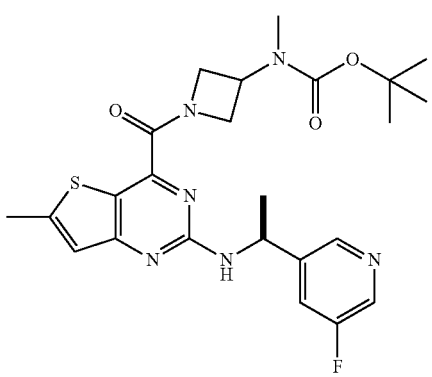 [SMILES: Cc1cc2nc(N[C@@H](C)c3cncc(F)c3)nc(C(=O)N3CC(N(C)C(=O)OC(C)(C)C)C3)c2s1]

(Z484)

Synthesis of tert-butyl (S)-(1-(2-((1-(5-fluoropyridin-3-yl)ethyl)amino)-6-methylthieno[3,2-d]pyrimidine-4-carbonyl)azetidin-3-yl)(methyl)carbamate (Z484): The title compound (Z484) was prepared from (S)-2-((1-(5-fluoropyridin-3-yl)ethyl)amino)-6-methylthieno[3,2-d]pyrimidine-4-carboxylic acid di-hydrochloride using chemistry similar to that described in Example Z17 using tert-butyl N-(azetidin-3-yl)-N-methyl-carbamate hydrochloride (commercially obtained from PharmaBlock, Sunnyvale, Calif.) in place of (3R)-3-methoxypyrrolidine hydrochloride (56% yield). ¹H NMR (400 MHz, CDCl₃) δ 1.48 (9H, s), 1.63 (3H, d, J=6.8 Hz), 2.60 (3H, s), 2.91 (3H, d, J=31.2 Hz), 4.19-4.27 (1H, m), 4.40 (2H, m), 4.60-4.70 (1H, m), 4.86 (1H, m), 5.21 (1H, q, J=6.4 Hz), 5.31 (1H, m), 6.85 (1H, m), 7.41 (1H, tt, J=6.8, 2.0 Hz), 8.34 (1H, t, J=2.4 Hz), 8.49 (1H, d, J=5.6 Hz) ppm. LCMS m/z=501.2 [M+H⁺].

Example Z485. tert-Butyl (S)-3-(2-(2-((1-(5-fluoropyridin-3-yl)ethyl)amino)-6-methylthieno[3,2-d]pyrimidine-4-carboxamido)ethyl)azetidine-1-carboxylate

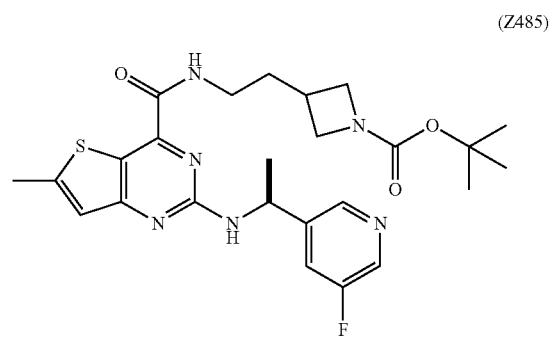

(Z485)

Synthesis of tert-butyl (S)-3-(2-(2-((1-(5-fluoropyridin-3-yl)ethyl)amino)-6-methylthieno[3,2-d]pyrimidine-4-carboxamido)ethyl)azetidine-1-carboxylate (485): The title compound (485) was prepared from (S)-2-((1-(5-fluoropyridin-3-yl)ethyl)amino)-6-methyl-thieno[3,2-d]pyrimidine-4-carboxylic acid di-hydrochloride using chemistry similar to that described in Example Z17 using tert-butyl 3-(2-aminoethyl)azetidine-1-carboxylate (commercially obtained from PharmaBlock, Sunnyvale, Calif.) in place of (3R)-3-methoxypyrrolidine hydrochloride (79% yield). LCMS m/z=515.3 [M+H⁺].

Example Z486. (S)-(3-Methoxy-3-methylazetidin-1-yl)(2-((1-(pyridin-2-yl)ethyl)amino)thieno[3,2-d]pyrimidin-4-yl)methanone

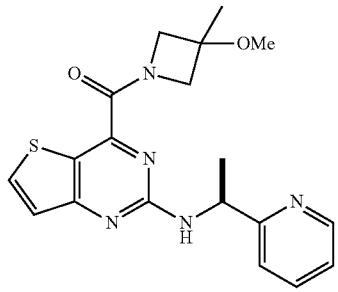 [SMILES: COC1(C)CN(C(=O)c2nc(N[C@@H](C)c3ccccn3)nc3ccsc23)C1]

(Z486)

Synthesis of (S)-(3-methoxy-3-methylazetidin-1-yl)(2-((1-(pyridin-2-yl)ethyl)amino)thieno[3,2-d]pyrimidin-4-yl)methanone (Z486): The title compound (Z486) was prepared from (S)-2-((1-(pyridin-2-yl)ethyl)amino)thieno[3,2-d]pyrimidine-4-carboxylic acid di-hydrochloride (37 mg, 0.10 mmol) using chemistry similar to that described in Example Z8 using 3-methoxy-3-methylazetidine in place of (R)-3-fluoropyrrolidine (13 mg, 34% yield). $^1$H NMR (400 MHz, CDCl$_3$) δ 1.48 (3H, s), 1.63 (3H, d, J=6.8 Hz), 3.27 (3H, s), 3.96 (1H, m), 4.08-4.40 (2H, m), 4.55 (1H, d, J=11.2 Hz), 5.22 (1H, m), 5.99 (1H, m), 7.18 (1H, m), 7.19 (1H, d, J=8.0 Hz), 7.35 (1H, dd, J=8.0, 4.8 Hz), 7.63 (1H, tt, J=8.0, 1.6 Hz), 7.96 (1H, d, J=4.8 Hz), 8.58 (1H, d, J=4.0 Hz) ppm. LCMS m/z=384.1 [M+H$^+$].

Example Z487. tert-Butyl (S)-4-(2-(2-((1-(5-fluoropyridin-3-yl)ethyl)amino)-6-methylthieno[3,2-d]pyrimidine-4-carboxamido)ethyl)piperidine-1-carboxylate

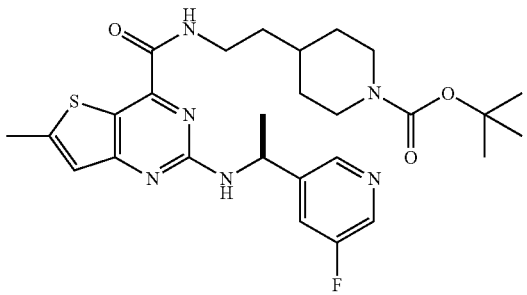 [SMILES: Cc1cc2nc(N[C@@H](C)c3cncc(F)c3)nc(C(=O)NCCC3CCN(C(=O)OC(C)(C)C)CC3)c2s1]

(Z487)

Synthesis of tert-butyl (S)-4-(2-(2-((1-(5-fluoropyridin-3-yl)ethyl)amino)-6-methyl-thieno[3,2-d]pyrimidine-4-carboxamido)ethyl)piperidine-1-carboxylate (Z487): The title compound (Z487) was prepared from (S)-2-((1-(5-fluoropyridin-3-yl)ethyl)amino)-6-methylthieno[3,2-d]pyrimidine-4-carboxylic acid di-hydrochloride using chemistry similar to that described in Example Z17 using tert-butyl 4-(2-aminoethyl)piperidine-1-carboxylate (commercially obtained from Combi Blocks, San Diego, Calif.) in place of (3R)-3-methoxy-pyrrolidine hydrochloride (78% yield). $^1$H NMR (400 MHz, CDCl$_3$) δ 1.10-1.20 (2H, m), 1.46 (9H, s), 1.45-1-50 (1H m), 1.51-1.57 (2H, m), 1.63 (3H, d, J=6.8 Hz), 1.67-1.73 (2H, m), 2.61 (3H, d, J=1.2 Hz), 2.66-2.72 (2H, m), 3.42-3.49 (2H, m), 4.08 (2H, m), 5.17 (1H, q, J=6.4 Hz), 5.80 (1H, m), 6.88 (1H, d, J=1.2 Hz), 7.41 (1H, dt, J=9.6, 2.4 Hz), 7.57 (1H, br s), 8.34 (1H, d, J=2.4 Hz), 8.53 (1H, t, J=1.6 Hz) ppm. LCMS m/z=543.2 [M+H$^+$].

Example Z488. (S)—N-(4-Acetamidophenethyl)-2-((1-(5-fluoropyridin-3-yl)ethyl)amino)-6-methylthieno[3,2-d]pyrimidine-4-carboxamide

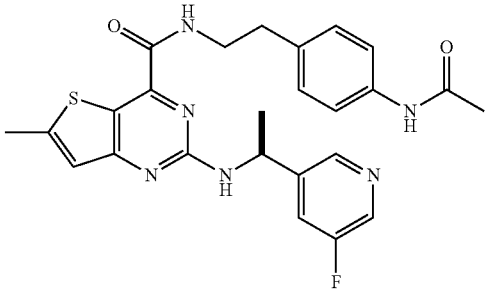 [SMILES: CC(=O)Nc1ccc(CCNC(=O)c2nc(N[C@@H](C)c3cncc(F)c3)nc3cc(C)sc23)cc1]

(Z488)

Synthesis of (S)—N-(4-acetamidophenethyl)-2-((1-(5-fluoropyridin-3-yl)ethyl)amino)-6-methylthieno[3,2-d]pyrimidine-4-carboxamide (Z488): The title compound (Z488) was prepared from (S)-2-((1-(5-fluoropyridin-3-yl)ethyl)amino)-6-methylthieno[3,2-d]pyrimidine-4-carboxylic acid di-hydrochloride using chemistry similar to that described in Example Z17 using N-[4-(2-aminoethyl)phenyl]acetamide (commercially obtained from Enamine, Monmouth Jct., N.J.) in place of (3R)-3-methoxypyrrolidine hydrochloride (44% yield). $^1$H NMR (400 MHz, CDCl$_3$) δ 1.60 (3H, d, J=6.8 Hz), 2.17 (3H, s), 2.61 (3H, d, J=0.8 Hz), 2.87 (2H, t, J=6.8 Hz), 3.56-3.66 (1H, m), 3.67-3.76 (1H, m), 5.14 (1H, q, J=6.4 Hz), 5.36 (1H, d, J=6.8 Hz), 6.84 (1H, d, J=1.2 Hz), 7.19 (2H, d, J=8.8 Hz), 7.37 (2H, dd, J=9.6, 2.0 Hz), 7.49 (2H, d, J=8.4 Hz), 7.64-7.72 (1H, m), 8.33 (1H, d, J=2.8 Hz), 8.38 (1H, br s) ppm. LCMS m/z=493.2 [M+H$^+$].

Example Z489. 2-(((S)-1-(5-Fluoropyridin-3-yl)ethyl)amino)-6-methyl-N-(2-((S)-pyrrolidin-3-yl)ethyl)thieno[3,2-d]pyrimidine-4-carboxamide

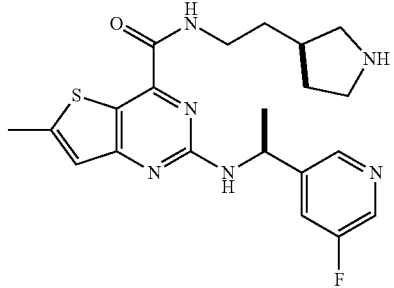 [SMILES: Cc1cc2nc(N[C@@H](C)c3cncc(F)c3)nc(C(=O)NCC[C@@H]3CCNC3)c2s1]

(Z489)

Synthesis of 2-(((S)-1-(5-fluoropyridin-3-yl)ethyl)amino)-6-methyl-N-(2-((S)-pyrrolidin-3-yl)ethyl)thieno[3,2-d]pyrimidine-4-carboxamide (Z489): The title compound (Z489) was prepared from (S)-2-((1-(5-fluoropyridin-3-yl)ethyl)amino)-6-methylthieno[3,2-d]pyrimidine-4-carboxylic acid di-hydrochloride (40.5 mg, 0.10 mmol) using chemistry similar to that described in Example Z463 using tert-butyl (R)-3-(2-aminoethyl)pyrrolidine-1-carboxylate (commercially obtained from Ark Pham, Arlington Heights, Ill.) in place of tert-butyl (S)-3-(2-aminoethyl)pyrrolidine-1-carboxylate (41 mg, 100% yield). $^1$H NMR (400 MHz, CDCl$_3$) δ 1.62 (3H, d, J=6.8 Hz), 1.66-1.80 (4H, m), 2.26 (1H, m), 2.38 (1H, m), 2.60 (3H, d, J=1.2 Hz), 2.93 (1H, dd, J=11.2, 8.8 Hz), 3.27 (1H, m), 3.39-3.52 (4H, m), 5.17 (1H, quintet, J=6.8 Hz), 5.52 (1H, d, J=6.8 Hz), 6.85 (1H, d, J=1.2 Hz), 7.47 (1H, d, J=8.0 Hz), 7.74 (1H, m), 8.34 (1H, s), 8.54 (1H, s), 9.81 (1H, m) ppm. LCMS m/z=429.2 [M+H$^+$].

Example Z490. (S)—N-((1-(2-((1-(5-Fluoropyridin-3-yl)ethyl)amino)-6-methylthieno[3,2-d]pyrimidine-4-carbonyl)azetidin-3-yl)methyl)pivalamide

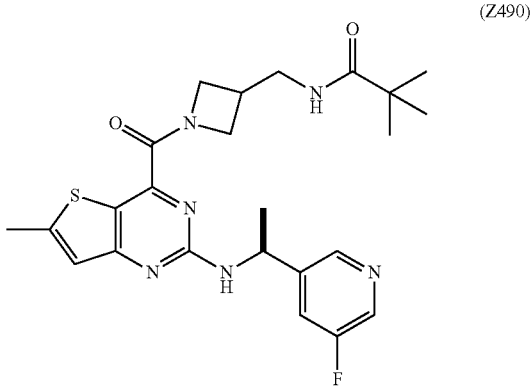

(Z490)

Synthesis of (S)—N-((1-(2-((1-(5-fluoropyridin-3-yl)ethyl)amino)-6-methylthieno[3,2-d]pyrimidine-4-carbonyl)azetidin-3-yl)methyl)pivalamide (Z490): Pivaloyl chloride (commercially obtained from Sigma-Aldrich, St. Louis, Mo.) (3.6 mg, 0.03 mmol) was added to a mixture of (S)-(3-(aminomethyl)azetidin-1-yl)(2-((1-(5-fluoropyridin-3-yl)ethyl)amino)-6-methylthieno[3,2-d]pyrimidin-4-yl)methanone di-hydrochloride (10 mg, 0.025 mmol) and DIEA (6.5 mg, 0.05 mmol) in DCM (0.7 mL), a resulting mixture was stirred at room temperature for 2 hours, concentrated and purified by flash chromatography (12 g, HP silica, Teledyne Isco) eluting with 0% to 10% MeOH in DCM to give (S)—N-((1-(2-((1-(5-fluoropyridin-3-yl)ethyl)amino)-6-methylthieno[3,2-d]pyrimidine-4-carbonyl)azetidin-3-yl)methyl)pivalamide (81% yield). $^1$H NMR (400 MHz, CDCl$_3$) δ 1.23 (9H, d, J=6.0 Hz), 1.62 (3H, dd, J=7.2, 3.2 Hz), 2.61 (3H, t, J=0.8 Hz), 2.79-2.89 (1H, m), 3.48-3.60 (2H, m), 3.79 (1H, q, J=5.2 Hz), 3.87 (1H, q, J=5.2 Hz), 4.21-4.32 (2H, m), 5.16 (1H, q, J=6.4 Hz), 5.32 (1H, dd, J=10.4, 5.6 Hz), 5.93 (1H, m), 6.84 (1H, t, J=1.2 Hz), 7.49 (1H, dd, J=9.6, 2.0 Hz), 8.33 (1H, dd, J=8.0, 2.8 Hz), 8.44-8.49 (1H, m) ppm. LCMS m/z=485.1 [M+H$^+$].

Example Z491. Benzyl ((R)-1-(2-(((S)-1-(5-fluoropyridin-3-yl)ethyl)amino)-6-methylthieno[3,2-d]pyrimidine-4-carbonyl)pyrrolidin-3-yl)carbamate

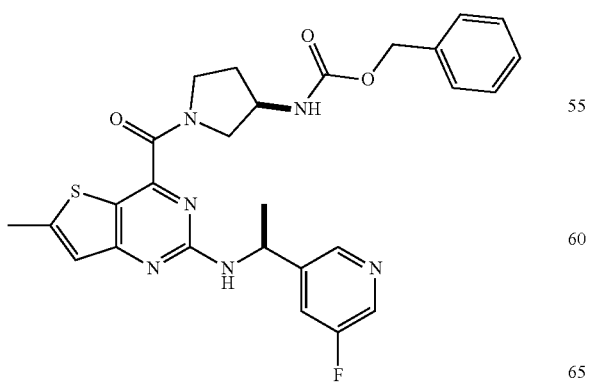

(Z491)

Synthesis of benzyl ((R)-1-(2-(((S)-1-(5-fluoropyridin-3-yl)ethyl)amino)-6-methylthieno[3,2-d]pyrimidine-4-carbonyl)pyrrolidin-3-yl)carbamate (Z491): The title compound (Z491) was prepared from (S)-2-((1-(5-fluoropyridin-3-yl)ethyl)amino)-6-methylthieno[3,2-d]pyrimidine-4-carboxylic acid di-hydrochloride using chemistry similar to that described in Example Z17 using benzyl N-[(3R)-pyrrolidin-3-yl]carbamate (commercially obtained from Cambridge Chemical, Cambridge, UK) in place of (3R)-3-methoxypyrrolidine hydrochloride (76% yield). LCMS m/z=535.1 [M+H$^+$].

Example Z492. (S)-6-Methyl-2-((1-(pyridin-2-yl)ethyl)amino)-N-(thiazol-2-ylmethyl)thieno[3,2-d]pyrimidine-4-carboxamide

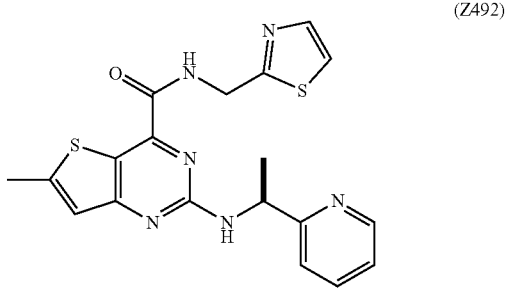

(Z492)

Synthesis of (S)-6-methyl-2-((1-(pyridin-2-yl)ethyl)amino)-N-(thiazol-2-ylmethyl)thieno[3,2-d]pyrimidine-4-carboxamide (Z492): The title compound (Z492) was prepared from (S)-6-methyl-2-((1-(pyridin-2-yl)ethyl)amino)thieno[3,2-d]pyrimidine-4-carboxylic acid di-hydrochloride (39 mg, 0.10 mmol) using chemistry similar to that described in Example Z8 using thiazol-2-ylmethanamine (commercially obtained from Ark Pham, Arlington Heights, Ill.) in place of (R)-3-fluoropyrrolidine (26 mg, 63% yield). $^1$H NMR (400 MHz, CDCl$_3$) δ 1.60 (3Hm d, J=6.8 Hz), 2.62 (3H, d, J=0.8 Hz), 4.94 (1H, dd, J=8.0, 6.0 Hz), 5.00 (1H, dd, J=8.0, 6.0 Hz), 5.22 (1H, quintet, J=6.8 Hz), 6.08 (1H, d, J=6.8 Hz), 6.88 (1H, d, J=0.8 Hz), 7.12 (1H, dd, J=8.0, 4.8 Hz), 7.32 (1H, d, J=3.2 Hz), 7.34 (1H, d, J=8.0 Hz), 7.60 (1H, td, J=8.0, 1.6 Hz), 7.77 (1H, d, J=3.2 Hz), 8.51-8.54 (2H, m) ppm. LCMS m/z=411.0 [M+H$^+$].

Example Z493. (S)—N-(4-Aminophenethyl)-2-((1-(5-fluoropyridin-3-yl)ethyl)amino)thieno[3,2-d]pyrimidine-4-carboxamide

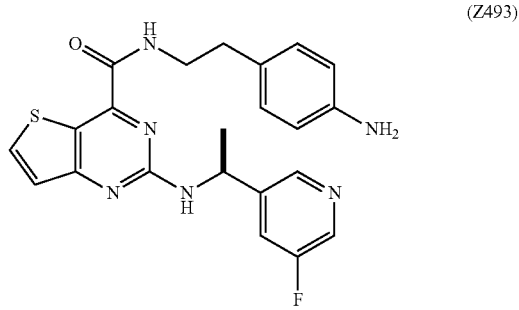

(Z493)

Synthesis of (S)—N-(4-aminophenethyl)-2-((1-(5-fluoropyridin-3-yl)ethyl)amino)thieno[3,2-d]pyrimidine-4-carboxamide (Z493): The title compound (Z493) was prepared from tert-butyl (S)-(4-(2-(2-((1-(5-fluoropyridin-3-yl)ethyl)amino)thieno[3,2-d]pyrimidine-4-carboxamido)ethyl)-phenyl)carbamate using chemistry similar to that described in Example Z358 (53% yield). $^1$H NMR (400 MHz, CDCl$_3$) δ 1.62 (3H, d, J=6.8 Hz), 2.81 (2H, q, J=6.0 Hz), 3.56-3.65 (2H, m), 3.69-3.78 (1H, m), 5.14 (1H, q, J=6.4 Hz), 5.39 (1H, d, J=6.8 Hz), 6.84 (2H, dt, J=8.4, 2.4 Hz), 7.03 (2H, dt, J=8.4, 2.4 Hz), 7.17 (1H, d, J=5.6 Hz), 7.37 (2H, dt, J=9.2, 2.0 Hz), 7.74 (1H, m), 8.00 (1H, d, J=5.6 Hz), 8.33 (1H, d, J=2.8 Hz), 8.42 (1H, s) ppm. LCMS m/z=437.1[M+H$^+$].

Example Z494. (S)-(2-((1-(5-Fluoropyridin-3-yl)ethyl)amino)-6-methylthieno[3,2-d]pyrimidin-4-yl)(3-(hydroxymethyl)azetidin-1-yl)methanone

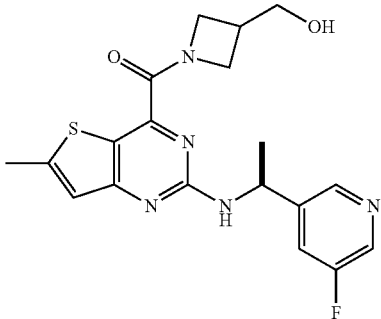 [SMILES: Cc1cc2nc(N[C@@H](C)c3cncc(F)c3)nc(C(=O)N3CC(CO)C3)c2s1]
(Z494)

Synthesis of (S)-(2-((1-(5-fluoropyridin-3-yl)ethyl)amino)-6-methylthieno[3,2-d]pyrimidin-4-yl)(3-(hydroxymethyl)azetidin-1-yl)methanone (Z494): The title compound (Z494) was prepared from (S)-2-((1-(5-fluoropyridin-3-yl)ethyl)amino)-6-methylthieno[3,2-d]pyrimidine-4-carboxylic acid di-hydrochloride (40.5 mg, 0.10 mmol) using chemistry similar to that described in Example Z8 using azetidin-3-ylmethanol (commercially obtained from Ark Pham, Arlington Heights, Ill.) in place of (R)-3-fluoropyrrolidine (12 mg, 30% yield). $^1$H NMR (400 MHz, CDCl$_3$) δ 1.62 (3H, d, J=6.8 Hz), 2.60 (3H, s), 2.82 (1H, m), 3.62-4.04 (4H, m), 4.22-4.34 (2H, m), 5.16 (1H, quintet, J=6.8 Hz), 5.32 (1H, d, J=6.8 Hz), 6.84 (1H, s), 7.44 (1H, m), 8.33 (1H, d, J=6.8 Hz), 8.48 (1H, dt, J=11.2, 1.6 Hz) ppm. LCMS m/z=402.2 [M+H$^+$].

Example Z495. (S)—N-Ethyl-2-(1-(2-((1-(5-fluoropyridin-3-yl)ethyl)amino)-6-methylthieno[3,2-d]pyrimidine-4-carbonyl)azetidin-3-yl)acetamide

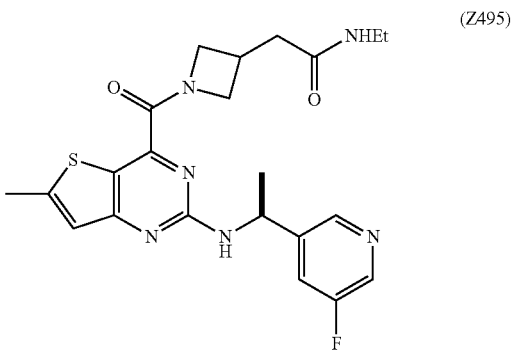
(Z495)

Synthesis of tert-butyl 3-(2-(ethylamino)-2-oxoethyl)azetidine-1-carboxylate: The title compound was prepared from 2-(1-tert-butoxycarbonylazetidin-3-yl)acetic acid (commercially obtained from PharmaBlock, Sunnyvale, Calif.) using chemistry similar to that described in Example Z17 using ethanamine hydrochloride (commercially obtained from TCI America, Portland, Oreg.) in place of (3R)-3-methoxypyrrolidine hydrochloride (100% yield). LCMS m/z=265.3 [M+Na].

Synthesis of 2-(azetidin-3-yl)-N-ethylacetamide hydrochloride: To a solution of tert-butyl 3-(2-(ethylamino)-2-oxoethyl)azetidine-1-carboxylate (112 mg, 0.46 mmol) in DCM (1 mL) was added a solution of 4 M hydrogen chloride in 1,4-dioxane (0.2 mL), the resulting mixture was stirred at room temperature for 1 hour, concentrated, and dried in vacuo to give crude 2-(azetidin-3-yl)-N-ethylacetamide hydrochloride which was used in next step without further purification (80 mg, 96% yield). LCMS m/z=143.1 [M+H$^+$].

Synthesis of (S)—N-ethyl-2-(1-(2-((1-(5-fluoropyridin-3-yl)ethyl)amino)-6-methylthieno[3,2-d]pyrimidine-4-carbonyl)azetidin-3-yl)acetamide (Z495): The title compound (Z495) was prepared from (S)-2-((1-(5-fluoropyridin-3-yl)ethyl)amino)-6-methylthieno[3,2-d]pyrimidine-4-carboxylic acid di-hydrochloride using chemistry similar to that described in Example Z17 using 2-(azetidin-3-yl)-N-ethylacetamide hydrochloride in place of (3R)-3-methoxypyrrolidine hydrochloride (18% yield). LCMS m/z=457.3 [M+H$^+$].

Example Z496. (S)-2-((1-(5-Fluoropyridin-3-yl)ethyl)amino)-6-methyl-N-(2-(piperidin-4-yl)ethyl)thieno[3,2-d]pyrimidine-4-carboxamide

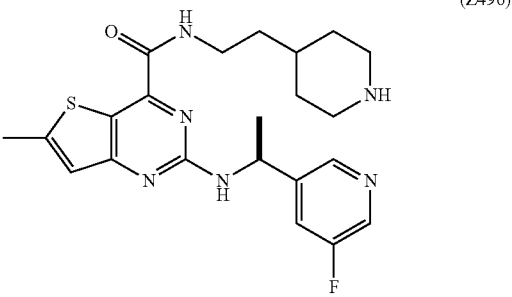
(Z496)

Synthesis of (S)-2-((1-(5-fluoropyridin-3-yl)ethyl)amino)-6-methyl-N-(2-(piperidin-4-yl)ethyl)thieno[3,2-d]pyrimidine-4-carboxamide (Z496): The title compound (Z496) was prepared from (S)-2-((1-(5-fluoropyridin-3-yl)ethyl)amino)-6-methylthieno[3,2-d]pyrimidine-4-carboxylic acid di-hydrochloride (81 mg, 0.20 mmol) using chemistry similar to that described in Example Z463 using tert-butyl 4-(2-aminoethyl)piperidine-1-carboxylate in place of tert-butyl (S)-3-(2-aminoethyl)pyrrolidine-1-carboxylate (88 mg, 100% yield). $^1$H NMR (400 MHz, CDCl$_3$) δ 1.51-1.62 (5H, m), 1.64 (3H, d, J=7.2 Hz), 1.93-2.02 (2H, m), 2.61 (3H, s), 2.80-2.94 (2H, m), 3.38-3.54 (4H, m), 5.17 (1H, m), 5.52 (1H, br s), 6.86 (1H, s), 7.45 (1H, dt, J=9.6, 2.0 Hz), 7.62 (1H, br s), 8.34 (1H, d, J=2.0 Hz), 8.53 (1H, s) ppm. LCMS m/z=443.1 [M+H$^+$].

Example Z497. (S)—N-(4-Acetamidophenethyl)-6-methyl-2-((1-(pyridin-3-yl)ethyl)amino)thieno[3,2-d]pyrimidine-4-carboxamide

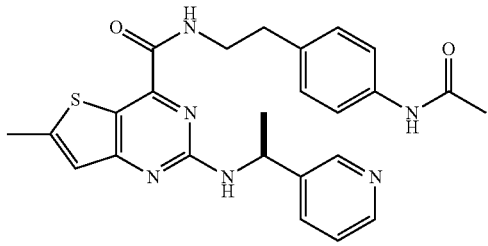 [SMILES: CC(=O)Nc1ccc(CCNC(=O)c2nc(N[C@@H](C)c3cccnc3)nc3cc(C)sc23)cc1]

(Z497)

Synthesis of (S)—N-(4-acetamidophenethyl)-6-methyl-2-((1-(pyridin-3-yl)ethyl)amino)thieno[3,2-d]pyrimidine-4-carboxamide (Z497): The title compound (Z497) was prepared from (S)-6-methyl-2-((1-(pyridin-3-yl)ethyl)amino)thieno[3,2-d]pyrimidine-4-carboxylic acid di-hydrochloride using chemistry similar to that described in Example Z8 using N-[4-(2-aminoethyl)phenyl]acetamide (commercially obtained from Enamine, Monmouth Jct., N.J.) in place of (R)-3-fluoropyrrolidine (23% yield). $^1$H NMR (400 MHz, CDCl$_3$) δ 1.58 (3H, d, J=7.2 Hz), 2.17 (3H, s), 3.33 (3H, m), 2.87 (2H, t, J=6.8 Hz), 3.62-3.71 (2H, m), 5.11 (1H, q, J=6.8 Hz), 5.38 (1H, d, J=7.2 Hz), 6.84 (1H, d, J=0.8 Hz), 7.16 (2H, d, J=8.0 Hz), 7.23 (1H, dd, J=8.0, 4.8 Hz), 7.44 (2H, d, J=8.8 Hz), 7.62-7.00 (3H, m), 8.47 (1H, dd, J=4.8, 1.2 Hz), 8.54 (1H, s) ppm. LCMS m/z=483.2 [M+H$^+$].

Example Z498. tert-Butyl (S)-((1-(6-methyl-2-((1-(pyridin-3-yl)ethyl)amino)thieno[3,2-d]pyrimidine-4-carbonyl)azetidin-3-yl)methyl)carbamate

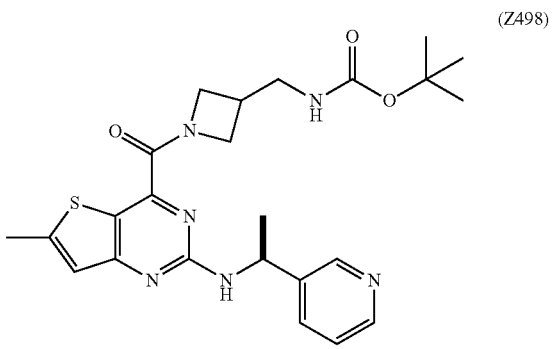

(Z498)

Synthesis of tert-butyl (S)-((1-(6-methyl-2-((1-(pyridin-3-yl)ethyl)amino)thieno[3,2-d]pyrimidine-4-carbonyl)azetidin-3-yl)methyl)carbamate (Z498): The title compound (Z498) was prepared from (S)-6-methyl-2-((1-(pyridin-3-yl)ethyl)amino)thieno[3,2-d]pyrimidine-4-carboxylic acid di-hydrochloride using chemistry similar to that described in Example Z8 using tert-butyl N-(azetidin-3-ylmethyl)carbamate hydrochloride (commercially obtained from PharmaBlock, Sunnyvale, Calif.) in place of (R)-3-fluoropyrrolidine (27% yield). $^1$H NMR (400 MHz, CDCl$_3$) δ 1.46 (9H, d, J=2.0 Hz), 1.61 (3H, dd, J=6.4, 4.0 Hz), 2.59 (3H, d, J=0.8 Hz), 3.29-3.38 (2H, m), 3.76-3.86 (2H, m), 4.22 (2H, dd, J=9.2, 1.2 Hz), 4.94 (1H, m), 5.13 (1H, q, J=6.4 Hz), 5.31 (1H, m), 6.84 (1H, d, J=1.2 Hz), 7.23-7.27 (2H, m), 7.67-7.71 (1H, m), 8.48-8.51 (1H, m), 8.65 (1H, dd, J=6.4, 2.4 Hz) ppm. LCMS m/z=483.2 [M+H$^+$].

Example Z499. (S)-(3-(Aminomethyl)azetidin-1-yl)(6-methyl-2-((1-(pyridin-3-yl)ethyl)amino)thieno[3,2-d]pyrimidin-4-yl)methanone

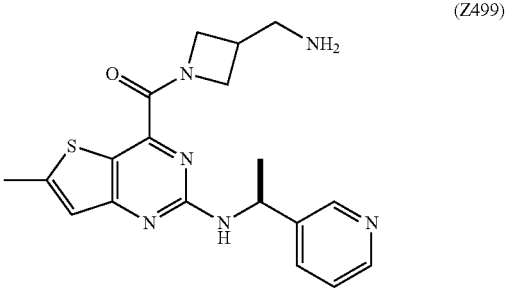

(Z499)

Synthesis of (S)-(3-(aminomethyl)azetidin-1-yl)(6-methyl-2-((1-(pyridin-3-yl)ethyl)amino)thieno[3,2-d]pyrimidin-4-yl)methanone (Z499): The title compound (Z499) was prepared from tert-butyl (S)-((1-(6-methyl-2-((1-(pyridin-3-yl)ethyl)amino)thieno[3,2-d]pyrimidine-4-carbonyl)azetidin-3-yl)methyl)carbamate using chemistry similar to that described in Example Z358 (116% yield). LCMS m/z=383.1[M+H$^+$].

Example Z500. 6-Methyl-2-(((S)-1-(pyridin-3-yl)ethyl)amino)-N-(2-((S)-pyrrolidin-3-yl)ethyl)thieno[3,2-d]pyrimidine-4-carboxamide

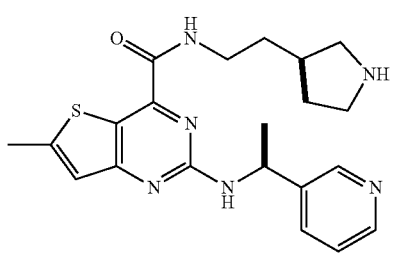 [SMILES: Cc1cc2nc(N[C@@H](C)c3cccnc3)nc(C(=O)NCC[C@@H]3CCNC3)c2s1]
(Z500)

Synthesis of 6-methyl-2-(((S)-1-(pyridin-3-yl)amino)-N-(2-((S)-pyrrolidin-3-yl)ethyl)thieno[3,2-d]pyrimidine-4-carboxamide (Z500): The title compound (Z500) was prepared from (S)-6-methyl-2-((1-(pyridin-3-yl)ethyl)amino)thieno[3,2-d]pyrimidine-4-carboxylic acid di-hydrochloride (39 mg, 0.10 mmol) using chemistry similar to that described in Example Z463 using tert-butyl (R)-3-(2-aminoethyl)pyrrolidine-1-carboxylate in place of tert-butyl (S)-3-(2-aminoethyl)pyrrolidine-1-carboxylate (35 mg, 68% yield). LCMS m/z=411.2 [M+H$^+$].

Example Z501. 6-Methyl-2-(((S)-1-(pyridin-3-yl)ethyl)amino)-N-(2-((R)-pyrrolidin-3-yl)ethyl)thieno[3,2-d]pyrimidine-4-carboxamide

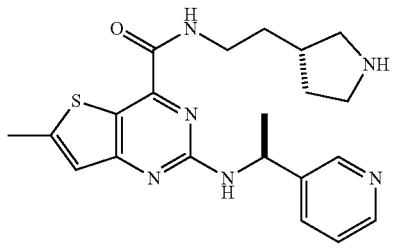 [SMILES: Cc1cc2nc(N[C@@H](C)c3cccnc3)nc(C(=O)NCC[C@H]3CCNC3)c2s1]
(Z501)

Synthesis of 6-methyl-2-(((S)-1-(pyridin-3-yl)amino)-N-(2-((R)-pyrrolidin-3-yl)ethyl)thieno[3,2-d]pyrimidine-4-carboxamide (Z501): The title compound (Z501) was prepared from (S)-6-methyl-2-((1-(pyridin-3-yl)ethyl)amino)thieno[3,2-d]pyrimidine-4-carboxylic acid di-hydrochloride (39 mg, 0.10 mmol) using chemistry similar to that described in Example Z463. (33 mg, 65% yield). $^1$H NMR (400 MHz, CDCl$_3$) δ 1.63 (3H, d, J=6.8 Hz), 1.67-1.81 (2H, m), 2.23 (1H, m), 2.27-2.43 (3H, m), 2.60 (3H, s), 3.03 (1H, t, J=9.2 Hz), 3.26 (1H, m), 3.41-3.52 (4H, m), 5.20 (1H, m), 5.90 (1H, m), 6.84 (1H, s), 7.37 (1H, m), 7.80-7.88 (2H, m), 8.48 (1H, m), 8.78 (1H, m) ppm. LCMS m/z=411.2 [M+H$^+$].

Example Z502. (S)-(3-((Dimethylamino)methyl)azetidin-1-yl)(2-((1-(5-fluoropyridin-3-yl)ethyl)amino)-6-methylthieno[3,2-d]pyrimidin-4-yl)methanone

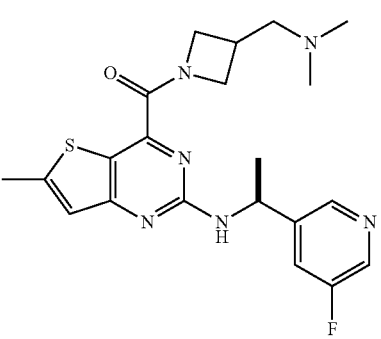 [SMILES: Cc1cc2nc(N[C@@H](C)c3cncc(F)c3)nc(C(=O)N3CC(CN(C)C)C3)c2s1]
(Z502)

Synthesis of (S)-(3-((dimethylamino)methyl)azetidin-1-yl)(2-((1-(5-fluoropyridin-3-yl)ethyl)amino)-6-methylthieno[3,2-d]pyrimidin-4-yl)methanone (Z502): The title compound (Z502) was prepared from (S)-2-((1-(5-fluoropyridin-3-yl)ethyl)amino)-6-methylthieno[3,2-d]pyrimidine-4-carboxylic acid di-hydrochloride (40.5 mg, 0.10 mmol) using chemistry similar to that described in Example Z8 using 1-(azetidin-3-yl)-N,N-dimethylmethanamine di-hydrochloride in place of (R)-3-fluoropyrrolidine (23 mg, 54% yield). $^1$H NMR (400 MHz, CDCl$_3$) δ 1.62 (3H, d, J=6.8 Hz), 2.24 (3H, s), 2.26 (3H, s), 2.45-2.57 (2H, m), 2.60 (3H, s), 2.82 (1H, m), 2.84 (1H, m), 4.29 (1H, t, J=9.6 Hz), 4.31 (1H, m), 4.55 (1H, t, J=9.6 Hz), 5.22 (1H, quintet, J=6.8 Hz), 5.29 (1H, d, J=6.8 Hz), 6.84 (1H, s), 7.41 (1H, d, J=9.2 Hz), 8.33 (1H, d, J=2.8 Hz), 8.49 (1H, s) ppm. LCMS m/z=429.2 [M+H$^+$].

Example Z503. N-((1s,3R)-3-hydroxycyclobutyl)-6-methyl-2-(((S)-1-(pyridin-3-yl)ethyl)amino)thieno[3,2-d]pyrimidine-4-carboxamide

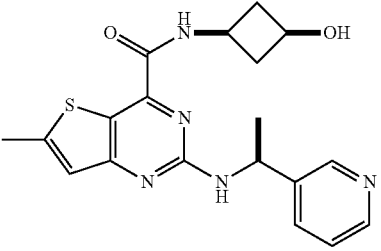
(Z503)

Synthesis of N-((1s,3R)-3-hydroxycyclobutyl)-6-methyl-2-(((S)-1-(pyridin-3-yl)ethyl)amino)thieno[3,2-d]pyrimidine-4-carboxamide (Z503): The title compound (Z503) was prepared from (S)-6-methyl-2-((1-(pyridin-3-yl)ethyl)amino)thieno[3,2-d]pyrimidine-4-carboxylic acid di-hydrochloride using chemistry similar to that described in Example Z8 using cis-3-aminocyclobutanol hydrochloride in place of (R)-3-fluoropyrrolidine (38% yield). $^1$H NMR (400 MHz, DMSO-d$_6$) δ 1.25 (1H, m), 1.51 (3H, d, J=7.2 Hz), 1.90-2.05 (2H m), 2.55 (3H, d, J=1.2 Hz), 2.57-2.60 (2H, m), 3.88-3.92 (2H, m), 5.25-5.40 (1H, m), 6.92 (1H, d, J=1.2 Hz), 7.32 (1H, ddd, J=8.2, 4.6, 0.8 Hz), 7.75-7.81 (1H, m), 7.86 (1H, d, J=8.0 Hz), 8.39 (1H, dd, J=4.4, 1.6 Hz), 8.5 (1H, d, J=8.4 Hz), 8.71 (1H, br s) ppm. LCMS m/z=384.2 [M+H$^+$].

Example Z504. (S)-1-(2-((1-(5-Fluoropyridin-3-yl)ethyl)amino)-6-methylthieno[3,2-d]pyrimidine-4-carbonyl)azetidine-3-carboxamide

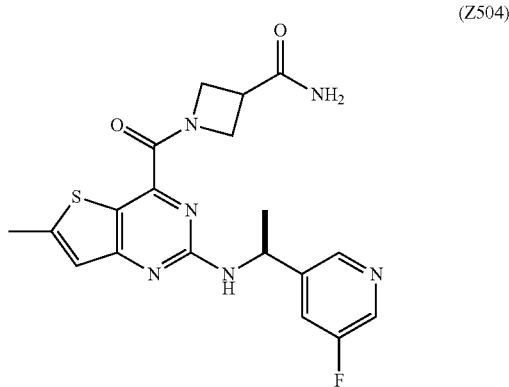

Synthesis of (S)-1-(2-((1-(5-fluoropyridin-3-yl)ethyl)amino)-6-methylthieno[3,2-d]pyrimidine-4-carbonyl)azetidine-3-carboxamide (Z504): The title compound (Z504) was prepared from (S)-2-((1-(5-fluoropyridin-3-yl)ethyl)amino)-6-methylthieno[3,2-d]pyrimidine-4-carboxylic acid di-hydrochloride using chemistry similar to that described in Example Z17 using azetidine-3-carboxamide hydrochloride (commercially obtained from PharmaBlock, Sunnyvale, Calif.) in place of (3R)-3-methoxypyrrolidine hydrochloride (26% yield). $^1$H NMR (400 MHz, DMSO-d$_6$) δ 1.51 (3H, d, J=6.8 Hz), 2.55 (3H, d, J=1.2 Hz), 3.35-3.37 (1H, m), 4.03-4.06 (1H, m), 4.17 (1H, t, J=10.0 Hz), 4.65-4.85 (2H, m), 5.20 (1H, m), 6.93 (1H s), 7.08 (1H, d, J=5.6 Hz), 7.52 (1H, d, J=10.0 Hz), 7.70-7.74 (1H, m), 7.79 (1H, s), 8.40 (1H, dd, J=5.2, 2.8 Hz), 8.51 (1H, br s) ppm. LCMS m/z=415.1 [M+H$^+$].

Example Z505. (S)—N-((1-(6-Methyl-2-((1-(pyridin-3-yl)ethyl)amino)thieno[3,2-d]pyrimidine-4-carbonyl)azetidin-3-yl)methyl)pivalamide

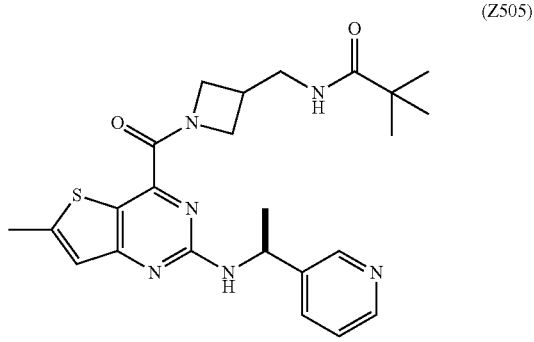

Synthesis of (S)—N-((1-(6-methyl-2-((1-(pyridin-3-yl)ethyl)amino)thieno[3,2-d]pyrimidine-4-carbonyl)azetidin-3-yl)methyl)pivalamide (Z505): The title compound (Z505) was prepared from (S)-(3-(aminomethyl)azetidin-1-yl)(6-methyl-2-((1-(pyridin-2-yl)ethyl)amino)thieno[3,2-d]pyrimidin-4-yl)methanone using chemistry similar to that described in Example Z490 (81% yield). LCMS m/z=485.1 [M+H$^+$].

Example Z506. (S)—N-(4-(Ethylcarbamoyl)phenethyl)-2-((1-(5-fluoropyridin-3-yl)ethyl)amino)-6-methylthieno[3,2-d]pyrimidine-4-carboxamide

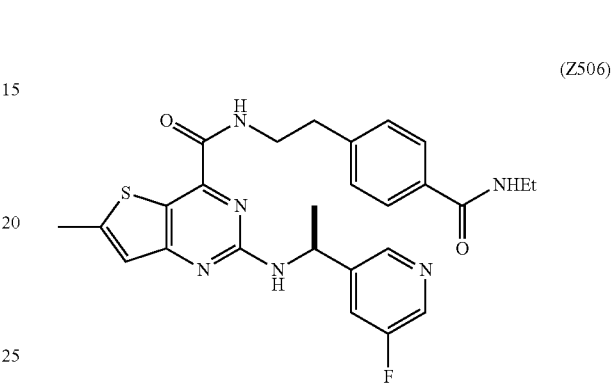

Synthesis of methyl 4-(2-((tert-butoxycarbonyl)amino)ethyl)benzoate: A suspension of methyl 4-(2-aminoethyl)benzoate hydrochloride (250 mg, 1.16 mmol) (commercially obtained from J&W Pharmalab, Levittown, Pa.) in THF (20 mL) and MeOH (10 mL) mixture was treated with DIEA (0.22 mL, 1.28 mmol) and di-tert-butyl dicarbonate (379.4 mg, 1.74 mmol) (commercially obtained from Sigma-Aldrich, St. Louis, Mo.). The reaction mixture was stirred at room temperature under N$_2$ overnight. Solvents were evaporated in vacuo and the residue was dissolved in ethyl acetate. The solution was washed with water and saturated sodium chloride, dried over magnesium sulfate, filtered, and evaporated in vacuo. The residue was triturated with cold ether, formed precipitate was filtered and dried in vacuo to give methyl 4-(2-(tert-butoxycarbonyl)amino)-ethyl)benzoate (225 mg, 70% yield). LCMS m/z=302.1 [M+Na].

Synthesis of 4-(2-((tert-butoxycarbonyl)amino)ethyl)benzoic acid: The title compound was prepared from methyl 4-(2-(tert-butoxycarbonyl)amino)ethyl)benzoate using chemistry similar to that described in Example Z435 (51% yield). LCMS m/z=288.2 [M+Na].

Synthesis of 4-(2-aminoethyl)-N-ethylbenzamide hydrochloride: The title compound was prepared from 4-(2-((tert-butoxycarbonyl)amino)ethyl)benzoic acid and ethylamine using chemistry similar to that described in Example Z495 (80% yield). LCMS m/z=193.3 [M+H$^+$].

Synthesis of (S)—N-(4-(ethylcarbamoyl)phenethyl)-2-((1-(5-fluoropyridin-3-yl)ethyl)amino)-6-methylthieno[3,2-d]pyrimidine-4-carboxamide (Z506): The title compound (Z506) was prepared from (S)-2-((1-(5-fluoropyridin-3-yl)ethyl)amino)-6-methylthieno[3,2-d]pyrimidine-4-carboxylic acid di-hydrochloride using chemistry similar to that described in Example Z17 using ethyl 4-(2-aminoethyl)benzoate hydrochloride in place of (3R)-3-methoxypyrrolidine hydrochloride (77% yield). $^1$H NMR (400 MHz, DMSO-d$_6$) δ 1.10 (3H, t, J=7.6 Hz), 1.51 (3H, d, J=6.8 Hz), 2.55 (3H, d, J=1.2 Hz), 2.88-2.97 (2H, m), 3.22-3.29 (2H, m), 3.53-3.66 (2H, m), 5.40-5.44 (1H, br s), 6.93 (1H, d, J=1.2 Hz), 7.32 (2H, d, J=8.4 Hz), 7.76 (2H, d, J=8.4 Hz), 7.78-7.81 (2H, m), 8.37 (1H, m), 8.40 (1H, d, J=2.8 Hz), 8.51 (1H, br s) 8.75 (1H, s) ppm. LCMS m/z=507.2 [M+H$^+$].

Example Z507. Ethyl (S)-(1-(2-((1-(5-fluoropyridin-3-yl)ethyl)amino)-6-methylthieno[3,2-d]pyrimidine-4-carbonyl)azetidin-3-yl)(methyl)carbamate

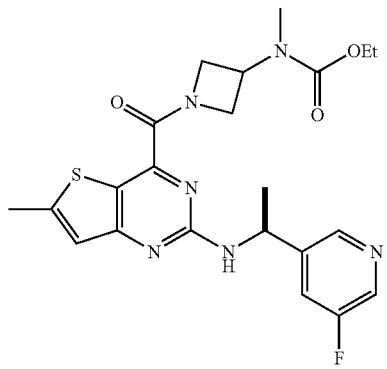 [SMILES: CCOC(=O)N(C)C1CN(C(=O)c2nc(N[C@@H](C)c3cncc(F)c3)nc3cc(C)sc23)C1]
(Z507)

Synthesis of ethyl (S)-(1-(2-((1-(5-fluoropyridin-3-yl)ethyl)amino)-6-methylthieno[3,2-d]pyrimidine-4-carbonyl)azetidin-3-yl)(methyl)carbamate (Z507): The title compound (Z507) was prepared from (S)-(2-((1-(5-fluoropyridin-3-yl)ethyl)amino)-6-methylthieno[3,2-d]pyrimidin-4-yl)(3-(methylamino)azetidin-1-yl)methanone using chemistry similar to that described in Example Z490 using ethyl chloroformate (commercially obtained from Sigma-Aldrich, St. Louis, Mo.) in place of pivaloyl chloride (58% yield). $^1$H NMR (400 MHz, DMSO-d$_6$) δ 1.20 (3H, t, J=7.6 Hz), 1.50 (3H, d, J=7.2 Hz), 2.55 (3H, s), 3.32 (3H, s), 4.03-4.09 (3H, m), 4.26 (2H, m), 4.82-4.95 (1H, m), 5.14-5.24 (1H, m), 6.94 (1H, d, J=1.2 Hz), 7.78-7.81 (2H, m), 8.40 (1H, t, J=2.8 Hz), 8.52 (1H, dd, J=4.0, 1.6 Hz) ppm. LCMS m/z=473.1 [M+H$^+$].

Example Z508. (S)—N-(1-(2-((1-(5-Fluoropyridin-3-yl)ethyl)amino)-6-methylthieno[3,2-d]pyrimidine-4-carbonyl)azetidin-3-yl)-N,3,3-trimethylbutanamide

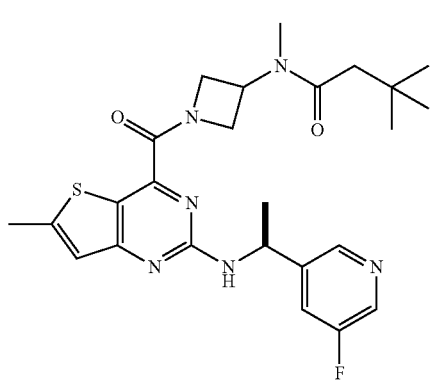 [SMILES: Cc1cc2nc(N[C@@H](C)c3cncc(F)c3)nc(C(=O)N3CC(N(C)C(=O)CC(C)(C)C)C3)c2s1]
(Z508)

Synthesis of (S)—N-(1-(2-((1-(5-fluoropyridin-3-yl)ethyl)amino)-6-methylthieno[3,2-d]pyrimidine-4-carbonyl)azetidin-3-yl)-N,3,3-trimethylbutanamide (Z508): The title compound (Z508) was prepared from (S)-(2-((1-(5-fluoropyridin-3-yl)ethyl)amino)-6-methylthieno[3,2-d]pyrimidin-4-yl)(3-(methylamino)azetidin-1-yl)methanone using chemistry similar to that described in Example Z490 using tert-butylacetyl chloride (commercially obtained from Sigma-Aldrich, St. Louis, Mo.) in place of pivaloyl chloride (53% yield). $^1$H NMR (400 MHz, DMSO-d$_6$) δ 0.96-1.01 (9H, m), 1.50 (3H, d, J=7.2 Hz), 2.55 (3H, s), 2.25 (2H, s), 3.32 (3H, s), 4.05-4.20 (1H, m), 4.23-4.30 (1H, m), 4.52-4.95 (1H, m), 5.19-5.24 (2H, m), 6.95 (1H, s), 7.71-7.78 (2H, m), 8.40 (1H, d, J=2.8 Hz), 8.50 (1H, s) ppm. LCMS m/z=499.3 [M+H$^+$].

Example Z509. (S)—N-(1-(2-((1-(5-Fluoropyridin-3-yl)ethyl)amino)-6-methylthieno[3,2-d]pyrimidine-4-carbonyl)azetidin-3-yl)-N-methylacetamide

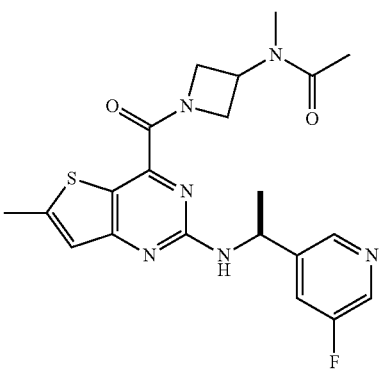 [SMILES: CC(=O)N(C)C1CN(C(=O)c2nc(N[C@@H](C)c3cncc(F)c3)nc3cc(C)sc23)C1]
(Z509)

Synthesis of (S)—N-(1-(2-((1-(5-fluoropyridin-3-yl)ethyl)amino)-6-methylthieno[3,2-d]pyrimidine-4-carbonyl)azetidin-3-yl)-N-methylacetamide (Z509): The title compound (Z509) was prepared from (S)-(2-((1-(5-fluoropyridin-3-yl)ethyl)amino)-6-methylthieno[3,2-d]pyrimidin-4-yl)(3-(methylamino)azetidin-1-yl)methanone using chemistry similar to that described in Example Z490 using acetyl chloride (commercially obtained from Sigma-Aldrich, St. Louis, Mo.) in place of pivaloyl chloride (83% yield). $^1$H NMR (400 MHz, DMSO-d$_6$) δ 1.51 (3H, d, J=6.8 Hz), 2.04 (3H, d, J=7.6 Hz), 2.51 (3H, s), 3.32 (3H, s), 4.00-4.20 (2H, m), 4.60-4.95 (2H, m), 5.17-5.28 (2H, m), 6.94 (1H, s), 7.73-7.85 (2H, m), 8.40 (1H, m), 8.51 (1H, d, J=4.4 Hz) ppm. LCMS m/z=443.1 [M+H$^+$].

Example Z510. Isopropyl (S)-(1-(2-((1-(5-fluoropyridin-3-yl)ethyl)amino)thieno[3,2-d]pyrimidine-4-carbonyl)azetidin-3-yl)carbamate

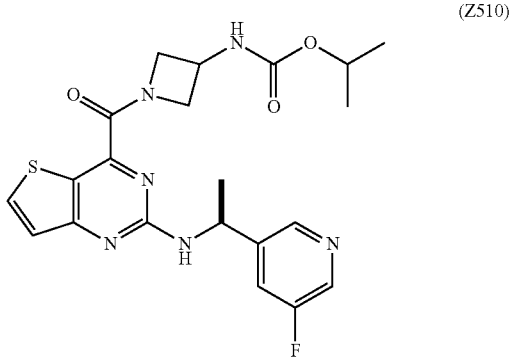

(Z510)

Synthesis of isopropyl (S)-(1-(2-((1-(5-fluoropyridin-3-yl)ethyl)amino)thieno[3,2-d]pyrimidine-4-carbonyl)azetidin-3-yl)carbamate (Z510): The title compound (Z510) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using isopropyl N-(azetidin-3-yl)carbamate hydrochloride (commercially obtained from PharmaBlock, Sunnyvale, Calif.) in place of (3R)-3-methoxypyrrolidine hydrochloride (56% yield). $^1$H NMR (400 MHz, DMSO-$d_6$) δ 1.18 (6H, d, J=6.4 Hz), 1.52 (3H, d, J=7.2 Hz), 3.93-3.95 (1H, m), 4.28-4.41 (3H, m), 4.76 (1H, td, J=6.0, 1.2 Hz), 4.92-5.05 (1H, m), 5.22 (1H, q, J=7.2 Hz), 7.19 (1H, d, J=5.6 Hz), 7.78-7.81 (2H, m), 7.87-7.89 (1H, m), 8.29 (1H, d, J=5.6 Hz), 8.40 (1H, t, J=2.8 Hz), 8.51 (1H, m) ppm. LCMS m/z=459.3 [M+H$^+$].

Example Z511. Isopropyl (S)-(1-(2-((1-(5-fluoropyridin-3-yl)ethyl)amino)-6-methylthieno[3,2-d]pyrimidine-4-carbonyl)azetidin-3-yl)carbamate

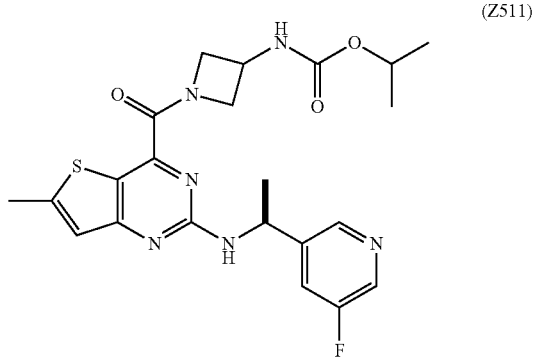

(Z511)

Synthesis of isopropyl (S)-(1-(2-((1-(5-fluoropyridin-3-yl)ethyl)amino)-6-methylthieno[3,2-d]pyrimidine-4-carbonyl)azetidin-3-yl)carbamate (Z511): The title compound (Z511) was prepared from (S)-2-((1-(5-fluoropyridin-3-yl)ethyl)amino)-6-methylthieno[3,2-d]pyrimidine-4-carboxylic acid di-hydrochloride using chemistry similar to that described in Example Z17 using isopropyl N-(azetidin-3-yl)carbamate hydrochloride (commercially obtained from PharmaBlock, Sunnyvale, Calif.) in place of (3R)-3-methoxypyrrolidine hydrochloride (34% yield). $^1$H NMR (400 MHz, DMSO-$d_6$) δ 1.18 (6H, d, J=6.0 Hz), 1.51 (3H, d, J=6.8 Hz), 2.55 (3H, s), 3.93-3.92 (1H, m), 4.28-4.46 (3H, m), 4.78 (1H, td, J=6.4, 1.6 Hz), 4.92-5.05 (1H, m), 5.20 (1H, q, J=7.2 Hz), 6.92 (1H, d, J=0.8 Hz), 7.68-7.71 (2H, m), 7.71-7.80 (3H, m), 8.40 (1H, t, J=3.2 Hz), 8.52 (1H, d, J=1.6 Hz) ppm. LCMS m/z=473.1 [M+H$^+$].

Example Z512. (S)—N-(2-((1-(2-((1-(5-Fluoropyridin-3-yl)ethyl)amino)-6-methylthieno[3,2-d]pyrimidine-4-carbonyl)azetidin-3-yl)amino)-2-oxoethyl)benzamide

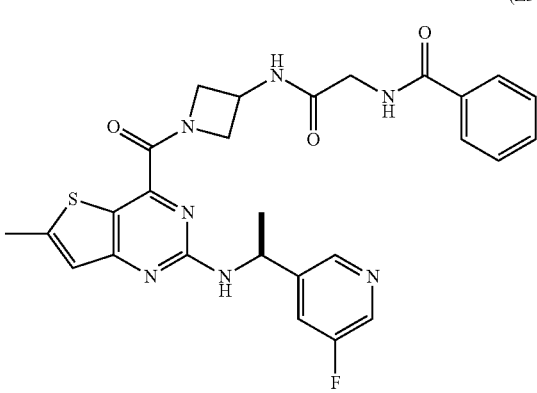

(Z512)

Synthesis of N-(2-(azetidin-3-ylamino)-2-oxoethyl)benzamide hydrochloride: The title compound was prepared from tert-butyl 3-aminoazetidine-1-carboxylate (commercially obtained from PharmaBlock, Sunnyvale, Calif.) using chemistry similar to that described in Example Z495 using 2-benzamidoacetic acid (commercially obtained from Oakwood Chemicals, Estill, S.C.) in place of ethylamine (96% yield). LCMS m/z=234.2 [M+H$^+$].

Synthesis of (S)—N-(2-((1-(2-((1-(5-fluoropyridin-3-yl)ethyl)amino)-6-methylthieno[3,2-d]pyrimidine-4-carbonyl)azetidin-3-yl)amino)-2-oxoethyl)benzamide (Z512): The title compound (Z512) was prepared from (S)-2-((1-(5-fluoropyridin-3-yl)ethyl)amino)-6-methylthieno[3,2-d]pyrimidine-4-carboxylic acid di-hydrochloride using chemistry similar to that described in Example Z17 using N-(2-(azetidin-3-ylamino)-2-oxoethyl)benzamide hydrochloride in place of (3R)-3-methoxypyrrolidine hydrochloride (19% yield). $^1$H NMR (400 MHz, DMSO-$d_6$) δ 1.51 (3H, d, J=6.8 Hz), 2.54 (3H, s), 3.87-3.91 (2H, m), 3.93-4.00 (1H, m), 4.34 (2H, t, J=8.0 Hz), 4.60-4.62 (2H, m), 4.95-5.01 (1H, m), 5.20 (1H, q, J=7.6 Hz), 6.93 (1H, s), 7.46-7.49 (2H, m), 7.71-7.74 (1H, m), 7.77-7.86 (1H, m), 7.89 (1H, m), 7.91 (1H, m), 8.40 (1H, d, J=2.8 Hz), 8.52 (1H, t, J=1.6 Hz), 8.60-8.68 (1H, m), 8.77 (1H, m) ppm. LCMS m/z=548.2 [M+H$^+$].

Example Z513. (S)—N-(1-(2-((1-(5-Fluoropyridin-3-yl)ethyl)amino)-6-methylthieno[3,2-d]pyrimidine-4-carbonyl)azetidin-3-yl)pivalamide

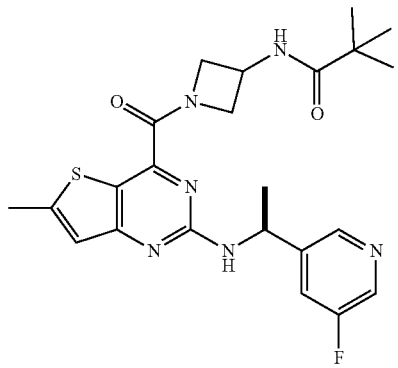

(Z513)

Synthesis of (S)—N-(1-(2-((1-(5-fluoropyridin-3-yl)ethyl)amino)-6-methylthieno[3,2-d]pyrimidine-4-carbonyl)azetidin-3-yl)pivalamide (Z513): The title compound (Z513) was prepared from (S)-(3-aminoazetidin-1-yl)(2-((1-(5-fluoropyridin-3-yl)ethyl)amino)-6-methylthieno[3,2-d]pyrimidin-4-yl)methanone using chemistry similar to that described in Example Z490 (65% yield). $^1$H NMR (400 MHz, DMSO-$d_6$) δ 1.12 (9H, d, J=3.6 Hz), 1.51 (3H, dd, J=7.2, 4.8 Hz), 2.55 (3H, s), 3.95-3.99 (1H, m), 4.27-4.32 (1H, m), 4.54-4.60 (2H, m), 4.92-5.05 (1H, m), 5.19 (1H, q, J=6.8 Hz), 6.93 (1H, m), 7.68-7.74 (1H, m), 7.80-7.82 (1H, s), 7.87-8.15 (1H, m), 8.39 (1H, dd, J=4.8, 2.8 Hz), 8.47-8.51 (1H, m) ppm. LCMS m/z=471.2 [M+H$^+$].

Example Z514. (S)-(3-(Methoxymethyl)azetidin-1-yl)(6-methyl-2-((1-(pyridin-2-yl)ethyl)amino)thieno[3,2-d]pyrimidin-4-yl)methanone

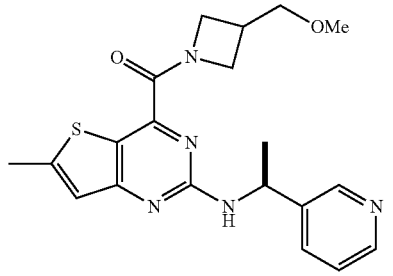

(Z514)

Synthesis of (S)-(3-(methoxymethyl)azetidin-1-yl)(6-methyl-2-((1-(pyridin-2-yl)ethyl)amino)thieno[3,2-d]pyrimidin-4-yl)methanone (Z514): The title compound (Z514) was prepared from (S)-6-methyl-2-((1-(pyridin-2-yl)ethyl)amino)thieno[3,2-d]pyrimidine-4-carboxylic acid di-hydrochloride (39 mg, 0.10 mmol) using chemistry similar to that described in Example Z8 using 3-(methoxymethyl)azetidine hydrochloride in place of (R)-3-fluoropyrrolidine (16 mg, 40% yield). $^1$H NMR (400 MHz, CDCl$_3$) δ 1.61 (3H, d, J=6.8 Hz), 2.60 (3H, s), 2.87 (1H, m), 3.39 (3H, s), 3.47 (1H, d, J=6.4 Hz), 3.56 (1H, d, J=6.4 Hz), 3.90-4.10 (2H, m), 4.25 (1H, t, J=10.0 Hz), 4.44 (1H, m), 5.18 (1H, m), 5.89 (1H, m), 6.86 (1H, s), 7.16 (1H, dd, J=8.0, 4.8 Hz), 7.34 (1H, d, J=8.0 Hz), 7.62 (1H, td, J=8.0, 1.6 Hz), 8.57 (1H, m) ppm. LCMS m/z=398.1 [M+H$^+$].

Example Z515. (S)-(3-(Hydroxymethyl)azetidin-1-yl)(6-methyl-2-((1-(pyridin-3-yl)ethyl)amino)thieno[3,2-d]pyrimidin-4-yl)methanone

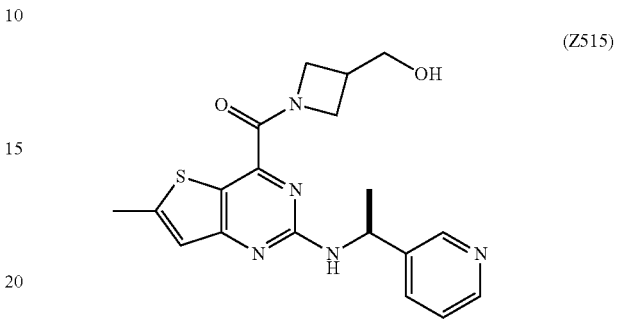

(Z515)

Synthesis of (S)-(3-(hydroxymethyl)azetidin-1-yl)(6-methyl-2-((1-(pyridin-3-yl)ethyl)amino)thieno[3,2-d]pyrimidin-4-yl)methanone (Z515): The title compound (Z515) was prepared from (S)-6-methyl-2-((1-(pyridin-3-yl)ethyl)amino)thieno[3,2-d]pyrimidine-4-carboxylic acid di-hydrochloride (52 mg, 0.13 mmol) using chemistry similar to that described in Example Z8 using azetidin-3-ylmethanol in place of (R)-3-fluoropyrrolidine (8 mg, 16% yield). LCMS m/z=384.2 [M+H$^+$].

Example Z516. (S)-(3-((Dimethylamino)methyl)azetidin-1-yl)(6-methyl-2-((1-(pyridin-3-yl)ethyl)amino)thieno[3,2-d]pyrimidin-4-yl)methanone

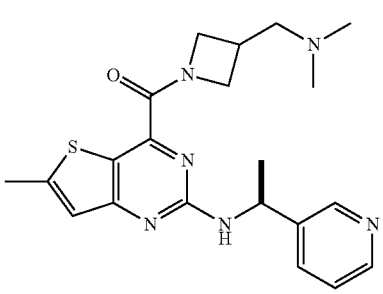 [SMILES: Cc1cc2nc(N[C@@H](C)c3cccnc3)nc(C(=O)N3CC(CN(C)C)C3)c2s1]

(Z516)

Synthesis of (S)-(3-((dimethylamino)methyl)azetidin-1-yl)(6-methyl-2-((1-(pyridin-3-yl)ethyl)amino)thieno[3,2-d]pyrimidin-4-yl)methanone (Z516): The title compound (Z516) was prepared from (S)-6-methyl-2-((1-(pyridin-3-yl)ethyl)amino)thieno[3,2-d]pyrimidine-4-carboxylic acid di-hydrochloride (39 mg, 0.10 mmol) using chemistry similar to that described in Example Z8 using 1-(azetidin-3-yl)-N,N-dimethylmethanamine di-hydrochloride in place of (R)-3-fluoropyrrolidine (12 mg, 29% yield). $^1$H NMR (400 MHz, CDCl$_3$) δ 1.61 (3H, d, J=6.8 Hz), 2.24 (3H, s), 2.25 (3H, s), 2.40-2.58 (2H, m), 2.60 (3H, s), 2.81 (1H, m), 3.84 (1H, m), 4.28 (1H, m), 4.30 (1H, m), 4.53 (1H, m), 5.19 (1H, m), 5.30 (1H, d, J=7.2 Hz), 6.84 (1H, s), 7.23 (1H, dd, J=8.0, 4.8 Hz), 7.68 (1H, dt, J=8.0, 2.0 Hz), 8.48 (1H, dd, J=4.8, 2.0 Hz), 8.66 (1H, d, J=2.0 Hz) ppm. LCMS m/z=411.2 [M+H$^+$].

Example Z517. (S)—N-(1-(2-((1-(5-Fluoropyridin-3-yl)ethyl)amino)thieno[3,2-d]pyrimidine-4-carbonyl)azetidin-3-yl)cyclopropanecarboxamide

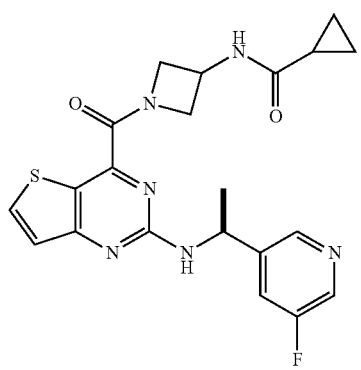 [SMILES: C[C@H](Nc1nc(C(=O)N2CC(NC(=O)C3CC3)C2)c2sccc2n1)c1cncc(F)c1]

(Z517)

Synthesis of (S)—N-(1-(2-((1-(5-fluoropyridin-3-yl)ethyl)amino)thieno[3,2-d]pyrimidine-4-carbonyl)azetidin-3-yl) (517): The title compound (Z517) was prepared from (S)-(3-aminoazetidin-1-yl)(2-((1-(5-fluoropyridin-3-yl)ethyl)amino)thieno[3,2-d]pyrimidin-4-yl)methanone and cyclopropanecarbonyl chloride (commercially obtained from Sigma-Aldrich, St. Louis, Mo.) using chemistry similar to that described in Example Z490 (56% yield). $^1$H NMR (400 MHz, DMSO-d$_6$) δ 0.67-0.69 (4H, m), 1.52 (4H, dd, J=7.2, 2.4 Hz), 3.93-3.95 (1H, m), 4.35 (2H, t, J=9.2 Hz), 4.55-4.58 (1H, m), 4.92-5.05 (1H, m), 5.23 (1H, q, J=7.2 Hz), 7.19 (1H, d, J=5.6 Hz), 7.71-7.75 (1H, m), 7.87-7.89 (1H, m), 8.28 (1H, d, J=5.2 Hz), 8.40 (1H, d, J=2.8 Hz), 8.52 (1H, m), 8.72-8.78 (1H, m) ppm. LCMS m/z=441.2 [M+H$^+$].

Example Z518. (S)—N-(1-(2-((1-(5-Fluoropyridin-3-yl)ethyl)amino)-6-methylthieno[3,2-d]pyrimidine-4-carbonyl)azetidin-3-yl)-3-methoxypropanamide

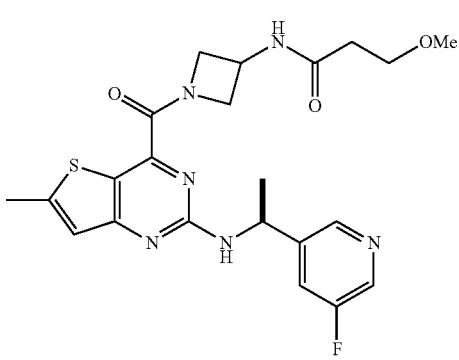 [SMILES: COCCC(=O)NC1CN(C(=O)c2nc(N[C@@H](C)c3cncc(F)c3)nc3cc(C)sc23)C1]

(Z518)

Synthesis of (S)—N-(1-(2-((1-(5-fluoropyridin-3-yl)ethyl)amino)-6-methylthieno[3,2-d]pyrimidine-4-carbonyl)azetidin-3-yl)-3-methoxypropanamide (Z518): The title compound (Z518) was prepared from (S)-(3-aminoazetidin-1-yl)(2-((1-(5-fluoropyridin-3-yl)ethyl)amino)-6-methylthieno[3,2-d]pyrimidin-4-yl)methanone using chemistry similar to that described in Example Z17 using 3-methoxypropionic acid (commercially obtained from Sigma-Aldrich, St. Louis, Mo.) in place of (3R)-3-methoxypyrrolidine hydrochloride (62% yield). $^1$H NMR (400 MHz, DMSO-d$_6$) δ 1.51 (3H, dd, J=7.2, 2.4 Hz), 2.31-2.35 (2H, m), 2.54 (3H, s), 3.21 (3H, s), 3.53 (2H, t, J=6.4 Hz), 3.87-3.89 (1H, m), 4.30-4.35 (1H, m), 4.52-4.55 (2H, m), 5.17-5.21 (1H, m), 6.91 (1H, s), 7.69-7.73 (1H, m), 7.75-7.79 (1H, m), 7.87-8.15 (1H, m), 8.39 (1H, d, J=2.8 Hz), 8.48-8.54 (1H, m), 8.51-8.51 (1H, m) ppm. LCMS m/z=473.1 [M+H$^+$].

Example Z519. N-(1-(2-(((S)-1-(5-Fluoropyridin-3-yl)ethyl)amino)thieno[3,2-d]pyrimidine-4-carbonyl)azetidin-3-yl)tetrahydrofuran-3-carboxamide

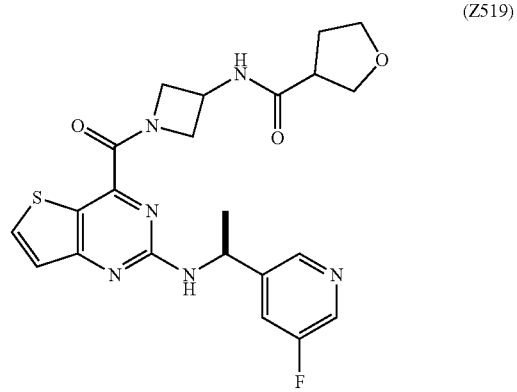

(Z519)

Synthesis of N-(1-(2-(((S)-1-(5-fluoropyridin-3-yl)ethyl)amino)thieno[3,2-d]pyrimidine-4-carbonyl)azetidin-3-yl)tetrahydrofuran-3-carboxamide (Z519): The title compound (Z519) was prepared from (S)-(3-aminoazetidin-1-yl)(2-((1-(5-fluoropyridin-3-yl)ethyl)amino)thieno[3,2-d]pyrimidin-4-yl)methanone using chemistry similar to that described in Example Z490 using tetrahydrofuran-3-carbonyl chloride (commercially obtained from Enamine, Monmouth Jct., N.J.) in place of pivaloyl chloride (86% yield). $^1$H NMR (400 MHz, DMSO-d$_6$) δ 1.52 (3H, d, J=7.2 Hz), 1.91-2.02 (2H, m), 2.90 (1H, q, J=7.2 Hz), 3.60-3.79 (3H, m), 3.80-4.00 (2H, m), 4.35 (2H, t, J=9.2 Hz), 4.55-4.58 (1H, m), 4.35-4.61 (1H, m), 5.23 (1H, m), 7.19 (1H, dd, J=6.4, 1.2 Hz), 7.72-7.75 (1H, m), 7.87-7.89 (1H, m), 8.28 (1H, d, J=4.4 Hz), 8.40 (1H, d, J=2.8 Hz), 8.50-8.52 (1H, m), 8.65-8.70 (1H, m) ppm. LCMS m/z=471.2 [M+H$^+$].

Example Z520. N-Ethyl-1-(2-(((S)-1-(5-fluoropyridin-3-yl)ethyl)amino)thieno[3,2-d]pyrimidine-4-carbonyl)pyrrolidine-3-carboxamide

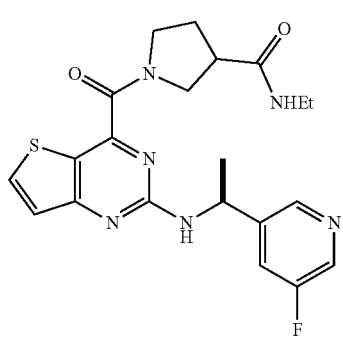

(Z520)

Synthesis of tert-butyl 1-(2-(((S)-1-(5-fluoropyridin-3-yl)ethyl)amino)thieno[3,2-d]pyrimidine-4-carbonyl)pyrrolidine-3-carboxylate: The title compound was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using tert-butyl pyrrolidine-3-carboxylate (commercially obtained from Accella Bio, Shanghai, Conn.) in place of (3R)-3-methoxypyrrolidine hydrochloride (66% yield). LCMS m/z=472.3 [M+H$^+$].

Synthesis of 1-(2-(((S)-1-(5-fluoropyridin-3-yl)ethyl)amino)thieno[3,2-d]pyrimidine-4-carbonyl)pyrrolidine-3-carboxylic acid di-hydrochloride: Hydrogen chloride, 4 M solution in 1,4-dioxane, (0.2 mL) was added to a solution of tert-butyl 1-(2-(((S)-1-(5-fluoropyridin-3-yl)ethyl)amino)thieno[3,2-d]pyrimidine-4-carbonyl)pyrrolidine-3-carboxylate (40 mg, 0.08 mmol) in DCM (0.5 mL), a resulting mixture was stirred at room temperature for 18 hours and concentrated to provide 1-(2-(((S)-1-(5-fluoropyridin-3-yl)ethyl)amino)thieno[3,2-d]pyrimidine-4-carbonyl)pyrrolidine-3-carboxylic acid di-hydrochloride (40 mg, 100% yield). LCMS m/z=416.1 [M+H$^+$].

Synthesis of N-ethyl-1-(2-(((S)-1-(5-fluoropyridin-3-yl)ethyl)amino)thieno[3,2-d]pyrimidine-4-carbonyl)pyrrolidine-3-carboxamide (Z520): The title compound (Z520) was prepared from 1-(2-(((S)-1-(5-fluoropyridin-3-yl)ethyl)amino)thieno[3,2-d]pyrimidine-4-carbonyl)pyrrolidine-3-carboxylic acid di-hydrochloride using chemistry similar to that described in Example Z17 using ethylamine in place of (3R)-3-methoxypyrrolidine hydrochloride (63% yield). $^1$H NMR (400 MHz, DMSO-d$_6$) δ 0.99-1.04 (3H, m), 1.51 (3H, d, J=7.2 Hz), 1.87-2.07 (2H, m), 2.90-2.92 (1H, m), 3.03-3.11 (2H, m), 3.51-3.61 (1H, m), 3.62-3.70 (2H, m), 3.95 (1H, t, J=2.8 Hz), 5.19-5.25 (1H, m), 7.19 (1H, dd, J=5.6, 1.2 Hz), 7.73 (1H, d, J=9.6 Hz), 7.91 (1H, t, J=7.6 Hz), 7.99 (1H, dt, J=28.0, 17.2 Hz), 8.26 (1H, d, J=5.6 Hz), 8.37-8.40 (1H, m), 8.49-8.51 (1H, m) ppm. LCMS m/z=443.1 [M+H$^+$].

Example Z521. (S)-2-((1-(5-Fluoropyridin-3-yl)ethyl)amino)-6-methyl-N-(2-(1-(2,2,2-trifluoroacetyl)azetidin-3-yl)ethyl)thieno[3,2-d]pyrimidine-4-carboxamide

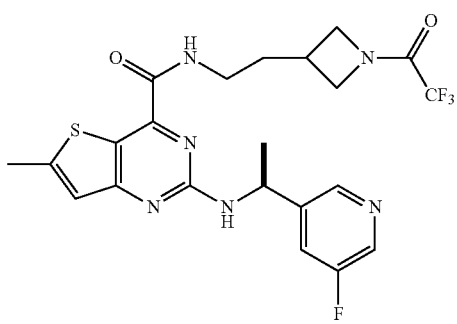 [SMILES: Cc1cc2nc(N[C@@H](C)c3cncc(F)c3)nc(C(=O)NCCC3CN(C(=O)C(F)(F)F)C3)c2s1]

(Z521)

Synthesis of (S)-2-((1-(5-fluoropyridin-3-yl)ethyl)amino)-6-methyl-N-(2-(1-(2,2,2-trifluoro-acetyl)azetidin-3-yl)ethyl)thieno[3,2-d]pyrimidine-4-carboxamide (Z521): A mixture of tert-butyl (S)-3-(2-(2-((1-(5-fluoropyridin-3-yl)ethyl)amino)-6-methylthieno[3,2-d]pyrimidine-4-carboxamido)ethyl)azetidine-1-carboxylate (21 mg, 0.04 mmol) and TFA (0.03 mL, 0.4 mmol) in DCM (1 mL) was stirred for 30 min, then trifluoroacetic anhydride (0.008 mL, 0.06 mmol) and DIEA (0.1 mL, 0.6 mmol) were added, the resulting mixture was stirred at room temperature for 30 minutes, transferred without concentration onto silica gel column (12 g, HP silica, Teledyne Isco) and purified by flash chromatography eluting with 0% to 10% MeOH in DCM to provide (S)-2-((1-(5-fluoropyridin-3-yl)ethyl)amino)-6-methyl-N-(2-(1-(2,2,2-trifluoro-acetyl)azetidin-3-yl)ethyl)thieno[3,2-d]pyrimidine-4-carboxamide (3.7 mg, 35% yield). LCMS m/z=511.1 [M+H$^+$].

Example Z522. (S)—N-(1-(2-((1-(5-Fluoropyridin-3-yl)ethyl)amino)-6-methylthieno[3,2-d]pyrimidine-4-carbonyl)azetidin-3-yl)cyclopropanecarboxamide

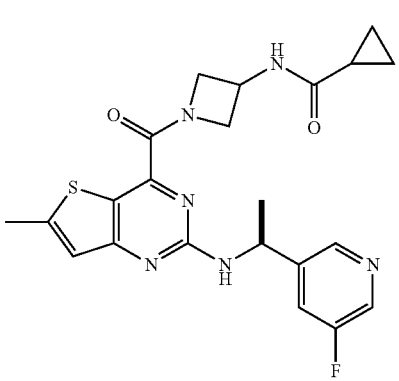 [SMILES: Cc1cc2nc(N[C@@H](C)c3cncc(F)c3)nc(C(=O)N3CC(NC(=O)C4CC4)C3)c2s1]

(Z522)

Synthesis of (S)—N-(1-(2-((1-(5-fluoropyridin-3-yl)ethyl)amino)-6-methylthieno[3,2-d]pyrimidine-4-carbonyl)azetidin-3-yl)cyclopropanecarboxamide (Z522): The title compound (Z522) was prepared from (S)-(3-aminoazetidin-1-yl)(2-((1-(5-fluoropyridin-3-yl)ethyl)amino)-6-methylthieno[3,2-d]pyrimidin-4-yl)methanone using chemistry similar to that described in Example Z490 using cyclopropanecarbonyl chloride in place of pivaloyl chloride (90% yield). ¹H NMR (400 MHz, DMSO-d₆) δ 0.68-0.70 (4H, m), 1.52 (3H, dd, J=7.2, 3.2 Hz), 2.55 (3H, s), 3.90-3.93 (1H, m), 4.33 (2H, t, J=8.0 Hz), 4.53-4.58 (2H, m), 5.23 (1H, q, J=6.8 Hz), 6.93 (1H, s), 7.69-7.74 (1H, m), 7.87-7.79-7.81 (1H, m), 8.40 (1H, d, J=2.8 Hz), 8.48-8.52 (1H, m), 8.78-8.82 (1H, m) ppm. LCMS m/z=455.1 [M+H⁺].

Example Z523. N-(1-(2-(((S)-1-(5-Fluoropyridin-3-yl)ethyl)amino)-6-methylthieno[3,2-d]pyrimidine-4-carbonyl)azetidin-3-yl)tetrahydrofuran-3-carboxamide

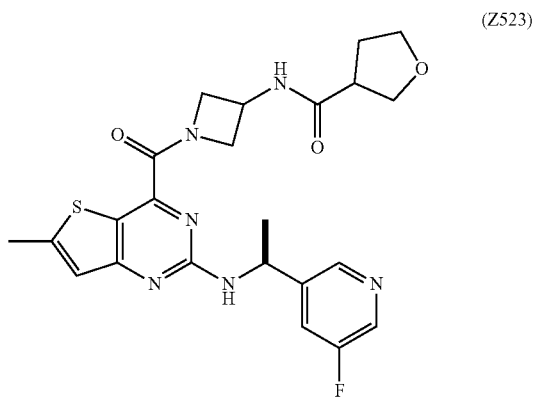

(Z523)

Synthesis of N-(1-(2-(((S)-1-(5-fluoropyridin-3-yl)ethyl)amino)-6-methylthieno[3,2-d]pyrimidine-4-carbonyl)azetidin-3-yl)tetrahydrofuran-3-carboxamide (Z523): The title compound (Z523) was prepared from (S)-(3-aminoazetidin-1-yl)(2-((1-(5-fluoropyridin-3-yl)ethyl)amino)-6-methylthieno[3,2-d]pyrimidin-4-yl)methanone using chemistry similar to that described in Example Z490 using tetrahydrofuran-3-carbonyl chloride in place of pivaloyl chloride (46% yield). ¹H NMR (400 MHz, DMSO-d₆) δ 1.52 (3H, d, J=6.8 Hz), 1.96-2.03 (2H, m), 2.55 (3H, s), 2.9 (1H, q, J=7.2 Hz), 3.62-3.76 (3H, m), 3.83-3.93 (2H, m), 4.33 (2H, t, J=8.0 Hz), 4.51-4.57 (2H, m), 5.51-5.21 (1H, m), 6.93 (1H, s), 7.69-7.73 (1H, m), 7.87-7.82 (1H, m), 8.40 (1H, d, J=2.8 Hz), 8.50-8.52 (1H, m), 8.65-8.70 (1H, m) ppm. LCMS m/z=485.1 [M+H⁺].

Example Z524. (2-(((S)-1-(5-Fluoropyridin-3-yl)ethyl)amino)thieno[3,2-d]pyrimidin-4-yl)(2-methylazetidin-1-yl)methanone

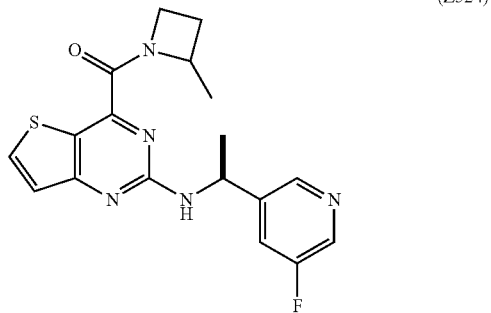

(Z524)

Synthesis of (2-(((S)-1-(5-fluoropyridin-3-yl)ethyl)amino)thieno[3,2-d]pyrimidin-4-yl)(2-methylazetidin-1-yl)methanone (Z524): The title compound (Z524) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using 2-methylazetidine (commercially obtained from Synnovator, Durham, N.C.) in place of (3R)-3-methoxypyrrolidine hydrochloride (52% yield). ¹H NMR (400 MHz, DMSO-d₆) δ 1.44-1.47 (3H, m), 1.51-1.54 (3H, m), 1.84-1.90 (1H, m), 3.96-4.09 (1H, m), 4.52-4.65 (2H, m), 5.22-5.27 (1H, m), 7.19 (1H, dd, J=5.2, 3.6 Hz), 7.71-7.77 (1H, m), 7.82-7.85 (1H, m), 8.27 (1H, d, J=5.2 Hz), 8.41 (1H, dd, J=4.0, 2.8 Hz), 8.52-8.55 (1H, m) ppm. LCMS m/z=372.2 [M+H⁺].

Example Z525. tert-Butyl (S)-((1-(2-((1-(5-Fluoropyridin-3-yl)ethyl)amino)thieno[3,2-d]pyrimidine-4-carbonyl)azetidin-3-yl)methyl)(methyl)carbamate

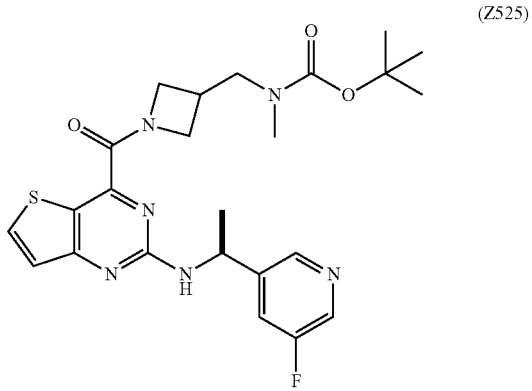

(Z525)

Synthesis of tert-butyl (S)-((1-(2-((1-(5-fluoropyridin-3-yl)ethyl)amino)thieno[3,2-d]pyrimidine-4-carbonyl)azetidin-3-yl)methyl)(methyl)carbamate (Z525): The title compound (Z525) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using tert-butyl N-(azetidin-3-ylmethyl)-N-methyl-carbamate (commercially obtained from Small Molecules, Hoboken, N.J.) in place of (3R)-3-methoxypyrrolidine hydrochloride (70% yield). ¹H NMR (400 MHz, DMSO-d₆) δ 1.36-1.37 (9H, m), 1.52 (3H, d, J=6.8 Hz), 1.84-1.90 (1H, m), 2.78-2.81 (3H, m), 3.41-3.49 (2H, m), 3.80-3.84 (1H, m), 4.14 (1H, t, J=9.6 Hz), 4.36-4.45 (2H, m), 5.23 (1H, q, J=6.8 Hz), 7.19 (1H, d, J=5.6 Hz), 7.71-7.73 (1H, m), 7.85-7.87 (1H, m), 8.28 (1H, d, J=5.6 Hz), 8.41 (1H, t, J=2.8 Hz), 8.52-8.52 (1H, d, J=9.6 Hz) ppm. LCMS m/z=501.2 [M+H⁺].

Example Z526. (S)—N-(1-(2-(((5-Fluoropyridin-3-yl)methyl)amino)thieno[3,2-d]pyrimidine-4-carbonyl)pyrrolidin-3-yl)pivalamide

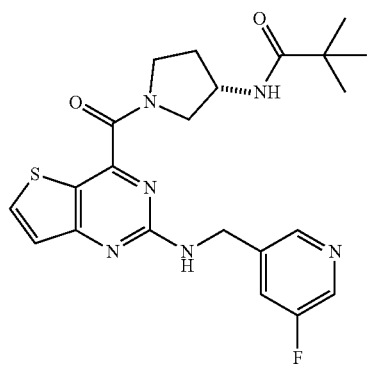

(Z526)

Synthesis of (S)—N-((1-(2-((1-(5-fluoropyridin-3-yl)ethyl)amino)thieno[3,2-d]pyrimidine-4-carbonyl)azetidin-3-yl)methyl)acetamide (Z526): The title compound (Z526) was prepared from (S)-(3-aminopyrrolidin-1-yl)(2-(((5-fluoropyridin-3-yl)methyl)amino)thieno[3,2-d]pyrimidine-4-yl)methanone using chemistry similar to that described in Example Z490 (41% yield). $^1$H NMR (400 MHz, DMSO-d$_6$) δ 1.06 (5H, s), 1.11 (4H, s), 1.80-1.85 (1H, m), 1.95-2.01 (1H, m), 3.59-3.65 (1H, m), 3.70-3.75 (1H, m), 3.90-4.15-4.14 (1H, m), 4.22-4.27 (2H, m), 4.64 (2H, d, J=6.0 Hz), 7.23 (1H, dd, J=5.2, 0.8 Hz), 7.44-7.46 (1H, m), 7.62-7.66 (1H, m), 7.94 (1H, q, J=6.0 Hz), 8.12 (1H, dd, J=8.8, 2.8 Hz), 8.29 (1H, dd, J=5.6, 2.0 Hz), 8.46 (1H, s) ppm. LCMS m/z=457.3 [M+H$^+$].

Example Z527. (S)—N-((1-(6-Methyl-2-((1-(pyridin-2-yl)ethyl)amino)thieno[3,2-d]pyrimidine-4-carbonyl)azetidin-3-yl)methyl)pivalamide

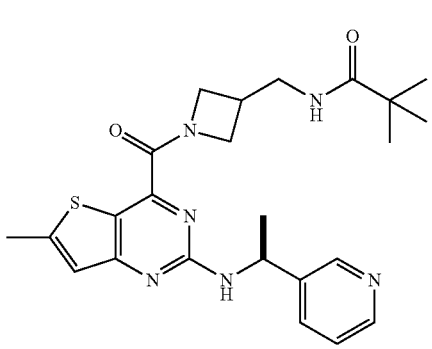

(Z527)

Synthesis of (S)—N-((1-(6-methyl-2-((1-(pyridin-2-yl)ethyl)amino)thieno[3,2-d]pyrimidine-4-carbonyl)azetidin-3-yl)methyl)pivalamide (Z527): The title compound (Z527) was prepared from (S)-(3-(aminomethyl)azetidin-1-yl)(6-methyl-2-((1-(pyridin-2-yl)ethyl)amino)thieno[3,2-d]pyrimidin-4-yl)methanone using chemistry similar to that described in Example Z490 (77% yield). $^1$H NMR (400 MHz, DMSO-d$_6$) δ 1.07 (9H, d, J=5.6 Hz), 1.49 (3H, d, J=7.2 Hz), 1.95-2.01 (1H, m), 2.55 (3H, s), 2.66-2.77 (1H, m), 3.19-3.25 (2H, m), 3.76-3.81 (1H, m), 4.01-4.06 (1H, m), 4.33-4.35 (1H, m), 4.50-4.75 (1H, m), 5.11-5.14 (1H, m), 6.92 (1H, d, J=0.8 Hz), 7.20-7.24 (1H, m), 7.39 (1H, t, J=6.4 Hz), 7.58-7.73 (3H, m) ppm. LCMS m/z=467.3 [M+H$^+$].

Example Z528. (S)—N-((1-(2-((1-(5-Fluoropyridin-3-yl)ethyl)amino)thieno[3,2-d]pyrimidine-4-carbonyl)azetidin-3-yl)methyl)acetamide

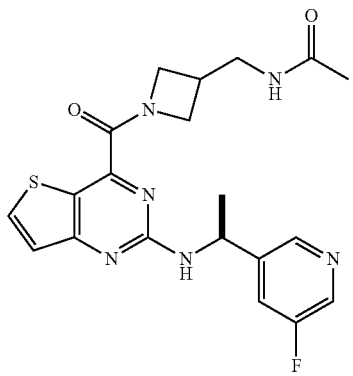 [SMILES: CC(=O)NCC1CN(C(=O)c2nc(N[C@@H](C)c3cncc(F)c3)nc3ccsc23)C1]

(Z528)

Synthesis of (S)—N-((1-(2-((1-(5-fluoropyridin-3-yl)ethyl)amino)thieno[3,2-d]pyrimidine-4-carbonyl)azetidin-3-yl)methyl)acetamide (Z528): The title compound (Z528) was prepared from (S)-(3-(aminomethyl)azetidin-1-yl)(2-((1-(5-fluoropyridin-3-yl)ethyl)amino)thieno[3,2-d]pyrimidin-4-yl)methanone using chemistry similar to that described in Example Z490 using acetyl chloride in place of pivaloyl chloride (76% yield). LCMS m/z=429.2 [M+H$^+$].

Example Z529. (S)—N-((1-(2-((1-(5-Fluoropyridin-3-yl)ethyl)amino)thieno[3,2-d]pyrimidine-4-carbonyl)azetidin-3-yl)methyl)pivalamide

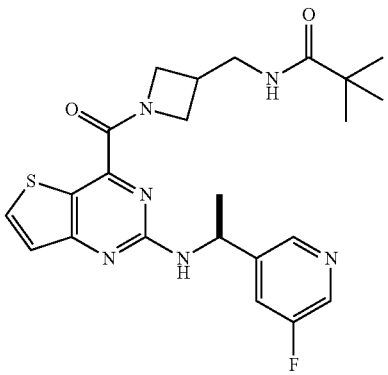 [SMILES: C[C@H](Nc1nc(C(=O)N2CC(CNC(=O)C(C)(C)C)C2)c2sccc2n1)c1cncc(F)c1]

(Z529)

Synthesis of (S)—N-((1-(2-((1-(5-fluoropyridin-3-yl)ethyl)amino)thieno[3,2-d]pyrimidine-4-carbonyl)azetidin-3-yl)methyl)pivalamide (Z529): The title compound (Z529) was prepared from (S)-(3-(aminomethyl)azetidin-1-yl)(2-((1-(5-fluoropyridin-3-yl)ethyl)amino)thieno[3,2-d]pyrimidin-4-yl)methanone using chemistry similar to that described in Example Z490 (74% yield). $^1$H NMR (400 MHz, DMSO-d$_6$) δ 1.07 (9H, d, J=5.6 Hz), 1.52 (3H, d, J=7.2 Hz), 2.77-2.78 (1H, m), 3.32 (3H, m), 3.82-3.86 (1H, m), 4.04-4.10 (1H, m), 4.41-4.44 (1H, dd, J=10.0, 6.0 Hz), 4.65-4.78 (1H, m), 5.25 (1H, q, J=6.8 Hz), 7.19 (1H, d, J=5.6 Hz), 7.65-7.79 (2H, m), 8.28 (1H, d, J=5.6 Hz), 8.41 (1H, d, J=2.8 Hz), 8.53-8.56 (1H, m) ppm. LCMS m/z=471.2 [M+H$^+$].

Example Z530. (S)—N-(1-(2-((1-(5-Fluoropyridin-3-yl)ethyl)amino)thieno[3,2-d]pyrimidine-4-carbonyl)azetidin-3-yl)acetamide

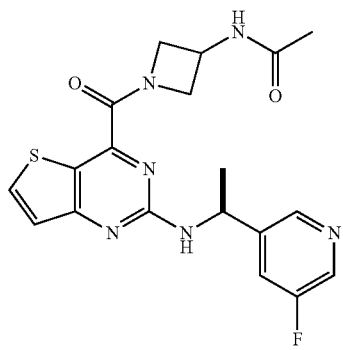 [SMILES: CC(=O)NC1CN(C(=O)c2nc(N[C@@H](C)c3cncc(F)c3)nc3ccsc23)C1]

(Z530)

Synthesis of (S)—N-(1-(2-((1-(5-fluoropyridin-3-yl)ethyl)amino)thieno[3,2-d]pyrimidine-4-carbonyl)azetidin-3-yl)acetamide (Z530): The title compound (Z530) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using N-(azetidin-3-yl)acetamide hydrochloride (commercially obtained from Enamine, Monmouth Jct., N.J.) in place of (3R)-3-methoxypyrrolidine hydrochloride (50% yield). $^1$H NMR (400 MHz, DMSO-d$_6$) δ 1.52 (3H, d, J=7.2 Hz), 1.85 (3H, d, J=1.4 Hz), 3.91-3.93 (1H, m), 4.34 (1H, t, J=6.4 Hz), 4.50-4.56 (1H, m), 4.99 (1H, m), 5.21-5.25 (1H, m), 7.19 (1H, d, J=5.6 Hz), 7.71-7.76 (1H, m), 7.88-7.90 (1H, m), 8.28 (1H, d, J=5.6 Hz), 8.41 (1H, dd, J=2.4, 1.2 Hz), 8.51-8.58 (2H, m) ppm. LCMS m/z=415.1 [M+H$^+$].

Example Z531. (S)—N-((1-(2-((1-(5-Fluoropyridin-3-yl)ethyl)amino)thieno[3,2-d]pyrimidine-4-carbonyl)azetidin-3-yl)methyl)methanesulfonamide

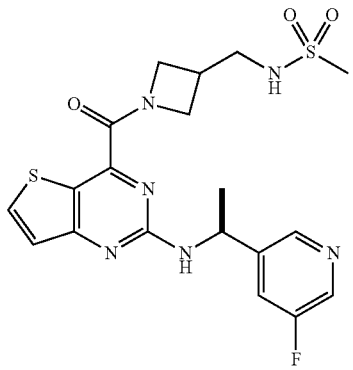 [SMILES: C[C@H](Nc1nc(C(=O)N2CC(CNS(C)(=O)=O)C2)c2sccc2n1)c1cncc(F)c1]

(Z531)

Synthesis of (S)—N-((1-(2-((1-(5-fluoropyridin-3-yl)ethyl)amino)thieno[3,2-d]pyrimidine-4-carbonyl)azetidin-3-yl)methyl)methanesulfonamide (Z531): The title compound (Z531) was prepared from (S)-(3-(aminomethyl)azetidin-1-yl)(2-((1-(5-fluoropyridin-3-yl)ethyl)amino)thieno[3,2-d]pyrimidin-4-yl)methanone using chemistry similar to that described in Example Z490 using methanesulfonyl chloride (commercially obtained from Sigma-Aldrich, St. Louis, Mo.) in place of pivaloyl chloride (42% yield). $^1$H NMR (400 MHz, DMSO-d$_6$) δ 1.52 (3H, d, J=7.2 Hz), 2.93 (3H, d, J=3.2 Hz), 3.15-0.23 (2H, m), 3.83 (1H, dd, J=10.4, 5.6 Hz), 3.93 (1H, m), 4.12 (1H, m), 4.40-4.50 (1H, m), 4.72-4.82 (1H, m), 5.25 (1H, q, J=8.0 Hz), 7.19 (1H, dd, J=5.6, 0.8 Hz), 7.24 (1H, m), 7.73-7.77 (1H, m), 7.82-7.90 (1H, m), 8.28 (1H, d, J=5.6 Hz), 8.16 (1H, dd, J=2.8, 1.2 Hz), 8.53-8.58 (1H, m) ppm. LCMS m/z=465.2 [M+H$^+$].

Example Z532. N—((R)-1-(2-(((S)-1-(5-Fluoropyridin-3-yl)ethyl)amino)-6-methylthieno[3,2-d]pyrimidine-4-carbonyl)pyrrolidin-3-yl)acetamide

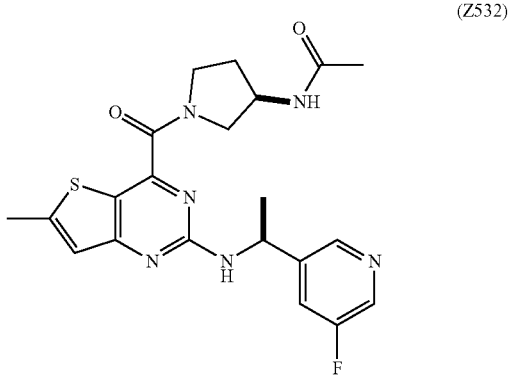

(Z532)

Synthesis of N—((R)-1-(2-(((S)-1-(5-fluoropyridin-3-yl)ethyl)amino)-6-methylthieno[3,2-d]pyrimidine-4-carbonyl)pyrrolidin-3-yl)acetamide (Z532): The title compound (Z532) was prepared from (S)-2-((1-(5-fluoropyridin-3-yl)ethyl)amino)-6-methylthieno[3,2-d]pyrimidine-4-carboxylic acid di-hydrochloride (40.5 mg, 0.10 mmol) using chemistry similar to that described in Example Z8 using (R)—N-(pyrrolidin-3-yl)acetamide in place of (R)-3-fluoropyrrolidine (36 mg, 81% yield). $^1$H NMR (400 MHz, CDCl$_3$) δ 1.62 (3H, d, J=6.8 Hz), 1.86 (1H, m), 2.02 (3H, s), 2.19 (1H, m), 2.60 (3H, d, J=1.2 Hz), 3.72-3.82 (3H, m), 3.90 (1H, m), 4.44 (1H, m), 5.17 (1H, quintet, J=6.8 Hz), 5.37 (1H, d, J=6.8 Hz), 5.68 (1H, d, J=6.8 Hz), 6.85 (1H, d, J=1.2 Hz), 7.45 (1H, dt, J=9.2, 2.0 Hz), 8.32 (1H, d, J=2.8 Hz), 8.50 (1H, m) ppm. LCMS m/z=443.1 [M+H$^+$].

Example Z533. (S)—N-(1-(2-((1-(pyridin-2-yl)ethyl)amino)thieno[3,2-d]pyrimidine-4-carbonyl)azetidin-3-yl)acetamide

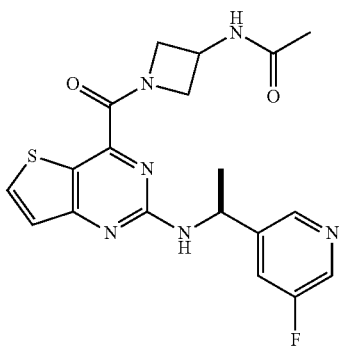

(Z533)

Synthesis of (S)—N-(1-(2-((1-(pyridin-2-yl)ethyl)amino)thieno[3,2-d]pyrimidine-4-carbonyl)azetidin-3-yl)acetamide (Z533): The title compound (Z533) was prepared from (S)-2-((1-(pyridin-2-yl)ethyl)amino)thieno[3,2-d]pyrimidine-4-carboxylic acid di-hydrochloride using chemistry similar to that described in Example Z17 using N-(azetidin-3-yl)acetamide hydrochloride in place of (3R)-3-methoxypyrrolidine hydrochloride (25% yield). $^1$H NMR (400 MHz, DMSO-$d_6$) δ 1.51 (3H, d, J=7.2 Hz), 1.85 (3H, d, J=4.4 Hz), 3.90 (1H, m), 4.32-4.58 (3H, m), 4.80-5.00 (1H, m), 5.14 (1H, m), 7.17-7.23 (2H, m), 7.40 (1H, d, J=8.0 Hz), 7.72 (1H, td, J=7.6, 1.6 Hz), 7.77-7.79 (1H, m), 8.28 (1H, d, J=4.4 Hz), 8.49-8.58 (2H, m) ppm. LCMS m/z=391.1 [M+H$^+$].

Example Z534. (S)-2-((1-(5-Fluoropyridin-3-yl)ethyl)amino)-6-methyl-N-(piperidin-4-ylmethyl)thieno[3,2-d]pyrimidine-4-carboxamide

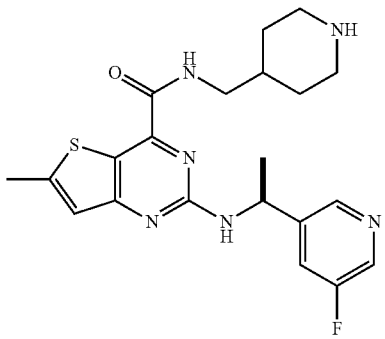 [SMILES: Cc1cc2nc(N[C@@H](C)c3cncc(F)c3)nc(C(=O)NCC3CCNCC3)c2s1]

(Z534)

Synthesis of (S)-2-((1-(5-fluoropyridin-3-yl)ethyl)amino)-6-methyl-N-(piperidin-4-ylmethyl)thieno[3,2-d]pyrimidine-4-carboxamide (Z534): The title compound (Z534) was prepared from (S)-2-((1-(5-fluoropyridin-3-yl)ethyl)amino)-6-methylthieno[3,2-d]pyrimidine-4-carboxylic acid di-hydrochloride (40.5 mg, 0.10 mmol) using chemistry similar to that described in Example Z463 using tert-butyl 4-(aminomethyl)piperidine-1-carboxylate in place of tert-butyl (S)-3-(2-aminoethyl)pyrrolidine-1-carboxylate (18 mg, 70% yield). $^1$H NMR (400 MHz, CDCl$_3$) δ 1.24-1.37 (3H, m), 1.62 (3H, d, J=6.8 Hz), 1.74 (1H, m), 1.98 (1H, m), 2.60 (3H, s), 2.70 (1H, m), 3.00 (1H, m), 3.21-3.44 (3H, m), 5.16 (1H, quintet, J=6.8 Hz), 5.40 (1H, d, J=6.8 Hz), 6.84 (1H, s), 7.43 (1H, m), 7.73 (1H, m), 7.83 (1H, d, J=2.4 Hz), 8.51 (1H, d, J=1.6 Hz) ppm. LCMS m/z=429.2 [M+H$^+$].

Example Z535. (S)-2-((1-(5-Fluoropyridin-3-yl)ethyl)amino)-6-methyl-N-(2-(1-methylazetidin-3-yl)ethyl)thieno[3,2-d]pyrimidine-4-carboxamide

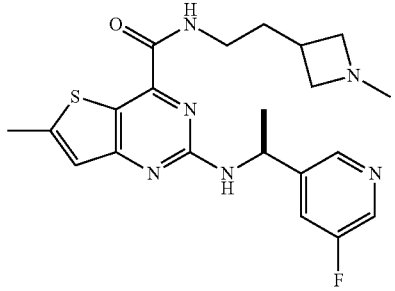

(Z535)

Synthesis of (S)-2-((1-(5-fluoropyridin-3-yl)ethyl)amino)-6-methyl-N-(2-(1-methylazetidin-3-yl)ethyl)thieno[3,2-d]pyrimidine-4-carboxamide (Z535): The title compound (Z535) was prepared from (S)-2-((1-(5-fluoropyridin-3-yl)ethyl)amino)-6-methylthieno[3,2-d]pyrimidine-4-carboxylic acid di-hydrochloride (40.5 mg, 0.10 mmol) using chemistry similar to that described in Example Z8 using 2-(1-methylazetidin-3-yl)ethan-1-amine in place of (R)-3-fluoropyrrolidine (14 mg, 33% yield). $^1$H NMR (400 MHz, CDCl$_3$) δ 1.61 (3H, d, J=6.8 Hz), 2.03 (1H, m), 2.20-2.38 (2H, m), 2.46 (3H, s), 2.53-2.66 (2H, m), 2.60 (3H, s), 3.34 (1H, m), 3.46-3.68 (2H, m), 3.77-4.02 (2H, m), 5.20 (1H, m), 5.38 (1H, m), 6.85 (1H, s), 7.44 (1H, m), 8.33 (1H, m), 8.50 (1H, m) ppm. LCMS m/z=429.2 [M+H$^+$].

Example Z536. (S)—N-(2-Aminoethyl)-2-((1-(5-fluoropyridin-3-yl)ethyl)amino)thieno[3,2-d]pyrimidine-4-carboxamide

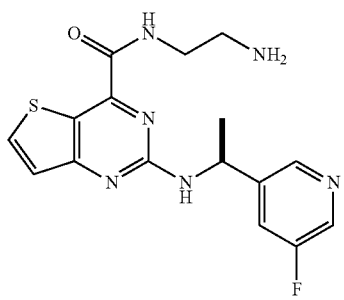

(Z536)

Synthesis of tert-butyl (S)-(2-(2-((1-(5-fluoropyridin-3-yl)ethyl)amino)thieno[3,2-d]pyrimidine-4-carboxamido)ethyl)carbamate: The title compound was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using tert-butyl N-(2-aminoethyl)carbamate (commercially obtained from Sigma-Aldrich, St. Louis, Mo.) in place of (3R)-3-methoxypyrrolidine hydrochloride (81 yield). LCMS m/z=461.1 [M+H⁺].

Synthesis of (S)—N-(2-aminoethyl)-2-((1-(5-fluoropyridin-3-yl)ethyl)amino)thieno[3,2-d]pyrimidine-4-carboxamide (Z536): The title compound (Z536) was prepared from tert-butyl (S)-(2-(2-((1-(5-fluoropyridin-3-yl)ethyl)amino)thieno[3,2-d]pyrimidine-4-carboxamido)ethyl)-carbamate using chemistry similar to that described in Example Z358 (102% yield). ¹H NMR (400 MHz, DMSO-d₆) δ 1.55 (3H, d, J=5.6 Hz), 3.00-3.08 (2H, m), 3.61 (2H, q, J=5.6 Hz), 5.52 (1H, m), 7.22 (1H, d, J=5.6 Hz), 7.77-7.84 (4H, m), 8.34 (1H, d, J=6.0 Hz), 8.40 (1H, d, J=2.8 Hz), 8.63 (1H, m), 8.94-8.95 (1H, m) ppm. LCMS m/z=361.1 [M+H⁺].

Example Z537. (S)-2-((1-(5-Fluoropyridin-3-yl)ethyl)amino)-N-(2-pivalamidoethyl)thieno[3,2-d]pyrimidine-4-carboxamide

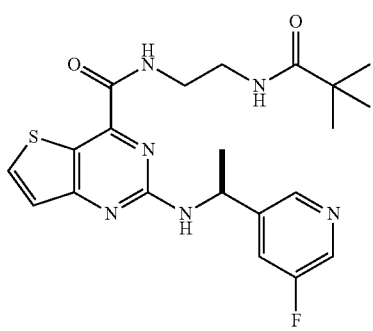 [SMILES: C[C@H](Nc1nc(C(=O)NCCNC(=O)C(C)(C)C)c2sccc2n1)c1cncc(F)c1]

(Z537)

Synthesis of (S)-2-((1-(5-fluoropyridin-3-yl)ethyl)amino)-N-(2-pivalamidoethyl)thieno[3,2-d]pyrimidine-4-carboxamide (Z537): The title compound (Z537) was prepared from (S)—N-(2-aminoethyl)-2-((1-(5-fluoropyridin-3-yl)ethyl)amino)thieno[3,2-d]pyrimidine-4-carboxamide using chemistry similar to that described in Example Z490 (39% yield). ¹H NMR (400 MHz, DMSO-d₆) δ 1.07 (9H, s), 1.53 (3H, d, J=2.8 Hz), 3.00-3.08 (1H, m), 3.30-3.35 (1H, m), 3.40-3.44 (2H, m), 5.62 (1H, m), 7.19 (1H, d, J=5.6 Hz), 7.69 (1H, m), 7.83-7.86 (2H, m), 8.32 (1H, d, J=5.2 Hz), 8.40 (1H, d, J=2.8 Hz), 8.66 (1H, s), 8.80-9.00 (1H, br s) ppm. LCMS m/z=445.3 [M+H⁺].

Example Z538. (S)-2-((1-(5-Fluoropyridin-3-yl)ethyl)amino)-N-(2-(methylsulfonamido)ethyl)thieno[3,2-d]pyrimidine-4-carboxamide

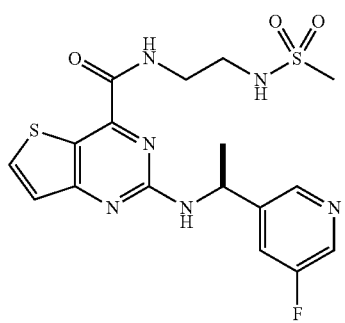 [SMILES: C[C@H](Nc1nc(C(=O)NCCNS(C)(=O)=O)c2sccc2n1)c1cncc(F)c1]

(Z538)

Synthesis of (S)-2-((1-(5-fluoropyridin-3-yl)ethyl)amino)-N-(2-(methylsulfon-amido)ethyl)thieno[3,2-d]pyrimidine-4-carboxamide (Z538): The title compound (Z538) was prepared from (S)—N-(2-aminoethyl)-2-((1-(5-fluoropyridin-3-yl)ethyl)amino)thieno[3,2-d]pyrimidine-4-carboxamide using chemistry similar to that described in Example Z490 using methanesulfonyl chloride in place of pivaloyl chloride (42% yield). ¹H NMR (400 MHz, DMSO-d₆) δ 1.53 (3H, d, J=7.2 Hz), 2.92 (3H, s), 3.17 (2H, q, J=6.4 Hz), 3.47 (2H, q, J=6.4 Hz), 5.50 (1H, m), 7.20 (1H, d, J=5.2 Hz), 7.25 (1H, m), 7.80-7.89 (2H, m), 8.32 (1H, d, J=5.2 Hz), 8.40 (1H, d, J=2.8 Hz), 8.66 (1H, s), 8.80-9.00 (1H, br s) ppm. LCMS m/z=439.1 [M+H⁺].

Example Z539. (S)—N-(2-(1-Acetylazetidin-3-yl)ethyl)-2-((1-(5-fluoropyridin-3-yl)ethyl)amino)thieno[3,2-d]pyrimidine-4-carboxamide

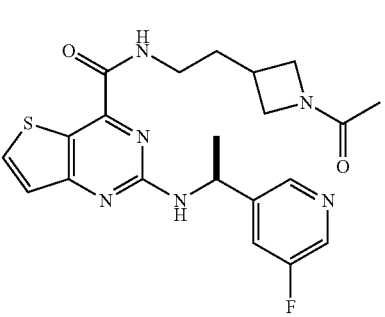 [SMILES: CC(=O)N1CC(CCNC(=O)c2nc(N[C@@H](C)c3cncc(F)c3)nc3ccsc23)C1]

(Z539)

Synthesis of (S)—N-(2-(1-acetylazetidin-3-yl)ethyl)-2-((1-(5-fluoropyridin-3-yl)ethyl)amino)-6-methylthieno[3,2-d]pyrimidine-4-carboxamide (Z539): The title compound (Z539) was prepared from tert-butyl (S)-3-(2-(2-((1-(5-fluoropyridin-3-yl)ethyl)amino)-6-methylthieno[3,2-d]pyrimidine-4-carboxamido)ethyl)azetidine-1-carboxylate using chemistry similar to that described in Example Z521 using acetyl chloride in place of trifluoroacetic anhydride (42% yield). LCMS m/z=457.3 [M+H⁺].

Example Z540. (S)-(2-((1-(5-Fluoropyridin-3-yl)ethyl)amino)-6-methylthieno[3,2-d]pyrimidin-4-yl)(3-(pyrrolidin-1-yl)azetidin-1-yl)methanone

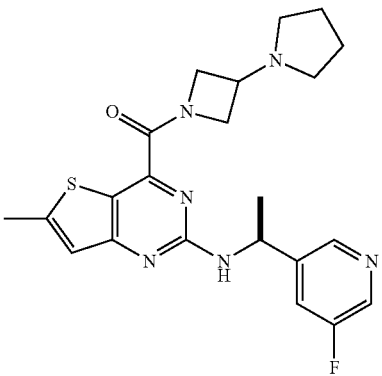 [SMILES: Cc1cc2nc(N[C@@H](C)c3cncc(F)c3)nc(C(=O)N3CC(N4CCCC4)C3)c2s1]

(Z540)

Synthesis of (S)-(2-((1-(5-fluoropyridin-3-yl)ethyl)amino)-6-methylthieno[3,2-d]pyrimidin-4-yl)(3-(pyrrolidin-1-yl)azetidin-1-yl)methanone (Z540): The title compound (Z540) was prepared from (S)-2-((1-(5-fluoropyridin-3-yl)ethyl)amino)-6-methylthieno[3,2-d]pyrimidine-4-carboxylic acid di-hydrochloride (40.5 mg, 0.10 mmol) using chemistry similar to that described in Example Z8 using 1-(azetidin-3-yl)pyrrolidine di-hydrochloride (commercially obtained from PharmBlock, Sunnyvale, Calif.) in place of (R)-3-fluoropyrrolidine (28 mg, 64% yield). $^1$H NMR (400 MHz, CDCl$_3$) δ 1.62 (3H, d, J=6.8 Hz), 1.80-1.87 (4H, m), 2.42-2.53 (4H, m), 2.60 (3H, d, J=1.2 Hz), 3.27 (1H, m), 4.05-4.25 (3H, m), 4.52 (1H, m), 5.20 (1H, quintet, J=6.8 Hz), 5.29 (1H, d, J=6.8 Hz), 6.84 (1H, d, J=1.2 Hz), 7.42 (1H, dt, J=9.6, 2.0 Hz), 8.33 (1H, dd, J=5.2, 2.8 Hz), 8.48 (1H, d, J=2.0 Hz) ppm. LCMS m/z=441.2 [M+H$^+$].

Example Z541. N-(1-(2-(((S)-1-(5-Fluoropyridin-3-yl)ethyl)amino)-6-methylthieno[3,2-d]pyrimidine-4-carbonyl)azetidin-3-yl)tetrahydrofuran-2-carboxamide

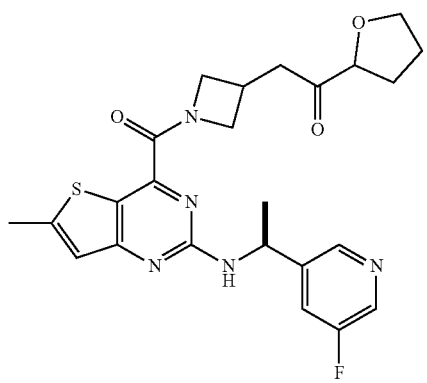 [SMILES: Cc1cc2nc(N[C@@H](C)c3cncc(F)c3)nc(C(=O)N3CC(NC(=O)C4CCCO4)C3)c2s1]

(Z541)

Synthesis of N-(1-(2-(((S)-1-(5-fluoropyridin-3-yl)ethyl)amino)-6-methylthieno[3,2-d]pyrimidine-4-carbonyl)azetidin-3-yl)tetrahydrofuran-2-carboxamide (Z541): The title compound (Z541) was prepared from (S)-(3-aminoazetidin-1-yl)(2-((1-(5-fluoropyridin-3-yl)ethyl)amino)-6-methylthieno[3,2-d]pyrimidin-4-yl)methanone using chemistry similar to that described in Example Z490 using tetrahydrofuran-2-carbonyl chloride (commercially obtained from Enamine, Monmouth Jct., N.J.) in place of pivaloyl chloride (72% yield). $^1$H NMR (400 MHz, DMSO-d$_6$) δ 1.51 (3H, dd, J=7.2, 2.8 Hz), 1.79-1.84 (3H, m), 2.13 (1H, m), 2.55 (3H, s), 3.77 (1H, m), 3.90 (1H, m), 3.97-4.07 (1H, m), 4.21-4.35 (2H, m), 4.55-4.65 (1H, m), 4.90-5.02 (1H, m), 5.19 (1H, m), 6.93 (1H, s), 7.71 (1H, m), 7.75-7.85 (1H, m), 8.35-8.39 (1H, m), 8.40 (1H, t, J=2.8 Hz), 8.49-8.51 (1H, m) ppm. LCMS m/z=485.1 [M+H$^+$].

Example Z542. (S)—N-(1-(2-((1-(5-Fluoropyridin-3-yl)ethyl)amino)-6-methylthieno[3,2-d]pyrimidine-4-carbonyl)azetidin-3-yl)cyclobutanecarboxamide

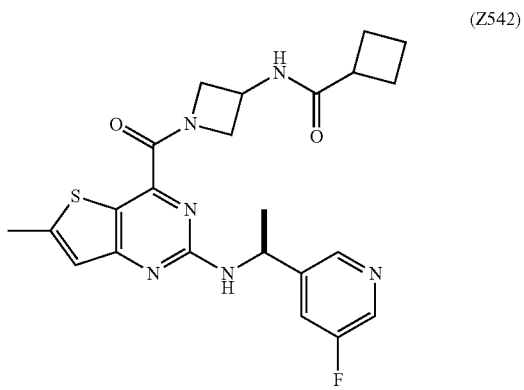

(Z542)

Synthesis of (S)—N-(1-(2-((1-(5-fluoropyridin-3-yl)ethyl)amino)-6-methylthieno[3,2-d]pyrimidine-4-carbonyl)azetidin-3-yl)cyclobutanecarboxamide (Z542): The title compound (Z542) was prepared from (S)-(3-aminoazetidin-1-yl)(2-((1-(5-fluoropyridin-3-yl)ethyl)amino)-6-methylthieno[3,2-d]pyrimidin-4-yl)methanone using chemistry similar to that described in Example Z490 using cyclobutanecarbonyl chloride (commercially obtained from Enamine, Monmouth Jct., N.J.) in place of pivaloyl chloride (42% yield). $^1$H NMR (400 MHz, DMSO-d$_6$) δ 1.51 (3H, dd, J=6.8, 2.4 Hz), 1.70-1.80 (1H, m), 1.85-1.90 (1H, m), 2.00-2.05 (2H, m), 2.11-2.16 (2H, m), 2.55 (3H, s), 3.49 (1H, q, J=8.0 Hz), 3.88-3.91 (1H, m), 4.31 (1H, t, J=6.8 Hz), 4.51-4.56 (2H, m), 4.90-5.02 (1H, m), 5.19 (1H, m), 6.93 (1H, s), 7.71 (1H, m), 7.75-7.85 (1H, m), 8.35-8.39 (1H, m), 8.40 (1H, t, J=2.8 Hz), 8.49-8.51 (1H, m) ppm. LCMS m/z=469.3 [M+H$^+$].

Example Z543. (S)—N-(1-(2-((1-(5-Fluoropyridin-3-yl)ethyl)amino)-6-methylthieno[3,2-d]pyrimidine-4-carbonyl)azetidin-3-yl)acetamide

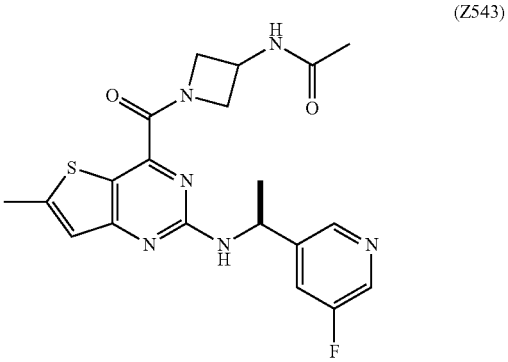

(Z543)

Synthesis of (S)—N-(1-(2-((1-(5-fluoropyridin-3-yl)ethyl)amino)-6-methylthieno[3,2-d]pyrimidine-4-carbonyl)azetidin-3-yl)acetamide (Z543): The title compound (Z543) was prepared from (S)-2-((1-(5-fluoropyridin-3-yl)ethyl)amino)-6-methylthieno[3,2-d]pyrimidine-4-carboxylic acid di-hydrochloride using chemistry similar to that described in Example Z17 using N-(azetidin-3-yl)acetamide hydrochloride in place of (3R)-3-methoxypyrrolidine hydrochloride (48% yield). ¹H NMR (400 MHz, DMSO-d₆) δ 1.51 (3H, d, J=7.2 Hz), m), 1.85 (3H, d, J=1.6 Hz), 2.55 (3H, s), 3.87-3.91 (1H, m), 4.32 (1H, t, J=8.4 Hz), 4.48-4.53 (1H, m), 4.90-5.02 (1H, m), 5.17-5.21 (1H, m), 6.93 (1H, s), 7.71 (1H, m), 7.71-7.74 (1H, m), 7.80-7.82 (1H, m), 8.40 (1H, m), 8.49-8.58 (2H, m) ppm. LCMS m/z=429.2 [M+H⁺].

Example Z544. (S)-(2-((1-(5-Fluoropyridin-3-yl)ethyl)amino)thieno[3,2-d]pyrimidin-4-yl)(3-((methylamino)methyl)azetidin-1-yl)methanone

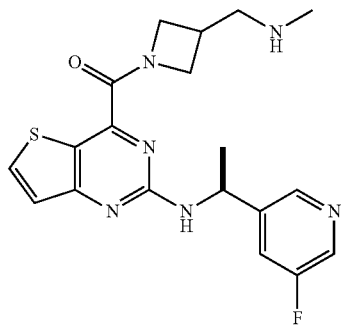 [SMILES: CNCC1CN(C(=O)c2nc(N[C@@H](C)c3cncc(F)c3)nc3ccsc23)C1]

(Z544)

Synthesis of (S)-(2-((1-(5-fluoropyridin-3-yl)ethyl)amino)thieno[3,2-d]pyrimidin-4-yl)(3-((methylamino)methyl)azetidin-1-yl)methanone (Z544): The title compound (Z544) was prepared from tert-butyl (S)-((1-(2-((1-(5-fluoropyridin-3-yl)ethyl)amino)thieno[3,2-d]pyrimidine-4-carbonyl)azetidin-3-yl)methyl)(methyl)carbamate using chemistry similar to that described in Example Z358 (70% yield). ¹H NMR (400 MHz, DMSO-d₆) δ 1.51 (3H, d, J=6.4 Hz), 2.34 (3H, d, J=5.6 Hz), 2.73-2.78 (3H, m), 3.77-3.80 (1H, m), 4.13 (1H, t, J=6.0 Hz), 4.30-4.50 (1H, m), 4.70-4.85 (1H, m), 5.21-5.25 (1H, m), 6.93 (1H, s), 7.19 (1H, d, J=5.2 Hz), 7.39 (1H, d, J=10.4 Hz), 7.86-7.88 (1H, m), 8.28 (1H, d, J=5.2 Hz), 8.41 (1H, d, J=2.4 Hz), 8.53 (1H, d, J=1.2 Hz) ppm. LCMS m/z=401.1[M+H⁺].

Example Z545. (S)-2-((1-(5-Fluoropyridin-3-yl)ethyl)amino)-N-(1-pivaloylazetidin-3-yl)thieno[3,2-d]pyrimidine-4-carboxamide

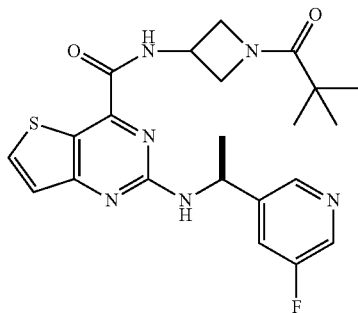 [SMILES: C[C@H](Nc1nc(C(=O)NC2CN(C(=O)C(C)(C)C)C2)c2sccc2n1)c1cncc(F)c1]

(Z545)

Synthesis of (S)-2-((1-(5-fluoropyridin-3-yl)ethyl)amino)-N-(1-pivaloylazetidin-3-yl)thieno[3,2-d]pyrimidine-4-carboxamide (Z545): The title compound (Z545) was prepared from (S)-(3-aminoazetidin-1-yl)(2-((1-(5-fluoropyridin-3-yl)ethyl)amino)-6-methylthieno[3,2-d]pyrimidin-4-yl)methanone using chemistry similar to that described in Example Z490 (46% yield). ¹H NMR (400 MHz, DMSO-d₆) δ 1.42 (9H, s), 1.54 (3H, d, J=1.6 Hz), 3.90-4.05 (1H, m), 4.10-4.25 (1H, m), 4.35-4.48 (1H, m), 4.73-4.77 (2H, m), 5.17-5.21 (1H, m), 7.21 (1H, d, J=5.6 Hz), 7.82-7.95 (2H, m), 8.33 (1H, d, J=5.6 Hz), 8.39 (1H, d, J=2.4 Hz), 8.63 (1H, s), 9.25-9.27 (1H, m) ppm. LCMS m/z=485.1 [M+H⁺].

Example Z546. (S)—N-(1-(2-((1-(5-Fluoropyridin-3-yl)ethyl)amino)-6-methylthieno[3,2-d]pyrimidine-4-carbonyl)azetidin-3-yl)furan-3-carboxamide

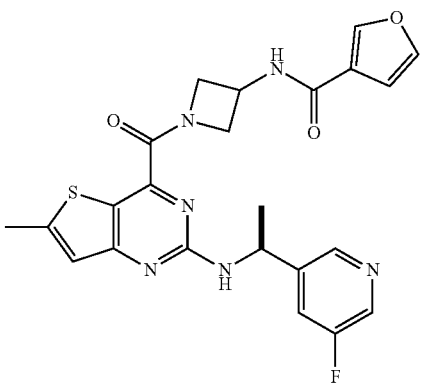 [SMILES: Cc1cc2nc(N[C@@H](C)c3cncc(F)c3)nc(C(=O)N3CC(NC(=O)c4ccoc4)C3)c2s1]

(Z546)

Synthesis of (S)—N-(1-(2-((1-(5-fluoropyridin-3-yl)ethyl)amino)-6-methylthieno[3,2-d]pyrimidine-4-carbonyl)azetidin-3-yl)furan-3-carboxamide (Z546): The title compound (Z546) was prepared from (S)-(3-aminoazetidin-1-yl)(2-((1-(5-fluoropyridin-3-yl)ethyl)amino)-6-methylthieno[3,2-d]pyrimidin-4-yl)methanone using chemistry similar to that described in Example Z490 using furan-3-carbonyl chloride (commercially obtained from Enamine, Monmouth Jct., N.J.) in place of pivaloyl chloride (38% yield). ¹H NMR (400 MHz, DMSO-d₆) δ 1.51 (3H, d, J=6.8 Hz), 2.55 (3H, s), 3.97-4.10 (1H, m), 4.40 (1H, t, J=2.0 Hz), 4.68-4.80 (2H, m), 5.02-5.20 (1H, m), 5.17-5.21 (1H, m), 6.87 (1H, dd, J=7.6, 0.8 Hz), 6.94 (1H, s), 7.71-7.75 (2H, m), 7.79-7.87 (1H, m), 8.21 (1H, d, J=7.6 Hz), 8.39 (1H, dd, J=5.6, 2.8 Hz), 8.51 (1H, dd, J=8.0, 1.2 Hz), 8.72-8.85 (1H, m) ppm. LCMS m/z=481.1 [M+H⁺].

Example Z547. (S)-1-(2-((1-(5-Fluoropyridin-3-yl)ethyl)amino)thieno[3,2-d]pyrimidine-4-carbonyl)-N-(2-hydroxyethyl)azetidine-3-carboxamide

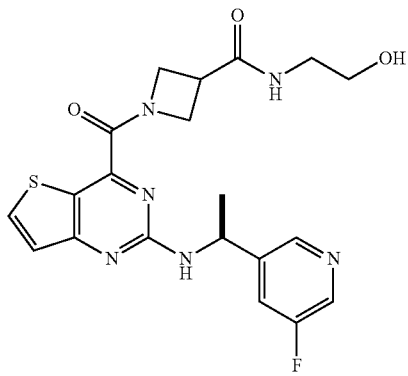 [SMILES: C[C@H](Nc1nc(C(=O)N2CC(C(=O)NCCO)C2)c2sccc2n1)c1cncc(F)c1]

(Z547)

Synthesis of (S)-1-(2-((1-(5-fluoropyridin-3-yl)ethyl)amino)thieno[3,2-d]pyrimidine-4-carbonyl)azetidine-3-carboxylic acid di-hydrochloride: The title compound was prepared from (S)-2-((1-(5-fluoropyridin-3-yl)ethyl)amino)-thieno[3,2-d]pyrimidine-4-carboxylic acid di-hydrochloride using chemistry similar to that described in Example Z520 using tert-butyl azetidine-3-carboxylate hydrochloride (commercially obtained from Ark Pharm, Libertyville, Ill.) in place of tert-butyl pyrrolidine-3-carboxylate (48% yield). LCMS m/z=402.0 [M+H⁺].

Synthesis of (S)-1-(2-((1-(5-fluoropyridin-3-yl)ethyl)amino)thieno[3,2-d]pyrimidine-4-carbonyl)-N-(2-hydroxyethyl)azetidine-3-carboxamide (Z547): The title compound (Z547) was prepared from (S)-1-(2-((1-(5-fluoropyridin-3-yl)ethyl)amino)thieno[3,2-d]pyrimidine-4-carbonyl)azetidine-3-carboxylic acid di-hydrochloride using chemistry similar to that described in Example Z17 using 2-aminoethanol in place of tert-butyl pyrrolidine-3-carboxylate (24% yield). LCMS m/z=445.3 [M+H⁺].

Example Z548. N-(tert-Butyl)-1-(2-(((S)-1-(5-fluoropyridin-3-yl)ethyl)amino)thieno[3,2-d]pyrimidine-4-carbonyl)pyrrolidine-3-carboxamide

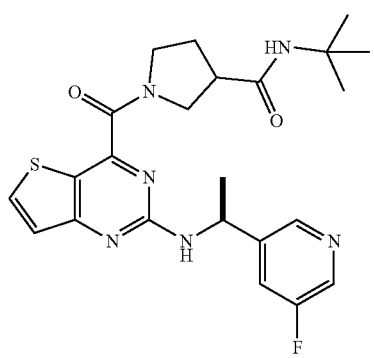 [SMILES: C[C@H](Nc1nc(C(=O)N2CCC(C(=O)NC(C)(C)C)C2)c2sccc2n1)c1cncc(F)c1]

(Z548)

Synthesis of N-(tert-butyl)-1-(2-(((S)-1-(5-fluoropyridin-3-yl)ethyl)amino)thieno[3,2-d]pyrimidine-4-carbonyl)pyrrolidine-3-carboxamide (Z548): The title compound (Z548) was prepared from 1-(2-(((S)-1-(5-fluoropyridin-3-yl)ethyl)amino)thieno[3,2-d]pyrimidine-4-carbonyl)pyrrolidine-3-carboxylic acid di-hydrochloride using chemistry similar to that described in Example Z17 using tert-butylamine in place of (3R)-3-methoxypyrrolidine hydrochloride (73% yield). ¹H NMR (400 MHz, DMSO-d₆) δ 1.25 (9H, dd, J=7.2, 3.2 Hz), 1.50 (3H, d, J=7.2 Hz), 1.83-2.02 (2H, m), 2.86-2.95 (1H, m), 3.50-3.58 (1H, m), 3.64-3.58 (2H, m), 3.96 (1H, m), 5.19-5.27 (1H, m), 7.19 (1H, dt, J=5.6, 1.2 Hz), 7.62 (1H, s), 7.72 (1H, m), 7.89-7.94 (1H, m), 8.26 (1H, d, J=5.2 Hz), 8.39 (1H, d, J=2.8 Hz), 8.51 (1H, s) ppm. LCMS m/z=571.2 [M+H⁺].

Example Z549. N-(tert-Butoxy)-1-(2-(((S)-1-(5-fluoropyridin-3-yl)ethyl)amino)thieno[3,2-d]pyrimidine-4-carbonyl)pyrrolidine-3-carboxamide (Z549)

Synthesis of N-(tert-butoxy)-1-(2-(((S)-1-(5-fluoropyridin-3-yl)ethyl)amino)thieno[3,2-d]pyrimidine-4-carbonyl)pyrrolidine-3-carboxamide (Z549): The title compound (Z549) was prepared from 1-(2-(((S)-1-(5-fluoropyridin-3-yl)ethyl)amino)thieno[3,2-d]pyrimidine-4-carbonyl)pyrrolidine-3-carboxylic acid di-hydrochloride using chemistry similar to that described in Example Z17 using O-tert-butylhydroxylamine hydrochloride (commercially obtained from Sigma-Aldrich, St. Louis, Mo.) in place of (3R)-3-methoxypyrrolidine hydrochloride (54% yield). ¹H NMR (400 MHz, DMSO-d₆) δ 1.13-1.16 (9H, m), 1.50 (3H, dd, J=7.2, 4.0 Hz), 1.95-2.03 (2H, m), 2.85-2.93 (1H, m), 3.53-3.60 (1H, m), 3.65-3.74 (2H, m), 4.02 (1H, m), 5.19-5.25 (1H, m), 7.19 (1H, dd, J=5.2, 2.4 Hz), 7.72 (1H, d, J=10.0 Hz), 7.90-7.94 (1H, m), 8.26 (1H, d, J=5.2 Hz), 8.37-8.39 (1H, m), 8.51 (1H, s) 10.50 (1H, dd, J=19.2, 2.8 Hz) ppm. LCMS m/z=487.3 [M+H⁺].

Example Z550. (S)—N-((1-(2-((1-(5-Fluoropyridin-3-yl)ethyl)amino)thieno[3,2-d]pyrimidine-4-carbonyl)azetidin-3-yl)methyl)-N,3,3-trimethylbutanamide

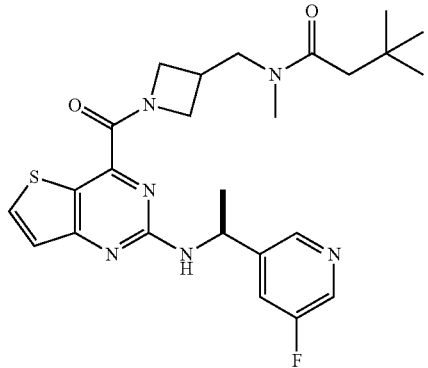

(Z550)

Synthesis of (S)—N-((1-(2-((1-(5-fluoropyridin-3-yl)ethyl)amino)thieno[3,2-d]pyrimidine-4-carbonyl)azetidin-3-yl)methyl)-N,3,3-trimethylbutanamide (Z550): The title compound (Z550) was prepared from (S)-(2-((1-(5-fluoropyridin-3-yl)ethyl)amino)thieno[3,2-d]pyrimidin-4-yl)(3-((methylamino)methyl)azetidin-1-yl)methanone using chemistry similar to that described in Example Z490 using tert-butylacetyl chloride (commercially obtained from Sigma-Aldrich, St. Louis, Mo.) in place of pivaloyl chloride (74% yield). $^1$H NMR (400 MHz, DMSO-$d_6$) δ 0.97 (9H, d, J=3.6 Hz), 1.49-1.53 (3H, m), 2.15-2.26 (2H, m), 2.77-2.80 (1H, m), 2.87-2.92 (1H, m), 3.53-3.60 (1H, m), 2.98 (1H, s), 3.99 (3H, s), 3.54-3.66 (2H, m), 4.08-4.12 (1H, m), 5.21-5.24 (1H, m), 7.19 (1H, d, J=5.6 Hz), 7.69-7.77 (1H, m), 7.90-7.94 (1H, m), 8.27 (1H, d, J=5.6 Hz), 8.40 (1H, t, J=2.4 Hz), 8.49-8.54 (1H, m) ppm. LCMS m/z=499.3 [M+H$^+$].

Example Z551. (S)—N-((1-(2-((1-(5-Fluoropyridin-3-yl)ethyl)amino)thieno[3,2-d]pyrimidine-4-carbonyl)azetidin-3-yl)methyl)-N-methylpivalamide

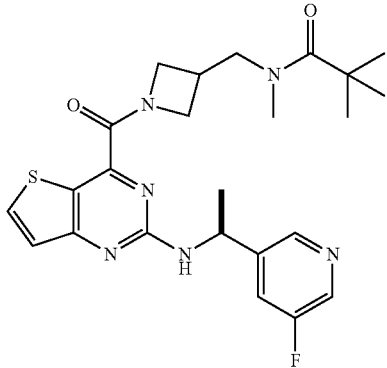 [SMILES: C[C@H](Nc1nc(C(=O)N2CC(CN(C)C(=O)C(C)(C)C)C2)c2sccc2n1)c1cncc(F)c1]

(Z551)

Synthesis of (S)—N-((1-(2-((1-(5-fluoropyridin-3-yl)ethyl)amino)thieno[3,2-d]pyrimidine-4-carbonyl)azetidin-3-yl)methyl)-N-methylpivalamide (Z551): The title compound (Z551) was prepared from (S)-(2-((1-(5-fluoropyridin-3-yl)ethyl)amino)thieno[3,2-d]pyrimidin-4-yl)(3-((methylamino)methyl)azetidin-1-yl)methanone using chemistry similar to that described in Example Z490 (83% yield). $^1$H NMR (400 MHz, DMSO-$d_6$) δ 1.19 (9H, dd, J=15.2, 8.0 Hz), 1.53 (3H, d, J=7.2 Hz), 2.87-2.91 (1H, m), 3.02 (3H, m), 3.54-3.61 (2H, m), 3.81-3.84 (1H, s), 4.13 (1H, t, J=9.2 Hz), 4.45-4.78 (1H, m), 4.78 (1H, m), 5.23 (1H, q, J=7.2 Hz), 7.19 (1H, d, J=5.6 Hz), 7.70-7.77 (1H, m), 7.87 (1H, m), 8.27 (1H, d, J=5.6 Hz), 8.40 (1H, dd, J=2.8, 1.6 Hz), 8.50-8.54 (1H, m) ppm. LCMS m/z=485.1 [M+H$^+$].

Example Z552. tert-Butyl (S)-1-(6-methyl-2-((1-(pyridin-2-yl)ethyl)amino)thieno[3,2-d]pyrimidine-4-carbonyl)azetidine-3-carboxylate

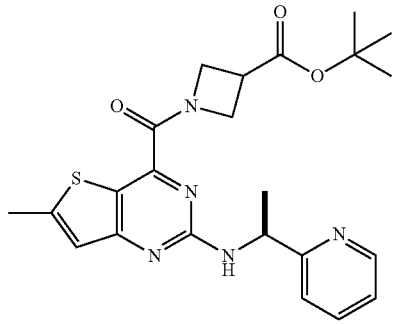 [SMILES: Cc1cc2nc(N[C@@H](C)c3ccccn3)nc(C(=O)N3CC(C(=O)OC(C)(C)C)C3)c2s1]

(Z552)

Synthesis of tert-butyl (S)-1-(6-methyl-2-((1-(pyridin-2-yl)ethyl)amino)thieno[3,2-d]pyrimidine-4-carbonyl)azetidine-3-carboxylate (Z552): The title compound (Z552) was prepared from (S)-6-methyl-2-((1-(pyridin-2-yl)ethyl)amino)thieno[3,2-d]pyrimidine-4-carboxylic acid di-hydrochloride (39 mg, 0.10 mmol) using chemistry similar to that described in Example Z8 using tert-butyl azetidine-3-carboxylate hydrochloride (commercially obtained from Ark Pham, Arlington Heights, Ill.) in place of (R)-3-fluoropyrrolidine (8 mg, 18% yield). $^1$H NMR (400 MHz, CDCl$_3$) δ 1.49 (9H, br s), 1.59 (3H, d, J=4.0 Hz), 2.60 (3H, s), 3.37 (1H, m), 4.26-4.36 (2H, m), 4.69 (1H, m), 4.85 (1H, m), 5.20 (1H, m), 5.95 (1H, m), 5.95 (1H, m), 6.86 (1H, s), 7.16 (1H, q, J=4.0 Hz), 7.33 (1H, t, J=8.0 Hz), 7.62 (1H, m), 8.57 (1H, dd, J=4.8, 4.0 Hz) ppm. LCMS m/z=454.3 [M+H$^+$].

Example Z553. (S)-(3-(Methoxymethyl)azetidin-1-yl)(7-methyl-2-((1-(pyridin-2-yl)ethyl)amino)thieno[3,2-d]pyrimidin-4-yl)methanone

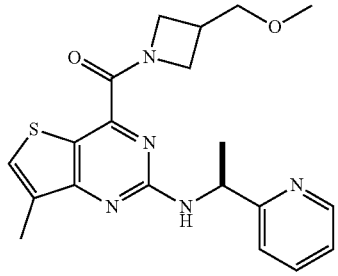 [SMILES: COCC1CN(C(=O)c2nc(N[C@@H](C)c3ccccn3)nc3c(C)csc23)C1]

(Z553)

Synthesis of (S)-(3-(methoxymethyl)azetidin-1-yl)(7-methyl-2-((1-(pyridin-2-yl)ethyl)amino)thieno[3,2-d]pyrimidin-4-yl)methanone (Z553): The title compound (Z553) was prepared from (S)-7-methyl-2-((1-(pyridin-2-yl)ethyl)amino)thieno[3,2-d]pyrimidine-4-carboxylic acid di-hydrochloride (39 mg, 0.10 mmol) using chemistry similar to that described in Example Z8 using 3-(methoxymethyl)azetidine hydrochloride in place of (R)-3-fluoropyrrolidine (13 mg, 33% yield). $^1$H NMR (400 MHz, CDCl$_3$) δ 1.60 (3H, d, J=6.4 Hz), 2.60 (3H, s), 2.86 (1H, m), 3.38 (3H, br s), 3.47 (1H, d, J=6.8 Hz), 3.55 (1H, d, J=6.8 Hz), 3.93 (1H, td, J=11.2. 5.6 Hz), 4.25 (1H, t, J=9.2 Hz), 4.44 (1H, m), 4.76 (1H, t, J=9.2 Hz), 5.19 (1H, m), 5.88 (1H, br s), 6.85 (1H, s), 7.16 (1H, m), 7.33 (1H, d, J=7.6 Hz), 7.62 (1H, td, J=8.0, 2.0 Hz), 8.56 (1H, m) ppm. LCMS m/z=398.1 [M+H$^+$].

Example Z554. ((R)-3-(Aminomethyl)pyrrolidin-1-yl)(2-(((S)-1-(5-fluoropyridin-3-yl)ethyl)amino)-6-methylthieno[3,2-d]pyrimidin-4-yl)methanone

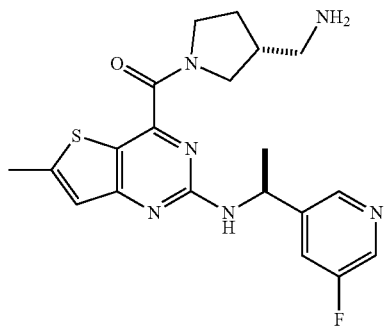 [SMILES: Cc1cc2nc(N[C@@H](C)c3cncc(F)c3)nc(C(=O)N3CC[C@H](CN)C3)c2s1]

(Z554)

Synthesis of ((R)-3-(aminomethyl)pyrrolidin-1-yl)(2-(((S)-1-(5-fluoropyridin-3-yl)ethyl)amino)-6-methylthieno[3,2-d]pyrimidin-4-yl)methanone (Z554): The title compound (Z554) was prepared from (S)-2-((1-(5-fluoropyridin-3-yl)ethyl)amino)-6-methylthieno[3,2-d]pyrimidine-4-carboxylic acid di-hydrochloride (40.5 mg, 0.10 mmol) using chemistry similar to that described in Example Z463 using tert-butyl (S)-(pyrrolidin-3-ylmethyl)carbamate (commercially obtained from Ark Pharm, Libertyville, Ill.) in place of tert-butyl (S)-3-(2-aminoethyl)pyrrolidine-1-carboxylate (36 mg, 88% yield). $^1$H NMR (400 MHz, CDCl$_3$) δ 1.61 (3H, d, J=6.8 Hz), 2.03 (1H, m), 2.22 (1H, m), 2.60 (3H, s), 2.65-2.81 (2H, m), 3.32-3.52 (1H, m), 3.61-3.88 (3H, m), 5.20 (1H, m), 5.37 (1H, m), 6.85 (1H, s), 7.42 (1H, m), 8.33 (1H, t, J=3.2 Hz), 8.49 (1H, m) ppm. LCMS m/z=415.3 [M+H$^+$].

Example Z555. Isopropyl (S)-(1-(2-((1-(4-methoxyphenyl)ethyl)amino)-6-methylthieno[3,2-d]pyrimidine-4-carbonyl)azetidin-3-yl)carbamate

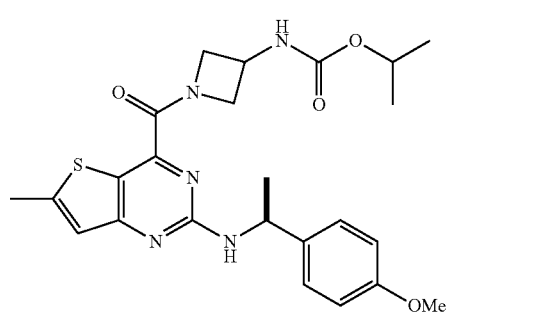 [SMILES: COc1ccc([C@H](C)Nc2nc(C(=O)N3CC(NC(=O)OC(C)C)C3)c3sc(C)cc3n2)cc1]

(Z555)

Synthesis of (S)-2-((1-(4-methoxyphenyl)ethyl)amino)-6-methylthieno[3,2-d]pyrimidine-4-carboxylic acid: The title compound was prepared from ethyl 2-chlorothieno[3,2-d]pyrimidine-4-carboxylate using chemistry similar to that described in Example Z465 using (1S)-1-(4-methoxyphenyl)ethanamine (commercially obtained from Cambridge, Cambridge, UK) in place of (6-methoxypyridin-3-yl)methanamine hydrochloride to provide (S)-2-((1-(4-methoxyphen-yl)ethyl)amino)-6-methylthieno[3,2-d]pyrimidine-4-carboxylic acid (25% yield). LCMS m/z=344.1 [M+H$^+$].

Synthesis of isopropyl (S)-(1-(2-((1-(4-methoxyphenyl)ethyl)amino)-6-methylthieno[3,2-d]pyrimidine-4-carbonyl)azetidin-3-yl)carbamate (Z555): The title compound (Z555) was prepared from (S)-2-((1-(4-methoxyphenyl)ethyl)amino)-6-methylthieno[3,2-d]pyrimidine-4-carboxylic acid using chemistry similar to that described in Example Z17 using isopropyl N-(azetidin-3-yl)carbamate hydrochloride (commercially obtained from PharmaBlock. Sunnyvale, Calif.) in place of (3R)-3-methoxypyrrolidine hydrochloride (15% yield). LCMS m/z=484.3 [M+H$^+$].

Example Z556. (S)—N-(1-(2-((1-(4-Methoxyphenyl)ethyl)amino)-6-methylthieno[3,2-d]pyrimidine-4-carbonyl)azetidin-3-yl)acetamide

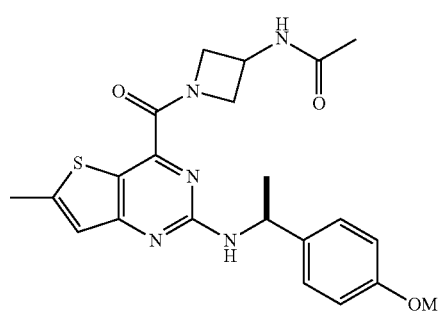

(Z556)

Synthesis of (S)—N-(1-(2-((1-(4-methoxyphenyl)ethyl)amino)-6-methylthieno[3,2-d]pyrimidine-4-carbonyl)azetidin-3-yl)acetamide (Z556): The title compound (Z556) was prepared from (S)-2-((1-(4-methoxyphenyl)ethyl)amino)-6-methylthieno[3,2-d]pyrimidine-4-carboxylic acid using chemistry similar to that described in Example Z17 using N-(azetidin-3-yl)acetamide hydrochloride in place of (3R)-3-methoxypyrrolidine hydrochloride (15% yield). ¹H NMR (400 MHz, DMSO-d₆) δ 1.43 (3H, dd, J=6.8, 2.8 Hz), 1.85 (3H, d, J=2.0 Hz), 2.53 (3H, s), 3.69 (3H, s), 3.87-3.90 (1H, s), 4.32 (1H, t, J=8.4 Hz), 4.50-4.53 (1H, m), 4.78 (1H, m), 5.03-5.05 (1H, m), 6.81-6.85 (2H, d, J=5.6 Hz), 6.91 (1H, t, J=0.8 Hz), 7.27-7.31 (2H, m), 7.60-7.70 (1H, m), 8.53 (1H, dd, J=8.4, 1.6 Hz), 8.55-8.60 (1H, m), ppm. LCMS m/z=440.2 [M+H⁺].

Example Z557. (S)—N-(1-(2-((1-(5-Fluoropyridin-3-yl)ethyl)amino)thieno[3,2-d]pyrimidine-4-carbonyl)azetidin-3-yl)-3,3-dimethylbutanamide

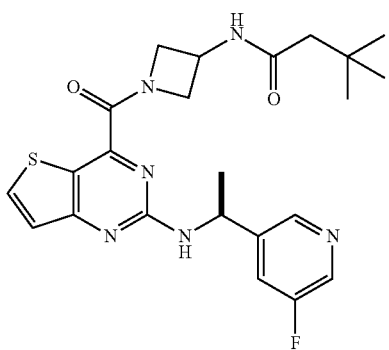

(Z557)

Synthesis of (S)—N-(1-(2-((1-(5-fluoropyridin-3-yl)ethyl)amino)thieno[3,2-d]pyrimidine-4-carbonyl)azetidin-3-yl)-3,3-dimethylbutanamide (Z557): The title compound (Z557) was prepared from (S)-(3-aminoazetidin-1-yl)(2-((1-(5-fluoropyridin-3-yl)ethyl)amino)-6-methylthieno[3,2-d]pyrimidin-4-yl)methanone using chemistry similar to that described in Example Z490 using tert-butylacetyl chloride in place of cyclopropanecarbonyl chloride (52% yield). ¹H NMR (400 MHz, DMSO-d₆) δ 0.97 (9H, d, J=2.4 Hz), 1.54 (3H, dd, J=6.8, 2.0 Hz), 1.98 (2H, d, J=5.6 Hz), 3.89-3.92 (1H, m), 4.34 (1H, td, J=9.2, 3.6 Hz), 4.51-4.57 (2H, m), 4.59.5-20 (1H, m), 5.23 (1H, q, J=7.2 Hz), 7.19 (1H, d, J=5.2 Hz), 7.71-7.75 (1H, m), 7.87-7.91 (1H, m), 8.27 (1H, d, J=5.2 Hz), 8.40 (1H, dd, J=4.4, 2.4 Hz), 8.47-8.52 (2H, m) ppm. LCMS m/z=471.2 [M+H⁺].

Example Z558. (S)—N-(1-(2-((1-(5-Fluoropyridin-3-yl)ethyl)amino)thieno[3,2-d]pyrimidine-4-carbonyl)azetidin-3-yl)isobutyramide (Z558)

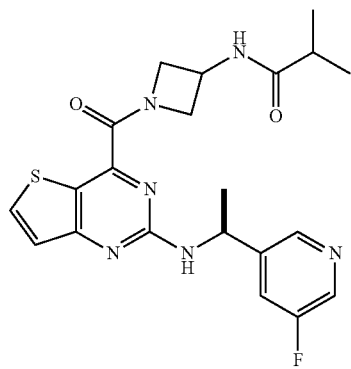

Synthesis of (S)—N-(1-(2-((1-(5-fluoropyridin-3-yl)ethyl)amino)thieno[3,2-d]pyrimidine-4-carbonyl)azetidin-3-yl)isobutyramide (Z558): The title compound (Z558) was prepared from (S)-(3-aminoazetidin-1-yl)(2-((1-(5-fluoropyridin-3-yl)ethyl)amino)-6-methylthieno[3,2-d]pyrimidin-4-yl)methanone using chemistry similar to that described in Example Z490 using isobutyryl chloride (commercially obtained from Sigma-Aldrich, St. Louis, Mo.) in place of pivaloyl chloride (47% yield). ¹H NMR (400 MHz, DMSO-d₆) δ 1.01-1.04 (6H, dd, J=15.2, 8.0 Hz), 1.53 (3H, dd, J=7.2, 2.8 Hz), 2.32-2.38 (1H, m), 3.91-3.94 (1H, s), 4.34 (1H, t, J=8.0 Hz), 4.53-4.57 (2H, m), 4.95-5.05 (1H, m), 5.23 (1H, q, J=11.62 Hz), 7.20 (1H, dd, J=5.6, 1.2 Hz), 7.71-7.76 (1H, m), 7.89 (1H, m), 8.28 (1H, d, J=4.8 Hz), 8.40 (1H, t, J=2.4 Hz), 8.43 (1H, m), 8.50-8.54 (1H, m) ppm. LCMS m/z=443.1 [M+H⁺].

Example Z559. (S)—N-(1-(7-Methyl-2-((1-(pyridin-2-yl)ethyl)amino)thieno[3,2-d]pyrimidine-4-carbonyl)azetidin-3-yl)pivalamide (Z559)

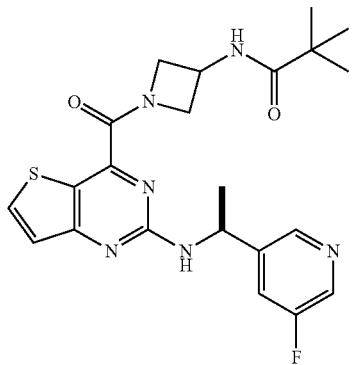

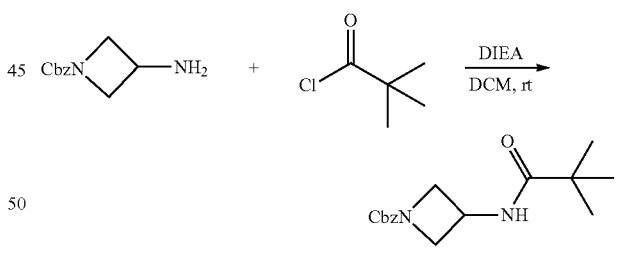

Synthesis of benzyl 3-pivalamidoazetidine-1-carboxylate: To a solution of benzyl 3-aminoazetidine-1-carboxylate (516 mg, 2.5 mmol) in DCM (5 mL) were added DIEA (871 uL, 5 mmol) and pivaloyl chloride (370 uL, 3 mmol) and the mixture thus obtained was stirred at room temperature for 2 h. The reaction mixture was concentrated and the residue was purified by flash chromatography on silica gel (80 g HP silica, Teledyne Isco) eluting with 15% to 50% ethyl acetate in hexane to provide benzyl 3-pivalamidoazetidine-1-carboxylate as a white solid (696 mg, 98% yield). ¹H NMR (400 MHz, CDCl₃) δ 1.20 (9H, s), 3.78 (2H, dd, J=10.0, 9.2 Hz), 4.34 (2H, d, J=9.2, 8.8 Hz), 4.64 (1H, m), 5.10 (2H, s), 5.96 (1H, br s), 7.30-7.38 (5H, m) ppm. LCMS m/z=291.2 [M+H⁺].

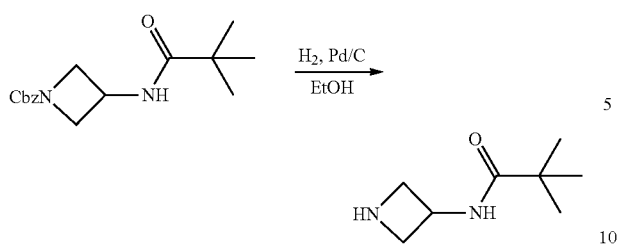

Synthesis of N-(azetidin-3-yl)pivalamide: To a solution of benzyl 3-(2,2-dimethylpropanoylamino)azetidine-1-carboxylate (690 mg, 2.36 mmol) in ethanol (10 mL) was added 10% palladium on carbon (wet, 690 mg). The reaction mixture was purged three times with hydrogen gas and stirred at hydrogen atmosphere for 1 hour and LCMS analysis indicated completion of the reaction. The reaction mixture was filtered through Celite and the filtrate was concentrated under reduced pressure to provide N-(azetidin-3-yl)pivalamide as a white solid (370 mg, 100% yield) which was used in next step without further purification. LCMS m/z=157.1 [M+H$^+$]).

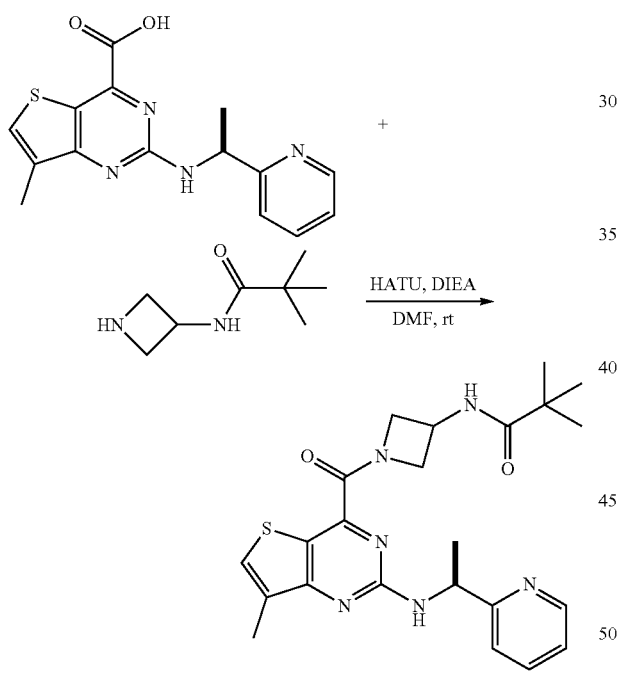

Synthesis of ((S)—N-(1-(7-methyl-2-((1-(pyridin-2-yl) ethyl)amino)thieno[3,2-d]pyrimidine-4-carbonyl)azetidin-3-yl)pivalamide (Z559): The title compound (Z559) was prepared from (S)-7-methyl-2-((1-(pyridin-2-yl)ethyl) amino)thieno[3,2-d]pyrimidine-4-carboxylic acid di-hydrochloride (39 mg, 0.10 mmol) using chemistry similar to that described in Example Z8 using N-(azetidin-3-yl)pivalamide in place of (R)-3-fluoropyrrolidine (15 mg, 41% yield). $^1$H NMR (400 MHz, CDCl$_3$) δ 1.24 (9H, br s), 1.61 (3H, d, J=6.8 Hz), 2.60 (3H, s), 3.94 (1H, m), 4.43 (1H, m), 4.53 (1H, m), 4.68 (1H, m), 5.07 (1H, m), 5.17 (1H, m), 5.92 (1H, m), 6.10 (1H, m), 6.86 (1H, dd, J=2.4, 1.2 Hz), 7.16 (1H, m), 7.34 (1H, dd, J=7.6, 1.2 Hz), 7.63 (1H, tt, J=7.6, 1.6 Hz), 8.56 (1H, tt, J=4.0, 1.2 Hz) ppm. LCMS m/z=453.2 [M+H$^+$].

Example Z560. (2-(((S)-1-(5-Fluoropyridin-3-yl) ethyl)amino)-6-methylthieno[3,2-d]pyrimidin-4-yl) ((R)-3-(methylamino)pyrrolidin-1-yl)methanone

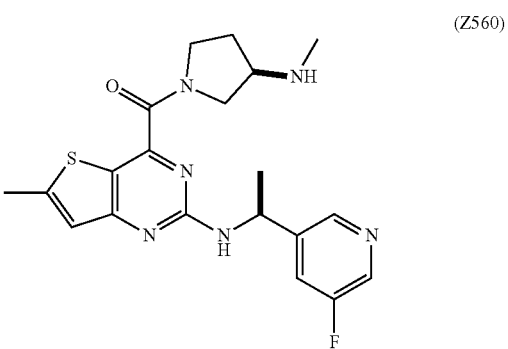

(Z560)

Synthesis of (2-(((S)-1-(5-fluoropyridin-3-yl)ethyl) amino)-6-methylthieno[3,2-d]pyrimidin-4-yl)((R)-3-(methylamino)pyrrolidin-1-yl)methanone (Z560): The title compound (Z560) was prepared from (S)-2-((1-(5-fluoropyridin-3-yl)ethyl)amino)-6-methylthieno[3,2-d]pyrimidine-4-carboxylic acid di-hydrochloride (40.5 mg, 0.10 mmol) using chemistry similar to that described in Example Z463 using tert-butyl (R)-methyl(pyrrolidin-3-yl)carbamate (commercially obtained from Ark Pharm, Libertyville, Ill.) in place of tert-butyl (S)-3-(2-aminoethyl)pyrrolidine-1-carboxylate (36 mg, 88% yield). $^1$H NMR (400 MHz, CDCl$_3$) δ 1.61 (3H, d, J=7.6 Hz), 1.74 (1H, m), 2.04 (1H, m), 2.44 (3H, br. s), 2.60 (3H, s), 3.25 (1H, m), 3.48-3.75 (2H, m), 3.76-3.90 (2H, m), 5.20 (1H, m), 5.34 (1H, dd, J=6.4, 2.8 Hz), 6.85 (1H, s), 7.48 (1H, m), 8.33 (1H, t, J=2.4 Hz), 8.50 (1H, dt, J=6.4, 1.6 Hz) ppm. LCMS m/z=415.3 [M+H$^+$].

Example Z561. (2-(((S)-1-(5-Fluoropyridin-3-yl) ethyl)amino)-6-methylthieno[3,2-d]pyrimidin-4-yl) ((S)-3-(methylamino)pyrrolidin-1-yl)methanone

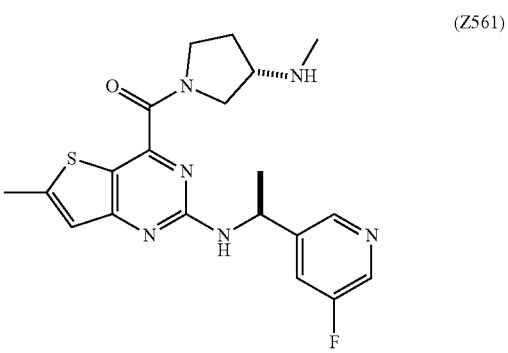

(Z561)

Synthesis of (2-(((S)-1-(5-fluoropyridin-3-yl)ethyl) amino)-6-methylthieno[3,2-d]pyrimidin-4-yl)((S)-3-(methylamino)pyrrolidin-1-yl)methanone (Z561): The title compound (Z561) was prepared from (S)-2-((1-(5-fluoropyridin-3-yl)ethyl)amino)-6-methylthieno[3,2-d]pyrimidine-4-carboxylic acid di-hydrochloride (40.5 mg, 0.10 mmol) using chemistry similar to that described in Example Z463 using tert-butyl (S)-methyl(pyrrolidin-3-yl)carbamate (commercially obtained from Ark Pharm, Libertyville, Ill.) in place of tert-butyl (S)-3-(2-aminoethyl)pyrrolidine-1-carboxylate (36 mg, 88% yield). ¹H NMR (400 MHz, CDCl₃) δ 1.61 (3H, d, J=6.8 Hz), 1.74 (1H, m), 2.00 (1H, m), 2.41 (3H, br. s), 2.60 (3H, s), 3.24 (1H, m), 3.35-3.78 (2H, m), 3.81 (1H, m), 3.94 (1H, m), 5.20 (1H, m), 5.34 (1H, d, J=6.4 Hz), 6.85 (1H, s), 7.43 (1H, m), 8.33 (1H, t, J=2.4 Hz), 8.49 (1H, dt, J=6.8, 1.6 Hz) ppm. LCMS m/z=415.1 [M+H⁺].

Example Z562. (S)-2-((1-(5-Fluoropyridin-3-yl)ethyl)amino)-6-methyl-N-(2-(1-methylpiperidin-4-yl)ethyl)thieno[3,2-d]pyrimidine-4-carboxamide

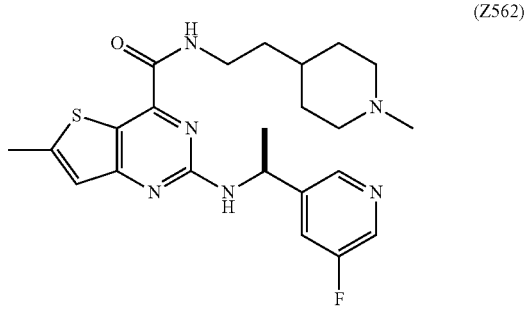

(Z562)

Synthesis of (S)-2-((1-(5-fluoropyridin-3-yl)ethyl)amino)-6-methyl-N-(2-(1-methylpiperidin-4-yl)ethyl)thieno[3,2-d]pyrimidine-4-carboxamide (Z562): The title compound (Z562) was prepared from (S)-2-((1-(5-fluoropyridin-3-yl)ethyl)amino)-6-methylthieno[3,2-d]pyrimidine-4-carboxylic acid di-hydrochloride (40.5 mg, 0.10 mmol) using chemistry similar to that described in Example Z8 using 2-(1-methylpiperidin-4-yl)ethan-1-amine (commercially obtained from PharmBlock, Sunnyvale, Calif.) in place of (R)-3-fluoropyrrolidine (27 mg, 60% yield). ¹H NMR (400 MHz, CDCl₃) δ 1.25-1.39 (3H, m), 1.52-1.52 (2H, m), 1.63 (3H, d, J=6.8 Hz), 1.68-1.78 (2H, m), 1.94 (2H, t, J=7.2 Hz), 2.28 (3H, s), 2.61 (3H, s), 2.87 (2H, d, J=7.2 Hz), 3.43-3.49 (2H, m), 5.18 (1H, m), 5.37 (1H, d, J=6.4 Hz), 6.85 (1H, s), 7.45 (1H, dt, J=7.6, 2.4 Hz), 7.59 (1H, s), 8.34 (1H, d, J=2.4 Hz), 8.53 (1H, s) ppm. LCMS m/z=457.1 [M+H⁺].

Example Z563. (S)-1-(2-((1-(5-Fluoropyridin-3-yl)ethyl)amino)thieno[3,2-d]pyrimidine-4-carbonyl)azetidine-3-carboxamide

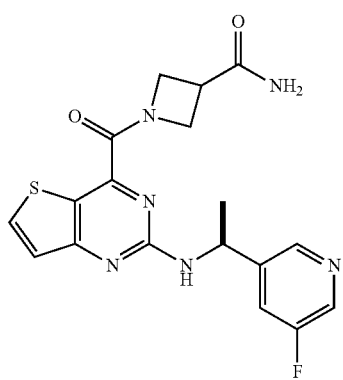 [SMILES: C[C@H](Nc1nc(C(=O)N2CC(C(N)=O)C2)c2sccc2n1)c1cncc(F)c1]

(Z563)

Synthesis of (S)-1-(2-((1-(5-fluoropyridin-3-yl)ethyl)amino)thieno[3,2-d]pyrimidine-4-carbonyl)azetidine-3-carboxamide (Z563): The title compound (Z563) was prepared from (S)-2-((1-(5-fluoropyridin-3-yl)ethyl)amino)-thieno[3,2-d]pyrimidine-4-carboxylic acid di-hydrochloride using chemistry similar to that described in Example Z17 using tert-butyl azetidine-3-carboxyamide hydrochloride (commercially obtained from PharmaBlock, Sunnyvale, Calif.) in place of (3R)-3-methoxypyrrolidine hydrochloride (19% yield). ¹H NMR (400 MHz, DMSO-d₆) δ 1.53 (3H, d, J=7.6 Hz), 3.35-3.41 (1H, m), 4.05-4.09 (1H, m), 4.20 (1H, t, J=9.6 Hz), 4.62-4.95 (1H, m), 4.81 (1H, t, J=9.2 Hz), 5.24 (1H, q, J=7.2 Hz), 7.08-7.09 (1H, d, J=5.6 Hz) 7.20 (1H, dd, J=5.6, 1.2 Hz), 7.52 (1H, d, J=4.8 Hz), 7.72-7.76 (1H, m), 7.85-7.88 (1H, m), 8.28 (1H, d, J=5.2 Hz), 8.40 (1H, dd, J=4.4, 2.8 Hz), 8.52 (1H, m) ppm. LCMS m/z=401.1 [M+H⁺].

Example Z564. (S)-1-(3-(2-((1-(5-Fluoropyridin-3-yl)ethyl)amino)thieno[3,2-d]pyrimidine-4-carbonyl)imidazolidin-1-yl)-2-methylpropan-1-one

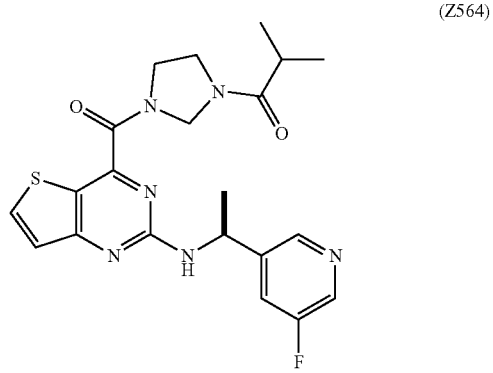

(Z564)

Synthesis of (S)-1-(3-(2-((1-(5-fluoropyridin-3-yl)ethyl)amino)thieno[3,2-d]pyrimidine-4-carbonyl)imidazolidin-1-yl)-2-methylpropan-1-one (Z564): The title compound (Z564) was prepared from (S)-(2-((1-(5-fluoropyridin-3-yl)ethyl)amino)thieno[3,2-d]pyrimidin-4-yl)(imidazolidin-1-yl)methanone using chemistry similar to that described in Example Z490 using isobutyryl chloride in place of pivaloyl chloride (33% yield). ¹H NMR (400 MHz, DMSO-d₆) δ 1.05 (5H, d, J=6.4 Hz), 1.23 (2H, m), 1.50-1.55 (3H, m), 2.74-2.79 (1H, m), 3.80 (2H, m), 3.94 (1H, m), 5.14-5.29 (1H, m), 5.37 (1H, d, J=9.6 Hz), 5.42-5.60 (1H, m), 7.22 (1H, d, J=5.6 Hz), 7.74-7.81 (1H, m), 7.97-8.10 (1H, m), 8.30-8.31 (1H, d, J=5.2 Hz), 8.40-8.42 (1H, d, J=5.6 Hz), 8.55-8.60 (1H, m) ppm. LCMS m/z=443.1 [M+H⁺].

Example Z565. (S)-1-(3-(2-((1-(5-Fluoropyridin-3-yl)ethyl)amino)thieno[3,2-d]pyrimidine-4-carbonyl)imidazolidin-1-yl)-2,2-dimethylpropan-1-one

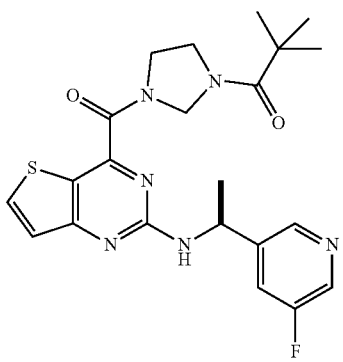 [SMILES: CC(C)C(=O)N1CCN(C(=O)c2nc(N[C@@H](C)c3cncc(F)c3)nc3ccsc23)C1]

(Z565)

Synthesis of (S)-1-(3-(2-((1-(5-fluoropyridin-3-yl)ethyl)amino)thieno[3,2-d]pyrimidine-4-carbonyl)imidazolidin-1-yl)-2,2-dimethylpropan-1-one (Z565): The title compound (Z565) was prepared from (S)-(2-((1-(5-fluoropyridin-3-yl)ethyl)amino)thieno[3,2-d]pyrimidin-4-yl)(imidazolidin-1-yl)methanone using chemistry similar to that described in Example Z490 (54% yield). $^1$H NMR (400 MHz, DMSO-$d_6$) δ 1.20 (9H, m), 1.53 (3H, d, J=6.8 Hz), 3.81-3.91 (4H m), 5.03 (1H, m), 5.25 (1H, dq, J=36.4, 7.6 Hz), 5.49 (1H, dd, J=39.2, 10.0 Hz), 7.22 (1H, dd, J=5.6, 1.2 Hz), 7.43-7.82 (1H, m), 7.97 (1H, d, J=4.0 Hz), 8.31 (1H, d, J=5.2 Hz), 8.41 (1H, dd, J=5.2, 2.8 Hz), 8.55-8.59 (1H, m) ppm. LCMS m/z=457.3 [M+H$^+$].

Example Z566. Neopentyl (S)-3-(2-((1-(5-fluoropyridin-3-yl)ethyl)amino)thieno[3,2-d]pyrimidine-4-carbonyl)imidazolidine-1-carboxylate

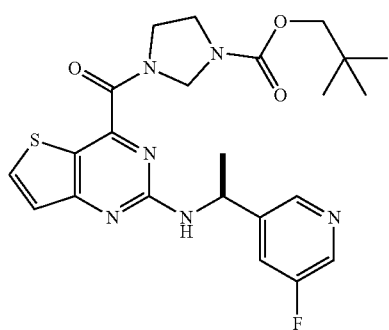 [SMILES: C[C@H](Nc1nc(C(=O)N2CCN(C(=O)OCC(C)(C)C)C2)c2sccc2n1)c1cncc(F)c1]

(Z566)

Synthesis of neopentyl (S)-3-(2-((1-(5-fluoropyridin-3-yl)ethyl)amino)thieno[3,2-d]pyrimidine-4-carbonyl)imidazolidine-1-carboxylate (Z566): The title compound (Z566) was prepared from (S)-(2-((1-(5-fluoropyridin-3-yl)ethyl)amino)thieno[3,2-d]pyrimidin-4-yl)(imidazolidin-1-yl)methanone using chemistry similar to that described in Example Z490 using 2,2-dimethylpropyl chloroformate (commercially obtained from Enamine, Monmouth Jct., N.J.) in place of pivaloyl chloride (47% yield). $^1$H NMR (400 MHz, DMSO-$d_6$) δ 0.93 (9H, m), 1.53 (3H, d, J=7.2 Hz), 3.57-3.64 (2H, m), 3.78 (2H, m), 3.88-3.91 (2H m), 4.92 (1H, s), 5.20-5.28 (1H, m), 5.44 (1H, d, J=8.8 Hz), 7.22 (1H, d, J=5.6 Hz), 7.74-7.80 (1H, m), 7.97 (1H, d, J=7.6 Hz), 8.31 (1H, d, J=5.2 Hz), 8.41 (1H, d, J=2.8 Hz), 8.55 (1H, m) ppm. LCMS m/z=487.3 [M+H$^+$].

Example Z567. (2-(((S)-1-(5-Fluoropyridin-3-yl)ethyl)amino)thieno[3,2-d]pyrimidin-4-yl)((S)-2-(methoxymethyl)azetidin-1-yl)methanone

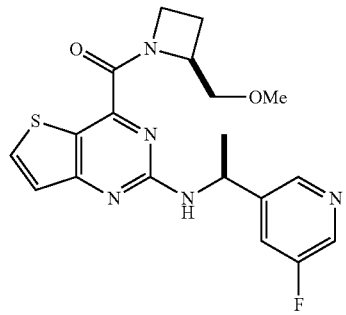 [SMILES: COC[C@@H]1CCN1C(=O)c1nc(N[C@@H](C)c2cncc(F)c2)nc2ccsc12]

(Z567)

Synthesis of (2-(((S)-1-(5-fluoropyridin-3-yl)ethyl)amino)thieno[3,2-d]pyrimidin-4-yl)((S)-2-(methoxymethyl)azetidin-1-yl)methanone (Z567): The title compound (Z567) was prepared from (S)-2-((1-(5-fluoropyridin-3-yl)ethyl)amino)-thieno[3,2-d]pyrimidine-4-carboxylic acid di-hydrochloride using chemistry similar to that described in Example Z17 using (2S)-2-(methoxymethyl)azetidine (commercially obtained from PharmaBlock, Sunnyvale, Calif.) in place of (3R)-3-methoxypyrrolidine hydrochloride (53% yield). $^1$H NMR (400 MHz, DMSO-$d_6$) δ 1.53 (3H, d, J=7.2 Hz), 2.10-2.22 (1H, m), 2.35-2.45 (1H, m), 3.31 (3H, m), 3.55-3.59 (1H, m), 3.78-3.82 (1H, d, J=10.4, 4.4 Hz), 3.93-4.01 (2H, m), 4.55-4.62 (1H, m), 5.23 (1H, q, J=7.2 Hz), 7.19 (1H, d, J=5.2 Hz), 7.72-7.77 (1H, m), 7.82-7.87 (1H, m), 8.28 (1H, d, J=5.6 Hz), 8.41 (1H, d, J=2.8 Hz), 8.52 (1H, m) ppm. LCMS m/z=402.2 [M+H$^+$].

Example Z568. (2-(((S)-1-(5-Fluoropyridin-3-yl)ethyl)amino)thieno[3,2-d]pyrimidin-4-yl)((R)-2-(methoxymethyl)azetidin-1-yl)methanone

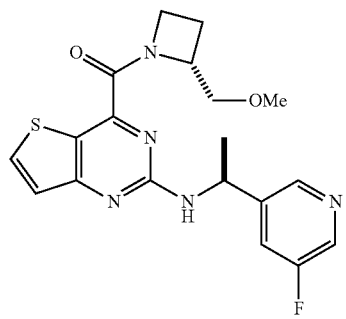 [SMILES: COC[C@H]1CCN1C(=O)c1nc(N[C@@H](C)c2cncc(F)c2)nc2ccsc12]

(Z568)

Synthesis of (2-(((S)-1-(5-fluoropyridin-3-yl)ethyl)amino)thieno[3,2-d]pyrimidin-4-yl)((R)-2-(methoxymethyl)ethyl)azetidin-1-yl)methanone (Z567): The title compound (Z567) was prepared from (S)-2-((1-(5-fluoropyridin-3-yl)ethyl)amino)-thieno[3,2-d]pyrimidine-4-carboxylic acid dihydrochloride using chemistry similar to that described in Example Z17 using (2R)-2-(methoxymethyl)azetidine (commercially obtained from PharmaBlock, Sunnyvale, Calif.) in place of (3R)-3-methoxypyrrolidine hydrochloride (33% yield). $^1$H NMR (400 MHz, DMSO-$d_6$) δ 1.53 (3H, d, J=7.2 Hz), 2.10-2.22 (1H, m), 2.35-2.45 (1H, m), 3.31 (3H, m), 3.57 (1H, dd, J=10.4, 3.2 Hz), 3.80 (2H, dd, J=6.0, 0.8 Hz), 3.90-4.00 (1H, m), 4.55-4.69 (1H, m), 5.25 (1H, q, J=7.6 Hz), 7.19 (1H, dd, J=5.6, 2.4 Hz), 7.73 (1H, dd, J=10.4, 2.4 Hz), 7.82-7.87 (1H, m), 8.28 (1H, d, J=5.6 Hz), 8.41 (1H, d, J=2.8 Hz), 8.52-8.55 (1H, m) ppm. LCMS m/z=402.2 [M+H$^+$].

Example Z569. (2-(((S)-1-(5-Fluoropyridin-3-yl)ethyl)amino)-6-methylthieno[3,2-d]pyrimidin-4-yl)((S)-2-(methoxymethyl)azetidin-1-yl)methanone

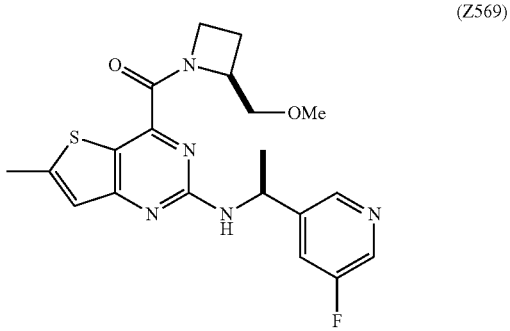

(Z569)

Synthesis of (2-(((S)-1-(5-fluoropyridin-3-yl)amino)-6-methylthieno[3,2-d]pyrimidin-4-yl)((S)-2-(methoxymethyl)azetidin-1-yl)methanone (Z569): The title compound (Z569) was prepared from (S)-2-((1-(5-fluoropyridin-3-yl)ethyl)amino)-6-methylthieno[3,2-d]pyrimidine-4-carboxylic acid di-hydrochloride using chemistry similar to that described in Example Z17 using (2S)-2-(methoxymethyl)azetidine in place of (3R)-3-methoxypyrrolidine hydrochloride (57% yield). $^1$H NMR (400 MHz, DMSO-$d_6$) δ 1.53 (3H, d, J=7.2 Hz), 2.18-2.40 (1H, m), 2.50 (3H, s), 2.54 (2H, m), 3.29 (3H, m), 3.55-3.59 (1H, m), 3.80 (1H, d, J=10.4, 4.8 Hz), 3.93-4.01 (1H, m), 4.55-4.62 (1H, m), 5.23 (1H, q, J=7.2 Hz), 6.93 (1H, d, J=0.8 Hz), 7.71-7.75 (2H, m), 8.41 (1H, d, J=2.8 Hz), 8.52 (1H, m) ppm. LCMS m/z=416.1 [M+H$^+$].

Example Z570. (2-(((S)-1-(5-Fluoropyridin-3-yl)ethyl)amino)-6-methylthieno[3,2-d]pyrimidin-4-yl)((R)-2-(methoxymethyl)azetidin-1-yl)methanone

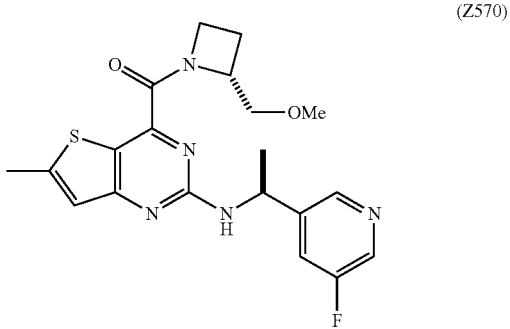

(Z570)

Synthesis of (2-(((S)-1-(5-fluoropyridin-3-yl)ethyl)amino)-6-methylthieno[3,2-d]pyrimidin-4-yl)((R)-2-(methoxymethyl)azetidin-1-yl)methanone (Z570): The title compound (Z570) was prepared from (S)-2-((1-(5-fluoropyridin-3-yl)ethyl)amino)-6-methylthieno[3,2-d]pyrimidine-4-carboxylic acid di-hydrochloride using chemistry similar to that described in Example Z17 using (2R)-2-(methoxymethyl)azetidine in place of (3R)-3-methoxypyrrolidine hydrochloride (47% yield). $^1$H NMR (400 MHz, DMSO-$d_6$) δ 1.50 (3H, d, J=7.2 Hz), 2.18-2.40 (1H, m), 2.50 (2H, m), 2.55 (3H, s), 3.29 (3H, m), 3.56 (1H, dd, J=10.0, 2.4 Hz), 3.81 (1H, dd, J=10.0, 4.8 Hz), 3.93-4.01 (1H, m), 4.58 (1H, m), 5.23 (1H, q, J=7.2 Hz), 6.93 (1H, d, J=0.8 Hz), 7.71-7.75 (2H, m), 8.41 (1H, td, J=6.4, 2.4 Hz), 8.50-8.54 (1H, m) ppm. LCMS m/z=416.1 [M+H$^+$].

Example Z571. (S)—N-(tert-Butyl)-2-(1-(2-((1-(5-fluoropyridin-3-yl)ethyl)amino)thieno[3,2-d]pyrimidine-4-carbonyl)azetidin-3-yl)acetamide

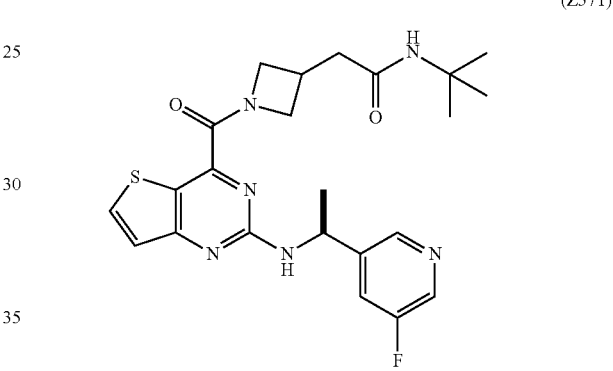

(Z571)

Synthesis of methyl (S)-2-(1-(2-((1-(5-fluoropyridin-3-yl)ethyl)amino)thieno[3,2-d]pyrimidine-4-carbonyl)azetidin-3-yl)acetate: The title compound was prepared from (S)-2-((1-(5-fluoropyridin-3-yl)ethyl)amino)-thieno[3,2-d]pyrimidine-4-carboxylic acid di-hydrochloride using chemistry similar to that described in Example Z17 using methyl 2-(azetidin-3-yl)acetate hydrochloride (commercially obtained from J&W Pharmalab, Levittown, Pa.) in place of (3R)-3-methoxypyrrolidine hydrochloride (82% yield). LCMS m/z=430.2 [M+H$^+$].

Synthesis of (S)-2-(1-(2-((1-(5-fluoropyridin-3-yl)ethyl)amino)thieno[3,2-d]pyrimidine-4-carbonyl)azetidin-3-yl)acetic acid: The title compound was prepared from methyl (S)-2-(1-(2-((1-(5-fluoropyridin-3-yl)ethyl)amino)thieno[3,2-d]pyrimidine-4-carbonyl)azetidin-3-yl)acetate using chemistry similar to that described in Example Z435 (45% yield). LCMS m/z=416.1 [M+H$^+$].

Synthesis of (S)—N-(tert-butyl)-2-(1-(2-((1-(5-fluoropyridin-3-yl)ethyl)amino)thieno[3,2-d]pyrimidine-4-carbonyl)azetidin-3-yl)acetamide (Z571): The title compound (Z571) was prepared from (S)-2-(1-(2-((1-(5-fluoropyridin-3-yl)ethyl)amino)thieno[3,2-d]pyrimidine-4-carbonyl)azetidin-3-yl)acetic acid using chemistry similar to that described in Example Z17 using tert-butylamine in place of (3R)-3-methoxypyrrolidine hydrochloride (33% yield). $^1$H NMR (400 MHz, DMSO-$d_6$) δ 1.24 (9H, t, J=1.2 Hz), 1.53 (3H, d, J=6.4 Hz), 2.37-2.42 (2H, m), 2.90 (1H, m), 3.78 (1H, dd, J=10.4, 5.2 Hz), 4.16 (1H, t, J=9.2 Hz), 4.41 (1H, dd, J=16.4, 10.0 Hz), 4.84 (1H, m), 5.23 (1H, q, J=6.4 Hz), 7.19 (1H, d, J=5.6 Hz), 7.51 (1H, d, J=7.2 Hz), 7.75 (1H, d, J=10.0 Hz), 7.86 (1H, d, J=6.4 Hz), 8.27 (1H, d, J=5.6 Hz), 8.41 (1H, dd, J=5.6, 1.6 Hz), 8.52 (1H, s) ppm. LCMS m/z=471.2 [M+H⁺].

Example Z572. tert-Butyl (S)-1-(2-((1-(5-fluoropyridin-3-yl)ethyl)amino)thieno[3,2-d]pyrimidine-4-carbonyl)azetidine-3-carboxylate

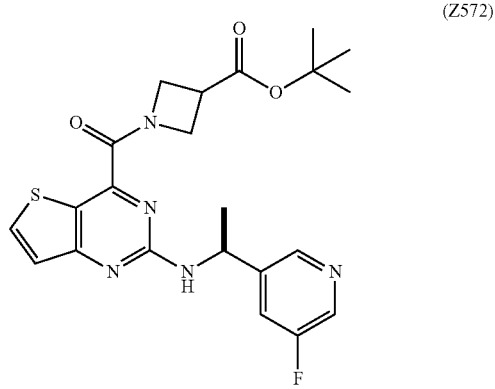

(Z572)

Synthesis of tert-butyl (S)-1-(2-((1-(5-fluoropyridin-3-yl)ethyl)amino)thieno[3,2-d]pyrimidine-4-carbonyl)azetidine-3-carboxylate (Z572): The title compound (Z572) was prepared from (S)-2-((1-(5-fluoropyridin-3-yl)ethyl)amino)-thieno[3,2-d]pyrimidine-4-carboxylic acid di-hydrochloride using chemistry similar to that described in Example Z17 using tert-butyl azetidine-3-carboxylate hydrochloride in place of (3R)-3-methoxypyrrolidine hydrochloride (68% yield). ¹H NMR (400 MHz, DMSO-d₆) δ 1.46 (9H, d, J=6.8 Hz), 1.53 (3H, d, J=7.2 Hz), 3.44-3.54 (1H, in), 3.78 (1H, dd, J=10.4, 5.2 Hz), 4.10 (1H, in), 4.41 (1H, m), 4.89 (1H, m), 5.21 (1H, q, J=6.8 Hz), 7.19 (1H, d, J=5.6 Hz), 7.70-7.77 (1H, m), 7.89 (1H, m), 8.27 (1H, d, J=5.2 Hz), 8.41 (1H, dd, J=4.8, 2.8 Hz), 8.52 (1H, d, J=6.0 Hz) ppm. LCMS m/z=458.1 [M+H⁺].

Example Z573. tert-Butyl (S)-1-(2-((1-(5-fluoropyridin-3-yl)ethyl)amino)-6-methylthieno[3,2-d]pyrimidine-4-carbonyl)azetidine-3-carboxylate

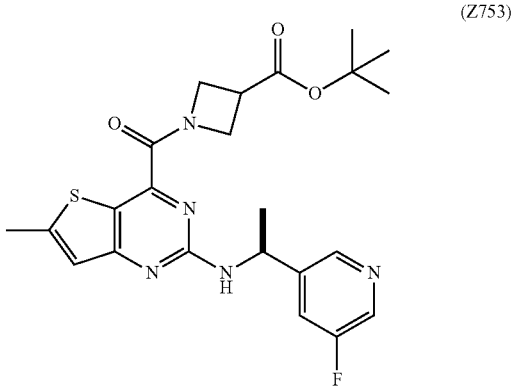

(Z753)

Synthesis of tert-butyl (S)-1-(2-((1-(5-fluoropyridin-3-yl)ethyl)amino)-6-methylthieno[3,2-d]pyrimidine-4-carbonyl) azetidine-3-carboxylate (Z573): The title compound (Z573) was prepared from (S)-2-((1-(5-fluoropyridin-3-yl)ethyl)amino)-6-methylthieno[3,2-d]pyrimidine-4-carboxylic acid di-hydrochloride using chemistry similar to that described in Example Z17 using tert-butyl azetidine-3-carboxylate hydrochloride (commercially obtained from Ark Pharm, Libertyville, Ill.) in place of (3R)-3-methoxypyrrolidine hydrochloride (68% yield). ¹H NMR (400 MHz, DMSO-d₆) δ 1.45 (9H, d, J=7.2 Hz), 1.53 (3H, d, J=6.8 Hz), 2.55 (3H, s), 3.45-3.55 (1H, m), 4.08 (1H, m), 4.22 (1H, t, J=9.6 Hz), 4.50-4.70 (1H, m), 4.85-4.95 (1H, m), 5.21 (1H, q, J=6.8 Hz), 6.94 (1H, s), 7.68-7.75 (1H, m), 7.77-7.85 (1H, m), 8.41 (1H, dd, J=5.6, 2.8 Hz), 8.52 (1H, d, J=6.4 Hz) ppm. LCMS m/z=472.3 [M+H⁺].

Example Z574. (S)-(3-(Ethylamino)azetidin-1-yl)(2-((1-(5-fluoropyridin-3-yl)ethyl)amino)-6-methylthieno[3,2-d]pyrimidin-4-yl)methanone

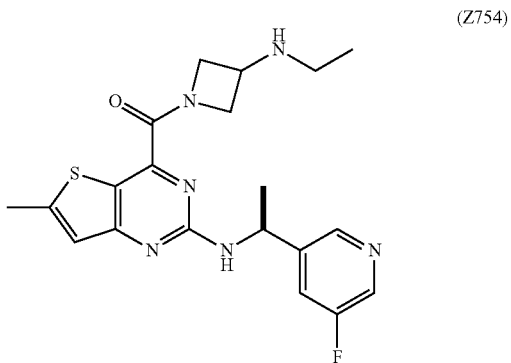

(Z754)

Synthesis of benzyl (S)-(1-(2-((1-(5-fluoropyridin-3-yl)ethyl)amino)-6-methylthieno[3,2-d]pyrimidine-4-carbonyl) azetidin-3-yl)carbamate: The title compound was prepared from (S)-2-((1-(5-fluoropyridin-3-yl)ethyl)amino)-6-methylthieno[3,2-d]pyrimidine-4-carboxylic acid di-hydrochloride (40.5 mg, 0.10 mmol) using chemistry similar to that described in Example Z8 using benzyl azetidin-3-ylcarbamate in place of (R)-3-fluoropyrrolidine (37 mg, 71% yield). LCMS m/z=521.2 [M+H⁺].

Synthesis of (S)-(3-(ethylamino)azetidin-1-yl)(2-((1-(5-fluoropyridin-3-yl)ethyl)amino)-6-methylthieno[3,2-d]pyrimidin-4-yl)methanone (Z574): To a solution of benzyl (S)-(1-(2-((1-(5-fluoropyridin-3-yl)ethyl)amino)-6-methylthieno[3,2-d]pyrimidine-4-carbonyl)azetidin-3-yl)carbamate (37 mg, 0.071 mmol) in ethanol (5 mL) was added 10% palladium on carbon (wet, 37 mg). The reaction mixture was purged three times with hydrogen gas and stirred at hydrogen atmosphere overnight. The reaction mixture was filtered through Celite and the filtrate was concentrated under reduced pressure and the residue was purified by flash chromatography on silica gel (12 g HP silica, Teledyne Isco) eluting with 15% to 50% solvent A (DCM/MeOH/NH₄OH, 100/10/1) in DCM to provide (S)-(3-(ethylamino)azetidin-1-yl)(2-((1-(5-fluoropyridin-3-yl)ethyl)amino)-6-methylthieno[3,2-d]pyrimidin-4-yl)methanone as a white solid (7 mg, 24% yield). ¹H NMR (400 Hz, CDCl₃) δ 1.14 (3H, t, J=7.2 Hz), 1.62 (3H, d, J=6.8 Hz), 2.59-2.68 (2H, m), 2.62 (3H, s), 3.67 (1H, m), 3.89 (1H, m), 4.26 (1H, m), 4.38 (1H, m), 4.55 (1H, m), 5.21 (1H, m), 5.39 (1H, d, J=6.4 Hz), 6.84

(1H, s), 7.42 (1H, dt, J=9.6, 2.4 Hz), 8.34 (1H, d, J=2.4 Hz), 8.49 (1H, s) ppm. LCMS m/z=415.1 [M+H⁺].

Example Z575. (S)-(2-((1-(5-Fluoropyridin-3-yl)ethyl)amino)-6-methylthieno[3,2-d]pyrimidin-4-yl)(3-((methylsulfonyl)methyl)azetidin-1-yl)methanone

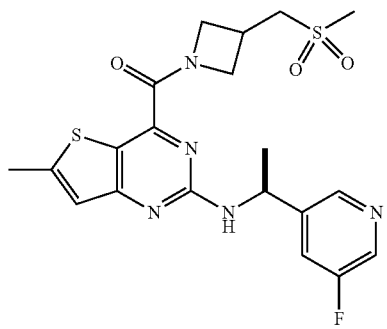 [SMILES: Cc1cc2nc(N[C@@H](C)c3cncc(F)c3)nc(C(=O)N3CC(CS(C)(=O)=O)C3)c2s1]

Synthesis of (S)-(2-((1-(5-fluoropyridin-3-yl)ethyl)amino)-6-methylthieno[3,2-d]pyrimidin-4-yl)(3-((methylsulfonyl)methyl)azetidin-1-yl)methanone (Z575): The title compound (Z575) was prepared from (S)-2-((1-(5-fluoropyridin-3-yl)ethyl)amino)-6-methylthieno[3,2-d]pyrimidine-4-carboxylic acid di-hydrochloride (40.5 mg, 0.10 mmol) using chemistry similar to that described in Example Z8 using 3-methanesulfonylmethyl-azetidine p-toluenesulfonic acid salt (commercially obtained from J&W Pharmlab, Levittown, Pa.) in place of (R)-3-fluoropyrrolidine (15 mg, 32% yield). ¹H NMR (400 MHz, CDCl₃) δ 1.62 (3H, d, J=6.8 Hz), 2.60 (3H, s), 3.00 (3H, s), 3.20-3.35 (2H, m), 3.39 (1H, m), 4.01 (1H, td, J=11.2, 5.6 Hz), 4.46 (1H, m), 4.67 (1H, m), 4.70 (1H, m), 5.19 (1H, m), 5.34 (1H, t, J=6.4 Hz), 6.84 (1H, s), 7.44 (1H, dt, J=9.2, 1.2 Hz), 8.34 (1H, dd, J=2.8, 1.2 Hz), 8.51 (1H, dd, J=2.8, 1.2 Hz) ppm. LCMS m/z=464.1 [M+H⁺].

Example Z576. (S)-1-((1-(2-((1-(5-Fluoropyridin-3-yl)ethyl)amino)thieno[3,2-d]pyrimidine-4-carbonyl)azetidin-3-yl)methyl)-3-methylurea

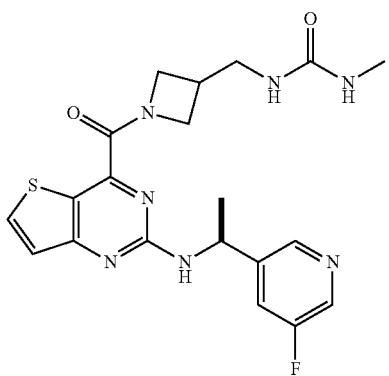 [SMILES: CNC(=O)NCC1CN(C(=O)c2nc(N[C@@H](C)c3cncc(F)c3)nc3ccsc23)C1]

Synthesis of (S)-1-((1-(2-((1-(5-fluoropyridin-3-yl)ethyl)amino)thieno[3,2-d]pyrimidine-4-carbonyl)azetidin-3-yl)methyl)-3-methylurea (Z576): The title compound (Z576) was prepared from (S)-(3-(aminomethyl)azetidin-1-yl)(2-((1-(5-fluoropyridin-3-yl)ethyl)amino)thieno[3,2-d]pyrimidin-4-yl)methanone using chemistry similar to that described in Example Z490 using N-methylcarbamoyl chloride (commercially obtained from Sigma-Aldrich, St. Louis, Mo.) in place of pivaloyl chloride (34% yield). LCMS m/z=444.2 [M+H⁺].

Example Z577. (S)-3-((1-(2-((1-(5-Fluoropyridin-3-yl)ethyl)amino)thieno[3,2-d]pyrimidine-4-carbonyl)azetidin-3-yl)methyl)-1,1-dimethylurea

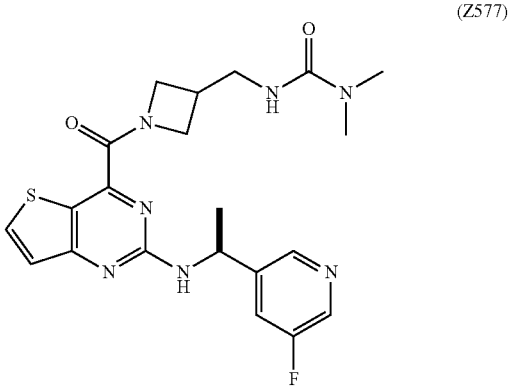

Synthesis of (S)-3-((1-(2-((1-(5-fluoropyridin-3-yl)ethyl)amino)thieno[3,2-d]pyrimidine-4-carbonyl)azetidin-3-yl)methyl)-1,1-dimethylurea (Z577): The title compound (Z577) was prepared from (S)-(3-(aminomethyl)azetidin-1-yl)(2-((1-(5-fluoropyridin-3-yl)ethyl)amino)thieno[3,2-d]pyrimidin-4-yl)methanone using chemistry similar to that described in Example Z490 using dimethylcarbamyl chloride (commercially obtained from Sigma-Aldrich, St. Louis, Mo.) in place of pivalonyl chloride (62% yield). ¹H NMR (400 MHz, CDCl₃) δ 1.63 (3H, dd, J=5.6, 2.4 Hz), 2.96 (6H, d, J=6.0 Hz), 2.80-2.89 (1H, m), 3.54 (1H, dq, J=29.2, 5.2 Hz), 3.87 (1H, ddd, J=39.6, 9.2, 4.0 Hz), 4.23-4.28 (1H, m), 4.33-4.46 (1H, m), 4.72 (1H, m), 5.18 (1H, dq, J=23.2, 5.6 Hz), 5.42 (1H, dd, J=12.8, 4.8 Hz), 7.19 (1H, dd, J=4.0, 1.2 Hz), 7.44-7.47 (1H, m), 7.97 (1H, t, J=4.8 Hz), 8.33 (1H, t, J=2.0 Hz), 8.48 (1H, d, J=10.4 Hz) ppm. LCMS m/z=458.1 [M+H⁺].

Example Z578. (S)—N-((1-(2-((1-(5-Fluoropyridin-3-yl)ethyl)amino)thieno[3,2-d]pyrimidine-4-carbonyl)azetidin-3-yl)methyl)isobutyramide

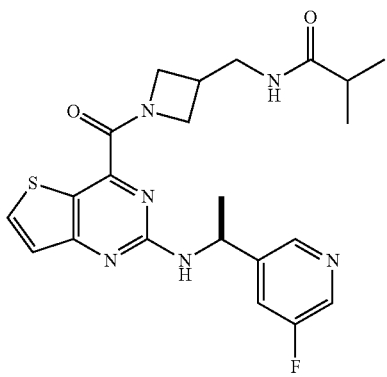 [SMILES: CC(C)C(=O)NCC1CN(C(=O)c2nc(N[C@@H](C)c3cncc(F)c3)nc3ccsc23)C1]

Synthesis of (S)—N-((1-(2-((1-(5-fluoropyridin-3-yl)ethyl)amino)thieno[3,2-d]pyrimidine-4-carbonyl)azetidin-3-yl)methyl)isobutyramide (Z578): The title compound (Z578) was prepared from (S)-(3-(aminomethyl)azetidin-1-yl)(2-((1-(5-fluoropyridin-3-yl)ethyl)amino)thieno[3,2-d]pyrimidin-4-yl)methanone using chemistry similar to that described in Example Z490 using isobutyryl chloride (commercially obtained from Sigma-Aldrich, St. Louis, Mo.) in place of pivaloyl chloride (95% yield). $^1$H NMR (400 MHz, CDCl$_3$) δ 1.19 (6H, d, J=8.4 Hz), 1.63 (3H, dd, J=10.0, 4.0 Hz), 2.46 (1H, m), 2.88-2.97 (2H, m), 3.46-3.66 (2H, m), 3.83 (1H, ddd, J=26.8, 10.8, 6.0 Hz), 4.24-4.31 (2H, m), 5.21 (1H, q, J=6.4 Hz), 5.41 (1H, dd, J=8.0, 6.4 Hz), 5.88 (1H, m), 7.17 (1H, dd, J=5.6, 0.8 Hz), 7.47 (1H, dt, J=9.6, 2.0 Hz), 7.98 (1H, dd, J=5.6, 4.4 Hz), 8.41 (1H, dd, J=6.8, 2.8 Hz), 8.48 (1H, d, J=18.4 Hz) ppm. LCMS m/z=457.3 [M+H$^+$].

Example Z579. (S)—N-(tert-Butoxy)-1-(2-((1-(5-fluoropyridin-3-yl)ethyl)amino)thieno[3,2-d]pyrimidine-4-carbonyl)azetidine-3-carboxamide

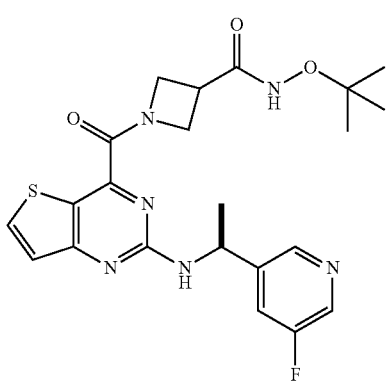 [SMILES: C[C@H](Nc1nc(C(=O)N2CC(C(=O)NOC(C)(C)C)C2)c2sccc2n1)c1cncc(F)c1]

Synthesis of (S)-1-(2-((1-(5-fluoropyridin-3-yl)ethyl)amino)thieno[3,2-d]pyrimidine-4-carbonyl)azetidine-3-carboxylic acid di-hydrochloride: The title compound was prepared from tert-butyl (S)-1-(2-((1-(5-fluoropyridin-3-yl)ethyl)amino)thieno[3,2-d]pyrimidine-4-carbonyl)azetidine-3-carboxylate using chemistry similar to that described in Example Z520 (99% yield). LCMS m/z=402.0 [M+H$^+$].

Synthesis of (S)—N-(tert-butoxy)-1-(2-((1-(5-fluoropyridin-3-yl)ethyl)amino)thieno[3,2-d]pyrimidine-4-carbonyl)azetidine-3-carboxamide (Z579): The title compound (Z579) was prepared from (S)-2-((1-(5-fluoropyridin-3-yl)ethyl)amino)-thieno[3,2-d]pyrimidine-4-carboxylic acid di-hydrochloride using chemistry similar to that described in Example Z17 using O-tert-butylhydroxylamine hydrochloride in place of (3R)-3-methoxypyrrolidine hydrochloride (64% yield). $^1$H NMR (400 MHz, CDCl$_3$) δ 1.29 (9H, s), 1.63 (3H, dd, J=5.6, 1.2 Hz), 3.18-3.30 (1H, m), 3.83 (1H, m), 4.34-4.43 (2H, m), 4.79-4.84 (1H, m), 5.18-5.27 (1H, m), 5.39-5.42 (1H, m), 7.19 (1H, dd, J=5.6, 1.6 Hz), 7.41-7.46 (1H, m), 7.67-7.70 (1H, m), 7.97 (1H, t, J=4.8 Hz), 8.33 (1H, d, J=2.4 Hz), 8.48 (1H, d, J=5.6 Hz) ppm. LCMS m/z=473.1 [M+H$^+$].

Example Z580. tert-Butyl (S)-2-(1-(2-((1-(5-Fluoropyridin-3-yl)ethyl)amino)-6-methylthieno[3,2-d]pyrimidine-4-carbonyl)azetidin-3-yl)acetate

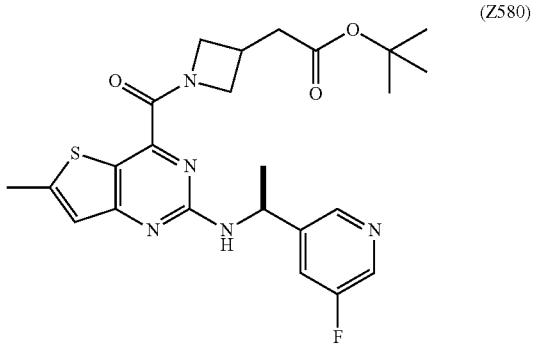

Synthesis of tert-butyl (S)-2-(1-(2-((1-(5-fluoropyridin-3-yl)ethyl)amino)-6-methylthieno[3,2-d]pyrimidine-4-carbonyl)azetidin-3-yl)acetate (Z580): The title compound (Z580) was prepared from (S)-2-((1-(5-fluoropyridin-3-yl)ethyl)amino)-6-methylthieno[3,2-d]pyrimidine-4-carboxylic acid di-hydrochloride using chemistry similar to that described in Example Z17 using tert-butyl 2-(azetidin-3-yl)acetate hydrochloride in place of (3R)-3-methoxypyrrolidine hydrochloride (83% yield). $^1$H NMR (400 MHz, CDCl$_3$) δ 1.45 (9H, d, J=3.6 Hz), 1.64 (3H, d, J=6.8 Hz), 2.52 (1H, d, J=8.0 Hz), 2.58-2.60 (1H, dd, J=4.8, 1.6 Hz) 2.61 (3H, d, J=0.8 Hz), 2.95-3.01 (1H, m), 3.87 (1H, dt, J=9.6, 2.4 Hz), 4.50-4.65 (1H, m), 4.24-4.32-4.38 (2H, m), 5.21 (1H, m), 5.61 (1H, m), 6.88 (1H, t, J=1.2 Hz), 7.42-7.45 (1H, m), 8.35 (1H, d, J=2.8 Hz), 8.48 (1H, dt, J=5.2, 1.6 Hz) ppm. LCMS m/z=486.2 [M+H$^+$].

Example Z581. Neopentyl (S)-((1-(2-((1-(5-fluoropyridin-3-yl)ethyl)amino)thieno[3,2-d]pyrimidine-4-carbonyl)azetidin-3-yl)methyl)carbamate

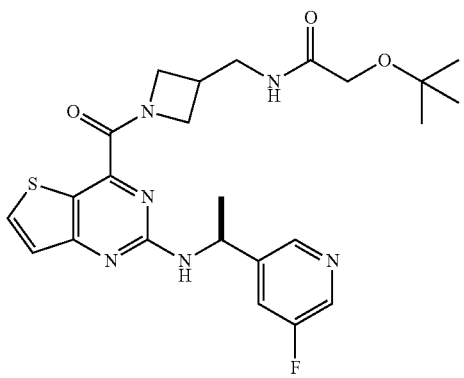 [SMILES: C[C@H](Nc1nc(C(=O)N2CC(CNC(=O)OCC(C)(C)C)C2)c2sccc2n1)c1cncc(F)c1]

(Z581)

Synthesis of neopentyl (S)-((1-(2-((1-(5-fluoropyridin-3-yl)ethyl)amino)thieno[3,2-d]pyrimidine-4-carbonyl)azetidin-3-yl)methyl)carbamate (Z581): The title compound (Z581) was prepared from (S)-(3-(aminomethyl)azetidin-1-yl)(2-((1-(5-fluoropyridin-3-yl)ethyl)amino)thieno[3,2-d]pyrimidin-4-yl)methanone using chemistry similar to that described in Example Z490 using isobutyryl chloride (commercially obtained from Sigma-Aldrich, St. Louis, Mo.) in place of pivaloyl chloride (51% yield). $^1$H NMR (400 MHz, CDCl$_3$) δ 0.94 (9H, d, J=2.0 Hz), 1.65 (3H, dd, J=6.8, 2.0 Hz), 2.80 (1H, m), 3.43-3.48 (2H, m), 3.78-3.88 (3H, m), 3.90-4.05 (1H, m), 4.28 (2H, m), 4.62-4.75 (1H, m), 5.20 (1H, q, J=6.0 Hz), 5.38 (1H, t, J=6.0 Hz), 7.17 (1H, d, J=5.6 Hz), 7.45 (1H, dd, J=9.2, 1.6 Hz), 7.98 (1H, dd, J=5.2, 2.8 Hz), 8.35 (1H, t, J=2.8 Hz), 8.50 (1H, d, J=8.0 Hz) ppm. LCMS m/z=501.2 [M+H$^+$].

Example Z582. (R)—N-((1-(2-(((S)-1-(5-Fluoropyridin-3-yl)ethyl)amino)thieno[3,2-d]pyrimidine-4-carbonyl)azetidin-3-yl)methyl)tetrahydrofuran-3-carboxamide

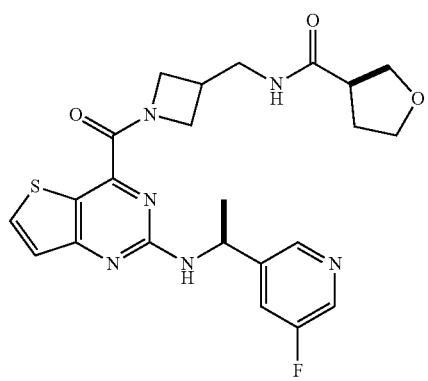

(Z582)

Synthesis of (R)—N-((1-(2-(((S)-1-(5-fluoropyridin-3-yl)ethyl)amino)thieno[3,2-d]pyrimidine-4-carbonyl)azetidin-3-yl)methyl)tetrahydrofuran-3-carboxamide (Z582): The title compound (Z582) was prepared from (S)-(3-(aminomethyl)azetidin-1-yl)(2-((1-(5-fluoropyridin-3-yl)ethyl)amino)thieno[3,2-d]pyrimidin-4-yl)methanone using chemistry similar to that described in Example Z17 using (3R)-tetrahydrofuran-3-carboxylic (commercially obtained from Ark Pharm, Libertyville, Ill.) in place of (3R)-3-methoxypyrrolidine hydrochloride (47% yield). $^1$H NMR (400 MHz, CDCl$_3$) δ 1.65 (3H, dd, J=6.8, 2.0 Hz), 3.16-3.25 (6H, m), 3.27-3.42 (2H, m), 3.55-3.65 (1H, m), 3.77 (1H, m), 4.34-4.42 (1H, m), 4.76 (2H, s), 5.2 (1H, m), 5.30 (1H, q, J=5.2 Hz), 5.42 (1H, m), 7.16 (1H, dd, J=4.4, 1.6 Hz), 7.66 (1H, dd, J=34.0, 7.6 Hz), 7.93 (1H, dd, J=5.6, 2.0 Hz), 8.31 (1H, t, J=0.8 Hz), 8.55 (1H, d, J=7.6 Hz) ppm. LCMS m/z=485.3 [M+H$^+$].

Example Z583. tert-Butyl (S)-(1-(2-((1-(5-fluoropyridin-3-yl)ethyl)amino)thieno[3,2-d]pyrimidine-4-carbonyl)azetidin-3-yl)carbamate

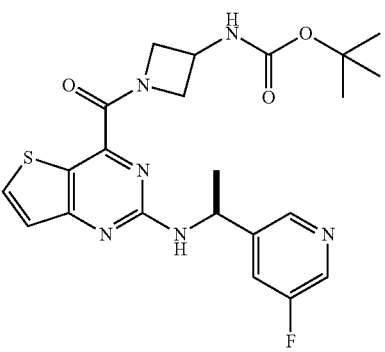

(Z583)

Synthesis of tert-butyl (S)-(1-(2-((1-(5-fluoropyridin-3-yl)ethyl)amino)thieno[3,2-d]pyrimidine-4-carbonyl)azetidin-3-yl)carbamate (Z583): The title compound (Z583) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using tert-butyl N-(azetidin-3-yl)carbamate (commercially obtained from Ark Pharm, Libertyville, Ill.) in place of (3R)-3-methoxypyrrolidine hydrochloride (62% yield). $^1$H NMR (400 MHz, CDCl$_3$) δ 1.47 (9H, d, J=9.6 Hz), 1.65 (3H, d, J=7.2 Hz), 4.00-4.05 (1H, m), 4.47-4.56 (3H, m), 4.90-5.02 (2H, s), 5.22-5.27 (1H, m), 5.24-5.48 (1H, m), 7.17 (1H, dd, J=5.6, 0.8 Hz), 7.42-7.60 (1H, m), 7.97 (1H, dd, J=5.6, 1.6 Hz), 8.35 (1H, dd, J=2.8, 1.2 Hz), 8.51 (1H, dd, J=3.2, 1.6 Hz) ppm. LCMS m/z=473.1 [M+H$^+$].

Example Z584. tert-Butyl (S)-3-(2-((1-(5-fluoropyridin-3-yl)ethyl)amino)thieno[3,2-d]pyrimidine-4-carbonyl)imidazolidine-1-carboxylate

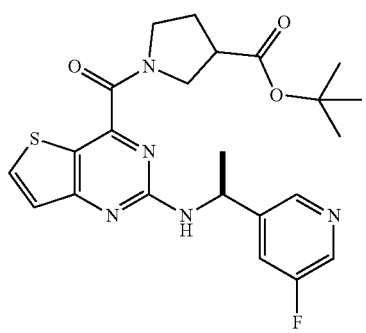 [SMILES: C[C@H](Nc1nc(C(=O)N2CCN(C(=O)OC(C)(C)C)C2)c2sccc2n1)c1cncc(F)c1]

Synthesis of tert-butyl (S)-3-(2-((1-(5-fluoropyridin-3-yl)ethyl)amino)thieno[3,2-d]pyrimidine-4-carbonyl)imidazolidine-1-carboxylate (Z584): The title compound (Z584) was prepared from (S)-2-((1-(5-fluoropyridin-3-yl)ethyl)amino)thieno[3,2-d]pyrimidine-4-carboxylic acid di-hydrochloride using chemistry similar to that described in Example Z17 using tert-butyl imidazolidine-1-carboxylate (commercially obtained from Oxchem, Wood Dale, Ill.) in place of (3R)-3-methoxypyrrolidine hydrochloride (59% yield). $^1$H NMR (400 MHz, CDCl$_3$) δ 1.50 (9H, d, J=9.6 Hz), 1.65 (3H, dd, J=6.8, 1.2 Hz), 3.59-3.65 (2H, m), 3.93-4.01 (2H, m), 5.02 (1H, s), 5.27-5.38 (2H, m), 5.42-5.50 (2H, m), 7.18 (1H, dd, J=5.6, 3.2 Hz), 7.42-7.60 (1H, m), 7.97 (1H, dd, J=5.6, 3.6 Hz), 8.34 (1H, t, J=3.2 Hz), 8.51-8.55 (1H, d, J=16.4 Hz) ppm. LCMS m/z=473.1 [M+H$^+$].

Example Z585. (S)-3-(2-((1-(5-Fluoropyridin-3-yl)ethyl)amino)thieno[3,2-d]pyrimidine-4-carbonyl)-N-methylimidazolidine-1-carboxamide

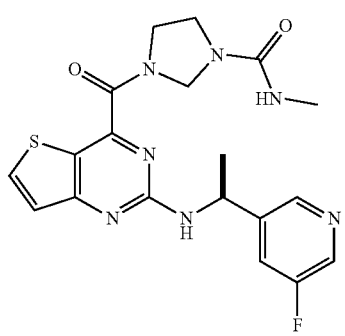 [SMILES: CNC(=O)N1CCN(C(=O)c2nc(N[C@@H](C)c3cncc(F)c3)nc3ccsc23)C1]

Synthesis of (S)-3-(2-((1-(5-fluoropyridin-3-yl)ethyl)amino)thieno[3,2-d]pyrimidine-4-carbonyl)-N-methylimidazolidine-1-carboxamide (Z585): The title compound (Z585) was prepared from (S)-(2-((1-(5-fluoropyridin-3-yl)ethyl)amino)thieno[3,2-d]pyrimidin-4-yl)(imidazolidin-1-yl)methanone using chemistry similar to that described in Example Z490 using N-methylcarbamoyl chloride in place of pivaloyl chloride (31% yield). $^1$H NMR (400 MHz, CDCl$_3$) δ 1.50 (9H, d, J=9.6 Hz), 1.65 (3H, dd, J=6.8, 1.2 Hz), 3.59-3.65 (2H, m), 3.93-4.01 (2H, m), 5.02 (1H, s), 5.27-5.38 (2H, m), 5.42-5.50 (2H, m), 7.18 (1H, dd, J=5.6, 3.2 Hz), 7.42-7.60 (1H, m), 7.97 (1H, dd, J=5.6, 3.6 Hz), 8.34 (1H, t, J=3.2 Hz), 8.51-8.55 (1H, d, J=16.4 Hz) ppm. LCMS m/z=430.1 [M+H$^+$].

Example Z586. (S)—N-((1-(2-((1-(5-Fluoropyridin-3-yl)ethyl)amino)-6-methylthieno[3,2-d]pyrimidine-4-carbonyl)azetidin-3-yl)methyl)-3,3-dimethylbutanamide

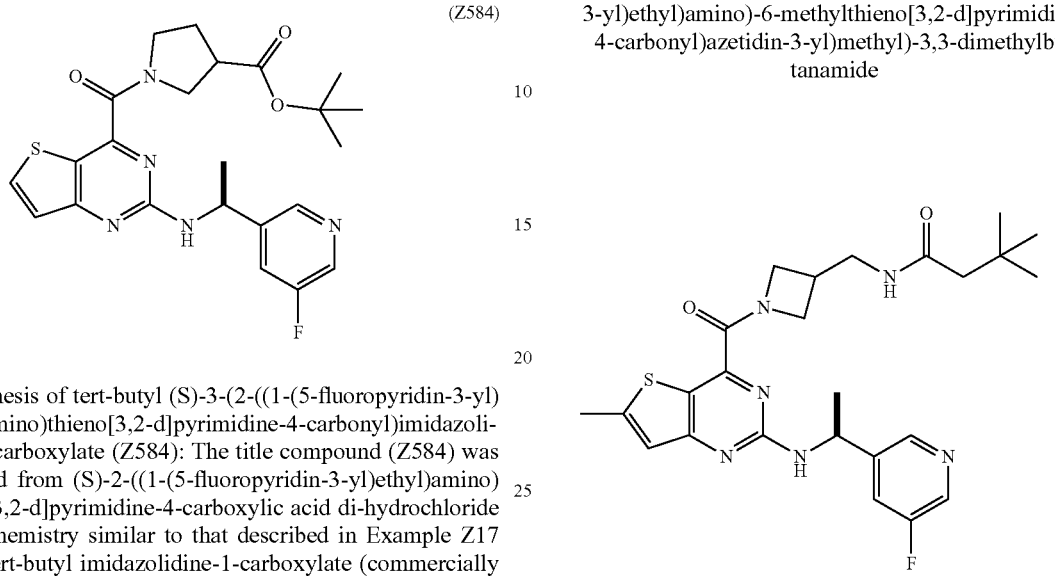

Synthesis of (S)—N-((1-(2-((1-(5-fluoropyridin-3-yl)ethyl)amino)-6-methylthieno[3,2-d]pyrimidine-4-carbonyl)azetidin-3-yl)methyl)-3,3-dimethylbutanamide (Z586): The title compound (Z586) was prepared from (S)-(3-(aminomethyl)azetidin-1-yl)(2-((1-(5-fluoropyridin-3-yl)ethyl)amino)-6-methylthieno[3,2-d]pyrimidin-4-yl)methanone using chemistry similar to that described in Example Z17 using tert-butylacetyl chloride in place of pivaloyl chloride (54% yield). $^1$H NMR (400 MHz, CDCl$_3$) δ 1.05 (9H, d, J=6.4 Hz), 1.62 (3H, dd, J=7.2, 2.4 Hz), 2.16 (2H, dd, J=8.4, 2.4 Hz), 2.30 (3H, s), 2.76-2.90 (1H, m), 3.55-3.69 (1H, m), 3.82 (1H, dq, J=31.6, 5.6 Hz), 4.21-4.29 (2H, m), 4.70 (1H, t, J=9.2 Hz), 5.13 (1H, q, J=7.2 Hz), 5.34 (1H, dd, J=15.6, 5.2 Hz), 5.81 (1H, m), 6.30 (1H, m), 7.45-7.50 (1H, m), 7.97 (1H, dd, J=5.6, 3.6 Hz), 8.34 (1H, t, J=3.2 Hz), 8.43-8.48 (1H, d, J=20.8 Hz) ppm. LCMS m/z=499.3 [M+H$^+$].

Example Z587. (S)-3-(2-((1-(5-Fluoropyridin-3-yl)ethyl)amino)thieno[3,2-d]pyrimidine-4-carbonyl)-N-isopropylimidazolidine-1-carboxamide

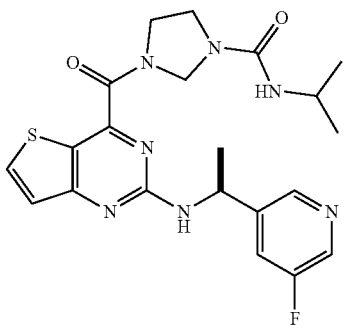 [SMILES: CC(C)NC(=O)N1CCN(C(=O)c2nc(N[C@@H](C)c3cncc(F)c3)nc3ccsc23)C1]

Synthesis of (S)-3-(2-((1-(5-fluoropyridin-3-yl)ethyl)amino)thieno[3,2-d]pyrimidine-4-carbonyl)-N-isopropylimidazolidine-1-carboxamide (Z587): The title compound (Z587) was prepared from (S)-(2-((1-(5-fluoropyridin-3-yl)ethyl)amino)thieno[3,2-d]pyrimidin-4-yl)(imidazolidin-1-yl)methanone using chemistry similar to that described in Example Z490 using isopropyl isocyanate, 0.5 M solution in o-xylene (commercially obtained from Enamine, Monmouth Jct., N.J.) in place of pivaloyl chloride (63% yield). $^1$H NMR (400 MHz, CDCl$_3$) δ 1.20 (6H, dd, J=8.0, 5.6 Hz), 1.64 (3H, dd, J=7.2, 2.8 Hz), 3.50 (1H, t, J=6.8 Hz), 3.55-3.68 (1H, m), 3.59-3.65 (2H, m), 3.99-4.15 (2H, m), 5.01 (1H, m), 5.20-5.32 (1H, m), 5.41 (1H, d, J=18.0, 9.6 Hz), 5.58 (1H, d, J=8.8 Hz), 7.18 (1H, d, J=5.6 Hz), 7.45-7.54 (1H, m), 7.97 (1H, dd, J=10.4, 5.6 Hz), 8.34 (1H, dd, J=9.6, 2.4 Hz), 8.51-8.58 (1H, d, J=28.0 Hz) ppm. LCMS m/z=458.1 [M+H$^+$].

Example Z588. (S)—N-(1-(2-((1-(5-Fluoropyridin-3-yl)ethyl)amino)-6-methylthieno[3,2-d]pyrimidine-4-carbonyl)azetidin-3-yl)isobutyramide

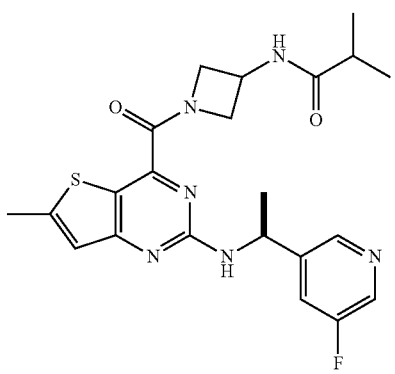 [SMILES: Cc1cc2nc(N[C@@H](C)c3cncc(F)c3)nc(C(=O)N3CC(NC(=O)C(C)C)C3)c2s1]

(Z588)

Synthesis of (S)—N-(1-(2-((1-(5-fluoropyridin-3-yl)ethyl)amino)-6-methylthieno[3,2-d]pyrimidine-4-carbonyl)azetidin-3-yl)isobutyramide (Z588): The title compound (Z588) was prepared from (S)-(3-aminoazetidin-1-yl)(2-((1-(5-fluoropyridin-3-yl)ethyl)amino)-6-methy-lthieno[3,2-d]pyrimidin-4-yl)methanone using chemistry similar to that described in Example Z490 using isobutyryl chloride in place of pivaloyl chloride (52% yield). $^1$H NMR (400 MHz, CDCl$_3$) δ 1.18-1.21 (6H, m), 1.60 (3H, t, J=3.2 Hz), 2.39-2.44 (1H, m), 2.59 (3H, s), 4.01 (1H, dt, J=5.6, 4.0 Hz), 4.18-4.4- (1H, m), 4.51-4.58 (1H, m), 4.62-4.82 (2H, m), 5.17 (1H, q, J=7.2 Hz), 5.29 (1H, dd, J=9.6, 6.8 Hz), 6.84 (1H, d, J=1.2 Hz), 6.96 (1H, dd, J=10.8, 6.0 Hz), 7.38-7.43 (1H, m), 8.35 (1H, t, J=2.4 Hz), 8.49 (1H, dt, J=8.0, 2.0 Hz) ppm. LCMS m/z=457.3 [M+H$^+$].

Example Z589. (S)-1-(3-(2-((1-(5-Fluoropyridin-3-yl)ethyl)amino)thieno[3,2-d]pyrimidine-4-carbonyl)imidazolidin-1-yl)-3-methoxypropan-1-one

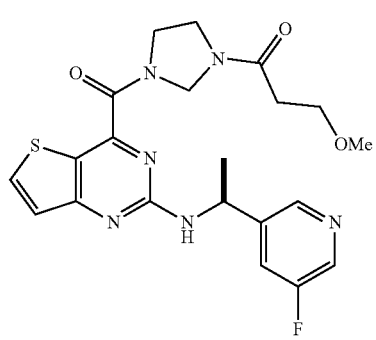 [SMILES: COCCC(=O)N1CCN(C(=O)c2nc(N[C@@H](C)c3cncc(F)c3)nc3ccsc23)C1]

(Z589)

Synthesis of (S)-1-(3-(2-((1-(5-fluoropyridin-3-yl)ethyl)amino)thieno[3,2-d]pyrimidine-4-carbonyl)imidazolidin-1-yl)-3-methoxypropan-1-one (Z589): The title compound (Z589) was prepared from (S)-(2-((1-(5-fluoropyridin-3-yl)ethyl)amino)thieno[3,2-d]pyrimidin-4-yl)(imidazolidin-1-yl)methanone using chemistry similar to that described in Example Z490 using 3-methoxypropionic acid (commercially obtained from Sigma-Aldrich, St. Louis, Mo.) in place of (3R)-3-methoxypyrrolidine hydrochloride (36% yield). $^1$H NMR (400 MHz, CDCl$_3$) δ 1.64 (3H, dd, J=7.2, 2.8 Hz), 2.56-2.63 (2H, m), 3.35-3.38 (2H, m), 3.59-3.71-3.82 (3H, m), 3.95-4.17 (2H, m), 5.17-5.24 (1H, m), 5.28-5.38 (1H, m), 5.40-5.48 (1H, m), 5.50-5.60 (1H, m), 5.65-5.71 (1H, m), 7.18 (1H, m), 7.42-7.54 (1H, m), 7.97 (1H, dd, J=9.6, 6.0 Hz), 8.34 (1H, dd, J=10.4, 2.8 Hz), 8.51-8.58 (1H, m) ppm. LCMS m/z=459.2 [M+H$^+$].

Example Z590. (S)-3-(2-((1-(5-Fluoropyridin-3-yl)ethyl)amino)thieno[3,2-d]pyrimidine-4-carbonyl)-N,N-dimethylimidazolidine-1-carboxamide

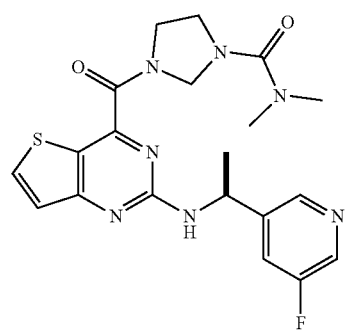 [SMILES: C[C@H](Nc1nc(C(=O)N2CCN(C(=O)N(C)C)C2)c2sccc2n1)c1cncc(F)c1]

(Z590)

Synthesis of (S)-3-(2-((1-(5-fluoropyridin-3-yl)ethyl)amino)thieno[3,2-d]pyrimidine-4-carbonyl)-N,N-dimethylimidazolidine-1-carboxamide (Z590): The title compound (Z590) was prepared from (S)-(2-((1-(5-fluoropyridin-3-yl)ethyl)amino)thieno[3,2-d]pyrimidin-4-yl)(imidazolidin-1-yl)methanone using chemistry similar to that described in Example Z490 using dimethylcarbamyl chloride in place of pivaloyl chloride (31% yield). $^1$H NMR (400 MHz, CDCl$_3$) δ 1.45 (1H, dd, J=17.6, 6.4 Hz), 1.64 (3H, d, J=7.2 Hz), 2.95

(3H, d, J=7.2 Hz), 3.35-3.38 (2H, m), 3.57-3.64 (2H, m), 3.70-78 (1H, m), 3.82-3.88 (1H, m), 3.95-4.17 (2H, m), 4.96-5.05 (1H, m), 5.25-5.35 (1H, m), 5.40-5.48 (1H, m), 5.50-5.60 (1H, m), 5.65-5.71 (1H, m), 7.18 (1H, dd, J=6.0, 2.4 Hz), 7.41-7.50 (1H, m), 7.97 (1H, dd, J=7.2, 3.6 Hz), 8.34 (1H, dd, J=10.4, 2.8 Hz), 8.49 (1H, d, J=14.8 Hz) ppm. LCMS m/z=444.2 [M+H$^+$].

Example Z591. Neopentyl (S)-(1-(2-((1-(5-fluoropyridin-3-yl)ethyl)amino)-6-methylthieno[3,2-d]pyrimidine-4-carbonyl)azetidin-3-yl)carbamate

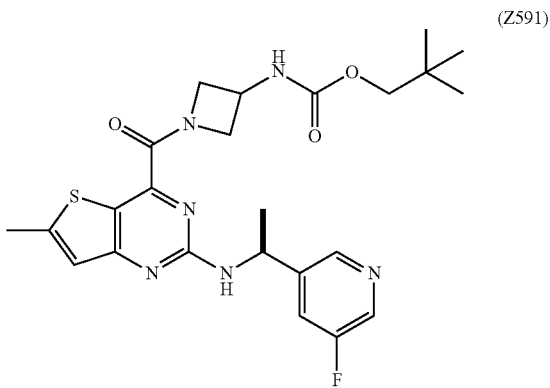

(Z591)

Synthesis of neopentyl (S)-(1-(2-((1-(5-fluoropyridin-3-yl)ethyl)amino)-6-methylthieno[3,2-d]pyrimidine-4-carbonyl)azetidin-3-yl)carbamate (Z591): The title compound (Z591) was prepared from (S)-(3-aminoazetidin-1-yl)(2-((1-(5-fluoropyridin-3-yl)ethyl)amino)-6-methylthieno[3,2-d]pyrimidin-4-yl)methanone using chemistry similar to that described in Example Z490 using 2,2-dimethylpropyl chloroformate in place of pivaloyl chloride (88% yield). $^1$H NMR (400 MHz, CDCl$_3$) δ 0.94 (9H, s), 1.62 (3H, dd, J=6.8, 1.2 Hz), 2.60 (3H, s), 3.80 (2H, s), 3.99-4.05 (1H, m), 4.10-4.40 (3H, m), 4.46-4.56 (3H, m), 4.98-5.11 (1H, m), 5.17 (1H, q, J=6.4 Hz), 5.28 (1H, t, J=6.0 Hz), 6.84 (1H, d, J=1.6 Hz), 7.40 (1H, ddd, J=7.2, 4.0, 1.6 Hz), 8.35 (1H, t, J=2.4 Hz), 8.49 (1H, dd, J=4.0, 2.4 Hz) ppm. LCMS m/z=501.2 [M+H$^+$].

Example Z592. (S)—N-(tert-Butoxy)-1-(2-((1-(5-fluoropyridin-3-yl)ethyl)amino)-6-methylthieno[3,2-d]pyrimidine-4-carbonyl)azetidine-3-carboxamide

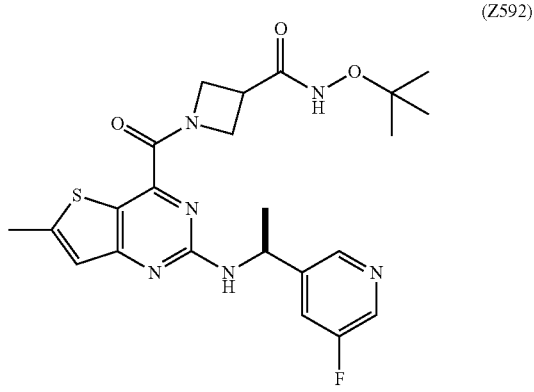

(Z592)

Synthesis of (S)-1-(2-((1-(5-fluoropyridin-3-yl)ethyl)amino)-6-methylthieno[3,2-d]pyrimidine-4-carbonyl)azetidine-3-carboxylic acid di-hydrochloride: The title compound was prepared from tert-butyl (S)-1-(2-((1-(5-fluoropyridin-3-yl)ethyl)amino)-6-methylthieno[3,2-d]pyrimidine-4-carbonyl)azetidine-3-carboxylate using chemistry similar to that described in Example Z520 (95% yield). LCMS m/z=416.1 [M+H$^+$].

Synthesis of (S)—N-(tert-butoxy)-1-(2-((1-(5-fluoropyridin-3-yl)ethyl)amino)-6-methylthieno[3,2-d]pyrimidine-4-carbonyl)azetidine-3-carboxamide (Z592): The title compound (Z592) was prepared from (S)-1-(2-((1-(5-fluoropyridin-3-yl)ethyl)amino)-6-methylthieno[3,2-d]pyrimidine-4-carbonyl)azetidine-3-carboxylic acid di-hydrochloride using chemistry similar to that described in Example Z17 using O-tert-butylhydroxylamine hydrochloride in place of (3R)-3-methoxypyrrolidine hydrochloride (45% yield). $^1$H NMR (400 MHz, CDCl$_3$) δ 1.29 (9H, s), 1.63 (3H, dd, J=9.6, 1.6 Hz), 2.60 (3H, t, J=1.2 Hz), 3.78-4.15 (1H, m), 4.28-4.38 (2H, m), 4.72-4.81 (1H, m), 5.13-5.25 (1H, m), 5.31 (1H, m), 6.84 (1H, t, J=1.2 Hz), 7.44 (1H, m), 7.62-7.83 (1H, m), 8.35 (1H, d, J=2.8 Hz), 8.48 (1H, d, J=8.4 Hz) ppm. LCMS m/z=487.3 [M+H$^+$].

Example Z593. (S)-3-(2-((1-(5-Fluoropyridin-3-yl)ethyl)amino)-6-methylthieno[3,2-d]pyrimidine-4-carbonyl)-N-isopropylimidazolidine-1-carboxamide

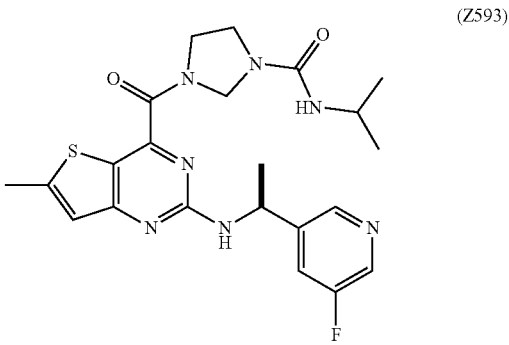

(Z593)

Synthesis of (S)-3-(2-((1-(5-fluoropyridin-3-yl)ethyl)amino)-6-methylthieno[3,2-d]pyrimidine-4-carbonyl)-N-isopropylimidazolidine-1-carboxamide (Z593): The title compound (Z593) was prepared from (S)-(2-((1-(5-fluoropyridin-3-yl)ethyl)amino)-6-methhylthieno[3,2-d]pyrimidin-4-yl)(imidazolidin-1-yl)methanone using chemistry similar to that described in Example Z490 using isopropyl isocyanate, 0.5 M solution in o-xylene in place of pivaloyl chloride (54% yield). $^1$H NMR (400 MHz, CDCl$_3$) δ 1.21 (6H, dd, J=14.0, 8.0 Hz), 1.63 (3H, dd, J=10.0, 1.2 Hz), 2.60 (3H, dd, J=2.8, 0.8 Hz), 3.45-3.65 (2H, m), 3.98-4.15 (4H, m), 4.91 (1H, d, J=2.0 Hz), 5.14-5.30 (1H, m), 5.33-5.40 (1H, m), 5.48-5.58 (1H, m), 6.85-6.88 (1H, m), 7.42-7.55 (1H, m), 8.35 (1H, dd, J=5.2, 2.8 Hz), 8.47-8.57 (1H, m) ppm. LCMS m/z=472.3 [M+H$^+$].

Example Z594. (S)—N-(1-(2-((1-(5-Fluoropyridin-3-yl)ethyl)amino)thieno[3,2-d]pyrimidine-4-carbonyl)azetidin-3-yl)pivalamide

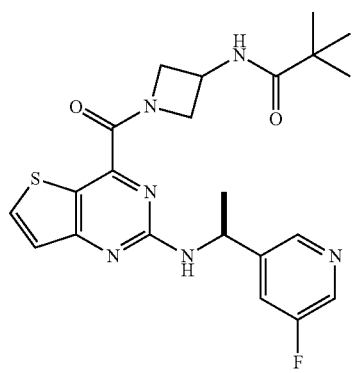 [SMILES: C[C@H](Nc1nc(C(=O)N2CC(NC(=O)C(C)(C)C)C2)c2sccc2n1)c1cncc(F)c1]
(Z594)

Synthesis of (S)—N-(1-(2-((1-(5-fluoropyridin-3-yl)ethyl)amino)thieno[3,2-d]pyrimidine-4-carbonyl)azetidin-3-yl)isobutyramide (Z594): The title compound (Z594) was prepared from (S)-(3-aminoazetidin-1-yl)(2-((1-(5-fluoropyridin-3-yl)ethyl)amino)thieno[3,2-d]pyrimidin-4-yl)methanone using chemistry similar to that described in Example Z490 (62% yield). $^1$H NMR (400 MHz, CDCl$_3$) δ 1.24 (9H, d, J=2.0 Hz), 1.65 (3H, dd, J=7.2, 2.4 Hz), 4.03 (1H, dt, J=8.8, 7.2 Hz), 4.23 (1H, m), 4.40 (1H dd, J=10.8, 7.6 Hz), 4.54-4.59 (1H, dt, J=8.4, 1.2 Hz), 4.62-4.71 (1H, s), 5.21 (1H, q, J=6.8 Hz), 5.37 (1H, dd, J=8.8, 7.2 Hz), 6.04 (1H dd, J=37.2, 6.0 Hz), 7.16 (1H, dd, J=5.6, 2.4 Hz), 7.42 (1H, dd, J=8.8, 2.0 Hz), 7.96 (1H, dd, J=5.6, 4.8 Hz), 8.34 (1H, t, J=4.4, 2.4 Hz), 8.49-8.52 (1H, d, J=11.6 Hz) ppm. LCMS m/z=457.3 [M+H$^+$].

Example Z595. (2-(((S)-1-(5-Fluoropyridin-3-yl)ethyl)amino)-6-methylthieno[3,2-d]pyrimidin-4-yl)((R)-2-methylazetidin-1-yl)methanone

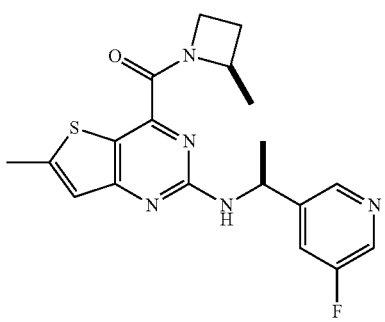 [SMILES: Cc1cc2nc(N[C@@H](C)c3cncc(F)c3)nc(C(=O)N3CC[C@H]3C)c2s1]
(Z595)

Synthesis of (2-(((S)-1-(5-fluoropyridin-3-yl)amino)-6-methylthieno[3,2-d]pyrimidin-4-yl)((R)-2-methylazetidin-1-yl)methanone (Z595): The title compound (Z595) was prepared from (S)-2-((1-(5-fluoropyridin-3-yl)ethyl)amino)-6-methylthieno[3,2-d]pyrimidine-4-carboxylic acid di-hydrochloride (40.5 mg, 0.10 mmol) using chemistry similar to that described in Example Z8 using (R)-2-methylazetidine hydrochloride (commercially obtained from NetChem, New Brunswick, N.J.) in place of (R)-3-fluoropyrrolidine (26 mg, 67% yield). $^1$H NMR (400 MHz, CDCl$_3$) δ 1.55 (3H, d, J=6.4 Hz), 1.63 (3H, d, J=6.8 Hz), 1.91 (1H, m), 2.53 (1H, m), 2.61 (3H, s), 4.15 (1H, m), 4.26 (1H, m), 4.58 (1H, m), 4.69 (1H, m), 5.24 (1H, m), 6.89 (1H, s), 7.45 (1H, m), 8.36 (1H, m), 8.48 (1H, m) ppm. LCMS m/z=386.1 [M+H$^+$].

Example Z596. (2-(((S)-1-(5-Fluoropyridin-3-yl-ethyl)amino)-6-methylthieno[3,2-d]pyrimidin-4-yl)((S)-2-methylazetidin-1-yl)methanone

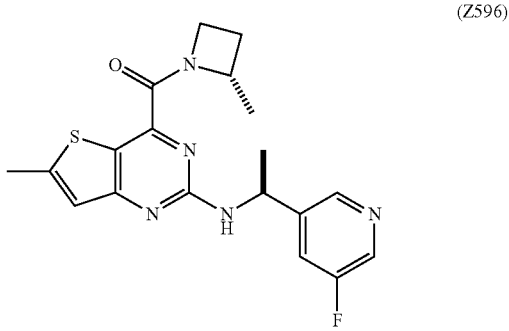
(Z596)

Synthesis of (2-(((S)-1-(5-fluoropyridin-3-yl)ethyl)amino)-6-methylthieno[3,2-d]pyrimidin-4-yl)((S)-2-methylazetidin-1-yl)methanone (Z596): The title compound (Z596) was prepared from (S)-2-((1-(5-fluoropyridin-3-yl)ethyl)amino)-6-methylthieno[3,2-d]pyrimidine-4-carboxylic acid di-hydrochloride (40.5 mg, 0.10 mmol) using chemistry similar to that described in Example Z8 using (S)-2-methylazetidine hydrochloride (commercially obtained from NetChem, New Brunswick, N.J.) in place of (R)-3-fluoropyrrolidine (19 mg, 49% yield). $^1$H NMR (400 MHz, CDCl$_3$) δ 1.56 (3H, d, J=6.4 Hz), 1.63 (3H, d, J=6.8 Hz), 1.91 (1H, m), 2.43 (1H, m), 2.61 (3H, s), 4.15 (1H, m), 4.26 (1H, m), 4.58-4.68 (2H, m), 5.24 (1H, m), 5.74 (1H, br s), 6.87 (1H, s), 7.44 (1H, m), 8.34 (1H, m), 8.49 (1H, m) ppm. LCMS m/z=386.1 [M+H$^+$].

Example Z597. ((S)-3-(Aminomethyl)pyrrolidin-1-yl)(2-(((S)-1-(5-fluoropyridin-3-yl)ethyl)amino)-6-methylthieno[3,2-d]pyrimidin-4-yl)methanone

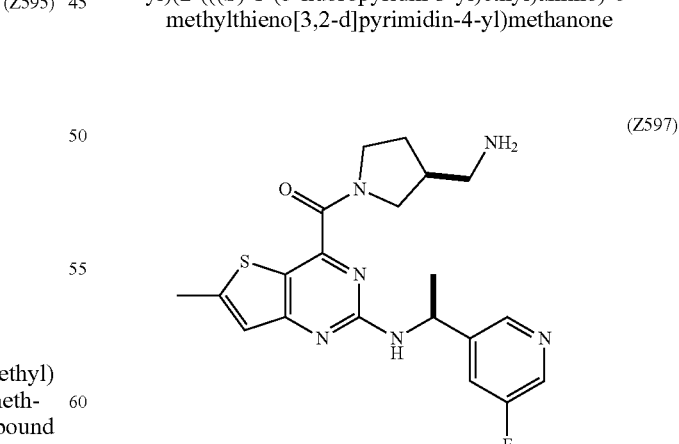
(Z597)

Synthesis of ((S)-3-(aminomethyl)pyrrolidin-1-yl)(2-(((S)-1-(5-fluoropyridin-3-yl)ethyl)amino)-6-methylthieno[3,2-d]pyrimidin-4-yl)methanone: The title compound (Z597) was prepared from (S)-2-((1-(5-fluoropyridin- 3-yl)ethyl)amino)-6-methylthieno[3,2-d]pyrimidine-4-carboxylic acid di-hydrochloride (40.5 mg, 0.10 mmol) using chemistry similar to that described in Example Z463 using tert-butyl (R)-(pyrrolidin-3-ylmethyl)carbamate (commercially obtained from Ark Pharm, Libertyville, Ill.) in place of tert-butyl (S)-3-(2-aminoethyl)pyrrolidine-1-carboxylate (34 mg, 82% yield). $^1$H NMR (400 MHz, CDCl$_3$) δ 1.61 (3H, d, J=6.8 Hz), 2.03 (1H, m), 2.22 (1H, m), 2.60 (3H, s), 2.65-2.81 (2H, m), 3.36 (1H, m), 3.65 (1H, m), 3.77-3.87 (2H, m), 4.02 (1H, m), 5.20 (1H, m), 5.37 (1H, m), 6.85 (1H, s), 7.44 (1H, m), 8.33 (1H, m), 8.49 (1H, m) ppm. LCMS m/z=415.2 [M+H$^+$].

Example Z598. (R)—N-(1-(2-(((S)-1-(5-Fluoropyridin-3-yl)ethyl)amino)-6-methylthieno[3,2-d]pyrimidine-4-carbonyl)azetidin-3-yl)tetrahydrofuran-3-carboxamide

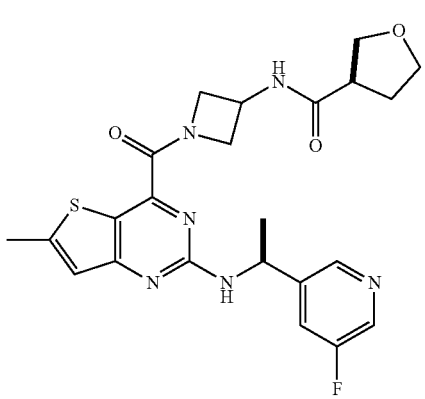
(Z598)

Synthesis of (R)—N-(1-(2-(((S)-1-(5-fluoropyridin-3-yl)ethyl)amino)-6-methylthieno[3,2-d]pyrimidine-4-carbonyl)azetidin-3-yl)tetrahydrofuran-3-carboxamide (Z598): A mixture of (3R)-tetrahydrofuran-3-carboxylic acid (4.5 mg, 0.039 mmol) (commercially obtained from Ark Pharm, Arlington Heights, Ill.) and HATU (15 mg, 0.039 mmol) in DMF (0.5 mL) was added to a solution of (S)-(3-aminoazetidin-1-yl)(2-((1-(5-fluoropyridin-3-yl)ethyl)amino)-6-methylthieno[3,2-d]pyrimidin-4-yl)methanone trihydrochloride (15 mg, 0.03 mmol) and DIEA (37 uL, 0.21 mmol) in DMF (0.3 mL). The resulting mixture was stirred at room temperature for 3 hours, concentrated on rotary evaporator, and the residue was purified by flash chromatography on silica gel eluting with 0% to 10% methanol in DCM to provide compound 598 (70% yield). $^1$H NMR (400 MHz, CDCl$_3$) δ 1.62 (3H, dd, J=7.2 Hz), 2.17-2.21 (2H, m), 2.60 (3H, t, J=0.8 Hz), 2.94-2.98 (1H, m), 3.80-4.03 (5H, m), 4.15-4.40 (1H, m), 4.55 (1H, t, J=9.2 Hz), 4.66-4.71 (1H, m), 4.65-5.05 (1H, m), 5.15 (1H, q, J=7.2 Hz), 5.34 (1H, dd, J=19.2, 6.4 Hz), 6.21 (1H, dd, J=49.6, 6.4 Hz), 6.84 (1H, d, J=0.8 Hz), 7.40 (1H, m), 8.33 (1H, d, J=2.8 Hz), 8.47 (1H, d, J=6.4 Hz) ppm. MS m/z=485.1 [M+H$^+$].

Example Z599. (S)—N-(1-(2-(((S)-1-(5-Fluoropyridin-3-yl)ethyl)amino)-6-methylthieno[3,2-d]pyrimidine-4-carbonyl)azetidin-3-yl)tetrahydrofuran-3-carboxamide

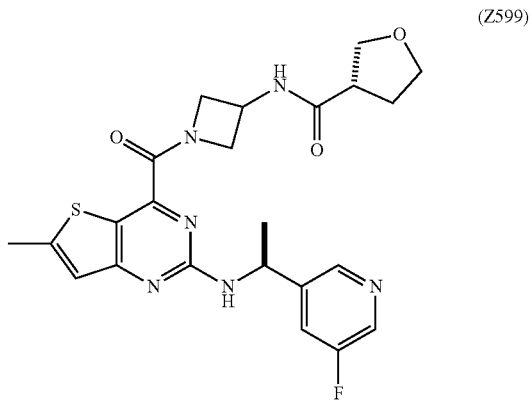
(Z599)

Synthesis of (S)—N-(1-(2-(((S)-1-(5-fluoropyridin-3-yl)ethyl)amino)-6-methylthieno[3,2-d]pyrimidine-4-carbonyl)azetidin-3-yl)tetrahydrofuran-3-carboxamide (Z599): The title compound (Z599) was prepared from (S)-(3-aminoazetidin-1-yl)(2-((1-(5-fluoropyridin-3-yl)ethyl)amino)-6-methylthieno[3,2-d]pyrimidin-4-yl)methanone using chemistry similar to that described in Example Z598 using (3S)-tetrahydrofuran-3-carboxylic acid (commercially obtained from Advanced Chem Blocks, Burlingame, Calif.) in place of (3R)-tetrahydrofuran-3-carboxylic acid (15% yield). $^1$H NMR (400 MHz, CDCl$_3$) δ 1.62 (3H, d, J=6.8 Hz), 2.16-2.23 (2H, m), 2.60 (3H, s), 2.93-3.01 (1H, m), 3.79-3.85 (1H, m), 3.86-4.03 (4H, m), 4.15-4.40 (1H, m), 4.55 (1H, t, J=9.2 Hz), 4.66-4.71 (1H, m), 4.65-5.05 (1H, m), 5.15 (1H, q, J=6.8 Hz), 5.34 (1H, dd, J=19.2, 6.4 Hz), 6.31 (1H, dd, J=10.0, 5.6 Hz), 6.84 (1H, d, J=0.8 Hz), 7.40 (1H, m), 8.33 (1H, t, J=3.2 Hz), 8.47 (1H, d, J=6.4 Hz) ppm. MS m/z=485.1 [M+H$^+$].

Example Z600. (S)—N-(1-(2-((1-(5-Fluoropyridin-3-yl)ethyl)amino)thieno[3,2-d]pyrimidine-4-carbonyl)azetidin-3-yl)furan-3-carboxamide

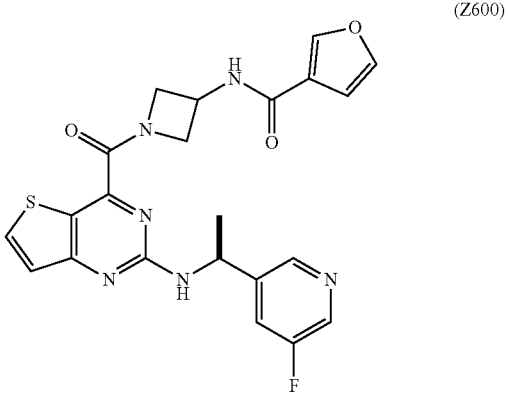
(Z600)

Synthesis of (S)—N-(1-(2-((1-(5-fluoropyridin-3-yl)ethyl)amino)thieno[3,2-d]pyrimidine-4-carbonyl)azetidin- 3-yl)furan-3-carboxamide (Z600): The title compound (Z600) was prepared from (S)-(3-aminoazetidin-1-yl)(2-((1-(5-fluoropyridin-3-yl)ethyl)aminothieno[3,2-d]pyrimidin-4-yl)methanone using chemistry similar to that described in Example 490 using furan-3-carbonyl chloride (commercially obtained from Enamine, Monmouth Jct., N.J.) in place of pivaloyl chloride (20% yield). $^1$H NMR (400 MHz, CDCl$_3$) δ 1.62 (3H, d, J=7.2 Hz), 4.12 (1H, td, J=10.8, 4.6 Hz), 4.36-4.50 (1H, m), 4.58-4.65 (1H, m), 4.75-4.85 (1H, m), 5.08 (1H, t, J=8.0 Hz), 5.21 (1H, m), 5.34 (1H, t, J=7.2 Hz), 6.39-6.60 (1H, m), 6.73 (1H, d, J=13.2 Hz), 7.16 (1H, d, J=5.6 Hz), 7.43 (1H, d, J=9.2 Hz), 7.47 (1H, m), 7.97 (1H, dd, J=5.6, 4.0 Hz), 8.04 (1H, d, J=6.8 Hz), 8.33 (1H, dd, J=7.6, 2.8 Hz), 8.50 (1H, m) ppm. MS m/z=467.1 [M+H$^+$].

Example Z601. (S)—N-(1-(2-((1-(5-Fluoropyridin-3-yl)ethyl)amino)thieno[3,2-d]pyrimidine-4-carbonyl)azetidin-3-yl)benzamide

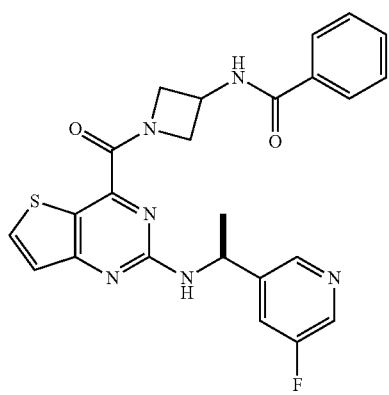

Synthesis of (S)—N-(1-(2-((1-(5-fluoropyridin-3-yl)ethyl)amino)thieno[3,2-d]pyrimidine-4-carbonyl)azetidin-3-yl)benzamide (Z601): The title compound (Z601) was prepared from (S)-(3-aminoazetidin-1-yl)(2-((1-(5-fluoropyridin-3-yl)ethyl)aminothieno[3,2-d]pyrimidin-4-yl)methanone using chemistry similar to that described in Example 490 using benzoyl chloride (commercially obtained from Oakwood Chemical, Estill, S.C.) in place of pivaloyl chloride (20% yield). $^1$H NMR (400 MHz, CDCl$_3$) δ 1.62 (3H, dd, J=6.8 Hz), 4.12-4.20 (1H, td, J=12.0, 3.6 Hz), 4.35-4.58 (1H, m), 4.62-4.68 (1H, m), 4.86-4.94 (1H, m), 5.12-5.24 (2H, m), 5.39 (1H, t, J=8.4 Hz), 6.60-6.74 (1H, m), 7.16 (1H, dd, J=5.6, 1.2 Hz), 7.42-7.49 (3H, m), 7.52-7.57 (1H, m), 7.82 (2H, td, J=8.4, 1.2 Hz), 7.96 (1H, t, J=5.2 Hz), 8.33 (1H, dd, J=13.6, 2.8 Hz), 8.52 (1H, d, J=6.0 Hz) ppm. MS m/z=477.2 [M+H$^+$].

Example Z602. N-(tert-Butoxy)-1-(2-(((S)-1-(5-fluoropyridin-3-yl)ethyl)amino)-6-methylthieno[3,2-d]pyrimidine-4-carbonyl)pyrrolidine-3-carboxamide

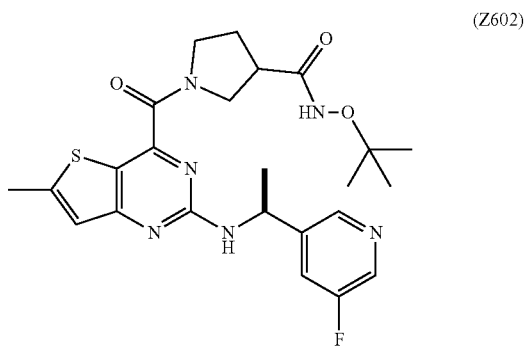

Synthesis of N-(tert-butoxy)-1-(2-(((S)-1-(5-fluoropyridin-3-yl)ethyl)amino)-6-methylthieno[3,2-d]pyrimidine-4-carbonyl)pyrrolidine-3-carboxamide (Z602): The title compound (Z602) was prepared from 1-(2-(((S)-1-(5-fluoropyridin-3-yl)ethyl)amino)-6-methylthieno[3,2-d]pyrimidine-4-carbonyl)pyrrolidine-3-carboxylic acid di-hydrochloride using chemistry similar to that described in Example 17 using O-tert-butylhydroxylamine hydrochloride (commercially obtained from Sigma-Aldrich, St. Louis, Mo.) in place of (3R)-3-methoxypyrrolidine hydrochloride (25% yield). $^1$H NMR (400 MHz, CDCl$_3$) δ 1.25-1.33 (9H, m), 1.44-1.52 (1H, m), 1.62 (3H, m), 2.00-2.28 (2H, m), 2.60 (3H, m), 3.65-3.85 (2H, m), 3.92-4.02 (2H, m), 4.02-4.20 (1H, m), 5.12-5.28 (1H, m), 5.35-5.55 (1H, m), 6.85 (1H, m), 7.52-7.57 (1H, m), 8.33 (1H, d, J=2.8 Hz), 8.48 (1H, m) ppm. MS m/z=501.2 [M+H$^+$].

Example Z603. (S)—N-(1-(2-((1-(5-Fluoropyridin-3-yl)ethyl)amino)thieno[3,2-d]pyrimidine-4-carbonyl)azetidin-3-yl)-1-methylcyclopropane-1-carboxamide

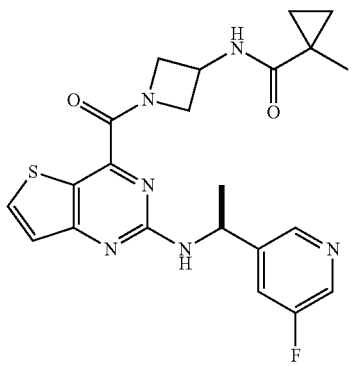

Synthesis of (S)—N-(1-(2-((1-(5-fluoropyridin-3-yl)ethyl)amino)thieno[3,2-d]pyrimidine-4-carbonyl)azetidin-3-yl)-1-methylcyclopropane-1-carboxamide (Z603): To a solution of (S)-(3-aminoazetidin-1-yl)(2-((1-(5-fluoropyridin-3-yl)ethyl)amino)thieno[3,2-d]pyrimidin-4-yl)methanone (37 mg, 0.1 mmol) in DCM (2 mL) were added DIEA (35 uL, 0.20 mmol) and 1-methylcyclopropanecarbonyl chloride (15 uL, 0.12 mmol) and the mixture thus obtained was stirred at room temperature for 1 h and LCMS analysis indicated completion of the reaction. The reaction mixture was concentrated and the residue was purified by flash chromatography on silica gel (4 g HP silica, Teledyne Isco) eluting with 10% to 50% solvent A (DCM/MeOH/NH$_4$OH, 100/10/1) in DCM to provide compound 603 as an off-white solid (36 mg, 79% yield). $^1$H NMR (400 MHz, CDCl$_3$) δ 0.63-0.67 (2H, m), 1.21-1.25 (2H, m), 1.38 (3H, s), 1.63 (3H, d, J=6.8 Hz), 4.05 (1H, m), 4.56 (1H, m), 4.69 (1H, m), 4.77 (1H, m), 5.22 (1H, m), 5.37 (1H, m), 6.15 (1H, m), 7.17 (1H, dd, J=5.6, 1.2 Hz), 7.43 (1H, m), 7.97 (1H, dd, J=5.6, 4.8 Hz), 8.35 (1H, d, J=2.8 Hz), 8.51 (1H, d, J=8.8 Hz) ppm. MS m/z=455.1 [M+H$^+$].

Example Z604. (S)—N-(1-(2-((1-(5-Fluoropyridin-3-yl)ethyl)amino)thieno[3,2-d]pyrimidine-4-carbonyl)azetidin-3-yl)bicyclo[1.1.1]pentane-1-carboxamide

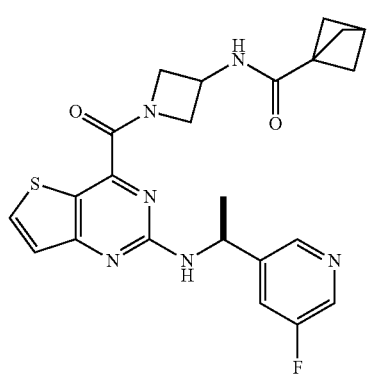

(Z604)

Synthesis of (S)—N-(1-(2-((1-(5-fluoropyridin-3-yl)ethyl)amino)thieno[3,2-d]pyrimidine-4-carbonyl)azetidin-3-yl)bicyclo[1.1.1]pentane-1-carboxamide (Z604): To a solution of (S)-(3-aminoazetidin-1-yl)(2-((1-(5-fluoropyridin-3-yl)ethyl)amino)thieno[3,2-d]pyrimidin-4-yl)methanone (37 mg, 0.1 mmol) in DMF (2 mL) were added bicyclo[1.1.1]pentane-2-carboxylic acid (17 mg, 0.15 mmol) (commercially obtained from PharmaBlock, Nanjing, China), HATU (57 mg, 0.15 mmol), and DIEA (52 uL, 0.3 mmol). The mixture thus obtained was stirred at room temperature for 2 h and LCMS analysis indicated completion of the reaction. The reaction mixture was diluted with ethyl acetate and washed with 5% NaHCO$_3$, water, and brine, then dried over MgSO$_4$. The solvent was evaporated in vacuo and the residue was purified flash chromatography on silica gel (4 g HP silica, Teledyne Isco) eluting with 10% to 50% solvent A (DCM/MeOH/NH$_4$OH, 100/10/1) in DCM to provide compound 604 as an off-white solid (35 mg, 75% yield). $^1$H NMR (400 MHz, CDCl$_3$) δ 1.63 (3H, d, J=6.8 Hz), 2.10 (6H, s), 2.51 (1H, d, J=1.2 Hz), 4.04 (1H, m), 4.56 (1H, m), 4.70 (1H, m), 4.47 (1H, m), 5.20 (1H, quintet, J=6.8 Hz), 5.37 (1H, m), 5.96 (1H, d, J=6.8 Hz), 7.16 (1H, dd, J=5.6, 2.0 Hz), 7.43 (1H, m), 7.97 (1H, dd, J=5.6, 4.0 Hz), 8.35 (1H, d, J=2.0 Hz), 8.50 (1H, d, J=9.2 Hz) ppm. MS m/z=467.1 [M+H$^+$].

Example Z605. (S)—N-(1-(2-((1-(5-Fluoropyridin-3-yl)ethyl)amino)thieno[3,2-d]pyrimidine-4-carbonyl)azetidin-3-yl)cyclopentanecarboxamide

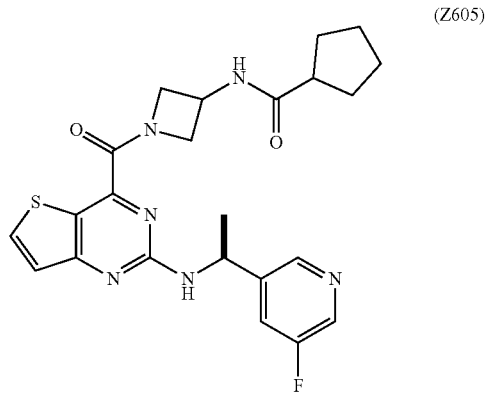

(Z605)

Synthesis of (S)—N-(1-(2-((1-(5-fluoropyridin-3-yl)ethyl)amino)thieno[3,2-d]pyrimidine-4-carbonyl)azetidin-3-yl)cyclopentanecarboxamide (Z605): The title compound (Z605) was prepared as a white solid from (S)-(3-aminoazetidin-1-yl)(2-((1-(5-fluoropyridin-3-yl)ethyl)amino)thieno[3,2-d]pyrimidin-4-yl)methanone (37 mg, 0.10 mmol) using chemistry similar to that described in Example Z603 using cyclopentanecarbonyl chloride (commercially obtained from Sigma-Aldrich, St. Louis, Mo.) in place of 1-methylcyclopropanecarbonyl chloride (37 mg, 79% yield). $^1$H NMR (400 MHz, CDCl$_3$) δ 1.59-1.65 (4H, m), 1.76-1.90 (6H, m), 2.57 (1H, m), 4.02 (1H, m), 4.36 (1H, m), 4.57 (1H, m), 4.71 (1H, m), 4.96 (1H, m), 5.21 (1H, quintet, J=6.4 Hz), 5.38 (1H, t, J=8.0 Hz), 5.95 (1H, d, J=6.4 Hz), 7.16 (1H, d, J=5.6 Hz), 7.43 (1H, m), 7.97 (1H, d, J=5.6 Hz), 8.43 (1H, m), 8.51 (1H, m) ppm. MS m/z=469.1 [M+H$^+$].

Example Z606. (S)-3,3,3-Trifluoro-N-(1-(2-((1-(5-fluoropyridin-3-yl)ethyl)amino)thieno[3,2-d]pyrimidine-4-carbonyl)azetidin-3-yl)-2,2-dimethylpropanamide

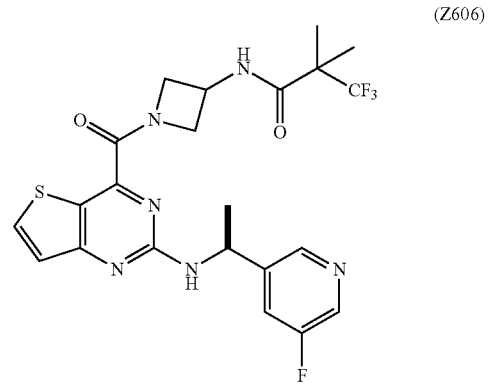

(Z606)

Synthesis of (S)-3,3,3-trifluoro-N-(1-(2-((1-(5-fluoropyridin-3-yl)ethyl)amino)thieno[3,2-d]pyrimidine-4-carbonyl)azetidin-3-yl)-2,2-dimethylpropanamide (Z606): The title compound (Z606) was prepared as an off-white solid from (S)-(3-aminoazetidin-1-yl)(2-((1-(5-fluoropyridin-3- yl)ethyl)amino)thieno[3,2-d]pyrimidin-4-yl)methanone (37 mg, 0.10 mmol) using chemistry similar to that described in Example Z604 using 3,3,3-trifluoro-2,2-dimethylpropanoic acid (commercially obtained from Ark Pharm, Arlington Heights, Ill.) in place of bicyclo[1.1.1]pentane-2-carboxylic acid (39 mg, 76% yield). $^1$H NMR (400 MHz, CDCl$_3$) δ 1.46 (6H, s), 1.64 (3H, d, J=7.2 Hz), 4.03 (1H, td, J=10.8, 4.8 Hz), 4.32 (1H, m), 4.58 (1H, m), 4.68 (1H, m), 4.96 (1H, m), 5.21 (1H, quintet, J=7.2 Hz), 5.38 (1H, m), 6.28 (1H, m), 7.18 (1H, d, J=5.6 Hz), 7.43 (1H, m), 7.97 (1H, d, J=5.6 Hz), 8.34 (1H, m), 8.51 (1H, m) ppm. MS m/z=511.2 [M+H$^+$].

Example Z607. (S)—N-(1-(2-((1-(5-Fluoropyridin-3-yl)ethyl)amino)thieno[3,2-d]pyrimidine-4-carbonyl)azetidin-3-yl)oxetane-3-carboxamide

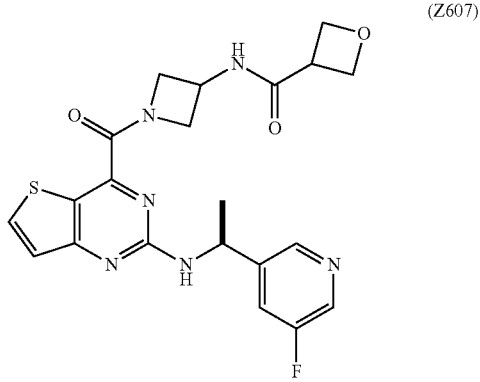

(Z607)

Synthesis of (S)—N-(1-(2-((1-(5-fluoropyridin-3-yl)ethyl)amino)thieno[3,2-d]pyrimidine-4-carbonyl)azetidin-3-yl)oxetane-3-carboxamide (Z607): The title compound (Z607) was prepared from (S)-(3-aminoazetidin-1-yl)(2-((1-(5-fluoropyridin-3-yl)ethyl)amino)thieno[3,2-d]pyrimidin-4-yl)methanone using chemistry similar to that described in Example Z598 using oxetane-3-carboxylic acid (commercially obtained from Enamine, Monmouth Jct, N.J.) in place of (3R)-tetrahydrofuran-3-carboxylic acid (21% yield). $^1$H NMR (400 MHz, CDCl$_3$) δ 1.63 (3H, d, J=6.4 Hz), 1.70-2.00 (1H, m), 3.75-3.80 (1H, m), 4.00-4.10 (1H, m), 4.24-4.46 (1H, m), 4.54-4.62 (1H, m), 4.68-4.86 (1H, m), 4.80-4.90 (4H, m), 5.02-5.10 (1H, m), 5.42-5.54 (1H, m), 7.17 (1H, dd, J=5.6, 2.0 Hz), 7.46 (1H, m), 7.96 (1H, t, J=5.6 Hz), 8.33 (1H, dd, J=6.4, 2.8 Hz), 8.52 (1H, m) ppm. MS m/z=457.1 [M+H$^+$].

Example Z608. N-(1-(2-(((S)-1-(5-Fluoropyridin-3-yl)ethyl)amino)thieno[3,2-d]pyrimidine-4-carbonyl)azetidin-3-yl)-3-methyltetrahydrofuran-3-carboxamide

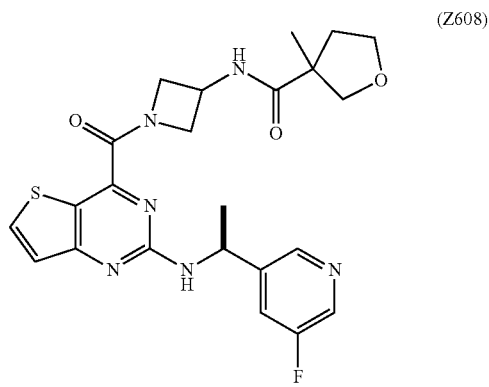

(Z608)

Synthesis of N-(1-(2-(((S)-1-(5-fluoropyridin-3-yl)ethyl)amino)thieno[3,2-d]pyrimidine-4-carbonyl)azetidin-3-yl)-3-methyltetrahydrofuran-3-carboxamide (Z608): The title compound (Z608) was prepared from (S)-(3-aminoazetidin-1-yl)(2-((1-(5-fluoropyridin-3-yl)ethyl)amino)thieno[3,2-d]pyrimidin-4-yl)methanone using chemistry similar to that described in Example Z598 using 3-methyltetrahydrofuran-3-carboxylic acid (commercially obtained from Advanced ChemBlocks, Burlingame, Calif.) in place of (3R)-tetrahydrofuran-3-carboxylic acid (19% yield). $^1$H NMR (400 MHz, CDCl$_3$) δ 1.36 (3H, d, J=2.8 Hz), 1.65 (3H, d, J=7.2 Hz), 1.85-1.95 (1H, m), 2.25-2.38 (1H, m), 3.44-3.46 (1H, m), 3.89-3.93 (1H, m), 3.98-4.12 (4H, m), 4.53-4.59 (1H, m), 4.42-4.72 (1H, m), 5.05 (1H, m), 5.17-5.23 (1H, m), 5.42-5.44 (1H, m), 6.54-6.66 (1H, m), 7.17 (1H, dd, J=5.2, 2.4 Hz), 7.41-7.46 (1H, m), 7.98 (1H, t, J=4.8 Hz), 8.34 (1H, t, J=3.2 Hz), 8.50 (1H, m) ppm. MS m/z=485.1 [M+H$^+$].

Example Z609. (S)—N-(1-(2-((1-(5-Fluoropyridin-3-yl)ethyl)amino)thieno[3,2-d]pyrimidine-4-carbonyl)azetidin-3-yl)-1-(trifluoromethyl)cyclopropane-1-carboxamide

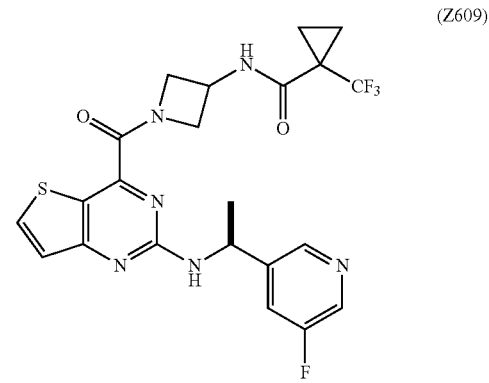

(Z609)

Synthesis of (S)—N-(1-(2-((1-(5-fluoropyridin-3-yl)ethyl)amino)thieno[3,2-d]pyrimidine-4-carbonyl)azetidin-3-yl)-1-(trifluoromethyl)cyclopropane-1-carboxamide (Z609): The title compound (Z609) was prepared as an off-white solid from (S)-(3-aminoazetidin-1-yl)(2-((1-(5-fluoropyridin-3-yl)ethyl)amino)thieno[3,2-d]pyrimidin-4-yl)methanone (37 mg, 0.10 mmol) using chemistry similar to that described in Example Z604 using 1-(trifluoromethyl)cyclopropane-1-carboxylic acid (commercially obtained from Ark Pharm, Arlington Heights, Ill.) in place of bicyclo[1.1.1]pentane-2-carboxylic acid (42 mg, 83% yield). $^1$H NMR (400 MHz, CDCl$_3$) δ 1.25-1.32 (2H, m), 1.46-1.55 (2H, m), 1.64 (3H, d, J=7.2 Hz), 4.08 (1H, m), 4.54 (1H, m), 4.58 (1H, m), 4.71 (1H, m), 4.78 (1H, m), 5.24 (1H, m), 5.40 (1H, m), 6.45 (1H, m), 7.17 (1H, d, J=5.6 Hz), 7.43 (1H, m), 7.98 (1H, d, J=5.6 Hz), 8.35 (1H, m), 8.51 (1H, m) ppm. MS m/z=509.1 [M+H$^+$].

Example Z610. (S)—N-(1-(2-((1-(5-Fluoropyridin-3-yl)ethyl)amino)thieno[3,2-d]pyrimidine-4-carbonyl)azetidin-3-yl)cyclohexanecarboxamide

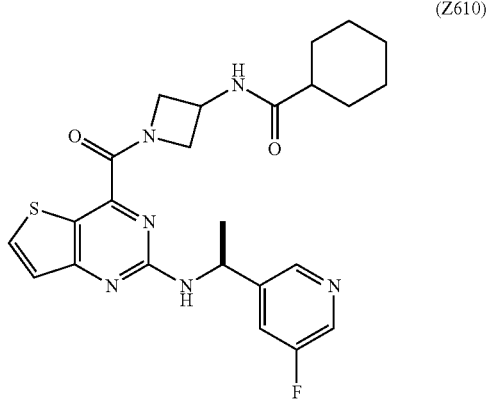

(Z610)

Synthesis of (S)—N-(1-(2-((1-(5-fluoropyridin-3-yl)ethyl)amino)thieno[3,2-d]pyrimidine-4-carbonyl)azetidin-3-yl)cyclohexanecarboxamide (Z610): The title compound (Z610) was prepared as a white solid from (S)-(3-aminoazetidin-1-yl)(2-((1-(5-fluoropyridin-3-yl)ethyl)amino)thieno[3,2-d]pyrimidin-4-yl)methanone (19 mg, 0.05 mmol) using chemistry similar to that described in Example Z603 using cyclohexanecarbonyl chloride (commercially obtained from Sigma-Aldrich, St. Louis, Mo.) in place of 1-methylcyclopropanecarbonyl chloride (20 mg, 83% yield). $^1$H NMR (400 MHz, CDCl$_3$) δ 1.21-1.35 (3H, m), 1.40-1.52 (2H, m), 1.64 (3H, d, J=6.8 Hz), 1.70 (1H, m), 1.78-1.93 (4H, m), 2.13 (1H, m), 4.01 (1H, td, J=8.0, 4.8 Hz), 4.34 (1H, m), 4.56 (1H, m), 4.70 (1H, m), 4.97 (1H, m), 5.21 (1H, quintet, J=6.8 Hz), 5.38 (1H, t, J=8.0 Hz), 5.94 (1H, d, J=6.8 Hz), 7.16 (1H, d, J=5.6 Hz), 7.43 (1H, m), 7.97 (1H, d, J=5.6 Hz), 8.43 (1H, m), 8.51 (1H, m) ppm. MS m/z=483.2 [M+H$^+$].

Example Z611. (S)-1-(tert-Butyl)-3-(1-(2-((1-(5-fluoropyridin-3-yl)ethyl)amino)thieno[3,2-d]pyrimidine-4-carbonyl)azetidin-3-yl)urea

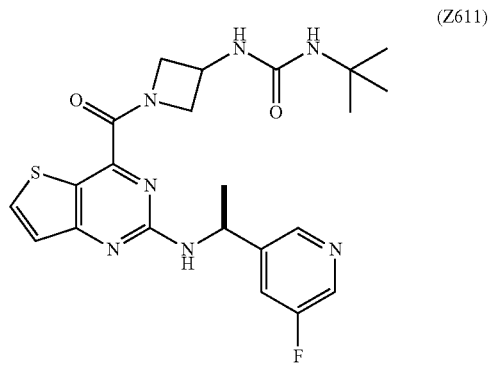

(Z611)

Synthesis of (S)-1-(tert-butyl)-3-(1-(2-((1-(5-fluoropyridin-3-yl)ethyl)amino)thieno[3,2-d]pyrimidine-4-carbonyl)azetidin-3-yl)urea (Z611): To a solution of (S)-(3-aminoazetidin-1-yl)(2-((1-(5-fluoropyridin-3-yl)ethyl)amino)thieno[3,2-d]pyrimidin-4-yl)methanone (37 mg, 0.1 mmol) in DCM (2 mL) were added DIEA (52 uL, 0.30 mmol) and tert-butyl isocyanate (23 uL, 0.2 mmol) (commercially obtained from Enamine, Monmouth Jct., N.J.) and the mixture thus obtained was stirred at room temperature for 2 h and 70% conversion was observed. Additional tert-butyl isocyanate (23 uL) was added and the reaction mixture was stirred additional 2 h and completion of the reaction was observed. The reaction mixture was concentrated and the residue was purified by flash chromatography on silica gel (4 g HP silica, Teledyne Isco) eluting with 15% to 50% solvent A (DCM/MeOH/NH$_4$OH, 100/10/1) in DCM to provide compound 611 (40 mg, 85% yield) as an off-white solid (40 mg, 85% yield). $^1$H NMR (400 MHz, CDCl$_3$) δ 1.35 (9H, s), 1.63 (3H, d, J=7.2 Hz), 3.95 (1H, m), 4.34-4.66 (4H, m), 4.78 (1H, m), 4.93 (1H, m), 5.21 (1H, quintet, J=7.2 Hz), 5.46 (1H, d, J=7.2 Hz), 7.15 (1H, d, J=5.6 Hz), 7.45 (1H, m), 7.95 (1H, d, J=5.6 Hz), 8.34 (1H, m), 8.51 (1H, m) ppm. MS m/z=472.3 [M+H$^+$].

Example Z612. (S)—N-(1-(2-((1-(5-Fluoropyridin-3-yl)ethyl)amino)thieno[3,2-d]pyrimidine-4-carbonyl)azetidin-3-yl)-3-(tetrahydro-2H-pyran-4-yl)propanamide

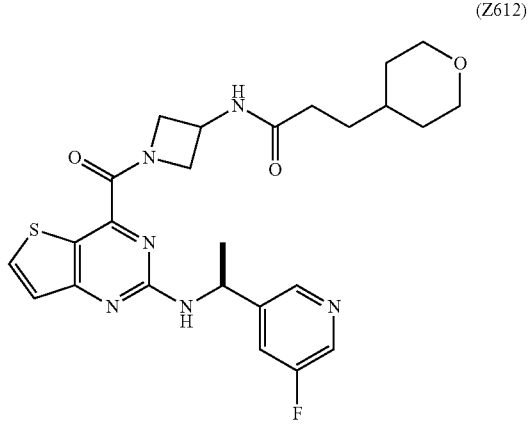

(Z612)

Synthesis of (S)—N-(1-(2-((1-(5-fluoropyridin-3-yl)ethyl)amino)thieno[3,2-d]pyrimidine-4-carbonyl)azetidin-3-yl)-3-(tetrahydro-2H-pyran-4-yl)propanamide (Z612): The title compound (Z612) was prepared as a white solid from (S)-(3-aminoazetidin-1-yl)(2-((1-(5-fluoropyridin-3-yl)ethyl)amino)thieno[3,2-d]pyrimidin-4-yl)methanone (37 mg, 0.10 mmol) using chemistry similar to that described in Example Z604 using 3-tetrahydropyran-4-ylpropanoic acid (commercially obtained from Enamine, Monmouth Jct., N.J.) in place of bicyclo[1.1.1]pentane-2-carboxylic acid (40 mg, 87% yield). $^1$H NMR (400 MHz, CDCl$_3$) δ 1.26-1.36 (2H, m), 1.54 (1H, m), 1.56-1.66 (7H, m), 2.25-2.29 (2H, m), 3.37 (2H, t, J=12.0 Hz), 3.94-4.05 (3H, m), 4.35 (1H, m), 4.55 (1H, m), 4.72 (1H, m), 4.93 (1H, m), 5.20 (1H, m), 5.37 (1H, d, J=6.8 Hz), 6.00 (1H, d, J=6.4 Hz), 7.16 (1H, d, J=5.6 Hz), 7.42 (1H, m), 7.97 (1H, d, J=5.6 Hz), 8.34 (1H, d, J=2.8 Hz), 8.50 (1H, m) ppm. MS m/z=513.2 [M+H$^+$].

Example Z613. (S)-3-Fluoro-N-(1-(2-((1-(5-fluoropyridin-3-yl)ethyl)amino)thieno[3,2-d]pyrimidine-4-carbonyl)azetidin-3-yl)benzamide

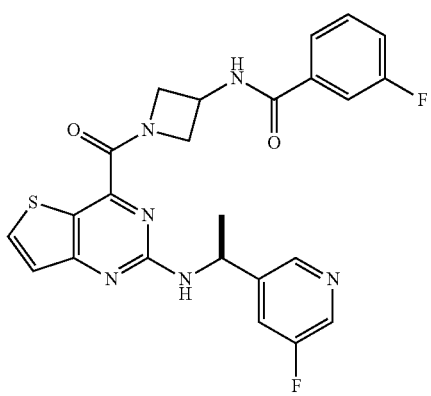

(Z613)

Synthesis of (S)-3-fluoro-N-(1-(2-((1-(5-fluoropyridin-3-yl)ethyl)amino)thieno[3,2-d]pyrimidine-4-carbonyl)azetidin-3-yl)benzamide (Z613): The title compound Z(613) was prepared as an off-white solid from (S)-(3-aminoazetidin-1-yl)(2-((1-(5-fluoropyridin-3-yl)ethyl)amino)thieno[3,2-d]pyrimidin-4-yl)methanone (19 mg, 0.05 mmol) using chemistry similar to that described in Example Z603 using 3-fluorobenzyl chloride (commercially obtained from Sigma-Aldrich, St. Louis, Mo.) in place of 1-methylcyclopropanecarbonyl chloride (20 mg, 81% yield). $^1$H NMR (400 MHz, CDCl$_3$) δ 1.64 (3H, d, J=6.8 Hz), 4.17 (1H, m), 4.48 (1H, m), 4.65 (1H, m), 4.86 (1H, m), 5.05 (1H, m), 5.12 (1H, m), 5.37 (1H, m), 6.80 (1H, m), 7.16 (1H, d, J=5.6 Hz), 7.25 (1H, m), 7.41-7.48 (2H, m), 7.56-7.65 (2H, m), 7.96 (1H, d, J=5.6 Hz), 8.33 (1H, d, J=2.8 Hz), 8.50 (1H, m) ppm. MS m/z=495.2 [M+H$^+$].

Example Z614. (S)-2-Fluoro-N-(1-(2-((1-(5-fluoropyridin-3-yl)ethyl)amino)thieno[3,2-d]pyrimidine-4-carbonyl)azetidin-3-yl)benzamide

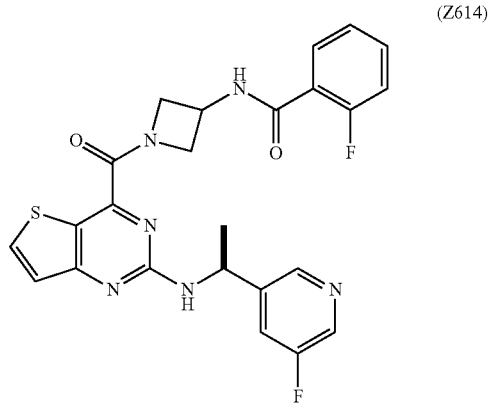

(Z614)

Synthesis of (S)-2-fluoro-N-(1-(2-((1-(5-fluoropyridin-3-yl)ethyl)amino)thieno[3,2-d]pyrimidine-4-carbonyl)azetidin-3-yl)benzamide (Z614): The title compound (Z614) was prepared as an off-white solid from (S)-(3-aminoazetidin-1-yl)(2-((1-(5-fluoropyridin-3-yl)ethyl)amino)thieno[3,2-d]pyrimidin-4-yl)methanone (19 mg, 0.05 mmol) using chemistry similar to that described in Example Z603 using 2-fluorobenzyl chloride (commercially obtained from Sigma-Aldrich, St. Louis, Mo.) in place of 1-methylcyclopropanecarbonyl chloride (18 mg, 73% yield). $^1$H NMR (400 MHz, CDCl$_3$) δ 1.64 (3H, d, J=7.2 Hz), 4.17 (1H, td. J=12.0, 5.6 Hz), 4.51 (1H, m), 4.66 (1H, m), 4.92 (1H, m), 5.06 (1H, m), 5.26 (1H, m), 5.38 (1H, m), 7.14-7.20 (3H, m), 7.25 (1H, m), 7.31 (1H, t, J=8.0 Hz), 7.44 (1H, m), 7.53 (1H, m), 7.98 (1H, d, J=5.6 Hz), 8.13 (1H, m), 8.33 (1H, d, J=2.8 Hz), 8.51 (1H, m) ppm. MS m/z=495.2 [M+H$^+$].

Example Z615. (S)-3-Chloro-N-(1-(2-((1-(5-fluoropyridin-3-yl)ethyl)amino)thieno[3,2-d]pyrimidine-4-carbonyl)azetidin-3-yl)benzamide

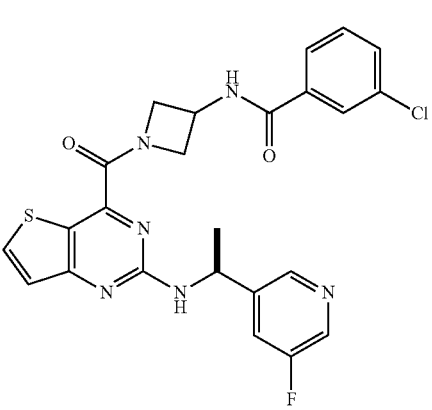

(Z615)

Synthesis of (S)-3-chloro-N-(1-(2-((1-(5-fluoropyridin-3-yl)ethyl)amino)thieno[3,2-d]pyrimidine-4-carbonyl)azetidin-3-yl)benzamide (Z615): The title compound (Z615) was prepared as an off-white solid from (S)-(3-aminoazetidin-1- yl)(2-((1-(5-fluoropyridin-3-yl)ethyl)amino)thieno[3,2-d]pyrimidin-4-yl)methanone (19 mg, 0.05 mmol) using chemistry similar to that described in Example Z603 using 3-chlorobenzyl chloride (commercially obtained from Sigma-Aldrich, St. Louis, Mo.) in place of 1-methylcyclopropanecarbonyl chloride (24 mg, 94% yield). $^1$H NMR (400 MHz, DMSO-$d_6$) δ 1.53 (3H, d, J=7.2 Hz), 4.14 (1H, m), 4.44 (1H, t, J=9.6 Hz), 4.67-4.86 (2H, m), 5.08 (1H, m), 5.25 (1H, m), 7.21 (1H, d, J=5.6 Hz), 7.54 (1H, td, J=8.0, 1.6 Hz), 7.64 (1H, m), 7.74 (1H, m), 7.84-7.94 (3H, m), 8.30 (1H, d, J=5.6 Hz), 8.37 (1H, m), 8.41 (1H, d, J=2.4 Hz), 8.53 (1H, m), 9.20 (1H, m) ppm. MS m/z=511.1 [M+H$^+$].

Example Z616. (S)-3,4-Difluoro-N-(1-(2-((1-(5-fluoropyridin-3-yl)ethyl)amino)thieno[3,2-d]pyrimidine-4-carbonyl)azetidin-3-yl)benzamide

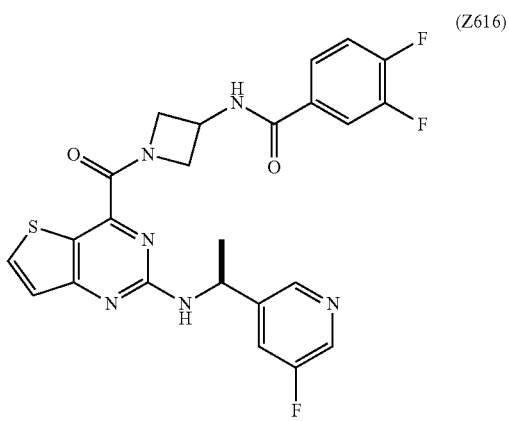

(Z616)

Synthesis of (S)-3,4-difluoro-N-(1-(2-((1-(5-fluoropyridin-3-yl)ethyl)amino)thieno[3,2-d]pyrimidine-4-carbonyl)azetidin-3-yl)benzamide (Z616): The title compound (Z616) was prepared as an off-white solid from (S)-(3-aminoazetidin-1-yl)(2-((1-(5-fluoropyridin-3-yl)ethyl)amino)thieno[3,2-d]pyrimidin-4-yl)methanone (19 mg, 0.05 mmol) using chemistry similar to that described in Example Z603 using 3,4-difluorobenzyl chloride (commercially obtained from Sigma-Aldrich, St. Louis, Mo.) in place of 1-methylcyclopropanecarbonyl chloride (21 mg, 82% yield). $^1$H NMR (400 MHz, DMSO-$d_6$) δ 1.53 (3H, d, J=7.2 Hz), 4.14 (1H, m), 4.44 (1H, t, J=9.6 Hz), 4.66-4.85 (2H, m), 5.10 (1H, m), 5.24 (1H, m), 7.21 (1H, d, J=5.6 Hz), 7.60 (1H, m), 7.71-7.83 (2H, m), 7.86-7.98 (2H, m), 8.30 (1H, d, J=5.6 Hz), 8.37 (1H, m), 8.41 (1H, d, J=2.8 Hz), 8.53 (1H, m), 9.18 (1H, m) ppm. MS m/z=513.2 [M+H$^+$].

Example Z617. (S)-4-Chloro-N-(1-(2-((1-(5-fluoropyridin-3-yl)ethyl)amino)thieno[3,2-d]pyrimidine-4-carbonyl)azetidin-3-yl)benzamide

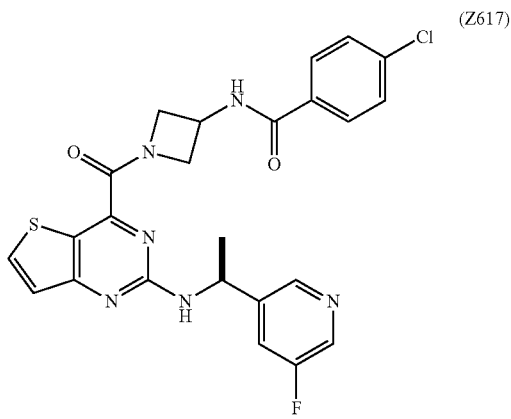

(Z617)

Synthesis of (S)-4-chloro-N-(1-(2-((1-(5-fluoropyridin-3-yl)ethyl)amino)thieno[3,2-d]pyrimidine-4-carbonyl)azetidin-3-yl)benzamide (Z617): The title compound Z(617) was prepared as a white solid from (S)-(3-aminoazetidin-1-yl)(2-((1-(5-fluoropyridin-3-yl)ethyl)amino)thieno[3,2-d]pyrimidin-4-yl)methanone (19 mg, 0.05 mmol) using chemistry similar to that described in Example Z603 using 4-chlorobenzyl chloride (commercially obtained from Sigma-Aldrich, St. Louis, Mo.) in place of 1-methylcyclopropanecarbonyl chloride (22 mg, 86% yield). $^1$H NMR (400 MHz, CDCl$_3$) δ 1.60 (3H, d, J=6.8 Hz), 4.16 (1H, m), 4.44 (1H, m), 4.70 (1H, m), 4.63 (1H, m), 4.75-5.10 (2H, m), 5.15 (1H, m), 5.34 (1H, m), 6.87 (1H, m), 7.16 (1H, d, J=5.6 Hz), 7.41-7.46 (3H, m), 7.80 (1H, d, J=8.4 Hz), 7.84 (1H, d, J=8.4 Hz), 7.96 (1H, d, J=5.6 Hz), 8.32 (1H, d, J=2.8 Hz), 8.49 (1H, m) ppm. MS m/z=511.1 [M+H$^+$].

Example Z618. Cyclopentyl (S)-(1-(2-((1-(5-fluoropyridin-3-yl)ethyl)amino)thieno[3,2-d]pyrimidine-4-carbonyl)azetidin-3-yl)carbamate

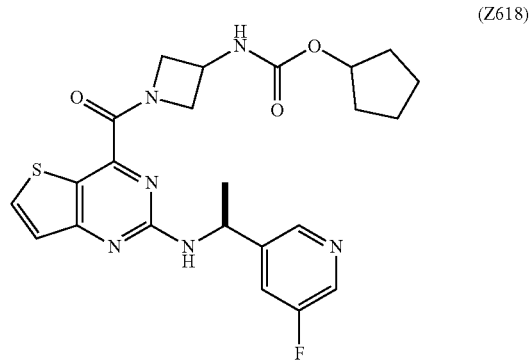

(Z618)

Synthesis of cyclopentyl (S)-(1-(2-((1-(5-fluoropyridin-3-yl)ethyl)amino)thieno[3,2-d]pyrimidine-4-carbonyl)azetidin-3-yl)carbamate (Z618): The title compound (Z618) was prepared from (S)-(3-aminoazetidin-1-yl)(2-((1-(5-fluoropyridin-3-yl)ethyl)aminothieno[3,2-d]pyrimidin-4-yl)methanone using chemistry similar to that described in Example 490 using cyclopentyl carbonochloridate (commercially obtained from Combi-Blocks, San Diego, Calif.) in place of pivaloyl chloride (20% yield). ¹H NMR (400 MHz, CDCl₃) δ 1.63 (3H, m), 1.68-1.76 (4H, m), 1.80-1.92 (2H, m), 4.01-4.05 (1H, m), 4.25-4.75 (1H, m), 4.52-4.59 (2H, m), 4.75-5.06 (2H, m), 5.13 (1H, m), 5.23 (1H, td, J=6.8, 2.4 Hz), 5.37 (1H, t, J=6.0 Hz), 7.16 (1H, d, J=5.6 Hz), 7.43 (1H, d, J=9.2 Hz), 7.53 (1H, dd, J=9.6, 2.4 Hz), 7.98 (1H, dd, J=5.6, 1.6 Hz), 8.34 (1H, d, J=2.4 Hz), 8.51 (1H, m) ppm. MS m/z=485.1 [M+H⁺].

Example Z619. (S)—N-(1-(2-((1-(5-Fluoropyridin-3-yl)ethyl)amino)thieno[3,2-d]pyrimidine-4-carbonyl)azetidin-3-yl)isonicotinamide

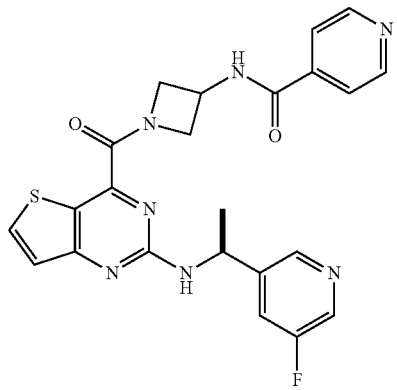

(Z619)

Synthesis of (S)—N-(1-(2-((1-(5-fluoropyridin-3-yl)ethyl)amino)thieno[3,2-d]pyrimidine-4-carbonyl)azetidin-3-yl)isonicotinamide (Z619): The title compound (Z619) was prepared from (S)-(3-aminoazetidin-1-yl)(2-((1-(5-fluoropyridin-3-yl)ethyl)amino)thieno[3,2-d]pyrimidin-4-yl)methanone using chemistry similar to that described in Example Z598 using isonicotinic acid (commercially obtained from TCI America, Portland, Oreg.) in place of (3R)-tetrahydrofuran-3-carboxylic acid (40% yield). ¹H NMR (400 MHz, CD₃OD) δ 1.62 (3H, d, J=3.2 Hz), 4.24 (1H, q, J=5.6 Hz), 4.57 (1H, t, J=4.8 Hz), 4.70-4.90 (2H, m), 5.20-5.35 (2H, m), 7.16 (1H, dd, J=5.6, 1.2 Hz), 7.67-7.72 (1H, m), 7.83 (2H, td, J=4.8, 2.0 Hz), 8.13 (1H, dd, J=6.0, 2.0 Hz), 8.28 (1H, dd, J=16.4, 3.2 Hz), 8.49 (1H, d, J=6.8 Hz), 8.72 (2H, dd, J=6.0, 0.8 Hz) ppm. MS m/z=478.1 [M+H⁺].

Example Z620. (S)—N-(1-(2-((1-(5-Fluoropyridin-3-yl)ethyl)amino)thieno[3,2d]pyrimidine-4-carbonyl)azetidin-3-yl)nicotinamide

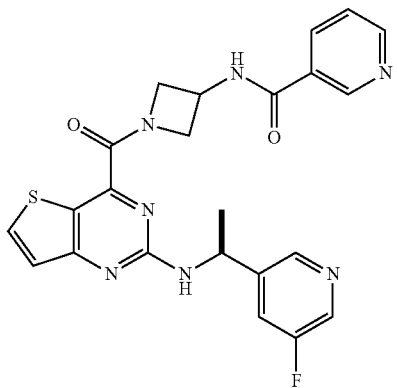

(620)

Synthesis of (S)—N-(1-(2-((1-(5-fluoropyridin-3-yl)ethyl)amino)thieno[3,2-d]pyrimidine-4-carbonyl)azetidin-3-yl)nicotinamide (Z620): The title compound (Z620) was prepared from (S)-(3-aminoazetidin-1-yl)(2-((1-(5-fluoropyridin-3-yl)ethyl)amino)thieno[3,2-d]pyrimidin-4-yl) methanone using chemistry similar to that described in Example Z598 using nicotinic acid (commercially obtained from Enamine, Monmouth Jct., N.J.) in place of (3R)-tetrahydrofuran-3-carboxylic acid (20% yield). ¹H NMR (400 MHz, CD₃OD) δ 1.62 (3H, d, J=7.2 Hz), 4.24 (1H, q, J=5.6 Hz), 4.57 (1H, t, J=4.8 Hz), 4.72-4.95 (2H, m), 5.20-5.35 (2H, m), 7.16 (1H, dd, J=5.6, 1.2 Hz), 7.56 (1H, dd, J=8.9, 5.2 Hz), 7.68-7.71 (1H, m), 8.13 (1H, dd, J=5.2, 2.0 Hz), 8.29-8.32 (2H, m), 8.49 (1H, d, J=7.2 Hz), 8.71 (1H, d, J=4.8 Hz), 9.03 (1H, dd, J=4.0, 2.0 Hz) ppm. MS m/z=478.1 [M+H⁺].

Example Z621. (S)—N-(1-(2-((1-(5-Fluoropyridin-3-yl)ethyl)amino)thieno[3,2-d]pyrimidine-4-carbonyl)-3-methylazetidin-3-yl)cyclopropanecarboxamide

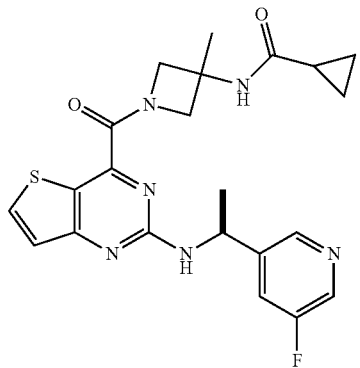

(Z621)

Synthesis of tert-butyl N-[1-[2-[[(1S)-1-(5-fluoro-3-pyridyl)ethyl]amino]thieno[3,2-d]pyrimidine-4-carbonyl]-3-methyl-azetidin-3-yl]carbamate: The title compound was prepared from (S)-2-((1-(5-fluoropyridin-3-yl)ethyl)amino)

thieno[3,2-d]pyrimidine-4-carboxylic acid di-hydrochloride using chemistry similar to that described in Example 17 using tert-butyl N-(3-methylazetidin-3-yl)carbamate (commercially obtained from J&W PharmLab, Levittown, Pa.) in place of (3R)-3-methoxypyrrolidine hydrochloride (95% yield). MS m/z=487.3 [M+H⁺].

Synthesis of (3-amino-3-methyl-azetidin-1-yl)-[2-[[(1S)-1-(5-fluoro-3-pyridyl)ethyl]amino]thieno[3,2-d]pyrimidin-4-yl]methanone trihydrochloride: The title compound was prepared from tert-butyl N-[1-[2-[[(1S)-1-(5-fluoro-3-pyridyl)ethyl]amino]thieno[3,2-d]pyrimidine-4-carbonyl]-3-methyl-azetidin-3-yl]carbamate using chemistry similar to that described in Example 358 (100% yield). MS m/z=387.2 [M+H⁺].

Synthesis of (S)—N-(1-(2-((1-(5-fluoropyridin-3-yl)ethyl)amino)thieno[3,2-d]pyrimidine-4-carbonyl)-3-methylazetidin-3-yl)cyclopropanecarboxamide (Z621): The title compound (Z621) was prepared from (3-amino-3-methyl-azetidin-1-yl)-[2-[[(1S)-1-(5-fluoro-3-pyridyl)ethyl]amino]thieno[3,2-d]pyrimidin-4-yl]methanone using chemistry similar to that described in Example 490 using cyclopropanecarbonyl chloride (commercially obtained from Sigma-Aldrich, St. Louis, Mo.) in place of pivaloyl chloride (20% yield). $^1$H NMR (400 MHz, CDCl$_3$) δ 0.78 (2H, dd, J=7.6, 2.8 Hz), 0.94-1.04 (2H, m), 1.35-1.40 (1H, m), 1.53 (3H, m), 1.64 (3H, s), 4.09 (1H, t, J=10.8 Hz), m), 4.27 (2H, dd, J=12.0, 10.8 Hz),), 4.64 (2H, m), 5.23 (1H, dd, J=13.6, 10.2 Hz), 5.41 (1H, d, J=6.4 Hz), 5.88 (1H, d, J=2.8 Hz), 7.16 (1H, d, J=5.6 Hz), 7.43-7.47 (1H, m), 7.95 (1H, d, J=5.6 Hz), 8.34 (1H, t, J=2.8 Hz), 8.51 (1H, d, J=8.0 Hz) ppm. MS m/z=455.1 [M+H⁺].

Example Z622. (S)—N-(1-(2-((1-(5-Fluoropyridin-3-yl)ethyl)amino)thieno[3,2-d]pyrimidine-4-carbonyl)azetidin-3-yl)tetrahydro-2H-pyran-4-carboxamide

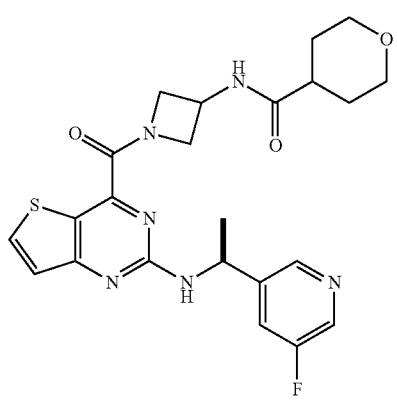

(Z622)

Synthesis of (S)—N-(1-(2-((1-(5-fluoropyridin-3-yl)ethyl)amino)thieno[3,2-d]pyrimidine-4-carbonyl)azetidin-3-yl)tetrahydro-2H-pyran-4-carboxamide (Z622): The title compound (Z622) was prepared as a white solid from (S)-(3-aminoazetidin-1-yl)(2-((1-(5-fluoropyridin-3-yl)ethyl)amino)thieno[3,2-d]pyrimidin-4-yl)methanone (19 mg, 0.05 mmol) using chemistry similar to that described in Example Z603 using tetrahydropyran-4-carbonyl chloride (commercially obtained from Ark Pharm, Arlington Heights, Ill.) in place of 1-methylcyclopropanecarbonyl chloride (20 mg, 83% yield). $^1$H NMR (400 MHz, CDCl$_3$) δ 1.21-1.35 (3H, m), 1.40-1.52 (2H, m), 1.64 (3H, d, J=6.8 Hz), 1.70 (1H, m), 1.78-1.93 (4H, m), 2.13 (1H, m), 4.01 (1H, td, J=8.0, 4.8 Hz), 4.34 (1H, m), 4.56 (1H, m), 4.70 (1H, m), 4.97 (1H, m), 5.21 (1H, quintet, J=6.8 Hz), 5.38 (1H, t, J=8.0 Hz), 5.94 (1H, d, J=6.8 Hz), 7.16 (1H, d, J=5.6 Hz), 7.43 (1H, m), 7.97 (1H, d, J=5.6 Hz), 8.43 (1H, m), 8.51 (1H, m) ppm. MS m/z=485.1 [M+H⁺].

Example Z623. (S)-1-Cyclobutyl-3-(1-(2-((1-(5-fluoropyridin-3-yl)ethyl)amino)thieno[3,2-d]pyrimidine-4-carbonyl)azetidin-3-yl)urea

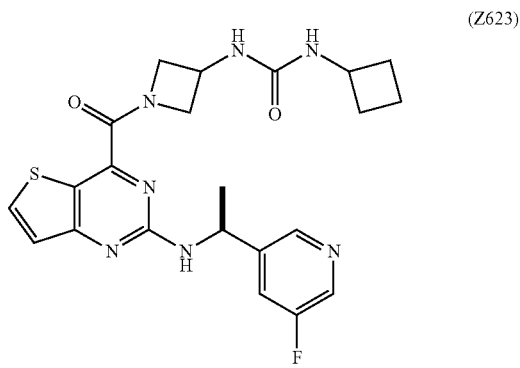

(Z623)

Synthesis of (S)-1-cyclobutyl-3-(1-(2-((1-(5-fluoropyridin-3-yl)ethyl)amino)thieno[3,2-d]pyrimidine-4-carbonyl)azetidin-3-yl)urea (Z623): The title compound (Z623) was prepared as an off-white solid from (S)-(3-aminoazetidin-1-yl)(2-((1-(5-fluoropyridin-3-yl)ethyl)amino)thieno[3,2-d]pyrimidin-4-yl)methanone (28 mg, 0.075 mmol) using chemistry similar to that described in Example Z611 using cyclobutyl isocyanate (commercially obtained from Oakwood Products, Estill, S.C.) in place of tert-butyl isocyanate (29 mg, 82% yield). $^1$H NMR (400 MHz, CDCl$_3$) δ 1.62 (3H, d, J=6.8 Hz), 1.67-1.74 (2H, m), 1.78-1.89 (2H, m), 2.31-2.38 (2H, m), 3.97 (1H, m), 4.16 (1H, m), 4.33 (1H, m), 4.49-4.65 (2H, m), 4.74-4.93 (2H, m), 500 (1H, m), 5.19 (1H, quintet, J=6.8 Hz), 5.46 (1H, d, J=6.8 Hz), 7.15 (1H, d, J=5.6 Hz), 7.45 (1H, m), 7.95 (1H, d, J=5.6 Hz), 8.34 (1H, m), 8.50 (1H, m) ppm. MS m/z=470.1 [M+H⁺].

Example Z624. (S)—N-(1-(2-((1-(5-Fluoropyridin-3-yl)ethyl)amino)-7-methylthieno[3,2-d]pyrimidine-4-carbonyl)azetidin-3-yl)pivalamide

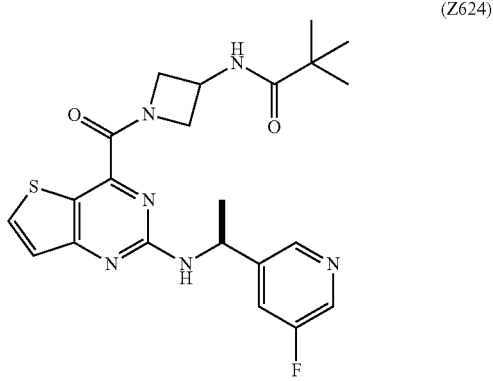

(Z624)

Synthesis of (S)—N-(1-(2-((1-(5-fluoropyridin-3-yl)ethyl)amino)-7-methylthieno[3,2-d]pyrimidine-4-carbonyl)azetidin-3-yl)pivalamide (Z624): The title compound (Z624) was prepared as a white solid from (S)-(3-aminoazetidin-1-yl)(2-((1-(5-fluoropyridin-3-yl)ethyl)amino)-7-methylthieno[3,2-d]pyrimidin-4-yl)methanone (10 mg, 0.026 mmol) using chemistry similar to that described in Example Z603 using pivaloyl chloride (commercially obtained from Sigma-Aldrich, St. Louis, Mo.) in place of 1-methylcyclopropanecarbonyl chloride (9.5 mg, 78% yield). $^1$H NMR (400 MHz, CDCl$_3$) δ 1.24 (9H, s), 1.65 (3H, d, J=7.2 Hz), 2.31 (3H, d, J=1.2 Hz), 4.00 (1H, m), 4.56 (1H, m), 4.57 (1H, m), 4.68 (1H, m), 4.47 (1H, m), 5.20 (1H, quintet, J=7.2 Hz), 5.42 (1H, d, J=7.2 Hz), 6.03 (1H, d, J=5.6 Hz), 7.45 (1H, dt, J=9.6, 2.0 Hz), 7.59 (1H, d, J=1.2 Hz), 8.33 (1H, d, J=2.0 Hz), 8.53 (1H, m) ppm. MS m/z=457.1 [M+H$^+$].

Example Z625. (S)-3-Chloro-N-(1-(2-((1-(5-fluoropyridin-3-yl)ethyl)amino)-7-methylthieno[3,2-d]pyrimidine-4-carbonyl)azetidin-3-yl)benzamide

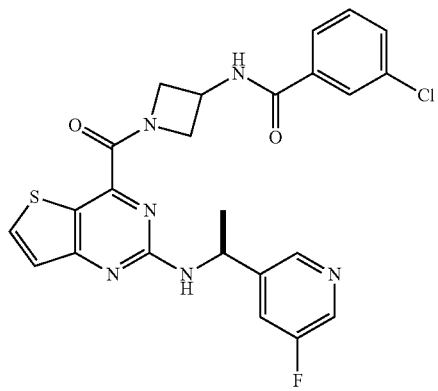

(Z625)

Synthesis of (S)-3-chloro-N-(1-(2-((1-(5-fluoropyridin-3-yl)ethyl)amino)-7-methylthieno[3,2-d]pyrimidine-4-carbonyl)azetidin-3-yl)benzamide (Z625): The title compound (Z625) was prepared as a light yellow solid from (S)-(3-aminoazetidin-1-yl)(2-((1-(5-fluoropyridin-3-yl)ethyl)amino)-7-methylthieno[3,2-d]pyrimidin-4-yl)methanone (10 mg, 0.026 mmol) using chemistry similar to that described in Example Z603 using 3-chlorobenzyl chloride in place of 1-methylcyclopropanecarbonyl chloride (12.5 mg, 92% yield). $^1$H NMR (400 MHz, DMSO-d$_6$ at 80° C.) δ 1.57 (3H, d, J=7.2 Hz), 2.6 (3H, d, J=1.2 Hz), 4.15 (1H, dd, J=10.8, 5.2 Hz), 4.43 (1H, t, J=8.4 Hz), 4.62 (1H, dd, J=10.8, 5.2 Hz), 4.79 (1H, m), 5.01 (1H, dd, J=9.6, 8.0 Hz), 5.25 (1H, quintet, J=7.2 Hz), 7.51 (1H, t, J=8.0 Hz), 7.60 (1H, m), 7.64 (1H, m), 7.71 (1H, m), 7.84 (1H, d, J=1.6 Hz), 7.93 (1H, m), 8.34 (1H, dd, J=11.2, 2.4 Hz), 8.55 (1H, t, J=2.0 Hz), 8.99 (1H, m) ppm. MS m/z=525.2 [M+H$^+$].

Example Z626. (S)—N-(1-(2-((1-(5-Fluoropyridin-3-yl)ethyl)amino)thieno[3,2-d]pyrimidine-4-carbonyl)azetidin-3-yl)-3-methylbenzamide

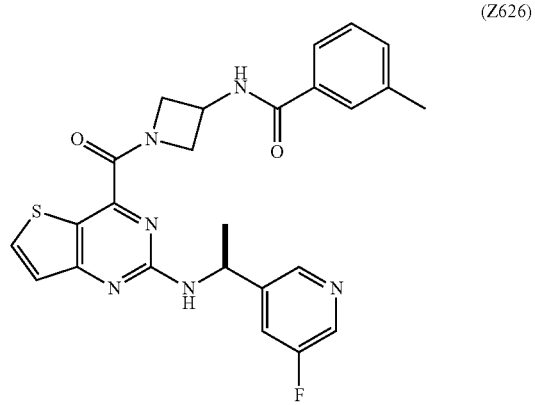

(Z626)

Synthesis of (S)—N-(1-(2-((1-(5-fluoropyridin-3-yl)ethyl)amino)thieno[3,2-d]pyrimidine-4-carbonyl)azetidin-3-yl)-3-methylbenzamide (Z626): The title compound (Z626) was prepared as an off-white solid from (S)-(3-aminoazetidin-1-yl)(2-((1-(5-fluoropyridin-3-yl)ethyl)amino)thieno[3,2-d]pyrimidin-4-yl)methanone (19 mg, 0.05 mmol) using chemistry similar to that described in Example Z603 using 3-methylbenzoyl chloride (commercially obtained from Oakwood Products, Estill, S.C.) in place of 1-methylcyclopropanecarbonyl chloride (15 mg, 61% yield). $^1$H NMR (400 MHz, DMSO-d$_6$ at 80° C.) δ 1.56 (3H, d, J=7.2 Hz), 2.37 (3H, s), 4.15 (1H, dd, J=10.8, 4.8 Hz), 4.43 (1H, t, J=10.0 Hz), 4.62 (1H, m), 4.80 (1H, m), 5.02 (1H, m), 5.28 (1H, quintet, J=7.2 Hz), 7.18 (1H, d, J=5.6 Hz), 7.34-7.37 (2H, m), 7.62 (1H, d, J=8.4 Hz), 7.67-7.72 (3H, m), 8.24 (1H, d, J=5.6 Hz), 8.35 (1H, dd, J=10.0, 2.8 Hz), 8.53 (1H, m), 8.81 (1H, m) ppm. MS m/z=491.1 [M+H$^+$].

Example Z627. (S)—N-(1-(2-((1-(5-Fluoropyridin-3-yl)ethyl)amino)thieno[3,2-d]pyrimidine-4-carbonyl)azetidin-3-yl)-1-methylcyclobutane-1-carboxamide

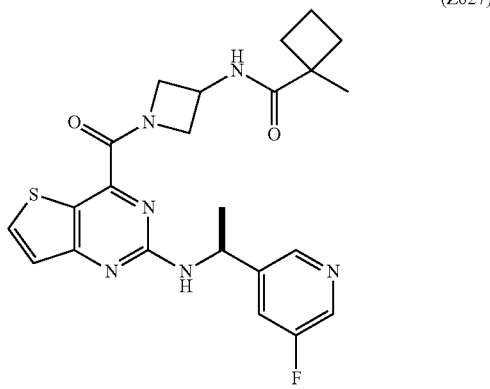

(Z627)

Synthesis of (S)—N-(1-(2-((1-(5-fluoropyridin-3-yl)ethyl)amino)thieno[3,2-d]pyrimidine-4-carbonyl)azetidin-3-yl)-1-methylcyclobutane-1-carboxamide (Z627): The title compound (Z627) was prepared from (S)-(3-aminoazetidin-1-yl)(2-((1-(5-fluoropyridin-3-yl)ethyl)amino)thieno[3,2-d]pyrimidin-4-yl)methanone using chemistry similar to that described in Example 490 using 1-methylcyclobutanecarbonyl chloride (commercially obtained from Enamine, Monmouth Jct., N.J.) in place of pivaloyl chloride (20% yield). ¹H NMR (400 MHz, CDCl₃) δ 1.46 (3H, d, J=2.8 Hz), 1.64 (3H, d, J=6.8 Hz), 1.82-1.90 (2H, m), 1.96-2.06 (1H, m), 2.38-2.48 (2H, m), 4.02 (1H, dt, J=16.8, 5.2 Hz), 4.20-4.47 (1H, m), 4.57 (1H, m), 4.65-4.78 (1H, m), 4.85-5.10 (1H, m), 5.13 (1H, m), 5.23 (1H, q, J=6.8 Hz), 5.37 (1H, t, J=7.2 Hz), 5.76-5.91 (1H, m), 7.16 (1H, dd, J=5.6, 1.6 Hz), 7.43 (1H, tt, J=9.2, 1.6 Hz), 7.98 (1H, dd, J=9.2, 4.4 Hz), 8.34 (1H, t, J=6.8 Hz), 8.51 (1H, d, J=11.6 Hz) ppm. MS m/z=469.3 [M+H⁺].

Example Z628. (R)—N-(Cyclopentyloxy)-1-(2-(((S)-1-(5-fluoropyridin-3-yl)ethyl)amino)thieno[3,2-d]pyrimidine-4-carbonyl)pyrrolidine-3-carboxamide

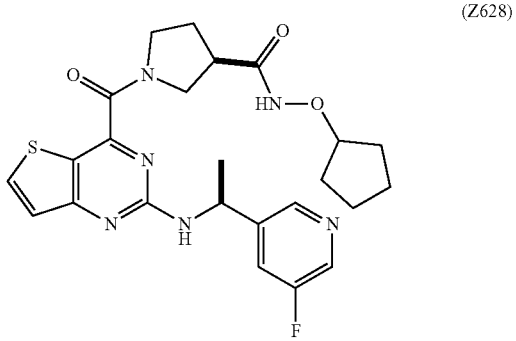

(Z628)

Synthesis of (R)—N-(cyclopentyloxy)-1-(2-(((S)-1-(5-fluoropyridin-3-yl)ethyl)amino)thieno[3,2-d]pyrimidine-4-carbonyl)pyrrolidine-3-carboxamide (Z628): The title compound (Z628) was prepared from (R)-1-(2-(((S)-1-(5-fluoropyridin-3-yl)ethyl)amino)-6-methylthieno[3,2-d]pyrimidine-4-carbonyl)pyrrolidine-3-carboxylic acid di-hydrochloride using chemistry similar to that described in Example Z17 using O-cyclopentylhydroxylamine (commercially obtained from Enamine, Monmouth Jct, N.J.) in place of (3R)-3-methoxypyrrolidine hydrochloride (26% yield). ¹H NMR (400 MHz, CDCl₃) δ 1.62 (3H, dd, J=13.2, 6.0 Hz), 1.65-1.82 (4H, m), 2.00-2.20 (4H, m), 2.60-2.80 (1H, m), 3.25-3.40 (1H, m), 3.60-3.85 (2H, m), 3.92-4.02 (2H, m), 4.02-4.20 (1H, m), 4.50-4.62 (1H, m), 5.12-5.28 (1H, m), 5.35-5.55 (1H, m), 6.85 (1H, m), 7.16 (1H, dd, J=5.6, 3.2 Hz), 7.42-7.45 (1H, m), 7.96 (1H, dt, J=7.2, 2.0 Hz), 8.33 (1H, t, J=3.2 Hz), 8.52 (1H, m) ppm. MS m/z=499.3 [M+H⁺].

Example Z629. (S)—N-(1-(2-((1-(5-Fluoropyridin-3-yl)ethyl)amino)thieno[3,2-d]pyrimidine-4-carbonyl)azetidin-3-yl)-5-(trifluoromethyl)furan-2-carboxamide

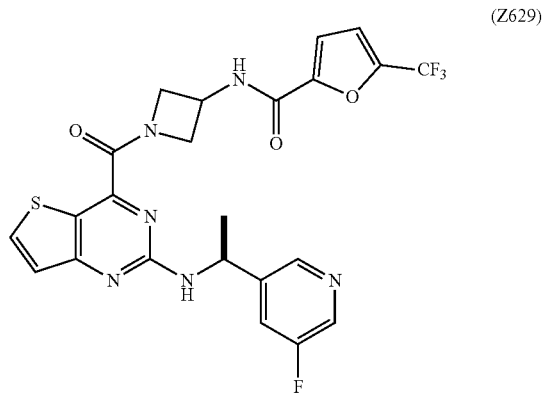

(Z629)

Synthesis of (S)—N-(1-(2-((1-(5-fluoropyridin-3-yl)ethyl)amino)thieno[3,2-d]pyrimidine-4-carbonyl)azetidin-3-yl)-5-(trifluoromethyl)furan-2-carboxamide (Z629): The title compound (Z629) was prepared from (S)-(3-aminoazetidin-1-yl)(2-((1-(5-fluoropyridin-3-yl)ethyl)amino)thieno[3,2-d]pyrimidin-4-yl)methanone using chemistry similar to that described in Example Z598 using 5-(trifluoromethyl)furan-2-carboxylic acid (commercially obtained from Enamine, Monmouth Jct., N.J.) in place of (3R)-tetrahydrofuran-3-carboxylic acid (22% yield). ¹H NMR (400 MHz, CD₃OD) δ 1.63 (3H, d, J=6.4 Hz), 4.24 (1H, dt, J=15.6, 3.6 Hz), 4.63-4.68 (1H, m), 4.82-5.15 (2H, m), 5.23 (1H, dd, J=14.4, 7.2 Hz), 5.36 (1H, t, J=6.4 Hz), 6.75-6.85 (1H, m), 6.92-6.94 (1H, m), 7.16 (1H, dd, J=5.6, 1.2 Hz), 7.22 (1H, d, J=3.6 Hz), 7.45 (1H, dq, J=7.2, 2.4 Hz), 7.98 (1H, dd, J=5.6, 3.2 Hz), 8.33 (1H, dd, J=12.0, 2.8 Hz), 8.52 (1H, dd, J=10.4, 2.0 Hz) ppm. MS m/z=535.1 [M+H⁺].

Example Z630. (S)-1-(1-(2-((1-(5-Fluoropyridin-3-yl)ethyl)amino)thieno[3,2-d]pyrimidine-4-carbonyl)azetidin-3-yl)-3-(pentan-3-yl)urea

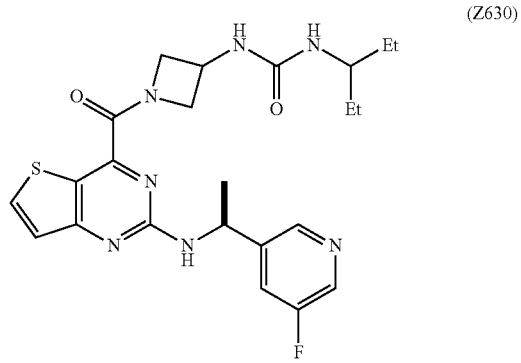

(Z630)

Synthesis of (S)-1-(1-(2-((1-(5-fluoropyridin-3-yl)ethyl)amino)thieno[3,2-d]pyrimidine-4-carbonyl)azetidin-3-yl)-3-(pentan-3-yl)urea (Z630): The title compound (Z630) was prepared from (S)-(3-aminoazetidin-1-yl)(2-((1-(5-fluoropyridin-3-yl)ethyl)amino)thieno[3,2-d]pyrimidin-4-yl) methanone using chemistry similar to that described in Example Z611 using 3-isocyanatopentane (commercially obtained from Enamine, Monmouth Jct., N.J.) in place of tert-butyl isocyanate (20% yield). $^1$H NMR (400 MHz, CDCl$_3$) δ 0.90-0.94 (6H, m), 1.34-1.42 (2H, m), 1.50-1.58 (2H, m), 1.64 (3H, d, J=6.8 Hz), 3.95-4.01 (1H, m), 4.21 (1H, dd, J=25.6, 8.8 Hz), 4.30-4.47 (1H, m), 4.50-4.70 (2H, m), 4.78 (1H, t, J=8.0 Hz), 4.75-5.01 (1H, m), 5.21 (1H, m), 5.41 (1H, t, J=6.4 Hz), 7.16 (1H, d, J=5.2 Hz), 7.43 (1H, tt, J=8.8 Hz), 7.95 (1H, dd, J=5.6, 4.0 Hz), 8.34 (1H, t, J=2.4 Hz), 8.52 (1H, d, J=8.8 Hz) ppm. MS m/z=486.2 [M+H$^+$].

Example Z631. (3S,5S,7S)—N-(1-(2-(((S)-1-(5-Fluoropyridin-3-yl)ethyl)amino)thieno[3,2-d]pyrimidine-4-carbonyl)azetidin-3-yl)adamantane-1-carboxamide

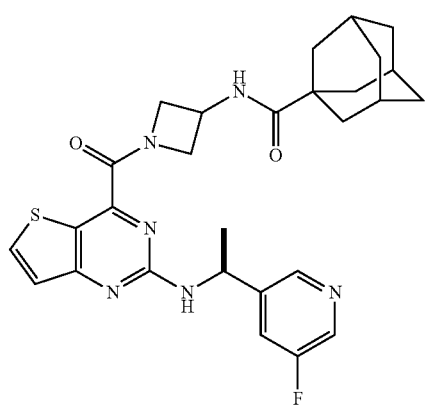

(Z631)

Synthesis of (3S,5S,7S)—N-(1-(2-(((S)-1-(5-fluoropyridin-3-yl)ethyl)amino)thieno[3,2-d]pyrimidine-4-carbonyl) azetidin-3-yl)adamantane-1-carboxamide (Z631): The title compound (Z631) was prepared from (S)-(3-aminoazetidin-1-yl)(2-((1-(5-fluoropyridin-3-yl)ethyl)amino)thieno[3,2-d] pyrimidin-4-yl)methanone using chemistry similar to that described in Example 490 using adamantane-1-carbonyl chloride (commercially obtained from Combi-Blocks, San Diego, Calif.) in place of pivaloyl chloride (23% yield). $^1$H NMR (400 MHz, DMSO-d$_6$) δ 1.56 (3H, d, J=5.6 Hz), 1.65-1.73 (6H, m), 1.82 (6H, s), 1.99 (3H, s), 3.95-4.05 (1H, m), 4.28-4.40 (1H, m), 4.52-4.58 (1H, m), 4.82-5.00 (1H, m), 5.27 (1H, t, J=8.0 Hz), 7.18 (1H, d, J=5.2 Hz), 7.61 (1H, d, J=8.4 Hz), 7.67-7.80 (2H, m), 8.25 (1H, d, J=6.0 Hz), 8.37 (1H, t, J=6.8 Hz), 8.53 (1H, d, J=8.0 Hz) ppm. MS m/z=535.3 [M+H$^+$].

Example Z632. (S)—N-(1-(2-((1-(5-Fluoropyridin-3-yl)ethyl)amino)-6-methylthieno[3,2-d]pyrimidine-4-carbonyl)azetidin-3-yl)-5-(trifluoromethyl)furan-2-carboxamide

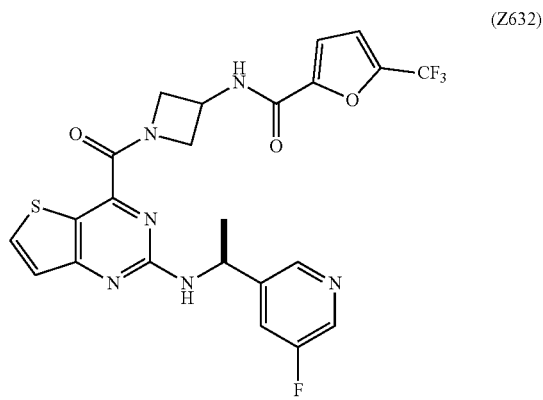

(Z632)

Synthesis of ((S)—N-(1-(2-((1-(5-fluoropyridin-3-yl) ethyl)amino)-6-methylthieno[3,2-d]pyrimidine-4-carbonyl) azetidin-3-yl)-5-(trifluoromethyl)furan-2-carboxamide (Z632): The title compound (Z632) was prepared from (S)-(3-aminoazetidin-1-yl)(2-((1-(5-fluoropyridin-3-yl) ethyl)amino)-6-methylthieno[3,2-d]pyrimidin-4-yl)methanone using chemistry similar to that described in Example Z598 using 5-(trifluoromethyl)furan-2-carboxylic acid (commercially obtained from Enamine, Monmouth Jct., N.J.) in place of (3R)-tetrahydrofuran-3-carboxylic acid (22% yield). $^1$H NMR (400 MHz, DMSO-d$_6$ at 80° C.) δ 1.55 (3H, d, J=6.8 Hz), 2.57 (3H, d, J=1.2 Hz), 4.15 (1H, dd, J=10.8, 5.6 Hz), 4.41 (1H, t, J=10.4 Hz), 4.70-4.82 (2H, m), 4.85-5.10 (1H, m), 5.24 (1H, t, J=7.2 Hz), 6.92 (1H, d, J=1.2 Hz), 7.30 (1H, t, J=4.4 Hz), 7.32 (1H, dd, J=3.6, 0.8 Hz), 7.51 (1H, d, J=8.0 Hz), 7.65-7.76 (1H, m), 8.33 (1H, dd, J=13.2, 2.8 Hz), 8.52 (1H, m), 9.10-0.915 (1H, m) ppm. MS m/z=549.2 [M+H$^+$].

Example Z633. (S)—N-(1-(2-((1-(5-Fluoropyridin-3-yl)ethyl)amino)thieno[3,2-d]pyrimidine-4-carbonyl)azetidin-3-yl)-3-(trifluoromethyl)benzamide

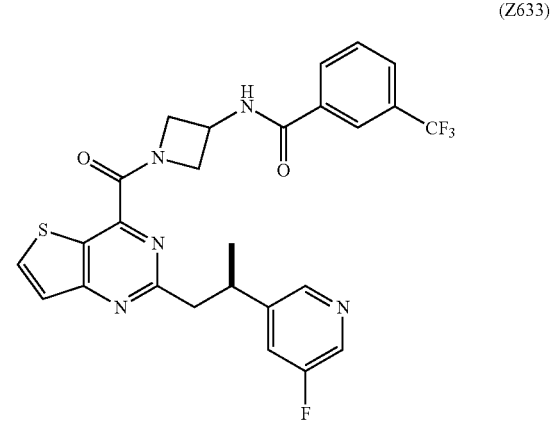

(Z633)

Synthesis of (S)—N-(1-(2-((1-(5-fluoropyridin-3-yl)ethyl)amino)thieno[3,2-d]pyrimidine-4-carbonyl)azetidin-3-yl)-3-(trifluoromethyl)benzamide (Z633): The title compound (Z633) was prepared as an off-white solid from (S)-(3-aminoazetidin-1-yl)(2-((1-(5-fluoropyridin-3-yl)ethyl)amino)thieno[3,2-d]pyrimidin-4-yl)methanone (19 mg, 0.05 mmol) using chemistry similar to that described in Example Z603 using 3-(trifluoromethyl)benzoyl chloride (commercially obtained from Oakwood Products, Estill, S.C.) in place of 1-methylcyclopropanecarbonyl chloride (18 mg, 66% yield). $^1$H NMR (400 MHz, DMSO-$d_6$ at 80° C.) δ 1.57 (3H, d, J=7.2 Hz), 4.19 (1H, dd, J=10.8, 5.2 Hz), 4.47 (1H, t, J=10.4 Hz), 4.65 (1H, m), 4.83 (1H, m), 5.05 (1H, m), 5.29 (1H, quintet, J=7.2 Hz), 7.19 (1H, d, J=5.6 Hz), 7.62 (1H, d, J=7.6 Hz), 7.71 (1H, m), 7.75 (1H, d, J=8.0 Hz), 7.91 (1H, d, J=7.6 Hz), 8.20 (1H, m), 8.23 (1H, m), 8.26 (1H, d, J=5.6 Hz), 8.35 (1H, m), 8.53 (1H, m), 9.13 (1H, m) ppm. MS m/z=545.2 [M+H$^+$].

Example Z634. (S)-1-(1-(2-((1-(5-Fluoropyridin-3-yl)ethyl)amino)thieno[3,2-d]pyrimidine-4-carbonyl)azetidin-3-yl)-3-phenylurea

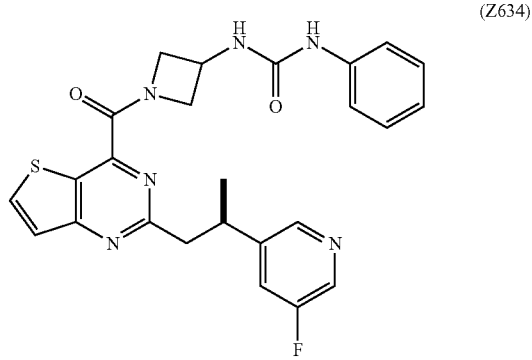

Synthesis of (S)-1-(1-(2-((1-(5-fluoropyridin-3-yl)ethyl)amino)thieno[3,2-d]pyrimidine-4-carbonyl)azetidin-3-yl)-3-phenylurea (Z634): The title compound (Z634) was prepared as an off-white solid from (S)-(3-aminoazetidin-1-yl)(2-((1-(5-fluoropyridin-3-yl)ethyl)amino)thieno[3,2-d]pyrimidin-4-yl)methanone (19 mg, 0.05 mmol) using chemistry similar to that described in Example Z611 using phenyl isocyanate (commercially obtained from Sigma-Aldrich, St. Louis, Mo.) in place of tert-butyl isocyanate (18 mg, 73% yield). $^1$H NMR (400 MHz, DMSO-$d_6$ at 80° C.) δ 1.57 (3H, d, J=7.2 Hz), 3.98 (1H, dd, J=10.8, 5.2 Hz), 4.40 (1H, t, J=10.4 Hz), 4.50 (1H, m), 4.52 (1H, m), 4.97 (1H, m), 5.29 (1H, quintet, J=7.2 Hz), 6.75 (1H, m), 6.98 (1H, tt, J=7.6, 1.2 Hz), 7.18 (1H, d, J=5.6 Hz), 7.21-7.25 (2H, m), 7.40 (1H, m), 7.42 (1H, m), 7.61 (1H, d, J=8.0 Hz), 7.72 (1H, dt, J=10.0, 2.0 Hz), 8.25 (1H, d, J=5.6 Hz), 8.37 (1H, m), 8.55 (1H, m) ppm. MS m/z=492.2 [M+H$^+$].

Example Z635. (S)—N-(1-(2-((1-(5-Fluoropyridin-3-yl)ethyl)amino)thieno[3,2-d]pyrimidine-4-carbonyl)azetidin-3-yl)-3-methoxybenzamide

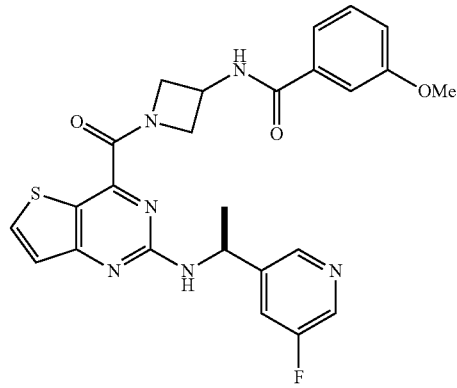

Synthesis of (S)—N-(1-(2-((1-(5-fluoropyridin-3-yl)ethyl)amino)thieno[3,2-d]pyrimidine-4-carbonyl)azetidin-3-yl)-3-methoxybenzamide (Z635): The title compound (Z635) was prepared as an off-white solid from (S)-(3-aminoazetidin-1-yl)(2-((1-(5-fluoropyridin-3-yl)ethyl)amino)thieno[3,2-d]pyrimidin-4-yl)methanone (19 mg, 0.05 mmol) using chemistry similar to that described in Example Z603 using 3-methoxybenzyl chloride (commercially obtained from Oakwood Products, Estill, S.C.) in place of 1-methylcyclopropanecarbonyl chloride (25 mg, 99% yield). $^1$H NMR (400 MHz, DMSO-$d_6$ at 80° C.) δ 1.55 (3H, d, J=7.2 Hz), 3.82 (3H, s), 4.16 (1H, dd, J=11.2, 5.6 Hz), 4.43 (1H, t, J=9.6 Hz), 4.63 (1H, m), 4.79 (1H, m), 5.02 (1H, m), 5.28 (1H, quintet, J=7.2 Hz), 7.10 (1H, m), 7.18 (1H, d, J=5.6 Hz), 7.38 (1H, t, J=8.0 Hz), 7.44-7.48 (2H, m), 7.61 (1H, d, J=8.0 Hz), 7.70 (1H, m), 8.24 (1H, d, J=5.6 Hz), 8.35 (1H, dd, J=9.6, 2.8 Hz), 8.53 (1H, m), 8.83 (1H, m) ppm. MS m/z=507.2 [M+H$^+$].

Example Z636. (S)-1-Cyano-N-(1-(2-((1-(5-fluoropyridin-3-yl)ethyl)amino)thieno[3,2-d]pyrimidine-4-carbonyl)azetidin-3-yl)cyclopropane-1-carboxamide

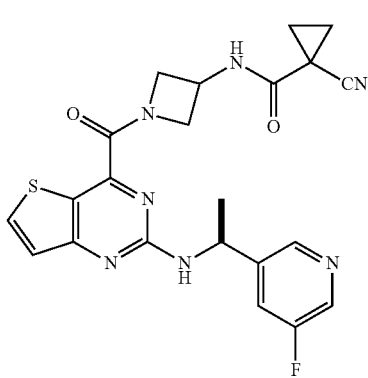

Synthesis of (S)-1-cyano-N-(1-(2-((1-(5-fluoropyridin-3-yl)ethyl)amino)thieno[3,2-d]pyrimidine-4-carbonyl)azetidin-3-yl)cyclopropane-1-carboxamide (Z636): The title compound (Z636) was prepared as an off-white solid from (S)-(3-aminoazetidin-1-yl)(2-((1-(5-fluoropyridin-3-yl)ethyl)amino)thieno[3,2-d]pyrimidin-4-yl)methanone (19 mg, 0.05 mmol) using chemistry similar to that described in Example Z604 using 1-cyanocyclopropanecarboxylic acid (commercially obtained from Ark Pharm, Arlington Heights, Ill.) in place of bicyclo[1.1.1]pentane-2-carboxylic acid (21 mg, 90% yield). $^1$H NMR (400 MHz, DMSO-d$_6$ at 80° C.) δ 1.56-1.58 (7H, m), 4.12 (1H, dd, J=11.2, 5.6 Hz), 4.34 (1H, t, J=9.4 Hz), 4.53 (1H, m), 4.64 (1H, m), 4.92 (1H, m), 5.28 (1H, m), 7.18 (1H, d, J=5.6 Hz), 7.61 (1H, d, J=8.0 Hz), 7.71 (1H, m), 8.25 (1H, d, J=5.6 Hz), 8.38 (1H, d, J=2.8 Hz), 8.53 (1H, d, J=8.0 Hz), 8.61 (1H, m) ppm. MS m/z=466.1 [M+H$^+$].

Example Z637. (S)—N-(1-(2-((1-(5-Fluoropyridin-3-yl)ethyl)amino)thieno[3,2-d]pyrimidine-4-carbonyl)azetidin-3-yl)bicyclo[2.2.2]octane-1-carboxamide

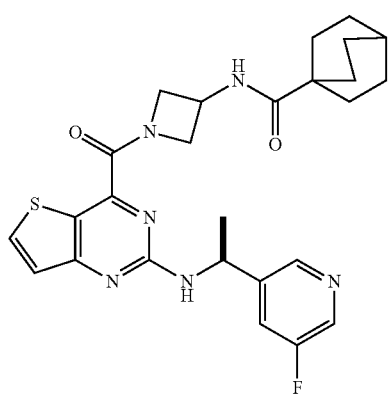

(Z637)

Synthesis of (S)—N-(1-(2-((1-(5-fluoropyridin-3-yl)ethyl)amino)thieno[3,2-d]pyrimidine-4-carbonyl)azetidin-3-yl)bicyclo[2.2.2]octane-1-carboxamide (Z637): The title compound (Z637) was prepared as an off-white solid from (S)-(3-aminoazetidin-1-yl)(2-((1-(5-fluoropyridin-3-yl)ethyl)amino)thieno[3,2-d]pyrimidin-4-yl)methanone (19 mg, 0.05 mmol) using chemistry similar to that described in Example Z604 using bicyclo[2.2.2]octane-4-carboxylic acid (commercially obtained from PharmaBlock, Nanjing, China) in place of bicyclo[1.1.1]pentane-2-carboxylic acid (21 mg, 83% yield). $^1$H NMR (400 MHz, DMSO-d$_6$ at 80° C.) δ 1.52-1.60 (10H, m), 1.63-1.69 (6H, m), 4.01 (1H, m), 4.31 (1H, m), 4.43 (1H, m), 4.55 (1H, m), 4.91 (1H, m), 5.27 (1H, quintet, J=6.8 Hz), 7.18 (1H, d, J=5.6 Hz), 7.61 (1H, d, J=8.0 Hz), 7.67-7.77 (2H, m), 8.24 (1H, d, J=5.6 Hz), 8.37 (1H, m), 8.53 (1H, d, J=8.0 Hz) ppm. MS m/z=509.1 [M+H$^+$].

Example Z638. (S)—N-(1-(2-((1-(5-Fluoropyridin-3-yl)ethyl)amino)thieno[3,2-d]pyrimidine-4-carbonyl)azetidin-3-yl)-3,3-dimethylcyclobutane-1-carboxamide

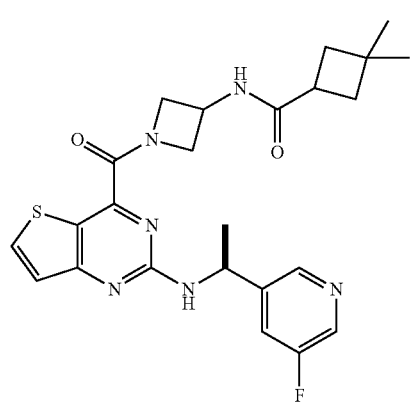

(Z638)

Synthesis of (S)—N-(1-(2-((1-(5-fluoropyridin-3-yl)ethyl)amino)thieno[3,2-d]pyrimidine-4-carbonyl)azetidin-3-yl)-3,3-dimethylcyclobutane-1-carboxamide (Z638): The title compound (Z638) was prepared as an off-white solid from (S)-(3-aminoazetidin-1-yl)(2-((1-(5-fluoropyridin-3-yl)ethyl)amino)thieno[3,2-d]pyrimidin-4-yl)methanone (19 mg, 0.05 mmol) using chemistry similar to that described in Example Z604 using 3,3-dimethylcyclobutanecarboxylic acid (commercially obtained from Ark Pharm, Arlington Heights, Ill.) in place of bicyclo[1.1.1]pentane-2-carboxylic acid (22 mg, 91% yield). $^1$H NMR (400 MHz, DMSO-d$_6$ at 80° C.) δ 1.05 (3H, s), 1.15 (3H, s), 1.56 (3H, d, J=7.2 Hz), 1.82-1.87 (2H, m), 1.93-1.98 (2H, m), 2.92 (1H, m), 3.96 (1H, m), 4.34 (1H, t, J=10.4 Hz), 4.43 (1H, m), 4.52 (1H, m), 4.91 (1H, m), 5.22 (1H, quintet, J=7.2 Hz), 7.17 (1H, d, J=5.6 Hz), 7.60 (1H, d, J=8.0 Hz), 7.70 (1H, m), 8.10 (1H, m), 8.23 (1H, d, J=5.6 Hz), 8.37 (1H, m), 8.52 (1H, m) ppm. MS m/z=483.2 [M+H$^+$].

Example Z639. Trans-N-(1-(2-(((S)-1-(5-fluoropyridin-3-yl)ethyl)amino)thieno[3,2-d]pyrimidine-4-carbonyl)azetidin-3-yl)-4-methylcyclohexane-1-carboxamide

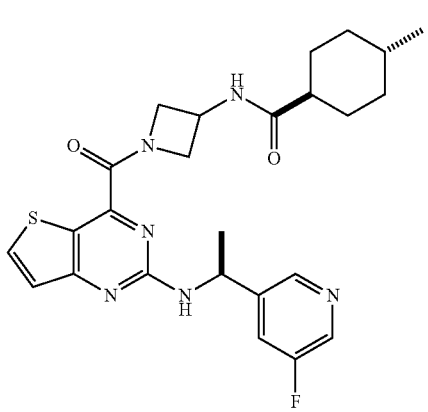

(Z639)

Synthesis of trans-N-(1-(2-(((S)-1-(5-fluoropyridin-3-yl)ethyl)amino)thieno[3,2-d]pyrimidine-4-carbonyl)azetidin-3-yl)-4-methylcyclohexane-1-carboxamide (Z639): The title compound (Z639) was prepared as an off-white solid from (S)-(3-aminoazetidin-1-yl)(2-((1-(5-fluoropyridin-3-yl)ethyl)amino)thieno[3,2-d]pyrimidin-4-yl)methanone (19 mg, 0.05 mmol) using chemistry similar to that described in Example Z604 using trans-4-methylcyclohexane-1-carboxylic acid (commercially obtained from Ark Pharm, Arlington Heights, Ill.) in place of bicyclo[1.1.1]pentane-2-carboxylic acid (23 mg, 93% yield). $^1$H NMR (400 MHz, DMSO-$d_6$ at 80° C.) δ 0.88 (3H, d, J=6.8 Hz), 0.90-0.97 (2H, m), 1.26-1.44 (3H, m), 1.56 (3H, d, J=7.2 Hz), 1.71-1.79 (4H, m), 2.05 (1H, m), 3.96 (1H, m), 4.34 (1H, m), 4.43 (1H, m), 4.53 (1H, m), 4.93 (1H, m), 5.27 (1H, quintet, J=7.2 Hz), 5.40 (1H, m), 7.18 (1H, d, J=5.2 Hz), 7.43 (1H, m), 7.62 (1H, d, J=8.0 Hz), 7.71 (1H, m), 8.15 (1H, m), 8.24 (1H, d, J=5.2 Hz), 8.38 (1H, m), 8.53 (1H, m) ppm. MS m/z=497.1 [M+H$^+$].

Example Z640. (S)-4,4-Difluoro-N-(1-(2-((1-(5-fluoropyridin-3-yl)ethyl)amino)thieno[3,2-d]pyrimidine-4-carbonyl)azetidin-3-yl)cyclohexane-1-carboxamide

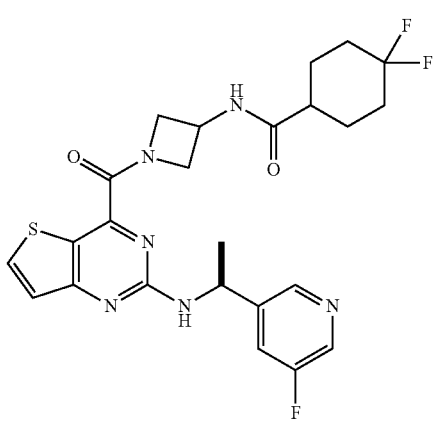

(Z640)

Synthesis of (S)-4,4-difluoro-N-(1-(2-((1-(5-fluoropyridin-3-yl)ethyl)amino)thieno[3,2-d]pyrimidine-4-carbonyl)azetidin-3-yl)cyclohexane-1-carboxamide (Z640): The title compound (Z640) was prepared as a white solid from (S)-(3-aminoazetidin-1-yl)(2-((1-(5-fluoropyridin-3-yl)ethyl)amino)thieno[3,2-d]pyrimidin-4-yl)methanone (19 mg, 0.05 mmol) using chemistry similar to that described in Example Z603 using 4,4-difluorocyclohexanecarbonyl chloride (commercially obtained from Enamine, Monmouth Jct., N.J.) in place of 1-methylcyclopropanecarbonyl chloride (24 mg, 93% yield). $^1$H NMR (400 MHz, DMSO-$d_6$ at 80° C.) δ 1.57 (3H, d, J=6.8 Hz), 1.63-1.80 (3H, m), 1.82-1.91 (3H, m), 2.05-2.12 (2H, m), 2.30 (1H, m), 3.98 (1H, m), 4.36 (1H, t, J=8.0 Hz), 4.43 (1H, m), 4.56 (1H, m), 4.94 (1H, m), 5.27 (1H, quintet, J=6.8 Hz), 7.18 (1H, d, J=5.6 Hz), 7.63 (1H, d, J=8.0 Hz), 7.71 (1H, m), 8.25 (1H, d, J=5.6 Hz), 8.31 (1H, m), 8.38 (1H, m), 8.53 (1H, m) ppm. MS m/z=519.2 [M+H$^+$].

Example Z641. (S)—N-(1-(2-((1-(5-Chloropyridin-3-yl)ethyl)amino)thieno[3,2-d]pyrimidine-4-carbonyl)azetidin-3-yl)-1-methylcyclopropane-1-carboxamide

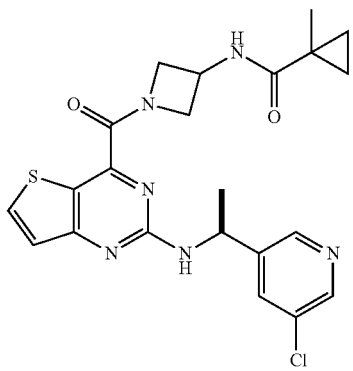

(Z641)

Synthesis of (S)—N-(1-(2-((1-(5-chloropyridin-3-yl)ethyl)amino)thieno[3,2-d]pyrimidine-4-carbonyl)azetidin-3-yl)-1-methylcyclopropane-1-carboxamide (Z641): The title compound (Z641) was prepared as a white solid from (S)-(3-aminoazetidin-1-yl)(2-((1-(5-chloropyridin-3-yl)ethyl)amino)thieno[3,2-d]pyrimidin-4-yl)methanone (19 mg, 0.05 mmol) using chemistry similar to that described in Example Z603 using 1-methylcyclopropanecarbonyl chloride in place of 1-methylcyclopropanecarbonyl chloride (21 mg, 89% yield). $^1$H NMR (400 MHz, DMSO-$d_6$ at 80° C.) δ 0.54-0.55 (2H, m), 1.00-1.02 (2H, m), 1.30 (3H, s), 1.56 (3H, d, J=6.8 Hz), 4.07 (1H, m), 4.33 (1H, m), 4.42 (1H, m), 4.61 (1H, m), 4.91 (1H, m), 5.24 (1H, quintet, J=6.8 Hz), 7.18 (1H, d, J=5.6 Hz), 7.63 (1H, d, J=8.0 Hz), 7.88 (1H, m), 7.93 (1H, m), 8.25 (1H, d, J=5.6 Hz), 8.44 (1H, d, J=2.4 Hz), 8.60 (1H, m) ppm. MS m/z=471.2 [M+H$^+$].

Example Z642. (S)—N-(1-(2-((1-(5-Chloropyridin-3-yl)ethyl)amino)thieno[3,2-d]pyrimidine-4-carbonyl)azetidin-3-yl)pivalamide

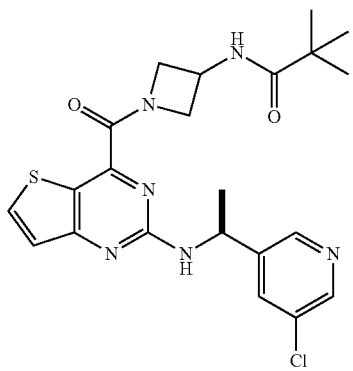

(Z642)

Synthesis of (S)—N-(1-(2-((1-(5-chloropyridin-3-yl)ethyl)amino)thieno[3,2-d]pyrimidine-4-carbonyl)azetidin-3-yl)pivalamide (Z642): The title compound (Z642) was prepared as an off-white solid from (S)-(3-aminoazetidin-1-yl)(2-((1-(5-chloropyridin-3-yl)ethyl)amino)thieno[3,2-d]

pyrimidin-4-yl)methanone (19 mg, 0.05 mmol) using chemistry similar to that described in Example Z603 using pivaloyl chloride in place of 1-methylcyclopropanecarbonyl chloride (21 mg, 89% yield). $^1$H NMR (400 MHz, DMSO-$d_6$ at 80° C.) δ 1.13 (9H, s), 1.55 (3H, d, J=7.2 Hz), 4.03 (1H, m), 4.44 (1H, m), 4.57 (1H, m), 4.92 (1H, m), 5.24 (1H, quintet, J=7.2 Hz), 7.17 (1H, d, J=5.6 Hz), 7.62 (1H, d, J=8.0 Hz), 7.84 (1H, m), 7.92 (1H, m), 8.24 (1H, d, J=5.6 Hz), 8.43 (1H, m), 8.59 (1H, m) ppm. MS m/z=473.1 [M+H$^+$].

Example Z643. (S)—N-(1-(2-((1-(5-Fluoropyridin-3-yl)ethyl)amino)thieno[3,2-d]pyrimidine-4-carbonyl)azetidin-3-yl)-1-(trifluoromethyl)cyclobutane-1-carboxamide

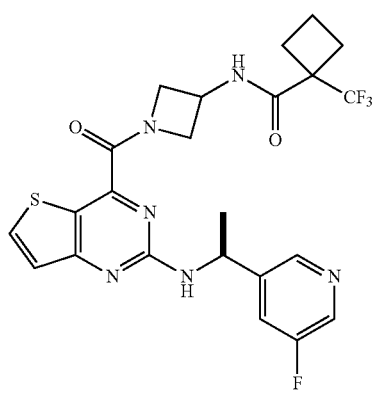

(Z643)

Synthesis of (S)—N-(1-(2-((1-(5-fluoropyridin-3-yl)ethyl)amino)thieno[3,2-d]pyrimidine-4-carbonyl)azetidin-3-yl)-1-(trifluoromethyl)cyclobutane-1-carboxamide (Z643): The title compound (Z643) was prepared as an off-white solid from (S)-(3-aminoazetidin-1-yl)(2-((1-(5-fluoropyridin-3-yl)ethyl)amino)thieno[3,2-d]pyrimidin-4-yl)methanone (37 mg, 0.1 mmol) using chemistry similar to that described in Example Z604 using 1-(trifluoromethyl)cyclobutane-1-carboxylic acid (commercially obtained from Oakwood Products, Estill, S.C.) in place of bicyclo[1.1.1]pentane-2-carboxylic acid (49 mg, 94% yield). $^1$H NMR (400 MHz, DMSO-$d_6$ at 80° C.) δ 1.56 (3H, d, J=6.8 Hz), 1.84-1.95 (2H, m), 2.32-2.41 (2H, m), 2.50-2.60 (2H, m), 4.06 (1H, m), 4.37 (1H, m), 4.50 (1H, m), 4.66 (1H, m), 4.96 (1H, m), 5.26 (1H, quintet, J=6.8 Hz), 5.40 (1H, m), 7.18 (1H, d, J=5.6 Hz), 7.62 (1H, d, J=8.0 Hz), 7.70 (1H, m), 8.24 (1H, d, J=5.6 Hz), 8.36 (1H, dd, J=6.0, 2.4 Hz), 8.48 (1H, d, J=6.8 Hz), 8.52 (1H, m) ppm. MS m/z=523.2 [M+H$^+$].

Example Z644. (S)—N-(1-(2-((1-(5-Chloropyridin-3-yl)ethyl)amino)thieno[3,2-d]pyrimidine-4-carbonyl)azetidin-3-yl)-1-methylcyclobutane-1-carboxamide

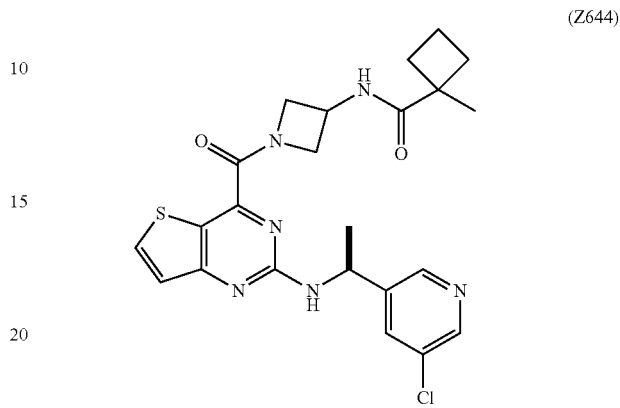

(Z644)

Synthesis of (S)—N-(1-(2-((1-(5-chloropyridin-3-yl)ethyl)amino)thieno[3,2-d]pyrimidine-4-carbonyl)azetidin-3-yl)-1-methylcyclobutane-1-carboxamide (Z644): The title compound (Z644) was prepared as an off-white solid from (S)-(3-aminoazetidin-1-yl)(2-((1-(5-chloropyridin-3-yl)ethyl)amino)thieno[3,2-d]pyrimidin-4-yl)methanone (19 mg, 0.05 mmol) using chemistry similar to that described in Example Z603 using 1-methylcyclobutanecarbonyl chloride in place of 1-methylcyclopropanecarbonyl chloride (20 mg, 91% yield). $^1$H NMR (400 MHz, DMSO-$d_6$ at 80° C.) δ 1.35 (3H, s), 1.55 (3H, d, J=6.8 Hz), 1.67-1.76 (3H, m), 1.88 (1H, m), 2.35-2.39 (2H, m), 4.02 (1H, m), 4.34 (1H, m), 4.46 (1H, m), 4.60 (1H, m), 4.93 (1H, m), 5.24 (1H, quintet, J=6.8 Hz), 7.17 (1H, d, J=5.6 Hz), 7.63 (1H, d, J=8.0 Hz), 7.87-7.93 (2H, m), 8.24 (1H, d, J=5.6 Hz), 8.43 (1H, m), 8.60 (1H, m) ppm. MS m/z=485.1 [M+H$^+$].

Example Z645. (S)—N-(1-(2-((1-(5-Fluoropyridin-3-yl)ethyl)amino)thieno[3,2-d]pyrimidine-4-carbonyl)azetidin-3-yl)-[1,1'-biphenyl]-4-carboxamide

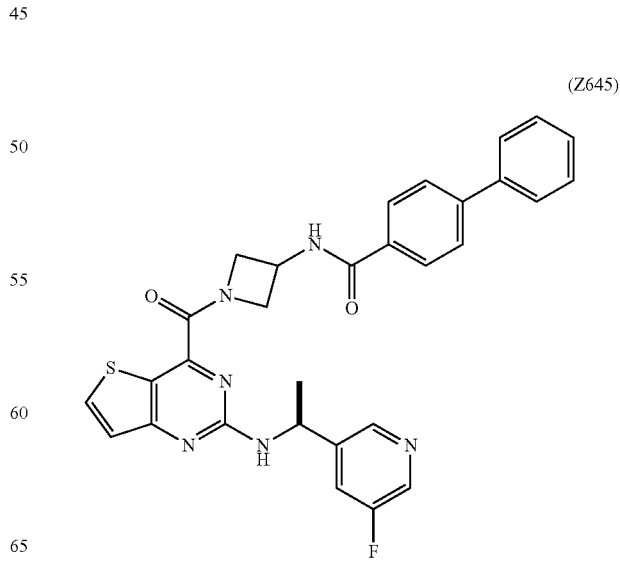

(Z645)

Synthesis of (S)—N-(1-(2-((1-(5-fluoropyridin-3-yl)ethyl)amino)thieno[3,2-d]pyrimidine-4-carbonyl)azetidin-3-yl)-[1,1'-biphenyl]-4-carboxamide (Z645): The title compound (Z645) was prepared as an off-white solid from (S)-(3-aminoazetidin-1-yl)(2-((1-(5-fluoropyridin-3-yl)ethyl)amino)-7-methylthieno[3,2-d]pyrimidin-4-yl)methanone (19 mg, 0.05 mmol) using chemistry similar to that described in Example Z603 using [1,1'-biphenyl]-4-carbonyl chloride (commercially obtained from Sigma-Aldrich, St. Louis, Mo.) in place of 1-methylcyclopropanecarbonyl chloride (27 mg, 98% yield). $^1$H NMR (400 MHz, DMSO-d$_6$ at 80° C.) δ 1.57 (3H, d, J=6.8 Hz), 4.19 (1H, dd, J=11.2, 5.6 Hz), 4.46 (1H, t, J=10.4 Hz), 4.66 (1H, m), 4.84 (1H, m), 5.05 (1H, m), 5.30 (1H, quintet, J=6.8 Hz), 7.19 (1H, d, J=5.6 Hz), 7.41 (1H, m), 7.48-7.52 (2H, m), 7.63 (1H, d, J=8.0 Hz), 7.70-7.74 (3H, m), 7.77-7.79 (2H, m), 7.98-8.01 (2H, m), 8.26 (1H, d, J=5.6 Hz), 8.55 (1H, m), 8.93 (1H, m) ppm. MS m/z=553.3 [M+H$^+$].

Example Z646. (S)—N-(1-(2-((1-(5-Fluoropyridin-3-yl)ethyl)amino)thieno[3,2-d]pyrimidine-4-carbonyl)azetidin-3-yl)-3,5-dimethylbenzamide

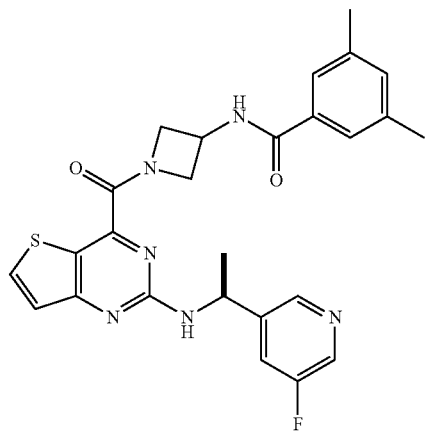

(Z646)

Synthesis of (S)—N-(1-(2-((1-(5-fluoropyridin-3-yl)ethyl)amino)thieno[3,2-d]pyrimidine-4-carbonyl)azetidin-3-yl)-3,5-dimethylbenzamide (646): The title compound (646) was prepared from (S)-(3-aminoazetidin-1-yl)(2-((1-(5-fluoropyridin-3-yl)ethyl)aminothieno[3,2-d]pyrimidin-4-yl)methanone using chemistry similar to that described in Example 490 using 3,5-dimethylbenzoyl chloride (commercially obtained from Oakwood Chemical, Estill, S.C.) in place of pivaloyl chloride (60% yield). $^1$H NMR (400 MHz, DMSO-d$_6$ at 80° C.) δ 1.56 (3H, d, J=7.2 Hz), 2.48 (6H, s), 4.14 (1H, dd, J=10.8, 5.2 Hz), 4.42 (1H, t, J=10.0 Hz), 4.53-4.81 (1H, m), 4.75-4.81 (1H, m), 4.91-5.01 (1H, m), 5.27 (1H, quintet, J=8.0 Hz), 7.17 (2H, d, J=5.6 Hz), 7.49 (2H, d, J=5.2 Hz), 7.61 (1H, d, J=10.0 Hz), 7.71 (1H, d, J=10.0 Hz), 8.24 (1H, d, J=5.6 Hz) 8.35 (1H, dd, J=10.0, 2.4 Hz), 8.53 (1H, s), 8.76 (1H, dd, J=10.0, 7.2 Hz ppm). MS m/z=505.3 [M+H$^+$].

Example Z647. (S)—N-(1-(2-((1-(5-Fluoropyridin-3-yl)ethyl)amino)thieno[3,2-d]pyrimidine-4-carbonyl)azetidin-3-yl)-2,5-dimethylfuran-3-carboxamide

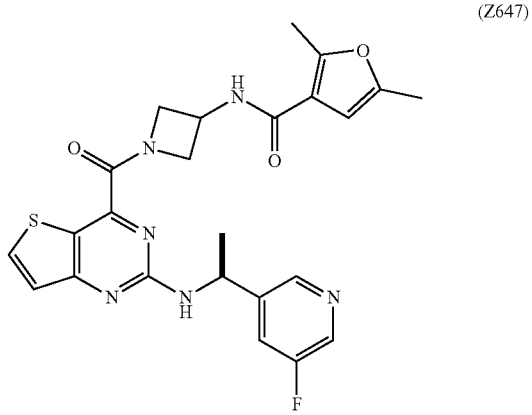

(Z647)

Synthesis of (S)—N-(1-(2-((1-(5-fluoropyridin-3-yl)ethyl)amino)thieno[3,2-d]pyrimidine-4-carbonyl)azetidin-3-yl)-2,5-dimethylfuran-3-carboxamide (647): The title compound (647) was prepared from (S)-(3-aminoazetidin-1-yl)(2-((1-(5-fluoropyridin-3-yl)ethyl)aminothieno[3,2-d]pyrimidin-4-yl)methanone using chemistry similar to that described in Example 490 using 2,5-dimethylfuran-3-carbonyl chloride (commercially obtained from ChemCruz Biotechnologies, Dallas, Tex.) in place of pivaloyl chloride (60% yield). $^1$H NMR (400 MHz, DMSO-d$_6$ at 80° C.) δ 1.56 (3H, d, J=7.2 Hz), 2.23 (6H, s), 4.05-4.12 (1H, m), 4.40 (1H, t, J=10.0 Hz), 4.53-4.68 (1H, m), 4.70-4.78 (1H, m), 4.90-5.08 (1H, m), 5.28 (1H, quintet, J=7.2 Hz), 6.44 (1H, d, J=8.8 Hz), 7.18 (1H, d, J=5.6 Hz), 7.62 (1H, d, J=8.0 Hz), 7.71 (1H, d, J=10.0 Hz), 8.24 (1H, d, J=6.0 Hz), 8.33 (1H, dd, J=6.8, 2.4 Hz), 8.53 (1H, s) ppm. MS m/z=495.2 [M+H$^+$].

Example 648: Compounds (e.g., Adenosine Receptor Modulators) and Activity Assay Results Table 1. Compounds (e.g., Adenosine Receptor modulators) and activity assay results. The legend is as follows: A=<10 nM; B=10-50 nM; C=50-100 nM; D=100-500; and E=>500 nM. The ratio corresponds to the A2A activity to the A2B activity; or A2A/A2B.

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/min/mg/protein) | Hep CLint (mL/min/10$^6$ cells) |
|---|---|---|---|---|---|---|---|---|
| 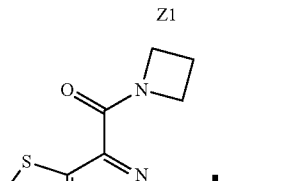 Z1 | D | C | 0.55 | | | | | |
| 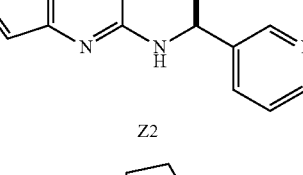 Z2 | A | D | 31.36 | E | E | CYP3A 4:66 CYP2D 6:38 | 27.86 (rat) 23.61 (human) | 37.66 (rat) 9.27 (human) |
| 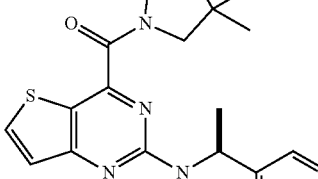 Z3 | D | D | 1.26 | | | | | |
| 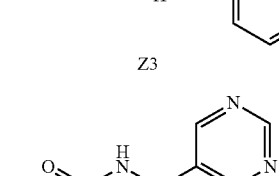 Z4 | E | E | 0.95 | | | | | |
| 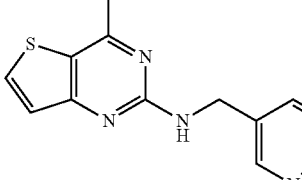 Z5 | D | E | 18.06 | | | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 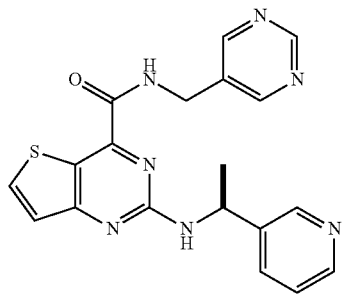 Z6 | E | E | 0.49 | | | | | |
| 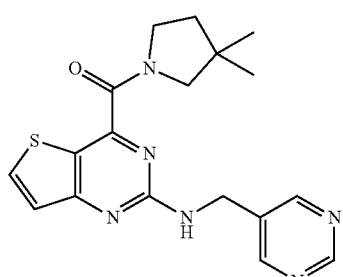 Z7 | E | E | 0.57 | | | | | |
| 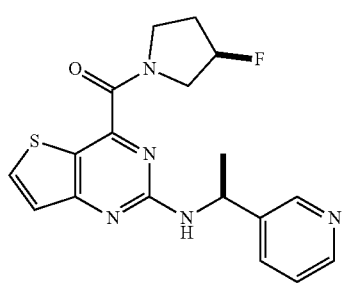 Z8 | B | D | 7.83 | E | E | CYP3A 4:74 CYP2D 6:41 | 20.43 (rat) 17.06 (human) | 47.60 (rat) 7.75 (human) |
| 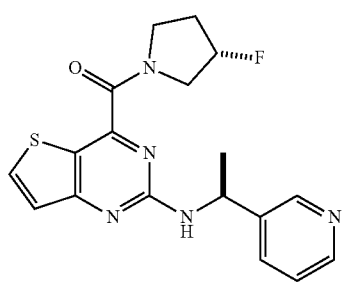 Z9 | B | C | 2.55 | | | CYP3A 4:71 CYP2D 6:20 | 28.41 (rat) 15.83 (human) | 70.12 (rat) 11.36 (human) |

-continued

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/min/mg/protein) | Hep CLint (mL/min/$10^6$ cells) |
|---|---|---|---|---|---|---|---|---|
| Z10 | A | C | 7.99 | E | E | CYP3A 4:0 CYP2D 6:8 | 15.05 (rat) 16.29 (human) | 26.71 (rat) 46.15 (dog) 17.94 (monkey) 6.53 (human) |
| Z11 | E | E | 4.88 | | | | | |
| Z12 | E | C | 0.15 | | | | | |
| Z13 | B | D | 3.93 | E | E | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 µM | LM CLint (µL/ min/mg/ protein) | Hep CLint (mL/ min/ 10$^6$ cells) |
|---|---|---|---|---|---|---|---|---|
| Z14 | D | D | 1.35 | | | | | |
| Z15 | D | E | 9.43 | | | | | |
| Z16 | B | C | 1.67 | E | E | CYP3A 4:46 CYP2D 6:13 | 32.42 (rat) 17.68 (human) | 58.59 (rat) 14.48 (human) |
| Z17 | D | C | 0.19 | | | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z18 | C | C | 0.88 | E | E | CYP3A 4:52 CYP2D 6:44 | 44.15 (rat) 14.28 (human) | 68.42 (rat) 12.30 (human) |
| Z19 | B | B | 1.37 | E | C | CYP3A 4:42 CYP2D 6:51 | 63.06 (rat) 17.60 (human) | 83.36 (rat) 12.91 (human) |
| Z20 | D | D | 0.62 | | | | | |
| Z21 | A | D | 113.57 | E | E | CYP3A 4:45 CYP2D 6:4 CYP3A 4 IC$_{50}$ = 12.4 μM | 89.01 (rat) 43.24 (human) | 71.20 (rat) 23.09 (human) |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z22 | E | E | 7.49 | | | | | |
| Z23 | E | E | 5.63 | | | | | |
| Z24 | D | E | 2.92 | | | | | |
| Z25 | B | D | 8.72 | | | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 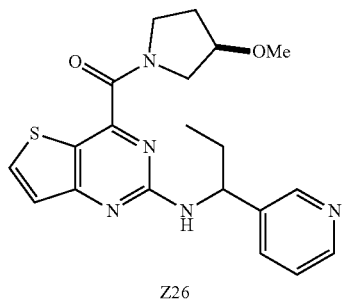 Z26 | B | C | 2.58 | | | | | |
| 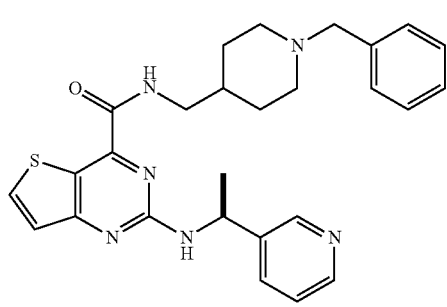 Z27 | C | D | 1.97 | | | | | |
| 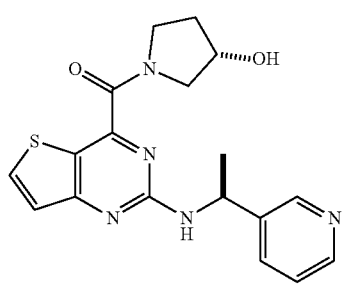 Z28 | C | E | 39.41 | E | E | CYP3A 4:35 CYP2D 6:11 | 9.33 (rat) 4.55 (human) | 34.68 (rat) 2.59 (dog) 0.62 (monkey) 3.48 (human) |
| 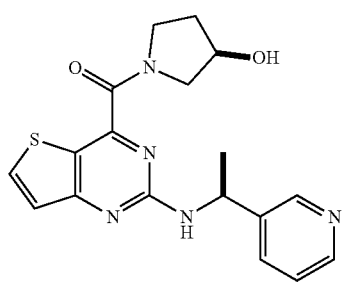 Z29 | C | E | 24.95 | E | E | CYP3A 4:26 CYP2D 6:16 | 9.22 (rat) 4.28 (human) | 44.02 (rat) 4.27 (human) |

-continued

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 µM | LM CLint (µL/ min/mg/ protein) | Hep CLint (mL/ min/ $10^6$ cells) |
|---|---|---|---|---|---|---|---|---|
| Z30 | D | E | 8.34 | | | | | |
| Z31 | D | E | 40.00 | | | | | |
| Z32 | B | D | 6.64 | E | E | CYP3A 4:49 CYP2D 6:7 | 33.25 (rat) 51.28 (human) | 76.25 (rat) 63.21 (human) |
| Z33 | E | E | 4.57 | | | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 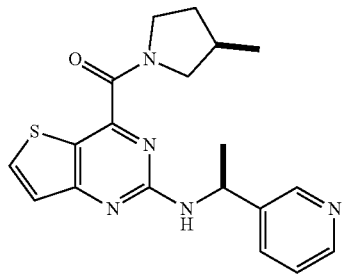 Z34 | B | D | 4.99 | E | E | CYP3A 4:82 CYP2D 6:22 | 81.23 (rat) 53.26 (human) | 130.82 (rat) 23.49 (human) |
| 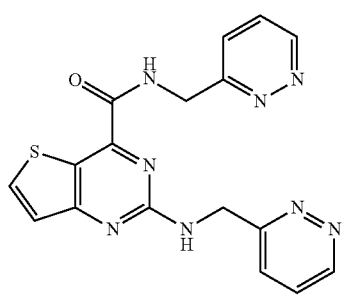 Z35 | E | E | 1.00 | | | | | |
| 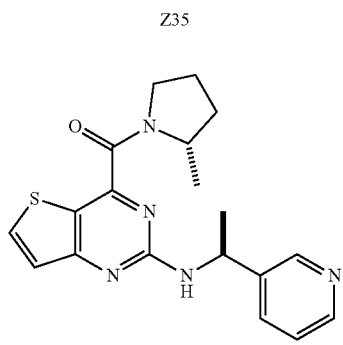 Z36 | D | D | 1.55 | | | | | |
| 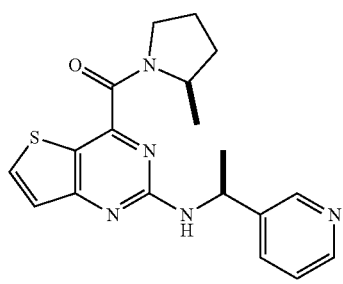 Z37 | D | E | 64.10 | | | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 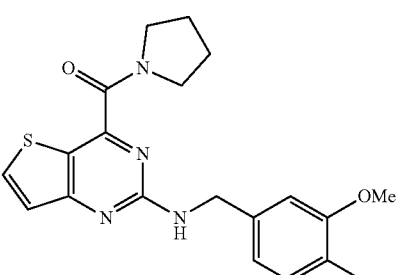 Z38 | E | E | 1.00 | | | | | |
| 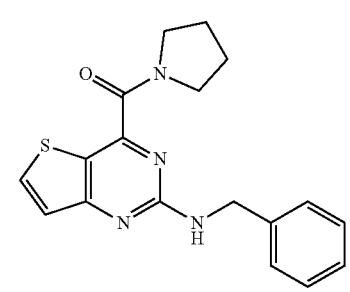 Z39 | D | D | 1.22 | | | | | |
| 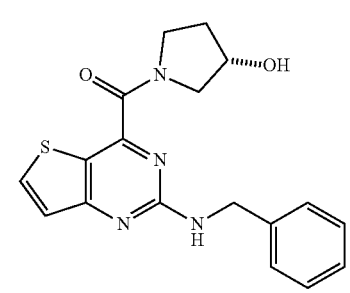 Z40 | D | E | 21.05 | | | | | |
| 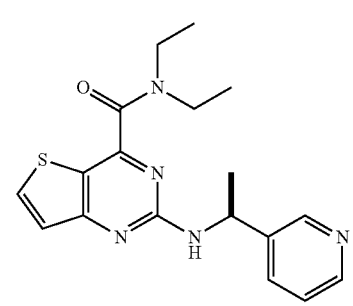 Z41 | E | E | 1.00 | | | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z42 | D | B | 0.20 | D | C | | | |
| Z43 | D | E | 33.44 | | | | | |
| Z44 | D | E | 44.44 | | | | | |
| Z45 | E | E | 1.00 | | | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 µM | LM CLint (µL/ min/mg/ protein) | Hep CLint (mL/ min/ 10$^6$ cells) |
|---|---|---|---|---|---|---|---|---|
| Z46 | D | E | 30.80 | | | | | |
| Z47 | E | E | 1.00 | | | | | |
| Z48 | B | D | 9.26 | | | | | |
| Z49 | D | D | 0.62 | | | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 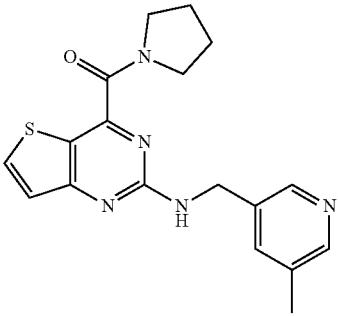 Z50 | B | E | 5.23 | | | CYP3A 4:79 CYP2D 6:32 | 129.90 (rat) 126.01 (human) | 149.26 (rat) 48.96 (human) |
| 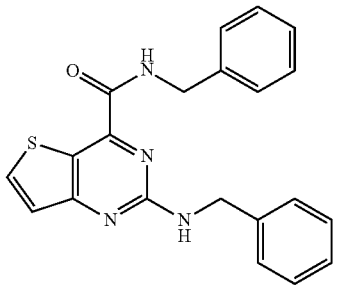 Z51 | D | D | 0.40 | | | | | |
| 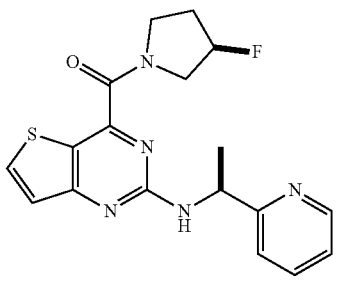 Z52 | A | B | 5.74 | E | E | CYP3A 4:7 CYP2D 6:0 | 11.87 (rat) 11.20 (human) | 45.29 (rat) 41.73 (dog) 18.66 (monkey) 12.68 (human) |
| 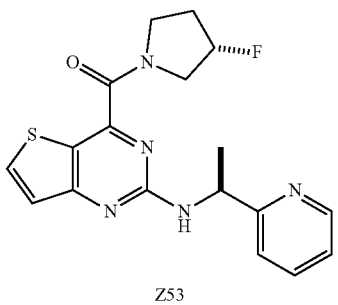 Z53 | A | C | 7.15 | | | CYP3A 4:10 CYP2D 6:0 | 14.92 (rat) 13.51 (human) | 42.72 (rat) 10.91 (human) |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 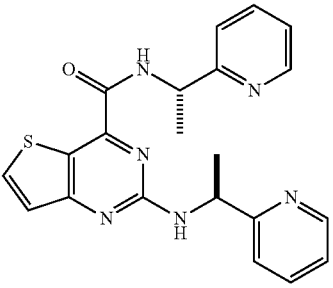 Z54 | B | B | 1.42 | E | C | CYP3A 4:38 CYP2D 6:3 | 39.84 (rat) 14.10 (human) | 125.73 (rat) 24.93 (human) |
| 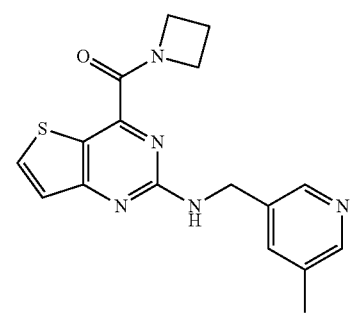 Z55 | B | E | 127.22 | E | E | CYP3A 4:76 CYP2D 6:19 | 94.74 (rat) 63.74 (human) | 64.67 (rat) 25.59 (human) |
| 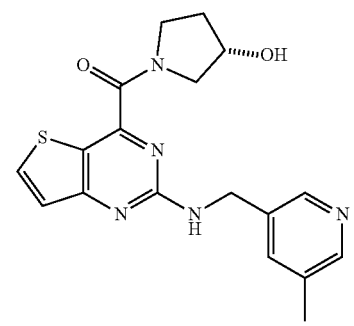 Z56 | D | E | 50.76 | | | | | |
| 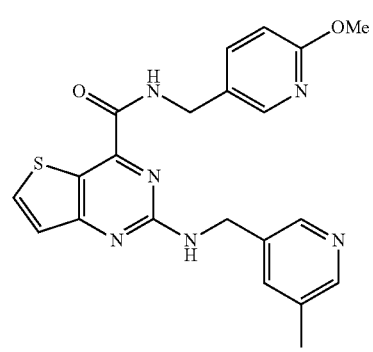 Z57 | D | D | 1.41 | | | | | |

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| Z58 | C | E | 15.14 | E | E | CYP3A 4:0<br>CYP2D 6:10 | 0.0 (rat)<br>5.60 (human) | 4.46 (rat)<br>1.73 (dog)<br>0.19 (monkey)<br>2.21 (human) |
| Z59 | B | D | 12.76 | E | E | CYP3A 4:0<br>CYP2D 6:15 | 4.86 (rat)<br>4.87 (human) | 8.70 (rat)<br>4.19 (dog)<br>0 (monkey)<br>1.50 (human) |
| Z60 | A | D | 66.23 | E | E | CYP3A 4:65<br>CYP2D 6:11 | 46.03 (rat)<br>34.26 (human) | 63.11 (rat)<br>22.84 (human) |
| Z61 | A | D | 84.42 | E | E | CYP3A 4:38<br>CYP2D 6:10 | 44.58 (rat)<br>33.16 (human) | 44.85 (rat)<br>15.45 (human) |

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 µM | LM CLint (µL/ min/mg/ protein) | Hep CLint (mL/ min/ $10^6$ cells) |
|---|---|---|---|---|---|---|---|---|
| Z62 | B | E | 60.76 | E | E | CYP3A 4:34 CYP2D 6:5 | 12.51 (rat) 10.76 (human) | 25.63 (rat) 7.12 (human) |
| Z63 | B | D | 12.78 | E | E | CYP3A 4:83 CYP2D 6:39 | 71.55 (rat) 47.64 (human) | 65.92 (rat) 24.52 (human) |
| Z64 | D | D | 1.94 | | | | | |
| Z65 | C | E | 14.95 | | | | | |

-continued

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 µM | LM CLint (µL/ min/mg/ protein) | Hep CLint (mL/ min/ $10^6$ cells) |
|---|---|---|---|---|---|---|---|---|
| Z66 | B | D | 15.71 | | | CYP3A 4:24 CYP2D 6:4 | 14.07 (rat) 16.45 (human) | 21.17 (rat) 7.10 (human) |
| Z67 | B | D | 5.07 | E | E | | | |
| Z68 | C | C | 0.92 | | | | | |
| Z69 | E | E | 0.92 | | | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z70 | C | E | 10.89 | | | | | |
| Z71 | C | E | 12.97 | | | | | |
| Z72 | E | E | 1.00 | | | | | |
| Z73 | B | C | 3.11 | E | C | | | |

-continued

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| Z74 | D | D | 1.74 | | | | | |
| Z75 | E | E | 1.00 | | | | | |
| Z76 | E | D | 0.22 | | | | | |
| Z77 | D | D | 3.77 | | | | | |

-continued

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| Z78 | C | D | 2.02 | | | | | |
| Z79 | C | D | 1.20 | | | | | |
| Z80 | E | E | 1.00 | | | | | |
| Z81 | C | D | 2.77 | | | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 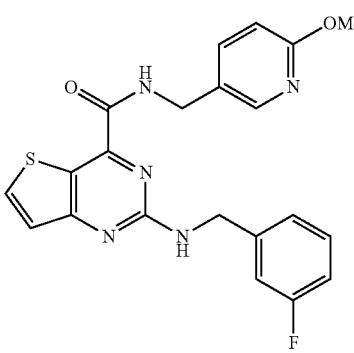 Z82 | C | C | 1.03 | | | | | |
| 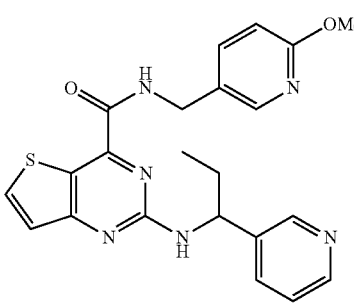 Z83 | E | D | 0.40 | | | | | |
| 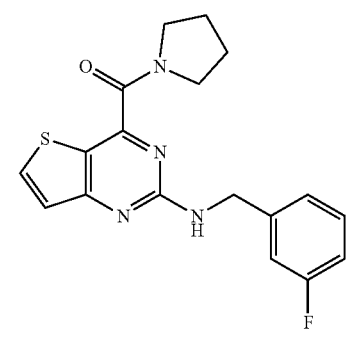 Z84 | B | E | 18.10 | E | E | | | |
| 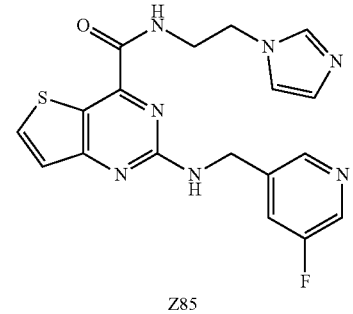 Z85 | E | E | 1.04 | | | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z86 | B | C | 4.25 | E | E | CYP3A4:18.99 | | 55.06 (rat) 11.84 (human) |
| Z87 | B | D | 11.70 | E | E | CYP3A4:19.92 | | 57.62 (rat) 13.33 (human) |
| Z88 | E | E | 1.00 | | | | | |
| Z89 | B | B | 0.89 | E | C | | | |
| Z90 | A | C | 18.88 | E | E | CYP3A4:0 | | 33.32 (rat) 6.32 (human) |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 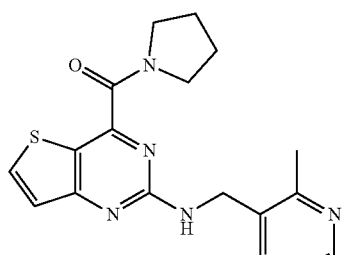 Z91 | B | D | 16.69 | | | CYP3A 4:18.99 | | 47.07 (rat) 7.19 (human) |
| 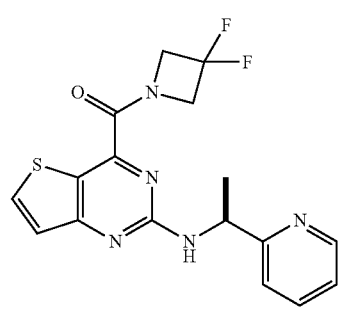 Z92 | B | D | 10.92 | E | E | CYP3A 4:0 | | 46.48 (rat) 45.20 (human) |
| 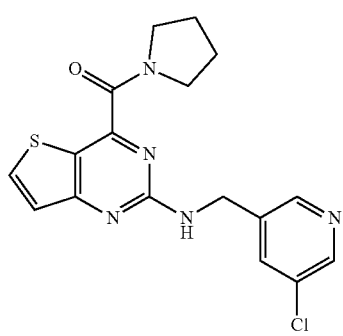 Z93 | B | E | 57.59 | E | E | | | |
| 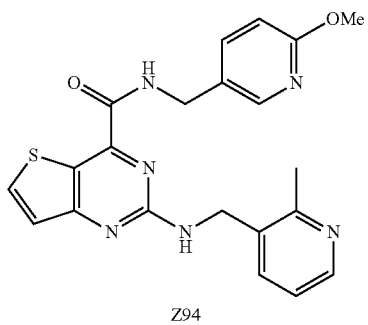 Z94 | D | D | 1.00 | | | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/min/mg/protein) | Hep CLint (mL/min/10$^6$ cells) |
|---|---|---|---|---|---|---|---|---|
| Z95 | B | D | 8.80 | E | E | | | |
| Z96 | B | D | 5.59 | E | E | CYP3A 4:0 | | 40.70 (rat) 16.80 (human) |
| Z97 | B | E | 30.97 | E | E | CYP3A 4:53.77 | | 61.43 (rat) 41.33 (human) |
| Z98 | B | E | 22.37 | | | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 µM | LM CLint (µL/ min/mg/ protein) | Hep CLint (mL/ min/ $10^6$ cells) |
|---|---|---|---|---|---|---|---|---|
| 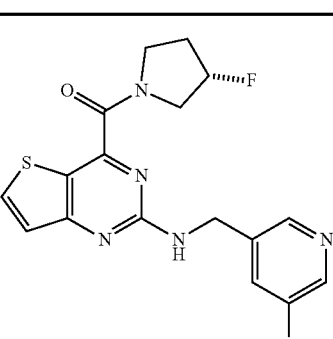 Z99 | B | E | 37.02 | E | E | CYP3A 4:48.87 | | 65.26 (rat) 21.15 (human) |
| 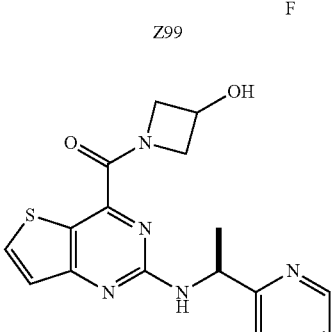 Z100 | B | D | 11.09 | E | E | CYP3A 4:7.65 | | 22.17 (rat) 1.89 (human) |
| 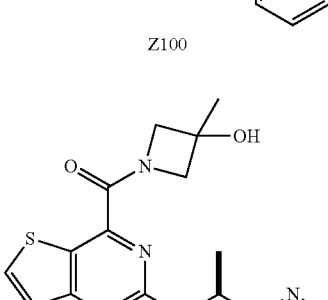 Z101 | B | D | 3.70 | | | | | |
| 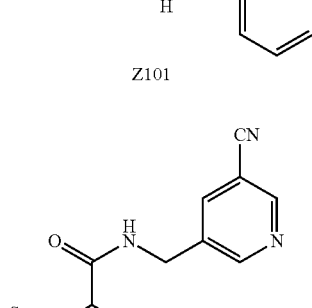 Z102 | D | D | 2.24 | | | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z103 | D | E | 3.68 | | | | | |
| Z104 | E | D | 0.50 | | | | | |
| Z105 | A | D | 19.04 | E | E | CYP3A 4:1.91 | | 27.66 (rat) 58.85 (human) |
| Z106 | B | D | 2.95 | | | | | |

-continued
| Compound | Ave A2B cAMP IC50 | Ave A2A cAMP IC50 | Ratio | A1 cAMP IC50 | A3 cAMP IC50 | CYP 450 % INH @ 10 µM | LM CLint (µL/ min/mg/ protein) | Hep CLint (mL/ min/ 10^6 cells) |
|---|---|---|---|---|---|---|---|---|
| Z107 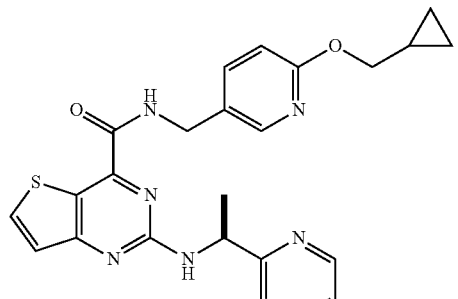 | C | C | 0.84 | D | D | | | |
| Z108 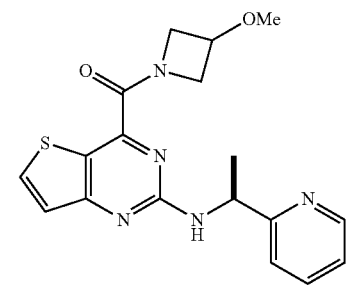 | B | ID | 10.93 | E | E | CYP3A 4:30.97 | | 23.36 (rat) 5.66 (human) |
| Z109 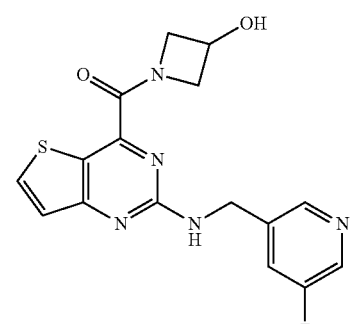 | A | E | 68.08 | E | E | CYP3A 4:28.38 | | 19.89 (rat) 4.11 (human) |
| Z110 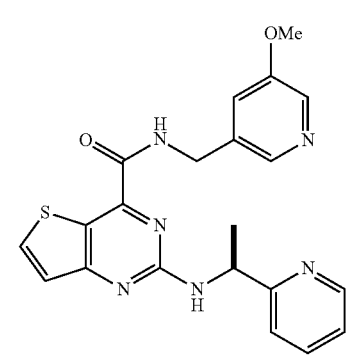 | C | ID | 3.23 | | | | | |

-continued

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| Z111 | A | C | 15.70 | E | E | CYP3A 4:19.88 | | 45.35 (rat) 8.64 (human) |
| Z112 | D | E | 7.09 | | | | | |
| Z113 | E | E | 1.00 | | | | | |
| Z114 | D | E | 5.15 | | | | | |

-continued

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| Z115 | A | D | 71.92 | E | E | CYP3A 4:75.00 | | 51.68 (rat) 13.93 (human) |
| Z116 | D | E | 4.17 | | | | | |
| Z117 | C | E | 10.87 | | | | | |
| Z118 | C | E | 13.75 | | | | | |

| Compound | Ave A<sub>2B</sub> cAMP IC$_{50}$ | Ave A<sub>2A</sub> cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 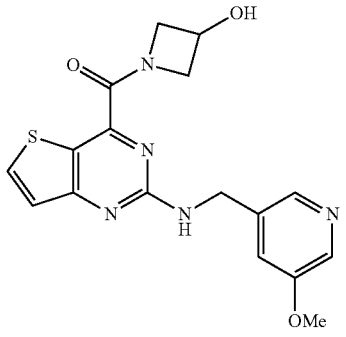 Z119 | D | E | 2.08 | | | | | |
| 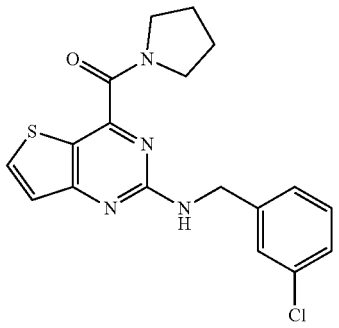 Z120 | B | D | 13.39 | | | | | |
| 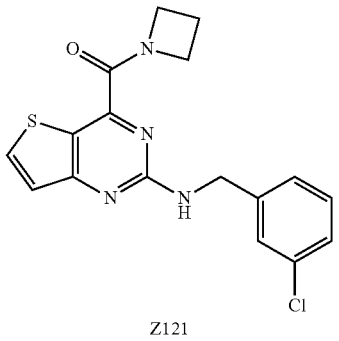 Z121 | B | D | | | | CYP3A 4:48.65 | | 249.09 (rat) 85.11 (human) |
| 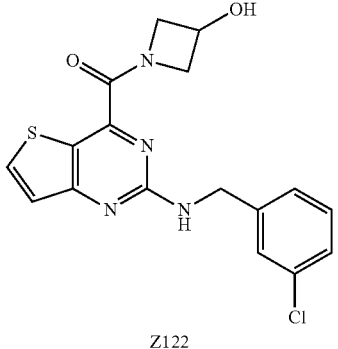 Z122 | B | D | | | | CYP3A 4:22.86 | | 112.00 (rat) 68.38 (human) |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 µM | LM CLint (µL/ min/mg/ protein) | Hep CLint (mL/ min/ 10$^6$ cells) |
|---|---|---|---|---|---|---|---|---|
| 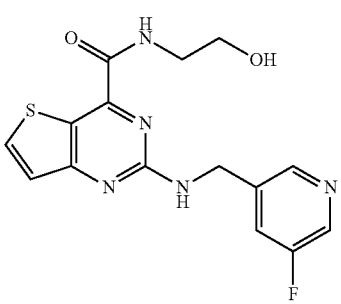<br>Z123 | B | E | 42.97 | E | E | CYP3A 4:76.52 | | 21.96 (rat) 5.54 (human) |
| 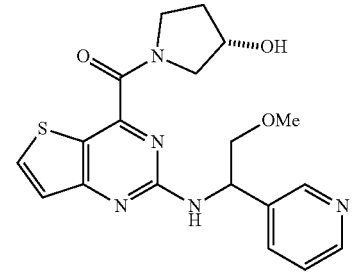<br>Z124 | D | E | 2.13 | | | | | |
| 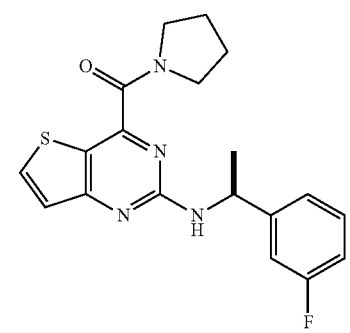<br>Z125 | A | D | 15.42 | E | E | CYP3A 4: −50.90 | | 144.17 (rat) 42.82 (human) |
| 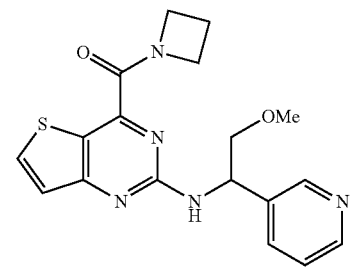<br>Z126 | B | E | 27.98 | | | | | |

-continued

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| Z127 | B | D | 4.85 | | | | | |
| Z128 | A | C | 32.43 | E | E | | | |
| Z129 | B | D | 22.27 | E | C | | | 42.98 (rat) 9.59 (human) |
| Z130 | D | E | 6.11 | | | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z131 | E | E | 6.72 | | | | | |
| Z132 | A | D | 20.13 | E | E | | | |
| Z133 | B | B | 3.85 | | | | | |
| Z134 | A | D | 72.09 | E | E | CYP3A 4:62.74 | | 72.88 (rat) 17.88 (human) |

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 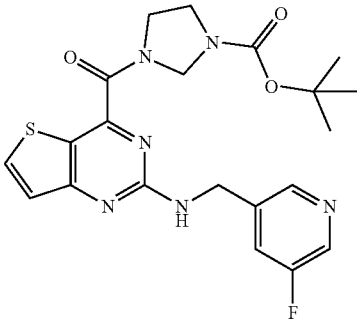 Z135 | D | E | 3.11 | | | | | |
| 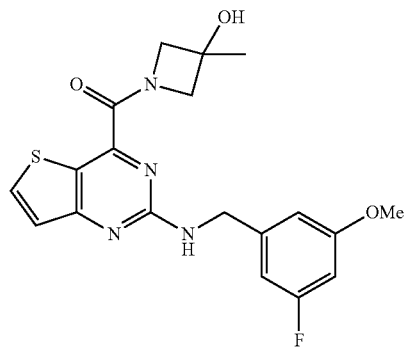 Z136 | C | E | 11.51 | | | | | |
| 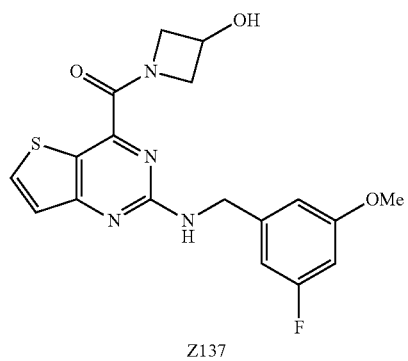 Z137 | B | D | 19.91 | E | B | | | 66.77 (rat) 74.83 (human) |
| 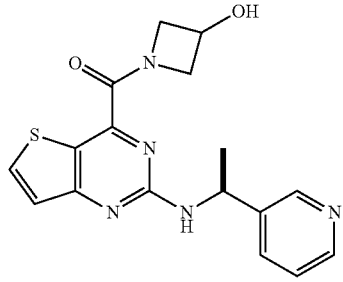 Z138 | B | D | 14.05 | E | E | 26.08 | | 10.29 (rat) 1.14 (human) |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 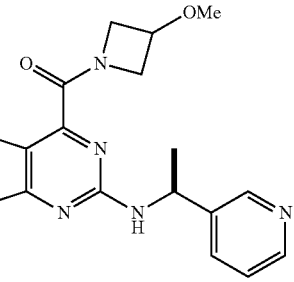 Z139 | A | C | 8.08 | E | E | 90.42 | | 24.18 (rat) 7.67 (human) |
| 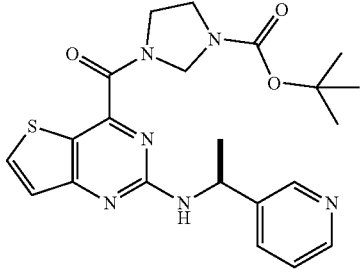 Z140 | E | E | 1.36 | | | | | |
| 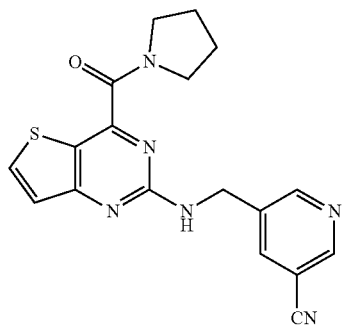 Z141 | B | E | 35.53 | E | E | 75.21 | | 101.57 (rat) 38.69 (human) |
| 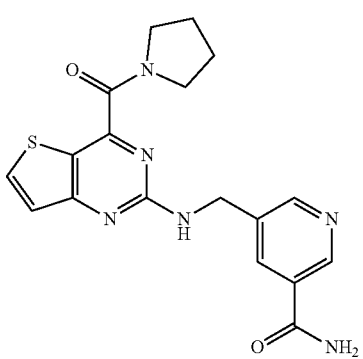 Z142 | E | E | 2.76 | | | | | |

-continued

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| Z143 | C | B | 0.44 | E | B | | | |
| Z144 | B | C | 1.52 | E | C | | | |
| Z145 | B | D | 8.90 | E | E | 26.71 | | 8.46 (rat) 1.92 (human) |
| Z146 | B | D | 7.16 | | | | | |
| Z147 | A | B | 2.82 | E | D | 24.42 | | 68.26 (rat) 43.54 (human) |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z148 | E | E | 4.87 | | | | | |
| Z149 | E | E | 14.43 | | | | | |
| Z150 | E | E | 7.05 | | | | | |
| Z151 | D | D | 0.83 | | | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/min/mg/protein) | Hep CLint (mL/min/10$^6$ cells) |
|---|---|---|---|---|---|---|---|---|
| Z152 | A | D | 53.70 | E | C | 62.36 | | 38.27 (rat) 12.35 (human) |
| Z153 | A | D | 46.65 | E | C | | | |
| Z154 | C | D | 4.52 | | | | | |
| Z155 | C | E | 18.83 | | | | | |
| Z156 | E | E | 14.60 | | | | | |

-continued

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| Z157 | E | E | 3.17 | | | | | |
| Z158 | A | B | 9.39 | D | E | 13.41 | | 22.60 (rat) 20.65 (human) |
| Z159 | B | D | 5.18 | E | E | | | |
| Z160 | B | E | 22.65 | E | C | | | |
| Z161 | A | D | 29.83 | E | C | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 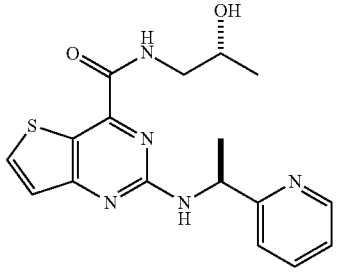 Z162 | B | D | 5.97 | E | E | | | |
| 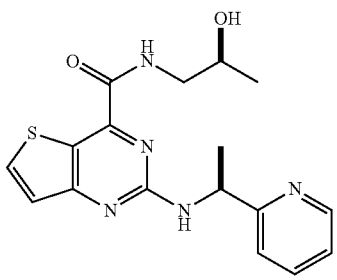 Z163 | C | D | 4.38 | E | E | | | |
| 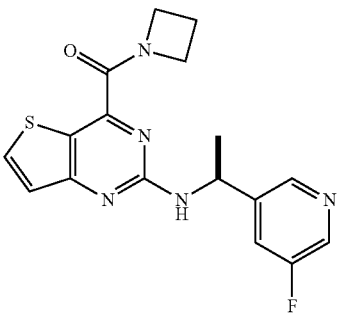 Z164 | A | C | 49.96 | E | E | 77.96 | 34.00 | 34.00 (rat) 13.48 (human) |
| 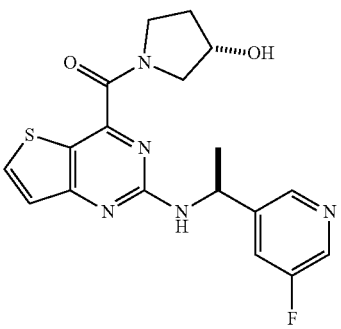 Z165 | A | E | 73.68 | E | E | 26.67 | 14.83 (rat) 5.66 (human) |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z166 | B | E | 62.32 | E | E | 20.66 | | 16.59 (rat) 4.51 (human) |
| Z167 | B | D | 16.55 | E | C | | | |
| Z168 | B | D | 36.14 | | | | | |
| Z169 | A | D | 26.40 | E | E | 0 | | 43.67 (rat) 55.57 (human) |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 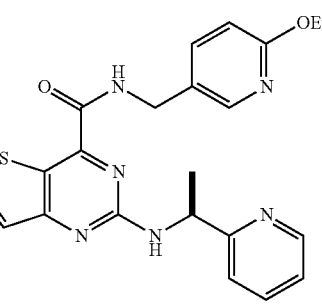 Z170 | C | C | 1.24 | D | D | | | |
| 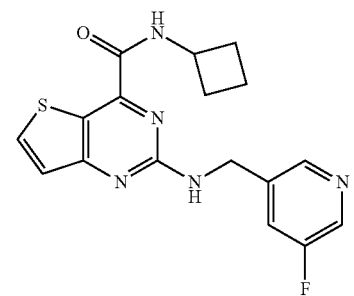 Z171 | A | C | 22.94 | D | E | 73.15 | | 91.38 (rat) 51.44 (human) |
| 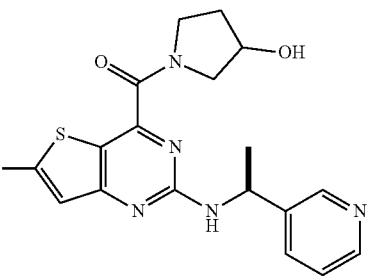 Z172 | C | E | 54.37 | E | E | | | |
| 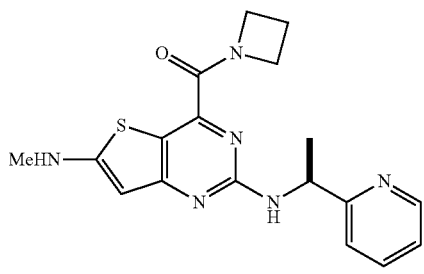 Z173 | A | D | 45.26 | E | C | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z174 | B | D | 15.05 | | | | | |
| Z175 | A | D | 22.59 | E | C | | | |
| Z176 | B | E | 27.44 | E | C | | | |
| Z177 | B | C | 7.01 | C | E | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z178 | D | D | 3.76 | | | | | |
| Z179 | C | C | 1.09 | | | | | |
| Z180 | B | B | 1.80 | D | D | | | |
| Z181 | C | D | 5.43 | | | | | |
| Z182 | C | D | 5.92 | | | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 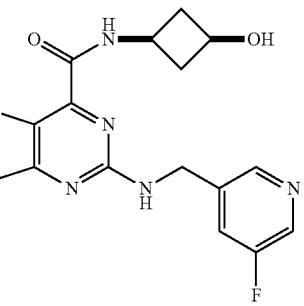<br>Z183 | A | D | 37.09 | E | E | 58.1 | | 23.73 (rat) 24.95 (human) |
| 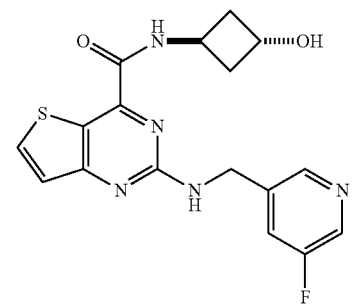<br>Z184 | B | E | 25.53 | E | E | | | |
| 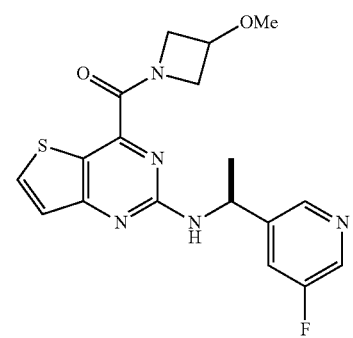<br>Z185 | A | D | 46.14 | E | E | 80.42 | | 37.02 (rat) 12.01 (human) |
| 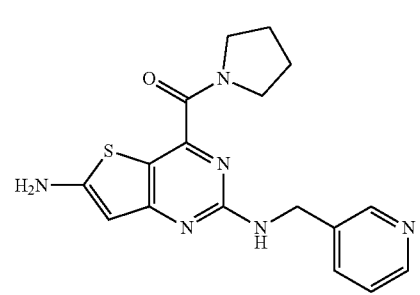<br>Z186 | C | E | 29.35 | | | | | |

-continued

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| Z187 | A | D | 48.67 | E | C | | | |
| Z188 | B | E | 114.79 | E | E | 37.03 | | 10.02 (rat) 2.16 (human) |
| Z189 | A | D | 36.15 | E | C | | | |
| Z190 | A | C | 34.96 | E | E | 39.64 | | 23.70 (rat) 10.09 (human) |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 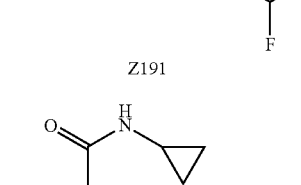  Z191 | A | D | 45.25 | E | E | 40.96 | | 26.67 (rat) 10.57 (human) |
| 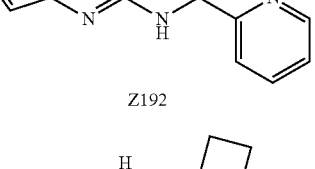  Z192 | A | B | 6.93 | C | E | | | |
| 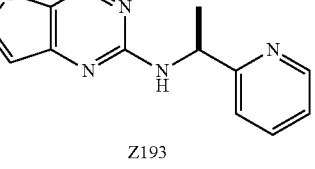  Z193 | B | C | 4.46 | | | | | |
| 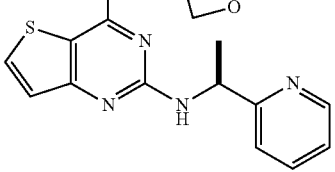  Z194 | B | D | 5.79 | | | | | |
| 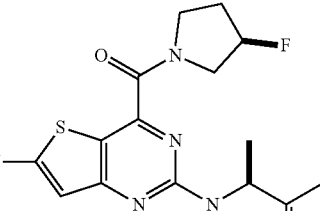  Z195 | B | D | 17.59 | | | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z196 | B | E | 102.27 | | | | | |
| Z197 | A | E | 298.42 | E | E | 25 | | 16.22 (rat) 3.34 (human) |
| Z198 | A | D | 52.81 | E | E | 27 | | 20.61 (rat) 6.78 (human) |
| Z199 | A | B | 3.51 | E | C | | | |

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/min/mg/protein) | Hep CLint (mL/min/$10^6$ cells) |
|---|---|---|---|---|---|---|---|---|
| Z200 | D | D | 1.81 | | | | | |
| Z201 | B | C | 2.22 | C | C | | | |
| Z202 | B | C | 3.91 | | | | | |
| Z203 | B | D | 33.74 | | | | | |
| Z204 | B | D | 13.13 | | | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z205 | B | D | 27.10 | | | | | |
| Z206 | B | D | 8.53 | | | | | |
| Z207 | B | D | 14.35 | | | | | |
| Z208 | C | E | 18.79 | | | | | |
| Z209 | B | E | 30.22 | | | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 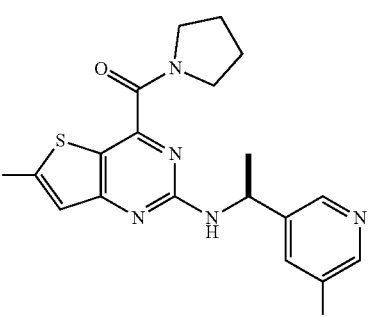 Z210 | A | D | 162.88 | E | C | 46 | | 51.73 (rat) 20.27 (human) |
| 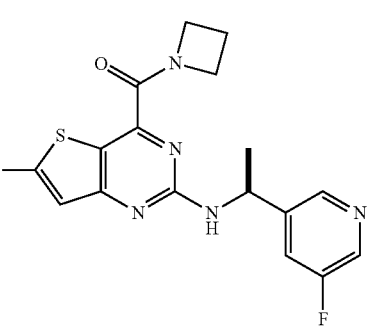 Z211 | A | D | 201.82 | E | C | 67 | | 53.21 (rat) 15.84 (human) |
| 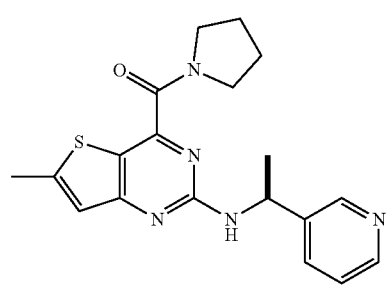 Z212 | A | E | 149.76 | E | E | 19.6 | | 5.95 (rat) 1.64 (human) |
| 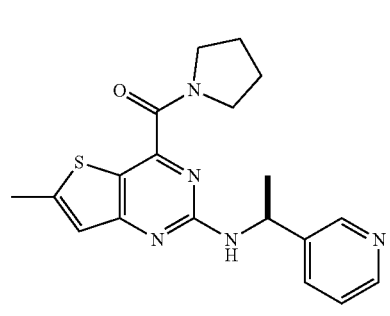 Z213 | A | D | 127.82 | E | E | 90 | | 25.29 (rat) 59.58 (human) |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/min/mg/protein) | Hep CLint (mL/min/10$^6$ cells) |
|---|---|---|---|---|---|---|---|---|
| Z214 | D | E | 6.84 | | | | | |
| Z215 | D | D | 2.95 | | | | | |
| Z216 | B | D | 5.35 | | | | | |
| Z217 | B | C | 5.70 | | | | | |
| Z218 | B | D | 8.99 | | | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 µM | LM CLint (µL/ min/mg/ protein) | Hep CLint (mL/ min/ $10^6$ cells) |
|---|---|---|---|---|---|---|---|---|
| 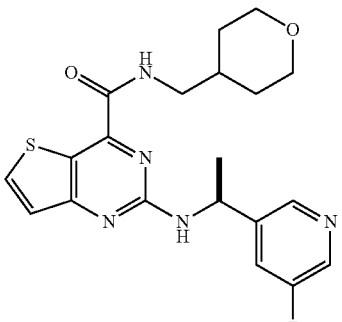 Z219 | B | D | 8.45 | | | | | |
| 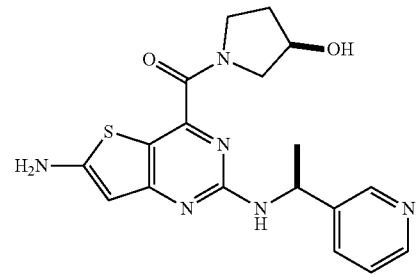 Z220 | D | E | 44.45 | | | | | |
| 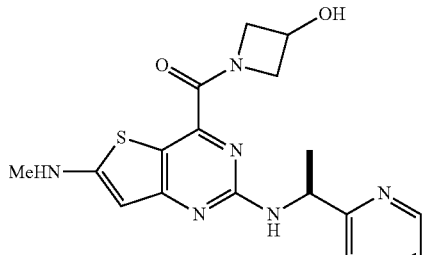 Z221 | B | E | 52.95 | E | C | | | |
| 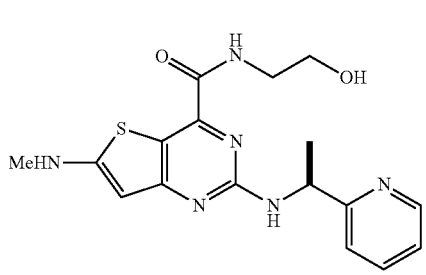 Z222 | B | E | 44.93 | E | E | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 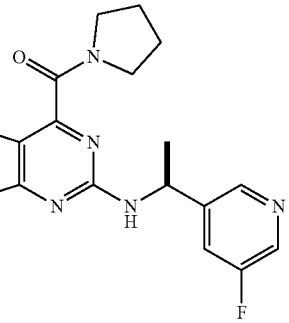 Z223 | A | D | 158.10 | E | E | | | |
| 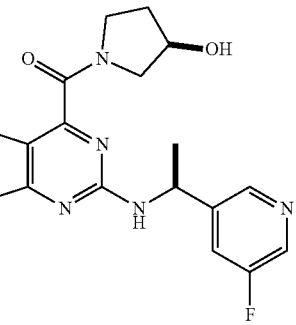 Z224 | A | E | 340.19 | E | C | 52.5 | | 4.61 (rat) 16.13 (human) |
| 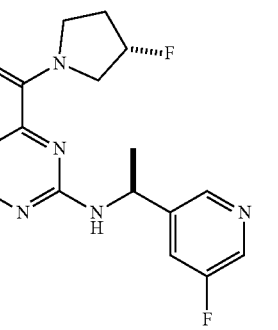 Z225 | A | D | 43.99 | E | E | 57 | | 21.11 (rat) 44.47 (human) |
| 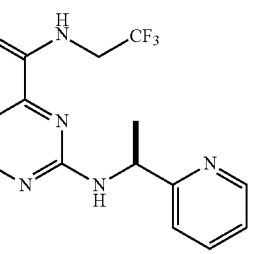 Z226 | A | C | 11.22 | E | E | | | |

-continued

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/min/mg/protein) | Hep CLint (mL/min/$10^6$ cells) |
|---|---|---|---|---|---|---|---|---|
| Z227 | B | D | 4.59 | | | | | |
| Z228 | E | E | 2.80 | | | | | |
| Z229 | E | E | 1.29 | | | | | |
| Z230 | D | E | 7.45 | | | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 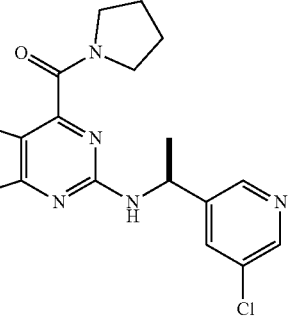 Z231 | A | D | 88.17 | E | E | 75 | | 41.06 (rat) 72.74 (human) |
| 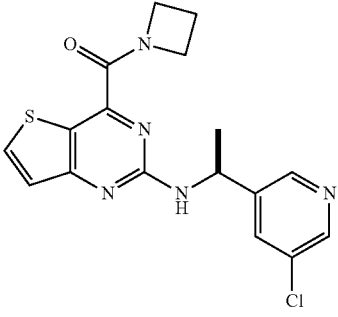 Z232 | A | D | 60.88 | E | E | | | |
| 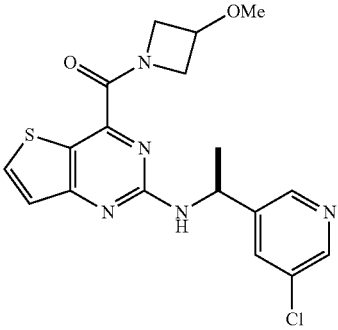 Z233 | A | D | 51.97 | E | E | | | |
| 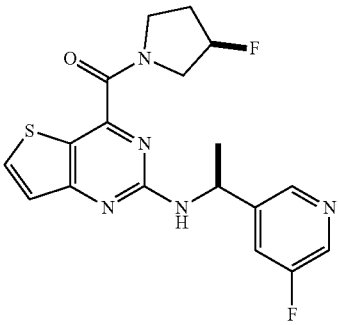 Z234 | A | D | 58.04 | E | E | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z235 | C | D | 2.57 | | | | | |
| Z236 | B | E | 57.61 | E | E | | | |
| Z237 | B | E | 65.87 | E | E | | | |
| Z238 | A | D | 22.98 | E | E | | | |
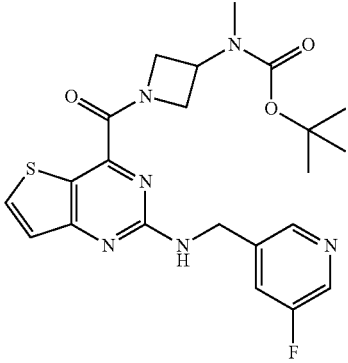
Z235
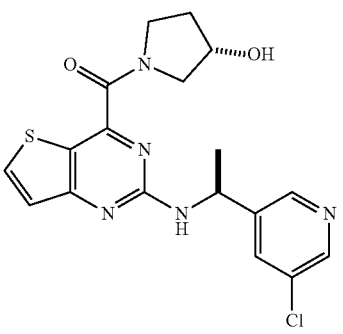
Z236
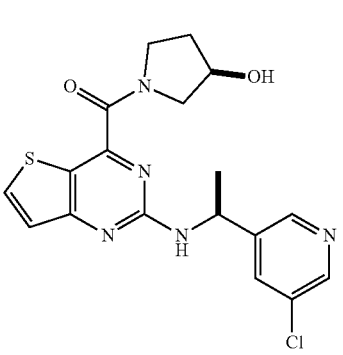
Z237
Z238

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 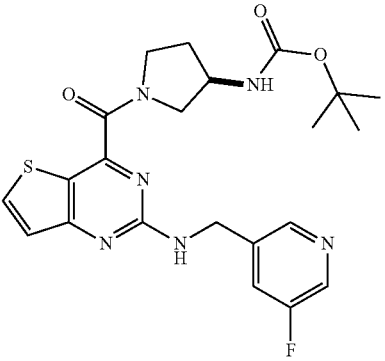 Z239 | A | D | 14.97 | E | B | | | |
| 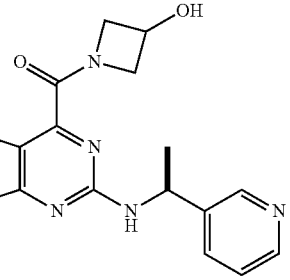 Z240 | B | E | 23.69 | E | E | | | |
| 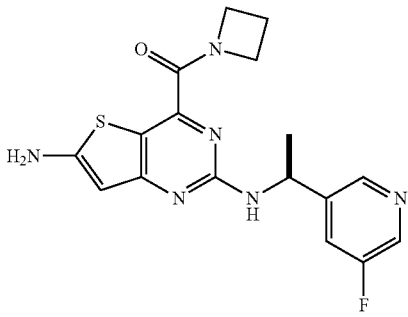 Z241 | A | C | 78.77 | E | E | | | |
| 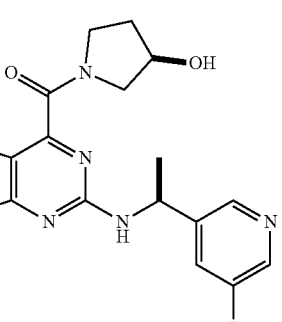 Z242 | A | D | 45.21 | E | E | | | |

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 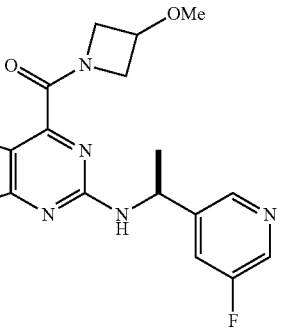 Z243 | A | D | 112.45 | E | C | | | |
| 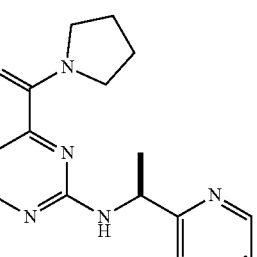 Z244 | A | B | 18.24 | C | C | | | |
| 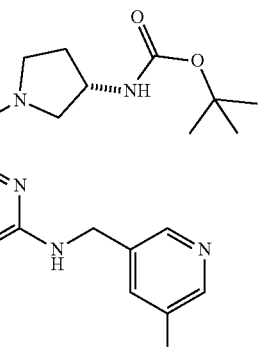 Z245 | C | D | 1.87 | | | | | |
| 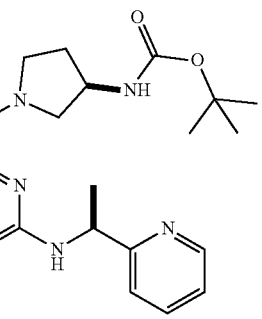 Z246 | B | D | 5.12 | E | E | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z247 | B | C | 2.54 | E | E | | | |
| Z248 | C | E | 15.23 | | | | | |
| Z249 | A | D | 197.12 | E | E | | | 20.85 (rat) 4.53 (human) |
| Z250 | A | D | 179.59 | E | E | | | 23.90 (rat) 11.95 (human) |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 µM | LM CLint (µL/ min/mg/ protein) | Hep CLint (mL/ min/ $10^6$ cells) |
|---|---|---|---|---|---|---|---|---|
| 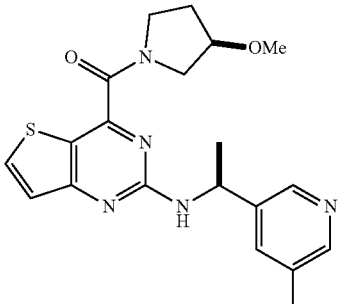 Z251 | A | D | 19.74 | E | E | 49.1 | | |
| 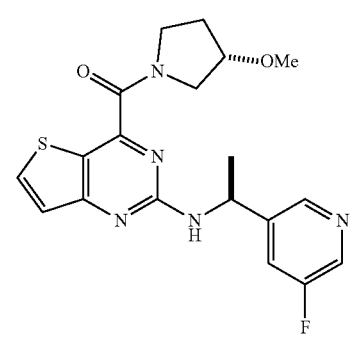 Z252 | B | D | 19.78 | E | E | 55.9 | | |
| 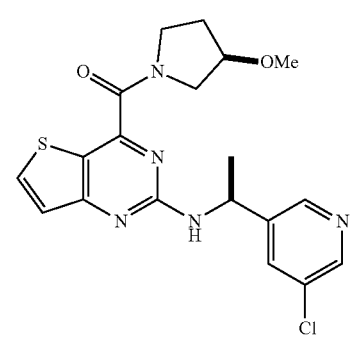 Z253 | B | D | 10.26 | E | E | | | |
| 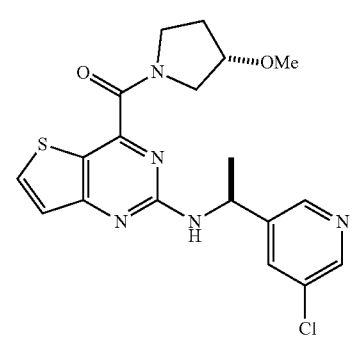 Z254 | B | D | 9.38 | E | E | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z255 | B | B | 1.81 | E | E | | | |
| Z256 | D | E | 5.57 | | | | | |
| Z257 | C | E | 9.16 | | | | | |
| Z258 | D | D | 1.70 | | | | | |
| Z259 | B | D | 31.95 | E | E | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/min/mg/protein) | Hep CLint (mL/min/$10^6$ cells) |
|---|---|---|---|---|---|---|---|---|
| 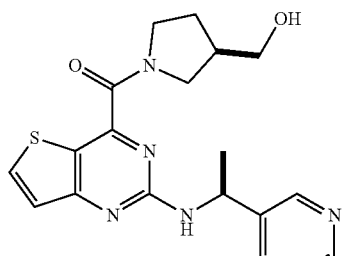 Z260 | B | D | 16.27 | E | E | | | |
| 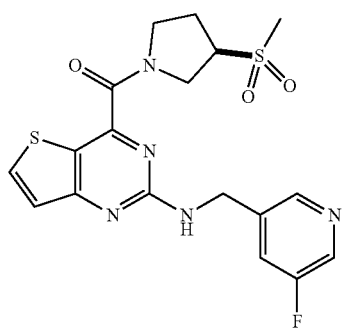 Z261 | D | E | 10.23 | | | | | |
| 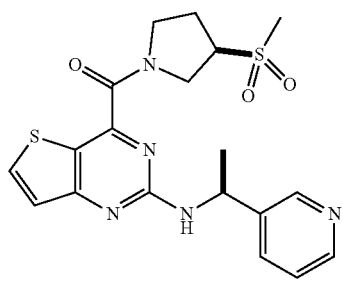 Z262 | E | E | 1.12 | | | | | |
| 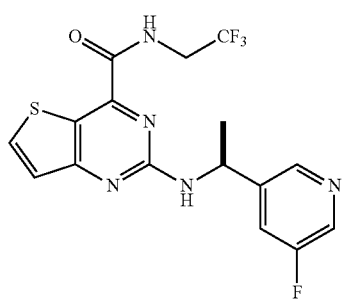 Z263 | B | D | 9.48 | E | E | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z264 | E | E | 13.34 | | | | | |
| Z265 | D | E | 16.94 | | | | | |
| Z266 | D | E | 34.17 | | | | | |
| Z267 | A | C | 105.81 | C | C | | | 45.89 (rat) 9.44 (human) |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 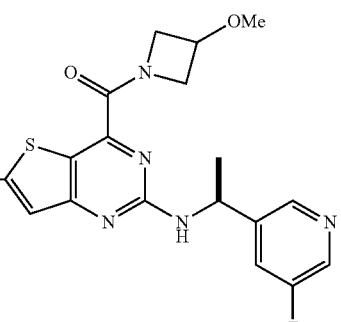 Z268 | A | C | 57.63 | C | C | | | |
| 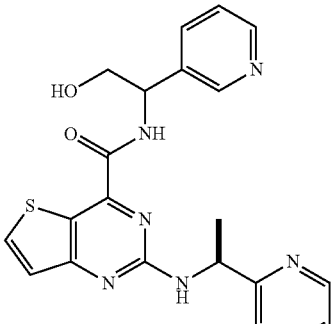 Z269 | E | D | 0.36 | | | | | |
| 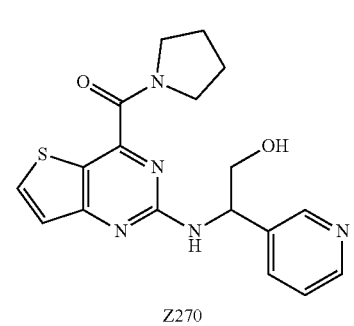 Z270 | B | E | 27.81 | | | | | |
| 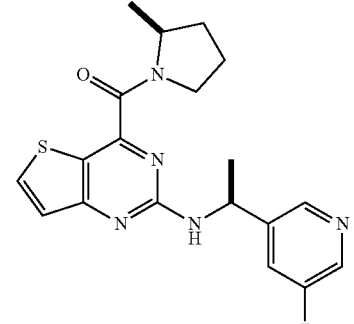 Z271 | B | D | 9.24 | E | E | | | |

-continued

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| Z272 | B | D | 9.34 | E | E | | | |
| Z273 | E | E | 2.15 | | | | | |
| Z274 | D | D | 1.11 | | | | | |
| Z275 | A | D | 24.38 | E | E | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 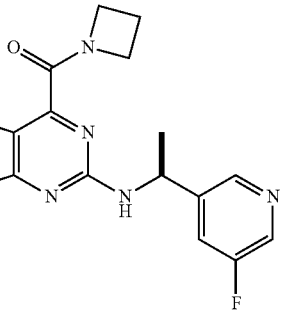 Z276 | A | C | 92.47 | C | C | | | |
| 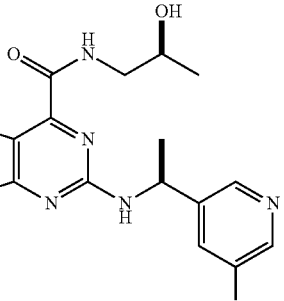 Z277 | A | D | 167.29 | C | C | | | 65.94 (rat) 16.45 (human) |
| 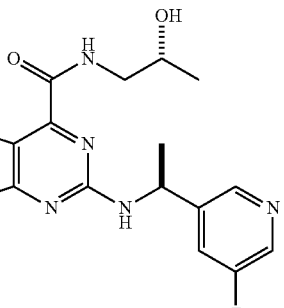 Z278 | A | C | 87.33 | C | C | | | 43.33 (rat) 14.84 (human) |
| 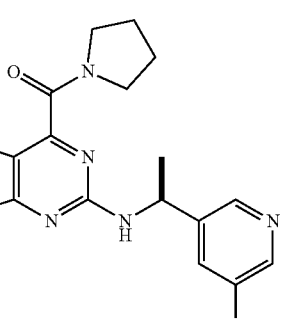 Z279 | A | C | 86.81 | C | C | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z280 | A | B | 24.55 | B | C | | | |
| Z281 | B | E | 88.64 | E | E | | | 18.59 (rat) 5.45 (human) |
| Z282 | B | E | 77.76 | E | E | −18.84 | | 17.17 (rat) 4.11 (human) |
| Z283 | A | D | 54.37 | E | E | 80.45 | | 42.74 (rat) 26.49 (human) |
| Z284 | A | C | 56.67 | C | C | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 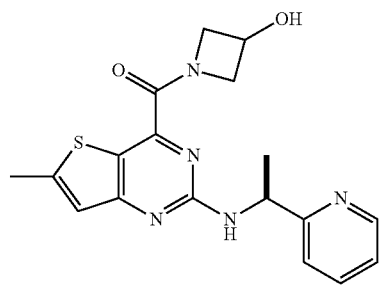 Z285 | A | D | 51.08 | C | C | | | |
| 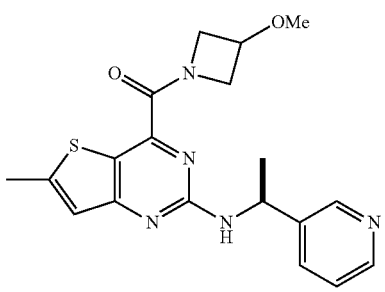 Z286 | A | C | 26.11 | E | E | | | |
| 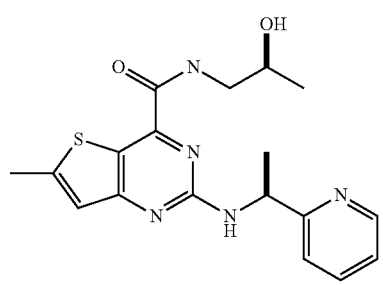 Z287 | B | D | 23.71 | E | C | | | |
| 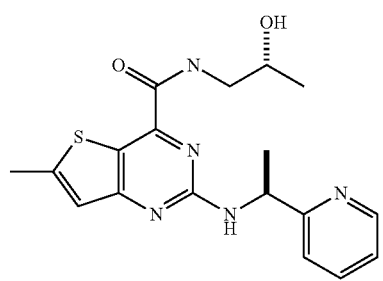 Z288 | A | D | 35.51 | E | C | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z289 | D | E | 14.69 | | | | | |
| Z290 | E | E | 1.63 | | | | | |
| Z291 | B | E | 50.12 | C | E | | | |
| Z292 | B | E | 60.59 | C | C | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 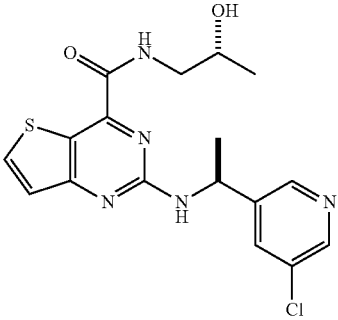 Z293 | A | D | 41.78 | C | C | | | |
| 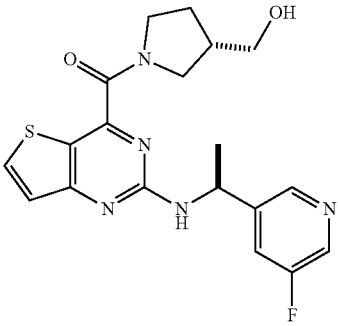 Z294 | A | D | 84.08 | E | E | 37.58 | 17.18 (rat) 15.63 (human) | |
| 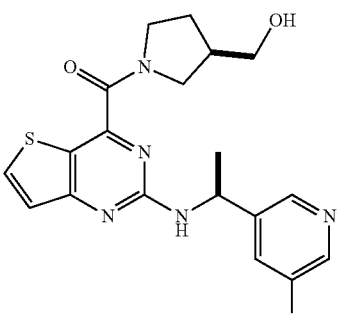 Z295 | A | D | 68.33 | E | E | | | |
| 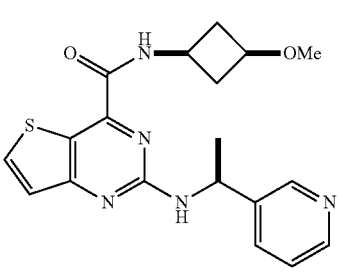 Z296 | D | D | 1.07 | | | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/min/mg/protein) | Hep CLint (mL/min/10$^6$ cells) |
|---|---|---|---|---|---|---|---|---|
| 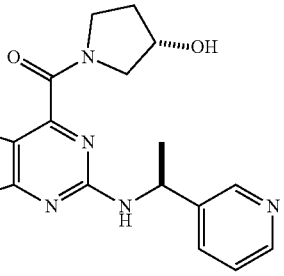 Z297 | A | E | 227.82 | E | E | | | 22.63 (rat) 3.47 (human) |
| 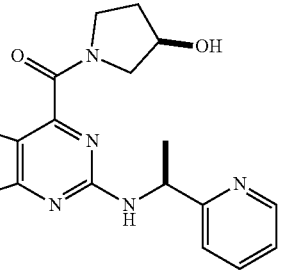 Z298 | A | D | 64.00 | E | E | −13.89 | | 18.84 (rat) 5.35 (human) |
| 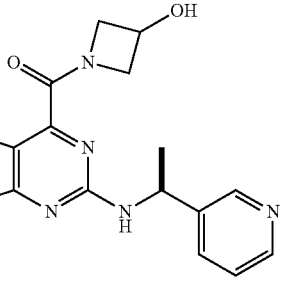 Z299 | A | D | 39.68 | E | E | | | |
| 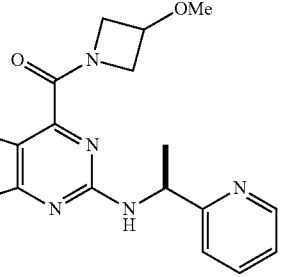 Z300 | A | B | 21.89 | C | C | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/min/mg/protein) | Hep CLint (mL/min/10$^6$ cells) |
|---|---|---|---|---|---|---|---|---|
| Z301 | A | D | 83.47 | E | C | 52.05 | | 51.66 (rat) 23.80 (human) |
| Z302 | A | C | 35.54 | E | C | | | |
| Z303 | C | D | 3.08 | | | | | |
| Z304 | D | D | 2.03 | | | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z305 | A | C | 38.51 | E | E | | | |
| Z306 | B | E | 40.62 | | | | | |
| Z307 | B | D | 5.89 | | | | | |
| Z308 | A | C | 29.96 | C | C | | | |

-continued
| Compound | Ave A2B cAMP IC50 | Ave A2A cAMP IC50 | Ratio | A1 cAMP IC50 | A3 cAMP IC50 | CYP 450 % INH @ 10 μM | LM CLint (μL/ min/mg/ protein) | Hep CLint (mL/ min/ 10^6 cells) |
|---|---|---|---|---|---|---|---|---|
| Z309 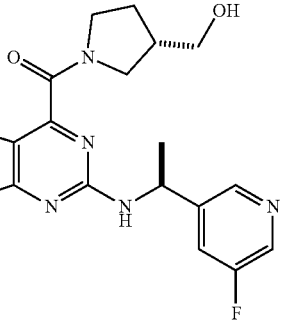 | A | C | 37.14 | E | E | | | |
| Z310 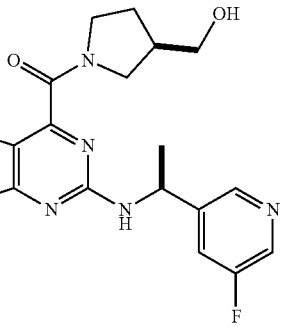 | A | D | 71.73 | E | E | | | |
| Z311 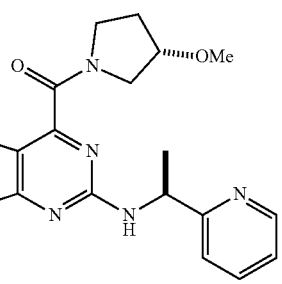 | B | C | 3.82 | E | C | | | |
| Z312 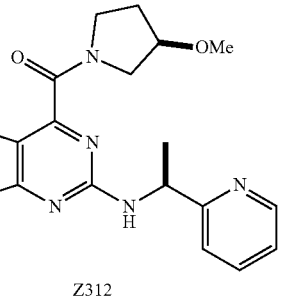 | A | B | 3.05 | E | C | | 57.04 (rat) 10.94 (huma) | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z313 | E | D | 0.29 | | | | | |
| Z314 | D | C | 0.46 | | | | | |
| Z315 | C | C | 0.67 | | | | | |
| Z316 | E | E | 2.06 | | | | | |
| Z317 | E | E | 6.69 | | | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z318 | E | E | 17.41 | | | | | |
| Z319 | C | E | 22.72 | | | | | |
| Z320 | C | D | 3.92 | | | | | |
| Z321 | C | D | 3.66 | | | | | |
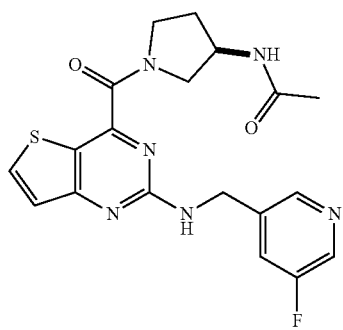
Z318
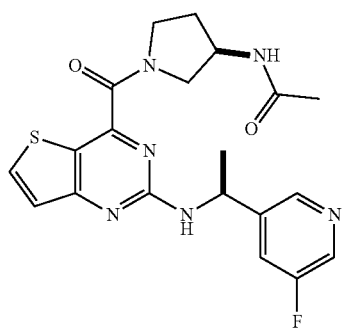
Z319
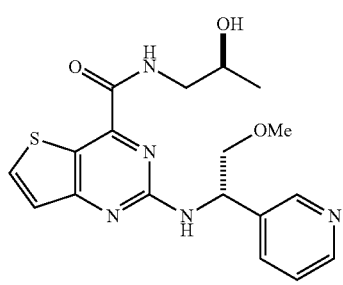
Z320
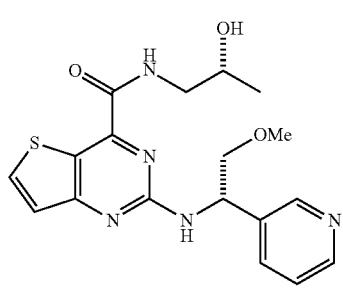
Z321

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z322 | D | E | 6.33 | | | | | |
| Z323 | E | E | 3.30 | | | | | |
| Z324 | B | E | 28.39 | | | | | |
| Z325 | E | E | 1.87 | | | | | |
| Z326 | C | B | 0.54 | E | B | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z327 | A | E | 143.99 | E | E | | | |
| Z328 | A | D | 107.75 | E | C | | | |
| Z329 | A | B | 26.05 | C | C | | | |
| Z330 | A | E | 196.86 | | | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z331 | A | D | 61.94 | E | E | | | |
| Z332 | A | D | 10.21 | E | E | | | |
| Z333 | B | E | 146.28 | E | E | | | 25.74 (rat) 19.53 (human) |
| Z334 | A | D | 171.86 | E | C | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z335 | A | E | 200.00 | E | E | | 33.31 (rat) 10.36 (human) | |
| Z336 | A | E | 136.91 | E | E | | | |
| Z337 | B | E | 120.82 | E | E | | 13.69 (rat) 20.68 (human) | |
| Z338 | D | E | 1.50 | | | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 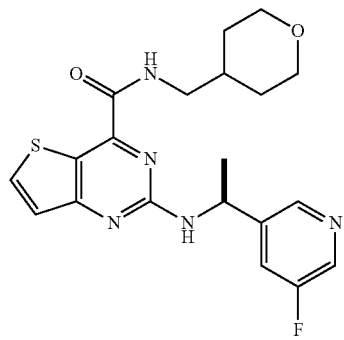 Z339 | A | C | 10.57 | E | E | | | |
| 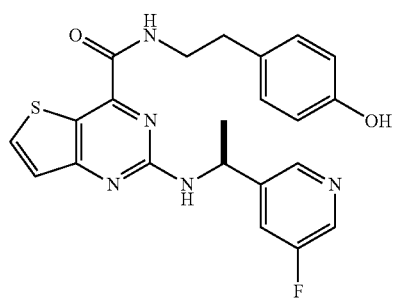 Z340 | A | D | 95.47 | E | E | | 504.21 (rat) 258.52 (human) | |
| 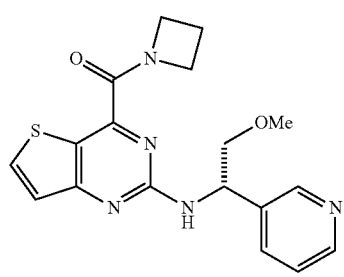 Z341 | A | D | 30.12 | E | E | | | |
| 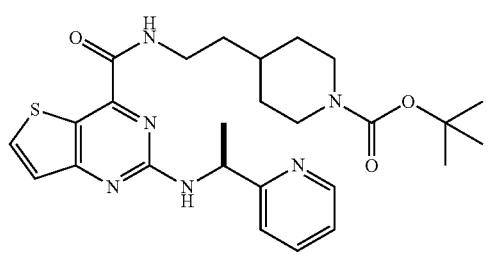 Z342 | D | D | 2.11 | | | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 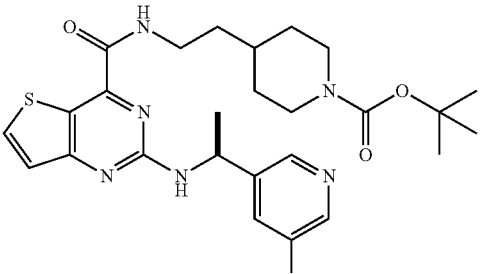 Z343 | C | D | 6.45 | | | | | |
| 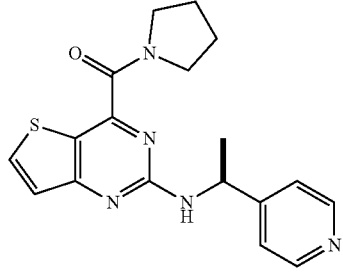 Z344 | B | D | 8.03 | | | | | |
| 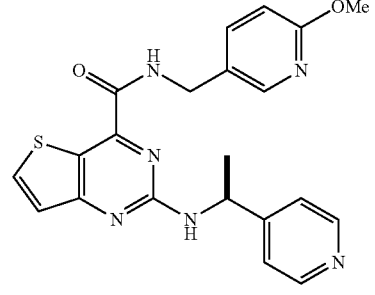 Z345 | C | D | 1.41 | | | | | |
| 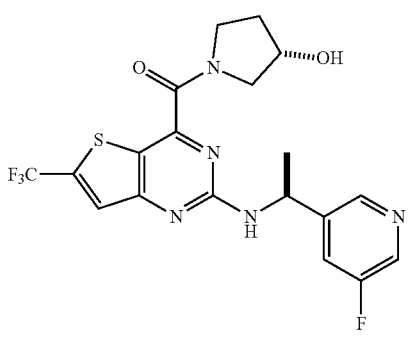 Z346 | A | E | 448.66 | E | E | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z347 | B | E | 98.22 | E | C | | | |
| Z348 | B | E | 92.29 | E | C | | | |
| Z349 | B | E | 46.63 | | | | | |
| Z350 | B | D | 4.80 | | | | | |
| Z351 | A | C | 10.17 | | | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z352 | A | B | 9.52 | C | C | | | |
| Z353 | A | D | 53.12 | C | C | | | |
| Z354 | B | D | 6.35 | | | | | |
| Z355 | D | E | 1.96 | | | | | |
| Z356 | E | E | 3.31 | | | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 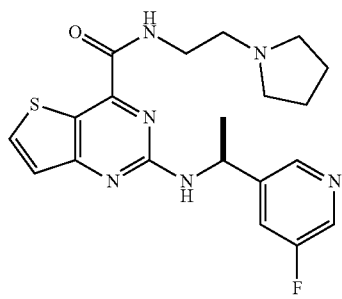 Z357 | E | E | 3.03 | | | | | |
| 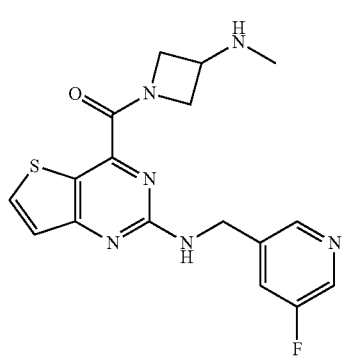 Z358 | D | E | 69.69 | | | | | |
| 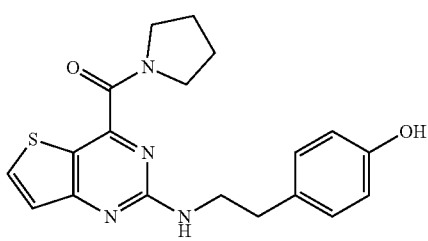 Z359 | D | D | 2.57 | | | | | |
| 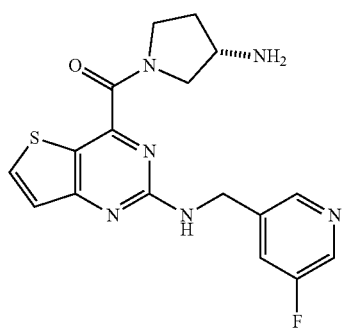 Z360 | D | E | 72.24 | | | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z361 | D | E | 28.33 | | | | | |
| Z362 | B | E | 95.57 | | | | | |
| Z363 | D | E | 23.53 | | | | | |
| Z364 | D | E | 11.16 | | | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 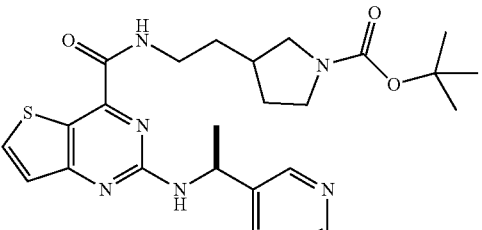 Z365 | B | C | 2.19 | | | | | |
| 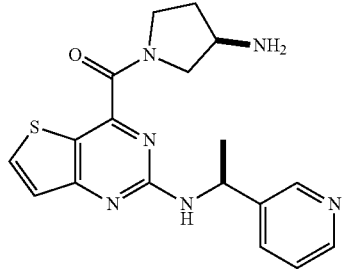 Z366 | E | E | 1.86 | | | | | |
| 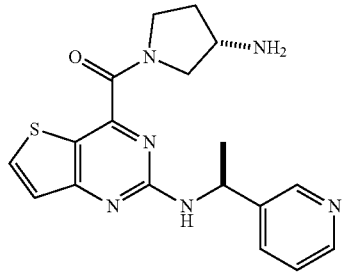 Z367 | E | E | 5.78 | | | | | |
| 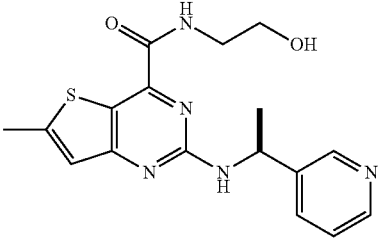 Z368 | A | D | 74.02 | C | C | | | |

-continued
| Compound | Ave A2B cAMP IC50 | Ave A2A cAMP IC50 | Ratio | A1 cAMP IC50 | A3 cAMP IC50 | CYP 450 % INH @ 10 μM | LM CLint (μL/ min/mg/ protein) | Hep CLint (mL/ min/ 10^6 cells) |
|---|---|---|---|---|---|---|---|---|
| Z369 | E | E | 2.26 | | | | | |
| Z370 | E | E | 1.81 | | | | | |
| Z371 | E | E | 11.56 | | | | | |
| Z372 | C | E | 33.10 | | | | | |
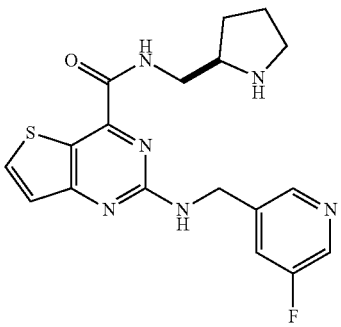
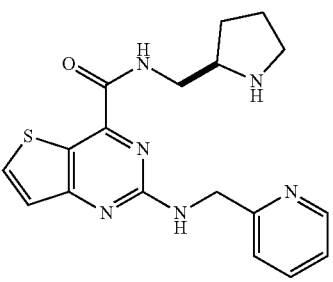
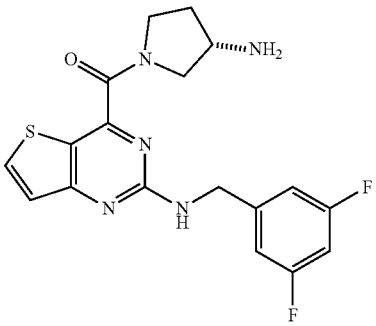
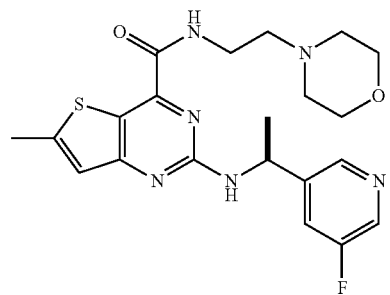

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 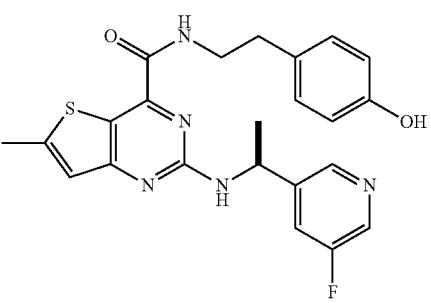 Z373 | A | D | 75.08 | C | B | | | |
| 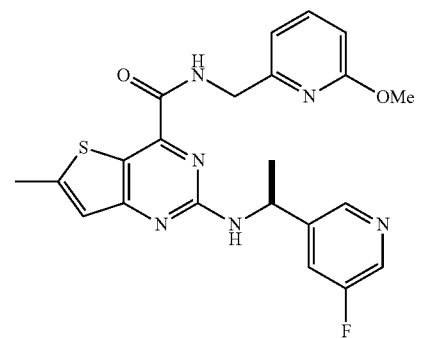 Z374 | A | D | 19.21 | C | B | | | |
| 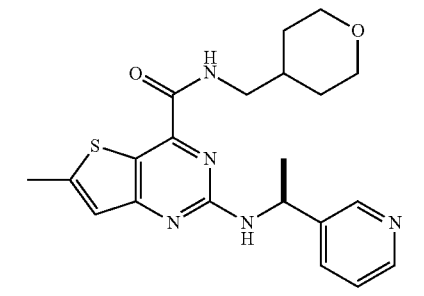 Z375 | B | D | 7.89 | | | | | |
| 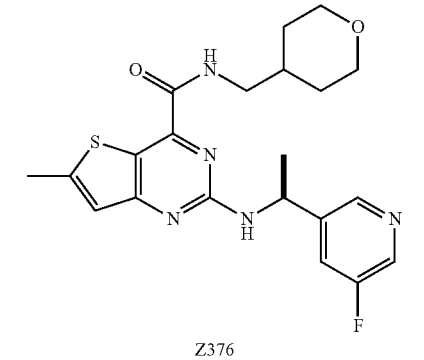 Z376 | A | D | 32.01 | C | C | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 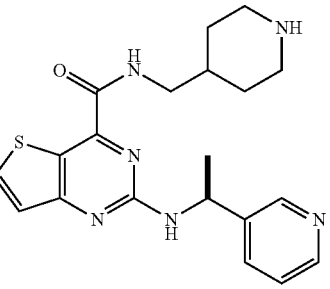 Z377 | D | E | 39.59 | | | | | |
| 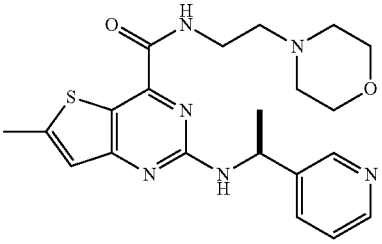 Z378 | D | E | 15.93 | | | | | |
| 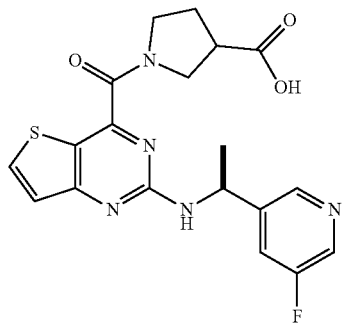 Z379 | D | E | 68.03 | | | | | |
| 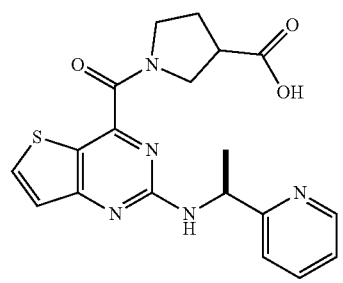 Z380 | E | E | 13.21 | | | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 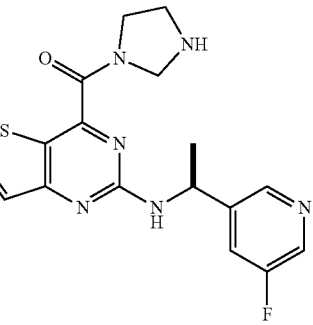 Z381 | B | E | 47.20 | | | | | |
| 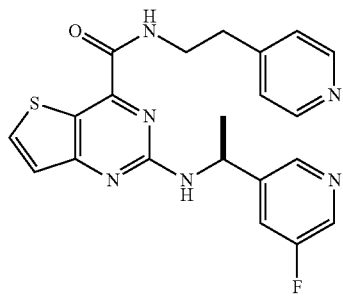 Z382 | B | E | 18.44 | E | E | | | |
| 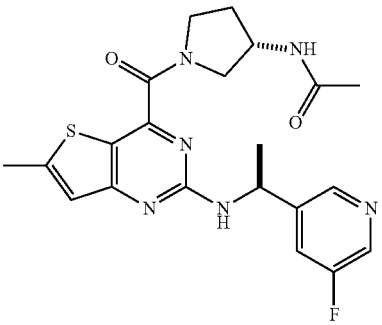 Z383 | B | E | 55.83 | E | B | | | |
| 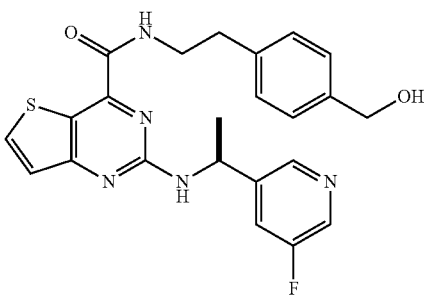 Z384 | B | D | 13.78 | C | E | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 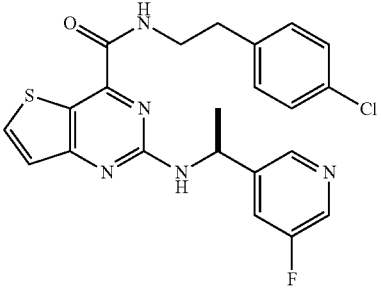 Z385 | C | E | 7.44 | | | | | |
| 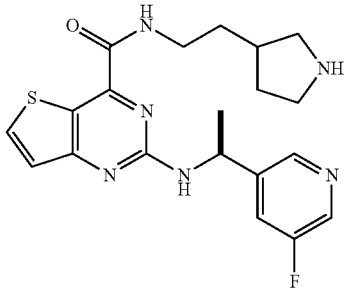 Z386 | B | E | 100.94 | E | E | | | |
| 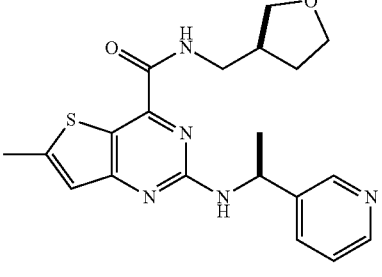 Z387 | C | E | 20.10 | | | | | |
| 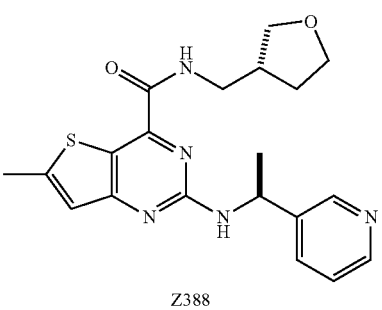 Z388 | C | E | 10.69 | | | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 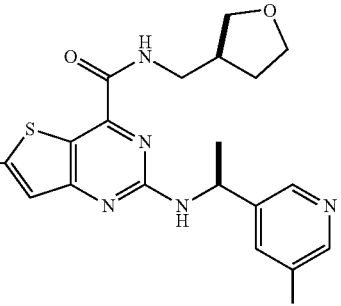 Z389 | A | E | 50.96 | C | C | | | |
| 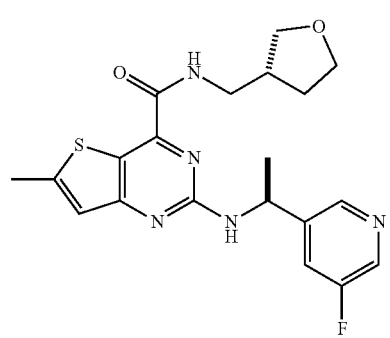 Z390 | A | D | 68.99 | C | C | | | |
| 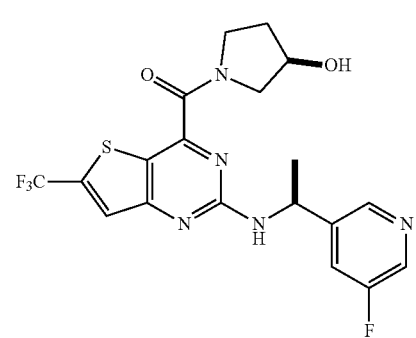 Z391 | A | E | 288.73 | E | E | | 7.73 (rat) 12.73 (human) | |
| 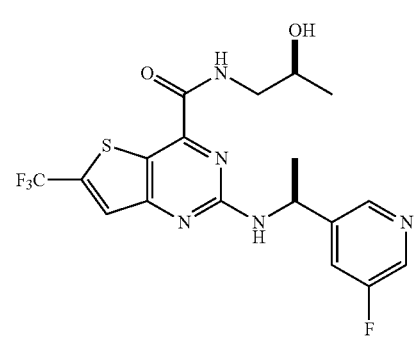 Z392 | A | E | 248.84 | C | C | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 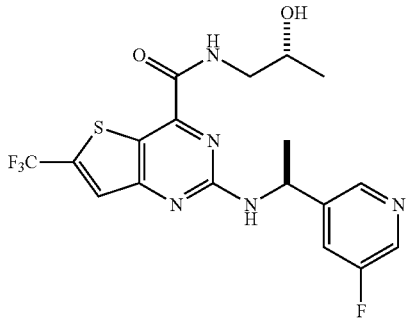 Z393 | A | E | 399.70 | C | C | | | |
| 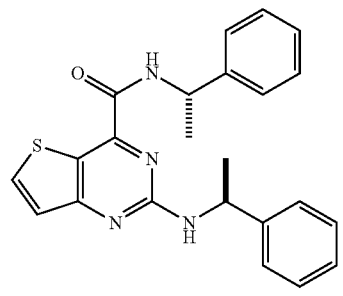 Z394 | D | D | 0.87 | | | | | |
| 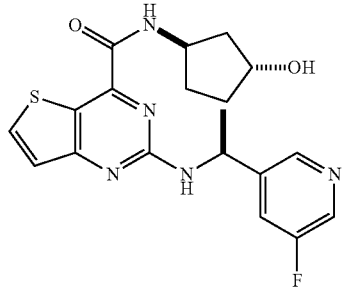 Z395 | B | D | 32.64 | | | | | |
| 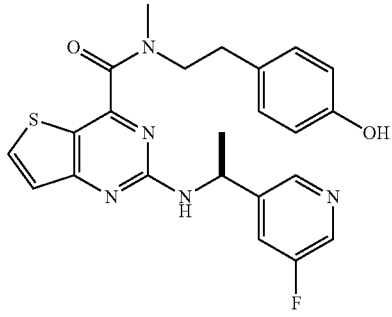 Z396 | E | E | 6.83 | | | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 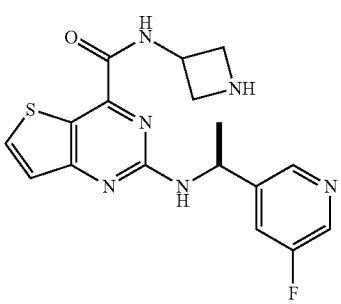 Z397 | E | E | 11.51 | | | | | |
| 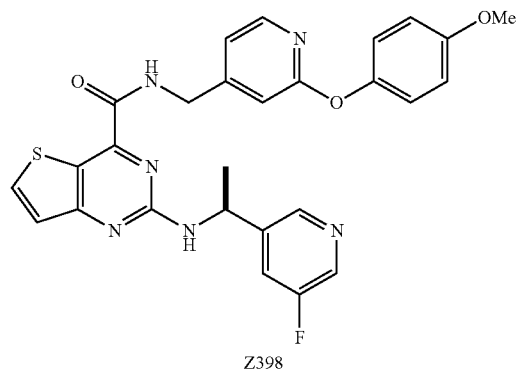 Z398 | D | D | 2.82 | | | | | |
| 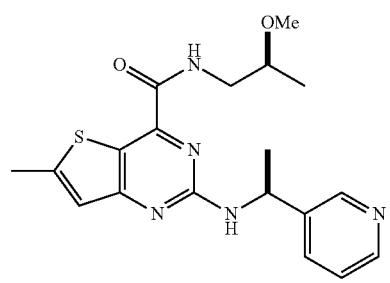 Z399 | B | E | 161.94 | | | | | |
| 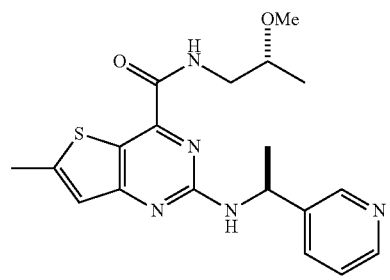 Z400 | C | E | 12.22 | | | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/min/mg/protein) | Hep CLint (mL/min/10$^6$ cells) |
|---|---|---|---|---|---|---|---|---|
| Z401 | B | E | 72.32 | E | E | | 5.32 (rat) 2.64 (human) | |
| Z402 | A | C | 38.37 | D | C | | | |
| Z403 | B | E | 42.24 | E | E | | | |
| Z404 | A | B | 5.80 | E | E | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z405 | A | D | 28.50 | E | E | | | |
| Z406 | B | D | 5.89 | | | | | |
| Z407 | D | E | 8.11 | | | | | |
| Z408 | C | E | 6.69 | | | | | |
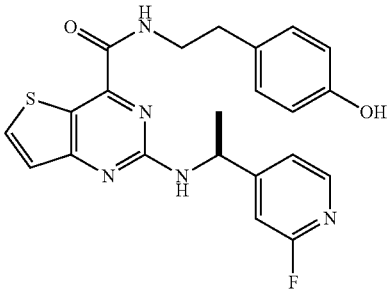
Z405
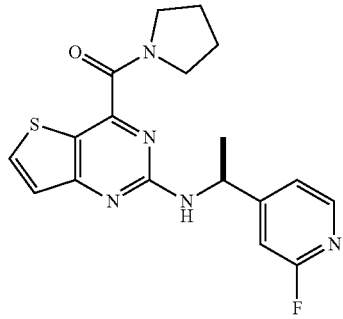
Z406
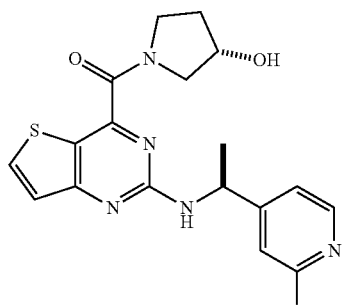
Z407
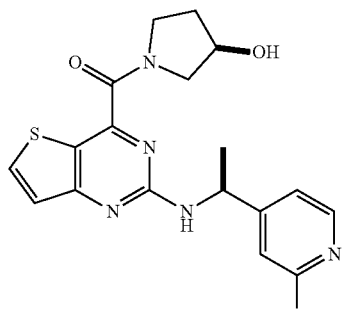
Z408

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 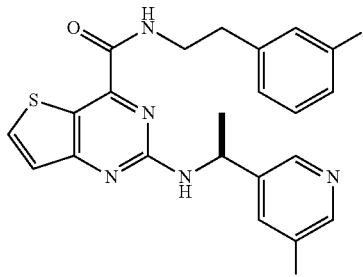 Z409 | A | B | 5.96 | C | C | | | |
| 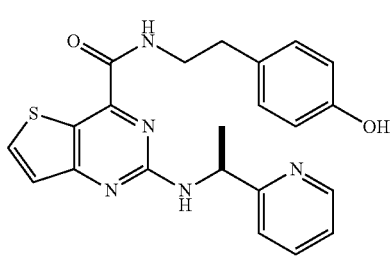 Z410 | A | D | 69.41 | E | E | | | |
| 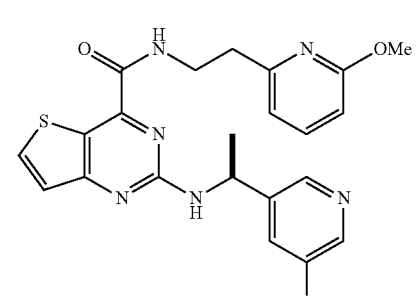 Z411 | A | D | 19.23 | E | E | | | |
| 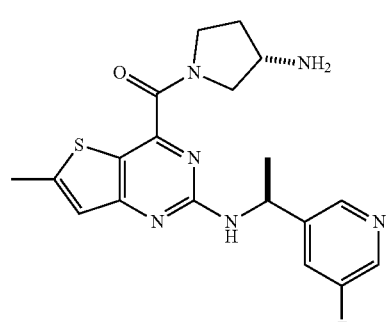 Z412 | B | E | 166.77 | E | E | | 26.34 (rat) 0.15 (human) | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 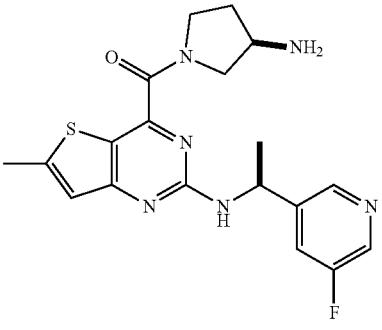 Z413 | B | E | 126.84 | E | E | | | |
| 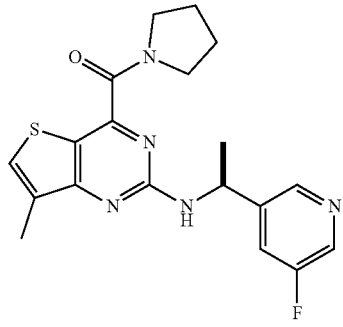 Z414 | A | B | 19.11 | C | C | | | |
| 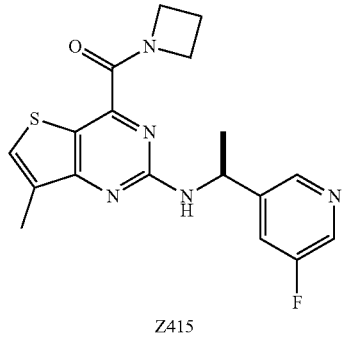 Z415 | A | B | 21.01 | C | E | | 56.26 (rat) 82.97 (human) | |
| 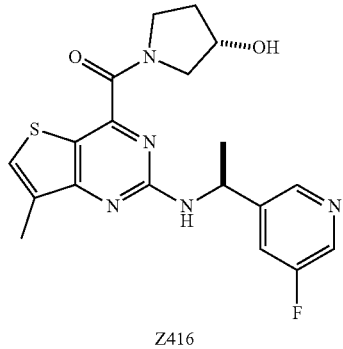 Z416 | A | D | 52.64 | E | E | | | |

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 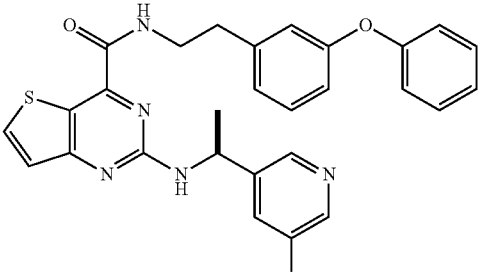 Z417 | D | E | 4.87 | | | | | |
| 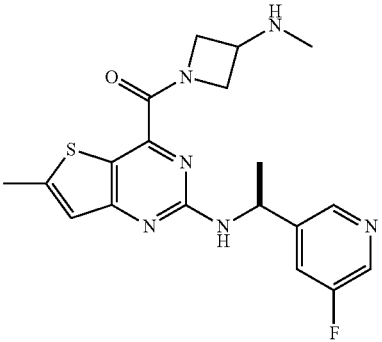 Z418 | B | E | 207.31 | E | E | | | |
| 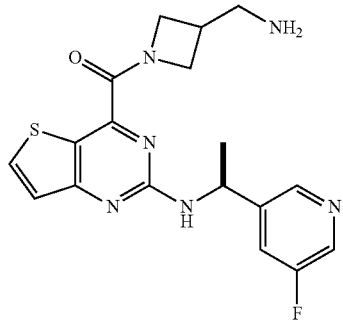 Z419 | B | E | 124.30 | E | E | | 9.09 (rat) 0.69 (human) | |
| 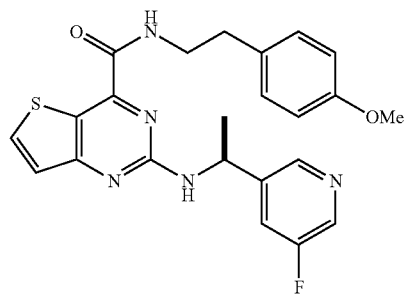 Z420 | C | D | 5.38 | | | | | |

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/min/mg/protein) | Hep CLint (mL/min/$10^6$ cells) |
|---|---|---|---|---|---|---|---|---|
| 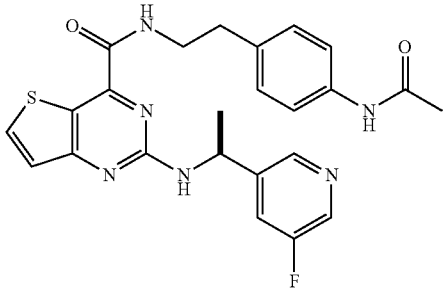 Z421 | B | E | 48.43 | E | E | | 85.16 (rat) 228.45 (human) | |
| 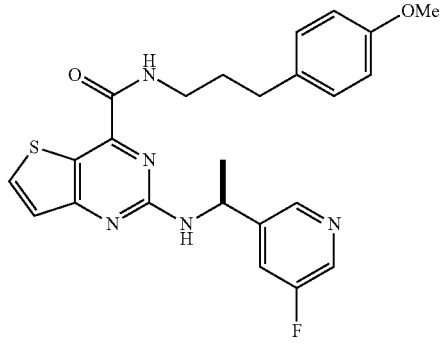 Z422 | B | D | 7.52 | E | E | | | |
| 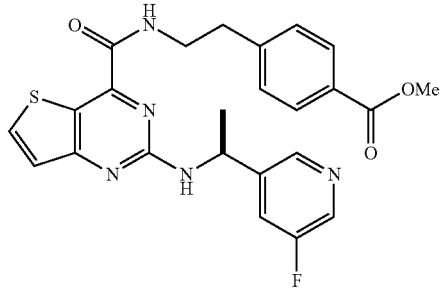 Z423 | D | E | 5.22 | | | | | |
| 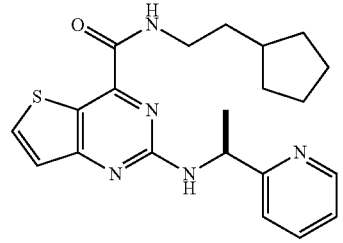 Z424 | C | C | 1.46 | | | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| Z425 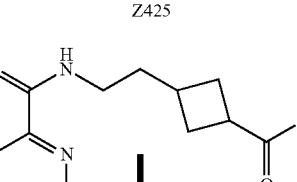 | D | C | 0.82 | | | | | |
| Z426 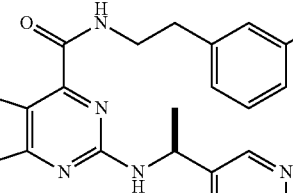 | C | D | 3.47 | | | | | |
| Z427 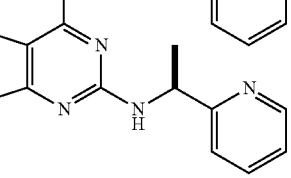 | C | D | 5.03 | D | D | | | |
| Z428 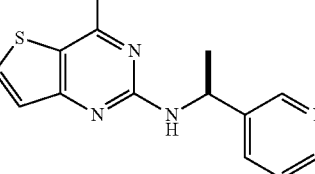 | B | D | 10.94 | E | E | | | |
| Z429  | A | B | 4.15 | C | B | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/min/mg/protein) | Hep CLint (mL/min/10$^6$ cells) |
|---|---|---|---|---|---|---|---|---|
| Z430 | A | E | 177.08 | E | E | | 4.83 (rat) 5.77 (human) | |
| Z431 | D | E | 37.04 | | | | | |
| Z432 | D | E | 57.47 | | | | | |
| Z433 | E | D | 0.22 | | | | | |
| Z434 | E | C | 0.08 | | | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 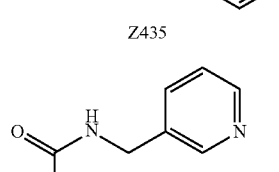 Z435 | D | B | 0.04 | D | C | | | |
| 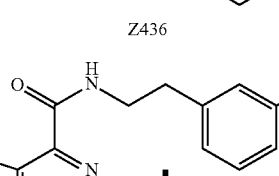 Z436 | E | D | 0.15 | | | | | |
| 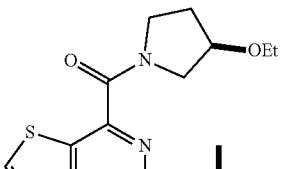 Z437 | D | D | 2.08 | | | | | |
| 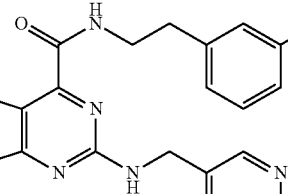 Z438 | B | C | 2.65 | | | | | |
|  Z439 | E | D | 0.29 | | | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z440 | D | D | 1.91 | | | | | |
| Z441 | B | B | 1.21 | | | | | |
| Z442 | D | D | 2.19 | | | | | |
| Z443 | C | B | 0.44 | | | | | |
| Z444 | D | C | 0.35 | | | | | |
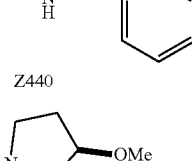
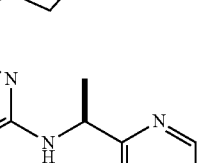
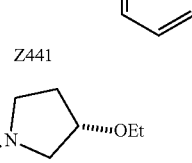
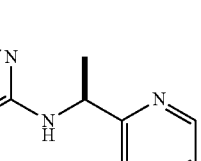
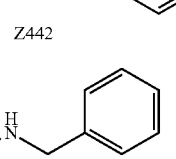

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 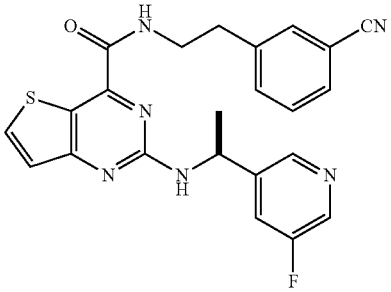 Z445 | C | E | 9.62 | | | | | |
| 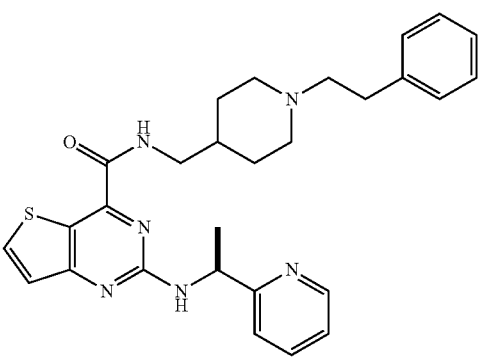 Z446 | E | E | 0.56 | | | | | |
| 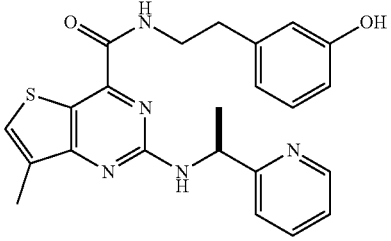 Z447 | C | C | 1.23 | | | | | |
| 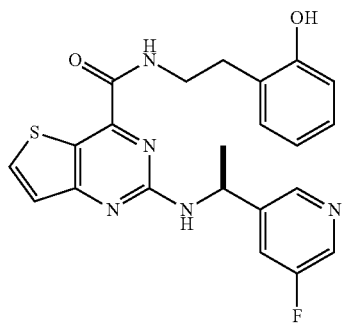 Z448 | A | D | 12.69 | | | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 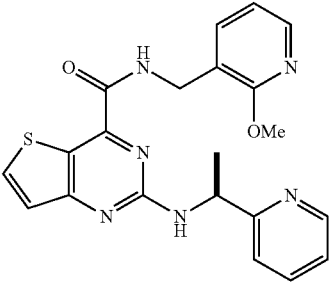 Z449 | E | E | 0.91 | | | | | |
| 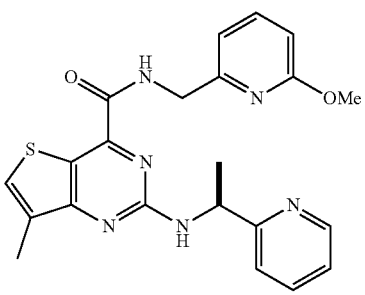 Z450 | B | B | 0.64 | E | C | | 314.14 (rat) 82.93 (human) | |
| 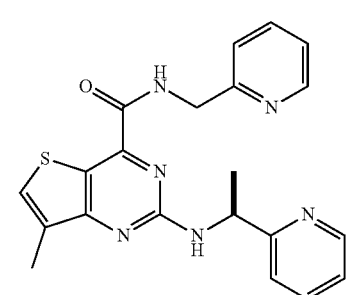 Z451 | B | B | 0.35 | C | B | | | |
| 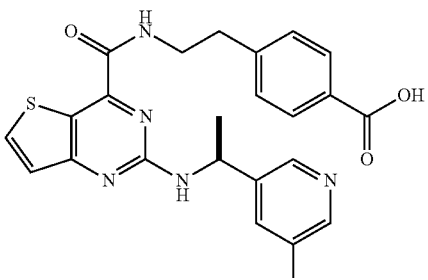 Z452 | D | E | 19.85 | | | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z453 | D | D | 0.43 | | | | | |
| Z454 | B | E | 38.75 | | | | | |
| Z455 | D | E | 3.91 | | | | | |
| Z456 | A | B | 2.47 | E | C | | | |
| Z457 | C | D | 2.73 | | | | | |
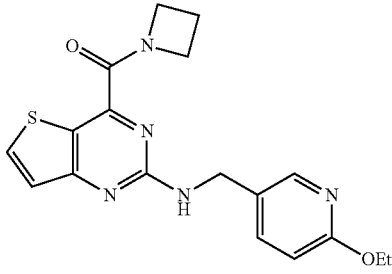
Z453
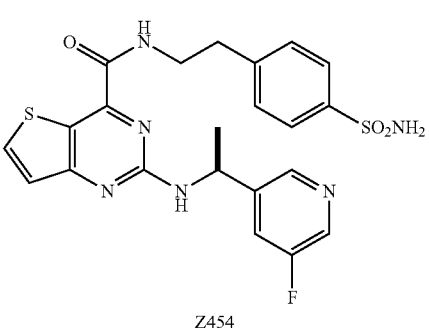
Z454
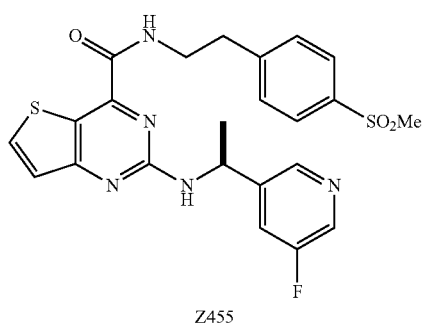
Z455
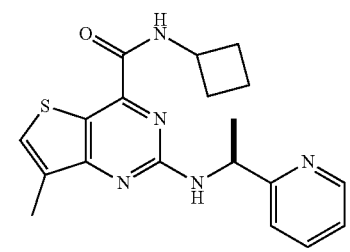
Z456
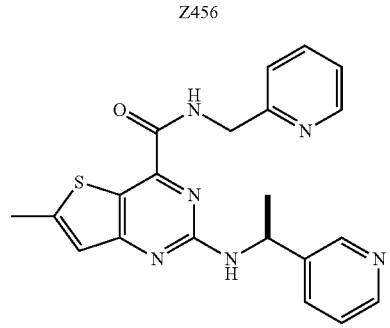
Z457

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/min/mg/protein) | Hep CLint (mL/min/10$^6$ cells) |
|---|---|---|---|---|---|---|---|---|
| Z458 | B | B | 0.72 | E | E | | | |
| Z459 | B | B | 2.40 | E | E | | | |
| Z460 | D | D | 0.84 | | | | | |
| Z461 | B | B | 3.15 | E | C | | | |
| Z462 | B | C | 2.70 | E | C | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 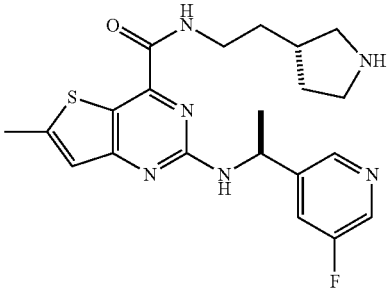<br>Z463 | B | E | 159.87 | E | E | | 48.47 (rat) 4.85 (human) | |
| 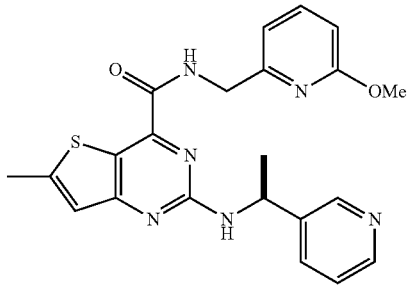<br>Z464 | A | D | 19.50 | E | C | | | |
| 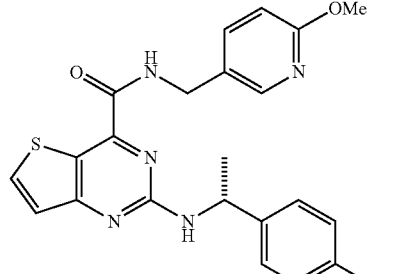<br>Z465 | E | B | 0.22 | E | E | | 75.91 (rat) 35.20 (human) | |
| 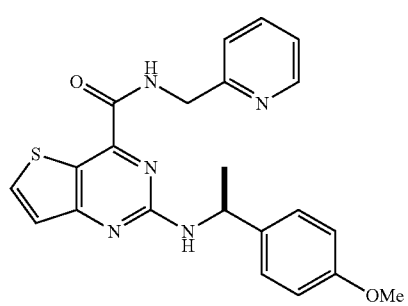<br>Z466 | E | B | 0.05 | | | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 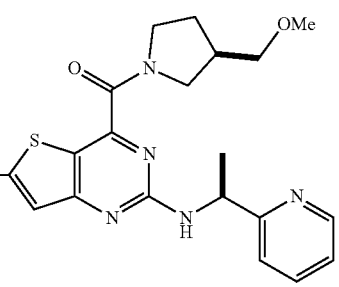 Z467 | B | D | 4.90 | E | C | | | |
| 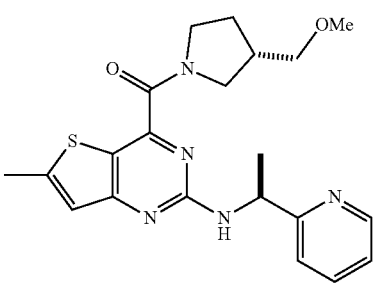 Z468 | B | E | 24.67 | E | E | | | |
| 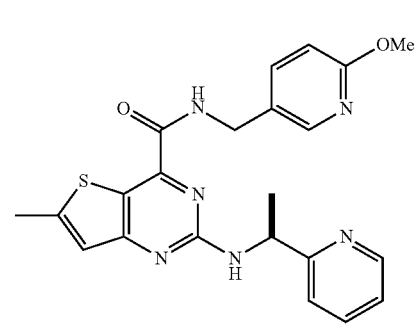 Z469 | B | E | 36.71 | E | E | | | |
| 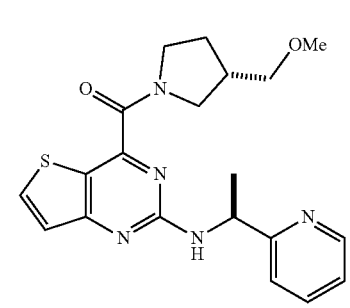 Z470 | C | D | 1.07 | | | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z471 | C | D | 7.81 | | | | | |
| Z472 | B | E | 8.61 | | | | | |
| Z473 | B | E | 20.60 | E | E | | | |
| Z474 | C | C | 0.80 | | | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 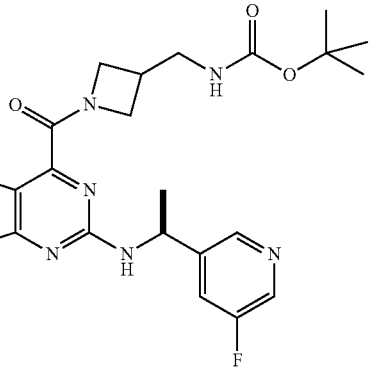 Z475 | B | D | 7.45 | E | E | | | |
| 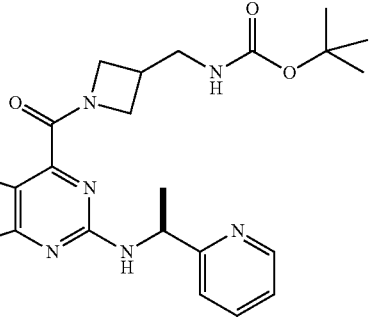 Z476 | B | D | 5.27 | E | E | | | |
| 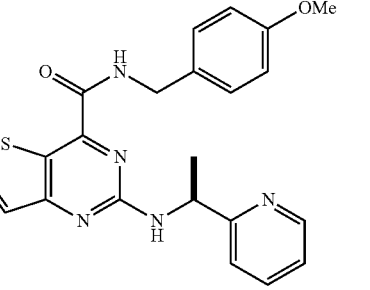 Z477 | B | D | 9.73 | C | C | | | |
| 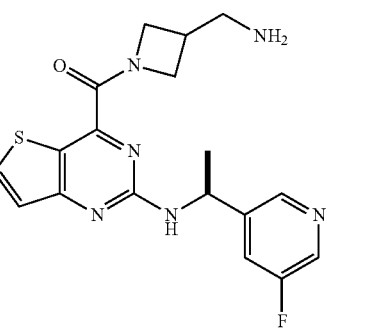 Z478 | B | E | 167.42 | E | E | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 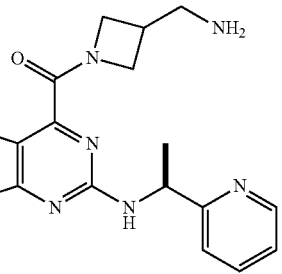 Z479 | B | E | 96.36 | E | E | | | |
| 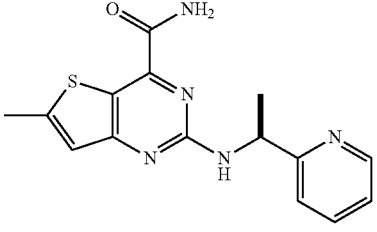 Z480 | B | E | 47.68 | E | E | | | |
| 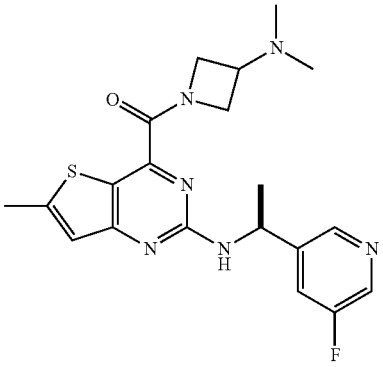 Z481 | B | E | 111.93 | E | E | | | |
| 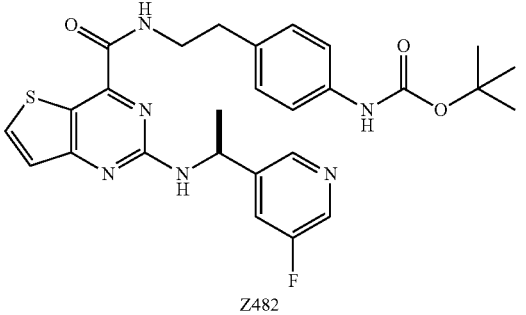 Z482 | D | E | 5.32 | | | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 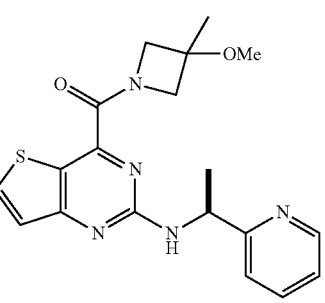<br>Z483 | B | D | 30.60 | E | E | | | |
| 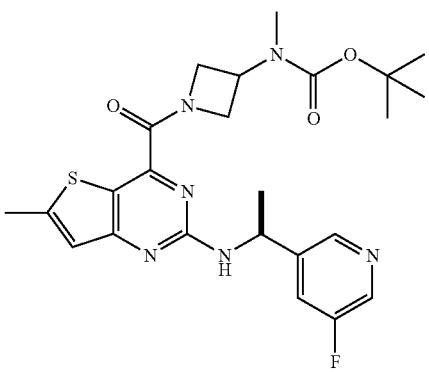<br>Z484 | B | D | 4.16 | | | | | |
| 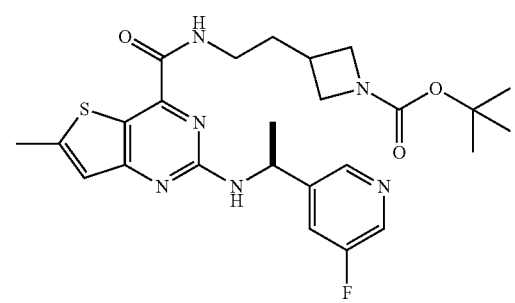<br>Z485 | B | D | 8.16 | D | E | | | |
| 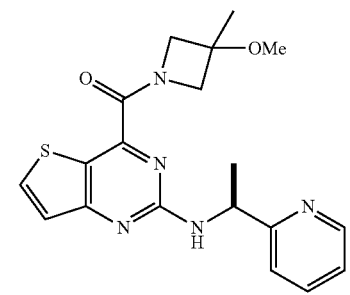<br>Z486 | C | E | 10.58 | | | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 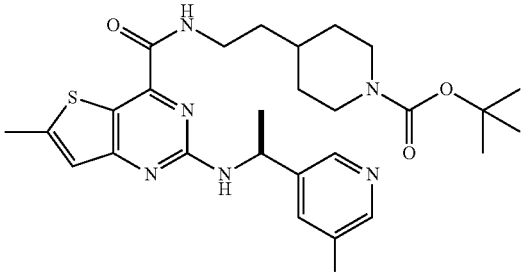 Z487 | D | E | 6.54 | | | | | |
| 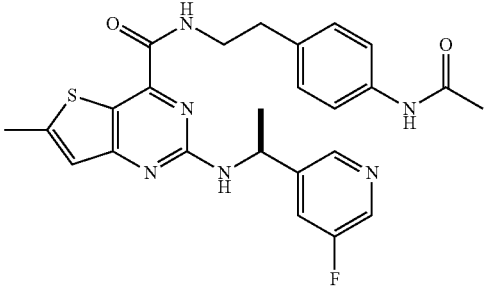 Z488 | A | E | 147.08 | E | E | | | |
| 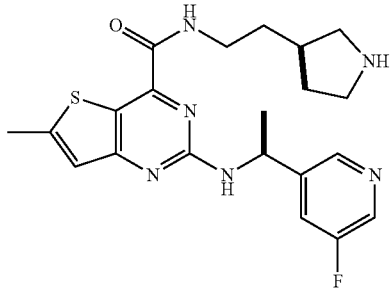 Z489 | B | E | 365.84 | E | E | | | |
| 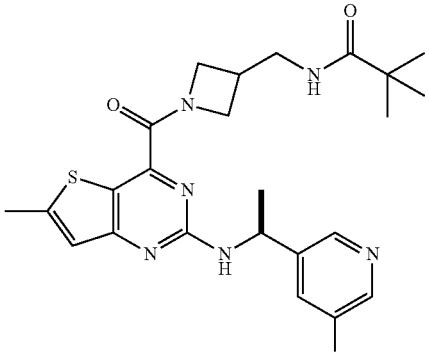 Z490 | B | D | 10.96 | E | E | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 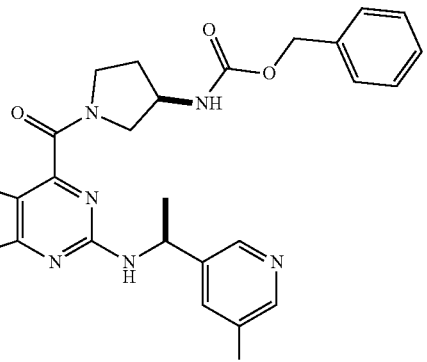 Z491 | B | E | 86.94 | E | E | | | |
| 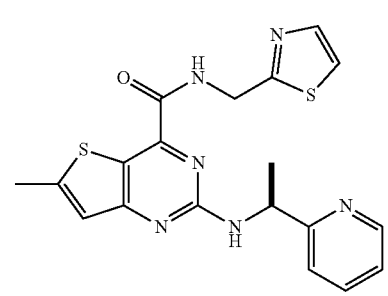 Z492 | B | D | 8.25 | E | B | | | |
| 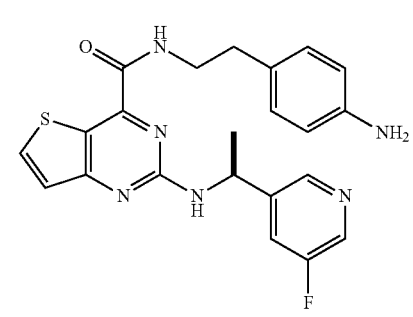 Z493 | C | E | 17.90 | | | | | |
| 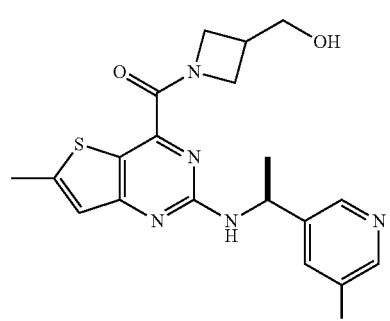 Z494 | A | D | 146.92 | E | E | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 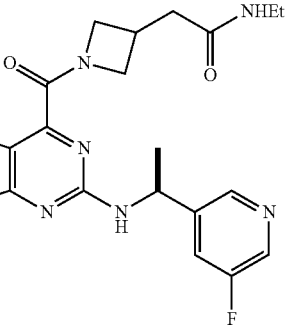 Z495 | A | C | 23.37 | E | C | | | |
| 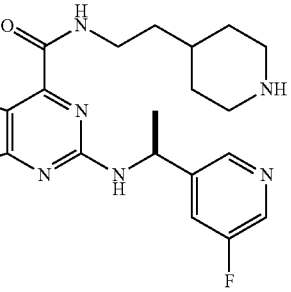 Z496 | B | E | 524.78 | E | E | | | |
| 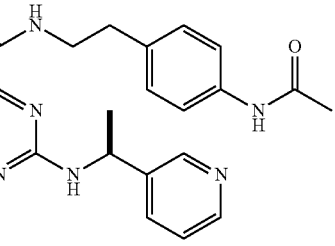 Z497 | B | E | 20.07 | E | C | | | |
| 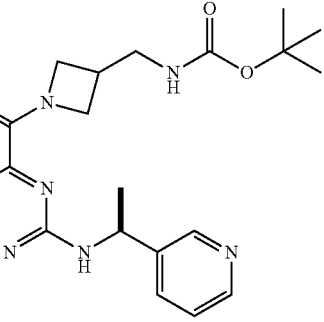 Z498 | D | E | 5.78 | | | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z499 | E | E | 13.99 | | | | | |
| Z500 | E | E | 12.75 | | | | | |
| Z501 | E | E | 8.68 | | | | | |
| Z505 | B | C | 4.89 | | | | | |
| Z503 | B | E | 18.01 | | | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| Z504 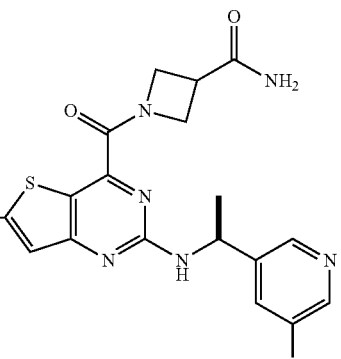 | A | E | 287.41 | E | E | | | |
| Z505 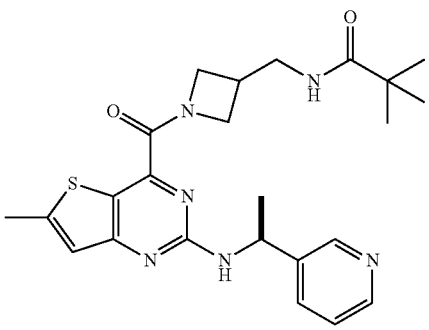 | D | D | 1.20 | | | | | |
| Z506 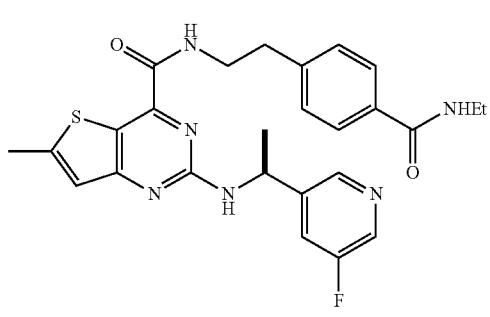 | B | E | 22.42 | E | E | | | |
| Z507 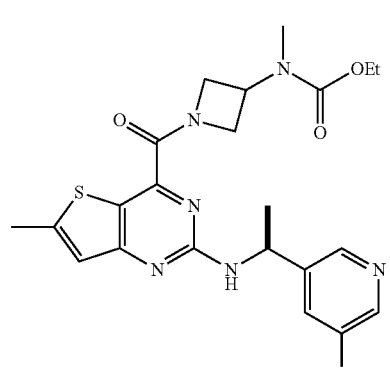 | B | C | 5.66 | E | E | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/min/mg/protein) | Hep CLint (mL/min/10$^6$ cells) |
|---|---|---|---|---|---|---|---|---|
| Z508 | B | B | 1.06 | E | E | | | |
| Z509 | A | E | 80.91 | E | E | | | |
| Z510 | B | B | 2.03 | E | E | | | |
| Z511 | B | B | 2.90 | E | C | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z512 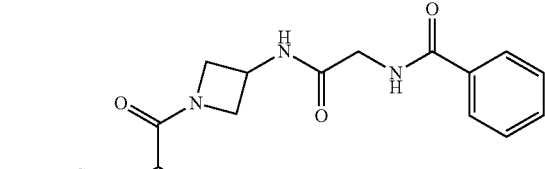 | B | E | 33.02 | E | E | | | |
| Z513 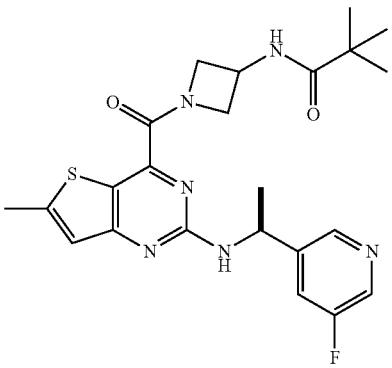 | B | A | 0.18 | D | B | | | |
| Z514 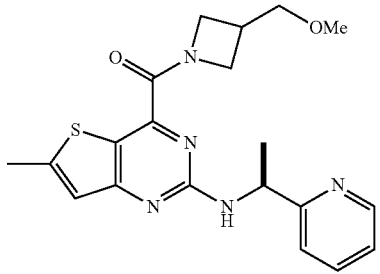 | A | B | 5.47 | | | | | |
| Z515 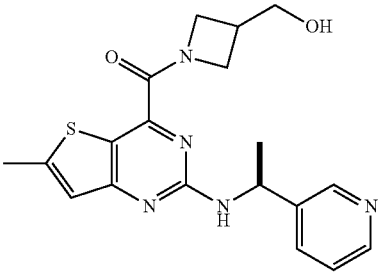 | B | E | 53.11 | E | E | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z516 | E | E | 8.08 | | | | | |
| Z517 | A | B | 4.68 | E | E | | 16.99 (rat) 6.17 (human) | |
| Z518 | A | B | 5.46 | E | E | | | |
| Z519 | A | B | 3.87 | E | E | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/min/mg/protein) | Hep CLint (mL/min/10$^6$ cells) |
|---|---|---|---|---|---|---|---|---|
| Z520 | A | D | 27.57 | E | E | | | |
| Z521 | E | E | 0.06 | | | | | |
| Z522 | A | B | 1.58 | E | D | | | |
| Z523 | A | B | 1.40 | E | D | | | |

-continued

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/min/mg/protein) | Hep CLint (mL/min/$10^6$ cells) |
|---|---|---|---|---|---|---|---|---|
| Z524 | A | C | 11.94 | E | E | | | |
| Z525 | C | D | 3.05 | | | | | |
| Z526 | B | C | 4.26 | E | E | | | |
| Z527 | C | E | 7.31 | | | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 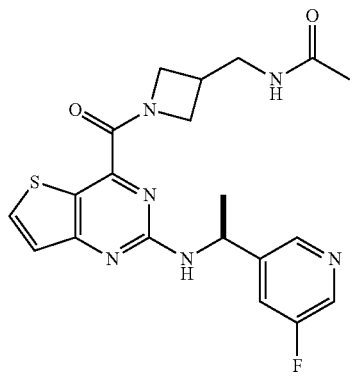 Z528 | A | D | 44.92 | E | E | | | |
| 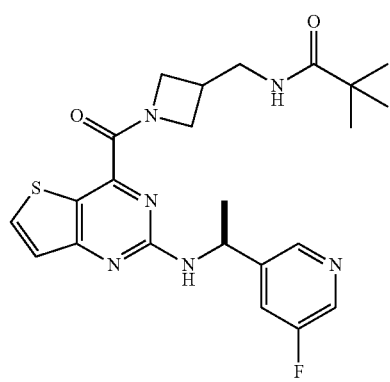 Z529 | B | D | 4.15 | E | E | | | |
| 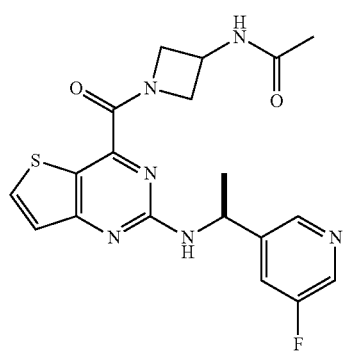 Z530 | B | D | 6.99 | E | E | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 µM | LM CLint (µL/min/mg/protein) | Hep CLint (mL/min/10$^6$ cells) |
|---|---|---|---|---|---|---|---|---|
| Z531 | B | D | 19.43 | E | E | | | |
| Z532 | B | E | 149.69 | E | E | | | |
| Z533 | D | D | 1.68 | | | | | |
| Z534 | C | E | 57.93 | | | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 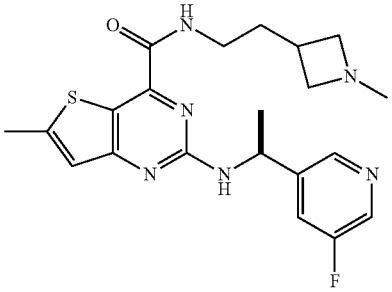 Z535 | B | E | 244.67 | E | E | | | |
| 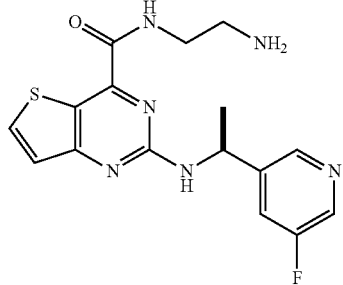 Z536 | E | E | 10.26 | | | | | |
| 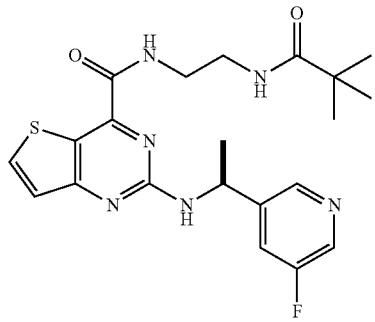 Z537 | D | D | 0.87 | | | | | |
| 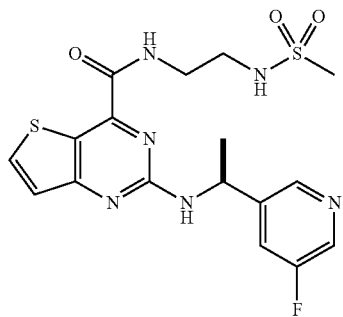 Z538 | B | E | 12.33 | | | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z539 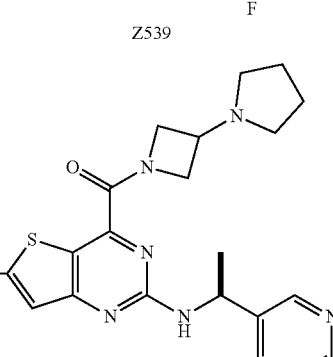 | B | D | 10.59 | | | | | |
| Z540 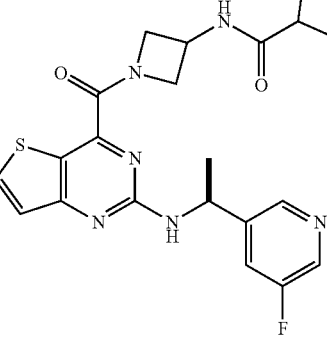 | B | D | 33.20 | E | E | | | |
| Z541 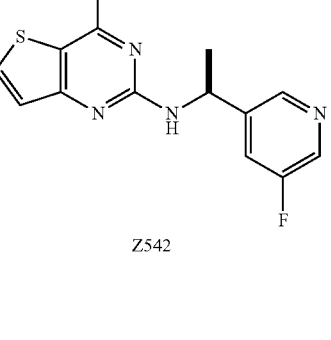 | B | B | 1.64 | D | D | | | |
| Z542  | B | B | 1.45 | E | C | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z543 | | D | 18.71 | E | E | | | |
| Z544 | | D | | | | | | |
| Z545 | D | D | 1.58 | | | | | |
| Z546 | A | B | 3.52 | E | E | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z547 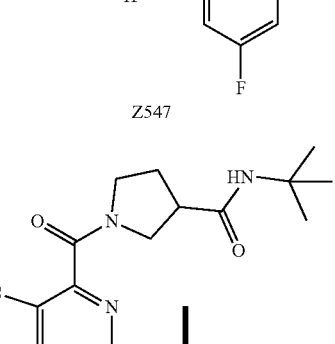 | C | E | 43.40 | | | | | |
| Z548 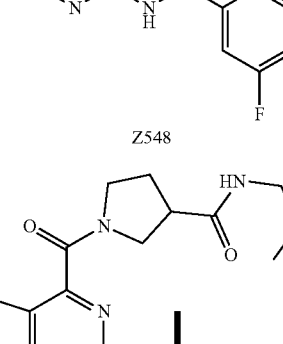 | B | D | 6.19 | | | | | |
| Z549 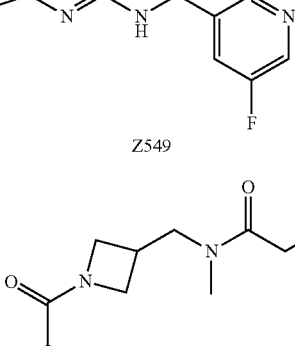 | B | A | 0.63 | E | E | | | |
| Z550 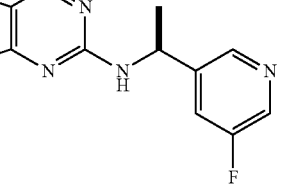 | B | C | 4.79 | | | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z551 | B | B | 1.68 | E | E | | | |
| Z552 | B | B | 2.32 | E | D | | | |
| Z553 | A | B | 3.87 | E | D | | | |
| Z554 | A | E | 547.59 | E | E | | | |
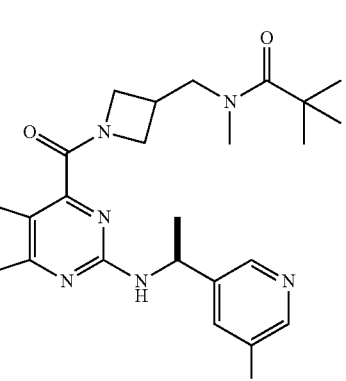
Z551
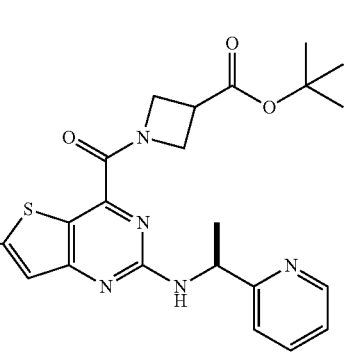
Z552
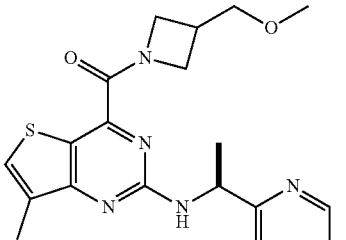
Z553
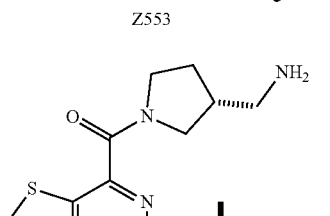
Z554

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 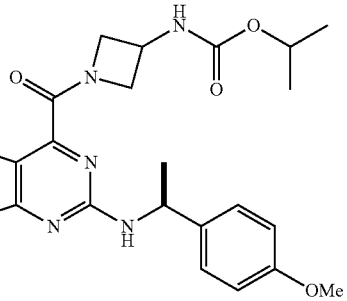 Z555 | D | C | 0.18 | | | | | |
| 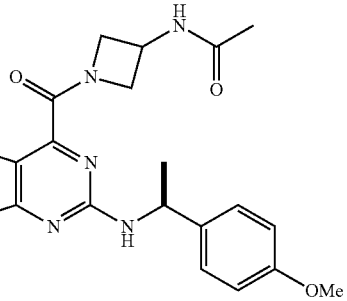 Z556 | D | C | 0.22 | | | | | |
| 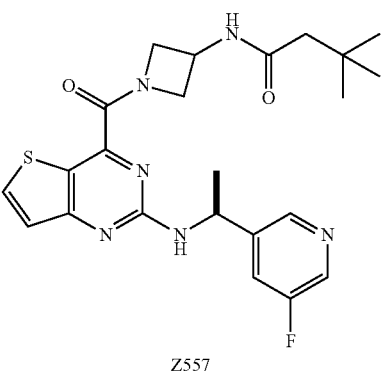 Z557 | B | B | 1.92 | E | E | | | |
| 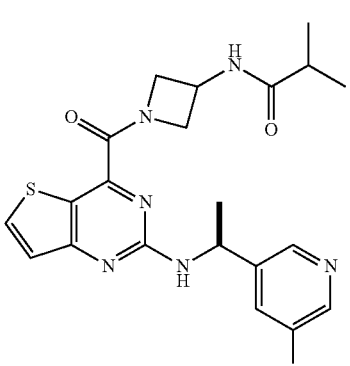 Z558 | A | B | 3.43 | E | E | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 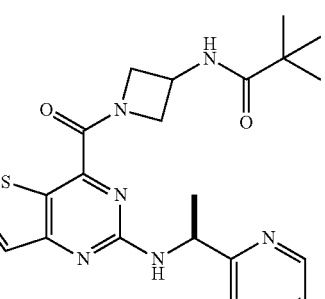 Z559 | B | B | 1.93 | E | D | | | |
| 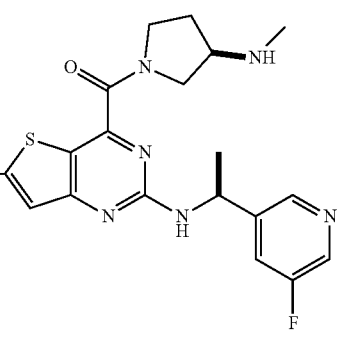 Z560 | C | E | 59.47 | E | E | | | |
| 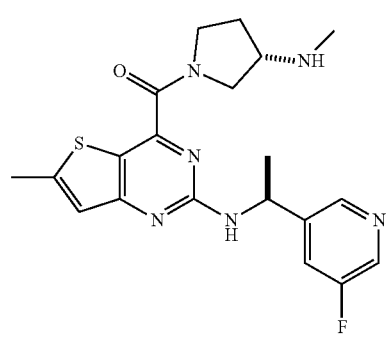 Z561 | C | E | 140.19 | E | E | | | |
| 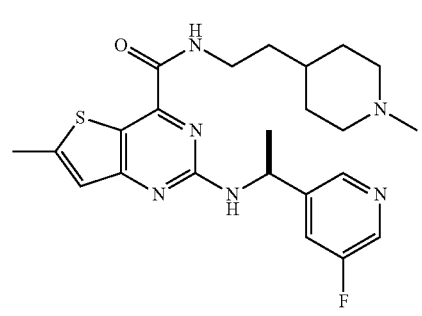 Z562 | B | E | 127.97 | E | E | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z563 | B | E | 16.87 | | | | | |
| Z564 | D | E | 18.15 | | | | | |
| Z565 | E | E | 6.39 | | | | | |
| Z566 | E | E | 3.10 | | | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z567 | D | E | 8.82 | | | | | |
| Z568 | C | E | 12.84 | | | | | |
| Z569 | D | E | 40.75 | | | | | |
| Z570 | B | E | 84.36 | | | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 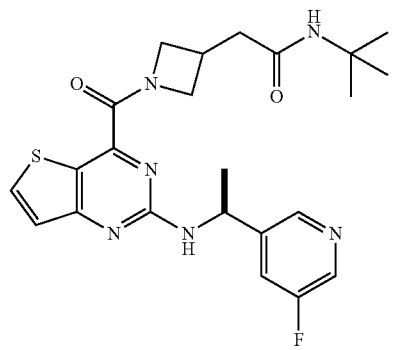 Z571 | B | B | 1.51 | E | E | | | |
| 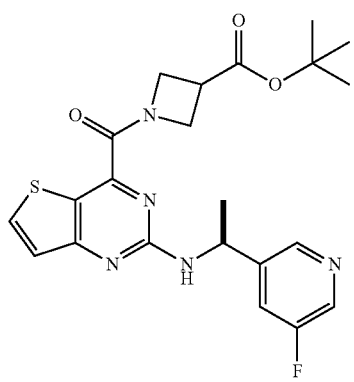 Z572 | B | D | 2.90 | | | | | |
| 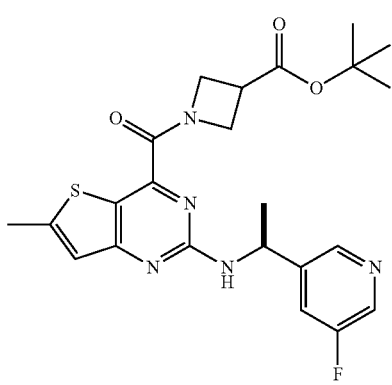 Z573 | B | D | 3.44 | E | E | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 µM | LM CLint (µL/min/mg/protein) | Hep CLint (mL/min/10$^6$ cells) |
|---|---|---|---|---|---|---|---|---|
| Z574 | B | E | 58.55 | | | | | |
| Z575 | A | E | 75.64 | E | E | | | |
| Z576 | A | D | 26.03 | E | E | | | |
| Z577 | B | C | 6.37 | E | E | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z578 | B | C | 4.95 | E | E | | | |
| Z579 | C | C | 1.29 | E | E | | | |
| Z580 | B | B | 1.19 | E | D | | | |
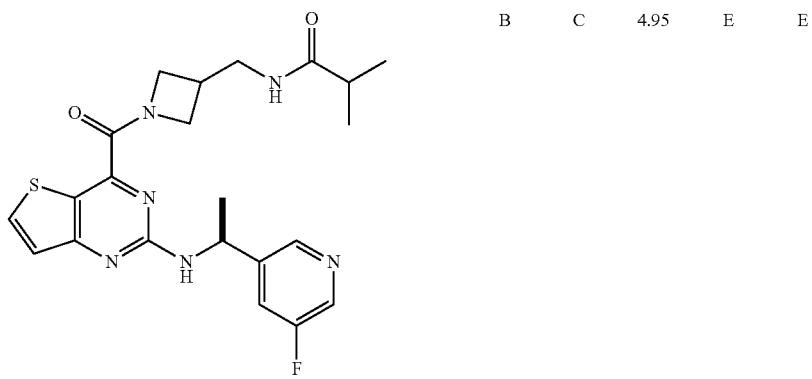
Z578
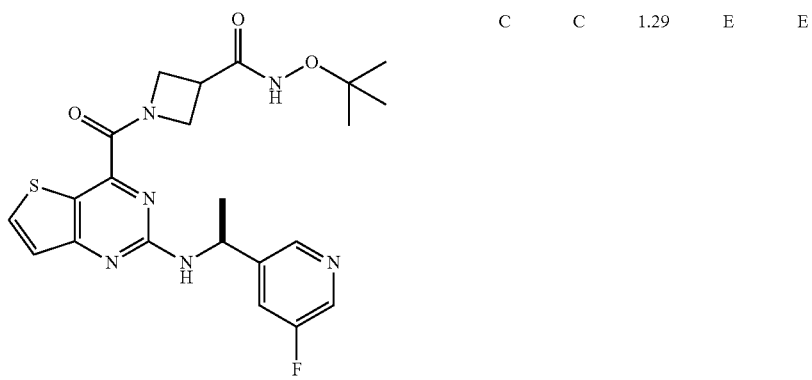
Z579
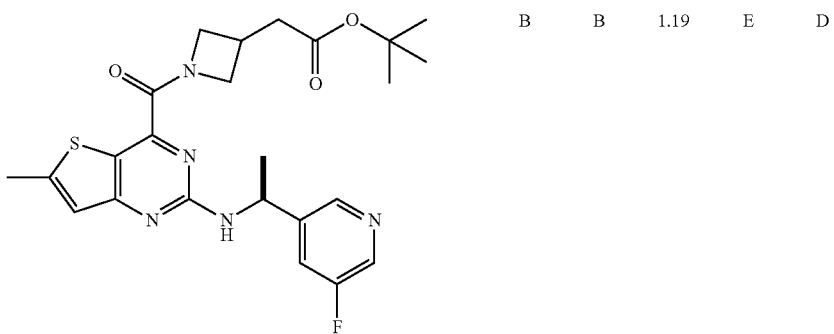
Z580

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z581 | B | B | 1.68 | E | E | | | |
| Z582 | | | | | | | | |
| Z583 | B | B | 0.37 | E | E | | | |
| Z584 | D | E | 2.34 | | | | | |

-continued

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z585 | B | D | 21.44 | E | E | | | |
| Z586 | B | C | 2.27 | E | E | | | |
| Z587 | C | D | 1.63 | | | | | |
| Z588 | B | A | 0.26 | E | D | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/min/mg/protein) | Hep CLint (mL/min/10$^6$ cells) |
|---|---|---|---|---|---|---|---|---|
| Z589 | B | E | 17.96 | | | | | |
| Z590 | B | D | 11.22 | | | | | |
| Z591 | B | A | 0.14 | E | B | | | |
| Z592 | B | C | 4.67 | E | E | | | |

| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z593 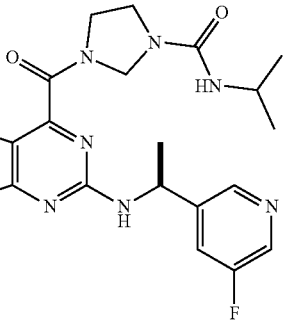 | B | C | 3.25 | E | E | | | |
| Z594 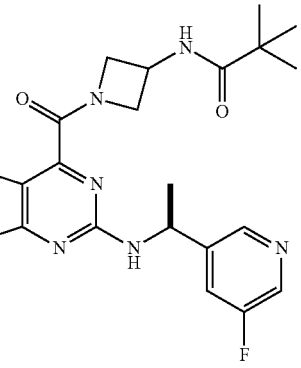 | B | A | 0.15 | E | C | | | |
| Z595 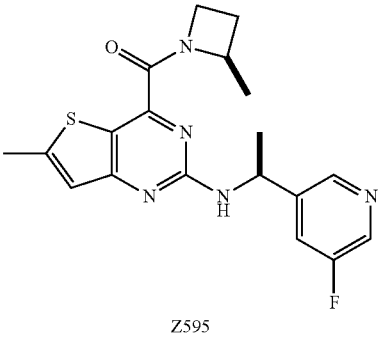 | A | B | 9.45 | A | A | | | |
| Z596 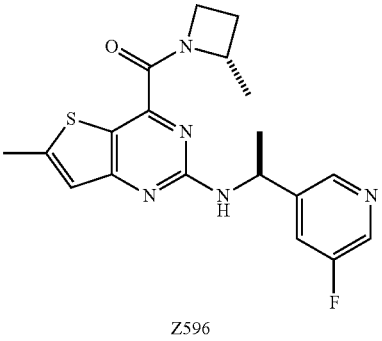 | A | B | 10.34 | A | A | | | |

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/min/mg/protein) | Hep CLint (mL/min/$10^6$ cells) |
|---|---|---|---|---|---|---|---|---|
| 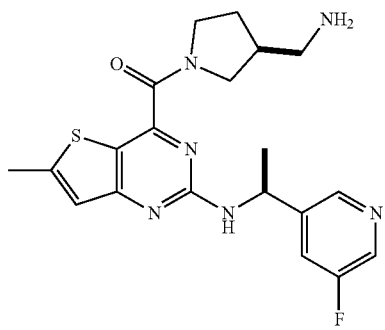 Z597 | B | E | 99.33 | A | A | | | |
| 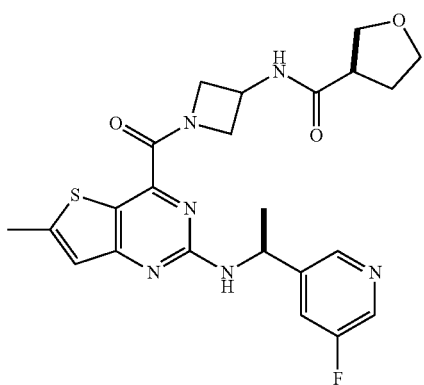 Z598 | B | B | 0.68 | E | D | | | |
| 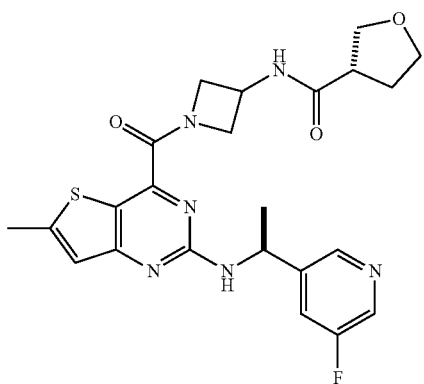 Z599 | B | B | 1.22 | E | D | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 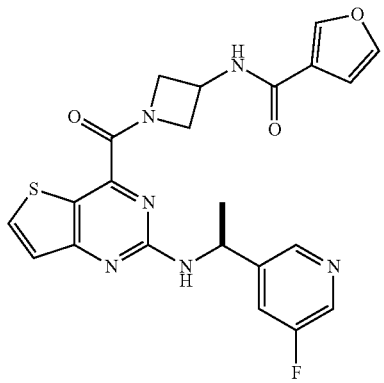 Z600 | A | B | 1.90 | E | D | | | |
| 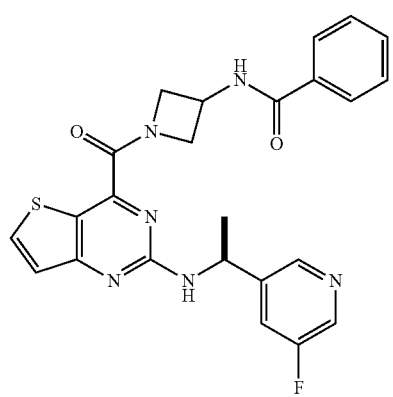 Z601 | B | B | 0.90 | E | D | | | |
| 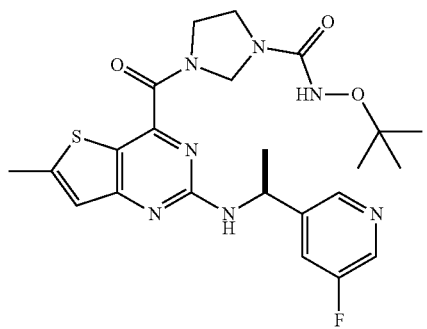 Z602 | B | A | 0.49 | E | D | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/min/mg/protein) | Hep CLint (mL/min/$10^6$ cells) |
|---|---|---|---|---|---|---|---|---|
| 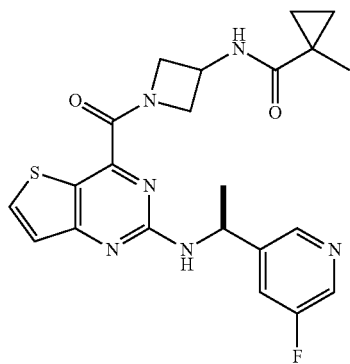 Z603 | A | A | 1.00 | E | D | | | |
| 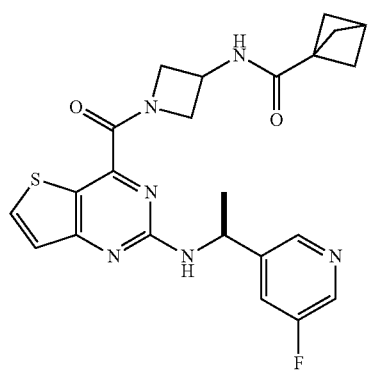 Z604 | A | A | 0.88 | E | D | | | |
| 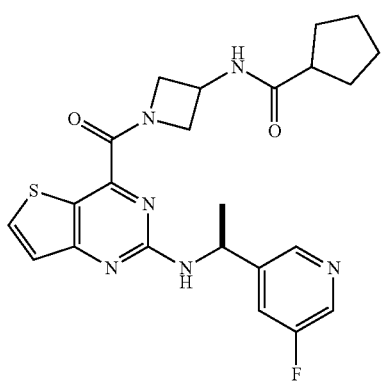 Z605 | A | A | 0.77 | E | D | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 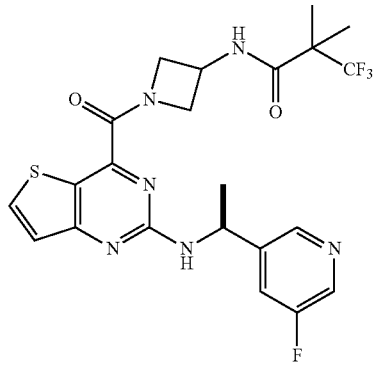 Z606 | A | A | 0.47 | E | D | | | |
| 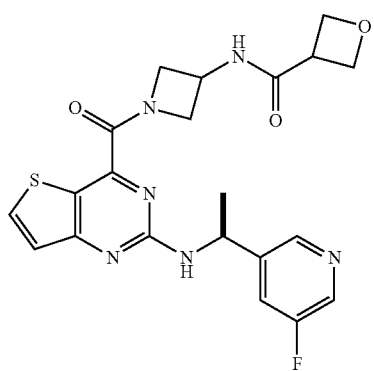 Z607 | B | C | 4.49 | E | E | | | |
| 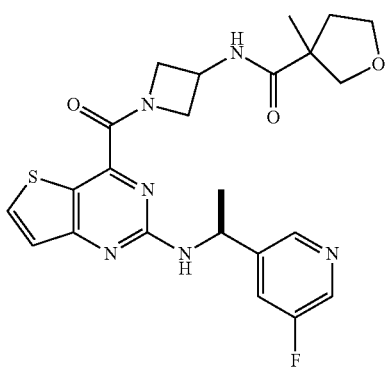 Z608 | B | A | 0.42 | E | E | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 µM | LM CLint (µL/min/mg/protein) | Hep CLint (mL/min/$10^6$ cells) |
|---|---|---|---|---|---|---|---|---|
| Z609 | A | A | 0.98 | E | D | | | |
| Z610 | A | A | 0.24 | E | B | | | |
| Z611 | A | A | 0.80 | E | D | | | |
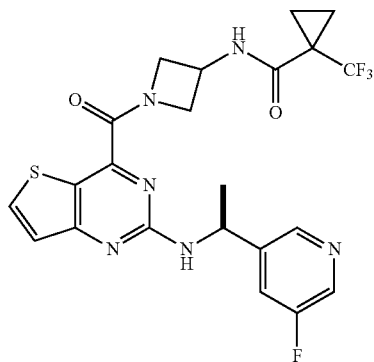 [SMILES: C[C@H](Nc1nc(C(=O)N2CC(NC(=O)C3(C(F)(F)F)CC3)C2)c2sccc2n1)c1cncc(F)c1]
Z609
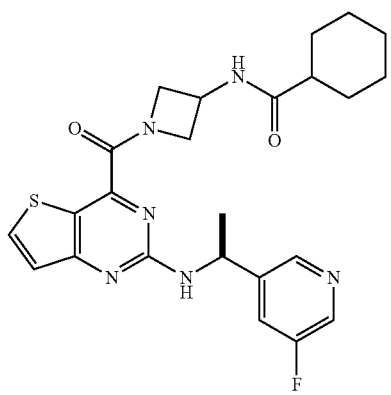 [SMILES: C[C@H](Nc1nc(C(=O)N2CC(NC(=O)C3CCCCC3)C2)c2sccc2n1)c1cncc(F)c1]
Z610
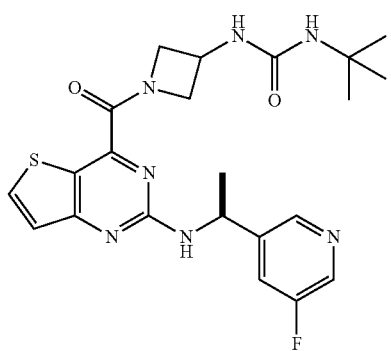 [SMILES: C[C@H](Nc1nc(C(=O)N2CC(NC(=O)NC(C)(C)C)C2)c2sccc2n1)c1cncc(F)c1]
Z611

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/min/mg/protein) | Hep CLint (mL/min/$10^6$ cells) |
|---|---|---|---|---|---|---|---|---|
| 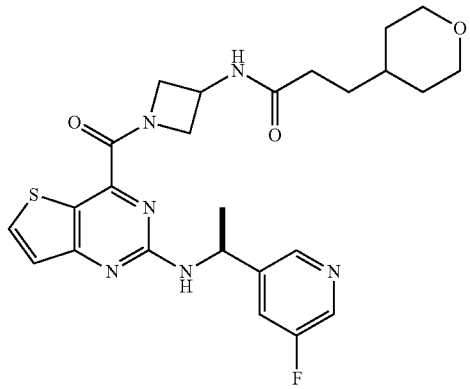 [SMILES: C[C@H](Nc1nc(C(=O)N2CC(NC(=O)CCC3CCOCC3)C2)c2sccc2n1)c1cncc(F)c1]<br>Z612 | B | B | 1.02 | E | D | | | |
| 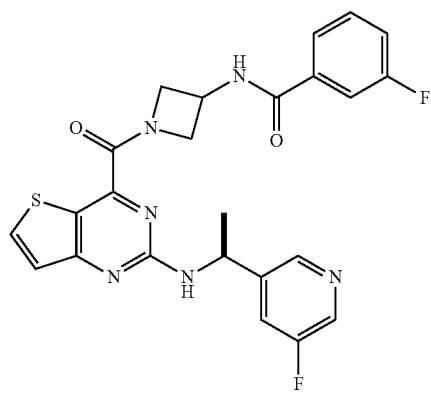 [SMILES: C[C@H](Nc1nc(C(=O)N2CC(NC(=O)c3cccc(F)c3)C2)c2sccc2n1)c1cncc(F)c1]<br>Z613 | A | A | 2.55 | E | D | | | |
| 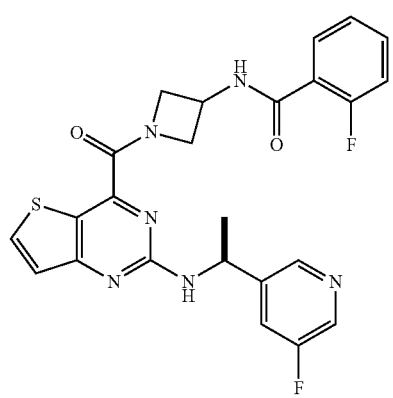 [SMILES: C[C@H](Nc1nc(C(=O)N2CC(NC(=O)c3ccccc3F)C2)c2sccc2n1)c1cncc(F)c1]<br>Z614 | A | A | 1.76 | E | D | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 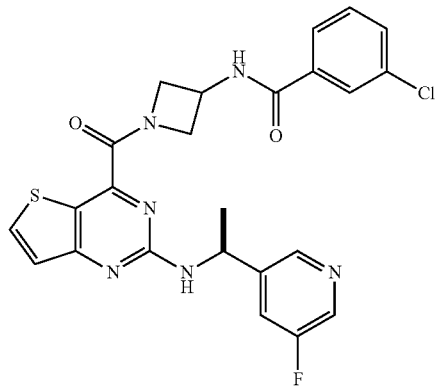 [SMILES: C[C@H](Nc1nc(C(=O)N2CC(NC(=O)c3cccc(Cl)c3)C2)c2sccc2n1)c1cncc(F)c1]<br>Z615 | A | A | 2.10 | E | D | | | |
| 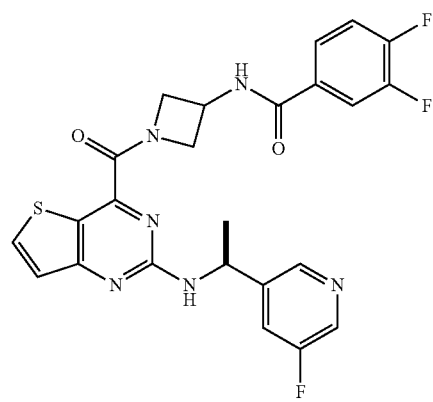 [SMILES: C[C@H](Nc1nc(C(=O)N2CC(NC(=O)c3ccc(F)c(F)c3)C2)c2sccc2n1)c1cncc(F)c1]<br>Z616 | A | B | 4.32 | E | E | | | |
| 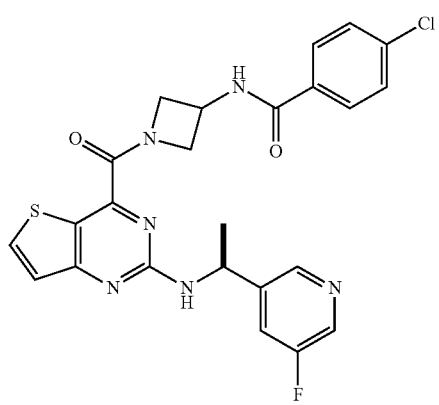 [SMILES: C[C@H](Nc1nc(C(=O)N2CC(NC(=O)c3ccc(Cl)cc3)C2)c2sccc2n1)c1cncc(F)c1]<br>Z617 | A | B | 3.67 | E | E | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 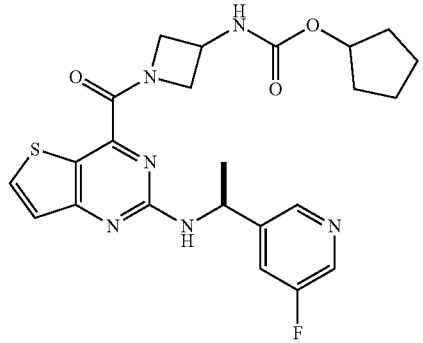 Z618 | B | B | 1.31 | E | D | | | |
| 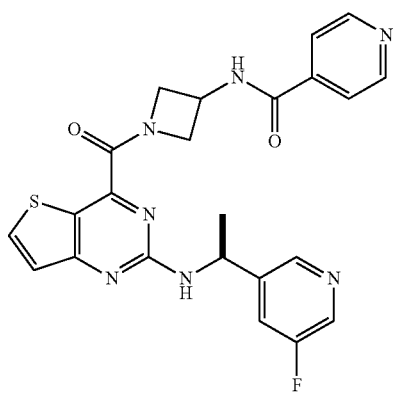 Z619 | B | C | 6.42 | E | E | | | |
| 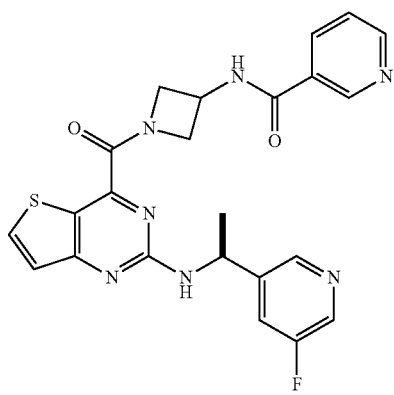 Z620 | B | C | 3.94 | E | E | | | |

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 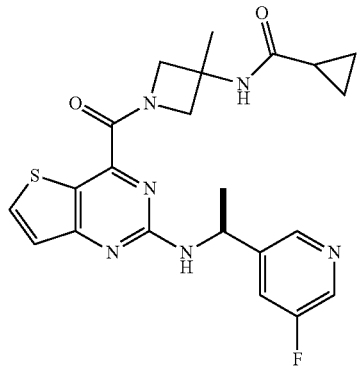 [SMILES: C[C@H](Nc1nc(C(=O)N2CC(C)(NC(=O)C3CC3)C2)c2sccc2n1)c1cncc(F)c1]<br>Z621 | B | C | 1.86 | E | A | | | |
| 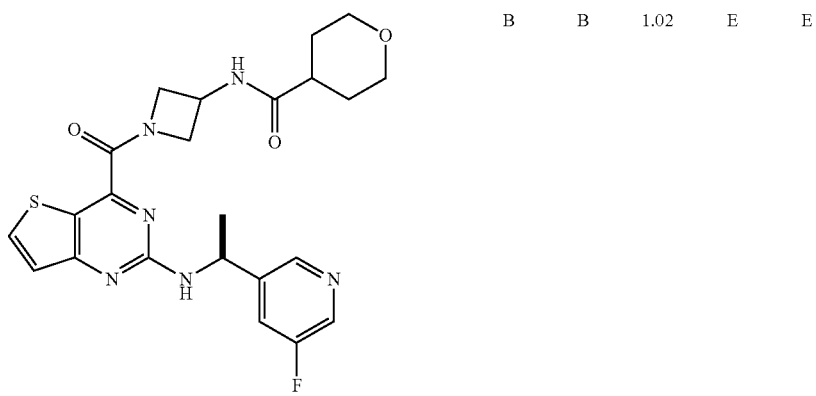<br>Z622 | B | B | 1.02 | E | E | | | |
| 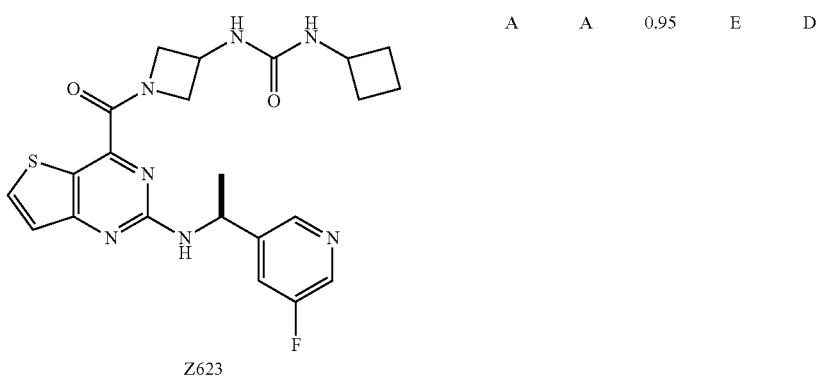<br>Z623 | A | A | 0.95 | E | D | | | |

-continued
| Compound | Ave A2B cAMP IC50 | Ave A2A cAMP IC50 | Ratio | A1 cAMP IC50 | A3 cAMP IC50 | CYP 450 % INH @ 10 μM | LM CLint (μL/ min/mg/ protein) | Hep CLint (mL/ min/ 10^6 cells) |
|---|---|---|---|---|---|---|---|---|
| 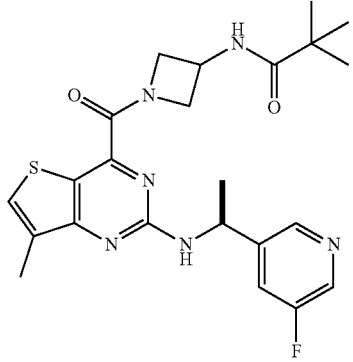<br>Z624 | B | A | 0.18 | E | D | | | |
| 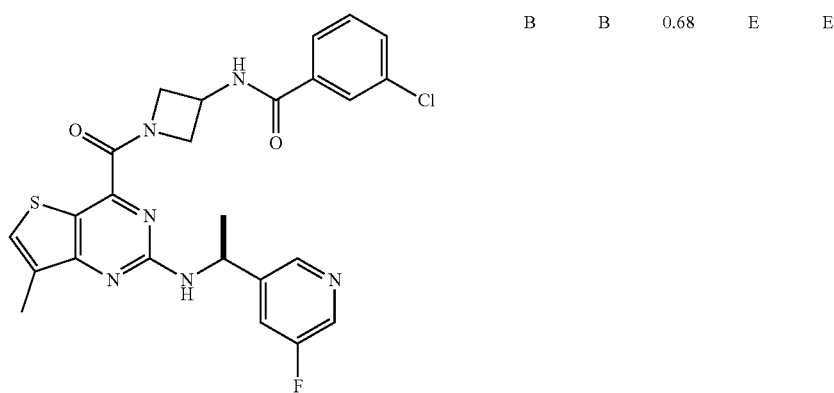<br>Z625 | B | B | 0.68 | E | E | | | |
| 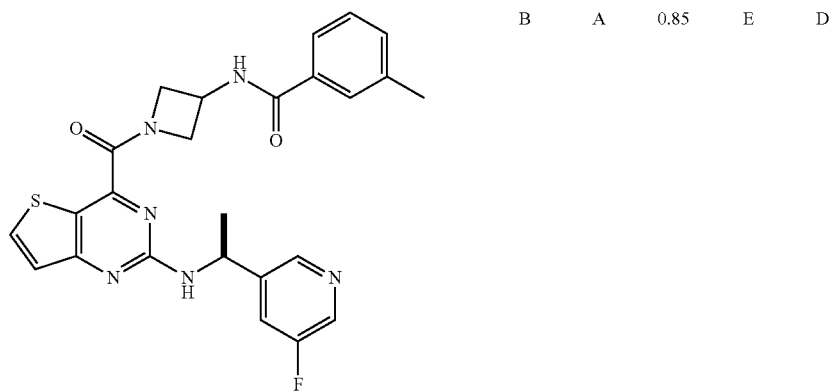<br>Z626 | B | A | 0.85 | E | D | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/min/mg/protein) | Hep CLint (mL/min/10$^6$ cells) |
|---|---|---|---|---|---|---|---|---|
| 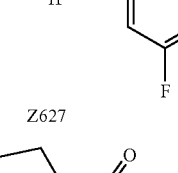 Z627 | B, B | A, A | 0.15, 0.25 | E, E | D, D | | | |
| 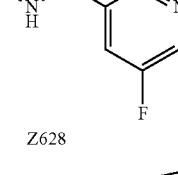 Z628 | A | A | 1.25 | E | D | | | |
| 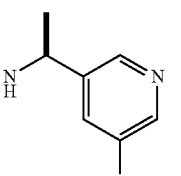 Z629 | B | B | 2.40 | E | E | | | |
| 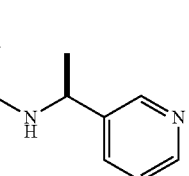 Z630 | B | A | 0.33 | E | B | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/min/mg/protein) | Hep CLint (mL/min/10$^6$ cells) |
|---|---|---|---|---|---|---|---|---|
| Z631 | B | A | 0.09 | E | B | | | |
| Z632 | A | A | 1.12 | E | D | | | |
| Z633 | A | B | 1.62 | E | D | | | |
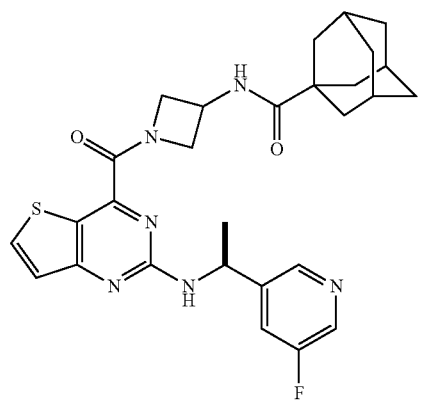 [SMILES: C[C@H](Nc1nc(C(=O)N2CC(NC(=O)C34CC5CC(CC(C5)C3)C4)C2)c2sccc2n1)c1cncc(F)c1]
Z631
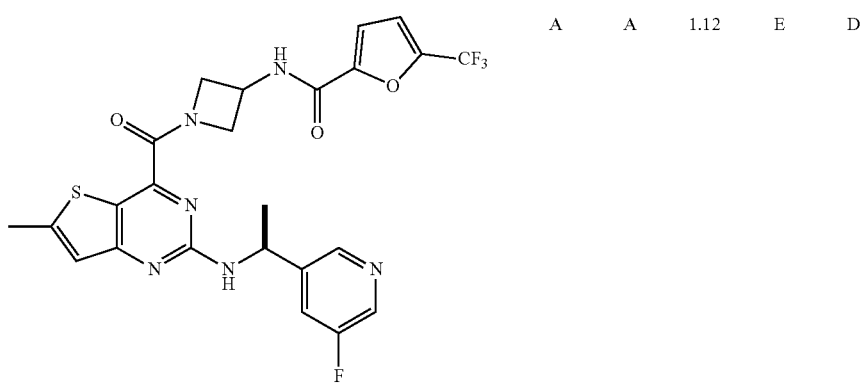
Z632
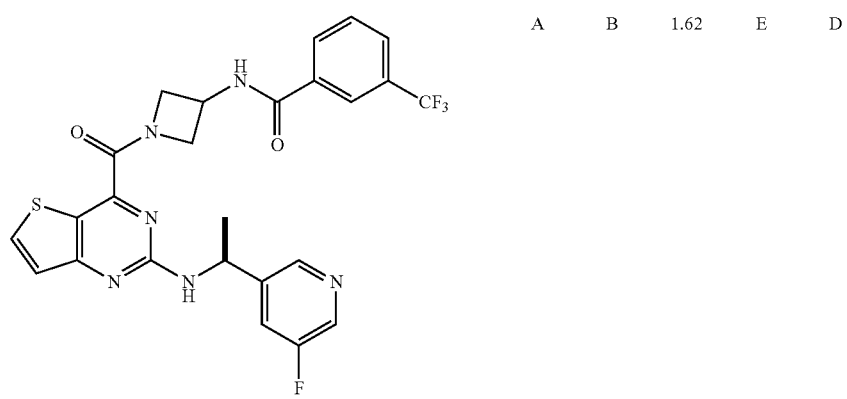
Z633

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| 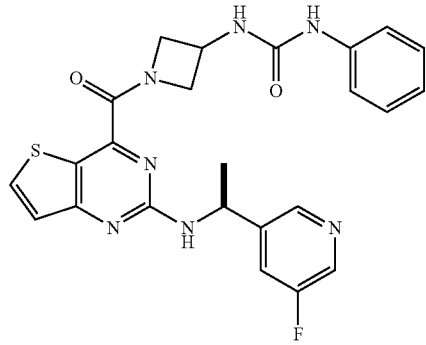 Z634 | A | B | 2.22 | E | D | | | |
| 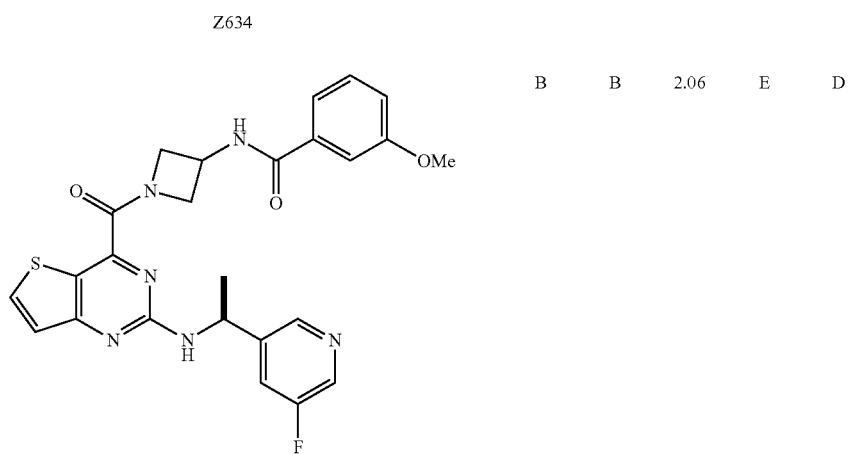 Z635 | B | B | 2.06 | E | D | | | |
| 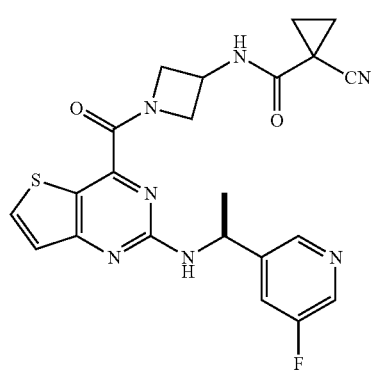 Z636 | B | C | 3.72 | E | E | | | |

-continued
| Compound | Ave A2B cAMP IC50 | Ave A2A cAMP IC50 | Ratio | A1 cAMP IC50 | A3 cAMP IC50 | CYP 450 % INH @ 10 μM | LM CLint (μL/ min/mg/ protein) | Hep CLint (mL/ min/ 10^6 cells) |
|---|---|---|---|---|---|---|---|---|
| 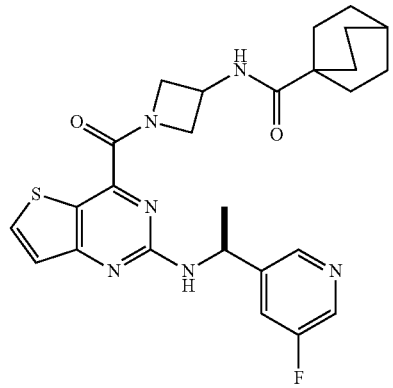 Z637 | B | A | 0.13 | E | B | | | |
| 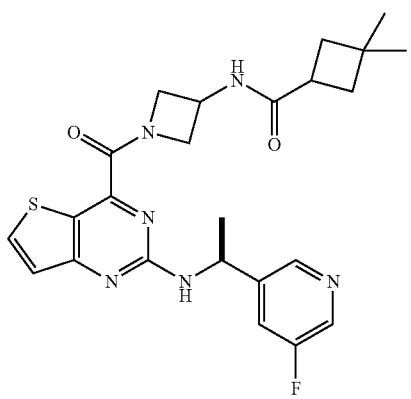 Z638 | B | A | 0.52 | E | C | | | |
| 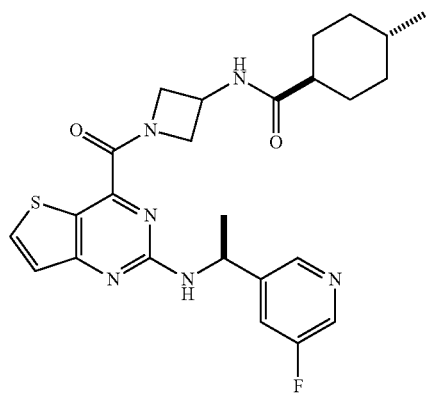 Z639 | B | B | 0.98 | E | D | | | |

-continued
| Compound | Ave A$_{2B}$ cAMP IC$_{50}$ | Ave A$_{2A}$ cAMP IC$_{50}$ | Ratio | A$_1$ cAMP IC$_{50}$ | A$_3$ cAMP IC$_{50}$ | CYP 450 % INH @ 10 μM | LM CLint (μL/ min/mg/ protein) | Hep CLint (mL/ min/ 10$^6$ cells) |
|---|---|---|---|---|---|---|---|---|
| Z640 | B | B | 1.24 | E | D | | | |
| Z641 | A | B | 1.81 | E | D | | | |
| Z642 | B | A | 0.57 | E | D | | | |
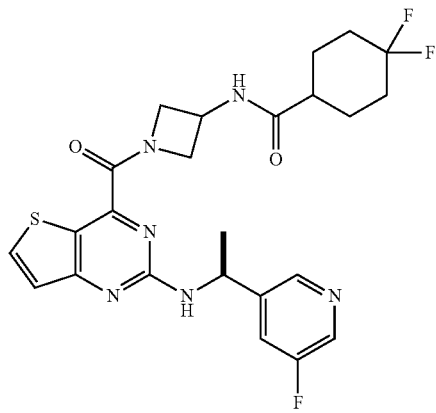 [SMILES: C[C@H](Nc1nc(C(=O)N2CC(NC(=O)C3CCC(F)(F)CC3)C2)c2sccc2n1)c1cncc(F)c1]
Z640
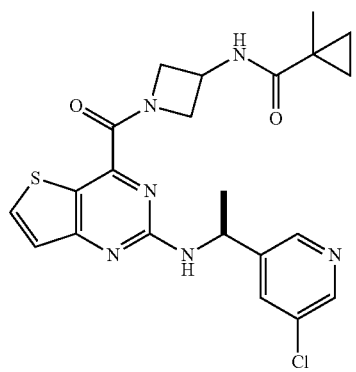 [SMILES: C[C@H](Nc1nc(C(=O)N2CC(NC(=O)C3(C)CC3)C2)c2sccc2n1)c1cncc(Cl)c1]
Z641
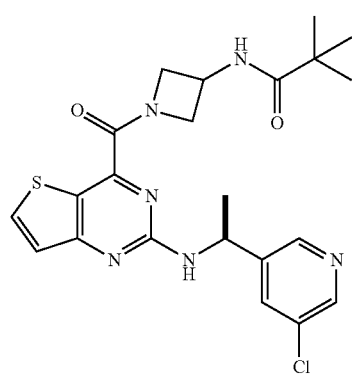
Z642

-continued
| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| 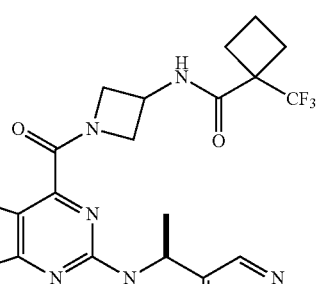 Z643 | B | A | 0.19 | E | D | | | |
| 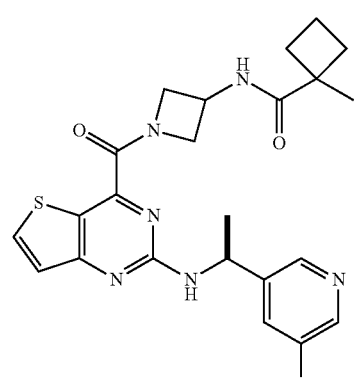 Z644 | B | A | 0.59 | E | D | | | |
| 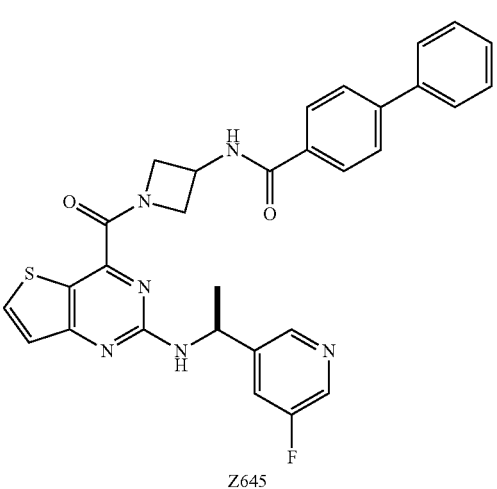 Z645 | C | B | 0.48 | E | C | | | |

-continued

| Compound | Ave $A_{2B}$ cAMP $IC_{50}$ | Ave $A_{2A}$ cAMP $IC_{50}$ | Ratio | $A_1$ cAMP $IC_{50}$ | $A_3$ cAMP $IC_{50}$ | CYP 450 % INH @ 10 μM | LM CLint (μL/ min/mg/ protein) | Hep CLint (mL/ min/ $10^6$ cells) |
|---|---|---|---|---|---|---|---|---|
| Z646 | B | B | 0.65 | E | D | | | |
| Z647 | B | B | 1.16 | E | D | | | |

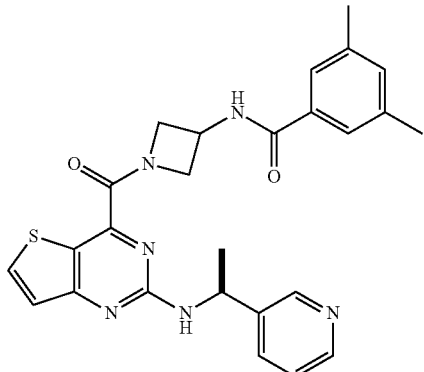

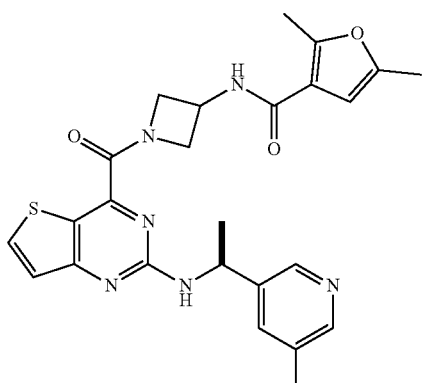

What is claimed is:

1. A compound having the formula:

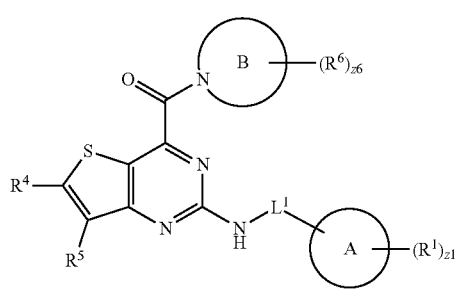

wherein $L^1$ is substituted or unsubstituted $C_1$-$C_3$ alkylene;

Ring A is phenyl, pyridyl, pyrimidinyl, pyridazinyl, or pyrazinyl;

Ring B is heterocycloalkyl;

$R^1$ is independently halogen, $-CX^1_3$, $-CHX^1_2$, $-CH_2X^1$, $-OCX^1_3$, $-OCH_2X^1$, $-OCHX^1_2$, $-CN$, $-SR^{1D}$, $-NR^{1A}R^{1B}$, $-C(O)R^{1C}$, $-C(O)OR^{1C}$, $-C(O)NR^{1A}R^{1B}$, $-OR^{1D}$, $-NR^{1A}C(O)R^{1C}$, $-NR^{1A}C(O)OR^{1C}$, $-SO_2R^{1D}$, $-SO_2NR^{1A}R^{1B}$, $-NR^{1A}SO_2R^{1D}$, substituted or unsubstituted alkyl, or substituted or unsubstituted heteroalkyl;

z1 is an integer from 0 to 5;

$R^4$ is hydrogen, $-CX^4_3$, $-NR^{4A}R^{4B}$, or substituted or unsubstituted $C_1$-$C_6$ alkyl;

$R^5$ is hydrogen or substituted or unsubstituted $C_1$-$C_6$ alkyl;

R$^6$ is independently halogen, —CX$^6_3$, —CHX$^6_2$, —CH$_2$X$^6$, —OCX$^6_3$, —OCH$_2$X$^6$, —OCHX$^6_2$, —CN, —SR$^{6D}$, —SO$_2$R$^{6D}$, —NR$^{6A}$R$^{6B}$, —C(O)R$^{6C}$, —C(O)OR$^{6C}$, —C(O)NR$^{6A}$R$^{6B}$, —C(O)NR$^{6A}$OR$^{6B}$, —OR$^{6D}$, —NR$^{6A}$C(O)R$^{6C}$, —NR$^{6A}$C(O)OR$^{6C}$, substituted or unsubstituted alkyl, or substituted or unsubstituted heteroalkyl;

z6 is an integer from 1 to 10;

each R$^{1A}$, R$^{1B}$, R$^{1C}$, R$^{1D}$, R$^{4A}$, R$^{4B}$, R$^{6A}$, R$^{6B}$, R$^{6C}$, and R$^{6D}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$ and R$^{1B}$ substituents bonded to the same nitrogen atom may optionally be joined to form a substituted or unsubstituted heterocycloalkyl;

R$^{4A}$ and R$^{4B}$ substituents bonded to the same nitrogen atom may optionally be joined to form a substituted or unsubstituted heterocycloalkyl;

R$^{6A}$ and R$^{6B}$ substituents bonded to the same nitrogen atom may optionally be joined to form a substituted or unsubstituted heterocycloalkyl; and each X$^1$, X$^4$, and X$^6$ is independently —F, —Cl, —Br, or —I.

2. The compound of claim 1, wherein Ring B is pyrrolidinyl or piperidinyl.

3. The compound of claim 1, wherein Ring A is pyridyl.

4. The compound of claim 1, having the formula:

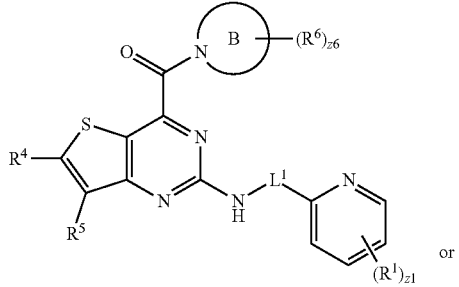

or

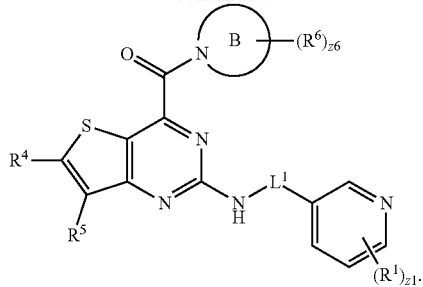

5. The compound of claim 1, wherein L$^1$ is unsubstituted C$_1$-C$_3$ alkylene.

6. The compound of claim 1, wherein R$^4$ is hydrogen or unsubstituted methyl.

7. The compound of claim 1, wherein R$^5$ is hydrogen or unsubstituted methyl.

8. The compound of claim 1, wherein z6 is 1.

9. The compound of claim 1, wherein R$^6$ is independently —NR$^{6A}$R$^{6B}$, —C(O)NR$^{6A}$R$^{6B}$, —C(O)NR$^{6A}$OR$^{6B}$, —OR$^{6D}$, —NR$^{6A}$C(O)R$^{6C}$, substituted or unsubstituted C$_1$-C$_6$ alkyl, substituted or unsubstituted 2 to 6 membered heteroalkyl.

10. The compound of claim 1, wherein R is independently —OH, —OCH$_3$, —OCH$_2$CH$_3$, —CH$_2$OH, or —CH$_2$OCH$_3$.

11. The compound of claim 1, having the formula:

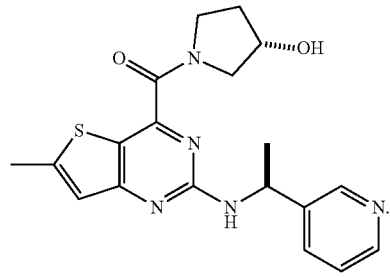 [SMILES: Cc1cc2nc(N[C@@H](C)c3cccnc3)nc(C(=O)N3CC[C@H](O)C3)c2s1]

12. The compound of claim 1, wherein R$^1$ is independently halogen, —CF$_3$, —CN, —OH, —OCH$_3$, —OCH$_2$CH$_3$, or —CH$_3$.

13. The compound of claim 1, wherein z1 is 0, 1, or 2.

14. The compound of claim 1, wherein z6 is 2.

15. A pharmaceutical composition comprising the compound of claim 1, and a pharmaceutically acceptable excipient.

* * * * *

SEQUENCE LISTING

<160> NUMBER OF SEQ ID NOS: 2

<210> SEQ ID NO 1
<211> LENGTH: 411
<212> TYPE: PRT
<213> ORGANISM: Artificial Sequence
<220> FEATURE:
<223> OTHER INFORMATION: Synthetic polypeptide

<400> SEQUENCE: 1

```
Met Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
            20                  25                  30

Leu Asn Ser Asn Leu Gln Asn Val Thr Asn Tyr Phe Val Val Ser Leu
        35                  40                  45

Ala Ala Ala Asp Ile Ala Val Gly Val Leu Ala Ile Pro Phe Ala Ile
    50                  55                  60

Thr Ile Ser Thr Gly Phe Cys Ala Ala Cys His Gly Cys Leu Phe Ile
65                  70                  75                  80
```

```
Ala Cys Phe Val Leu Val Leu Thr Gln Ser Ser Ile Phe Ser Leu Leu
                85                  90                  95

Ala Ile Ala Ile Asp Arg Tyr Ile Ala Ile Arg Ile Pro Leu Arg Tyr
            100                 105                 110

Asn Gly Leu Val Thr Gly Thr Arg Ala Lys Gly Ile Ile Ala Ile Cys
            115                 120                 125

Trp Val Leu Ser Phe Ala Ile Gly Leu Thr Pro Met Leu Gly Trp Asn
    130                 135                 140

Asn Cys Gly Gln Pro Lys Glu Gly Lys Asn His Ser Gln Cys Gly
145                 150                 155                 160

Glu Gly Gln Val Ala Cys Leu Phe Glu Asp Val Pro Met Asn Tyr Met
                165                 170                 175

Val Tyr Phe Asn Phe Phe Ala Cys Val Leu Val Pro Leu Leu Leu Met
                180                 185                 190

Leu Gly Val Tyr Leu Arg Ile Phe Leu Ala Ala Arg Arg Gln Leu Lys
            195                 200                 205

Gln Met Glu Ser Gln Pro Leu Pro Gly Glu Arg Ala Arg Ser Thr Leu
    210                 215                 220

Gln Lys Glu Val His Ala Ala Lys Ser Leu Ala Ile Ile Val Gly Leu
225                 230                 235                 240

Phe Ala Leu Cys Trp Leu Pro Leu His Ile Ile Asn Cys Phe Thr Phe
                245                 250                 255

Phe Cys Pro Asp Cys Ser His Ala Pro Leu Trp Leu Met Tyr Leu Ala
                260                 265                 270

Ile Val Leu Ser His Thr Asn Ser Val Val Asn Pro Phe Ile Tyr Ala
            275                 280                 285

Tyr Arg Ile Arg Glu Phe Arg Gln Thr Phe Arg Lys Ile Ile Arg Ser
    290                 295                 300

His Val Leu Arg Gln Gln Glu Pro Phe Lys Ala Gly Thr Ser Ala
305                 310                 315                 320

Arg Val Leu Ala Ala His Gly Ser Asp Gly Glu Gln Val Ser Leu Arg
                325                 330                 335

Leu Asn Gly His Pro Pro Gly Val Trp Ala Asn Gly Ser Ala Pro His
            340                 345                 350

Pro Glu Arg Arg Pro Asn Gly Tyr Ala Leu Gly Leu Val Ser Gly Gly
    355                 360                 365

Ser Ala Gln Glu Ser Gln Gly Asn Thr Gly Leu Pro Asp Val Glu Leu
    370                 375                 380

Leu Ser His Glu Leu Lys Gly Val Cys Pro Glu Pro Pro Gly Leu Asp
385                 390                 395                 400

Asp Pro Leu Ala Gln Asp Gly Ala Gly Val Ser
                405                 410

<210> SEQ ID NO 2
<211> LENGTH: 332
<212> TYPE: PRT
<213> ORGANISM: Artificial Sequence
<220> FEATURE:
<223> OTHER INFORMATION: Synthetic polypeptide

<400> SEQUENCE: 2

Met Leu Leu Glu Thr Gln Asp Ala Leu Tyr Val Ala Leu Glu Leu Val
1               5                   10                  15

Ile Ala Ala Leu Ser Val Ala Gly Asn Val Leu Val Cys Ala Ala Val
            20                  25                  30
```

```
Gly Thr Ala Asn Thr Leu Gln Thr Pro Thr Asn Tyr Phe Leu Val Ser
        35                  40                  45

Leu Ala Ala Ala Asp Val Ala Val Gly Leu Phe Ala Ile Pro Phe Ala
    50                  55                  60

Ile Thr Ile Ser Leu Gly Phe Cys Thr Asp Phe Tyr Gly Cys Leu Phe
65                  70                  75                  80

Leu Ala Cys Phe Val Leu Val Leu Thr Gln Ser Ser Ile Phe Ser Leu
                85                  90                  95

Leu Ala Val Ala Val Asp Arg Tyr Leu Ala Ile Cys Val Pro Leu Arg
                100                 105                 110

Tyr Lys Ser Leu Val Thr Gly Thr Arg Ala Arg Gly Val Ile Ala Val
            115                 120                 125

Leu Trp Val Leu Ala Phe Gly Ile Gly Leu Thr Pro Phe Leu Gly Trp
    130                 135                 140

Asn Ser Lys Asp Ser Ala Thr Asn Asn Cys Thr Glu Pro Trp Asp Gly
145                 150                 155                 160

Thr Thr Asn Glu Ser Cys Cys Leu Val Lys Cys Leu Phe Glu Asn Val
                165                 170                 175

Val Pro Met Ser Tyr Met Val Tyr Phe Asn Phe Phe Gly Cys Val Leu
            180                 185                 190

Pro Pro Leu Leu Ile Met Leu Val Ile Tyr Ile Lys Ile Phe Leu Val
    195                 200                 205

Ala Cys Arg Gln Leu Gln Arg Thr Glu Leu Met Asp His Ser Arg Thr
210                 215                 220

Thr Leu Gln Arg Glu Ile His Ala Ala Lys Ser Leu Ala Met Ile Val
225                 230                 235                 240

Gly Ile Phe Ala Leu Cys Trp Leu Pro Val His Ala Val Asn Cys Val
                245                 250                 255

Thr Leu Phe Gln Pro Ala Gln Gly Lys Asn Lys Pro Lys Trp Ala Met
                260                 265                 270

Asn Met Ala Ile Leu Leu Ser His Ala Asn Ser Val Val Asn Pro Ile
    275                 280                 285

Val Tyr Ala Tyr Arg Asn Arg Asp Phe Arg Tyr Thr Phe His Lys Ile
    290                 295                 300

Ile Ser Arg Tyr Leu Leu Cys Gln Ala Asp Val Lys Ser Gly Asn Gly
305                 310                 315                 320

Gln Ala Gly Val Gln Pro Ala Leu Gly Val Gly Leu
                325                 330
```